US012344869B2

(12) United States Patent
Liu et al.

(10) Patent No.: US 12,344,869 B2
(45) Date of Patent: *Jul. 1, 2025

(54) NUCLEOBASE EDITORS AND USES THEREOF

(71) Applicant: President and Fellows of Harvard College, Cambridge, MA (US)

(72) Inventors: David R. Liu, Cambridge, MA (US); Alexis Christine Komor, Cambridge, MA (US); Holly A. Rees, Cambridge, MA (US); Yongjoo Kim, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 437 days.

This patent is subject to a terminal disclaimer.

(21) Appl. No.: 17/527,011

(22) Filed: Nov. 15, 2021

(65) Prior Publication Data

US 2022/0220462 A1    Jul. 14, 2022

Related U.S. Application Data

(63) Continuation of application No. 15/960,171, filed on Apr. 23, 2018, now Pat. No. 11,214,780, which is a continuation of application No. 15/331,852, filed on Oct. 22, 2016, now Pat. No. 10,167,457, and a continuation of application No. PCT/US2016/058344, filed on Oct. 22, 2016.

(60) Provisional application No. 62/408,686, filed on Oct. 14, 2016, provisional application No. 62/398,490, filed on Sep. 22, 2016, provisional application No. 62/370,700, filed on Aug. 3, 2016, provisional application No. 62/357,332, filed on Jun. 30, 2016, provisional application No. 62/357,352, filed on Jun. 30, 2016, provisional application No. 62/322,178, filed on Apr. 13, 2016, provisional application No. 62/311,763, filed on Mar. 22, 2016, provisional application No. 62/279,346, filed on Jan. 15, 2016, provisional application No. 62/245,828, filed on Oct. 23, 2015.

(51) Int. Cl.
| | | |
|---|---|---|
| *C12N 15/10* | (2006.01) | |
| *C07K 14/32* | (2006.01) | |
| *C12N 9/22* | (2006.01) | |
| *C12N 9/24* | (2006.01) | |
| *C12N 9/78* | (2006.01) | |
| *C12N 15/11* | (2006.01) | |
| *C12N 15/90* | (2006.01) | |

(52) U.S. Cl.
CPC ............... *C12N 9/22* (2013.01); *C07K 14/32* (2013.01); *C12N 9/2497* (2013.01); *C12N 9/78* (2013.01); *C12N 15/11* (2013.01); *C12N 15/907* (2013.01); *C12Y 305/04005* (2013.01); *C07K 2319/00* (2013.01); *C07K 2319/09* (2013.01); *C07K 2319/80* (2013.01); *C12N 2310/20* (2017.05); *C12N 2800/80* (2013.01)

(58) Field of Classification Search
CPC .................. C12N 9/22; C12N 2310/20; C12Y 305/04005; C07K 2319/00
See application file for complete search history.

(56) References Cited

U.S. PATENT DOCUMENTS

| | | |
|---|---|---|
| 4,182,449 A | 1/1980 | Kozlow |
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,663,290 A | 5/1987 | Weis et al. |
| 4,737,323 A | 4/1988 | Martin et al. |
| 4,774,085 A | 9/1988 | Fidler |
| 4,797,368 A | 1/1989 | Carter et al. |
| 4,837,028 A | 6/1989 | Allen |
| 4,873,316 A | 10/1989 | Meade et al. |
| 4,880,635 A | 11/1989 | Janoff et al. |
| 4,889,818 A | 12/1989 | Gelfand et al. |
| 4,897,355 A | 1/1990 | Eppstein et al. |
| 4,906,477 A | 3/1990 | Kurono et al. |

(Continued)

FOREIGN PATENT DOCUMENTS

| | | |
|---|---|---|
| AU | 2012244264 A1 | 11/2012 |
| AU | 2012354062 A1 | 7/2014 |

(Continued)

OTHER PUBLICATIONS

Mariani et al, Cell 114:21-31, 2003.*

(Continued)

*Primary Examiner* — Mark Halvorson
(74) *Attorney, Agent, or Firm* — Wolf, Greenfield & Sacks, P.C.

(57) ABSTRACT

Some aspects of this disclosure provide strategies, systems, reagents, methods, and kits that are useful for the targeted editing of nucleic acids, including editing a single site within the genome of a cell or subject, e.g., within the human genome. In some embodiments, fusion proteins of Cas9 and nucleic acid editing proteins or protein domains, e.g., deaminase domains, are provided. In some embodiments, methods for targeted nucleic acid editing are provided. In some embodiments, reagents and kits for the generation of targeted nucleic acid editing proteins, e.g., fusion proteins of Cas9 and nucleic acid editing proteins or domains, are provided.

34 Claims, 138 Drawing Sheets
Specification includes a Sequence Listing.

(56) References Cited

U.S. PATENT DOCUMENTS

| | | |
|---|---|---|
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 4,946,787 A | 8/1990 | Eppstein et al. |
| 4,965,185 A | 10/1990 | Grischenko et al. |
| 5,017,492 A | 5/1991 | Kotewicz et al. |
| 5,047,342 A | 9/1991 | Chatterjee |
| 5,049,386 A | 9/1991 | Eppstein et al. |
| 5,057,432 A | 10/1991 | Wangersky et al. |
| 5,079,352 A | 1/1992 | Gelfand et al. |
| 5,139,941 A | 8/1992 | Muzyczka et al. |
| 5,173,414 A | 12/1992 | Lebkowski et al. |
| 5,223,409 A | 6/1993 | Ladner et al. |
| 5,244,797 A | 9/1993 | Kotewicz et al. |
| 5,270,179 A | 12/1993 | Chatterjee |
| 5,374,553 A | 12/1994 | Gelfand et al. |
| 5,405,776 A | 4/1995 | Kotewicz et al. |
| 5,436,149 A | 7/1995 | Barnes |
| 5,449,639 A | 9/1995 | Wei et al. |
| 5,496,714 A | 3/1996 | Comb et al. |
| 5,512,462 A | 4/1996 | Cheng |
| 5,580,737 A | 12/1996 | Polisky et al. |
| 5,614,365 A | 3/1997 | Tabor et al. |
| 5,652,094 A | 7/1997 | Usman et al. |
| 5,658,727 A | 8/1997 | Barbas et al. |
| 5,668,005 A | 9/1997 | Kotewicz et al. |
| 5,677,152 A | 10/1997 | Birch et al. |
| 5,712,089 A | 1/1998 | Borrebaeck et al. |
| 5,767,099 A | 6/1998 | Harris et al. |
| 5,780,053 A | 7/1998 | Ashley et al. |
| 5,821,047 A | 10/1998 | Garrard et al. |
| 5,830,430 A | 11/1998 | Unger et al. |
| 5,834,247 A | 11/1998 | Comb et al. |
| 5,835,699 A | 11/1998 | Kimura |
| 5,844,075 A | 12/1998 | Kawakami et al. |
| 5,849,548 A | 12/1998 | Haseloff et al. |
| 5,851,548 A | 12/1998 | Dattagupta et al. |
| 5,855,910 A | 1/1999 | Ashley et al. |
| 5,856,463 A | 1/1999 | Blankenborg et al. |
| 5,880,275 A | 3/1999 | Fischhoff et al. |
| 5,962,313 A | 10/1999 | Podsakoff et al. |
| 5,965,124 A | 10/1999 | Feinberg et al. |
| 5,981,182 A | 11/1999 | Jacobs, Jr. et al. |
| 6,015,794 A | 1/2000 | Haseloff et al. |
| 6,033,874 A | 3/2000 | Baum et al. |
| 6,057,153 A | 5/2000 | George et al. |
| 6,063,608 A | 5/2000 | Kotewicz et al. |
| 6,077,705 A | 6/2000 | Duan et al. |
| 6,156,509 A | 12/2000 | Schellenberger |
| 6,183,998 B1 | 2/2001 | Ivanov et al. |
| 6,355,415 B1 | 3/2002 | Wagner et al. |
| 6,429,298 B1 | 8/2002 | Ellington et al. |
| 6,453,242 B1 | 9/2002 | Eisenberg et al. |
| 6,479,264 B1 | 11/2002 | Louwrier |
| 6,503,717 B2 | 1/2003 | Case et al. |
| 6,534,261 B1 | 3/2003 | Cox, III et al. |
| 6,589,768 B1 | 7/2003 | Kotewicz et al. |
| 6,599,692 B1 | 7/2003 | Case et al. |
| 6,607,882 B1 | 8/2003 | Cox, III et al. |
| 6,610,522 B1 | 8/2003 | Kotewicz et al. |
| 6,689,558 B2 | 2/2004 | Case |
| 6,713,063 B1 | 3/2004 | Malvar et al. |
| 6,716,973 B2 | 4/2004 | Baskerville et al. |
| 6,824,978 B1 | 11/2004 | Cox, III et al. |
| 6,933,113 B2 | 8/2005 | Case et al. |
| 6,962,705 B2 | 11/2005 | Malvar et al. |
| 6,969,731 B1 | 11/2005 | Tang et al. |
| 6,979,539 B2 | 12/2005 | Cox, III et al. |
| 7,013,219 B2 | 3/2006 | Case et al. |
| 7,045,337 B2 | 5/2006 | Schultz et al. |
| 7,064,249 B2 | 6/2006 | Corbin et al. |
| 7,067,650 B1 | 6/2006 | Tanaka |
| 7,070,928 B2 | 7/2006 | Liu et al. |
| 7,070,982 B2 | 7/2006 | Malvar et al. |
| 7,078,208 B2 | 7/2006 | Smith et al. |
| 7,083,970 B2 | 8/2006 | Schultz et al. |
| 7,163,824 B2 | 1/2007 | Cox, III et al. |
| 7,192,739 B2 | 3/2007 | Liu et al. |
| 7,223,545 B2 | 5/2007 | Liu et al. |
| 7,354,761 B2 | 4/2008 | Schultz et al. |
| 7,368,275 B2 | 5/2008 | Schultz et al. |
| 7,419,669 B2 | 9/2008 | Kosmatopoulos et al. |
| 7,442,160 B2 | 10/2008 | Liu et al. |
| 7,476,500 B1 | 1/2009 | Liu et al. |
| 7,476,734 B2 | 1/2009 | Liu |
| 7,479,573 B2 | 1/2009 | Chu et al. |
| 7,488,718 B2 | 2/2009 | Scheinberg et al. |
| 7,491,494 B2 | 2/2009 | Liu et al. |
| 7,541,450 B2 | 6/2009 | Liu et al. |
| 7,557,068 B2 | 7/2009 | Liu et al. |
| 7,595,179 B2 | 9/2009 | Chen et al. |
| 7,638,300 B2 | 12/2009 | Schultz et al. |
| 7,670,807 B2 | 3/2010 | Lampson et al. |
| 7,678,554 B2 | 3/2010 | Liu et al. |
| 7,713,721 B2 | 5/2010 | Schultz et al. |
| 7,771,935 B2 | 8/2010 | Liu et al. |
| 7,794,931 B2 | 9/2010 | Breaker et al. |
| 7,807,408 B2 | 10/2010 | Liu et al. |
| 7,851,658 B2 | 12/2010 | Liu et al. |
| 7,915,025 B2 | 3/2011 | Schultz et al. |
| 7,919,277 B2 | 4/2011 | Russell et al. |
| 7,993,672 B2 | 8/2011 | Huang et al. |
| 7,998,904 B2 | 8/2011 | Liu et al. |
| 7,999,071 B2 | 8/2011 | Schlom et al. |
| 8,012,739 B2 | 9/2011 | Schultz et al. |
| 8,017,323 B2 | 9/2011 | Liu et al. |
| 8,017,755 B2 | 9/2011 | Liu et al. |
| 8,030,074 B2 | 10/2011 | Schultz et al. |
| 8,067,556 B2 | 11/2011 | Hogrefe et al. |
| 8,114,648 B2 | 2/2012 | Schultz et al. |
| 8,173,364 B2 | 5/2012 | Schultz et al. |
| 8,173,392 B2 | 5/2012 | Schultz et al. |
| 8,183,012 B2 | 5/2012 | Schultz et al. |
| 8,183,178 B2 | 5/2012 | Liu et al. |
| 8,206,914 B2 | 6/2012 | Liu et al. |
| 8,354,380 B2 | 1/2013 | Liu et al. |
| 8,361,725 B2 | 1/2013 | Russell et al. |
| 8,394,604 B2 | 3/2013 | Liu et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,492,082 B2 | 7/2013 | De Franciscis et al. |
| 8,546,553 B2 | 10/2013 | Terns et al. |
| 8,569,256 B2 | 10/2013 | Heyes et al. |
| 8,586,363 B2 | 11/2013 | Voytas et al. |
| 8,680,069 B2 | 3/2014 | De Fougerolles et al. |
| 8,691,729 B2 | 4/2014 | Liu et al. |
| 8,691,750 B2 | 4/2014 | Constien et al. |
| 8,697,359 B1 | 4/2014 | Zhang |
| 8,697,853 B2 | 4/2014 | Voytas et al. |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,822,663 B2 | 9/2014 | Schrum et al. |
| 8,835,148 B2 | 9/2014 | Janulaitis et al. |
| 8,846,578 B2 | 9/2014 | McCray et al. |
| 8,871,445 B2 | 10/2014 | Cong et al. |
| 8,889,418 B2 | 11/2014 | Zhang et al. |
| 8,900,814 B2 | 12/2014 | Yasukawa et al. |
| 8,945,839 B2 | 2/2015 | Zhang |
| 8,975,232 B2 | 3/2015 | Liu et al. |
| 8,993,233 B2 | 3/2015 | Zhang et al. |
| 8,999,641 B2 | 4/2015 | Zhang et al. |
| 9,023,594 B2 | 5/2015 | Liu et al. |
| 9,023,649 B2 | 5/2015 | Mali et al. |
| 9,034,650 B2 | 5/2015 | Padidam |
| 9,068,179 B1 | 6/2015 | Liu et al. |

(56) References Cited

U.S. PATENT DOCUMENTS

| | | |
|---|---|---|
| 9,150,626 B2 | 10/2015 | Liu et al. |
| 9,163,271 B2 | 10/2015 | Schultz et al. |
| 9,163,284 B2 | 10/2015 | Liu et al. |
| 9,181,535 B2 | 11/2015 | Liu et al. |
| 9,200,045 B2 | 12/2015 | Liu et al. |
| 9,221,886 B2 | 12/2015 | Liu et al. |
| 9,228,207 B2 | 1/2016 | Liu et al. |
| 9,234,213 B2 | 1/2016 | Wu |
| 9,243,038 B2 | 1/2016 | Liu et al. |
| 9,267,127 B2 | 2/2016 | Liu et al. |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,388,430 B2 | 7/2016 | Liu et al. |
| 9,394,537 B2 | 7/2016 | Liu et al. |
| 9,434,774 B2 | 9/2016 | Liu et al. |
| 9,458,484 B2 | 10/2016 | Ma et al. |
| 9,512,446 B1 | 12/2016 | Joung et al. |
| 9,526,724 B2 | 12/2016 | Oshlack et al. |
| 9,526,784 B2 | 12/2016 | Liu et al. |
| 9,534,210 B2 | 1/2017 | Park et al. |
| 9,567,589 B2 | 2/2017 | Jin et al. |
| 9,580,698 B1 | 2/2017 | Xu et al. |
| 9,610,322 B2 | 4/2017 | Liu et al. |
| 9,637,739 B2 | 5/2017 | Siksnys et al. |
| 9,663,770 B2 | 5/2017 | Rogers et al. |
| 9,737,604 B2 | 8/2017 | Jin et al. |
| 9,738,693 B2 | 8/2017 | Telford et al. |
| 9,753,340 B2 | 9/2017 | Saitou |
| 9,766,216 B2 | 9/2017 | Wada et al. |
| 9,771,574 B2 | 9/2017 | Liu et al. |
| 9,783,791 B2 | 10/2017 | Hogrefe et al. |
| 9,816,093 B1 | 11/2017 | Donohoue et al. |
| 9,840,538 B2 | 12/2017 | Telford et al. |
| 9,840,690 B2 | 12/2017 | Karli et al. |
| 9,840,699 B2 | 12/2017 | Liu et al. |
| 9,840,702 B2 | 12/2017 | Collingwood et al. |
| 9,850,521 B2 | 12/2017 | Braman et al. |
| 9,873,907 B2 | 1/2018 | Zeiner et al. |
| 9,879,270 B2 | 1/2018 | Hittinger et al. |
| 9,914,939 B2 | 3/2018 | Church et al. |
| 9,932,567 B1 | 4/2018 | Xu et al. |
| 9,938,288 B1 | 4/2018 | Kishi et al. |
| 9,944,933 B2 | 4/2018 | Storici et al. |
| 9,982,279 B1 | 5/2018 | Gill et al. |
| 9,999,671 B2 | 6/2018 | Liu et al. |
| 10,011,868 B2 | 7/2018 | Liu et al. |
| 10,053,725 B2 | 8/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,150,955 B2 | 12/2018 | Lambowitz et al. |
| 10,167,457 B2 | 1/2019 | Liu et al. |
| 10,179,911 B2 | 1/2019 | Liu et al. |
| 10,189,831 B2 | 1/2019 | Arrington et al. |
| 10,202,658 B2 | 2/2019 | Parkin et al. |
| 10,227,581 B2 | 3/2019 | Liu et al. |
| 10,323,236 B2 | 6/2019 | Liu et al. |
| 10,336,997 B2 | 7/2019 | Liu et al. |
| 10,358,670 B2 | 7/2019 | Janulaitis et al. |
| 10,392,674 B2 | 8/2019 | Liu et al. |
| 10,407,697 B2 | 9/2019 | Doudna et al. |
| 10,465,176 B2 | 11/2019 | Liu et al. |
| 10,508,298 B2 | 12/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |
| 10,704,062 B2 | 7/2020 | Liu et al. |
| 10,745,677 B2 | 8/2020 | Maianti et al. |
| 10,858,639 B2 | 12/2020 | Liu et al. |
| 10,912,833 B2 | 2/2021 | Liu et al. |
| 10,920,208 B2 | 2/2021 | Liu et al. |
| 10,930,367 B2 | 2/2021 | Zhang et al. |
| 10,947,530 B2 | 3/2021 | Liu et al. |
| 10,954,548 B2 | 3/2021 | Liu et al. |
| 11,046,948 B2 | 6/2021 | Liu et al. |
| 11,053,481 B2 | 7/2021 | Liu et al. |
| 11,124,782 B2 | 9/2021 | Liu et al. |
| 11,214,780 B2 | 1/2022 | Liu et al. |
| 11,268,082 B2 | 3/2022 | Liu et al. |
| 11,299,755 B2 | 4/2022 | Liu et al. |
| 11,306,324 B2 | 4/2022 | Liu et al. |
| 11,319,532 B2 | 5/2022 | Liu et al. |
| 11,447,770 B1 | 9/2022 | Liu et al. |
| 11,542,496 B2 | 1/2023 | Liu et al. |
| 11,542,509 B2 | 1/2023 | Maianti et al. |
| 11,560,566 B2 | 1/2023 | Liu et al. |
| 11,578,343 B2 | 2/2023 | Liu et al. |
| 11,643,652 B2 | 5/2023 | Liu et al. |
| 11,661,590 B2 | 5/2023 | Liu et al. |
| 11,702,651 B2 | 7/2023 | Liu et al. |
| 11,732,274 B2 | 8/2023 | Liu et al. |
| 11,795,443 B2 | 10/2023 | Liu et al. |
| 11,795,452 B2 | 10/2023 | Liu et al. |
| 11,820,969 B2 | 11/2023 | Maianti et al. |
| 11,898,179 B2 | 2/2024 | Maianti et al. |
| 11,912,985 B2 | 2/2024 | Liu et al. |
| 11,920,181 B2 | 3/2024 | Liu et al. |
| 11,932,884 B2 | 3/2024 | Liu et al. |
| 11,999,947 B2 | 6/2024 | Liu et al. |
| 12,006,520 B2 | 6/2024 | Liu et al. |
| 12,031,126 B2 | 7/2024 | Liu et al. |
| 2002/0132327 A1 | 9/2002 | Hay et al. |
| 2003/0082575 A1 | 5/2003 | Schultz et al. |
| 2003/0087817 A1 | 5/2003 | Cox et al. |
| 2003/0096337 A1 | 5/2003 | Hillman et al. |
| 2003/0108885 A1 | 6/2003 | Schultz et al. |
| 2003/0119764 A1 | 6/2003 | Loeb et al. |
| 2003/0167533 A1 | 9/2003 | Yadav et al. |
| 2003/0203480 A1 | 10/2003 | Kovesdi et al. |
| 2004/0003420 A1 | 1/2004 | Kuhn et al. |
| 2004/0115184 A1 | 6/2004 | Smith et al. |
| 2004/0197892 A1 | 10/2004 | Moore et al. |
| 2004/0203109 A1 | 10/2004 | Lal et al. |
| 2005/0100973 A1 | 5/2005 | Steward et al. |
| 2005/0136429 A1 | 6/2005 | Guarente et al. |
| 2005/0222030 A1 | 10/2005 | Allison |
| 2005/0260626 A1 | 11/2005 | Lorens et al. |
| 2006/0088864 A1 | 4/2006 | Smolke et al. |
| 2006/0104984 A1 | 5/2006 | Littlefield et al. |
| 2006/0112447 A1 | 5/2006 | Bogdanova et al. |
| 2006/0160222 A1 | 7/2006 | Rozwadowski et al. |
| 2006/0166319 A1 | 7/2006 | Chan et al. |
| 2006/0246568 A1 | 11/2006 | Honjo et al. |
| 2007/0015238 A1 | 1/2007 | Snyder et al. |
| 2007/0264692 A1 | 11/2007 | Liu et al. |
| 2007/0269817 A1 | 11/2007 | Shapero |
| 2008/0008697 A1 | 1/2008 | Mintier et al. |
| 2008/0051317 A1 | 2/2008 | Church et al. |
| 2008/0124725 A1 | 5/2008 | Barrangou et al. |
| 2008/0182254 A1 | 7/2008 | Hall et al. |
| 2008/0220502 A1 | 9/2008 | Schellenberger et al. |
| 2008/0241917 A1 | 10/2008 | Akita et al. |
| 2008/0268516 A1 | 10/2008 | Perreault et al. |
| 2009/0111119 A1 | 4/2009 | Doyon et al. |
| 2009/0130718 A1 | 5/2009 | Short |
| 2009/0215110 A1 | 8/2009 | Gibson et al. |
| 2009/0215878 A1 | 8/2009 | Tan et al. |
| 2009/0227463 A1 | 9/2009 | Reif et al. |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0273857 A1 | 10/2010 | Thakker et al. |
| 2010/0297180 A1 | 11/2010 | Shone |
| 2010/0305197 A1 | 12/2010 | Che |
| 2010/0316643 A1 | 12/2010 | Eckert et al. |
| 2011/0016540 A1 | 1/2011 | Weinstein et al. |
| 2011/0059160 A1 | 3/2011 | Essner et al. |
| 2011/0059502 A1 | 3/2011 | Chalasani |
| 2011/0104787 A1 | 5/2011 | Church et al. |
| 2011/0177495 A1 | 7/2011 | Liu et al. |

(56) References Cited

U.S. PATENT DOCUMENTS

| | | |
|---|---|---|
| 2011/0189775 A1 | 8/2011 | Ainley et al. |
| 2011/0189776 A1 | 8/2011 | Terns et al. |
| 2011/0217739 A1 | 9/2011 | Terns et al. |
| 2011/0301073 A1 | 12/2011 | Gregory et al. |
| 2012/0128649 A1 | 5/2012 | Chaddock et al. |
| 2012/0129759 A1 | 5/2012 | Liu et al. |
| 2012/0141523 A1 | 6/2012 | Castado et al. |
| 2012/0244601 A1 | 9/2012 | Bertozzi et al. |
| 2012/0270273 A1 | 10/2012 | Zhang et al. |
| 2012/0322861 A1 | 12/2012 | Byrne et al. |
| 2013/0022980 A1 | 1/2013 | Nelson et al. |
| 2013/0059931 A1 | 3/2013 | Petersen-Mahrt et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0212725 A1 | 8/2013 | Kuhn et al. |
| 2013/0309720 A1 | 11/2013 | Schultz et al. |
| 2013/0344117 A1 | 12/2013 | Mirosevich et al. |
| 2013/0345064 A1 | 12/2013 | Liu et al. |
| 2013/0345065 A1 | 12/2013 | Hassibi et al. |
| 2014/0004280 A1 | 1/2014 | Loomis |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0128449 A1 | 5/2014 | Liu et al. |
| 2014/0141094 A1 | 5/2014 | Smyth et al. |
| 2014/0141487 A1 | 5/2014 | Feldman et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0201858 A1 | 7/2014 | Ostertag et al. |
| 2014/0234289 A1 | 8/2014 | Liu et al. |
| 2014/0248702 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273234 A1 | 9/2014 | Zhang et al. |
| 2014/0283156 A1 | 9/2014 | Zador et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0128300 A1 | 5/2015 | Warming et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166983 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens |
| 2015/0218573 A1 | 8/2015 | Loque et al. |
| 2015/0225773 A1 | 8/2015 | Farmer et al. |
| 2015/0241440 A1 | 8/2015 | Fasan et al. |
| 2015/0252358 A1 | 9/2015 | Maeder et al. |
| 2015/0259721 A1 | 9/2015 | Brunt et al. |
| 2015/0275202 A1 | 10/2015 | Liu et al. |
| 2015/0291965 A1 | 10/2015 | Zhang et al. |
| 2015/0307889 A1 | 10/2015 | Petolino et al. |
| 2015/0315252 A1 | 11/2015 | Haugwitz et al. |
| 2015/0344549 A1 | 12/2015 | Muir et al. |
| 2016/0002301 A1 | 1/2016 | Je et al. |
| 2016/0015682 A2 | 1/2016 | Cawthorne et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0040155 A1 | 2/2016 | Maizels et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |
| 2016/0115488 A1 | 4/2016 | Zhang et al. |
| 2016/0138046 A1 | 5/2016 | Wu |
| 2016/0153003 A1 | 6/2016 | Joung et al. |
| 2016/0186214 A1 | 6/2016 | Brouns et al. |
| 2016/0200779 A1 | 7/2016 | Liu et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0264934 A1 | 9/2016 | Giallourakis et al. |
| 2016/0272593 A1 | 9/2016 | Ritter et al. |
| 2016/0272965 A1 | 9/2016 | Zhang et al. |
| 2016/0281072 A1 | 9/2016 | Zhang |
| 2016/0298136 A1 | 10/2016 | Chen et al. |
| 2016/0304846 A1 | 10/2016 | Liu et al. |
| 2016/0304855 A1 | 10/2016 | Stark et al. |
| 2016/0312304 A1 | 10/2016 | Sorrentino et al. |
| 2016/0319262 A1 | 11/2016 | Doudna et al. |
| 2016/0333389 A1 | 11/2016 | Liu et al. |
| 2016/0340622 A1 | 11/2016 | Abdou |
| 2016/0340661 A1 | 11/2016 | Cong et al. |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0348096 A1 | 12/2016 | Liu et al. |
| 2016/0350476 A1 | 12/2016 | Quake et al. |

(56) References Cited

U.S. PATENT DOCUMENTS

| | | |
|---|---|---|
| 2016/0355796 A1 | 12/2016 | Davidson et al. |
| 2016/0369262 A1 | 12/2016 | Reik et al. |
| 2017/0009224 A1 | 1/2017 | Liu et al. |
| 2017/0009242 A1 | 1/2017 | Mckinley et al. |
| 2017/0014449 A1 | 1/2017 | Bangera et al. |
| 2017/0020922 A1 | 1/2017 | Wagner et al. |
| 2017/0022251 A1 | 1/2017 | Rammensee et al. |
| 2017/0029844 A1 | 2/2017 | Ball et al. |
| 2017/0037432 A1 | 2/2017 | Donohoue et al. |
| 2017/0044520 A1 | 2/2017 | Liu et al. |
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0073670 A1 | 3/2017 | Nishida et al. |
| 2017/0087224 A1 | 3/2017 | Quake |
| 2017/0087225 A1 | 3/2017 | Quake |
| 2017/0088587 A1 | 3/2017 | Quake |
| 2017/0088828 A1 | 3/2017 | Quake |
| 2017/0107536 A1 | 4/2017 | Zhang et al. |
| 2017/0107560 A1 | 4/2017 | Peter et al. |
| 2017/0114367 A1 | 4/2017 | Hu et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0211061 A1 | 7/2017 | Weiss et al. |
| 2017/0224843 A1 | 8/2017 | Deglon et al. |
| 2017/0226522 A1 | 8/2017 | Hu et al. |
| 2017/0233703 A1 | 8/2017 | Xie et al. |
| 2017/0233708 A1 | 8/2017 | Liu et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0275648 A1 | 9/2017 | Barrangou et al. |
| 2017/0275665 A1 | 9/2017 | Silas et al. |
| 2017/0283797 A1 | 10/2017 | Robb et al. |
| 2017/0283831 A1 | 10/2017 | Zhang et al. |
| 2017/0306306 A1 | 10/2017 | Potter et al. |
| 2017/0314016 A1 | 11/2017 | Kim et al. |
| 2017/0362635 A1 | 12/2017 | Chamberlain et al. |
| 2018/0023062 A1 | 1/2018 | Lamb et al. |
| 2018/0057545 A9 | 3/2018 | Liu et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0080051 A1 | 3/2018 | Sheikh et al. |
| 2018/0087046 A1 | 3/2018 | Badran et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127759 A1 | 5/2018 | Lu et al. |
| 2018/0127780 A1 | 5/2018 | Liu et al. |
| 2018/0155708 A1 | 6/2018 | Church et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237758 A1 | 8/2018 | Liu et al. |
| 2018/0237787 A1 | 8/2018 | Maianti et al. |
| 2018/0245066 A1 | 8/2018 | Yao et al. |
| 2018/0245075 A1 | 8/2018 | Khalil et al. |
| 2018/0258418 A1 | 9/2018 | Kim |
| 2018/0265864 A1 | 9/2018 | Li et al. |
| 2018/0273939 A1 | 9/2018 | Yu et al. |
| 2018/0282722 A1 | 10/2018 | Jakimo et al. |
| 2018/0298391 A1 | 10/2018 | Jakimo et al. |
| 2018/0305688 A1 | 10/2018 | Zhong |
| 2018/0305704 A1 | 10/2018 | Zhang |
| 2018/0312822 A1 | 11/2018 | Lee et al. |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2019/0010481 A1 | 1/2019 | Joung et al. |
| 2019/0055543 A1 | 2/2019 | Tran et al. |
| 2019/0093099 A1 | 3/2019 | Liu et al. |
| 2019/0185883 A1 | 6/2019 | Liu et al. |
| 2019/0219575 A1 | 7/2019 | Gray et al. |
| 2019/0225955 A1 | 7/2019 | Liu et al. |
| 2019/0233847 A1 | 8/2019 | Savage et al. |
| 2019/0241633 A1 | 8/2019 | Fotin-Mleczek et al. |
| 2019/0256842 A1 | 8/2019 | Liu et al. |
| 2019/0264202 A1 | 8/2019 | Church et al. |
| 2019/0276816 A1 | 9/2019 | Liu et al. |
| 2019/0276873 A1 | 9/2019 | Dong et al. |
| 2019/0322992 A1 | 10/2019 | Liu et al. |
| 2019/0352632 A1 | 11/2019 | Liu et al. |
| 2019/0367891 A1 | 12/2019 | Liu et al. |
| 2020/0010818 A1 | 1/2020 | Liu et al. |
| 2020/0010835 A1 | 1/2020 | Maianti et al. |
| 2020/0063127 A1 | 2/2020 | Lu et al. |
| 2020/0071722 A1 | 3/2020 | Liu et al. |
| 2020/0172931 A1 | 6/2020 | Liu et al. |
| 2020/0181619 A1 | 6/2020 | Tang et al. |
| 2020/0190493 A1 | 6/2020 | Liu et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2020/0399619 A1 | 12/2020 | Maianti et al. |
| 2020/0399626 A1 | 12/2020 | Liu et al. |
| 2021/0054416 A1 | 2/2021 | Liu et al. |
| 2021/0115428 A1 | 4/2021 | Maianti et al. |
| 2021/0196809 A1 | 7/2021 | Maianti et al. |
| 2021/0198330 A1 | 7/2021 | Liu et al. |
| 2021/0214698 A1 | 7/2021 | Liu et al. |
| 2021/0230577 A1 | 7/2021 | Liu et al. |
| 2021/0254127 A1 | 8/2021 | Liu et al. |
| 2021/0315994 A1 | 10/2021 | Liu et al. |
| 2021/0317440 A1 | 10/2021 | Liu et al. |
| 2022/0033785 A1 | 2/2022 | Liu et al. |
| 2022/0119785 A1 | 4/2022 | Liu et al. |
| 2022/0170013 A1 | 6/2022 | Liu et al. |
| 2022/0177877 A1 | 6/2022 | Church et al. |
| 2022/0204975 A1 | 6/2022 | Liu et al. |
| 2022/0213507 A1 | 7/2022 | Liu et al. |
| 2022/0238182 A1 | 7/2022 | Shen et al. |
| 2022/0249697 A1 | 8/2022 | Liu et al. |
| 2022/0282275 A1 | 9/2022 | Liu et al. |
| 2022/0290115 A1 | 9/2022 | Liu et al. |
| 2022/0307001 A1 | 9/2022 | Liu et al. |
| 2022/0307003 A1 | 9/2022 | Liu et al. |
| 2022/0315906 A1 | 10/2022 | Liu et al. |
| 2022/0356469 A1 | 11/2022 | Liu et al. |
| 2022/0380740 A1 | 12/2022 | Liu et al. |
| 2022/0389395 A1 | 12/2022 | Liu et al. |
| 2023/0002745 A1 | 1/2023 | Liu et al. |
| 2023/0021641 A1 | 1/2023 | Liu et al. |
| 2023/0056852 A1 | 2/2023 | Liu et al. |
| 2023/0058176 A1 | 2/2023 | Liu et al. |
| 2023/0078265 A1 | 3/2023 | Liu et al. |
| 2023/0086199 A1 | 3/2023 | Liu et al. |
| 2023/0090221 A1 | 3/2023 | Liu et al. |

(56) References Cited

U.S. PATENT DOCUMENTS

| | | |
|---|---|---|
| 2023/0108687 A1 | 4/2023 | Liu et al. |
| 2023/0123669 A1 | 4/2023 | Liu et al. |
| 2023/0127008 A1 | 4/2023 | Liu et al. |
| 2023/0159913 A1 | 5/2023 | Liu et al. |
| 2023/0193295 A1 | 6/2023 | Maianti et al. |
| 2023/0220374 A1 | 7/2023 | Liu et al. |
| 2023/0272425 A1 | 8/2023 | Liu et al. |
| 2023/0279443 A1 | 9/2023 | Liu et al. |
| 2023/0332144 A1 | 10/2023 | Liu et al. |
| 2023/0340465 A1 | 10/2023 | Liu et al. |
| 2023/0340466 A1 | 10/2023 | Liu et al. |
| 2023/0340467 A1 | 10/2023 | Liu et al. |
| 2023/0348883 A1 | 11/2023 | Liu et al. |
| 2023/0357766 A1 | 11/2023 | Liu et al. |
| 2023/0383289 A1 | 11/2023 | Liu et al. |
| 2024/0035017 A1 | 2/2024 | Liu et al. |
| 2024/0076652 A1 | 3/2024 | Liu et al. |
| 2024/0110166 A1 | 4/2024 | Maianti et al. |
| 2024/0124866 A1 | 4/2024 | Liu et al. |
| 2024/0173430 A1 | 5/2024 | Liu et al. |

FOREIGN PATENT DOCUMENTS

| | | |
|---|---|---|
| AU | 2015252023 A1 | 11/2015 |
| AU | 2015101792 A4 | 1/2016 |
| BR | 112015013786 A2 | 7/2017 |
| CA | 2894668 A1 | 6/2014 |
| CA | 2894681 A1 | 6/2014 |
| CA | 2894684 A1 | 6/2014 |
| CA | 2852593 A1 | 11/2015 |
| CA | 3193022 A1 | 3/2022 |
| CN | 1069962 A | 3/1993 |
| CN | 101460619 A | 6/2009 |
| CN | 101873862 A | 10/2010 |
| CN | 102892777 A | 1/2013 |
| CN | 103224947 A | 7/2013 |
| CN | 103233028 A | 8/2013 |
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 103088008 A | 8/2014 |
| CN | 103981211 A | 8/2014 |
| CN | 103981212 A | 8/2014 |
| CN | 104004778 A | 8/2014 |
| CN | 104004782 A | 8/2014 |
| CN | 104017821 A | 9/2014 |
| CN | 104109687 A | 10/2014 |
| CN | 104178461 A | 12/2014 |
| CN | 104342457 A | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104561095 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |
| CN | 104725626 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 105039339 A | 11/2015 |
| CN | 105039399 A | 11/2015 |
| CN | 105063061 A | 11/2015 |
| CN | 105087620 A | 11/2015 |
| CN | 105112422 A | 12/2015 |
| CN | 105112445 A | 12/2015 |
| CN | 105112519 A | 12/2015 |
| CN | 105121648 A | 12/2015 |
| CN | 105132427 A | 12/2015 |
| CN | 105132451 A | 12/2015 |
| CN | 105177038 A | 12/2015 |
| CN | 105177126 A | 12/2015 |
| CN | 105210981 A | 1/2016 |
| CN | 105219799 A | 1/2016 |
| CN | 105238806 A | 1/2016 |
| CN | 105255937 A | 1/2016 |
| CN | 105274144 A | 1/2016 |
| CN | 105296518 A | 2/2016 |
| CN | 105296537 A | 2/2016 |
| CN | 105316324 A | 2/2016 |
| CN | 105316327 A | 2/2016 |
| CN | 105316337 A | 2/2016 |
| CN | 105331607 A | 2/2016 |
| CN | 105331608 A | 2/2016 |
| CN | 105331609 A | 2/2016 |
| CN | 105331627 A | 2/2016 |
| CN | 105400773 A | 3/2016 |
| CN | 105400779 A | 3/2016 |
| CN | 105400810 A | 3/2016 |
| CN | 105441451 A | 3/2016 |
| CN | 105462968 A | 4/2016 |
| CN | 105463003 A | 4/2016 |
| CN | 105463027 A | 4/2016 |
| CN | 105492608 A | 4/2016 |
| CN | 105492609 A | 4/2016 |
| CN | 105505976 A | 4/2016 |
| CN | 105505979 A | 4/2016 |
| CN | 105518134 A | 4/2016 |
| CN | 105518135 A | 4/2016 |
| CN | 105518137 A | 4/2016 |
| CN | 105518138 A | 4/2016 |
| CN | 105518139 A | 4/2016 |
| CN | 105518140 A | 4/2016 |
| CN | 105543228 A | 5/2016 |
| CN | 105543266 A | 5/2016 |
| CN | 105543270 A | 5/2016 |
| CN | 105567688 A | 5/2016 |
| CN | 105567689 A | 5/2016 |
| CN | 105567734 A | 5/2016 |
| CN | 105567735 A | 5/2016 |
| CN | 105567738 A | 5/2016 |
| CN | 105593367 A | 5/2016 |
| CN | 105594664 A | 5/2016 |
| CN | 105602987 A | 5/2016 |
| CN | 105624146 A | 6/2016 |
| CN | 105624187 A | 6/2016 |
| CN | 105646719 A | 6/2016 |
| CN | 105647922 A | 6/2016 |
| CN | 105647962 A | 6/2016 |
| CN | 105647968 A | 6/2016 |
| CN | 105647969 A | 6/2016 |
| CN | 105671070 A | 6/2016 |
| CN | 105671083 A | 6/2016 |
| CN | 105695485 A | 6/2016 |
| CN | 105779448 A | 7/2016 |
| CN | 105779449 A | 7/2016 |
| CN | 105802980 A | 7/2016 |
| CN | 105821039 A | 8/2016 |
| CN | 105821040 A | 8/2016 |
| CN | 105821049 A | 8/2016 |
| CN | 105821072 A | 8/2016 |

(56) References Cited

FOREIGN PATENT DOCUMENTS

| | | | |
|---|---|---|---|
| CN | 105821075 A | 8/2016 |
| CN | 105821116 A | 8/2016 |
| CN | 105838733 A | 8/2016 |
| CN | 105861547 A | 8/2016 |
| CN | 105861552 A | 8/2016 |
| CN | 105861554 A | 8/2016 |
| CN | 105886498 A | 8/2016 |
| CN | 105886534 A | 8/2016 |
| CN | 105886616 A | 8/2016 |
| CN | 105907758 A | 8/2016 |
| CN | 105907785 A | 8/2016 |
| CN | 105925608 A | 9/2016 |
| CN | 105934516 A | 9/2016 |
| CN | 105950560 A | 9/2016 |
| CN | 105950626 A | 9/2016 |
| CN | 105950633 A | 9/2016 |
| CN | 105950639 A | 9/2016 |
| CN | 105985985 A | 10/2016 |
| CN | 106011104 A | 10/2016 |
| CN | 106011150 A | 10/2016 |
| CN | 106011167 A | 10/2016 |
| CN | 106011171 A | 10/2016 |
| CN | 106032540 A | 10/2016 |
| CN | 106047803 A | 10/2016 |
| CN | 106047877 A | 10/2016 |
| CN | 106047930 A | 10/2016 |
| CN | 106086008 A | 11/2016 |
| CN | 106086028 A | 11/2016 |
| CN | 106086061 A | 11/2016 |
| CN | 106086062 A | 11/2016 |
| CN | 106109417 A | 11/2016 |
| CN | 106119275 A | 11/2016 |
| CN | 106119283 A | 11/2016 |
| CN | 106148286 A | 11/2016 |
| CN | 106148370 A | 11/2016 |
| CN | 106148416 A | 11/2016 |
| CN | 106167525 A | 11/2016 |
| CN | 106167808 A | 11/2016 |
| CN | 106167810 A | 11/2016 |
| CN | 106167821 A | 11/2016 |
| CN | 106172238 A | 12/2016 |
| CN | 106190903 A | 12/2016 |
| CN | 106191057 A | 12/2016 |
| CN | 106191061 A | 12/2016 |
| CN | 106191062 A | 12/2016 |
| CN | 106191064 A | 12/2016 |
| CN | 106191071 A | 12/2016 |
| CN | 106191099 A | 12/2016 |
| CN | 106191107 A | 12/2016 |
| CN | 106191113 A | 12/2016 |
| CN | 106191114 A | 12/2016 |
| CN | 106191116 A | 12/2016 |
| CN | 106191124 A | 12/2016 |
| CN | 106222177 A | 12/2016 |
| CN | 106222193 A | 12/2016 |
| CN | 106222203 A | 12/2016 |
| CN | 106244555 A | 12/2016 |
| CN | 106244557 A | 12/2016 |
| CN | 106244591 A | 12/2016 |
| CN | 106244609 A | 12/2016 |
| CN | 106282241 A | 1/2017 |
| CN | 106318934 A | 1/2017 |
| CN | 106318973 A | 1/2017 |
| CN | 106350540 A | 1/2017 |
| CN | 106367435 A | 2/2017 |
| CN | 106399306 A | 2/2017 |
| CN | 106399311 A | 2/2017 |
| CN | 106399360 A | 2/2017 |
| CN | 106399367 A | 2/2017 |
| CN | 106399375 A | 2/2017 |
| CN | 106399377 A | 2/2017 |
| CN | 106434651 A | 2/2017 |
| CN | 106434663 A | 2/2017 |
| CN | 106434688 A | 2/2017 |
| CN | 106434737 A | 2/2017 |
| CN | 106434748 A | 2/2017 |
| CN | 106434752 A | 2/2017 |
| CN | 106434782 A | 2/2017 |
| CN | 106446600 A | 2/2017 |
| CN | 106479985 A | 3/2017 |
| CN | 106480027 A | 3/2017 |
| CN | 106480036 A | 3/2017 |
| CN | 106480067 A | 3/2017 |
| CN | 106480080 A | 3/2017 |
| CN | 106480083 A | 3/2017 |
| CN | 106480097 A | 3/2017 |
| CN | 106544351 A | 3/2017 |
| CN | 106544353 A | 3/2017 |
| CN | 106544357 A | 3/2017 |
| CN | 106554969 A | 4/2017 |
| CN | 106566838 A | 4/2017 |
| CN | 106701763 A | 5/2017 |
| CN | 106701808 A | 5/2017 |
| CN | 106701818 A | 5/2017 |
| CN | 106701823 A | 5/2017 |
| CN | 106701830 A | 5/2017 |
| CN | 106754912 A | 5/2017 |
| CN | 106755026 A | 5/2017 |
| CN | 106755077 A | 5/2017 |
| CN | 106755088 A | 5/2017 |
| CN | 106755091 A | 5/2017 |
| CN | 106755097 A | 5/2017 |
| CN | 106755424 A | 5/2017 |
| CN | 106801056 A | 6/2017 |
| CN | 106834323 A | 6/2017 |
| CN | 106834341 A | 6/2017 |
| CN | 106834347 A | 6/2017 |
| CN | 106845151 A | 6/2017 |
| CN | 106868008 A | 6/2017 |
| CN | 106868031 A | 6/2017 |
| CN | 106906240 A | 6/2017 |
| CN | 106906242 A | 6/2017 |
| CN | 106916820 A | 7/2017 |
| CN | 106916852 A | 7/2017 |
| CN | 106939303 A | 7/2017 |
| CN | 106947750 A | 7/2017 |
| CN | 106947780 A | 7/2017 |
| CN | 106957830 A | 7/2017 |
| CN | 106957831 A | 7/2017 |
| CN | 106957844 A | 7/2017 |
| CN | 106957855 A | 7/2017 |
| CN | 106957858 A | 7/2017 |
| CN | 106967697 A | 7/2017 |
| CN | 106967726 A | 7/2017 |
| CN | 106978428 A | 7/2017 |
| CN | 106987570 A | 7/2017 |
| CN | 106987757 A | 7/2017 |
| CN | 107012164 A | 8/2017 |
| CN | 107012174 A | 8/2017 |
| CN | 107012213 A | 8/2017 |
| CN | 107012250 A | 8/2017 |
| CN | 107022562 A | 8/2017 |
| CN | 107034188 A | 8/2017 |
| CN | 107034218 A | 8/2017 |
| CN | 107034229 A | 8/2017 |
| CN | 107043775 A | 8/2017 |
| CN | 107043779 A | 8/2017 |
| CN | 107043787 A | 8/2017 |
| CN | 107058320 A | 8/2017 |
| CN | 107058328 A | 8/2017 |
| CN | 107058358 A | 8/2017 |
| CN | 107058372 A | 8/2017 |
| CN | 107083392 A | 8/2017 |
| CN | 107099533 A | 8/2017 |
| CN | 107099850 A | 8/2017 |
| CN | 107119053 A | 9/2017 |
| CN | 107119071 A | 9/2017 |
| CN | 107129999 A | 9/2017 |
| CN | 107130000 A | 9/2017 |
| CN | 107142272 A | 9/2017 |
| CN | 107142282 A | 9/2017 |
| CN | 107177591 A | 9/2017 |
| CN | 107177595 A | 9/2017 |
| CN | 107177625 A | 9/2017 |

(56) References Cited

FOREIGN PATENT DOCUMENTS

| | | |
|---|---|---|
| CN | 107177631 A | 9/2017 |
| CN | 107190006 A | 9/2017 |
| CN | 107190008 A | 9/2017 |
| CN | 107217042 A | 9/2017 |
| CN | 107217075 A | 9/2017 |
| CN | 107227307 A | 10/2017 |
| CN | 107227352 A | 10/2017 |
| CN | 107236737 A | 10/2017 |
| CN | 107236739 A | 10/2017 |
| CN | 107236741 A | 10/2017 |
| CN | 107245502 A | 10/2017 |
| CN | 107254485 A | 10/2017 |
| CN | 107266541 A | 10/2017 |
| CN | 107267515 A | 10/2017 |
| CN | 107287245 A | 10/2017 |
| CN | 107298701 A | 10/2017 |
| CN | 107299114 A | 10/2017 |
| CN | 107304435 A | 10/2017 |
| CN | 107312785 A | 11/2017 |
| CN | 107312793 A | 11/2017 |
| CN | 107312795 A | 11/2017 |
| CN | 107312798 A | 11/2017 |
| CN | 107326042 A | 11/2017 |
| CN | 107326046 A | 11/2017 |
| CN | 107354156 A | 11/2017 |
| CN | 107354173 A | 11/2017 |
| CN | 107356793 A | 11/2017 |
| CN | 107362372 A | 11/2017 |
| CN | 107365786 A | 11/2017 |
| CN | 107365804 A | 11/2017 |
| CN | 107384894 A | 11/2017 |
| CN | 107384922 A | 11/2017 |
| CN | 107384926 A | 11/2017 |
| CN | 107400677 A | 11/2017 |
| CN | 107418974 A | 12/2017 |
| CN | 107435051 A | 12/2017 |
| CN | 107435069 A | 12/2017 |
| CN | 104446922 A | 12/2017 |
| CN | 104446923 A | 12/2017 |
| CN | 104446924 A | 12/2017 |
| CN | 104446932 A | 12/2017 |
| CN | 107446951 A | 12/2017 |
| CN | 107446954 A | 12/2017 |
| CN | 107460196 A | 12/2017 |
| CN | 107474129 A | 12/2017 |
| CN | 107475300 A | 12/2017 |
| CN | 104488649 A | 12/2017 |
| CN | 107502608 A | 12/2017 |
| CN | 107502618 A | 12/2017 |
| CN | 107513531 A | 12/2017 |
| CN | 107519492 A | 12/2017 |
| CN | 107523567 A | 12/2017 |
| CN | 107523583 A | 12/2017 |
| CN | 107541525 A | 1/2018 |
| CN | 107557373 A | 1/2018 |
| CN | 107557378 A | 1/2018 |
| CN | 107557381 A | 1/2018 |
| CN | 107557390 A | 1/2018 |
| CN | 107557393 A | 1/2018 |
| CN | 107557394 A | 1/2018 |
| CN | 107557455 A | 1/2018 |
| CN | 107574179 A | 1/2018 |
| CN | 107586777 A | 1/2018 |
| CN | 107586779 A | 1/2018 |
| CN | 107604003 A | 1/2018 |
| CN | 107619829 A | 1/2018 |
| CN | 107619837 A | 1/2018 |
| CN | 107630006 A | 1/2018 |
| CN | 107630041 A | 1/2018 |
| CN | 107630042 A | 1/2018 |
| CN | 107630043 A | 1/2018 |
| CN | 107641631 A | 1/2018 |
| CN | 107653256 A | 2/2018 |
| CN | 107686848 A | 2/2018 |
| CN | 206970581 U | 2/2018 |
| CN | 107760652 A | 3/2018 |
| CN | 107760663 A | 3/2018 |
| CN | 107760684 A | 3/2018 |
| CN | 107760715 A | 3/2018 |
| CN | 107784200 A | 3/2018 |
| CN | 107794272 A | 3/2018 |
| CN | 107794276 A | 3/2018 |
| CN | 107815463 A | 3/2018 |
| CN | 107828738 A | 3/2018 |
| CN | 107828794 A | 3/2018 |
| CN | 107828826 A | 3/2018 |
| CN | 107828874 A | 3/2018 |
| CN | 107858346 A | 3/2018 |
| CN | 107858373 A | 3/2018 |
| CN | 107880132 A | 4/2018 |
| CN | 107881184 A | 4/2018 |
| CN | 107893074 A | 4/2018 |
| CN | 107893075 A | 4/2018 |
| CN | 107893076 A | 4/2018 |
| CN | 107893080 A | 4/2018 |
| CN | 107893086 A | 4/2018 |
| CN | 107904261 A | 4/2018 |
| CN | 107937427 A | 4/2018 |
| CN | 107937432 A | 4/2018 |
| CN | 107937501 A | 4/2018 |
| CN | 107974466 A | 5/2018 |
| CN | 107988229 A | 5/2018 |
| CN | 107988246 A | 5/2018 |
| CN | 107988256 A | 5/2018 |
| CN | 107988268 A | 5/2018 |
| CN | 108018316 A | 5/2018 |
| CN | 108034656 A | 5/2018 |
| CN | 108048466 A | 5/2018 |
| CN | 108102940 A | 6/2018 |
| CN | 108103090 A | 6/2018 |
| CN | 108103092 A | 6/2018 |
| CN | 108103098 A | 6/2018 |
| CN | 108103586 A | 6/2018 |
| CN | 108148835 A | 6/2018 |
| CN | 108148837 A | 6/2018 |
| CN | 108148873 A | 6/2018 |
| CN | 108192956 A | 6/2018 |
| CN | 108251423 | 7/2018 |
| CN | 108251451 A | 7/2018 |
| CN | 108251452 | 7/2018 |
| CN | 108342480 A | 7/2018 |
| CN | 108359691 A | 8/2018 |
| CN | 108359712 A | 8/2018 |
| CN | 108384784 A | 8/2018 |
| CN | 108396027 A | 8/2018 |
| CN | 108410877 | 8/2018 |
| CN | 108410906 A | 8/2018 |
| CN | 108410907 A | 8/2018 |
| CN | 108410911 A | 8/2018 |
| CN | 108424931 A | 8/2018 |
| CN | 108441519 A | 8/2018 |
| CN | 108441520 A | 8/2018 |
| CN | 108486108 A | 9/2018 |
| CN | 108486111 A | 9/2018 |
| CN | 108486145 A | 9/2018 |
| CN | 108486146 A | 9/2018 |
| CN | 108486154 A | 9/2018 |
| CN | 108486159 A | 9/2018 |
| CN | 108486234 A | 9/2018 |
| CN | 108504657 A | 9/2018 |
| CN | 108504685 A | 9/2018 |
| CN | 108504693 A | 9/2018 |
| CN | 108546712 A | 9/2018 |
| CN | 108546717 A | 9/2018 |
| CN | 108546718 A | 9/2018 |
| CN | 108559730 A | 9/2018 |
| CN | 108559732 A | 9/2018 |
| CN | 108559745 A | 9/2018 |
| CN | 108559760 A | 9/2018 |
| CN | 108570479 A | 9/2018 |
| CN | 108588071 A | 9/2018 |
| CN | 108588123 A | 9/2018 |
| CN | 108588128 A | 9/2018 |
| CN | 108588182 A | 9/2018 |

(56) References Cited

FOREIGN PATENT DOCUMENTS

| | | |
|---|---|---|
| CN | 108610399 A | 10/2018 |
| CN | 108611364 A | 10/2018 |
| CN | 108624622 A | 10/2018 |
| CN | 108642053 A | 10/2018 |
| CN | 108642055 A | 10/2018 |
| CN | 108642077 A | 10/2018 |
| CN | 108642078 A | 10/2018 |
| CN | 108642090 A | 10/2018 |
| CN | 108690844 A | 10/2018 |
| CN | 108707604 A | 10/2018 |
| CN | 108707620 A | 10/2018 |
| CN | 108707621 A | 10/2018 |
| CN | 108707628 A | 10/2018 |
| CN | 108707629 A | 10/2018 |
| CN | 108715850 A | 10/2018 |
| CN | 108728476 A | 11/2018 |
| CN | 108728486 A | 11/2018 |
| CN | 108753772 A | 11/2018 |
| CN | 108753783 A | 11/2018 |
| CN | 108753813 A | 11/2018 |
| CN | 108753817 A | 11/2018 |
| CN | 108753832 A | 11/2018 |
| CN | 108753835 A | 11/2018 |
| CN | 108753836 A | 11/2018 |
| CN | 108795902 A | 11/2018 |
| CN | 108822217 A | 11/2018 |
| CN | 108823248 A | 11/2018 |
| CN | 108823249 A | 11/2018 |
| CN | 108823291 A | 11/2018 |
| CN | 108841845 A | 11/2018 |
| CN | 108853133 A | 11/2018 |
| CN | 108866093 A | 11/2018 |
| CN | 108893529 A | 11/2018 |
| CN | 108913664 A | 11/2018 |
| CN | 108913691 A | 11/2018 |
| CN | 108913714 A | 11/2018 |
| CN | 108913717 A | 11/2018 |
| EP | 264166 A1 | 4/1988 |
| EP | 0289479 A2 | 11/1988 |
| EP | 321201 B2 | 6/1989 |
| EP | 519463 A1 | 12/1992 |
| EP | 2604255 A1 | 6/2013 |
| EP | 2840140 A1 | 2/2015 |
| EP | 2877490 A2 | 6/2015 |
| EP | 2966170 A1 | 1/2016 |
| EP | 3009511 A2 | 4/2016 |
| EP | 3031921 A1 | 6/2016 |
| EP | 3045537 A1 | 7/2016 |
| EP | 3115457 A1 | 1/2017 |
| EP | 3144390 A1 | 3/2017 |
| EP | 3199632 A1 | 8/2017 |
| EP | 3216867 A1 | 9/2017 |
| EP | 3252160 A1 | 12/2017 |
| EP | 3450553 B1 | 12/2019 |
| GB | 2528177 A | 1/2016 |
| GB | 2531454 A1 | 4/2016 |
| GB | 2542653 A | 3/2017 |
| HK | 1208045 A1 | 2/2016 |
| JP | H0937764 A | 2/1997 |
| JP | 2007-501626 A | 2/2007 |
| JP | 2008-515405 A | 5/2008 |
| JP | 2010-033344 A | 2/2010 |
| JP | 2010-535744 A | 11/2010 |
| JP | 2010-539929 A | 12/2010 |
| JP | 2011-081011 A | 4/2011 |
| JP | 2011-523353 A | 8/2011 |
| JP | 2012-525146 A | 10/2012 |
| JP | 2012-210172 | 11/2012 |
| JP | 2012-531909 A | 12/2012 |
| JP | 2015-532654 A | 11/2015 |
| JP | 2016-525888 A | 9/2016 |
| JP | 2016-534132 A | 11/2016 |
| JP | 2017-500035 A | 1/2017 |
| JP | 2018-521045 A | 8/2018 |
| JP | 6629734 B2 | 1/2020 |
| JP | 6633524 B2 | 1/2020 |
| KR | 2015-523856 A | 8/2015 |
| KR | 101584933 B1 | 1/2016 |
| KR | 2016-0050069 A | 5/2016 |
| KR | 20160133380 A | 11/2016 |
| KR | 20170037025 A | 4/2017 |
| KR | 20170037028 A | 4/2017 |
| KR | 101748575 B1 | 6/2017 |
| KR | 20170128137 A | 11/2017 |
| KR | 2018-0022465 A | 3/2018 |
| RU | 2016104674 A | 8/2017 |
| RU | 2634395 C1 | 10/2017 |
| RU | 2652899 C1 | 5/2018 |
| RU | 2015128057 A | 3/2019 |
| RU | 2015128098 A | 3/2019 |
| RU | 2687451 C1 | 5/2019 |
| RU | 2019112514 A | 6/2019 |
| RU | 2019127300 A | 9/2019 |
| SG | 10201707569 Y | 10/2017 |
| SG | 10201710486X | 1/2018 |
| SG | 10201710487 | 1/2018 |
| SG | 10201710488 T | 1/2018 |
| TW | I608100 B | 12/2017 |
| TW | 2018-29773 A | 8/2018 |
| WO | 1990/002809 A1 | 3/1990 |
| WO | 1991/003162 A1 | 3/1991 |
| WO | WO 1991/016024 A1 | 10/1991 |
| WO | WO 1991/017271 A1 | 11/1991 |
| WO | WO 1991/017424 A1 | 11/1991 |
| WO | WO 1992/001047 A1 | 1/1992 |
| WO | 1992/007065 A1 | 4/1992 |
| WO | WO 1992/006188 A2 | 4/1992 |
| WO | WO 1992/006200 A1 | 4/1992 |
| WO | WO 1992/009690 A2 | 6/1992 |
| WO | WO 1992/015679 A1 | 9/1992 |
| WO | WO 1992/018619 A1 | 10/1992 |
| WO | WO 1992/020791 A1 | 11/1992 |
| WO | WO 1993/001288 A1 | 1/1993 |
| WO | 1993/015187 A1 | 8/1993 |
| WO | WO 1993/024641 A2 | 12/1993 |
| WO | WO 1994/018316 A2 | 8/1994 |
| WO | WO 1994/026877 A1 | 11/1994 |
| WO | WO 1996/004403 A1 | 2/1996 |
| WO | WO 1996/010640 A1 | 4/1996 |
| WO | WO 1998/032845 A1 | 7/1998 |
| WO | WO 00/71694 A1 | 11/2000 |
| WO | WO 01/05950 A2 | 1/2001 |
| WO | WO 2001/036452 A2 | 5/2001 |
| WO | WO 2001/038547 A2 | 5/2001 |
| WO | WO 01/61049 A1 | 8/2001 |
| WO | WO 2002/059296 A2 | 8/2002 |
| WO | WO 2002/068676 A2 | 9/2002 |
| WO | WO 2002/103028 A2 | 12/2002 |
| WO | WO 2004/007684 A2 | 1/2004 |
| WO | WO 2005/014791 A2 | 2/2005 |
| WO | WO 2005/019415 A2 | 3/2005 |
| WO | WO 2005/081632 A2 | 9/2005 |
| WO | WO 2006/002547 A1 | 1/2006 |
| WO | WO 2006/042112 A2 | 4/2006 |
| WO | WO 2007/025097 A2 | 3/2007 |
| WO | 2007/037444 A1 | 4/2007 |
| WO | WO 2007/066923 A1 | 6/2007 |
| WO | WO 2007/136815 A2 | 11/2007 |
| WO | WO 2007/143574 A1 | 12/2007 |
| WO | WO 2008/005529 A2 | 1/2008 |
| WO | WO 2008/108989 A2 | 9/2008 |
| WO | 2009/002418 A2 | 12/2008 |
| WO | WO 2009/019317 A1 | 2/2009 |
| WO | WO 2009/082488 A2 | 7/2009 |
| WO | 2009/098290 A1 | 8/2009 |
| WO | WO 2009/108180 A2 | 9/2009 |
| WO | WO 2009/134808 A1 | 11/2009 |
| WO | WO 2010/011961 A2 | 1/2010 |
| WO | 2010/012902 A1 | 2/2010 |
| WO | WO 2010/028347 A2 | 3/2010 |
| WO | WO 2010/054108 A2 | 5/2010 |
| WO | WO 2010/054154 A2 | 5/2010 |
| WO | WO 2010/068289 A2 | 6/2010 |
| WO | WO 2010/075424 A2 | 7/2010 |

(56) References Cited

FOREIGN PATENT DOCUMENTS

| | | | |
|---|---|---|---|
| WO | 2010/104749 A2 | 9/2010 |
| WO | WO 2010/102257 A2 | 9/2010 |
| WO | WO 2010/129019 A2 | 11/2010 |
| WO | WO 2010/129023 A2 | 11/2010 |
| WO | WO 2010/132092 42 | 11/2010 |
| WO | WO 2010/144150 A2 | 12/2010 |
| WO | WO 2011/002503 A1 | 1/2011 |
| WO | WO 2011/017293 A2 | 2/2011 |
| WO | WO 2011/039518 A2 | 4/2011 |
| WO | WO 2011/053868 A1 | 5/2011 |
| WO | WO 2011/053982 A2 | 5/2011 |
| WO | WO 2011/066747 A1 | 6/2011 |
| WO | WO 2011/068810 A1 | 6/2011 |
| WO | WO 2011/075627 A1 | 6/2011 |
| WO | 2011/091396 A1 | 7/2011 |
| WO | WO 2011/091311 A2 | 7/2011 |
| WO | WO 2011/109031 A1 | 9/2011 |
| WO | WO 2011/143124 A2 | 11/2011 |
| WO | WO 2011/147590 A2 | 12/2011 |
| WO | WO 2011/159369 A1 | 12/2011 |
| WO | WO 2012/054726 A1 | 4/2012 |
| WO | WO 2012/065043 A2 | 5/2012 |
| WO | WO 2012/088381 A2 | 6/2012 |
| WO | WO 2012/125445 A2 | 9/2012 |
| WO | WO 2012/138927 A2 | 10/2012 |
| WO | WO 2012/149470 A1 | 11/2012 |
| WO | WO 2012/158985 A2 | 11/2012 |
| WO | WO 2012/158986 A2 | 11/2012 |
| WO | WO 2012/164565 A1 | 12/2012 |
| WO | WO 2012/170930 A1 | 12/2012 |
| WO | WO 2013/012674 A1 | 1/2013 |
| WO | WO 2013/013105 A1 | 1/2013 |
| WO | WO 2013/013105 A2 | 1/2013 |
| WO | WO 2013/039857 A1 | 3/2013 |
| WO | WO 2013/039861 A2 | 3/2013 |
| WO | WO 2013/045632 A1 | 4/2013 |
| WO | WO 2013/047844 A1 | 4/2013 |
| WO | WO 2013/066438 A2 | 5/2013 |
| WO | 2013/086441 A2 | 6/2013 |
| WO | 2013/086444 A2 | 6/2013 |
| WO | WO 2013/098244 A1 | 7/2013 |
| WO | WO 2013/119602 A1 | 8/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142578 A1 | 9/2013 |
| WO | WO 2013/142578 A2 | 9/2013 |
| WO | WO 2013/152359 A1 | 10/2013 |
| WO | WO 2013/160230 A1 | 10/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A1 | 11/2013 |
| WO | WO 2013/176915 A1 | 11/2013 |
| WO | WO 2013/176916 A1 | 11/2013 |
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2013/142378 A9 | 1/2014 |
| WO | WO 2014/004336 A2 | 1/2014 |
| WO | WO 2014/005042 A2 | 1/2014 |
| WO | WO 2014/011237 A1 | 1/2014 |
| WO | WO 2014/011901 A2 | 1/2014 |
| WO | WO 2014/018423 A2 | 1/2014 |
| WO | WO 2014/020608 A1 | 2/2014 |
| WO | WO 2014/022120 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039585 A2 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |
| WO | WO 2014/043143 A1 | 3/2014 |
| WO | WO 2014/047103 A2 | 3/2014 |
| WO | WO 2014/055782 A1 | 4/2014 |
| WO | WO 2014/059173 A2 | 4/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/110006 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/125668 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/152940 A1 | 9/2014 |
| WO | WO 2014/153118 A1 | 9/2014 |
| WO | WO 2014/153470 A2 | 9/2014 |
| WO | WO 2014/157820 A1 | 10/2014 |
| WO | WO 2014/158593 A1 | 10/2014 |
| WO | WO 2014/161821 A1 | 10/2014 |

(56) References Cited

FOREIGN PATENT DOCUMENTS

| | | |
|---|---|---|
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/007194 A1 | 1/2015 |
| WO | WO 2015/010114 A1 | 1/2015 |
| WO | WO 2015/011483 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | 2015/042393 A2 | 3/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/048707 A2 | 4/2015 |
| WO | WO 2015/048801 A2 | 4/2015 |
| WO | WO 2015/049897 A1 | 4/2015 |
| WO | WO 2015/051191 A1 | 4/2015 |
| WO | WO 2015/052133 A1 | 4/2015 |
| WO | WO 2015/052231 A1 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/054315 A1 | 4/2015 |
| WO | WO 2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066634 A2 | 5/2015 |
| WO | WO 2015/066636 A2 | 5/2015 |
| WO | WO 2015/066637 A1 | 5/2015 |
| WO | WO 2015/066638 A2 | 5/2015 |
| WO | WO 2015/066643 A1 | 5/2015 |
| WO | WO 2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075175 A1 | 5/2015 |
| WO | WO 2015/075195 A1 | 5/2015 |
| WO | WO 2015/075557 A2 | 5/2015 |
| WO | WO 2015/077058 A2 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A1 | 6/2015 |
| WO | WO 2015/086798 A2 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A2 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/109752 A1 | 7/2015 |
| WO | WO 2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/114365 A1 | 8/2015 |
| WO | WO 2015/115903 A1 | 8/2015 |
| WO | WO 2015/116686 A1 | 8/2015 |
| WO | WO 2015/116969 A2 | 8/2015 |
| WO | WO 2015/117021 A1 | 8/2015 |

(56) References Cited

FOREIGN PATENT DOCUMENTS

| | | |
|---|---|---|
| WO | WO 2015/117041 A1 | 8/2015 |
| WO | WO 2015/117081 A2 | 8/2015 |
| WO | WO 2015/118156 A1 | 8/2015 |
| WO | WO 2015/119941 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/124715 A1 | 8/2015 |
| WO | WO 2015/124718 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/129686 A1 | 9/2015 |
| WO | WO 2015/131101 A1 | 9/2015 |
| WO | WO 2015/133554 A1 | 9/2015 |
| WO | WO 2015/134121 A2 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO 2015/143177 A1 | 9/2015 |
| WO | WO 2015/145417 A1 | 10/2015 |
| WO | WO 2015/148431 A1 | 10/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153889 A2 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164740 A1 | 10/2015 |
| WO | WO 2015/164748 A1 | 10/2015 |
| WO | WO 2015/165274 A1 | 11/2015 |
| WO | WO 2015/165275 A1 | 11/2015 |
| WO | WO 2015/165276 A1 | 11/2015 |
| WO | WO 2015/166272 A2 | 11/2015 |
| WO | WO 2015/167766 A1 | 11/2015 |
| WO | WO 2015/167956 A1 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |
| WO | WO 2015/171894 A1 | 11/2015 |
| WO | WO 2015/171932 A1 | 11/2015 |
| WO | WO 2015/172128 A1 | 11/2015 |
| WO | WO 2015/173436 A1 | 11/2015 |
| WO | WO 2015/175642 A2 | 11/2015 |
| WO | WO 2015/179540 A1 | 11/2015 |
| WO | WO 2015/183025 A1 | 12/2015 |
| WO | WO 2015/183026 A1 | 12/2015 |
| WO | WO 2015/183885 A1 | 12/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188056 A1 | 12/2015 |
| WO | WO 2015/188065 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A1 | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 A2 | 12/2015 |
| WO | WO 2015/193858 A1 | 12/2015 |
| WO | WO 2015/193897 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A1 | 12/2015 |
| WO | WO 2016/001978 A1 | 1/2016 |
| WO | WO 2016/004010 A1 | 1/2016 |
| WO | WO 2016/004318 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO 2016/011210 A2 | 1/2016 |
| WO | WO 2016/011428 A1 | 1/2016 |
| WO | WO 2016/012544 A2 | 1/2016 |
| WO | WO 2016/012552 A1 | 1/2016 |
| WO | WO 2016/014409 A1 | 1/2016 |
| WO | WO 2016/014565 A2 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |
| WO | WO 2016/022363 A2 | 2/2016 |
| WO | WO 2016/022866 A1 | 2/2016 |
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |
| WO | WO 2016/026444 A1 | 2/2016 |
| WO | WO 2016/028682 A1 | 2/2016 |
| WO | WO 2016/028843 A2 | 2/2016 |
| WO | WO 2016/028887 A1 | 2/2016 |
| WO | WO 2016/033088 A1 | 3/2016 |
| WO | WO 2016/033230 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/035918 A1 | 3/2016 |
| WO | WO 2016/036754 A1 | 3/2016 |
| WO | WO 2016/037157 A2 | 3/2016 |
| WO | WO 2016/040030 A1 | 3/2016 |
| WO | WO 2016/040594 A1 | 3/2016 |
| WO | WO 2016/044182 A1 | 3/2016 |
| WO | WO 2016/044416 A1 | 3/2016 |
| WO | WO 2016/046635 A1 | 3/2016 |
| WO | WO 2016/049024 A2 | 3/2016 |
| WO | WO 2016/049163 A1 | 3/2016 |
| WO | WO 2016/049230 A1 | 3/2016 |
| WO | WO 2016/049251 A1 | 3/2016 |
| WO | WO 2016/049258 A2 | 3/2016 |
| WO | 2016/065364 A1 | 4/2016 |
| WO | WO 2016/053397 A1 | 4/2016 |
| WO | WO 2016/054326 A1 | 4/2016 |
| WO | WO 2016/057061 A2 | 4/2016 |
| WO | WO 2016/057821 A2 | 4/2016 |
| WO | WO 2016/057835 A2 | 4/2016 |
| WO | WO 2016/057850 A1 | 4/2016 |
| WO | WO 2016/057951 A2 | 4/2016 |
| WO | WO 2016/057961 A1 | 4/2016 |

(56) References Cited

FOREIGN PATENT DOCUMENTS

| | | |
|---|---|---|
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/064894 A2 | 4/2016 |
| WO | WO 2016/069282 A1 | 5/2016 |
| WO | WO 2016/069283 A1 | 5/2016 |
| WO | WO 2016/069591 A2 | 5/2016 |
| WO | WO 2016/069774 A1 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/072399 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO 2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO 2016/080795 A1 | 5/2016 |
| WO | WO 2016/081923 A2 | 5/2016 |
| WO | WO 2016/081924 A1 | 5/2016 |
| WO | WO 2016/082135 A1 | 6/2016 |
| WO | WO 2016/083811 A1 | 6/2016 |
| WO | WO 2016/084084 A1 | 6/2016 |
| WO | WO 2016/084088 A1 | 6/2016 |
| WO | WO 2016/086177 A2 | 6/2016 |
| WO | WO 2016/089433 A1 | 6/2016 |
| WO | WO 2016/089866 A1 | 6/2016 |
| WO | WO 2016/089883 A1 | 6/2016 |
| WO | WO 2016/090385 A1 | 6/2016 |
| WO | WO 2016/094679 A1 | 6/2016 |
| WO | WO 2016/094845 A2 | 6/2016 |
| WO | WO 2016/094867 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/094888 A1 | 6/2016 |
| WO | WO 2016/097212 A1 | 6/2016 |
| WO | WO 2016/097231 A2 | 6/2016 |
| WO | WO 2016/097751 A1 | 6/2016 |
| WO | WO 2016/099887 A1 | 6/2016 |
| WO | WO 2016/100272 A1 | 6/2016 |
| WO | WO 2016/100389 A1 | 6/2016 |
| WO | WO 2016/100568 A1 | 6/2016 |
| WO | WO 2016/100571 A1 | 6/2016 |
| WO | WO 2016/100951 A2 | 6/2016 |
| WO | WO 2016/100955 A2 | 6/2016 |
| WO | WO 2016/100974 A1 | 6/2016 |
| WO | WO 2016/103233 A2 | 6/2016 |
| WO | WO 2016/104716 A1 | 6/2016 |
| WO | WO 2016/106236 A1 | 6/2016 |
| WO | WO 2016/106239 A1 | 6/2016 |
| WO | WO 2016/106244 A1 | 6/2016 |
| WO | WO 2016/106338 A2 | 6/2016 |
| WO | 2016/113357 A1 | 7/2016 |
| WO | WO 2016/108926 A1 | 7/2016 |
| WO | WO 2016/109255 A1 | 7/2016 |
| WO | WO 2016/109840 A2 | 7/2016 |
| WO | WO 2016/110214 A1 | 7/2016 |
| WO | WO 2016/110453 A1 | 7/2016 |
| WO | WO 2016/110511 A1 | 7/2016 |
| WO | WO 2016/110512 A1 | 7/2016 |
| WO | WO 2016/111546 A2 | 7/2016 |
| WO | WO 2016/112242 A1 | 7/2016 |
| WO | WO 2016/112351 A1 | 7/2016 |
| WO | WO 2016/112963 A1 | 7/2016 |
| WO | WO 2016/114972 A1 | 7/2016 |
| WO | WO 2016/115179 A1 | 7/2016 |
| WO | WO 2016/115326 A1 | 7/2016 |
| WO | WO 2016/115355 A1 | 7/2016 |
| WO | WO 2016/116032 A1 | 7/2016 |
| WO | WO 2016/120480 A1 | 8/2016 |
| WO | WO 2016/123071 A1 | 8/2016 |
| WO | WO 2016/123230 A1 | 8/2016 |
| WO | WO 2016/123243 A1 | 8/2016 |
| WO | WO 2016/123578 A1 | 8/2016 |
| WO | WO 2016/126747 A1 | 8/2016 |
| WO | WO 2016/130600 A2 | 8/2016 |
| WO | WO 2016/130697 A1 | 8/2016 |
| WO | WO 2016/131009 A1 | 8/2016 |
| WO | WO 2016/132122 A1 | 8/2016 |
| WO | WO 2016/133165 A1 | 8/2016 |
| WO | WO 2016/077052 A9 | 9/2016 |
| WO | WO 2016/135507 A1 | 9/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/137774 A1 | 9/2016 |
| WO | WO 2016/137949 A1 | 9/2016 |
| WO | WO 2016/141224 A1 | 9/2016 |
| WO | WO 2016/141893 A1 | 9/2016 |
| WO | WO 2016/142719 A1 | 9/2016 |
| WO | WO 2016/145150 A2 | 9/2016 |
| WO | WO 2016/148994 A1 | 9/2016 |
| WO | WO 2016/149484 A2 | 9/2016 |
| WO | WO 2016/149547 A1 | 9/2016 |
| WO | WO 2016/150336 A1 | 9/2016 |
| WO | WO 2016/150855 A1 | 9/2016 |
| WO | WO 2016/154016 A2 | 9/2016 |
| WO | WO 2016/154579 A2 | 9/2016 |
| WO | WO 2016/154596 A1 | 9/2016 |
| WO | WO 2016/155482 A1 | 10/2016 |
| WO | WO 2016/161004 A1 | 10/2016 |
| WO | WO 2016/161207 A1 | 10/2016 |
| WO | WO 2016/161260 A1 | 10/2016 |
| WO | WO 2016/161380 A1 | 10/2016 |
| WO | WO 2016/161446 A1 | 10/2016 |
| WO | WO 2016/164356 A1 | 10/2016 |
| WO | WO 2016/164797 A1 | 10/2016 |
| WO | WO 2016/166340 A1 | 10/2016 |
| WO | WO 2016/167300 A1 | 10/2016 |
| WO | WO 2016/168631 A1 | 10/2016 |
| WO | WO 2016/170484 A1 | 10/2016 |
| WO | WO 2016/172359 A2 | 10/2016 |
| WO | WO 2016/172727 A1 | 10/2016 |
| WO | WO 2016/174056 A1 | 11/2016 |
| WO | WO 2016/174151 A1 | 11/2016 |
| WO | WO 2016/174250 A1 | 11/2016 |
| WO | WO 2016/176191 A1 | 11/2016 |
| WO | WO 2016/176404 A1 | 11/2016 |
| WO | WO 2016/176690 A2 | 11/2016 |
| WO | WO 2016/177682 A1 | 11/2016 |
| WO | WO 2016/178207 A1 | 11/2016 |
| WO | WO 2016/179038 A1 | 11/2016 |
| WO | WO 2016/179112 A1 | 11/2016 |
| WO | WO 2016/181357 A1 | 11/2016 |
| WO | WO 2016/182893 A1 | 11/2016 |
| WO | WO 2016/182917 A1 | 11/2016 |
| WO | WO 2016/182959 A1 | 11/2016 |
| WO | WO 2016/183236 A1 | 11/2016 |
| WO | WO 2016/183298 A2 | 11/2016 |
| WO | WO 2016/183345 A1 | 11/2016 |
| WO | WO 2016/183402 A2 | 11/2016 |
| WO | WO 2016/183438 A1 | 11/2016 |
| WO | WO 2016/183448 A1 | 11/2016 |
| WO | WO 2016/184955 A2 | 11/2016 |
| WO | WO 2016/184989 A1 | 11/2016 |
| WO | WO 2016/185411 A1 | 11/2016 |
| WO | WO 2016/186745 A1 | 11/2016 |
| WO | WO 2016/186772 A2 | 11/2016 |
| WO | WO 2016/186946 A1 | 11/2016 |
| WO | WO 2016/186953 A1 | 11/2016 |
| WO | WO 2016/187717 A1 | 12/2016 |
| WO | WO 2016/187904 A1 | 12/2016 |
| WO | WO 2016/191684 A1 | 12/2016 |
| WO | WO 2016/191869 A1 | 12/2016 |
| WO | WO 2016/196273 A1 | 12/2016 |
| WO | WO 2016/196282 A1 | 12/2016 |

(56) References Cited

FOREIGN PATENT DOCUMENTS

| | | |
|---|---|---|
| WO | WO 2016/196308 A1 | 12/2016 |
| WO | WO 2016/196361 A1 | 12/2016 |
| WO | WO 2016/196499 A1 | 12/2016 |
| WO | WO 2016/196539 A2 | 12/2016 |
| WO | WO 2016/196655 A1 | 12/2016 |
| WO | WO 2016/196805 A1 | 12/2016 |
| WO | WO 2016/196887 A1 | 12/2016 |
| WO | WO 2016/197132 A1 | 12/2016 |
| WO | WO 2016/197133 A1 | 12/2016 |
| WO | WO 2016/197354 A1 | 12/2016 |
| WO | WO 2016/197355 A1 | 12/2016 |
| WO | WO 2016/197356 A1 | 12/2016 |
| WO | WO 2016/197357 A1 | 12/2016 |
| WO | WO 2016/197358 A1 | 12/2016 |
| WO | WO 2016/197359 A1 | 12/2016 |
| WO | WO 2016/197360 A1 | 12/2016 |
| WO | WO 2016/197361 A1 | 12/2016 |
| WO | WO 2016/197362 A1 | 12/2016 |
| WO | WO 2016/198361 A1 | 12/2016 |
| WO | WO 2016/198500 A1 | 12/2016 |
| WO | WO 2016/200263 A1 | 12/2016 |
| WO | WO 2016/201047 A1 | 12/2016 |
| WO | WO 2016/201138 A1 | 12/2016 |
| WO | WO 2016/201152 A1 | 12/2016 |
| WO | WO 2016/201153 A1 | 12/2016 |
| WO | WO 2016/201155 A1 | 12/2016 |
| WO | WO 2016/205276 A1 | 12/2016 |
| WO | WO 2016/205613 A1 | 12/2016 |
| WO | WO 2016/205623 A1 | 12/2016 |
| WO | WO 2016/205680 A1 | 12/2016 |
| WO | WO 2016/205688 A2 | 12/2016 |
| WO | WO 2016/205703 A1 | 12/2016 |
| WO | WO 2016/205711 A1 | 12/2016 |
| WO | WO 2016/205728 A1 | 12/2016 |
| WO | WO 2016/205745 A2 | 12/2016 |
| WO | WO 2016/205749 A1 | 12/2016 |
| WO | WO 2016/205759 A1 | 12/2016 |
| WO | WO 2016/205764 A1 | 12/2016 |
| WO | WO 2017/001572 A1 | 1/2017 |
| WO | WO 2017/001988 A1 | 1/2017 |
| WO | WO 2017/004261 A1 | 1/2017 |
| WO | WO 2017/004279 A2 | 1/2017 |
| WO | WO 2017/004616 A1 | 1/2017 |
| WO | WO 2017/005807 A1 | 1/2017 |
| WO | WO 2017/009399 A1 | 1/2017 |
| WO | WO 2017/010556 A1 | 1/2017 |
| WO | WO 2017/011519 A1 | 1/2017 |
| WO | WO 2017/011721 A1 | 1/2017 |
| WO | WO 2017/011804 A1 | 1/2017 |
| WO | WO 2017/015015 A1 | 1/2017 |
| WO | WO 2017/015101 A1 | 1/2017 |
| WO | WO 2017/015545 A1 | 1/2017 |
| WO | WO 2017/015559 A2 | 1/2017 |
| WO | WO 2017/015567 A1 | 1/2017 |
| WO | WO 2017/015637 A1 | 1/2017 |
| WO | WO 2017/017016 A1 | 2/2017 |
| WO | WO 2017/019867 A1 | 2/2017 |
| WO | WO 2017/019895 A1 | 2/2017 |
| WO | WO 2017/023803 A1 | 2/2017 |
| WO | WO 2017/023974 A1 | 2/2017 |
| WO | WO 2017/024047 A1 | 2/2017 |
| WO | WO 2017/024319 A1 | 2/2017 |
| WO | WO 2017/024343 A1 | 2/2017 |
| WO | WO 2017/024602 A1 | 2/2017 |
| WO | WO 2017/025323 A1 | 2/2017 |
| WO | WO 2017/027423 A1 | 2/2017 |
| WO | WO 2017/028768 A1 | 2/2017 |
| WO | WO 2017/029664 A1 | 2/2017 |
| WO | WO 2017/031360 A1 | 2/2017 |
| WO | WO 2017/031483 A1 | 2/2017 |
| WO | WO 2017/035416 A2 | 3/2017 |
| WO | WO 2017/040348 A1 | 3/2017 |
| WO | WO 2017/040511 A1 | 3/2017 |
| WO | WO 2017/040709 A1 | 3/2017 |
| WO | WO 2017/040786 A1 | 3/2017 |
| WO | WO 2017/040793 A1 | 3/2017 |
| WO | WO 2017/040813 A2 | 3/2017 |
| WO | WO 2017/043573 A1 | 3/2017 |
| WO | WO 2017/043656 A1 | 3/2017 |
| WO | WO 2017/044419 A1 | 3/2017 |
| WO | WO 2017/044776 A1 | 3/2017 |
| WO | WO 2017/044857 A2 | 3/2017 |
| WO | WO 2017/048390 A1 | 3/2017 |
| WO | WO 2017/049129 A2 | 3/2017 |
| WO | WO 2017/050963 A1 | 3/2017 |
| WO | WO 2017/053312 A1 | 3/2017 |
| WO | WO 2017/053431 A2 | 3/2017 |
| WO | WO 2017/053713 A1 | 3/2017 |
| WO | WO 2017/053729 A1 | 3/2017 |
| WO | WO 2017/053753 A1 | 3/2017 |
| WO | WO 2017/053762 A1 | 3/2017 |
| WO | WO 2017/053879 A1 | 3/2017 |
| WO | WO 2017/054721 A1 | 4/2017 |
| WO | WO 2017/058658 A2 | 4/2017 |
| WO | WO 2017/059241 A1 | 4/2017 |
| WO | WO 2017/062605 A1 | 4/2017 |
| WO | WO 2017/062723 A1 | 4/2017 |
| WO | WO 2017/062754 A1 | 4/2017 |
| WO | WO 2017/062855 A1 | 4/2017 |
| WO | WO 2017/062886 A1 | 4/2017 |
| WO | WO 2017/062983 A1 | 4/2017 |
| WO | WO 2017/064439 A1 | 4/2017 |
| WO | WO 2017/064546 A1 | 4/2017 |
| WO | WO 2017/064566 A2 | 4/2017 |
| WO | WO 2017/066175 A1 | 4/2017 |
| WO | WO 2017/066497 A2 | 4/2017 |
| WO | WO 2017/066588 A2 | 4/2017 |
| WO | WO 2017/066707 A1 | 4/2017 |
| WO | WO 2017/066781 A1 | 4/2017 |
| WO | WO 2017/068077 A1 | 4/2017 |
| WO | WO 2017/068377 A1 | 4/2017 |
| WO | WO 2017/069829 A2 | 4/2017 |
| WO | WO 2017/070029 A1 | 4/2017 |
| WO | WO 2017/070032 A1 | 4/2017 |
| WO | WO 2017/070169 A1 | 4/2017 |
| WO | WO 2017/070284 A1 | 4/2017 |
| WO | WO 2017/070598 A1 | 4/2017 |
| WO | WO 2017/070605 A1 | 4/2017 |
| WO | WO 2017/070632 A2 | 4/2017 |
| WO | WO 2017/070633 A2 | 4/2017 |
| WO | WO 2017/072590 A1 | 5/2017 |
| WO | WO 2017/074526 A1 | 5/2017 |
| WO | WO 2017/074962 A1 | 5/2017 |
| WO | WO 2017/075261 A1 | 5/2017 |
| WO | WO 2017/075335 A1 | 5/2017 |
| WO | WO 2017/075475 A1 | 5/2017 |
| WO | WO 2017/077135 A1 | 5/2017 |
| WO | WO 2017/077329 A2 | 5/2017 |
| WO | WO 2017/078751 A1 | 5/2017 |
| WO | WO 2017/079400 A1 | 5/2017 |
| WO | WO 2017/079428 A1 | 5/2017 |
| WO | WO 2017/079673 A1 | 5/2017 |
| WO | WO 2017/079724 A1 | 5/2017 |
| WO | WO 2017/081097 A1 | 5/2017 |
| WO | WO 2017/081288 A1 | 5/2017 |
| WO | WO 2017/083368 A1 | 5/2017 |
| WO | WO 2017/083722 A1 | 5/2017 |
| WO | WO 2017/083766 A1 | 5/2017 |
| WO | WO 2017/087395 A1 | 5/2017 |
| WO | WO 2017/090724 A1 | 6/2017 |
| WO | WO 2017/091510 A1 | 6/2017 |
| WO | WO 2017/091630 A1 | 6/2017 |
| WO | WO 2017/092201 A1 | 6/2017 |
| WO | WO 2017/093370 A1 | 6/2017 |
| WO | WO 2017/093969 A1 | 6/2017 |
| WO | WO 2017/095111 A1 | 6/2017 |
| WO | WO 2017/096041 A1 | 6/2017 |
| WO | WO 2017/096237 A1 | 6/2017 |
| WO | WO 2017/100158 A1 | 6/2017 |
| WO | WO 2017/100431 A2 | 6/2017 |
| WO | WO 2017/104404 A1 | 6/2017 |
| WO | WO 2017/105251 A1 | 6/2017 |
| WO | WO 2017/105350 A1 | 6/2017 |
| WO | WO 2017/105991 A1 | 6/2017 |

(56) References Cited

FOREIGN PATENT DOCUMENTS

| | | |
|---|---|---|
| WO | WO 2017/106414 A1 | 6/2017 |
| WO | WO 2017/106528 A2 | 6/2017 |
| WO | WO 2017/106537 A2 | 6/2017 |
| WO | WO 2017/106569 A1 | 6/2017 |
| WO | WO 2017/106616 A1 | 6/2017 |
| WO | WO 2017/106657 A1 | 6/2017 |
| WO | WO 2017/106767 A1 | 6/2017 |
| WO | WO 2017/109134 A1 | 6/2017 |
| WO | WO 2017/109757 A1 | 6/2017 |
| WO | WO 2017/112620 A1 | 6/2017 |
| WO | WO 2017/115268 A1 | 7/2017 |
| WO | WO 2017/117395 A1 | 7/2017 |
| WO | WO 2017/118598 A1 | 7/2017 |
| WO | WO 2017/118720 A1 | 7/2017 |
| WO | WO 2017/123609 A1 | 7/2017 |
| WO | WO 2017/123910 A1 | 7/2017 |
| WO | WO 2017/124086 A1 | 7/2017 |
| WO | WO 2017/124100 A1 | 7/2017 |
| WO | WO 2017/124652 A1 | 7/2017 |
| WO | WO 2017/126987 A1 | 7/2017 |
| WO | WO 2017/127807 A1 | 7/2017 |
| WO | 2017/142923 A1 | 8/2017 |
| WO | 2017/147056 A1 | 8/2017 |
| WO | WO 2017/131237 A1 | 8/2017 |
| WO | WO 2017/132112 A1 | 8/2017 |
| WO | WO 2017/132580 A2 | 8/2017 |
| WO | WO 2017/136520 A1 | 8/2017 |
| WO | WO 2017/136629 A1 | 8/2017 |
| WO | WO 2017/136794 A1 | 8/2017 |
| WO | WO 2017/139264 A1 | 8/2017 |
| WO | WO 2017/139505 A2 | 8/2017 |
| WO | WO 2017/141173 A2 | 8/2017 |
| WO | WO 2017/142835 A1 | 8/2017 |
| WO | WO 2017/142999 A2 | 8/2017 |
| WO | WO 2017/143042 A2 | 8/2017 |
| WO | WO 2017/147278 A1 | 8/2017 |
| WO | WO 2017/147432 A1 | 8/2017 |
| WO | WO 2017/147446 A1 | 8/2017 |
| WO | WO 2017/147555 A1 | 8/2017 |
| WO | WO 2017/151444 A1 | 9/2017 |
| WO | WO 2017/151719 A1 | 9/2017 |
| WO | WO 2017/152015 A1 | 9/2017 |
| WO | WO 2017/155717 A1 | 9/2017 |
| WO | WO 2017/157422 A1 | 9/2017 |
| WO | WO 2017/158153 A1 | 9/2017 |
| WO | WO 2017/160689 A1 | 9/2017 |
| WO | WO 2017/160752 A1 | 9/2017 |
| WO | WO 2017/160890 A1 | 9/2017 |
| WO | WO 2017/161068 A1 | 9/2017 |
| WO | WO 2017/165826 A1 | 9/2017 |
| WO | WO 2017/165862 A1 | 9/2017 |
| WO | 2017/167712 A1 | 10/2017 |
| WO | WO 2017/172644 A2 | 10/2017 |
| WO | WO 2017/172645 A2 | 10/2017 |
| WO | WO 2017/172860 A1 | 10/2017 |
| WO | WO 2017/173004 A1 | 10/2017 |
| WO | WO 2017/173054 A1 | 10/2017 |
| WO | WO 2017/173092 A1 | 10/2017 |
| WO | WO 2017/174329 A1 | 10/2017 |
| WO | WO 2017/176529 A1 | 10/2017 |
| WO | WO 2017/176806 A1 | 10/2017 |
| WO | WO 2017/178590 A1 | 10/2017 |
| WO | WO 2017/180694 A1 | 10/2017 |
| WO | WO 2017/180711 A1 | 10/2017 |
| WO | WO 2017/180915 A2 | 10/2017 |
| WO | WO 2017/180926 A1 | 10/2017 |
| WO | WO 2017/181107 A2 | 10/2017 |
| WO | WO 2017/181735 A2 | 10/2017 |
| WO | WO 2017/184334 A1 | 10/2017 |
| WO | WO 2017/184768 A1 | 10/2017 |
| WO | WO 2017/184786 A1 | 10/2017 |
| WO | 2017/190041 A1 | 11/2017 |
| WO | 2017/191274 A2 | 11/2017 |
| WO | WO 2017/186550 A1 | 11/2017 |
| WO | WO 2017/189308 A1 | 11/2017 |
| WO | WO 2017/189336 A1 | 11/2017 |
| WO | WO 2017/190257 A1 | 11/2017 |
| WO | WO 2017/190664 A1 | 11/2017 |
| WO | WO 2017/191210 A1 | 11/2017 |
| WO | WO 2017/192172 A1 | 11/2017 |
| WO | WO 2017/192512 A2 | 11/2017 |
| WO | WO 2017/192544 A1 | 11/2017 |
| WO | WO 2017/192573 A1 | 11/2017 |
| WO | WO 2017/193029 A2 | 11/2017 |
| WO | WO 2017/193053 A1 | 11/2017 |
| WO | WO 2017/196768 A1 | 11/2017 |
| WO | WO 2017/197038 A1 | 11/2017 |
| WO | WO 2017/197238 A1 | 11/2017 |
| WO | WO 2017/197301 A1 | 11/2017 |
| WO | WO 2017/201476 A1 | 11/2017 |
| WO | WO 2017/205290 A1 | 11/2017 |
| WO | WO 2017/205423 A1 | 11/2017 |
| WO | WO 2017/207589 A1 | 12/2017 |
| WO | WO 2017/208247 A1 | 12/2017 |
| WO | WO 2017/209809 A1 | 12/2017 |
| WO | WO 2017/213896 A1 | 12/2017 |
| WO | WO 2017/213898 A2 | 12/2017 |
| WO | WO 2017/214460 A1 | 12/2017 |
| WO | WO 2017/216392 A1 | 12/2017 |
| WO | WO 2017/216771 A2 | 12/2017 |
| WO | WO 2017/218185 A1 | 12/2017 |
| WO | WO 2017/219027 A1 | 12/2017 |
| WO | WO 2017/219033 A1 | 12/2017 |
| WO | WO 2017/220751 A1 | 12/2017 |
| WO | WO 2017/222370 A1 | 12/2017 |
| WO | WO 2017/222773 A1 | 12/2017 |
| WO | WO 2017/222834 A1 | 12/2017 |
| WO | WO 2017/223107 A1 | 12/2017 |
| WO | WO 2017/223330 A1 | 12/2017 |
| WO | 2018/013932 A1 | 1/2018 |
| WO | WO 2018/000657 A1 | 1/2018 |
| WO | WO 2018/002719 A1 | 1/2018 |
| WO | WO 2018/005117 A1 | 1/2018 |
| WO | WO 2018/005289 A2 | 1/2018 |
| WO | WO 2018/005691 A1 | 1/2018 |
| WO | WO 2018/005782 AN | 1/2018 |
| WO | WO 2018/005873 A1 | 1/2018 |
| WO | WO 2018/06693 A1 | 1/2018 |
| WO | WO 2018/009520 A1 | 1/2018 |
| WO | WO 2018/009562 A1 | 1/2018 |
| WO | WO 2018/009822 A1 | 1/2018 |
| WO | WO 2018/009903 A2 | 1/2018 |
| WO | WO 2018/013821 A1 | 1/2018 |
| WO | WO 2018/013990 A1 | 1/2018 |
| WO | WO 2018/014384 A1 | 1/2018 |
| WO | WO 2018/015444 A1 | 1/2018 |
| WO | WO 2018/015936 A2 | 1/2018 |
| WO | WO 2018/017754 A1 | 1/2018 |
| WO | WO 2018/018979 A1 | 2/2018 |
| WO | WO 2018/020248 A1 | 2/2018 |
| WO | WO 2018/021878 A1 | 2/2018 |
| WO | WO 2018/022480 A1 | 2/2018 |
| WO | WO 2018/022634 A1 | 2/2018 |
| WO | WO 2018/025206 A1 | 2/2018 |
| WO | WO 2018/026723 A1 | 2/2018 |
| WO | WO 2018/026976 A1 | 2/2018 |
| WO | WO 2018/027078 A1 | 2/2018 |
| WO | WO 2018/030608 A1 | 2/2018 |
| WO | WO 2018/031683 A1 | 2/2018 |
| WO | WO 2018/035250 A1 | 2/2018 |
| WO | WO 2018/035300 A1 | 2/2018 |
| WO | WO 2018/035423 A1 | 2/2018 |
| WO | WO 2018/035503 A1 | 2/2018 |
| WO | 2018/049073 A1 | 3/2018 |
| WO | WO 2018/039145 A1 | 3/2018 |
| WO | WO 2018/039438 A1 | 3/2018 |
| WO | WO 2018/039440 A1 | 3/2018 |
| WO | WO 2018/039448 A1 | 3/2018 |
| WO | WO 2018/045630 A1 | 3/2018 |
| WO | WO 2018/048827 A1 | 3/2018 |
| WO | WO 2018/049168 A1 | 3/2018 |
| WO | WO 2018/051347 A1 | 3/2018 |
| WO | WO 2018/058064 A1 | 3/2018 |

(56) References Cited

FOREIGN PATENT DOCUMENTS

| | | |
|---|---|---|
| WO | WO 2018/062866 A2 | 4/2018 |
| WO | WO 2018/064352 A1 | 4/2018 |
| WO | WO 2018/064371 A1 | 4/2018 |
| WO | WO 2018/064516 A1 | 4/2018 |
| WO | WO 2018/067546 A1 | 4/2018 |
| WO | WO 2018/067846 A1 | 4/2018 |
| WO | WO 2018/068053 A2 | 4/2018 |
| WO | WO 2018/069474 A1 | 4/2018 |
| WO | WO 2018/071623 A2 | 4/2018 |
| WO | WO 2018/071663 A1 | 4/2018 |
| WO | WO 2018/071868 A1 | 4/2018 |
| WO | WO 2018/071892 A1 | 4/2018 |
| WO | WO 2018/074979 A1 | 4/2018 |
| WO | 2018/085414 A1 | 5/2018 |
| WO | WO 2018/079134 A1 | 5/2018 |
| WO | WO 2018/080573 A1 | 5/2018 |
| WO | WO 2018/081504 A1 | 5/2018 |
| WO | WO 2018/081535 A2 | 5/2018 |
| WO | WO 2018/081728 A1 | 5/2018 |
| WO | WO 2018/083128 A2 | 5/2018 |
| WO | WO 2018/083606 A1 | 5/2018 |
| WO | WO 2018/085288 A1 | 5/2018 |
| WO | WO 2018/086623 A1 | 5/2018 |
| WO | WO 2018/089664 A1 | 5/2018 |
| WO | WO 2018/093990 A1 | 5/2018 |
| WO | WO 2018/098383 A1 | 5/2018 |
| WO | WO 2018/098480 A1 | 5/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018/108272 A1 | 6/2018 |
| WO | WO 2018/109101 A1 | 6/2018 |
| WO | WO 2018/109447 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | WO 2018/119354 A1 | 6/2018 |
| WO | WO 2018/119359 A1 | 6/2018 |
| WO | WO 2018/120283 A1 | 7/2018 |
| WO | WO 2018/130830 A1 | 7/2018 |
| WO | WO 2018/135838 A2 | 7/2018 |
| WO | WO 2018/136396 A2 | 7/2018 |
| WO | WO 2018/136939 A1 | 7/2018 |
| WO | 2018/142364 A1 | 8/2018 |
| WO | 2018/149915 A1 | 8/2018 |
| WO | 2018/156824 A1 | 8/2018 |
| WO | WO 2018/138385 A1 | 8/2018 |
| WO | WO 2018/148246 A1 | 8/2018 |
| WO | WO 2018/148256 A1 | 8/2018 |
| WO | WO 2018/148647 A2 | 8/2018 |
| WO | WO 2018/149418 A1 | 8/2018 |
| WO | WO 2018/149888 A1 | 8/2018 |
| WO | WO 2018/152197 A1 | 8/2018 |
| WO | WO 2018/152418 A1 | 8/2018 |
| WO | WO 2018/154380 A1 | 8/2018 |
| WO | WO 2018/154387 A1 | 8/2018 |
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A2 | 8/2018 |
| WO | WO 2018/156372 A1 | 8/2018 |
| WO | WO 2018/161009 A1 | 9/2018 |
| WO | WO 2018/161032 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/176009 A1 | 9/2018 |
| WO | 2018/189184 A1 | 10/2018 |
| WO | 2018/191388 A1 | 10/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/195402 A1 | 10/2018 |
| WO | WO 2018/195545 A2 | 10/2018 |
| WO | WO 2018/195555 A1 | 10/2018 |
| WO | 2018/197020 A1 | 11/2018 |
| WO | 2018/202800 A1 | 11/2018 |
| WO | WO 2018/197495 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |
| WO | 2019/005884 A1 | 1/2019 |
| WO | WO 2019/005886 A1 | 1/2019 |
| WO | WO 2019/010384 A1 | 1/2019 |
| WO | WO 2019/023680 A1 | 1/2019 |
| WO | WO 2019/040935 A1 | 2/2019 |
| WO | WO 2019/079347 A1 | 4/2019 |
| WO | 2019/084062 A1 | 5/2019 |
| WO | WO 2019/118949 A1 | 6/2019 |
| WO | WO 2019/126709 A1 | 6/2019 |
| WO | WO 2019/139645 A2 | 7/2019 |
| WO | 2019/161251 A1 | 8/2019 |
| WO | 2019/168953 A1 | 9/2019 |
| WO | 2019/217942 A1 | 11/2019 |
| WO | WO 2019/226953 A1 | 11/2019 |
| WO | 2019/241649 A1 | 12/2019 |
| WO | WO 2020/014261 A1 | 1/2020 |
| WO | 2020/028555 A2 | 2/2020 |
| WO | WO 2020/041751 A1 | 2/2020 |
| WO | WO 2020/051360 A1 | 3/2020 |
| WO | WO 2020/086908 A1 | 4/2020 |
| WO | WO 2020/092453 A1 | 5/2020 |
| WO | WO 2020/102659 A1 | 5/2020 |
| WO | WO 2020/154500 A1 | 7/2020 |
| WO | 2020/180975 A1 | 9/2020 |
| WO | 2020/191153 A2 | 9/2020 |
| WO | WO 2020/181178 A1 | 9/2020 |
| WO | WO 2020/181180 A1 | 9/2020 |
| WO | WO 2020/181193 A1 | 9/2020 |
| WO | WO 2020/181195 A1 | 9/2020 |
| WO | WO 2020/181202 A1 | 9/2020 |
| WO | WO 2020/191153 A1 | 9/2020 |
| WO | WO 2020/191171 A1 | 9/2020 |
| WO | WO 2020/191233 A1 | 9/2020 |
| WO | WO 2020/191234 A1 | 9/2020 |
| WO | WO 2020/191239 A1 | 9/2020 |
| WO | WO 2020/191241 A1 | 9/2020 |
| WO | WO 2020/191242 A1 | 9/2020 |
| WO | WO 2020/191243 A1 | 9/2020 |
| WO | WO 2020/191245 A1 | 9/2020 |
| WO | WO 2020/191246 A1 | 9/2020 |
| WO | WO 2020/191248 A1 | 9/2020 |
| WO | WO 2020/191249 A1 | 9/2020 |
| WO | WO 2020/210751 A1 | 10/2020 |
| WO | WO 2020/214842 A1 | 10/2020 |
| WO | WO 2020/236982 A1 | 11/2020 |
| WO | WO 2021/025750 A1 | 2/2021 |
| WO | WO 2021/030666 A1 | 2/2021 |
| WO | 2021/072328 A1 | 4/2021 |
| WO | 2021/108717 A2 | 6/2021 |
| WO | 2021/138469 A1 | 7/2021 |
| WO | 2021/155065 A1 | 8/2021 |
| WO | 2021/158921 A2 | 8/2021 |
| WO | 2021/158995 A1 | 8/2021 |

(56) References Cited

FOREIGN PATENT DOCUMENTS

| | | |
|---|---|---|
| WO | 2021/158999 A1 | 8/2021 |
| WO | 2021/222318 A1 | 11/2021 |
| WO | 2021/226558 A1 | 11/2021 |
| WO | 2022/067130 A2 | 3/2022 |

OTHER PUBLICATIONS

U.S. Appl. No. 61/716,256, filed Oct. 19, 2012, Jinek et al..
U.S. Appl. No. 61/717,324, filed Oct. 23, 2012, Cho et al..
U.S. Appl. No. 61/734,256, filed Dec. 6, 2012, Chen et al..
U.S. Appl. No. 61/758,624, filed Jan. 30, 2013, Chen et al..
U.S. Appl. No. 61/761,046, filed Feb. 5, 2013, Knight et al..
U.S. Appl. No. 61/794,422, filed Mar. 15, 2013, Knight et al..
U.S. Appl. No. 61/803,599, filed Mar. 20, 2013, Kim et al..
U.S. Appl. No. 61/836,080.
U.S. Appl. No. 61/837,481, filed Jun. 20, 2013, Cho et al..
U.S. Appl. No. 61/838,178, filed Jun. 21, 2013, Joung et al..
U.S. Appl. No. 61/874,682, filed Sep. 6, 2013, Liu et al..
U.S. Appl. No. 61/874,746, filed Sep. 6, 2013, Liu et al..
U.S. Appl. No. 62/288,661, filed Jan. 29, 2016, Muir et al..
U.S. Appl. No. 62/357,332, filed Jun. 30, 2016, Liu et al..
U.S. Appl. No. 62/498,686.
Invitation to Pay Additional Fees for PCT/US2016/058344, mailed Mar. 1, 2017.
International Search Report and Written Opinion for PCT/US2016/058344, mailed Apr. 20, 2017.
International Preliminary Report on Patentability for PCT/US2016/058344, mailed May 3, 2018.
[No Author Listed] "FokI" from New England Biolabs Inc. Last accessed online via https://www.neb.com/products/r0109-foki#Product%20Information on Mar. 19, 2021. 1 page.
[No Author Listed] "Nucleic Acids Sizes and Molecular Weights." Printed Mar. 19, 2021. 2 pages.
[No Author Listed] "Zinc Finger Nuclease" from Wikipedia. Retrieved from https://en.wikipedia.org/w/index.php?title=Zinc_finger_nuclease&oldid=1007053318. Page last edited Feb. 16, 2021. Printed on Mar. 19, 2021.
[No Author Listed] HyPhy—Hypothesis testing using Phylogenies. Last modified Apr. 21, 2017. Accessed online via http://hyphy.org/w/index.php/Main_Page on Apr. 28, 2021.
[No Author Listed] NCBI Accession No. XP_015843220.1. C ->U editing enzyme APOBEC-1 [Peromyscus maniculatus bairdii], XP002793540. Mar. 21, 2016.
[No Author Listed] NCBI Accession No. XP_021505673.1. C ->U editing enzyme APOBEC-1 [Meriones unguiculatus], XP002793541. Jun. 27, 2017.
[No Author Listed] Score result for SEQ 355 to W02017032580. Muir et al. 2016.
[No Author Listed] Theoretical Biochemistry Group. Institute for Theoretical Chemistry. The ViennaRNA Package. Universitat Wien. https://www.tbi.univie.ac.at/RNA/. Last accessed Apr. 28, 2021.
[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Abremski et al., Bacteriophage P1 site-specific recombination. Purification and properties of the Cre recombinase protein. J Biol Chem. Feb. 10, 1984;259(3):1509-14.
Abudayyeh et al., C2c2 is a single-component programmable RNA-guided RNA-targeting CRISPR effector. Science Aug. 2016;353(6299):aaf5573. DOI: 10.1126/science.aaf5573.
Abudayyeh et al., RNA targeting with CRISPR-Cas13. Nature. Oct. 12, 2017;550(7675):280-284. doi: 10.1038/nature24049. Epub Oct. 4, 2017.
Ada et al., Carbohydrate-protein conjugate vaccines. Clin Microbiol Infect. Feb. 2003;9(2):79-85. doi: 10.1046/j.1469-0691.2003.00530.x.
Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.
Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Adli, The CRISPR tool kit for genome editing and beyond. Nat Commun. May 15, 2018;9(1):1911. doi: 10.1038/s41467-018-04252-2.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel.2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Aguilo et al., Coordination of m(6)A mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.
Ahmad et al., Antibody-mediated specific binding and cytotoxicity of liposome-entrapped doxorubicin to lung cancer cells in vitro. Cancer Res. Sep. 1, 1992;52(17):4817-20.
Aihara et al., A conformational switch controls the DNA cleavage activity of lambda integrase. Mol Cell. Jul. 2003; 12(1):187-98.
Aik et al., Structure of human RNA N ?-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.
Aird et al., Increasing Cas9-mediated homology-directed repair efficiency through covalent tethering of DNA repair template. Commun Biol. May 31, 2018;1:54. doi: 10.1038/s42003-018-0054-2.
Akcakaya et al., In vivo CRISPR editing with no detectable genome-wide off-target mutations. Nature. Sep. 2018;561(7723):416-419. doi: 10.1038/s41586-018-0500-9. Epub Sep. 12, 2018. PMID: 30209390; PMCID: PMC6194229.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Akins et al., Mitochondrial plasmids of Neurospora: integration into mitochondrial DNA and evidence for reverse transcription in mitochondria. Cell. Nov. 21, 1986;47(4):505-16. doi: 10.1016/0092-8674(86)90615-x.
Akinsheye et al., Fetal hemoglobin in sickle cell anemia. Blood. Jul. 7, 2011;118(1):19-27. doi: 10.1182/blood-2011-03-325258. Epub Apr. 13, 2011.
Akopian et al., Chimeric recombinases with designed DNA sequence recognition. Proc Natl Acad Sci U S A. Jul. 22, 2003;100(15):8688-91. Epub Jul. 1, 2003.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Alarcón et al., HNRNPA2B1 Is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.
Alarcón et al., N6-methyladenosine marks primary microRNAs for processing. Nature. Mar. 26, 2015;519(7544):482-5. doi: 10.1038/nature14281. Epub Mar. 18, 2015.

(56) References Cited

OTHER PUBLICATIONS

Alexander, HFE-associated hereditary hemochromatosis. Genet Med. May 2009;11(5):307-13. doi: 10.1097/GIM.0b013e31819d30f2.
Alexandrov et al., Signatures of mutational processes in human cancer. Nature. Aug. 22, 2013;500(7463):415-21. doi: 10.1038/nature12477. Epub Aug. 14, 2013.
Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Altschul et al., Basic local alignment search tool. J Mol Biol. Oct. 5, 1990;215(3):403-10. doi: 10.1016/S0022-2836(05)80360-2.
Amato et al., Interpreting elevated fetal hemoglobin in pathology and health at the basic laboratory level: new and known γ- gene mutations associated with hereditary persistence of fetal hemoglobin. Int J Lab Hematol. Feb. 2014;36(1):13-9. doi: 10.1111/ijlh.12094. Epub Apr. 29, 2013.
Amato et al., Interpreting elevated fetal hemoglobin in pathology and health at the basic laboratory level: new and known γ-gene mutations associated with hereditary persistence of fetal hemoglobin. Int J Lab Hematol. Feb. 2014;36(1):13-9. doi: 10.1111/ijlh.12094. Epub Apr. 29, 2013.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Amrann et al., Tightly regulated tac promoter vectors useful for the expression of unfused and fused proteins in *Escherichia coli*. Gene. Sep. 30, 1988;69(2):301-15.
Anders et al., Chapter One: In Vitro Enzymology of Cas9. in Methods in Enzymology, eds Doudna et al. 2014: 546:1-20.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014. Europe PMC Funders Group. Author manuscript. Available OMC Mar. 25, 2015.
Anderson, Human gene therapy. Science. May 8, 1992;256(5058):808-13. doi: 10.1126/science.1589762.
André et al., Axotomy-induced expression of calcium-activated chloride current in subpopulations of mouse dorsal root ganglion neurons. J Neurophysiol. Dec. 2003;90(6):3764- 73. doi: 10.1152/jn.00449.2003. Epub Aug. 27, 2003.
Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.
Anzalone et al., Search-and-replace genome editing without double-strand breaks or donor DNA. Nature. Dec. 2019;576(7785):149-157. doi: 10.1038/s41586-019-1711-4. Epub Oct. 21, 2019.
Aplan, Causes of oncogenic chromosomal translocation. Trends Genet. Jan. 2006;22(1):46-55. doi: 10.1016/j.tig.2005.10.002. Epub Oct. 28, 2005.
Arakawa et al., A method to convert mRNA into a gRNA library for CRISPR/Cas9 editing of any organism. Sci Adv. Aug. 24, 2016;2(8):e1600699. doi: 10.1126/sciadv.1600699.
Araki et al., Comparative analysis of right element mutant lox sites on recombination efficiency in embryonic stem cells. BMC Biotechnol. Mar. 31, 2010;10:29. doi: 10.1186/1472-6750-10-29.
Araki et al., Site-specific recombinase, R, encoded by yeast plasmid pSR1. J Mol Biol. May 5, 1992;225(1):25-37. doi: 10.1016/0022-2836(92)91023-i.
Araki et al., Targeted integration of DNA using mutant lox sites in embryonic stem cells. Nucleic Acids Res. Feb. 15, 1997;25(4):868-72. doi: 10.1093/nar/25.4.868.
Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.
Arazoe et al., Targeted Nucleotide Editing Technologies for Microbial Metabolic Engineering. Biotechnol J. Sep. 2018;13(9):e1700596. doi: 10.1002/biot.201700596. Epub Jun. 19, 2018.
Arbab et al., Cloning-free CRISPR. Stem Cell Reports. Nov. 10, 2015;5(5):908-917. doi: 10.1016/j.stemcr.2015.09.022. Epub Oct. 29, 2015.
Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.
Arnold et al., Mutants of Tn3 resolvase which do not require accessory binding sites for recombination activity. Embo J. Mar. 1, 1999;18(5):1407-14.
Asante et al., A naturally occurring variant of the human prion protein completely prevents prion disease. Nature. Jun. 25, 2015;522(7557):478-81. doi: 10.1038/nature14510. Epub Jun. 10, 2015.
Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.
Auer et al., Highly efficient CRISPR/Cas9-mediated knock-in in zebrafish by homology- independent DNA repair. Genome Res. Jan. 2014;24(1):142-53. doi: 10.1101/gr.161638.113. Epub Oct. 31, 2013.
Autieri et al., IRT-1, a novel interferon-gamma-responsive transcript encoding a growth- suppressing basic leucine zipper protein. J Biol Chem. Jun. 12, 1998;273(24):14731-7. doi: 10.1074/jbc.273.24.14731.
Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.
Babacic et al., CRISPR-cas gene-editing as plausible treatment of neuromuscular and nucleotide-repeat-expansion diseases: A systematic review. PLoS One. Feb. 22, 2019;14(2):e0212198. doi: 10.1371/journal.pone.0212198.
Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Bae et al., Microhomology-based choice of Cas9 nuclease target sites. Nat Methods. Jul. 2014;11(7):705-6. doi: 10.1038/nmeth.3015.
Bae et al., Protective anti-tumour immune responses by murine dendritic cells pulsed with recombinant Tat-carcinoembryonic antigen derived from Escherichia coli. Clin Exp Immunol. Jul. 2009; 157(1):128-38. doi: 10.1111/j.1365-2249.2009.03943.x.
Bagyinszky et al., Characterization of mutations in PRNP (prion) gene and their possible roles in neurodegenerative diseases. Neuropsychiatr Dis Treat. Aug. 14, 2018;14:2067-2085. doi: 10.2147/NDT.S165445.
Balakrishnan et al., Flap endonuclease 1. Annu Rev Biochem. 2013;82:119-38. doi: 10.1146/annurev-biochem-072511-122603. Epub Feb. 28, 2013.
Baldari et al., A novel leader peptide which allows efficient secretion of a fragment of human interleukin 1 beta in *Saccharomyces cerevisiae*. EMBO J. Jan. 1987;6(1):229-34.
Banerjee et al., Cadmium inhibits mismatch repair by blocking the ATPase activity of the MSH2-MSH6 complex [published correction appears in Nucleic Acids Res. 2005;33(5):1738]. Nucleic Acids Res. 2005;33(4):1410-1419. Published Mar. 3, 2005. doi: 10.1093/nar/gki291.

(56) References Cited

OTHER PUBLICATIONS

Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.

Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.

Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.

Barnes et al., Repair and genetic consequences of endogenous DNA base damage in mammalian cells. Annu Rev Genet. 2004;38:445-76.

Barnes et al., The fidelity of Taq polymerase catalyzing PCR is improved by an N-terminal deletion. Gene. Mar. 1, 1992;112(1):29-35. doi: 10.1016/0378-1119(92)90299-5.

Barrangou et al., CRISPR provides acquired resistance against viruses in prokaryotes. Science. Mar. 23, 2007;315(5819):1709-12.

Barrangou, RNA-mediated programmable DNA cleavage. Nat Biotechnol. Sep. 2012;30(9):836-8. doi: 10.1038/nbt.2357.

Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.

Bartosovic et al., N6-methyladenosine demethylase FTO targets pre-mRNAs and regulates alternative splicing and 3'-end processing. Nucleic Acids Res. Nov. 2, 2017;45(19):11356-11370. doi: 10.1093/nar/gkx778.

Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.

Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.

Batey et al., Structure of a natural guanine-responsive riboswitch complexed with the metabolite hypoxanthine. Nature. Nov. 18, 2004;432(7015):411-5.

Beale et al., Comparison of the differential context-dependence of DNA deamination by APOBEC enzymes: correlation with mutation spectra in vivo. J Mol Biol. Mar. 26, 2004;337(3):585-96.

Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.

Bedell et al., In vivo genome editing using a high-efficiency TALEN system. Nature. Nov. 1, 2012;491(7422):114-8. Doi: 10.1038/nature11537. Epub Sep. 23, 2012.

Begley, Scientists unveil the 'most clever CRISPR gadget' so far. STAT, Apr. 20, 2016. https://www.statnews.com/2016/04/20/clever-crispr-advance-unveiled/.

Behr, Gene transfer with synthetic cationic amphiphiles: prospects for gene therapy. Bioconjug Chem. Sep. -Oct. 1994;5(5):382-9. doi: 10.1021/bc00029a002.

Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.

Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.

Benarroch, HCN channels: function and clinical implications. Neurology. Jan. 15, 2013;80(3):304-10. doi: 10.1212/WNL.0b013e31827dec42.

Bennett et al., Painful and painless channelopathies. Lancet Neurol. Jun. 2014; 13(6):587-99. doi: 10.1016/S1474-4422(14)70024-9. Epub May 6, 2014.

Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.

Berges et al., Transduction of brain by herpes simplex virus vectors. Mol Ther. Jan. 2007;15(1):20-9. doi: 10.1038/sj.mt.6300018.

Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375.1999.

Bernhart et al., Local RNA base pairing probabilities in large sequences. Bioinformatics. Mar. 1, 2006;22(5):614-5. doi: 10.1093/bioinformatics/btk014. Epub Dec. 20, 2005.

Bernstein et al., Role for a bidentate ribonuclease in the initiation step of RNA interference. Nature. Jan. 18, 2001;409(6818):363-6. doi: 10.1038/35053110.

Bershtein et al., Advances in laboratory evolution of enzymes. Curr Opin; Chem Biol. Apr. 2008; 12(2):151-8. doi: 10.1016/j.cbpa.2008.01.027. Epub Mar. 7, 2008. Review.

Bertolotti et al., Toward genosafe endonuclease-boosted gene targeting using breakthrough CRISP/Cas9 for next generation stem cell gene therapy culminating in efficient ex VIVO in VIVO gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2015-May 16, 2015.

Bertrand et al., Localization of ASH1 mRNA particles in living yeast. Mol Cell. Oct. 1998;2(4):437-45. doi: 10.1016/s1097-2765(00)80143-4.

Beumer et al., Efficient gene targeting in *Drosophila* with zinc-finger nucleases. Genetics. Apr. 2006;172(4):2391-403. Epub Feb. 1, 2006.

Bhagwat, DNA-cytosine deaminases: from antibody maturation to antiviral defense. DNA Repair (Amst). Jan. 5, 2004;3(1):85-9.

Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.

Bibb et al., Integration and excision by the large serine recombinase phiRv1 integrase. Mol Microbiol. Mar. 2005;55(6):1896-910. doi: 10.1111/j.1365-2958.2005.04517.x.

Bibikova et al., Stimulation of homologous recombination through targeted cleavage by chimeric nucleases. Mol Cell Biol. Jan. 2001;21(1):289-97.

Bibikova et al., Targeted chromosomal cleavage and mutagenesis in *Drosophila* using zinc-finger nucleases. Genetics. Jul. 2002;161(3):1169-75.

Biehs et al., DNA Double-Strand Break Resection Occurs during Non-homologous End Joining in G1 but Is Distinct from Resection during Homologous Recombination. Mol Cell. Feb. 16, 2017;65(4):671-684.e5. doi: 10.1016/j.molcel.2016.12.016. Epub Jan. 26, 2017.

Billon et al., CRISPR-Mediated Base Editing Enables Efficient Disruption of Eukaryotic Genes through Induction of STOP Codons. Mol Cell. Sep. 21, 2017;67(6): 1068-1079.e4. doi: 10.1016/j.molcel.2017.08.008. Epub Sep. 7, 2017.

Birling et al., Site-specific recombinases for manipulation of the mouse genome. Methods Mol Biol. 2009;561:245-63. doi: 10.1007/978-1-60327-019-9_16.

Biswas et al., A structural basis for allosteric control of DNA recombination by lambda integrase. Nature. Jun. 23, 2005;435(7045):1059-66. doi: 10.1038/nature03657.

Bitinaite et al., FokI dimerization is required for DNA cleavage. Proc Natl Acad Sci U S A. Sep. 1, 1998;95(18):10570-5.

Blaese et al., Vectors in cancer therapy: how will they deliver? Cancer Gene Ther. Dec. 1995;2(4):291-7.

Blain et al., Nuclease activities of Moloney murine leukemia virus reverse transcriptase. Mutants with altered substrate specificities. J Biol Chem. Nov. 5, 1993;268(31):23585-92.

Blaisonneau et al., A circular plasmid from the yeast Torulaspora delbrueckii. Plasmid. 1997;38(3):202-9. doi: 10.1006/plas.1997.1315.

(56) References Cited

OTHER PUBLICATIONS

Blau et al., A proliferation switch for genetically modified cells. PNAS Apr. 1, 1997 94 (7) 3076-3081; https://doi.org/10.1073/pnas.94.7.3076.

Bloom et al., Evolving strategies for enzyme engineering. Curr Opin Struct Biol. Aug. 2005; 15(4):447-52.

Boch et al., Breaking the code of DNA binding specificity of TAL-type III effectors. Science. Dec. 11, 2009;326(5959):1509-12. Doi: 10.1126/science.1178811.

Boch, TALEs of genome targeting. Nat Biotechnol. Feb. 2011;29(2):135-6. Doi: 10.1038/nbt.1767.

Bodi et al., Yeast m6A Methylated mRNAs Are Enriched on Translating Ribosomes during Meiosis, and under Rapamycin Treatment. PLoS One. Jul. 17, 2015;10(7):e0132090. doi: 10.1371/journal.pone.0132090.

Boeckle et al., Melittin analogs with high lytic activity at endosomal pH enhance transfection with purified targeted PEI polyplexes. J Control Release. May 15, 2006;112(2):240-8. Epub Mar. 20, 2006.

Boersma et al., Selection strategies for improved biocatalysts. Febs J. May 2007;274(9):2181-95.

Bogdanove et al., Engineering altered protein-DNA recognition specificity. Nucleic Acids Res. Jun. 1, 2018;46(10):4845-4871. doi: 10.1093/nar/gky289.

Bogdanove et al., TAL effectors: customizable proteins for DNA targeting. Science. Sep. 30, 2011;333(6051):1843-6. doi: 10.1126/science.1204094.

Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.

Bolotin et al., Clustered regularly interspaced short palindrome repeats (CRISPRs) have spacers of extrachromosomal origin. Microbiology. Aug. 2005;151(Pt 8):2551-61.

Bolusani et al., Evolution of variants of yeast site-specific recombinase Flp that utilize native genomic sequences as recombination target sites. Nucleic Acids Res. 2006;34(18):5259-69. Epub Sep. 26, 2006.

Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.

Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.

Borman, Improved route to single-base genome editing. Chemical & Engineering News, Apr. 25, 2016;94(17)p. 5. http://cen.acs.org/articles/94/i17/Improved-route-single-base-genome.html.

Bourinet et al., Silencing of the Cav3.2 T-type calcium channel gene in sensory neurons demonstrates its major role in nociception. EMBO J. Jan. 26, 2005;24(2):315-24. doi: 10.1038/sj.emboj.7600515. Epub Dec. 16, 2004.

Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.

Box et al., A multi-domain protein system based on the HC fragment of tetanus toxin for targeting DNA to neuronal cells. J Drug Target. Jul. 2003;11(6):333-43. doi: 10.1080/10611860310001634667.

Branden and Tooze, Introduction to Protein Structure. 1999; 2nd edition. Garland Science Publisher: 3-12.

Braun et al., Immunogenic duplex nucleic acids are nuclease resistant. J Immunol. Sep. 15, 1988;141(6):2084-9.

Briner et al., Guide RNA functional modules direct Cas9 activity and orthogonality. Mol Cell. Oct. 23, 2014;56(2):333-339. doi: 10.1016/j.molcel.2014.09.019.

Britt et al., Re-engineering plant gene targeting. Trends Plant Sci. Feb. 2003;8(2):90-5.

Brouns et al., Small CRISPR RNAs guide antiviral defense in prokaryotes. Science. Aug. 15, 2008;321(5891):960-4. doi: 10.1126/science.1159689.

Brown et al., A mammalian protein targeted by G1-arresting rapamycin-receptor complex. Nature. Jun. 30, 1994;369(6483):756-8. doi: 10.1038/369756a0.

Brown et al., Characterization of the genetic elements required for site-specific integration of plasmid pSE211 in Saccharopolyspora erythraea. J Bacteriol. Apr. 1990;172(4):1877-88. doi: 10.1128/jb.172.4.1877-1888.1990.

Brown et al., Serine recombinases as tools for genome engineering. Methods. Apr. 2011;53(4):372-9. doi: 10.1016/j.ymeth.2010.12.031. Epub Dec. 30, 2010.

Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.

Brusse et al., Spinocerebellar ataxia associated with a mutation in the fibroblast growth factor 14 gene (SCA27): A new phenotype. Mov Disord. Mar. 2006;21(3):396-401.

Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gkl765. Epub Oct. 27, 2006.

Buchholz et al., Alteration of Cre recombinase site specificity by substrate-linked protein evolution. Nat Biotechnol. Nov. 2001;19(11):1047-52.

Buchschacher et al., Human immunodeficiency virus vectors for inducible expression of foreign genes. J Virol. May 1992;66(5):2731-9. doi: 10.1128/JVI.66.5.2731-2739.1992.

Buchwald et al., Long-term, continuous intravenous heparin administration by an implantable infusion pump in ambulatory patients with recurrent venous thrombosis. Surgery. Oct. 1980;88(4):507-16.

Buckley et al., Targeting the von Hippel-Lindau E3 ubiquitin ligase using small molecules to disrupt the VHL/HIF-1? interaction. J Am Chem Soc. Mar. 14, 2012;134(10):4465-8. doi: 10.1021/ja209924v. Epub Feb. 27, 2012.

Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.

Budker et al., Protein/amphipathic polyamine complexes enable highly efficient transfection with minimal toxicity. Biotechniques. Jul. 1997;23(1): 139, 142-7. doi: 10.2144/97231rr02.

Budworth et al., A brief history of triplet repeat diseases. Methods Mol Biol. 2013; 1010:3-17. doi: 10.1007/978-1-62703-411-1_1.

Bulow et al., Multienzyme systems obtained by gene fusion. Trends Biotechnol. Jul. 1991;9(7):226-31.

Bulyk et al., Exploring the DNA-binding specificities of zinc fingers with DNA microarrays. Proc Natl Acad Sci U S A. Jun. 19, 2001;98(13):7158-63. Epub Jun. 12, 2001.

Burke et al., Activating mutations of Tn3 resolvase marking interfaces important in recombination catalysis and its regulation. Mol Microbiol. Feb. 2004;51(4):937-48.

Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.

Burstein et al., New CRISPR-Cas systems from uncultivated microbes. Nature Feb. 2017;542(7640):237-240.

Burton et al., Gene delivery using herpes simplex virus vectors. DNA Cell Biol. Dec. 2002;21(12):915-36. doi: 10.1089/104454902762053864.

Buskirk et al., Directed evolution of ligand dependence: small-molecule-activated protein splicing. Proc Natl Acad Sci U S A. Jul. 20, 2004;101(29):10505-10. Epub Jul. 9, 2004.

Buskirk et al., In vivo evolution of an RNA-based transcriptional activator. Chem Biol. Jun. 2003; 10(6):533-40. doi: 10.1016/s1074-5521(03)00109-1.

Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.

Böck et al., Selenocysteine: the 21st amino acid. Mol Microbiol. Mar. 1991;5(3):515-20.

(56) References Cited

OTHER PUBLICATIONS

Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cadwell et al., Randomization of genes by PCR mutagenesis. PCR Methods Appl. Aug. 1992;2(1):28-33. doi: 10.1101/gr.2.1.28.
Cai et al., Reconstruction of ancestral protein sequences and its applications. BMC Evol Biol. Sep. 17, 2004;4:33. doi: 10.1186/1471-2148-4-33.
Calame et al., Transcriptional controlling elements in the immunoglobulin and T cell receptor loci. Adv Immunol. 1988;43:235-75. doi: 10.1016/s0065-2776(08)60367-3.
Caldecott et al., Single-strand break repair and genetic disease. Nat Rev Genet. Aug. 2008;9(8):619-31. doi: 10.1038/nrg2380.
Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.
Cameron, Recent advances in transgenic technology. Mol Biotechnol. Jun. 1997;7(3):253-65.
Camper et al., Postnatal repression of the alpha-fetoprotein gene is enhancer independent. Genes Dev. Apr. 1989;3(4):537-46. doi: 10.1101/gad.3.4.537.
Camps et al., Targeted gene evolution in Escherichia coli using a highly error-prone DNA polymerase I. Proc Natl Acad Sci U S A. Aug. 19, 2003;100(17):9727-32. Epub Aug. 8, 2003.
Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.
Canver et al., Customizing the genome as therapy for the β-hemoglobinopathies. Blood. May 26, 2016;127(21):2536-45. doi: 10.1182/blood-2016-01-678128. Epub Apr. 6, 2016.
Cargill et al., Characterization of single-nucleotide polymorphisms in coding regions of human genes. Nat Genet. Jul. 1999;22(3):231-8.
Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Caron et al., Intracellular delivery of a Tat-eGFP fusion protein into muscle cells. Mol Ther. Mar. 2001;3(3):310-8.
Carr et al., Genome engineering. Nat Biotechnol. Dec. 2009;27(12):1151-62. doi: 10.1038/nbt.1590.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Carroll, Genome engineering with zinc-finger nucleases. Genetics. Aug. 2011;188(4):773-82. doi: 10.1534/genetics.111.131433. Review.
Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.
Caspi et al., Distribution of split DnaE inteins in cyanobacteria. Mol Microbiol. Dec. 2003;50(5):1569-77. doi: 10.1046/j.1365-2958.2003.03825.x.
Cattaneo et al., SEL1L affects human pancreatic cancer cell cycle and invasiveness through modulation of PTEN and genes related to cell-matrix interactions. Neoplasia. 2005;7(11):1030-1038.
Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.
Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.
Chan et al., Molecular recording of mammalian embryogenesis. Nature. Jun. 2019;570(7759):77-82. doi: 10.1038/s41586-019-1184-5. Epub May 13, 2019.
Chan et al., Novel selection methods for DNA-encoded chemical libraries. Curr Opin Chem Biol. 2015;26:55-61. doi:10.1016/j.cbpa.2015.02.010.
Chan et al., The choice of nucleotide inserted opposite abasic sites formed within chromosomal DNA reveals the polymerase activities participating in translesion DNA synthesis. DNA Repair (Amst). Nov. 2013;12(11):878-89. doi: 10.1016/j.dnarep.2013.07.008. Epub Aug. 26, 2013.
Chang et al., Modification of DNA ends can decrease end joining relative to homologous recombination in mammalian cells. Proc Natl Acad Sci U S A. Jul. 1987; 84(14):4959-63.
Chapman et al., Playing the end game: DNA double-strand break repair pathway choice. Mol Cell. Aug. 24, 2012;47(4):497-510. doi: 10.1016/j.molcel.2012.07.029.
Chari et al., Unraveling CRISPR-Cas9 genome engineering parameters via a library-on-library approach. Nat Methods. Sep. 2015;12(9):823-6. doi: 10.1038/nmeth.3473. Epub Jul. 13, 2015.
Charpentier et al., Biotechnology: Rewriting a genome. Nature. Mar. 7, 2013;495(7439):50-1. doi: 10.1038/495050a.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chavez et al., Highly efficient Cas9-mediated transcriptional programming. Nat Methods. Apr. 2015; 12(4):326-8. doi: 10.1038/nmeth.3312. Epub Mar. 2, 2015.
Chavez et al., Precise Cas9 targeting enables genomic mutation prevention. bioRxiv. Jun. 14, 2016; http://dx/doi.oreg/10.1101/058974. 6 pages. bioRxiv preprint first posted online Jun. 14, 2016.
Chavez et al., Precise Cas9 targeting enables genomic mutation prevention. Jun. 14, 2016. doi:https://doi.org/10.1101/058974. [Preprint].
Chavez et al., Precise Cas9 targeting enables genomic mutation prevention. Proc Natl Acad Sci U S A. Apr. 3, 2018;115(14):3669-3673. doi: 10.1073/pnas.1718148115. Epub Mar. 19, 2018.
Chavez et al., Therapeutic applications of the ΦC31 integrase system. Curr Gene Ther. Oct. 2011;11(5):375-81. Review.
Chavez et al., Therapeutic applications of the PhiC31 integrase system. Curr Gene Ther. Oct. 2011; 11(5):375-81. Review.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.

(56) References Cited

OTHER PUBLICATIONS

Chen et al., Enhanced proofreading governs CRISPR-Cas9 targeting accuracy. Nature. Oct. 19, 2017;550(7676):407-410. doi: 10.1038/nature24268. Epub Sep. 20, 2017.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Chen et al., Genome-wide CRISPR screen in a mouse model of tumor growth and metastasis. Cell. Mar. 12, 2015;160(6):1246-60. doi: 10.1016/j.cell.2015.02.038. Epub Mar. 5, 2015.
Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.
Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Chesnoy et al., Structure and function of lipid-DNA complexes for gene delivery. Annu Rev Biophys Biomol Struct. 2000;29:27-47.
Chester et al., The apolipoprotein B mRNA editing complex performs a multifunctional cycle and suppresses nonsense-mediated decay. EMBO J. Aug. 1, 2003;22(15):3971-82. doi: 10.1093/emboj/cdg369.
Chew et al., A multifunctional AAV-CRISPR-Cas9 and its host response. Nat Methods. Oct. 2016; 13(10):868-74. doi: 10.1038/nmeth.3993. Epub Sep. 5, 2016.
Chew et al., A multifunctional AAV-CRISPR-Cas9 and its host response. Nat Methods. Oct. 2016;13(10):868-74. doi: 10.1038/nmeth.3993. Epub Sep. 5, 2016. Supplementary Information.
Chichili et al., Linkers in the structural biology of protein-protein interactions. Protein Science. 2013;22:153-67.
Chin, Expanding and reprogramming the genetic code of cells and animals. Annu Rev Biochem. 2014;83:379-408. doi: 10.1146/annurev-biochem-060713-035737. Epub Feb. 10, 2014.
Chipev et al., A leucine—proline mutation in the H1 subdomain of keratin 1 causes epidermolytic hyperkeratosis. Cell. Sep. 4, 1992;70(5):821-8.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Cho et al., Site-specific recombination of bacteriophage P22 does not require integration host factor. J Bacteriol. Jul. 1999; 181(14):4245-9. doi: 10.1128/JB.181.14.4245-4249.1999.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Cho et al., The calcium-activated chloride channel anoctamin 1 acts as a heat sensor in nociceptive neurons. Nat Neurosci. May 27, 2012;15(7):1015-21. doi: 10.1038/nn.3111.
Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.
Choi et al., N(6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 11, 2016.
Choi et al., Protein trans-splicing and characterization of a split family B-type DNA polymerase from the hyperthermophilic archaeal parasite Nanoarchaeum equitans. J Mol Biol. Mar. 10, 2006;356(5):1093-106. doi: 10.1016/j.jmb.2005.12.036. Epub Dec. 27, 2005.

Choi et at al., Translesion synthesis across abasic lesions by human B-family and Y-family DNA polymerases ?, ?, ?, ?, ?, and REV1. J Mol Biol. Nov. 19, 2010;404(1):34-44. doi: 10.1016/j.jmb.2010.09.015. Epub Oct. 1, 2010.
Chong et al., Modulation of protein splicing of the *Saccharomyces cerevisiae* vacuolar membrane ATPase intein. J Biol Chem. Apr. 24, 1998;273(17):10567-77. doi: 10.1074/jbc.273.17.10567.
Chong et al., Utilizing the C-terminal cleavage activity of a protein splicing element to purify recombinant proteins in a single chromatographic step. Nucleic Acids Res. Nov. 18, 1998;26(22):5109-15. doi: 10.1093/nar/26.22.5109.
Chong et al., Protein splicing involving the Saccharomyces cerevisiae VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.
Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.
Chong et al., Single-column purification of free recombinant proteins using a self-cleavable affinity tag derived from a protein splicing element. Gene. Jun. 19, 1997;192(2):271-81. doi: 10.1016/s0378-1119(97)00105-4.
Choudhury et al., Engineering RNA endonucleases with customized sequence specificities. Nat Commun. 2012;3:1147. doi: 10.1038/ncomms2154.
Choulika et al., Induction of homologous recombination in mammalian chromosomes by using the I-SceI system of Saccharomyces cerevisiae. Mol Cell Biol. Apr. 1995;15(4):1968-73. doi: 10.1128/MCB.15.4.1968.
Christian et al., Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Christiansen et al., Characterization of the lactococcal temperate phage TP901-1 and its site-specific integration. J Bacteriol. Feb. 1994;176(4):1069-76. doi: 10.1128/jb.176.4.1069-1076.1994.
Chu et al., Increasing the efficiency of homology-directed repair for CRISPR-Cas9-induced precise gene editing in mammalian cells. Nat Biotech. Feb. 13, 2015;33:543-8.
Chu et al., Increasing the efficiency of homology-directed repair for CRISPR-Cas9-induced precise gene editing in mammalian cells. Nat Biotech. Feb. 13, 2015;33:543-8. doi: 10.1038/nbt.3198. Epub Mar. 24, 2015.
Chuai et al., DeepCRISPR: optimized CRISPR guide RNA design by deep learning. Genome Biol. Jun. 26, 2018;19(1):80. doi: 10.1186/s13059-018-1459-4.
Chuai et al., In Silico Meets In Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.
Chuang et al., Novel Heterotypic Rox Sites for Combinatorial Dre Recombination Strategies. G3 (Bethesda). Dec. 29, 2015;6(3):559-71. doi: 10.1534/g3.115.025841.
Chujo et al., Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.
Clement et al., CRISPResso2 provides accurate and rapid genome editing sequence analysis. Nat Biotechnol. Mar. 2019;37(3):224-226. doi: 10.1038/s41587-019-0032-3.

(56) References Cited

OTHER PUBLICATIONS

Cobb et al., Directed evolution as a powerful synthetic biology tool. Methods. Mar. 15, 2013;60(1):81-90. doi: 10.1016/j.ymeth.2012.03.009. Epub Mar. 23, 2012.

Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012. Review.

Coelho et al., Safety and efficacy of RNAi therapy for transthyretin amyloidosis. Engl J Med. Aug. 29, 2013;369(9):819-29. doi: 10.1056/NEJMoa1208760.

Coffey et al., The Economic Impact of BSE on the U.S. Beef Industry: Product Value Losses, Regulatory Costs, and Consumer Reactions. Kansas State University Agricultural Experiment Station and Cooperative Extension Service. MF-2678. May 2005. 68 pages. Accessed via https://bookstore.ksre.ksu.edu/pubs/MF2678.pdf.

Cokol et al., Finding nuclear localization signals. EMBO Rep. Nov. 2000;1(5):411-5. doi: 10.1093/embo-reports/kvd092.

Cole et al., Reconstructing evolutionary adaptive paths for protein engineering. Methods Mol Biol. 2013;978:115-25. doi: 10.1007/978-1-62703-293-3_8.

Cole-Strauss et al., Correction of the mutation responsible for sickle cell anemia by an RNA-DNA oligonucleotide. Science. Sep. 6, 1996;273(5280):1386-9.

Colletier et al., Protein encapsulation in liposomes: efficiency depends on interactions between protein and phospholipid bilayer. BMC Biotechnol. May 10, 2002;2:9.

Collinge, Prion diseases of humans and animals: their causes and molecular basis. Annu Rev Neurosci. 2001;24:519-50. doi: 10.1146/annurev.neuro.24.1.519.

Cong et al., Comprehensive interrogation of natural TALE DNA-binding modules and transcriptional repressor domains. Nat Commun. Jul. 24, 2012;3:968. doi: 10.1038/ncomms1962.

Cong et al., Multiplex genome engineering using CRISPR/Cas systems. Science. Feb. 15, 2013;339(6121):819-23. doi: 10.1126/science.1231143. Epub Jan. 3, 2013.

Conrad et al., A Kaposi's sarcoma virus RNA element that increases the nuclear abundance of intronless transcripts. Embo J. May 18, 2005;24(10):1831-41. doi: 10.1038/sj.emboj.7600662. Epub Apr. 28, 2005.

Conticello, The AID/APOBEC family of nucleic acid mutators. Genome Biol. 2008;9(6):229. doi: 10.1186/GB-2008-9-6-229. Epub Jun. 17, 2008.

Cornu et al., DNA-binding specificity is a major determinant of the activity and toxicity of zinc-finger nucleases. Mol Ther. Feb. 2008;16(2):352-8. Epub Nov. 20, 2007.

Cornu et al., Refining strategies to translate genome editing to the clinic. Nat Med. Apr. 3, 2017;23(4):415-423. doi: 10.1038/nm.4313.

Costa et al., Frequent use of the same tertiary motif by self-folding RNAs. EMBO J. Mar. 15, 1995;14(6):1276-85.

Cotton et al., Insertion of a Synthetic Peptide into a Recombinant Protein Framework: A Protein Biosensor. J. Am. Chem. Soc. Jan. 22, 1999; 121(5):1100-1. https://doi.org/10.1021/ja983804b.

Covino et al., The CCL2/CCR2 Axis in the Pathogenesis of HIV-1 Infection: A New Cellular Target for Therapy? Current Drug Targets Dec. 2016;17(1):76-110. DOI 10.2174/1389450117011521710917.

Cox et al., An SCN9A channelopathy causes congenital inability to experience pain. Nature. Dec. 14, 2006;444(7121):894-8. doi: 10.1038/nature05413.

Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.

Cox et al., Congenital insensitivity to pain: novel SCN9A missense and in-frame deletion mutations. Hum Mutat. Sep. 2010;31(9):E1670-86. doi: 10.1002/humu.21325.

Cox et al., RNA editing with CRISPR-Cas13. Science. Nov. 24, 2017;358(6366):1019-1027. doi: 10.1126/science.aaq0180. Epub Oct. 25, 2017.

Cox et al., Therapeutic genome editing: prospects and challenges. Nat Med. Feb. 2015;21(2):121-31. doi: 10.1038/nm.3793.

Cox, Proteins pinpoint double strand breaks. Elife. Oct. 29, 2013;2:e01561. doi: 10.7554/eLife.01561.

Crabtree et al., Three-part inventions: intracellular signaling and induced proximity. Trends Biochem Sci. Nov. 1996;21(11):418-22. doi: 10.1016/s0968-0004(96)20027-1.

Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.

Cradick et al., ZFN-site searches genomes for zinc finger nuclease target sites and off-target sites. BMC Bioinformatics. May 13, 2011;12:152. doi: 10.1186/1471-2105-12-152.

Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.

Crick, On protein synthesis. Symp Soc Exp Biol. 1958;12:138-63.

Cronican et al., A class of human proteins that deliver functional proteins into mammalian cells in vitro and in vivo. Chem Biol. Jul. 2, 20119;18(7):833-8. doi: 10.1016/j.chembiol.2011.07.003.

Cronican et al., Potent delivery of functional proteins into mammalian cells in vitro and in vivo using a supercharged protein. ACS Chem Biol. Aug. 20, 2010;5(8):747-52. doi: 10.1021/cb1001153.

Crystal, Transfer of genes to humans: early lessons and obstacles to success. Science. Oct. 20, 1995;270(5235):404-10. doi: 10.1126/science.270.5235.404.

Cui et al., Consequences of Cas9 cleavage in the chromosome of *Escherichia coli*. Nucleic Acids Res. May 19, 2016;44(9):4243-51. doi: 10.1093/nar/gkw223. Epub Apr. 8, 2016.

Cui et al., m6A RNA Methylation Regulates the Self-Renewal and Tumorigenesis of Glioblastoma Stem Cells. Cell Rep. Mar. 14, 2017;18(11):2622-2634. doi: 10.1016/j.celrep.2017.02.059.

Cui et al., Review of CRISPR/Cas9 sgRNA Design Tools. Interdiscip Sci. Jun. 2018;10(2):455-465. doi: 10.1007/s12539-018-0298-z. Epub Apr. 11, 2018.

Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.

Cunningham et al., Ensembl 2015. Nucleic Acids Res. Jan. 2015;43(Database issue):D662-9. doi: 10.1093/nar/gku1010. Epub Oct. 28, 2014.

Cupples et al., A set of lacZ mutations in *Escherichia coli* that allow rapid detection of each of the six base substitutions. Proc Natl Acad Sci U S A. Jul. 1989;86(14):5345-9.

Czerwinski et al., Cytotoxic agents directed to peptide hormone receptors: defining the requirements for a successful drug. Proc Natl Acad Sci U S A. Sep. 29, 1998;95(20):11520-5.

D'adda di fagagna et al., The Gam protein of bacteriophage Mu is an orthologue of eukaryotic Ku. EMBO Rep. Jan. 2003;4(1):47-52.

Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.

Dahlgren et al., A novel mutation in ribosomal protein S4 that affects the function of a mutated RF1. Biochimie. Aug. 2000;82(8):683-91.

Dahlman et al., Orthogonal gene knockout and activation with a catalytically active Cas9 nuclease. Nat Biotechnol. Nov. 2015;33(11):1159-61. doi: 10.1038/nbt.3390.

Dang et al., Optimizing sgRNA structure to improve CRISPR-Cas9 knockout efficiency. Genome Biol. Dec. 15, 2015;16:280. doi: 10.1186/s13059-015-0846-3.

Daniels et al., Intrinsically cell-permeable miniature proteins based on a minimal cationic PPII motif. J Am Chem Soc. Nov. 28, 2007;129(47):14578-9. Epub Nov. 6, 2007.

Das et al., The crystal structure of the monomeric reverse transcriptase from Moloney murine leukemia virus. Structure. May 2004;12(5):819-29. doi: 10.1016/j.str.2004.02.032.

Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.

(56) References Cited

OTHER PUBLICATIONS

Dassa et al., Trans protein splicing of cyanobacterial split inteins in endogenous and exogenous combinations. Biochemistry. Jan. 9, 2007;46(1):322-30. doi: 10.1021/bi0611762.
Database EBI Accession No. ADE34233 Jan. 29, 2004.
Database EBI Accession No. BFF09785. May 31, 2018. 2 pages.
Database EBI Accession No. BGE38086. Jul. 25, 2019. 2 pages.
Database UniProt Accession No. G813E0. Jan. 14, 2012.
Datsenko et al., One-step inactivation of chromosomal genes in *Escherichia coli* K-12 using PCR products. Proc Natl Acad Sci U S A. Jun. 6, 2000;97(12):6640-5.
Davidson et al., Viral vectors for gene delivery to the nervous system. Nat Rev Neurosci. May 2003;4(5):353-64. doi: 10.1038/nrn1104.
Davis et al., DNA double strand break repair via non-homologous end-joining. Transl Cancer Res. Jun. 2013;2(3):130-143.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
De Felipe et al., Co-translational, intraribosomal cleavage of polypeptides by the foot-and- mouth disease virus 2A peptide. J Biol Chem. Mar. 28, 2003;278(13):11441-8. doi: 10.1074/jbc.M211644200. Epub Jan. 8, 2003.
De Souza, Primer: genome editing with engineered nucleases. Nat Methods. Jan. 2012;9(1):27.
De Wit et al., The Human CD4+ T Cell Response against Mumps Virus Targets a Broadly Recognized Nucleoprotein Epitope. J Virol. Mar. 5, 2019;93(6):e01883-18. doi: 10.1128/JVI.01883-18.
Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. Sep. 27, 1996;273(5283):1856-62. doi: 10.1126/science.273.5283.1856.
Dekosky et al., Large-scale sequence and structural comparisons of human naive and antigen-experienced antibody repertoires. Proc Natl Acad Sci U S A. May 10, 2016;113(19):E2636-45. doi: 10.1073/pnas.1525510113. Epub Apr. 25, 2016.
Delebecque et al., Organization of intracellular reactions with rationally designed RNA assemblies. Science. Jul. 22, 2011;333(6041):470-4. doi: 10.1126/science.1206938. Epub Jun. 23, 2011.
Deltcheva et al., CRISPR RNA maturation by trans-encoded small RNA and host factor RNase III. Nature. Mar. 31, 2011;471(7340):602-7. doi: 10.1038/nature09886.
Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.
Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dever et al., CRISPR/Cas9 ?—globin gene targeting in human haematopoietic stem cells. Nature. Nov. 17, 2016;539(7629):384-389. doi: 10.1038/nature20134. Epub Nov. 7, 2016.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Devigili et al., Paroxysmal itch caused by gain-of-function Nav1.7 mutation. Pain. Sep. 2014;155(9):1702-1707. doi: 10.1016/j.pain.2014.05.006. Epub May 10, 2014.
Dianov et al., Mammalian base excision repair: the forgotten archangel. Nucleic Acids Res. Apr. 1, 2013;41(6):3483-90. doi: 10.1093/nar/gkt076. Epub Feb. 13, 2013.
Dicarlo et al., Genome engineering in Saccharomyces cerevisiae using CRISPR-Cas systems. Nucleic Acids Research Apr. 2013;41(7):4336-43.

Dicarlo et al., Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.
Dickey et al., Single-stranded DNA-binding proteins: multiple domains for multiple functions. Structure. Jul. 2, 2013;21(7):1074-84. doi: 10.1016/j.str.2013.05.013.
Dickinson et al., Experimental interrogation of the path dependence and stochasticity of protein evolution using phage-assisted continuous evolution. Proc Natl Acad Sci USA. May 2013;110(22):9007-12.
Dillon, Regulating gene expression in gene therapy. Trends Biotechnol. May 1993;11(5):167-73. doi: 10.1016/0167-7799(93)90109-M.
Ding et al., A Talen genome-editing system for generating human stem cell-based disease models. Cell Stem Cell. Feb. 7, 2013;12(2):238-51. Doi: 10.1016/j.stem.2012.11.011. Epub Dec. 13, 2012.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Dingwall et al., Nuclear targeting sequences—a consensus? Trends Biochem Sci. Dec. 1991;16(12):478-81. doi: 10.1016/0968-0004(91)90184-w.
Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Doench et al., Optimized sgRNA design to maximize activity and minimize off-target effects of CRISPR-Cas9. Nat Biotechnol. Feb. 2016;34(2):184-191. doi: 10.1038/nbt.3437.
Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.
Doman et al., Evaluation and minimization of Cas9-independent off-target DNA editing by cytosine base editors. Nat Biotechnol. May 2020;38(5):620-628. doi: 10.1038/s41587-020-0414- 6. Epub Feb. 10, 2020.
Dominissini et al., Topology of the human and mouse m6A RNA methylomes revealed by m6A-seq. Nature. Apr. 29, 2012;485(7397):201-6. doi: 10.1038/nature11112.
Dorgan et al., An enzyme-coupled continuous spectrophotometric assay for S-adenosylmethionine-dependent methyltransferases. Anal Biochem. Mar. 15, 2006;350(2):249-55. doi: 10.1016/j.ab.2006.01.004. Epub Feb. 7, 2006.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.
Doudna et al., Genome editing. The new frontier of genome engineering with CRISPR-Cas9. Science. Nov. 28, 2014;346(6213):1258096. doi: 10.1126/science.1258096.
Dove et al., Conversion of the omega subunit of Escherichia coli RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.
Doyon et al., Heritable targeted gene disruption in zebrafish using designed zinc-finger nucleases. Nat Biotechnol. Jun. 2008;26(6):702-8. Doi: 10.1038/nbt1409. Epub May 2, 20085.
Drake, A constant rate of spontaneous mutation in DNA-based microbes. Proc Natl Acad Sci USA. Aug. 15, 1991;88(16):7160-4.

(56) References Cited

OTHER PUBLICATIONS

Dubois et al., Retroviral RNA Dimerization: From Structure to Functions. Front Microbiol. Mar. 22, 2018;9:527. doi: 10.3389/fmicb.2018.00527.

Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.

Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.

Dunbar et al., Gene therapy comes of age. Science. Jan. 12, 2018;359(6372):eaan4672. doi: 10.1126/science.aan4672.

Dupuy et al., Le syndrome de De La Chapelle [De La Chapelle syndrome]. Presse Med. Mar. 3, 2001;30(8):369-72. French.

Durai et al., A bacterial one-hybrid selection system for interrogating zinc finger-DNA interactions. Comb Chem High Throughput Screen. May 2006;9(4):301-11.

Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.

During et al., Controlled release of dopamine from a polymeric brain implant: in vivo characterization. Ann Neurol. Apr. 1989;25(4):351-6.

East-Seletsky et al., Two distinct RNase activities of CRISPR-C2c2 enable guide-RNA processing and RNA detection. Nature Oct. 2016;538(7624):270-3.

Edlund et al., Cell-specific expression of the rat insulin gene: evidence for role of two distinct 5' flanking elements. Science. Nov. 22, 1985;230(4728):912-6. doi: 10.1126/science.3904002.

Edwards et al., An *Escherichia coli* tyrosine transfer RNA is a leucine-specific transfer RNA in the yeast Saccharomyces cerevisiae. Proc Natl Acad Sci U S A. Feb. 15, 1991;88(4):1153-6.

Edwards et al., Crystal structures of the thi-box riboswitch bound to thiamine pyrophosphate analogs reveal adaptive RNA-small molecule recognition. Structure. Sep. 2006;14(9):1459-68.

Edwards et al., Structural basis for recognition of S-adenosylhomocysteine by riboswitches. RNA. Nov. 2010;16(11):2144-55. doi:10.1261/rna.2341610. Epub Sep. 23, 2010.

Eick et al., Robustness of Reconstructed Ancestral Protein Functions to Statistical Uncertainty. Mol Biol Evol. Feb. 1, 2017;34(2):247-261. doi: 10.1093/molbev/msw223.

Eiler et al., Structural Basis for the Fast Self-Cleavage Reaction Catalyzed by the Twister Ribozyme. Proc Natl Acad Sci U S A. Sep. 9, 2014;111(36):13028-33. doi: 10.1073/pnas.1414571111. Epub Aug. 25, 2014.

Ellington et al., In vitro selection of RNA molecules that bind specific ligands. Nature. Aug. 30, 1990;346(6287):818-22.

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

Emery et al., HCN2 ion channels play a central role in inflammatory and neuropathic pain. Science. Sep. 9, 2011;333(6048):1462-6. doi: 10.1126/science.1206243.

Endo et al., Toward establishing an efficient and versatile gene targeting system in higher plants. Biocatalysis and Agricultural Biotechnology 2014;3,(1):2-6.

Engel et al., The emerging role of mRNA methylation in normal and pathological behavior. Genes Brain Behav. Mar. 2018;17(3):e12428. doi: 10.1111/gbb.12428. Epub Nov. 17, 2017.

Engelward et al., Base excision repair deficient mice lacking the Aag alkyladenine DNA glycosylase. Proc Natl Acad Sci U S A. Nov. 25, 1997;94(24):13087-92.

England, Unnatural amino acid mutagenesis: a precise tool for probing protein structure and function. Biochemistry. Sep. 21, 2004;43(37):11623-9.

Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.

Epstein, HSV-1-based amplicon vectors: design and applications. Gene Ther. Oct. 2005;12 Suppl 1:S154-8. doi: 10.1038/sj.gt.3302617.

Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.

Esvelt et al., A system for the continuous directed evolution of biomolecules. Nature. Apr. 28, 2011;472(7344):499-503. doi: 10.1038/nature09929. Epub Apr. 10, 2011.

Esvelt et al., Genome-scale engineering for systems and synthetic biology. Mol Syst Biol. 2013;9:641. doi: 10.1038/msb.2012.66.

Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.

Evans et al., Protein trans-splicing and cyclization by a naturally split intein from the dnaE gene of *Synechocystis* species PCC6803. J Biol Chem. Mar. 31, 2000;275(13):9091-4. doi: 10.1074/jbc.275.13.9091.

Evans et al., Semisynthesis of cytotoxic proteins using a modified protein splicing element. Protein Sci. Nov. 1998;7(11):2256-64. doi: 10.1002/pro.5560071103.

Evans et al., The cyclization and polymerization of bacterially expressed proteins using modified self-splicing inteins. J Biol Chem. Jun. 25, 1999;274(26): 18359-63. doi: 10.1074/jbc.274.26.18359.

Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.

Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.

Extended European Search Report for EP 15830407.1, mailed Mar. 2, 2018.

Extended European Search Report for EP 19181479.7, mailed Oct. 31, 2019.

Extended European Search Report for EP 19187331.4, mailed Mar. 25, 2020.

Extended European Search Report for EP18199195.1, mailed Feb. 12, 2019.

Fagerlund et al., The Cpf1 CRISPR-Cas protein expands genome-editing tools. Genome Biology Nov. 17, 2015;16:251. https://doi.org/10.1186/s13059-015-0824-9.

Falnes et al., DNA repair by bacterial AlkB proteins. Res Microbiol. Oct. 2003;154(8):531-8. doi: 10.1016/S0923-2508(03)00150-5.

Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.

Fang et al., Synthetic Studies Towards Halichondrins: Synthesis of the Left Halves of Norhalichondrins and Homohalichondrins. Tetrahedron Letters 1992;33(12):1557-1560.

Farboud et al., Dramatic enhancement of genome editing by CRISPR/Cas9 through improved guide RNA design. Genetics. Apr. 2015;199(4):959-71. doi: 10.1534/genetics.115.175166. Epub Feb. 18, 2015.

Farhood et al., Codelivery to mammalian cells of a transcriptional factor with cis-acting element using cationic liposomes. Anal Biochem. Feb. 10, 1995;225(1):89-93.

Fawcett et al., Transposable elements controlling I-R hybrid dysgenesis in D. melanogaster are similar to mammalian LINEs. Cell. Dec. 26, 1986;47(6):1007-15. doi: 10.1016/0092-8674(86)90815-9.

Feldstein et al., Two sequences participating in the autolytic processing of satellite tobacco ringspot virus complementary RNA. Gene. Oct. 15, 1989;82(1):53-61. doi: 10.1016/0378-1119(89)90029-2.

Felletti et al., Twister Ribozymes as Highly Versatile Expression Platforms for Artificial Riboswitches. Nat Commun. Sep. 27, 2016;7:12834. doi: 10.1038/ncomms12834.

(56) References Cited

OTHER PUBLICATIONS

Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.
Feng et al., Human L1 retrotransposon encodes a conserved endonuclease required for retrotransposition. Cell. Nov. 29, 1996;87(5):905-16. doi: 10.1016/s0092-8674(00)81997-2.
Ferretti et al., Complete genome sequence of an M1 strain of Streptococcus pyogenes. Proc Natl Acad Sci U S A. Apr. 10, 2001;98(8):4658-63.
Ferry et al., Rational design of inducible CRISPR guide RNAs for de novo assembly of transcriptional programs. Nat Commun. Mar. 3, 2017;8:14633. doi: 10.1038/ncomms14633.
Feuk, Inversion variants in the human genome: role in disease and genome architecture. Genome Med. Feb. 12, 2010;2(2):11. doi: 10.1186/gm132.
Filippov et al., A novel type of RNase III family proteins in eukaryotes. Gene. Mar. 7, 2000;245(1):213-21. doi: 10.1016/s0378-1119(99)00571-5.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fire et al., Potent and specific genetic interference by double-stranded RNA in Caenorhabditis elegans. Nature. Feb. 19, 1998;391(6669):806-11. doi: 10.1038/35888.
Fischbach et al., Directed evolution can rapidly improve the activity of chimeric assembly- line enzymes. Proc Natl Acad Sci U S A. Jul. 17, 2007;104(29):11951-6. doi: 10.1073/pnas.0705348104. Epub Jul. 9, 2007.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fitzjohn, Diversitree: comparative phylogenetic analyses of diversification in R. Methods in Evology and Evolution. Dec. 2012;3(6):1084-92 .doi: 10.1111/j.2041-210X.2012.00234.x.
Flajolet et al., Woodchuck hepatitis virus enhancer I and enhancer II are both involved in N- myc2 activation in woodchuck liver tumors. J Virol. Jul. 1998;72(7):6175-80. doi: 10.1128/JVI.72.7.6175-6180.1998.
Flaman et al., A rapid PCR fidelity assay. Nucleic Acids Res. Aug. 11, 1994;22(15):3259-60. doi: 10.1093/nar/22.15.3259.
Flynn et al., CRISPR-mediated genotypic and phenotypic correction of a chronic granulomatous disease mutation in human iPS cells. Exp Hematol. Oct. 2015;43(10):838-848.e3. doi: 10.1016/j.exphem.2015.06.002. Epub Jun. 19, 2015. Including supplementary figures and data.
Fogg et al., New applications for phage integrases. J Mol Biol. Jul. 29, 2014;426(15):2703-16. doi: 10.1016/j.jmb.2014.05.014. Epub May 22, 2014.
Fogg et al., Genome Integration and Excision by a New Streptomyces Bacteriophage, ?Joe. Appl Environ Microbiol. Feb. 15, 2017;83(5):e02767-16. doi: 10.1128/AEM.02767-16.
Fonfara et al., Phylogeny of Cas9 determines functional exchange-ability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Fonfara et al., Phylogeny of Cas9 determines functional exchange-ability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Including Supplementary Information.
Forster et al., Self-cleavage of virusoid RNA is performed by the proposed 55-nucleotide active site. Cell. Jul. 3, 1987;50(1):9-16. doi: 10.1016/0092-8674(87)90657-x.
Fortini et al., Different DNA polymerases are involved in the short- and long-patch base excision repair in mammalian cells. Biochemistry. Mar. 17, 1998;37(11):3575-80. doi: 10.1021/bi972999h.

Fouts et al., Sequencing Bacillus anthracis typing phages gamma and cherry reveals a common ancestry. J Bacteriol. May 2006;188(9):3402-8. doi: 10.1128/JB.188.9.3402-3408.2006.
Freitas et al., Mechanisms and signals for the nuclear import of proteins. Curr Genomics. Dec. 2009;10(8):550-7. doi: 10.2174/138920209789503941.
Freshney, Culture of Animal Cells. A Manual of Basic Technique. Alan R. Liss, Inc. New York. 1983;4.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fu et al., Promises and Pitfalls of Intracellular Delivery of Proteins. Bioconjugate Chemistry. Aug. 2014;25:1602-8.
Fuchs et al., Polyarginine as a multifunctional fusion tag. Protein Sci. Jun. 2005;14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Furukawa et al., In vitro selection of allosteric ribozymes that sense the bacterial second messenger c-di-GMP. Methods Mol Biol. 2014;1111:209-20. doi: 10.1007/978-1-62703-755-6_15.
Fusi et al., In Silico Predictive Modeling of CRISPR/Cas9 guide efficiency. Jun. 26, 2015; bioRxiv. http://dx.doi.org/10.1101/021568.
Gabriel et al., An unbiased genome-wide analysis of zinc-finger nuclease specificity. Nat Biotechnol. Aug. 7, 2011;29(9):816-23. doi: 10.1038/nbt.1948.
Gaj et al., 3rd. Genome engineering with custom recombinases. Methods Enzymol. 2014;546:79-91. doi: 10.1016/B978-0-12-801185-0.00004-0.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gajula, Designing an Elusive CoG?GoC CRISPR Base Editor. Trends Biochem Sci. Feb. 2019;44(2):91-94. doi: 10.1016/j.tibs.2018.10.004. Epub Nov. 13, 2018.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gao et al., Cationic liposome-mediated gene transfer. Gene Ther. Dec. 1995;2(10):710-22.
Gao et al., Crystal structure of a TALE protein reveals an extended N-terminal DNA binding region. Cell Res. Dec. 2012;22(12):1716-20. doi: 10.1038/cr.2012.156. Epub Nov. 13, 2012.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.

(56) References Cited

OTHER PUBLICATIONS

Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.
Gao et al., Treatment of autosomal dominant hearing loss by in vivo delivery of genome editing agents. Nature. Jan. 11, 2018;553(7687):217-221. doi: 10.1038/nature25164. Epub Dec. 20, 2017.
Gapinske et al., CRISPR-SKIP: programmable gene splicing with single base editors. Genome Biol. Aug. 15, 2018;19(1):107. doi: 10.1186/s13059-018-1482-5.
Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.
Gardlik et al., Vectors and delivery systems in gene therapy. Med Sci Monit. Apr. 2005; 11(4):RA110-21. Epub Mar. 24, 2005.
Garibyan et al., Use of the rpoB gene to determine the specificity of base substitution mutations on the *Escherichia coli* chromosome. DNA Repair (Amst). May 12, 2003;2(5):593-608.
Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gaudelli et al., Programmable base editing of AoT to GoC in genomic DNA without DNA cleavage. Nature. Nov. 23, 2017;551(7681):464-471. doi: 10.1038/nature24644. Epub Oct. 25, 2017. Erratum in: Nature. May 2, 2018.
Gearing, Addgene blog. CRISPR 101: Cas9 nickase design and homology directed repair. 2018. pp. 1-12. https://blog.addgene.org/crispr-101-cas9-nickase-design-and-homlogy-directed-repair. Last retrieved online Jun. 25, 2021.
Gehrke et al., An APOBEC3A-Cas9 base editor with minimized bystander and off-target activities. Nat Biotechnol. Nov. 2018;36(10):977-982. doi: 10.1038/nbt.4199. Epub Jul. 30, 2018.
GenBank Accession No. J01600.1. Brooks et al., *E.coli* dam gene coding for DNA adenine methylase. Apr. 26, 1993.
GenBank Accession No. U07651.1. Lu, *Escherichia coli* K12 negative regulator of replication initiation (seqA) gene, complete cds. Jul. 19, 1994.
GenBank Submission; NIH/NCBI Accession No. NM_001319224.2. Umar et al., Apr. 21, 2021. 7 pages.
GenBank Submission; NIH/NCBI Accession No. NM_006027.4. Umar et al., Apr. 10, 2021. 7 pages. GENBANK Submission; NIH/NCBI, Accession No. AAA66622.1. Martinelli et al., May 18, 1995. 2 pages. GenBank Submission; NIH/NCBI, Accession No. AGT42196. Farzadfar et al., Nov. 2, 2013. 2 pages.
GenBank Submission; NIH/NCBI, Accession No. AAA66622.1. Martinelli Ct 211., May 18, 1995. 2 pages.
GenBank Submission; NIH/NCBI, Accession No. AGT42196. Farzadfar et al., Nov. 2, 2013. 2 pages.
GenBank Submission; NIH/NCBI, Accession No. APG80656.1. Burstein et al., Dec. 10, 2016. 1 pages.
GenBank Submission; NIH/NCBI, Accession No. AYD60528.1. Ram et al., Oct. 2, 2018. 1 page.
GenBank Submission; NIH/NCBI, Accession No. BDB43378. Zhang et al., Aug. 11, 2016. 2 pages.
GenBank Submission; NIH/NCBI, Accession No. J04623. Kita et al., Apr. 26, 1993. 2 pages.
GenBank Submission; NIH/NCBI, Accession No. KR710351.1. Sahni et al., Jun. 1, 2015. 2 pages.
GenBank Submission; NIH/NCBI, Accession No. NC 002737.2. Nasser et al., Feb. 7, 2021. 2 pages.
GenBank Submission; NIH/NCBI, Accession No. NC_002737.1. Ferretti et al., Jun. 27, 2013. page.
GenBank Submission; NIH/NCBI, Accession No. NC_015683.1. Trost et al., Jul. 6, 2013. 1 page.
GenBank Submission; NIH/NCBI, Accession No. NC_016782.1. Trost et al., Jun. 11, 2013. 1 page.
GenBank Submission; NIH/NCBI, Accession No. NC_016786.1. Trost et al., Aug. 28, 2013. 1 page.
GenBank Submission; NIH/NCBI, Accession No. NC_017053.1. Fittipaldi et al., Jul. 6, 2013. 1 page.
GenBank Submission; NIH/NCBI, Accession No. NC_017317.1. Trost et al., Jun. 11, 2013. 1 page.
GenBank Submission; NIH/NCBI, Accession No. NC_017861.1. Heidelberg et al., Jun. 11, 2013. 1 page.
GenBank Submission; NIH/NCBI, Accession No. NC_018010.1. Lucas et al., Jun. 11, 2013. 2 pages.
GenBank Submission; NIH/NCBI, Accession No. NC_018721.1. Feng et al., Jun. 11, 2013. 1 pages.
GenBank Submission; NIH/NCBI, Accession No. NC_021284.1. Ku et al., Jul. 12, 2013. 1 page.
GenBank Submission; NIH/NCBI, Accession No. NC_021314.1. Zhang et al., Jul. 15, 2013. 1 page.
GenBank Submission; NIH/NCBI, Accession No. NC_021846.1. Lo et al., Jul. 22, 2013. 1 page.
GenBank Submission; NIH/NCBI, Accession No. NM_000311.5. Alves et al., Mar. 7, 2021. 5 pages.
GenBank Submission; NIH/NCBI, Accession No. NM_001319224. Umar et al., Apr. 21, 2021. 7 pages.
GenBank Submission; NIH/NCBI, Accession No. NM_002945.3. Weiser et al., Sep. 3, 2017. 5 pages.
GenBank Submission; NIH/NCBI, Accession No. NM_003686. Umar et al., Apr. 9, 2021. 7 pages.
GenBank Submission; NIH/NCBI, Accession No. NM_003686.4. Umar et al., Apr. 9, 2021. 7 pages.
GenBank Submission; NIH/NCBI, Accession No. NM_006027. Umar et al., Apr. 10, 2021. 7 pages.
GenBank Submission; NIH/NCBI, Accession No. NM_174936. Guo et al., Oct. 28, 2015. 6 pages.
GenBank Submission; NIH/NCBI, Accession No. NP_000302.1. Alves et al., Mar. 7, 2021. 4 pages.
GenBank Submission; NIH/NCBI, Accession No. NP_358988.1. Hoskins et al., Jan. 11, 2017. 2 pages.
GenBank Submission; NIH/NCBI, Accession No. NP_472073.1. Glaser et al., Jun. 27, 2013. 2 pages.
GenBank Submission; NIH/NCBI, Accession No. NP_628093.1. Hsiao et al., Aug. 3, 2016. 2 pages.
GenBank Submission; NIH/NCBI, Accession No. NP_955579.1. Chen et al., Aug. 13, 2018. 5 pages.
GenBank Submission; NIH/NCBI, Accession No. P42212. Prasher et al., Mar. 19, 2014. 7 pages.
GenBank Submission; NIH/NCBI, Accession No. QBJ66766. Duan et al. Aug. 12, 2020. 2 pages.
GenBank Submission; NIH/NCBI, Accession No. RFF81513.1. Zhou et al., Aug. 21, 2018. 2 pages.
GenBank Submission; NIH/NCBI, Accession No. SNX31424.1. Weckx, S., Feb. 16, 2018. 2 pages.
GenBank Submission; NIH/NCBI, Accession No. TGH57013. Xu et al., Apr. 9, 2019. 2 pages.
GenBank Submission; NIH/NCBI, Accession No. WP_016631044.1. Haft et al., Sep. 22, 2020. 1 page.
GenBank Submission; NIH/NCBI, Accession No. WP_031386437. No Author Listed., Sep. 23, 2019. 1 page.
GenBank Submission; NIH/NCBI, Accession No. WP_031589969.1. Haft et al., Oct. 9, 2019. 2 pages.
GenBank Submission; NIH/NCBI, Accession No. WP_044924278.1. Haft et al., Oct. 9, 2019. 2 pages.
GenBank Submission; NIH/NCBI, Accession No. WP_047338501.1. Haft et al., Oct. 9, 2019. 2 pages.
GenBank Submission; NIH/NCBI, Accession No. WP_060798984.1. Haft et al., Oct. 9, 2019. 2 pages.
GenBank Submission; NIH/NCBI, Accession No. WP_062913273.1. Haft et al., Oct. 9, 2019, 2 pages.

(56) References Cited

OTHER PUBLICATIONS

GenBank Submission; NIH/NCBI, Accession No. WP_072754838. No Author Listed., Sep. 23, 2019. 1 page.
GenBank Submission; NIH/NCBI, Accession No. WP_095142515. 1. No Author Listed., Sep. 23, 2019. 1 page.
GenBank Submission; NIH/NCBI, Accession No. WP_118538418. 1. No Author Listed., Oct. 13, 2019. 1 page.
GenBank Submission; NIH/NCBI, Accession No. WP_119223642. 1. No Author Listed., Oct. 13, 2019. 1 page.
GenBank Submission; NIH/NCBI, Accession No. WP_119227726. 1. No Author Listed., Oct. 13, 2019. 1 page.
GenBank Submission; NIH/NCBI, Accession No. WP_119623382. 1. No Author Listed., Oct. 13, 2019. 1 page.
GenBank Submission; NIH/NCBI, Accession No. WP_132221894. 1. No Author Listed., Sep. 23, 2019. 1 page.
GenBank Submission; NIH/NCBI, Accession No. WP_133478044. 1. Haft et al., Oct. 9, 2019. 2 pages.
GenBank Submission; NIH/NCBI, Accession No. YP_002342100. 1. Bernardini et al., Jun. 10, 2013. 2 pages.
GenBank Submission; NIH/NCBI, Accession No. YP_002344900. 1. Gundogdu et al., Mar. 19, 2014. 2 pages.
GenBank Submission; NIH/NCBI, Accession No. YP_009137104. 1. Davison, Aug. 13, 2018. 2 pages.
GenBank Submission; NIH/NCBI, Accession No. YP_009283008. 1. Bernardini et al., Sep. 23, 2016. 2 pages.
GenBank Submission; NIH/NCBI, Accession No. YP_820832.1. Makarova et al., Aug. 27, 2013. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.
Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.
Gerard et al., The role of template-primer in protection of reverse transcriptase from thermal inactivation. Nucleic Acids Res. Jul. 15, 2002;30(14):3118-29. doi: 10.1093/nar/gkf417.
Gerber et al., An adenosine deaminase that generates inosine at the wobble position of tRNAs. Science. Nov. 5, 1999;286(5442):1146-9. doi: 10.1126/science.286.5442.1146.
Gerber et al., RNA editing by base deamination: more enzymes, more targets, new mysteries. Trends Biochem Sci. Jun. 2001;26(6):376-84.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.
Ghahfarokhi et al., Blastocyst Formation Rate and Transgene Expression are Associated with Gene Insertion into Safe and Non-Safe Harbors in the Cattle Genome. Sci Rep. Nov. 13, 20173;7(1):15432. doi: 10.1038/s41598-017-15648-3.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Glasgow et al., DNA-binding properties of the Hin recombinase. J Biol Chem. Jun. 15, 1989;264(17):10072-82.
Glassner et al., Generation of a strong mutator phenotype in yeast by imbalanced base excision repair. Proc Natl Acad Sci U S A. Aug. 18, 1998;95(17):9997-10002.
Goldberg et al., Epigenetics: a landscape takes shape. Cell. Feb. 23, 2007;128(4):635-8. doi: 10.1016/j.cell.2007.02.006.
Goldberg et al., Loss-of-function mutations in the Nav1.7 gene underlie congenital indifference to pain in multiple human populations. Clin Genet. Apr. 2007;71(4):311-9. doi: 10.1111/j.1399-0004.2007.00790.x.
Gong et al., Active DNA demethylation by oxidation and repair. Cell Res. Dec. 2011;21(12):1649-51. doi: 10.1038/cr.2011.140. Epub Aug. 23, 2011.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.
Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Grainge et al., The integrase family of recombinase: organization and function of the active site. Mol Microbiol. Aug. 1999;33(3):449-56.
Gregory et al., Integration site for Streptomyces phage phiBT1 and development of site- specific integrating vectors. J Bacteriol. Sep. 2003;185(17):5320-3. doi: 10.1128/jb.185.17.5320-5323.2003.
Griffiths, Endogenous retroviruses in the human genome sequence. Genome Biol. 2001;2(6):Reviews1017. doi: 10.1186/GB-2001-2-6-reviews1017. Epub Jun. 5, 2001.
Grindley et al., Mechanisms of site-specific recombination. Annu Rev Biochem. 2006;75:567-605. doi: 10.1146/annurev.biochem.73.011303.073908.
Grishok et al., Genes and Mechanisms Related to RNA Interference Regulate Expression of the Small Temporal RNAs that Control *C. elegans* Developmental Timing. Jul. 13, 2001:106(1):P23-4.
Groth et al., Construction of transgenic Drosophila by using the site-specific integrase from phage phiC31. Genetics. Apr. 2004; 166(4): 1775-82. doi: 10.1534/genetics.166.4.1775.
Groth et al., Phage integrases: biology and applications. J Mol Biol. Jan. 16, 2004;335(3):667-78.
Gruber et al., Strategies for measuring evolutionary conservation of RNA secondary structures. BMC Bioinformatics. Feb. 26, 2008;9:122. doi: 10.1186/1471-2105-9-122.
Gruber et al., The Vienna RNA websuite. Nucleic Acids Res. Jul. 1, 2008;36(Web Server issue): W70-4. doi: 10.1093/nar/gkn188. Epub Apr. 19, 2008.
Grundy et al., The L box regulon: lysine sensing by leader RNAs of bacterial lysine biosynthesis genes. Proc Natl Acad Sci U S A. Oct. 14, 2003;100(21):12057-62. Epub Oct. 2003.
Grunebaum et al., Recent advances in understanding and managing adenosine deaminase and purine nucleoside phosphorylase deficiencies. Curr Opin Allergy Clin Immunol. Dec. 2013; 13(6):630-8. doi: 10.1097/ACI.0000000000000006.
Grünewald et al., Transcriptome-wide off-target RNA editing induced by CRISPR-guided DNA base editors. Nature. May 2019;569(7756):433-437. doi: 10.1038/s41586-019-1161-z. Epub Apr. 1, 20197.
Guilinger et al., Broad specificity profiling of TALENs results in engineered nucleases with improved DNA-cleavage specificity. Nat Methods. Apr. 2014; 11(4):429-35. doi: 10.1038/nmeth.2845. Epub Feb. 16, 2014.

(56) References Cited

OTHER PUBLICATIONS

Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Gumulya et al., Exploring the past and the future of protein evolution with ancestral sequence reconstruction: the 'retro' approach to protein engineering. Biochem J. Jan. 1, 2017;474(1):1-19. doi: 10.1042/BCJ20160507.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Guo et al., Facile functionalization of FK506 for biological studies by the thiol-ene 'click' reaction. RSC Advances. 2014;22:11400-3.
Guo et al., Protein tolerance to random amino acid change. Proc Natl Acad Sci U S A. Jun. 22, 2004;101(25):9205-10. Epub Jun. 14, 2004.
Guo et al., Structure of Cre recombinase complexed with DNA in a site-specific recombination synapse. Nature. Sep. 4, 1997;389(6646):40-6.
Gupta et al., Cross-talk between cognate and noncognate RpoE sigma factors and Zn(2+)-binding anti-sigma factors regulates photooxidative stress response in Azospirillum brasilense. Antioxid Redox Signal. Jan. 1, 2014;20(1):42-59. doi: 10.1089/ars.2013.5314. Epub Jul. 19, 2013.
Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.
Gupta et al., Zinc finger protein-dependent and -independent contributions to the in vivo off-target activity of zinc finger nucleases. Nucleic Acids Res. Jan. 2011;39(1):381-92. doi: 10.1093/nar/gkq787. Epub Sep. 14, 2010.
Guzman et al., Tight regulation, modulation, and high-level expression by vectors containing the arabinose PBAD promoter. J Bacteriol. 1995;177(14):4121-4130.
Haapaniemi et al., CRISPR-Cas9 genome editing induces a p53-mediated DNA damage response. Nat Med. Jul. 2018;24(7):927-930. doi: 10.1038/s41591-018-0049-z. Epub Jun. 11, 2018.
Haddada et al., Gene therapy using adenovirus vectors. Curr Top Microbiol Immunol. 1995;199 ( Pt 3):297-306. doi: 10.1007/978-3-642-79586-2_14.
Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.
Hale et al., RNA-guided RNA cleavage by a CRISPR RNA-Cas protein complex. Cell. Nov. 25, 2009;139(5):945-56. doi: 10.1016/j.cell.2009.07.040.
Halmai et al., Targeted CRIPSR/dCas9-mediated reactivation of epigenetically silenced genes suggests limited escape from the inactive X chromosome. 2nd Intl Conf on Epigenetics and Bioengineering. Oct. 4, 2018; Retrieved from the Internet: https://aiche.confex.com/aiche/epibiol8/webprogram/paper544785.html. Retrieved Jun. 29, 2020.
Halperin et al., CRISPR-guided DNA polymerases enable diversification of all nucleotides in a tunable window. Nature. Aug. 2018;560(7717):248-252. doi: 10.1038/s41586-018-0384-8. Epub Aug. 1, 2018.
Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.
Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.
Hampel et al., Evidence for preorganization of the glmS ribozyme ligand binding pocket. Biochemistry. 2006; 45(25):7861-71.

Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Handa et al., Template-assisted synthesis of adenine-mutagenized cDNA by a retroelement protein complex. Nucleic Acids Res. Oct. 12, 2018;46(18):9711-9725. doi: 10.1093/nar/gky620.
Hanson et al., Codon optimality, bias and usage in translation and mRNA decay. Nat Rev Mol Cell Biol. Jan. 2018; 19(1):20-30. doi: 10.1038/nrm.2017.91. Epub Oct. 11, 2017.
Harms et al., Evolutionary biochemistry: revealing the historical and physical causes of protein properties. Nat Rev Genet. Aug. 2013;14(8):559-71. doi: 10.1038/nrg3540.
Harrington et al., A thermostable Cas9 with increased lifetime in human plasma. Nat Commun. Nov. 10, 2017;8(1):1424. doi: 10.1038/s41467-017-01408-4.
Harrington et al., A thermostable Cas9 with increased lifetime in human plasma. Nat Commun. Nov. 10, 2017;8(1):1424. doi: 10.1038/s41467-017-01408-4. Posted May 16, 2017 as bioRxiv preprint. Doi.org/10.1101/138867.
Harris et al., RNA Editing Enzyme APOBEC1 and Some of Its Homologs Can Act as DNA Mutators. Mol Cell. Nov. 2002; 10(5):1247-53.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hartung et al., Cre mutants with altered DNA binding properties. J Biol Chem. Sep. 4, 1998;273(36):22884-91.
Hasadsri et al., Functional protein delivery into neurons using polymeric nanoparticles. J Biol Chem. Mar. 1, 20093;284(11):6972-81. doi: 10.1074/jbc.M805956200. Epub Jan. 7, 2009.
Hasegawa et al., Spontaneous mutagenesis associated with nucleotide excision repair in *Escherichia coli*. Genes Cells. May 2008;13(5):459-69. doi: 10.1111/j.1365-2443.2008.01185.x.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Hector et al., CDKL5 variants: Improving our understanding of a rare neurologic disorder. Neurol Genet. Dec. 15, 2017;3(6):e200. doi: 10.1212/NXG.0000000000000200.
Heidenreich et al., Non-homologous end joining as an important mutagenic process in cell cycle-arrested cells. Embo J. May 1, 2003;22(9):2274-83. doi: 10.1093/emboj/cdg203.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Held et al., In vivo correction of murine hereditary tyrosinemia type I by phiC31 integrase- mediated gene delivery. Mol Ther. Mar. 2005;11(3):399-408. doi: 10.1016/j.ymthe.2004.11.001.
Heller et al., Replisome assembly and the direct restart of stalled replication forks. Nat Rev Mol Cell Biol. Dec. 2006;7(12):932-43. Epub Nov. 8, 2006.
Hendricks et al., The S. cerevisiae Mag1 3-methyladenine DNA glycosylase modulates susceptibility to homologous recombination. DNA Repair (Amst). 2002;1(8):645-659.
Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.
Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.

(56) References Cited

OTHER PUBLICATIONS

Hida et al., Directed evolution for drug and nucleic acid; delivery. Adv Drug Deliv Rev. Dec. 22, 2007;59(15):1562-78. Epub Aug. 28, 2007.; Review.
Higgs et al., Genetic complexity in sickle cell disease. Proc Natl Acad Sci U S A. Aug. 19, 2008;105(33):11595-6. doi: 10.1073/pnas.0806633105. Epub Aug. 11, 2008.
Hill et al., Functional analysis of conserved histidines in ADP-glucose pyrophosphorylase from *Escherichia coli*.Biochem Biophys Res Commun. Mar. 17, 1998;244(2):573-7.
Hille et al., The Biology of CRISPR-Cas: Backward and Forward. Cell. Mar. 8, 2018;172(6):1239-1259. doi: 10.1016/j.cell.2017.11.032.
Hilton et al., Enabling functional genomics with genome engineering. Genome Res. Oct. 2015;25(10):1442-55. doi: 10.1101/gr.190124.115.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.
Hirano et al., Structural Basis for the Altered PAM Specificities of Engineered CRISPR-Cas9. Mol Cell. Mar. 17, 2016;61(6):886-94. doi: 10.1016/j.molcel.2016.02.018.
Hoang et al., UFBoot2: Improving the Ultrafast Bootstrap Approximation. Mol Biol Evol. Feb. 1, 2018;35(2):518-522. doi: 10.1093/molbev/msx281.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Hoernes et al., Translating the epitranscriptome. Wiley Interdiscip Rev RNA. Jan. 2017;8(1):e1375. doi: 10.1002/wrna.1375. Epub Jun. 27, 2016.
Hoess et al., DNA specificity of the Cre recombinase resides in the 25 kDa carboxyl domain of the protein. J Mol Biol. Dec. 20, 1990;216(4):873-82. doi: 10.1016/S0022-2836(99)80007-2.
Holden et al., Crystal structure of the anti-viral APOBEC3G catalytic domain and functional implications. Nature. Nov. 6, 2008;456(7218):121-4. doi: 10.1038/nature07357. Epub Oct. 2008.
Hollis et al., Phage integrases for the construction and manipulation of transgenic mammals. Reprod Biol Endocrinol. Nov. 7, 2003;1:79. doi: 10.1186/1477-7827-1-79.
Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.
Holt et al., Human hematopoietic stem/progenitor cells modified by zinc-finger nucleases targeted to CCR5 control HIV-1 in vivo. Nat Biotechnol. Aug. 2010;28(8):839-47. doi: 10.1038/nbt.1663. Epub Jul. 2, 2010.
Hondares et al., Peroxisome Proliferator-activated Receptor a (PPARa) Induces PPARY Coactivator 1a (PGC-1a) Gene Expression and Contributes to Thermogenic Activation of Brown Fat. J Biol. Chem Oct. 2011; 286(50):43112-22. doi: 10.1074/jbc.M111.252775.
Hoogenboom et al., Natural and designer binding sites made by phage display technology. Immunol Today. Aug. 2000;21(8):371-8.
Hope et al., Cationic lipids, phosphatidylethanolamine and the intracellular delivery of polymeric, nucleic acid-based drugs (review). Mol Membr Biol. Jan. 1998-Mar. 15(1):1-14.
Horvath et al., CRISPR/Cas, the immune system of bacteria and archaea. Science. Jan. 8, 2010;327(5962):167-70. doi: 10.1126/science.1179555.
Horvath et al., Diversity, Activity, and Evolution of CRISPR Loci in *Streptococcus thermophilus*. J Bacteriol. Feb. 2008;190(4):1401-12. doi: 10.1128/JB.01415-07. Epub Dec. 2007.
Hotta et al., [Neurotropic viruses—classification, structure and characteristics]. Nihon Rinsho. Apr. 1997;55(4):777-82. Japanese.
Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.
Houdebine, The methods to generate transgenic animals and to control transgene expression. Biotechnol. Sep. 25, 2002;98(2-3):145-60.
Housden et al., Identification of potential drug targets for tuberous sclerosis complex by synthetic screens combining CRISPR-based knockouts with RNAi. Sci Signal. Sep. 8, 2015;8(393):rs9. doi: 10.1126/scisignal.aab3729.
Howard et al., Intracerebral drug delivery in rats with lesion-induced memory deficits. J Neurosurg. Jul. 1989;71(1):105-12.
Hower et al., Shape-based peak identification for ChIP-Seq. BMC Bioinformatics. Jan. 12, 2011;12:15. doi: 10.1186/1471-2105-12-15.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.
Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.
Hu et al., Evolved Cas9 variants with broad PAM compatibility and high DNA specificity. Nature. Apr. 5, 2018;556(7699):57-63. doi: 10.1038/nature26155. Epub Feb. 28, 2018.
Huang et al., Circularly permuted and PAM-modified Cas9 variants broaden the targeting scope of base editors. Nat Biotechnol. Jun. 2019;37(6):626-631. doi: 10.1038/s41587-019-0134-y. Epub May 20, 2019. Including Supplementary Information.
Huang et al., Heritable gene targeting in zebrafish using customized TALENs. Nat Biotechnol. Aug. 5, 2011;29(8):699-700. doi: 10.1038/nbt.1939.
Huang et al., Long-range pseudoknot interactions dictate the regulatory response in the tetrahydrofolate riboswitch. Proc Natl Acad Sci U S A. Sep. 6, 2011;108(36):14801-6. doi: 10.1073/pnas.1111701108. Epub Aug. 22, 2011.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015.
Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.
Humbert et al., Targeted gene therapies: tools, applications, optimization. Crit Rev Biochem Mol Biol. May-Jun. 2012;47(3):264-81. doi: 10.3109/10409238.2012.658112.
Hung et al., Protein localization in disease and therapy. J Cell Sci. Oct. 15, 2011;124(Pt 20):3381-92. doi: 10.1242/jcs.089110.
Hurt et al., Highly specific zinc finger proteins obtained by directed domain shuffling and cell- based selection. Proc Natl Acad Sci U S A. Oct. 14, 2003;100(21):12271-6. Epub Oct. 3, 2003.
Husimi, Selection and evolution of bacteriophages in cellstat. Adv Biophys.; 1989;25:1-43. Review.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Hwang et al., Efficient In Vivo Genome Editing Using RNA-Guided Nucleases. Nat Biotechnol. Mar. 2013; 31(3):227-229. doi: 10.1038/nbt.2501. Epub Jan. 29, 2013.
Hwang et al., Web-based design and analysis tools for CRISPR base editing. BMC Bioinformatics. Dec. 27, 2018;19(1):542. doi: 10.1186/s12859-018-2585-4.
Händel et al., Expanding or restricting the target site repertoire of zinc-finger nucleases: the inter-domain linker as a major determinant of target site selectivity. Mol Ther. Jan. 2009;17(1):104-11. doi: 10.1038/mt.2008.233. Epub Nov. 11, 2008.
Ibba et al., Relaxing the substrate specificity of an aminoacyl-tRNA synthetase allows in vitro and in vivo synthesis of proteins containing unnatural amino acids. FEBS Lett. May 15, 1995;364(3):272-5.

(56) References Cited

OTHER PUBLICATIONS

Ibba et al., Substrate specificity is determined by amino acid binding pocket size in *Escherichia coli* phenylalanyl-tRNA synthetase. Biochemistry. Jun. 14, 1994;33(23):7107-12.

Ihry et al., p53 inhibits CRISPR-Cas9 engineering in human pluripotent stem cells. Nat Med. Jul. 2018;24(7):939-946. doi: 10.1038/s41591-018-0050-6. Epub Jun. 11, 2018.

Iida et al., A site-specific, conservative recombination system carried by bacteriophage P1. Mapping the recombinase gene cin and the cross-over sites cix for the inversion of the C segment. EMBO J. 1982;1(11):1445-53.

Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.

Ikediobi et al., Mutation analysis of 24 known cancer genes in the NCI-60 cell line set. Mol Cancer Ther. Nov. 2006;5(11):2606-12. Epub Nov. 6, 2006.

Imanishi et al., Detection of N6-methyladenosine based on the methyl-sensitivity of MazF RNA endonuclease. Chem Commun (Camb). Nov. 30, 2017;53(96):12930-12933. doi: 10.1039/c7cc07699a.

Imburgio et al., Studies of promoter recognition and start site selection by T7 RNA polymerase using a comprehensive collection of promoter variants. Biochemistry. Aug. 29, 2000;39(34):10419-30.

Ingram, A specific chemical difference between the globins of normal human and sickle-cell anaemia haemoglobin. Nature. Oct. 13, 1956;178(4537):792-4. doi: 10.1038/178792a0.

Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.

Irrthum et al., Congenital hereditary lymphedema caused by a mutation that inactivates VEGFR3 tyrosine kinase. Am J Hum Genet. Aug. 2000;67(2):295-301. Epub Jun. 9, 2000.

Ishino et al., Nucleotide sequence of the iap gene, responsible for alkaline phosphatase isozyme conversion in *Escherichia coli*, and identification of the gene product. J Bacteriol. Dec. 1987; 169(12):5429-33.

Iwai et al., Circular beta-lactamase: stability enhancement by cyclizing the backbone. FEBS Lett. Oct. 8, 1999;459(2):166-72. doi: 10.1016/s0014-5793(99)01220-x.

Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.

Jaffrey et al., Emerging links between m6A and misregulated mRNA methylation in cancer. Genome Med. Jan. 12, 2017;9(1):2. doi: 10.1186/s13073-016-0395-8.

Jamieson et al., Drug discovery with engineered zinc-finger proteins. Nat Rev Drug Discov. May 2003;2(5):361-8.

Jansen et al., Backbone and nucleobase contacts to glucosamine-6-phosphate in the glmS ribozyme. Nat Struct Mol Biol. Jun. 2006;13(6):517-23. Epub May 14, 2006.

Jansen et al., Identification of genes that are associated with DNA repeats in prokaryotes. Mol Microbiol. Mar. 2002;43(6):1565-75.

Jardine et al., HIV-1 Vaccines. Priming a broadly neutralizing antibody response to HIV-1 using a germline-targeting immunogen. Science. Jul. 10, 2015;349(6244):156-61. doi: 10.1126/science.aac5894. Epub Jun. 18, 2015.

Jasin et al., Repair of strand breaks by homologous recombination. Cold Spring Harb Perspect Biol. Nov. 1, 2013;5(11):a012740. doi: 10.1101/cshperspect.a012740.

Jeggo, DNA breakage and repair. Adv Genet. 1998;38:185-218. doi: 10.1016/s0065-2660(08)60144-3.

Jemielity et al., Novel "anti-reverse" cap analogs with superior translational properties. RNA. Sep. 2003;9(9):1108-22. doi: 10.1261/rna.5430403.

Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.

Jeong et al., Measurement of deoxyinosine adduct: Can it be a reliable tool to assess oxidative or nitrosative DNA damage? Toxicol Lett. Oct. 17, 2012;214(2):226-33. doi: 10.1016/j.toxlet.2012.08.013. Epub Aug. 23, 2012.

Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jiang et al., Structural Biology. A Cas9-guide RNA Complex Preorganized for Target DNA Recognition. Science. Jun. 26, 2015;348(6242):1477-81. doi: 10.1126/science.aab1452.

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Jiricny, The multifaceted mismatch-repair system. Nat Rev Mol Cell Biol. May 2006;7(5):335-46. doi: 10.1038/nrm1907.

Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.

Johansson et al., RNA Recognition by the MS2 Phage Coat Protein. Seminars in Virology. 1997;8(3):176-85. https://doi.org/10.1006/smvy.1997.0120.

Johansson et al., Selenocysteine in proteins-properties and biotechnological use. Biochim Biophys Acta. Oct. 30, 2005;1726(1):1-13. Epub Jun. 1, 2005.

Johns et al., The promise and peril of continuous in vitro evolution. J Mol Evol. Aug. 2005;61(2):253-63. Epub Jun. 7, 2005.

Joho et al., Identification of a region of the bacteriophage T3 and T7 RNA polymerases that determines promoter specificity. J Mol Biol. Sep. 5, 1990;215(1):31-9.

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.

Joung et al., TALENs: a widely applicable technology for targeted genome editing. Nat Rev Mol Cell Biol. Jan. 2013; 14(1):49-55. doi: 10.1038/nrm3486. Epub Nov. 21, 2012.

Joyce et al., Amplification, mutation and selection of catalytic RNA. Gene. Oct. 15, 1989;82(1):83-7. doi: 10.1016/0378-1119(89)90033-4.

Jyothy et al., Translocation Down syndrome. Indian J Med Sci. Mar. 2002;56(3):122-6.

Kacian et al., Purification of the DNA polymerase of avian myeloblastosis virus. Biochim Biophys Acta. Sep. 24, 1971;246(3):365-83. doi: 10.1016/0005-2787(71)90773-8.

Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.

Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.

Kahmann et al., G inversion in bacteriophage Mu DNA is stimulated by a site within the invertase gene and a host factor. Cell. Jul. 1985;41(3):771-80. doi: 10.1016/s0092-8674(85)80058-1.

Kaiser et al., Gene therapy. Putting the fingers on gene repair. Science. Dec. 23, 2005;310(5756):1894-6.

Kakiyama et al., A peptide release system using a photo-cleavable linker in a cell array format for cell-toxicity analysis. Polymer J. Feb. 27, 2013;45:535-9.

(56) References Cited

OTHER PUBLICATIONS

Kalyaanamoorthy et al., ModelFinder: fast model selection for accurate phylogenetic estimates. Nat Methods. Jun. 2017; 14(6):587-589. doi: 10.1038/nmeth.4285. Epub May 8, 2017.

Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.

Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

Kao et al., Cleavage specificity of Saccharomyces cerevisiae flap endonuclease 1 suggests a double-flap structure as the cellular substrate. J Biol Chem. Apr. 26, 2002;277(17):14379-89. doi: 10.1074/jbc.M110662200. Epub Feb. 1, 2002.

Kappel et al., Regulating gene expression in transgenic animals. Curr Opin Biotechnol. Oct. 1992;3(5):548-53.

Karimova et al., Discovery of Nigri/nox and Panto/pox site-specific recombinase systems facilitates advanced genome engineering. Sci Rep. Jul. 22, 2016;6:30130. doi: 10.1038/srep30130.

Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.

Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.

Karpinsky et al., Directed evolution of a recombinase that excises the provirus of most HIV-primary isolates with high specificity. Nat Biotechnol. Apr. 2016;34(4):401-9. doi: 10.1038/nbt.3467. Epub Feb. 22, 2016.

Katafuchi et al., DNA polymerases involved in the incorporation of oxidized nucleotides into DNA: their efficiency and template base preference. Mutat Res. Nov. 28, 2010;703(1):24-31. doi: 10.1016/j.mrgentox.2010.06.004. Epub Jun. 11, 2010.

Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.

Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.

Kaufman et al., Translational efficiency of polycistronic mRNAs and their utilization to express heterologous genes in mammalian cells. EMBO J. Jan. 1987;6(1):187-93.

Kavli et al., Excision of cytosine and thymine from DNA by mutants of human uracil-DNA glycosylase. EMBO J. Jul. 1, 1996;15(13):3442-7.

Kawarasaki et al., Enhanced crossover SCRATCHY: construction and high-throughput screening of a combinatorial library containing multiple non-homologous crossovers. Nucleic Acids Res. Nov. 1, 2003;31(21):e126.

Kay et al., Viral vectors for gene therapy: the art of turning infectious agents into vehicles of therapeutics. Nat Med. Jan. 2001;7(1):33-40.

Kaya et al., A bacterial Argonaute with noncanonical guide RNA specificity. Proc. Natl. Acad. Sci. USA Apr. 2016;113(15):4057-62.

Keijzers et al., Human exonuclease 1 (EXO1) activity characterization and its function on flap structures. Biosci Rep. Apr. 25, 2015;35(3):e00206. doi: 10.1042/BSR20150058.

Kellendonk et al., Regulation of Cre recombinase activity by the synthetic steroid RU 486. Nucleic Acids Res. Apr. 15, 1996;24(8):1404-11.

Kelman, PCNA: structure, functions and interactions. Oncogene. Feb. 13, 1997;14(6):629-40. doi: 10.1038/sj.onc.1200886.

Keravala et al., A diversity of serine phage integrases mediate site-specific recombination in mammalian cells. Mol Genet Genomics. Aug. 2006;276(2):135-46. doi: 10.1007/s00438-006-0129-5. Epub May 13, 2006.

Kessel et al., Murine developmental control genes. Science. Jul. 27, 1990;249(4967):374-9. doi: 10.1126/science.1974085.

Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.

Ketha et al., Application of bioinformatics-coupled experimental analysis reveals a new transport-competent nuclear localization signal in the nucleoprotein of Influenza A virus strain. BMC Cell Biol. Apr. 28, 2008; 9:22. https://doi.org/10.1186/1471-2121-9-22.

Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.

Kilbride et al., Determinants of product topology in a hybrid Cre-Tn3 resolvase site-specific recombination system. J Mol Biol. Jan. 13, 2006;355(2):185-95. Epub Nov. 9, 2005.

Kilcher et al., Brochothrix thermosphacta bacteriophages feature heterogeneous and highly mosaic genomes and utilize unique prophage insertion sites. J Bacteriol. Oct. 2010; 192(20):5441-53. doi: 10.1128/JB.00709-10. Epub Aug. 13, 2010.

Kim et al., DJ-1, a novel regulator of the tumor suppressor PTEN. Cancer Cell. 2005;7(3):263-273.

Kim et al., A library of TAL effector nucleases spanning the human genome. Nat Biotechnol. Mar. 2013;31(3):251-8. Doi: 10.1038/nbt.2517. Epub Feb. 17, 2013.

Kim et al., Genome-wide target specificities of CRISPR RNA-guided programmable deaminases. Nat Biotechnol. May 2017;35(5):475-480. doi: 10.1038/nbt.3852. Epub Apr. 10, 2017.

Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.

Kim et al., Highly efficient RNA-guided base editing in mouse embryos. Nat Biotechnol. May 2017;35(5):435-437. doi: 10.1038/nbt.3816. Epub Feb. 27, 2017.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Kim et al., Hybrid restriction enzymes: zinc finger fusions to Fok I cleavage domain. Proc Natl Acad Sci U S A. Feb. 6, 1996;93(3):1156-60.

Kim et al., In vivo genome editing with a small Cas9 orthologue derived from Campylobacter jejuni. Nat Commun. Feb. 21, 2017;8:14500. doi: 10.1038/ncomms14500. PMID: 28220790; PMCID: PMC5473640.

Kim et al., In vivo high-throughput profiling of CRISPR-Cpf1 activity. Nat Methods. Feb. 2017;14(2):153-159. doi: 10.1038/nmeth.4104. Epub Dec. 19, 2016.

Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.

Kim et al., Mycobacteriophage Bxb1 integrates into the *Mycobacterium smegmatis* groEL1 gene. Mol Microbiol. Oct. 2003;50(2):463-73. doi: 10.1046/j.1365-2958.2003.03723.x.

Kim et al., Rescue of high-specificity Cas9 variants using sgRNAs with matched 5' nucleotides. Genome Biol. Nov. 15, 2017;18(1):218. doi: 10.1186/s13059-017-1355-3.

Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.

Kim et al., TALENs and ZFNs are associated with different mutationsignatures. Nat Methods. Mar. 2013;10(3):185. doi: 10.1038/nmeth.2364. Epub Feb. 10, 2013.

(56) References Cited

OTHER PUBLICATIONS

Kim et al., Targeted genome editing in human cells with zinc finger nucleases constructed via modular assembly. Genome Res. Jul. 2009;19(7):1279-88. doi: 10.1101/gr.089417.108. Epub May 21, 2009.

Kim et al., The role of apolipoprotein E in Alzheimer's disease. Neuron. Aug. 13, 2009;63(3):287-303. doi: 10.1016/j.neuron.2009.06.026.

Kim et al., Transcriptional repression by zinc finger peptides. Exploring the potential for applications in gene therapy. J Biol Chem. Nov. 21, 1997;272(47):29795-800.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.

Klapacz et al., Frameshift mutagenesis and microsatellite instability induced by human alkyladenine DNA glycosylase. Mol Cell. Mar. 26, 2010;37(6):843-53. doi: 10.1016/j.molcel.2010.01.038.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Klein et al., Cocrystal structure of a class I preQ1 riboswitch reveals a pseudoknot recognizing an essential hypermodified nucleobase. Nat Struct Mol Biol. Mar. 2009; 16(3):343-4. doi: 10.1038/nsmb.1563.Epub Feb. 22, 2009.

Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.

Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.

Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

Kleinstiver et al., High-fidelity CRISPR-Cas9 nucleases with No. detectable genome-wide off-target effects. Nature. Jan. 28, 2016;529(7587):490-5. doi: 10.1038/nature16526. Epub Jan. 6, 2016.

Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.

Klement et al., Discrimination between bacteriophage T3 and T7 promoters by the T3 and T7 Rna polymerases depends primarily upon a three base-pair region located 10 to 12 base-pairs upstream from the start site. J Mol Biol. Sep. 5, 1990;215(1):21-9.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. EMBO J. Apr. 1988;7(4):1229-37.

Klompe et al., Transposon-encoded CRISPR-Cas systems direct RNA-guided DNA integration. Nature. Jul. 2019;571(7764):219-225. doi: 10.1038/s41586-019-1323-z. Epub Jun. 12, 2019.

Klug et al., Zinc fingers: a novel protein fold for nucleic acid recognition. Cold Spring Harb Symp Quant Biol. 1987;52:473-82.

Knott et al., Guide-bound structures of an RNA-targeting A-cleaving CRISPR-Cas13a enzyme. Nat Struct Mol Biol. Oct. 2017;24(10):825-833. doi: 10.1038/nsmb.3466. Epub Sep. 1, 20171.

Koblan et al., Improving cytidine and adenine base editors by expression optimization and ancestral reconstruction. Nat Biotechnol. Oct. 2018;36(9):843-846. doi: 10.1038/nbt.4172. Epub May 29, 2018.

Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 2017.

Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.

Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.

Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.

Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.

Kolot et al., Site-specific recombination in mammalian cells expressing the Int recombinase of bacteriophage HK022. Mol Biol Rep. Aug. 1999;26(3):207-13. doi: 10.1023/a:1007096701720.

Komor et al., CRISPR-Based Technologies for the Manipulation of Eukaryotic Genomes. Cell. Jan. 12, 2017;168(1-2):20-36. doi: 10.1016/j.cell.2016.10.044.

Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.

Komor et al., Programmable editing of a target base in genomic DNA without double-stranded DNA cleavage. Nature. Apr. 20, 2016;533(7603):420-4. doi: 10.1038/nature17946.

Komor, Editing the Genome Without Double-Stranded DNA Breaks. ACS Chem Biol. Feb. 16, 2018;13(2):383-388. doi: 10.1021/acschembio.7b00710. Epub Oct. 9, 2017.

Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.

Koonin et al., Diversity, classification and evolution of CRISPR-Cas systems. Curr Opin Microbiol. 2017;37:67?78. doi:10.1016/j.mib.2017.05.008.

Kosicki et al., Repair of double-strand breaks induced by CRISPR-Cas9 leads to large deletions and complex rearrangements. Nat Biotechnol. Sep. 2018;36(8):765-771. doi: 10.1038/nbt.4192. Epub Jul. 16, 2018.

Kotewicz et al., Cloning and overexpression of Moloney murine leukemia virus reverse transcriptase in *Escherichia coli*. Gene. 1985;35(3):249-58. doi: 10.1016/0378-1119(85)90003-4.

Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.

Kotin, Prospects for the use of adeno-associated virus as a vector for human gene therapy. Hum Gene Ther. Jul. 1994;5(7):793-801. doi: 10.1089/hum.1994.5.7-793.

Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.

Kowal et al., Exploiting unassigned codons in Micrococcus luteus for tRNA-based amino acid mutagenesis. Nucleic Acids Res. Nov. 15, 1997;25(22):4685-9.

Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.

Kozak, An analysis of 5'-noncoding sequences from 699 vertebrate messenger RNAs. Nucleic Acids Res. Oct. 26, 1987;15(20):8125-48. doi: 10.1093/nar/15.20.8125.

Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.

Kremer et al., Adenovirus and adeno-associated virus mediated gene transfer. Br Med Bull. Jan. 1995;51(1):31-44. doi: 10.1093/oxfordjournals.bmb.a072951.

Krishna et al., Structural classification of zinc fingers: survey and summary. Nucleic Acids Res. Jan. 15, 2003;31(2):532-50.

(56) References Cited

OTHER PUBLICATIONS

Krokan et al., Uracil in DNA—occurrence, consequences and repair. Oncogene. Dec. 16, 2002;21(58):8935-48. doi: 10.1038/sj.onc.1205996.

Krokan et al., Base excision repair. Cold Spring Harb Perspect Biol. Apr. 1, 2013;5(4):a012583. doi: 10.1101/cshperspect.a012583.

Krzywkowski et al., Limited reverse transcriptase activity of phi29 DNA polymerase. Nucleic Acids Res. Apr. 20, 2018;46(7):3625-3632. doi: 10.1093/nar/gky190.

Kumar et al., Structural and functional consequences of the mutation of a conserved arginine residue in alphaA and alphaB crystallins. J Biol Chem. Aug. 20, 1999;274(34):24137-41.

Kundu et al., Leucine to proline substitution by SNP at position 197 in Caspase-9 gene expression leads to neuroblastoma: a bioinformatics analysis. 3 Biotech. 2013; 3:225-34.

Kunkel et al., Eukaryotic Mismatch Repair in Relation to DNA Replication. Annu Rev Genet. 2015;49:291-313. doi: 10.1146/annurev-genet-112414-054722.

Kunz et al., DNA Repair in mammalian cells: Mismatched repair: variations on a theme. Cell Mol Life Sci. Mar. 2009;66(6):1021-38. doi: 10.1007/s00018-009-8739-9.

Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.

Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.

Kuscu et al., CRISPR-Cas9-AID base editor is a powerful gain-of-function screening tool. Nat Methods. Nov. 29, 2016;13(12):983-984. doi: 10.1038/nmeth.4076.

Kuscu et al., CRISPR-STOP: gene silencing through base-editing-induced nonsense mutations. Nat Methods. Jul. 2017; 14(7):710-712. doi: 10.1038/nmeth.4327. Epub Jun. 5, 2017.

Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.

Kwart et al., Precise and efficient scarless genome editing in stem cells using CORRECT. Nat Protoc. Feb. 2017; 12(2):329-354. doi: 10.1038/nprot.2016.171. Epub Jan. 19, 2017.

Kweon et al., Fusion guide RNAs for orthogonal gene manipulation with Cas9 and Cpf1. Nat Commun. Nov. 23, 2017;8(1):1723. doi: 10.1038/s41467-017-01650-w. Erratum in: Nat Commun. Jan. 16, 2018;9(1):303.

Kwon et al., Chemical basis of glycine riboswitch cooperativity. RNA. Jan. 2008;14(1):25-34. Epub Nov. 27, 2007.

Köhrer et al., A possible approach to site-specific insertion of two different unnatural amino acids into proteins in mammalian cells via nonsense suppression. Chem Biol. Nov. 2003;10(11):1095-102.

Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.

Kügler et al., Human synapsin 1 gene promoter confers highly neuron-specific long-term transgene expression from an adenoviral vector in the adult rat brain depending on the transduced area. Gene Ther. Feb. 2003; 10(4):337-47. doi: 10.1038/sj.gt.3301905.

Lada et al., Mutator effects and mutation signatures of editing deaminases produced in bacteria and yeast. Biochemistry (Mosc). Jan. 2011;76(1):131-46.

Lakich et al., Inversions disrupting the factor VIII gene are a common cause of severe haemophilia A. Nat Genet. Nov. 1993;5(3):236-41. doi: 10.1038/ng1193-236.

Lancaster et al., Limited trafficking of a neurotropic virus through inefficient retrograde axonal transport and the type I interferon response. PLoS Pathog. Mar. 5, 2010;6(3):e1000791. doi: 10.1371/journal.ppat.1000791.

Landrum et al., Clin Var: public archive of interpretations of clinically relevant variants. Nucleic Acids Res. Jan. 4, 2016;44(D1):D862-8. doi: 10.1093/nar/gkv1222. Epub Nov. 17, 2015.

Landrum et al., ClinVar: public archive of relationships among sequence variation and human phenotype. Nucleic Acids Res. Jan. 2014;42(Database issue): D980-5. doi: 10.1093/nar/gkt1113. Epub Nov. 14, 2013.

Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.

Langer et al., New methods of drug delivery. Science. Sep. 2, 19908;249(4976): 1527-33.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Lau et al., Molecular basis for discriminating between normal and damaged bases by the human alkyladenine glycosylase, AAG. Proc Natl Acad Sci U S A. Dec. 5, 2000;97(25):13573-8.

Lauer et al., Construction, characterization, and use of two Listeria monocytogenes site- specific phage integration vectors. J Bacteriol. Aug. 2002; 184(15):4177-86. doi: 10.1128/jb.184.15.4177-4186.2002.

Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.

Lawrence et al., Supercharging proteins can impart unusual resilience. J Am Chem Soc. Aug. 22, 2007;129(33):10110-2. Epub Aug. 1, 2007.

Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.

Lazar et al., Transforming growth factor alpha: mutation of aspartic acid 47 and leucine 48 results in different biological activities. Mol Cell Biol. Mar. 1988;8(3):1247-52.

Lazarevic et al., Nucleotide sequence of the Bacillus subtilis temperate bacteriophage SPbetac2. Microbiology (Reading). May 1999;145 ( Pt 5): 1055-1067. doi: 10.1099/13500872-145-5-1055.

Le Grice et al., Purification and characterization of recombinant equine infectious anemia virus reverse transcriptase. J Virol. Dec. 1991;65(12):7004-7. doi: 10.1128/JVI.65.12.7004-7007.1991.

Leaver-Fay et al., ROSETTA3: an object-oriented software suite for the simulation and design of macromolecules. Methods Enzymol. 2011;487:545-74. doi: 10.1016/B978-0-12-381270-4.00019-6.

Leconte et al., A population-based experimental model for protein evolution: effects of mutation rate and selection stringency on evolutionary outcomes. Biochemistry. Feb. 26, 2013;52(8): 1490-9. doi: 10.1021/bi3016185. Epub Feb. 14, 2013.

Ledford, Gene-editing hack yields pinpoint precision. Nature, Apr. 20, 2016. http://www.nature.com/news/gene-editing-hack-yields-pinpoint-precision-1.19773.

Lee et al., A chimeric thyroid hormone receptor constitutively bound to DNA requires retinoid receptor for hormone-dependent transcriptional activation in yeast. Mol Endocrinol. Sep. 1994;8(9):1245-52.

Lee et al., An allosteric self-splicing ribozyme triggered by a bacterial second messenger. Science. Aug. 13, 2010;329(5993):845-8. doi: 10.1126/science.1190713.

Lee et al., Failure to detect DNA-guided genome editing using Natronobacterium gregoryi Argonaute. Nat Biotechnol. Nov. 28, 2016;35(1):17-18. doi: 10.1038/nbt.3753.

Lee et al., Group I Intron-Based Therapeutics Through Trans-Splicing Reaction. Prog Mol Biol Transl Sci. 2018;159:79-100. doi: 10.1016/bs.pmbts.2018.07.001. Epub Aug. 9, 2018.

Lee et al., PIK3CA gene is frequently mutated in breast carcinomas and hepatocellular carcinomas. Oncogene. Feb. 17, 2005;24(8):1477-80.

(56) References Cited

OTHER PUBLICATIONS

Lee et al., Recognition of liposomes by cells: in vitro binding and endocytosis mediated by specific lipid headgroups and surface charge density. Biochim Biophys Acta. Jan. 31, 1992;1103(2):185-97.
Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.
Lee et al., Site-specific integration of mycobacteriophage L5: integration-proficient vectors for *Mycobacterium smegmatis*, *Mycobacterium tuberculosis*, and bacille Calmette-Guérin. Proc Natl Acad Sci U S A. Apr. 15, 1991;88(8):3111-5. doi: 10.1073/pnas.88.8.3111.
Lee et al., Synthetically modified guide RNA and donor DNA are a versatile platform for CRISPR-Cas9 engineering. Elife. May 2, 2017;6:e25312. doi: 10.7554/eLife.25312.
Lee et al., Targeted chromosomal deletions in human cells using zinc finger nucleases. Genome Res. Jan. 2010 20: 81-89; Published in Advance Dec. 1, 2009, doi:10.1101/gr.099747.109.
Lee et al., Transcriptional regulation and its misregulation in disease. Cell. Mar. 14, 2013;152(6):1237-51. doi: 10.1016/j.cell.2013.02.014.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Lei et al., Site-specificity of serine integrase demonstrated by the attB sequence preference of ?BT1 integrase. FEBS Lett. Apr. 2018;592(8):1389-1399. doi: 10.1002/1873-3468.13023. Epub Mar. 25, 2018.
Leipold et al., A de novo gain-of-function mutation in SCN11A causes loss of pain perception. Nat Genet. Nov. 2013;45(11):1399-404. doi: 10.1038/ng.2767. Epub Sep. 15, 2013.
Lemos et al., CRISPR/Cas9 cleavages in budding yeast reveal templated insertions and strand- specific insertion/deletion profiles. Proc Natl Acad Sci U S A. Feb. 27, 2018;115(9):E2040-E2047. doi: 10.1073/pnas.1716855115. Epub Feb. 13, 2018.
Lenk et al., Pathogenic mechanism of the FIG4 mutation responsible for Charcot-Marie-Tooth disease CMT4J. Plos Genet. Jun. 2011;7(6):e1002104. doi: 10.1371/journal.pgen.1002104. Epub Jun. 2, 2011.
Levy et al., Cytosine and adenine base editing of the brain, liver, retina, heart and skeletal muscle of mice via adeno-associated viruses. Nat Biomed Eng. 2020;4(1):97-110. doi:10.1038/s41551-019-0501-5.
Levy et al., Inhibition of calcification of bioprosthetic heart valves by local controlled-release diphosphonate. Science. Apr. 12, 1985;228(4696):190-2.
Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.
Lew et al., Protein splicing in vitro with a semisynthetic two-component minimal intein. J Biol Chem. Jun. 26, 1998;273(26):15887-90. doi: 10.1074/jbc.273.26.15887.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lewis et al., Building the Class 2 CRISPR-Cas Arsenal. Mol Cell 2017;65(3);377-379.
Lewis et al., Codon 129 polymorphism of the human prion protein influences the kinetics of amyloid formation. J Gen Virol. Aug. 2006;87(Pt 8):2443-9.
Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.
Lewis et al., RNA modifications and structures cooperate to guide RNA-protein interactions. Nat Rev Mol Cell Biol. Mar. 2017;18(3):202-210. doi: 10.1038/nrm.2016.163. Epub Feb. 1, 2017.
Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Current approaches for engineering proteins with diverse biological properties. Adv Exp Med Biol. 2007;620:18-33.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.
Li et al., Loss of post-translational modification sites in disease. Pac Symp Biocomput. 2010:337-47. doi: 10.1142/9789814295291_0036.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.
Li et al., Protein trans-splicing as a means for viral vector-mediated in vivo gene therapy. Hum Gene Ther. Sep. 2008;19(9):958-64. doi: 10.1089/hum.2008.009.
Li et al., RSEM: accurate transcript quantification from RNA-Seq data with or without a reference genome. BMC Bioinformatics. Aug. 4, 2011;12:323. doi: 10.1186/1471-2105-12-323.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Li, Mechanisms and functions of DNA mismatch repair. Cell Res. Jan. 2008;18(1):85-98. doi: 10.1038/cr.2007.115.
Liang et al., Correction of ?thalassemia mutant by base editor in human embryos. Protein Cell. Nov. 2017;8(11):811-822. doi: 10.1007/s13238-017-0475-6. Epub Sep. 23, 2017.
Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Lieber et al., Mechanism and regulation of human non-homologous DNA end-joining. Nat Rev Mol Cell Biol. Sep. 2003;4(9):712-20.
Lienert et al., Two- and three-input TALE-based AND logic computation in embryonic stem cells. Nucleic Acids Res. Nov. 2013;41(21):9967-75. doi: 10.1093/nar/gkt758. Epub Aug. 27, 2013.
Lilley, D.M. The Varkud Satellite Ribozyme. RNA. Feb. 2004; 10(2):151-8.doi: 10.1261/rna.5217104.
Lim et al., Crystal structure of the moloney murine leukemia virus RNase H domain. J Virol. Sep. 2006;80(17):8379-89. doi: 10.1128/JVI.00750-06.
Lim et al., Viral vectors for neurotrophic factor delivery: a gene therapy approach for neurodegenerative diseases of the CNS. Pharmacol Res. Jan. 2010;61(1):14-26. doi: 10.1016/j.phrs.2009.10.002. Epub Oct. 17, 2009.
Lin et al., Enhanced homology-directed human genome engineering by controlled timing of CRISPR/Cas9 delivery. Elife. Dec. 15, 2014;3:e04766. doi: 10.7554/eLife.04766.
Lin et al., The human REV1 gene codes for a DNA template-dependent dCMP transferase. Nucleic Acids Res. Nov. 15, 1999;27(22):4468-75. doi: 10.1093/nar/27.22.4468.

(56) References Cited

OTHER PUBLICATIONS

Link et al., Engineering ligand-responsive gene-control elements: lessons learned from natural riboswitches. Gene Ther. Oct. 2009; 16(10):1189-201. doi: 10.1038/gt.2009.81. Epub Jul. 9, 2009. Review.
Liu et al., C2c1-sgRNA Complex Structure Reveals RNA-Guided DNA Cleavage Mechanism. Molecular Cell Jan. 2017;65(2):310-22.
Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.
Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.
Liu et al., Adding new chemistries to the genetic code. Annu Rev Biochem. 2010;79:413-44. doi: 10.1146/annurev.biochem.052308.105824.
Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.
Liu et al., Balancing AID and DNA repair during somatic hypermutation. Trends Immunol. Apr. 2009;30(4):173-81. doi: 10.1016/j.it.2009.01.007.
Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.
Liu et al., CasX enzymes comprise a distinct family of RNA-guided genome editors. Nature. Feb. 2019;566(7743):218-223. doi: 10.1038/s41586-019-0908-x. Epub Feb. 4, 2019. Author manuscript entitled CRISPR-CasX is an RNA-dominated enzyme active for human genome editing.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Design of polydactyl zinc-finger proteins for unique addressing within complex genomes. Proc Natl Acad Sci U S A. May 27, 1997;94(11):5525-30.
Liu et al., Direct Promoter Repression by BCL11A Controls the Fetal to Adult Hemoglobin Switch. Cell. Apr. 5, 2018;173(2):430-442.e17. doi: 10.1016/j.cell.2018.03.016. Epub Mar. 29, 2018.
Liu et al., Distance determination by GIY-YIG intron endonucleases: discrimination between repression and cleavage functions. Nucleic Acids Res. Mar. 31, 2006;34(6):1755-64. Print 2006.
Liu et al., Editing DNA Methylation in the Mammalian Genome. Cell. Sep. 22, 2016;167(1):233- 247.e17. doi: 10.1016/j.cell.2016.08.056.
Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.
Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.
Liu et al., Fast Colorimetric Sensing of Adenosine and Cocaine Based on a General Sensor Design Involving Aptamers and Nanoparticles. Angew Chem. 2006;118(1):96-100.
Liu et al., Flap endonuclease 1: a central component of DNA metabolism. Annu Rev Biochem. 2004;73:589-615. doi: 10.1146/annurev.biochem.73.012803.092453.
Liu et al., Functional Nucleic Acid Sensors. Chem Rev. May 2009; 109(5):1948-98. doi: 10.1021/cr030183i.
Liu et al., Genetic incorporation of unnatural amino acids into proteins in mammalian cells. Nat Methods. Mar. 2007;4(3):239-44. Epub Feb. 25, 2007.
Liu et al., Highly efficient RNA-guided base editing in rabbit. Nat Commun. Jul. 13, 2018;9(1):2717. doi: 10.1038/s41467-018-05232-2.
Liu et al., N(6)-methyladenosine-dependent RNA structural switches regulate RNA-protein interactions. Nature. Feb. 26, 2015;518(7540):560-4. doi: 10.1038/nature14234.
Liu et al., Probing N6-methyladenosine RNA modification status at single nucleotide resolution in mRNA and long noncoding Rna. Rna. Dec. 2013;19(12):1848-56. doi: 10.1261/rna.041178.113. Epub Oct. 18, 2013.
Liu et al., Reverse transcriptase of foamy virus. Purification of the enzymes and immunological identification. Arch Virol. 1977;55(3):187-200. doi: 10.1007/BF01319905.
Liu et al., Reverse transcriptase-mediated tropism switching in Bordetella bacteriophage. Science. Mar. 15, 2002;295(5562):2091-4. doi: 10.1126/science.1067467.
Liu et al., *Saccharomyces cerevisiae* flap endonuclease 1 uses flap equilibration to maintain triplet repeat stability. Mol Cell Biol. May 2004;24(9):4049-64. doi: 10.1128/MCB.24.9.4049-4064.2004.
Liu et al., The Molecular Architecture for RNA-Guided RNA Cleavage by Cas13a. Cell. Aug. 10, 2017;170(4):714-726.e10. doi: 10.1016/j.cell.2017.06.050. Epub Jul. 27, 2017.
Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.
Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.
Losey et al., Crystal structure of *Staphylococcus sureus* tRNA adenosine deaminase tadA in complex with RNA. Nature Struct. Mol. Biol. Feb. 2006;13(2):153-9.
Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.
Luan et al., Reverse transcription of R2Bm RNA is primed by a nick at the chromosomal target site: a mechanism for non-LTR retrotransposition. Cell. Feb. 26, 1993;72(4):595-605. doi: 10.1016/0092-8674(93)90078-5.
Luckow et al., High level expression of nonfused foreign genes with Autographa californica nuclear polyhedrosis virus expression vectors. Virology. May 1989;170(1):31-9. doi: 10.1016/0042-6822(89)90348-6.
Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.
Lundberg et al., Delivery of short interfering RNA using endosomolytic cell-penetrating peptides. Faseb J. Sep. 2007;21(11):2664-71. Epub Apr. 26, 2007.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Lynch, Evolution of the mutation rate. Trends Genet. Aug. 2010;26(8):345-52. doi: 10.1016/j.tig.2010.05.003. Epub Jun. 3, 20100.
Lyons et al., Efficient Recognition of an Unpaired Lesion by a DNA Repair Glycosylase. J. Am. Chem. Soc., 2009;131(49):17742-3. DOI: 10.1021/ja908378y.
Luke et al., Partial purification and characterization of the reverse transcriptase of the simian immunodeficiency virus TYO-7 isolated from an African green monkey. Biochemistry. Feb. 2, 19900;29(7):1764-9. doi: 10.1021/bi00459a015.
Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.

(56) References Cited

OTHER PUBLICATIONS

Ma et al., In vitro protein engineering using synthetic tRNA(Ala) with different anticodons. Biochemistry. Aug. 10, 1993;32(31):7939-45.

Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.

Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.

Ma et al., Targeted AID-mediated mutagenesis (TAM) enables efficient genomic diversification in mammalian cells. Nature Methods. Oct. 2016; 13:1029-35. doi:10.1038/nmeth.4027 .

Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.

Macbeth et al., Inositol hexakisphosphate is bound in the ADAR2 core and required for RNA editing. Science. Sep. 2, 2005;309(5740):1534-9. doi: 10.1126/science.1113150.

Macrae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.

Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.

Maeder et al., Robust, synergistic regulation of human gene expression using TALE activators. Nat Methods. Mar. 2013;10(3):243-5. doi: 10.1038/nmeth.2366. Epub Feb. 10, 2013.

Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.

Maizels et al., Initiation of homologous recombination at DNA nicks. Nucleic Acids Res. Aug. 21, 2018;46(14):6962-6973. doi: 10.1093/nar/gky588.

Mak et al., The crystal structure of TAL effector PthXo1 bound to its DNA target. Science. Feb. 10, 2012;335(6069):716-9. doi: 10.1126/science.1216211. Epub Jan. 5, 2012.

Makarova et al., Prokaryotic homologs of Argonaute proteins are predicted to function as key components of a novel system of defense against mobile genetic elements. Biology Direct 2009;4:29.

Makarova et al., An updated evolutionary classification of CRISPR-Cas systems. Nat Rev Microbiol. Nov. 2015;13(11):722-36. doi: 10.1038/nrmicro3569. Epub Sep. 28, 2015.

Makarova et al., Classification and Nomenclature of CRISPR-Cas Systems: Where from Here? Crispr J. Oct. 2018; 1(5):325-336. doi: 10.1089/crispr.2018.0033.

Makarova et al., Evolution and classification of the CRISPR-Cas systems. Nat Rev Microbiol. Jun. 2011;9(6):467-77. doi: 10.1038/nrmicro2577. Epub May 9, 2011.

Makarova et al., Prokaryotic homologs of Argonaute proteins are predicted to function as key components of a novel system of defense against mobile genetic elements. Biology Direct 2009;4:29. doi: 10.1186/1745-6150-4-29.

Makeyev et al., Evolutionary potential of an RNA virus. J Virol. Feb. 2004;78(4):2114-20.

Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).

Mali et al., Cas9 as a versatile tool for engineering biology. Nat Methods. Oct. 2013; 10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science.1232033. Epub Jan. 3, 2013.

Malito et al., Structural basis for lack of toxicity of the diphtheria toxin mutant CRM197. Proc Natl Acad Sci U S A. Apr. 3, 2012;109(14):5229-34. doi: 10.1073/pnas.1201964109. Epub Mar. 19, 2012.

Mandal et al., A glycine-dependent riboswitch that uses cooperative binding to control gene expression. Science. Oct. 8, 2004;306(5694):275-9.

Mandal et al., Adenine riboswitches and gene activation by disruption of a transcription terminator. Nat Struct Mol Biol. Jan. 2004; 11(1):29-35. Epub Dec. 29, 2003.

Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.

Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.

Mani et al., Design, engineering, and characterization of zinc finger nucleases. Biochem Biophys Res Commun. Sep. 23, 2005;335(2):447-57.

Marceau, Functions of single-strand DNA-binding proteins in DNA replication, recombination, and repair. Methods Mol Biol. 2012;922:1-21. doi: 10.1007/978-1-62703-032-8_1.

Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.

Marioni et al., DNA methylation age of blood predicts all-cause mortality in later life. Genome Biol. Jan. 30, 2015;16:25. doi: 10.1186/s13059-015-0584-6.

Marraffini et al., CRISPR interference limits horizontal gene transfer in staphylococci by targeting DNA. Science. Dec. 19, 2008;322(5909):1843-5. doi: 10.1126/science.1165771.

Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.

Martsolf et al., Complete trisomy 17p a relatively new syndrome. Ann Genet. 1988;31(3):172-4.

Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.

Mascola et al., HIV-1 neutralizing antibodies: understanding nature's pathways. Immunol Rev. Jul. 2013;254(1):225-44. doi: 10.1111/imr.12075.

Mathys et al., Characterization of a self-splicing mini-intein and its conversion into autocatalytic N- and C-terminal cleavage elements: facile production of protein building blocks for protein ligation. Gene. Apr. 29, 1999;231(1-2):1-13. doi: 10.1016/s0378-1119(99)00103-1.

Matsuura et al., A gene essential for the site-specific excision of actinophage r4 prophage genome from the chromosome of a lysogen. J Gen Appl Microbiol. 1995;41(1):53-61.

Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.

May et al., Emergent lineages of mumps virus suggest the need for a polyvalent vaccine. Int J Infect Dis. Jan. 2018;66:1-4. doi: 10.1016/j.ijid.2017.09.024. Epub Oct. 4, 2017.

McCarroll et al., Copy-number variation and association studies of human disease. Nat Genet. Jul. 2007;39(7 Suppl):S37-42. doi: 10.1038/ng2080.

(56) References Cited

OTHER PUBLICATIONS

McDonald et al., Characterization of mutations at the mouse phenylalanine hydroxylase locus. Genomics. Feb. 1, 1997;39(3):402-5. doi: 10.1006/geno.1996.4508.

McInerney et al., Error Rate Comparison during Polymerase Chain Reaction by DNA Polymerase. Mol Biol Int. 2014;2014:287430. doi: 10.1155/2014/287430. Epub Aug. 1, 20147.

McKenna et al., Recording development with single cell dynamic lineage tracing. Development. Jun. 27, 20197146(12):dev169730. doi: 10.1242/dev.169730.

McKenna et al., Whole-organism lineage tracing by combinatorial and cumulative genome editing. Science. Jul. 29, 2016;353(6298):aaf7907. doi: 10.1126/science.aaf7907. Epub May 26, 2016.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.

Mead et al., A novel protective prion protein variant that colocalizes with kuru exposure. N Engl J Med. Nov. 19, 2009;361(21):2056-65. doi: 10.1056/NEJMoa0809716.

Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.

Mei et al., Recent Progress in CRISPR/Cas9 Technology. J Genet Genomics. Feb. 20, 2016;43(2):63-75. doi: 10.1016/j.jgg.2016.01.001. Epub Jan. 16, 2016.

Meinke et al., Cre Recombinase and Other Tyrosine Recombinases. Chem Rev. Oct. 26, 2016;116(20):12785-12820. doi: 10.1021/acs.chemrev.6b00077. Epub May 10, 2016.

Meng et al., Profiling the DNA-binding specificities of engineered Cys2His2 zinc finger domains using a rapid cell-based method. Nucleic Acids Res. 2007;35(11):e81. Epub May 30, 2007.

Meng et al., Targeted gene inactivation in zebrafish using engineered zinc-finger nucleases. Nat Biotechnol. Jun. 2008;26(6):695-701. doi: 10.1038/nbt1398. Epub May 25, 2008.

Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.

Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.

Mertens et al., Site-specific recombination in bacteriophage Mu: characterization of binding sites for the DNA invertase Gin. Embo J. Apr. 1988;7(4):1219-27.

Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.

Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.

Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.

Meyer et al., Library generation by gene shuffling. Curr Protoc Mol Biol. Jan. 6, 2014;105: Unit 15.12 . . . doi: 10.1002/0471142727.mb1512s105.

Meyer et al., The dynamic epitranscriptome: N6-methyladenosine and gene expression control. Nat Rev Mol Cell Biol. May 2014;15(5):313-26. doi: 10.1038/nrm3785. Epub Apr. 9, 2014.

Michel et al., Mitochondrial class II introns encode proteins related to the reverse transcriptases of retroviruses. Nature. Aug. 15-21, 1985;316(6029):641-3. doi: 10.1038/316641a0.

Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.

Mihai et al., PTEN inhibition improves wound healing in lung epithelia through changes in cellular mechanics that enhance migration. Am J Physiol Lung Cell Mol Physiol. 2012;302(3):L287-L299.

Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.

Miller et al., A Tale nuclease architecture for efficient genome editing. Nat Biotechnol. Feb. 2011;29(2):143-8. doi:10.1038/nbt.1755. Epub Dec. 22, 2010.

Miller et al., An improved zinc-finger nuclease architecture for highly specific genome editing. Nat Biotechnol. Jul. 2007;25(7):778-85. Epub Jul. 1, 2007.

Miller et al., Construction and properties of retrovirus packaging cells based on gibbon ape leukemia virus. J Virol. May 1991;65(5):2220-4. doi: 10.1128/JVI.65.5.2220-2224.1991.

Miller, Human gene therapy comes of age. Nature. Jun. 11, 1992;357(6378):455-60. doi: 10.1038/357455a0.

Mills et al., Protein splicing in trans by purified N- and C-terminal fragments of the *Mycobacterium tuberculosis* RecA intein. Proc Natl Acad Sci U S A. Mar. 31, 1998;95(7):3543-8. doi: 10.1073/pnas.95.7.3543.

Minoche et al., Evaluation of genomic high-throughput sequencing data generated on Illumina HiSeq and genome analyzer systems. Genome Biol. Nov. 8, 2011;12(11):R112. doi: 10.1186/GB-2011-12-11-r112.

Minoretti et al., A W148R mutation in the human FOXD4 gene segregating with dilated cardiomyopathy, obsessive-compulsive disorder, and suicidality. Int J Mol Med. Mar. 2007;19(3):369-72.

Mir et al., Two Active Site Divalent Ions in the Crystal Structure of the Hammerhead Ribozyme Bound to a Transition State Analogue. Biochemistry . . . Feb. 2, 2016;55(4):633-6. doi: 10.1021/acs.biochem.5b01139. Epub Jan. 19, 2016.

Mir et al., Type II-C CRISPR-Cas9 Biology, Mechanism, and Application. ACS Chem Biol. Feb. 16, 2018;13(2):357-365. doi: 10.1021/acschembio.7b00855. Epub Dec. 20, 2017.

Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.

Mitani et al., Delivering therapeutic genes—matching approach and application. Trends Biotechnol. May 1993;11(5):162-6. doi: 10.1016/0167-7799(93)90108-L.

Mitton-Fry et al., Poly(A) tail recognition by a viral RNA element through assembly of a triple helix. Science. Nov. 26, 2010;330(6008):1244-7. doi: 10.1126/science.1195858.

Miyaoka et al., Systematic quantification of HDR and NHEJ reveals effects of locus, nuclease, and cell type on genome-editing. Sci Rep. Mar. 31, 2016;6:23549. doi: 10.1038/srep23549.

Moede et al., Identification of a nuclear localization signal, RRMKWKK, in the homeodomain transcription factor PDX-1. Febs Lett. Nov. 19, 1999;461(3):229-34. doi: 10.1016/s0014-5793(99)01446-5.

Mohr et al., A Reverse Transcriptase-Cas1 Fusion Protein Contains a Cas6 Domain Required for Both Crispr RNA Biogenesis and RNA Spacer Acquisition. Mol Cell. Nov. 15, 2018;72(4):700-714.e8. doi: 10.1016/j.molcel.2018.09.013. Epub Oct. 18, 2018.

Mohr et al., A Reverse Transcriptase-Cas1 Fusion Protein Contains a Cas6 Domain Required for Both Crispr Rna Biogenesis and RNA Spacer Acquisition. Mol Cell. Nov. 15, 2018;72(4):700-714.e8. doi: 10.1016/j.molcel.2018.09.013. Epub Oct. 18, 2018. Including Supplemental Information.

Mohr et al., Thermostable group II intron reverse transcriptase fusion proteins and their use in cDNA synthesis and next-generation RNA sequencing. RNA. Jul. 2013;19(7):958-70. doi: 10.1261/rna.039743.113. Epub May 22, 2013.

Mojica et al., Intervening sequences of regularly spaced prokaryotic repeats derive from foreign genetic elements. J Mol Evol. Feb. 2005;60(2):174-82.

(56) References Cited

OTHER PUBLICATIONS

Mol et al., Crystal structure and mutational analysis of human uracil-DNA glycosylase: structural basis for specificity and catalysis. Cell. Mar. 24, 1995;80(6):869-78. doi: 10.1016/0092-8674(95)90290-2.
Mol et al., Crystal structure of human uracil-DNA glycosylase in complex with a protein inhibitor: protein mimicry of DNA. Cell. Sep. 8, 1995;82(5):701-8.
Monahan et al., Site-specific incorporation of unnatural amino acids into receptors expressed in Mammalian cells. Chem Biol. Jun. 2003; 10(6):573-80.
Monot et al., The specificity and flexibility of l1 reverse transcription priming at imperfect T- tracts. PLOS Genet. May 2013;9(5):e1003499. doi: 10.1371/journal.pgen.1003499. Epub May 9, 2013.
Montange et al., Structure of the S-adenosylmethionine riboswitch regulatory mRNA element. Nature. Jun. 29, 2006;441(7097):1172-5.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Mootz et al., Conditional protein splicing: a new tool to control protein structure and function in vitro and in vivo. J Am Chem Soc. Sep. 3, 2003;125(35):10561-9.
Mootz et al., Protein splicing triggered by a small molecule. J Am Chem Soc. Aug. 7, 2002;124(31):9044-5.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.
Moreno-Mateos et al., CRISPRscan: designing highly efficient sgRNAs for CRISPR-Cas9 targeting in vivo. Nat Methods. Oct. 2015;12(10):982-8. doi: 10.1038/nmeth.3543. Epub Aug. 31, 2015.
Morita et al., The site-specific recombination system of actinophage TG1. Fems Microbiol Lett. Aug. 2009;297(2):234-40. doi: 10.1111/j.1574-6968.2009.01683.x. Morris et al., A peptide carrier for the delivery of biologically active proteins into mammalian cells. Nat Biotechnol. Dec. 2001;19(12):1173-6.
Morris et al., A peptide carrier for the delivery of biologically active proteins into mammalian cells. Nat Biotechnol. Dec. 2001;9(12):1173-6.
Moscou et al., A simple cipher governs DNA recognition by TAL effectors. Science. Dec. 11, 2009;326(5959):1501. doi: 10.1126/science.1178817.
Mougiakos et al., Characterizing a thermostable Cas9 for bacterial genome editing and silencing. Nat Commun. Nov. 21, 2017;8(1):1647. doi: 10.1038/s41467-017-01591-4.
Muller et al., Nucleotide exchange and excision technology (Next) Dna shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.
Mullins et al., Transgenesis in nonmurine species. Hypertension. Oct. 1993;22(4):630-3.
Mumtsidu et al., Structural features of the single-stranded DNA-binding protein of Epstein-Barr virus. J Struct Biol. Feb. 2008;161(2):172-87. doi: 10.1016/j.jsb.2007.10.014. Epub Nov. 1, 2007.
Murphy, Phage recombinases and their applications. Adv Virus Res. 2012;83:367-414. doi: 10.1016/B978-0-12-394438-2.00008-6. Review.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Muzyczka et al., Adeno-associated virus (AAV) vectors: will they work? J Clin Invest. Oct. 1994;94(4):1351. doi: 10.1172/JCI117468.

Myerowitz et al., The major defect in Ashkenazi Jews with Tay-Sachs disease is an insertion in the gene for the alpha-chain of beta-hexosaminidase. J Biol Chem. Dec. 15, 1988;263(35):18587-9.
Myers et al., Insulin signal transduction and the IRS proteins. Annu Rev Pharmacol Toxicol. 1996;36:615-58. doi: 10.1146/annurev.pa.36.040196.003151.
Nabel et al., Direct gene transfer for immunotherapy and immunization. Trends Biotechnol. May 1993;11(5):211-5. doi: 10.1016/0167-7799(93)90117-R.
Nahar et al., A G-quadruplex motif at the 3' end of sgRNAs improves CRISPR-Cas9 based genome editing efficiency. Chem Commun (Camb). Mar. 7, 2018;54(19):2377-2380. doi: 10.1039/c7cc08893k. Epub Feb. 16, 2018.
Nahvi et al., Coenzyme B12 riboswitches are widespread genetic control elements in prokaryotes. Nucleic Acids Res. Jan. 2, 2004;32(1):143-50.
Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.
Nakamura et al., Codon usage tabulated from international DNA sequence databases: status for the year 2000. Nucleic Acids Res. Jan. 1, 2000;28(1):292. doi: 10.1093/nar/28.1.292.
Naorem et al., DGR mutagenic transposition occurs via hypermutagenic reverse transcription primed by nicked template RNA. Proc Natl Acad Sci U S A. Nov. 21, 2017;114(47):E10187-E10195. doi: 10.1073/pnas.1715952114. Epub Nov. 6, 2017.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Neel et al., Riboswitches: Classification, function and in silico approach, International Journal of Pharma Sciences and Research. 2010;1(9):409-420.
Nelson et al., Filamentous phage DNA cloning vectors: a noninfective mutant with a nonpolar deletion in gene III. Virology. 1981; 108(2): 338-50.
Nern et al., Multiple new site-specific recombinases for use in manipulating animal genomes. Proc Natl Acad Sci U S A. Aug. 23, 2011;108(34): 14198-203. doi: 10.1073/pnas.1111704108. Epub Aug. 9, 2011.
Nguyen et al., Evolutionary drivers of thermoadaptation in enzyme catalysis. Science. Jan. 20, 2017;355(6322):289-294. doi: 10.1126/science.aah3717. Epub Dec. 22, 2016.
Nguyen et al., IQ-TREE: a fast and effective stochastic algorithm for estimating maximum- likelihood phylogenies. Mol Biol Evol. Jan. 2015;32(1):268-74. doi: 10.1093/molbev/msu300. Epub Nov. 3, 2014.
Ni et al., A PCSK9-binding antibody that structurally mimics the EGF(A) domain of LDL-receptor reduces LDL cholesterol in vivo. J Lipid Res. 2011;52:76-86.
Ni et al., Nucleic acid aptamers: clinical applications and promising new horizons. Curr Med Chem. 2011;18(27):4206-14. Review.
Nishida et al., Targeted nucleotide editing using hybrid prokaryotic and vertebrate adaptive immune systems. Science. Sep. 16, 2016;353(6305). pii: aaf8729. doi: 10.1126/science.aaf8729. Epub Aug. 4, 2016.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Nishikura, Functions and regulation of RNA editing by ADAR deaminases. Annu Rev Biochem. 2010;79:321-349. doi:10.1146/annurev-biochem-060208-105251.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

(56) References Cited

OTHER PUBLICATIONS

Nishimasu et al., Crystal Structure of Staphylococcus Aureus Cas9. Cell. Aug. 27, 2015;162(5):1113-26. doi: 10.1016/j.cell.2015.08.007.
Nishimasu et al., Engineered CRISPR-Cas9 nuclease with expanded targeting space. Science. Sep. 21, 2018;361(6408):1259-1262. doi: 10.1126/science.aas9129. Epub Aug. 30, 2018.
Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Noris et al., A phenylalanine-55 to serine amino-acid substitution in the human glycoprotein IX leucine-rich repeat is associated with Bernard-Soulier syndrome. Br J Haematol. May 1997;97(2):312-20.
Nottingham et al., RNA-seq of human reference RNA samples using a thermostable group II intron reverse transcriptase. RNA. Apr. 2016;22(4):597-613. doi: 10.1261/rna.055558.115. Epub Jan. 29, 2016.
Nowak et al., Characterization of single-stranded DNA-binding proteins from the psychrophilic bacteria Desulfotalea psychrophila, Flavobacterium psychrophilum, Psychrobacter arcticus, Psychrobacter cryohalolentis, Psychromonas ingrahamii, Psychroflexus torquis, and Photobacterium profundum. BMC Microbiol. Apr. 14, 2014;14:91. doi: 10.1186/1471-2180-14-91.
Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.
Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.
Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.
Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
O'Maille et al., Structure-based combinatorial protein engineering (SCOPE). J Mol Biol. Aug. 23, 2002;321(4):677-91.
Oakes et al., CRISPR-Cas9 Circular Permutants as Programmable Scaffolds for Genome Modification. Cell. Jan. 1, 20190;176(1-2):254-267.e16. doi: 10.1016/j.cell.2018.11.052.
Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.
Oakes et al., Protein engineering of Cas9 for enhanced function. Methods Enzymol. 2014;546:491-511.
Odsbu et al., Specific N-terminal interactions of the Escherichia coli SeqA protein are required to form multimers that restrain negative supercoils and form foci. Genes Cells. Nov. 2005;10(11):1039-49.
Oeemig et al., Solution structure of DnaE intein from Nostoc punctiforme: structural basis for the design of a new split intein suitable for site-specific chemical modification. FEBS Lett. May 6, 2009;583(9):1451-6.
Offord, Advances in Genome Editing. The Scientist, Apr. 20, 2016. http://www.the-scientist.com/?articles.view/articleNo/45903/title/Advances-in-Genome-Editing/.
Oh et al., Positional cloning of a gene for Hermansky-Pudlak syndrome, a disorder of cytoplasmic organelles. Nat Genet. Nov. 1996;14(3):300-6. doi: 10.1038/ng1196-300.
Ohe et al., Purification and properties of xanthine dehydrogenase from Streptomyces cyanogenus. J Biochem. Jul. 1979;86(1):45-53.
Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.
Olorunniji et al., Purification and In Vitro Characterization of Zinc Finger Recombinases. Methods Mol Biol. 2017;1642:229-245. doi: 10.1007/978-1-4939-7169-5_15.
Olorunniji et al., Site-specific recombinases: molecular machines for the Genetic Revolution. Biochem J. Mar. 15, 2016;473(6):673-84. doi: 10.1042/BJ20151112.
Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.
Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Orthwein et al., A mechanism for the suppression of homologous recombination in G1 cells. Nature. Dec. 17, 2015;528(7582):422-6. doi: 10.1038/nature16142. Epub Dec. 9, 2015.
Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.
Osborn et al., TALEN-based gene correction for epidermolysis bullosa. Mol Ther. Jun. 2013;21(6):1151-9. doi: 10.1038/mt.2013.56. Epub Apr. 2, 2013.
Ostermeier et al., A combinatorial approach to hybrid enzymes independent of DNA homology. Nat Biotechnol. Dec. 1999;17(12):1205-9.
Ostertag et al., Biology of mammalian L1 retrotransposons. Annu Rev Genet. 2001;35:501- 38. doi: 10.1146/annurev.genet.35.102401.091032.
Otomo et al., Improved segmental isotope labeling of proteins and application to a larger protein. J Biomol NMR. Jun. 1999;14(2):105-14. doi: 10.1023/a:1008308128050.
Otomo et al., NMR observation of selected segments in a larger protein: central-segment isotope labeling through intein-mediated ligation. Biochemistry. Dec. 7, 1999;38(49):16040-4. doi: 10.1021/bi991902j.
Otto et al., The probability of fixation in populations of changing size. Genetics. Jun. 1997; 146(2):723-33.
Pabo et al., Design and selection of novel Cys2His2 zinc finger proteins. Annu Rev Biochem. 2001;70:313-40.
Packer et al., Phage-assisted continuous evolution of proteases with altered substrate specificity. Nat Commun. Oct. 16, 2017;8(1):956. doi: 10.1038/s41467-017-01055-9.
Paige et al., RNA mimics of green fluorescent protein. Science. Jul. 29, 2011;333(6042):642-6. doi:10.1126/science.1207339.
Pan et al., Biological and biomedical applications of engineered nucleases. Mol Biotechnol. Sep. 2013;55(1):54-62. doi: 10.1007/s12033-012-9613-9.
Paquet et al., Efficient introduction of specific homozygous and heterozygous mutations using CRISPR/Cas9. Nature. May 5, 2016;533(7601): 125-9. doi: 10.1038/nature17664. Epub Apr. 27, 2016.
Park et al., Digenome-seq web tool for profiling CRISPR specificity. Nat Methods. May 30, 2017;14(6):548-549. doi: 10.1038/nmeth.4262.
Park et al., Highly efficient editing of the ?-globin gene in patient-derived hematopoietic stem and progenitor cells to treat sickle cell disease. Nucleic Acids Res. Sep. 5, 2019;47(15):7955-7972. doi: 10.1093/nar/gkz475.
Park et al., Sendai virus, an RNA virus with No. risk of genomic integration, delivers CRISPR/Cas9 for efficient gene editing. Mol Ther Methods Clin Dev. Aug. 24, 2016;3:16057. doi: 10.1038/mtm.2016.57.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Partial European Search Report for Application No. EP 19187331.4, mailed Dec. 19, 2019.
Partial Supplementary European Search Report for Application No. EP 12845790.0, mailed Mar. 18, 2015.

(56) References Cited

OTHER PUBLICATIONS

Patel et al., Flap endonucleases pass 5'-flaps through a flexible arch using a disorder-thread- order mechanism to confer specificity for free 5'-ends. Nucleic Acids Res. May 2012;40(10):4507-19. doi: 10.1093/nar/gks051. Epub Feb. 8, 2012.
Pattanayak et al., Determining the specificities of TALENs, Cas9, and other genome- editing enzymes. Methods Enzymol. 2014;546:47-78. doi: 10.1016/B978-0-12-801185-0.00003-9.
Pattanayak et al., High-throughput profiling of off-target DNA cleavage reveals RNA- programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pawson et al., Protein phosphorylation in signaling—50 years and counting. Trends Biochem Sci. Jun. 2005;30(6):286-90. doi: 10.1016/j.tibs.2005.04.013.
Pearl, Structure and function in the uracil-DNA glycosylase superfamily. Mutat Res. Aug. 30, 2000;460(3-4):165-81.
Peck et al., Directed evolution of a small-molecule-triggered intein with improved splicing properties in mammalian cells. Chem Biol. May 27, 2011;18(5):619-30. doi: 10.1016/j.chembiol.2011.02.014.
Pellenz et al., New human chromosomal safe harbor sites for genome engineering with CRISPR/Cas9, TAL effector and homing endonucleases. Aug. 20, 2018. bioRxiv doi: https://doi.org/10.1101/396390.
Pelletier, CRISPR-Cas systems for the study of the immune function. Nov. 15, 2016. https://doi.org/10.1002/9780470015902.a0026896.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perach et al., Catalytic features of the recombinant reverse transcriptase of bovine leukemia virus expressed in bacteria. Virology. Jun. 20, 1999;259(1):176-89. doi: 10.1006/viro. 1999.9761.
Perez et al., Establishment of HIV-1 resistance in CD4+ T cells by genome editing using zinc- finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012; 16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Perler et al., Protein splicing and autoproteolysis mechanisms. Curr Opin Chem Biol. Oct. 1997;1(3):292-9. doi: 10.1016/s1367-5931(97)80065-8.
Perler et al., Protein splicing elements: inteins and exteins—a definition of terms and recommended nomenclature. Nucleic Acids Res. Apr. 11, 1994;22(7):1125-7. doi: 10.1093/nar/22.7.1125.
Perler, InBase, the New England Biolabs Intein Database. Nucleic Acids Res. Jan. 1, 1999;27(1):346-7. doi: 10.1093/nar/27.1.346.
Perler, Protein splicing of inteins and hedgehog autoproteolysis: structure, function, and evolution. Cell. Jan. 9, 1998;92(1):1-4. doi: 10.1016/s0092-8674(00)80892-2.
Petek et al., Frequent endonuclease cleavage at off-target locations in vivo. Mol Ther. May 2010;18(5):983-6. Doi: 10.1038/mt.2010.35. Epub Mar. 9, 2010.
Petersen-Mahrt et al., AID mutates *E. coli* suggesting a DNA deamination mechanism for antibody diversification. Nature. Jul. 4, 2002;418(6893):99-103.
Petolino et al., Editing Plant Genomes: a new era of crop improvement. Plant Biotechnol J. Feb. 2016;14(2):435-6. doi: 10.1111/pbi.12542.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pfeiffer et al., Mechanisms of DNA double-strand break repair and their potential to induce chromosomal aberrations. Mutagenesis. Jul. 2000;15(4):289-302. doi: 10.1093/mutage/15.4.289.
Pham et al., Reward versus risk: DNA cytidine deaminases triggering immunity and disease. Biochemistry. Mar. 1, 2005;44(8):2703-15.
Phillips, The challenge of gene therapy and DNA delivery. J Pharm Pharmacol. Sep. 2001;53(9):1169-74.
Pickart et al., Ubiquitin: structures, functions, mechanisms. Biochim Biophys Acta. Nov. 29, 2004;1695(1-3):55-72. doi: 10.1016/j.bbamcr.2004.09.019.
Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.
Pirakitikulr et al., PCRless library mutagenesis via oligonucleotide recombination in yeast. Protein Sci. Dec. 2010; 19(12):2336-46. doi: 10.1002/pro.513.
Plasterk et al., DNA inversions in the chromosome of Escherichia coli and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutLa endonuclease in mismatch repair. Proc Natl Acad Sci U S A. Sep. 14, 2010;107(37):16066-71. doi: 10.1073/pnas.1010662107. Epub Aug. 16, 2010.
Poller et al., A leucine-to-proline substitution causes a defective alpha 1-antichymotrypsin allele associated with familial obstructive lung disease. Genomics. Sep. 1993;17(3):740-3.
Popp et al., Sortagging: a versatile method for protein labeling. Nat Chem Biol. Nov. 2007;3(11):707-8. doi: 10.1038/nchembio.2007.31. Epub Sep. 23, 2007.
Porteus, Design and testing of zinc finger nucleases for use in mammalian cells. Methods Mol Biol. 2008;435:47-61. doi: 10.1007/978-1-59745-232-8_4.
Posnick et al., Imbalanced base excision repair increases spontaneous mutation and alkylation sensitivity in *Escherichia coli*. J Bacteriol. Nov. 1999;181(21):6763-71.
Pospíšilová et al., Hydrolytic cleavage of N6-substituted adenine derivatives by eukaryotic adenine and adenosine deaminases. Biosci Rep. 2008;28(6):335-347. doi:10.1042/BSR20080081.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prasad et al., Rev1 is a base excision repair enzyme with 5'-deoxyribose phosphate lyase activity. Nucleic Acids Res. Dec. 15, 2016;44(22):10824-10833. doi: 10.1093/nar/gkw869. Epub Sep. 28, 2016.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.
Proudfoot et al., Zinc finger recombinases with adaptable DNA sequence specificity. PLOS One. Apr. 29, 2011;6(4):e19537. doi: 10.1371/journal.pone.0019537.
Pruschy et al., Mechanistic studies of a signaling pathway activated by the organic dimerizer FK1012. Chem Biol. Nov. 1994;1(3):163-72. doi: 10.1016/1074-5521(94)90006-x.
Prykhozhij et al., CRISPR multitargeter: a web tool to find common and unique CRISPR single guide RNA targets in a set of similar sequences. PLOS One. Mar. 5, 2015;10(3):e0119372. doi: 10.1371/journal.pone.0119372. eCollection 2015.

(56) References Cited

OTHER PUBLICATIONS

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.

Putney et al., Improving protein therapeutics with sustained-release formulations. Nat Biotechnol. Feb. 1998;16(2):153-7.

Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.

Qi et al., Repurposing CRISPR as an RNA-guided platform for sequence-specific control of gene expression. Cell. Feb. 28, 2013;152(5):1173-83. doi: 10.1016/j.cell.2013.02.022.

Qu et al., Global mapping of binding sites for phic31 integrase in transgenic maden-darby bovine kidney cells using ChIP-seq. Hereditas. Jan. 14, 2019;156:3. doi: 10.1186/s41065-018-0079-z.

Queen et al., Immunoglobulin gene transcription is activated by downstream sequence elements. Cell. Jul. 1983;33(3):741-8. doi: 10.1016/0092-8674(83)90016-8.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.

Rakonjac et al., Roles of PIII in filamentous phage assembly. J Mol Biol. 1998; 282(1)25-41.

Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.

Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.

Ramirez et al., Unexpected failure rates for modular assembly of engineered zinc fingers. Nat Methods. May 2008;5(5):374-5. Doi: 10.1038/nmeth0508-374.

Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.

Ran et al., Genome engineering using the CRISPR-Cas9 system. Nat Protoc. Nov. 2013;8(11):2281-308. doi: 10.1038/nprot.2013.143. Epub Oct. 24, 2013.

Ran et al., In vivo genome editing using Staphylococcus aureus Cas9. Nature. Apr. 9, 2015;520(7546):186-91. doi: 10.1038/nature14299. Epub Apr. 1, 2015.

Ranzau et al., Genome, Epigenome, and Transcriptome Editing via Chemical Modification of Nucleobases in Living Cells. Biochemistry. Feb. 5, 2019;58(5):330-335. doi: 10.1021/acs.biochem.8b00958. Epub Dec. 12, 2018.

Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.

Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rath et al., Fidelity of end joining in mammalian episomes and the impact of Metnase on joint processing. BMC Mol Biol. Mar. 22, 2014;15:6. doi: 10.1186/1471-2199-15-6.

Rauch et al., Programmable RNA Binding Proteins for Imaging and Therapeutics. Biochemistry. Jan. 30, 2018;57(4):363-364. doi: 10.1021/acs.biochem.7b01101. Epub Nov. 17, 2017.

Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).

Ray et al., A compendium of RNA-binding motifs for decoding gene regulation. Nature. Jul. 11, 2013;499(7457):172-7. doi: 10.1038/nature12311.

Ray et al., Homologous recombination: ends as the means. Trends Plant Sci. Oct. 2002;7(10):435-40.

Rebar et al., Phage display methods for selecting zinc finger proteins with novel DNA-binding specificities. Methods Enzymol. 1996;267:129-49.

Rebuzzini et al., New mammalian cellular systems to study mutations introduced at the break site by non-homologous end-joining. DNA Repair (Amst). May 2, 2005;4(5):546-55.

Rees et al., Analysis and minimization of cellular RNA editing by DNA adenine base editors. Sci Adv. May 8, 2019;5(5):eaax5717. doi: 10.1126/sciadv.aax5717.

Rees et al., Base editing: precision chemistry on the genome and transcriptome of living cells. Nat Rev Genet. Dec. 2018;19(12):770-788. doi: 10.1038/s41576-018-0059-1.

Rees et al., Development of hRad51-Cas9 nickase fusions that mediate HDR without double-stranded breaks. Nat Commun. May 17, 2019;10(1):2212. doi: 10.1038/s41467-019-09983-4.

Rees et al., Improving the DNA specificity and applicability of base editing through protein engineering and protein delivery. Nat Commun. Jun. 6, 2017;8:15790. doi: 10.1038/ncomms15790.

Relph et al., Recent developments and current status of gene therapy using viral vectors in the United Kingdom. BMJ. 2004;329(7470):839-842. doi:10.1136/bmj.329.7470.839.

Remy et al., Gene transfer with a series of lipophilic DNA-binding molecules. Bioconjug Chem. Nov.-Dec. 1994;5(6):647-54. doi: 10.1021/bc00030a021.

Ren et al., In-line Alignment and Mg2? Coordination at the Cleavage Site of the env22 Twister Ribozyme. Nat Commun. Nov. 20, 2014;5:5534. doi: 10.1038/ncomms6534.

Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.

Reynaud et al., What role for AID: mutator, or assembler of the immunoglobulin mutasome? Nat Immunol. Jul. 2003;4(7):631-8.

Reyon et al., FLASH assembly of TALENs for high-throughput genome editing. Nat Biotechnol. May 2012;30(5):460-5. doi: 10.1038/nbt.2170.

Ribeiro et al., Protein Engineering Strategies to Expand CRISPR-Cas9 Applications. Int J Genomics. Aug. 2, 2018;2018:1652567. doi: 10.1155/2018/1652567.

Richardson et al., Enhancing homology-directed genome editing by catalytically active and inactive CRISPR-Cas9 using asymmetric donor DNA. Nat Biotechnol. Mar. 2016; 34(3):339-44. doi: 10.1038/nbt.3481. Epub Jan. 20, 2016.

Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.

Riechmann et al., The C-terminal domain of TolA is the coreceptor for filamentous phage infection of *E. coli*. Cell. 1997; 90(2):351-60. PMID:9244308.

Ringrose et al., The Kw recombinase, an integrase from Kluyveromyces waltii. Eur J Biochem. Sep. 15, 1997;248(3):903-12. doi: 10.1111/j.1432-1033.1997.00903.x.

(56) References Cited

OTHER PUBLICATIONS

Risso et al., Hyperstability and substrate promiscuity in laboratory resurrections of Precambrian ?-lactamases. J Am Chem Soc. Feb. 27, 2013;135(8):2899-902. doi: 10.1021/ja311630a. Epub Feb. 14, 2013.
Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.
Rizk et al., An engineered substance P variant for receptor-mediated delivery of synthetic antibodies into tumor cells. Proc Natl Acad Sci U S A. Jul. 7, 2009;106(27):11011-5. doi: 10.1073/pnas.0904907106. Epub Jun. 22, 2009.
Robertson et al., DNA repair in mammalian cells: Base excision repair: the long and short of it. Cell Mol Life Sci. Mar. 2009;66(6):981-93. doi: 10.1007/s00018-009-8736-z.
Robinson et al., The protein tyrosine kinase family of the human genome. Oncogene. Nov. 20, 2000;19(49):5548-57. doi: 10.1038/sj.onc.1203957.
Rogozin et al., Evolution and diversification of lamprey antigen receptors: evidence for involvement of an AID-APOBEC family cytosine deaminase. Nat Immunol. Jun. 2007;8(6):647- 56. doi: 10.1038/ni1463. Epub Apr. 29, 2007.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rongrong et al., Effect of deletion mutation on the recombination activity of Cre recombinase. Acta Biochim Pol. 2005;52(2):541-4. Epub May 15, 2005.
Roth et al., A riboswitch selective for the queuosine precursor preQ1 contains an unusually small aptamer domain. Nat Struct Mol Biol. Apr. 2007;14(4):308-17. Epub Mar. 25, 2007.
Roth et al., A widespread self-cleaving ribozyme class is revealed by bioinformatics. Nat Chem Biol. Jan. 2014;10(1):56-60. doi: 10.1038/nchembio.1386. Epub Nov. 17, 2013.
Roth et al., Purification and characterization of murine retroviral reverse transcriptase expressed in *Escherichia coli*. J Biol Chem. Aug. 5, 1985;260(16):9326-35.
Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.
Rouet et al., Introduction of double-strand breaks into the genome of mouse cells by expression of a rare-cutting endonuclease. Mol Cell Biol. Dec. 1994; 14(12):8096-106. doi: 10.1128/mcb.14.12.8096.
Rouet et al., Receptor-Mediated Delivery of CRISPR-Cas9 Endonuclease for Cell-Type- Specific Gene Editing. J Am Chem Soc. May 30, 2018;140(21):6596-6603. doi: 10.1021/jacs.8b01551. Epub May 18, 2018.
Roundtree et al., YTHDC1 mediates nuclear export of N6-methyladenosine methylated mRNAs. Elife. Oct. 6, 2017;6:e31311. doi: 10.7554/eLife.31311.
Rowland et al., Regulatory mutations in Sin recombinase support a structure-based model of the synaptosome. Mol Microbiol. Oct. 2009;74(2):282-98. doi: 10.1111/j.1365- 2958.2009.06756.x. Epub Jun. 8, 2009.
Rowland et al., Sin recombinase from *Staphylococcus aureus*: synaptic complex architecture and transposon targeting. Mol Microbiol. May 2002;44(3):607-19. doi: 10.1046/j.1365-2958.2002.02897.x.
Rowley, Chromosome translocations: dangerous liaisons revisited. Nat Rev Cancer. Dec. 2001;1(3):245-50. doi: 10.1038/35106108.
Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.
Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.
Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.
Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.
Ryu et al., Adenine base editing in mouse embryos and an adult mouse model of Duchenne muscular dystrophy. Nat Biotechnol. Jul. 2018;36(6):536-539. doi: 10.1038/nbt.4148. Epub Apr. 27, 2018.
Rüfer et al., Non-contact positions impose site selectivity on Cre recombinase. Nucleic Acids Res. Jul. 1, 2002;30(13):2764-71. doi: 10.1093/nar/gkf399.
Sadelain et al., Safe harbours for the integration of new DNA in the human genome. Nat Rev Cancer. Dec. 1, 2011;12(1):51-8. doi: 10.1038/nrc3179.
Sadowski, The Flp recombinase of the 2-microns plasmid of *Saccharomyces cerevisiae*. Prog Nucleic Acid Res Mol Biol. 1995;51:53-91.
Sage et al., Proliferation of functional hair cells in vivo in the absence of the retinoblastoma protein. Science. Feb. 18, 2005;307(5712):1114-8. Epub Jan. 13, 2005.
Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.
Sale et al., Y-family DNA polymerases and their role in tolerance of cellular DNA damage. Nat Rev Mol Cell Biol. Feb. 23, 2012;13(3):141-52. doi: 10.1038/nrm3289.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Samal et al., Cationic polymers and their therapeutic potential. Chem Soc Rev. Nov. 7, 2012;41(21):7147-94. doi: 10.1039/c2cs35094g. Epub Aug. 10, 2012.
Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang et al., A unique uracil-DNA binding protein of the uracil DNA glycosylase superfamily. Nucleic Acids Res. Sep. 30, 2015;43(17):8452-63. doi: 10.1093/nar/gkv854. Epub Aug. 24, 2015.
Sang, Prospects for transgenesis in the chick. Mech Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Santoro et al., Directed evolution of the site specificity of Cre recombinase. Proc Natl Acad Sci U S A. Apr. 2, 2002;99(7):4185-90. Epub Mar. 19, 2002.
Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

(56) References Cited

OTHER PUBLICATIONS

Sapunar et al., Dorsal root ganglion—a potential new therapeutic target for neuropathic pain. J Pain Res. 2012;5:31-8. doi: 10.2147/JPR.S26603. Epub Feb. 16, 2012.

Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.

Sarkar et al., HIV-1 proviral DNA excision using an evolved recombinase. Science. Jun. 29, 2007;316(5833):1912-5. doi: 10.1126/science.1141453.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Sasidharan et al., The selection of acceptable protein mutations. PNAS; Jun. 12, 2007;104(24):10080-5. www.pnas.org/cgi/doi/10.1073.pnas.0703737104.

Satomura et al., Precise genome-wide base editing by the CRISPR Nickase system in yeast. Sci Rep. May 18, 2017;7(1):2095. doi: 10.1038/s41598-017-02013-7.

Saudek et al., A preliminary trial of the programmable implantable medication system for insulin delivery. N Engl J Med. Aug. 31, 1989;321(9):574-9.

Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.

Savic et al., Covalent linkage of the DNA repair template to the CRISPR-Cas9 nuclease enhances homology-directed repair. Elife. May 29, 2018;7:e33761. doi: 10.7554/eLife.33761.

Saville et al., A site-specific self-cleavage reaction performed by a novel RNA in Neurospora mitochondria. Cell. May 18, 1990;61(4):685-96. doi: 10.1016/0092-8674(90)90480-3.

Savva et al., The structural basis of specific base-excision repair by uracil-DNA glycosylase. Nature. Feb. 9, 1995;373(6514):487-93. doi: 10.1038/373487a0.

Schaaper et al., Base selection, proofreading, and mismatch repair during DNA replication in *Escherichia coli*. J Biol Chem. Nov. 15, 1993;268(32):23762-5.

Schaaper et al., Spectra of spontaneous mutations in Escherichia coli strains defective in mismatch correction: the nature of in vivo DNA replication errors. Proc Natl Acad Sci U S A. Sep. 1987;84(17):6220-4.

Schaefer et al., Understanding RNA modifications: the promises and technological bottlenecks of the 'epitranscriptome'. Open Biol. May 2017;7(5):170077. doi: 10.1098/rsob.170077.

Schechner et al., Multiplexable, locus-specific targeting of long RNAs with CRISPR-Display. Nat Methods. Jul. 2015; 12(7):664-70. doi: 10.1038/nmeth.3433. Epub Jun. 1, 2015.

Schechner et al., Multiplexable, locus-specific targeting of long RNAs with CRISPR-Display. Nat Methods. Jul. 2015; 12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.

Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.

Schellenberger et al., A recombinant polypeptide extends the in vivo half-life of peptides and proteins in a tunable manner. Nat Biotechnol. Dec. 2009;27(12):1186-90. doi: 10.1038/nbt.1588.

Schenk et al., MPDU1 mutations underlie a novel human congenital disorder of glycosylation, designated type If. J Clin Invest. Dec. 2001; 108(11):1687-95. doi: 10.1172/JCI13419.

Schmitz et al., Behavioral abnormalities in prion protein knockout mice and the potential relevance of PrP(C) for the cytoskeleton. Prion. 2014;8(6):381-6. doi: 10.4161/19336896.2014.983746.

Schneider et al., NIH Image to ImageJ: 25 years of image analysis. Nat Methods. Jul. 2012;9(7):671-5.

Schriefer et al., Low pressure DNA shearing: a method for random DNA sequence analysis. Nucleic Acids Res. Dec. 25, 1990;18(24):7455-6.

Schultz et al., Expression and secretion in yeast of a 400-kDa envelope glycoprotein derived from Epstein-Barr virus. Gene. 1987;54(1):113-23. doi: 10.1016/0378-1119(87)90353-2.

Schultz et al., Oligo-2'-fluoro-2'-deoxynucleotide N3' -- >P5' phosphoramidates: synthesis and properties. Nucleic Acids Res. Aug. 1, 1996;24(15):2966-73.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schwartz et al., Post-translational enzyme activation in an animal via optimized conditional protein splicing. Nat Chem Biol. Jan. 2007;3(1):50-4. Epub Nov. 26, 2006.

Schwarze et al., In vivo protein transduction: delivery of a biologically active protein into the mouse. Science. Sep. 3, 1999;285(5433):1569-72.

Schöller et al., Interactions, localization, and phosphorylation of the m6A generating METTL3-METTL14-WTAP complex. RNA. Apr. 2018;24(4):499-512. doi: 10.1261/rna.064063.117. Epub Jan. 18, 2018.

Sclimenti et al., Directed evolution of a recombinase for improved genomic integration at a native human sequence. Nucleic Acids Res. Dec. 15, 2001;29(24):5044-51.

Scott et al., Production of cyclic peptides and proteins in vivo. Proc Natl Acad Sci U S A. Nov. 23, 1999;96(24):13638-43. doi: 10.1073/pnas.96.24.13638.

Sebastián-Martín et al., Transcriptional inaccuracy threshold attenuates differences in RNA-dependent DNA synthesis fidelity between retroviral reverse transcriptases. Sci Rep. Jan. 12, 2018;8(1):627. doi: 10.1038/s41598-017-18974-8.

Seed, An LFA-3 cDNA encodes a phospholipid-linked membrane protein homologous to its receptor CD2. Nature. Oct. 29-Nov. 4, 1987;329(6142):840-2. doi: 10.1038/329840a0.

Sefton et al., Implantable pumps. Crit Rev Biomed Eng. 1987;14(3):201-40.

Segal et al., Evaluation of a modular strategy for the construction of novel polydactyl zinc finger DNA-binding proteins. Biochemistry. Feb. 25, 2003;42(7):2137-48.

Segal et al., Toward controlling gene expression at will: selection and design of zinc finger domains recognizing each of the 5'-GNN-3' Dna target sequences. Proc Natl Acad Sci U S A. Mar. 16, 1999;96(6):2758-63.

Sells et al., Delivery of protein into cells using polycationic liposomes. Biotechniques. Jul. 1995;19(1):72-6, 78.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Semple et al., Rational design of cationic lipids for siRNA delivery. Nat Biotechnol. Feb. 2010;28(2):172-6. doi: 10.1038/nbt.1602. Epub Jan. 17, 2010.

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.

Serganov et al., Structural basis for discriminative regulation of gene expression by adenine- and guanine-sensing mRNAs. Chem Biol. Dec. 2004; 11(12):1729-41.

Serganov et al., Structural basis for gene regulation by a thiamine pyrophosphate-sensing riboswitch. Nature. Jun. 29, 2006;441(7097):1167-71. Epub May 21, 2006.

Seripa et al., The missing ApoE allele. Ann Hum Genet. Jul. 2007;71(Pt 4):496-500. Epub Jan. 22, 2007.

Serrano-Heras et al., Protein p56 from the Bacillus subtilis phage phi29 inhibits DNA- binding ability of uracil-DNA glycosylase. Nucleic Acids Res. 2007;35(16):5393-401. Epub Aug. 13, 2007.

Severinov et al., Expressed protein ligation, a novel method for studying protein-protein interactions in transcription. J Biol Chem. Jun. 26, 1998;273(26):16205-9. doi: 10.1074/jbc.273.26.16205.

Sha et al., Monobodies and other synthetic binding proteins for expanding protein science. Protein Sci. May 2017;26(5):910-924. doi: 10.1002/pro.3148. Epub Mar. 24, 2017.

(56) References Cited

OTHER PUBLICATIONS

Shah et al., Inteins: nature's gift to protein chemists. Chem Sci. 2014;5(1):446-461.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.
Shah et al., Protospacer recognition motifs: mixed identities and functional diversity. RNA Biol. May 2013;10(5):891-9. doi: 10.4161/rna.23764. Epub Feb. 12, 2013.
Shah et al., Target-specific variants of Flp recombinase mediate genome engineering reactions in mammalian cells. Febs J. Sep. 2015;282(17):3323-33. doi: 10.1111/febs.13345. Epub Jul. 1, 2015.
Shaikh et al., Chimeras of the Flp and Cre recombinases: tests of the mode of cleavage by Flp and Cre. J Mol Biol. Sep. 8, 2000;302(1):27-48.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Shalem et al., High-throughput functional genomics using CRISPR-Cas9. Nat Rev Genet. May 2015;16(5):299-311. doi: 10.1038/nrg3899. Epub Apr. 9, 2015.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharma et al., Efficient introduction of aryl bromide functionality into proteins in vivo. FEBS Lett. Feb. 4, 2000;467(1):37-40.
Sharon et al., Functional Genetic Variants Revealed by Massively Parallel Precise Genome Editing. Cell. Oct. 4, 2018;175(2):544-557.e16. doi: 10.1016/j.cell.2018.08.057. Epub Sep. 20, 2018.
Shaw et al., Implications of human genome architecture for rearrangement-based disorders: the genomic basis of disease. Hum Mol Genet. Apr. 1, 2004;13 Spec No. 1:R57-64. doi: 10.1093/hmg/ddh073. Epub Feb. 5, 2004.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shee et al., Engineered proteins detect spontaneous DNA breakage in human and bacterial cells. Elife. Oct. 29, 2013;2:e01222. doi: 10.7554/eLife.01222.
Shen et al., Herpes simplex virus 1 (HSV-1) for cancer treatment. Cancer Gene Ther. Nov. 2006;13(11):975-92. doi: 10.1038/sj.cgt.7700946. Epub Apr. 7, 2006.
Shen et al., Predictable and precise template-free CRISPR editing of pathogenic variants. Nature. Nov. 2018;563(7733):646-651. doi: 10.1038/s41586-018-0686-x. Epub Nov. 7, 2018. Erratum in: Nature. Mar. 2019;567(7746):E1-E2.
Shen, Data processing, Modeling and Analysis scripts for CRISPR-inDelphi. GitHub—maxwshen/indelphi-dataprocessinganalysis at 6b68e3cec73c9358fef6e5f178a935f3c2a4118f. Apr. 10, 2018. Retrieved online via https://github.com/maxwshen/indelphi-sataprocessinganalysis/tree/6b68e3cec73c9358fef6e5f178a935f3c2a4118f Last retrieved on Jul. 26, 2021. 2 pages.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.
Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.
Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimizu et al., Adding fingers to an engineered zinc finger nuclease can reduce activity. Biochemistry. Jun. 7, 2011;50(22):5033-41. doi: 10.1021/bi200393g. Epub May 11, 2011.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.
Shin et al., CRISPR/Cas9 targeting events cause complex deletions and insertions at 17 sites in the mouse genome. Nat Commun. May 31, 2017;8:15464. doi: 10.1038/ncomms15464.
Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.
Shingledecker et al., Molecular dissection of the *Mycobacterium tuberculosis* RecA intein: design of a minimal intein and of a trans-splicing system involving two intein fragments. Gene. Jan. 30, 1998;207(2):187-95. doi: 10.1016/s0378-1119(97)00624-0.
Shmakov et al., Discovery and Functional Characterization of Diverse Class 2 CRISPR Cas Systems. Molecular Cell Nov. 2015;60(3):385-97.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.
Shultz et al., A genome-wide analysis of FRT-like sequences in the human genome. PLoS One. Mar. 23, 2011;6(3):e18077. doi: 10.1371/journal.pone.0018077.
Siebert et al., An improved PCR method for walking in uncloned genomic DNA. Nucleic Acids Res. Mar. 25, 1995;23(6): 1087-8.
Silas et al., Direct CRISPR spacer acquisition from RNA by a natural reverse transcriptase-Cas1 fusion protein. Science. Feb. 26, 2016;351(6276):aad4234. doi: 10.1126/science.aad4234.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Simonelli et al., Base excision repair intermediates are mutagenic in mammalian cells. Nucleic Acids Res. Aug. 2, 2005;33(14):4404-11. Print 2005.
Singh et al., Cross-talk between diverse serine integrases. J Mol Biol. Jan. 23, 2014;426(2):318- 31. doi: 10.1016/j.jmb.2013.10.013. Epub Oct. 22, 2013.
Singh et al., Real-time observation of DNA recognition and rejection by the RNA-guided endonuclease Cas9. Nat Commun. Sep. 14, 2016;7:12778. doi: 10.1038/ncomms12778.
Singh et al., Real-time observation of DNA target interrogation and product release by the RNA-guided endonuclease CRISPR Cpf1 (Cas12a). Proc Natl Acad Sci U S A. May 22, 2018;115(21):5444-5449. doi: 10.1073/pnas.1718686115. Epub May 7, 2018.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005; 14(2):523-32. Epub Jan. 4, 2005.
Slaymaker et al., Rationally engineered Cas9 nucleases with improved specificity. Science. Jan. 1, 2016;351(6268):84-8. doi: 10.1126/science.aad5227. Epub Dec. 1, 2015.
Sledz et al., Structural insights into the molecular mechanism of the m(6)A writer complex. Elife. Sep. 14, 2016;5:e18434. doi: 10.7554/eLife.18434.

(56) References Cited

OTHER PUBLICATIONS

Slupphaug et al., A nucleotide-flipping mechanism from the structure of human uracil-DNA glycosylase bound to DNA. Nature. Nov. 7, 1996;384(6604):87-92. doi: 10.1038/384087a0.
Smargon et al., Cas13b Is a Type VI-B CRISPR-Associated RNA-Guided RNase Differentially Regulated by Accessory Proteins Csx27 and Csx28. Mol Cell. Feb. 16, 2017;65(4):618-630.e7. doi: 10.1016/j.molcel.2016.12.023. Epub Jan. 5, 2017.
Smith et al., Diversity in the serine recombinases. Mol Microbiol. Apr. 2002;44(2):299-307. Review.
Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.
Smith et al., Herpesvirus transport to the nervous system and back again. Annu Rev Microbiol. 2012;66:153-76. doi: 10.1146/annurev-micro-092611-150051. Epub Jun. 15, 2012.
Smith et al., Production of human beta interferon in insect cells infected with a baculovirus expression vector. Mol Cell Biol. Dec. 1983;3(12):2156-65. doi: 10.1128/mcb.3.12.2156.
Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.
Smith, Filamentous fusion phage: novel expression vectors that display cloned antigens on the virion surface. Science. Jun. 1, 19854;228(4705): 1315-7.
Smith, Phage-encoded Serine Integrases and Other Large Serine Recombinases. Microbiol Spectr. Aug. 2015;3(4). doi: 10.1128/microbiolspec.MDNA3-0059-2014.
Sommerfelt et al., Receptor interference groups of 20 retroviruses plating on human cells. Virology. May 1990;176(1):58-69. doi: 10.1016/0042-6822(90)90230-o.
Song et al., Antibody mediated in vivo delivery of small interfering RNAs via cell-surface receptors. Nat Biotechnol. Jun. 2005;23(6):709-17. Epub May 22, 2005.
Southworth et al., Control of protein splicing by intein fragment reassembly. Embo J. Feb. 16, 1998;17(4):918-26. doi: 10.1093/emboj/17.4.918.
Southworth et al., Purification of proteins fused to either the amino or carboxy terminus of the *Mycobacterium xenopi* gyrase A intein. Biotechniques. Jul. 1999;27(1):110-4, 116, 118-20. doi: 10.2144/99271st04.
Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.
Spencer et al., Controlling signal transduction with synthetic ligands. Science. Nov. 12, 1993;262(5136):1019-24. doi: 10.1126/science.7694365.
Spencer et al., Functional analysis of Fas signaling in vivo using synthetic inducers of dimerization. Curr Biol. Jul. 1, 1996;6(7):839-47. doi: 10.1016/s0960-9822(02)00607-3.
Srivastava et al., An inhibitor of nonhomologous end-joining abrogates double-strand break repair and impedes cancer progression. Cell. Dec. 21, 2012;151(7):1474-87. doi: 10.1016/j.cell.2012.11.054.
Stadtman, Selenocysteine. Annu Rev Biochem. 1996;65:83-100.
Stamos et al., Structure of a Thermostable Group II Intron Reverse Transcriptase with Template-Primer and Its Functional and Evolutionary Implications. Mol Cell. Dec. 7, 2017;68(5):926-939.e4. doi: 10.1016/j.molcel.2017.10.024. Epub Nov. 16, 2017.
Steele et al., The prion protein knockout mouse: a phenotype under challenge. Prion. Apr.-Jun. 2007;1(2):83-93. doi: 10.4161/pri.1.2.4346. Epub Apr. 25, 2007.
Steiner et al., The neurotropic herpes viruses: herpes simplex and varicella-zoster. Lancet Neurol. Nov. 2007;6(11):1015-28. doi: 10.1016/S1474-4422(07)70267-3.
Stella et al., Structure of the Cpf1 endonuclease R-loop complex after target DNA cleavage. Nature. Jun. 22, 2017;546(7659):559-563. doi: 10.1038/nature22398. Epub May 31, 2017.
Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.
Stenson et al., The Human Gene Mutation Database: towards a comprehensive repository of inherited mutation data for medical research, genetic diagnosis and next-generation sequencing studies. Hum Genet. Jun. 2017;136(6):665-677. doi: 10.1007/s00439-017-1779-6. Epub Mar. 27, 2017.
Stephens et al., The landscape of cancer genes and mutational processes in breast cancer. Nature Jun. 2012;486:400-404. doi: 10.1038/nature11017.
Sternberg et al., Conformational control of DNA target cleavage by CRISPR-Cas9. Nature. Nov. 5, 2015;527(7576):110-3. doi: 10.1038/nature15544. Epub Oct. 28, 2015.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.
Sterne-Weiler et al., Exon identity crisis: disease-causing mutations that disrupt the splicing code. Genome Biol. Jan. 23, 2014;15(1):201. doi: 10.1186/gb4150.
Stevens et al., A promiscuous split intein with expanded protein engineering applications. Proc Natl Acad Sci U S A. Aug. 8, 2017;114(32):8538-8543. doi: 10.1073/pnas.1701083114. Epub Jul. 24, 2017.
Stevens et al., Design of a Split Intein with Exceptional Protein-Splicing Activity. J Am Chem Soc. Feb. 26, 2016;138(7):2162-5. doi: 10.1021/jacs.5b13528. Epub Feb. 8, 2016.
Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.
Strecker et al., RNA-guided DNA insertion with CRISPR-associated transposases. Science. Jul. 5, 2019;365(6448):48-53. doi: 10.1126/science.aax9181. Epub Jun. 6, 2019.
Strutt et al., RNA-dependent RNA targeting by CRISPR-Cas9. Elife. Jan. 5, 2018;7:e32724. doi: 10.7554/eLife.32724.
Su et al., Human DNA polymerase η has reverse transcriptase activity in cellular environments. J Biol Chem. Apr. 12, 2019;294(15):6073-6081. doi: 10.1074/jbc.RA119.007925. Epub Mar. 6, 2019.
Sudarsan et al., An mRNA structure in bacteria that controls gene expression by binding lysine. Genes Dev. Nov. 1, 2003;17(21):2688-97.
Sudarsan et al., Riboswitches in eubacteria sense the second messenger cyclic di-GMP. Science. Jul. 18, 2008;321(5887):411-3. doi: 10.1126/science.1159519.
Suess et al., A theophylline responsive riboswitch based on helix slipping controls gene expression in vivo. Nucleic Acids Res. Mar. 5, 2004;32(4):1610-4.
Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Sun et al., The CRISPR/Cas9 system for gene editing and its potential application in pain research. Transl Periop & Pain Med. Aug. 3, 2016;1(3):22-33.
Supplementary European Search Report for Application No. EP 12845790.0, mailed Oct. 12, 2015.
Surun et al., High Efficiency Gene Correction in Hematopoietic Cells by Donor-Template- Free CRISPR/Cas9 Genome Editing. Mol Ther Nucleic Acids. Mar. 2, 2018;10:1-8. doi: 10.1016/j.omtn.2017.11.001. Epub Nov. 10, 2017.
Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.
Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.
Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.

(56) References Cited

OTHER PUBLICATIONS

Swarts et al., DNA-guided DNA interference by a prokaryotic Argonaute. Nature. Mar. 13, 2014;507(7491):258-61. doi: 10.1038/nature12971. Epub Feb. 16, 2014.

Swarts et al., The evolutionary journey of Argonaute proteins. Nat Struct Mol Biol. Sep. 2014;21(9):743-53. doi: 10.1038/nsmb.2879.

Szczepek et al., Structure-based redesign of the dimerization interface reduces the toxicity of zinc-finger nucleases. Nat Biotechnol. Jul. 2007;25(7):786-93. Epub Jul. 1, 2007.

Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.

Tagalakis et al., Lack of RNA-DNA oligonucleotide (chimeraplast) mutagenic activity in mouse embryos. Mol Reprod Dev. Jun. 2005;71(2):140-4.

Tahara et al., Potent and Selective Inhibitors of 8-Oxoguanine DNA Glycosylase. J Am Chem Soc. Feb. 14, 2018;140(6):2105-2114. doi: 10.1021/jacs.7b09316. Epub Feb. 5, 2018.

Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.

Takimoto et al., Stereochemical basis for engineered pyrrolysyl-tRNA synthetase and the efficient in vivo incorporation of structurally divergent non-native amino acids. ACS Chem Biol. Jul. 15, 2011;6(7):733-43. doi: 10.1021/cb200057a. Epub May 5, 2011.

Tambunan et al., Vaccine Design for H5N1 Based on B- and T-cell Epitope Predictions. Bioinform Biol Insights. Apr. 28, 2016;10:27-35. doi: 10.4137/BBI.S38378.

Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.

Tanese et al., Expression of enzymatically active reverse transcriptase in *Escherichia coli*. Proc Natl Acad Sci U S A. Aug. 1985;82(15):4944-8. doi: 10.1073/pnas.82.15.4944.

Tang et al., Aptazyme-embedded guide RNAs enable ligand-responsive genome editing and transcriptional activation. Nat Commun. Jun. 28, 2017;8:15939. doi: 10.1038/ncomms15939.

Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.

Tang et al., Rewritable multi-event analog recording in bacterial and mammalian cells. Science. Apr. 13, 2018;360(6385):eaap8992. doi: 10.1126/science.aap8992. Epub Feb. 15, 2018.

Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.

Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.

Tebas et al., Gene editing of CCR5 in autologous CD4 T cells of persons infected with Hiv. N Engl J Med. Mar. 6, 2014;370(10):901-10. doi: 10.1056/NEJMoa1300662.

Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.

Telenti et al., The *Mycobacterium xenopi* GyrA protein splicing element: characterization of a minimal intein. J Bacteriol. Oct. 1997;179(20):6378-82. doi: 10.1128/jb.179.20.6378-6382.1997.

Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.

Teng et al., Mutational analysis of apolipoprotein B mRNA editing enzyme (APOBEC1). structure-function relationships of RNA editing and dimerization. J Lipid Res. Apr. 1999;40(4):623-35.

Tessarollo et al., Targeted mutation in the neurotrophin-3 gene results in loss of muscle sensory neurons. Proc Natl Acad Sci U S A. Dec. 6, 1994;91(25):11844-8.

Tesson et al., Knockout rats generated by embryo microinjection of TALENs. Nat Biotechnol. Aug. 5, 2011;29(8):695-6. doi: 10.1038/nbt.1940.

Thompson et al., Cellular uptake mechanisms and endosomal trafficking of supercharged proteins. Chem Biol. Jul. 27, 2012;19(7):831-43. doi: 10.1016/j.chembiol.2012.06.014.

Thompson et al., Engineering and identifying supercharged proteins for macromolecule delivery into mammalian cells. Methods Enzymol. 2012;503:293-319. doi: 10.1016/B978-0-12-396962-0.00012-4.

Thomson et al., Mutational analysis of loxP sites for efficient Cre-mediated insertion into genomic DNA. Genesis. Jul. 2003;36(3):162-7. doi: 10.1002/gene.10211.

Thorpe et al., Functional correction of episomal mutations with short DNA fragments and RNA-DNA oligonucleotides. J Gene Med. Mar.-Apr. 2002;4(2):195-204.

Thuronyi et al., Continuous evolution of base editors with expanded target compatibility and improved activity. Nat Biotechnol. Sep. 2019;37(9):1070-1079. doi: 10.1038/s41587-019-0193-0. Epub Jul. 22, 2019.

Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.

Thyagarajan et al., Mammalian genomes contain active recombinase recognition sites. Gene. Feb. 22, 2000;244(1-2):47-54.

Thyagarajan et al., Site-specific genomic integration in mammalian cells mediated by phage phiC31 integrase. Mol Cell Biol. Jun. 2001;21(12):3926-34.

Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.

Tirumalai et al., Recognition of core-type DNA sites by lambda integrase. J Mol Biol. Jun. 12, 1998;279(3):513-27.

Tom et al., Mechanism whereby proliferating cell nuclear antigen stimulates flap endonuclease 1. J Biol Chem. Apr. 7, 2000;275(14):10498-505. doi: 10.1074/jbc.275.14.10498.

Tone et al., Single-stranded DNA binding protein Gp5 of Bacillus subtilis phage ?29 is required for viral DNA replication in growth-temperature dependent fashion. Biosci Biotechnol Biochem. 2012;76(12):2351-3. doi: 10.1271/bbb.120587. Epub Dec. 7, 2012.

Toor et al., Crystal structure of a self-spliced group II intron. Science. Apr. 4, 2008;320(5872):77-82. doi: 10.1126/science.1153803.

Toro et al., On the Origin and Evolutionary Relationships of the Reverse Transcriptases Associated With Type III CRISPR-Cas Systems. Front Microbiol. Jun. 15, 2018;9:1317. doi: 10.3389/fmicb.2018.01317.

Toro et al., The Reverse Transcriptases Associated with CRISPR-Cas Systems. Sci Rep. Aug. 2, 2017;7(1):7089. doi: 10.1038/s41598-017-07828-y.

Torres et al., Non-integrative lentivirus drives high-frequency cre-mediated cassette exchange in human cells. PLoS One. 2011;6(5):e19794. doi: 10.1371/journal.pone.0019794. Epub May 23, 2011.

Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.

Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.

Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6. Erratum in: Lancet Jul. 13, 2002;360(9327):176.

Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.

(56) References Cited

OTHER PUBLICATIONS

Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.
Tratschin et al., Adeno-associated virus vector for high-frequency integration, expression, and rescue of genes in mammalian cells. Mol Cell Biol. Nov. 1985;5(11):3251-60. doi: 10.1128/mcb.5.11. 3251.
Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Traxler et al., A genome-editing strategy to treat ?-hemoglobinopathies that recapitulates a mutation associated with a benign genetic condition. Nat Med. Sep. 2016;22(9):987-90. doi: 10.1038/nm. 4170. Epub Aug. 15, 2016.
Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.
Tsai et al., CIRCLE-seq: a highly sensitive in vitro screen for genome-wide CRISPR-Cas9 nuclease off-targets. Nat Methods. Jun. 2017; 14(6):607-614. doi: 10.1038/nmeth.4278. Epub May 1, 2017.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Tsang et al., Specialization of the DNA-cleaving activity of a group I ribozyme through in vitro evolution. J Mol Biol. Sep. 13, 1996;262(1):31-42. doi: 10.1006/jmbi.1996.0496.
Tsutakawa et al., Human flap endonuclease structures, DNA double-base flipping, and a unified understanding of the FEN1 superfamily. Cell. Apr. 15, 2011;145(2): 198-211. doi: 10.1016/j.cell.2011.03. 004.
Turan et al., Recombinase-mediated cassette exchange (RMCE) - a rapidly-expanding toolbox for targeted genomic modifications. Gene. Feb. 15, 2013;515(1):1-27. doi: 10.1016/j.gene.2012.11.016. Epub Nov. 29, 2012.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Turan et al., Site-specific recombinases: from tag-and-target- to tag-and-exchange-based genomic modifications. Faseb J. Dec. 2011;25(12):4088-107. doi: 10.1096/fj.11-186940. Epub Sep. 2, 2011. Review.
Tycko et al., Pairwise library screen systematically interrogates *Staphylococcus aureus* Cas9 specificity in human cells. bioRxiv. doi: https://doi.org/10.1101/269399 Posted Feb. 22, 2018.
Tyszkiewicz et al., Activation of protein splicing with light in yeast. Nat Methods. Apr. 2008;5(4):303-5. doi: 10.1038/nmeth.1189. Epub Feb. 13, 2008.
UniProt Consortium, UniProt: the universal protein knowledgebase. Nucleic Acids Res. Mar. 16, 2018;46(5):2699. doi: 10.1093/nar/gky092.
UniProt Submission; UniProt, Accession No. P01011. Last modified Jun. 11, 2014, version 2. 15 pages.
UniProt Submission; UniProt, Accession No. P01011. Last modified Sep. 18, 2013, version 2. 15 pages.
UniProt Submission; UniProt, Accession No. P04264. Last modified Jun. 11, 2014, version 6. 15 pages.
UniProt Submission; UniProt, Accession No. P04275. Last modified Jul. 9, 2014, version 107. 29 pages.
UniProTKB Submission; Accession No. FONH53. May 3, 2011. 4 pages.
UniProTKB Submission; Accession No. FONN87. May 3, 2011. 4 pages.
UniProTKB Submission; Accession No. G3ECR1.2. No Author Listed., Aug. 12, 2020, 8 pages.
UniProTKB Submission; Accession No. P04264. No Author Listed., Apr. 7, 2021. 12 pages.
UniProTKB Submission; Accession No. PODOC6. No Author Listed., Oct. 5, 2016. 5 pages.
UniProTKB Submission; Accession No. TOD7A2. Oct. 16, 2013. 10 pages.
UniProTKB Submission; Accession No. U2UMQ6. No Author Listed., Apr. 7, 2021, 11 pages.
Urasaki et al., Functional dissection of the Tol2 transposable element identified the minimal cis-sequence and a highly repetitive sequence in the subterminal region essential for transposition. Genetics. Oct. 2006;174(2):639-49. doi: 10.1534/genetics.106. 060244. Epub Sep. 7, 2006.
Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Vagner et al., Efficiency of homologous DNA recombination varies along the Bacillus subtilis chromosome. J Bacteriol. Sep. 1988;170(9):3978-82.
Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem. 5b00359. Epub Sep. 11, 2015.
Van Brunt et al., Molecular Farming: Transgenic Animals as Bioreactors. Biotechnology (NY). 1988;6(10):1149-1154. doi: 10.1038/nbt1088-1149.
Van Duyne et al., Teaching Cre to follow directions. Proc Natl Acad Sci U S A. Jan. 6, 2009;106(1):4-5. doi: 10.1073/pnas.0811624106. Epub Dec. 31, 2008.
Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.
Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.
Van Wijk et al., Identification of 51 novel exons of the Usher syndrome type 2A (USH2A) gene that encode multiple conserved functional domains and that are mutated in patients with Usher syndrome type II. Am J Hum Genet. Apr. 2004;74(4):738-44. doi: 10.1086/383096. Epub Mar. 10, 2004.
Vanamee et al., FokI requires two specific DNA sites for cleavage. J Mol Biol. May 25, 2001;309(1):69-78.
Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas. 0600012103. Epub Feb. 21, 2006.
Vasey et al., Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee.
Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.
Venken et al., Genome-wide manipulations of Drosophila melanogaster with transposons, Flp recombinase, and ΦC31 integrase. Methods Mol Biol. 2012;859:203-28. doi: 10.1007/978-1-61779-603-6_12.
Verma, The reverse transcriptase. Biochim Biophys Acta. Mar. 21, 1977;473(1):1-38. doi: 10.1016/0304-419x(77)90005-1.

(56) References Cited

OTHER PUBLICATIONS

Vigne et al., Third-generation adenovectors for gene therapy. Restor Neurol Neurosci. Jan. 1, 1995;8(1):35-6. doi: 10.3233/RNN-1995-81208.
Vik et al., Endonuclease V cleaves at inosines in RNA. Nat Commun. 2013;4:2271. doi: 10.1038/ncomms3271.
Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas.2135498100. Epub Oct. 17, 2003.
Vitreschak et al., Regulation of the vitamin B12 metabolism and transport in bacteria by a conserved RNA structural element. RNA. Sep. 2003;9(9):1084-97.
Voigt et al., Rational evolutionary design: the theory of in vitro protein evolution. Adv Protein Chem. 2000;55:79-160.
Vriend et al., Nick-initiated homologous recombination: Protecting the genome, one strand at a time. DNA Repair (Amst). Feb. 2017;50:1-13. doi: 10.1016/j.dnarep.2016.12.005. Epub Dec. 29, 2016.
Wacey et al., Disentangling the perturbational effects of amino acid substitutions in the DNA-binding domain of p53. Hum Genet. Jan. 1999; 104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wah et al., Structure of FokI has implications for DNA cleavage. Proc Natl Acad Sci U S A. Sep. 1, 1998;95(18):10564-9.
Wals et al., Unnatural amino acid incorporation in E. coli: current and future applications in the design of therapeutic proteins. Front Chem. Apr. 1, 2014;2:15. doi: 10.3389/fchem.2014.00015. eCollection 2014.
Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.
Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.
Wang et al., Continuous directed evolutions of proteins with improved soluble expression. Nature Chemical Biology. Nat Publishing Group. Aug. 20, 2018; 14(10):972-980.
Wang et al., CRISPR-Cas9 Targeting of PCSK9 in Human Hepatocytes In Vivo-Brief Report. Arterioscler Thromb Vasc Biol. May 2016;36(5):783-6. doi: 10.1161/ATVBAHA.116.307227. Epub Mar. 3, 2016.
Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Enhanced base editing by co-expression of free uracil DNA glycosylase inhibitor. Cell Res. Oct. 2017;27(1):1289-92. doi: 10.1038/cr.2017.111. Epub Aug. 29, 2017.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Expanding the genetic code. Annu Rev Biophys Biomol Struct. 2006;35:225-49. Review.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., Highly efficient CRISPR/HDR-mediated knock-in for mouse embryonic stem cells and zygotes. Biotechniques. 2015:59,201-2;204;206-8.
Wang et al., N(6)-methyladenosine Modulates Messenger RNA Translation Efficiency. Cell. Jun. 4, 2015;161(6):1388-99. doi: 10.1016/j.cell.2015.05.014.
Wang et al., N6-methyladenosine-dependent regulation of messenger RNA stability. Nature. Jan. 2, 2014;505(7481):117-20. doi: 10.1038/nature12730. Epub Nov. 27, 2013.
Wang et al., Neutralizing antibodies to therapeutic enzymes: considerations for testing, prevention and treatment. Nat Biotechnol. Aug. 2008;26(8):901-8. doi: 10.1038/nbt.1484.
Wang et al., Nucleation, propagation and cleavage of target RNAs in Ago silencing complexes. Nature. Oct. 8, 2009;461(7265):754-61. doi: 10.1038/nature08434.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Optimized paired-sgRNA/Cas9 cloning and expression cassette triggers high-efficiency multiplex genome editing in kiwifruit. Plant Biotechnol J. Aug. 2018;16(8):1424-1433. doi: 10.1111/pbi.12884. Epub Feb. 6, 2018.
Wang et al., Programming cells by multiplex genome engineering and accelerated evolution. Nature. Aug. 13, 2009;460(7257):894-8. Epub Jul. 26, 2009.
Wang et al., Reading RNA methylation codes through methyl-specific binding proteins. RNA Biol. 2014;11(6):669-72. doi: 10.4161/rna.28829. Epub Apr. 24, 2014.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.
Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.
Wang et al., Structural basis of N(6)-adenosine methylation by the METTL3-METTL14 complex. Nature. Jun. 23, 2016;534(7608):575-8. doi: 10.1038/nature18298. Epub May 25, 2016.
Wang et al., Targeted gene addition to a predetermined site in the human genome using a ZFN- based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.
Warren et al., A chimeric Cre recombinase with regulated directionality. Proc Natl Acad Sci USA. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Watowich, The erythropoietin receptor: molecular structure and hematopoietic signaling pathways. J Investig Med. Oct. 2011;59(7):1067-72. doi: 10.2310/JIM.0b013e31820fb28c.
Waxman et al., Regulating excitability of peripheral afferents: emerging ion channel targets. Nat Neurosci. Feb. 2014;17(2):153-63. doi: 10.1038/nn.3602. Epub Jan. 28, 2014.
Weber et al., Assembly of designer TAL effectors by Golden Gate cloning. PLoS One. 2011;6(5):e19722. doi: 10.1371/journal.pone.0019722. Epub May 19, 2011.
Weill et al., DNA polymerases in adaptive immunity. Nat Rev Immunol. Apr. 2008;8(4):302- 12. doi: 10.1038/nri2281. Epub Mar. 14, 2008.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human ClC-1 chloride channels in myotonia congenita. J Physiol. Aug. 1, 2012;590(Pt 15):3449-64. doi: 0.1113/jphysiol.2012.232785. Epub May 28, 2012.

(56) References Cited

OTHER PUBLICATIONS

Weiss et al., Loss-of-function mutations in sodium channel Nav1.7 cause anosmia. Nature. Apr. 14, 2011;472(7342):186-90. doi: 10.1038/nature09975. Epub Mar. 23, 2011.

Wen et al., Inclusion of a universal tetanus toxoid CD4(+) T cell epitope P2 significantly enhanced the immunogenicity of recombinant rotavirus ?VP8* subunit parenteral vaccines. Vaccine. Jul. 31, 2014;32(35):4420-4427. doi: 10.1016/j.vaccine.2014.06.060. Epub Jun. 21, 2014.

West et al., Gene expression in adeno-associated virus vectors: the effects of chimeric mRNA structure, helper virus, and adenovirus VA1 RNA. Virology. Sep. 1987;160(1):38-47. doi: 10.1016/0042-6822(87)90041-9.

Wharton et al., A new-specificity mutant of 434 repressor that defines an amino acid-base pair contact. Nature. Apr. 30-May 6, 1987;326(6116):888-91.

Wharton et al., Changing the binding specificity of a repressor by redesigning an alpha-helix. Nature. Aug. 15-21, 1985;316(6029):601-5.

Wheeler et al., The thermostability and specificity of ancient proteins. Curr Opin Struct Biol. Jun. 2016;38:37-43. doi: 10.1016/j.sbi.2016.05.015. Epub Jun. 9, 2016.

Wiedenheft et al., RNA-guided genetic silencing systems in bacteria and archaea. Nature. Feb. 15, 2012;482(7385):331-8. doi: 10.1038/nature10886. Review.

Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.

Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.

Wijnker et al., Managing meiotic recombination in plant breeding. Trends Plant Sci. Dec. 2008;13(12):640-6. doi: 10.1016/j.tplants.2008.09.004. Epub Oct. 22, 2008.

Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.

Wilson et al., Assessing annotation transfer for genomics: quantifying the relations between protein sequence, structure and function through traditional and probabilistic scores. J Mol Biol 2000;297:233-49.

Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.

Wilson et al., In Vitro Selection of Functional Nucleic Acids. Annu Rev Biochem. 1999;68:611-47. doi: 10.1146/annurev.biochem.68.1.611.

Wilson et al., Kinase dynamics. Using ancient protein kinases to unravel a modern cancer drug's mechanism. Science. Feb. 20, 2015;347(6224):882-6. doi: 10.1126/science.aaa1823.

Winkler et al., An mRNA structure that controls gene expression by binding FMN. Proc Natl Acad Sci U S A. Dec. 10, 2002;99(25):15908-13. Epub Nov. 27, 2002.

Winkler et al., An mRNA structure that controls gene expression by binding S-adenosylmethionine. Nat Struct Biol.Sep. 2003;10(9):701-7. Epub Aug. 10, 2003.

Winkler et al., Control of gene expression by a natural metabolite-responsive ribozyme. Nature. Mar. 18, 2004;428(6980):281-6.

Winkler et al., Thiamine derivatives bind messenger RNAs directly to regulate bacterial gene expression. Nature. Oct. 31, 2002;419(6910):952-6. Epub Oct. 16, 2002.

Winoto et al., A novel, inducible and T cell-specific enhancer located at the 3' end of the T cell receptor alpha locus. Embo J. Mar. 1989;8(3):729-33.

Winter et al., Drug Development. Phthalimide conjugation as a strategy for in vivo target protein degradation. Science. Jun. 19, 2015;348(6241):1376-81. doi:; 10.1126/science.aab1433. Epub May 21, 2015.

Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1.61.

Wolf et al., tadA, an essential tRNA-specific adenosine deaminase from *Escherichia coli*. EMBO J. Jul. 15, 2002;21(14):3841-51.

Wolfe et al., Analysis of zinc fingers optimized via phage display: evaluating the utility of a recognition code. J Mol Biol. Feb. 5, 1999;285(5):1917-34.

Wong et al., A statistical analysis of random mutagenesis methods used for directed protein evolution. J Mol Biol. Jan. 27, 2006;355(4):858-71. Epub Nov. 17, 2005.

Wong et al., The Diversity Challenge in Directed Protein Evolution. Comb Chem High Throughput Screen. May 2006;9(4):271-88.

Wood et al., A genetic system yields self-cleaving inteins for bioseparations. Nat Biotechnol. Sep. 1999;17(9):889-92. doi: 10.1038/12879.

Wood et al., Targeted genome editing across species using ZFNs and TALENs. Science. Jul. 15, 2011;333(6040):307. doi: 10.1126/science.1207773. Epub Jun. 23, 2011.

Woods et al., The phenotype of congenital insensitivity to pain due to the NaV1.9 variant p.L811P. Eur J Hum Genet. May 2015;23(5):561-3. doi: 10.1038/ejhg.2014.166. Epub Aug. 13, 2014.

Wright et al., Continuous in vitro evolution of catalytic function. Science. Apr. 25, 1997;276(5312):614-7.

Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.

Wu et al., Correction of a genetic disease in mouse via use of CRISPR-Cas9. Cell Stem Cell. Dec. 5, 2013;13(6):659-62. doi: 10.1016/j.stem.2013.10.016.

Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.

Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.

Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.

Wu et al., Protein trans-splicing by a split intein encoded in a split DnaE gene of *Synechocystis* sp. PCC6803. Proc Natl Acad Sci U S A. Aug. 4, 1998;95(16):9226-31. doi: 10.1073/pnas.95.16.9226.

Wu et al., Readers, writers and erasers of N6-methylated adenosine modification. Curr Opin Struct Biol. Dec. 2017;47:67-76. doi: 10.1016/j.sbi.2017.05.011. Epub Jun. 16, 2017.

Xiang et al., RNA m6A methylation regulates the ultraviolet-induced DNA damage response. Nature. Mar. 23, 2017;543(7646):573-576. doi: 10.1038/nature21671. Epub Mar. 15, 2017.

Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.

Xiao et al., Nuclear m(6)A Reader YTHDC1 Regulates mRNA Splicing. Mol Cell. Feb. 18, 2016;61(4):507-519. doi: 10.1016/j.molcel.2016.01.012. Epub Feb. 11, 2016.

Xie et al., Adjusting the attB site in donor plasmid improves the efficiency of ?C31 integrase system. DNA Cell Biol. Jul. 2012;31(7):1335-40. doi: 10.1089/dna.2011.1590. Epub Apr. 10, 2012.

Xiong et al., Origin and evolution of retroelements based upon their reverse transcriptase sequences. EMBO J. Oct. 1990;9(10):3353-62.

Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.

(56) References Cited

OTHER PUBLICATIONS

Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.

Xu et al., Protein splicing: an analysis of the branched intermediate and its resolution by succinimide formation. EMBO J. Dec. 1, 1994;13(23):5517-22.

Xu et al., PTMD: A Database of Human Disease-associated Post-translational Modifications. Genomics Proteomics Bioinformatics. Aug. 2018; 16(4):244-251. doi: 10.1016/j.gpb.2018.06.004. Epub Sep. 21, 2018.

Xu et al., Sequence determinants of improved CRISPR sgRNA design. Genome Res. Aug. 2015;25(8):1147-57. doi: 10.1101/gr.191452.115. Epub Jun. 10, 2015.

Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.

Xu et al., The mechanism of protein splicing and its modulation by mutation. EMBO J. Oct. 1, 1996;15(19):5146-53.

Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.

Yamada et al., Crystal Structure of the Minimal Cas9 from Campylobacter jejuni Reveals the Molecular Diversity in the CRISPR-Cas9 Systems. Mol Cell. Mar. 16, 2017;65(6):P1109-1121. /doi.org/10.1016/j.molcel.2017.02.007.

Yamamoto et al., The ons and offs of inducible transgenic technology: a review. Neurobiol Dis. Dec. 2001;8(6):923-32.

Yamamoto et al., Virological and immunological bases for HIV-1 vaccine design. Uirusu 2007;57(2):133-139. https://doi.org/10.2222/jsv.57.133.

Yamano et al., Crystal Structure of Cpf1 in Complex with Guide RNA and Target DNA. Cell. May 5, 2016;165(4):949-62 and Supplemental Info. doi: 10.1016/j.cell.2016.04.003. Epub Apr. 21, 2016.

Yamano et al., Crystal Structure of Cpf1 in Complex with Guide RNA and Target DNA. Cell. May 5, 2016;165(4):949-62. doi: 10.1016/j.cell.2016.04.003. Epub Apr. 21, 2016.

Yamazaki et al., Segmental Isotope Labeling for Protein NMR Using Peptide Splicing. J. Am. Chem. Soc. May 22, 1998; 120(22):5591-2. https://doi.org/10.1021/ja9807760.

Yan et al., Cas13d Is a Compact RNA-Targeting Type Vi Crispr Effector Positively Modulated by a WYL-Domain-Containing Accessory Protein. Mol Cell. Apr. 19, 2018;70(2):327- 339.e5. doi: 10.1016/j.molcel.2018.02.028. Epub Mar. 15, 2018.

Yang et al., APOBEC: From mutator to editor. J Genet Genomics. Sep. 20, 2017;44(9):423-437. doi: 10.1016/j.jgg.2017.04.009. Epub Aug. 7, 2017.

Yang et al., Construction of an integration-proficient vector based on the site-specific recombination mechanism of enterococcal temperate phage phiFC1. J Bacteriol. Apr. 2002; 184(7):1859-64. doi: 10.1128/jb.184.7.1859-1864.2002.

Yang et al., Engineering and optimising deaminase fusions for genome editing. Nat Commun. Nov. 2, 2016;7:13330. doi: 10.1038/ncomms13330.

Yang et al., Genome editing with targeted deaminases. BioRxiv. Preprint. First posted online Jul. 28, 2016.

Yang et al., Increasing targeting scope of adenosine base editors in mouse and rat embryos through fusion of TadA deaminase with Cas9 variants. Protein Cell. Sep. 2018;9(9):814-819. doi: 10.1007/s13238-018-0568-x.

Yang et al., Mutations in SCN9A, encoding a sodium channel alpha subunit, in patients with primary erythermalgia. J Med Genet. Mar. 2004;41(3):171-4. doi: 10.1136/jmg.2003.012153.

Yang et al., New CRISPR-Cas systems discovered. Cell Res. Mar. 2017;27(3):313-314. doi: 10.1038/cr.2017.21. Epub Feb. 21, 2017.

Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.

Yang et al., PAM-dependent Target DNA Recognition and Cleavage by C2C1 CRISPR-Cas endonuclease. Cell Dec. 2016;167(7):1814-28.

Yang et al., Permanent genetic memory with >1-byte capacity. Nat Methods. Dec. 2014;11(12):1261-6. doi: 10.1038/nmeth.3147. Epub Oct. 26, 2014.

Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.

Yang et al., Small-molecule control of insulin and PDGF receptor signaling and the role of membrane attachment. Curr Biol. Jan. 1, 1998;8(1):11-8. doi: 10.1016/s0960-9822(98)70015-6.

Yang, Development of Human Genome Editing Tools for the Study of Genetic Variations and Gene Therapies. Doctoral Dissertation. Harvard University. 2013. Accessible via nrs.harvard.edu/urn-3:HUL.InstRepos: 11181072. 277 pages.

Yang, Nucleases: diversity of structure, function and mechanism. Q Rev Biophys. Feb. 2011;44(1):1-93. doi: 10.1017/S0033583510000181. Epub Sep. 21, 2010.

Yang, Paml 4: phylogenetic analysis by maximum likelihood. Mol Biol Evol. Aug. 2007;24(8):1586-91. doi: 10.1093/molbev/msm088. Epub May 4, 2007.

Yang, Phylogenetic Analysis by Maximum Likelihood (PAML). //abacus.gene.ucl.ac.uk/software/paml.html Last accessed Apr. 28, 2021.

Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.

Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.

Yasui, Alternative excision repair pathways. Cold Spring Harb Perspect Biol. Jun. 1, 2013;5(6):a012617. doi: 10.1101/cshperspect.a012617.

Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.

Yazaki et al., Hereditary systemic amyloidosis associated with a new apolipoprotein AII stop codon mutation Stop78Arg. Kidney Int. Jul. 2003;64(1):11-6.

Yeh et al., In vivo base editing of post-mitotic sensory cells. Nat Commun. Jun. 5, 2018;9(1):2184. doi: 10.1038/s41467-018-04580-3.

Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.

Yokoe et al., Spatial dynamics of GFP-tagged proteins investigated by local fluorescence enhancement. Nat Biotechnol. Oct. 1996; 14(10):1252-6. doi: 10.1038/nbt1096-1252.

Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.

Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.

Yu et al., Liposome-mediated in vivo ELA gene transfer suppressed dissemination of ovarian cancer cells that overexpress HER-2/neu. Oncogene. Oct. 5, 1995;11(7):1383-8.

Yu et al., Progress towards gene therapy for HIV infection. Gene Ther. Jan. 1994; 1(1):13-26.

Yu et al., Small molecules enhance CRISPR genome editing in pluripotent stem cells. Cell Stem Cell. Feb. 5, 2015;16(2):142-7. doi: 10.1016/j.stem.2015.01.003.

(56) References Cited

OTHER PUBLICATIONS

Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.

Yuan et al., Laboratory-directed protein evolution. Microbiol Mol Biol Rev. 2005; 69(3):373-92. PMID: 16148303.

Yuan et al., Tetrameric structure of a serine integrase catalytic domain. Structure. Aug. 6, 2008;16(8):1275-86. doi: 10.1016/j.str.2008.04.018.

Yuen et al., Control of transcription factor activity and osteoblast differentiation in mammalian cells using an evolved small-molecule-dependent intein. J Am Chem Soc. Jul. 12, 2006;128(27):8939-46.

Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.

Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 18, 2014.

Zelphati et al., Intracellular delivery of proteins with a new lipid-mediated delivery system. J Biol Chem. Sep. 14, 2001;276(37):35103-10. Epub Jul. 10, 2001.

Zetsche et al., A split-Cas9 architecture for inducible genome editing and transcription modulation. Nat Biotechnol. Feb. 2015;33(2):139-42. doi: 10.1038/nbt.3149.

Zetsche et al., Cpf1 is a single RNA-guided endonuclease of a class 2 CRISPR-Cas system. Cell. Oct. 22, 2015;163(3):759-71 and Supplemental Info. doi: 10.1016/j.cell.2015.09.038. Epub Sep. 25, 2015.

Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.

Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.

Zhang et al., Π-Clamp-mediated cysteine conjugation. Nat Chem. Feb. 2016;8(2):120-8. doi: 10.1038/nchem.2413. Epub Dec. 21, 2015.

Zhang et al., A new strategy for the site-specific modification of proteins in vivo. Biochemistry. Jun. 10, 2003;42(22):6735-46.

Zhang et al., Circular intronic long noncoding RNAs. Mol Cell. Sep. 26, 2013;51(6):792-806. doi: 10.1016/j.molcel.2013.08.017. Epub Sep. 12, 2013.

Zhang et al., Comparison of non-canonical PAMs for CRISPR/Cas9-mediated DNA cleavage in human cells. Sci Rep. Jun. 2014;4:5405.

Zhang et al., Conditional gene manipulation: Cre-ating a new biological era. J Zhejiang Univ Sci B. Jul. 2012;13(7):511-24. doi: 10.1631/jzus.B1200042. Review.

Zhang et al., Copy number variation in human health, disease, and evolution. Annu Rev Genomics Hum Genet. 2009;10:451-81. doi: 10.1146/annurev.genom.9.081307.164217.

Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.

Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.

Zhang et al., Myoediting: Toward Prevention of Muscular Dystrophy by Therapeutic Genome Editing. Physiol Rev. Jul. 1, 2018;98(3):1205-1240. doi: 10.1152/physrev.00046.2017.

Zhang et al., Π-Clamp-mediated cysteine conjugation. Nat Chem. Feb. 2016;8(2):120-8. doi: 10.1038/nchem.2413. Epub Dec. 2, 20151.

Zhang et al., Programmable base editing of zebrafish genome using a modified CRISPR-Cas9 system. Nat Commun. Jul. 25, 2017;8(1):118. doi: 10.1038/s41467-017-00175-6.

Zhang et al., Ribozymes and Riboswitches: Modulation of RNA Function by Small Molecules. Biochemistry. Nov. 2, 2010;49(43):9123-31. doi: 10.1021/bi1012645.

Zhang et al., Stabilized plasmid-lipid particles for regional gene therapy: formulation and transfection properties. Gene Ther. Aug. 1999;6(8):1438-47.

Zhao et al., An ultraprocessive, accurate reverse transcriptase encoded by a metazoan group II intron. RNA. Feb. 2018;24(2):183-195. doi: 10.1261/rna.063479.117. Epub Nov. 6, 2017.

Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.

Zhao et al., Post-transcriptional gene regulation by mRNA modifications. Nat Rev Mol Cell Biol. Jan. 2017;18(1):31-42. doi: 10.1038/nrm.2016.132. Epub Nov. 3, 2016.

Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.

Zheng et al., DNA editing in DNA/RNA hybrids by adenosine deaminases that act on RNA. Nucleic Acids Res. Apr. 7, 2017;45(6):3369-3377. doi: 10.1093/nar/gkx050.

Zheng et al., Highly efficient base editing in bacteria using a Cas9-cytidine deaminase fusion. Commun Biol. Apr. 19, 2018;1:32. doi: 10.1038/s42003-018-0035-5.

Zheng et al., Structural basis for the complete resistance of the human prion protein mutant G127V to prion disease. Sci Rep. Sep. 4, 2018;8(1):13211. doi: 10.1038/s41598-018-31394-6.

Zhong et al., Rational Design of Aptazyme Riboswitches for Efficient Control of Gene Expression in Mammalian Cells. Elife. Nov. 2, 2016;5:e18858. doi: 10.7554/eLife.18858.

Zhou et al., Generation of induced pluripotent stem cells using recombinant proteins. Cell Stem Cell. May 8, 2009;4(5):381-4. doi: 10.1016/j.stern.2009.04.005. Epub Apr. 23, 2009.

Zhou et al., Dynamic m(6)A mRNA methylation directs translational control of heat shock response. Nature. Oct. 22, 2015;526(7574):591-4. doi: 10.1038/nature15377. Epub Oct. 12, 2015. Zhou et al., Generation of induced pluripotent stem cells using recombinant proteins. Cell Stem Cell. May 8, 2009;4(5):381-4. doi: 10.1016/j.stem.2009.04.005. Epub Apr. 23, 2009.

Zhou et al., Protective V127 prion variant prevents prion disease by interrupting the formation of dimer and fibril from molecular dynamics simulations. Sci Rep. Feb. 24, 2016;6:21804. doi: 10.1038/srep21804.

Zhou et al., Seamless Genetic Conversion of SMN2 to SMN1 via CRISPR/Cpf1 and Single-Stranded Oligodeoxynucleotides in Spinal Muscular Atrophy Patient-Specific Induced Pluripotent Stem Cells. Hum Gene Ther. Nov. 2018;29(11):1252-1263. doi: 10.1089/hum.2017.255. Epub May 9, 2018.

Zielenski, Genotype and phenotype in cystic fibrosis. Respiration. 2000;67(2):117-33. doi: 10.1159/000029497.

Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.

Zimmerly et al., Group II intron mobility occurs by target DNA-primed reverse transcription. Cell. Aug. 25, 1995;82(4):545-54. doi: 10.1016/0092-8674(95)90027-6.

Zimmermann et al., Molecular interactions and metal binding in the theophylline-binding core of an RNA aptamer. RNA. May 2000;6(5):659-67.

Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.

Zorko et al., Cell-penetrating peptides: mechanism and kinetics of cargo delivery. Adv Drug Deliv Rev. Feb. 28, 2005;57(4):529-45. Epub Jan. 22, 2005.

Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.

(56) References Cited

OTHER PUBLICATIONS

Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.
Zuker et al., Optimal computer folding of large RNA sequences using thermodynamics and auxiliary information. Nucleic Acids Res. Jan. 10, 1981;9(1):133-48. doi: 10.1093/nar/9.1.133.
Zuo et al., Cytosine base editor generates substantial off-target single-nucleotide variants in mouse embryos. Science. Apr. 19, 2019;364(6437):289-292. doi: 10.1126/science.aav9973. Epub Feb. 28, 2019.
Zuris et al., Cationic lipid-mediated delivery of proteins enables efficient protein-based genome editing in vitro and in vivo. Nat Biotechnol. 2015;33:73-80.
Extended European Search Report for EP 23181576.2, mailed Dec. 20, 2023.
[No. Author Listed] Beast2: Bayesian evolutionary analysis by sampling trees. http://www.beast2.org/ Last accessed Apr. 28, 2021.
[No. Author Listed] NCBI Reference Sequence: WP_001516895.1. Mar. 13, 2021. 2 pages.
[No. Author Listed] NCBI Reference Sequence: WP_087959824.1. Oct. 9, 2019. 2 pages.
[No. Author Listed] Nucleic Acid Data from New England Biolabs. Printed Sep. 28, 2021. 1 page.
[No. Author Listed] Transcription activator-like effector nuclease. Wikipedia. Last edited Sep. 27, 2021. Accessed via https://en.wikipedia.org/w/index.php?title=Transcription_activator-like_effector_nuclease&oldid=1046813325 on Sep. 28, 2021. 9 pages.
[No. Author Listed], "Human genome." Encyclopedia Britannica. Encyclopedia Brittanica, Inc. Published Feb. 15, 2019. Last accessed online via https://www.britannica.com/science/human-genome on Mar. 19, 2021. 2 pages.
[No. Author Listed], "Lambda DNA" from Catalog & Technical Reference. New England Biolabs Inc. 2002/2003. pp. 133 and 270-273.
[No Author Listed], Mus musculus (Mouse). UniProtKB Accession No. P51908 (ABEC1_MOUSE). Oct. 1, 1996. 10 pages.
[No. Author Listed], MutL homolog 1. UniProtKB Acc. No. F1MPG0. May 3, 2011. Accessible at https://rest.uniprot.org/unisave/F1MPG0?format=txt&versions=1. 1 page.
Abudayyeh et al., A cytosine deaminase for programmable single-base RNA editing. Science. Jul. 26, 2019;365(6451):382-386. doi: 10.1126/science.aax7063. Epub Jul. 11, 2019.
Acharya et al., hMSH2 forms specific mispair-binding complexes with hMSH3 and hMSH6. Proc Natl Acad Sci U S A. Nov. 26, 1996;93(24):13629-34. doi: 10.1073/pnas.93.24.13629.
Ai et al., C-terminal Loop Mutations Determine Folding and Secretion Properties of PCSK9. iMedPub J: Biochem Mol Biol J. Nov. 5, 2016;2(3):17. doi: 10.21767/2471-8084.100026. 12 pages.
Asokan et al., The AAV vector toolkit: poised at the clinical crossroads. Mol Ther. Apr. 2012;20(4):699-708. doi: 10.1038/mt.2011.287. Epub Jan. 24, 2012.
Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.
Avidan et al., Expression and characterization of a recombinant novel reverse transcriptase of a porcine endogenous retrovirus. Virology. Mar. 15, 2003;307(2):341-57. doi: 10.1016/s0042-6822(02)00131-9.
Baba et al., Construction of *Escherichia coli* K-12 in-frame, single-gene knockout mutants: the Keio collection. Mol Syst Biol. 2006;2:2006.0008. doi: 10.1038/msb4100050. Epub Feb. 21, 2006.
Bae et al., Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014.
Bae et al., Heteroclitic CD33 peptide with enhanced anti-acute myeloid leukemic immunogenicity. Clin Cancer Res. Oct. 15, 2004;10(20):7043-52. doi: 10.1158/1078-0432.CCR-04-0322.
Bagal et al., Recent progress in sodium channel modulators for pain. Bioorg Med Chem Lett. Aug. 15, 2014;24(16):3690-9. doi: 10.1016/j.bmcl.2014.06.038. Epub Jun. 21, 2014.
Banno et al., Deaminase-mediated multiplex genome editing in *Escherichia coli*. Nat Microbiol. Apr. 2018;3(4):423-429. doi: 10.1038/s41564-017-0102-6. Epub Feb. 5, 2018.
Baños-Sanz et al., Crystal structure and functional insights into uracil-DNA glycosylase inhibition by phage @29 DNA mimic protein p56. Nucleic Acids Res. Jul. 2013;41(13):6761-73. doi: 10.1093/nar/gkt395. Epub May 13, 2013.
Barmania et al., C—C chemokine receptor type five (CCR5): An emerging target for the control of HIV infection. Appl Transl Genom. May 26, 2013;2:3-16. doi: 10.1016/j.atg.2013.05.004.
Basila et al., Minimal 2'-O-methyl phosphorothioate linkage modification pattern of synthetic guide RNAs for increased stability and efficient CRISPR-Cas9 gene editing avoiding cellular toxicity. PLoS One. Nov. 27, 2017;12(11):e0188593. doi: 10.1371/journal.pone.0188593.
Bass, B.L., RNA editing by adenosine deaminases that act on RNA. Annu Rev Biochem. 2002;71:817-46. doi: 10.1146/annurev.biochem.71.110601.135501. Epub Nov. 9, 2001.
Beaudry et al., Directed evolution of an RNA enzyme. Science. Jul. 31, 1992;257(5070):635- 41. doi: 10.1126/science.1496376.
Bell et al., Ribozyme-catalyzed excision of targeted sequences from within RNAs. Biochemistry. Dec. 24, 2002;41(51):15327-33. doi: 10.1021/bi0267386.
Bentin, T., A ribozyme transcribed by a ribozyme. Artif DNA PNA XNA. Apr. 2011;2(2):40-42. doi: 10.4161/adna.2.2.16852.
Bertsimas et al., Simulated annealing. Statistical Science. Feb. 1993;8(1):10-15. doi: 10.1214/ss/1177011077.
Bibikova et al., Targeted chromosomal cleavage and mutagenesis in Drosophila using zinc-finger nucleases. Genetics. Jul. 2002;161(3):1169-75. doi: 10.1093/genetics/161.3.1169.
Blauw et al., SMN1 gene duplications are associated with sporadic ALS. Neurology. Mar. 13, 2012;78(11):776-80. doi: 10.1212/WNL.0b013e318249f697. Epub Feb. 8, 2012.
Bothmer et al., Characterization of the interplay between DNA repair and CRISPR/Cas9-induced DNA lesions at an endogenous locus. Nat Commun. Jan. 9, 2017;8:13905. doi: 10.1038/ncomms13905.
Brierley et al., Viral RNA pseudoknots: versatile motifs in gene expression and replication. Nat Rev Microbiol. Aug. 2007;5(8):598-610. doi: 10.1038/nrmicro1704.
Brutlag et al., Improved sensitivity of biological sequence database searches. Comput Appl Biosci. Jul. 1990;6(3):237-45. doi: 10.1093/bioinformatics/6.3.237.
Butt et al., Efficient CRISPR/Cas9-Mediated Genome Editing Using a Chimeric Single-Guide RNA Molecule. Front Plant Sci. Aug. 24, 2017;8:1441(1-8). doi: 10.3389/fpls.2017.01441.
Canny et al., Inhibition of 53BP1 Favors Homology-Dependent DNA Repair and Increases CRISPR-Cas9 Genome-Editing Efficiency. Nat Biotechnol. Jan. 2018;36(1):95-102. doi: 10.1038/nbt.4021. Epub Nov. 27, 2017.
Cao et al., Rapamycin reverses cellular phenotypes and enhances mutant protein clearance in Hutchinson-Gilford progeria syndrome cells. Sci Transl Med. Jun. 2, 20119;3(89):89ra58. doi: 10.1126/scitranslmed.3002346.
Carlier et al., Genome Sequence of Burkholderia cenocepacia H111, a Cystic Fibrosis Airway Isolate. Genome Announc. Apr. 10, 2014;2(2):e00298-14. doi: 10.1128/genomeA.00298-14.
Cartegni et al., Determinants of exon 7 splicing in the spinal muscular atrophy genes, SMN1 and SMN2. Am J Hum Genet. Jan. 2006;78(1):63-77. doi: 10.1086/498853. Epub Nov. 16, 2005.
Chang et al., Degradation of survival motor neuron (SMN) protein is mediated via the ubiquitin/proteasome pathway. Neurochem Int. Dec. 2004;45(7):1107-12. doi: 10.1016/j.neuint.2004.04.005.
Chawla et al., An atlas of RNA base pairs involving modified nucleobases with optimal geometries and accurate energies. Nucleic Acids Res. Aug. 18, 2015;43(14):6714-29. doi: 10.1093/nar/gkv606. Epub Jun. 27, 2015.

(56) References Cited

OTHER PUBLICATIONS

Chen et al., Alterations in PMS2, MSH2 and MLH1 expression in human prostate cancer. Int J Oncol. May 2003;22(5):1033-43.

Chen et al., Dynamic imaging of genomic loci in living human cells by an optimized CRISPR/Cas system. Cell. Dec. 19, 2013;155(7):1479-91. doi: 10.1016/j.cell.2013.12.001. Erratum in: Cell. Jan. 16, 2014;156(1-2):373.

Chen et al., Targeting genomic rearrangements in tumor cells through Cas9-mediated insertion of a suicide gene. Nat Biotechnol. Jun. 2017;35(6):543-550. doi: 10.1038/nbt.3843. Epub May 1, 2017.

Cheng et al., [Cloning,expression and activity identification of human innate immune protein apolipoprotein B mRNA editing enzyme catalytic subunit 3A(APOBEC3A)]. Xi Bao Yu Fen Zi Mian Yi Xue Za Zhi. Chinese Journal of Cellular and Molecular Immunology, Feb. 2017;33(2):179-84. Chinese.

Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.

Cho et al., A degron created by SMN2 exon 7 skipping is a principal contributor to spinal muscular atrophy severity. Genes Dev. Mar. 1, 2010;24(5):438-42. doi: 10.1101/gad.1884910.

Choi et al., Optimization of AAV expression cassettes to improve packaging capacity and transgene expression in neurons. Mol Brain. Mar. 11, 2014;7:17. doi: 10.1186/1756-6606-7-17.

Choudhury et al., CRISPR-dCas9 mediated TET1 targeting for selective DNA demethylation at BRCA1 promoter. Oncotarget. Jul. 19, 2016;7(29):46545-46556. doi: 10.18632/oncotarget.10234.

Corcia et al., The importance of the SMN genes in the genetics of sporadic ALS. Amyotroph Lateral Scler. Oct.-Dec. 2009;10(5-6):436-40. doi: 10.3109/17482960902759162.

Corti et al., Genetic correction of human induced pluripotent stem cells from patients with spinal muscular atrophy. Sci Transl Med. Dec. 19, 2012;4(165):165ra162. doi: 10.1126/scitranslmed.3004108.

Cucchiarini et al., Enhanced expression of the central survival of motor neuron (SMN) protein during the pathogenesis of osteoarthritis. J Cell Mol Med. Jan. 2014;18(1):115-24. doi: 10.1111/jcmm.12170. Epub Nov. 17, 2013.

D'ydewalle et al., The Antisense Transcript SMN-AS1 Regulates SMN Expression and Is a Novel Therapeutic Target for Spinal Muscular Atrophy. Neuron. Jan. 4, 2017;93(1):66-79 and Supplemental Information. doi: 10.1016/j.neuron.2016.11.033. Epub Dec. 22, 2016.

Damdindorj et al., A comparative analysis of constitutive promoters located in adeno- associated viral vectors. PLoS One. Aug. 29, 2014;9(8):e106472. doi: 10.1371/journal.pone.0106472.

Davis et al., Assaying Repair at DNA Nicks. Methods Enzymol. 2018;601:71-89. doi: 10.1016/bs.mie.2017.12.001. Epub Feb. 1, 2018.

Davis et al., Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014.

Davis et al., Two Distinct Pathways Support Gene Correction by Single-Stranded Donors at DNA Nicks. Cell Rep. Nov. 8, 2016;17(7):1872-1881. doi: 10.1016/j.celrep.2016.10.049.

De La Peña et al., The Hammerhead Ribozyme: A Long History for a Short RNA. Molecules. Jan. 4, 2017;22(1):78. doi: 10.3390/molecules22010078.

De Sandre-Giovannoli et al., Lamin a truncation in Hutchinson-Gilford progeria. Science. Jun. 27, 2003;300(5628):2055. doi: 10.1126/science.1084125. Epub Apr. 17, 2003.

Denizio et al., Harnessing natural DNA modifying activities for editing of the genome and epigenome. Curr Opin Chem Biol. Aug. 2018;45:10-17. doi: 10.1016/j.cbpa.2018.01.016. Epub Feb. 13, 2018.

Dickinson et al., A system for the continuous directed evolution of proteases rapidly reveals drug-resistance mutations. Nat Commun. Oct. 30, 2014;5:5352. doi: 10.1038/ncomms6352.

Ding et al., Gene therapy for cardiovascular disease. Journal of Shanghai University (Natural Science Edition). 2016;3:270-9 . DOI: 10.3969/j.issn.1007-2861.2016.03.013.

Dolan et al., Trans-splicing with the group I intron ribozyme from Azoarcus. RNA. Feb. 2014;20(2):202-13. doi: 10.1261/rna.041012.113. Epub Dec. 16, 2013.

Drenth et al., Mutations in sodium-channel gene SCN9A cause a spectrum of human genetic pain disorders. J Clin Invest. Dec. 2007;117(12):3603-9. doi: 10.1172/JCI33297.

Drost et al., Inactivation of DNA mismatch repair by variants of uncertain significance in the PMS2 gene. Hum Mutat. Nov. 2013;34(11):1477-80. doi: 10.1002/humu.22426. Epub Sep. 11, 2013.

Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.

Dugar et al., CRISPR RNA-Dependent Binding and Cleavage of Endogenous RNAs by the Campylobacter jejuni Cas9. Mol Cell. Mar. 1, 2018;69(5):893-905.e7. doi: 10.1016/j.molcel.2018.01.032.

Eisenberg et al., A-to-I RNA editing—immune protector and transcriptome diversifier. Nat Rev Genet. Aug. 2018; 19(8):473-490. doi: 10.1038/s41576-018-0006-1.

Ekstrand et al., Frequent alterations of the PI3K/AKT/mTOR pathways in hereditary nonpolyposis colorectal cancer. Fam Cancer. Jun. 2010;9(2):125-9. doi: 10.1007/s10689-009-9293-1.

Entin-Meer et al., The role of phenylalanine-119 of the reverse transcriptase of mouse mammary tumour virus in DNA synthesis, ribose selection and drug resistance. Biochem J. Oct. 15, 2002;367(Pt 2):381-91. doi: 10.1042/BJ20020712.

Eriksen et al., Occlusion of the Ribosome Binding Site Connects the Translational Initiation Frequency, mRNA Stability and Premature Transcription Termination. Front Microbiol. Mar. 14, 2017;8:362. doi: 10.3389/fmicb.2017.00362.

Estacion et al., A sodium channel gene SCN9A polymorphism that increases nociceptor excitability. Ann Neurol. Dec. 2009;66(6):862-6. doi: 10.1002/ana.21895.

Fang et al., Human strand-specific mismatch repair occurs by a bidirectional mechanism similar to that of the bacterial reaction. J Biol Chem. Jun. 5, 1993;268(16):11838-44.

Fang et al., The Menu of Features that Define Primary MicroRNAs and Enable De Novo Design of MicroRNA Genes. Mol Cell. Oct. 15, 201;60(1):131-45. doi: 10.1016/j.molcel.2015.08.015. Epub Sep. 24, 2015.

Feng et al., Efficient genome editing in plants using a CRISPR/Cas system. Cell Res. Oct. 2013;23(10):1229-32. doi: 10.1038/cr.2013.114. Epub Aug. 20, 2013.

Fikes et al., Design of multi-epitope, analogue-based cancer vaccines. Expert Opin Biol Ther. Sep. 2003;3(6):985-93. doi: 10.1517/14712598.3.6.985.

Fishel et al., The human mutator gene homolog MSH2 and its association with hereditary nonpolyposis colon cancer. Cell. Dec. 3, 1993;75(5):1027-38. doi: 10.1016/0092-8674(93)90546-3. Erratum in: Cell. Apr. 8, 1994;77(1):1 p following 166.

Friedman, J. H., Greedy function approximation: A gradient boosting machine. Ann. Statist. Oct. 2001;29(5):1189-232. doi: 10.1214/aos/1013203451.

Fu et al., Targeted genome editing in human cells using CRISPR/Cas nucleases and truncated guide RNAs. Methods Enzymol. 2014;546:21-45. doi: 10.1016/B978-0-12-801185-0.00002-7.

Gaudelli et al., Programmable base editing of A•T to G•C in genomic DNA without DNA cleavage. Nature. Nov. 23, 2017;551(7681):464-471. doi: 10.1038/nature24644. Epub Oct. 25, 2017. Erratum in: Nature. May 2, 2018.

Geisberg et al., Global analysis of mRNA isoform half-lives reveals stabilizing and destabilizing elements in yeast. Cell. Feb. 13, 2014;156(4):812-24. doi: 10.1016/j.cell.2013.12.026.

Genbank Submission; NIH/NCBI Accession No. 4UN5_B. Anders et al., Jul. 23, 2014. 5 pages.

(56) References Cited

OTHER PUBLICATIONS

Genbank Submission; NIH/NCBI, Accession No. AIT42264.1. Hyun et al., Oct. 15, 2014. 2 pages.
Genbank Submission; NIH/NCBI, Accession No. AKA60242.1. Tong et al., Apr. 5, 2015. 1 page.
Genbank Submission; NIH/NCBI, Accession No. AKQ21048.1. Gilles et al., Jul. 19, 2015. 1 page.
Genbank Submission; NIH/NCBI, Accession No. AKS40380.1. Nodvig et al., Aug. 2, 2015. 1 page.
Genbank Submission; NIH/NCBI, Accession No. NC_000001.11. Gregory et al., Jun. 6, 2016. 3 pages.
Genbank Submission; NIH/NCBI, Accession No. NG_008692.2. McClintock et al., Aug. 27, 2018. 33 pages.
Genbank Submission; NIH/NCBI, Accession No. NM_206933.2. Khalaileh et al., Sep. 16, 2018. 12 pages.
Genbank Submission; NIH/NCBI, Accession No. NP_001075493.1. Schiaffella et al., Jun. 24, 2018. 2 pages.
Genbank Submission; NIH/NCBI, Accession No. NP_001157741.1. Zeng et al., Sep. 17, 2018. 3 pages.
Genbank Submission; NIH/NCBI, Accession No. NP_001157742.1. Zeng et al., Oct. 21, 2018. 3 pages.
Genbank Submission; NIH/NCBI, Accession No. NP_001243439.1. Lee et al., Jul. 26, 2021. 4 pages.
Genbank Submission; NIH/NCBI, Accession No. NP_033040.2. Liu et al., Jun. 23, 2018. 2 pages.
Genbank Submission; NIH/NCBI, Accession No. NP_060228.2. Bi et al., Dec. 21, 2005. 1 page.
Genbank Submission; NIH/NCBI, Accession No. NP_062826.2. Bokar et al., Sep. 18, 2004. 2 pages.
Genbank Submission; NIH/NCBI, Accession No. NP_066012.1. Ota et al., Apr. 3, 2005. 2 pages.
Genbank Submission; NIH/NCBI, Accession No. WP_002989955.1. No Author Listed, May 6, 2013. 1 page.
Genbank Submission; NIH/NCBI, Accession No. WP_010922251.1. No Author Listed, May 15, 2013. 1 page.
Genbank Submission; NIH/NCBI, Accession No. WP_011054416.1. No Author Listed, May 15, 2013. 1 page.
Genbank Submission; NIH/NCBI, Accession No. WP_011284745.1. No Author Listed, May 16, 2013. 1 page.
Genbank Submission; NIH/NCBI, Accession No. WP_011285506.1. No Author Listed, May 16, 2013. 1 page.
Genbank Submission; NIH/NCBI, Accession No. WP_011527619.1. No Author Listed, May 16, 2013. 1 page.
Genbank Submission; NIH/NCBI, Accession No. WP_012560673.1. No Author Listed, May 17, 2013. 1 page.
Genbank Submission; NIH/NCBI, Accession No. WP_014407541.1. No Author Listed, May 18, 2013. 1 page.
Genbank Submission; NIH/NCBI, Accession No. WP_020905136.1. No Author Listed, Jul. 25, 2013. 1 page.
Genbank Submission; NIH/NCBI, Accession No. WP_023080005.1. No Author Listed, Oct. 27, 2013. 1 page.
Genbank Submission; NIH/NCBI, Accession No. WP_023610282.1. No Author Listed, Nov. 27, 2013. 1 page.
Genbank Submission; NIH/NCBI, Accession No. WP_030125963.1. No Author Listed, Jul. 9, 2014. 1 page.
Genbank Submission; NIH/NCBI, Accession No. WP_030126706.1. No Author Listed, Jul. 9, 2014. 1 page.
Genbank Submission; NIH/NCBI, Accession No. WP_031488318.1. No Author Listed., Aug. 5, 2014. 1 page.
Genbank Submission; NIH/NCBI, Accession No. WP_032460140.1. No Author Listed, Oct. 4, 2014. 1 page.
Genbank Submission; NIH/NCBI, Accession No. WP_032461047.1. No Author Listed, Oct. 4, 2014. 1 page.
Genbank Submission; NIH/NCBI, Accession No. WP_032462016.1. Haft et al., Oct. 4, 2014. 1 page.
Genbank Submission; NIH/NCBI, Accession No. WP_032462936.1. No Author Listed, Oct. 4, 2014. 1 page.
Genbank Submission; NIH/NCBI, Accession No. WP_032464890.1. No Author Listed, Oct. 4, 2014. 1 page.
Genbank Submission; NIH/NCBI, Accession No. WP_038431314.1. No Author Listed, Dec. 26, 2014. 1 page.
Genbank Submission; NIH/NCBI, Accession No. WP_038432938.1. No Author Listed, Dec. 26, 2014. 1 page.
Genbank Submission; NIH/NCBI, Accession No. WP_038434062.1. No Author Listed, Dec. 26, 2014. 1 page.
Genbank Submission; NIH/NCBI, Accession No. WP_042518169.1. No Author, Feb. 10, 2015. 1 page.
Genbank Submission; NIH/NCBI, Accession No. WP_048327215.1. No Author Listed, Jun. 26, 2015. 1 page.
Genbank Submission; NIH/NCBI, Accession No. WP_049519324.1. No Author Listed, Jul. 20, 2015. 1 page.
Genbank Submission; NIH/NCBI, Accession No. XP_003314669.1. No Author Listed, Mar. 20, 2018. 2 pages.
Genbank Submission; NIH/NCBI, Accession No. XP_026671085.1. No Author Listed, Oct. 17, 2018. 1 page.
Geng et al., In vitro studies of DNA mismatch repair proteins. Anal Biochem. Jun. 15, 2011;413(2):179-84. doi: 10.1016/j.ab.2011.02.017. Epub Feb. 15, 2011.
Genschel et al., Human exonuclease I is required for 5' and 3' mismatch repair. J Biol Chem. Apr. 12, 2002;277(15):13302-11. doi: 10.1074/jbc.M111854200. Epub Jan. 24, 2002.
Genschel et al., Isolation of MutSbeta from human cells and comparison of the mismatch repair specificities of MutSbeta and MutSalpha. J Biol Chem. Jul. 31, 1998;273(31):19895-901. doi: 10.1074/jbc.273.31.19895. Erratum in: J Biol Chem Oct. 9, 1998;273(41):27034.
Grati et al., Localization of PDZD7 to the stereocilia ankle-link associates this scaffolding protein with the Usher syndrome protein network. J Neurosci. Oct. 10, 2012;32(41):14288-93. doi: 10.1523/JNEUROSCI.3071-12.2012.
Green et al., Characterization of the mechanical unfolding of RNA pseudoknots. J Mol Biol. Jan. 11, 2008;375(2):511-28. doi: 10.1016/j.jmb.2007.05.058. Epub May 26, 2007.
Groher et al., Synthetic riboswitches - A tool comes of age. Biochim Biophys Acta. Oct. 2014; 1839(10):964-973. doi: 10.1016/j.bbagrm.2014.05.005. Epub May 17, 2014.
Guedon et al., Current gene therapy using viral vectors for chronic pain. Mol Pain. May 13, 2015;11:27. doi: 10.1186/s12990-015-0018-1.
Gueneau et al., Structure of the MutLa C-terminal domain reveals how Mlh1 contributes to Pms1 endonuclease site. Nat Struct Mol Biol. Apr. 2013;20(4):461-8. doi: 10.1038/nsmb.2511. Epub Feb. 24, 2013.
Guerrette et al., The interaction of the human MutL homologues in hereditary nonpolyposis colon cancer. J Biol Chem. Mar. 5, 1999;274(10):6336-41. doi: 10.1074/jbc.274.10.6336.
Guo et al., Evolution of Tetrahymena ribozyme mutants with increased structural stability. Nat Struct Biol. Nov. 2002;9(11):855-61. doi: 10.1038/nsb850.
Gupta et al., Mechanism of mismatch recognition revealed by human MutSß bound to unpaired DNA loops. Nat Struct Mol Biol. Dec. 18, 2011;19(1):72-8. doi: 10.1038/nsmb.2175.
Gutschner et al., Post-translational Regulation of Cas9 during G1 Enhances Homology- Directed Repair. Cell Rep. Feb. 16, 2016;14(6):1555-1566. doi: 10.1016/j.celrep.2016.01.019. Epub Feb. 4, 2016.
Halbert et al., Repeat transduction in the mouse lung by using adeno-associated virus vectors with different serotypes. J Virol. Feb. 2000;74(3): 1524-32. doi: 10.1128/jvi.74.3.1524-1532.2000.
Hardt et al., Missense variants in hMLH1 identified in patients from the German HNPCC consortium and functional studies. Fam Cancer. Jun. 2011;10(2):273-84. doi: 10.1007/s10689-011-9431-4.
Harmsen et al., DNA mismatch repair and oligonucleotide end-protection promote base-pair substitution distal from a CRISPR/Cas9-induced DNA break. Nucleic Acids Res. Apr. 6, 2018;46(6):2945-2955. doi: 10.1093/nar/gky076.
Hart et al., High-Resolution CRISPR Screens Reveal Fitness Genes and Genotype-Specific Cancer Liabilities. Cell. Dec. 3, 2015;163(6):1515-26. doi: 10.1016/j.cell.2015.11.015. Epub Nov. 25, 2015.

(56) References Cited

OTHER PUBLICATIONS

Hawley-Nelson et al., Transfection of Cultured Eukaryotic Cells Using Cationic Lipid Reagents. Curr Prot Mol Biol. Jan. 2008;9.4. 1-9.4.17. doi: 10.102/0471142727.mb0904s81. 17 pages.
Hendel et al., Chemically modified guide RNAs enhance CRISPR-Cas genome editing in human primary cells. Nat Biotechnol. Sep. 2015;33(9):985-989. doi: 10.1038/nbt.3290. Epub Jun. 29, 2015. Author Manuscript. 14 pages.
Herschhorn et al., Retroviral reverse transcriptases. Cell Mol Life Sci. Aug. 2010;67(16):2717-47. doi: 10.1007/s00018-010-0346-2. Epub Apr. 1, 2010.
Heyer et al., Regulation of homologous recombination in eukaryotes. Annu Rev Genet. 2010;44:113-39. doi: 10.1146/annurev-genet-051710-150955. Author Manuscript. 33 pages.
Hilbers et al., New developments in structure determination of pseudoknots. Biopolymers. 1998;48(2-3):137-53. doi: 10.1002/(SICI)1097-0282(1998)48:2<137::AID-BIP4>3.0.CO;2-H.
Hizi et al., Retroviral reverse transcriptases (other than those of HIV-1 and murine leukemia virus): a comparison of their molecular and biochemical properties. Virus Res. Jun. 2008;134(1-2):203-20. doi: 10.1016/j.virusres.2007.12.008. Epub Mar. 3, 2008.
Houck-Loomis et al., An equilibrium-dependent retroviral mRNA switch regulates translational recoding. Nature. Nov. 27, 2011;480(7378):561-4. doi: 10.1038/nature 10657.
Houghton et al., Immunological validation of the EpitOptimizer program for streamlined design of heteroclitic epitopes. Vaccine. Jul. 20, 2007;25(29):5330-42. doi: 10.1016/j.vaccine.2007.05.008. Epub Jun. 4, 2007.
Houseley et al., The many pathways of RNA degradation. Cell. Feb. 20, 2009;136(4):763-76. doi: 10.1016/j.cell.2009.01.019.
Hu et al., Evolved Cas9 variants with broad PAM compatibility and high DNA specificity. Nature. Apr. 5, 2018;556(7699):57-63 and Extended/Supplementary Data. doi: 10.1038/nature26155. Epub Feb. 28, 2018. 21 pages.
Hua et al., Precise A•T to G•C Base Editing in the Rice Genome. Mol Plant. Apr. 2, 2018;11(4):627-630. doi: 10.1016/j.molp.2018.02.007. Epub Feb. 21, 2018.
Huang et al., Gain-of-function mutations in sodium channel Na(v)1.9 in painful neuropathy. Brain. Jun. 2014;137(Pt 6):1627-42. doi: 10.1093/brain/awu079. Epub Apr. 27, 2014.
Hwang et al., Heritable and precise zebrafish genome editing using a CRISPR-Cas system. PLOS One. Jul. 9, 2013;8(7):e68708. doi: 10.1371/journal.pone.0068708.
Hänsel-Hertsch et al., DNA G-quadruplexes in the human genome: detection, functions and therapeutic potential. Nat Rev Mol Cell Biol. May 2017;18(5):279-284. doi: 10.1038/nrm.2017.3. Epub Feb. 22, 2017.
Iaccarino et al., hMSH2 and hMSH6 play distinct roles in mismatch binding and contribute differently to the ATPase activity of hMutSalpha. EMBO J. May 1, 1998;17(9):2677-86. doi: 10.1093/emboj/17.9.2677.
Ibrahim et al., RNA recognition by 3'-to-5' exonucleases: the substrate perspective. Biochim Biophys Acta. Apr. 2008;1779(4):256-65. doi: 10.1016/j.bbagrm.2007.11.004. Epub Dec. 3, 2007.
Isaacs et al., Engineered riboregulators enable post-transcriptional control of gene expression. Nat Biotechnol. Jul. 2004;22(7):841-7. doi: 10.1038/nbt986. Epub Jun. 20, 2004.
Iyama et al., DNA repair mechanisms in dividing and non-dividing cells. DNA Repair (Amst). Aug. 2013;12(8):620-36. doi: 10.1016/j.dnarep.2013.04.015. Epub May 16, 2013.
Iyer et al., DNA mismatch repair: functions and mechanisms. Chem Rev. Feb. 2006; 106(2):302-23. doi: 10.1021/cr0404794.
Jakimo et al., A Cas9 with Complete PAM Recognition for Adenine Dinucleotides. bioRxiv preprint. Sep. 27, 2018. doi.org/10.1101/429654. 29 pages.
Jia et al., The MLH1 ATPase domain is needed for suppressing aberrant formation of interstitial telomeric sequences. DNA Repair (Amst). May 2018;65:20-25. doi: 10.1016/j.dnarep.2018.03.002. Epub Mar. 7, 2018.
Johnson et al., Trans insertion-splicing: ribozyme-catalyzed insertion of targeted sequences into RNAs. Biochemistry. Aug. 9, 2005;44(31):10702-10. doi: 10.1021/bi0504815.
Kadyrov et al., Endonucleolytic function of MutLalpha in human mismatch repair. Cell. Jul. 28, 2006;126(2):297-308. doi: 10.1016/j.cell.2006.05.039.
Kan et al., Mechanisms of precise genome editing using oligonucleotide donors. Genome Res. Jul. 2017;27(7):1099-1111. doi: 10.1101/gr.214775.116. Epub Mar. 29, 2017.
Kang et al., Precision genome engineering through adenine base editing in plants. Nat Plants. Jul. 2018;4(7):427-431. doi: 10.1038/s41477-018-0178-x. Epub Jun. 4, 2018. Erratum in: Nat Plants. Sep. 2018;4(9):730.
Kim et al., RAD51 mutants cause replication defects and chromosomal instability. Mol Cell Biol. Sep. 2012;32(18):3663-80. doi: 10.1128/MCB.00406-12. Epub Jul. 9, 2012.
King et al., No gain, no pain: NaV1.7 as an analgesic target. ACS Chem Neurosci. Sep. 17, 2014;5(9):749-51. doi: 10.1021/cn500171p. Epub Aug. 11, 2014.
Kirshenboim et al., Expression and characterization of a novel reverse transcriptase of the LTR retrotransposon Tf1. Virology. Sep. 30, 2007;366(2):263-76. doi: 10.1016/j.virol.2007.04.002. Epub May 23, 2007.
Kleinstiver et al., Engineered CRISPR-Cas9 nucleases with altered PAM specificities. Nature. Jul. 23, 2015;523(7561):481-5 and Supplementary Materials. doi: 10.1038/nature14592. Epub Jun. 22, 2015. 27 pages.
Knott et al., CRISPR-Cas guides the future of genetic engineering. Science. Aug. 31, 2018;361(6405):866-869. doi: 10.1126/science.aat5011.
Konishi et al., Amino acid substitutions away from the RNase H catalytic site increase the thermal stability of Moloney murine leukemia virus reverse transcriptase through RNase H inactivation. Biochem Biophys Res Commun. Nov. 14, 2014;454(2):269-74. doi: 10.1016/j.bbrc.2014.10.044. Epub Oct. 17, 2014.
Ku et al., Nucleic Acid Aptamers: An Emerging Tool for Biotechnology and Biomedical Sensing. Sensors (Basel). Jul. 6, 2015;15(7):16281-313. doi: 10.3390/s150716281.
Kuan et al., A systematic evaluation of nucleotide properties for CRISPR sgRNA design. BMC Bioinformatics. Jun. 6, 2017;18(1):297. doi: 10.1186/s12859-017-1697-6.
Kumar et al., Gene therapy for chronic neuropathic pain: how does it work and where do we stand today? Pain Med. May 2011;12(5):808-22. doi: 10.1111/j.1526-4637.2011.01120.x.
Kunkel et al., DNA mismatch repair. Annu Rev Biochem. 2005;74:681-710. doi: 10.1146/annurev.biochem.74.082803.133243.
Kwok et al., G-Quadruplexes: Prediction, Characterization, and Biological Application. Trends Biotechnol. Oct. 2017;35(10):997-1013. doi: 10.1016/j.tibtech.2017.06.012. Epub Jul. 26, 2017.
Lahue et al., DNA mismatch correction in a defined system. Science. Jul. 14, 1989;245(4914):160-4. doi: 10.1126/science.2665076.
Langer et al., Chemical and Physical Structure of Polymers as Carriers for Controlled Release of Bioactive Agents: A Review. J Macromol Sci, Part C, 1983;23(1):61-126. doi: 10.1080/07366578308079439.
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. doi: 10.1093/hmg/ddi078. Epub Feb. 9, 2005.
Leach et al., Mutations of a mutS homolog in hereditary nonpolyposis colorectal cancer. Cell. Dec. 17, 1993;75(6):1215-25. doi: 10.1016/0092-8674(93)90330-s.
Lee et al., A monoclonal antibody that targets a NaV1.7 channel voltage sensor for pain and itch relief. Cell. Jun. 5, 2014;157(6):1393-1404. doi: 10.1016/j.cell.2014.03.064. Epub May 22, 2014. Retraction in: Cell. Jun. 25, 2020;181(7):1695.
Lefebvre et al., Identification and characterization of a spinal muscular atrophy-determining gene. Cell. Jan. 13, 1995;80(1):155-65. doi: 10.1016/0092-8674(95)90460-3.

(56) References Cited

OTHER PUBLICATIONS

Lesinski et al., The potential for targeting the STAT3 pathway as a novel therapy for melanoma. Future Oncol. Jul. 2013;9(7):925-7. doi: 10.2217/fon.13.83. Author Manuscript. 4 pages.

Li et al., Programmable Single and Multiplex Base-Editing in Bombyx mori Using RNA-Guided Cytidine Deaminases. G3 (Bethesda). May 4, 2018;8(5):1701-1709. doi: 10.1534/g3.118.200134.

Liao et al., One-step assembly of large CRISPR arrays enables multi-functional targeting and reveals constraints on array design. bioRxiv. May 2, 2018. doi: 10.1101/312421. 45 pages.

Liefke et al., The oxidative demethylase ALKBH3 marks hyperactive gene promoters in human cancer cells. Genome Med. Jun. 30, 2015;7(1):66. doi: 10.1186/s13073-015-0180-0.

Lin et al., [Construction and evaluation of DnaB split intein high expression vector and a six amino acids cyclic peptide library]. Sheng Wu Gong Cheng Xue Bao. Nov. 2008;24(11):1924-30. Chinese.

Lindahl, T., Instability and decay of the primary structure of DNA. Nature. Apr. 22, 1993;362(6422):709-15. doi: 10.1038/362709a0.

Liu et al., Human BRCA2 protein promotes RAD51 filament formation on RPA-covered single-stranded DNA. Nat Struct Mol Biol. Oct. 2010; 17(10):1260-2. doi: 10.1038/nsmb.1904. Epub Aug. 22, 2010.

Liu et al., Intrinsic Nucleotide Preference of Diversifying Base Editors Guides Antibody Ex Vivo Affinity Maturation. Cell Rep. Oct. 23, 2018;25(4):884-892.e3. doi: 10.1016/j.celrep.2018.09.090.

Liu et al., Usherin is required for maintenance of retinal photoreceptors and normal development of cochlear hair cells. Proc Natl Acad Sci U S A. Mar. 13, 2007;104(11):4413-8. doi: 10.1073/pnas.0610950104. Epub Mar. 5, 2007.

Lorenz et al., ViennaRNA Package 2.0. Algorithms Mol Biol. Nov. 24, 2011;6:26. doi: 10.1186/1748-7188-6-26.

Lorson et al., A single nucleotide in the SMN gene regulates splicing and is responsible for spinal muscular atrophy. Proc Natl Acad Sci U S A. May 25, 1999;96(11):6307-11. doi: 10.1073/pnas.96.11.6307.

Lujan et al., Heterogeneous polymerase fidelity and mismatch repair bias genome variation and composition. Genome Res. Nov. 2014;24(11):1751-64. doi: 10.1101/gr.178335.114. Epub Sep. 12, 2014.

Lutz et al., Postsymptomatic restoration of SMN rescues the disease phenotype in a mouse model of severe spinal muscular atrophy. J Clin Invest. Aug. 2011;121(8):3029-41. doi: 10.1172/JCI57291. Epub Jul. 25, 2011.

Ma et al., Human RAD52 interactions with replication protein A and the RAD51 presynaptic complex. J Biol Chem. Jul. 14, 2017;292(28):11702-11713. doi: 10.1074/jbc.M117.794545. Epub May 27, 2017.

Macfadden et al., Mechanism and structural diversity of exoribonuclease-resistant RNA structures in flaviviral RNAs. Nat Commun. Jan. 9, 2018;9(1):119. doi: 10.1038/s41467-017-02604-y.

Madura et al., Structural basis for ineffective T-cell responses to MHC anchor residue- improved "heteroclitic" peptides. Eur J Immunol. Feb. 2015;45(2):584-91. doi: 10.1002/eji.201445114. Epub Dec. 28, 2014.

Maerker et al., A novel Usher protein network at the periciliary reloading point between molecular transport machineries in vertebrate photoreceptor cells. Hum Mol Genet. Jan. 1, 2008;17(1):71-86. doi: 10.1093/hmg/ddm285. Epub Sep. 28, 2007.

Mahoney et al., The Next Immune-Checkpoint Inhibitors: PD-1/PD-L1 Blockade in Melanoma. Clin Ther. Apr. 1, 2015;37(4):764-82. doi: 10.1016/j.clinthera.2015.02.018. Epub Mar. 29, 2015.

Marcovitz et al., Frustration in protein-DNA binding influences conformational switching and target search kinetics. Proc Natl Acad Sci U S A. Nov. 1, 2011;108(44):17957-62. doi: 10.1073/pnas.1109594108. Epub Oct. 14, 2011.

Marsden et al., The Tumor-Associated Variant RAD51 G151D Induces a Hyper- Recombination Phenotype. PLoS Genet. Aug. 11, 2016;12(8):e1006208. doi: 10.1371/journal.pgen.1006208.

Martz, L., Nav-i-gating antibodies for pain. Science-Business eXchange. Jun. 12, 2014;7(662):1-2. doi: 10.1038/scibx.2014.662.

Mendell et al., Single-Dose Gene-Replacement Therapy for Spinal Muscular Atrophy. N Engl J Med. Nov. 2, 2017;377(18): 1713-1722. doi: 10.1056/NEJMoa1706198.

Meyer et al., Ribosome biogenesis factor Tsr3 is the aminocarboxypropyl transferase responsible for 18S rRNA hypermodification in yeast and humans. Nucleic Acids Res. May 19, 2016;44(9):4304-16. doi: 10.1093/nar/gkw244. Epub Apr. 15, 2016.

Micozzi et al., Human cytidine deaminase: a biochemical characterization of its naturally occurring variants. Int J Biol Macromol. Feb. 2014;63:64-74. doi: 10.1016/j.ijbiomac.2013.10.029. Epub Oct. 29, 2013. Erratum in: Int J Biol Macromol. Feb. 2014;63:262.

Millevoi et al., G-quadruplexes in RNA biology. Wiley Interdiscip Rev RNA. Jul.-Aug. 2012;3(4):495-507. doi: 10.1002/wrna. 1113. Epub Apr. 4, 2012.

Min et al., Deep learning in bioinformatics. Brief Bioinform. Sep. 1, 2017;18(5):851-869. doi: 10.1093/bib/bbw068.

Misra et al., An enzymatically active chimeric HIV-1 reverse transcriptase (RT) with the RNase-H domain of murine leukemia virus RT exists as a monomer. J Biol Chem. Apr. 17, 1998;273(16):9785-9. doi: 10.1074/jbc.273.16.9785.

Monani et al., A single nucleotide difference that alters splicing patterns distinguishes the SMA gene SMN1 from the copy gene SMN2. Hum Mol Genet. Jul. 1999;8(7):1177-83. doi: 10.1093/hmg/8.7.1177.

Mootz et al., Protein splicing triggered by a small molecule. J Am Chem Soc. Aug. 7, 2002;124(31):9044-5 and Supporting Information. doi: 10.1021/ja0267690. 4 pages.

Muir et al., Expressed protein ligation: a general method for protein engineering. Proc Natl Acad Sci U S A. Jun. 9, 1998;95(12):6705-10. doi: 10.1073/pnas.95.12.6705.

Muller, U.F., Design and Experimental Evolution of trans-Splicing Group I Intron Ribozymes. Molecules. Jan. 2, 2017;22(1):75. doi: 10.3390/molecules22010075.

Murray et al., Selective vulnerability of motor neurons and dissociation of pre- and post-synaptic pathology at the neuromuscular junction in mouse models of spinal muscular atrophy. Hum Mol Genet. Apr. 1, 2008;17(7):949-62. doi: 10.1093/hmg/ddm367. Epub Dec. 8, 2007.

Murugan et al., The Revolution Continues: Newly Discovered Systems Expand the CRISPR-Cas Toolkit. Mol Cell. Oct. 5, 2017;68(1):15-25. doi: 10.1016/j.molcel.2017.09.007.

Nelson et al., In vivo genome editing improves muscle function in a mouse model of Duchenne muscular dystrophy. Science. Jan. 22, 2016;351(6271):403-7. doi: 10.1126/science.aad5143. Epub Dec. 31, 2015.

Nelson et al., The unstable repeats—three evolving faces of neurological disease. Neuron. Mar. 6, 2013;77(5):825-43. doi: 10.1016/j.neuron.2013.02.022.

Niemeyer, C.M., Semisynthetic DNA-protein conjugates for biosensing and nanofabrication. Angew Chem Int Ed Engl. Feb. 8, 2010;49(7):1200-16. doi: 10.1002/anie.200904930.

Noack et al., Epitranscriptomics: A New Regulatory Mechanism of Brain Development and Function. Front Neurosci. Feb. 20, 2018;12:85. doi: 10.3389/fnins.2018.00085. 9 pages.

Nowak et al., Ty3 reverse transcriptase complexed with an RNA-DNA hybrid shows structural and functional asymmetry. Nat Struct Mol Biol. Apr. 2014;21(4):389-96. doi: 10.1038/nsmb.2785. Epub Mar. 9, 2014. Author Manuscript, 22 pages.

Ottesen, ISS-N1 makes the First FDA-approved Drug for Spinal Muscular Atrophy. Transl Neurosci. Jan. 26, 2017;8:1-6. doi: 10.1515/tnsci-2017-0001.

Ousterout et al., Multiplex CRISPR/Cas9-based genome editing for correction of dystrophin mutations that cause Duchenne muscular dystrophy. Nat Commun. Feb. 18, 2015;6:6244. doi: 10.1038/ncomms7244.

Packer et al., Methods for the directed evolution of proteins. Nat Rev Genet. Jul. 2015;16(7):379-94. doi: 10.1038/nrg3927. Epub Jun. 9, 2015.

(56) References Cited

OTHER PUBLICATIONS

Pandey et al., Effect of loops and G-quartets on the stability of RNA G-quadruplexes. J Phys Chem B. Jun. 13, 2013;117(23):6896-905. doi: 10.1021/jp401739m. Epub May 29, 2013. Supplementary Information, 21 pages.
Parente et al., Advances in spinal muscular atrophy therapeutics. Ther Adv Neurol Disord. Feb. 5, 2018;11:1756285618754501. doi: 10.1177/1756285618754501. 13 pages.
Parsons et al., Hypermutability and mismatch repair deficiency in RER+ tumor cells. Cell. Dec. 17, 1993;75(6):1227-36. doi: 10.1016/0092-8674(93)90331-j.
Passini et al., Antisense oligonucleotides delivered to the mouse CNS ameliorate symptoms of severe spinal muscular atrophy. Sci Transl Med. Mar. 2, 2011;3(72):72ra18. doi: 10.1126/scitranslmed. 3001777.
Pellegrini et al., Insights into DNA recombination from the structure of a RAD51-BRCA2 complex. Nature. Nov. 21, 2002;420(6913):287-93. doi: 10.1038/nature01230. Epub Nov. 10, 2002.
Perreault et al., Mixed deoxyribo- and ribo-oligonucleotides with catalytic activity. Nature. Apr. 5, 1990;344(6266):565-7. doi: 10.1038/344565a0.
Petit et al., Powerful mutators lurking in the genome. Philos Trans R Soc Lond B Biol Sci. Mar. 12, 2009;364(1517):705-15. doi: 10.1098/rstb.2008.0272.
Pieken et al., Kinetic characterization of ribonuclease-resistant 2'-modified hammerhead ribozymes. Science. Jul. 19, 1991;253(5017):314-7. doi: 10.1126/science.1857967.
Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.
Plotz et al., N-terminus of hMLH1 confers interaction of hMutLalpha and hMutLbeta with hMutSalpha. Nucleic Acids Res. Jun. 15, 2003;31(12):3217-26. doi: 10.1093/nar/gkg420.
Porensky et al., A single administration of morpholino antisense oligomer rescues spinal muscular atrophy in mouse. Hum Mol Genet. Apr. 1, 2012;21(7):1625-38. doi: 10.1093/hmg/ddr600. Epub Dec. 20, 2011.
Prasad et al., Visualizing the assembly of human Rad51 filaments on double-stranded Dna. J Mol Biol. Oct. 27, 2006;363(3):713-28. doi: 10.1016/j.jmb.2006.08.046. Epub Aug. 22, 2006.
Raghavan et al., Abstract 27: Therapeutic Targeting of Human Lipid Genes with in vivo CRISPR-Cas9 Genome Editing. Oral Abstract Presentations: Lipoprotein Metabolism and Therapeutic Targets. Arterioscler THromb Vasc Biol. 2015;35(Suppl. 1):Abstract 27. 5 pages.
Raillard et al., Targeting sites within HIV-1 cDNA with a DNA-cleaving ribozyme. Biochemistry. Sep. 10, 1996;35(36):11693-701. doi: 10.1021/bi960845g.
Rajagopal et al., High-throughput mapping of regulatory DNA. Nat Biotechnol. Feb. 2016;34(2):167-74. doi: 10.1038/nbt.3468. Epub Jan. 25, 2016.
Reiners et al., Scaffold protein harmonin (USH1C) provides molecular links between Usher syndrome type 1 and type 2. Hum Mol Genet. Dec. 15, 2005;14(24):3933-43. doi: 10.1093/hmg/ddi417. Epub Nov. 21, 2005.
Richardson et al., CRISPR-Cas9 genome editing in human cells occurs via the Fanconi anemia pathway. Nat Genet. Aug. 2018;50(8):1132-1139. doi: 10.1038/s41588-018-0174-0. Epub Jul. 27, 2018.
Richardson et al., Frequent chromosomal translocations induced by DNA double-strand breaks. Nature. Jun. 8, 2000;405(6787):697-700. doi: 10.1038/35015097.
Riddle et al., Frameshift suppression: a nucleotide addition in the anticodon of a glycine transfer RNA. Nat New Biol. Apr. 25, 1973;242(121):230-4. doi: 10.1038/newbio242230a0.
Riddle et al., Frameshift suppressors. II. Genetic mapping and dominance studies. J Mol Biol. May 28, 1972;66(3):483-93. doi: 10.1016/0022-2836(72)90428-7.
Riddle et al., Suppressors of frameshift mutations in Salmonella typhimurium. J Mol Biol. Nov. 28, 1970;54(1):131-44. doi: 10.1016/0022-2836(70)90451-1.
Robert et al., Virus-Like Particles Derived from HIV-1 for Delivery of Nuclear Proteins: Improvement of Production and Activity by Protein Engineering. Mol Biotechnol. Jan. 2017;59(1):9-23. doi: 10.1007/s12033-016-9987-1.
Robertson et al., Selection in vitro of an RNA enzyme that specifically cleaves single- stranded DNA. Nature. Mar. 29, 1990;344(6265):467-8. doi: 10.1038/344467a0.
Rodriguez-Muela et al., Single-Cell Analysis of SMN Reveals Its Broader Role in Neuromuscular Disease. Cell Rep. Feb. 7, 2017;18(6):1484-1498 and Supplemental Information. doi: 10.1016/j.celrep.2017.01.035.
Räschle et al., Mutations within the hMLH1 and hPMS2 subunits of the human MutLalpha mismatch repair factor affect its ATPase activity, but not its ability to interact with hMutSalpha. J Biol Chem. Jun. 14, 2002;277(24):21810-20. doi: 10.1074/jbc.M108787200. Epub Apr. 10, 2002.
Saayman et al., The therapeutic application of CRISPR/Cas9 technologies for HIV. Expert Opin Biol Ther. Jun. 2015;15(6):819-30. doi: 10.1517/14712598.2015.1036736. Epub Apr. 12, 2015.
Sadowski et al., The sequence-structure relationship and protein function prediction. Curr Opin Struct Biol. Jun. 2009;19(3):357-62. doi: 10.1016/j.sbi.2009.03.008. Epub May 4, 2009.
Samanta et al., A reverse transcriptase ribozyme. Elife. Sep. 26, 2017;6:e31153. doi: 10.7554/eLife.31153.
San Filippo et al., Mechanism of eukaryotic homologous recombination. Annu Rev Biochem. 2008;77:229-57. doi: 10.1146/annurev.biochem.77.061306.125255.
Schlacher et al., Double-strand break repair-independent role for BRCA2 in blocking stalled replication fork degradation by MRE11. Cell. May 13, 2011;145(4):529-42. doi: 10.1016/j.cell.2011.03.041. Erratum in: Cell. Jun. 10, 2011;145(6):993.
Schrank et al., Inactivation of the survival motor neuron gene, a candidate gene for human spinal muscular atrophy, leads to massive cell death in early mouse embryos. Proc Natl Acad Sci USA. Sep. 2, 1997;94(18):9920-5. doi: 10.1073/pnas.94.18.9920.
Score Results for Luetticken et al., Complete genome sequence of a Streptococcus dysgalactiae subsp. RT equisimilis strain possessing Lancefield's group A antigen. RL Submitted to the EMBL/GenBank/DDBJ databases. May 2012. 3 pages.
Score Results for Okumura et al., Evolutionary paths of streptococcal and staphylococcal superantigens. RL BMC Genomics. 2012;13:404-404. 3 pages.
Score Results for SHIMOMURA et al., Complete Genome Sequencing and Analysis of a Lancefield Group G RT *Streptococcus dysagalactiae* Subsp. Equisimilis Strain Causing Streptococcal RT Toxic Shock Syndrome (STSS). RL BMC Genomics. 2011;12:17-17. 3 pages.
Seffernick et al., Melamine deaminase and atrazine chlorohydrolase: 98 percent identical but functionally different. J Bacteriol. Apr. 2001;183(8):2405-10. doi: 10.1128/JB.183.8.2405-2410.2001.
Sharma et al., Identification of novel methyltransferases, Bmt5 and Bmt6, responsible for the m3U methylations of 25S rRNA in *Saccharomyces cerevisiae*. Nucleic Acids Res. Mar. 2014;42(5):3246-60. doi: 10.1093/nar/gkt1281. Epub Dec. 11, 2013.
Shcherbakova et al., Mutator phenotypes conferred by MLH1 overexpression and by heterozygosity for mlh1 mutations. Mol Cell Biol. Apr. 1999;19(4):3177-83. doi: 10.1128/MCB.19.4.3177.
Shechner et al., Multiplexable, locus-specific targeting of long RNAs with CRISPR-Display. Nat Methods. Jul. 2015; 12(7):664-70. doi: 10.1038/nmeth.3433. Epub Jun. 1, 2015.
Shen et al., Efficient genome modification by CRISPR-Cas9 nickase with minimal off-target effects. Nat Methods. Apr. 2014;11(4):399-402. doi: 10.1038/nmeth.2857. Epub Mar. 2, 2014.
Singh et al., Protein Engineering Approaches in the Post-Genomic Era. Curr Protein Pept Sci. 2018;19(1):5-15. doi: 10.2174/1389203718666161117114243.
Singh et al., Splicing of a critical exon of human Survival Motor Neuron is regulated by a unique silencer element located in the last intron. Mol Cell Biol. Feb. 2006;26(4):1333-46. doi: 10.1128/MCB.26.4.1333-1346.2006.

(56) References Cited

OTHER PUBLICATIONS

Somanathan et al., AAV vectors expressing LDLR gain-of-function variants demonstrate increased efficacy in mouse models of familial hypercholesterolemia. Circ Res. Aug. 29, 2014;115(6):591-9. doi: 10.1161/CIRCRESAHA.115.304008. Epub Jul. 14, 2014.

Song et al., RS-1 enhances CRISPR/Cas9- and TALEN-mediated knock-in efficiency. Nat Commun. Jan. 2, 20168;7:10548. doi: 10.1038/ncomms10548.

Sorusch et al., Characterization of the ternary Usher syndrome SANS/ush2a/whirlin protein complex. Hum Mol Genet. Mar. 15, 2017;26(6):1157-1172. doi: 10.1093/hmg/ddx027.

Stark et al., ATP hydrolysis by mammalian RAD51 has a key role during homology-directed DNA repair. J Biol Chem. Jun. 7, 2002;277(23):20185-94. doi: 10.1074/jbc.M112132200. Epub Mar. 28, 2002.

Steckelberg et al., A folded viral noncoding RNA blocks host cell exoribonucleases through a conformationally dynamic RNA structure. Proc Natl Acad Sci U S A. Jun. 19, 2018;115(25):6404-6409. doi: 10.1073/pnas.1802429115. Epub Jun. 4, 2018.

Strand et al., Destabilization of tracts of simple repetitive DNA in yeast by mutations affecting DNA mismatch repair. Nature. Sep. 16, 1993;365(6443):274-6. doi: 10.1038/365274a0. Erratum in: Nature Apr. 7, 1994;368(6471);569.

Studebaker et al., Depletion of uracil-DNA glycosylase activity is associated with decreased cell proliferation. Biochem Biophys Res Commun. Aug. 26, 2005;334(2):509-15. doi: 10.1016/j.bbrc.2005.06.118.

Su et al., Mispair specificity of methyl-directed DNA mismatch correction in vitro. J Biol Chem. May 15, 1988;263(14):6829-35. Erratum in: J Biol Chem Aug. 5, 1988;263(22):11015.

Sugawara et al., Heteroduplex rejection during single-strand annealing requires Sgs1 helicase and mismatch repair proteins Msh2 and Msh6 but not Pms1. Proc Natl Acad Sci U S A. Jun. 22, 2004;101(25):9315-20. doi: 10.1073/pnas.0305749101. Epub Jun. 15, 2004.

Sullenger et al., Ribozyme-mediated repair of defective mRNA by targeted, trans-splicing. Nature. Oct. 13, 1994;371(6498):619-22. doi: 10.1038/371619a0.

Sumner et al., Two breakthrough gene-targeted treatments for spinal muscular atrophy: challenges remain. J Clin Invest. Aug. 1, 2018;128(8):3219-3227. doi: 10.1172/JCI121658. Epub Jul. 9, 2018.

Supek et al., Differential DNA mismatch repair underlies mutation rate variation across the human genome. Nature. May 7, 2015;521(7550):81-4. doi: 10.1038/nature14173. Epub Feb. 23, 2015.

Suzuki et al., Crystal structures reveal an elusive functional domain of pyrrolysyl-tRNA synthetase. Nat Chem Biol. Dec. 2017;13(12):1261-1266. doi: 10.1038/nchembio.2497. Epub Oct. 16, 2017.

Svitashev et al., Targeted Mutagenesis, Precise Gene Editing, and Site-Specific Gene Insertion in Maize Using Cas9 and Guide RNA. Plant Physiol. Oct. 2015; 169(2):931-45. doi: 10.1104/pp.15.00793. Epub Aug. 12, 2015.

Talbot et al., Spinal muscular atrophy. Semin Neurol. Jun. 2001;21(2):189-97. doi: 10.1055/s-2001-15264.

Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.

Thomas et al., Heteroduplex repair in extracts of human HeLa cells. J Biol Chem. Feb. 25, 1991;266(6):3744-51.

Thompson et al., The Future of Multiplexed Eukaryotic Genome Engineering. ACS Chem Biol. Feb. 16, 2018;13(2):313-325. doi: 10.1021/acschembio.7b00842. Epub Dec. 28, 2017.

Tomer et al., Contribution of human mlh1 and pms2 ATPase activities to DNA mismatch repair. J Biol Chem. Jun. 14, 2002;277(24):21801-9. doi: 10.1074/jbc.M111342200. Epub Mar. 15, 2002.

Toro et al., Comprehensive phylogenetic analysis of bacterial reverse transcriptases. PLoS One. Nov. 25, 2014;9(11):e114083. doi: 10.1371/journal.pone.0114083.

Tran et al., Hypermutability of homonucleotide runs in mismatch repair and DNA polymerase proofreading yeast mutants. Mol Cell Biol. May 1997;17(5):2859-65. doi: 10.1128/MCB.17.5.2859.

Trojan et al., Functional analysis of hMLH1 variants and HNPCC-related mutations using a human expression system. Gastroenterology. Jan. 2002;122(1):211-9. doi: 10.1053/gast.2002.30296.

Umar et al., DNA loop repair by human cell extracts. Science. Nov. 4, 1994;266(5186): 814-6. doi: 10.1126/science.7973637.

Usman et al., Exploiting the chemical synthesis of RNA. Trends Biochem Sci. Sep. 1992;17(9):334-9. doi: 10.1016/0968-0004(92)90306-t.

Vakulskas et al., A high-fidelity Cas9 mutant delivered as a ribonucleoprotein complex enables efficient gene editing in human hematopoietic stem and progenitor cells. Nat Med. Aug. 2018;24(8):1216-1224. doi: 10.1038/s41591-018-0137-0. Epub Aug. 6, 2018.

Van Den Oord et al., Pixel Recurrent Neural Networks. Proceedings of the 33rd International Conference on Machine Learning. Journal of Machine Learning Research. Aug. 19, 2016. vol. 48. 11 pages.

Vidal et al., Yeast forward and reverse 'n'-hybrid systems. Nucleic Acids Res. Feb. 19, 1999;27(4):919-29. doi: 10.1093/nar/27.4.919.

Villiger et al., Treatment of a metabolic liver disease by in vivo genome base editing in adult mice. Nat Med. Oct. 2018;24(10):1519-1525. doi: 10.1038/s41591-018-0209-1. Epub Oct. 8, 2018.

Warren et al., Structure of the human MutSalpha DNA lesion recognition complex. Mol Cell. May 25, 2007;26(4):579-92. doi: 10.1016/j.molcel.2007.04.018.

Wills et al., Pseudoknot-dependent read-through of retroviral gag termination codons: importance of sequences in the spacer and loop 2. EMBO J. Sep. 1, 1994;13(17):4137-44. doi: 10.1002/j.1460-2075.1994.tb06731.x.

Wirth et al., Mildly affected patients with spinal muscular atrophy are partially protected by an increased SMN2 copy number Hum Genet. May 2006;119(4):422-8. doi: 10.1007/s00439-006-0156-7. Epub Mar. 1, 2006.

Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

Woo et al., Gene activation of SMN by selective disruption of lncRNA-mediated recruitment of PRC2 for the treatment of spinal muscular atrophy. Proc Natl Acad Sci U S A. Feb. 21, 2017;114(8):E1509-E1518. doi:10.1073/pnas.1616521114. Epub Feb. 13, 2017.

Wu et al., A novel SCN9A mutation responsible for primary erythromelalgia and is resistant to the treatment of sodium channel blockers. PLoS One. 2013;8(1):e55212. doi: 10.1371/journal.pone.0055212. Epub Jan. 31, 2013. 15 pages.

Wu et al., MLV based viral-like-particles for delivery of toxic proteins and nuclear transcription factors. Biomaterials. Sep. 2014;35(29):8416-26. doi: 10.1016/j.biomaterials.2014.06.006. Epub Jul. 3, 2014.

Wu et al., Widespread Influence of 3'-End Structures on Mammalian mRNA Processing and Stability. Cell. May 18, 2017;169(5):905-917.e11. doi: 10.1016/j.cell.2017.04.036.

Xi et al., C-terminal Loop Mutations Determine Folding and Secretion Properties of PCSK9. Biochem Mol Biol J. 2016;2(3):17. doi: 10.21767/2471-8084.100026. 12 pages.

Yamane et al., Deep-sequencing identification of the genomic targets of the cytidine deaminase AID and its cofactor RPA in B lymphocytes. Nat Immunol. Jan. 2011;12(1):62-9. doi: 10.1038/ni.1964. Epub Nov. 28, 2010.

Yan et al., Highly Efficient A•T to G•C Base Editing by Cas9n-Guided tRNA Adenosine Deaminase in Rice. Mol Plant. Apr. 2, 2018;11(4):631-634. doi: 10.1016/j.molp.2018.02.008. Epub Feb. 22, 2018.

Yang et al., BRCA2 function in DNA binding and recombination from a BRCA2-DSS1-ssDNA structure. Science. Sep. 13, 2002;297(5588):1837-48. doi: 10.1126/science.297.5588.1837.

Yang et al., Genome-wide inactivation of porcine endogenous retroviruses (PERVs). Science. Nov. 27, 2015;350(6264):1101-4. doi: 10.1126/science.aad1191. Epub Oct. 11, 2015.

(56) References Cited

OTHER PUBLICATIONS

Yang et al., The BRCA2 homologue Brh2 nucleates RAD51 filament formation at a dsDNA-ssDNA junction. Nature. Feb. 10, 2005;433(7026):653-7. doi: 10.1038/nature03234.
Yi et al., Engineering of TEV protease variants by yeast ER sequestration screening (YESS) of combinatorial libraries. Proc Natl Acad Sci U S A. Apr. 30, 2013;110(18):7229-34. doi: 10.1073/pnas.1215994110. Epub Apr. 15, 2013.
Yu et al., Dynamic control of Rad51 recombinase by self-association and interaction with BRCA2. Mol Cell. Oct. 2003;12(4):1029-41. doi: 10.1016/s1097-2765(03)00394-0.
Zhang et al., Efficient precise knockin with a double cut HDR donor after CRISPR/Cas9- mediated double-stranded DNA cleavage. Genome Biol. Feb. 20, 2017;18(1):35. doi: 10.1186/s13059-017-1164-8.
Zhang et al., Global analysis of small RNA and mRNA targets of Hfq. Mol Microbiol. Nov. 2003;50(4):1111-24. doi: 10.1046/j.1365-2958.2003.03734.x.
Zhang et al., Large genomic fragment deletions and insertions in mouse using CRISPR/Cas9. PLoS One. Mar. 24, 2015;10(3):e0120396. doi: 10.1371/journal.pone.0120396. 14 pages.
Zhang et al., Reconstitution of 5'-directed human mismatch repair in a purified system. Cell. Sep. 9, 2005;122(5):693-705. doi: 10.1016/j.cell.2005.06.027.
Zhang et al., Reversible RNA Modification N1-methyladenosine (m1A) in mRNA and tRNA. Genomics Proteomics Bioinformatics. Jun. 2018; 16(3):155-161. doi: 10.1016/j.gpb.2018.03.003. Epub Jun. 14, 2018.
Zhou et al., GISSD: Group I Intron Sequence and Structure Database. Nucleic Acids Res. Jan. 2008;36(Database issue):D31-7. doi: 10.1093/nar/gkm766. Epub Oct. 16, 2007.
Zhu et al., Novel Thrombotic Function of a Human SNP in STXBP5 Revealed by CRISPR/Cas9 Gene Editing in Mice. Arterioscler Thromb Vasc Biol. Feb. 2017;37(2):264-270. doi: 10.1161/ATVBAHA.116.308614. Epub Dec. 29, 2016.
Zolotukhin et al., Production and purification of serotype 1, 2, and 5 recombinant adeno- associated viral vectors. Methods. Oct. 2002;28(2):158-67. doi: 10.1016/s1046-2023(02)00220-7.
†U.S. Appl. No. 17/289,665, filed Apr. 28, 2021, Liu et al.
†U.S. Appl. No. 16/756,432, filed Apr. 15, 2020, Liu et al.
†U.S. Appl. No. 18/460,178, filed Sep. 1, 2023, Liu et al.
†U.S. Appl. No. 16/772,747, filed Jun. 12, 2020, Shen et al.
†U.S. Appl. No. 17/425,261, filed Jul. 22, 2021, Kim et al.
†U.S. Appl. No. 17/057,398, filed Nov. 20, 2020, Liu et al.
†U.S. Appl. No. 17/259,147, filed Jan. 8, 2021, Liu et al.
†U.S. Appl. No. 17/270,396, filed Feb. 22, 2021, Liu et al.
†U.S. Appl. No. 17/273,688, filed Mar. 4, 2021, Liu et al.
†U.S. Appl. No. 17/294,287, filed May 14, 2021, Liu et al.
†U.S. Appl. No. 17/288,504, filed Apr. 23, 2021, Liu et al.
†U.S. Appl. No. 17/633,573, filed Feb. 7, 2022, Liu et al.
†U.S. Appl. No. 17/910,552, filed Sep. 9, 2022, Liu et al.
†U.S. Appl. No. 17/436,048, filed Sep. 2, 2021, Liu et al.
†U.S. Appl. No. 17/219,590, filed Mar. 31, 2021, Liu et al.
†U.S. Appl. No. 17/603,917, filed Oct. 14, 2021, Liu et al.
†U.S. Appl. No. 17/797,700, filed Aug. 4, 2022, Liu et al.
†U.S. Appl. No. 17/602,738, filed Oct. 8, 2021, Liu et al.
†U.S. Appl. No. 17/613,025, filed Nov. 19, 2021, Liu et al.
†U.S. Appl. No. 17/300,668, filed Sep. 17, 2021, Liu et al.
†U.S. Appl. No. 17/795,819, filed Jul. 27, 2022, Liu et al.
†U.S. Appl. No. 17/779,953, filed May 25, 2022, Liu et al.
†U.S. Appl. No. 17/767,777, filed Apr. 8, 2022, Liu et al.
†U.S. Appl. No. 17/797,701, filed Aug. 4, 2022, Liu et al.
†U.S. Appl. No. 18/053,269, filed Nov. 7, 2022, Liu et al.
†U.S. Appl. No. 18/534,489, filed Dec. 8, 2023, Liu et al.
†U.S. Appl. No. 18/619,518, filed Mar. 28, 2024, Liu et al.
†U.S. Appl. No. 17/797,697, filed Aug. 4, 2022, Liu et al.
†U.S. Appl. No. 17/921,971, filed Oct. 27, 2022, Liu et al.
†U.S. Appl. No. 17/219,635, filed Mar. 31, 2021, Liu et al.
†U.S. Appl. No. 18/064,738, filed Dec. 12, 2022, Liu et al.
†U.S. Appl. No. 18/326,588, filed May 31, 2023, Liu et al.
†U.S. Appl. No. 18/326,634, filed May 31, 2023, Liu et al.
†U.S. Appl. No. 18/326,689, filed May 31, 2023, Liu et al.
†U.S. Appl. No. 18/326,708, filed May 31, 2023, Liu et al.
†U.S. Appl. No. 18/646,267, filed Apr. 25, 2024, Liu et al.
†U.S. Appl. No. 17/219,672, filed Mar. 31, 2021, Liu et al.
†U.S. Appl. No. 17/751,599, filed May 23, 2022, Liu et al.
†U.S. Appl. No. 18/323,245, filed May 24, 2023, Liu et al.
†U.S. Appl. No. 17/440,682, filed Sep. 17, 2021, Liu et al.
†U.S. Appl. No. 18/028,183, filed Mar. 23, 2023, Liu et al.
†U.S. Appl. No. 18/271,656, filed Jul. 10, 2023, Liu et al.
†U.S. Appl. No. 18/579,685, filed Jan. 16, 2024, Liu et al.
†U.S. Appl. No. 18/286,547, filed Oct. 11, 2023, Liu et al.
†U.S. Appl. No. 18/568,796, filed Dec. 8, 2023, Liu et al.
†U.S. Appl. No. 18/704,328, filed Apr. 24, 2024, Liu et al.
†U.S. Appl. No. 18/681,490, filed Feb. 5, 2024, Liu et al.
†U.S. Appl. No. 14/234,031, filed Mar. 24, 2014, Liu et al.
†U.S. Appl. No. 14/320,271, filed Jun. 30, 2014, Liu et al.
†U.S. Appl. No. 16/441,751, filed Jun. 14, 2019, Liu et al.
†U.S. Appl. No. 18/654,704, filed May 3, 2024, Liu et al.
†U.S. Appl. No. 14/320,519, filed Jun. 30, 2014, Liu et al.
†U.S. Appl. No. 14/913,458, filed Feb. 22, 2016, Liu et al.
†U.S. Appl. No. 16/266,937, filed Feb. 4, 2019, Liu et al.
†U.S. Appl. No. 14/320,370, filed Jun. 30, 2014, Liu et al.
†U.S. Appl. No. 14/320,413, filed Jun. 30, 2014, Liu et al.
†U.S. Appl. No. 14/874,123, filed Oct. 2, 2015, Liu et al.
†U.S. Appl. No. 14/911,117, filed Feb. 9, 2016, Liu et al.
†U.S. Appl. No. 17/160,329, filed Jan. 27, 2021, Liu et al.
†U.S. Appl. No. 15/029,602, filed Apr. 14, 2016, Ritter et al.
†U.S. Appl. No. 14/462,163, filed Aug. 18, 2014, Liu et al.
†U.S. Appl. No. 14/462,189, filed Aug. 18, 2014, Liu et al.
†U.S. Appl. No. 14/916,679, filed Mar. 4, 2016, Liu et al.
†U.S. Appl. No. 16/860,639, filed Apr. 28, 2020, Liu et al.
†U.S. Appl. No. 14/320,498, filed Jun. 30, 2014, Liu et al.
†U.S. Appl. No. 14/320,467, filed Jun. 30, 2014, Liu et al.
†U.S. Appl. No. 14/916,681, filed Mar. 4, 2016, Liu et al.
†U.S. Appl. No. 17/103,233, filed Nov. 24, 2020, Liu et al.
†U.S. Appl. No. 17/937,203, filed Sep. 30, 2022, Liu et al.
†U.S. Appl. No. 14/326,329, filed Jul. 8, 2014, Liu et al.
†U.S. Appl. No. 14/326,340, filed Jul. 8, 2014, Liu et al.
†U.S. Appl. No. 14/326,361, filed Jul. 8, 2014, Liu et al.
†U.S. Appl. No. 14/916,683, filed Mar. 4, 2016, Liu et al.
†U.S. Appl. No. 16/796,323, filed Feb. 20, 2020, Liu et al.
†U.S. Appl. No. 17/688,416, filed Mar. 7, 2022, Liu et al.
†U.S. Appl. No. 14/325,815, filed Jul. 8, 2014, Liu et al.
†U.S. Appl. No. 14/326,109, filed Jul. 8, 2014, Liu et al.
†U.S. Appl. No. 14/326,140, filed Jul. 8, 2014, Liu et al.
†U.S. Appl. No. 14/326,269, filed Jul. 8, 2014, Liu et al.
†U.S. Appl. No. 14/326,290, filed Jul. 8, 2014, Liu et al.
†U.S. Appl. No. 14/326,318, filed Jul. 8, 2014, Liu et al.
†U.S. Appl. No. 14/326,303, filed Jul. 8, 2014, Liu et al.
†U.S. Appl. No. 15/103,608, filed Jun. 10, 2016, Liu et al.
†U.S. Appl. No. 16/374,634, filed Apr. 3, 2019, Liu et al.
†U.S. Appl. No. 17/408,306, filed Aug. 20, 2021, Liu et al.
†U.S. Appl. No. 15/329,925, filed Jan. 27, 2017, Liu et al.
†U.S. Appl. No. 16/132,276, filed Sep. 14, 2018, Liu et al.
†U.S. Appl. No. 16/888,646, filed May 29, 2020, Liu et al.
†U.S. Appl. No. 18/069,898, filed Dec. 21, 2022, Liu et al.
†U.S. Appl. No. 14/529,010, filed Oct. 30, 2014, Liu et al.
†U.S. Appl. No. 15/958,721, filed Apr. 20, 2018, Liu et al.
†U.S. Appl. No. 17/130,812, filed Dec. 22, 2020, Liu et al.
†U.S. Appl. No. 15/331,852, filed Oct. 22, 2016, Liu et al.
†U.S. Appl. No. 15/960,171, filed Apr. 23, 2018, Liu et al.
†U.S. Appl. No. 15/770,076, filed Apr. 20, 2018, Liu et al.
†U.S. Appl. No. 18/732,559, filed Jun. 3, 2024, Liu et al.
†U.S. Appl. No. 16/327,744, filed Feb. 22, 2019, Maianti et al.
†U.S. Appl. No. 18/055,274, filed Nov. 14, 2022, Maianti et al.
†U.S. Appl. No. 15/852,891, filed Dec. 22, 2017, Maianti et al.
†U.S. Appl. No. 16/926,436, filed Jul. 10, 2020, Maianti et al.
†U.S. Appl. No. 18/484,381, filed Oct. 10, 2023, Maianti et al..
†U.S. Appl. No. 15/852,526, filed Dec. 22, 2017, Maianti et al.
†U.S. Appl. No. 16/492,534, filed Sep. 9, 2019, Liu et al.
†U.S. Appl. No. 16/324,476, filed Feb. 8, 2019, Liu et al.
†U.S. Appl. No. 18/324,394, filed May 26, 2023, Liu et al.
†U.S. Appl. No. 15/791,085, filed Oct. 23, 2017, Liu et al.

(56) References Cited

OTHER PUBLICATIONS

†U.S. Appl. No. 16/143,370, filed Sep. 26, 2018, Liu et al.
†U.S. Appl. No. 17/148,059, filed Jan. 13, 2021, Liu et al.
†U.S. Appl. No. 18/174,569, filed Feb. 24, 2023, Liu et al.
†U.S. Appl. No. 18/641,299, filed Apr. 19, 2024, Liu et al.
†U.S. Appl. No. 16/492,548, filed Sep. 9, 2019, Maianti et al.
†U.S. Appl. No. 18/545,977, filed Dec. 19, 2023, Maianti et al.
†U.S. Appl. No. 15/784,033, filed Oct. 13, 2017, Liu et al.
†U.S. Appl. No. 17/692,925, filed Mar. 11, 2022, Liu et al.
†U.S. Appl. No. 16/492,553, filed Sep. 9, 2019, Liu et al.
†U.S. Appl. No. 18/059,308, filed Nov. 28, 2022, Liu et al.
†U.S. Appl. No. 15/934,945, filed Mar. 23, 2018, Liu et al.
†U.S. Appl. No. 17/586,688, filed Jan. 27, 2022, Liu et al.
†U.S. Appl. No. 18/066,878, filed Dec. 15, 2022, Liu et al.
†U.S. Appl. No. 16/643,376, filed Feb. 28, 2020, Liu et al.
†U.S. Appl. No. 17/700,109, filed Mar. 21, 2022, Liu et al.
†U.S. Appl. No. 16/612,988, filed Nov. 12, 2019, Liu et al.
†U.S. Appl. No. 16/634,405, filed Jan. 27, 2020, Liu et al.
†U.S. Appl. No. 18/178,048, filed Mar. 3, 2023, Liu et al.
†U.S. Appl. No. 16/976,047, filed Aug. 26, 2020, Liu et al.
†U.S. Appl. No. 17/593,020, filed Sep. 3, 2021, Church et al.
†U.S. Appl. No. 18/460,178, Liu et al.
[No. Author Listed] NCBI Reference Sequence: WP_032188360.1. Apr. 6, 2015. 1 page.
[No Author Listed], dCas9-5xPlat2AfID-P2A-scFvGCN4sfGFPTET1CD [Cloning vector pPlatTET-gRNA2]. GenBank No. BAV54124. Apr. 18, 2017. 5 pages.
[No. Author Listed], tRNA-specific adenosine deaminase [*Escherichia coli*]. GenBank Acc. No. CTS26096.1. Accessible at https://www.ncbi.nlm.nih.gov/protein/CTS26096.1. Aug. 22, 2015. 1 page.
Cheriyan et al., Faster protein splicing with the Nostoc punctiforme DnaE intein using non- native extein residues. J Biol Chem. Mar. 1, 2013;288(9):6202-11. doi: 10.1074/jbc.M112.433094. Epub Jan. 10, 2013.
GenBank Access No. BAP64357. Aug 1, 2013. 1 page.
Ghosh et al., Synapsis in phage Bxb1 integration: selection mechanism for the correct pair of recombination sites. J Mol Biol. Jun. 3, 2005;349(2):331-48. doi: 10.1016/j.jmb.2005.03.043. Epub Apr. 7, 2005.
Haeussler et al., Genome Editing with CRISPR-Cas9: Can It Get Any Better? J Genet Genomics. May 20, 2016;43(5):239-50. doi: 10.1016/j.jgg.2016.04.008. Epub Apr. 24, 2016. Author Manuscript. 22 pages.
Kizer et al., Application of functional genomics to pathway optimization for increased isoprenoid production. Appl Environ Microbiol. May 2008;74(10):3229-41. doi: 10.1128/AEM.02750-07. Epub Mar. 14, 2008.
Kueh et al., The new editor-targeted genome engineering in the absence of homology-directed repair. Cell Death Discov. Jun. 13, 2016;2:16042. doi: 10.1038/cddiscovery.2016.42.
Lu, periodic chart of amino acid.pdf. Accessed on the internet at https://figshare.com/articles/figure/periodic_chart_of_amino_acid_pdf/3445001/1. Posted Jun. 21, 2016. www.bachem.com. 1 page.
Mali et al., CAS9 transcriptional activators for target specificity screening and paired nickases for cooperative genome engineering. Nat Biotechnol. Sep. 2013;31(9):833-8, Supplemental Info. doi: 10.1038/nbt.2675. Epub Aug. 1, 2013.
Mariani et al., Species-specific exclusion of APOBEC3G from HIV-1 virions by Vif. Cell. Jul. 11, 2003;114(1):21-31. doi: 10.1016/s0092-8674(03)00515-4.
Momose et al., Diving into marine genomics with CRISPR/Cas9 systems. Mar Genomics. Dec. 2016;30:55-65. doi: 10.1016/j.margen.2016.10.003. Epub Oct. 12, 2016.
Prather et al., De novo biosynthetic pathways: rational design of microbial chemical factories. Curr Opin Biotechnol. Oct. 2008;19(5):468-74. doi: 10.1016/j.copbio.2008.07.009. Epub Sep. 5, 2008.
Rusk, Cas9 and the importance of asymmetry. Nat Methods. Apr. 2016;13(4):286-7. doi: 10.1038/nmeth.3826.
Score Results for US 2014-0186919 A1 to Zhang et al. Aug. 28, 2014. 3 pages.
Tuorto et al., Genome recoding by tRNA modifications. Open Biol. Dec. 2016;6(12):160287. doi: 10.1098/rsob.160287.
Tycko et al., Methods for Optimizing CRISPR-Cas9 Genome Editing Specificity. Mol Cell. Aug. 4, 2016;63(3):355-70. doi: 10.1016/j.molcel.2016.07.004.
Wang et al., CRISPR/Cas9 in Genome Editing and Beyond. Annu Rev Biochem. Jun. 2, 2016;85:227-64. doi: 10.1146/annurev-biochem-060815-014607. Epub Apr. 25, 2016.

* cited by examiner

| EMX1 | | $C_5$ | $C_6$ | $C_{10}$ |
|---|---|---|---|---|
| 0 uM XTEN | A | 0.1% | 0.1% | 0.1% |
| | C | 99.8% | 99.8% | 99.8% |
| | G | 0.0% | 0.0% | 0.1% |
| | T | 0.0% | 0.1% | 0.0% |
| 1.85 uM XTEN | A | 0.1% | 0.0% | 0.1% |
| | C | 60.4% | 61.0% | 99.1% |
| | G | 0.0% | 0.0% | 0.1% |
| | T | 39.5% | 39.0% | 0.7% |

| FANCF | | $C_6$ | $C_7$ | $C_8$ | $C_{11}$ |
|---|---|---|---|---|---|
| 0 uM XTEN | A | 0.1% | 0.1% | 0.1% | 0.1% |
| | C | 99.8% | 99.8% | 99.9% | 99.9% |
| | G | 0.0% | 0.1% | 0.0% | 0.0% |
| | T | 0.0% | 0.0% | 0.0% | 0.0% |
| 1.85 uM XTEN | A | 0.1% | 0.1% | 0.1% | 0.1% |
| | C | 63.9% | 64.7% | 65.0% | 72.6% |
| | G | 0.0% | 0.0% | 0.0% | 0.0% |
| | T | 36.0% | 35.1% | 34.9% | 27.3% |

| HEK293 site 2 | | $C_4$ | $C_6$ | $C_{11}$ |
|---|---|---|---|---|
| 0 uM XTEN | A | 0.1% | 0.1% | 0.1% |
| | C | 99.9% | 99.9% | 99.9% |
| | G | 0.0% | 0.0% | 0.0% |
| | T | 0.0% | 0.0% | 0.1% |
| 1.85 uM XTEN | A | 0.1% | 0.1% | 0.1% |
| | C | 80.6% | 76.9% | 99.6% |
| | G | 0.0% | 0.0% | 0.0% |
| | T | 19.3% | 22.9% | 0.3% |

| HEK293 site 3 | | $C_3$ | $C_4$ | $C_5$ | $C_9$ |
|---|---|---|---|---|---|
| 0 uM XTEN | A | 0.1% | 0.1% | 0.0% | 0.1% |
| | C | 99.8% | 99.9% | 99.9% | 99.9% |
| | G | 0.0% | 0.0% | 0.0% | 0.0% |
| | T | 0.1% | 0.0% | 0.0% | 0.0% |
| 1.85 uM XTEN | A | 0.1% | 0.1% | 0.0% | 0.1% |
| | C | 92.2% | 74.8% | 71.5% | 96.6% |
| | G | 0.0% | 0.0% | 0.0% | 0.0% |
| | T | 7.7% | 25.1% | 28.5% | 3.3% |

| HEK293 site 4 | | $C_3$ | $C_5$ | $C_8$ | $C_{11}$ |
|---|---|---|---|---|---|
| 0 uM XTEN | A | 0.1% | 0.0% | 0.1% | 0.0% |
| | C | 99.8% | 99.9% | 99.8% | 99.9% |
| | G | 0.0% | 0.0% | 0.0% | 0.0% |
| | T | 0.0% | 0.0% | 0.1% | 0.0% |
| 1.85 uM XTEN | A | 0.1% | 0.1% | 0.1% | 0.1% |
| | C | 98.8% | 60.1% | 97.0% | 99.4% |
| | G | 0.0% | 0.0% | 0.0% | 0.0% |
| | T | 1.1% | 39.8% | 2.9% | 0.5% |

| RNF2 | | $C_3$ | $C_6$ |
|---|---|---|---|
| 0 uM XTEN | A | 0.1% | 0.0% |
| | C | 99.9% | 99.9% |
| | G | 0.0% | 0.0% |
| | T | 0.0% | 0.0% |
| 1.85 uM XTEN | A | 0.1% | 0.0% |
| | C | 59.1% | 57.8% |
| | G | 0.0% | 0.0% |
| | T | 40.8% | 42.1% |

FIGURE 9

| EMX1 |   | $C_5$ | $C_6$ | $C_{10}$ |
|---|---|---|---|---|
| untreated | A | 0.0% | 0.0% | 0.0% |
|  | C | 99.5% | 99.7% | 100.0% |
|  | G | 0.0% | 0.1% | 0.0% |
|  | T | 0.5% | 0.2% | 0.0% |
| XTEN | A | 0.7% | 0.5% | 0.0% |
|  | C | 93.5% | 95.8% | 100.0% |
|  | G | 2.1% | 0.3% | 0.0% |
|  | T | 3.6% | 3.3% | 0.0% |
| XTEN-UGI | A | 0.2% | 0.0% | 0.0% |
|  | C | 81.8% | 82.5% | 100.0% |
|  | G | 0.6% | 0.3% | 0.0% |
|  | T | 17.4% | 17.1% | 0.0% |

| FANCF |   | $C_6$ | $C_7$ | $C_8$ | $C_{11}$ |
|---|---|---|---|---|---|
| untreated | A | 0.0% | 0.0% | 0.2% | 0.1% |
|  | C | 99.9% | 99.8% | 99.8% | 99.9% |
|  | G | 0.0% | 0.0% | 0.0% | 0.0% |
|  | T | 0.1% | 0.1% | 0.0% | 0.0% |
| XTEN | A | 0.3% | 0.1% | 0.0% | 0.0% |
|  | C | 98.1% | 99.2% | 99.0% | 99.8% |
|  | G | 0.4% | 0.0% | 0.0% | 0.0% |
|  | T | 1.2% | 0.7% | 1.0% | 0.2% |
| XTEN-UGI | A | 0.0% | 0.0% | 0.1% | 0.0% |
|  | C | 93.2% | 93.5% | 93.4% | 98.2% |
|  | G | 0.0% | 0.0% | 0.0% | 0.0% |
|  | T | 6.7% | 6.5% | 6.5% | 1.8% |

| HEK293 site 2 |   | $C_4$ | $C_6$ | $C_{11}$ |
|---|---|---|---|---|
| untreated | A | 0.3% | 0.2% | 0.2% |
|  | C | 99.7% | 99.7% | 99.7% |
|  | G | 0.0% | 0.0% | 0.0% |
|  | T | 0.0% | 0.0% | 0.0% |
| XTEN | A | 0.3% | 0.3% | 0.3% |
|  | C | 99.7% | 99.4% | 99.7% |
|  | G | 0.0% | 0.3% | 0.0% |
|  | T | 0.0% | 0.0% | 0.0% |
| XTEN-UGI | A | 0.3% | 0.2% | 0.2% |
|  | C | 98.8% | 98.2% | 99.8% |
|  | G | 0.0% | 0.3% | 0.0% |
|  | T | 0.9% | 1.3% | 0.0% |

| HEK293 site 2 |   | $C_3$ | $C_4$ | $C_5$ | $C_9$ |
|---|---|---|---|---|---|
| untreated | A | 0.0% | 0.0% | 0.0% | 0.0% |
|  | C | 100.0% | 100.0% | 100.0% | 99.9% |
|  | G | 0.0% | 0.0% | 0.0% | 0.0% |
|  | T | 0.0% | 0.0% | 0.0% | 0.1% |
| XTEN | A | 0.0% | 0.6% | 0.3% | 0.1% |
|  | C | 100.0% | 95.8% | 95.8% | 99.2% |
|  | G | 0.0% | 0.2% | 0.7% | 0.4% |
|  | T | 0.0% | 3.4% | 3.2% | 0.3% |
| XTEN-UGI | A | 0.0% | 0.3% | 0.3% | 0.0% |
|  | C | 96.8% | 83.0% | 79.2% | 98.5% |
|  | G | 0.0% | 0.0% | 1.1% | 0.2% |
|  | T | 3.2% | 16.8% | 19.4% | 1.3% |

| HEK293 site 4 |   | $C_3$ | $C_5$ | $C_8$ | $C_{11}$ |
|---|---|---|---|---|---|
| untreated | A | 0.0% | 0.4% | 0.0% | 0.0% |
|  | C | 99.8% | 97.6% | 99.9% | 100.0% |
|  | G | 0.0% | 1.0% | 0.0% | 0.0% |
|  | T | 0.2% | 1.0% | 0.0% | 0.0% |
| XTEN | A | 0.0% | 1.1% | 0.0% | 0.0% |
|  | C | 99.6% | 92.2% | 99.9% | 100.0% |
|  | G | 0.0% | 2.2% | 0.0% | 0.0% |
|  | T | 0.4% | 4.5% | 0.0% | 0.0% |
| XTEN-UGI | A | 0.0% | 0.5% | 0.0% | 0.0% |
|  | C | 99.4% | 86.7% | 99.1% | 100.0% |
|  | G | 0.0% | 1.8% | 0.0% | 0.0% |
|  | T | 0.6% | 11.0% | 0.9% | 0.0% |

| RNF2 |   | $C_3$ | $C_6$ |
|---|---|---|---|
| untreated | A | 0.0% | 0.0% |
|  | C | 99.9% | 99.5% |
|  | G | 0.0% | 0.2% |
|  | T | 0.0% | 0.3% |
| XTEN | A | 0.0% | 0.0% |
|  | C | 99.8% | 99.3% |
|  | G | 0.0% | 0.2% |
|  | T | 0.2% | 0.5% |
| XTEN-UGI | A | 0.0% | 0.0% |
|  | C | 99.6% | 99.1% |
|  | G | 0.0% | 0.4% |
|  | T | 0.4% | 0.5% |

FIGURE 10

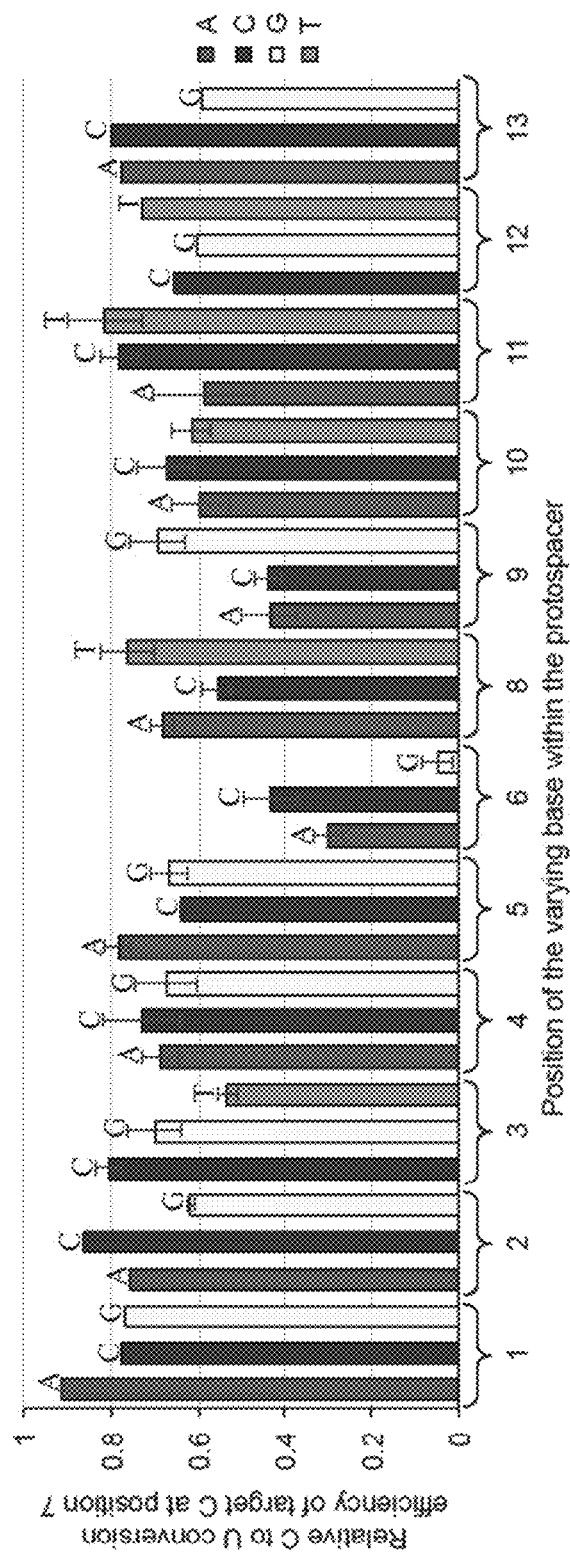

EMX1: GAGTC$_5$C$_8$GAGCAGAAGAAGAAGGG
FANCF: GGAATC$_6$C$_7$C$_8$TTC$_{11}$TGCAGCACCTGG
HEK293 site 2: GAAC$_4$AC$_6$AAAGCATAGACTGCGGG
HEK293 site 3: GGCC$_4$C$_5$AGACTGAGCACGTGATGG
HEK293 site 4: GGCAC$_5$TGCGGCTGGAGGTCCGGG
RNF2: GTC$_3$ATC$_6$TTAGTC$_{12}$ATTACCTGAGG

APOE4 Cys112Arg:   5'-GGAGGACGTGC$_{11}$GCGGCCGCCTGG
APOE4 Cys158Arg:   5'-GAAGC$_5$GCCTGGCAGTGTACCAGG
CTNNB1 Thr41Ala:   5'-CTGTGGC$_7$AGTGGCACCAGAATGG
HRAS Gln61Arg:     5'-CCTCCC$_6$GGCCGGCGGTATCCAGG
p53 Tyr163Cys:     5'-GCTTGC$_6$AGATGGCCATGGCGCGG
p53 Tyr236Cys:     5'-ACACATGC$_8$AGTTGTAGTGGATGG
p53 Asn239Asp:     5'-TGTC$_4$ACACATGTAGTTGTAGTGG

FIGURE 16A

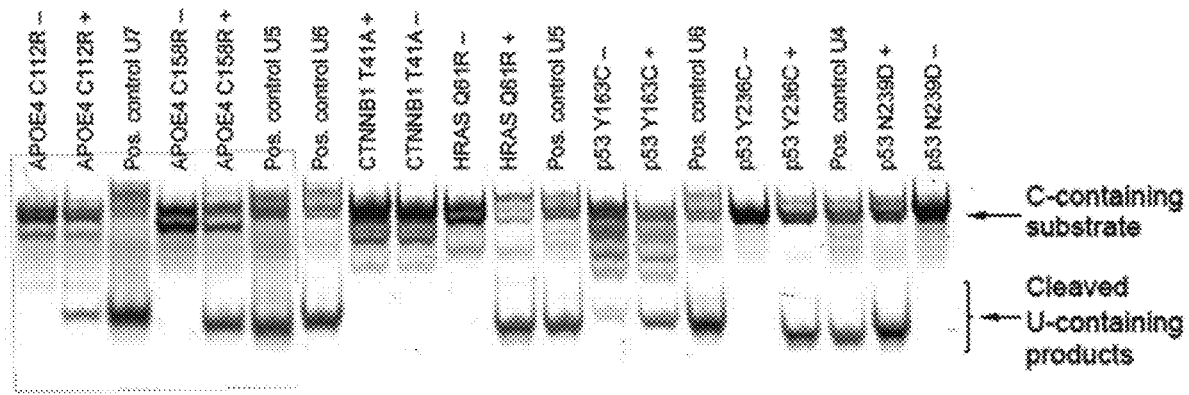

FIGURE 16B

Protospacer and PAM sequence:   5'-TTCCCCCCCGATTTATTTATGG-3'

| Sequence | % of total reads |
|---|---|
| CCCCCCCC | 62.4 |
| TTTTTTCC | 18.2 |
| TTTTTTTC | 13.4 |
| TTTTTTTT | 3.3 |
| TCCCCCCC | 0.8 |
| CCCCTTCC | 0.3 |
| CCCTTTCC | 0.3 |
| TTTTTCCC | 0.3 |
| CCCCTCCC | 0.3 |

FIGURE 17

EMX1:         GAGTC$_5$C$_6$GAGCAGAAGAAGAAGGG
FANCF:        GGAATC$_6$C$_7$C$_8$TTC$_{11}$TGCAGCACCTGG
HEK293 site 2: GAAC$_4$AC$_6$AAAGCATAGACTGCGGG
HEK293 site 3: GGCC$_4$C$_5$AGACTGAGCACGTGATGG
HEK293 site 4: GGCAC$_5$TGCGGCTGGAGGTCCGGG
RNF2:         GTC$_3$ATC$_6$TTAGTCATTACCTGAGG

FIGURE 18A

| EMX1 | C$_5$ | C$_6$ |
|---|---|---|
| NBE1 | 6.2% | 6.5% |
| NBE1 + UGI | 9.7% | 10.1% |
| NBE2 | 8.0% | 8.7% |

FIGURE 18B

| FANCF | C$_6$ | C$_7$ | C$_8$ | C$_{10}$ |
|---|---|---|---|---|
| NBE1 | 3.7% | 3.2% | 3.4% | 2.4% |
| NBE1 + UGI | 7.5% | 7.6% | 7.5% | 1.6% |
| NBE2 | 4.7% | 4.6% | 4.6% | 0.8% |

FIGURE 18C

| HEK293 site 2 | C$_4$ | C$_6$ |
|---|---|---|
| NBE1 | 0.4% | 0.4% |
| NBE1 + UGI | 1.6% | 2.6% |
| NBE2 | 3.4% | 5.9% |

FIGURE 18D

| HEK293 site 3 | $C_4$ | $C_5$ |
|---|---|---|
| NBE1 | 2.0% | 1.9% |
| NBE1 + UGI | 6.5% | 6.7% |
| NBE2 | 10.0% | 12.5% |

FIGURE 18E

| HEK293 site 4 | $C_5$ |
|---|---|
| NBE1 | 1.4% |
| NBE1 + UGI | 5.4% |
| NBE2 | 8.2% |

FIGURE 18F

| RNF2 | $C_3$ | $C_6$ |
|---|---|---|
| NBE1 | 0.7% | 1.4% |
| NBE1 + UGI | 3.4% | 3.9% |
| NBE2 | 2.5% | 3.7% |

FIGURE 18G

| Non-protospacer Cs | C | T |
|---|---|---|
| untreated | 99.93% | 0.03% |
| NBE1 | 99.95% | 0.03% |
| NBE1 + UGI | 99.91% | 0.06% |
| NBE2 | 99.92% | 0.04% |

EMX1 off target 3 — 708

| G | A | G | C | C | G | A | G | C | A | G | A | A | G | A | A | A | G | A | C | G |
|---|---|---|---|---|---|---|---|---|---|---|---|---|---|---|---|---|---|---|---|---|
|   |   |   |   |   |   |   |   |   |   |   |   |   |   |   |   |   |   |   |   |   |

| | | | | | | | | | |
|---|---|---|---|---|---|---|---|---|---|
| untreated | | 0.0 | 0.0 | | | 0.0 | | | | | 0.0 |
| NBE1 | | 0.0 | 0.0 | | | 0.0 | | | | | 0.0 |
| NBE2 | | 0.8 | 0.9 | | | 0.0 | | | | | 0.0 |
| NBE3 | | 5.1 | 5.2 | | | 0.0 | | | | | 0.0 |

EMX1 off target 4 — 393

| G | A | G | T | C | C | T | A | G | C | A | G | A | A | G | A | A | G | A | G | G |
|---|---|---|---|---|---|---|---|---|---|---|---|---|---|---|---|---|---|---|---|---|

| | | | | | | | | | |
|---|---|---|---|---|---|---|---|---|---|
| untreated | | 0.0 | 0.0 | | | 0.0 | | | | | 0.0 |
| NBE1 | | 0.2 | 0.2 | | | 0.0 | | | | | 0.0 |
| NBE2 | | 0.5 | 0.5 | | | 0.0 | | | | | 0.0 |
| NBE3 | | 2.2 | 2.2 | | | 0.0 | | | | | 0.0 |

EMX1 off target 6 — 216

| G | A | G | T | C | C | G | G | G | A | G | A | A | G | A | A | A | G | A | A | G |
|---|---|---|---|---|---|---|---|---|---|---|---|---|---|---|---|---|---|---|---|---|

| | | | |
|---|---|---|---|
| untreated | | 0.0 | 0.1 |
| NBE1 | | 0.1 | 0.1 |
| NBE2 | | 0.2 | 0.3 |
| NBE3 | | 1.0 | 1.0 |

| Non-protospacer Cs | C (%) | T (%) |
|---|---|---|
| untreated | 99.94 | 0.04 |
| NBE1 | 99.92 | 0.05 |
| NBE2 | 99.92 | 0.05 |
| NBE3 | 99.94 | 0.03 |

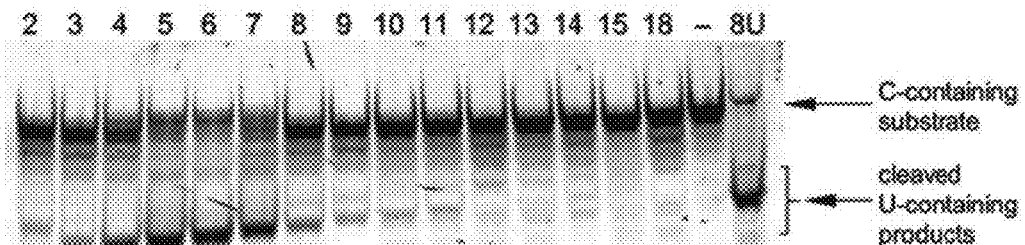
FIGURE 36D
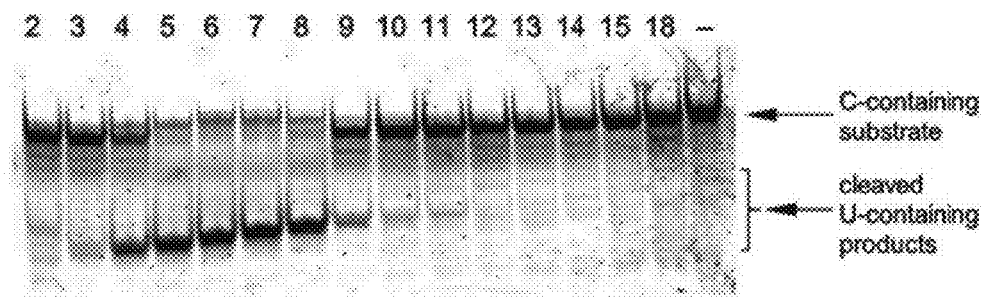
FIGURE 36E
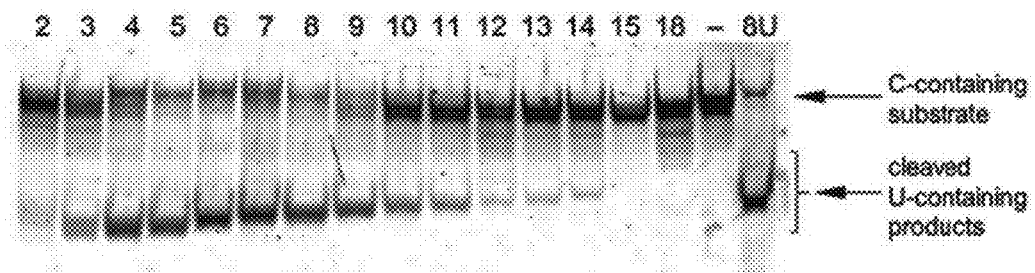
FIGURE 36F
EMX1:          GAGTC$_5$C$_6$GAGCAGAAGAAGAAGGG
FANCF:         GGAATC$_6$C$_7$C$_8$TTC$_{11}$TGCAGCACCTGG
HEK293 site 2: GAAC$_4$AC$_6$AAAGCATAGACTGCGGG
HEK293 site 3: GGCC$_4$C$_5$AGACTGAGCACGTGATGG
HEK293 site 4: GGCAC$_5$TGCGGCTGGAGGTCCGGG
RNF2:          GTC$_3$ATC$_6$TTAGTC$_{12}$ATTACCTGAGG
FIGURE 37A

FIGURE 37B

| non-protospacer C/Gs | average C/G (%) | average T/A (%) | lowest T/A (%) | highest T/A (%) |
|---|---|---|---|---|
| untreated | 99.95 ± 0.14 | 0.02 ± 0.02 | 0.00 | 2.44 |
| BE1 | 99.95 ± 0.24 | 0.03 ± 0.03 | 0.00 | 1.84 |
| BE2 | 99.95 ± 0.13 | 0.03 ± 0.03 | 0.00 | 1.92 |
| BE3 | 99.97 ± 0.09 | 0.02 ± 0.02 | 0.00 | 2.52 |

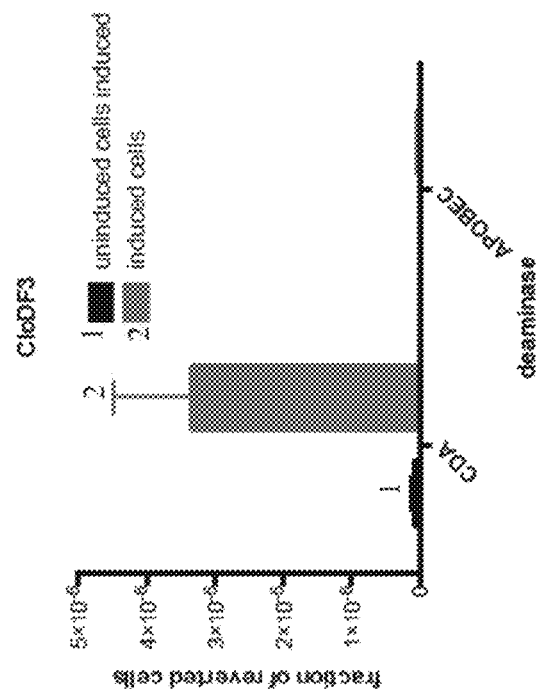
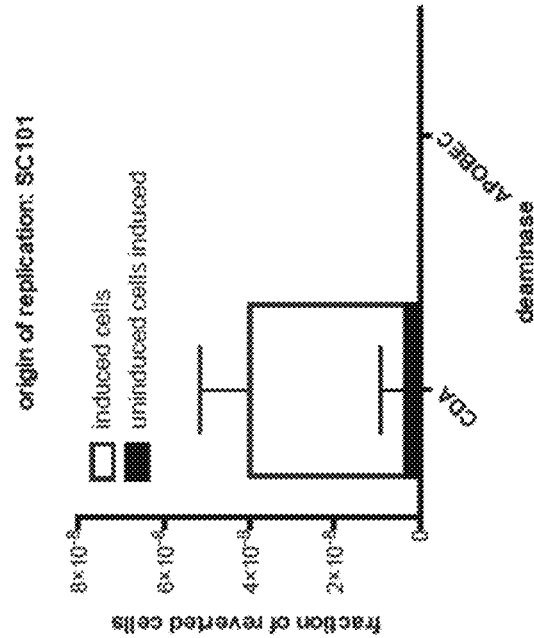
FIGURE 49

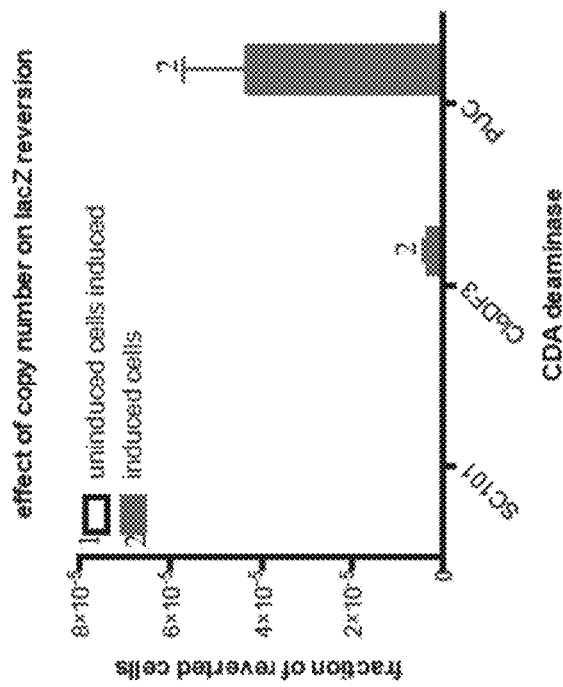
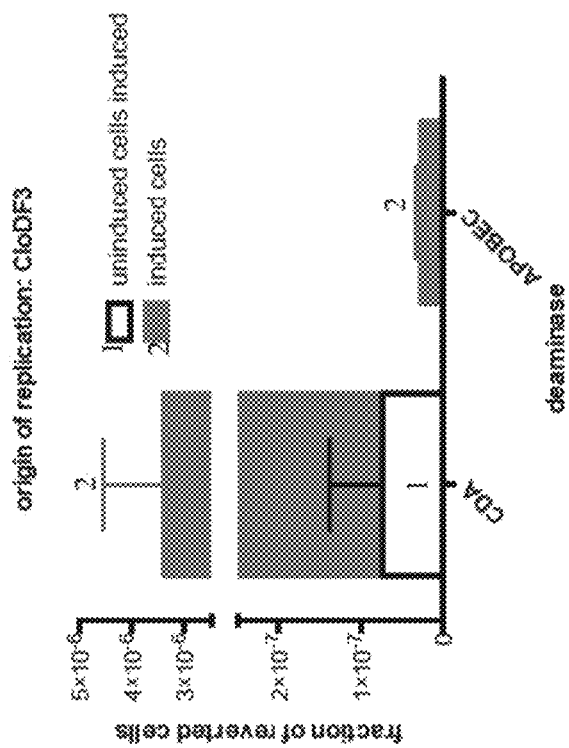
FIGURE 49 (CONTINUED)

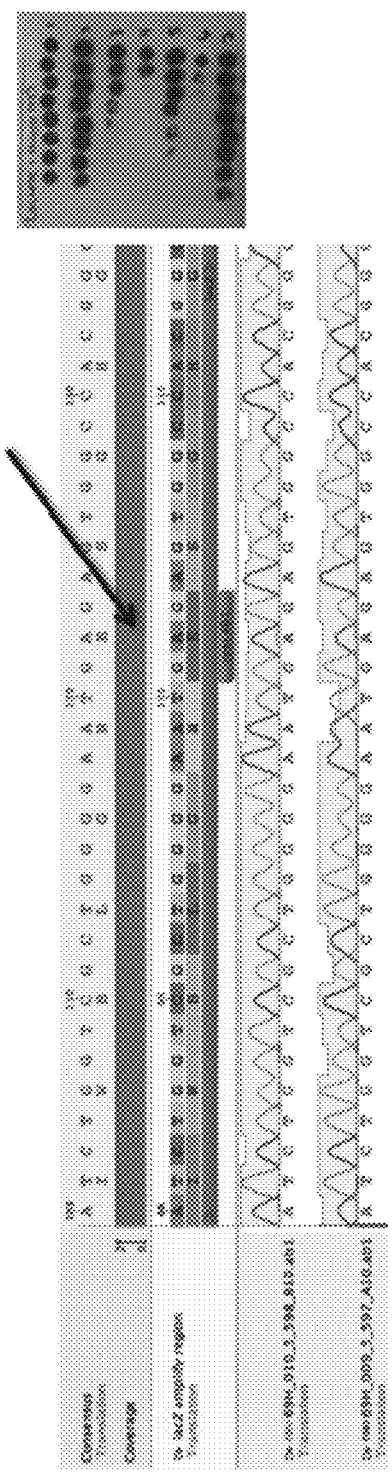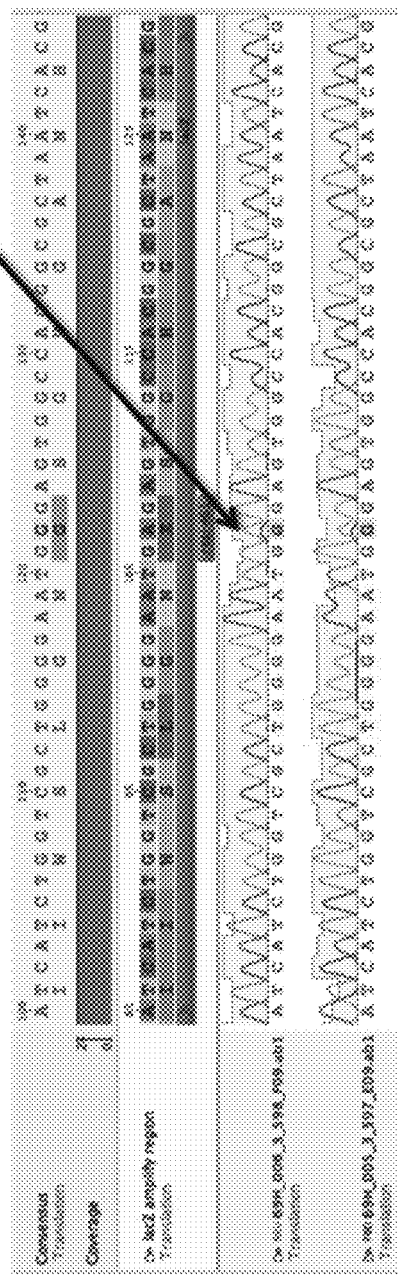
FIGURE 50

Row 1: CDA-dCas9 + selection plasmid (chlor$^S$)

Row 2: CDA-dCas9 + pos. control selection (chlor$^R$)

Row 3: rAPOBEC-dCas9 + selection plasmid (chlor$^S$)

Row 4: rAPOBEC-dCas9 + pos. control selection (chlor$^R$)

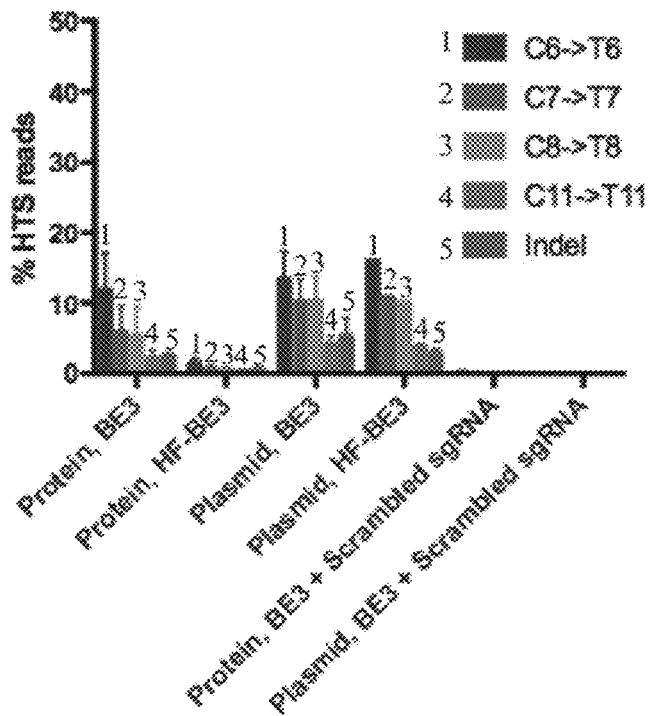
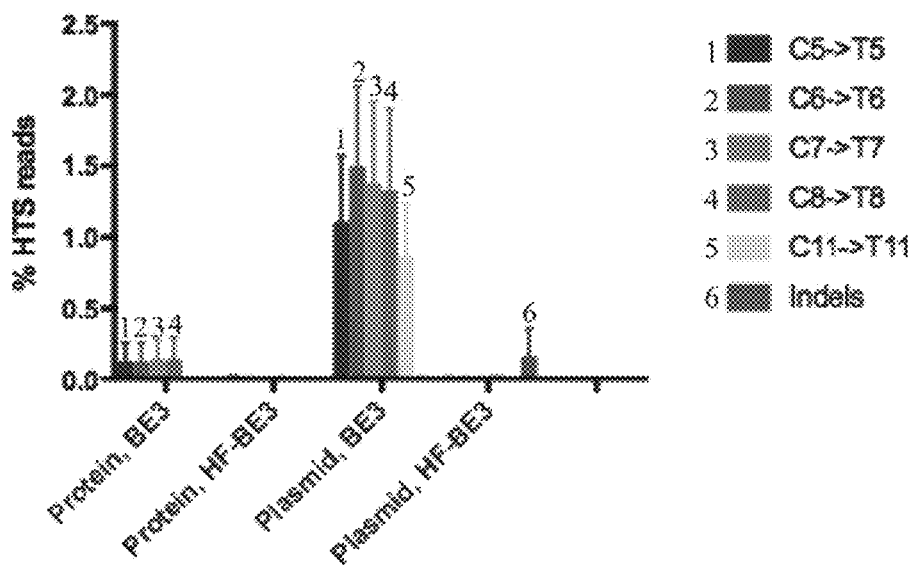
FIGURE 78

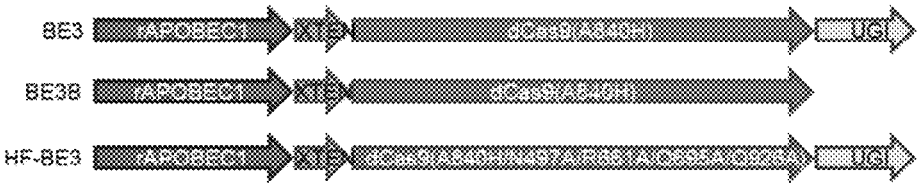
FIGURE 91

| Species | PAM | Base editor | Reference |
|---|---|---|---|
| S. pyogenes | NGG | BE3 | Wild-type |
| | NGA | VQR, EQR BE3 | Ref#7 |
| | NGCG | VRER BE3 | Ref#7 |
| S. aureus | NNGRRT | SaBE3 | Wild-type |
| | NNNRRT | SaKKHBE3 | Ref#8 |

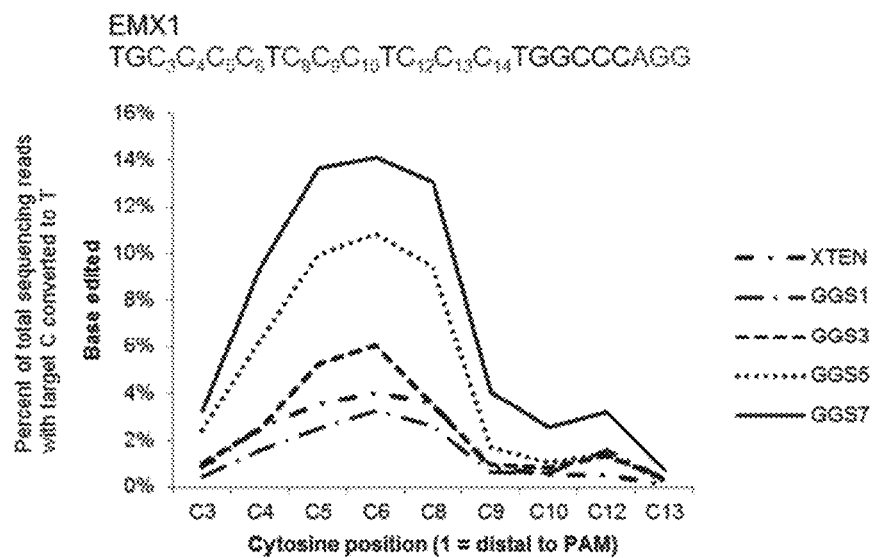
FIGURE 96
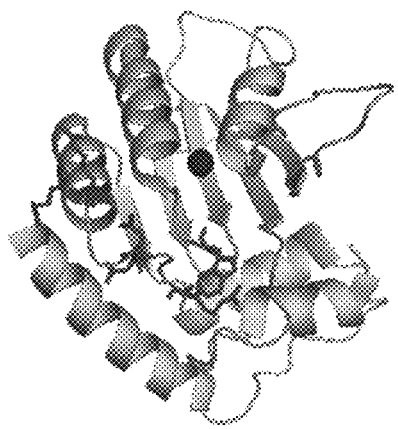
FIGURE 97A
| APOBEC1 mutation | APOBEC3G mutation | Reference |
|---|---|---|
| R126A | R320A | #9,10 |
| R126E | R320E | #9,10 |
| W90A | W285A | #9,10 |
| W90Y | W285Y | This work |
| R132E | R326E | This work |
FIGURE 97B

NUCLEOBASE EDITORS AND USES THEREOF

RELATED APPLICATIONS

This application is a continuation of and claims priority under 35 U.S.C. § 120 to U.S. application, U.S. Ser. No. 15/960,171, filed Apr. 23, 2018, which is a continuation of and claims priority under 35 U.S.C. § 120 to international PCT Application, PCT/US2016/058344, filed Oct. 22, 2016, and is a continuation of and claims priority under 35 U.S.C. § 120 to U.S. application, U.S. Ser. No. 15/331,852, filed Oct. 22, 2016, which claims priority under 35 U.S.C. § 119(e) to U.S. provisional patent applications, U.S. Ser. No. 62/245,828 filed Oct. 23, 2015, U.S. Ser. No. 62/279,346 filed Jan. 15, 2016, U.S. Ser. No. 62/311,763 filed Mar. 22, 2016, U.S. Ser. No. 62/322,178 filed Apr. 13, 2016, U.S. Ser. No. 62/357,352 filed Jun. 30, 2016, U.S. Ser. No. 62/370,700 filed Aug. 3, 2016, U.S. Ser. No. 62/398,490 filed Sep. 22, 2016, U.S. Ser. No. 62/408,686 filed Oct. 14, 2016, and U.S. Ser. No. 62/357,332 filed Jun. 30, 2016; each of which is incorporated herein by reference.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Nov. 9, 2021, is named H082470213US10-SEQ-EPG and is 4,463,178 bytes in size.

GOVERNMENT SUPPORT

This invention was made with Government support under grant number EB022376 (formerly GM065400) awarded by the National Institutes of Health. The Government has certain rights in the invention.

BACKGROUND OF THE INVENTION

Targeted editing of nucleic acid sequences, for example, the targeted cleavage or the targeted introduction of a specific modification into genomic DNA, is a highly promising approach for the study of gene function and also has the potential to provide new therapies for human genetic diseases.[1] An ideal nucleic acid editing technology possesses three characteristics: (1) high efficiency of installing the desired modification; (2) minimal off-target activity; and (3) the ability to be programmed to edit precisely any site in a given nucleic acid, e.g., any site within the human genome.[2] Current genome engineering tools, including engineered zinc finger nucleases (ZFNs),[3] transcription activator like effector nucleases (TALENs),[4] and most recently, the RNA-guided DNA endonuclease Cas9,[5] effect sequence-specific DNA cleavage in a genome. This programmable cleavage can result in mutation of the DNA at the cleavage site via non-homologous end joining (NHEJ) or replacement of the DNA surrounding the cleavage site via homology-directed repair (HDR).[6,7]

One drawback to the current technologies is that both NHEJ and HDR are stochastic processes that typically result in modest gene editing efficiencies as well as unwanted gene alterations that can compete with the desired alteration.[8] Since many genetic diseases in principle can be treated by effecting a specific nucleotide change at a specific location in the genome (for example, a C to T change in a specific codon of a gene associated with a disease),[9] the development of a programmable way to achieve such precision gene editing would represent both a powerful new research tool, as well as a potential new approach to gene editing-based human therapeutics.

SUMMARY OF THE INVENTION

The clustered regularly interspaced short palindromic repeat (CRISPR) system is a recently discovered prokaryotic adaptive immune system[10] that has been modified to enable robust and general genome engineering in a variety of organisms and cell lines.[11] CRISPR-Cas (CRISPR associated) systems are protein-RNA complexes that use an RNA molecule (sgRNA) as a guide to localize the complex to a target DNA sequence via base-pairing.[12] In the natural systems, a Cas protein then acts as an endonuclease to cleave the targeted DNA sequence.[13] The target DNA sequence must be both complementary to the sgRNA, and also contain a "protospacer-adjacent motif" (PAM) at the 3'-end of the complementary region in order for the system to function.[14]

Among the known Cas proteins, S. pyogenes Cas9 has been mostly widely used as a tool for genome engineering.[15] This Cas9 protein is a large, multi-domain protein containing two distinct nuclease domains. Point mutations can be introduced into Cas9 to abolish nuclease activity, resulting in a dead Cas9 (dCas9) that still retains its ability to bind DNA in a sgRNA-programmed manner.[16] In principle, when fused to another protein or domain, dCas9 can target that protein to virtually any DNA sequence simply by co-expression with an appropriate sgRNA.

The potential of the dCas9 complex for genome engineering purposes is immense. Its unique ability to bring proteins to specific sites in a genome programmed by the sgRNA in theory can be developed into a variety of site-specific genome engineering tools beyond nucleases, including transcriptional activators, transcriptional repressors, histone-modifying proteins, integrases, and recombinases.[11] Some of these potential applications have recently been implemented through dCas9 fusions with transcriptional activators to afford RNA-guided transcriptional activators,[17,18] transcriptional repressors,[16,19,20] and chromatin modification enzymes.[21] Simple co-expression of these fusions with a variety of sgRNAs results in specific expression of the target genes. These seminal studies have paved the way for the design and construction of readily programmable sequence-specific effectors for the precise manipulation of genomes.

Significantly, 80-90% of protein mutations responsible for human disease arise from the substitution, deletion, or insertion of only a single nucleotide.[6] Most current strategies for single-base gene correction include engineered nucleases (which rely on the creation of double-strand breaks, DSBs, followed by stochastic, inefficient homology-directed repair, HDR), and DNA-RNA chimeric oligonucleotides.[22] The latter strategy involves the design of a RNA/DNA sequence to base pair with a specific sequence in genomic DNA except at the nucleotide to be edited. The resulting mismatch is recognized by the cell's endogenous repair system and fixed, leading to a change in the sequence of either the chimera or the genome. Both of these strategies suffer from low gene editing efficiencies and unwanted gene alterations, as they are subject to both the stochasticity of HDR and the competition between HDR and non-homologous end-joining, NHEJ.[23-25] HDR efficiencies vary according to the location of the target gene within the genome,[26] the state of the cell cycle,[27] and the type of cell/tissue.[28] The development of a direct, programmable way to install a specific type of base modification at a precise location in genomic DNA with enzyme-like efficiency and no stochasticity therefore represents a powerful new approach to gene editing-based research tools and human therapeutics.

Some aspects of the disclosure are based on the recognition that certain configurations of a dCas9 domain, and a cytidine deaminase domain fused by a linker are useful for efficiently deaminating target cytidine residues. Other aspects of this disclosure relate to the recognition that a nucleobase editing fusion protein with a cytidine deaminase domain fused to the N-terminus of a nuclease inactive Cas9 (dCas9) via a linker was capable of efficiently deaminating target nucleic acids in a double stranded DNA target molecule. See for example, Examples 3 and 4 below, which demonstrate that the fusion proteins, which are also referred to herein as base editors, generate less indels and more efficiently deaminate target nucleic acids than other base editors, such as base editors without a UGI domain. In some embodiments, the fusion protein comprises a nuclease-inactive Cas9 (dCas9) domain and an apolipoprotein B mRNA-editing complex 1 (APOBEC1) deaminase domain, where the deaminase domain is fused to the N-terminus of the dCas9 domain via a linker comprising the amino acid sequence SGSETPGTSESATPES (SEQ ID NO: 7). In some embodiments, the nuclease-inactive Cas9 (dCas9) domain of comprises the amino acid sequence set forth in SEQ ID NO: 263. In some embodiments, the deaminase is rat APOBEC1 (SEQ ID NO: 284). In some embodiments, the deaminase is human APOBEC1 (SEQ ID NO: 282). In some embodiments, the deaminase is pmCDA1 (SEQ ID NO: 5738). In some embodiments, the deaminase is human APOBEC3G (SEQ ID NO: 275). In some embodiments, the deaminase is a human APOBEC3G variant of any one of (SEQ ID NOs: 5739-5741).

Some aspects of the disclosure are based on the recognition that certain configurations of a dCas9 domain, and a cytidine deaminase domain fused by a linker are useful for efficiently deaminating target cytidine residues. Other aspects of this disclosure relate to the recognition that a nucleobase editing fusion protein with an apolipoprotein B mRNA-editing complex 1 (APOBEC1) deaminase domain fused to the N-terminus of a nuclease inactive Cas9 (dCas9) via a linker comprising the amino acid sequence SGSETPGTSESATPES (SEQ ID NO: 7) was capable of efficiently deaminating target nucleic acids in a double stranded DNA target molecule. In some embodiments, the fusion protein comprises a nuclease-inactive Cas9 (dCas9) domain and an apolipoprotein B mRNA-editing complex 1 (APOBEC1) deaminase domain, where the deaminase domain is fused to the N-terminus of the dCas9 domain via a linker comprising the amino acid sequence SGSETPGT-SESATPES (SEQ ID NO: 7).

In some embodiments, the fusion protein comprises the amino acid residues 11-1629 of the amino acid sequence set forth in SEQ ID NO: 591. In some embodiments, the fusion protein comprises the amino acid sequence set forth in SEQ ID NO: 591. In some embodiments, the fusion protein comprises the amino acid sequence of any one of SEQ ID NOs: 5737, 5743, 5745, and 5746.

Some aspects of this disclosure provide strategies, systems, reagents, methods, and kits that are useful for the targeted editing of nucleic acids, including editing a single site within a subject's genome, e.g., a human's genome. In some embodiments, fusion proteins of Cas9 (e.g., dCas9, nuclease active Cas9, or Cas9 nickase) and deaminases or deaminase domains, are provided. In some embodiments, methods for targeted nucleic acid editing are provided. In some embodiments, reagents and kits for the generation of targeted nucleic acid editing proteins, e.g., fusion proteins of Cas9 and deaminases or deaminase domains, are provided.

Some aspects of this disclosure provide fusion proteins comprising a Cas9 protein as provided herein that is fused to a second protein (e.g., an enzymatic domain such as a cytidine deaminase domain), thus forming a fusion protein. In some embodiments, the second protein comprises an enzymatic domain, or a binding domain. In some embodiments, the enzymatic domain is a nuclease, a nickase, a recombinase, a deaminase, a methyltransferase, a methylase, an acetylase, an acetyltransferase, a transcriptional activator, or a transcriptional repressor domain. In some embodiments, the enzymatic domain is a nucleic acid editing domain. In some embodiments, the nucleic acid editing domain is a deaminase domain. In some embodiments, the deaminase is a cytosine deaminase or a cytidine deaminase. In some embodiments, the deaminase is an apolipoprotein B mRNA-editing complex (APOBEC) family deaminase. In some embodiments, the deaminase is an APOBEC1 deaminase. In some embodiments, the deaminase is an APOBEC2 deaminase. In some embodiments, the deaminase is an APOBEC3 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, the deaminase is an APOBEC3E deaminase. In some embodiments, the deaminase is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). It should be appreciated that the deaminase may be from any suitable organism (e.g., a human or a rat). In some embodiments, the deaminase is from a human, chimpanzee, gorilla, monkey, cow, dog, rat, or mouse. In some embodiments, the deaminase is rat APOBEC1 (SEQ ID NO: 284). In some embodiments, the deaminase is human APOBEC1 (SEQ ID NO: 282). In some embodiments, the deaminase is pmCDA1.

Some aspects of this disclosure provide fusion proteins comprising: (i) a nuclease-inactive Cas9 (dCas9) domain comprising the amino acid sequence of SEQ ID NO: 263; and (ii) an apolipoprotein B mRNA-editing complex 1 (APOBEC1) deaminase domain, wherein the deaminase domain is fused to the N-terminus of the dCas9 domain via a linker comprising the amino acid sequence of SGSETPGT-SESATPES (SEQ ID NO: 7). In some embodiments, the deaminase is rat APOBEC1 (SEQ ID NO: 284). In some embodiments, the deaminase is human APOBEC1 (SEQ ID NO: 282). In some embodiments, the fusion protein comprises the amino acid sequence of SEQ ID NO: 591. In some embodiments, the fusion protein comprises the amino acid sequence of SEQ ID NO: 5737. In some embodiments, the deaminase is pmCDA1 (SEQ ID NO: 5738). In some embodiments, the deaminase is human APOBEC3G (SEQ ID NO: 275). In some embodiments, the deaminase is a human APOBEC3G variant of any one of SEQ ID NOs: 5739-5741.

Some aspects of this disclosure provide fusion proteins comprising: (i) a Cas9 nickase domain and (ii) an apolipoprotein B mRNA-editing complex 1 (APOBEC1) deaminase domain, wherein the deaminase domain is fused to the N-terminus of the Cas9 nickase domain. In some embodiments, the Cas9 nickase domain comprises a D10X mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the Cas9 nickase domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the Cas9 nickase domain comprises a histidine at amino acid position 840 of the amino acid sequence provided in SEQ ID NO: 10, or a corresponding amino acid position in any of the amino acid sequences provided in SEQ ID NOs: 11-260. In some embodiments, the amino acid sequence of the Cas9 nickase domain comprises the amino acid sequence as set forth in SEQ ID NO: 267. In some embodiments, the deaminase is rat APOBEC1 (SEQ ID NO: 284). In some embodiments, the deaminase is human APOBEC1 (SEQ ID NO: 282). In some embodiments, the deaminase is pmCDA1.

Some aspects of this disclosure provide fusion proteins comprising: (i) a Cas9 nickase domain and (ii) an apolipoprotein B mRNA-editing complex 1 (APOBEC1) deaminase domain, wherein the deaminase domain is fused to the N-terminus of the Cas9 nickase domain. In some embodiments, the Cas9 nickase domain comprises a D10× mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the Cas9 nickase domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the Cas9 nickase domain comprises a histidine at amino acid position 840 of the amino acid sequence provided in SEQ ID NO: 10, or a corresponding amino acid position in any of the amino acid sequences provided in SEQ ID NOs: 11-260. In some embodiments, the amino acid sequence of the Cas9 nickase domain comprises the amino acid sequence as set forth in SEQ ID NO: 267. In some embodiments, the deaminase is rat APOBEC1 (SEQ ID NO: 284). In some embodiments, the deaminase is human APOBEC1 (SEQ ID NO: 282). In some embodiments, the deaminase is pmCDAL.

Other aspects of this disclosure relate to the recognition that fusion proteins comprising a deaminase domain, a dCas9 domain and a uracil glycosylase inhibitor (UGI) domain demonstrate improved efficiency for deaminating target nucleotides in a nucleic acid molecule. Without wishing to be bound by any particular theory, cellular DNA-repair response to the presence of U:G heteroduplex DNA may be responsible for a decrease in nucleobase editing efficiency in cells. Uracil DNA glycosylase (UDG) catalyzes removal of U from DNA in cells, which may initiate base excision repair, with reversion of the U:G pair to a C:G pair as the most common outcome. As demonstrated herein, Uracil DNA Glycosylase Inhibitor (UGI) may inhibit human UDG activity. Without wishing to be bound by any particular theory, base excision repair may be inhibited by molecules that bind the single strand, block the edited base, inhibit UGI, inhibit base excision repair, protect the edited base, and/or promote "fixing" of the non-edited strand, etc.Thus, this disclosure contemplates fusion proteins comprising a dCas9-cytidine deaminase domain that is fused to a UGI domain.

In some embodiments, the fusion protein comprises a nuclease-inactive Cas9 (dCas9) domain; a nucleic acid editing domain; and a uracil glycosylase inhibitor (UGI) domain. In some embodiments, the dCas9 domain comprises a D10× mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the dCas9 domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the dCas9 domain comprises an H840X mutation of the amino acid sequence provided in SEQ ID NO: 10, or a corresponding mutation in any of the amino acid sequences provided in SEQ ID NOs: 11-260, wherein X is any amino acid except for H. In some embodiments, the amino acid sequence of the dCas9 domain comprises an H840A mutation of the amino acid sequence provided in SEQ ID NO: 10, or a corresponding mutation in any of the amino acid sequences provided in SEQ ID NOs: 11-260. In some embodiments, the dCas9 domain comprises the amino acid sequence as set forth in SEQ ID NO: 263.

Further aspects of this disclosure relate to the recognition that fusion proteins using a Cas9 nickase as the Cas9 domain demonstrate improved efficiency for editing nucleic acids. For example, aspects of this disclosure relate to the recognition that fusion proteins comprising a Cas9 nickase, a deaminase domain and a UGI domain demonstrate improved efficiency for editing nucleic acids. For example, the improved efficiency for editing nucleotides is described below in the Examples section.

Some aspects of the disclosure are based on the recognition that any of the base editors provided herein are capable of modifying a specific nucleotide base without generating a significant proportion of indels. An "indel", as used herein, refers to the insertion or deletion of a nucleotide base within a nucleic acid. Such insertions or deletions can lead to frame shift mutations within a coding region of a gene. In some embodiments, it is desirable to generate base editors that efficiently modify (e.g. mutate or deaminate) a specific nucleotide within a nucleic acid, without generating a large number of insertions or deletions (i.e., indels) in the nucleic acid. In certain embodiments, any of the base editors provided herein are capable of generating a greater proportion of intended modifications (e.g., point mutations or deaminations) versus indels.

Some aspects of the disclosure are based on the recognition that any of the base editors provided herein are capable of efficiently generating an intended mutation, such as a point mutation, in a nucleic acid (e.g. a nucleic acid within a genome of a subject) without generating a significant number of unintended mutations, such as unintended point mutations.

In some embodiments, a fusion protein comprises a Cas9 nickase domain, a nucleic acid editing domain; and a uracil glycosylase inhibitor (UGI) domain. In some embodiments, the amino acid sequence of the Cas9 nickase domain comprises a D10X mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the Cas9 nickase domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the Cas9 nickase domain comprises a histidine at amino acid position 840 of the amino acid sequence provided in SEQ ID NO: 10, or a corresponding amino acid position in any of the amino acid sequences provided in SEQ ID NOs: 11-260. In some embodiments, the amino acid sequence of the Cas9 nickase domain comprises the amino acid sequence as set forth in SEQ ID NO: 267.

In some embodiments, the deaminase domain of the fusion protein is fused to the N-terminus of the dCas9 domain or the Cas9 nickase. In some embodiments, the UGI domain is fused to the C-terminus of the dCas9 domain or the Cas9 nickase. In some embodiments, the dCas9 domain or the Cas9 nickase and the nucleic acid editing domain are fused via a linker. In some embodiments, the dCas9 domain or the Cas9 nickase and the UGI domain are fused via a linker.

In certain embodiments, linkers may be used to link any of the peptides or peptide domains of the invention. The linker may be as simple as a covalent bond, or it may be a polymeric linker many atoms in length. In certain embodiments, the linker is a polpeptide or based on amino acids. In other embodiments, the linker is not peptide-like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker is based on a phenyl ring. The linker may included funtionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In some embodiments, the linker comprises the amino acid sequence $(GGGGS)_n$ (SEQ ID NO: 5), $(G)_n$, $(EAAAK)_n$ (SEQ ID NO: 6), $(GGS)_n$, (SGGS), (SEQ ID NO: 4288), SGSETPGTSESATPES (SEQ ID NO: 7), $(XP)_n$, or any combination thereof, wherein n is independently an integer between 1 and 30, and wherein X is any amino acid. In some embodiments, the linker comprises the amino acid sequence $(GGS)_n$, wherein n is 1, 3, or 7. In some embodiments, the linker comprises the amino acid sequence SGSETPGTSESATPES (SEQ ID NO: 7).

In some embodiments, the fusion protein comprises the structure [nucleic acid editing domain]-[optional linker sequence]-[dCas9 or Cas9 nickase]-[optional linker sequence]-[UGI]. In some embodiments, the fusion protein comprises the structure [nucleic acid editing domain]-[optional linker sequence]-[UGI]-[optional linker sequence]-[dCas9 or Cas9 nickase]; [UGI]-[optional linker sequence]-[nucleic acid editing domain]-[optional linker sequence]-[dCas9 or Cas9 nickase]; [UGI]-[optional linker sequence]-[dCas9 or Cas9 nickase]-[optional linker sequence]-[nucleic acid editing domain]; [dCas9 or Cas9 nickase]-[optional linker sequence]-[UGI]-[optional linker sequence]-[nucleic acid editing domain]; or [dCas9 or Cas9 nickase]-[optional linker sequence]-[nucleic acid editing domain]-[optional linker sequence]-[UGI].

In some embodiments, the nucleic acid editing domain comprises a deaminase. In some embodiments, the nucleic acid editing domain comprises a deaminase. In some embodiments, the deaminase is a cytidine deaminase. In some embodiments, the deaminase is an apolipoprotein B mRNA-editing complex (APOBEC) family deaminase. In some embodiments, the deaminase is an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, or an APOBEC4 deaminase. In some embodiments, the deaminase is an activation-induced deaminase (AID). In some embodiments, the deaminase is a Lamprey CDA1 (pmCDA1) deaminase.

In some embodiments, the deaminase is from a human, chimpanzee, gorilla, monkey, cow, dog, rat, or mouse. In some embodiments, the deaminase is from a human. In some embodiments the deaminase is from a rat. In some embodiments, the deaminase is a rat APOBEC1 deaminase comprising the amino acid sequence set forth in (SEQ ID NO: 284). In some embodiments, the deaminase is a human APOBEC1 deaminase comprising the amino acid sequence set forth in (SEQ ID NO: 282). In some embodiments, the deaminase is pmCDA1 (SEQ ID NO: 5738). In some embodiments, the deaminase is human APOBEC3G (SEQ ID NO: 275). In some embodiments, the deaminase is a human APOBEC3G variant of any one of (SEQ ID NOs: 5739-5741). In some embodiments, the deaminase is at least 80%, at least 85%, at least 90%, at least 92%, at least 95%, at least 96%, at least 97%, at least 98%, at least 99%, or at least 99.5% identical to any one of the amino acid sequences set forth in SEQ ID NOs: 266-284 or 5725-5741.

In some embodiments, the UGI domain comprises an amino acid sequence that is at least 80%, at least 85%, at least 90%, at least 92%, at least 95%, at least 96%, at least 97%, at least 98%, at least 99%, or at least 99.5% identical to SEQ ID NO: 600. In some embodiments, the UGI domain comprises the amino acid sequence as set forth in SEQ ID NO: 600.

Some aspects of this disclosure provide complexes comprising a Cas9 protein or a Cas9 fusion protein as provided herein, and a guide RNA bound to the Cas9 protein or the Cas9 fusion protein.

Some aspects of this disclosure provide methods of using the Cas9 proteins, fusion proteins, or complexes provided herein. For example, some aspects of this disclosure provide methods comprising contacting a DNA molecule (a) with a Cas9 protein or a fusion protein as provided herein and with a guide RNA, wherein the guide RNA is about 15-100 nucleotides long and comprises a sequence of at least 10 contiguous nucleotides that is complementary to a target sequence; or (b) with a Cas9 protein, a Cas9 fusion protein, or a Cas9 protein or fusion protein complex with a gRNA as provided herein.

Some aspects of this disclosure provide kits comprising a nucleic acid construct, comprising (a) a nucleotide sequence encoding a Cas9 protein or a Cas9 fusion protein as provided herein; and (b) a heterologous promoter that drives expression of the sequence of (a). In some embodiments, the kit further comprises an expression construct encoding a guide RNA backbone, wherein the construct comprises a cloning site positioned to allow the cloning of a nucleic acid sequence identical or complementary to a target sequence into the guide RNA backbone.

Some aspects of this disclosure provide polynucleotides encoding a Cas9 protein of a fusion protein as provided herein. Some aspects of this disclosure provide vectors comprising such polynucleotides. In some embodiments, the vector comprises a heterologous promoter driving expression of polynucleotide.

Some aspects of this disclosure provide cells comprising a Cas9 protein, a fusion protein, a nucleic acid molecule, and/or a vector as provided herein.

The description of exemplary embodiments of the reporter systems above is provided for illustration purposes only and not meant to be limiting. Additional reporter systems, e.g., variations of the exemplary systems described in detail above, are also embraced by this disclosure.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 9 shows in vitro C→T editing efficiencies using His6-rAPOBEC1-XTEN-dCas9.

FIG. 10 shows C→T editing efficiencies in HEK293T cells is greatly enhanced by fusion with UGI.

FIG. 11A: Nucleobase editing strategy. DNA with a target C (red) at a locus specified by a guide RNA (green) is bound by dCas9 (blue), which mediates the local denaturation of the DNA substrate. Cytidine deamination by a tethered APOBEC1 enzyme (orange) converts the target C to U. The resulting G:U heteroduplex can be permanently converted to an A:T base pair following DNA replication or repair. If the U is in the template DNA strand, it will also result in an RNA transcript containing a G to A mutation following transcription. FIG. 11B: Deamination assay showing an activity window of approximately five nucleotides. Following incubation of NBE1-sgRNA complexes with dsDNA substrates at 37° C. for 2 h, the 5' fluorophore-labeled DNA was isolated and incubated with USER enzyme (uracil DNA glycosylase and endonuclease VIII) at 37° C. for 1 h to induce DNA cleavage at the site of any uracils. The resulting DNA was resolved on a denaturing polyacrylamide gel, and any fluorophore-linked strands were visualized. Each lane is labeled according to the position of the target C within the protospacer, or with "—" if no target C is present, counting the base distal from the PAM as position 1. FIG. 11C: Deaminase assay showing the sequence specificity and sgRNA-dependence of NBE1. The DNA substrate with a target C at position 7 was incubated with NBE1 as in FIG. 11B with either the correct sgRNA, a mismatched sgRNA, or no sgRNA. No C to U editing is observed with the mismatched sgRNA or with no sgRNA. The positive control sample contains a DNA sequence with a U synthetically incorporated at position 7.

FIGS. 12A to 12B show effects of sequence context and target C position on nucleobase editing efficiency in vitro. FIG. 12A: Effect of changing the sequence surrounding the target C on editing efficiency in vitro. The deamination yield of 80% of targeted strands (40% of total sequencing reads from both strands) for $C_7$ in the protospacer sequence 5'-TTATTTCGTGGATTTATTTA-3'(SEQ ID NO: 264) was defined as 1.0, and the relative deamination efficiencies of substrates containing all possible single-base mutations at positions 1-6 and 8-13 are shown. Values and error bars reflect the mean and standard deviation of two or more independent biological replicates performed on different days. FIG. 12B: Positional effect of each NC motif on editing efficiency in vitro. Each NC target motif was varied from positions 1 to 8 within the protospacer as indicated in the sequences shown on the right (the PAM shown in red, the protospacer plus one base 5' to the protospacer are also shown). The percentage of total sequence reads containing T at each of the numbered target C positions following incubation with NBE1 is shown in the graph. Note that the maximum possible deamination yield in vitro is 50% of total sequencing reads (100% of targeted strands). Values and error bars reflect the mean and standard deviation of two or three independent biological replicates performed on different days. FIG. 12B depicts SEQ ID NOs: 285 through 292 from top to bottom, respectively.

FIGS. 13A to 13C show nucleobase editing in human cells. FIG. 13A: Protospacer (black) and PAM (red) sequences of the six mammalian cell genomic loci targeted by nucleobase editors. Target Cs are indicated with subscripted numbers corresponding to their positions within the protospacer. FIG. 13A depicts SEQ ID NOs: 293 through 298 from top to bottom, respectively. FIG. 13B: HEK293T cells were transfected with plasmids expressing NBE1, NBE2, or NBE3 and an appropriate sgRNA. Three days after transfection, genomic DNA was extracted and analyzed by high-throughput DNA sequencing at the six loci. Cellular C to T conversion percentages, defined as the percentage of total DNA sequencing reads with Ts at the target positions indicated, are shown for NBE1, NBE2, and NBE3 at all six genomic loci, and for wt Cas9 with a donor HDR template at three of the six sites (EMX1, HEK293 site 3, and HEK293 site 4). Values and error bars reflect the mean and standard deviation of three independent biological replicates performed on different days. FIG. 13C: Frequency of indel formation, calculated as described in the Methods, is shown following treatment of HEK293T cells with NBE2 and NBE3 for all six genomic loci, or with wt Cas9 and a single-stranded DNA template for HDR at three of the six sites (EMX1, HEK293 site 3, and HEK293 site 4). Values reflect the mean of at least three independent biological replicates performed on different days.

Figures 14A, 14B, 14C:
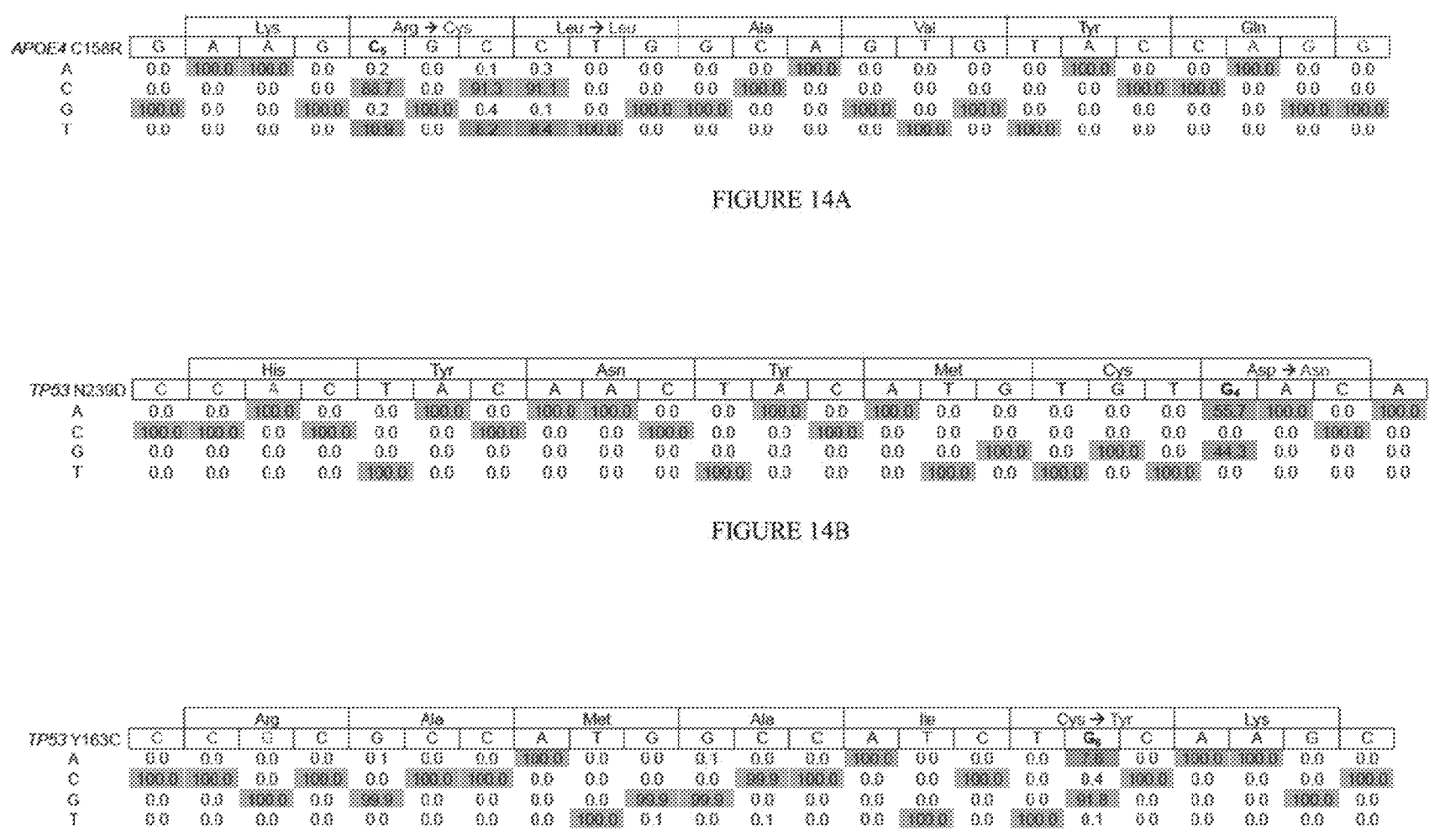

FIGS. 14A to 14C show NBE2- and NBE3-mediated correction of three disease-relevant mutations in mammalian cells. For each site, the sequence of the protospacer is indicated to the right of the name of the mutation, with the PAM highlighted in green and the base responsible for the mutation indicated in bold with a subscripted number corresponding to its position within the protospacer. The amino acid sequence above each disease-associated allele is shown, together with the corrected amino acid sequence following nucleobase editing in red. Underneath each sequence are the percentages of total sequencing reads with the corresponding base. Cells were nucleofected with plasmids encoding NBE2 or NBE3 and an appropriate sgRNA. Two days after nucleofection, genomic DNA was extracted and analyzed by HTS to assess pathogenic mutation correction. FIG. 14A: The Alzheimer's disease-associated APOE4 allele is converted to APOE3' in mouse astrocytes by NBE3 in 11% of total reads (44% of nucleofected astrocytes). Two nearby Cs are also converted to Ts, but with no change to the predicted sequence of the resulting protein (SEQ ID NO: 299). FIG. 14B The cancer-associated p53 N239D mutation is corrected by NBE2 in 11% of treated human lymphoma cells (12% of nucleofected cells) that are heterozygous for the mutation (SEQ ID NO: 300). FIG. 14C The p53 Y163C mutation is corrected by NBE3 in 7.6% of nucleofected human breast cancer cells (SEQ ID NO: 301).

FIGS. 16A to 16B show NBE1 is capable of correcting disease-relevant mutations in vitro. FIG. 16A: Protospacer and PAM sequences (red) of seven disease-relevant mutations. The disease-associated target C in each case is indicated with a subscripted number reflecting its position within the protospacer. For all mutations except both APOE4 SNPs, the target C resides in the template (non-coding) strand. FIG. 16A depicts SEQ ID NOs: 302 through 308 from top to bottom, respectively. FIG. 16B: Deaminase assay showing each dsDNA oligonucleotide before (−) and after (+) incubation with NBE1, DNA isolation, and incubation with USER enzymes to cleave DNA at positions containing U. Positive control lanes from incubation of synthetic oligonucleotides containing U at various positions within the protospacer with USER enzymes are shown with the corresponding number indicating the position of the U.

FIG. 17 shows processivity of NBE1. The protospacer and PAM (red) of a 60-mer DNA oligonucleotide containing eight consecutive Cs is shown at the top. The oligonucleotide (125 nM) was incubated with NBE1 (2 µM) for 2 h at 37° C. The DNA was isolated and analyzed by high-throughput sequencing. Shown are the percent of total reads for the most frequent nine sequences observed. The vast majority of edited strands (>93%) have more than one C converted to T. This figure depicts SEQ ID NO: 309.

FIGS. 18A to 18H show the effect of fusing UGI to NBE1 to generate NBE2. FIG. 18A: Protospacer and PAM (red) sequences of the six mammalian cell genomic loci targeted with nucleobase editors. Editable Cs are indicated with labels corresponding to their positions within the protospacer. FIG. 18A depicts SEQ ID NOs: 293 through 298 from top to bottom, respectively. FIGS. 18B to 18G: HEK293T cells were transfected with plasmids expressing NBE1, NBE2, or NBE1 and UGI, and an appropriate sgRNA. Three days after transfection, genomic DNA was extracted and analyzed by high-throughput DNA sequencing at the six loci. Cellular C to T conversion percentages, defined as the percentage of total DNA sequencing reads with Ts at the target positions indicated, are shown for NBE1, NBE1 and UGI, and NBE2 at all six genomic loci. FIG. 18H: C to T mutation rates at 510 Cs surrounding the protospacers of interest for NBE1, NBE1 plus UGI on a separate plasmid, NBE2, and untreated cells are shown. The data show the results of 3,000,000 DNA sequencing reads from 1.5×106 cells. Values reflect the mean of at least two biological experiments conducted on different days.

Figure 22:
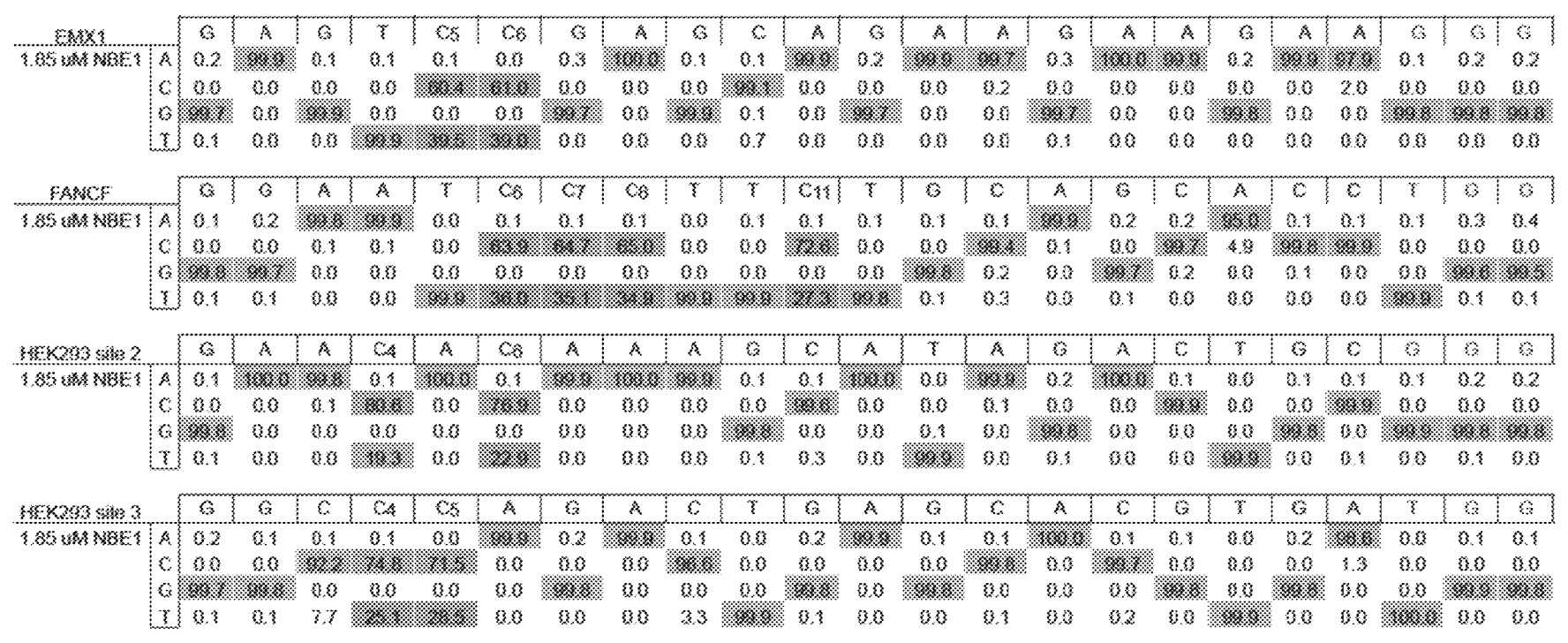
Figure 22:
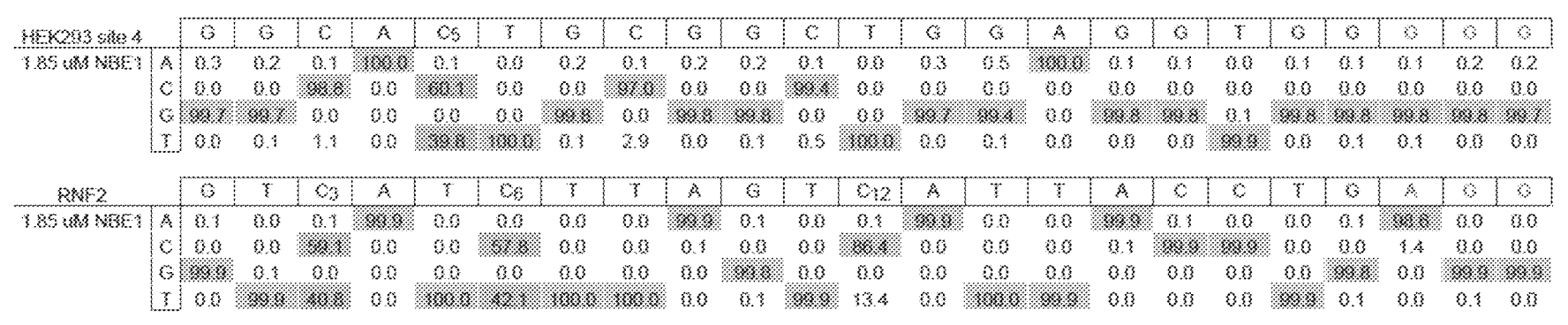

FIG. 22 shows in vitro identification of editable Cs in six genomic loci. Synthetic 80-mers with sequences matching six different genomic sites were incubated with NBE1 then analyzed for nucleobase editing via HTS. For each site, the sequence of the protospacer is indicated to the right of the name of the site, with the PAM highlighted in red. Underneath each sequence are the percentages of total DNA sequencing reads with the corresponding base. A target C was considered as "editable" if the in vitro conversion efficiency is >10%. Note that maximum yields are 50% of total DNA sequencing reads since the non-targeted strand is not a substrate for nucleobase editing. This figure depicts SEQ ID NOs: 293 through 298 from top to bottom, respectively.

Figure 24:
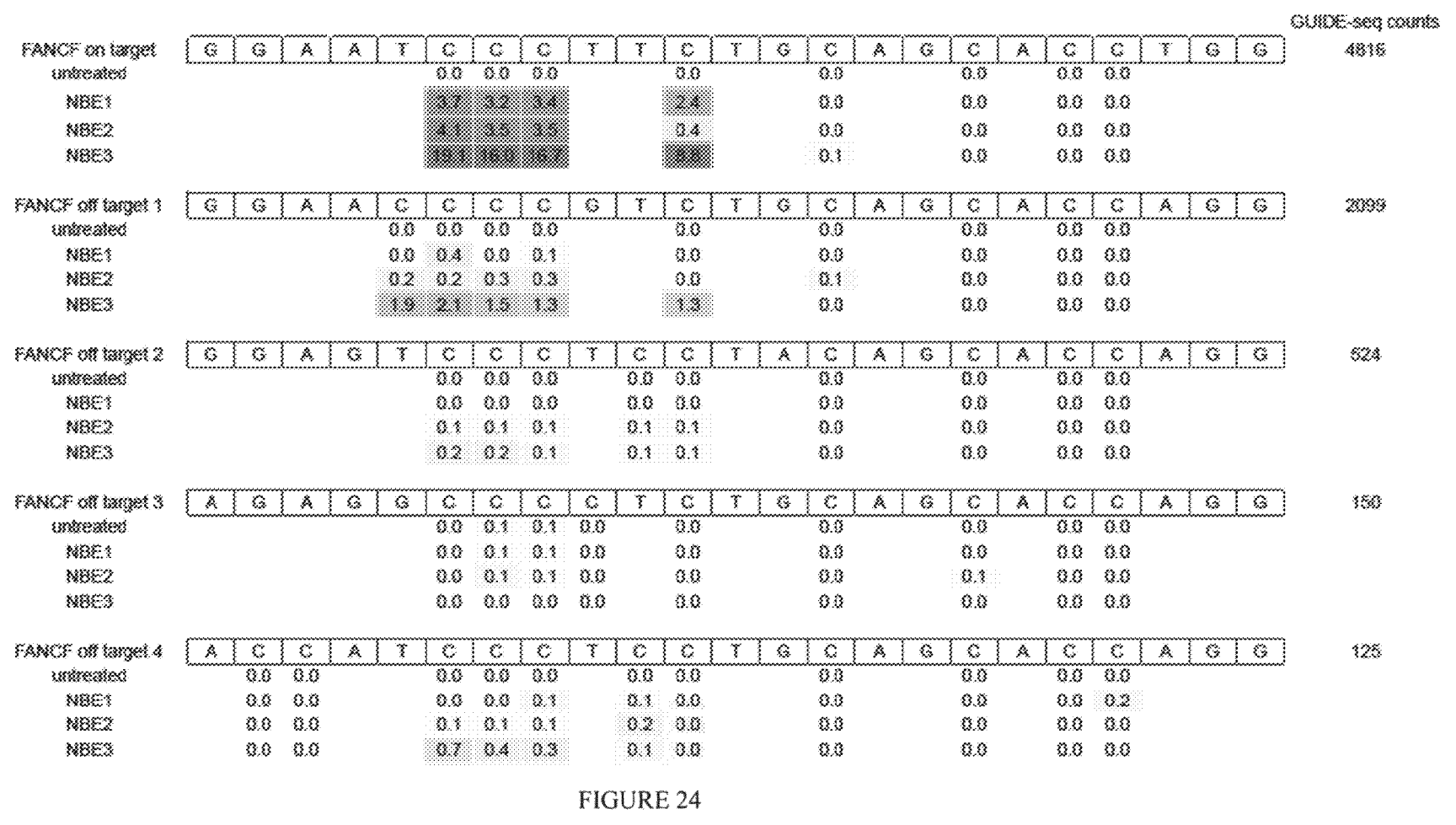
Figure 24:
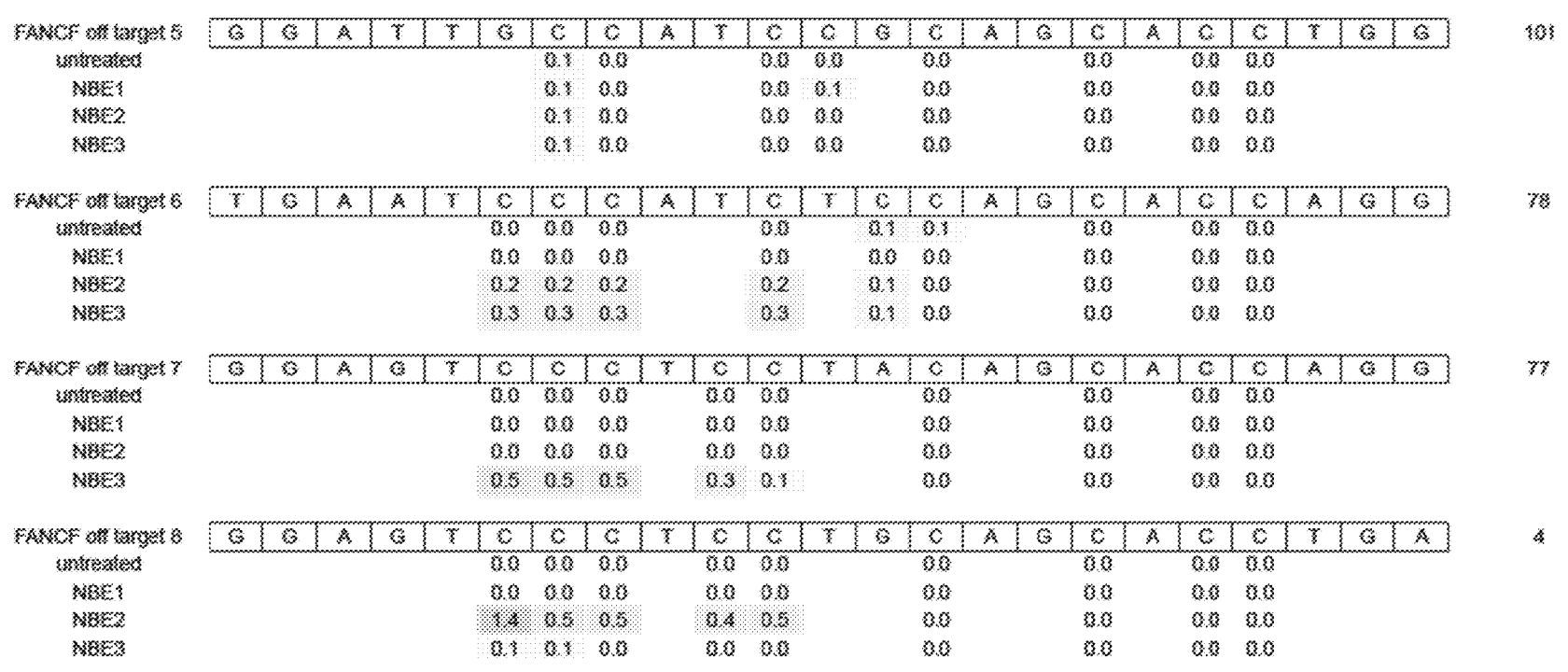

FIG. 24 shows activities of NBE1, NBE2, and NBE3 at FANCF off-targets. HEK293T cells were transfected with plasmids expressing NBE1, NBE2, or NBE3 and a sgRNA matching the FANCF sequence using Lipofectamine 2000. Three days after transfection, genomic DNA was extracted, amplified by PCR, and analyzed by high-throughput DNA sequencing at the on-target loci, plus all of the known Cas9 off-target loci for the FANCF sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 294 and 319 through 326 from top to bottom, respectively.

Figure 26:
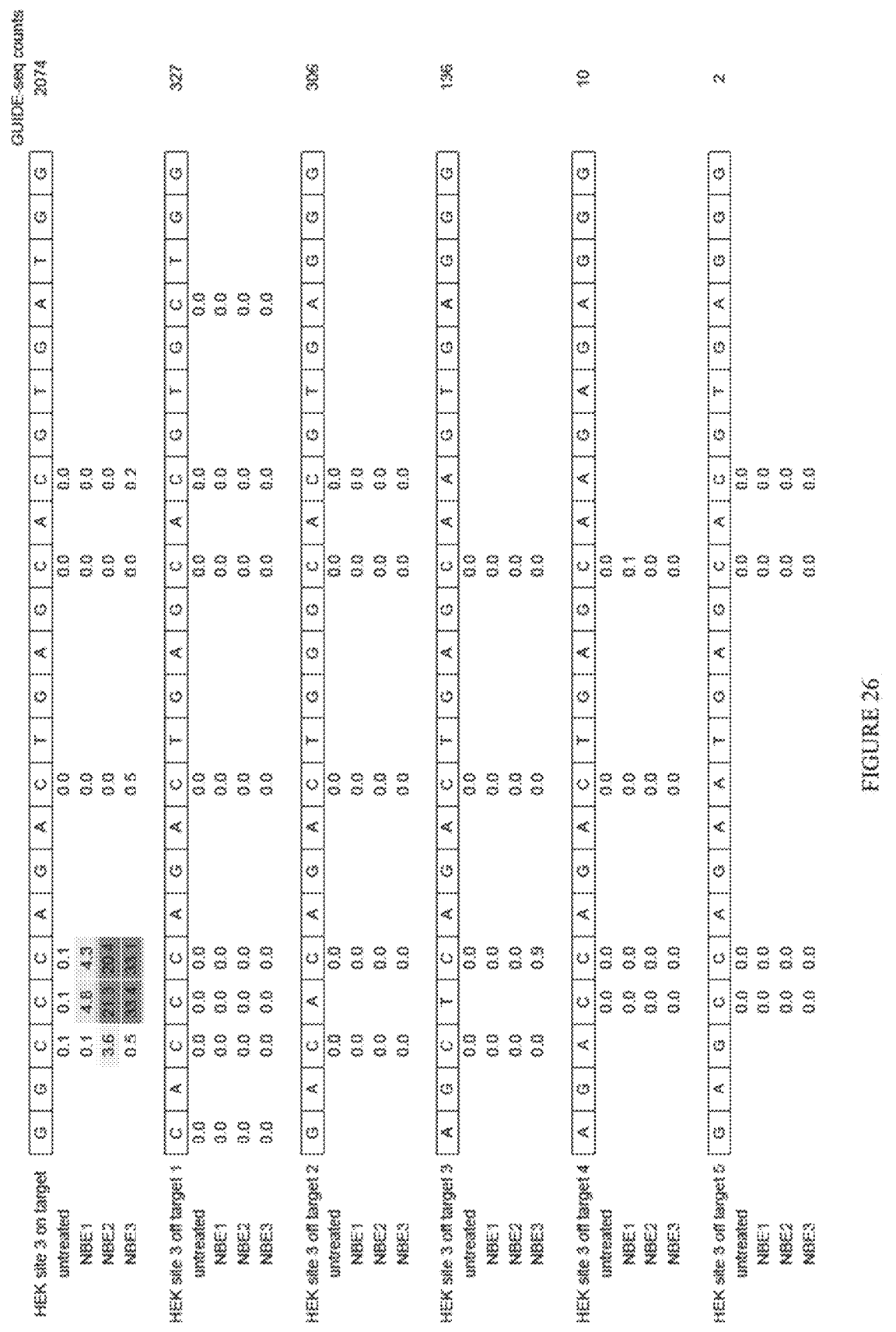

FIG. 26 shows activities of NBE1, NBE2, and NBE3 at HEK293 site 3 off-targets. HEK293T cells were transfected with plasmids expressing NBE1, NBE2, or NBE3 and a sgRNA matching the HEK293 site 3 sequence using Lipofectamine 2000. Three days after transfection, genomic DNA was extracted, amplified by PCR, and analyzed by high-throughput DNA sequencing at the on-target loci, plus all of the known Cas9 off-target loci for the HEK293 site 3 sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 296 and 659 through 663 from top to bottom, respectively.

Figure 27:
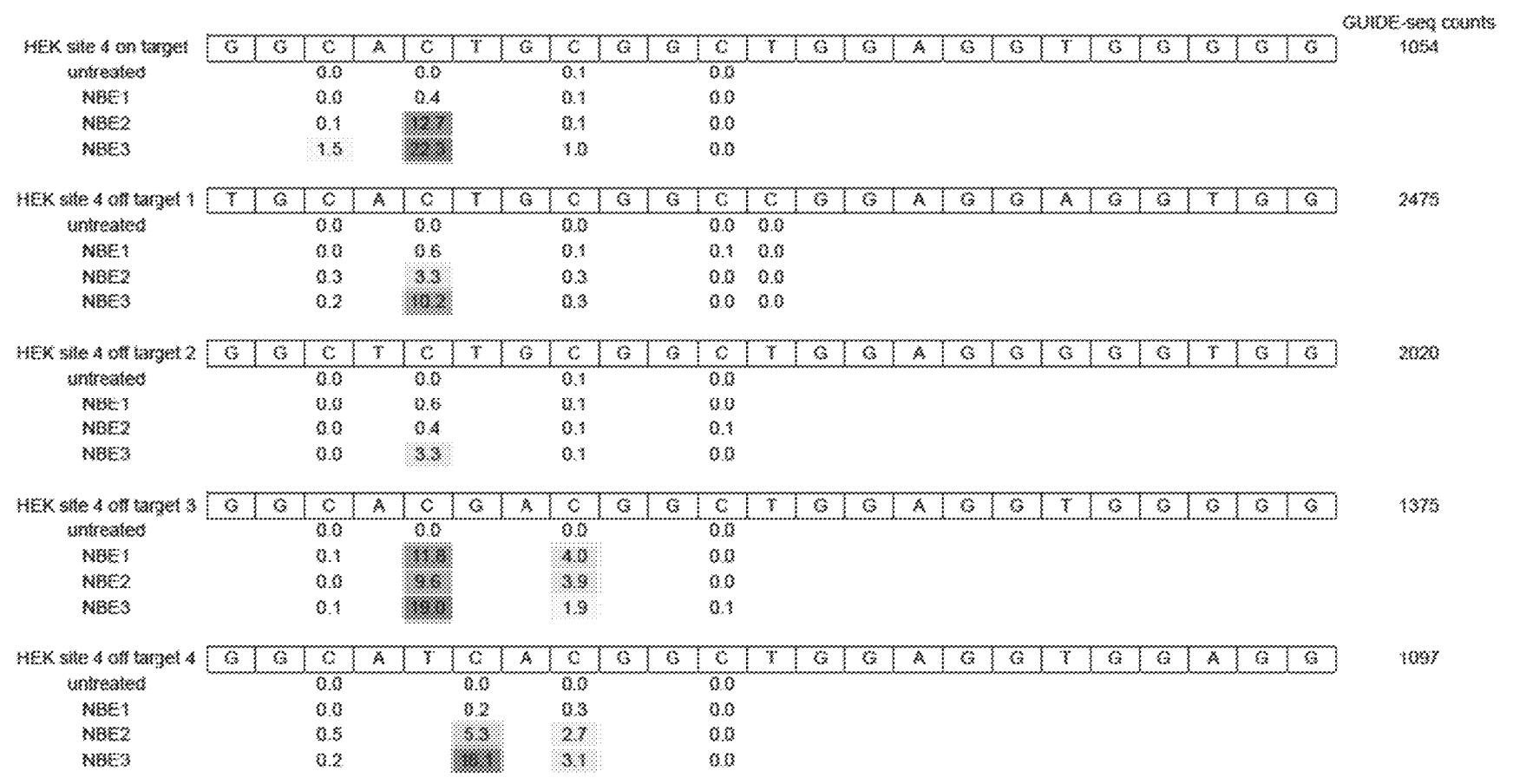
Figure 27:
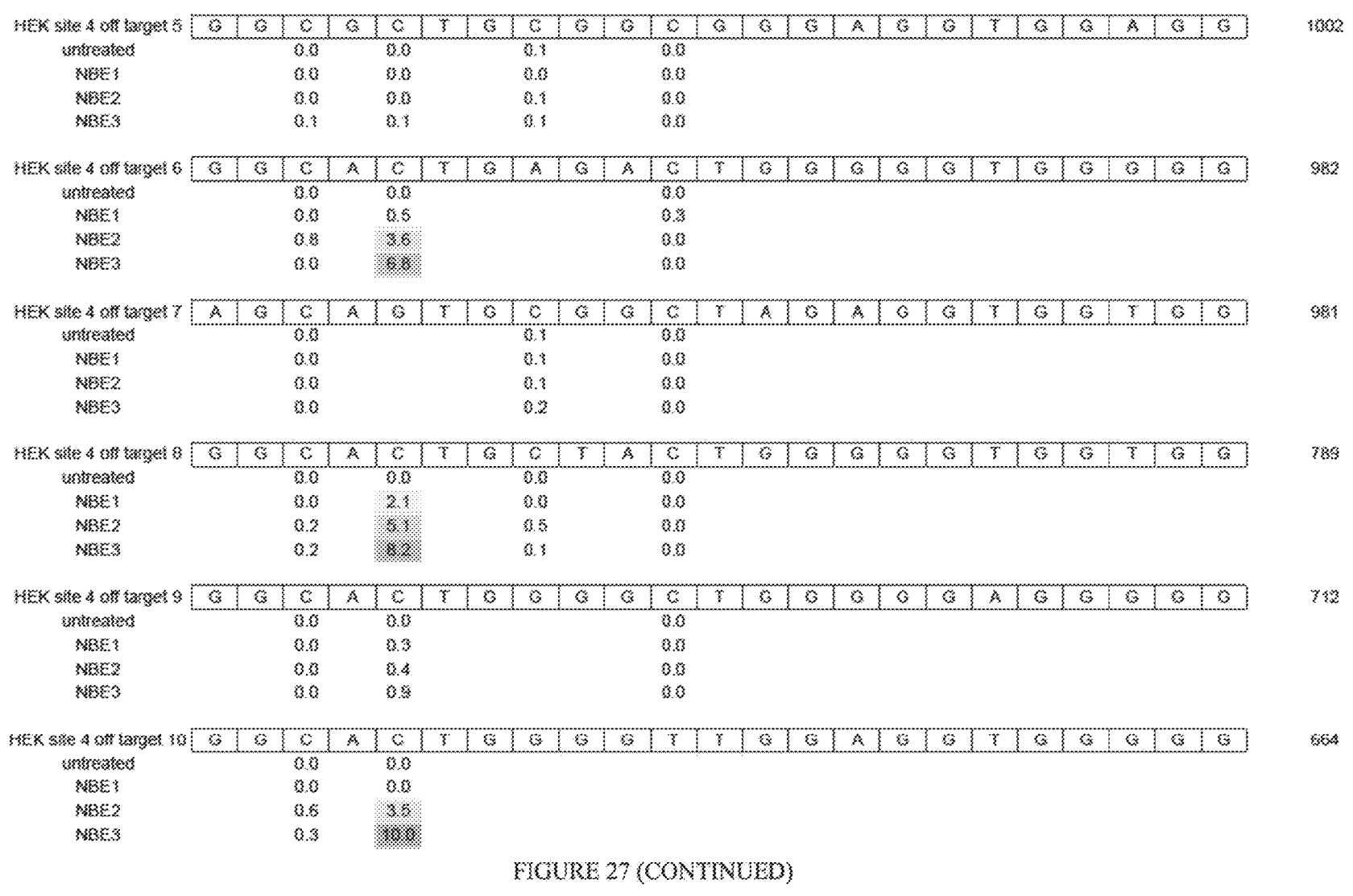

FIG. 27 shows activities of NBE1, NBE2, and NBE3 at HEK293 site 4 off-targets. HEK293T cells were transfected with plasmids expressing NBE1, NBE2, or NBE3 and a sgRNA matching the HEK293 site 4 sequence using Lipofectamine 2000. Three days after transfection, genomic DNA was extracted, amplified by PCR, and analyzed by high-throughput DNA sequencing at the on-target loci, plus the top ten known Cas9 off-target loci for the HEK293 site 4 sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 297 and 664 through 673 from top to bottom, respectively.

FIG. 29A shows possible base editing outcomes in mammalian cells. Initial editing resulted in a U:G mismatch. Recognition and excision of the U by uracil DNA glycosylase (UDG) initiated base excision repair (BER), which lead to reversion to the C:G starting state. BER was impeded by BE2 and BE3, which inhibited UDG. The U:G mismatch was also processed by mismatch repair (MMR), which preferentially repaired the nicked strand of a mismatch. BE3 nicked the non-edited strand containing the G, favoring resolution of the U:G mismatch to the desired U:A or T:A outcome. FIG. 29B shows HEK293T cells treated as described in the Materials and Methods in the Examples below. The percentage of total DNA sequencing read with Ts at the target positions indicated show treatment with BE1, BE2, or BE3, or for treatment with wt Cas9 with a donor HDR template. FIG. 29C shows frequency of indel formation following the treatment in FIG. 29B. Values are listed in FIG. 34. For FIGS. 29B and 29C, values and error bars reflect the mean and s.d. of three independent biological replicates performed on different days.

Figure 30A:
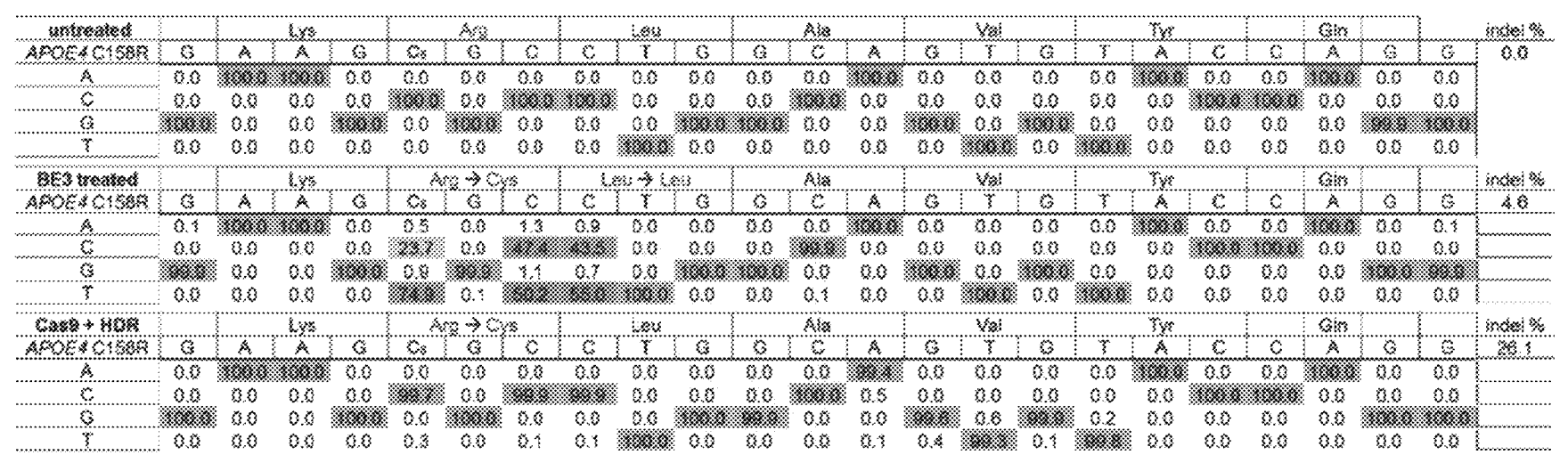
Figure 30B:
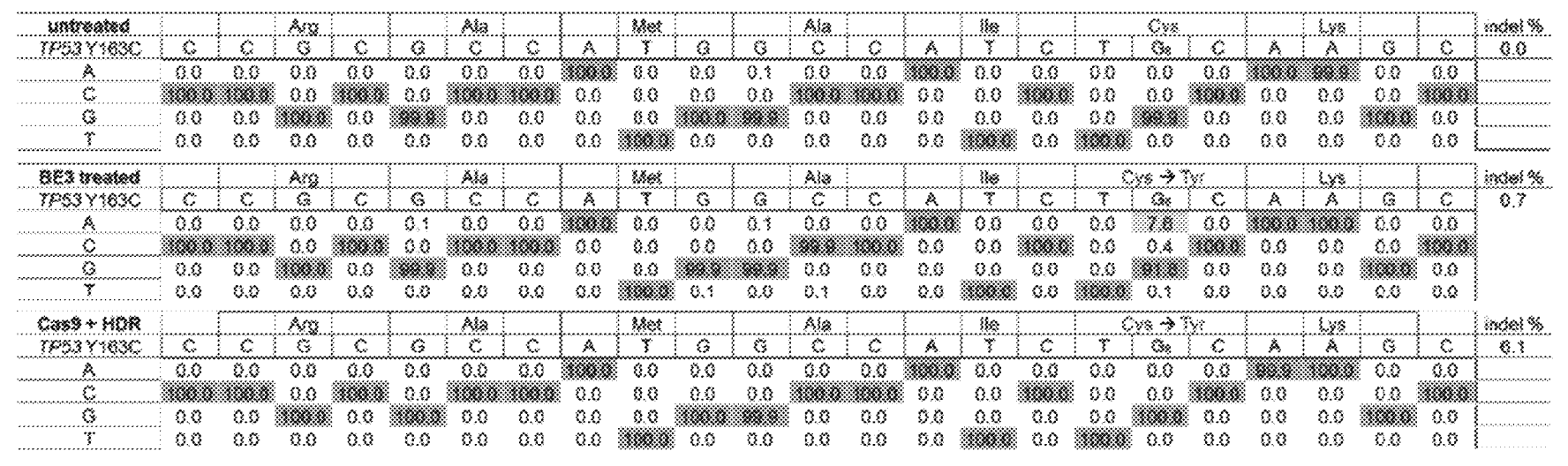

FIGS. 30A to 30B show BE3-mediated correction of two disease-relevant mutations in mammalian cells. The sequence of the protospacer is shown to the right of the mutation, with the PAM in blue and the target base in red with a subscripted number indicating its position within the protospacer. Underneath each sequence are the percentages of total sequencing reads with the corresponding base. Cells were treated as described in the Materials and Methods. FIG. 30A shows the Alzheimer's disease-associated APOE4 allele converted to APOE3r in mouse astrocytes by BE3 in 74.9% of total reads. Two nearby Cs were also converted to Ts, but with no change to the predicted sequence of the resulting protein. Identical treatment of these cells with wt Cas9 and donor ssDNA results in only 0.3% correction, with 26.1% indel formation. FIG. 30B shows the cancer associated p53 Y163C mutation corrected by BE3 in 7.6% of nucleofected human breast cancer cells with 0.7% indel formation. Identical treatment of these cells with wt Cas9 and donor ssDNA results in no mutation correction with 6.1% indel formation. This figure depicts SEQ ID NOs: 675 to 680 from top to bottom, respectively.

Figure 32:
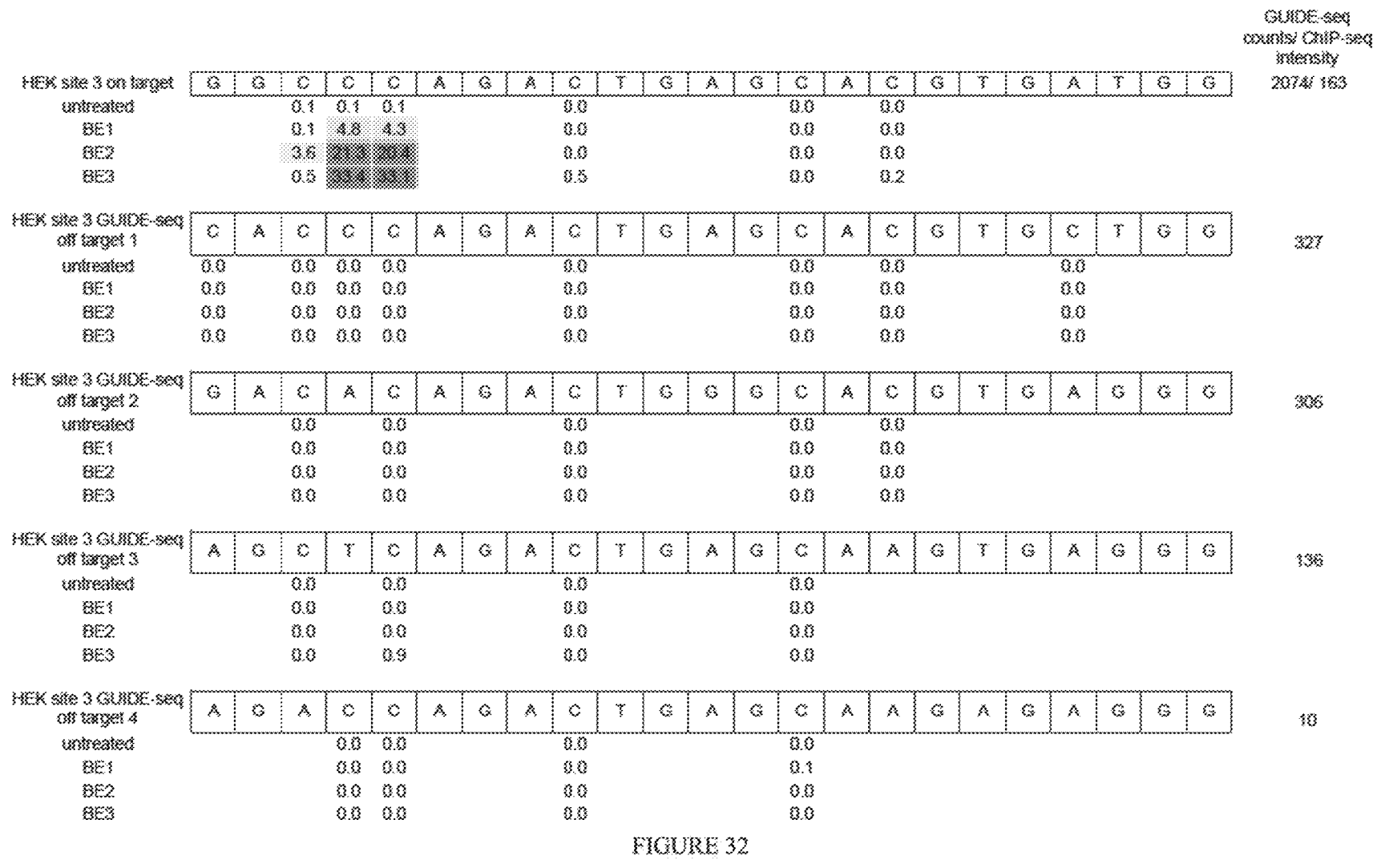
Figure 32:
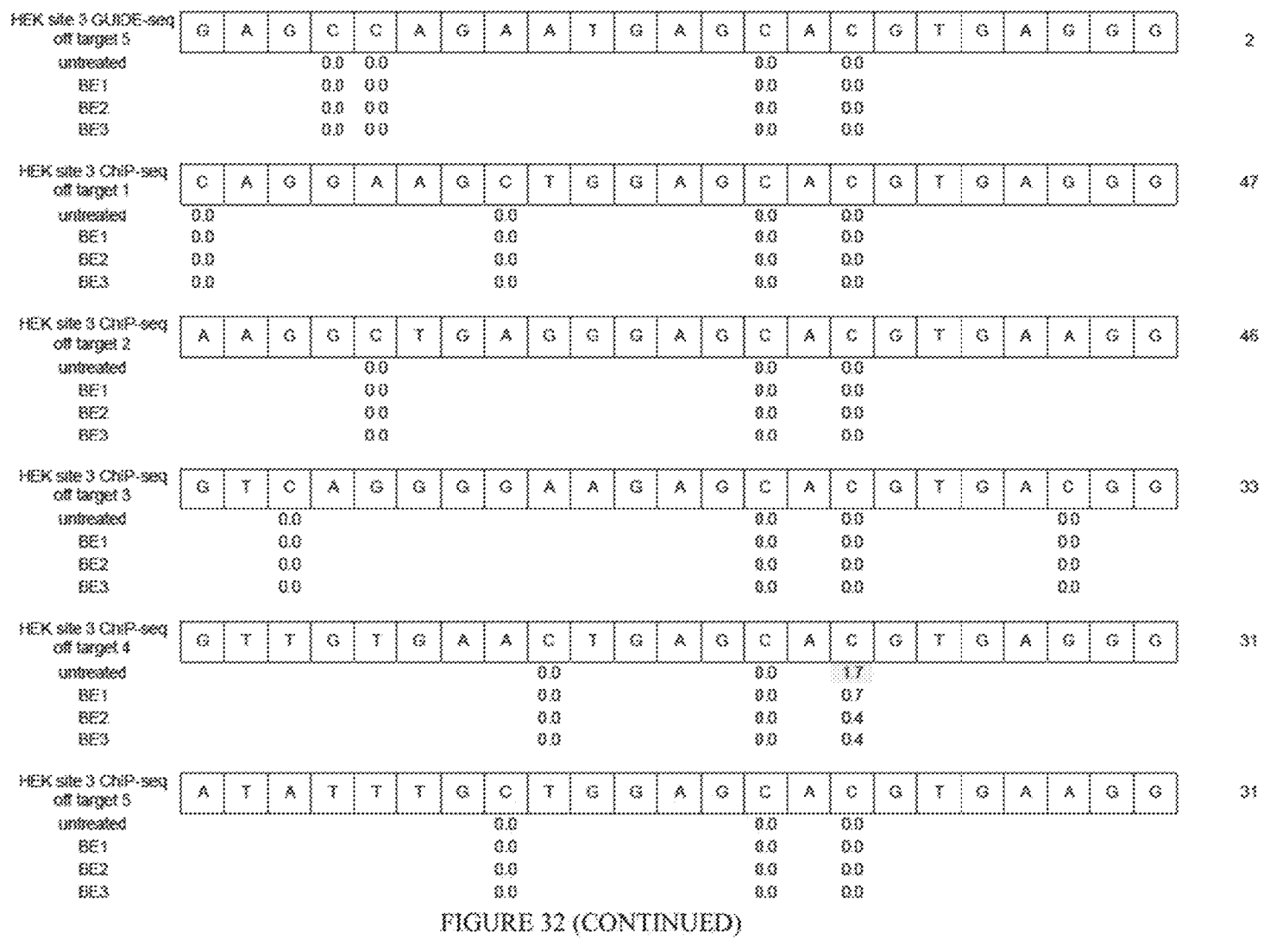

FIG. 32 shows activities of BE1, BE2, and BE3 at HEK293 site 3 off-targets. HEK293T cells were transfected with plasmids expressing BE1, BE2, or BE3 and a sgRNA matching the HEK293 site 3 sequence using Lipofectamine 2000. Three days after transfection, genomic DNA was extracted, amplified by PCR, and analyzed by high-throughput DNA sequencing at the on-target loci, plus all of the known Cas9 off-target loci and the top five known dCas9 off-target loci for the HEK293 site 3 sgRNA, as previously determined by Joung and coworkers using the GUIDE-seq method[54], and using chromatin immunoprecipitation high-throughput sequencing (ChIP-seq) experiments[61]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for BE1, BE2, and BE3. On the far right are displayed the total number of sequencing reads reported, and the ChIP-seq signal intensity reported for each sequence. This figure depicts SEQ ID NOs: 689 to 699 from top to bottom, respectively.

Figure 34:
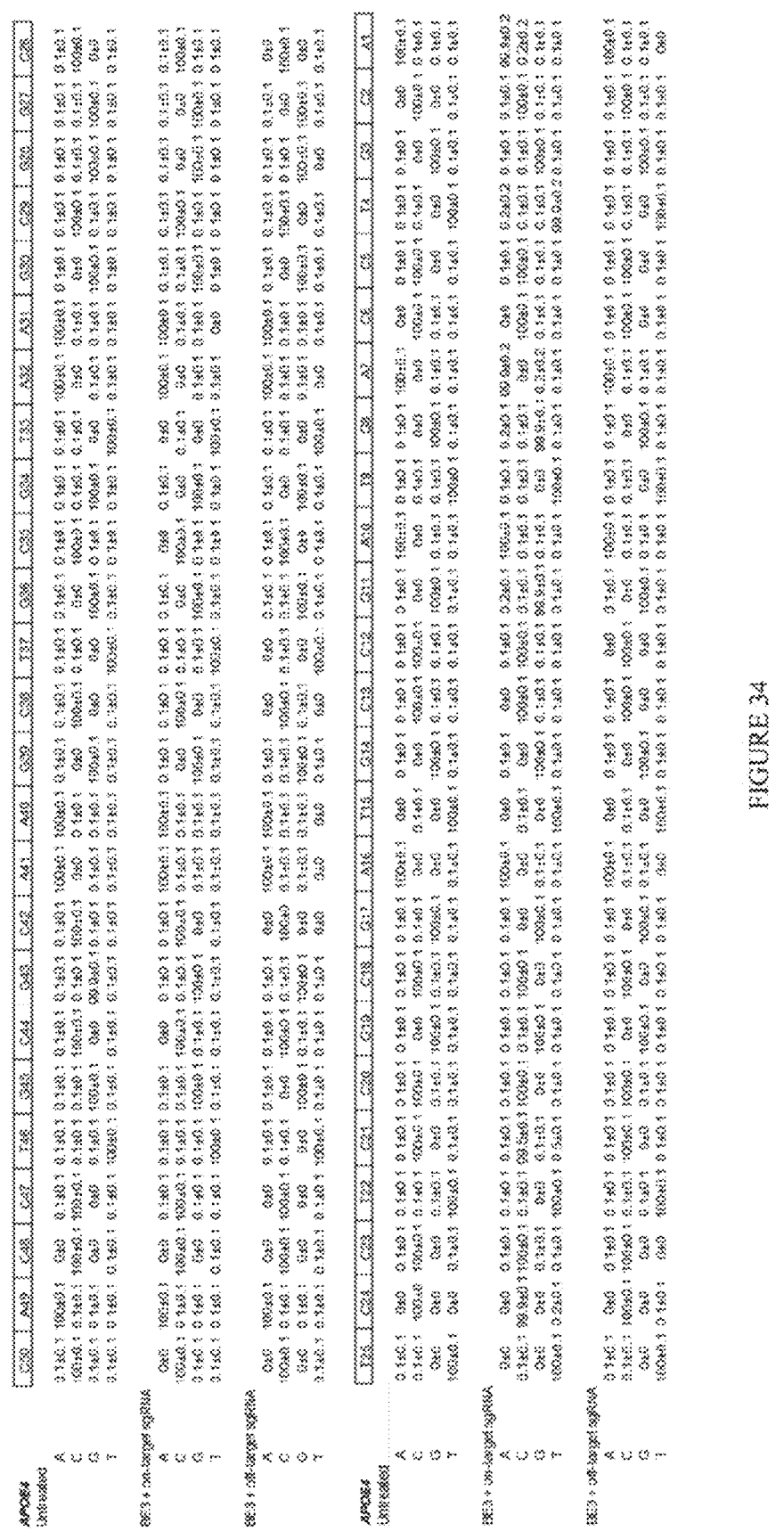

FIG. 34 shows mutation rates of non-protospacer bases following BE3-mediated correction of the Alzheimer's disease-associated APOE4 allele to APOE3r in mouse astrocytes. The DNA sequence of the 50 bases on either side of the protospacer from FIG. 30A and FIG. 34B is shown with each base's position relative to the protospacer. The side of the protospacer distal to the PAM is designated with positive numbers, while the side that includes the PAM is designated with negative numbers, with the PAM shown in blue. Underneath each sequence are the percentages of total DNA sequencing reads with the corresponding base for untreated cells, for cells treated with BE3 and an sgRNA targeting the APOE4 C158R mutation, or for cells treated with BE3 and an sgRNA targeting the VEGFA locus. Neither BE3-treated sample resulted in mutation rates above those of untreated controls. This figure depicts SEQ ID NOs: 713 to 716 from top to bottom, respectively.

Figure 35:
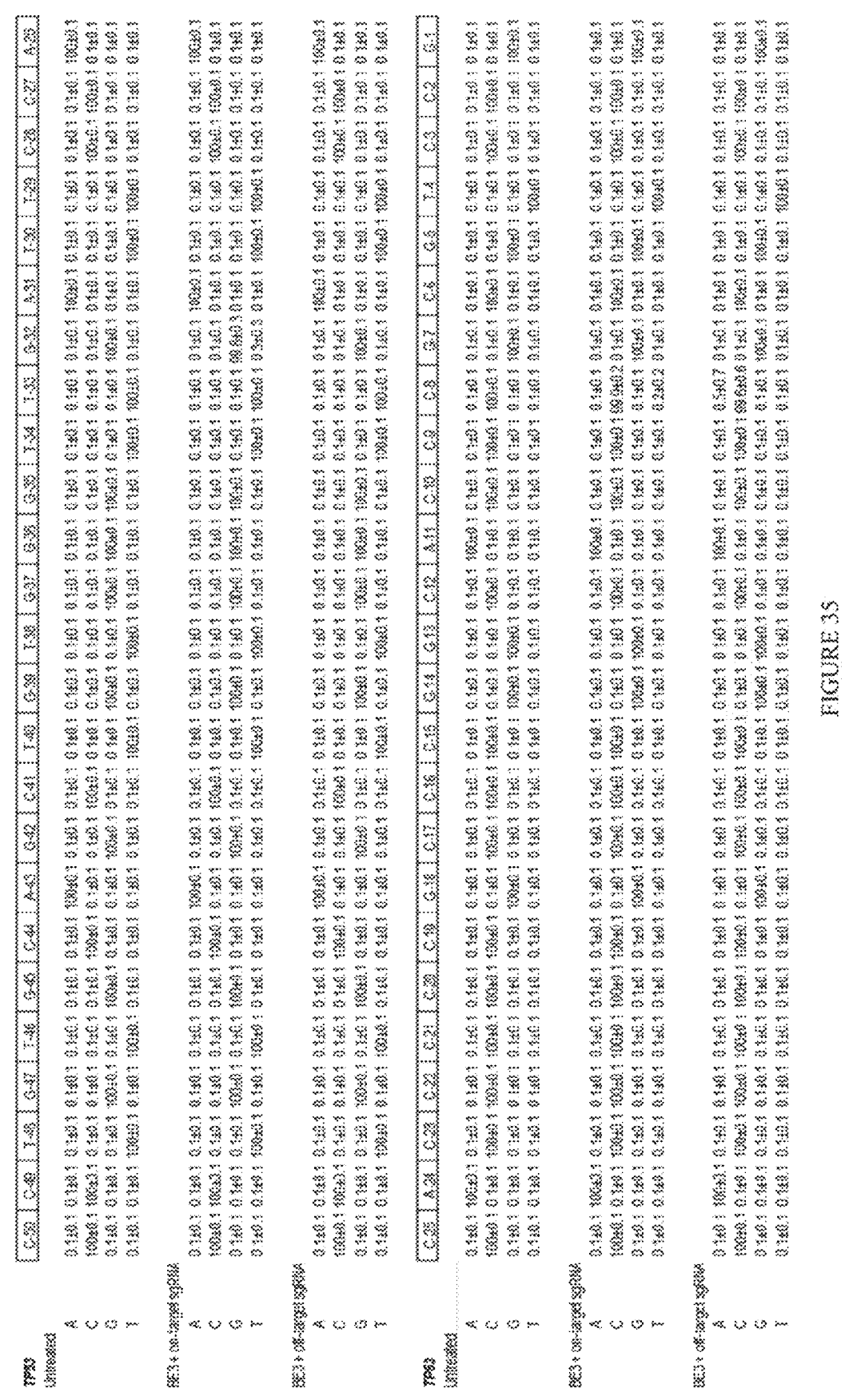
Figure 35:
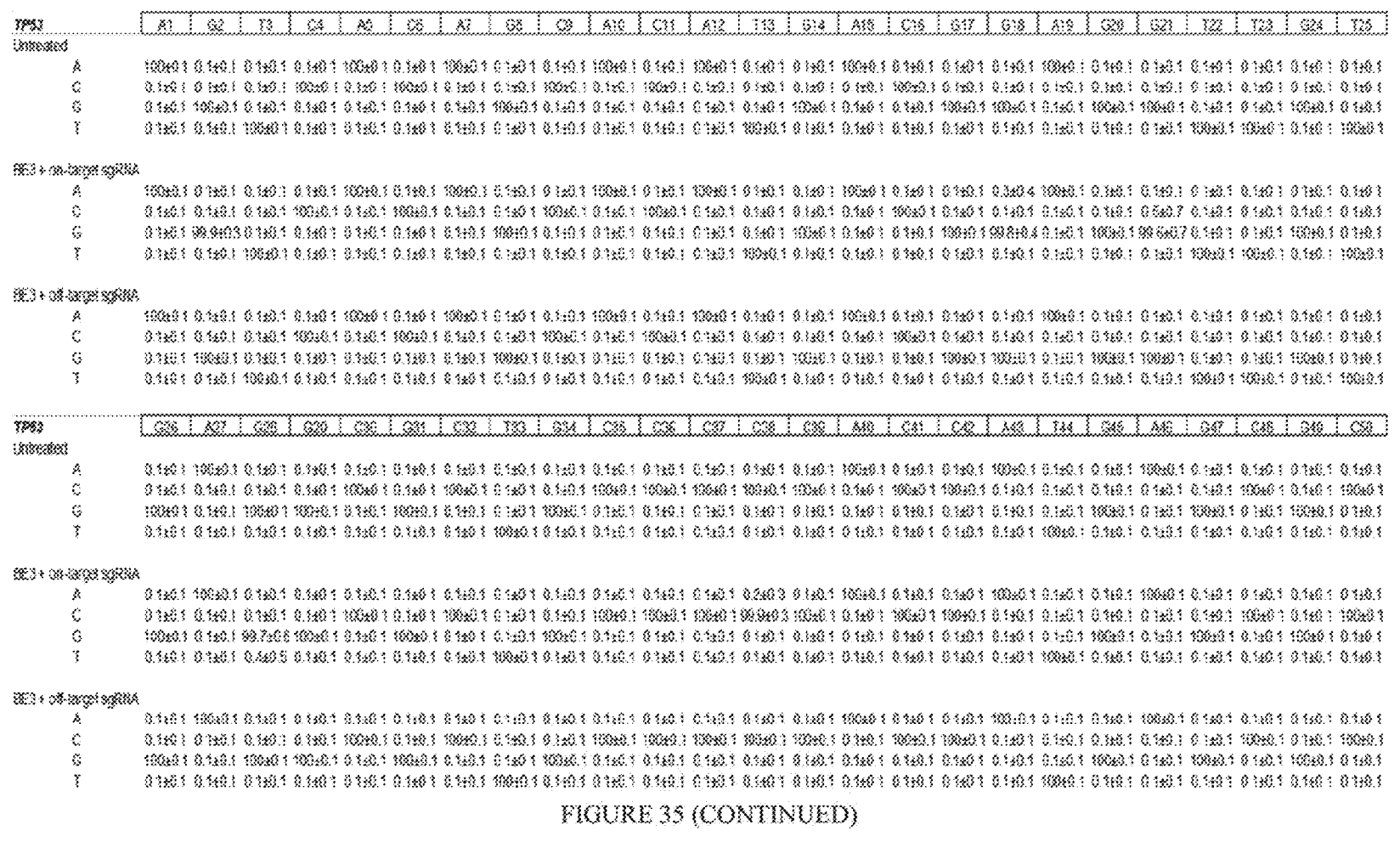

FIG. 35 shows mutation rates of non-protospacer bases following BE3-mediated correction of the cancer-associated p53 Y163C mutation in HCC1954 human cells. The DNA sequence of the 50 bases on either side of the protospacer from FIG. 30B

FIGS. 36A to 36F show the effects of deaminase, linker length, and linker composition on base editing. FIG. 36A shows a gel-based deaminase assay showing activity of rAPOBEC1, pmCDA1, hAID, hAPOBEC3G, rAPOBEC1-GGS-dCas9, rAPOBEC1-(GGS)$_3$(SEQ ID NO: 596)-dCas9, and dCas9-(GGS)$_3$(SEQ ID NO: 596)-rAPOBEC1 on ssDNA. Enzymes were expressed in a mammalian cell lysate-derived in vitro transcription-translation system and incubated with 1.8 µM dye-conjugated ssDNA and USER enzyme (uracil DNA glycosylase and endonuclease VIII) at 37° C. for 2 hours. The resulting DNA was resolved on a denaturing polyacrylamide gel and imaged. The positive control is a sequence with a U synthetically incorporated at the same position as the target C. FIG. 36B shows coomassie-stained denaturing PAGE gel of the expressed and purified proteins used in FIGS. 36C to 36F. FIGS. 36C to 36F show gel-based deaminase assay showing the deamination window of base editors with deaminase-Cas9 linkers of GGS (FIG. 36C), (GGS)$_3$ (SEQ ID NO: 596) (FIG. 36D), XTEN (FIG. 36E), or (GGS)$_7$ (SEQ ID NO: 597) (FIG. 36F). Following incubation of 1.85 µM deaminase-dCas9 fusions complexed with sgRNA with 125 nM dsDNA substrates at 37° C. for 2 hours, the dye-conjugated DNA was isolated and incubated with USER enzyme at 37° C. for 1 hour to cleave the DNA backbone at the site of any uracils.

The resulting DNA was resolved on a denaturing polyacrylamide gel, and the dye-conjugated strand was imaged. Each lane is numbered according to the position of the target C within the protospacer, or with—if no target C is present. 8U is a positive control sequence with a U synthetically incorporated at position 8.

Figure 37B:
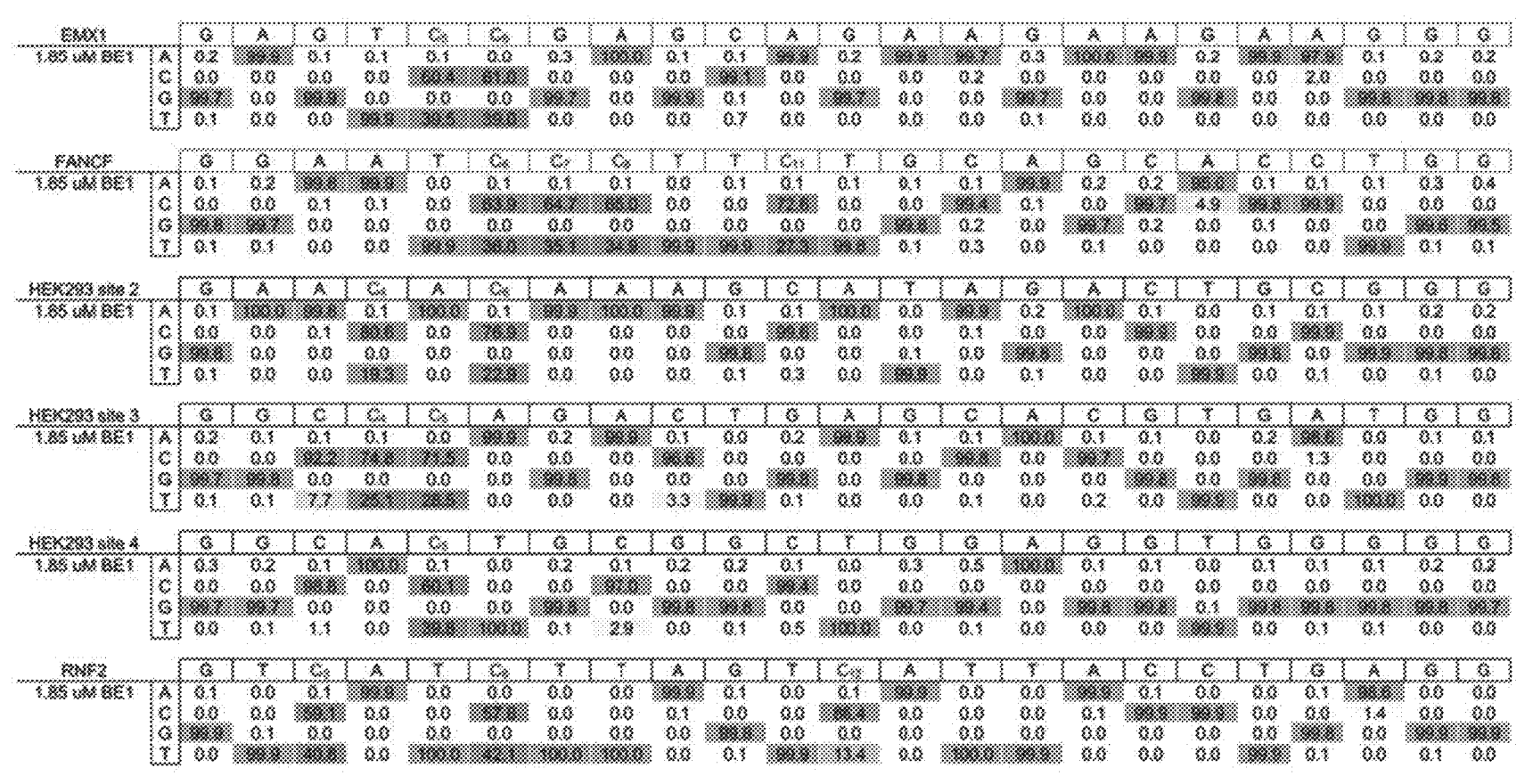
Figure 37C:
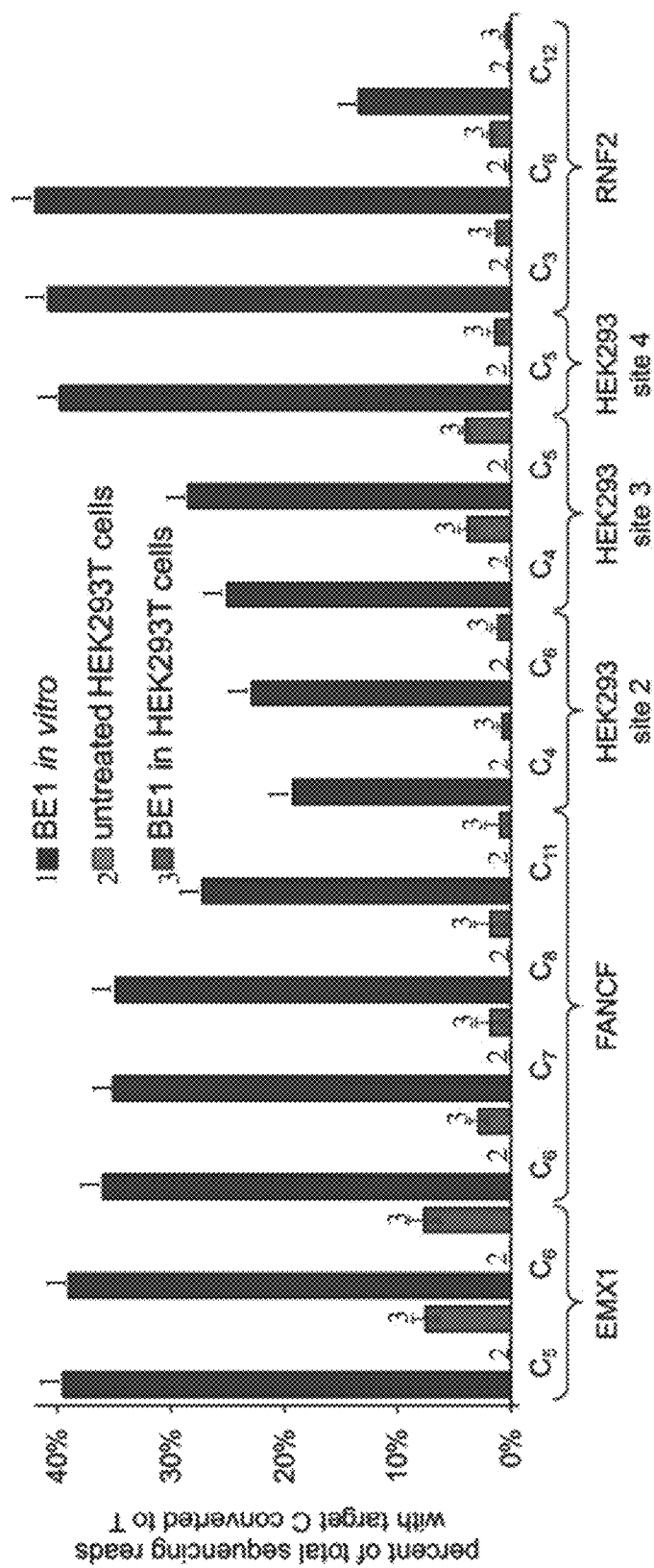

FIGS. 37A to 37C show BE1 base editing efficiencies are dramatically decreased in mammalian cells. FIG. 37A Protospacer (black and red) and PAM (blue) sequences of the six mammalian cell genomic loci targeted by base editors. Target Cs are indicated in red with subscripted numbers corresponding to their positions within the protospacer. FIG. 37B shows synthetic 80-mers with sequences matching six different genomic sites were incubated with BE1 then analyzed for base editing by HTS. For each site, the sequence of the protospacer is indicated to the right of the name of the site, with the PAM highlighted in blue. Underneath each sequence are the percentages of total DNA sequencing reads with the corresponding base. We considered a target C as "editable" if the in vitro conversion efficiency is >10%. Note that maximum yields are 50% of total DNA sequencing reads since the non-targeted strand is unaffected by BE1. Values are shown from a single experiment. FIG. 37C shows HEK293T cells were transfected with plasmids encoding BE1 and an appropriate sgRNA. Three days after transfection, genomic DNA was extracted and analyzed by high-throughput DNA sequencing at the six loci. Cellular C to T conversion percentages, defined as the percentage of total DNA sequencing reads with Ts at the target positions indicated, are shown for BE1 at all six genomic loci. Values and error bars of all data from HEK293T cells reflect the mean and standard deviation of three independent biological replicates performed on different days. FIG. 37A depicts SEQ ID NOs: 721 to 726 from top to bottom, respectively. FIG. 37B depicts SEQ ID NOs: 727 to 732 from top to bottom, respectively.

Figure 38:
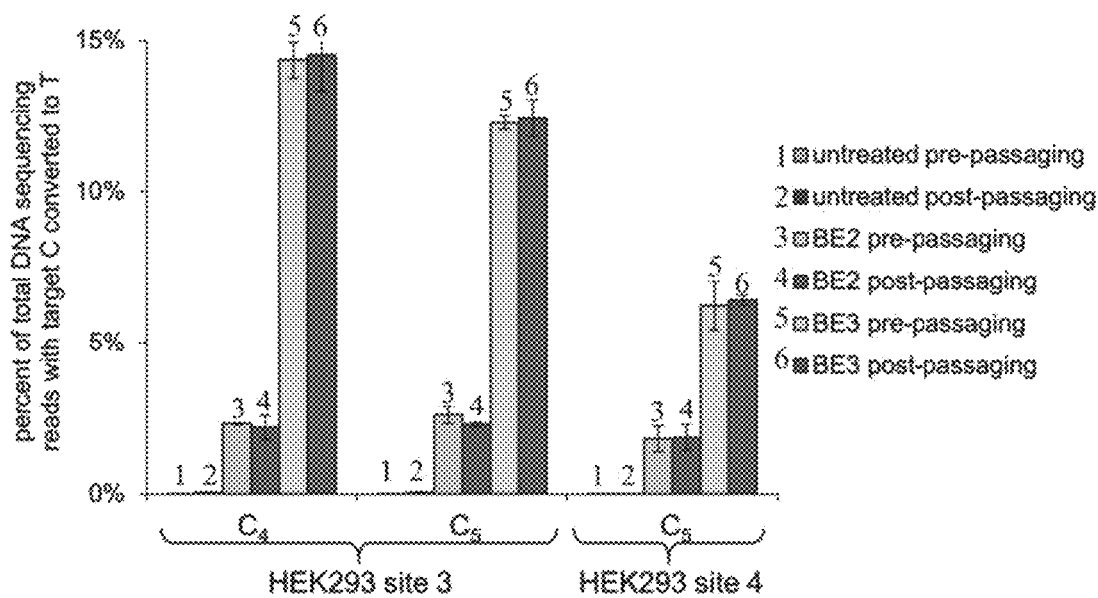

FIG. 38 shows base editing persists over multiple cell divisions. Cellular C to T conversion percentages by BE2 and BE3 are shown for HEK293 sites 3 and 4 in HEK293T cells before and after passaging the cells. HEK293T cells were nucleofected with plasmids expressing BE2 or BE3 and an sgRNA targeting HEK293 site 3 or 4. Three days after nucleofection, the cells were harvested and split in half. One half was subjected to HTS analysis, and the other half was allowed to propagate for approximately five cell divisions, then harvested and subjected to HTS analysis. Values and error bars reflect the mean and standard deviation of at least two biological experiments.

Figure 39A:
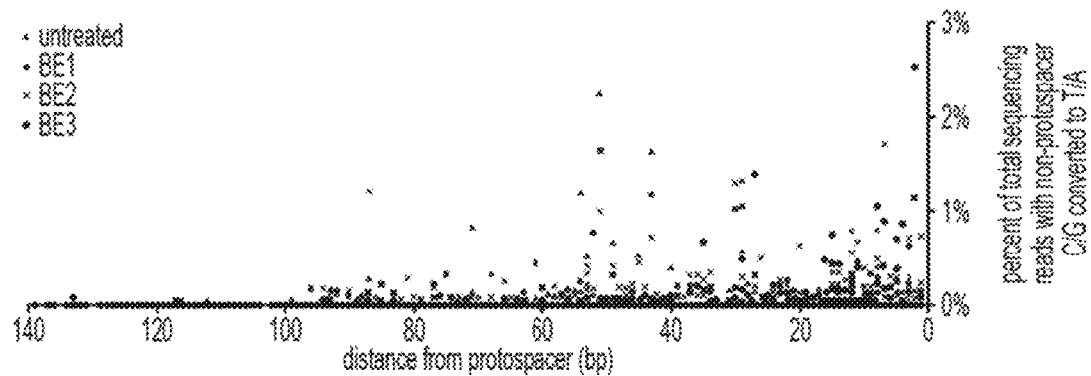
FIG. 39B is shown with each base's position relative to the protospacer. The side of the protospacer distal to the PAM is designated with positive numbers, while the side that includes the PAM is designated with negative numbers, with the PAM shown in blue. Underneath each sequence are the percentages of total sequencing reads with the corresponding base for untreated cells, for cells treated with BE3 and an sgRNA targeting the TP53 Y163C mutation, or for cells treated with BE3 and an sgRNA targeting the VEGFA locus. Neither BE3-treated sample resulted in mutational rates above those of untreated controls. This figure depicts SEQ ID NOs: 717 to 720 from top to bottom, respectively.
Figures 39B, 39C:
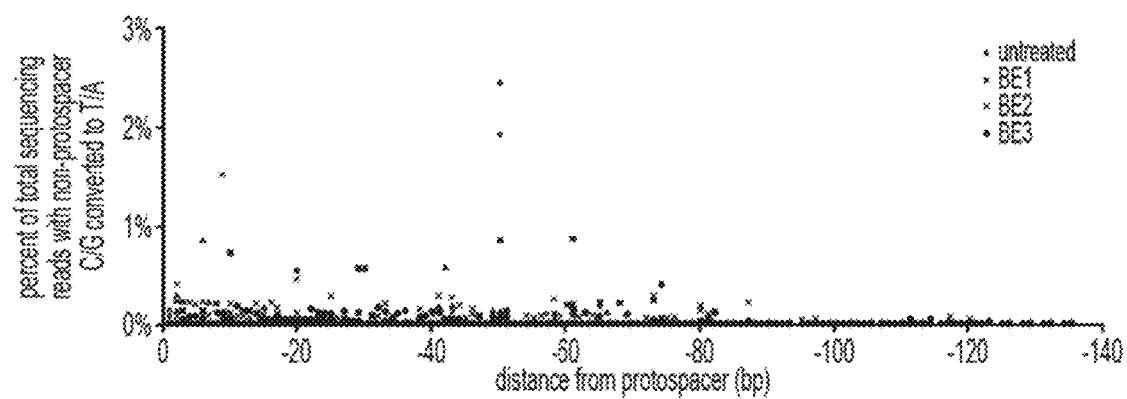

FIGS. 39A to 39C show non-target C/G mutation rates. Shown here are the C to T and G to A mutation rates at 2,500 distinct cytosines and guanines surrounding the six on-target and 34 off-target loci tested, representing a total of 14,700,000 sequence reads derived from approximately $1.8 \times 10^6$ cells. FIGS. 39A and 39B show cellular non-target C to T and G to A conversion percentages by BE1, BE2, and BE3 are plotted individually against their positions relative to a protospacer for all 2,500 cytosines/guanines. The side of the protospacer distal to the PAM is designated with positive numbers, while the side that includes the PAM is designated with negative numbers. FIG. 39C shows average non-target cellular C to T and G to A conversion percentages by BE1, BE2, and BE3 are shown, as well as the highest and lowest individual conversion percentages.

Figure 40A:
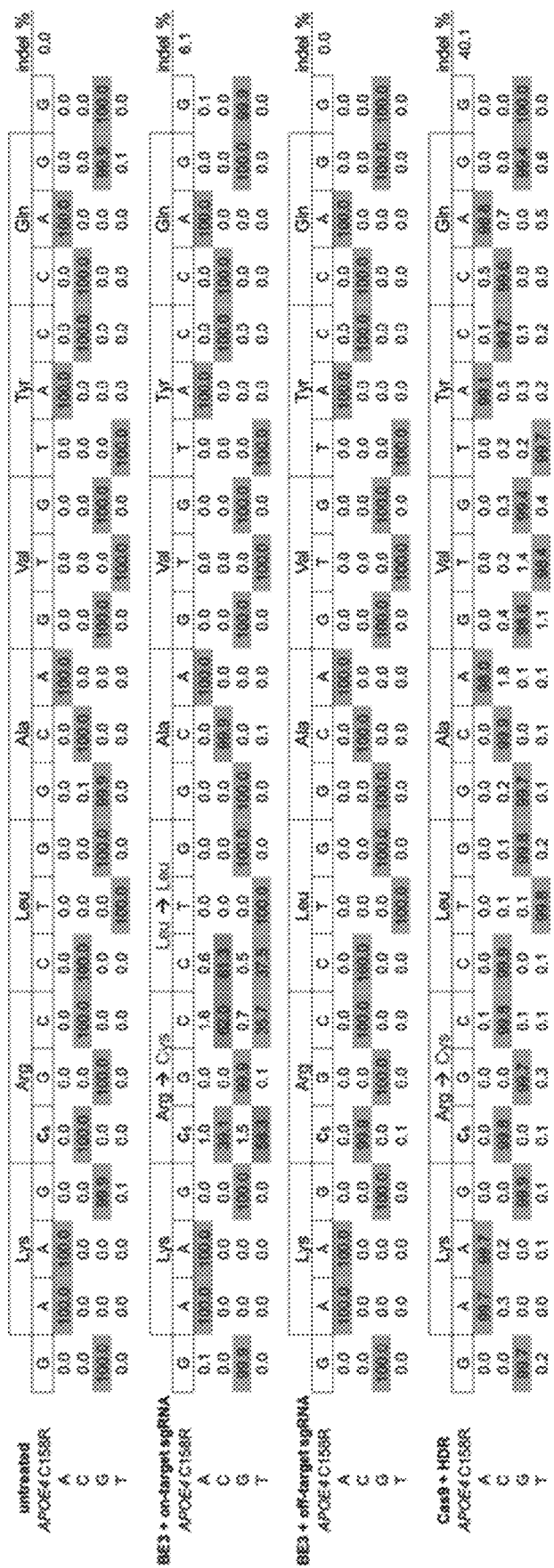
Figure 40B:
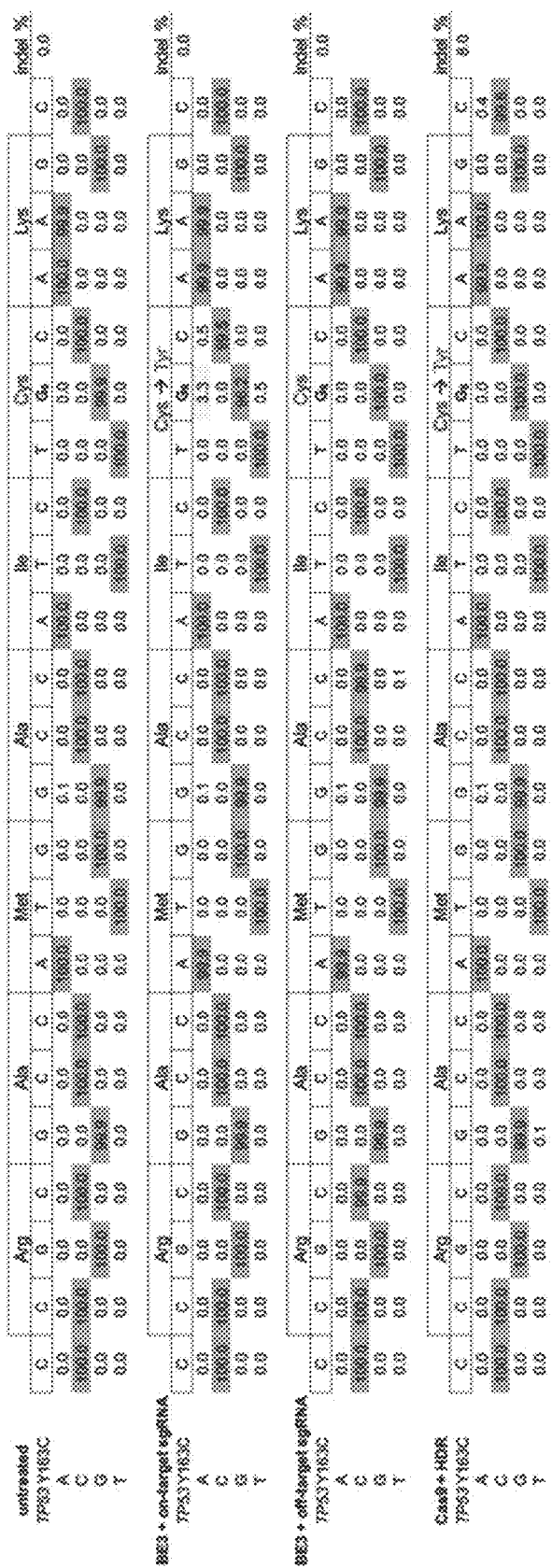

FIGS. 40A to 40B show additional data sets of BE3-mediated correction of two disease-relevant mutations in mammalian cells. For each site, the sequence of the protospacer is indicated to the right of the name of the mutation, with the PAM highlighted in blue and the base responsible for the mutation indicated in red bold with a subscripted number corresponding to its position within the protospacer. The amino acid sequence above each disease-associated allele is shown, together with the corrected amino acid sequence following base editing in green. Underneath each sequence are the percentages of total sequencing reads with the corresponding base. Cells were nucleofected with plasmids encoding BE3 and an appropriate sgRNA. Two days after nucleofection, genomic DNA was extracted from the nucleofected cells and analyzed by HTS to assess pathogenic mutation correction. FIG. 40A shows the Alzheimer's disease-associated APOE4 allele is converted to APOE3r in mouse astrocytes by BE3 in 58.3% of total reads only when treated with the correct sgRNA. Two nearby Cs are also converted to Ts, but with no change to the predicted sequence of the resulting protein. Identical treatment of these cells with wt Cas9 and donor ssDNA results in 0.2% correction, with 26.7% indel formation. FIG. 40B shows the cancer-associated p53 Y163C mutation is corrected by BE3 in 3.3% of nucleofected human breast cancer cells only when treated with the correct sgRNA. Identical treatment of these cells with wt Cas9 and donor ssDNA results in no detectable mutation correction with 8.0% indel formation. FIGS. 40A to 40B depict SEQ ID NOs: 733 to 740 from top to bottom, respectively.

Figure 41:
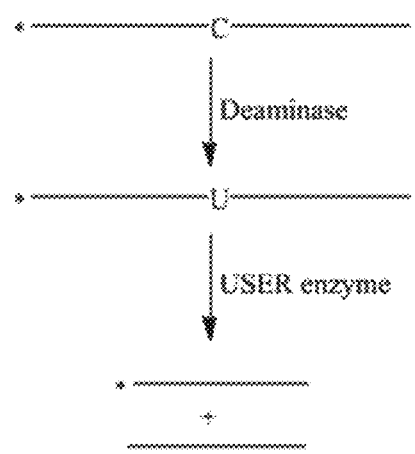

FIG. 41 shows a schematic representation of an exemplary USER (Uracil-Specific Excision Reagent) Enzyme-based assay, which may be used to test the activity of various deaminases on single-stranded DNA (ssDNA) substrates.

Figure 42:
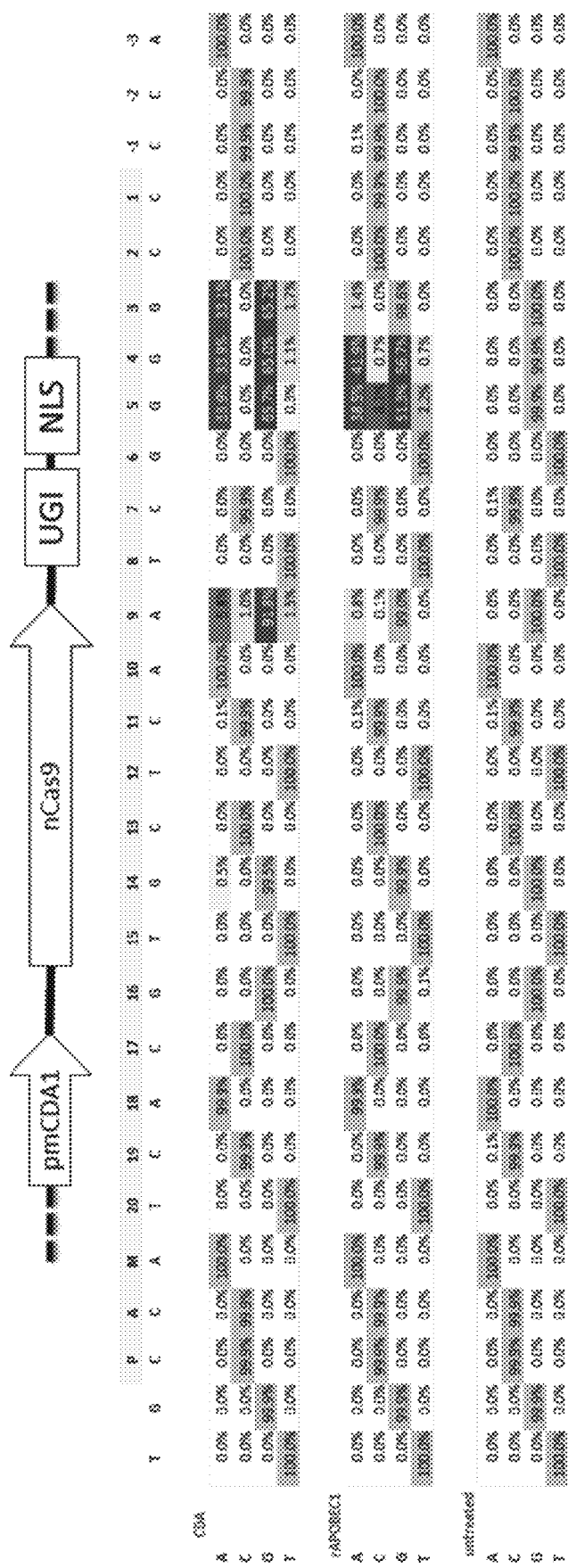

FIG. 42 is a schematic of the pmCDA-nCas9-UGI-NLS construct and its activity at the HeK-3 site relative to the base editor (rAPOBEC1) and the negative control (untreated).

Figure 43:
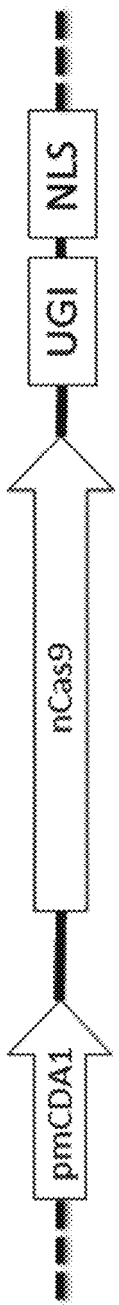

FIG. 43 is a schematic of the pmCDA1-XTEN-nCas9-UGI-NLS construct and its activity at the HeK-3 site relative to the base editor (rAPOBEC1) and the negative control (untreated).

Figure 44:
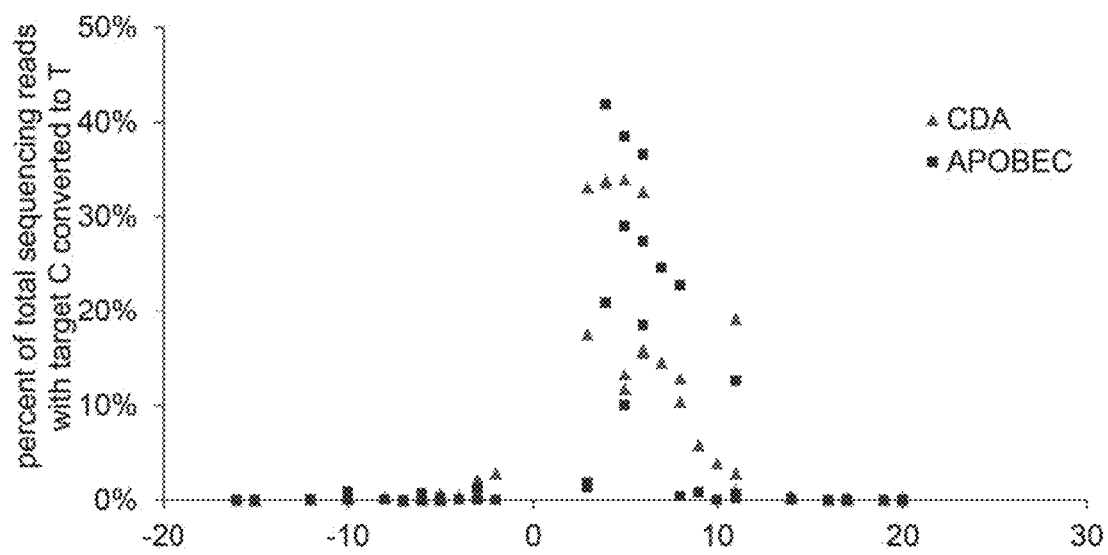

FIG. 44 shows the percent of total sequencing reads with target C converted to T using cytidine deaminases (CDA) or APOBEC.

Figure 45:
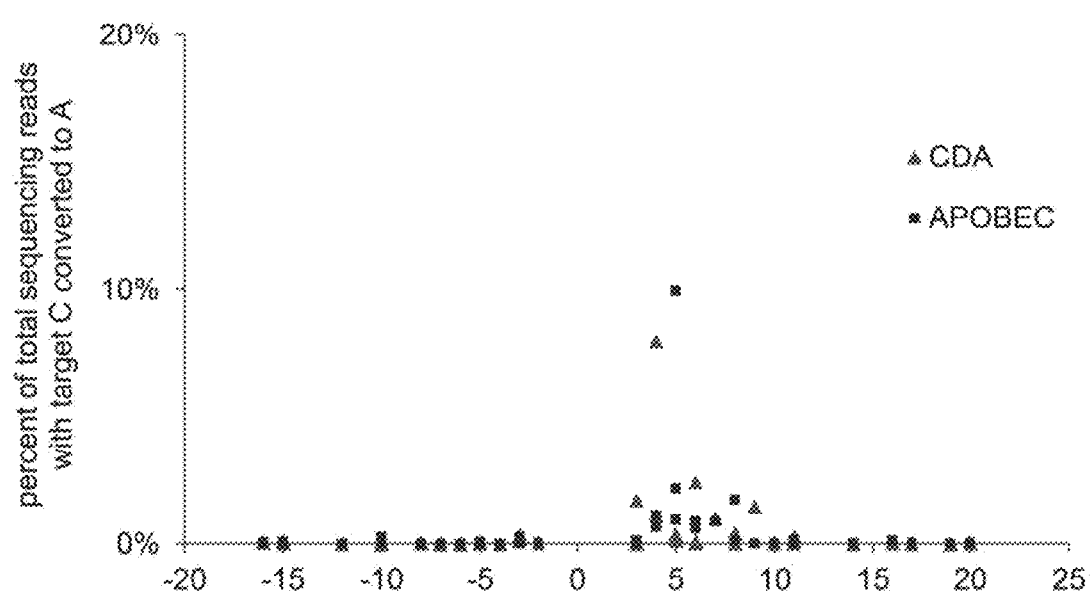

FIG. 45 shows the percent of total sequencing reads with target C converted to A using deaminases (CDA) or APOBEC.

Figure 46:
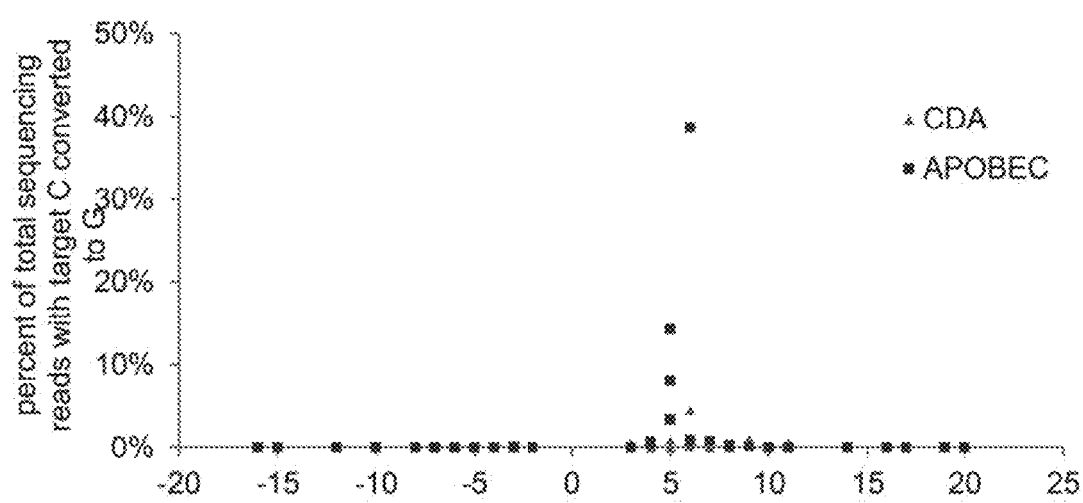

FIG. 46 shows the percent of total sequencing reads with target C converted to G using deaminases (CDA) or APOBEC.

Figure 47:
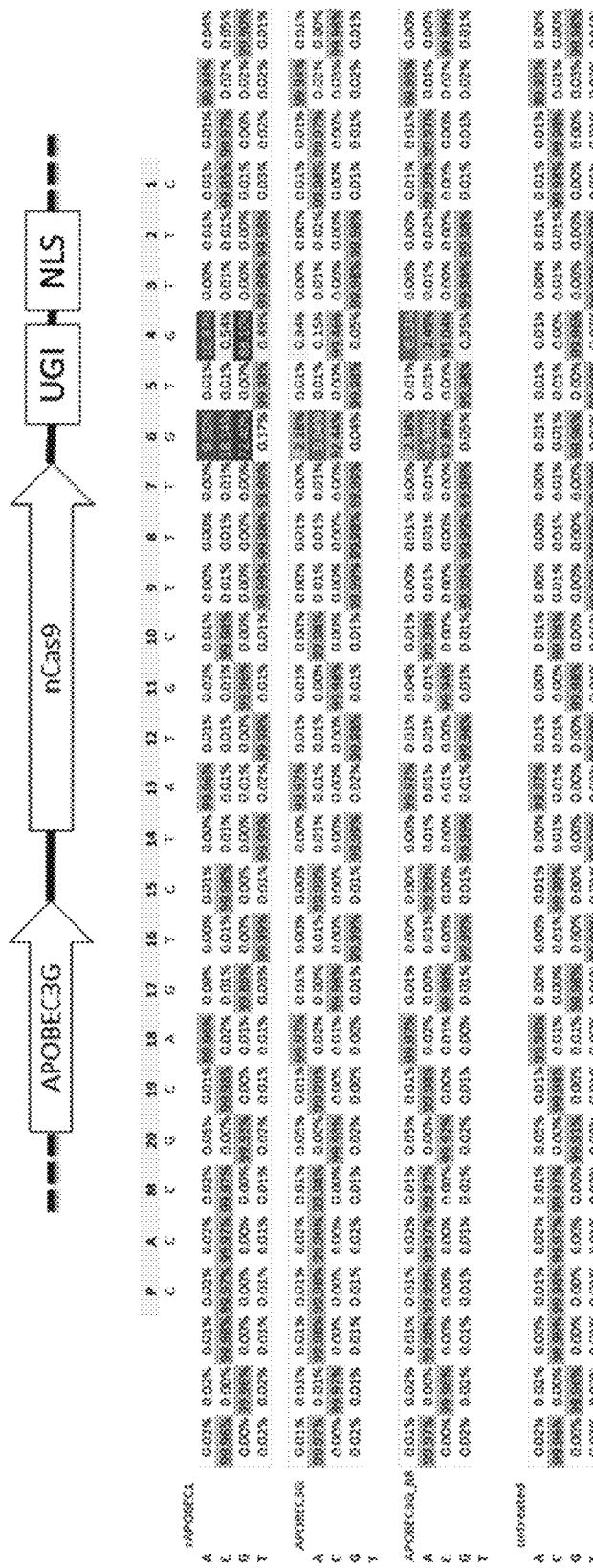

FIG. 47 is a schematic of the huAPOBEC3G-XTEN-nCas9-UGI-NLS construct and its activity at the HeK-2 site relative to a mutated form (huAPOBEC3G* (D316R_D317R)-XTEN-nCas9-UGI-NLS, the base editor (rAPOBEC1) and the negative control (untreated).

Figure 48:
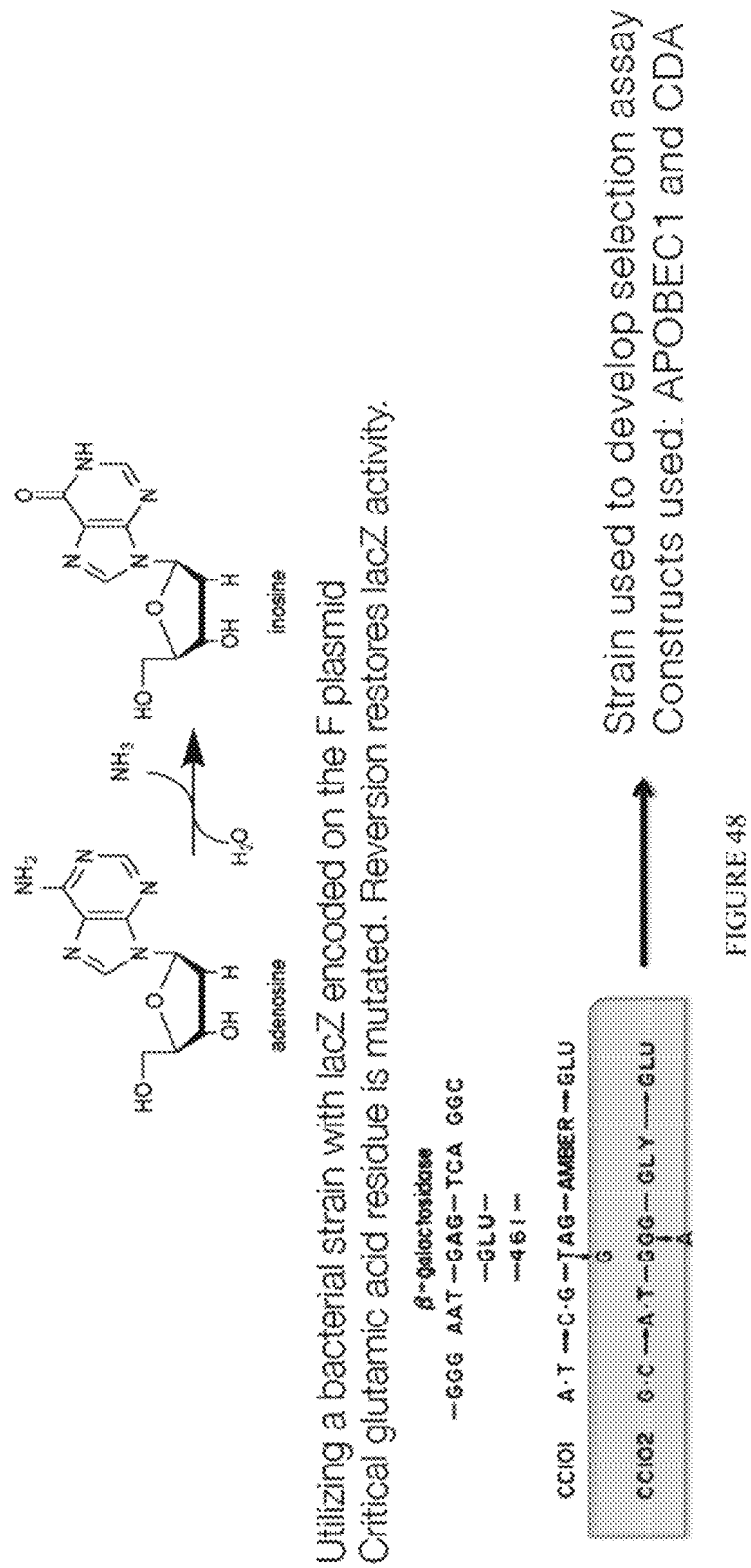

FIG. 48 shows the schematic of the LacZ construct used in the selection assay of Example 7.

FIG. 49 shows reversion data from different plasmids and constructs.

FIG. 50 shows the verification of lacZ reversion and the purification of reverted clones.

Figure 51:
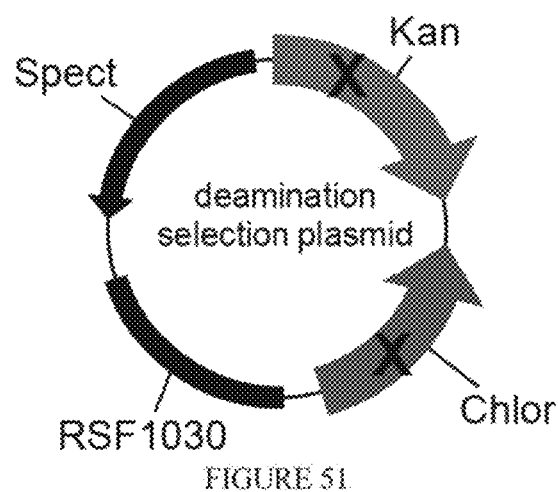

FIG. 51 is a schematic depicting a deamination selection plasmid used in Example 7.

Figure 52:
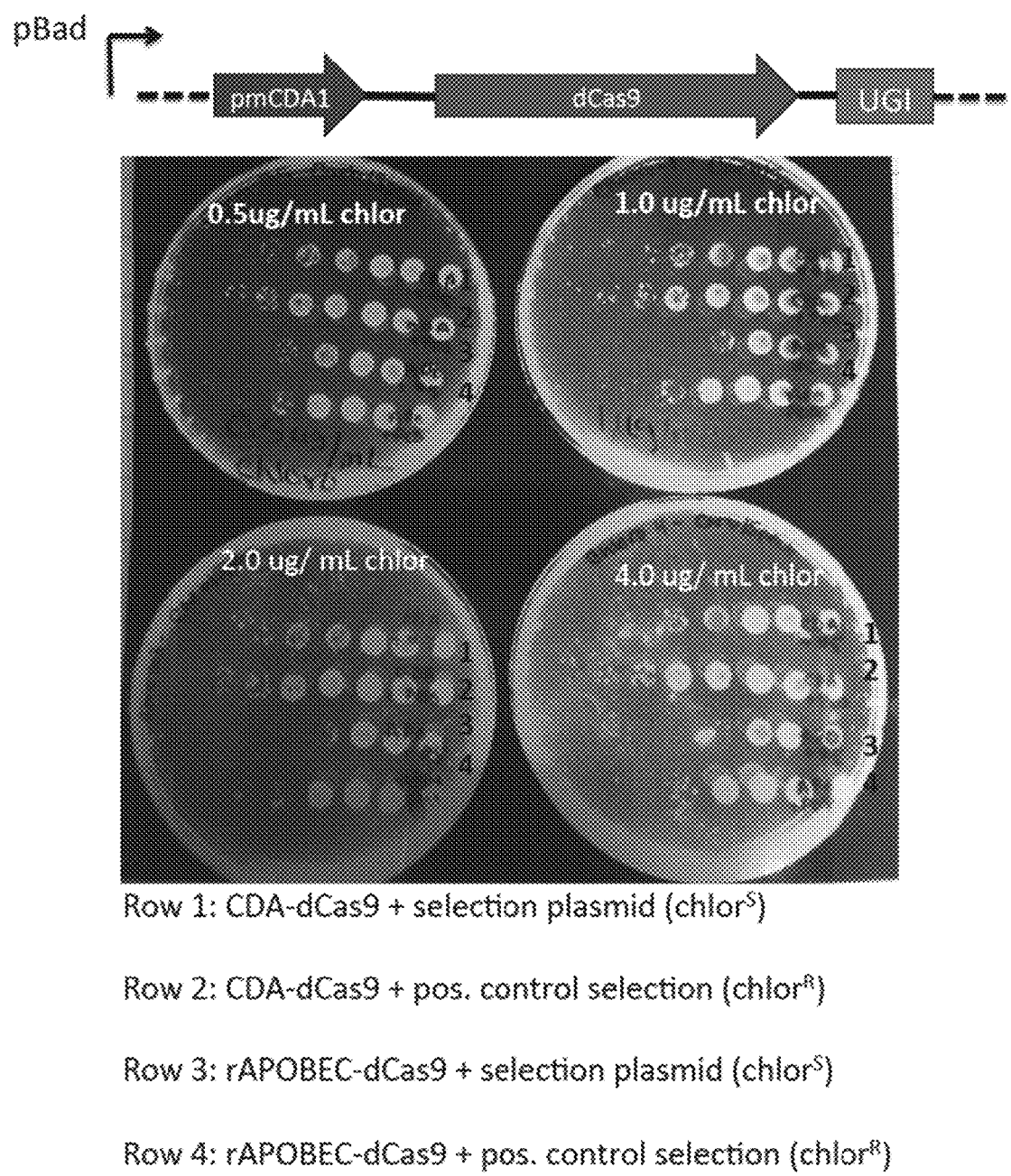

FIG. 52 shows the results of a chloramphenicol reversion assay (pmCDA1 fusion).

Figure 53A:
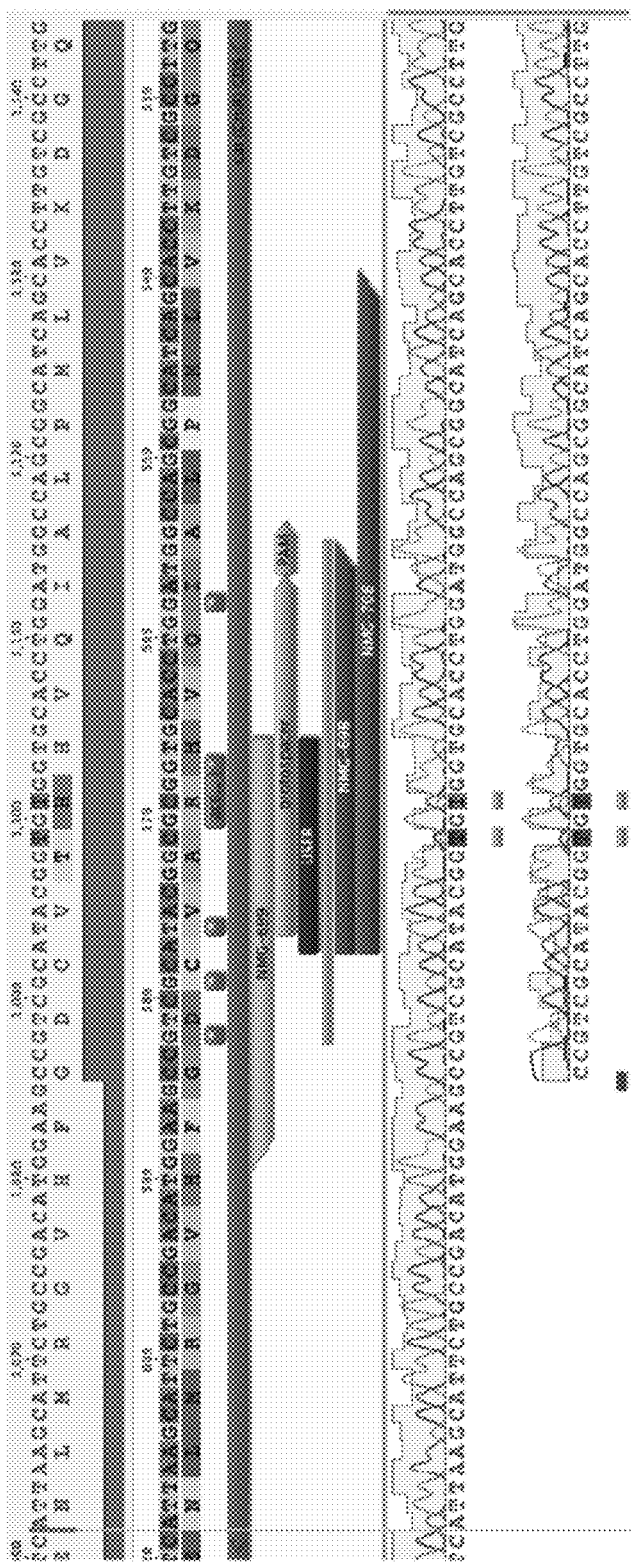
Figure 53B:
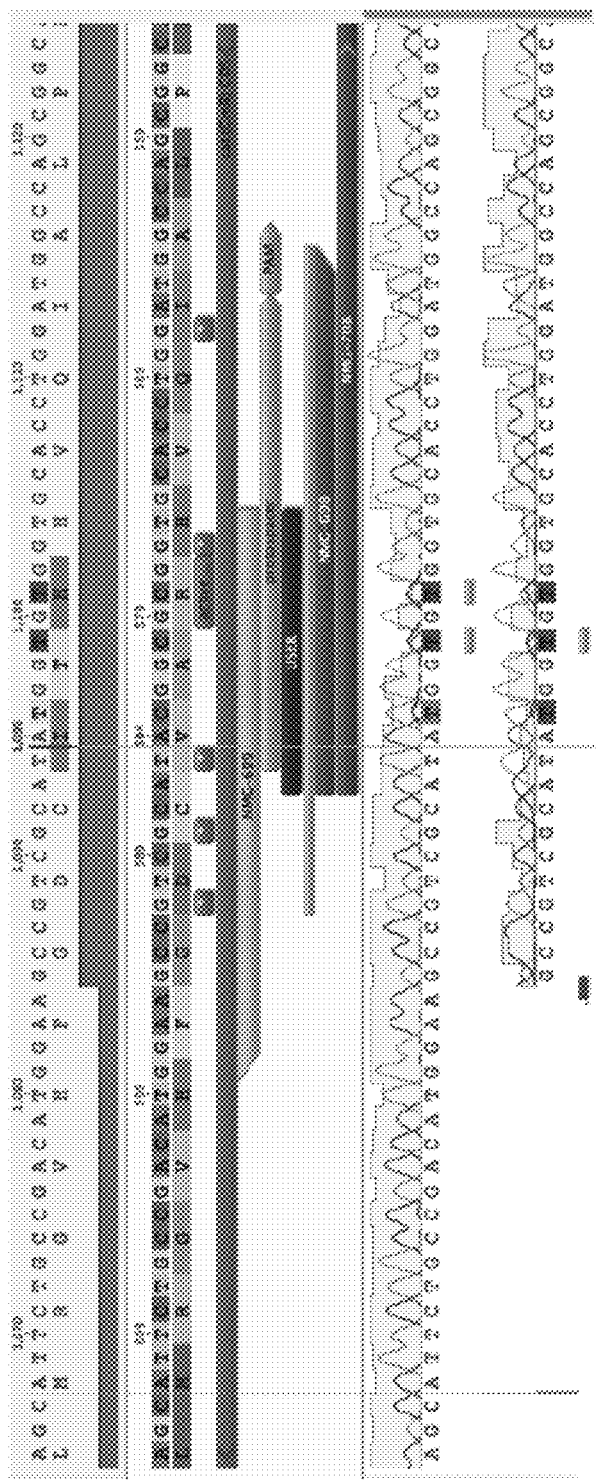

FIGS. 53A to 53B demonstrated DNA correction induction of two constructs.

Figure 54:
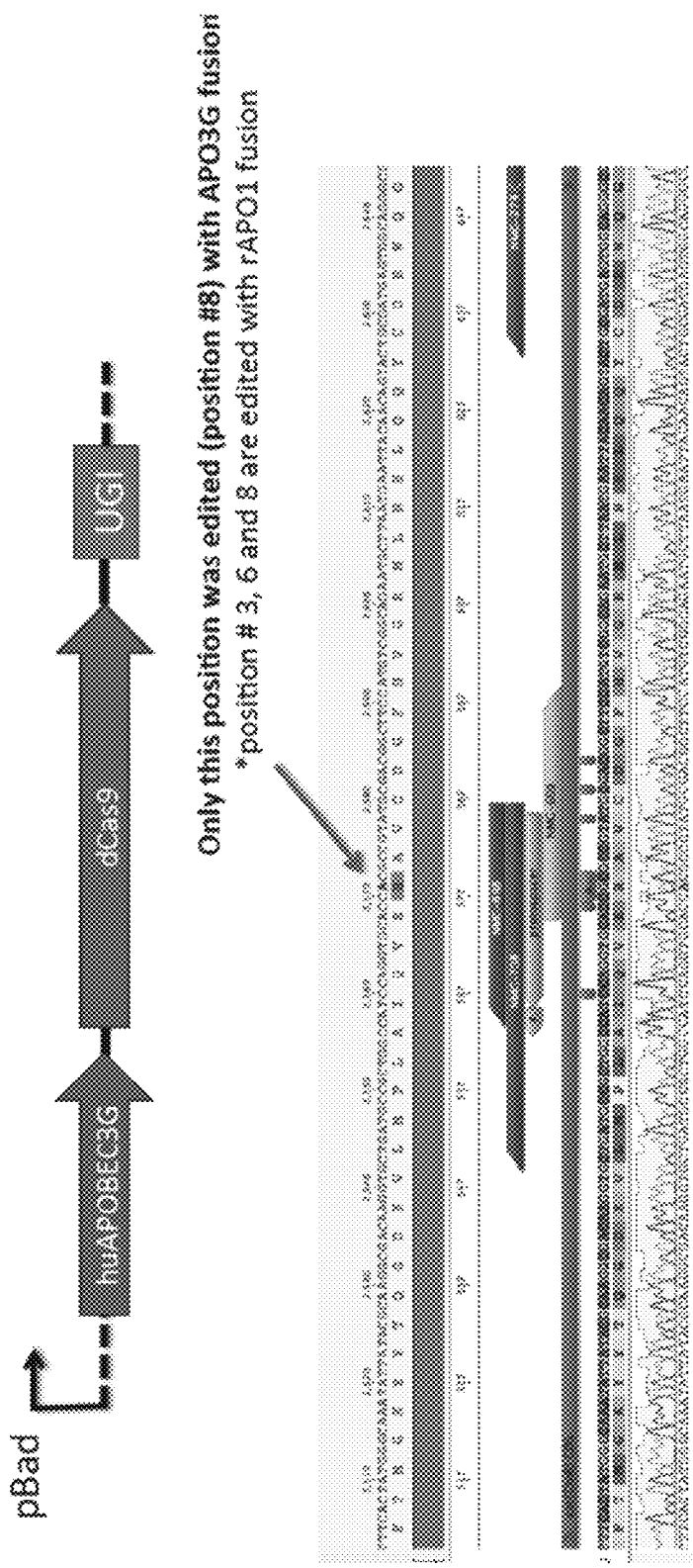

FIG. 54 shows the results of a chloramphenicol reversion assay (huAPOBEC3G fusion).

Figure 55:
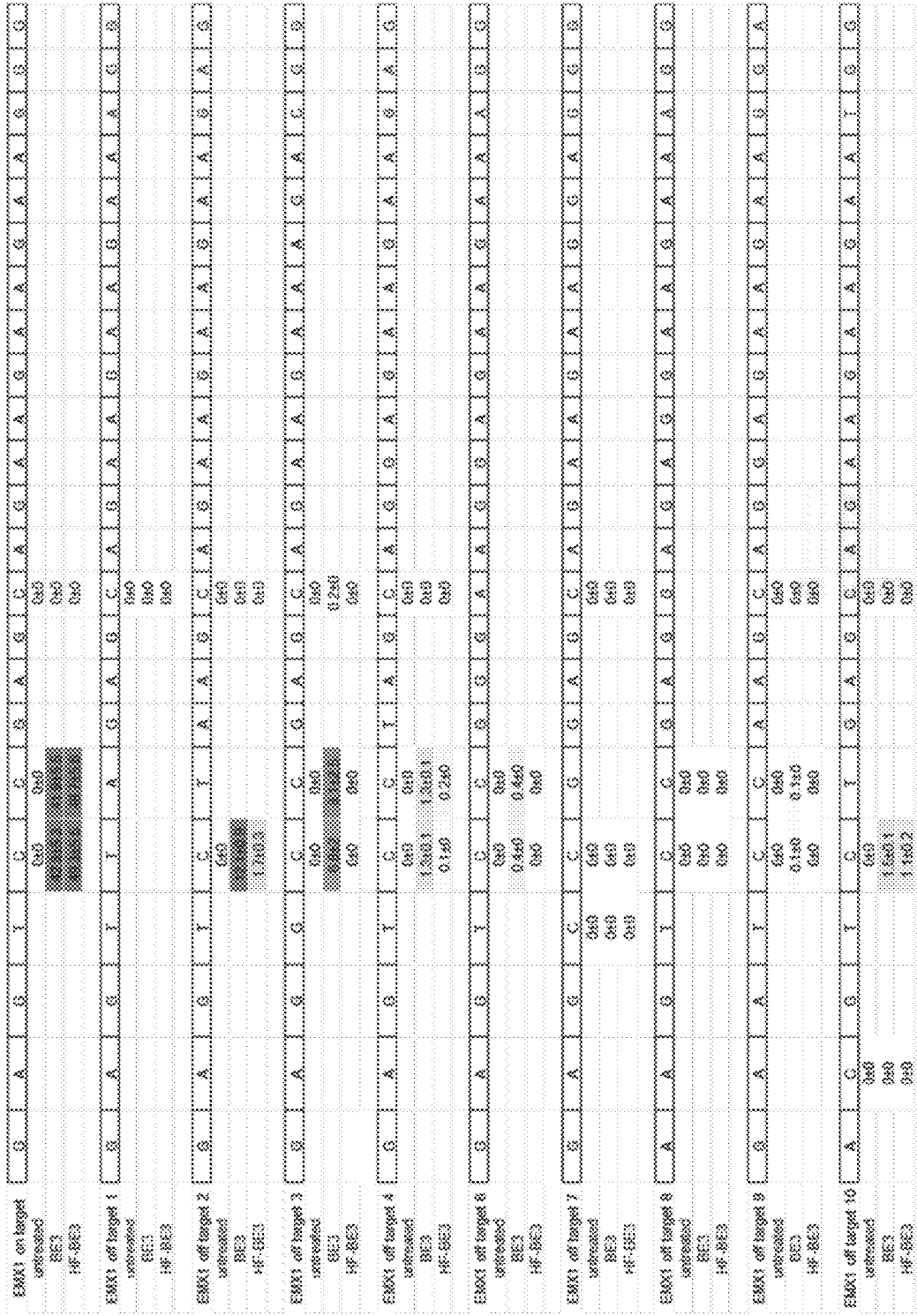

FIG. 55 shows the activities of BE3 and HF-BE3 at EMX1 off-targets. The sequences, from top to bottom, correspond to SEQ ID NOs: 286-292, 299-301.

Figure 56:
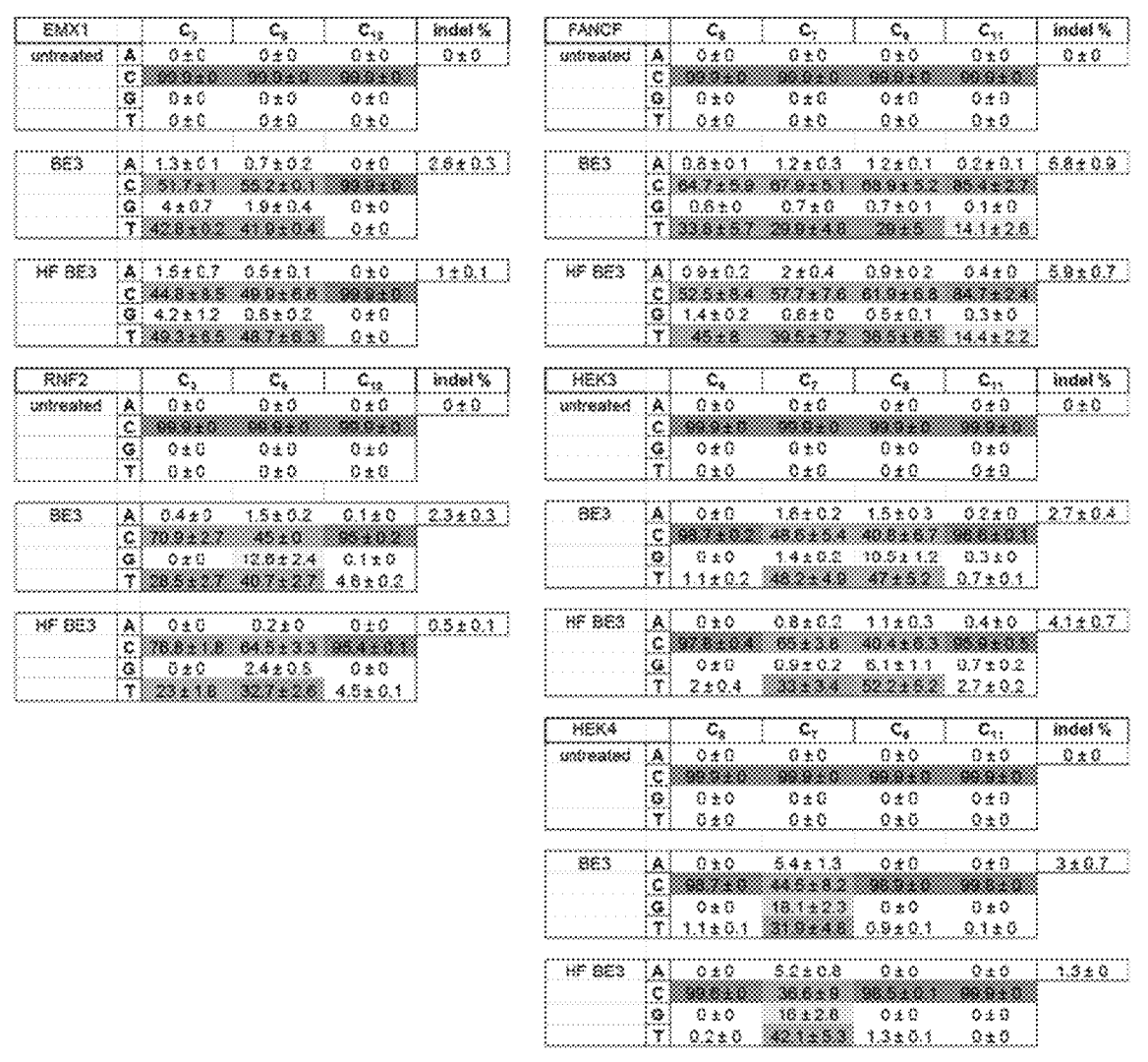

FIG. 56 shows on-target base editing efficiencies of BE3 and HF-BE3.

Figure 57:
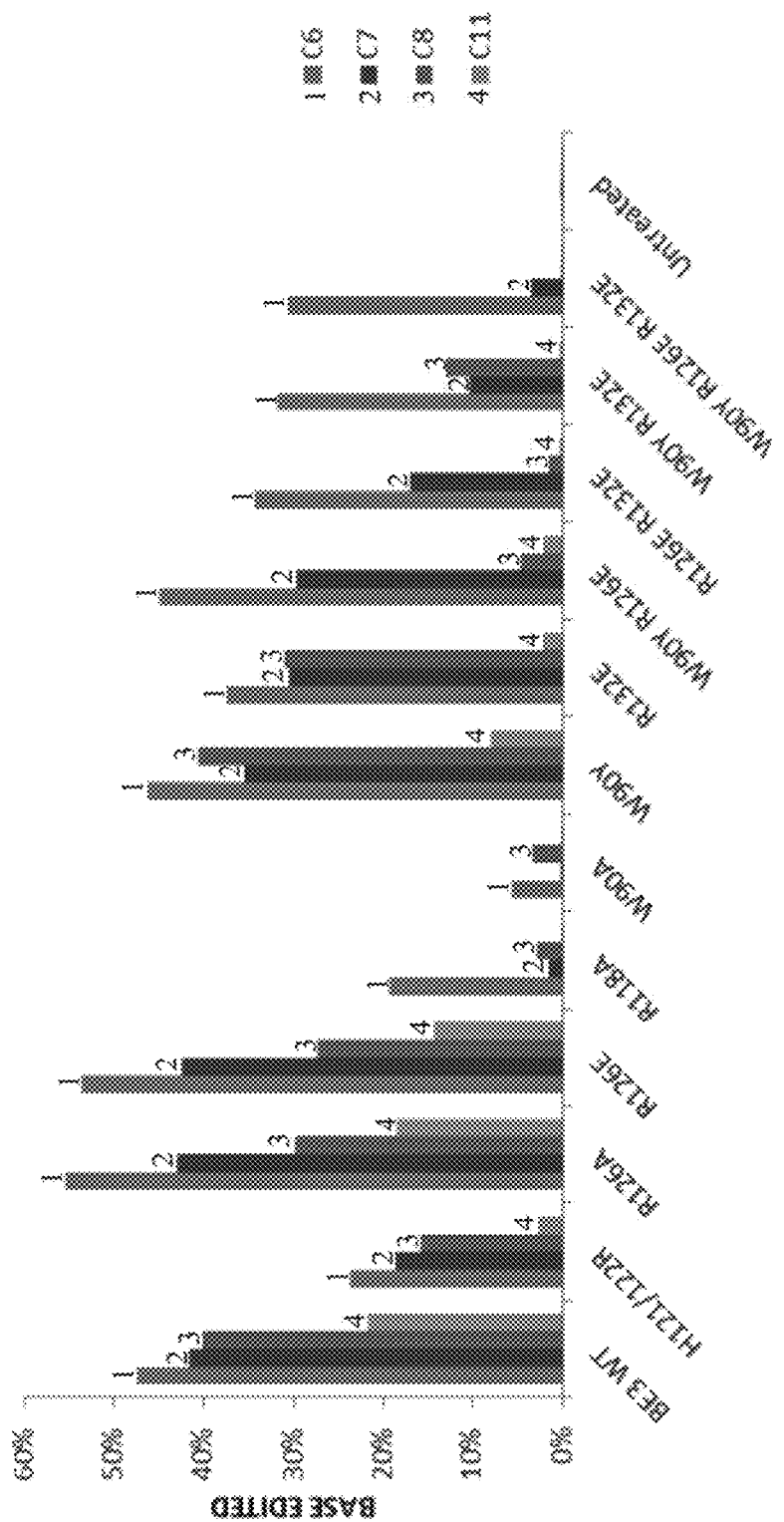

FIG. 57 is a graph demonstrating that mutations affect cytidine deamination with varying degrees. Combinations of mutations that each slightly impairs catalysis allow selective deamination at one position over others. The FANCF site was GGAATC$_6$C$_7$C$_8$TTC$_{11}$TGCAGCACCTGG (SEQ ID NO: 303).

Figure 58:
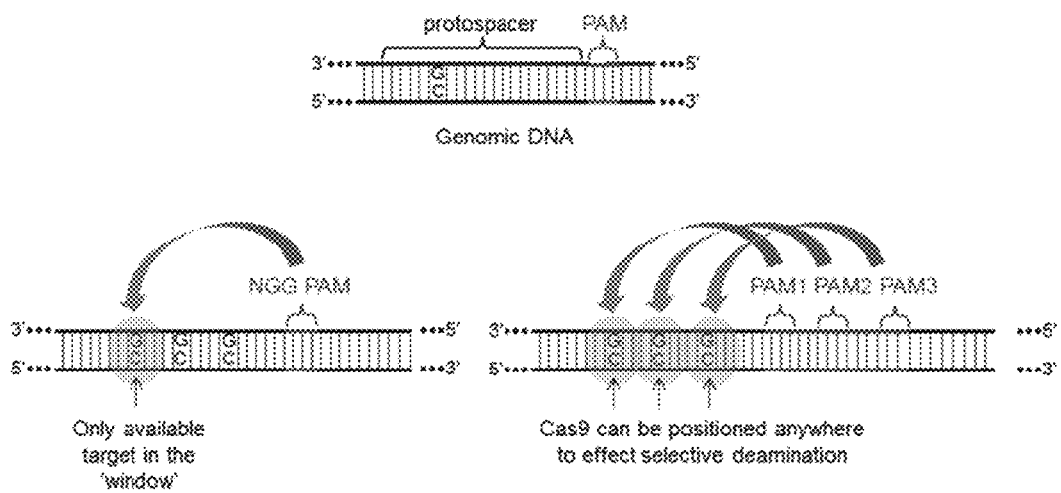

FIG. 58 is a schematic depicting next generation base editors.

Figure 59:
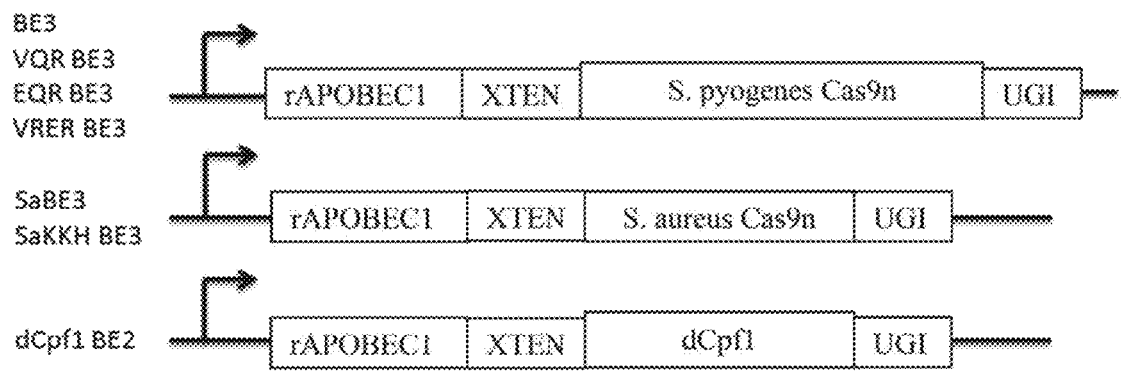

FIG. 59 is a schematic illustrating new base editors made from Cas9 variants.

Figure 60:
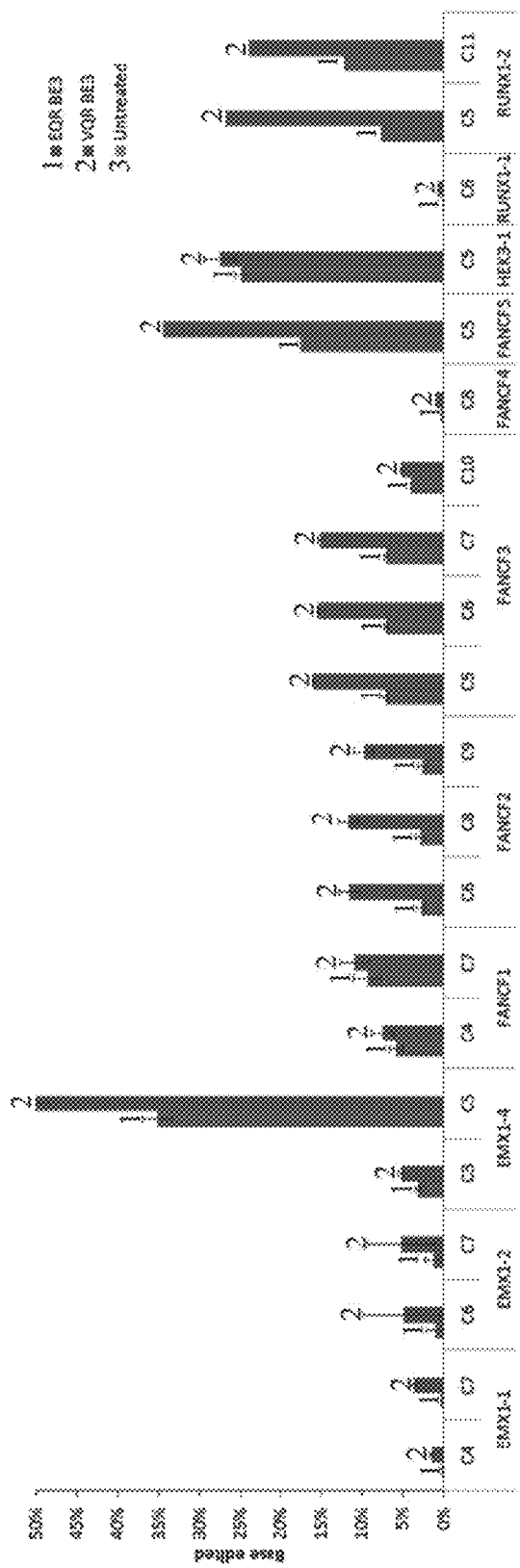

FIG. 60 shows the base-edited percentage of different NGA PAM sites.

Figure 61:
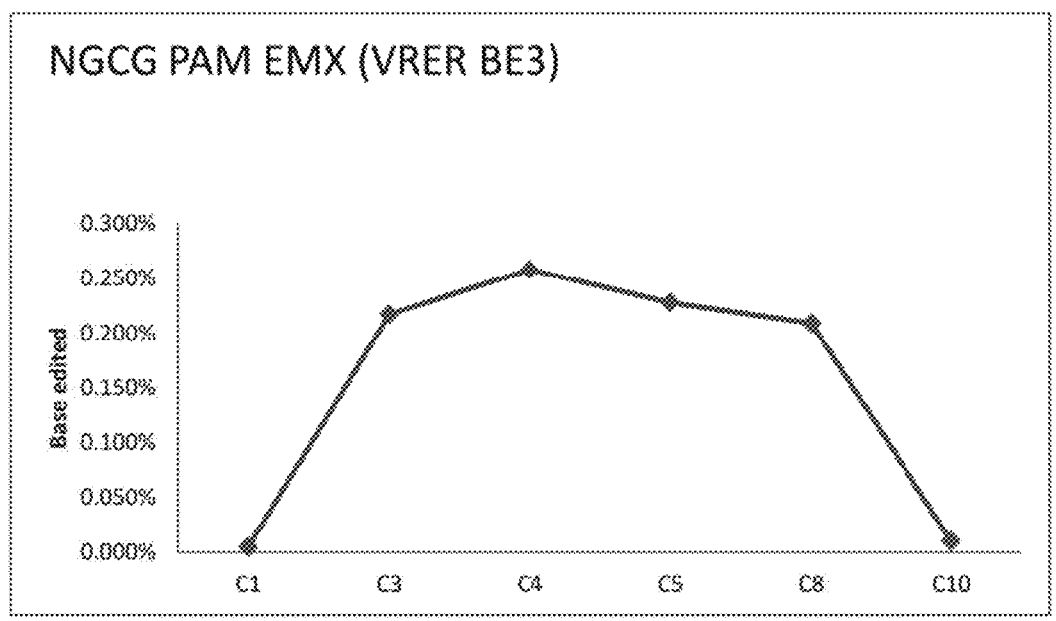

FIG. 61 shows the base-edited percentage of cytidines using NGCG PAM EMX (VRER BE3) and the C$_1$TC$_3$C$_4$C$_5$ATC$_8$AC$_{10}$ATCAACCGGT (SEQ ID NO: 304) spacer.

Figure 62:
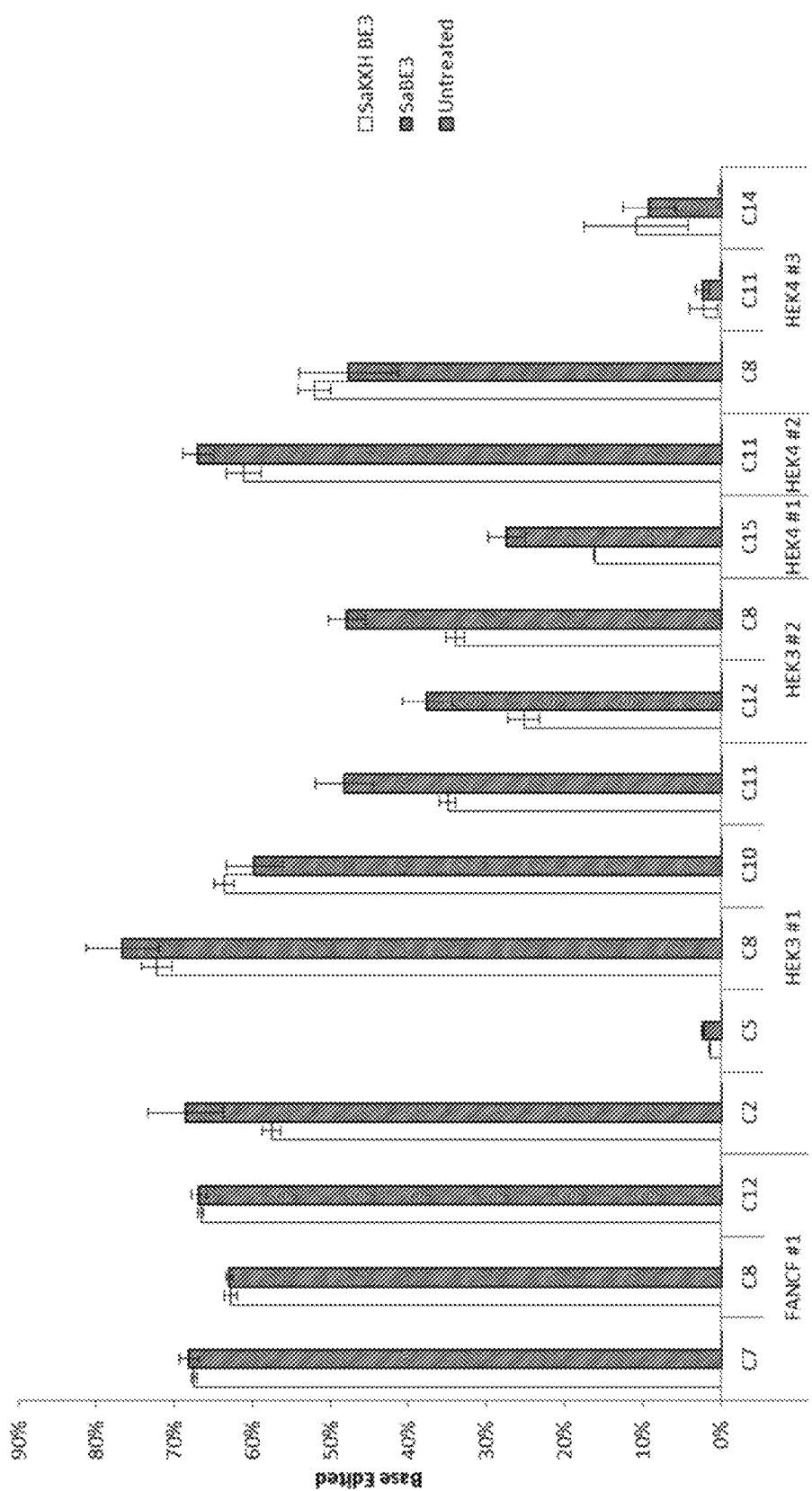

FIG. 62 shows the based-edited percentages resulting from different NNGRRT PAM sites.

Figure 63:
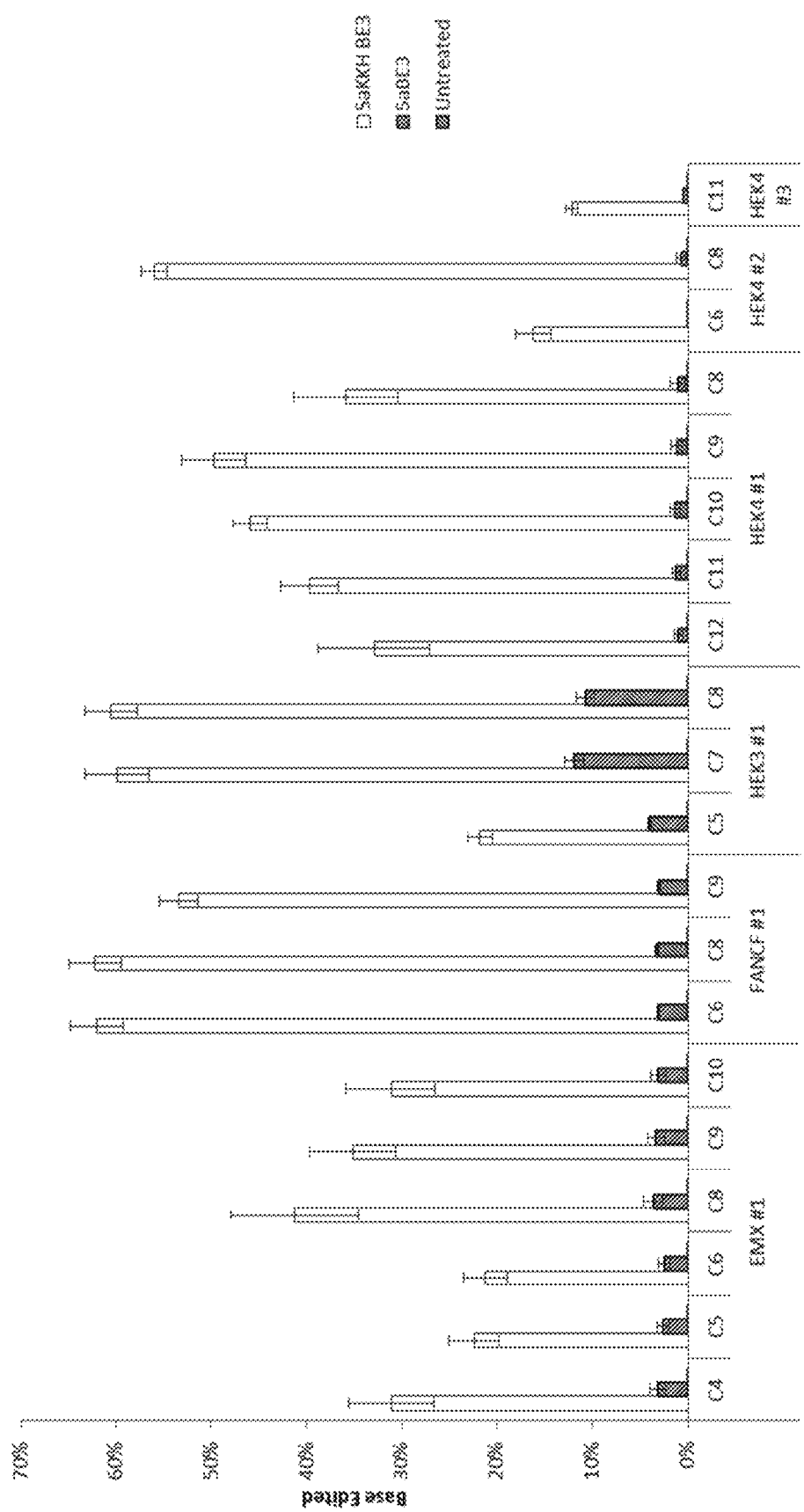

FIG. 63 shows the based-edited percentages resulting from different NNHRRT PAM sites.

Figure 64A:
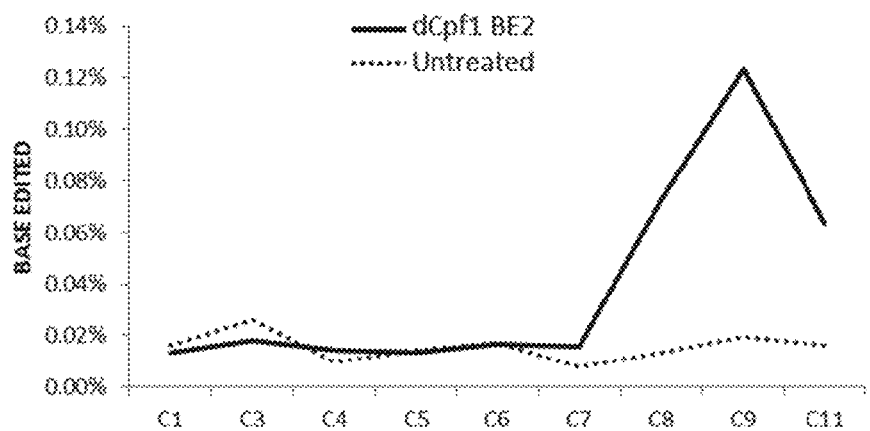
Figure 64B:
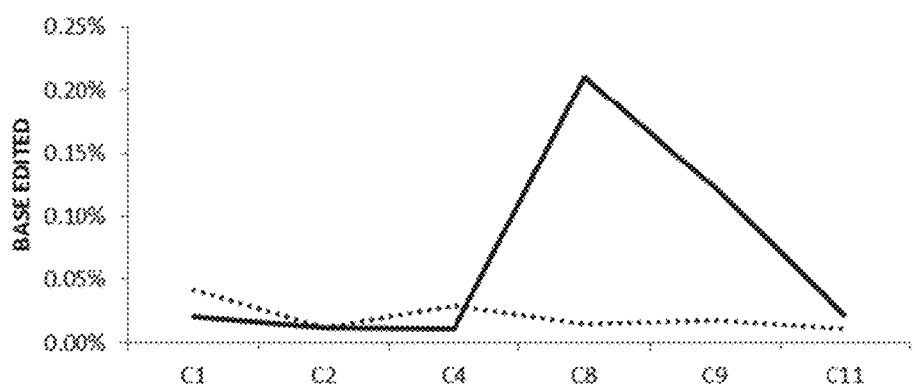
Figure 64C:
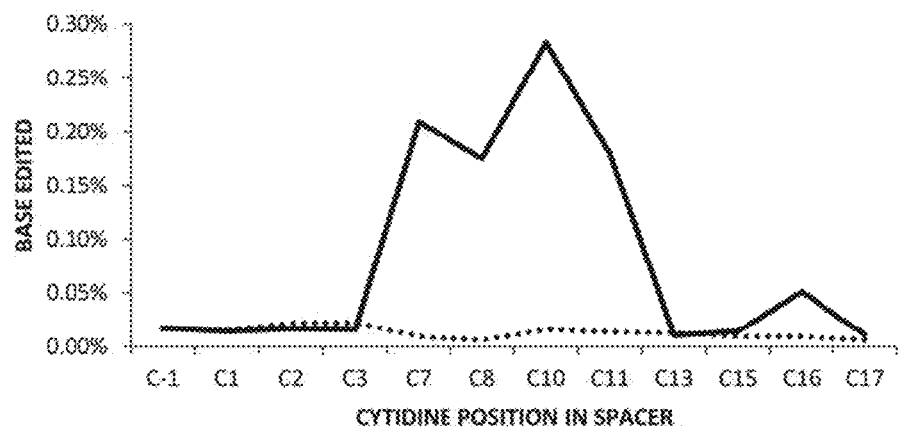

FIGS. 64A to 64C show the base-edited percentages resulting from different TTTN PAM sites using Cpf1 BE2. The spacers used were: TTTCCTC$_3$C$_4$C$_5$C$_6$C$_7$C$_8$C$_9$AC$_{10}$iAGGTAGAACAT (FIG. 64A, SEQ ID NO: 305), TTTCC$_1$C$_2$TC$_4$TGTC$_8$C$_9$AC$_{11}$ACCCTCATCCTG (FIG. 64B, SEQ ID NO: 306), and TTTCC$_1$C$_2$C$_3$AGTC$_7$C$_8$TC$_{10}$C$_{11}$AC$_{13}$AC$_{15}$C$_{16}$C$_{17}$TGAAAC (FIG. 64C, SEQ ID NO: 307).

Figure 65:
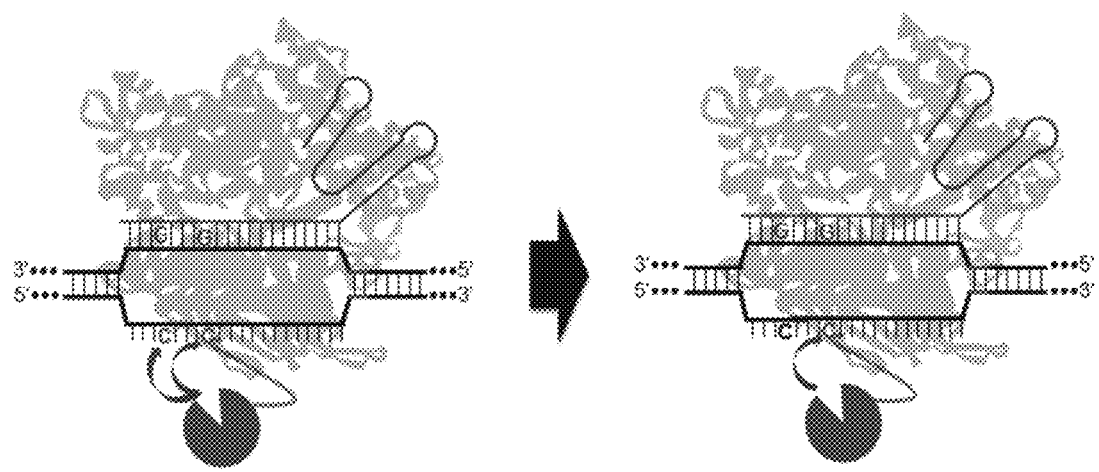

FIG. 65 is a schematic depicting selective deamination as achieved through kinetic modulation of cytidine deaminase point mutagenesis.

Figure 66:
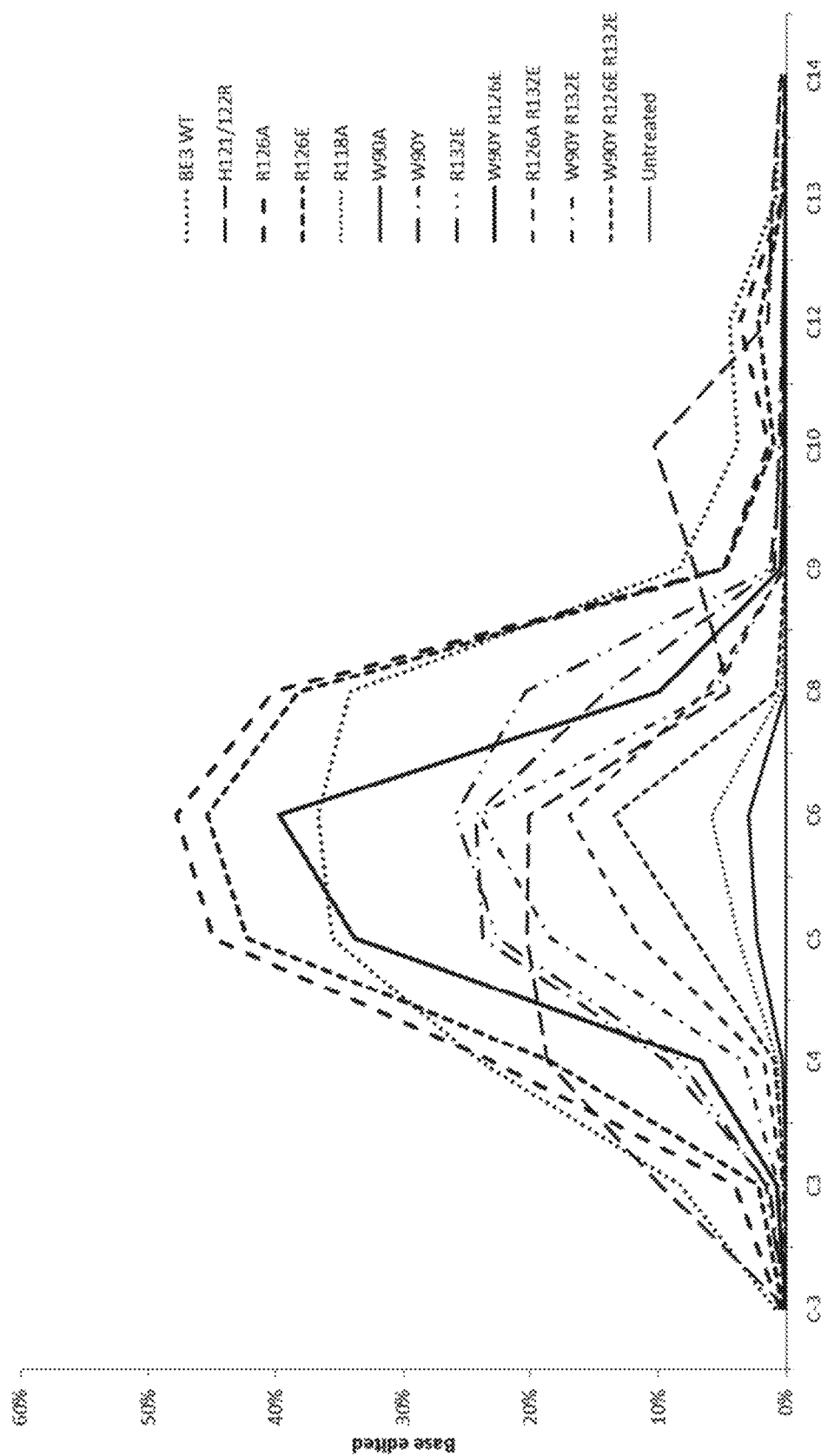

FIG. 66 is a graph showing the effect of various mutations on the deamination window probed in cell culture with multiple cytidines in the spacer. The spacer used was: TGC$_3$C$_4$C$_5$C$_6$TC$_8$C$_9$C$_{10}$TC$_{12}$C$_{13}$C$_{14}$TGGCCC (SEQ ID NO: 308).

Figure 67:
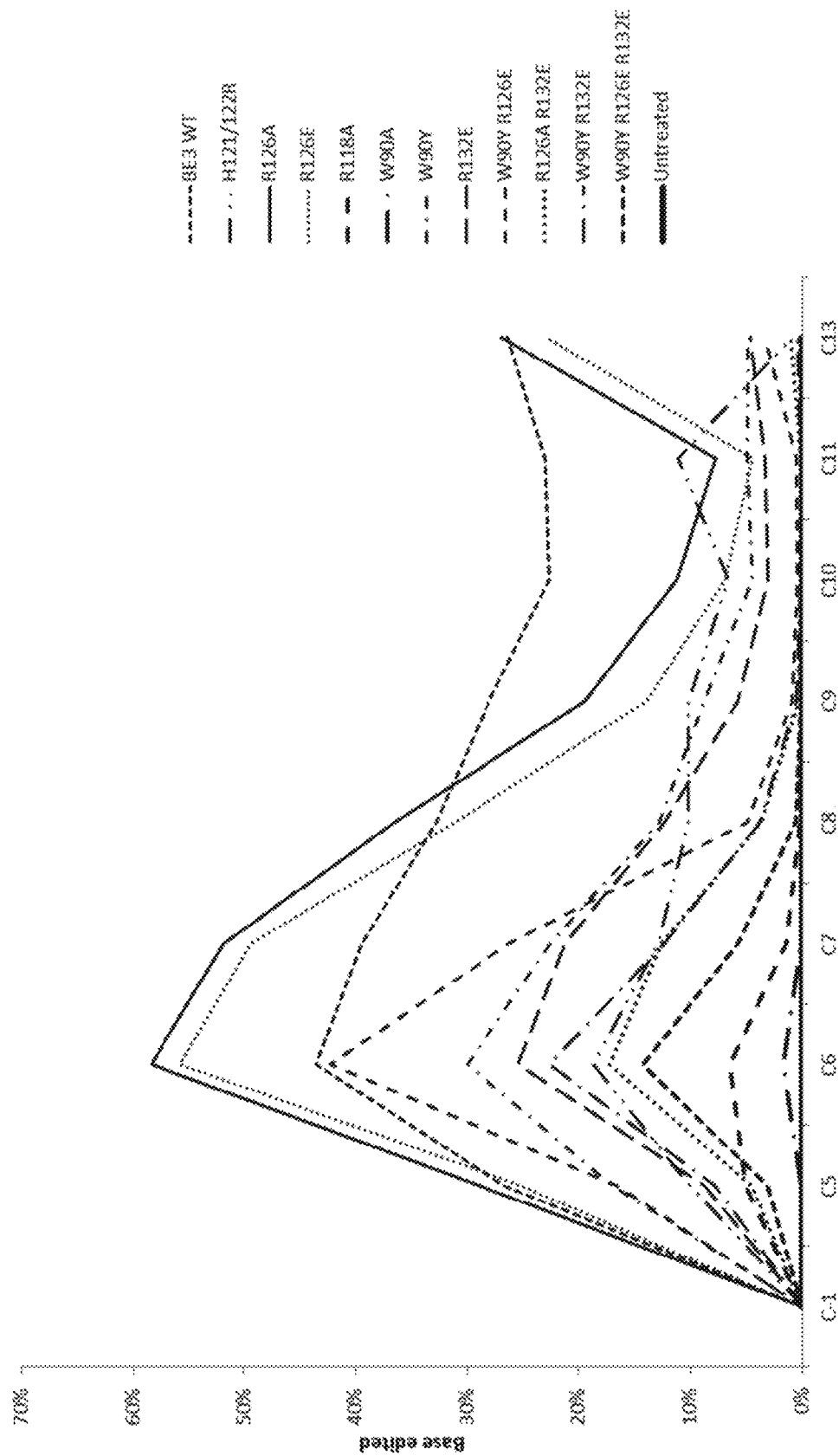

FIG. 67 is a graph showing the effect of various mutations on the deamination window probed in cell culture with multiple cytidines in the spacer. The spacer used was: AGAGC5C$_6$C$_7$C$_8$C$_9$C$_{10}$C$_{11}$TC$_{13}$AAAGAGA (SEQ ID NO: 309).

Figure 68:
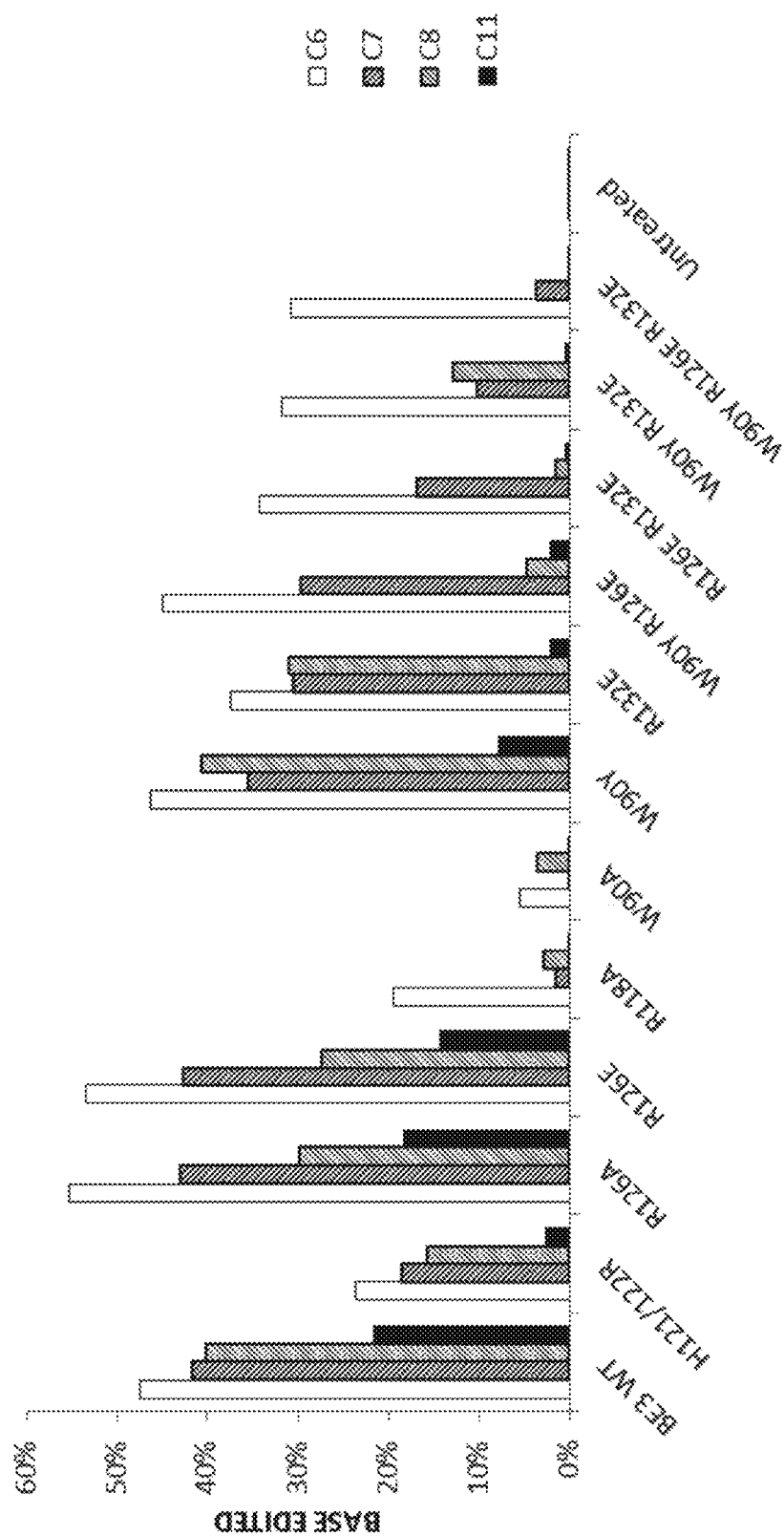

FIG. 68 is a graph showing the effect of various mutations on the FANCF site with a limited number of cytidines. The spacer used was: GGAATC$_6$C$_7$C$_8$TTC$_{11}$TGCAGCA-CCTGG (SEQ ID NO: 303). Note that the triple mutant (W90Y, R126E, R132E) preferentially edits the cytidine at the sixth position.

Figure 69:
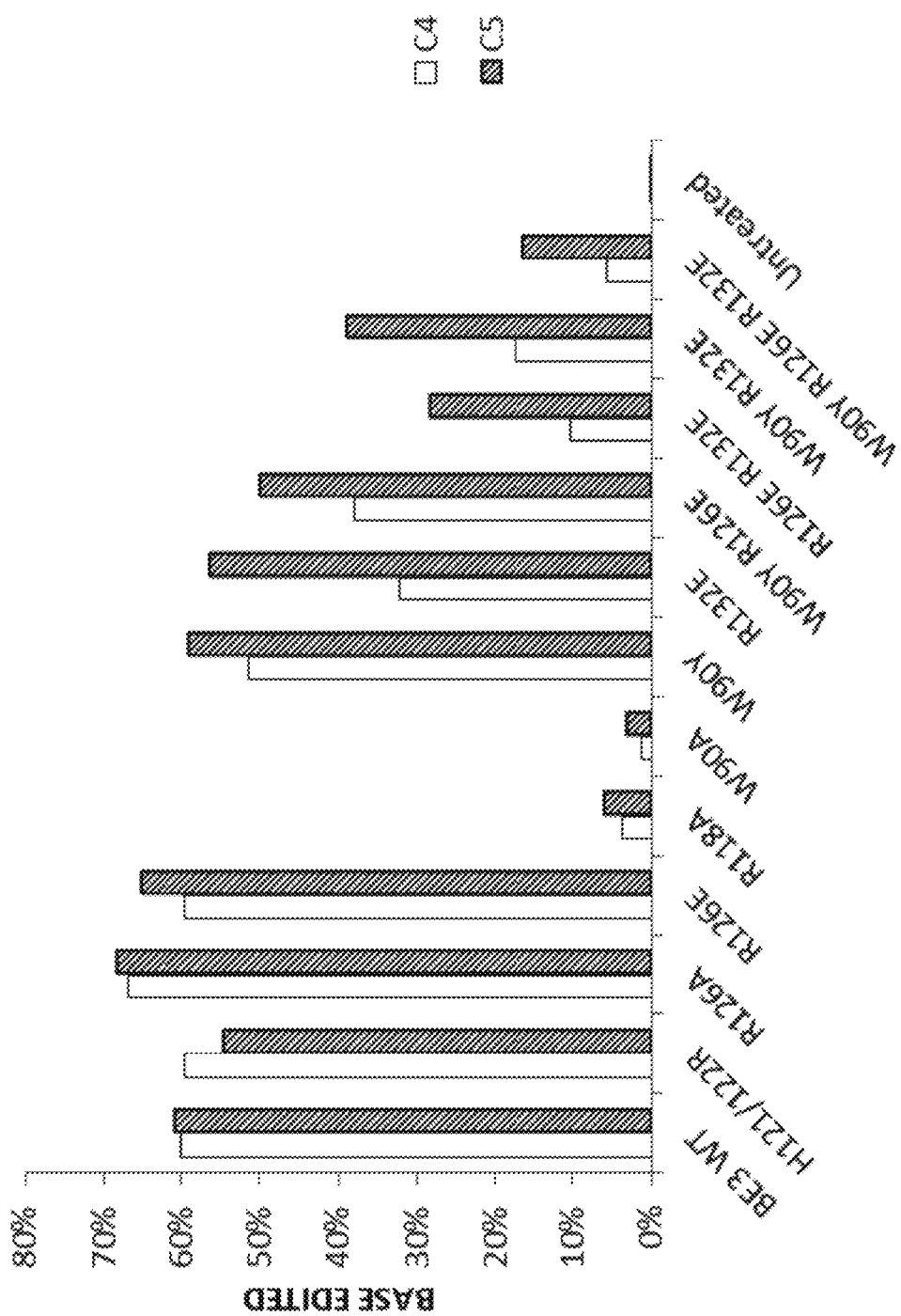

FIG. 69 is a graph showing the effect of various mutations on the HEK3 site with a limited number of cytidines. The spacer used was: GGCC$_4$C$_5$AGACTGAGCACGTGATGG (SEQ ID NO: 310). Note that the double and triple mutants preferentially edit the cytidine at the fifth position over the cytidine in the fourth position.

Figure 70:
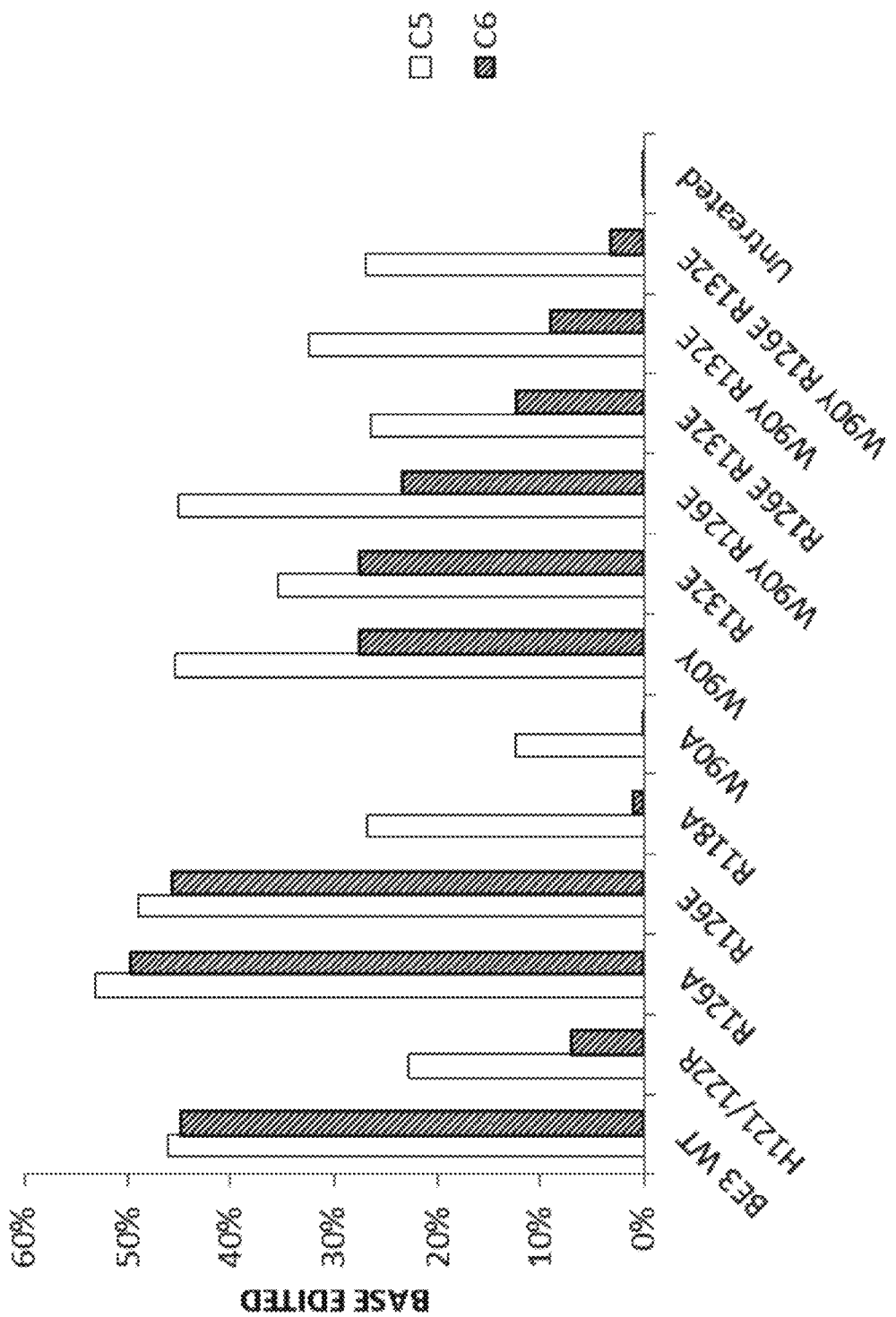

FIG. 70 is a graph showing the effect of various mutations on the EMX1 site with a limited number of cytidines. The spacer used was: GAGTC$_5$C$_6$GAGCAGAAGAAGAAGGG (SEQ ID NO: 311). Note that the triple mutant only edits the cytidine at the fifth position, not the sixth.

Figure 71:
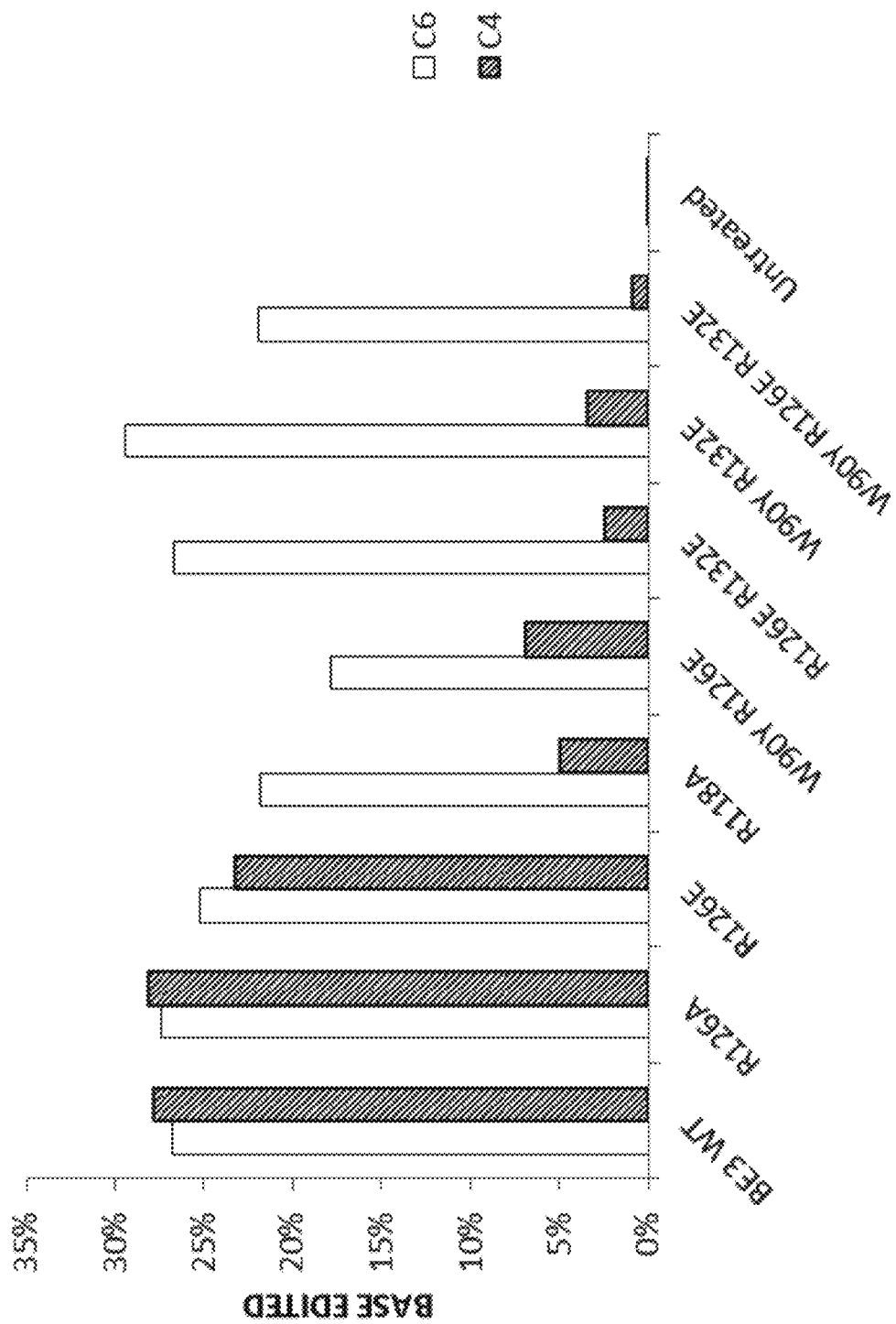

FIG. 71 is a graph showing the effect of various mutations on the HEK2 site with a limited number of cytidines. The spacer used was: GAAC$_4$AC$_6$AAAGCATAGACTGCGGG (SEQ ID NO: 312).

Figure 72:
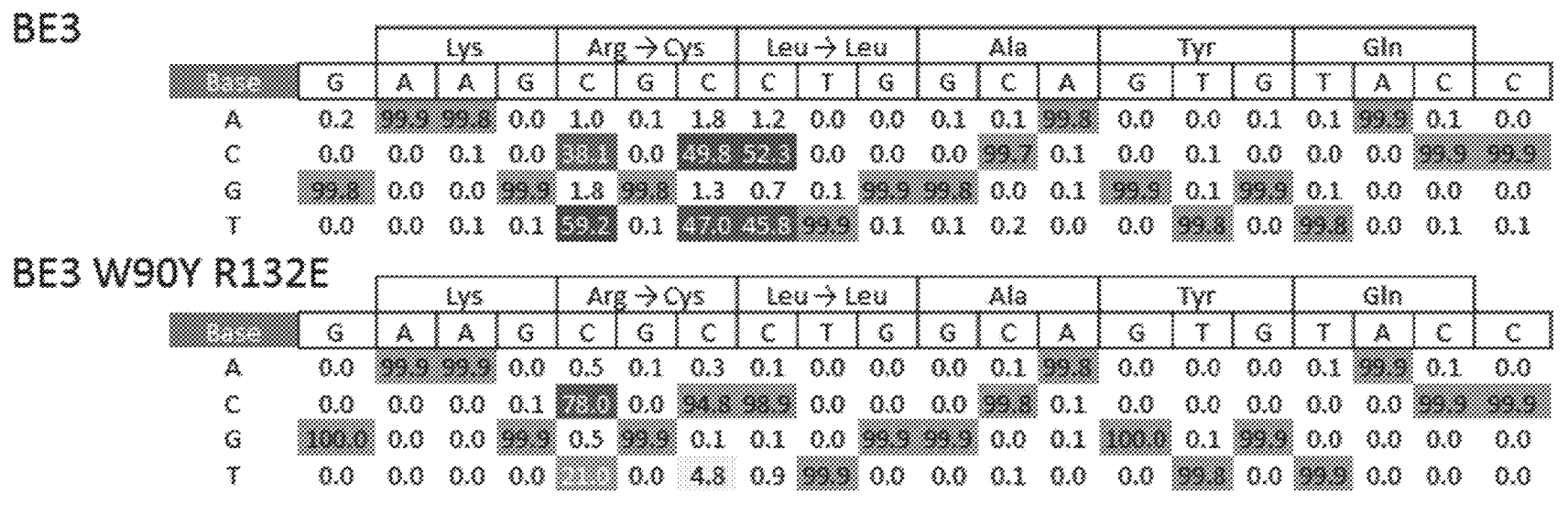

FIG. 72 shows on-target base editing efficiencies of BE3 and BE3 comprising mutations W90Y R132E in immortalized astrocytes.

Figure 73:
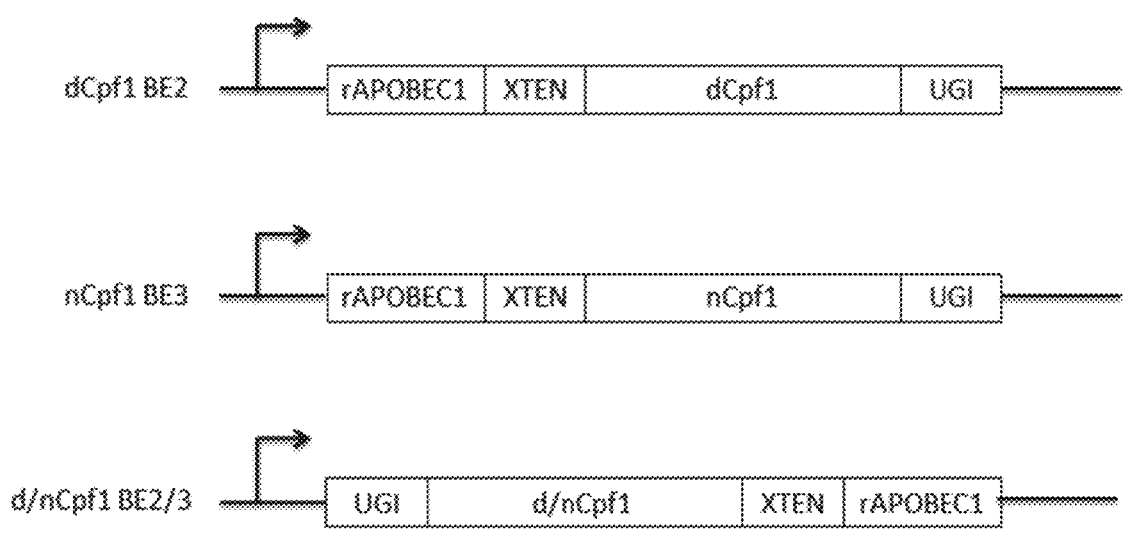

FIG. 73 depicts a schematic of three Cpf1 fusion constructs.

Figure 74:
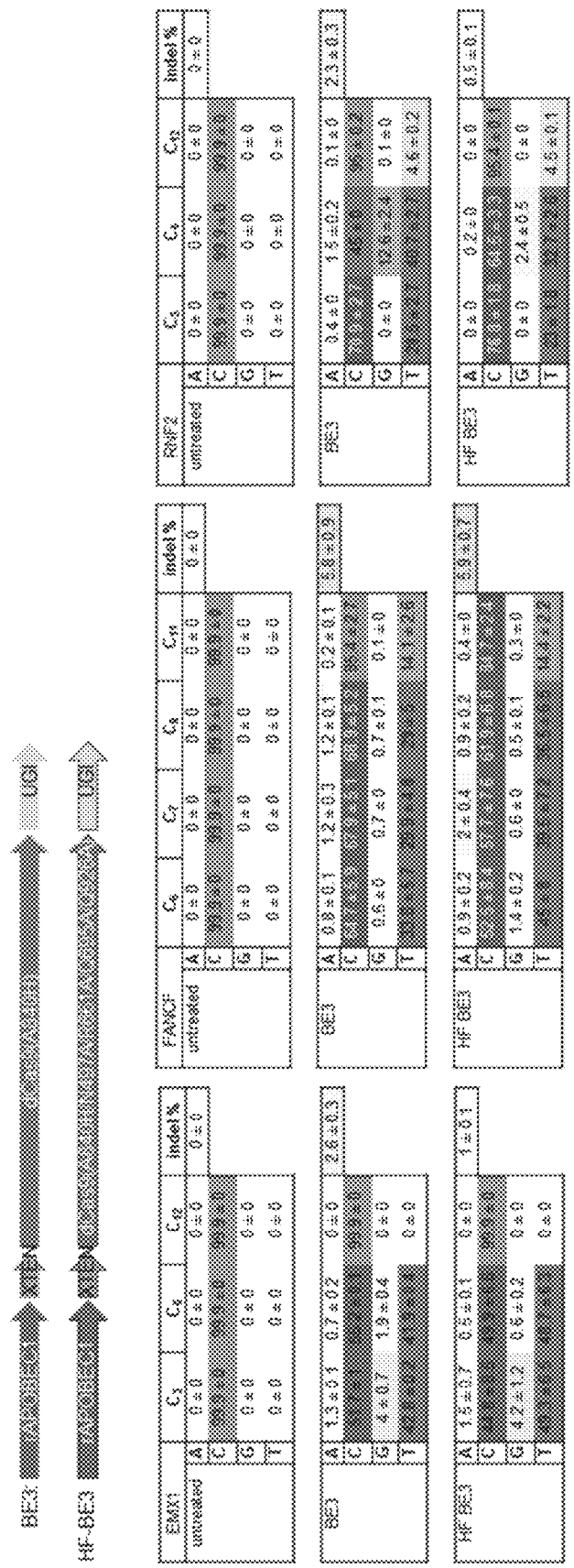

FIG. 74 shows a comparison of plasmid delivery of BE3 and HF-BE3 (EMX1, FANCF, and RNF2).

Figure 75:
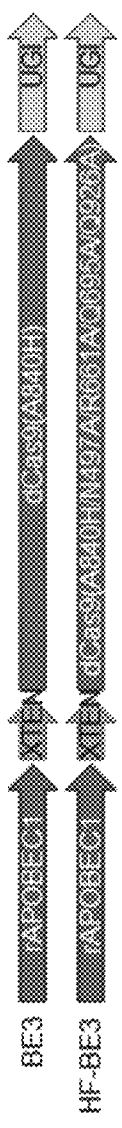

FIG. 75 shows a comparison of plasmid delivery of BE3 and HF-BE3 (HEK3 and HEK 4).

Figure 76:
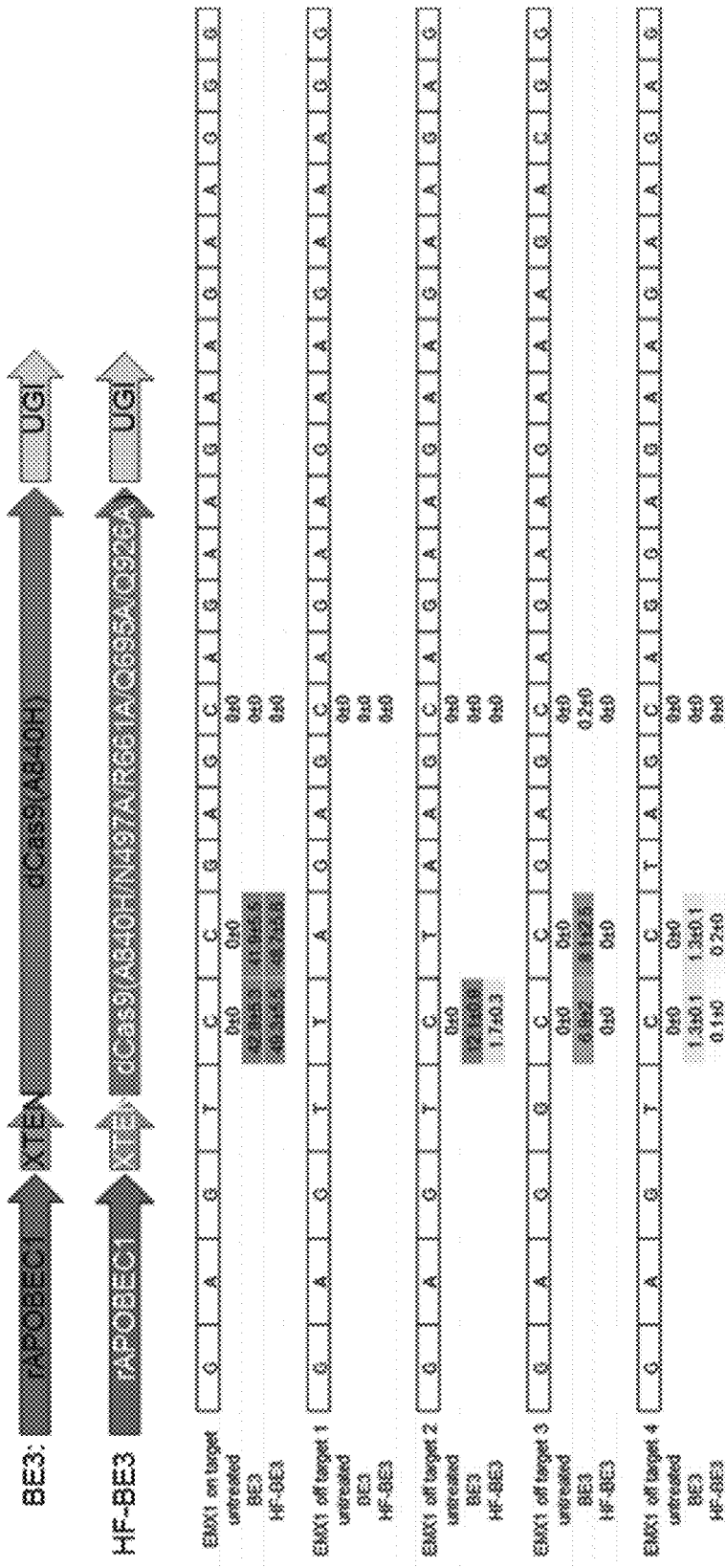
Figure 76:
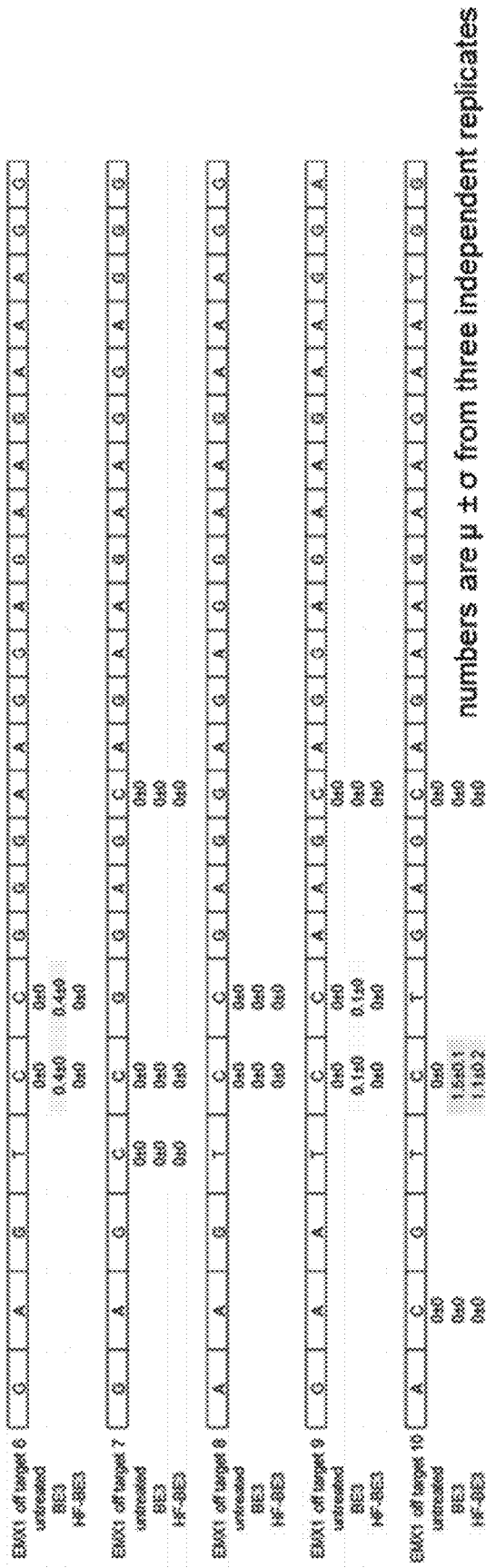

FIG. 76 shows off-target editing of EMX-1 at all 10 sites.

Figure 77:
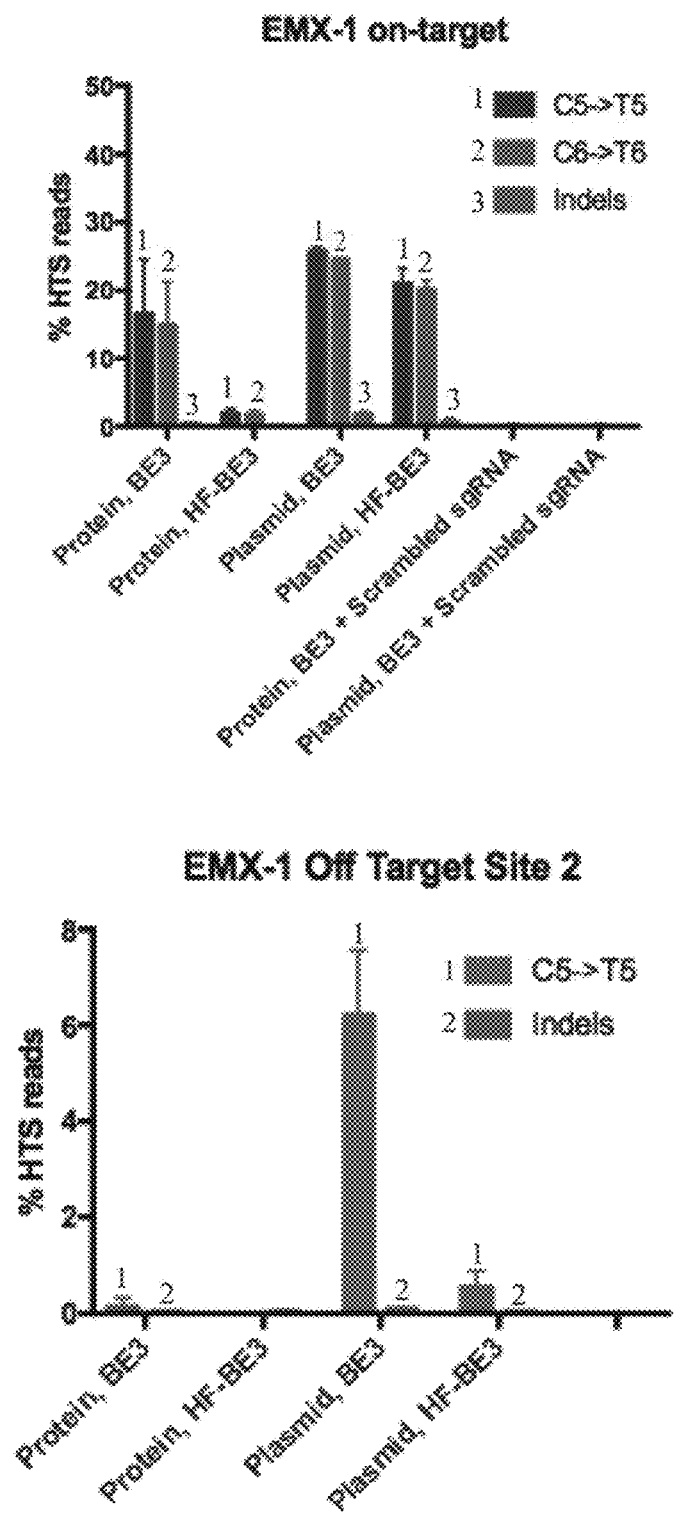

FIG. 77 shows deaminase protein lipofection to HEK cells using a GAGTCCGAGCAGAAGAAGAAG (SEQ ID NO: 313) spacer. The EMX-1 on-target and EMX-1 off target site 2 were examined.

FIG. 78 shows deaminase protein lipofection to HEK cells using a GGAATCCCTTCTGCAGCACCTGG (SEQ ID NO: 314) spacer. The FANCF on target and FANCF off target site 1 were examined.

Figure 79:
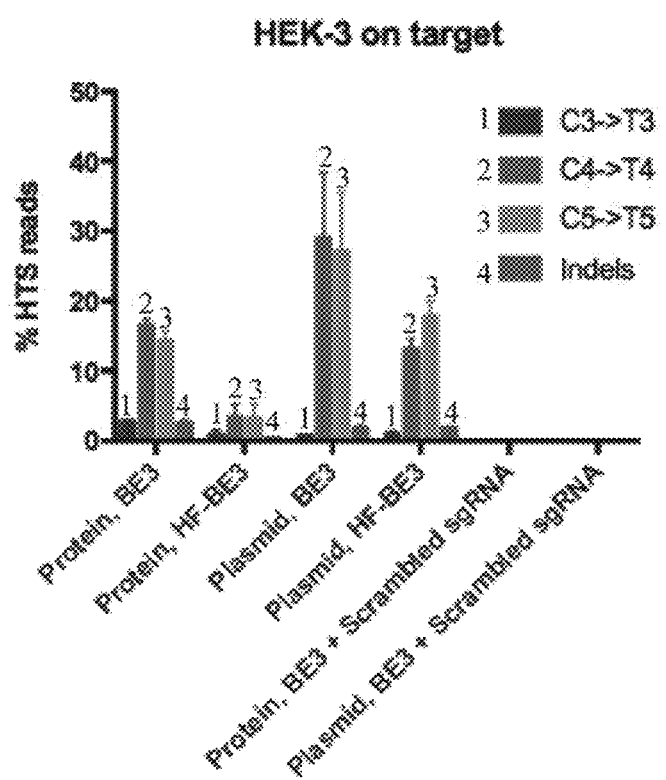

FIG. 79 shows deaminase protein lipofection to HEK cells using a GGCCCAGACTGAGCACGTGA (SEQ ID NO: 315) spacer. The HEK-3 on target site was examined.

Figure 80:
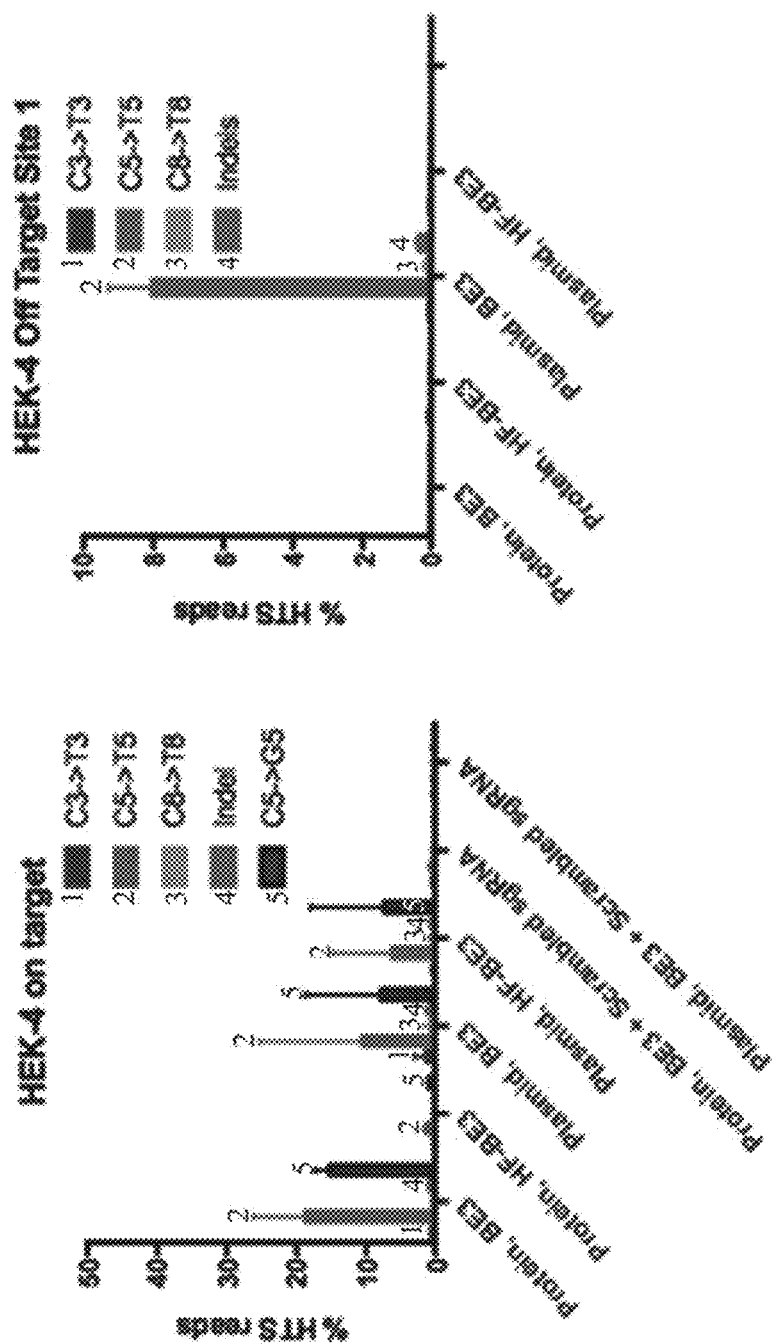
Figure 80:
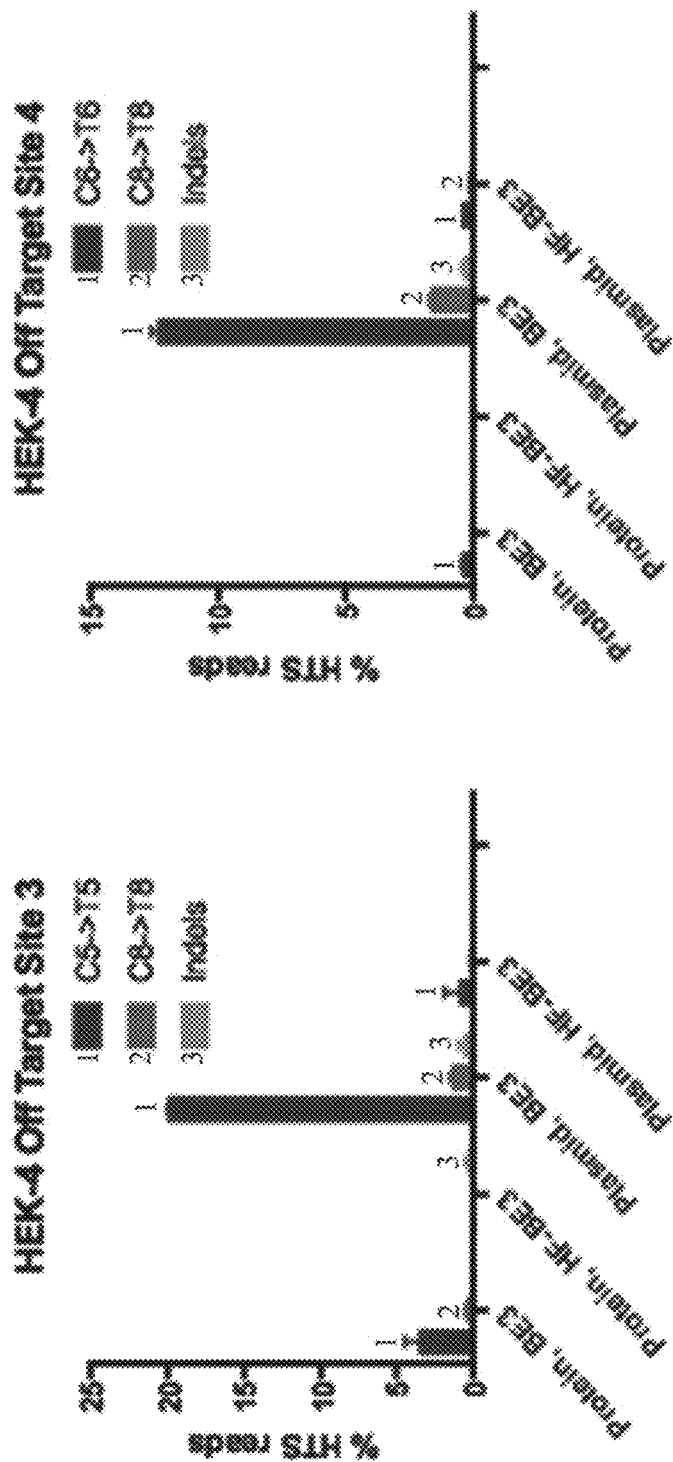

FIG. 80 shows deaminase protein lipofection to HEK cells using a GGCACTGCGGCTGGAGGTGGGGG (SEQ ID NO: 316) spacer. The HEK-4 on target, off target site 1, site 3, and site 4.

Figure 81:
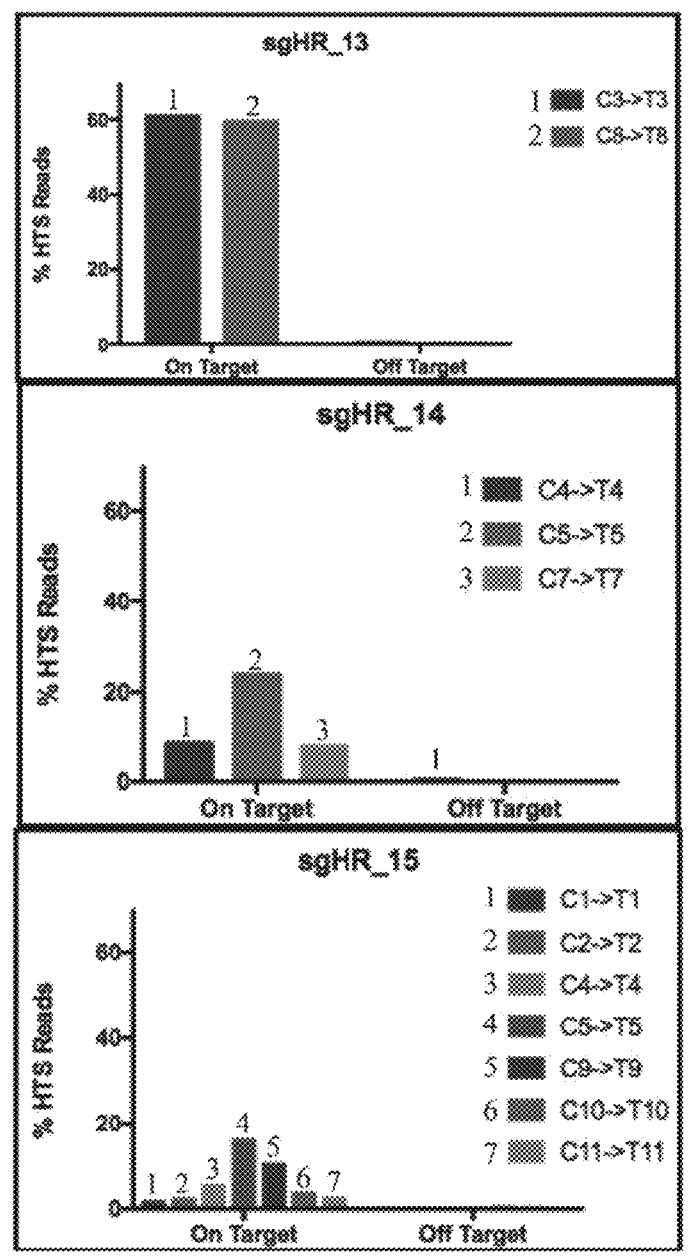

FIG. 81 shows the results of an in vitro assay for sgRNA activity for sgHR_13 (GTCAGGTCGAGGGTTCTGTC (SEQ ID NO: 317) spacer; C8 target: G51 to STOP), sgHR_14 (GGGCCGCAGTATCCTCACTC (SEQ ID NO: 318) spacer; C7 target; C7 target: Q68 to STOP), and sgHR_15 (CCGCCAGTCCCAGTACGGGA (SEQ ID NO: 319) spacer; C10 and C11 are targets: W239 or W237 to STOP).

Figure 82:
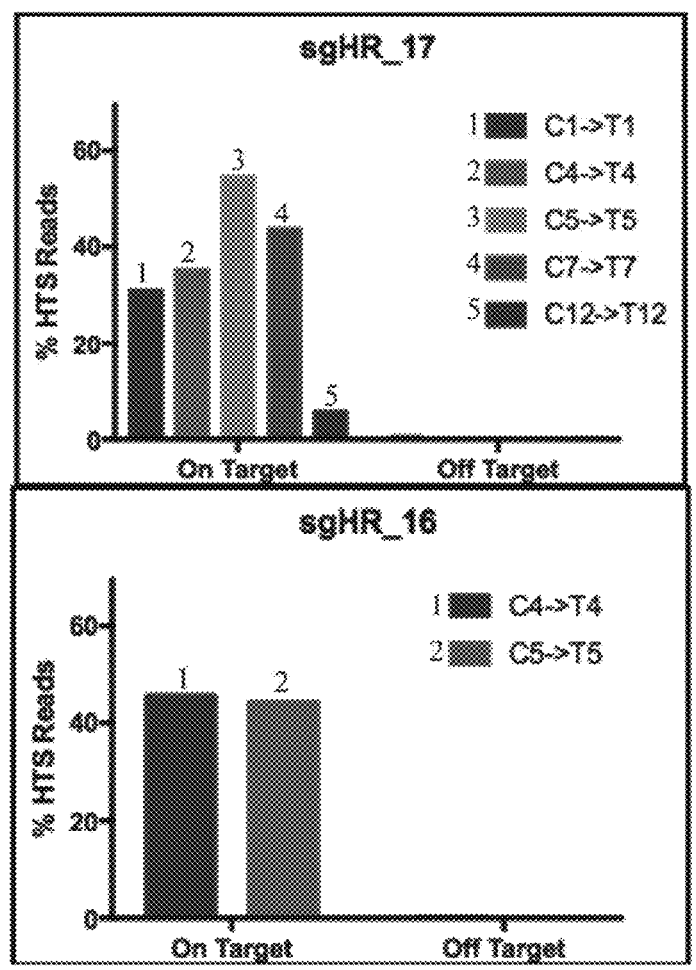

FIG. 82 shows the results of an in vitro assay for sgHR_17 (CAACCACTGCTCAAAGATGC (SEQ ID NO: 320) spacer; C4 and C5 are targets: W410 to STOP), and sgHR_16 (CTTCCAGGATGAGAACACAG (SEQ ID NO: 321) spacer; C4 and C5 are targets: W273 to STOP).

Figure 83:
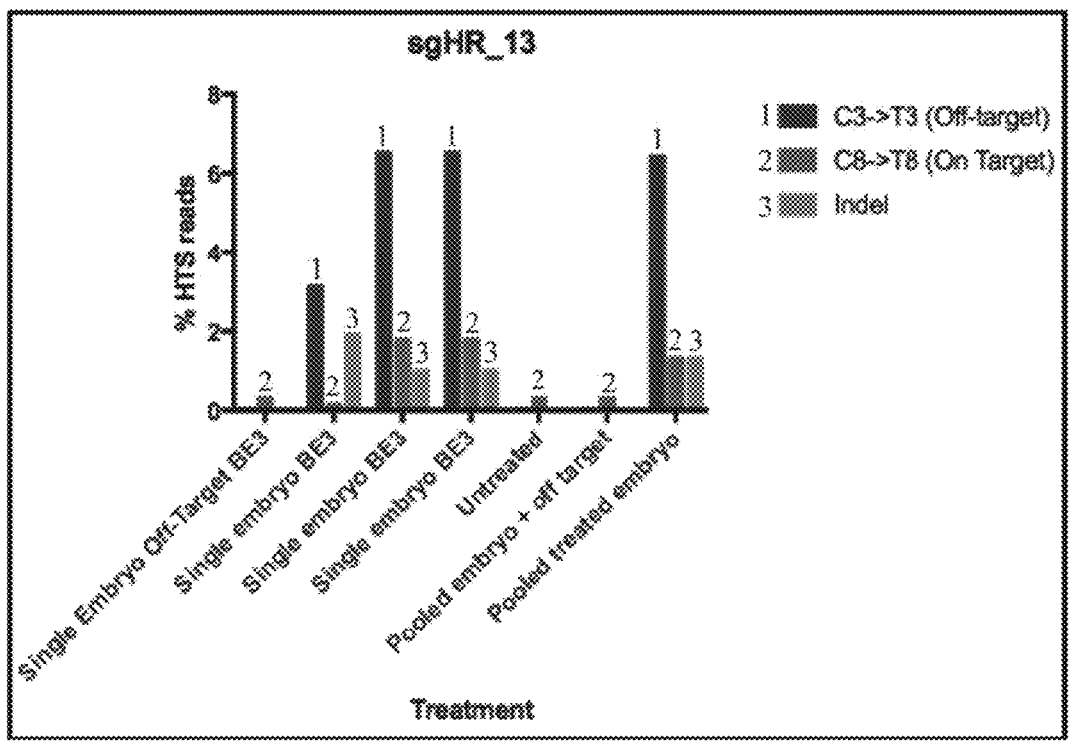

FIG. 83 shows the direct injection of BE3 protein complexed with sgHR_13 in zebrafish embryos.

Figure 84:
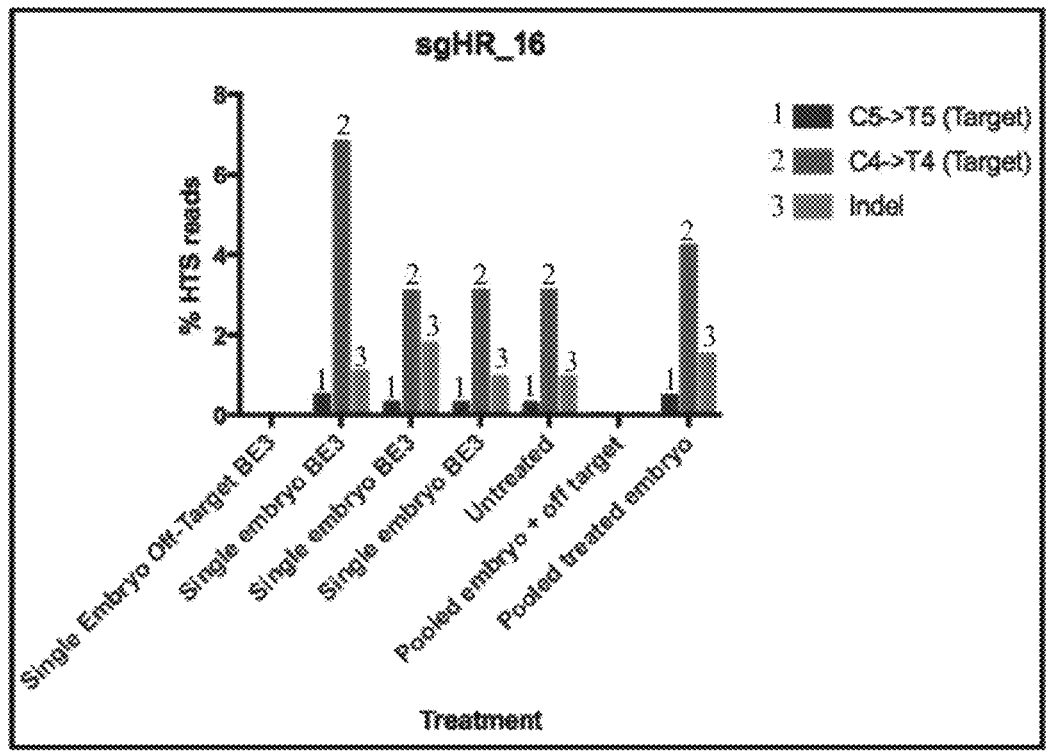

FIG. 84 shows the direct injection of BE3 protein complexed with sgHR_16 in zebrafish embryos.

Figure 85:
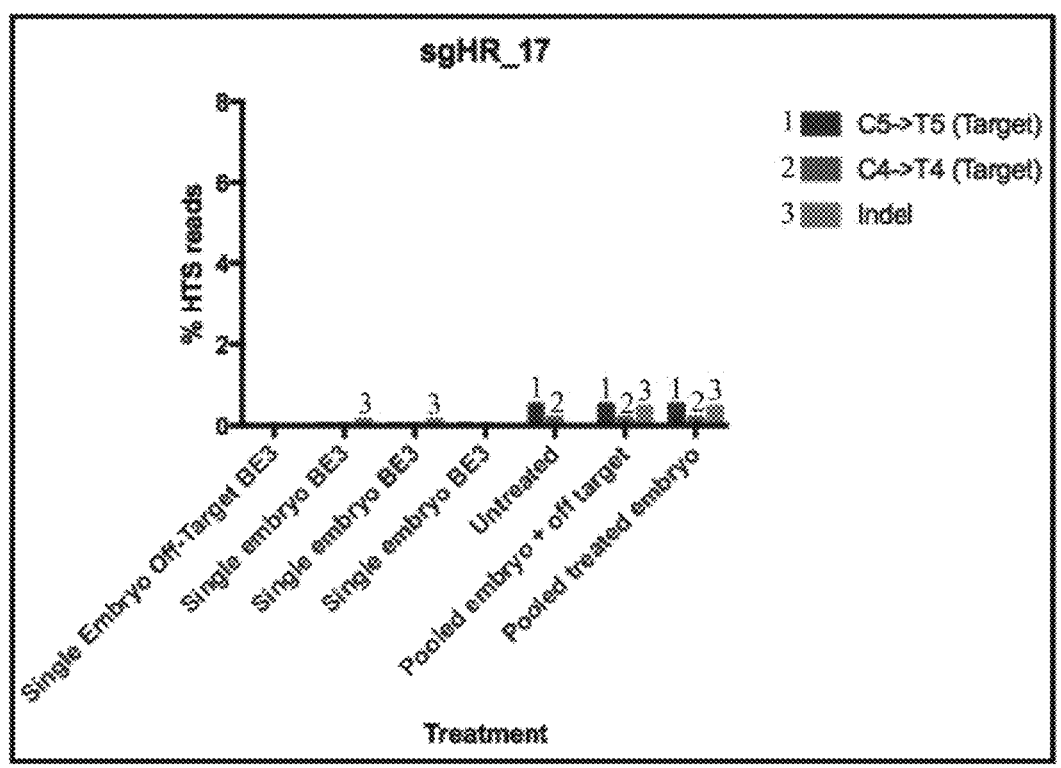

FIG. 85 shows the direct injection of BE3 protein complexed with sgHR_17 in zebrafish embryos.

Figure 86:
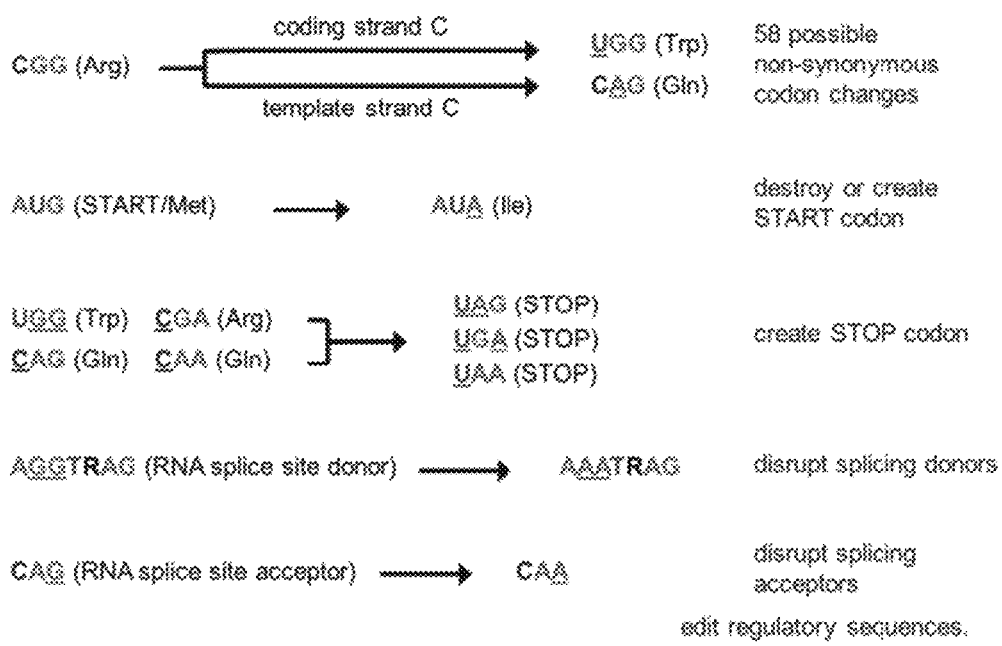

FIG. 86 shows exemplary nucleic acid changes that may be made using base editors that are capable of making a cytosine to thymine change.

Figure 87:
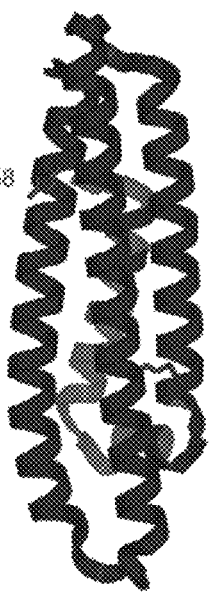

FIG. 87 shows an illustration of apolipoprotein E (APOE) isoforms, demonstrating how a base editor (e.g., BE3) may be used to edit one APOE isoform (e.g., APOE4) into another APOE isoform (e.g., APOE3r) that is associated with a decreased risk of Alzheimer's disease.

Figure 88:
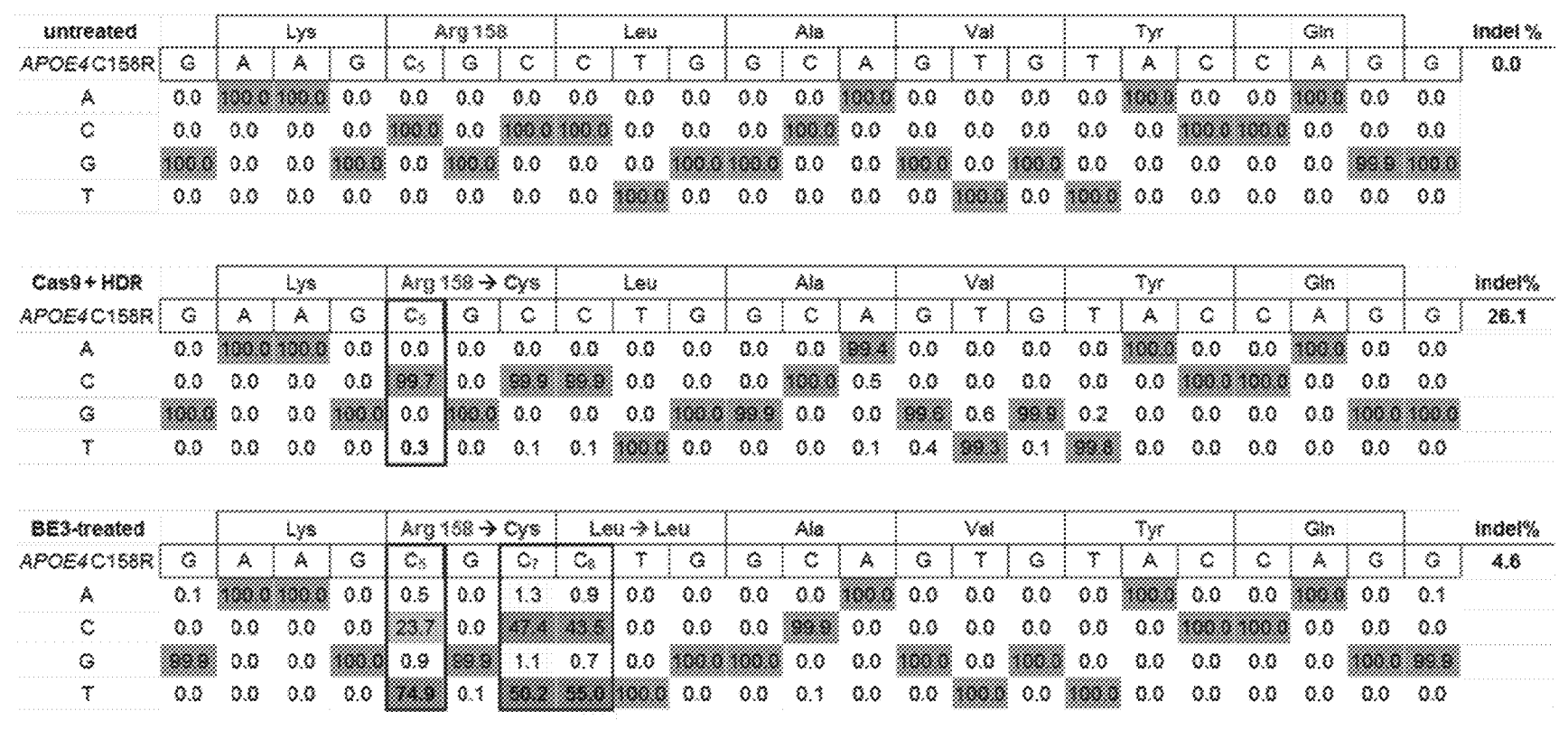

FIG. 88 shows base editing of APOE4 to APOE3r in mouse astrocytes.

Figure 89:
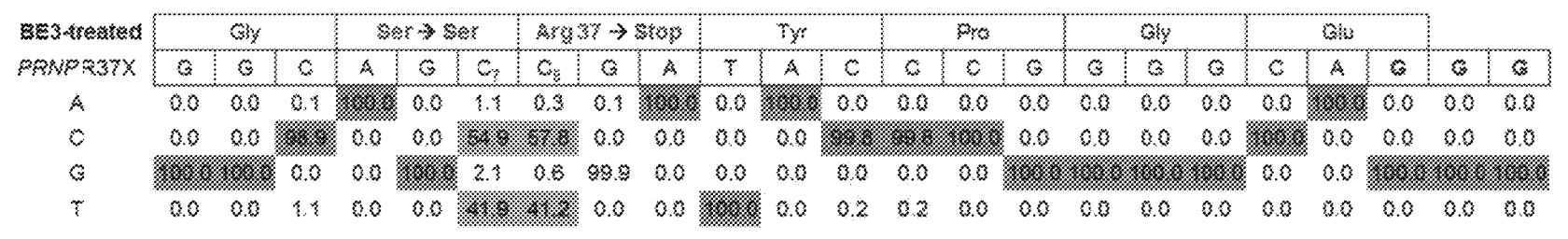

FIG. 89 shows base editing of PRNP to cause early truncation of the protein at arginine residue 37.

Figure 90:
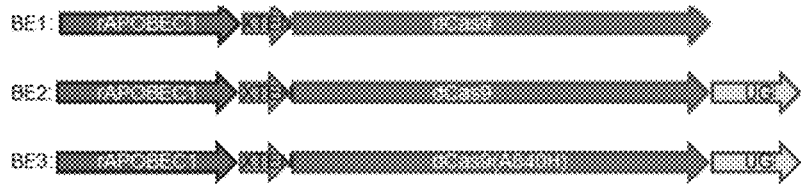

FIG. 90 shows that knocking out UDG (which UGI inhibits) dramatically improves the cleanliness of efficiency of C to T base editing.

FIG. 91 shows that use of a base editor with the nickase but without UGI leads to a mixture of outcomes, with very high indel rates.

Figures 92A, 92B:
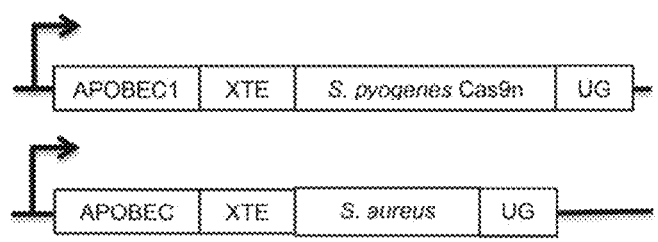
Figure 92C:
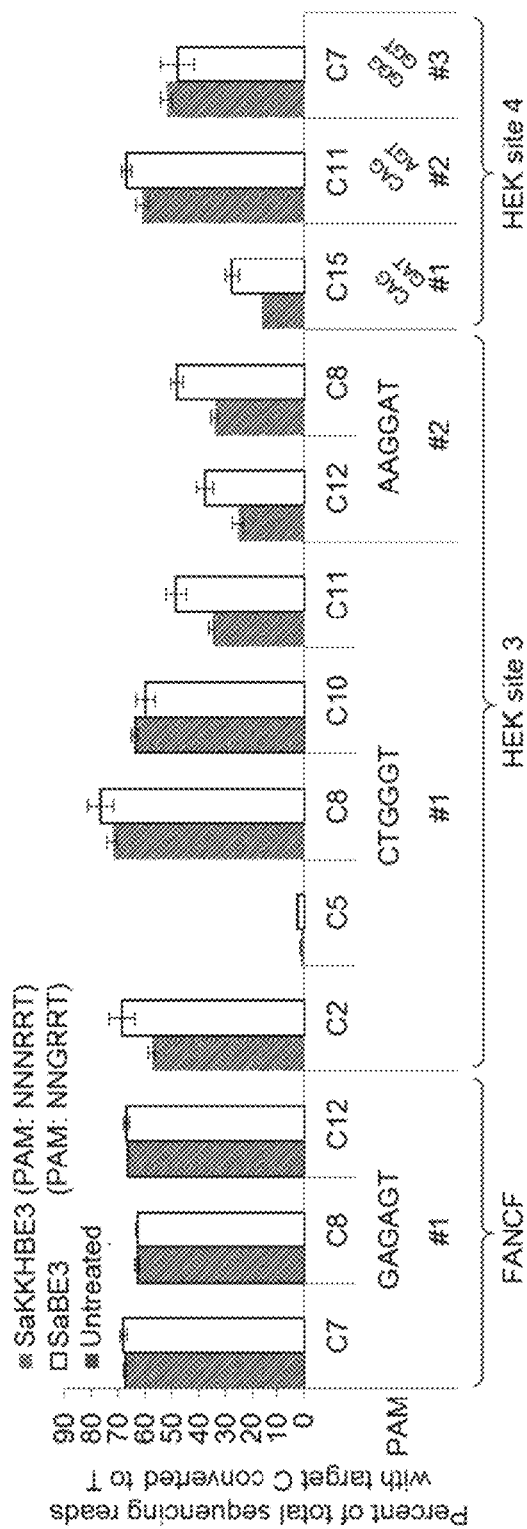
Figure 92D:
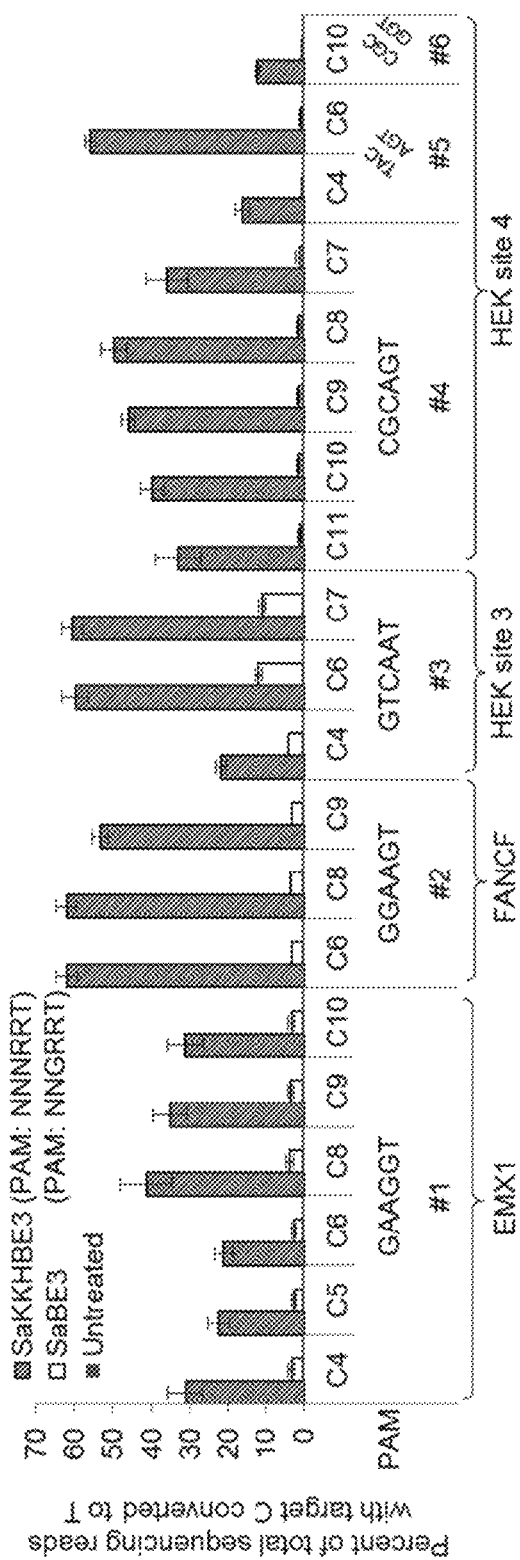
Figure 92E:
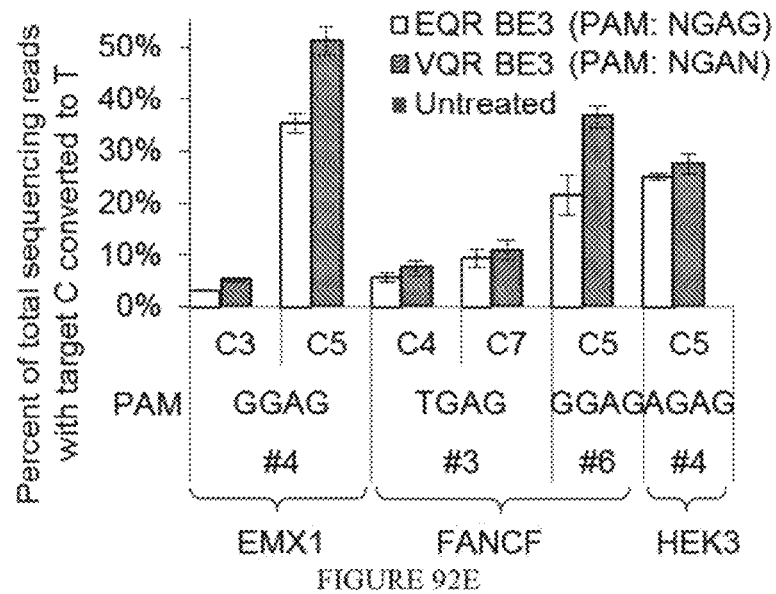
Figure 92F:
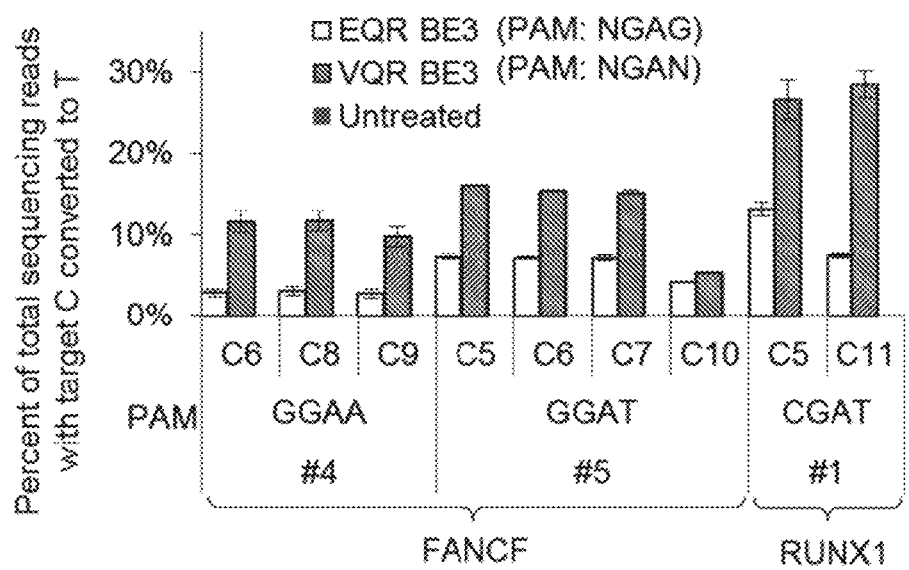
Figure 92G:
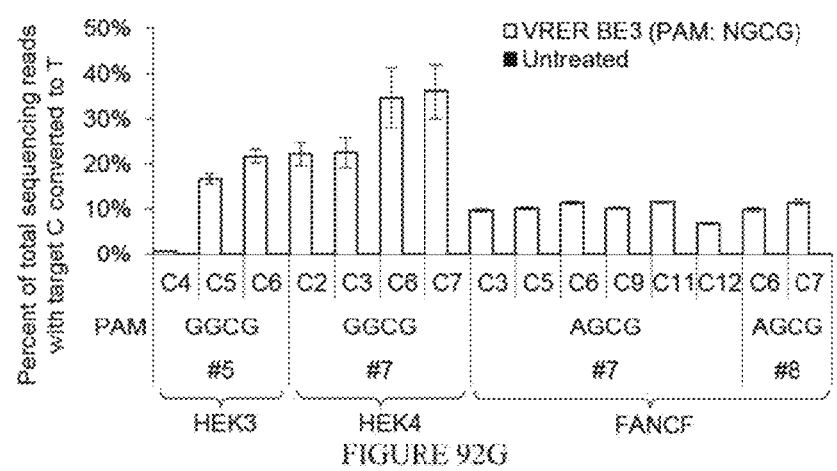

FIGS. 92A to 92G show that SaBE3, SaKKH-BE3, VQR-BE3, EQR-BE3, and VRER-BE3 mediate efficient base editing at target sites containing non-NGG PAMs in human cells. FIG. 92A shows base editor architectures using *S. pyogenes* and *S. aureus* Cas9. FIG. 92B shows recently characterized Cas9 variants with alternate or relaxed PAM requirements. FIGS. 92C and 92D show HEK293T cells treated with the base editor variants shown as described in Example 12. The percentage of total DNA sequencing reads (with no enrichment for transfected cells) with C converted to T at the target positions indicated are shown. The PAM sequence of each target tested is shown below the X-axis. The charts show the results for SaBE3 and SaKKH-BE3 at genomic loci with NNGRRT PAMs (FIG. 92C), SaBE3 and SaKKH-BE3 at genomic loci with NNNRRT PAMs (FIG. 92D), VQR-BE3 and EQR-BE3 at genomic loci with NGAG PAMs (FIG. 92E), and with NGAH PAMs (FIG. 92F), and VRER-BE3 at genomic loci with NGCG PAMs (FIG. 92G). Values and error bars reflect the mean and standard deviation of at least two biological replicates.

Figure 93A:
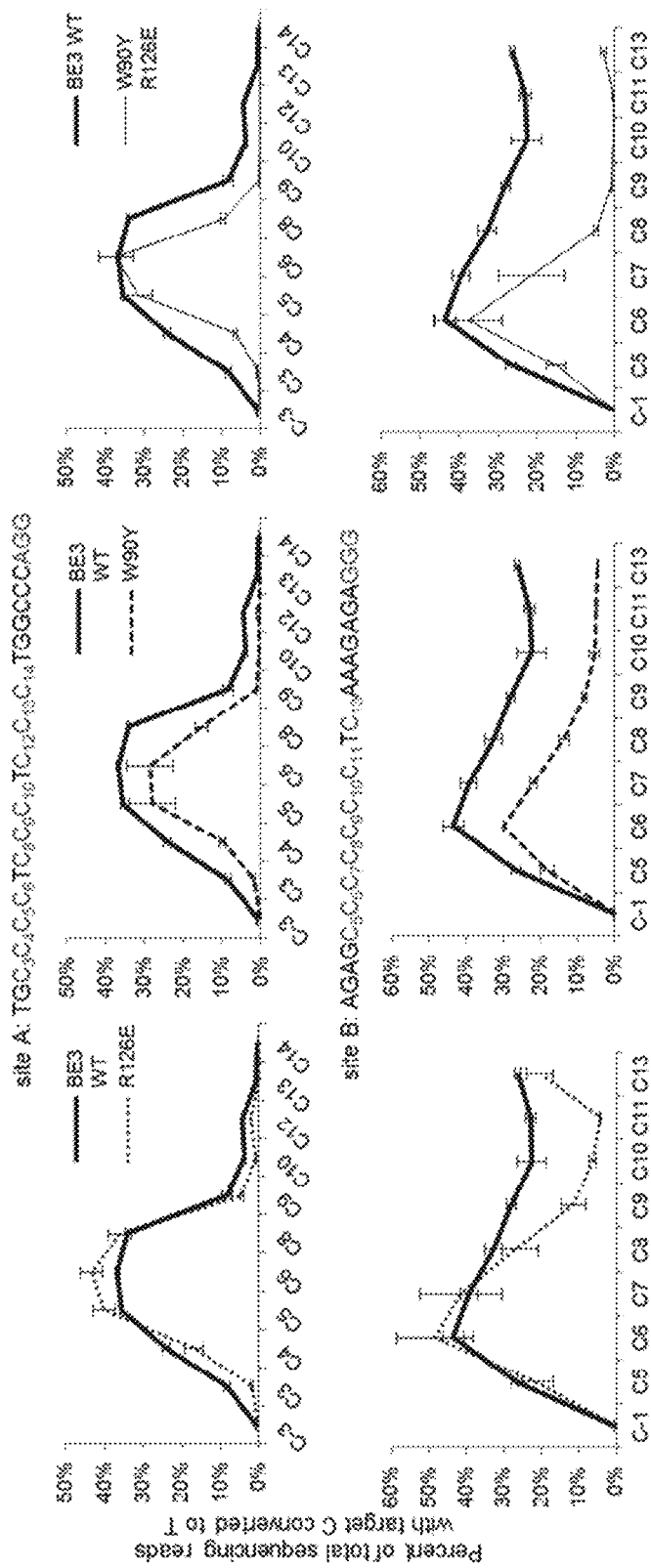
Figure 93B:
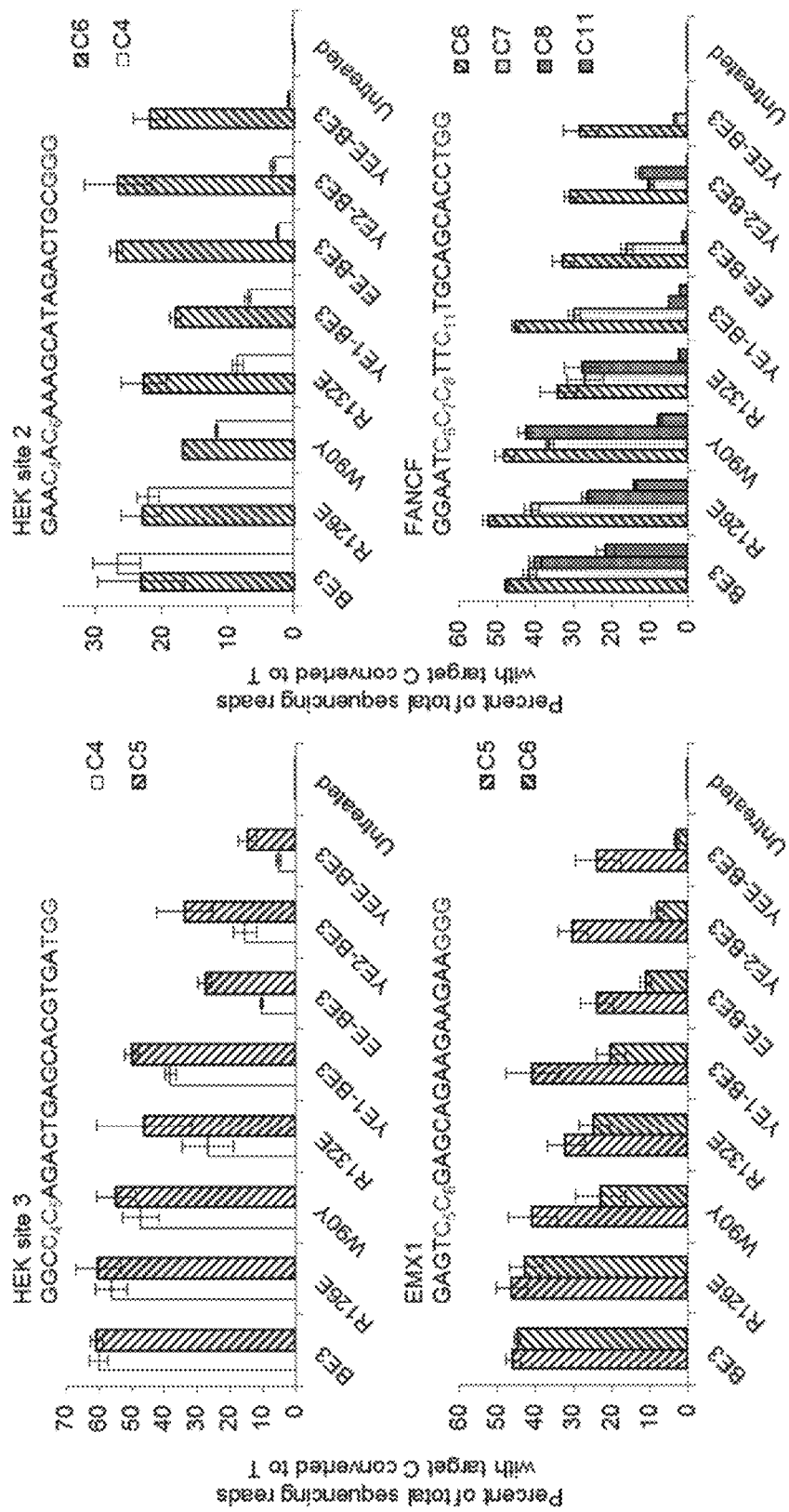
Figure 93C:
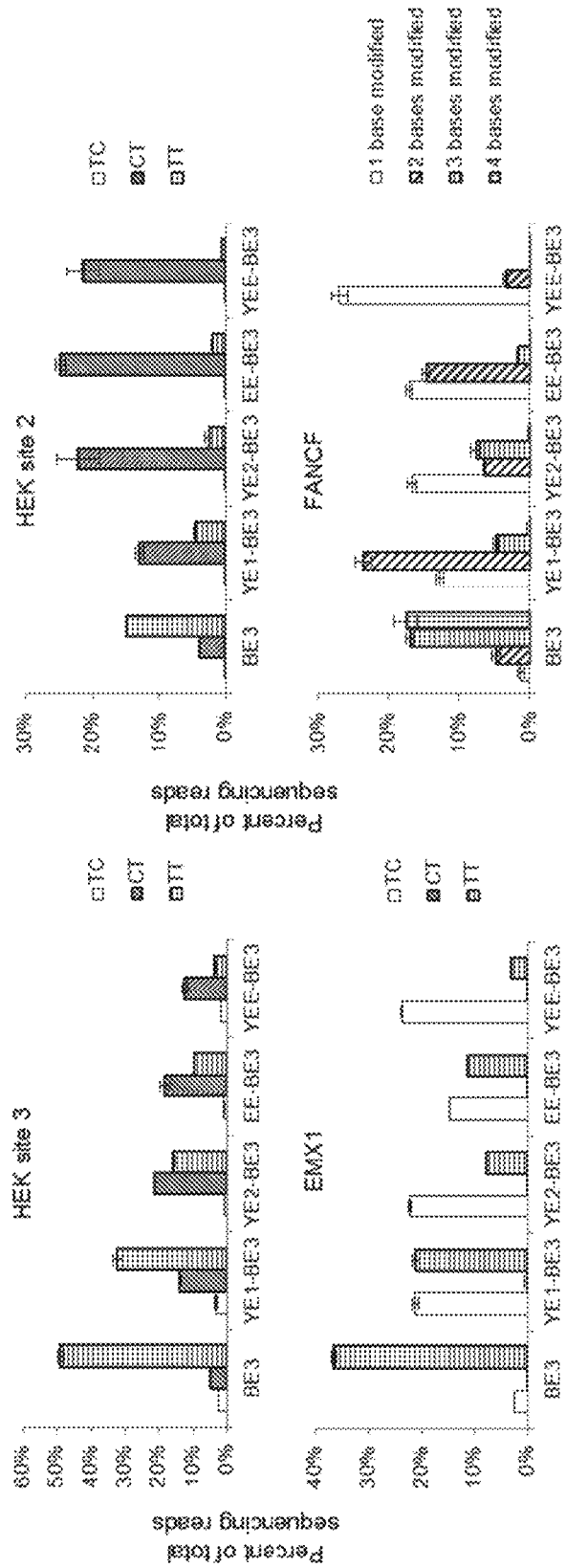

FIGS. 93A to 93C demonstrate that base editors with mutations in the cytidine deaminase domain exhibit narrowed editing windows. FIGS. 93A to 93C show HEK293T cells transfected with plasmids expressing mutant base editors and an appropriate sgRNA. Three days after transfection, genomic DNA was extracted and analyzed by high-throughput DNA sequencing at the indicated loci. The percentage of total DNA sequencing reads (without enrichment for transfected cells) with C changed to T at the target positions indicated are shown for the EMX1 site, HEK293 site 3, FANCF site, HEK293 site 2, site A, and site B loci. FIG. 93A illustrates certain cytidine deaminase mutations which narrow the base editing window. See FIG. 98 for the characterization of additional mutations. FIG. 93B shows the effect of cytidine deaminase mutations which effect the editing window width on genomic loci. Combining beneficial mutations has an additive effect on narrowing the editing window. FIG. 93C shows that YE1-BE3, YE2-BE3, EE-BE3, and YEE-BE3 effect the product distribution of base editing, producing predominantly singly-modified products in contrast with BE3. Values and error bars reflect the mean and standard deviation of at least two biological replicates.

Figure 94A:
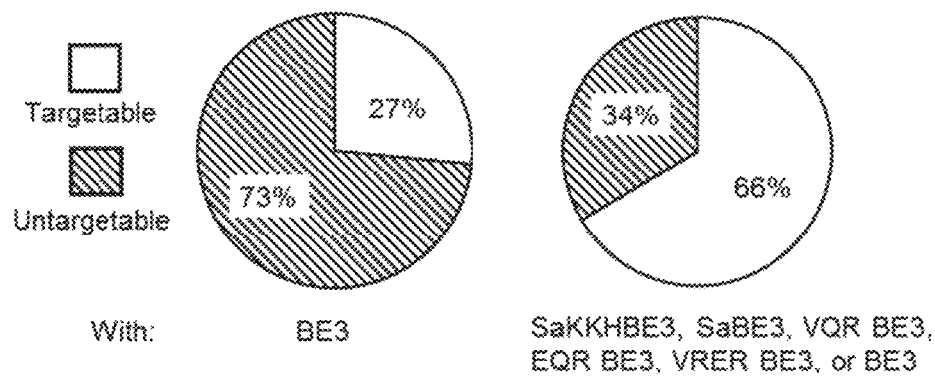
Figure 94B:
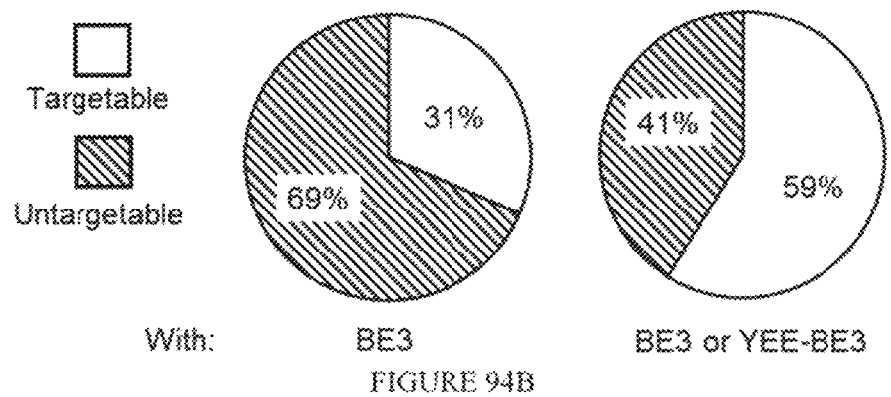

FIGS. 94A and 94B show genetic variants from ClinVar that in principle can be corrected by the base editors developed in this work. The NCBI ClinVar database of human genetic variations and their corresponding phenotypes was searched for genetic diseases that in theory can be corrected by base editing. FIG. 94A demonstrates improvement in base editing targeting scope among all pathogenic T→C mutations in the ClinVar database through the use of base editors with altered PAM specificities. The white fractions denote the proportion of pathogenic T→C mutations accessible on the basis of the PAM requirements of either BE3, or BE3 together with the five modified-PAM base editors developed in this work. FIG. 94B shows improvement in base editing targeting scope among all pathogenic T→C mutations in the ClinVar database through the use of base editors with narrowed activity windows. BE3 was assumed to edit Cs in positions 4-8 with comparable efficiency as shown in FIGS. 93A to 93C. YEE-BE3 was assumed to edit with C5>C6>C7>others preference within its activity window. The white fractions denote the proportion of pathogenic T→C mutations that can be edited BE3 without comparable editing of other Cs (left), or that can be edited BE3 or YEE-BE3 without comparable editing of other Cs (right).

Figure 95A:
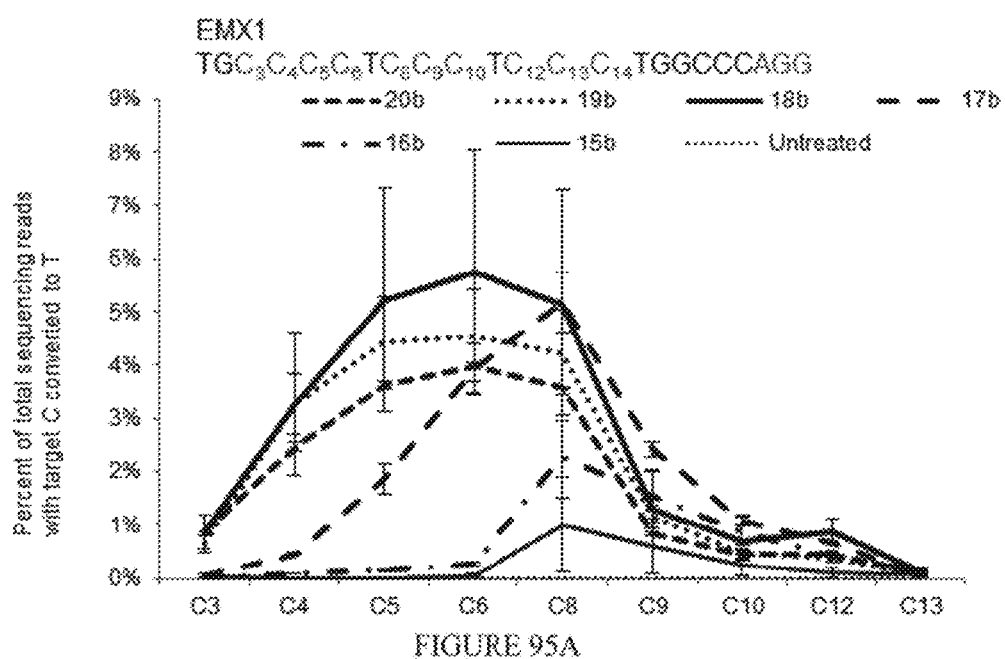
Figure 95B:
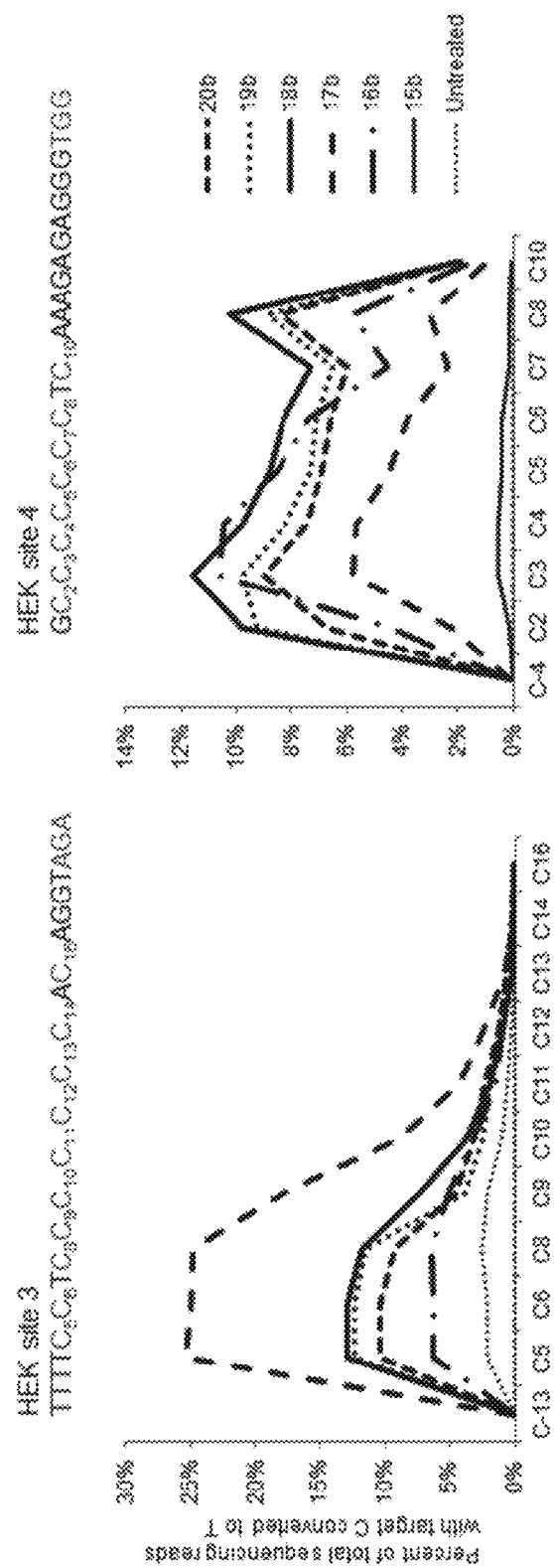

FIGS. 95A and 95B show the effect of truncated guide RNAs on base editing window width. HEK293T cells were transfected with plasmids expressing BE3 and sgRNAs of different 5' truncation lengths. The treated cells were analyzed as described in the Examples. FIG. 95A shows protospacer and PAM sequence (top, SEQ ID NO: 4270) and cellular C to T conversion percentages, defined as the percentage of total DNA sequencing reads with Ts at the target positions indicated, at a site within the EMX1 genomic locus. At this site, the base editing window was altered through the use of a 17-nt truncated gRNA. FIG. 95B shows protospacer and PAM sequences (top, SEQ ID NO: 4270) and cellular C to T conversion percentages, defined as the percentage of total DNA sequencing reads with Ts at the target positions indicated, at sites within the HEK site 3 and site 4 genomic loci. At these sites, no change in the base editing window was observed, but a linear decrease in editing efficiency for all substrate bases as the sgRNA is truncated was noted.

FIG. 96 shows the effect of APOBEC1-Cas9 linker lengths on base editing window width. HEK293T cells were transfected with plasmids expressing base editors with rAPOBEC1-Cas9 linkers of XTEN, GGS, (GGS)$_3$ (SEQ ID NO: 596), (GGS)$_5$(SEQ ID NO: 4271), or (GGS)$_7$ (SEQ ID NO: 597) and an sgRNA. The treated cells were analyzed as described in the Examples. Cellular C to T conversion percentages, defined as the percentage of total DNA sequencing reads with Ts at the target positions indicated, are shown for the various base editors with different linkers.

Figure 97C:
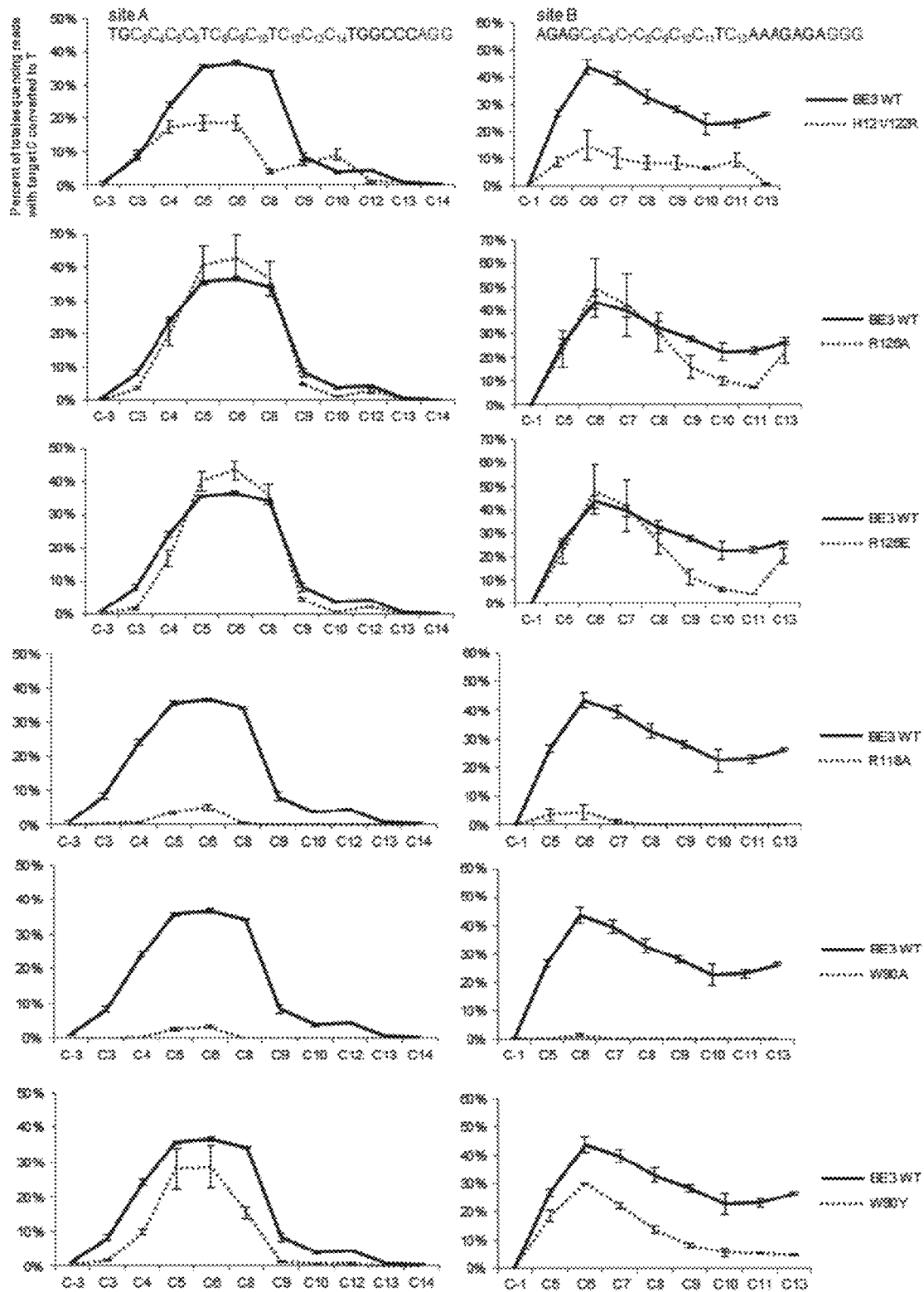
Figure 97C:
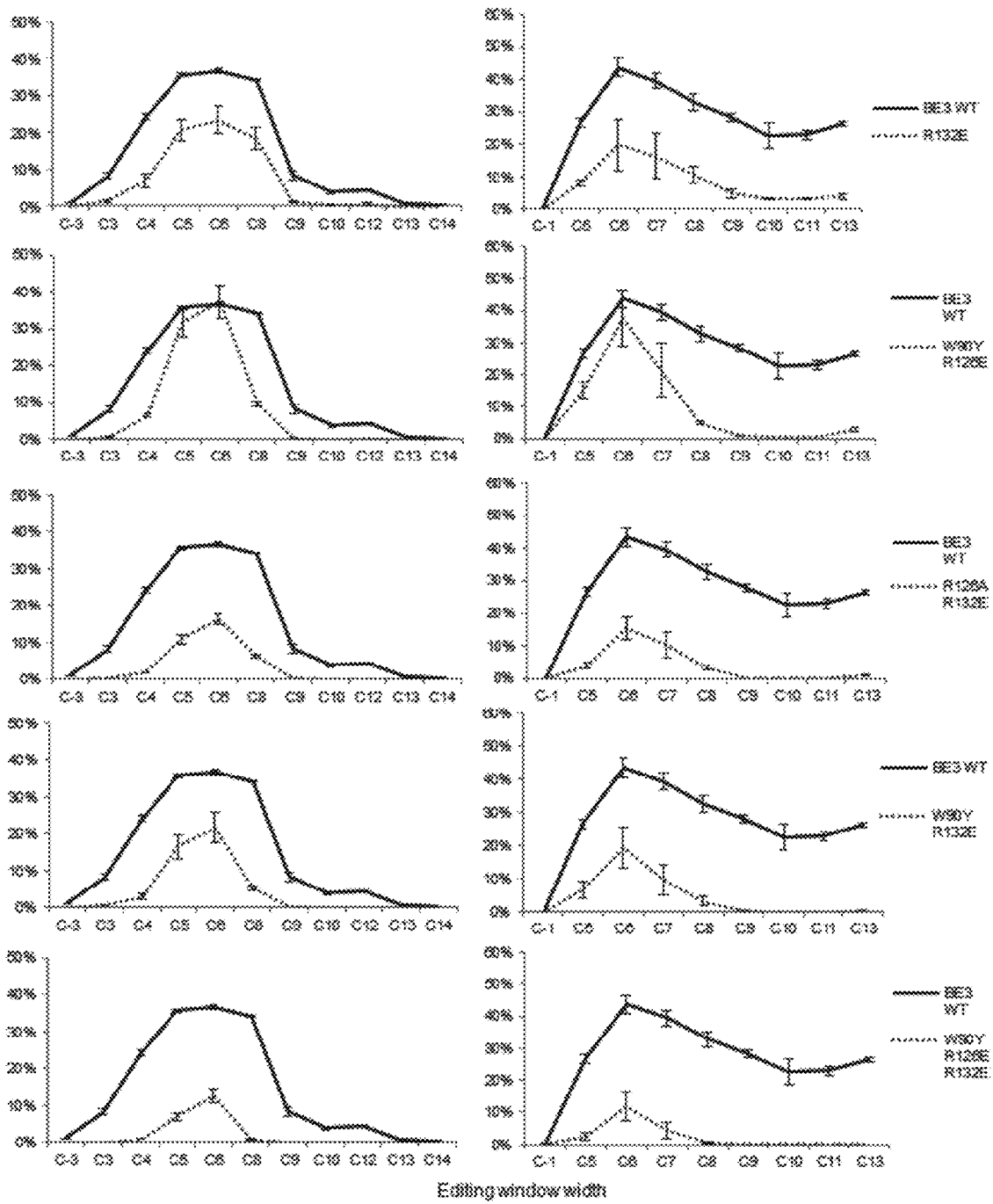

FIGS. 97A to 97C show the effect of rAPOBEC mutations on base editing window width. FIG. 97C shows HEK293T cells transfected with plasmids expressing an sgRNA targeting either Site A or Site B and the BE3 point mutants indicated. The treated cells were analyzed as described in the Examples. All C's in the protospacer and within three basepairs of the protospacer are displayed and the cellular C to T conversion percentages are shown. The 'editing window widths', defined as the calculated number of nucleotides within which editing efficiency exceeds the half-maximal value, are displayed for all tested mutants.

Figure 98:
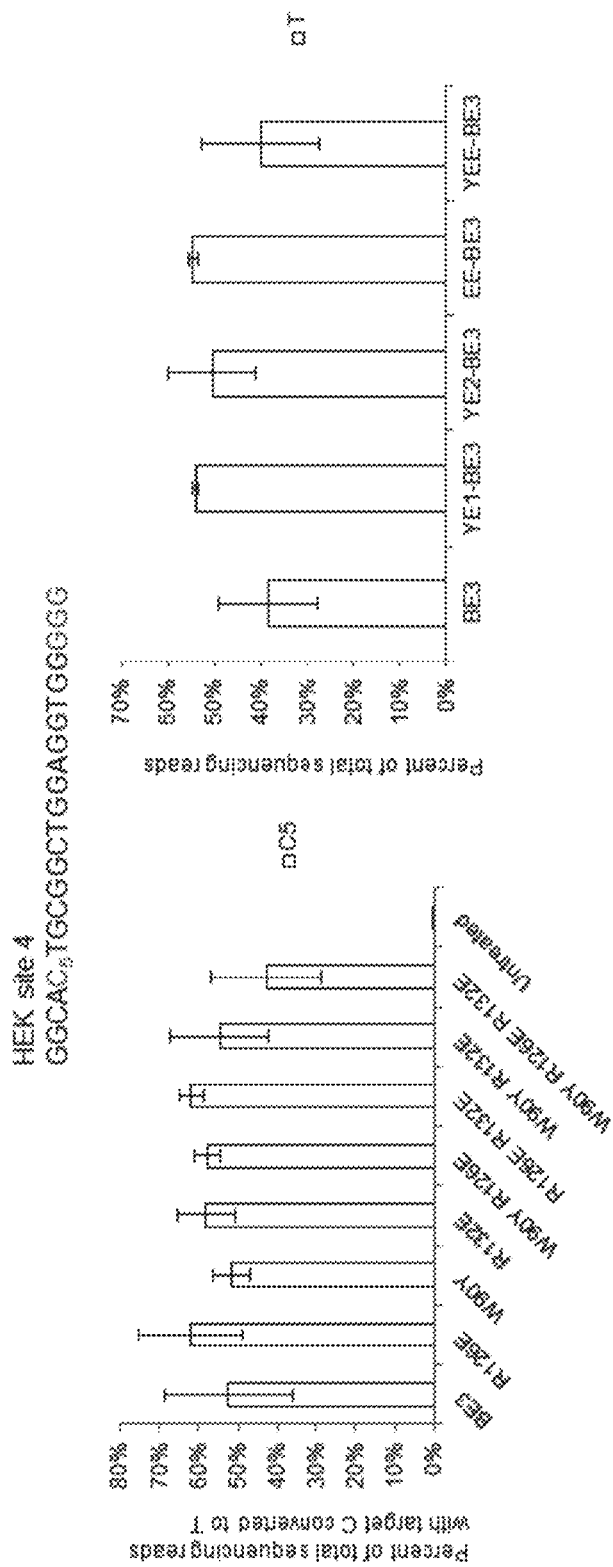

FIG. 98 shows the effect of APOBEC1 mutation son product distributions of base editing in mammalian cells. HEK293T cells were transfected with plasmids expressing BE3 or its mutants and an appropriate sgRNAs. The treated cells were analyzed as described in the Examples. Cellular C to T conversion percentages, defined as the percentage of total DNA sequencing reads with Ts at the target positions indicated, are shown (left). Percent of total sequencing reads containing the C to T conversion is shown on the right. The BE3 point mutants do not significantly affect base editing efficiencies at HEK site 4, a site with only one target cytidine.

Figure 99:
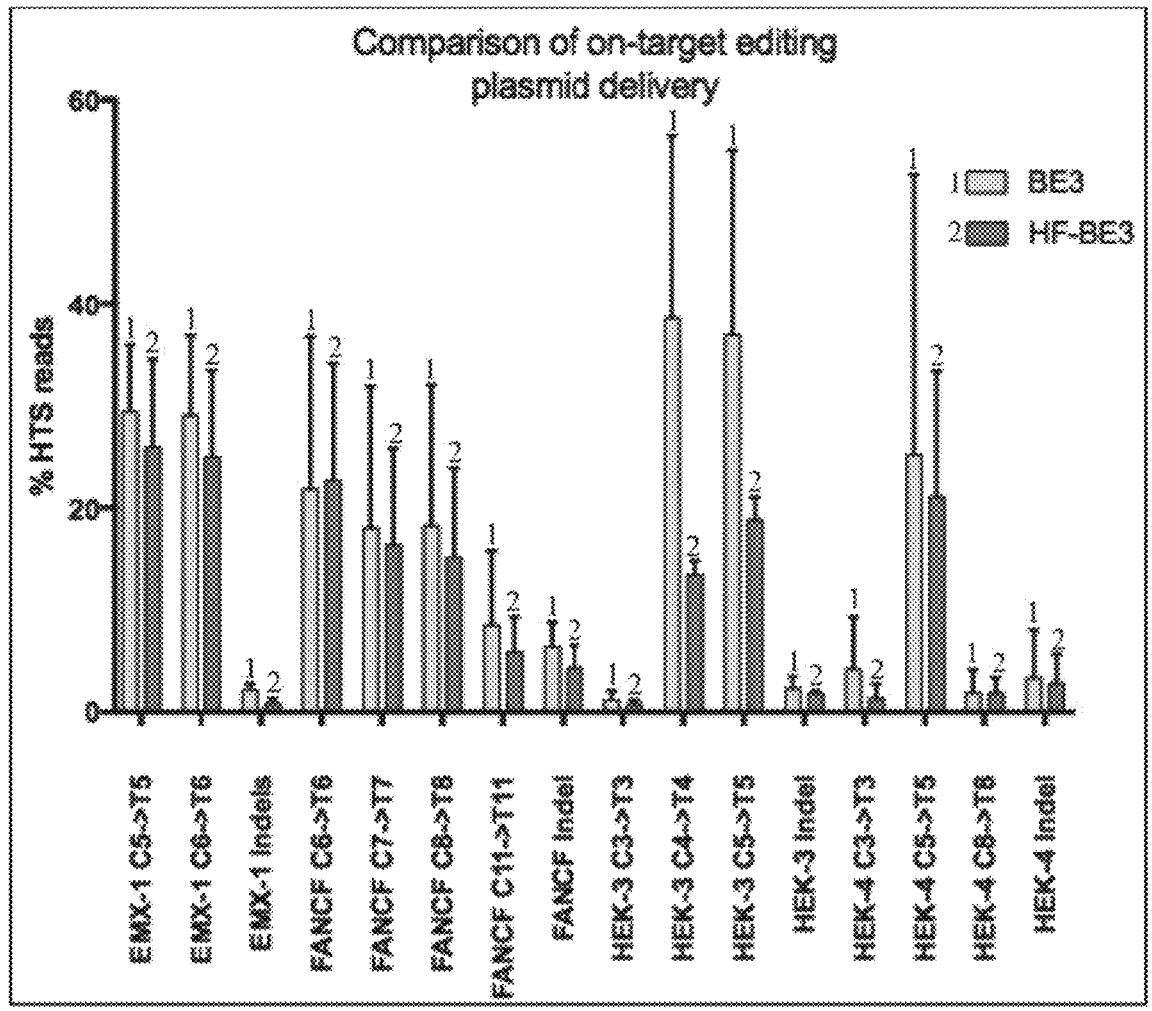

FIG. 99 shows a comparison of on-target editing plasma delivery in BE3 and HF-BE3.

Figure 100:
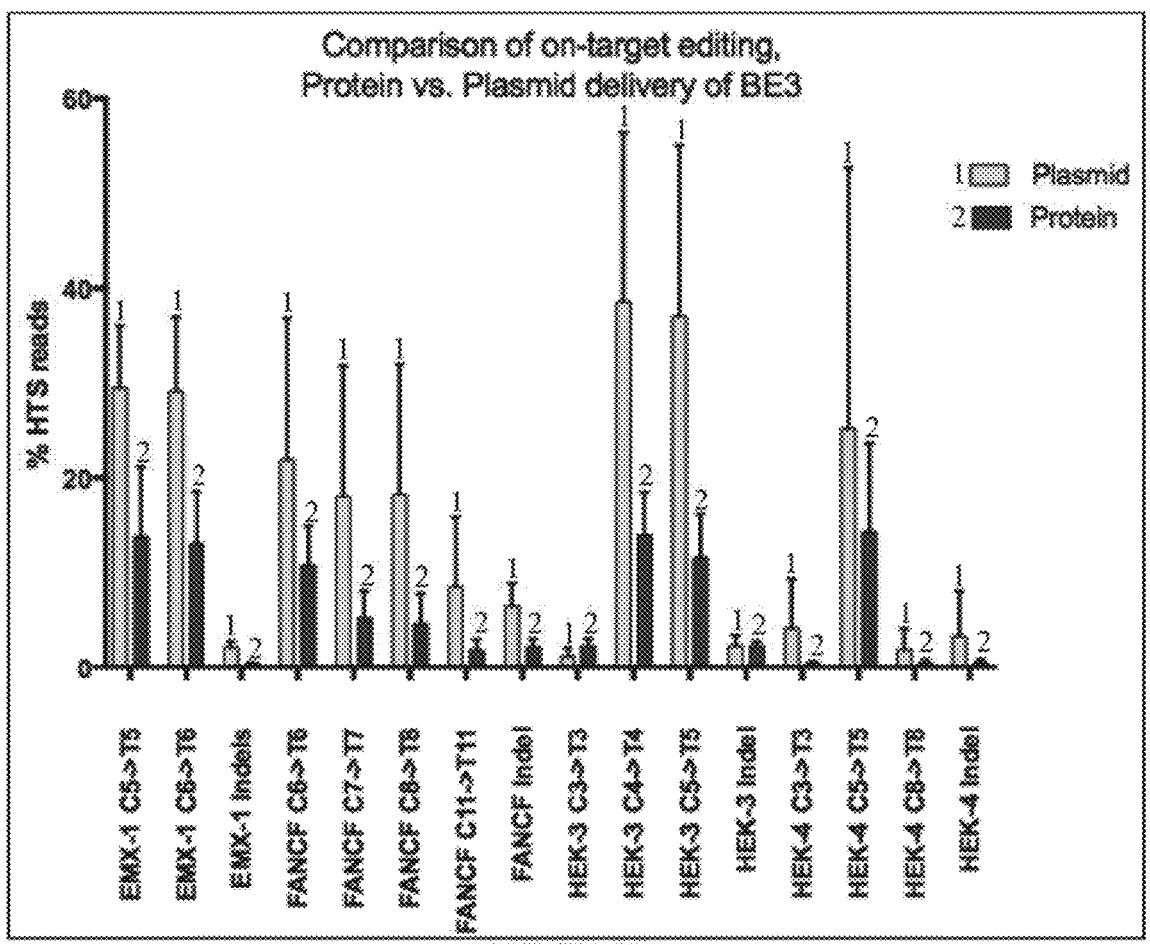

FIG. 100 shows a comparison of on-target editing in protein and plasma delivery of BE3.

Figure 101:
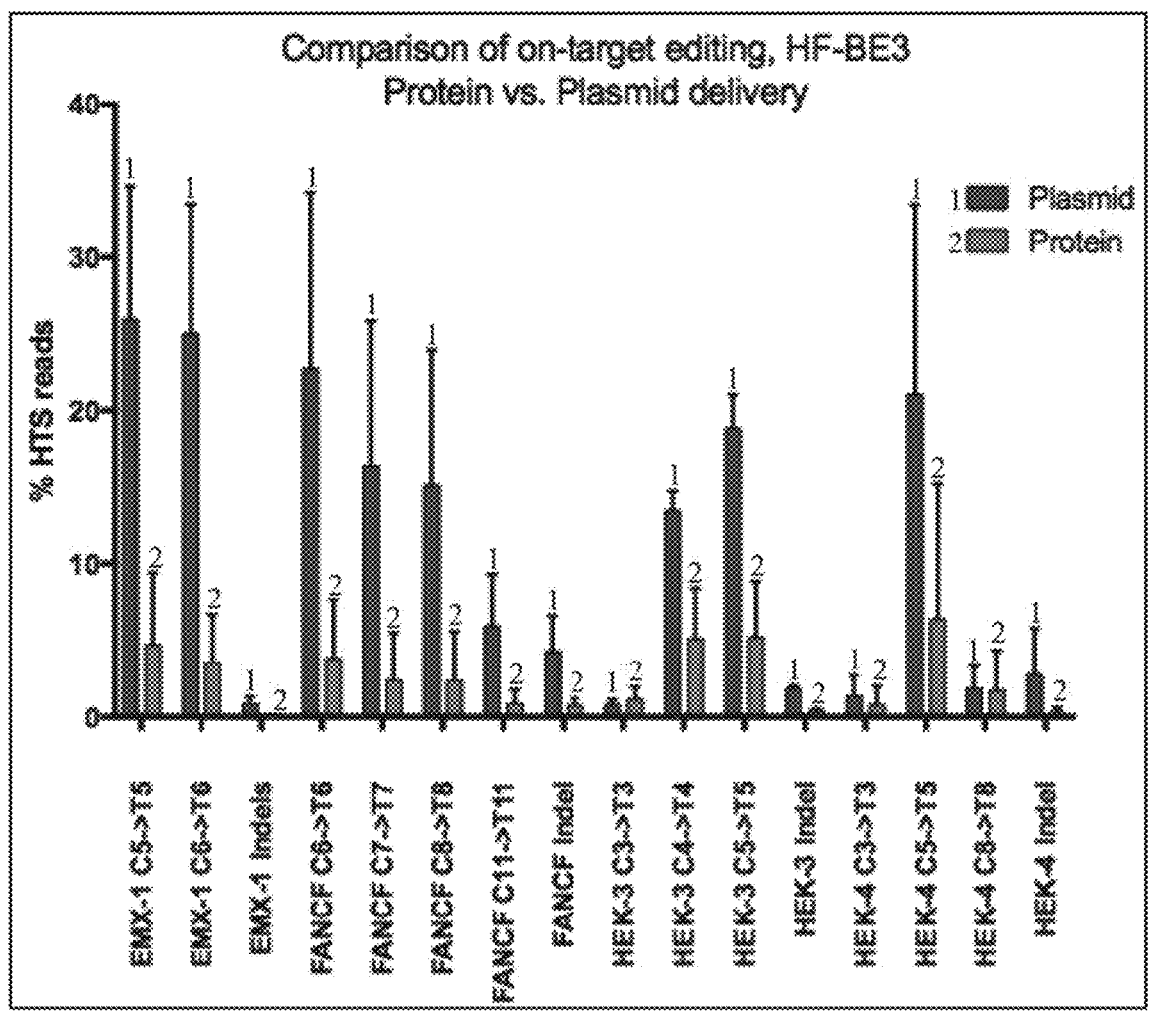

FIG. 101 shows a comparison of on-target editing in protein and plasma delivery of HF-BE3.

Figure 102:
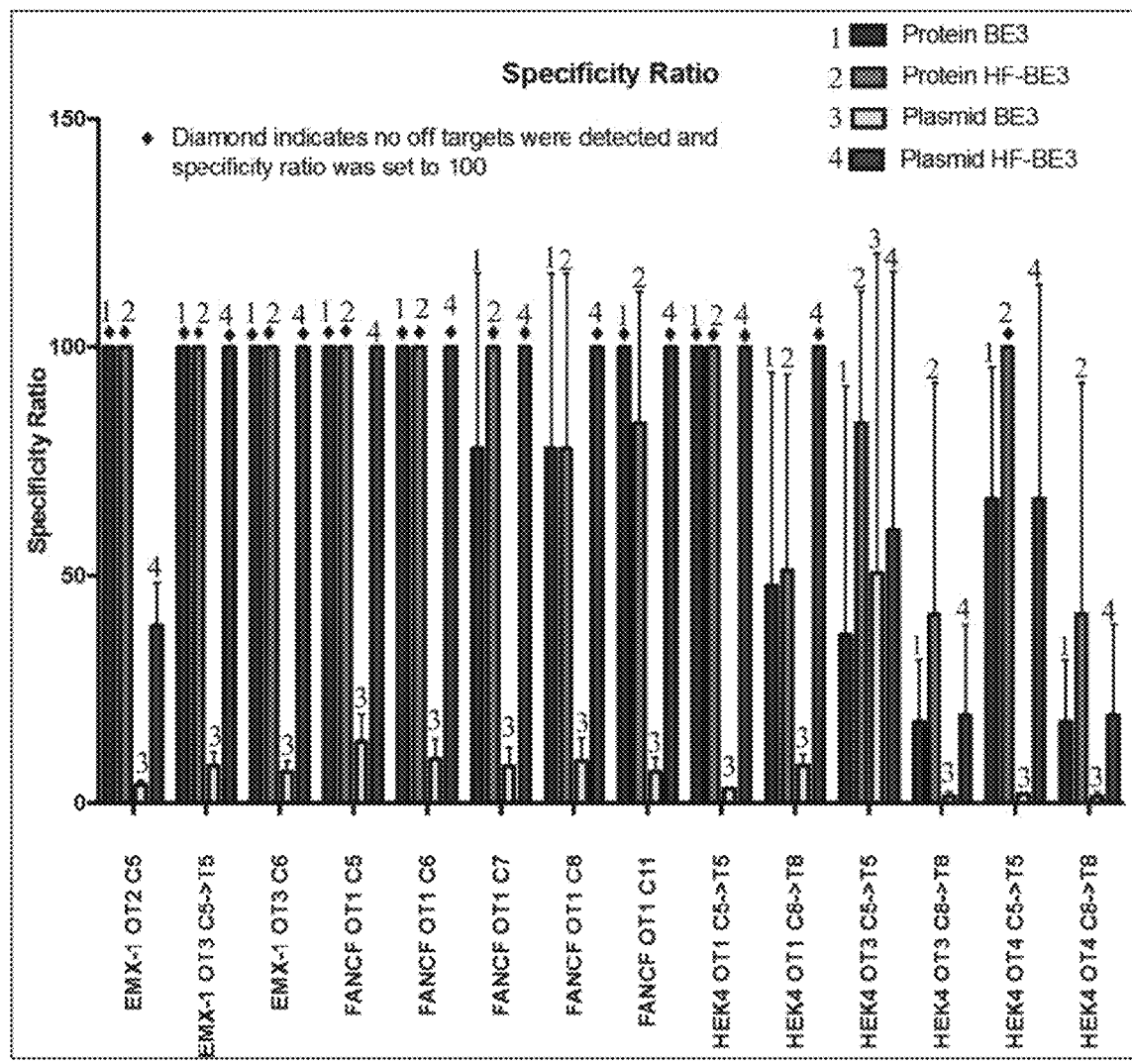

FIG. 102 shows that both lipofection and installing HF mutations decrease off-target deamination events. The diamond indicates no off targets were detected and the specificity ratio was set to 100.

Figure 103:
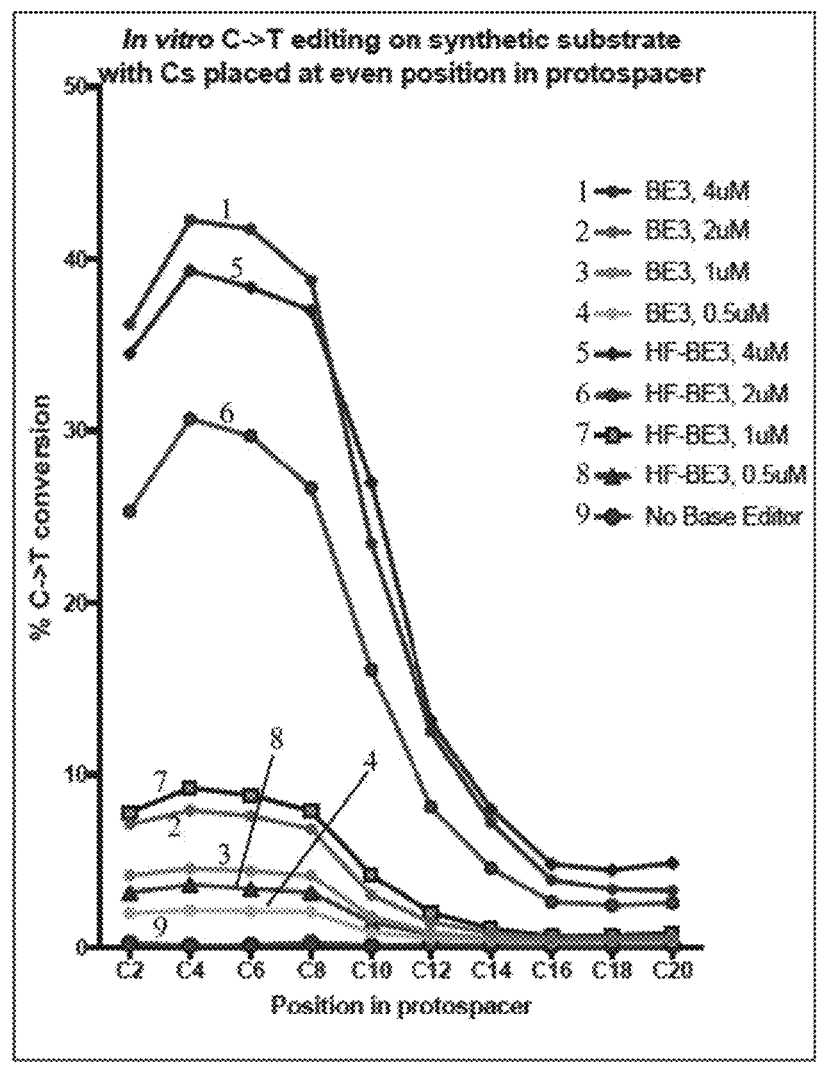

FIG. 103 shows in vitro C to T editing on a synthetic substrate with Cs placed at even positions in the protospacer (NNNNTC$_2$TC$_4$TC$_6$TC$_8$TC$_{10}$TC$_{12}$TC$_{14}$TC$_{16}$TC$_{18}$TC$_{20}$NGG, SEQ ID NO: 4272).

Figure 104:
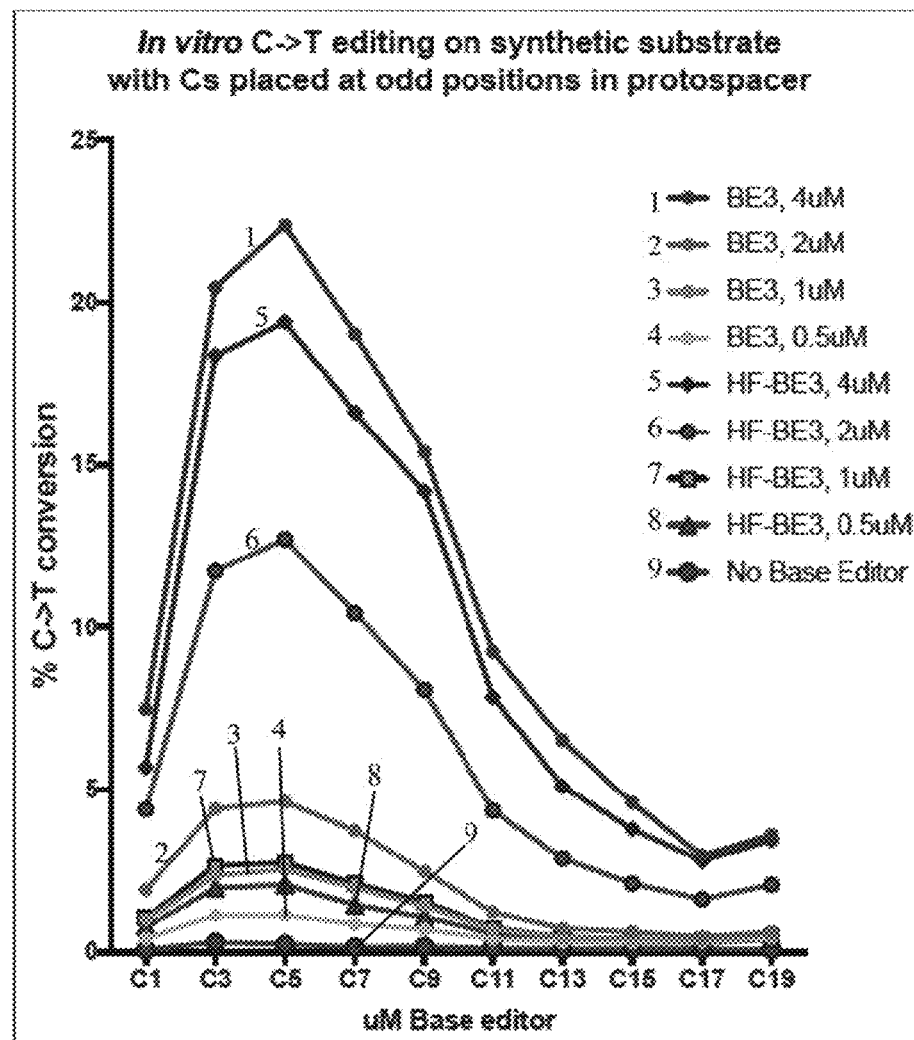

FIG. 104 shows in vitro C to T editing on a synthetic substrate with Cs placed at odd positions in the protospacer (NNNNTC$_2$TC$_4$TC$_6$TC$_8$TC$_{10}$TC$_{12}$TC$_{14}$TC$_{16}$TC$_{18}$TC$_{20}$NGG, SEQ ID NO: 4272).

Figure 105:
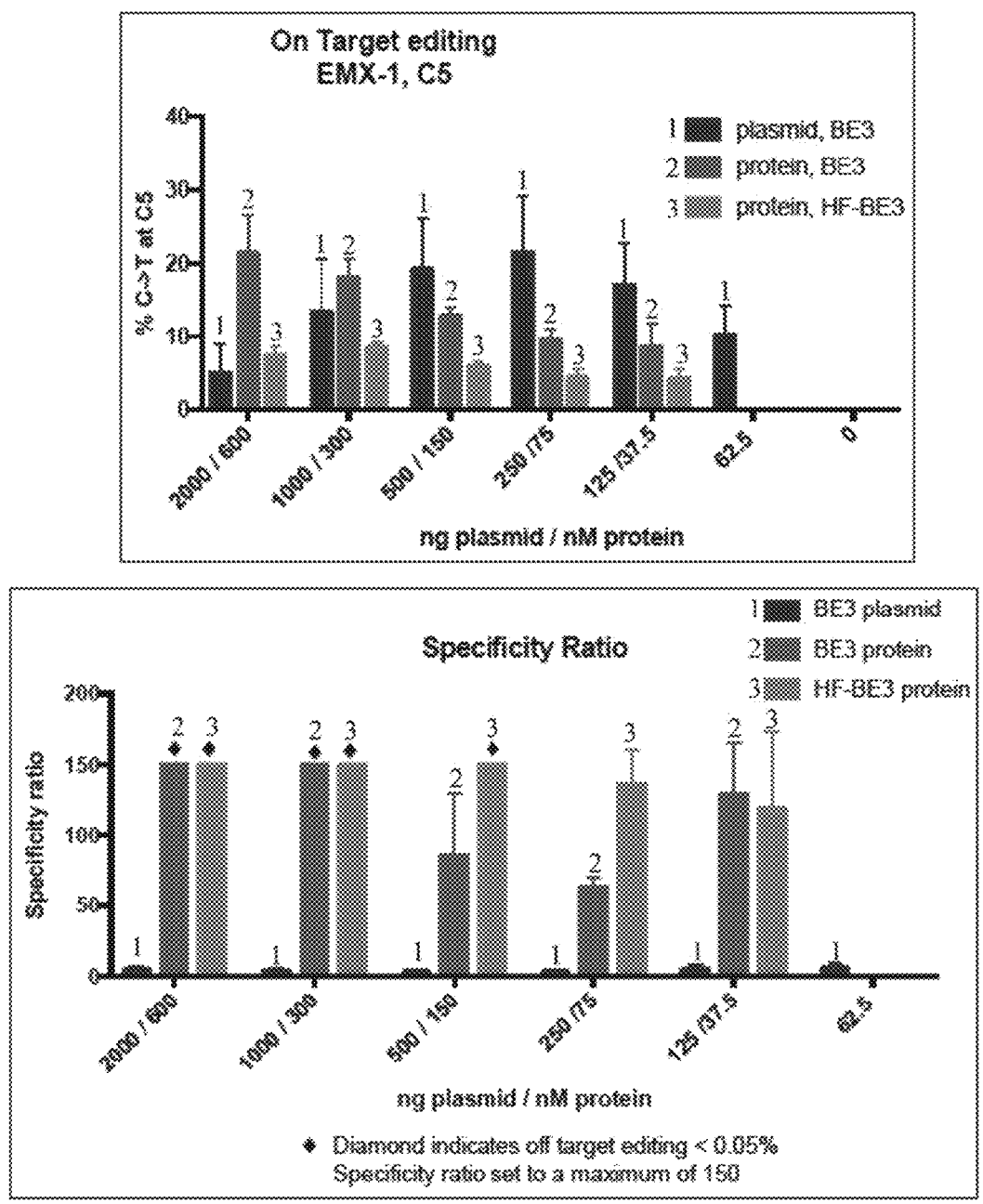

FIG. 105 includes two graphs depicting the specificity ratio of base editing with plasmid vs. protein delivery.

Figure 106A:
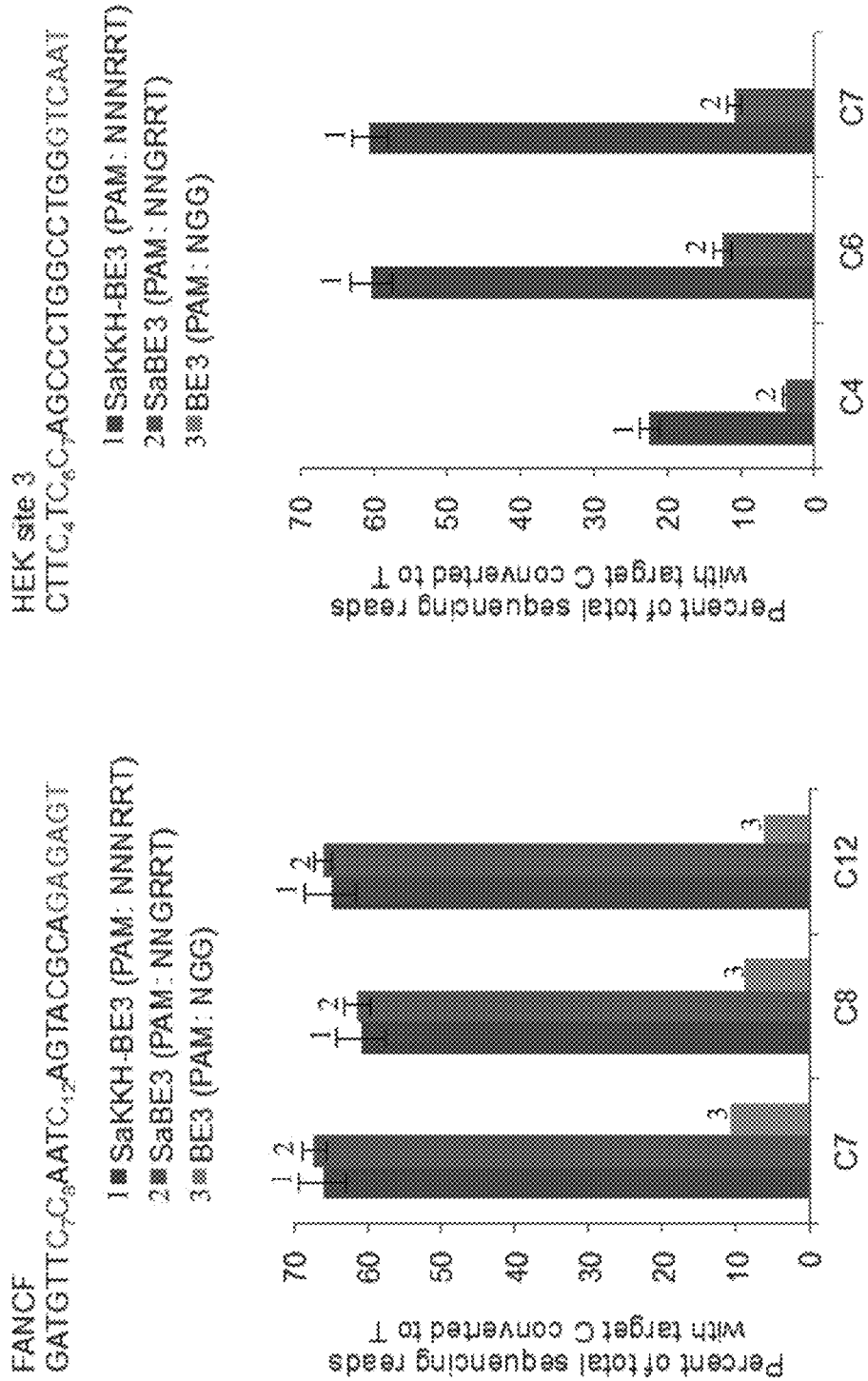
Figure 106B:
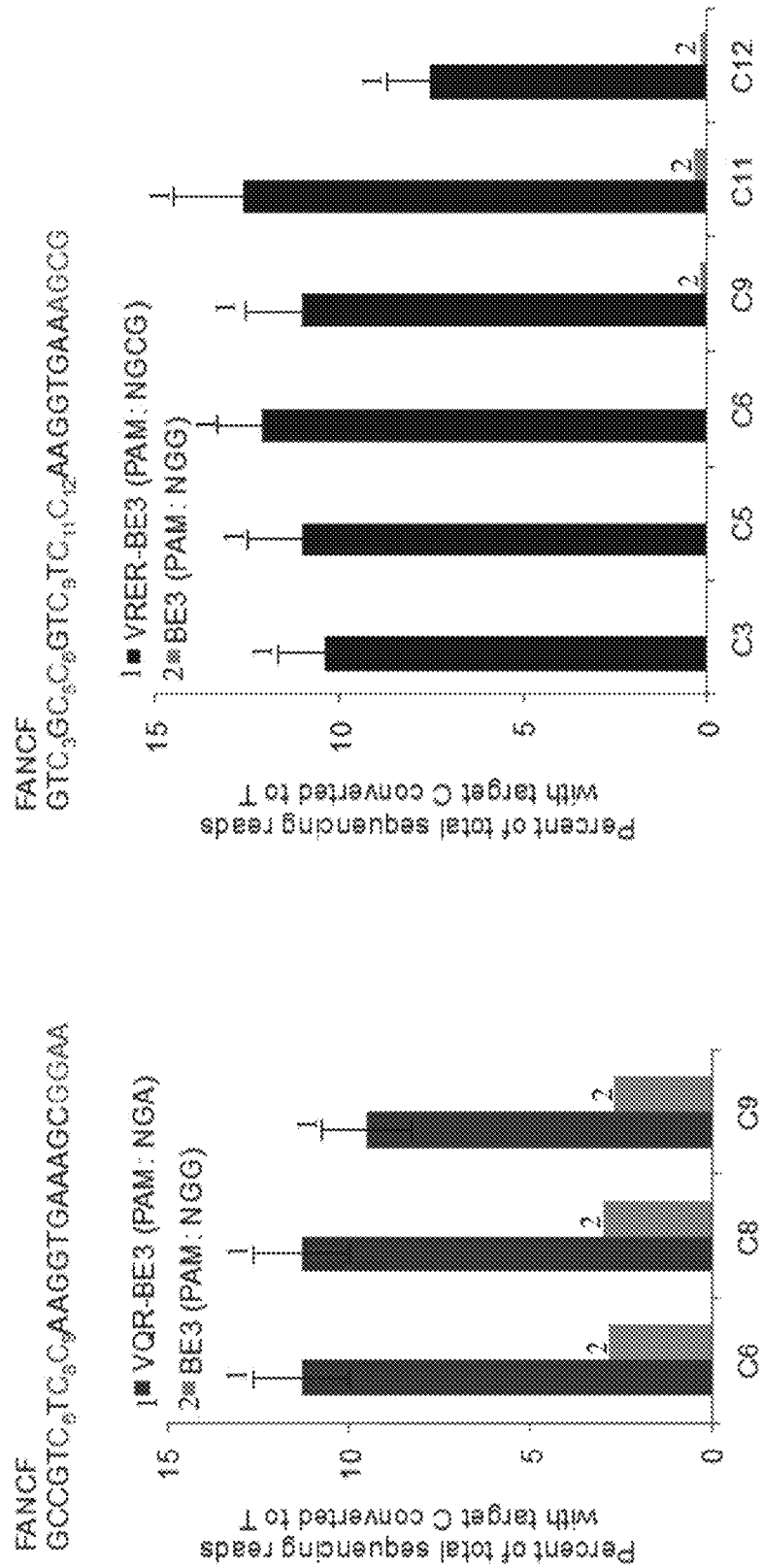

FIGS. 106A to 106B shows BE3 activity on non-NGG PAM sites. HEK293T cells were transfected with plasmids expressing BE3 and appropriate sgRNA. The treated cells were analyzed as described in the Examples. FIG. 106A shows BE3 activity on sites can be efficiently targeted by SaBE3 or SaKKH-BE3. BE3 shows low but significant activity on the NAG PAM. FIG. 106B shows BE3 has significantly reduced editing at sites with NGA or NGCG PAMs, in contrast to VQR-BE3 or VRER-BE3.

Figure 107A:
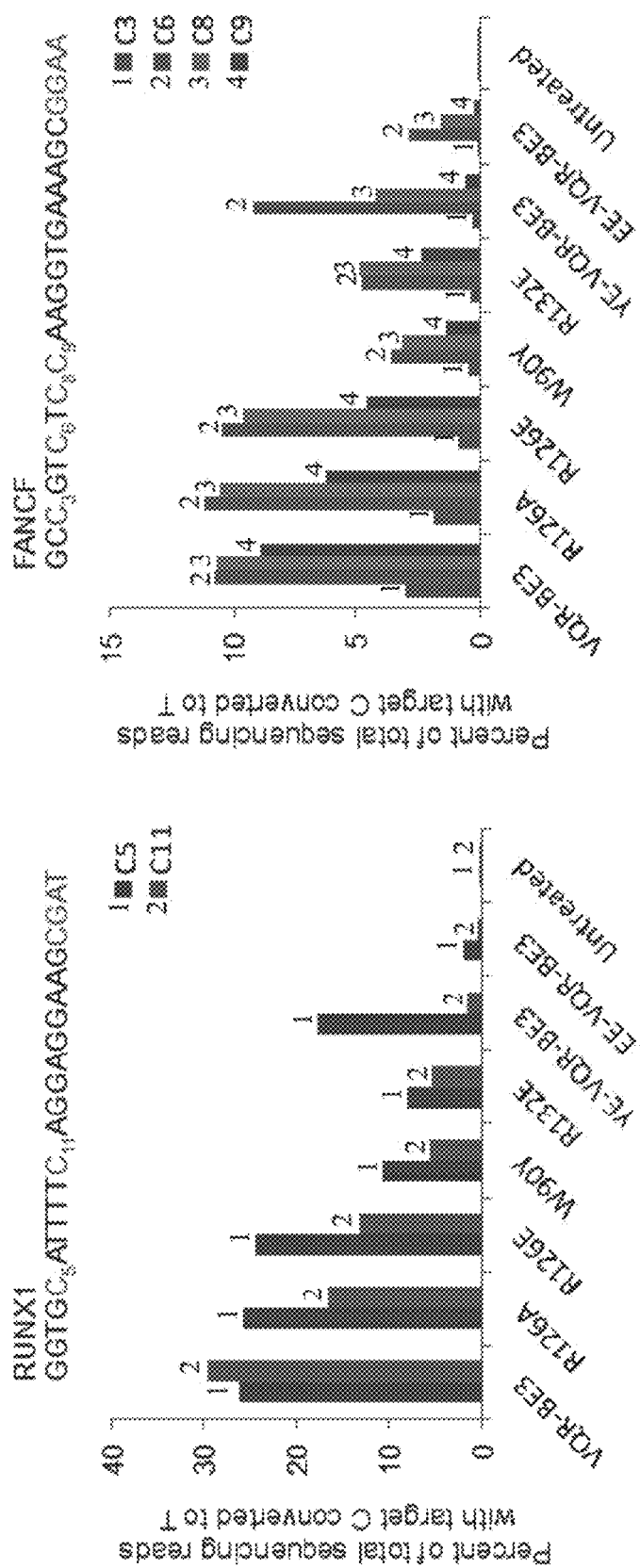
Figure 107B:
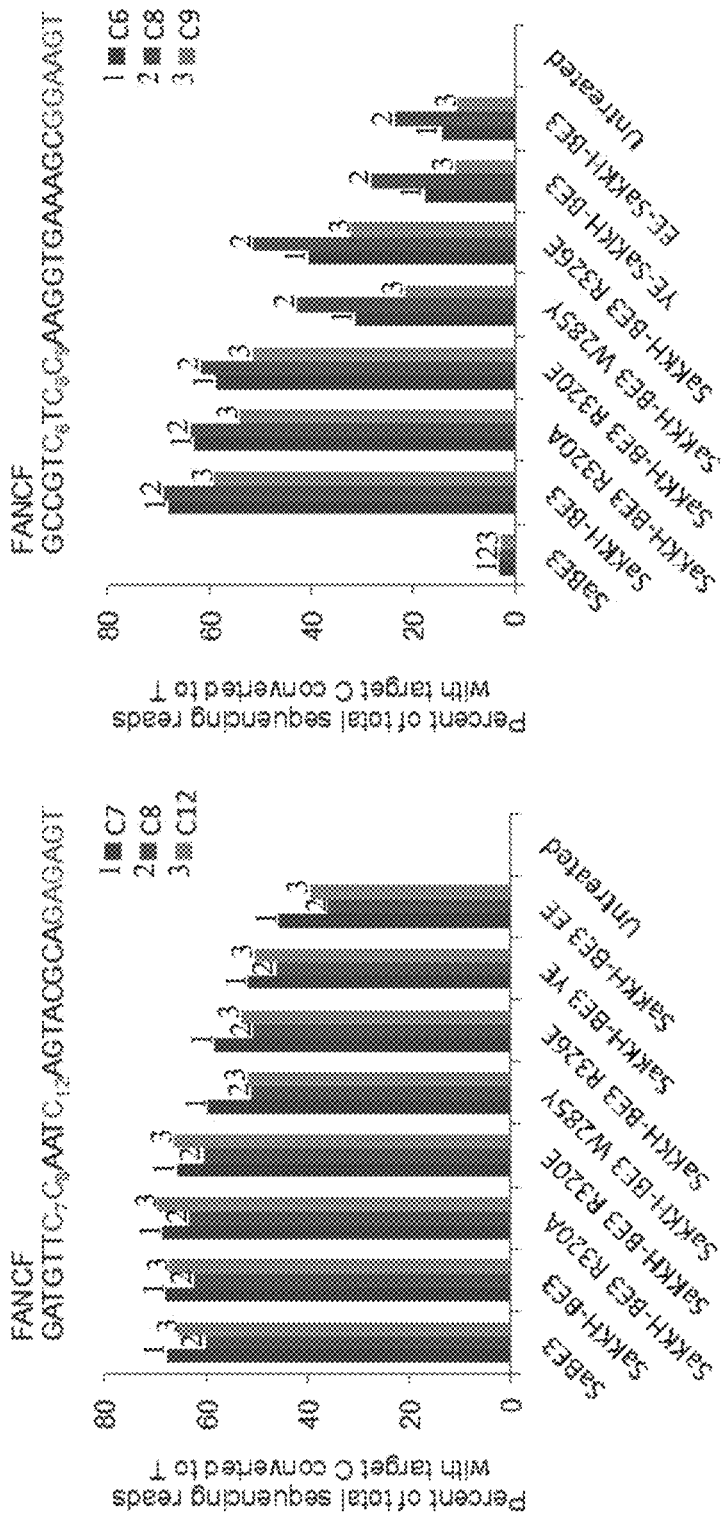

FIGS. 107A to 107B show the effect of APOBEC1 mutations on VQR-BE3 and SaKKH-BE3. HEK293T cells were transfected with plasmids expressing VQR-BE3, SaKKH-BE3 or its mutants and an appropriate sgRNAs. The treated cells were analyzed as described in the Methods. Cellular C to T conversion percentages, defined as the percentage of total DNA sequencing reads with Ts at the target positions indicated, are shown. FIG. 107A shows that the window-modulating mutations can be applied to VQR-BE3 to enable selective base editing at sites targetable by NGA PAM. FIG. 107B shows that, when applied to SaKKH-BE3, the mutations cause overall decrease in base editing efficiency without conferring base selectivity within the target window.

Figure 108:
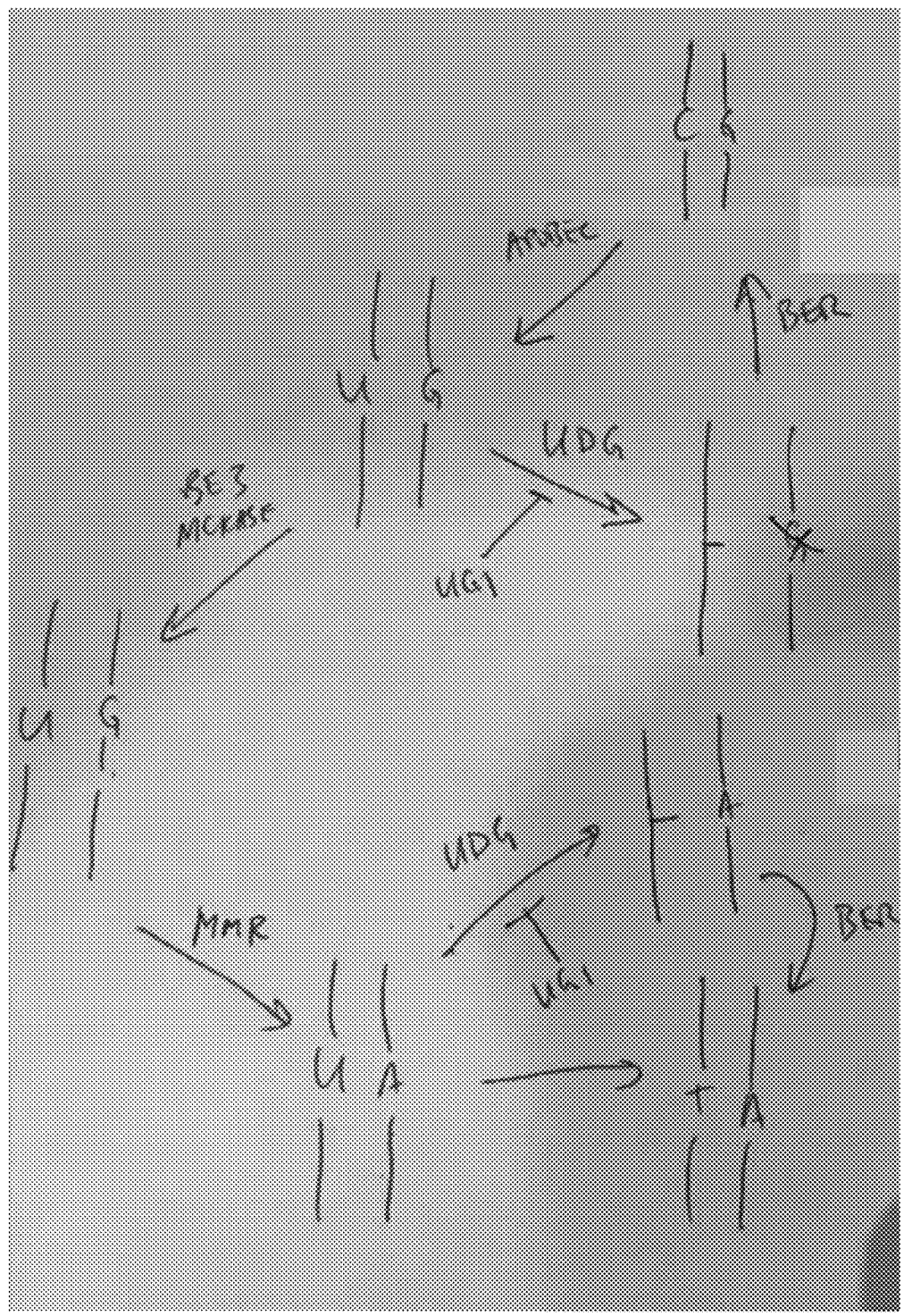

FIG. 108 shows a schematic representation of nucleotide editing. The following abbreviations are used: (MMR)—mismatch repair, (BE3 Nickase)—refers to base editor 3, which comprises a Cas9 nickase domain, (UGI)—uracil glycosylase inhibitor, UDG)—uracil DNA glycosylase, (APOBEC)—refers to an APOBEC cytidine deaminase.

DEFINITIONS

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof (e.g., a protein comprising an active, inactive, or partially active DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase.

A nuclease-inactivated Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., Science. 337:816-821(2012); Qi et al., "Repurposing CRISPR as an RNA-Guided Platform for Sequence-Specific Control of Gene Expression" (2013) Cell. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science*. 337:816-821(2012); Qi et al., *Cell*. 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to wild type Cas9. In some embodiments, the Cas9 variant may have 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more amino acid changes compared to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9. In some embodiments, the fragment is is at least 30%, at least 35%, at least 40%, at least 45%, at least 50%, at least 55%, at least 60%, at least 65%, at least 70%, at least 75%, at least 80%, at least 85%, at least 90%, at least 95% identical, at least 96%, at least 97%, at least 98%, at least 99%, or at least 99.5% of the amino acid length of a corresponding wild type Cas9.

In some embodiments, the fragment is at least 100 amino acids in length. In some embodiments, the fragment is at least 100, 150, 200, 250, 300, 350, 400, 450, 500, 550, 600, 650, 700, 750, 800, 850, 900, 950, 1000, 1050, 1100, 1150, 1200, 1250, or at least 1300 amino acids in length. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

```
                                              (SEQ ID NO: 1)
ATGGATAAGAAATACTCAATAGGCTTAGATATCGGCACAAATAGCGTCGGA

TGGGCGGTGATCACTGATGATTATAAGGTTCCGTCTAAAAAGTTCAAGGTT

CTGGGAAATACAGACCGCCACAGTATCAAAAAAATCTTATAGGGGCTCTT

TTATTTGGCAGTGGAGAGACAGCGGAAGCGACTCGTCTCAAACGGACAGCT

CGTAGAAGGTATACACGTCGGAAGAATCGTATTTGTTATCTACAGGAGATT

TTTTCAAATGAGATGGCGAAAGTAGATGATAGTTTCTTTCATCGACTTGAA

GAGTCTTTTTTGGTGGAAGAAGACAAGAAGCATGAACGTCATCCTATTTTT

GGAAATATAGTAGATGAAGTTGCTTATCATGAGAAATATCCAACTATCTAT

CATCTGCGAAAAAAATTGGCAGATTCTACTGATAAAGCGGATTTGCGCTTA

ATCTATTTGGCCTTAGCGCATATGATTAAGTTTCGTGGTCATTTTTTGATT

GAGGGAGATTTAAATCCTGATAATAGTGATGTGGACAAACTATTTATCCAG

TTGGTACAAATCTACAATCAATTATTTGAAGAAAACCCTATTAACGCAAGT

AGAGTAGATGCTAAAGCGATTCTTTCTGCACGATTGAGTAAATCAAGACGA

TTAGAAAATCTCATTGCTCAGCTCCCCGGTGAGAAGAGAAATGGCTTGTTT

GGGAATCTCATTGCTTTGTCATTGGGATTGACCCCTAATTTTAAATCAAAT

TTTGATTTGGCAGAAGATGCTAAATTACAGCTTTCAAAAGATACTTACGAT

GATGATTTAGATAATTTATTGGCGCAAATTGGAGATCAATATGCTGATTTG

TTTTTGGCAGCTAAGAATTTATCAGATGCTATTTTACTTTCAGATATCCTA

AGAGTAAATAGTGAAATAACTAAGGCTCCCCTATCAGCTTCAATGATTAAG

CGCTACGATGAACATCATCAAGACTTGACTCTTTTAAAAGCTTTAGTTCGA
```

```
                                -continued
CAACAACTTCCAGAAAAGTATAAAGAAATCTTTTTTGATCAATCAAAAAAC

GGATATGCAGGTTATATTGATGGGGGAGCTAGCCAAGAAGAATTTTATAAA

TTTATCAAACCAATTTTAGAAAAAATGGATGGTACTGAGGAATTATTGGTG

AAACTAAATCGTGAAGATTTGCTGCGCAAGCAACGGACCTTTGACAACGGC

TCTATTCCCCATCAAATTCACTTGGGTGAGCTGCATGCTATTTTGAGAAGA

CAAGAAGACTTTTATCCATTTTTAAAAGACAATCGTGAGAAGATTGAAAAA

ATCTTGACTTTTCGAATTCCTTATTATGTTGGTCCATTGGCGCGTGGCAAT

AGTCGTTTTGCATGGATGACTCGGAAGTCTGAAGAAACAATTACCCCATGG

AATTTTGAAGAAGTTGTCGATAAAGGTGCTTCAGCTCAATCATTTATTGAA

CGCATGACAAACTTTGATAAAAATCTTCCAAATGAAAAAGTACTACCAAAA

CATAGTTTGCTTTATGAGTATTTTACGGTTTATAACGAATTGACAAAGGTC

AAATATGTTACTGAGGGAATGCGAAAACCAGCATTTCTTTCAGGTGAACAG

AAGAAAGCCATTGTTGATTTACTCTTCAAAACAAATCGAAAAGTAACCGTT

AAGCAATTAAAAGAAGATTATTTCAAAAAAATAGAATGTTTTGATAGTGTT

GAAATTTCAGGAGTTGAAGATAGATTTAATGCTTCATTAGGCGCCTACCAT

GATTTGCTAAAAATTATTAAAGATAAAGATTTTTTGGATAATGAAGAAAT

GAAGATATCTTAGAGGATATTGTTTTAACATTGACCTTATTTGAAGATAGG

GGGATGATTGAGGAAAGACTTAAAACATATGCTCACCTCTTTGATGATAAG

GTGATGAAACAGCTTAAACGTCGCCGTTATACTGGTTGGGGACGTTTGTCT

CGAAAATTGATTAATGGTATTAGGGATAAGCAATCTGGCAAAACAATATTA

GATTTTTTGAAATCAGATGGTTTTGCCAATCGCAATTTTATGCAGCTGATC

CATGATGATAGTTTGACATTTAAAGAAGATATTCAAAAAGCACAGGTGTCT

GGACAAGGCCATAGTTTACATGAACAGATTGCTAACTTAGCTGGCAGTCCT

GCTATTAAAAAAGGTATTTTACAGACTGTAAAAATTGTTGATGAACTGGTC

AAAGTAATGGGGCATAAGCCAGAAAATATCGTTATTGAAATGGCACGTGAA

AATCAGACAACTCAAAAGGGCCAGAAAAATTCGCGAGAGCGTATGAAACGA

ATCGAAGAAGGTATCAAAGAATTAGGAAGTCAGATTCTTAAAGAGCATCCT

GTTGAAAATACTCAATTGCAAAATGAAAAGCTCTATCTCTATTATCTACAA

AATGGAAGAGACATGTATGTGGACCAAGAATTAGATATTAATCGTTTAAGT

GATTATGATGTCGATCACATTGTTCCACAAAGTTTCATTAAAGACGATTCA

ATAGACAATAAGGTACTAACGCGTTCTGATAAAAATCGTGGTAAATCGGAT

AACGTTCCAAGTGAAGAAGTAGTCAAAAAGATGAAAAACTATTGGAGACAA

CTTCTAAACGCCAAGTTAATCACTCAACGTAAGTTTGATAATTTAACGAAA

GCTGAACGTGGAGGTTTGAGTGAACTTGATAAAGCTGGTTTTATCAAACGC

CAATTGGTTGAAACTCGCCAAATCACTAAGCATGTGGCACAAATTTTGGAT

AGTCGCATGAATACTAAATACGATGAAAATGATAAACTTATTCGAGAGGTT

AAAGTGATTACCTTAAAATCTAAATTAGTTTCTGACTTCCGAAAAGATTTC

CAATTCTATAAAGTACGTGAGATTAACAATTACCATCATGCCCATGATGCG

TATCTAAATGCCGTCGTTGGAACTGCTTTGATTAAGAAATATCCAAAACTT

GAATCGGAGTTTGTCTATGGTGATTATAAAGTTTATGATGTTCGTAAAATG

ATTGCTAAGTCTGAGCAAGAAATAGGCAAAGCAACCGCAAAATATTTCTTT
```

-continued

```
TACTCTAATATCATGAACTTCTTCAAAACAGAAATTACACTTGCAAATGGA

GAGATTCGCAAACGCCCTCTAATCGAAACTAATGGGGAAACTGGAGAAATT

GTCTGGGATAAAGGGCGAGATTTTGCCACAGTGCGCAAAGTATTGTCCATG

CCCCAAGTCAATATTGTCAAGAAAACAGAAGTACAGACAGGCGGATTCTCC

AAGGAGTCAATTTTACCAAAAAGAAATTCGGACAAGCTTATTGCTCGTAAA

AAAGACTGGGATCCAAAAAAATATGGTGGTTTTGATAGTCCAACGGTAGCT

TATTCAGTCCTAGTGGTTGCTAAGGTGGAAAAAGGGAAATCGAAGAAGTTA

AAATCCGTTAAAGAGTTACTAGGGATCACAATTATGGAAAGAAGTTCCTTT

GAAAAAAATCCGATTGACTTTTTAGAAGCTAAAGGATATAAGGAAGTTAAA

AAAGACTTAATCATTAAACTACCTAAATATAGTCTTTTTGAGTTAGAAAAC

GGTCGTAAACGGATGCTGGCTAGTGCCGGAGAATTACAAAAAGGAAATGAG

CTGGCTCTGCCAAGCAAATATGTGAATTTTTTATATTTAGCTAGTCATTAT

GAAAAGTTGAAGGGTAGTCCAGAAGATAACGAACAAAAACAATTGTTTGTG

GAGCAGCATAAGCATTATTTAGATGAGATTATTGAGCAAATCAGTGAATTT

TCTAAGCGTGTTATTTTAGCAGATGCCAATTTAGATAAAGTTCTTAGTGCA

TATAACAAACATAGAGACAAACCAATACGTGAACAAGCAGAAAATATTATT

CATTTATTTACGTTGACGAATCTTGGAGCTCCCGCTGCTTTTAAATATTTT

GATACAACAATTGATCGTAAACGATATACGTCTACAAAAGAAGTTTTAGAT

GCCACTCTTATCCATCAATCCATCACTGGTCTTTATGAAACACGCATTGAT

TTGAGTCAGCTAGGAGGTGACTGA
```

(SEQ ID NO: 2)
MDKK<u>YSIGLDIGTNSVGWAVITDDYKVPSKKFKVLGNTDRHSIKKNLIGAL</u>
<u>LFGSGETAEATRLKRTARRRYTRRKNRICYLQEIFSNEMAKVDDSFFHRLE</u>
ESFLVEEDKKHERHPIFGNIVDEVAYHEKYPTIYHLRKKLADSTDKADLRL
IYLALAHMIKFRGHFLIEGDLNPDNSDVDKLFIQLVQIYNQLFEENPINAS
RVDAKAILSARLSKSRRLENLIAQLPGEKRNGLFGNLIALSLGLTPNFKSN
FDLAEDAKLQLSKDTYDDDLDNLLAQIGDQYADLFLAAKNLSDAILLSDIL
RVNSEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGN
SRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTV
KQLKEDYFKKIECFDSVEISGVEDRFNASLGAYHDLLKIIKDKDFLDNEEN
EDILEDIVLTLTLFEDRGMIEERLKTYAHLFDDKVMKQLKRRRYTGWGRLS
RKLINGIRDKQSGKTILDFLKSDGFANRNFMQLIHDDSLTFKEDIQKAQVS
GQG<u>HSLHEQIANLAGSPAIKKGILQTVKIVDELVKVMGHKPENIVIEMARE</u>
<u>NQTTQKGQKNSRERMKRIEEGIKELGSQILKEHPVENTQLQNEKLYLYYLQ</u>
<u>NGRDMYVDQELDINRLSDYDVDHIVPQSFIKDDSIDNKVLTRSDKNRGKSD</u>
<u>NVPSEEVVKKMKNYWRQLLNAKLITQRKFDNLTKAERGG</u>LS<u>ELDKAGFIKR</u>
<u>QLVETRQITKHVAQILDSRMNTKYDENDKLIREVKVITLKSKLVSDFRKDF</u>
<u>QFYKVREINNYHHAHDAYLNAVVGTALIKKYPKLESEFVYGDYKVYDVRKM</u>
<u>IAKSEQEIGKATAKYFFYSNIMNFFKTEITLANGEIRKRPLIETNGETGEI</u>
<u>VWDKGRDFATVRKVLSMPQVNIVKKTEVQT</u>GGFSKESILPKRNSDKLIARK
KDWDPKKYGGFDSPTVAYSVLVVAKVEKGKSKKLKSVKELLGITIMERSSF
EKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEF
SKRVILADANLDKVLSAYNKHRDKPIREQAENIIHLFTLTNLGAPAAFKYF
DTTIDRKRYTSTKEVLDATLIHQSITGLYETRIDLSQLGGD
(single underline: HNH domain; double underline: RuvC domain)

In some embodiments, wild type Cas9 corresponds to, or comprises SEQ ID NO:3 (nucleotide) and/or SEQ ID NO: 4 (amino acid):

(SEQ ID NO: 3)
```
ATGGATAAAAAGTATTCTATTGGTTTAGACATCGGCACTAATTCCGTTGGA
TGGGCTGTCATAACCGATGAATACAAAGTACCTTCAAAGAAATTTAAGGTG
TTGGGGAACACAGACCGTCATTCGATTAAAAAGAATCTTATCGGTGCCCTC
CTATTCGATAGTGGCGAAACGGCAGAGGCGACTCGCCTGAAACGAACCGCT
CGGAGAAGGTATACACGTCGCAAGAACCGAATATGTTACTTACAAGAAATT
TTTAGCAATGAGATGGCCAAAGTTGACGATTCTTTCTTTCACCGTTTGGAA
GAGTCCTTCCTTGTCGAAGAGGACAAGAAACATGAACGGCACCCCATCTTT
GGAAACATAGTAGATGAGGTGGCATATCATGAAAGTACCCAACGATTTAT
CACCTCAGAAAAAGCTAGTTGACTCAACTGATAAAGCGGACCTGAGGTTA
ATCTACTTGGCTCTTGCCCATATGATAAAGTTCCGTGGGCACTTTCTCATT
GAGGGTGATCTAAATCCGGACAACTCGGATGTCGACAAACTGTTCATCCAG
TTAGTACAAACCTATAATCAGTTGTTTGAAGAGAACCCTATAAATGCAAGT
GGCGTGGATGCGAAGGCTATTCTTAGCGCCCGCCTCTCTAAATCCCGACGG
CTAGAAAACCTGATCGCACAATTACCCGGAGAGAAGAAAAATGGGTTGTTC
GGTAACCTTATAGCGCTCTCACTAGGCCTGACACCAAATTTTAAGTCGAAC
TTCGACTTAGCTGAAGATGCCAAATTGCAGCTTAGTAAGGACACGTACGAT
GACGATCTCGACAATCTACTGGCACAAATTGGAGATCAGTATGCGGACTTA
TTTTTGGCTGCCAAAAACCTTAGCGATGCAATCCTCCTATCTGACATACTG
AGAGTTAATACTGAGATTACCAAGGCGCCGTTATCCGCTTCAATGATCAAA
AGGTACGATGAACATCACCAAGACTTGACACTTCTCAAGGCCCTAGTCCGT
CAGCAACTGCCTGAGAAATATAAGGAAATATTCTTTGATCAGTCGAAAAAC
GGGTACGCAGGTTATATTGACGGCGGAGCGAGTCAAGAGGAATTCTACAAG
TTTATCAAACCCATATTAGAGAAGATGGATGGGACGGAAGAGTTGCTTGTA
AAACTCAATCGCGAAGATCTACTGCGAAAGCAGCGGACTTTCGACAACGGT
AGCATTCCACATCAAATCCACTTAGGCGAATTGCATGCTATACTTAGAAGG
CAGGAGGATTTTTATCCGTTCCTCAAAGACAATCGTGAAAAGATTGAGAAA
ATCCTAACCTTTCGCATACCTTACTATGTGGGACCCCTGGCCCGAGGGAAC
TCTCGGTTCGCATGGATGACAAGAAGTCCGAAGAAACGATTACTCCATGG
AATTTTGAGGAAGTTGTCGATAAAGGTGCGTCAGCTCAATCGTTCATCGAG

```
AGGATGACCAACTTTGACAAGAATTTACCGAACGAAAAAGTATTGCCTAAG
CACAGTTTACTTTACGAGTATTTCACAGTGTACAATGAACTCACGAAAGTT
AAGTATGTCACTGAGGGCATGCGTAAACCCGCCTTTCTAAGCGGAGAACAG
AAGAAAGCAATAGTAGATCTGTTATTCAAGACCAACCGCAAAGTGACAGTT
AAGCAATTGAAAGAGGACTACTTTAAGAAAATTGAATGCTTCGATTCTGTC
GAGATCTCCGGGGTAGAAGATCGATTTAATGCGTCACTTGGTACGTATCAT
GACCTCCTAAAGATAATTAAAGATAAGGACTTCCTGGATAACGAAGAGAAT
GAAGATATCTTAGAAGATATAGTGTTGACTCTTACCCTCTTTGAAGATCGG
GAAATGATTGAGGAAAGACTAAAAACATACGCTCACCTGTTCGACGATAAG
GTTATGAAACAGTTAAAGAGGCGTCGCTATACGGGCTGGGGACGATTGTCG
CGGAAACTTATCAACGGGATAAGAGACAAGCAAAGTGGTAAAACTATTCTC
GATTTTCTAAAGAGCGACGGCTTCGCCAATAGGAACTTTATGCAGCTGATC
CATGATGACTCTTTAACCTTCAAAGAGGATATACAAAAGGCACAGGTTTCC
GGACAAGGGGACTCATTGCACGAACATATTGCGAATCTTGCTGGTTCGCCA
GCCATCAAAAAGGGCATACTCCAGACAGTCAAAGTAGTGGATGAGCTAGTT
AAGGTCATGGGACGTCACAAACCGGAAAACATTGTAATCGAGATGGCACGC
GAAAATCAAACGACTCAGAAGGGGCAAAAAAACAGTCGAGAGCGGATGAAG
AGAATAGAAGAGGGTATTAAAGAACTGGGCAGCCAGATCTTAAAGGAGCAT
CCTGTGGAAAATACCCAATTGCAGAACGAGAAACTTTACCTCTATTACCTA
CAAAATGGAAGGGACATGTATGTTGATCAGGAACTGGACATAAACCGTTTA
TCTGATTACGACGTCGATCACATTGTACCCCAATCCTTTTTGAAGGACGAT
TCAATCGACAATAAAGTGCTTACACGCTCGGATAAGAACCGAGGGAAAAGT
GACAATGTTCCAAGCGAGGAAGTCGTAAAGAAAATGAAGAACTATTGGCGG
CAGCTCCTAAATGCGAAACTGATAACGCAAAGAAAGTTCGATAACTTAACT
AAAGCTGAGAGGGGTGGCTTGTCTGAACTTGACAAGGCCGGATTTATTAAA
CGTCAGCTCGTGGAAACCCGCCAAATCACAAAGCATGTTGCACAGATACTA
GATTCCCGAATGAATACGAAATACGACGAGAACGATAAGCTGATTCGGGAA
GTCAAAGTAATCACTTTAAAGTCAAAATTGGTGTCGGACTTCAGAAAGGAT
TTTCAATTCTATAAAGTTAGGGAGATAAATAACTACCACCATGCGCACGAC
GCTTATCTTAATGCCGTCGTAGGGACCGCACTCATTAAGAAATACCCGAAG
CTAGAAAGTGAGTTTGTGTATGGTGATTACAAAGTTTATGACGTCCGTAAG
ATGATCGCGAAAAGCGAACAGGAGATAGGCAAGGCTACAGCCAAATACTTC
TTTTATTCTAACATTATGAATTTCTTTAAGACGGAAATCACTCTGGCAAAC
GGAGAGATACGCAAACGACCTTTAATTGAAACCAATGGGGAGACAGGTGAA
ATCGTATGGGATAAGGGCCGGGACTTCGCGACGGTGAGAAAAGTTTTGTCC
ATGCCCCAAGTCAACATAGTAAAGAAAACTGAGGTGCAGACCGGAGGGTTT
TCAAAGGAATCGATTCTTCCAAAAAGGAATAGTGATAAGCTCATCGCTCGT
AAAAAGGACTGGGACCCGAAAAAGTACGGTGGCTTCGATAGCCCTACAGTT
GCCTATTCTGTCCTAGTAGTGGCAAAAGTTGAGAAGGGAAAATCCAAGAAA
CTGAAGTCAGTCAAAGAATTATTGGGGATAACGATTATGGAGCGCTCGTCT
TTTGAAAAGAACCCCATCGACTTCCTTGAGGCGAAAGGTTACAAGGAAGTA
AAAAAGGATCTCATAATTAAACTACCAAAGTATAGTCTGTTTGAGTTAGAA
AATGGCCGAAAACGGATGTTGGCTAGCGCCGGAGAGCTTCAAAAGGGGAAC
GAACTCGCACTACCGTCTAAATACGTGAATTTCCTGTATTTAGCGTCCCAT
TACGAGAAGTTGAAAGGTTCACCTGAAGATAACGAACAGAAGCAACTTTTT
GTTGAGCAGCACAAACATTATCTCGACGAAATCATAGAGCAAATTTCGGAA
TTCAGTAAGAGAGTCATCCTAGCTGATGCCAATCTGGACAAAGTATTAAGC
GCATACAACAAGCACAGGGATAAACCCATACGTGAGCAGGCGGAAAATATT
ATCCATTTGTTTACTCTTACCAACCTCGGCGCTCCAGCCGCATTCAAGTAT
TTTGACACAACGATAGATCGCAAACGATACACTTCTACCAAGGAGGTGCTA
GACGCGACACTGATTCACCAATCCATCACGGGATTATATGAAACTCGGATA
GATTTGTCACAGCTTGGGGGTGACGGATCCCCCAAGAAGAAGAGGAAAGTC
TCGAGCGACTACAAAGACCATGACGGTGATTATAAAGATCATGACATCGAT
TACAAGGATGACGATGACAAGGCTGCAGGA
```

(SEQ ID NO: 4)

MDKK<u>YSIGLAIGTNSVGWAVITDEYKVPSKKFKVLGNTDRHSIKKNLIGAL</u>
<u>LFDSGETA</u>EATRLKRTARRRYTRRKNRICYLQEIFSNEMAKVDDSFFHRLE
ESFLVEEDKKHERHPIFGNIVDEVAYHEKYPTIYHLRKKLVDSTDKADLRL
IYLALAHMIKFRGHFLIEGDLNPDNSDVDKLFIQLVQTYNQLFEENPINAS
GVDAKAILSARLSKSRRLENLIAQLPGEKKNGLFGNLIALSLGLTPNFKSN
FDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGN
SRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTV
KQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVS
GQG<u>DSLHEHIANLAGSPAIKKGILQTVKVVDELVKVMGRHKPENIVIEMAR</u>
ENQTTQK<u>GQKNSRERMKRIEEGIKELGSQILKEHPVENTQLQNEKLYLYYL</u>
<u>QNGRDMYVDQELDINRLSDYDVDHIVPQSFLKDDSIDNKVLTRSDKNRGKS</u>
<u>DNVPSEEVVKKMKNYWRQLLNAKLITQRKFDNLTKAERG</u>GL<u>SELDKAGFIK</u>
<u>RQLVETRQITKHVAQILDSRMNTKYDENDKLIREVKVITLKSKLVSDFRKD</u>
<u>FQFYKVREINNYHHAHDAYLNAVVGTALIKKYPKLESEFVYGDYKVYDVRK</u>
<u>MIAKSEQEIGKATAKYFFYSNIMNFFKTEITLANGEIRKRPLIETNGETGE</u>
<u>IVWDKGRDFATVRKVLSMPQVNIVKKTEVQT</u>GGFSKESILPKRNSDKLIAR
KKDWDPKKYGGFDSPTVAYSVLVVAKVEKGKSKKLKSVKELLGITIMERSS
FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD
(single underline: HNH domain; double underline: RuvC domain)

In some embodiments, wild type Cas9 corresponds to Cas9 from *Streptococcus pyogenes* (NCBI Reference Sequence: NC_002737.2, SEQ ID NO: 8 (nucleotide); and Uniport Reference Sequence: Q99ZW2, SEQ ID NO: 10 (amino acid).

(SEQ ID NO: 8)
ATGGATAAGAAATACTCAATAGGCTTAGATATCGGCACAAATAGCGTCGGA

TGGGCGGTGATCACTGATGAATATAAGGTTCCGTCTAAAAAGTTCAAGGTT

CTGGGAAATACAGACCGCCACAGTATCAAAAAAAATCTTATAGGGGCTCTT

TTATTTGACAGTGGAGAGACAGCGGAAGCGACTCGTCTCAAACGGACAGCT

CGTAGAAGGTATACACGTCGGAAGAATCGTATTTGTTATCTACAGGAGATT

TTTTCAAATGAGATGGCGAAAGTAGATGATAGTTTCTTTCATCGACTTGAA

GAGTCTTTTTTGGTGGAAGAAGACAAGAAGCATGAACGTCATCCTATTTTT

GGAAATATAGTAGATGAAGTTGCTTATCATGAGAAATATCCAACTATCTAT

CATCTGCGAAAAAAATTGGTAGATTCTACTGATAAAGCGGATTTGCGCTTA

ATCTATTTGGCCTTAGCGCATATGATTAAGTTTCGTGGTCATTTTTTGATT

GAGGGAGATTTAAATCCTGATAATAGTGATGTGGACAAACTATTTATCCAG

TTGGTACAAACCTACAATCAATTATTTGAAGAAAACCCTATTAACGCAAGT

GGAGTAGATGCTAAAGCGATTCTTTCTGCACGATTGAGTAAATCAAGACGA

TTAGAAAATCTCATTGCTCAGCTCCCCGGTGAGAAGAAAAATGGCTTATTT

GGGAATCTCATTGCTTTGTCATTGGGTTTGACCCCTAATTTTAAATCAAAT

TTTGATTGGCAGAAGATGCTAAATTACAGCTTTCAAAAGATACTTACGAT

GATGATTTAGATAATTTATTGGCGCAAATTGGAGATCAATATGCTGATTTG

TTTTTGGCAGCTAAGAATTTATCAGATGCTATTTTACTTTCAGATATCCTA

AGAGTAAATACTGAAATAACTAAGGCTCCCCTATCAGCTTCAATGATTAAA

CGCTACGATGAACATCATCAAGACTTGACTCTTTTAAAAGCTTTAGTTCGA

CAACAACTTCCAGAAAAGTATAAAGAAATCTTTTTTGATCAATCAAAAAAC

GGATATGCAGGTTATATTGATGGGGGAGCTAGCCAAGAAGAATTTTATAAA

TTTATCAAACCAATTTTAGAAAAAATGGATGGTACTGAGGAATTATTGGTG

AAACTAAATCGTGAAGATTTGCTGCGCAAGCAACGGACCTTTGACAACGGC

TCTATTCCCCATCAAATTCACTTGGGTGAGCTGCATGCTATTTTGAGAAGA

CAAGAAGACTTTTATCCATTTTTAAAAGACAATCGTGAGAAGATTGAAAAA

ATCTTGACTTTTCGAATTCCTTATTATGTTGGTCCATTGGCGCGTGGCAAT

AGTCGTTTTGCATGGATGACTCGGAAGTCTGAAGAAACAATTACCCCATGG

AATTTTGAAGAAGTTGTCGATAAAGGTGCTTCAGCTCAATCATTTATTGAA

CGCATGACAAACTTTGATAAAAATCTTCCAAATGAAAAAGTACTACCAAAA

CATAGTTTGCTTTATGAGTATTTTACGGTTTATAACGAATTGACAAAGGTC

AAATATGTTACTGAAGGAATGCGAAAACCAGCATTTCTTTCAGGTGAACAG

AAGAAAGCCATTGTTGATTACTCTTCAAAACAAATCGAAAAGTAACCGTT

AAGCAATTAAAAGAAGATTATTTCAAAAAAATAGAATGTTTTGATAGTGTT

GAAATTTCAGGAGTTGAAGATAGATTTAATGCTTCATTAGGTACCTACCAT

GATTTGCTAAAAATTATTAAAGATAAAGATTTTTTGGATAATGAAGAAAAT

GAAGATATCTTAGAGGATATTGTTTTAACATTGACCTTATTTGAAGATAGG

GAGATGATTGAGGAAAGACTTAAAACATATGCTCACCTCTTTGATGATAAG

GTGATGAAACAGCTTAAACGTCGCCGTTATACTGGTTGGGGACGTTTGTCT

CGAAAATTGATTAATGGTATTAGGGATAAGCAATCTGGCAAAACAATATTA

GATTTTTTGAAATCAGATGGTTTTGCCAATCGCAATTTTATGCAGCTGATC

CATGATGATAGTTTGACATTTAAAGAAGACATTCAAAAAGCACAAGTGTCT

GGACAAGGCGATAGTTTACATGAACATATTGCAAATTTAGCTGGTAGCCCT

GCTATTAAAAAGGTATTTTACAGACTGTAAAAGTTGTTGATGAATTGGTC

AAAGTAATGGGCGGCATAAGCCAGAAAATATCGTTATTGAAATGGCACGT

GAAAATCAGACAACTCAAAAGGGCCAGAAAAATTCGCGAGAGCGTATGAAA

CGAATCGAAGAAGGTATCAAAGAATTAGGAAGTCAGATTCTTAAAGAGCAT

CCTGTTGAAAATACTCAATTGCAAATGAAAAGCTCTATCTCTATTATCTC

CAAAATGGAAGAGACATGTATGTGGACCAAGAATTAGATATTAATCGTTTA

AGTGATTATGATGTCGATCACATTGTTCCACAAAGTTTCCTTAAAGACGAT

TCAATAGACAATAAGGTCTTAACGCGTTCTGATAAAAATCGTGGTAAATCG

GATAACGTTCCAAGTGAAGAAGTAGTCAAAAAGATGAAAAACTATTGGAGA

CAACTTCTAAACGCCAAGTTAATCACTCAACGTAAGTTTGATAATTTAACG

AAAGCTGAACGTGGAGGTTTGAGTGAACTTGATAAAGCTGGTTTTATCAAA

CGCCAATTGGTTGAAACTCGCCAAATCACTAAGCATGTGGCACAAATTTTG

GATAGTCGCATGAATACTAAATACGATGAAAATGATAAACTTATTCGAGAG

GTTAAAGTGATTACCTTAAAATCTAAATTAGTTTCTGACTTCCGAAAAGAT

TTCCAATTCTATAAAGTACGTGAGATTAACAATTACCATCATGCCCATGAT

GCGTATCTAAATGCCGTCGTTGGAACTGCTTTGATTAAGAAATATCCAAAA

CTTGAATCGGAGTTTGTCTATGGTGATTATAAAGTTTATGATGTTCGTAAA

ATGATTGCTAAGTCTGAGCAAGAAATAGGCAAAGCAACCGCAAAATATTTC

TTTTACTCTAATATCATGAACTTCTTCAAAACAGAAATTACACTTGCAAAT

GGAGAGATTCGCAAACGCCCTCTAATCGAAACTAATGGGGAAACTGGAGAA

ATTGTCTGGGATAAAGGGCGAGATTTTGCCACAGTGCGCAAAGTATTGTCC

ATGCCCCAAGTCAATATTGTCAAGAAAACAGAAGTACAGACAGGCGGATTC

TCCAAGGAGTCAATTTTACCAAAAAGAAATTCGGACAAGCTTATTGCTCGT

AAAAAAGACTGGGATCCAAAAAAATATGGTGGTTTTGATAGTCCAACGGTA

GCTTATTCAGTCCTAGTGGTTGCTAAGGTGGAAAAAGGGAAATCGAAGAAG

TTAAAATCCGTTAAAGAGTTACTAGGGATCACAATTATGGAAAGAAGTTCC

TTTGAAAAAAATCCGATTGACTTTTTAGAAGCTAAAGGATATAAGGAAGTT

AAAAAAGACTTAATCATTAAACTACCTAAATATAGTCTTTTTGAGTTAGAA

AACGGTCGTAAACGGATGCTGGCTAGTGCCGGAGAATTACAAAAAGGAAAT

```
GAGCTGGCTCTGCCAAGCAAATATGTGAATTTTTTATATTTAGCTAGTCAT

TATGAAAAGTTGAAGGGTAGTCCAGAAGATAACGAACAAAAACAATTGTTT

GTGGAGCAGCATAAGCATTATTTAGATGAGATTATTGAGCAAATCAGTGAA

TTTTCTAAGCGTGTTATTTTAGCAGATGCCAATTTAGATAAAGTTCTTAGT

GCATATAACAAACATAGAGACAAACCAATACGTGAACAAGCAGAAAATATT

ATTCATTTATTTACGTTGACGAATCTTGGAGCTCCCGCTGCTTTTAAATAT

TTTGATACAACAATTGATCGTAAACGATATACGTCTACAAAAGAAGTTTTA

GATGCCACTCTTATCCATCAATCCATCACTGGTCTTTATGAAACACGCATT

GATTTGAGTCAGCTAGGAGGTGACTGA (SEQ ID NO: 10)
MDKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVS

GQGDSLHEHIANLAGSPAIKKGILQTVKVVDELVKVMGRHKPENIVIEMAR

ENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKS

DNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD
(single underline: HNH domain; double underline:
RuvC domain)
```

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria. meningitidis* (NCBI Ref: YP_002342100.1) or to a Cas9 from any of the organisms listed in Example 5.

In some embodiments, dCas9 corresponds to, or comprises in part or in whole, a Cas9 amino acid sequence having one or more mutations that inactivate the Cas9 nuclease activity. For example, in some embodiments, a dCas9 domain comprises D10A and/or H840A mutation. dCas9 (D10A and H840A):

```
                                            (SEQ ID NO: 9)
MDKKYSIGLAIGTNSVGWAVITDEYKVPSKKFKVLGNTDRHSIKKNLIGALLFDS

GETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQ

YADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYYVGPLARGNSR

FAWMTRKSEETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKEDYFKKIEC

FDSVETSGVEDRFNASLGTYHDLLKIIKDKDFLDNEENEDILEDIVLTLTLFEDREMIEE

RLKTYAHLFDDKVMKQLKRRRYTGWGRLSRKLINGIRDKQSGKTILDFLKSDGFAN

RNFMQLIHDDSLTFKEDIQKAQVSGQGDSLHEHIANLAGSPAIKKGILQTVKVVDEL
```

-continued

VKVMGRHKPENIVIEMARENQTTQKGQKNSRERMKRIEEGIKELGSQILKEHPVE

NTQLCINEKLYLYYLCINGRDMYVDQELDINRLSDYDVDAIVPQSFLKDDSIDNKV

LTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMI

AKSEQEIGKATAKYFFYSNIMNFFKTEITLANGEIRKRPLIETNGETGEIVWDKGRDF

ATVRKVLSMPQVNIVKKTEVQTGGFSKESILPKRNSDKLIARKKDWDPKKYGGFDSP

TVAYSVLVVAKVEKGKSKKLKSVKELLGITIMERSSFEKNPIDFLEAKGYKEVKKDLI

IKLPKYSLFELENGRKRMLASAGELQKGNELALPSKYVNFLYLASHYEKLKGSPEDN

EQKQLFVEQHKHYLDEIIEQISEFSKRVILADANLDKVLSAYNKHRDKPIREQAENIIH

LFTLTNLGAPAAFKYFDTTIDRKRYTSTKEVLDATLIHQSITGLYETRIDLSQLGGD
(single underline: HNH domain; double underline: RuvC domain).

In some embodiments, the Cas9 domain comprises a D10A mutation, while the residue at position 840 remains a histidine in the amino acid sequence provided in SEQ ID NO: 10, or at corresponding positions in any of the amino acid sequences provided in SEQ ID NOs: 11-260. Without wishing to be bound by any particular theory, the presence of the catalytic residue H840 restores the acvitity of the Cas9 to cleave the non-edited (e.g., non-deaminated) strand containing a G opposite the targeted C. Restoration of H840 (e.g., from A840) does not result in the cleavage of the target strand containing the C. Such Cas9 variants are able to generate a single-strand DNA break (nick) at a specific location based on the gRNA-defined target sequence, leading to repair of the non-edited strand, ultimately resulting in a G to A change on the non-edited strand. A schematic representation of this process is shown in FIG. 108. Briefly, the C of a C-G basepair can be deaminated to a U by a deaminase, e.g., an APOBEC deamonase. Nicking the non-edited strand, having the G, facilitates removal of the G via mismatch repair mechanisms. UGI inhibits UDG, which prevents removal of the U.

In other embodiments, dCas9 variants having mutations other than D10A and H840A are provided, which, e.g., result in nuclease inactivated Cas9 (dCas9). Such mutations, by way of example, include other amino acid substitutions at D10 and H820, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 10) are provided which are at least about 70% identical, at least about 80% identical, at least about 90% identical, at least about 95% identical, at least about 98% identical, at least about 99% identical, at least about 99.5% identical, or at least about 99.9% identical to SEQ ID NO: 10. In some embodiments, variants of dCas9 (e.g., variants of SEQ ID NO: 10) are provided having amino acid sequences which are shorter, or longer than SEQ ID NO: 10, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some embodiments, Cas9 fusion proteins as provided herein comprise the full-length amino acid sequence of a Cas9 protein, e.g., one of the Cas9 sequences provided herein. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all. Exemplary amino acid sequences of suitable Cas9 domains and Cas9 fragments are provided herein, and additional suitable sequences of Cas9 domains and fragments will be apparent to those of skill in the art.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

The term "deaminase" or "deaminase domain," as used herein, refers to a protein or enzyme that catalyzes a deamination reaction. In some embodiments, the deaminase or deaminase domain is a cytidine deaminase, catalyzing the hydrolytic deamination of cytidine or deoxycytidine to uridine or deoxyuridine, respectively. In some embodiments, the deaminase or deaminase domain is a cytidine deaminase domain, catalyzing the hydrolytic deamination of cytosine to uracil. In some embodiments, the deaminase or deaminase domain is a naturally-occurring deaminase from an organism, such as a human, chimpanzee, gorilla, monkey, cow, dog, rat, or mouse. In some embodiments, the deaminase or deaminase domain is a variant of a naturally-occurring deaminase from an organism, that does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring deaminase from an organism.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a fusion protein provided herein, e.g., of a fusion protein comprising a nuclease-inactive Cas9 domain and a nucleic acid editing domain (e.g., a deaminase domain) may refer to the amount of the fusion protein that is sufficient to induce editing of a target site specifically bound and edited by the fusion protein. As will be appreciated by the skilled artisan, the effective amount of an agent, e.g., a fusion protein, a nuclease, a deaminase, a recombinase, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

The term "linker," as used herein, refers to a chemical group or a molecule linking two molecules or moieties, e.g., two domains of a fusion protein, such as, for example, a nuclease-inactive Cas9 domain and a nucleic acid editing domain (e.g., a deaminase domain). In some embodiments, a linker joins a gRNA binding domain of an RNA-programmable nuclease, including a Cas9 nuclease domain, and the catalytic domain of a nucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "nucleic acid editing domain," as used herein refers to a protein or enzyme capable of making one or more modifications (e.g., deamination of a cytidine residue) to a nucleic acid (e.g., DNA or RNA). Exemplary nucleic acid editing domains include, but are not limited to a deaminase, a nuclease, a nickase, a recombinase, a methyltransferase, a methylase, an acetylase, an acetyltransferase, a transcriptional activator, or a transcriptional repressor domain. In some embodiments the nucleic acid editing domain is a deaminase (e.g., a cytidine deaminase, such as an APOBEC or an AID deaminase).

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4$^{th}$ ed., Cold Spring Harbor Laboratory Press, Cold Spring Harbor, N.Y. (2012)), the entire contents of which are incorporated herein by reference.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is identical or homologous to a tracrRNA as provided in Jinek et al., *Science* 337:816-821(2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof," and U.S. Provisional Patent Application, U.S. Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2), and may be referred to as an "extended gRNA." For example, an extended gRNA will, e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to target DNA cleavage sites, these proteins are able to be targeted, in principle, to any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); *Mali*, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The term "target site" refers to a sequence within a nucleic acid molecule that is deaminated by a deaminase or a fusion protein comprising a deaminase, (e.g., a dCas9-deaminase fusion protein provided herein).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

The term "nucleobase editors (NBEs)" or "base editors (BEs)," as used herein, refers to the Cas9 fusion proteins described herein. In some embodiments, the fusion protein comprises a nuclease-inactive Cas9 (dCas9) fused to a deaminase. In some embodiments, the fusion protein comprises a Cas9 nickase fused to a deaminase. In some embodiments, the fusion protein comprises a nuclease-inactive Cas9 fused to a deaminase and further fused to a UGI domain. In some embodiments, the fusion protein comprises a Cas9 nickase fused to a deaminase and further fused to a UGI domain. In some embodiments, the dCas9 of the fusion protein comprises a D10A and a H840A mutation of SEQ ID NO: 10, or a corresponding mutation in any of SEQ ID NOs: 11-260, which inactivates nuclease activity of the Cas9 protein. In some embodiments, the fusion protein comprises a D10A mutation and comprises a histidine at residue 840 of SEQ ID NO: 10, or a corresponding mutation in any of SEQ ID NOs: 11-260, which renders Cas9 capable of cleaving only one strand of a nucleic acid duplex. An example of a Cas9 nickase is shown below in SEQ ID NO: 674. The terms "nucleobase editors (NBEs)" and "base editors (BEs)" may be used interchangeably.

The term "uracil glycosylase inhibitor" or "UGI," as used herein, refers to a protein that is capable of inhibiting a uracil-DNA glycosylase base-excision repair enzyme.

The term "Cas9 nickase," as used herein, refers to a Cas9 protein that is capable of cleaving only one strand of a duplexed nucleic acid molecule (e.g., a duplexed DNA molecule). In some embodiments, a Cas9 nickase comprises a D10A mutation and has a histidine at position H840 of SEQ ID NO: 10, or a corresponding mutation in any of SEQ ID NOs: 11-260. For example, a Cas9 nickase may comprise the amino acid sequence as set forth in SEQ ID NO: 674. Such a Cas9 nickase has an active HNH nuclease domain and is able to cleave the non-targeted strand of DNA, i.e., the strand bound by the gRNA. Further, such a Cas9 nickase has an inactive RuvC nuclease domain and is not able to cleave the targeted strand of the DNA, i.e., the strand where base editing is desired.

Exemplary Cas9 nickase (Cloning vector pPlatTET-gRNA2; Accession No. BAV54124).

(SEQ ID NO: 674)
MDKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVS

GQGDSLHEHIANLAGSPAIKKGILQTVKVVDELVKVMGRHKPENIVIEMAR

ENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKS

DNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD

DETAILED DESCRIPTION OF CERTAIN EMBODIMENTS OF THE INVENTION

Some aspects of this disclosure provide fusion proteins that comprise a domain capable of binding to a nucleotide sequence (e.g., a Cas9, or a Cpf1 protein) and an enzyme domain, for example, a DNA-editing domain, such as, e.g., a deaminase domain. The deamination of a nucleobase by a deaminase can lead to a point mutation at the respective residue, which is referred to herein as nucleic acid editing. Fusion proteins comprising a Cas9 variant or domain and a DNA editing domain can thus be used for the targeted editing of nucleic acid sequences. Such fusion proteins are useful for targeted editing of DNA in vitro, e.g., for the generation of mutant cells or animals; for the introduction of targeted mutations, e.g., for the correction of genetic defects in cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a subject. Typically, the Cas9 domain of the fusion proteins described herein does not have any nuclease activity but instead is a Cas9 fragment or a dCas9 protein or domain. Methods for the use of Cas9 fusion proteins as described herein are also provided.

Cas9 Domains of Nucleobase Editors

Non-limiting, exemplary Cas9 domains are provided herein. The Cas9 domain may be a nuclease active Cas9 domain, a nucleasae inactive Cas9 domain, or a Cas9 nickase. In some embodiments, the Cas9 domain is a nuclease active domain. For example, the Cas9 domain may be a Cas9 domain that cuts both strands of a duplexed nucleic acid (e.g., both strands of a duplexed DNA molecule). In some embodiments, the Cas9 domain comprises any one of the amino acid sequences as set forth in SEQ ID NOs: 10-263. In some embodiments the Cas9 domain comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in SEQ ID NOs: 10-263. In some embodiments, the Cas9 domain comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more or more mutations compared to any one of the amino acid sequences set forth in SEQ ID NOs: 10-263. In some embodiments, the Cas9 domain comprises an amino acid sequence that has at least 10, at least 15, at least 20, at least 30, at least 40, at least 50, at least 60, at least 70, at least 80, at least 90, at least 100, at least 150, at least 200, at least 250, at least 300, at least 350, at least 400, at least 500, at least 600, at least 700, at least 800, at least 900, at least 1000, at least 1100, or at least 1200 identical contiguous amino acid residues as compared to any one of the amino acid sequences set forth in SEQ ID NOs: 10-263.

In some embodiments, the Cas9 domain is a nuclease-inactive Cas9 domain (dCas9). For example, the dCas9 domain may bind to a duplexed nucleic acid molecule (e.g., via a gRNA molecule) without cleaving either strand of the duplexed nucleic acid molecule. In some embodiments, the nuclease-inactive dCas9 domain comprises a D10X mutation and a H840X mutation of the amino acid sequence set forth in SEQ ID NO: 10, or a corresponding mutation in any of the amino acid sequences provided in SEQ ID NOs: 11-260, wherein X is any amino acid change. In some embodiments, the nuclease-inactive dCas9 domain comprises a D10A mutation and a H840A mutation of the amino acid sequence set forth in SEQ ID NO: 10, or a corresponding mutation in any of the amino acid sequences provided in SEQ ID NOs: 11-260. As one example, a nuclease-inactive Cas9 domain comprises the amino acid sequence set forth in SEQ ID NO: 263 (Cloning vector pPlatTET-gRNA2, Accession No. BAV54124).

(SEQ ID NO: 263
MDKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRLE
ESFLVEEDKKHERHPIFGNIVDEVAYHEKYPTIYHLRKKLVDSTDKADLRL
IYLALAHMIKFRGHFLIEGDLNPDNSDVDKLFIQLVQTYNQLFEENPINAS
GVDAKAILSARLSKSRRLENLIAQLPGEKKNGLFGNLIALSLGLTPNFKSN
FDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGN
SRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTV
KQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVS
GQGDSLHEHIANLAGSPAIKKGILQTVKVVDELVKVMGRHKPENIVIEMAR
ENQTTQKGQKNSRERMKRIEEGIKELGSQILKEHPVENTQLQNEKLYLYYL
QNGRDMYVDQELDINRLSDYDVDAIVPQSFLKDDSIDNKVLTRSDKNRGKS
DNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKD
FQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGE
IVWDKGRDFATVRKVLSMPQVNIVKKTEVQTGGFSKESILPKRNSDKLIAR
KKDWDPKKYGGFDSPTVAYSVLVVAKVEKGKSKKLKSVKELLGITIMERSS
FEKNPIDFLEAKGYKEVKKDLIIKLPKYSLFELENGRKRMLASAGELQKGN
ELALPSKYVNFLYLASHYEKLKGSPEDNEQKQLFVEQHKHYLDEIIEQISE
FSKRVILADANLDKVLSAYNKHRDKPIREQAENIIHLFTLTNLGAPAAFKY
FDTTIDRKRYTSTKEVLDATLIHQSITGLYETRIDLSQLGGD;

see e.g., Qi et al., Repurposing CRISPR as an RNA-guided platform for sequence-specific control of gene expression. Cell. 2013; 152(5):1173-83, the entire contents of which are incorporated herein by reference).

Additional suitable nuclease-inactive dCas9 domains will be apparent to those of skill in the art based on this disclosure and knowledge in the field, and are within the scope of this disclosure. Such additional exemplary suitable nuclease-inactive Cas9 domains include, but are not limited to, D10A/H840A, D10A/D839A/H840A, and D10A/D839A/H840A/N863A mutant domains (See, e.g., Prashant et al., CAS9 transcriptional activators for target specificity screening and paired nickases for cooperative genome engineering. *Nature Biotechnology.* 2013; 31(9): 833-838, the entire contents of which are incorporated herein by reference). In some embodiments the dCas9 domain comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the dCas9 domains provided herein. In some embodiments, the Cas9 domain comprises an amino acid sequences that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more or more mutations compared to any one of the amino acid sequences set forth in SEQ ID NOs: 10-263. In some embodiments, the Cas9 domain comprises an amino acid sequence that has at least 10, at least 15, at least 20, at least 30, at least 40, at least 50, at least 60, at least 70, at least 80, at least 90, at least 100, at least 150, at least 200, at least 250, at least 300, at least 350, at least 400, at least 500, at least 600, at least 700, at least 800, at least 900, at least 1000, at least 1100, or at least 1200 identical contiguous amino acid residues as compared to any one of the amino acid sequences set forth in SEQ ID NOs: 10-263.

In some embodiments, the Cas9 domain is a Cas9 nickase. The Cas9 nickase may be a Cas9 protein that is capable of cleaving only one strand of a duplexed nucleic acid molecule (e.g., a duplexed DNA molecule). In some embodiments the Cas9 nickase cleaves the target strand of a duplexed nucleic acid molecule, meaning that the Cas9 nickase cleaves the strand that is base paired to (complementary to) a gRNA (e.g., an sgRNA) that is bound to the Cas9. In some embodiments, a Cas9 nickase comprises a D10A mutation and has a histidine at position 840 of SEQ ID NO: 10, or a mutation in any of SEQ ID NOs: 11-260. For example, a Cas9 nickase may comprise the amino acid sequence as set forth in SEQ ID NO: 674. In some embodiments the Cas9 nickase cleaves the non-target, non-base-edited strand of a duplexed nucleic acid molecule, meaning that the Cas9 nickase cleaves the strand that is not base paired to a gRNA (e.g., an sgRNA) that is bound to the Cas9. In some embodiments, a Cas9 nickase comprises an H840A mutation and has an aspartic acid residue at position 10 of SEQ ID NO: 10, or a corresponding mutation in any of SEQ ID NOs: 11-260. In some embodiments the Cas9 nickase comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the Cas9 nickases provided herein. Additional suitable Cas9 nickases will be apparent to those of skill in the art based on this disclosure and knowledge in the field, and are within the scope of this disclosure.

Cas9 Domains with Reduced PAM Exclusivity

Some aspects of the disclosure provide Cas9 domains that have different PAM specificities. Typically, Cas9 proteins, such as Cas9 from *S. pyogenes* (spCas9), require a canonical NGG PAM sequence to bind a particular nucleic acid region. This may limit the ability to edit desired bases within a genome. In some embodiments, the base editing fusion proteins provided herein may need to be placed at a precise location, for example where a target base is placed within a 4 base region (e.g., a "deamination window"), which is approximately 15 bases upstream of the PAM. See Komor, A. C., et al., "Programmable editing of a target base in genomic DNA without double-stranded DNA cleavage" *Nature* 533, 420-424 (2016), the entire contents of which are hereby incorporated by reference. Accordingly, in some embodiments, any of the fusion proteins provided herein may contain a Cas9 domain that is capable of binding a nucleotide sequence that does not contain a canonical (e.g., NGG) PAM sequence. Cas9 domains that bind to non-canonical PAM sequences have been described in the art and would be apparent to the skilled artisan. For example, Cas9 domains that bind non-canonical PAM sequences have been described in Kleinstiver, B. P., et al., "Engineered CRISPR-Cas9 nucleases with altered PAM specificities" *Nature* 523, 481-485 (2015); and Kleinstiver, B. P., et al., "Broadening the targeting range of *Staphylococcus aureus* CRISPR-Cas9 by modifying PAM recognition" *Nature Biotechnology* 33, 1293-1298 (2015); the entire contents of each are hereby incorporated by reference.

In some embodiments, the Cas9 domain is a Cas9 domain from *Staphylococcus aureus* (SaCas9). In some embodiments, the SaCas9 domain is a nuclease active SaCas9, a nuclease inactive SaCas9 (SaCas9d), or a SaCas9 nickase (SaCas9n). In some embodiments, the SaCas9 comprises the amino acid sequence SEQ ID NO: 4273. In some embodiments, the SaCas9 comprises a N579X mutation of SEQ ID NO: 4273, or a corresponding mutation in any of the amino acid sequences provided in SEQ ID NOs: 11-260, wherein X is any amino acid except for N. In some embodiments, the SaCas9 comprises a N579A mutation of SEQ ID NO: 4273, or a corresponding mutation in any of the amino acid sequences provided in SEQ ID NOs: 11-260. In some embodiments, the SaCas9 domain, the SaCas9d domain, or the SaCas9n domain can bind to a nucleic acid sequence having a non-canonical PAM. In some embodiments, the SaCas9 domain, the SaCas9d domain, or the SaCas9n domain can bind to a nucleic acid sequence having a NNGRRT PAM sequence. In some embodiments, the SaCas9 domain comprises one or more of a E781X, a N967X, and a R1014X mutation of SEQ ID NO: 4273, or a corresponding mutation in any of the amino acid sequences provided in SEQ ID NOs: 11-260, wherein X is any amino acid. In some embodiments, the SaCas9 domain comprises one or more of a E781K, a N967K, and a R1014H mutation of SEQ ID NO: 4273, or one or more corresponding mutation in any of the amino acid sequences provided in SEQ ID NOs: 11-260. In some embodiments, the SaCas9 domain comprises a E781K, a N967K, or a R1014H mutation of SEQ ID NO: 4273, or corresponding mutations in any of the amino acid sequences provided in SEQ ID NOs: 11-260.

In some embodiments, the Cas9 domain of any of the fusion proteins provided herein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of SEQ ID NOs: 4273-4275. In some embodiments, the Cas9 domain of any of the fusion proteins provided herein comprises the amino acid sequence of any one of SEQ ID NOs: 4273-4275. In some embodiments, the Cas9 domain of any of the fusion proteins provided herein consists of the amino acid sequence of any one of SEQ ID NOs: 4273-4275.

Exemplary SaCas9 sequence
(SEQ ID NO: 4273)
KRNYILGLDIGITSVGYGIIDYETRDVIDAGVRLFKEANVENNEGRRSKRG

ARRLKRRRRHRIQRVKKLLFDYNLLTDHSELSGINPYEARVKGLSQKLSEE

EFSAALLHLAKRRGVHNVNEVEEDTGNELSTKEQISRNSKALEEKYVAELQ

LERLKKDGEVRGSINRFKTSDYVKEAKQLLKVQKAYHQLDQSFIDTYIDLL

ETRRTYYEGPGEGSPFGWKDIKEWYEMLMGHCTYFPEELRSVKYAYNADLY

NALNDLNNLVITRDENEKLEYYEKFQIIENVFKQKKKPTLKQIAKEILVNE

EDIKGYRVTSTGKPEFTNLKVYHDIKDITARKEIIENAELLDQIAKILTIY

QSSEDIQEELTNLNSELTQEEIEQISNLKGYTGTHNLSLKAINLILDELWH

```
TNDNQIAIFNRLKLVPKKVDLSQQKEIPTTLVDDFILSPVVKRSFIQSIKV

INAIIKKYGLPNDIIIELAREKNSKDAQKMINEMQKRNRQTNERIEEIIRT

TGKENAKYLIEKIKLHDMQEGKCLYSLEAIPLEDLLNNPFNYEVDHIIPRS

VSFDNSFNNKVLVKQEENSKKGNRTPFQYLSSSDSKISYETFKKHILNLAK

GKGRISKTKKEYLLEERDINRFSVQKDFINRNLVDTRYATRGLMNLLRSYF

RVNNLDVKVKSINGGFTSFLRRKWKFKKERNKGYKHHAEDALIIANADFIF

KEWKKLDKAKKVMENQMFEEKQAESMPEIETEQEYKEIFITPHQIKHIKDF

KDYKYSHRVDKKPNRELINDTLYSTRKDDKGNTLIVNNLNGLYDKDNDKLK

KLINKSPEKLLMYHHDPQTYQKLKLIMEQYGDEKNPLYKYYEETGNYLTKY

SKKDNGPVIKKIKYYGNKLNAHLDITDDYPNSRNKVVKLSLKPYRFDVYLD

NGVYKFVTVKNLDVIKKENYYEVNSKCYEEAKKLKKISNQAEFIASFYNND

LIKINGELYRVIGVNNDLLNRIEVNMIDITYREYLENMNDKRPPRIIKTIA

SKTQSIKKYSTDILGNLYEVKSKKHPQIIKKG
```

Residue N579 of SEQ ID NO: 4273, which is underlined and in bold, may be mutated (e.g., to a A579) to yield a SaCas9 nickase.

```
Exemplary SaCas9n sequence
                                          (SEQ ID NO: 4274)
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTKEQISRNSKALEEKYVA

ELQLERLKKDGEVRGSINRFKTSDYVKEAKQLLKVQKAYHQLDQSFIDTY

IDLLETRRTYYEGPGEGSPFGWKDIKEWYEMLMGHCTYFPEELRSVKYAY

NADLYNALNDLNNLVITRDENEKLEYYEKFQIIENVFKQKKKPTLKQIAK

EILVNEEDIKGYRVTSTGKPEFTNLKVYHDIKDITARKEIIENAELLDQI

AKILTIYQSSEDIQEELTNLNSELTQEEIEQISNLKGYTGTHNLSLKAIN

LILDELWHTNDNQIAIFNRLKLVPKKVDLSQQKEIPTTLVDDFILSPVVK

RSFIQSIKVINAIIKKYGLPNDIIIELAREKNSKDAQKMINEMQKRNRQT

NERIEEIIRTTGKENAKYLIEKIKLHDMQEGKCLYSLEAIPLEDLLNNPF

NYEVDHIIPRSVSFDNSFNNKVLVKQEEASKKGNRTPFQYLSSSDSKISY

ETFKKHILNLAKGKGRISKTKKEYLLEERDINRFSVQKDFINRNLVDTRY

ATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYK

EIFITPHQIKHIKDFKDYKYSHRVDKKPNRELINDTLYSTRKDDKGNTLI

VNNLNGLYDKDNDKLKKLINKSPEKLLMYHHDPQTYQKLKLIMEQYGDEK

NPLYKYYEETGNYLTKYSKKDNGPVIKKIKYYGNKLNAHLDITDDYPNSR

NKVVKLSLKPYRFDVYLDNGVYKFVTVKNLDVIKKENYYEVNSKCYEEAK

KLKKISNQAEFIASFYNNDLIKINGELYRVIGVNNDLLNRIEVNMIDITY

REYLENMNDKRPPRIIKTIASKTQSIKKYSTDILGNLYEVKSKKHPQIIK

KG.
```

Residue A579 of SEQ ID NO: xx, which can be mutated from N579 of SEQ ID NO: 4274 to yield a SaCas9 nickase, is underlined and in bold.

```
Exemplary SaKKH Cas9
                                          (SEQ ID NO: 4275)
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTKEQISRNSKALEEKYVA

ELQLERLKKDGEVRGSINRFKTSDYVKEAKQLLKVQKAYHQLDQSFIDTY

IDLLETRRTYYEGPGEGSPFGWKDIKEWYEMLMGHCTYFPEELRSVKYAY

NADLYNALNDLNNLVITRDENEKLEYYEKFQIIENVFKQKKKPTLKQIAK

EILVNEEDIKGYRVTSTGKPEFTNLKVYHDIKDITARKEIIENAELLDQI

AKILTIYQSSEDIQEELTNLNSELTQEEIEQISNLKGYTGTHNLSLKAIN

LILDELWHTNDNQIAIFNRLKLVPKKVDLSQQKEIPTTLVDDFILSPVVK

RSFIQSIKVINAIIKKYGLPNDIIIELAREKNSKDAQKMINEMQKRNRQT

NERIEEIIRTTGKENAKYLIEKIKLHDMQEGKCLYSLEAIPLEDLLNNPF

NYEVDHIIPRSVSFDNSFNNKVLVKQEEASKKGNRTPFQYLSSSDSKISY

ETFKKHILNLAKGKGRISKTKKEYLLEERDINRFSVQKDFINRNLVDTRY

ATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYK

EIFITPHQIKHIKDFKDYKYSHRVDKKPNRKLINDTLYSTRKDDKGNTLI

VNNLNGLYDKDNDKLKKLINKSPEKLLMYHHDPQTYQKLKLIMEQYGDEK

NPLYKYYEETGNYLTKYSKKDNGPVIKKIKYYGNKLNAHLDITDDYPNSR

NKVVKLSLKPYRFDVYLDNGVYKFVTVKNLDVIKKENYYEVNSKCYEEAK

KLKKISNQAEFIASFYKNDLIKINGELYRVIGVNNDLLNRIEVNMIDITY

REYLENMNDKRPPHIIKTIASKTQSIKKYSTDILGNLYEVKSKKHPQIIK

KG.
```

Residue A579 of SEQ ID NO: 4275, which can be mutated from N579 of SEQ ID NO: 4275 to yield a SaCas9 nickase, is underlined and in bold. Residues K781, K967, and H1014 of SEQ ID NO: 4275, which can be mutated from E781, N967, and R1014 of SEQ ID NO: 4275 to yield a SaKKH Cas9 are underlined and in italics.

In some embodiments, the Cas9 domain is a Cas9 domain from *Streptococcus pyogenes* (SpCas9). In some embodiments, the SpCas9 domain is a nuclease active SpCas9, a nuclease inactive SpCas9 (SpCas9d), or a SpCas9 nickase (SpCas9n). In some embodiments, the SpCas9 comprises the amino acid sequence SEQ ID NO: 4276. In some embodiments, the SpCas9 comprises a D9X mutation of SEQ ID NO: 4276, or a corresponding mutation in any of the amino acid sequences provided in SEQ ID NOs: 11-260, wherein X is any amino acid except for D. In some embodiments, the SpCas9 comprises a D9A mutation of SEQ ID NO: 4276, or a corresponding mutation in any of the amino acid sequences provided in SEQ ID NOs: 11-260. In some embodiments, the SpCas9 domain, the SpCas9d domain, or the SpCas9n domain can bind to a nucleic acid sequence having a non-canonical PAM. In some embodiments, the SpCas9 domain, the SpCas9d domain, or the SpCas9n domain can bind to a nucleic acid sequence having a NGG, a NGA, or a NGCG PAM sequence. In some embodiments, the SpCas9 domain comprises one or more of a D1134X, a R1334X, and a T1336X mutation of SEQ ID NO: 4276, or a corresponding mutation in any of the amino acid sequences provided in SEQ ID NOs: 11-260, wherein X is any amino acid. In some embodiments, the SpCas9 domain comprises one or more of a D1134E, R1334Q, and T1336R mutation of SEQ ID NO: 4276, or a corresponding mutation in any of the amino acid sequences provided in SEQ ID NOs: 11-260. In some embodiments, the SpCas9 domain comprises a D1134E, a R1334Q, and a T1336R mutation of SEQ ID NO: 4276, or corresponding mutations in any of the amino acid sequences provided in SEQ ID NOs: 11-260. In some embodiments, the SpCas9 domain comprises one or more of a D1134X, a R1334X, and a T1336X mutation of SEQ ID NO: 4276, or a corresponding mutation in any of the amino acid sequences provided in SEQ ID NOs: 11-260, wherein X is any amino acid. In some embodiments, the SpCas9 domain comprises one or more of a D1134V, a R1334Q, and a T1336R mutation of SEQ ID NO: 4276, or a corresponding mutation in any of the amino acid sequences provided in SEQ ID NOs: 11-260. In some embodiments, the SpCas9 domain comprises a D1134V, a R1334Q, and a T1336R mutation of SEQ ID NO: 4276, or corresponding mutations in any of the amino acid sequences provided in SEQ ID NOs: 11-260. In some embodiments, the SpCas9 domain comprises one or more of a D1134X, a G1217X, a R1334X, and a T1336X mutation of SEQ ID NO: 4276, or a corresponding mutation in any of the amino acid sequences provided in SEQ ID NOs: 11-260, wherein X is any amino acid. In some embodiments, the SpCas9 domain comprises one or more of a D1134V, a G1217R, a R1334Q, and a T1336R mutation of SEQ ID NO: 4276, or a corresponding mutation in any of the amino acid sequences provided in SEQ ID NOs: 11-260. In some embodiments, the SpCas9 domain comprises a D1134V, a G1217R, a R1334Q, and a T1336R mutation of SEQ ID NO: 4276, or corresponding mutations in any of the amino acid sequences provided in SEQ ID NOs: 11-260.

In some embodiments, the Cas9 domain of any of the fusion proteins provided herein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of SEQ ID NOs: 4276-4280. In some embodiments, the Cas9 domain of any of the fusion proteins provided herein comprises the amino acid sequence of any one of SEQ ID NOs: 4276-4280. In some embodiments, the Cas9 domain of any of the fusion proteins provided herein consists of the amino acid sequence of any one of SEQ ID NOs: 4276-4280.

Exemplary SpCas9
(SEQ ID NO: 4276)
DKKYSIGLDIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYF

DTTIDRKRYTSTKEVLDATLIHQSITGLYETRIDLSQLGGD

Exemplary SpCas9n
(SEQ ID NO: 4277)
DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYF

DTTIDRKRYTSTKEVLDATLIHQSITGLYETRIDLSQLGGD

Exemplary SpEQR Cas9

(SEQ ID NO: 4278)

DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFESPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYF

DTTIDRKQYRSTKEVLDATLIHQSITGLYETRIDLSQLGGD

Residues E1134, Q1334, and R1336 of SEQ ID NO: 4278, which can be mutated from D1134, R1334, and T1336 of SEQ ID NO: 4278 to yield a SpEQR Cas9, are underlined and in bold.

Exemplary SpVQR Cas9

(SEQ ID NO: 4279)

DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVETSGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFVSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKQYRSTKEVLDATLIHQS

ITGLYETRIDLSQLGGD

Residues V1134, Q1334, and R1336 of SEQ ID NO: 4279, which can be mutated from D1134, R1334, and T1336 of SEQ ID NO: 4279 to yield a SpVQR Cas9, are underlined and in bold.

Exemplary SpVRER Cas9

(SEQ ID NO: 4280)

DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVETSGVEDRFNASLGTYHDLLKII

-continued

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

-continued

TGGFSKESILPKRNSDKLIARKKDWDPKKYGGFVSPTVAYSVLVVAKVEK

GKSKKLKSVKELLGITIMERSSFEKNPIDFLEAKGYKEVKKDLIIKLPKY

SLFELENGRKRMLASARELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKEYRSTKEVLDATLIHQS

ITGLYETRIDLSQLGGD

Residues V1134, R1217, Q1334, and R1336 of SEQ ID NO: 4280, which can be mutated from D1134, G1217, R1334, and T1336 of SEQ ID NO: 4280 to yield a SpVRER Cas9, are underlined and in bold.

The following are exemplary fusion proteins (e.g., base editing proteins) capable of binding to a nucleic acid sequence having a non-canonical (e.g., a non-NGG) PAM sequence:

```
Exemplary SaBE3 (rAPOBEC1-XTEN-SaCas9n-UGI-NLS)
                                    (SEQ ID NO: 4281)
MSSETGPVAVDPTLRRRIEPHEFEVFFDPRELRKETCLLYEINWGGRHSIWRHTSQNTNKHVE

VNFIEKFTTERYFCPNTRCSITWFLSWSPCGECSRAITEFLSRYPHVTLFIYIARLYHHADPR

NRQGLRDLISSGVTIQIMTEQESGYCWRNFVNYSPSNEAHWPRYPHLWVRLYVLELYCIILGL

PPCLNILRRKQPQLTFFTIALQSCHYQRLPPHILWATGLKSGSETPGTSESATPESKRNYILG

LDIGITSVGYGIIDYETRDVIDAGVRLFKEANVENNEGRRSKRGARRLKRRRHRIQRVKKLL

FDYNLLTDHSELSGINPYEARVKGLSQKLSEEEFSAALLHLAKRRGVHNVNEVEEDTGNELST

KEQISRNSKALEEKYVAELQLERLKKDGEVRGSINRFKTSDYVKEAKQLLKVQKAYHQLDQSF

IDTYIDLLETRRTYYEGPGEGSPFGWKDIKEWYEMLMGHCTYFPEELRSVKYAYNADLYNALN

DLNNLVITRDENEKLEYYEKFQIIENVFKQKKKPTLKQIAKEILVNEEDIKGYRVTSTGKPEF

TNLKVYHDIKDITARKEIIENAELLDQIAKILTIYQSSEDIQEELTNLNSELTQEEIEQISNL

KGYTGTHNLSLKAINLILDELWHTNDNQIAIFNRLKLVPKKVDLSQQKEIPTTLVDDFILSPV

VKRSFIQSIKVINAIIKKYGLPNDIIIELAREKNSKDAQKMINEMQKRNRQTNERIEEIIRTT

GKENAKYLIEKIKLHDMQEGKCLYSLEAIPLEDLLNNPFNYEVDHIIPRSVSFDNSFNNKVLV

KQEEASKKGNRTPFQYLSSSDSKISYETFKKHILNLAKGKGRISKTKKEYLLEERDINRFSVQ

KDFINRNLVDTRYATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYKEIFITPHQIKHIK

DFKDYKYSHRVDKKPNRELINDTLYSTRKDDKGNTLIVNNLNGLYDKDNDKLKKLINKSPEKL

LMYHHDPQTYQKLKLIMEQYGDEKNPLYKYYEETGNYLTKYSKKDNGPVIKKIKYYGNKLNAH

LDITDDYPNSRNKVVKLSLKPYRFDVYLDNGVYKFVTVKNLDVIKKENYYEVNSKCYEEAKKL

KKISNQAEFIASFYNNDLIKINGELYRVIGVNNDLLNRIEVNMIDITYREYLENMNDKRPPRI

IKTIASKTQSIKKYSTDILGNLYEVKSKKHPQIIKKGSGGSTNLSDIIEKETGKQLVIQESIL

MLPEEVEEVIGNKPESDILVHTAYDESTDENVMLLTSDAPEYKPWALVIQDSNGENKIKMLSG

GSPKKKRKV

Exemplary SaKKH-BE3 (rAPOBEC1-XTEN-SaCas9n-UGI-NLS)
                                    (SEQ ID NO: 4282)
MSSETGPVAVDPTLRRRIEPHEFEVFFDPRELRKETCLLYEINWGGRHSIWRHTSQNTNKHVE

VNFIEKFTTERYFCPNTRCSITWFLSWSPCGECSRAITEFLSRYPHVTLFIYIARLYHHADPR

NRQGLRDLISSGVTIQIMTEQESGYCWRNFVNYSPSNEAHWPRYPHLWVRLYVLELYCIILGL
```

-continued

PPCLNILRRKQPQLTFFTIALQSCHYQRLPPHILWATGLKSGSETPGTSESATPES<u>KRNYILG</u>

<u>LDIGITSVGYGIIDYETRDVIDAGVRLFKEANVENNEGRRSKRGARRLKRRRRHRIQRVKKLL</u>

<u>FDYNLLTDHSELSGINPYEARVKGLSQKLSEEEFSAALLHLAKRRGVHNVNEVEEDTGNELST</u>

<u>KEQISRNSKALEEKYVAELQLERLKKDGEVRGSINRFKTSDYVKEAKQLLKVQKAYHQLDQSF</u>

<u>IDTYIDLLETRRTYYEGPGEGSPFGWKDIKEWYEMLMGHCTYFPEELRSVKYAYNADLYNALN</u>

<u>DLNNLVITRDENEKLEYYEKFQIIENVFKQKKKPTLKQIAKEILVNEEDIKGYRVTSTGKPEF</u>

<u>TNLKVYHDIKDITARKEIIENAELLDQIAKILTIYQSSEDIQEELTNLNSELTQEEIEQISNL</u>

<u>KGYTGTHNLSLKAINLILDELWHTNDNQIAIFNRLKLVPKKVDLSQQKEIPTTLVDDFILSPV</u>

<u>VKRSFIQSIKVINAIIKKYGLPNDIIIELAREKNSKDAQKMINEMQKRNRQTNERIEEIIRTT</u>

<u>GKENAKYLIEKIKLHDMQEGKCLYSLEAIPLEDLLNNPFNYEVDHIIPRSVSFDNSFNNKVLV</u>

<u>KQEEASKKGNRTPFQYLSSSDSKISYETFKKHILNLAKGKGRISKTKKEYLLEERDINRFSVQ</u>

<u>KDFINRNLVDTRYATRGLMNLLRSYFRVNNLDVKVKSINGGFTSFLRRKWKFKKERNKGYKHH</u>

<u>AEDALIIANADFIFKEWKKLDKAKKVMENQMFEEKQAESMPEIETEQEYKEIFITPHQIKHIK</u>

<u>DFKDYKYSHRVDKKPNR</u>KLINDTLYSTRKDDKGNTLIVNNLNGLYDKDNDKLKKLINKSPEKL

LMYHHDPQTYQKLKLIMEQYGDEKNPLYKYYEETGNYLTKYSKKDNGPVIKKIKYYGNKLNAH

LDITDDYPNSRNKVVKLSLKPYRFDVYLDNGVYKFVTVKNLDVIKKENYYEVNSKCYEEAKKL

KKISNQAEFIASFY<i>K</i>NDLIKINGELYRVIGVNNDLLNRIEVNMIDITYREYLENMNDKRPP<i>HI</i>

<u>IKTIASKTQSIKKYSTDILGNLYEVKSKKHPQIIKKGSGGSTNLSDIIEKETGKQLVIQESIL</u>

MLPEEVEEVIGNKPESDILVHTAYDESTDENVMLLTSDAPEYKPWALVIQDSNGENKIKMLSG

GSPKKKRKV

Exemplary EQR-BE3 (rAPOBEC1-XTEN-Cas9n-UGI-NLS)
(SEQ ID NO: 4283)
MSSETGPVAVDPTLRRRIEPHEFEVFFDPRELRKETCLLYEINWGGRHSIWRHTSQNTNKHVE

VNFIEKFTTERYFCPNTRCSITWFLSWSPCGECSRAITEFLSRYPHVTLFIYIARLYHHADPR

NRQGLRDLISSGVTIQIMTEQESGYCWRNFVNYSPSNEAHWPRYPHLWVRLYVLELYCIILGL

PPCLNILRRKQPQLTFFTIALQSCHYQRLPPHILWATGLKSGSETPGTSESATPES<u>DKKYSIG</u>

<u>LAIGTNSVGWAVITDEYKVPSKKFKVLGNTDRHSIKKNLIGALLFDSGETAEATRLKRTARRR</u>

<u>YTRRKNRICYLQEIFSNEMAKVDDSFFHRLEESFLVEEDKKHERHPIFGNIVDEVAYHEKYPT</u>

<u>IYHLRKKLVDSTDKADLRLIYLALAHMIKFRGHFLIEGDLNPDNSDVDKLFIQLVQTYNQLFE</u>

<u>ENPINASGVDAKAILSARLSKSRRLENLIAQLPGEKKNGLFGNLIALSLGLTPNFKSNFDLAE</u>

<u>DAKLQLSKDTYDDDLDNLLAQIGDQYADLFLAAKNLSDAILLSDILRVNTEITKAPLSASMIK</u>

<u>RYDEHHQDLTLLKALVRQQLPEKYKEIFFDQSKNGYAGYIDGGASQEEFYKFIKPILEKMDGT</u>

<u>EELLVKLNREDLLRKQRTFDNGSIPHQIHLGELHAILRRQEDFYPFLKDNREKIEKILTFRIP</u>

<u>YYVGPLARGNSRFAWMTRKSEETITPWNFEEVVDKGASAQSFIERMTNFDKNLPNEKVLPKHS</u>

<u>LLYEYFTVYNELTKVKYVTEGMRKPAFLSGEQKKAIVDLLFKTNRKVTVKQLKEDYFKKIECF</u>

<u>DSVEISGVEDRFNASLGTYHDLLKIIKDKDFLDNEENEDILEDIVLTLTLFEDREMIEERLKT</u>

<u>YAHLFDDKVMKQLKRRRYTGWGRLSRKLINGIRDKQSGKTILDFLKSDGFANRNFMQLIHDDS</u>

<u>LTFKEDIQKAQVSGQGDSLHEHIANLAGSPAIKKGILQTVKVVDELVKVMGRHKPENIVIEMA</u>

<u>RENQTTQKGQKNSRERMKRIEEGIKELGSQILKEHPVENTQLQNEKLYLYYLQNGRDMYVDQE</u>

<u>LDINRLSDYDVDHIVPQSFLKDDSIDNKVLTRSDKNRGKSDNVPSEEVVKKMKNYWRQLLNAK</u>

<u>LITQRKFDNLTKAERGGLSELDKAGFIKRQLVETRQITKHVAQILDSRMNTKYDENDKLIREV</u>

<u>KVITLKSKLVSDFRKDFQFYKVREINNYHHAHDAYLNAVVGTALIKKYPKLESEFVYGDYKVY</u>

DVRKMIAKSEQEIGKATAKYFFYSNIMNFFKTEITLANGEIRKRPLIETNGETGEIVWDKGRD

FATVRKVLSMPQVNIVKKTEVQTGGFSKESILPKRNSDKLIARKKDWDPKKYGGF*E*SPTVAYS

VLVVAKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNLGAPAAFKYFDTTI

DRK*Q*YRSTKEVLDATLIHQSITGLYETRIDLSQLGGDSGGSTNLSDIIEKETGKQLVIQESIL

MLPEEVEEVIGNKPESDILVHTAYDESTDENVMLLTSDAPEYKPWALVIQDSNGENKIKMLSG

GSPKKKRKV

VQR-BE3 (rAPOBEC1-XTEN-Cas9n-UGI-NLS)
(SEQ ID NO: 4284)

MSSETGPVAVDPTLRRRIEPHEFEVFFDPRELRKETCLLYEINWGGRHSIWRHTSQNTNKHVE

VNFIEKFTTERYFCPNTRCSITWFLSWSPCGECSRAITEFLSRYPHVTLFIYIARLYHHADPR

NRQGLRDLISSGVTIQIMTEQESGYCWRNFVNYSPSNEAHWPRYPHLWVRLYVLELYCIILGL

PPCLNILRRKQPQLTFFTIALQSCHYQRLPPHILWATGLKSGSETPGTSESATPESDKKYSIG

LAIGTNSVGWAVITDEYKVPSKKFKVLGNTDRHSIKKNLIGALLFDSGETAEATRLKRTARRR

YTRRKNRICYLQEIFSNEMAKVDDSFFHRLEESFLVEEDKKHERHPIFGNIVDEVAYHEKYPT

IYHLRKKLVDSTDKADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSLGLTPNFKSNFDLAE

DAKLQLSKDTYDDDLDNLLAQIGDQYADLFLAAKNLSDAILLSDILRVNTEITKAPLSASMIK

RYDEHHQDLTLLKALVRQQLPEKYKEIFFDQSKNGYAGYIDGGASQEEFYKFIKPILEKMDGT

EELLVKLNREDLLRKQRTFDNGSIPHQIHLGELHAILRRQEDFYPFLKDNREKIEKILTFRIP

YYVGPLARGNSRFAWMTRKSEETITPWNFEEVVDKGASAQSFIERMTNFDKNLPNEKVLPKHS

LLYEYFTVYNELTKVKYVTEGMRKPAFLSGEQKKAIVDLLFKTNRKVTVKQLKEDYFKKIECF

DSVEISGVEDRFNASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVMGRHKPENIVIEMA

RENQTTQKGQKNSRERMKRIEEGIKELGSQILKEHPVENTQLQNEKLYLYYLQNGRDMYVDQE

LDINRLSDYDVDHIVPQSFLKDDSIDNKVLTRSDKNRGKSDNVPSEEVVKKMKNYWRQLLNAK

LITQRKFDNLTKAERGGLSELDKAGFIKRQLVETRQITKHVAQILDSRMNTKYDENDKLIREV

KVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRD

FATVRKVLSMPQVNIVKKTEVQTGGFSKESILPKRNSDKLIARKKDWDPKKYGGF*V*SPTVAYS

VLVVAKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNLGAPAAFKYFDTTI

DRK*Q*YRSTKEVLDATLIHQSITGLYETRIDLSQLGGDSGGSTNLSDIIEKETGKQLVIQESIL

MLPEEVEEVIGNKPESDILVHTAYDESTDENVMLLTSDAPEYKPWALVIQDSNGENKIKMLSG

GSPKKKRKV

VRER-BE3 (rAPOBEC1-XTEN-Cas9n-UGI-NLS)
(SEQ ID NO: 4285)

MSSETGPVAVDPTLRRRIEPHEFEVFFDPRELRKETCLLYEINWGGRHSIWRHTSQNTNKHVE

VNFIEKFTTERYFCPNTRCSITWFLSWSPCGECSRAITEFLSRYPHVTLFIYIARLYHHADPR

-continued

```
NRQGLRDLISSGVTIQIMTEQESGYCWRNFVNYSPSNEAHWPRYPHLWVRLYVLELYCIILGL

PPCLNILRRKQPQLTFFTIALQSCHYQRLPPHILWATGLKSGSETPGTSESATPESDKKYSIG

LAIGTNSVGWAVITDEYKVPSKKFKVLGNTDRHSIKKNLIGALLFDSGETAEATRLKRTARRR

YTRRKNRICYLQEIFSNEMAKVDDSFFHRLEESFLVEEDKKHERHPIFGNIVDEVAYHEKYPT

IYHLRKKLVDSTDKADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSLGLTPNFKSNFDLAE

DAKLQLSKDTYDDDLDNLLAQIGDQYADLFLAAKNLSDAILLSDILRVNTEITKAPLSASMIK

RYDEHHQDLTLLKALVRQQLPEKYKEIFFDQSKNGYAGYIDGGASQEEFYKFIKPILEKMDGT

EELLVKLNREDLLRKQRTFDNGSIPHQIHLGELHAILRRQEDFYPFLKDNREKIEKILTFRIP

YYVGPLARGNSRFAWMTRKSEETITPWNFEEVVDKGASAQSFIERMTNFDKNLPNEKVLPKHS

LLYEYFTVYNELTKVKYVTEGMRKPAFLSGEQKKAIVDLLFKTNRKVTVKQLKEDYFKKIECF

DSVEISGVEDRFNASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVMGRHKPENIVIEMA

RENQTTQKGQKNSRERMKRIEEGIKELGSQILKEHPVENTQLQNEKLYLYYLQNGRDMYVDQE

LDINRLSDYDVDHIVPQSFLKDDSIDNKVLTRSDKNRGKSDNVPSEEVVKKMKNYWRQLLNAK

LITQRKFDNLTKAERGGLSELDKAGFIKRQLVETRQITKHVAQILDSRMNTKYDENDKLIREV

KVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRD

FATVRKVLSMPQVNIVKKTEVQTGGFSKESILPKRNSDKLIARKKDWDPKKYGGFVSPTVAYS

VLVVAKVEKGKSKKLKSVKELLGITIMERSSFEKNPIDFLEAKGYKEVKKDLIIKLPKYSLFE

LENGRKRMLASARELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNLGAPAAFKYFDTTI

DRK*EYRS*TKEVLDATLIHQSITGLYETRIDLSQLGGDSGGSTNLSDIIEKETGKQLVIQESIL

MLPEEVEEVIGNKPESDILVHTAYDESTDENVMLLTSDAPEYKPWALVIQDSNGENKIKMLSG

GSPKKKRKV
```

High Fidelity Base Editors

Some aspects of the disclosure provide Cas9 fusion proteins (e.g., any of the fusion proteins provided herein) comprising a Cas9 domain that has high fidelity. Additional aspects of the disclosure provide Cas9 fusion proteins (e.g., any of the fusion proteins provided herein) comprising a Cas9 domain with decreased electrostatic interactions between the Cas9 domain and a sugar-phosphate backbone of a DNA, as compared to a wild-type Cas9 domain. In some embodiments, a Cas9 domain (e.g., a wild type Cas9 domain) comprises one or more mutations that decreases the association between the Cas9 domain and a sugar-phosphate backbone of a DNA. In some embodiments, any of the Cas9 fusion proteins provided herein comprise one or more of a N497X, a R661X, a Q695X, and/or a Q926X mutation of the amino acid sequence provided in SEQ ID NO: 10, or a corresponding mutation in any of the amino acid sequences provided in SEQ ID NOs: 11-260, wherein X is any amino acid. In some embodiments, any of the Cas9 fusion proteins provided herein comprise one or more of a N497A, a R661A, a Q695A, and/or a Q926A mutation of the amino acid sequence provided in SEQ ID NO: 10, or a corresponding mutation in any of the amino acid sequences provided in SEQ ID NOs: 11-260. In some embodiments, the Cas9 domain comprises a D10A mutation of the amino acid sequence provided in SEQ ID NO: 10, or a corresponding mutation in any of the amino acid sequences provided in SEQ ID NOs: 11-260. In some embodiments, the Cas9 domain (e.g., of any of the fusion proteins provided herein) comprises the amino acid sequence as set forth in SEQ ID NO: 325. In some embodiments, the fusion protein comprises the amino acid sequence as set forth in SEQ ID NO: 285. Cas9 domains with high fidelity are known in the art and would be apparent to the skilled artisan. For example, Cas9 domains with high fidelity have been described in Kleinstiver, B. P., et al. "High-fidelity CRISPR-Cas9 nucleases with no detectable genome-wide off-target effects." *Nature* 529, 490-495 (2016); and Slaymaker, I. M., et al. "Rationally engineered Cas9 nucleases with improved specificity." *Science* 351, 84-88 (2015); the entire contents of each are incorporated herein by reference.

It should be appreciated that the base editors provided herein, for example base editor 2 (BE2) or base editor 3 (BE3), may be converted into high fidelity base editors by modifying the Cas9 domain as described herein to generate high fidelity base editors, for example high fidelity base editor 2 (HF-BE2) or high fidelity base editor 3 (HF-BE3). In some embodiments, base editor 2 (BE2) comprises a deaminase domain, a dCas9, and a UGI domain. In some embodiments, base editor 3 (BE3) comprises a deaminase domain an nCas9 domain and a UGI domain.

```
Cas9 domain where mutations relative to Cas9
of SEQ ID NO: 10 are shown in bold and
underlines
                                    (SEQ ID NO: 325)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTAFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGALSRKLINGIRDKQSGKTILDFLKSDGFANRNFMALIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRAITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

HF-BE3
                                    (SEQ ID NO: 285)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKSGSETPGTSESATPESDKKYS

IGLAIGTNSVGWAVITDEYKVPSKKFKVLGNTDRHSIKKNLIGALLFDSG

-continued
ETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYL

ALAHMIKFRGHFLIEGDLNPDNSDVDKLFIQLVQTYNQLFEENPINASGV

DAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSK

NGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLA

RGNSRFAWMTRKSEETITPWNFEEVVDKGASAQSFIERMTAFDKNLPNEK

VLPKHSLLYEYFTVYNELTKVKYVTEGMRKPAFLSGEQKKAIVDLLFKTN

RKVTVKQLKEDYFKKIECFDSVEISGVEDRFNASLGTYHDLLKIIKDKDF

LDNEENEDILEDIVLTLTLFEDREMIEERLKTYAHLFDDKVMKQLKRRRY

TGWGALSRKLINGIRDKQSGKTILDFLKSDGFANRNFMALIHDDSLTFKE

DIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKV

LTRSDKNRGKSDNVPSEEVVKKMKNYWRQLLNAKLITQRKFDNLTKAERG

GLSELDKAGFIKRQLVETRAITKHVAQILDSRMNTKYDENDKLIREVKVI

TLKSKLVSDFRKDFQFYKVREINNYHHAHDAYLNAVVGTALIKKYPKLES

EFVYGDYKVYDVRKMIAKSEQEIGKATAKYFFYSNIMNFFKTEITLANGE

IRKRPLIETNGETGEIVWDKGRDFATVRKVLSMPQVNIVKKTEVQTGGFS

KESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFEL

ENGRKRMLASAGELQKGNELALPSKYVNFLYLASHYEKLKGSPEDNEQKQ

LFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLY

ETRIDLSQLGGD
```

Cas9 Fusion Proteins

Any of the Cas9 domains (e.g., a nuclease active Cas9 protein, a nuclease-inactive dCas9 protein, or a Cas9 nickase protein) disclosed herein may be fused to a second protein, thus fusion proteins provided herein comprise a Cas9 domain as provided herein and a second protein, or a "fusion partner". In some embodiments, the second protein is fused to the N-terminus of the Cas9 domain. However, in other embodiments, the second protein is fused to the C-terminus of the Cas9 domain. In some embodiments, the second protein that is fused to the Cas9 domain is a nucleic acid editing domain. In some embodiments, the Cas9 domain and the nucleic acid editing domain are fused via a linker, while in other embodiments the Cas9 domain and the nucleic acid editing domain are fused directly to one another. In some embodiments, the linker comprises $(GGGS)_n$ (SEQ ID NO: 265), $(GGGGS)_n$ (SEQ ID NO: 5), $(G)_n$, $(EAAAK)_n$ (SEQ ID NO: 6), $(GGS)_n$, $(SGGS)_n$ (SEQ ID NO: 4288), SGSETPGTSESATPES (SEQ ID NO: 7), or $(XP)_n$ motif, or a combination of any of these, wherein n is independently an integer between 1 and 30, and wherein X is any amino acid. In some embodiments, the linker comprises a $(GGS)_n$ motif, wherein n is 1, 3, or 7. In some embodiments, the linker comprises a (GGS)$_n$ motif, wherein n is 1, 2, 3, 4, 5, 6, 7, 8, 9, 10, 11, 12, 13, 14, or 15. In some embodiments, the linker comprises an amino acid sequence of SGSETPGTSESAT-PES (SEQ ID NO: 7),also referred to as the XTEN linker in the Examples). The length of the linker can influence the base to be edited, as illustrated in the Examples. For example, a linker of 3-amino-acid long (e.g., (GGS)$_1$) may give a 2-5, 2-4, 2-3, 3-4 base editing window relative to the PAM sequence, while a 9-amino-acid linker (e.g., (GGS)$_3$ (SEQ ID NO: 596)) may give a 2-6, 2-5, 2-4, 2-3, 3-6, 3-5, 3-4, 4-6, 4-5, 5-6 base editing window relative to the PAM sequence. A 16-amino-acid linker (e.g., the XTEN linker) may give a 2-7, 2-6, 2-5, 2-4, 2-3, 3-7, 3-6, 3-5, 3-4, 4-7, 4-6, 4-5, 5-7, 5-6, 6-7 base window relative to the PAM sequence with exceptionally strong activity, and a 21-amino-acid linker (e.g., (GGS)$_7$ (SEQ ID NO: 597)) may give a 3-8, 3-7, 3-6, 3-5, 3-4, 4-8, 4-7, 4-6, 4-5, 5-8, 5-7, 5-6, 6-8, 6-7, 7-8 base editing window relative to the PAM sequence. The novel finding that varying linker length may allow the dCas9 fusion proteins of the disclosure to edit nucleobases different distances from the PAM sequence affords significant clinical importance, since a PAM sequence may be of varying distance to the disease-causing mutation to be corrected in a gene. It is to be understood that the linker lengths described as examples here are not meant to be limiting.

In some embodiments, the second protein comprises an enzymatic domain. In some embodiments, the enzymatic domain is a nucleic acid editing domain. Such a nucleic acid editing domain may be, without limitation, a nuclease, a nickase, a recombinase, a deaminase, a methyltransferase, a methylase, an acetylase, or an acetyltransferase. Non-limiting exemplary binding domains that may be used in accordance with this disclosure include transcriptional activator domains and transcriptional repressor domains.

Deaminase Domains

In some embodiments, second protein comprises a nucleic acid editing domain. In some embodiments, the nucleic acid editing domain can catalyze a C to U base change. In some embodiments, the nucleic acid editing domain is a deaminase domain. In some embodiments, the deaminase is a cytidine deaminase or a cytidine deaminase. In some embodiments, the deaminase is an apolipoprotein B mRNA-editing complex (APOBEC) family deaminase. In some embodiments, the deaminase is an APOBEC1 deaminase. In some embodiments, the deaminase is an APOBEC2 deaminase. In some embodiments, the deaminase is an APOBEC3 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, the deaminase is an APOBEC3E deaminase. In some embodiments, the deaminase is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). In some embodiments, the deaminase is a vertebrate deaminase. In some embodiments, the deaminase is an invertebrate deaminase. In some embodiments, the deaminase is a human, chimpanzee, gorilla, monkey, cow, dog, rat, or mouse deaminase. In some embodiments, the deaminase is a human deaminase. In some embodiments, the deaminase is a rat deaminase, e.g., rAPOBEC1. In some embodiments, the deaminase is a *Petromyzon marinus* cytidine deaminase 1 (pmCDA1). In some embodiments, the deminase is a human APOBEC3G (SEQ ID NO: 275). In some embodiments, the deaminase is a fragment of the human APOBEC3G (SEQ ID NO: 5740). In some embodiments, the deaminase is a human APOBEC3G variant comprising a D316R_D317R mutation (SEQ ID NO: 5739). In some embodiments, the deaminase is a frantment of the human APOBEC3G and comprising mutations corresponding to the D316R_D317R mutations in SEQ ID NO: 275 (SEQ ID NO: 5741).

In some embodiments, the nucleic acid editing domain is at least 80%, at least 85%, at least 90%, at least 92%, at least 95%, at least 96%, at least 97%, at least 98%, at least 99%, or at least 99.5% identical to the deaminase domain of any one of SEQ ID NOs: 266-284, 607-610, 5724-5736, or 5738-5741. In some embodiments, the nucleic acid editing domain comprises the amino acid sequence of any one of SEQ ID NOs: 266-284, 607-610, 5724-5736, or 5738-5741.

Deaminase Domains that Modulate the Editing Window of Base Editors

Some aspects of the disclosure are based on the recognition that modulating the deaminase domain catalytic activity of any of the fusion proteins provided herein, for example by making point mutations in the deaminase domain, affect the processivity of the fusion proteins (e.g., base editors). For example, mutations that reduce, but do not eliminate, the catalytic activity of a deaminase domain within a base editing fusion protein can make it less likely that the deaminase domain will catalyze the deamination of a residue adjacent to a target residue, thereby narrowing the deamination window. The ability to narrow the deamination window may prevent unwanted deamination of residues adjacent of specific target residues, which may decrease or prevent off-target effects.

In some embodiments, any of the fusion proteins provided herein comprise a deaminase domain (e.g., a cytidine deaminase domain) that has reduced catalytic deaminase activity. In some embodiments, any of the fusion proteins provided herein comprise a deaminase domain (e.g., a cytidine deaminase domain) that has a reduced catalytic deaminase activity as compared to an appropriate control. For example, the appropriate control may be the deaminase activity of the deaminase prior to introducing one or more mutations into the deaminase. In other embodiments, the appropriate control may be a wild-type deaminase. In some embodiments, the appropriate control is a wild-type apolipoprotein B mRNA-editing complex (APOBEC) family deaminase. In some embodiments, the appropriate control is an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, or an APOBEC3H deaminase. In some embodiments, the appropriate control is an activation induced deaminase (AID). In some embodiments, the appropriate control is a cytidine deaminase 1 from *Petromyzon marinus* (pmCDA1). In some embodiments, the deaminase domain may be a deaminase domain that has at least 1%, at least 5%, at least 15%, at least 20%, at least 25%, at least 30%, at least 40%, at least 50%, at least 60%, at least 70%, at least 80%, at least 90%, or at least 95% less catalytic deaminase activity as compared to an appropriate control.

In some embodiments, any of the fusion proteins provided herein comprise an APOBEC deaminase comprising one or more mutations selected from the group consisting of H121X, H122X, R126X, R126X, R118X, W90X, W90X, and R132X of rAPOBEC1 (SEQ ID NO: 284), or one or more corresponding mutations in another APOBEC deaminase, wherein X is any amino acid. In some embodiments, any of the fusion proteins provided herein comprise an APOBEC deaminase comprising one or more mutations selected from the group consisting of H121R, H122R, R126A, R126E, R118A, W90A, W90Y, and R132E of rAPOBEC1 (SEQ ID NO: 284), or one or more corresponding mutations in another APOBEC deaminase.

In some embodiments, any of the fusion proteins provided herein comprise an APOBEC deaminase comprising one or more mutations selected from the group consisting of D316X, D317X, R320X, R320X, R313X, W285X, W285X, R326X of hAPOBEC3G (SEQ ID NO: 275), or one or more corresponding mutations in another APOBEC deaminase, wherein X is any amino acid. In some embodiments, any of the fusion proteins provided herein comprise an APOBEC deaminase comprising one or more mutations selected from the group consisting of D316R, D317R, R320A, R320E, R313A, W285A, W285Y, R326E of hAPOBEC3G (SEQ ID NO: 275), or one or more corresponding mutations in another APOBEC deaminase.

In some embodiments, any of the fusion proteins provided herein comprise an APOBEC deaminase comprising a H121R and a H122R mutation of rAPOBEC1 (SEQ ID NO: 284), or one or more corresponding mutations in another APOBEC deaminase. In some embodiments, any of the fusion proteins provided herein comprise an APOBEC deaminase comprising a R126A mutation of rAPOBEC1 (SEQ ID NO: 284), or one or more corresponding mutations in another APOBEC deaminase. In some embodiments, any of the fusion proteins provided herein comprise an APOBEC deaminase comprising a R126E mutation of rAPOBEC1 (SEQ ID NO: 284), or one or more corresponding mutations in another APOBEC deaminase. In some embodiments, any of the fusion proteins provided herein comprise an APOBEC deaminase comprising a R118A mutation of rAPOBEC1 (SEQ ID NO: 284), or one or more corresponding mutations in another APOBEC deaminase. In some embodiments, any of the fusion proteins provided herein comprise an APOBEC deaminase comprising a W90A mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y mutation of rAPOBEC1 (SEQ ID NO: 284), or one or more corresponding mutations in another APOBEC deaminase. In some embodiments, any of the fusion proteins provided herein comprise an APOBEC deaminase comprising a R132E mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y and a R126E mutation of rAPOBEC1 (SEQ ID NO: 284), or one or more corresponding mutations in another APOBEC deaminase. In some embodiments, any of the fusion proteins provided herein comprise an APOBEC deaminase comprising a R126E and a R132E mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y and a R132E mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y, R126E, and R132E mutation of rAPOBEC1 (SEQ ID NO: 284), or one or more corresponding mutations in another APOBEC deaminase.

In some embodiments, any of the fusion proteins provided herein comprise an APOBEC deaminase comprising a D316R and a D317R mutation of hAPOBEC3G (SEQ ID NO: 275), or one or more corresponding mutations in another APOBEC deaminase. In some embodiments, any of the fusion proteins provided herein comprise an APOBEC deaminase comprising a R320A mutation of hAPOBEC3G (SEQ ID NO: 275), or one or more corresponding mutations in another APOBEC deaminase. In some embodiments, any of the fusion proteins provided herein comprise an APOBEC deaminase comprising a R320E mutation of hAPOBEC3G (SEQ ID NO: 275), or one or more corresponding mutations in another APOBEC deaminase. In some embodiments, any of the fusion proteins provided herein comprise an APOBEC deaminase comprising a R313A mutation of hAPOBEC3G (SEQ ID NO: 275), or one or more corresponding mutations in another APOBEC deaminase. In some embodiments, any of the fusion proteins provided herein comprise an APOBEC deaminase comprising a W285A mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y mutation of hAPOBEC3G (SEQ ID NO: 275), or one or more corresponding mutations in another APOBEC deaminase. In some embodiments, any of the fusion proteins provided herein comprise an APOBEC deaminase comprising a R326E mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y and a R320E mutation of hAPOBEC3G (SEQ ID NO: 275), or one or more corresponding mutations in another APOBEC deaminase. In some embodiments, any of the fusion proteins provided herein comprise an APOBEC deaminase comprising a R320E and a R326E mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y and a R326E mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y, R320E, and R326E mutation of hAPOBEC3G (SEQ ID NO: 275), or one or more corresponding mutations in another APOBEC deaminase.

Some aspects of this disclosure provide fusion proteins comprising (i) a nuclease-inactive Cas9 domain; and (ii) a nucleic acid editing domain. In some embodiments, a nuclease-inactive Cas9 domain (dCas9), comprises an amino acid sequence that is at least 80%, at least 85%, at least 90%, at least 92%, at least 95%, at least 96%, at least 97%, at least 98%, at least 99%, or at least 99.5% identical to the amino acid sequence of a Cas9 as provided by any one of SEQ ID NOs: 10-263, and comprises mutations that inactivate the nuclease activity of Cas9. Mutations that render the nuclease domains of Cas9 inactive are well-known in the art. For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science*. 337:816-821(2012); Qi et al., *Cell.* 28; 152(5):1173-83 (2013)). In some embodiments, the dCas9 of this disclosure comprises a D10A mutation of the amino acid sequence provided in SEQ ID NO: 10, or a corresponding mutation in any of the amino acid sequences provided in SEQ ID NOs: 11-260. In some embodiments, the dCas9 of this disclosure comprises a H840A mutation of the amino acid sequence provided in SEQ ID NO: 10, or a corresponding mutation in any of the amino acid sequences provided in SEQ ID NOs: 11-260. In some embodiments, the dCas9 of this disclosure comprises both D10A and H840A mutations of the amino acid sequence provided in SEQ ID NO: 10, or a corresponding mutation in any of the amino acid sequences provided in SEQ ID NOs: 11-260. In some embodiments, the Cas9 further comprises a histidine residue at position 840 of the amino acid sequence provided in SEQ ID NO: 10, or a corresponding mutation in any of the amino acid sequences provided in SEQ ID NOs: 11-260. The presence of the catalytic residue H840 restores the acvitity of the Cas9 to cleave the non-edited strand containing a G opposite the targeted C. Restoration of H840 does not result in the cleavage of the target strand containing the C. In some embodiments, the dCas9 comprises an amino acid sequence of SEQ ID NO: 263. It is to be understood that other mutations that inactivate the nuclease domains of Cas9 may also be included in the dCas9 of this disclosure.

The Cas9 or dCas9 domains comprising the mutations disclosed herein, may be a full-length Cas9, or a fragment thereof. In some embodiments, proteins comprising Cas9, or fragments thereof, are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9, e.g., a Cas9 comprising the amino acid sequence of SEQ ID NO: 10.

Any of the Cas9 fusion proteins of this disclosure may further comprise a nucleic acid editing domain (e.g., an enzyme that is capable of modifying nucleic acid, such as a deaminase). In some embodiments, the nucleic acid editing domain is a DNA-editing domain. In some embodiments, the nucleic acid editing domain has deaminase activity. In some embodiments, the nucleic acid editing domain comprises or consists of a deaminase or deaminase domain. In some embodiments, the deaminase is a cytidine deaminase. In some embodiments, the deaminase is an apolipoprotein B mRNA-editing complex (APOBEC) family deaminase. In some embodiments, the deaminase is an APOBEC1 family deaminase. In some embodiments, the deaminase is an activation-induced cytidine deaminase (AID). Some nucleic-acid editing domains as well as Cas9 fusion proteins including such domains are described in detail herein. Additional suitable nucleic acid editing domains will be apparent to the skilled artisan based on this disclosure and knowledge in the field.

Some aspects of the disclosure provide a fusion protein comprising a Cas9 domain fused to a nucleic acid editing domain, wherein the nucleic acid editing domain is fused to the N-terminus of the Cas9 domain. In some embodiments, the Cas9 domain and the nucleic acid editing-editing domain are fused via a linker. In some embodiments, the linker comprises a $(GGGS)_n$ (SEQ ID NO: 265), a $(GGGGS)_n$ (SEQ ID NO: 5), a $(G)_n$, an $(EAAAK)_n$ (SEQ ID NO: 6), a $(GGS)_n$, $(SGGS)_n$ (SEQ ID NO: 4288), an SGSETPGTS-ESATPES (SEQ ID NO: 7) motif (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference), or an $(XP)_n$ motif, or a combination of any of these, wherein n is independently an integer between 1 and 30. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. In some embodiments, the linker comprises a $(GGS)_n$ motif, wherein n is 1,2, 3, 4, 5, 6, 7, 8, 9, 10, 11, 12, 13, 14 or 15. In some embodiments, the linker comprises a $(GGS)_n$ motif, wherein n is 1, 3, or 7. In some embodiments, the linker comprises the amino acid sequence SGSETPGTSESATPES (SEQ ID NO: 7). Additional suitable linker motifs and linker configurations will be apparent to those of skill in the art. In some embodiments, suitable linker motifs and configurations include those described in Chen et al., Fusion protein linkers: property, design and functionality. *Adv Drug Deliv Rev.* 2013; 65(10):1357-69, the entire contents of which are incorporated herein by reference. Additional suitable linker sequences will be apparent to those of skill in the art based on the instant disclosure. In some embodiments, the general architecture of exemplary Cas9 fusion proteins provided herein comprises the structure:

[NH$_2$]-[nucleic acid editing domain]-[Cas9]-[COOH] or
[NH$_2$]-[nucleic acid editing domain]-[linker]-[Cas9]-[COOH], wherein NH$_2$ is the N-terminus of the fusion protein, and COOH is the C-terminus of the fusion protein.

The fusion proteins of the present disclosure may comprise one or more additional features. For example, in some embodiments, the fusion protein comprises a nuclear localization sequence (NLS). In some embodiments, the NLS of the fusion protein is localized between the nucleic acid editing domain and the Cas9 domain. In some embodiments, the NLS of the fusion protein is localized C-terminal to the Cas9 domain.

Other exemplary features that may be present are localization sequences, such as cytoplasmic localization sequences, export sequences, such as nuclear export sequences, or other localization sequences, as well as sequence tags that are useful for solubilization, purification, or detection of the fusion proteins. Suitable protein tags provided herein include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art. In some embodiments, the fusion protein comprises one or more His tags.

In some embodiments, the nucleic acid editing domain is a deaminase. For example, in some embodiments, the general architecture of exemplary Cas9 fusion proteins with a deaminase domain comprises the structure:

[NH$_2$]-[NLS]-[deaminase]-[Cas9]-[COOH],
[NH$_2$]-[Cas9]-[deaminase]-[COOH],
[NH$_2$]-[deaminase]-[Cas9]-[COOH], or
[NH$_2$]-[deaminase]-[Cas9]-[NLS]-[COOH]

wherein NLS is a nuclear localization sequence, NH$_2$ is the N-terminus of the fusion protein, and COOH is the C-terminus of the fusion protein. Nuclear localization sequences are known in the art and would be apparent to the skilled artisan. For example, NLS sequences are described in Plank et al., PCT/EP2000/011690, the contents of which are incorporated herein by reference for their disclosure of exemplary nuclear localization sequences. In some embodiments, a NLS comprises the amino acid sequence PKKKRKV (SEQ ID NO: 741) or MDSLLMNRRKFLYQFKNVRWAKGR-RETYLC (SEQ ID NO: 742). In some embodiments, a linker is inserted between the Cas9 and the deaminase. In some embodiments, the NLS is located C-terminal of the Cas9 domain. In some embodiments, the NLS is located N-terminal of the Cas9 domain. In some embodiments, the NLS is located between the deaminase and the Cas9 domain. In some embodiments, the NLS is located N-terminal of the deaminase domain. In some embodiments, the NLS is located C-terminal of the deaminase domain.

One exemplary suitable type of nucleic acid editing domain is a cytidine deaminase, for example, of the APOBEC family. The apolipoprotein B mRNA-editing complex (APOBEC) family of cytidine deaminase enzymes encompasses eleven proteins that serve to initiate mutagenesis in a controlled and beneficial manner.[29] One family member, activation-induced cytidine deaminase (AID), is responsible for the maturation of antibodies by converting cytosines in ssDNA to uracils in a transcription-dependent, strand-biased fashion.[30] The apolipoprotein B editing complex 3 (APOBEC3) enzyme provides protection to human cells against a certain HIV-1 strain via the deamination of cytosines in reverse-transcribed viral ssDNA.[31] These proteins all require a Zn$^{2+}$-coordinating motif (His-X-Glu-X$_{23-26}$-Pro-Cys-X$_{2-4}$-Cys; SEQ ID NO: 598) and bound water molecule for catalytic activity. The Glu residue acts to activate the water molecule to a zinc hydroxide for nucleophilic attack in the deamination reaction. Each family member preferentially deaminates at its own particular "hotspot", ranging from WRC (W is A or T, R is A or G) for hAID, to TTC for hAPOBEC3F.[32] A recent crystal structure of the catalytic domain of APOBEC3G revealed a secondary structure comprised of a five-stranded β-sheet core flanked by six α-helices, which is believed to be conserved across the entire family.[33] The active center loops have been shown to be responsible for both ssDNA binding and in determining "hotspot" identity.[34] Overexpression of these enzymes has been linked to genomic instability and cancer, thus highlighting the importance of sequence-specific targeting.[35]

Some aspects of this disclosure relate to the recognition that the activity of cytidine deaminase enzymes such as APOBEC enzymes can be directed to a specific site in genomic DNA. Without wishing to be bound by any particular theory, advantages of using Cas9 as a recognition agent include (1) the sequence specificity of Cas9 can be easily altered by simply changing the sgRNA sequence; and (2) Cas9 binds to its target sequence by denaturing the dsDNA, resulting in a stretch of DNA that is single-stranded and therefore a viable substrate for the deaminase. It should be understood that other catalytic domains, or catalytic domains from other deaminases, can also be used to generate fusion proteins with Cas9, and that the disclosure is not limited in this regard.

Figure 3:
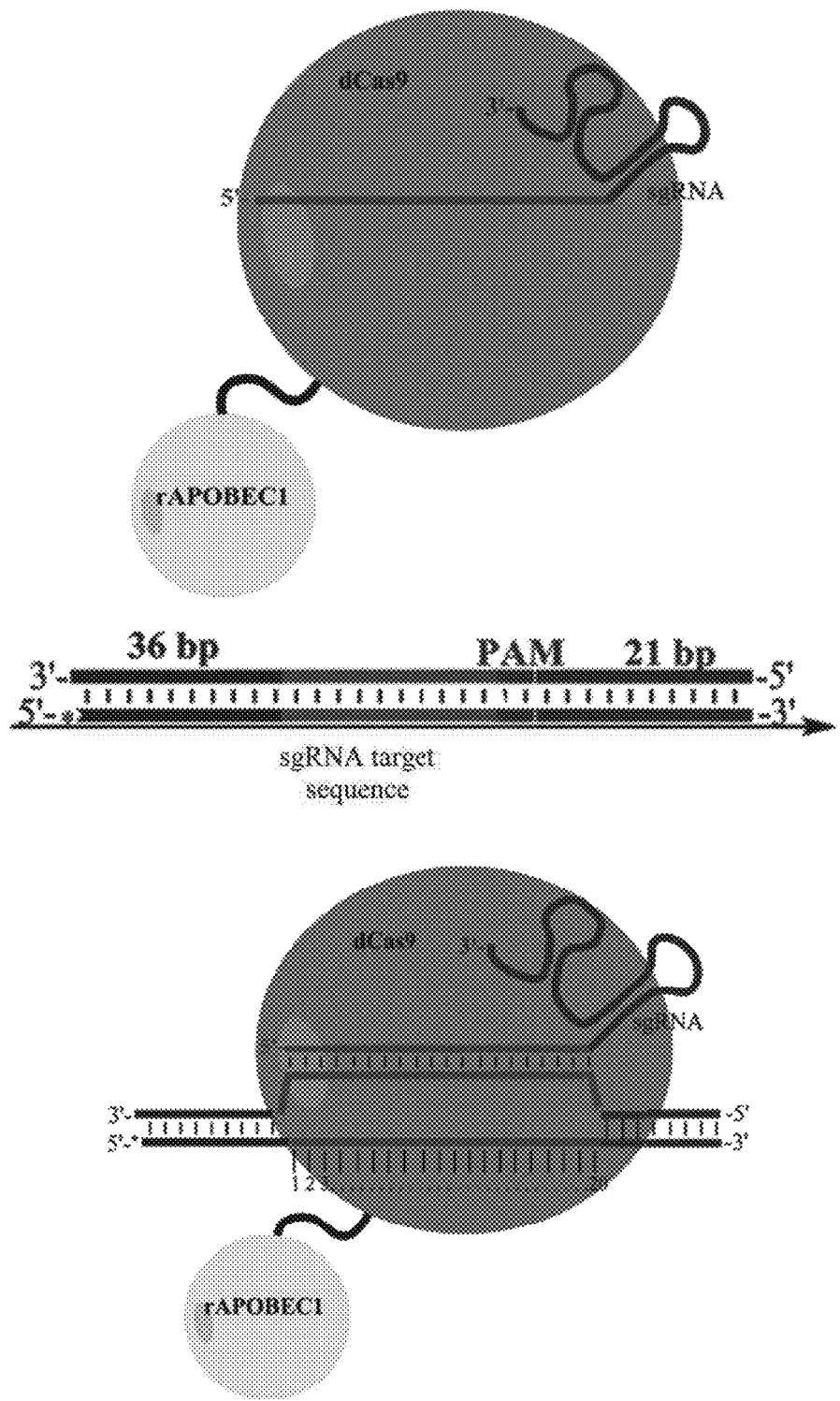
FIG. 3 illustrates double stranded DNA substrate binding by Cas9:deaminase:sgRNA complexes.

Some aspects of this disclosure are based on the recognition that Cas9:deaminase fusion proteins can efficiently deaminate nucleotides at positions 3-11 according to the numbering scheme in FIG. 3. In view of the results provided herein regarding the nucleotides that can be targeted by Cas9:deaminase fusion proteins, a person of skill in the art will be able to design suitable guide RNAs to target the fusion proteins to a target sequence that comprises a nucleotide to be deaminated.

In some embodiments, the deaminase domain and the Cas9 domain are fused to each other via a linker. Various linker lengths and flexibilities between the deaminase domain (e.g., AID) and the Cas9 domain can be employed (e.g., ranging from very flexible linkers of the form (GGGGS)$_n$ (SEQ ID NO: 5), (GGS)$_n$, and (G)$_n$ to more rigid linkers of the form (EAAAK)$_n$ (SEQ ID NO: 6), (SGGS)$_n$ (SEQ ID NO: 4288), SGSETPGTSESATPES (SEQ ID NO: 7) (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference) and (XP)$_n$)[36] in order to achieve the optimal length for deaminase activity for the specific application. In some embodiments, the linker comprises a (GGS)$_n$ motif, wherein n is 1, 3, or 7. In some embodiments, the linker comprises a (an SGSETPGTSESATPES (SEQ ID NO: 7) motif.

Some exemplary suitable nucleic-acid editing domains, e.g., deaminases and deaminase domains, that can be fused to Cas9 domains according to aspects of this disclosure are provided below. It should be understood that, in some embodiments, the active domain of the respective sequence can be used, e.g., the domain without a localizing signal (nuclear localization sequence, without nuclear export signal, cytoplasmic localizing signal).

Human AID:

(SEQ ID NO: 266)

<u>MDSLLMNRRKFLYQFKNVRWAKGRRETYLC</u>YVVKRRDSATSFSLDFGYLRNKNGCHVELLFLR

YISDWDLDPGRCYRVTWFTSWSPCYDCARHVADFLRGNPNLSLRIFTARLYFCEDRKAEPEGL

RRLHRAGVQIAIMTFKDYFYCWNTFVENHERTFKAWEGLHENSVRLSRQLRRILL<u><u>PLYEVDDL</u></u>

<u><u>RDAFRTLGL</u></u>
(underline: nuclear localization sequence;
double underline: nuclear export signal)

-continued

Mouse AID:
(SEQ ID NO: 267)
<u>MDSLLMKQKKFLYHFKNVRWAKGRHETYLC</u>YVVKRRDSATSCSLDFGHLRNKSGCHVELLFLR

YISDWDLDPGRCYRVTWFTSWSPCYDCARHVAEFLRWNPNLSLRIFTARLYFCEDRKAEPEGL

RRLHRAGVQIGIMTFKDYFYCWNTFVENRERTFKAWEGLHENSVRLTRQLRRILL<u>PLYEVDDL</u>

<u>RDAFRMLGF</u>
(underline: nuclear localization sequence;
double underline: nuclear export signal)

Dog AID:
(SEQ ID NO: 268)
<u>MDSLLMKQRKFLYHFKNVRWAKGRHETYLC</u>YVVKRRDSATSFSLDFGHLRNKSGCHVELLFLR

YISDWDLDPGRCYRVTWFTSWSPCYDCARHVADFLRGYPNLSLRIFAARLYFCEDRKAEPEGL

RRLHRAGVQIAIMTFKDYFYCWNTFVENREKTFKAWEGLHENSVRLSRQLRRILL<u>PLYEVDDL</u>

<u>RDAFRTLGL</u>
(underline: nuclear localization sequence;
double underline: nuclear export signal)

Bovine AID:
(SEQ ID NO: 269)
<u>MDSLLKKQRQFLYQFKNVRWAKGRHETYLC</u>YVVKRRDSPTSFSLDFGHLRNKAGCHVELLFLR

YISDWDLDPGRCYRVTWFTSWSPCYDCARHVADFLRGYPNLSLRIFTARLYFCDKERKAEPEG

LRRLHRAGVQIAIMTFKDYFYCWNTFVENHERTFKAWEGLHENSVRLSRQLRRILL<u>PLYEVDD</u>

<u>LRDAFRTLGL</u>
(underline: nuclear localization sequence;
double underline: nuclear export signal)

Rat AID
(SEQ ID NO: 5725)
<u>MAVGSKPKAALVGPHWERERIWCFLC</u>STGLGTQQTGQTSRWLRPAATQDPVSPPRSLLMKQRK

FLYHFKNVRWAKGRHETYLCYVVKRRDSATSFSLDFGYLRNKSGCHVELLFLRYISDWDLDPG

RCYRVTWFTSWSPCYDCARHVADFLRGNPNLSLRIFTARLTGWGALPAGLMSPARPSDYFYCW

NTFV<u>ENHERTFKAWEGLHENSVRLSRRLRRILLPLYEVDDLRDAFRTLGL</u>
(underline: nuclear localization sequence;
double underline: nuclear export signal)

Mouse APOBEC-3:
(SEQ ID NO: 270)
MGPFCLGCSHRKCYSPIRNLISQETFKFHFKNLGYAKGRKDTFLCYEVTRKDCDSPVSLHHGV

FKNKDNI*HAEICFLYWFHDKVLKVLSPREEFKITWYMSWSPCFEC*AEQIVRFLATHHNLSLDI

FSSRLYNVQDPETQQNLCRLVQEGAQVAAMDLYEFKKCWKKFVDNGGRRFRPWKRLLTNFRYQ

DSKLQEILRPCYIPVPSSSSSTLSNICLTKGLPETRFCVEGRRMDPLSEEEFYSQFYNQRVKH

LCYYHRMKPYLCYQLEQFNGQAPLKGCLLSEKGKQ*HAEILFLDKIRSMELSQVTITCYLTWSP

CPNC*AWQLAAFKRDRPDLILHIYTSRLYFHWKRPFQKGLCSLWQSGILVDVMDLPQFTDCWTN

FVNPKRPFWPWKGLEIISRRTQRRLRRIKESWGLQDLVNDFGNLQLGPPMS
(italic: nucleic acid editing domain)

Rat APOBEC-3:
(SEQ ID NO: 271)
MGPFCLGCSHRKCYSPIRNLISQETFKFHFKNLRYAIDRKDTFLCYEVTRKDCDSPVSLHHGV

FKNKDNI*HAEICFLYWFHDKVLKVLSPREEFKITWYMSWSPCFEC*AEQVLRFLATHHNLSLDI

FSSRLYNIRDPENQQNLCRLVQEGAQVAAMDLYEFKKCWKKFVDNGGRRFRPWKKLLTNFRYQ

DSKLQEILRPCYIPVPSSSSSTLSNICLTKGLPETRFCVERRRVHLLSEEEFYSQFYNQRVKH

LCYYHGVKPYLCYQLEQFNGQAPLKGCLLSEKGKQ*HAEILFLDKIRSMELSQVIITCYLTWSP

*CPNCAWQLAAFKRDRPDLILHIYTSRLYFHWKRPFQKGLCSLWQSGILVDVMDLPQFTDCWTN*

FVNPKRPFWPWKGLEIISRRTQRRLHRIKESWGLQDLVNDFGNLQLGPPMS
(italic: nucleic acid editing domain)

Rhesus macaque APOBEC-3G:
(SEQ ID NO: 272)

<u>MVEPMDPRTFVSNFNNRPILSGLNTVWLCCEVKTKDPSGPPLDAKIFQGKVYSKAKY</u>*HPEMRF*

*LRWFHKWRQLHHDQEYKVTWYVSWSPCTRC*ANSVATFLAKDPKVTLTIFVARLYYFWKPDYQQ

ALRILCQKRGGPHATMKIMNYNEFQDCWNKFVDGRGKPFKPRNNLPKHYTLLQATLGELLRHL

MDPGTFTSNFNNKPWVSGQHETYLCYKVERLHNDTWVPLNQHRGFLRNQAPNIHGFPKGR*HAE*

*LCFLDLIPFWKLDGQQYRVTCFTSWSPCFSC*AQEMAKFISNNEHVSLCIFAARIYDDQGRYQE

GLRALHRDGAKIAMMNYSEFEYCWDTFVDRQGRPFQPWDGLDEHSQALSGRLRAI
(italic: nucleic acid editing domain; underline: cytoplasmic localization signal)

Chimpanzee APOBEC-3G:
(SEQ ID NO: 273)

<u>MKPHFRNPVERMYQDTFSDNFYNRPILSHRNTVWLCYEVKTKGPSRPPLDAKIFRGQVYSKLK</u>

*YHPEMRFFHWFSKWRKLHRDQEYEVIWYISWSPCTK*CTRDVATFLAEDPKVTLTIFVARLYYF

WDPDYQEALRSLCQKRDGPRATMKIMNYDEFQHCWSKFVYSQRELFEPWNNLPKYYILLHIML

GEILRHSMDPPTFTSNFNNELWVRGRHETYLCYEVERLHNDTWVLLNQRRGFLCNQAPHKHGF

LEGR*HAELCFLDVIPFWKLDLHQDYRVTCFTSWSPCFSC*AQEMAKFISNNKHVSLCIFAARIY

DDQGRCQEGLRTLAKAGAKISIMTYSEFKHCWDTFVDHQGCPFQPWDGLEEHSQALSGRLRAI

LQNQGN
(italic: nucleic acid editing domain; underline: cytoplasmic localization signal)

Green monkey APOBEC-3G:
(SEQ ID NO: 274)

<u>MNPQIRNMVEQMEPDIFVYYFNNRPILSGRNTVWLCYEVKTKDPSGPPLDANIFQGKLYPEAK</u>

D*HPEMKFLHWFRKWRQLHRDQEYEVTWYVSWSPCTRC*ANSVATFLAEDPKVTLTIFVARLYYF

WKPDYQQALRILCQERGGPHATMKIMNYNEFQHCWNEFVDGQGKPFKPRKNLPKHYTLLHATL

GELLRHVMDPGTFTSNFNNKPWVSGQRETYLCYKVERSHNDTWVLLNQHRGFLRNQAPDRHGF

PKGR*HAELCFLDLIPFWKLDDQQYRVTCFTSWSPCFSC*AQKMAKFISNNKHVSLCIFAARIYD

DQGRCQEGLRTLHRDGAKIAVMNYSEFEYCWDTFVDRQGRPFQPWDGLDEHSQALSGRLRAI
(italic: nucleic acid editing domain; underline: cytoplasmic localization signal)

Human APOBEC-3G:
(SEQ ID NO: 275)

<u>MKPHFRNTVERMYRDTFSYNFYNRPILSRRNTVWLCYEVKTKGPSRPPLDAKIFRGQVYSELK</u>

*YHPEMRFFHWFSKWRKLHRDQEYEVTWYISWSPCTK*CTRDMATFLAEDPKVTLTIFVARLYYF

WDPDYQEALRSLCQKRDGPRATMKIMNYDEFQHCWSKFVYSQRELFEPWNNLPKYYILLHIML

GEILRHSMDPPTFTFNFNNEPWVRGRHETYLCYEVERMHNDTWVLLNQRRGFLCNQAPHKHGF

LEGR*HAELCFLDVIPFWKLDLDQDYRVTCFTSWSPCFSC*AQEMAKFISKNKHVSLCIFTARIY

DDQGRCQEGLRTLAEAGAKISIMTYSEFKHCWDTFVDHQGCPFQPWDGLDEHSQDLSGRLRAI

LQNQEN
(italic: nucleic acid editing domain; underline: cytoplasmic localization signal)

Human APOBEC-3F:
(SEQ ID NO: 276)
MKPHFRNTVERMYRDTFSYNFYNRPILSRRNTVWLCYEVKTKGPSRPRLDAKIFRGQ

VYSQPEH*HAEMCFLSWFCGNQLPAYKCFQITWFVSWTPCPDC*VAKLAEFLAEHPNVTL

TISAARLYYYWERDYRRALCRLSQAGARVKIMDDEEFAYCWENFVYSEGQPFMPW

-continued

YKFDDNYAFLHRTLKEILRNPMEAMYPHIFYFHFKNLRKAYGRNESWLCFTMEVVK

HHSPVSWKRGVFRNQVDPETHC*HAERCFLSWFCDDILSPNTNYEVTWYTSWSPCPEC*A

GEVAEFLARHSNVNLTIFTARLYYFWDTDYQEGLRSLSQEGASVEIMGYKDFKYCW

ENFVYNDDEPFKPWKGLKYNFLFLDSKLQEILE
(italic: nucleic acid editing domain)

Human APOBEC-3B:
(SEQ ID NO: 277)
MNPQIRNPMERMYRDTFYDNFENEPILYGRSYTWLCYEVKIKRGRSNLLWDTGVFR

GQVYFKPQY*HAEMCFLSWFCGNQLPAYKCFQITWFVSWTPCPDC*VAKLAEFLSEHPN

VTLTISAARLYYYWERDYRRALCRLSQAGARVTIMDYEEFAYCWENFVYNEGQQF

MPWYKFDENYAFLHRTLKEILRYLMDPDTFTFNFNNDPLVLRRRQTYLCYEVERLD

NGTWVLMDQHMGFLCNEAKNLLCGFY*GRHAELRFLDLVPSLQLDPAQIYRVTWFISWS*

*PCFSWGC*AGEVRAFLQENTHVRLRIFAARIYDYDPLYKEALQMLRDAGAQVSIMTY

DEFEYCWDTFVYRQGCPFQPWDGLEEHSQALSGRLRAILQNQGN
(italic: nucleic acid editing domain)

Rat APOBEC-3B:
(SEQ ID NO: 5729)
MQPQGLGPNAGMGPVCLGCSHRRPYSPIRNPLKKLYQQTFYFHFKNVRYAWGRKN

NFLCYEVNGMDCALPVPLRQGVFRKQGHIHAELCFIYWFHDKVLRVLSPMEEFKVT

WYMSWSPCSKCAEQVARFLAAHRNLSLAIFSSRLYYYLRNPNYQQKLCRLIQEGVH

VAAMDLPEFKKCWNKFVDNDGQPFRPWMRLRINFSFYDCKLQEIFSRMNLLREDVF

YLQFNNSHRVKPVQNRYYRRKSYLCYQLERANGQEPLKGYLLYKKGEQHVEILFLE

KMRSMELSQVRITCYLTWSPCPNCARQLAAFKKDHPDLILRIYTSRLYFYWRKKFQK

GLCTLWRSGIHVDVMDLPQFADCWTNFVNPQRPFRPWNELEKNSWRIQRRLRRIKE

SWGL

Bovine APOBEC-3B:
(SEQ ID NO: 5730)
DGWEVAFRSGTVLKAGVLGVSMTEGWAGSGHPGQGACVWTPGTRNTMNLLREVL

FKQQFGNQPRVPAPYYRRKTYLCYQLKQRNDLTLDRGCFRNKKQRHAEIRFIDKINS

LDLNPSQSYKIICYITWSPCPNCANELVNFITRNNHLKLEIFASRLYFHWIKSFKMGLQ

DLQNAGISVAVMTHTEFEDCWEQFVDNQSRPFQPWDKLEQYSASIRRRLQRILTAPI

Chimpanzee APOBEC-3B:
(SEQ ID NO: 5731)
MNPQIRNPMEWMYQRTFYYNFENEPILYGRSYTWLCYEVKIRRGHSNLLWDTGVFR

GQMYSQPEHHAEMCFLSWFCGNQLSAYKCFQITWFVSWTPCPDCVAKLAKFLAEHP

NVTLTISAARLYYYWERDYRRALCRLSQAGARVKIMDDEEFAYCWENFVYNEGQPF

MPWYKFDDNYAFLHRTLKEIIRHLMDPDTFTFNFNNDPLVLRRHQTYLCYEVERLD

NGTWVLMDQHMGFLCNEAKNLLCGFYGRHAELRFLDLVPSLQLDPAQIYRVTWFIS

WSPCFSWGCAGQVRAFLQENTHVRLRIFAARIYDYDPLYKEALQMLRDAGAQVSIM

TYDEFEYCWDTFVYRQGCPFQPWDGLEEHSQALSGRLRAILQVRASSLCMVPHRPPP

PPQSPGPCLPLCSEPPLGSLLPTGRPAPSLPFLLTASFSFPPPASLPPLPSLSLSPGHLPVP

SFHSLTSCSIQPPCSSRIRETEGWASVSKEGRDLG

Human APOBEC-3C:
(SEQ ID NO: 278)
MNPQIRNPMKAMYPGTFYFQFKNLWEANDRNETWLCFTVEGIKRRSVVSWKTGVF

RNQVDSETH*CHAERCFLSWFCDDILSPNTKYQVIWYTSWSPCPDC*AGEVAEFLARHSN

-continued

VNLTIFTARLYYFQYPCYQEGLRSLSQEGVAVEIMDYEDFKYCWENFVYNDNEPFKP

WKGLKTNFRLLKRRLRESLQ
(italic: nucleic acid editing domain)

Gorilla APOB EC3C
(SEQ ID NO: 5726)
MNPQIRNPMKAMYPGTFYFQFKNLWEANDRNETWLCFTVEGIKRRSVVSWKTGVF

RNQVDSETH*CHAERCFLSWFCDDILSPNTNYQVIWYTSWSPCPEC*AGEVAEFLARHSN

VNLTIFTARLYYFQDTDYQEGLRSLSQEGVAVKIMDYKDFKYCWENFVYNDDEPFK

PWKGLKYNFRFLKRRLQEILE
(italic: nucleic acid editing domain)

Human APOBEC-3A:
(SEQ ID NO: 279)
MEASPASGPRHLMDPHIFTSNFNNGIGRHKTYLCYEVERLDNGTSVKMDQHRGFLH

NQAKNLLCGFYGR*HAELRFLDLVPSLQLDPAQIYRVTWFISWSPCFSWGC*AGEVRAFLQ

ENTHVRLRIFAARIYDYDPLYKEALQMLRDAGAQVSIMTYDEFKHCWDTFVDHQGC

PFQPWDGLDEHSQALSGRLRAILQNGN
(italic: nucleic acid editing domain)

Rhesus macaque APOBEC-3A:
(SEQ ID NO: 5727)
MDGSPASRPRHLMDPNTFTFNFNNDLSVRGRHQTYLCYEVERLDNGTWVPMDERR

GFLCNKAKNVPCGDYGC*HVELRFLCEVPSWQLDPAQTYRVTWFISWSPC*FRRGCAGQ

VRVFLQENKHVRLRIFAARIYDYDPLYQEALRTLRDAGAQVSIMTYEEFKHCWDTF

VDRQGRPFQPWDGLDEHSQALSGRLRAILQNGN
(italic: nucleic acid editing domain)

Bovine APOBEC-3A:
(SEQ ID NO: 5728)
MDEYTFTENFNNQGWPSKTYLCYEMERLDGDATIPLDEYKGFVRNKGLDQPEKPC*H*

*AELYFLGKIHSWNLDRNQHYRLTCFISWSPC*YDCAQKLTTFLKENHHISLHILASRIYTH

NRFGCHQSGLCELQAAGARITIMTFEDFKHCWETFVDHKGKPFQPWEGLNVKSQAL

CTELQAILKTQQN
(italic: nucleic acid editing domain)

Human APOBEC-3H:
(SEQ ID NO: 280)
MALLTAETFRLQFNNKRRLRRPYYPRKALLCYQLTPQNGSTPTRGYFENKKKC*HAEI*

*CFINEIKSMGLDETQCYQVTCYLTWSPCSSC*AWELVDFIKAHDHLNLGIFASRLYYHWC

KPQQKGLRLLCGSQVPVEVMGFPKFADCWENFVDHEKPLSFNPYKMLEELDKNSRA

IKRRLERIKIPGVRAQGRYMDILCDAEV
(italic: nucleic acid editing domain)

Rhesus macaque APOBEC-3H:
(SEQ ID NO: 5732)
MALLTAKTFSLQFNNKRRVNKPYYPRKALLCYQLTPQNGSTPTRGHLKNKKKDHAE

IRFINKIKSMGLDETQCYQVTCYLTWSPCPSCAGELVDFIKAHRHLNLRIFASRLYYH

WRPNYQEGLLLLCGSQVPVEVMGLPEFTDCWENFVDHKEPPSFNPSEKLEELDKNS

QAIKRRLERIKSRSVDVLENGLRSLQLGPVTPSSSIRNSR

Human APOBEC-3D:
(SEQ ID NO: 281)
MNPQIRNPMERMYRDTFYDNFENEPILYGRSYTWLCYEVKIKRGRSNLLWDTGVFR

GPVLPKRQSNHRQEVYFRFEN*HAEMCFLSWFCGNRLPANRRFQITWFVSWNPCLPC*VV

KVTKFLAEHPNVTLTISAARLYYYRDRDWRWVLLRLHKAGARVKIMDYEDFAYCW

ENFVCNEGQPFMPWYKFDDNYASLHRTLKEILRNPMEAMYPHIFYFHFKNLLKACG

RNESWLCFTMEVTKHHSAVFRKRGVFRNQVDPETHC*HAERCFLSWFCDDILSPNTNY*

```
EVTWYTSWSPCPECAGEVAEFLARHSNVNLTIFTARLCYFWDTDYQEGLCSLSQEGAS

VKIMGYKDFVSCWKNFVYSDDEPFKPWKGLQTNFRLLKRRLREILQ
(italic: nucleic acid editing domain)

Human APOBEC-1:
                                        (SEQ ID NO: 282)
MTSEKGPSTGDPTLRRRIEPWEFDVFYDPRELRKEACLLYEIKWGMSRKIWRSSGKN

TTNHVEVNFIKKFTSERDFHPSMSCSITWFLSWSPCWECSQAIREFLSRHPGVTLVIYV

ARLFWHMDQQNRQGLRDLVNSGVTIQIMRASEYYHCWRNFVNYPPGDEAHWPQYP

PLWMMLYALELHCIILSLPPCLKISRRWQNHLTFFRLHLQNCHYQTIPPHILLATGLIH

PSVAWR

Mouse APOBEC-1:
                                        (SEQ ID NO: 283)
MSSETGPVAVDPTLRRRIEPHEFEVFFDPRELRKETCLLYEINWGGRHSVWRHTSQN

TSNHVEVNFLEKFTTERYFRPNTRCSITWFLSWSPCGECSRAITEFLSRHPYVTLFIYIA

RLYHHTDQRNRQGLRDLISSGVTIQIMTEQEYCYCWRNFVNYPPSNEAYWPRYPHL

WVKLYVLELYCIILGLPPCLKILRRKQPQLTFFTITLQTCHYQRIPPHLLWATGLK

Rat APOBEC-1:
                                        (SEQ ID NO: 284)
MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLW

VRLYVLELYCIILGLPPCLNILRRKQPQLTFFTIALQSCHYQRLPPHILWATGLK

Human APOBEC-2:
                                        (SEQ ID NO: 5733)
MAQKEEAAVATEAASQNGEDLENLDDPEKLKELIELPPFEIVTGERLPANFFKFQFRN

VEYSSGRNKTFLCYVVEAQGKGGQVQASRGYLEDEHAAAHAEEAFFNTILPAFDPALR

YNVTWYVSSSPCAACADRIIKTLSKTKNLRLLILVGRLFMWEEPEIQAALKKLKEAG

CKLRIMKPQDFEYVWQNFVEQEEGESKAFQPWEDIQENFLYYEEKLADILK

Mouse APOBEC-2:
                                        (SEQ ID NO: 5734)
MAQKEEAAEAAAPASQNGDDLENLEDPEKLKELIDLPPFEIVTGVRLPVNFFKFQFR

NVEYSSGRNKTFLCYVVEVQSKGGQAQATQGYLEDEHAGAHAEEAFFNTILPAFDP

ALKYNVTWYVSSSPCAACADRILKTLSKTKNLRLLILVSRLFMWEEPEVQAALKKLK

EAGCKLRIMKPQDFEYIWQNFVEQEEGESKAFEPWEDIQENFLYYEEKLADILK

Rat APOBEC-2:
                                        (SEQ ID NO: 5735)
MAQKEEAAEAAAPASQNGDDLENLEDPEKLKELIDLPPFEIVTGVRLPVNFFKFQFR

NVEYSSGRNKTFLCYVVEAQSKGGQVQATQGYLEDEHAGAHAEEAFFNTILPAFDP

ALKYNVTWYVSSSPCAACADRILKTLSKTKNLRLLILVSRLFMWEEPEVQAALKKLK

EAGCKLRIMKPQDFEYLWQNFVEQEEGESKAFEPWEDIQENFLYYEEKLADILK

Bovine APOBEC-2:
                                        (SEQ ID NO: 5736)
MAQKEEAAAAAEPASQNGEEVENLEDPEKLKELIELPPFEIVTGERLPAHYFKFQFRN

VEYSSGRNKTFLCYVVEAQSKGGQVQASRGYLEDEHATNHAEEAFFNSIMPTFDPALR

YMVTWYVSSSPCAACADRIVKTLNKTKNLRLLILVGRLFMWEEPEIQAALRKLKEA

GCRLRIMKPQDFEYIWQNFVEQEEGESKAFEPWEDIQENFLYYEEKLADILK
```

```
Petromyzon marinus CDA1 (pmCDA1)
                                                      (SEQ ID NO: 5738)
MTDAEYVRIHEKLDIYTFKKQFFNNKKSVSHRCYVLFELKRRGERRACFWGYAVNK

PQSGTERGIHAEIFSIRKVEEYLRDNPGQFTINWYSSWSPCADCAEKILEWYNQELRG

NGHTLKIWACKLYYEKNARNQIGLWNLRDNGVGLNVMVSEHYQCCRKIFIQSSHNQ

LNENRWLEKTLKRAEKRRSELSIMIQVKILHTTKSPAV

Human APOBEC3G D316R_D317R
                                                      (SEQ ID NO: 5739)
MKPHFRNTVERMYRDTFSYNFYNRPILSRRNTVWLCYEVKTKGPSRPPLDAKIFRGQ

VYSELKYHPEMRFFHWFSKWRKLHRDQEYEVTWYISWSPCTKCTRDMATFLAEDP

KVTLTIFVARLYYFWDPDYQEALRSLCQKRDGPRATMKIMNYDEFQHCWSKFVYSQ

RELFEPWNNLPKYYILLHIMLGEILRHSMDPPTFTFNFNNEPWVRGRHETYLCYEVER

MHNDTWVLLNQRRGFLCNQAPHKHGFLEGRHAELCFLDVIPFWKLDLDQDYRVTC

FTSWSPCFSCAQEMAKFISKNKHVSLCIFTARIYRRQGRCQEGLRTLAEAGAKISIMT

YSEFKHCWDTFVDHQGCPFQPWDGLDEHSQDLSGRLRAILQNQEN

Human APOBEC3G chain A
                                                      (SEQ ID NO: 5740)
MDPPTFTFNFNNEPWVRGRHETYLCYEVERMHNDTWVLLNQRRGFLCNQAPHKHG

FLEGRHAELCFLDVIPFWKLDLDQDYRVTCFTSWSPCFSCAQEMAKFISKNKHVSLCI

FTARIYDDQGRCQEGLRTLAEAGAKISIMTYSEFKHCWDTFVDHQGCPFQPWDGLD

EHSQDLSGRLRAILQ

Human APOBEC3G chain A D120R_D121R
                                                      (SEQ ID NO: 5741)
MDPPTFTFNFNNEPWVRGRHETYLCYEVERMHNDTWVLLNQRRGFLCNQAPHKHG

FLEGRHAELCFLDVIPFWKLDLDQDYRVTCFTSWSPCFSCAQEMAKFISKNKHVSLCI

FTARIYRRQGRCQEGLRTLAEAGAKISIMTYSEFKHCWDTFVDHQGCPFQPWDGLDE

HSQDLSGRLRAILQ
```

In some embodiments, fusion proteins as provided herein comprise the full-length amino acid of a nucleic acid editing enzyme, e.g., one of the sequences provided above. In other embodiments, however, fusion proteins as provided herein do not comprise a full-length sequence of a nucleic acid editing enzyme, but only a fragment thereof. For example, in some embodiments, a fusion protein provided herein comprises a Cas9 domain and a fragment of a nucleic acid editing enzyme, e.g., wherein the fragment comprises a nucleic acid editing domain. Exemplary amino acid sequences of nucleic acid editing domains are shown in the sequences above as italicized letters, and additional suitable sequences of such domains will be apparent to those of skill in the art.

Additional suitable nucleic-acid editing enzyme sequences, e.g., deaminase enzyme and domain sequences, that can be used according to aspects of this invention, e.g., that can be fused to a nuclease-inactive Cas9 domain, will be apparent to those of skill in the art based on this disclosure. In some embodiments, such additional enzyme sequences include deaminase enzyme or deaminase domain sequences that are at least 70%, at least 75%, at least 80%, at least 85%, at least 90%, at least 95%, at least 96%, at least 97%, at least 98%, or at least 99% similar to the sequences provided herein. Additional suitable Cas9 domains, variants, and sequences will also be apparent to those of skill in the art. Examples of such additional suitable Cas9 domains include, but are not limited to, D10A, D10A/D839A/H840A, and D10A/D839A/H840A/N863A mutant domains (See, e.g., Prashant et al., CAS9 transcriptional activators for target specificity screening and paired nickases for cooperative genome engineering. Nature Biotechnology. 2013; 31(9): 833-838 the entire contents of which are incorporated herein by reference). In some embodiments, the Cas9 comprises a histidine residue at position 840 of the amino acid sequence provided in SEQ ID NO: 10, or a corresponding mutation in any of the amino acid sequences provided in SEQ ID NOs: 11-260. The presence of the catalytic residue H840 restores the acvitity of the Cas9 to cleave the non-edited strand containing a G opposite the targeted C. Restoration of H840 does not result in the cleavage of the target strand containing the C.

Additional suitable strategies for generating fusion proteins comprising a Cas9 domain and a deaminase domain will be apparent to those of skill in the art based on this disclosure in combination with the general knowledge in the art. Suitable strategies for generating fusion proteins according to aspects of this disclosure using linkers or without the use of linkers will also be apparent to those of skill in the art in view of the instant disclosure and the knowledge in the art. For example, Gilbert et al., CRISPR-mediated modular RNA-guided regulation of transcription in eukaryotes. Cell. 2013; 154(2):442-51, showed that C-terminal fusions of Cas9 with VP64 using 2 NLS's as a linker (SPKKKRKVEAS, SEQ ID NO: 599), can be employed for transcriptional activation. Mali et al., CAS9 transcriptional activators for target specificity screening and paired nickases for cooperative genome engineering. *Nat Biotechnol.* 2013; 31(9):833-8, reported that C-terminal fusions with VP64 without linker can be employed for transcriptional activation. And Maeder et al., CRISPR RNA-guided activation of endogenous human genes. *Nat Methods.* 2013; 10: 977-979, reported that C-terminal fusions with VP64 using a Gly4Ser (SEQ ID NO: 5) linker can be used as transcriptional activators. Recently, dCas9—FokI nuclease fusions have successfully been generated and exhibit improved enzymatic specificity as compared to the parental Cas9 enzyme (In Guilinger J P, Thompson D B, Liu D R. Fusion of catalytically inactive Cas9 to FokI nuclease improves the specificity of genome modification. *Nat. Biotechnol.* 2014; 32(6): 577-82, and in Tsai S Q, Wyvekens N, Khayter C, Foden J A, Thapar V, Reyon D, Goodwin M J, Aryee M J, Joung J K. Dimeric CRISPR RNA-guided FokI nucleases for highly specific genome editing. *Nat Biotechnol.* 2014; 32(6):569-76. PMID: 24770325 a SGSETPGTSESATPES (SEQ ID NO: 7) or a GGGGS (SEQ ID NO: 5) linker was used in FokI-dCas9 fusion proteins, respectively).

Some aspects of this disclosure provide fusion proteins comprising (i) a Cas9 enzyme or domain (e.g., a first protein); and (ii) a nucleic acid-editing enzyme or domain (e.g., a second protein). In some aspects, the fusion proteins provided herein further include (iii) a programmable DNA-binding protein, for example, a zinc-finger domain, a TALE, or a second Cas9 protein (e.g., a third protein). Without wishing to be bound by any particular theory, fusing a programmable DNA-binding protein (e.g., a second Cas9 protein) to a fusion protein comprising (i) a Cas9 enzyme or domain (e.g., a first protein); and (ii) a nucleic acid-editing enzyme or domain (e.g., a second protein) may be useful for improving specificity of the fusion protein to a target nucleic acid sequence, or for improving specificity or binding affinity of the fusion protein to bind target nucleic acid sequence that does not contain a canonical PAM (NGG) sequence. In some embodiments, the third protein is a Cas9 protein (e.g, a second Cas9 protein). In some embodiments, the third protein is any of the Cas9 proteins provided herein. In some embodiments, the third protein is fused to the fusion protein N-terminal to the Cas9 protein (e.g., the first protein). In some embodiments, the third protein is fused to the fusion protein C-terminal to the Cas9 protein (e.g., the first protein). In some embodiments, the Cas9 domain (e.g., the first protein) and the third protein (e.g., a second Cas9 protein) are fused via a linker (e.g., a second linker). In some embodiments, the linker comprises a (GGGGS)n (SEQ ID NO: 5), a (G)n, an (EAAAK)n (SEQ ID NO: 6), a (GGS)n, (SGGS)$_n$ (SEQ ID NO: 4288), an SGSETPGTSESATPES (SEQ ID NO: 7), or an (XP)n motif, or a combination of any of these, wherein n is independently an integer between 1 and 30. In some embodiments, the general architecture of exemplary Cas9 fusion proteins provided herein comprises the structure:

[NH2]-[nucleic acid-editing enzyme or domain]-[Cas9]-[third protein]-[COOH];
[NH2]-[third protein]-[Cas9]-[nucleic acid-editing enzyme or domain]-[COOH];
[NH2]-[Cas9]-[nucleic acid-editing enzyme or domain]-[third protein]-[COOH];
[NH2]-[third protein]-[nucleic acid-editing enzyme or domain]-[Cas9]-[COOH];
[NH2]-[UGI]-[nucleic acid-editing enzyme or domain]-[Cas9]-[third protein]-[COOH];
[NH2]-[UGI]-[third protein]-[Cas9]-[nucleic acid-editing enzyme or domain]-[COOH];
[NH2]-[UGI]-[Cas9]-[nucleic acid-editing enzyme or domain]-[third protein]-[COOH];
[NH2]-[UGI]-[third protein]-[nucleic acid-editing enzyme or domain]-[Cas9]-[COOH];
[NH2]-[nucleic acid-editing enzyme or domain]-[Cas9]-[third protein]-[UGI]-[COOH];
[NH2]-[third protein]-[Cas9]-[nucleic acid-editing enzyme or domain]-[UGI]-[COOH];
[NH2]-[Cas9]-[nucleic acid-editing enzyme or domain]-[third protein]-[UGI]-[COOH]; or
[NH2]-[third protein]-[nucleic acid-editing enzyme or domain]-[Cas9]-[UGI]-[COOH];

wherein NH2 is the N-terminus of the fusion protein, and COOH is the C-terminus of the fusion protein. In some embodiments, the "]-[" used in the general architecture above indicates the presence of an optional linker sequence. In other examples, the general architecture of exemplary Cas9 fusion proteins provided herein comprises the structure:

[NH2]-[nucleic acid-editing enzyme or domain]-[Cas9]-[second Cas9 protein]-[COOH];
[NH2]-[second Cas9 protein]-[Cas9]-[nucleic acid-editing enzyme or domain]-[COOH];
[NH2]-[Cas9]-[nucleic acid-editing enzyme or domain]-[second Cas9 protein]-[COOH];
[NH2]-[second Cas9 protein]-[nucleic acid-editing enzyme or domain]-[Cas9]-[COOH];
[NH2]-[UGI]-[nucleic acid-editing enzyme or domain]-[Cas9]-[second Cas9 protein]-[COOH],
[NH2]-[UGI]-[second Cas9 protein]-[Cas9]-[nucleic acid-editing enzyme or domain]-[COOH];
[NH2]-[UGI]-[Cas9]-[nucleic acid-editing enzyme or domain]-[second Cas9 protein]-[COOH];
[NH2]-[UGI]-[second Cas9 protein]-[nucleic acid-editing enzyme or domain]-[Cas9]-[COOH];
[NH2]-[nucleic acid-editing enzyme or domain]-[Cas9]-[second Cas9 protein]-[UGI]-[COOH];
[NH2]-[second Cas9 protein]-[Cas9]-[nucleic acid-editing enzyme or domain]-[UGI]-[COOH];
[NH2]-[Cas9]-[nucleic acid-editing enzyme or domain]-[second Cas9 protein]-[UGI]-[COOH]; or
[NH2]-[second Cas9 protein]-[nucleic acid-editing enzyme or domain]-[Cas9]-[UGI]-[COOH];

wherein NH$_2$ is the N-terminus of the fusion protein, and COOH is the C-terminus of the fusion protein. In some embodiments, the "]-[" used in the general architecture above indicates the presence of an optional linker sequence. In some embodiments, the second Cas9 is a dCas9 protein. In some examples, the general architecture of exemplary Cas9 fusion proteins provided herein comprises a structure as shown in FIG. 3. It should be appreciated that any of the proteins provided in any of the general architectures of exemplary Cas9 fusion proteins may be connected by one or more of the linkers provided herein. In some embodiments, the linkers are the same. In some embodiments, the linkers are different. In some embodiments, one or more of the proteins provided in any of the general architectures of exemplary Cas9 fusion proteins are not fused via a linker. In some embodiments, the fusion proteins further comprise a nuclear targeting sequence, for example a nuclear localization sequence. In some embodiments, fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the third protein. In some embodiments, the NLS is fused to the C-terminus of the third protein. In some embodiments, the NLS is fused to the N-terminus of the Cas9 protein. In some embodiments, the NLS is fused to the C-terminus of the Cas9 protein. In some embodiments, the NLS is fused to the N-terminus of the nucleic acid-editing enzyme or domain. In some embodiments, the NLS is fused to the C-terminus of the nucleic acid-editing enzyme or domain. In some embodiments, the NLS is fused to the N-terminus of the UGI protein. In some embodiments, the NLS is fused to the C-terminus of the UGI protein. In some embodiments, the NLS is fused to the fusion protein via one or more linkers. In some embodiments, the NLS is fused to the fusion protein without a linker Uracil Glycosylase Inhibitor Fusion Proteins Some aspects of the disclosure relate to fusion proteins that comprise a uracil glycosylase inhibitor (UGI) domain. In some embodiments, any of the fusion proteins provided herein that comprise a Cas9 domain (e.g., a nuclease active Cas9 domain, a nuclease inactive dCas9 domain, or a Cas9 nickase) may be further fused to a UGI domain either directly or via a linker. Some aspects of this disclosure provide deaminase-dCas9 fusion proteins, deaminase-nuclease active Cas9 fusion proteins and deaminase-Cas9 nickase fusion proteins with increased nucleobase editing efficiency. Without wishing to be bound by any particular theory, cellular DNA-repair response to the presence of U:G heteroduplex DNA may be responsible for the decrease in nucleobase editing efficiency in cells. For example, uracil DNA glycosylase (UDG) catalyzes removal of U from DNA in cells, which may initiate base excision repair, with reversion of the U:G pair to a C:G pair as the most common outcome. As demonstrated in the Examples below, Uracil DNA Glycosylase Inhibitor (UGI) may inhibit human UDG activity. Thus, this disclosure contemplates a fusion protein comprising dCas9-nucleic acid editing domain futher fused to a UGI domain. This disclosure also contemplates a fusion protein comprising a Cas9 nickase-nucleic acid editing domain further fused to a UGI domain. It should be understood that the use of a UGI domain may increase the editing efficiency of a nucleic acid editing domain that is capable of catalyzing a C to U change. For example, fusion proteins comprising a UGI domain may be more efficient in deaminating C residues. In some embodiments, the fusion protein comprises the structure:

[deaminase]-[optional linker sequence]-[dCas9]-[optional linker sequence]-[UGI];
[deaminase]-[optional linker sequence]-[UGI]-[optional linker sequence]-[dCas9];
[UGI]-[optional linker sequence]-[deaminase]-[optional linker sequence]-[dCas9];
[UGI]-[optional linker sequence]-[dCas9]-[optional linker sequence]-[deaminase];
[dCas9]-[optional linker sequence]-[deaminase]-[optional linker sequence]-[UGI]; or
[dCas9]-[optional linker sequence]-[UGI]-[optional linker sequence]-[deaminase].

In other embodiments, the fusion protein comprises the structure:

[deaminase]-[optional linker sequence]-[Cas9 nickase]-[optional linker sequence]-[UGI];
[deaminase]-[optional linker sequence]-[UGI]-[optional linker sequence]-[Cas9 nickase];
[UGI]-[optional linker sequence]-[deaminase]-[optional linker sequence]-[Cas9 nickase];
[UGI]-[optional linker sequence]-[Cas9 nickase]-[optional linker sequence]-[deaminase];
[Cas9 nickase]-[optional linker sequence]-[deaminase]-[optional linker sequence]-[UGI]; or
[Cas9 nickase]-[optional linker sequence]-[UGI]-[optional linker sequence]-[deaminase].

In some embodiments, the fusion proteins provided herein do not comprise a linker sequence. In some embodiments, one or both of the optional linker sequences are present.

In some embodiments, the "-" used in the general architecture above indicates the presence of an optional linker sequence. In some embodiments, the fusion proteins comprising a UGI further comprise a nuclear targeting sequence, for example a nuclear localization sequence. In some embodiments, fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the UGI protein. In some embodiments, the NLS is fused to the C-terminus of the UGI protein. In some embodiments, the NLS is fused to the N-terminus of the Cas9 protein. In some embodiments, the NLS is fused to the C-terminus of the Cas9 protein. In some embodiments, the NLS is fused to the N-terminus of the deaminase. In some embodiments, the NLS is fused to the C-terminus of the deaminase. In some embodiments, the NLS is fused to the N-terminus of the second Cas9. In some embodiments, the NLS is fused to the C-terminus of the second Cas9. In some embodiments, the NLS is fused to the fusion protein via one or more linkers. In some embodiments, the NLS is fused to the fusion protein without a linker. In some embodiments, the NLS comprises an amino acid sequence of any one of the NLS sequences provided or referenced herein. In some embodiments, the NLS comprises an amino acid sequence as set forth in SEQ ID NO: 741 or SEQ ID NO: 742.

In some embodiments, a UGI domain comprises a wild-type UGI or a UGI as set forth in SEQ ID NO: 600. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 600. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 600. In some embodiments, a UGI comprises an amino acid sequence homologous to the amino acid sequence set forth in SEQ ID NO: 600 or an amino acid sequence homologous to a fragment of the amino acid sequence set forth in SEQ ID NO: 600. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 600. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 600. In some embodiments, the UGI comprises the following amino acid sequence:
>sp|P14739|UNGI_BPPB2 Uracil-DNA glycosylase inhibitor MTNLSDIIEKETGKQLVIQE-SILMLPEEVEEVIGNKPESDILVHTAYDEST-DENVMLLTSDA PEYKPWALVIQDSNGENKIKML (SEQ ID NO: 600)

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. J. Biol. Chem. 264: 1163-1171(1989); Lundquist et al., Site-directed mutagenesis and characterization of uracil-DNA glycosylase inhibitor protein. Role of specific carboxylic amino acids in complex formation with *Escherichia coli* uracil-DNA glycosylase. J. Biol. Chem. 272:21408-21419(1997); Ravishankar et al., X-ray analysis of a complex of *Escherichia coli* uracil DNA glycosylase (EcUDG) with a proteinaceous inhibitor. The structure elucidation of a prokaryotic UDG. Nucleic Acids Res. 26:4880-4887(1998); and Putnam et al., Protein mimicry of DNA from crystal structures of the uracil-DNA glycosylase inhibitor protein and its complex with *Escherichia coli* uracil-DNA glycosylase. J. Mol. Biol. 287:331-346(1999), the entire contents of each are incorporated herein by reference.

It should be appreciated that additional proteins may be uracil glycosylase inhibitors. For example, other proteins that are capable of inhibiting (e.g., sterically blocking) a uracil-DNA glycosylase base-excision repair enzyme are within the scope of this disclosure. Additionally, any proteins that block or inhibit base-excision repair as also within the scope of this disclosure. In some embodiments, a protein that binds DNA is used. In another embodiment, a substitute for UGI is used. In some embodiments, a uracil glycosylase inhibitor is a protein that binds single-stranded DNA. For example, a uracil glycosylase inhibitor may be a *Erwinia tasmaniensis* single-stranded binding protein. In some embodiments, the single-stranded binding protein comprises the amino acid sequence (SEQ ID NO: 322). In some embodiments, a uracil glycosylase inhibitor is a protein that binds uracil. In some embodiments, a uracil glycosylase inhibitor is a protein that binds uracil in DNA. In some embodiments, a uracil glycosylase inhibitor is a catalytically inactive uracil DNA-glycosylase protein. In some embodiments, a uracil glycosylase inhibitor is a catalytically inactive uracil DNA-glycosylase protein that does not excise uracil from the DNA. For example, a uracil glycosylase inhibitor is a UdgX. In some embodiments, the UdgX comprises the amino acid sequence (SEQ ID NO: 323). As another example, a uracil glycosylase inhibitor is a catalytically inactive UDG. In some embodiments, a catalytically inactive UDG comprises the amino acid sequence (SEQ ID NO: 324). It should be appreciated that other uracil glycosylase inhibitors would be apparent to the skilled artisan and are within the scope of this disclosure. In some embodiments, a uracil glycosylase inhibitor is a protein that is homologous to any one of SEQ ID NOs: 322-324. In some embodiments, a uracil glycosylase inhibitor is a protein that is at least 50% identical, at least 55% identical at least 60% identical, at least 65% identical, at least 70% identical, at least 75% identical, at least 80% identical at least 85% identical, at least 90% identical, at least 95% identical, at least 96% identical, at least 98% identical, at least 99% identical, or at least 99.5% identical to any one of SEQ ID NOs: 322-324.

```
Erwinia tasmaniensis SSB
(themostable single-stranded DNA binding protein)
                                          (SEQ ID NO: 322)
MASRGVNKVILVGNLGQDPEVRYMPNGGAVANITLATSESWRDKQTGETK

EKTEWHRVVLFGKLAEVAGEYLRKGSQVYIEGALQTRKWTDQAGVEKYTT

EVVVNVGGTMQMLGGRSQGGGASAGGQNGGSNNGWGQPQQPQGGNQFSGG

AQQQARPQQQPQQNNAPANNEPPIDFDDDIP

UdgX (binds to Uracil in DNA but does not excise)
                                          (SEQ ID NO: 323)
MAGAQDFVPHTADLAELAAAAGECRGCGLYRDATQAVFGAGGRSARIMMI

GEQPGDKEDLAGLPFVGPAGRLLDRALEAADIDRDALYVTNAVKHFKFTR

AAGGKRRIHKTPSRTEVVACRPWLIAEMTSVEPDVVVLLGATAAKALLGN

DFRVTQHRGEVLHVDDVPGDPALVATVHPSSLLRGPKEERESAFAGLVDD

LRVAADVRP

UDG (catalytically inactive human UDG, binds to
Uracil in DNA but does not excise)
                                          (SEQ ID NO: 324)
MIGQKTLYSFFSPSPARKRHAPSPEPAVQGTGVAGVPEESGDAAAIPAKK

APAGQEEPGTPPSSPLSAEQLDRIQRNKAAALLRLAARNVPVGFGESWKK

HLSGEFGKPYFIKLMGFVAEERKHYTVYPPPHQVFTWTQMCDIKDVKVVI

LGQEPYHGPNQAHGLCFSVQRPVPPPPSLENIYKELSTDIEDFVHPGHGD

LSGWAKQGVLLLNAVLTVRAHQANSHKERGWEQFTDAVVSWLNQNSNGLV

FLLWGSYAQKKGSAIDRKRHHVLQTAHPSPLSVYRGFFGCRHFSKTNELL

QKSGKKPIDWKEL
```

In some embodiments, the nucleic acid editing domain is a deaminase domain. In some embodiments, the deaminase is a cytosine deaminase or a cytidine deaminase. In some embodiments, the deaminase is an apolipoprotein B mRNA-editing complex (APOBEC) family deaminase. In some embodiments, the deaminase is an APOBEC1 deaminase. In some embodiments, the deaminase is an APOBEC2 deaminase. In some embodiments, the deaminase is an APOBEC3 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, the deaminase is an APOBEC3E deaminase. In some embodiments, the deaminase is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). In some embodiments, the deaminase is a rat APOBEC1 (SEQ ID NO: 282). In some embodiments, the deminase is a human APOBEC1 (SEQ ID No: 284). In some embodiments, the deaminase is a *Petromyzon marinus* cytidine deaminase 1 (pmCDA1). In some embodiments, the deminase is a human APOBEC3G (SEQ ID NO: 275). In some embodiments, the deaminase is a fragment of the human APOBEC3G (SEQ ID NO: 5740). In some embodiments, the deaminase is a human APOBEC3G variant comprising a D316R_D317R mutation (SEQ ID NO: 5739). In some embodiments, the deaminase is a frantment of the human APOBEC3G and comprising mutations corresponding to the D316R_D317R mutations in SEQ ID NO: 275 (SEQ ID NO: 5741).

In some embodiments, the linker comprises a $(GGGS)_n$ (SEQ ID NO: 265), $(GGGGS)_n$ (SEQ ID NO: 5), a $(G)_n$, an $(EAAAK)_n$ (SEQ ID NO: 6), a $(GGS)_n$, an SGSETPGTS-ESATPES (SEQ ID NO: 7), or an $(XP)_n$ motif, or a combination of any of these, wherein n is independently an integer between 1 and 30.

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. *J. Biol. Chem.* 264: 1163-1171(1989); Lundquist et al., Site-directed mutagenesis and characterization of uracil-DNA glycosylase inhibitor protein. Role of specific carboxylic amino acids in complex formation with *Escherichia coli* uracil-DNA glycosylase. *J. Biol. Chem.* 272:21408-21419(1997); Ravishankar et al., X-ray analysis of a complex of *Escherichia coli* uracil DNA glycosylase (EcUDG) with a proteinaceous inhibitor. The structure elucidation of a prokaryotic UDG. *Nucleic Acids Res.* 26:4880-4887(1998); and Putnam et al., Protein mimicry of DNA from crystal structures of the uracil-DNA glycosylase inhibitor protein and its complex with *Escherichia coli* uracil-DNA glycosylase. *J. Mol. Biol.* 287:331-346(1999), the entire contents of which are incorporated herein by reference. In some embodiments, the optional linker comprises a $(GGS)_n$ motif, wherein n is 1, 2, 3, 4, 5, 6, 7, 8, 9, 19, 11, 12, 13, 14, 15, 16, 17, 18, 19, or 20. In some embodiments, the optional linker comprises a (GGS)n motif, wherein n is 1, 3, or 7. In some embodiments, the optional linker comprises the amino acid sequence SGSETPGTSESATPES (SEQ ID NO: 7), which is also referred to as the XTEN linker in the Examples.

In some embodiments, a Cas9 nickase may further facilitate the removal of a base on the non-edited strand in an organism whose genome is edited in vivo. The Cas9 nickase, as described herein, may comprise a D10A mutation in SEQ ID NO: 10, or a corresponding mutation in any of SEQ ID NOs: 11-260. In some embodiments, the Cas9 nickase of this disclosure may comprise a histidine at mutation 840 of SEQ ID NO: 10, or a corresponding residue in any of SEQ ID NOs: 11-260. Such fusion proteins comprising the Cas9 nickase, can cleave a single strand of the target DNA sequence, e.g., the strand that is not being edited. Without wishing to be bound by any particular theory, this cleavage may inhibit mis-match repair mechanisms that reverse a C to U edit made by the deaminase.

Cas9 Complexes with Guide RNAs

Some aspects of this disclosure provide complexes comprising any of the fusion proteins provided herein, and a guide RNA bound to a Cas9 domain (e.g., a dCas9, a nuclease active Cas9, or a Cas9 nickase) of fusion protein.

In some embodiments, the guide RNA is from 15-100 nucleotides long and comprises a sequence of at least 10 contiguous nucleotides that is complementary to a target sequence. In some embodiments, the guide RNA is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some embodiments, the guide RNA comprises a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to a target sequence. In some embodiments, the target sequence is a DNA sequence. In some embodiments, the target sequence is a sequence in the genome of a mammal. In some embodiments, the target sequence is a sequence in the genome of a human. In some embodiments, the 3' end of the target sequence is immediately adjacent to a canonical PAM sequence (NGG). In some embodiments, the guide RNA is complementary to a sequence associated with a disease or disorder. In some embodiments, the guide RNA is complementary to a sequence associated with a disease or disorder having a mutation in a gene selected from the genes disclosed in any one of Tables 1-3. In some embodiments, the guide RNA comprises a nucleotide sequence of any one of the guide sequences provided in Table 2 or Table 3. Exemplary sequences in the human genome that may be targeted by the complexes of this disclosure are provided herein in Tables 1-3.

Methods of Using Cas9 Fusion Proteins

Some aspects of this disclosure provide methods of using the Cas9 proteins, fusion proteins, or complexes provided herein. For example, some aspects of this disclosure provide methods comprising contacting a DNA molecule (a) with any of the the Cas9 proteins or fusion proteins provided herein, and with at least one guide RNA, wherein the guide RNA is about 15-100 nucleotides long and comprises a sequence of at least 10 contiguous nucleotides that is complementary to a target sequence; or (b) with a Cas9 protein, a Cas9 fusion protein, or a Cas9 protein or fusion protein complex with at least one gRNA as provided herein. In some embodiments, the 3' end of the target sequence is not immediately adjacent to a canonical PAM sequence (NGG). In some embodiments, the 3' end of the target sequence is immediately adjacent to an AGC, GAG, TTT, GTG, or CAA sequence.

In some embodiments, the target DNA sequence comprises a sequence associated with a disease or disorder. In some embodiments, the target DNA sequence comprises a point mutation associated with a disease or disorder. In some embodiments, the activity of the Cas9 protein, the Cas9 fusion protein, or the complex results in a correction of the point mutation. In some embodiments, the target DNA sequence comprises a T→C point mutation associated with a disease or disorder, and wherein the deamination of the mutant C base results in a sequence that is not associated with a disease or disorder. In some embodiments, the target DNA sequence encodes a protein and wherein the point mutation is in a codon and results in a change in the amino acid encoded by the mutant codon as compared to the wild-type codon. In some embodiments, the deamination of the mutant C results in a change of the amino acid encoded by the mutant codon. In some embodiments, the deamination of the mutant C results in the codon encoding the wild-type amino acid. In some embodiments, the contacting is in vivo in a subject. In some embodiments, the subject has or has been diagnosed with a disease or disorder. In some embodiments, the disease or disorder is cystic fibrosis, phenylketonuria, epidermolytic hyperkeratosis (EHK), Charcot-Marie-Toot disease type 4J, neuroblastoma (NB), von Willebrand disease (vWD), myotonia congenital, hereditary renal amyloidosis, dilated cardiomyopathy (DCM), hereditary lymphedema, familial Alzheimer's disease, HIV, Prion disease, chronic infantile neurologic cutaneous articular syndrome (CINCA), desmin-related myopathy (DRM), a neoplastic disease associated with a mutant PI3KCA protein, a mutant CTNNB1 protein, a mutant HRAS protein, or a mutant p53 protein.

Some embodiments provide methods for using the Cas9 DNA editing fusion proteins provided herein. In some embodiments, the fusion protein is used to introduce a point mutation into a nucleic acid by deaminating a target nucleobase, e.g., a C residue. In some embodiments, the deamination of the target nucleobase results in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ a Cas9 DNA editing fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provide herein is to restore the function of a dysfunctional gene via genome editing. The Cas9 deaminase fusion proteins provided herein can be validated for gene editing-based human therapeutics in vitro, e.g., by correcting a disease-associated mutation in human cell culture. It will be understood by the skilled artisan that the fusion proteins provided herein, e.g., the fusion proteins comprising a Cas9 domain and a nucleic acid deaminase domain can be used to correct any single point T->C or A->G mutation. In the first case, deamination of the mutant C back to U corrects the mutation, and in the latter case, deamination of the C that is base-paired with the mutant G, followed by a round of replication, corrects the mutation.

An exemplary disease-relevant mutation that can be corrected by the provided fusion proteins in vitro or in vivo is the H1047R (A3140G) polymorphism in the PI3KCA protein. The phosphoinositide-3-kinase, catalytic alpha subunit (PI3KCA) protein acts to phosphorylate the 3-OH group of the inositol ring of phosphatidylinositol. The PI3KCA gene has been found to be mutated in many different carcinomas, and thus it is considered to be a potent oncogene.[37] In fact, the A3140G mutation is present in several NCI-60 cancer cell lines, such as, for example, the HCT116, SKOV3, and T47D cell lines, which are readily available from the American Type Culture Collection (ATCC).[38]

In some embodiments, a cell carrying a mutation to be corrected, e.g., a cell carrying a point mutation, e.g., an A3140G point mutation in exon 20 of the PI3KCA gene, resulting in a H1047R substitution in the PI3KCA protein, is contacted with an expression construct encoding a Cas9 deaminase fusion protein and an appropriately designed sgRNA targeting the fusion protein to the respective mutation site in the encoding PI3KCA gene. Control experiments can be performed where the sgRNAs are designed to target the fusion enzymes to non-C residues that are within the PI3KCA gene. Genomic DNA of the treated cells can be extracted, and the relevant sequence of the PI3KCA genes PCR amplified and sequenced to assess the activities of the fusion proteins in human cell culture.

It will be understood that the example of correcting point mutations in PI3KCA is provided for illustration purposes and is not meant to limit the instant disclosure. The skilled artisan will understand that the instantly disclosed DNA-editing fusion proteins can be used to correct other point mutations and mutations associated with other cancers and with diseases other than cancer including other proliferative diseases.

The successful correction of point mutations in disease-associated genes and alleles opens up new strategies for gene correction with applications in therapeutics and basic research. Site-specific single-base modification systems like the disclosed fusions of Cas9 and deaminase enzymes or domains also have applications in "reverse" gene therapy, where certain gene functions are purposely suppressed or abolished. In these cases, site-specifically mutating Trp (TGG), Gln (CAA and CAG), or Arg (CGA) residues to premature stop codons (TAA, TAG, TGA) can be used to abolish protein function in vitro, ex vivo, or in vivo.

The instant disclosure provides methods for the treatment of a subject diagnosed with a disease associated with or caused by a point mutation that can be corrected by a Cas9 DNA editing fusion protein provided herein. For example, in some embodiments, a method is provided that comprises administering to a subject having such a disease, e.g., a cancer associated with a PI3KCA point mutation as described above, an effective amount of a Cas9 deaminase fusion protein that corrects the point mutation or introduces a deactivating mutation into the disease-associated gene. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting a point mutation or introducing a deactivating mutation into a disease-associated gene will be known to those of skill in the art, and the disclosure is not limited in this respect.

The instant disclosure provides methods for the treatment of additional diseases or disorders, e.g., diseases or disorders that are associated or caused by a point mutation that can be corrected by deaminase-mediated gene editing. Some such diseases are described herein, and additional suitable diseases that can be treated with the strategies and fusion proteins provided herein will be apparent to those of skill in the art based on the instant disclosure. Exemplary suitable diseases and disorders are listed below. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment and determination of homologous residues. Exemplary suitable diseases and disorders include, without limitation, cystic fibrosis (see, e.g., Schwank et al., Functional repair of CFTR by CRISPR/Cas9 in intestinal stem cell organoids of cystic fibrosis patients. *Cell stem cell*. 2013; 13: 653-658; and Wu et. al., Correction of a genetic disease in mouse via use of CRISPR-Cas9. *Cell stem cell*. 2013; 13: 659-662, neither of which uses a deaminase fusion protein to correct the genetic defect); phenylketonuria—e.g., phenylalanine to serine mutation at position 835 (mouse) or 240 (human) or a homologous residue in phenylalanine hydroxylase gene (T>C mutation)—see, e.g., McDonald et al., *Genomics*. 1997; 39:402-405; Bernard-Soulier syndrome (BSS)—e.g., phenylalanine to serine mutation at position 55 or a homologous residue, or cysteine to arginine at residue 24 or a homologous residue in the platelet membrane glycoprotein IX (T>C mutation)—see, e.g., Noris et al., *British Journal of Haematology.* 1997; 97: 312-320, and Ali et al., *Hematol.* 2014; 93: 381-384; epidermolytic hyperkeratosis (EHK)—e.g., leucine to proline mutation at position 160 or 161 (if counting the initiator methionine) or a homologous residue in keratin 1 (T>C mutation)—see, e.g., Chipev et al., *Cell.* 1992; 70: 821-828, see also accession number P04264 in the UNIPROT database at www[dot]uniprot[dot]org; chronic obstructive pulmonary disease (COPD)—e.g., leucine to proline mutation at position 54 or 55 (if counting the initiator methionine) or a homologous residue in the processed form of $\alpha_1$-antitrypsin or residue 78 in the unprocessed form or a homologous residue (T>C mutation)—see, e.g., Poller et al., *Genomics.* 1993; 17: 740-743, see also accession number P01011 in the UNIPROT database; Charcot-Marie-Toot disease type 4J—e.g., isoleucine to threonine mutation at position 41 or a homologous residue in FIG. 4 (T>C mutation)—see, e.g., Lenk et al., PLoS Genetics. 2011; 7: e1002104; neuroblastoma (NB)—e.g., leucine to proline mutation at position 197 or a homologous residue in Caspase-9 (T>C mutation)—see, e.g., Kundu et al., 3 *Biotech.* 2013, 3:225-234; von Willebrand disease (vWD)—e.g., cysteine to arginine mutation at position 509 or a homologous residue in the processed form of von Willebrand factor, or at position 1272 or a homologous residue in the unprocessed form of von Willebrand factor (T>C mutation)—see, e.g., Lavergne et al., *Br. J. Haematol.* 1992, see also accession number P04275 in the UNIPROT database; 82: 66-72; myotonia congenital—e.g., cysteine to arginine mutation at position 277 or a homologous residue in the muscle chloride channel gene CLCN1 (T>C mutation)—see, e.g., Weinberger et al., *The J. of Physiology.* 2012; 590: 3449-3464; hereditary renal amyloidosis—e.g., stop codon to arginine mutation at position 78 or a homologous residue in the processed form of apolipoprotein AII or at position 101 or a homologous residue in the unprocessed form (T>C mutation)—see, e.g., Yazaki et al., *Kidney Int.* 2003; 64: 11-16; dilated cardiomyopathy (DCM)—e.g., tryptophan to Arginine mutation at position 148 or a homologous residue in the FOXD4 gene (T>C mutation), see, e.g., Minoretti et. al., *Int. J. of Mol. Med.* 2007; 19: 369-372; hereditary lymphedema—e.g., histidine to arginine mutation at position 1035 or a homologous residue in VEGFR3 tyrosine kinase (A>G mutation), see, e.g., Irrthum et al., *Am. J. Hum. Genet.* 2000; 67: 295-301; familial Alzheimer's disease—e.g., isoleucine to valine mutation at position 143 or a homologous residue in presenilin1 (A>G mutation), see, e.g., Gallo et. al., *J. Alzheimer's disease.* 2011; 25: 425-431; Prion disease—e.g., methionine to valine mutation at position 129 or a homologous residue in prion protein (A>G mutation)—see, e.g., Lewis et. al., *J. of General Virology.* 2006; 87: 2443-2449; chronic infantile neurologic cutaneous articular syndrome (CINCA)—e.g., Tyrosine to Cysteine mutation at position 570 or a homologous residue in cryopyrin (A>G mutation)—see, e.g., Fujisawa et. al. *Blood.* 2007; 109: 2903-2911; and desmin-related myopathy (DRM)—e.g., arginine to glycine mutation at position 120 or a homologous residue in $\alpha\beta$ crystallin (A>G mutation)—see, e.g., Kumar et al., *J. Biol. Chem.* 1999; 274: 24137-24141. The entire contents of all references and database entries is incorporated herein by reference.

The instant disclosure provides lists of genes comprising pathogenic T>C or A>G mutations. Provided herein, are the names of these genes, their respective SEQ ID NOs, their gene IDs, and sequences flanking the mutation site. (Tables 2 and 3). In some instances, the gRNA sequences that can be used to correct the mutations in these genes are disclosed (Tables 2 and 3).

In some embodiments, a Cas9-deaminase fusion protein recognizes canonical PAMs and therefore can correct the pathogenic T>C or A>G mutations with canonical PAMs, e.g., NGG (listed in Tables 2 and 3, SEQ ID NOs: 2540-2702 and 5084-5260), respectively, in the flanking sequences. For example, the Cas9 proteins that recognize canonical PAMs comprise an amino acid sequence that is at least 90% identical to the amino acid sequence of *Streptococcus pyogenes* Cas9 as provided by SEQ ID NO: 10, or to a fragment thereof comprising the RuvC and HNH domains of SEQ ID NO: 10.

It will be apparent to those of skill in the art that in order to target a Cas9:nucleic acid editing enzyme/domain fusion protein as disclosed herein to a target site, e.g., a site comprising a point mutation to be edited, it is typically necessary to co-express the Cas9:nucleic acid editing enzyme/domain fusion protein together with a guide RNA, e.g., an sgRNA. As explained in more detail elsewhere herein, a guide RNA typically comprises a tracrRNA framework allowing for Cas9 binding, and a guide sequence, which confers sequence specificity to the Cas9:nucleic acid editing enzyme/domain fusion protein. In some embodiments, the guide RNA comprises a structure 5'-[guide sequence]-guuuuagagcuagaaauagcaaguuaaaauaaaggcuagu-ccguuaucaacuugaaaaaguggcaccgagucggugcuuuuu-3' (SEQ ID NO: 601), wherein the guide sequence comprises a sequence that is complementary to the target sequence. The guide sequence is typically 20 nucleotides long. The sequences of suitable guide RNAs for targeting Cas9:nucleic acid editing enzyme/domain fusion proteins to specific genomic target sites will be apparent to those of skill in the art based on the instant disclosure. Such suitable guide RNA sequences typically comprise guide sequences that are complementary to a nucleic sequence within 50 nucleotides upstream or downstream of the target nucleotide to be edited. Some exemplary guide RNA sequences suitable for targeting Cas9:nucleic acid editing enzyme/domain fusion proteins to specific target sequences are provided below.

Base Editor Efficiency

Some aspects of the disclosure are based on the recognition that any of the base editors provided herein are capable of modifying a specific nucleotide base without generating a significant proportion of indels. An "indel", as used herein, refers to the insertion or deletion of a nucleotide base within a nucleic acid. Such insertions or deletions can lead to frame shift mutations within a coding region of a gene. In some embodiments, it is desirable to generate base editors that efficiently modify (e.g. mutate or deaminate) a specific nucleotide within a nucleic acid, without generating a large number of insertions or deletions (i.e., indels) in the nucleic acid. In certain embodiments, any of the base editors provided herein are capable of generating a greater proportion of intended modifications (e.g., point mutations or deaminations) versus indels. In some embodiments, the base editors provided herein are capable of generating a ratio of intended point mutations to indels that is greater than 1:1. In some embodiments, the base editors provided herein are capable of generating a ratio of intended point mutations to indels that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 200:1, at least 300:1, at least 400:1, at least 500:1, at least 600:1, at least 700:1, at least 800:1, at least 900:1, or at least 1000:1, or more. The number of intended mutations and indels may be determined using any suitable method, for example the methods used in the below Examples.

In some embodiments, the base editors provided herein are capable of limiting formation of indels in a region of a nucleic acid. In some embodiments, the region is at a nucleotide targeted by a base editor or a region within 2, 3, 4, 5, 6, 7, 8, 9, or 10 nucleotides of a nucleotide targeted by a base editor. In some embodiments, any of the base editors provided herein are capable of limiting the formation of indels at a region of a nucleic acid to less than 1%, less than 1.5%, less than 2%, less than 2.5%, less than 3%, less than 3.5%, less than 4%, less than 4.5%, less than 5%, less than 6%, less than 7%, less than 8%, less than 9%, less than 10%, less than 12%, less than 15%, or less than 20%. The number of indels formed at a nucleic acid region may depend on the amount of time a nucleic acid (e.g., a nucleic acid within the genome of a cell) is exposed to a base editor. In some embodiments, an number or proportion of indels is determined after at least 1 hour, at least 2 hours, at least 6 hours, at least 12 hours, at least 24 hours, at least 36 hours, at least 48 hours, at least 3 days, at least 4 days, at least 5 days, at least 7 days, at least 10 days, or at least 14 days of exposing a nucleic acid (e.g., a nucleic acid within the genome of a cell) to a base editor.

Some aspects of the disclosure are based on the recognition that any of the base editors provided herein are capable of efficiently generating an intended mutation, such as a point mutation, in a nucleic acid (e.g. a nucleic acid within a genome of a subject) without generating a significant number of unintended mutations, such as unintended point mutations. In some embodiments, a intended mutation is a mutation that is generated by a specific base editor bound to a gRNA, specifically designed to generate the intended mutation. In some embodiments, the intended mutation is a mutation associated with a disease or disorder. In some embodiments, the intended mutation is a cytosine (C) to thymine (T) point mutation associated with a disease or disorder. In some embodiments, the intended mutation is a guanine (G) to adenine (A) point mutation associated with a disease or disorder. In some embodiments, the intended mutation is a cytosine (C) to thymine (T) point mutation within the coding region of a gene. In some embodiments, the intended mutation is a guanine (G) to adenine (A) point mutation within the coding region of a gene. In some embodiments, the intended mutation is a point mutation that generates a stop codon, for example, a premature stop codon within the coding region of a gene. In some embodiments, the intended mutation is a mutation that eliminates a stop codon. In some embodiments, the intended mutation is a mutation that alters the splicing of a gene. In some embodiments, the intended mutation is a mutation that alters the regulatory sequence of a gene (e.g., a gene promotor or gene repressor). In some embodiments, any of the base editors provided herein are capable of generating a ratio of intended mutations to unintended mutations (e.g., intended point mutations:unintended point mutations) that is greater than 1:1. In some embodiments, any of the base editors provided herein are capable of generating a ratio of intended mutations to unintended mutations (e.g., intended point mutations:unintended point mutations) that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 150:1, at least 200:1, at least 250:1, at least 500:1, or at least 1000:1, or more. It should be appreciated that the characteristics of the base editors described in the "Base Editor Efficiency" section, herein, may be applied to any of the fusion proteins, or methods of using the fusion proteins provided herein.

Methods for Editing Nucleic Acids

Some aspects of the disclosure provide methods for editing a nucleic acid. In some embodiments, the method is a method for editing a nucleobase of a nucleic acid (e.g., a base pair of a double-stranded DNA sequence). In some embodiments, the method comprises the steps of: a) contacting a target region of a nucleic acid (e.g., a double-stranded DNA sequence) with a complex comprising a base editor (e.g., a Cas9 domain fused to a cytidine deaminase domain) and a guide nucleic acid (e.g., gRNA), wherein the target region comprises a targeted nucleobase pair, b) inducing strand separation of said target region, c) converting a first nucleobase of said target nucleobase pair in a single strand of the target region to a second nucleobase, and d) cutting no more than one strand of said target region, where a third nucleobase complementary to the first nucleobase base is replaced by a fourth nucleobase complementary to the second nucleobase; and the method results in less than 20% indel formation in the nucleic acid. It should be appreciated that in some embodiments, step b is omitted. In some embodiments, the first nucleobase is a cytosine. In some embodiments, the second nucleobase is a deaminated cytosine, or a uracil. In some embodiments, the third nucleobase is a guanine. In some embodiments, the fourth nucleobase is an adenine. In some embodiments, the first nucleobase is a cytosine, the second nucleobase is a deaminated cytosine, or a uracil, the third nucleobase is a guanine, and the fourth nucleobase is an adenine. In some embodiments, the method results in less than 19%, 18%, 16%, 14%, 12%, 10%, 8%, 6%, 4%, 2%, 1%, 0.5%, 0.2%, or less than 0.1% indel formation. In some embodiments, the method further comprises replacing the second nucleobase with a fifth nucleobase that is complementary to the fourth nucleobase, thereby generating an intended edited base pair (e.g., C:G→T:A). In some embodiments, the fifth nucleobase is a thymine. In some embodiments, at least 5% of the intended basepairs are edited. In some embodiments, at least 10%, 15%, 20%, 25%, 30%, 35%, 40%, 45%, or 50% of the intended basepairs are edited.

In some embodiments, the ratio of intended products to unintended products in the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand (nicked strand) is hybridized to the guide nucleic acid. In some embodiments, the cut single strand is opposite to the strand comprising the first nucleobase. In some embodiments, the base editor comprises a Cas9 domain. In some embodiments, the first base is cytosine, and the second base is not a G, C, A, or T. In some embodiments, the second base is uracil. In some embodiments, the first base is cytosine. In some embodiments, the second base is not a G, C, A, or T. In some embodiments, the second base is uracil. In some embodiments, the base editor inhibits base excision repair of the edited strand. In some embodiments, the base editor protects or binds the non-edited strand. In some embodiments, the base editor comprises UGI activity. In some embodiments, the base editor comprises nickase activity. In some embodiments, the intended edited basepair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepair is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair is within the target window. In some embodiments, the target window comprises the intended edited base pair. In some embodiments, the method is performed using any of the base editors provided herein. In some embodiments, a target window is a deamination window In some embodiments, the disclosure provides methods for editing a nucleotide. In some embodiments, the disclosure provides a method for editing a nucleobase pair of a double-stranded DNA sequence. In some embodiments, the method comprises a) contacting a target region of the double-stranded DNA sequence with a complex comprising a base editor and a guide nucleic acid (e.g., gRNA), where the target region comprises a target nucleobase pair, b) inducing strand separation of said target region, c) converting a first nucleobase of said target nucleobase pair in a single strand of the target region to a second nucleobase, d) cutting no more than one strand of said target region, wherein a third nucleobase complementary to the first nucleobase base is replaced by a fourth nucleobase complementary to the second nucleobase, and the second nucleobase is replaced with a fifth nucleobase that is complementary to the fourth nucleobase, thereby generating an intended edited basepair, wherein the efficiency of generating the intended edited basepair is at least 5%. It should be appreciated that in some embodiments, step b is omitted. In some embodiments, at least 5% of the intended basepairs are edited. In some embodiments, at least 10%, 15%, 20%, 25%, 30%, 35%, 40%, 45%, or 50% of the intended basepairs are edited. In some embodiments, the method causes less than 19%, 18%, 16%, 14%, 12%, 10%, 8%, 6%, 4%, 2%, 1%, 0.5%, 0.2%, or less than 0.1% indel formation. In some embodiments, the ratio of intended product to unintended products at the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand is hybridized to the guide nucleic acid. In some embodiments, the cut single strand is opposite to the strand comprising the first nucleobase. In some embodiments, the first base is cytosine. In some embodiments, the second nucleobase is not G, C, A, or T. In some embodiments, the second base is uracil. In some embodiments, the base editor inhibits base excision repair of the edited strand. In some embodiments, the base editor protects or binds the non-edited strand. In some embodiments, the nucleobase editor comprises UGI activity. In some embodiments, the nucleobase edit comprises nickase activity. In some embodiments, the intended edited basepair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepair is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, the linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. 108/663 H0824.70213w000 In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair occurs within the target window. In some embodiments, the target window comprises the intended edited base pair. In some embodiments, the nucleobase editor is any one of the base editors provided herein.

Kits, Vectors, Cells

Some aspects of this disclosure provide kits comprising a nucleic acid construct, comprising (a) a nucleotide sequence encoding a Cas9 protein or a Cas9 fusion protein as provided herein; and (b) a heterologous promoter that drives expression of the sequence of (a). In some embodiments, the kit further comprises an expression construct encoding a guide RNA backbone, wherein the construct comprises a cloning site positioned to allow the cloning of a nucleic acid sequence identical or complementary to a target sequence into the guide RNA backbone.

Some aspects of this disclosure provide polynucleotides encoding a Cas9 protein of a fusion protein as provided herein. Some aspects of this disclosure provide vectors comprising such polynucleotides. In some embodiments, the vector comprises a heterologous promoter driving expression of polynucleotide.

Some aspects of this disclosure provide cells comprising a Cas9 protein, a fusion protein, a nucleic acid molecule encoding the fusion protein, a complex comprise the Cas9 protein and the gRNA, and/or a vector as provided herein.

The description of exemplary embodiments of the reporter systems above is provided for illustration purposes only and not meant to be limiting. Additional reporter systems, e.g., variations of the exemplary systems described in detail above, are also embraced by this disclosure.

EXAMPLES

Example 1: Cas9 Deaminase Fusion Proteins

A number of Cas9:Deaminase fusion proteins were generated and deaminase activity of the generated fusions was characterized. The following deaminases were tested:

Human AID (hAID):
(SEQ ID NO: 607)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPYLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGLLD

Human AID-DC (hAID-DC, truncated version of hAID with 7-fold increased activity):
(SEQ ID NO: 608)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPNLSLRIFTARLYFCEDRKAEPEGLRRLHRAGVQIAIMTFKDYFYCWNT

FVENHERTFKAWEGLHENSVRLSRQLRRILL

Rat APOBEC1 (rAPOBEC1):
(SEQ ID NO: 284)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLK

Human APOBEC1 (hAPOBEC1)
(SEQ ID NO: 5724)
MTSEKGPSTGDPTLRRRIEPWEFDVFYDPRELRKEACLLYEIKWGMSRKI

WRSSGKNTTNHVEVNFIKKFTSERDFHPSMSCSITWFLSWSPCWECSQAI

REFLSRHPGVTLVIYVARLFWHMDQQNRQGLRDLVNSGVTIQIMRASEYY

HCWRNFVNYPPGDEAHWPQYPPLWMMLYALELHCIILSLPPCLKISRRWQ

NHLTFFRLHLQNCHYQTIPPHILLATGLIHPSVAWR

Petromyzon marinus (Lamprey) CDA1 (pmCDA1):
(SEQ ID NO: 609)
MTDAEYVRIHEKLDIYTFKKQFFNNKKSVSHRCYVLFELKRRGERRACFW

GYAVNKPQSGTERGIHAEIFSIRKVEEYLRDNPGQFTINWYSSWSPCADC

AEKILEWYNQELRGNGHTLKIWACKLYYEKNARNQIGLWNLRDNGVGLNV

MVSEHYQCCRKIFIQSSHNQLNENRWLEKTLKRAEKRRSELSIMIQVKIL

HTTKSPAV

Human APOBEC3G (hAPOBEC3G):
(SEQ ID NO: 610)
MELKYHPEMRFFHWFSKWRKLHRDQEYEVTWYISWSPCTKCTRDMATFLA

EDPKVTLTIFVARLYYFWDPDYQEALRSLCQKRDGPRATMKIMNYDEFQH

CWSKFVYSQRELFEPWNNLPKYYILLHIMLGEILRHSMDPPTFTFNFNNE

PWVRGRHETYLCYEVERMHNDTWVLLNQRRGFLCNQAPHKHGFLEGRHAE

LCFLDVIPFWKLDLDQDYRVTCFTSWSPCFSCAQEMAKFISKNKHVSLCI

FTARIYDDQGRCQEGLRTLAEAGAKISIMTYSEFKHCWDTFVDHQGCPFQ

PWDGLDEHSQDLSGRLRAILQNQEN

Deaminase Activity on ssDNA. A USER (Uracil-Specific Excision Reagent) Enzyme-based assay for deamination was employed to test the activity of various deaminases on single-stranded DNA (ssDNA) substrates. USER Enzyme was obtained from New England Biolabs. An ssDNA substrate was provided with a target cytosine residue at different positions. Deamination of the ssDNA cytosine target residue results in conversion of the target cytosine to a uracil. The USER Enzyme excises the uracil base and cleaves the ssDNA backbone at that position, cutting the ssDNA substrate into two shorter fragments of DNA. In some assays, the ssDNA substrate is labeled on one end with a dye, e.g., with a 5' Cy3 label (the * in the scheme below). Upon deamination, excision, and cleavage of the strand, the substrate can be subjected to electrophoresis, and the substrate and any fragment released from it can be visualized by detecting the label. Where Cy5 is images, only the fragment with the label will be visible via imaging.

In one USER Enzyme assay, ssDNA substrates were used that matched the target sequences of the various deaminases tested. Expression cassettes encoding the deaminases tested were inserted into a CMV backbone plasmid that has been used previously in the lab (Addgene plasmid 52970). The deaminase proteins were expressed using a TNT Quick Coupled Transcription/Translation System (Promega) according to the manufacturers recommendations. After 90 min of incubation, 5 mL of lysate was incubated with 5' Cy3-labeled ssDNA substrate and 1 unit of USER Enzyme (NEB) for 3 hours. The DNA was resolved on a 10% TBE PAGE gel and the DNA was imaged using Cy-dye imaging. A schematic representation of the USER Enzyme assay is shown in FIG. 41.

Figure 1:
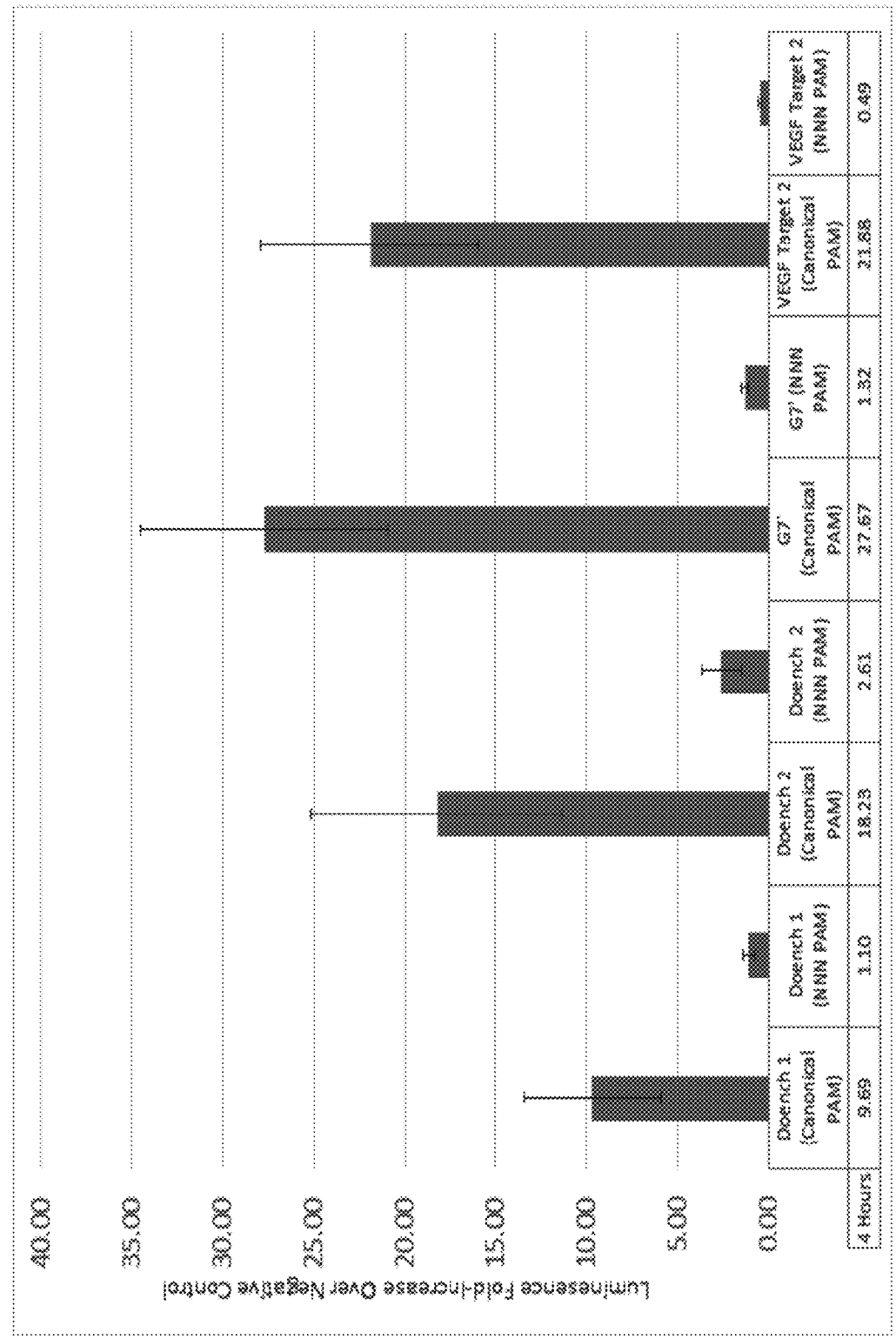
FIG. 1 shows the deaminase activity of deaminases on single stranded DNA substrates. Single stranded DNA substrates using randomized PAM sequences (NNN PAM) were used as negative controls. Canonical PAM sequences used (NGG PAM)

FIG. 1 shows the deaminase activity of the tested deaminases on ssDNA substrates, such as Doench 1, Doench 2, G7' and VEGF Target 2. The rAPOBEC1 enzyme exhibited a substantial amount of deamination on the single-stranded DNA substrate with a canonical NGG PAM, but not with a negative control non-canonical NNN PAM. Cas9 fusion proteins with APOBEC family deaminases were generated. The following fusion architectures were constructed and tested on ssDNA:

rAPOBEC1-GGS-dCas9 primary sequence
(SEQ ID NO: 611)
MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLW

VRLYVLELYCIILGLPPCLNILRRKQPQLTFFTIALQSCHYQRLPPHILWATGLKGGSD

*KKYSIGLAIGTNSVGWAVITDEYKVPSKKFKVLGNTDRHSIKKNLIGALLFDSGETAE*

*ATRLKRTARRRYTRRKNRICYLQEIFSNEMAKVDDSFFHRLEESFLVEEDKKHERHP*

-continued

*IFGNIVDEVAYHEKYPTIYHLRKKLVDSTDKADLRLIYLALAHMIKFRGHFLIEGDLN*

*PDNSDVDKLFIQLVQTYNQLFEENPINASGVDAKAILSARLSKSRRLENLIAQLPGEK*

*KNGLFGNLIALSLGLTPNFKSNFDLAEDAKLQLSKDTYDDDLDNLLAQIGDQYADLF*

*LAAKNLSDAILLSDILRVNTEITKAPLSASMIKRYDEHHQDLTLLKALVRQQLPEKYK*

*EIFFDQSKNGYAGYIDGGASQEEFYKFIKPILEKMDGTEELLVKLNREDLLRKQRTF*

*DNGSIPHQIHLGELHAILRRQEDFYPFLKDNREKIEKILTFRIPYYVGPLARGNSRFA*

*WMTRKSEETITPWNFEEVVDKGASAQSFIERMTNFDKNLPNEKVLPKHSLLYEYFT*

*VYNELTKVKYVTEGMRKPAFLSGEQKKAIVDLLFKTNRKVTVKQLKEDYFKKIECFD*

*SVEISGVEDRFNASLGTYHDLLKIIKDKDFLDNEENEDILEDIVLTLTLFEDREMIEE*

*RLKTYAHLFDDKVMKQLKRRRYTGWGRLSRKLINGIRDKQSGKTILDFLKSDGFANR*

*NFMQLIHDDSLTFKEDIQKAQVSGQGDSLHEHIANLAGSPAIKKGILQTVKVVDELV*

*KVMGRHKPENIVIEMARENQTTQKGQKNSRERMKRIEEGIKELGSQILKEHPVENTQ*

*LQNEKLYLYYLQNGRDMYVDQELDINRLSDYDVDAIVPQSFLKDDSIDNKVLTRSDK*

*NRGKSDNVPSEEVVKKMKNYWRQLLNAKLITQRKFDNLTKAERGGLSELDKAGFIK*

*RQLVETRQITKHVAQILDSRMNTKYDENDKLIREVKVITLKSKLVSDFRKDFQFYKVR*

*EINNYHHAHDAYLNAVVGTALIKKYPKLESEFVYGDYKVYDVRKMIAKSEQEIGKAT*

*AKYFFYSNIMNFFKTEITLANGEIRKRPLIETNGETGEIVWDKGRDFATVRKVLSMP*

*QVNIVKKTEVQTGGFSKESILPKRNSDKLIARKKDWDPKKYGGFDSPTVAYSVLVVAK*

*VEKGKSKKLKSVKELLGITIMERSSFEKNPIDFLEAKGYKEVKKDLIIKLPKYSLFELE*

*NGRKRMLASAGELQKGNELALPSKYVNFLYLASHYEKLKGSPEDNEQKQLFVEQHK*

*HYLDEIIEQISEFSKRVILADANLDKVLSAYNKHRDKPIREQAENIIHLFTLTNLGAPA*

*AFKYFDTTIDRKRYTSTKEVLDATLIHQSITGLYETRIDLSQLGGD* rAPOBEC1-(GGS)₃-dCas9 primary sequence
(SEQ ID NO: 612)

<u>MSSETGPVAVDPTLRRRIEPHEFEVFFDPRELRKETCLLYEINWGGRHSIWRHTSQNT</u>

<u>NKHVEVNFIEKFTTERYFCPNTRCSITWFLSWSPCGECSRAITEFLSRYPHVTLFIYIAR</u>

<u>LYHHADPRNRQGLRDLISSGVTIQIMTEQESGYCWRNFVNYSPSNEAHWPRYPHLW</u>

<u>VRLYVLELYCIILGLPPCLNILRRKQPQLTFFTIALQSCHYQRLPPHILWATGLK</u>GGSG

GSGGS*MDKKYSIGLAIGTNSVGWAVITDEYKVPSKKFKVLGNTDRHSIKKNLIGALLF*

*DSGETAEATRLKRTARRRYTRRKNRICYLQEIFSNEMAKVDDSFFHRLEESFLVEED*

*KKHERHPIFGNIVDEVAYHEKYPTIYHLRKKLVDSTDKADLRLIYLALAHMIKFRGH*

-continued

```
FLIEGDLNPDNSDVDKLFIQLVQTYNQLFEENPINASGVDAKAILSARLSKSRRLENLI

AQLPGEKKNGLFGNLIALSLGLTPNFKSNFDLAEDAKLQLSKDTYDDDLDNLLAQIG

DQYADLFLAAKNLSDAILLSDILRVNTEITKAPLSASMIKRYDEHHQDLTLLKALVRQ

QLPEKYKEIFFDQSKNGYAGYIDGGASQEEFYKFIKPILEKMDGTEELLVKLNREDLL

RKQRTFDNGSIPHQIHLGELHAILRRQEDFYPFLKDNREKIEKILTFRIPYYVGPLAR

GNSRFAWMTRKSEETITPWNFEEVVDKGASAQSFIERMTNFDKNLPNEKVLPKHSL

LYEYFTVYNELTKVKYVTEGMRKPAFLSGEQKKAIVDLLFKTNRKVTVKQLKEDYFK

KIECFDSVEISGVEDRFNASLGTYHDLLKIIKDKDFLDNEENEDILEDIVLTLTLFEDR

EMIEERLKTYAHLFDDKVMKQLKRRRYTGWGRLSRKLINGIRDKQSGKTILDFLKSD

GFANRNFMQLIHDDSLTFKEDIQKAQVSGQGDSLHEHIANLAGSPAIKKGILQTVKV

VDELVKVMGHKPENIVIEMARENQTTQKGQKNSRERMKRIEEGIKELGSQILKEHP

VENTQLQNEKLYLYYLQNGRDMYVDQELDINRLSDYDVDAIVPQSFLKDDSIDNKVL

TRSDKNRGKSDNVPSEEVVKKMKNYWRQLLNAKLITQRKFDNLTKAERGGLSELDK

AGFIKRQLVETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKMIAKSEQE

IGKATAKYFFYSNIMNFFKTEITLANGEIRKRPLIETNGETGEIVWDKGRDFATVRKV

LSMPQVNIVKKTEVQTGGFSKESILPKRNSDLIARKKDWDPKKYGGFDSPTVAYSVL

VVAKVEKGKSKKLKSVKELLGITIMERSSFEKNPIDFLEAKGYKEVKKDLIIKLPKYSL

FELENGRKRMLASAGELQKGNELALPSKYVNFLYLASHYEKLKGSPEDNEQKQLFV

EQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD
``` dCas9-GGS-rAPOBEC1

(SEQ ID NO: 613)

```
DKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY
```

-continued

*KEIFFDQSKNGYAGYIDGGASQEEFYKFIKPILEKMDGTEELLVKLNREDLLRKQRT*

*FDNGSIPHQIHLGELHAILRRQEDFYPFLKDNREKIEKILTFRIPYYVGPLARGNSRF*

*AWMTRKSEETITPWNFEEVVDKGASAQSFIERMTNFDKNLPNEKVLPKHSLLYEYF*

*TVYNELTKVKYVTEGMRKPAFLSGEQKKAIVDLLFKTNRKVTVKQLKEDYFKKIECF*

*DSVEISGVEDRFNASLGTYHDLLKIIKDKDFLDNEENEDILEDIVLTLTLFEDREMIE*

*ERLKTYAHLFDDKVMKQLKRRRYTGWGRLSRKLINGIRDKQSGKTILDFLKSDGFAN*

*RNFMQLIHDDSLTFKEDIQKAQVSGQGDSLHEHIANLAGSPAIKKGILQTVKVVDEL*

*VKVMGRHKPENIVIEMARENQTTQKGQKNSRERMKRIEEGIKELGSQILKEHPVENT*

*QLQNEKLYLYYLQNGRDMYVDQELDINRLSDYDVDAIVPQSFLKDDSIDNKVLTRSD*

*KNRGKSDNVPSEEVVKKMKNYWRQLLNAKLITQRKFDNLTKAERGGLSELDKAGFI*

*KRQLVETRQITKHVAQILDSRMNTKYDENDKLIREVKVITLKSKLVSDFRKDFQFYKV*

*REINNYHHAHDAYLNAVVGTALIKKYPKLESEFVYGDYKVYDVRKMIAKSEQEIGKA*

*TAKYFFYSNIMNFFKTEITLANGEIRKRPLIETNGETGEIVWDKGRDFATVRKVLSMP*

*QVNIVKKTEVQTGGFSKESILPKRNSDKLIARKKDWDPKKYGGFDSPTVAYSVLVVAK*

*VEKGKSKKLKSVKELLGITIMERSSFEKNPIDFLEAKGYKEVKKDLIIKLPKYSLFELE*

*NGRKRMLASAGELQKGNELALPSKYVNFLYLASHYEKLKGSPEDNEQKQLFVEQHK*

*HYLDEIIEQISEFSKRVILADANLDKVLSAYNKHRDKPIREQAENIIHLFTLTNLGAPA*

*AFKYFDTTIDRKRYTSTKEVLDATLIHQSITGLYETRIDLSQLGGD*GGS*MSSETGPVA*

VDPTLRRRIEPHEFEVFFDPRELRKETCLLYEINWGGRHSIWRHTSQNTNKHVEVNFI

EKFTTERYFCPNTRCSITWFLSWSPCGECSRAITEFLSRYPHVTLFIYIARLYHHADPR

NRQGLRDLISSGVTIQIMTEQESGYCWRNFVNYSPSNEAHWPRYPHLWVRLYVLEL

YCIILGLPPCLNILRRKQPQLTFFTIALQSCHYQRLPPHILWATGLK

*dCas9-* GGS₃ *-rAPOBEC1*

(SEQ ID NO: 614)

*DKKYSIGLAIGTNSVGWAVITDEYKVPSKKFKVLGNTDRHSIKKNLIGALLFDSGETA*

*EATRLKRTARRRYTRRKNRICYLQEIFSNEMAKVDDSFFHRLEESFLVEEDKKHERH*

*PIFGNIVDEVAYHEKYPTIYHLRKKLVDSTDKADLRLIYLALAHMIKFRGHFLIEGDL*

*NPDNSDVDKLFIQLVQTYNQLFEENPINASGVDAKAILSARLSKSRRLENLIAQLPGE*

*KKNGLFGNLIALSLGLTPNFKSNFDLAEDAKLQLSKDTYDDDLDNLLAQIGDQYADL*

*FLAAKNLSDAILLSDILRVNTEITKAPLSASMIKRYDEHHQDLTLLKALVRQQLPEKY*

*KEIFFDQSKNGYAGYIDGGASQEEFYKFIKPILEKMDGTEELLVKLNREDLLRKQRT*

FDNGSIPHQIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKEDYFKKIECF

DSVEISGVEDRFNASLGTYHDLLKIIKDKDFLDNEENEDILEDIVLTLTLFEDREMIE

ERLKTYAHLFDDKVMKQLKRRRYTGWGRLSRKLINGIRDKQSGKTILDFLKSDGFAN

RNFMQLIHDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILKEHPVENT

QLQNEKLYLYYLQNGRDMYVDQELDINRLSDYDVDAIVPQSFLKDDSIDNKVLTRSD

KNRGKSDNVPSEEVVKKMKNYWRQLLNAKLITQRKFDNLTKAERGGLSELDKAGFI

KRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKA

TAKYFFYSNIMNFFKTEITLANGEIRKRPLIETNGETGEIVWDKGRDFATVRKVLSMP

QVNIVKKTEVQTGGFSKESILPKRNSDKLIARKKDWDPKKYGGFDSPTVAYSVLVVAK

VEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHK

HYLDEIIEQISEFSKRVILADANLDKVLSAYNKHRDKPIREQAENIIHLFTLTNLGAPA

AFKYFDTTIDRKRYTSTKEVLDATLIHQSITGLYETRIDLSQLGGD GGSGGSGGS MSS

ETGPVAVDPTLRRRIEPHEFEVFFDPRELRKETCLLYEINWGGRHSIWRHTSQNTNKH

VEVNFIEKFTTERYFCPNTRCSITWFLSWSPCGECSRAITEFLSRYPHVTLFIYIARLYH

HADPRNRQGLRDLISSGVTIQIMTEQESGYCWRNFVNYSPSNEAHWPRYPHLWVRL

YVLELYCIILGLPPCLNILRRKQPQLTFFTIALQSCHYQRLPPHILWATGLK rAPOBEC1-XTEN-dCas9 primary sequence
(SEQ ID NO: 615)
MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLW

VRLYVLELYCIILGLPPCLNILRRKQPQLTFFTIALQSCHYQRLPPHILWATGLKS GSE

TPGTSESATPES DKKYSIGLAIGTNSVGWAVITDEYKVPSKKFKVLGNTDRHSIKKNLI

GALLFDSGETAEATRLKRTARRRYTRRKNRICYLQEIFSNEMAKVDDSFFHRLEESF

LVEEDKKHERHPIFGNIVDEVAYHEKYPTIYHLRKKLVDSTDKADLRLIYLALAHMIK

FRGHFLIEGDLNPDNSDVDKLFIQLVQTYNQLFEENPINASGVDAKAILSARLSKSRR

-continued

LENLIAQLPGEKKNGLFGNLIALSLGLTPNFKSNFDLAEDAKLQLSKDTYDDDLDNL

LAQIGDQYADLFLAAKNLSDAILLSDILRVNTEITKAPLSASMIKRYDEHHQDLTLLK

ALVRQQLPEKYKEIFFDQSKNGYAGYIDGGASQEEFYKFIKPILEKMDGTEELLVKLN

REDLLRKQRTFDNGSIPHQIHLGELHAILRRQEDFYPFLKDNREKIEKILTFRIPYYV

GPLARGNSRFAWMTRKSEETITPWNFEEVVDKGASAQSFIERMTNFDKNLPNEKVL

PKHSLLYEYFTVYNELTKVKYVTEGMRKPAFLSGEQKKAIVDLLFKTNRKVTVKQLK

EDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILD

FLKSDGFANRNFMQLIHDDSLTFKEDIQKAQVSGQGDSLHEHIANLAGSPAIKKGIL

QTVKVVDELVKVMGRHKPENIVIEMARENQTTQKGQKNSRERMKRIEEGIKELGSQI

LKEHPVENTQLQNEKLYLYYLQNGRDMYVDQELDINRLSDYDVDAIVPQSFLKDDSI

DNKVLTRSDKNKGKSDNVPSEEVVKKMKNYWRQLLNAKLITQRKFDNLTKAERGGL

SELDKAGFIKRQLVETRQITKHVAQILDSRMNTKYDENDKLIREVKVITLKSKLVSDF

RKDFQFYKVREINNYHHAHDAYLNAVVGTALIKKYPKLESEFVYGDYKVYDVRKMIA

KSEQEIGKATAKYFFYSNIMNFFKTEITLANGEIRKRPLIETNGETGEIVWDKGRDFA

TVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIK

LPKYSLFELENGRKRMLASAGELQKGNELALPSKYVNFLYLASHYEKLKGSPEDNEQ

KQLFVEQHKHYLDEIIEQISEFSKRVILADANLDKVLSAYNKHRDKPIREQAENIIHLF

TLTNLGAPAAFKYFDTTIDRKRYTSTKEVLDATLIHQSITGLYETRIDLSQLGGD

Figure 2:
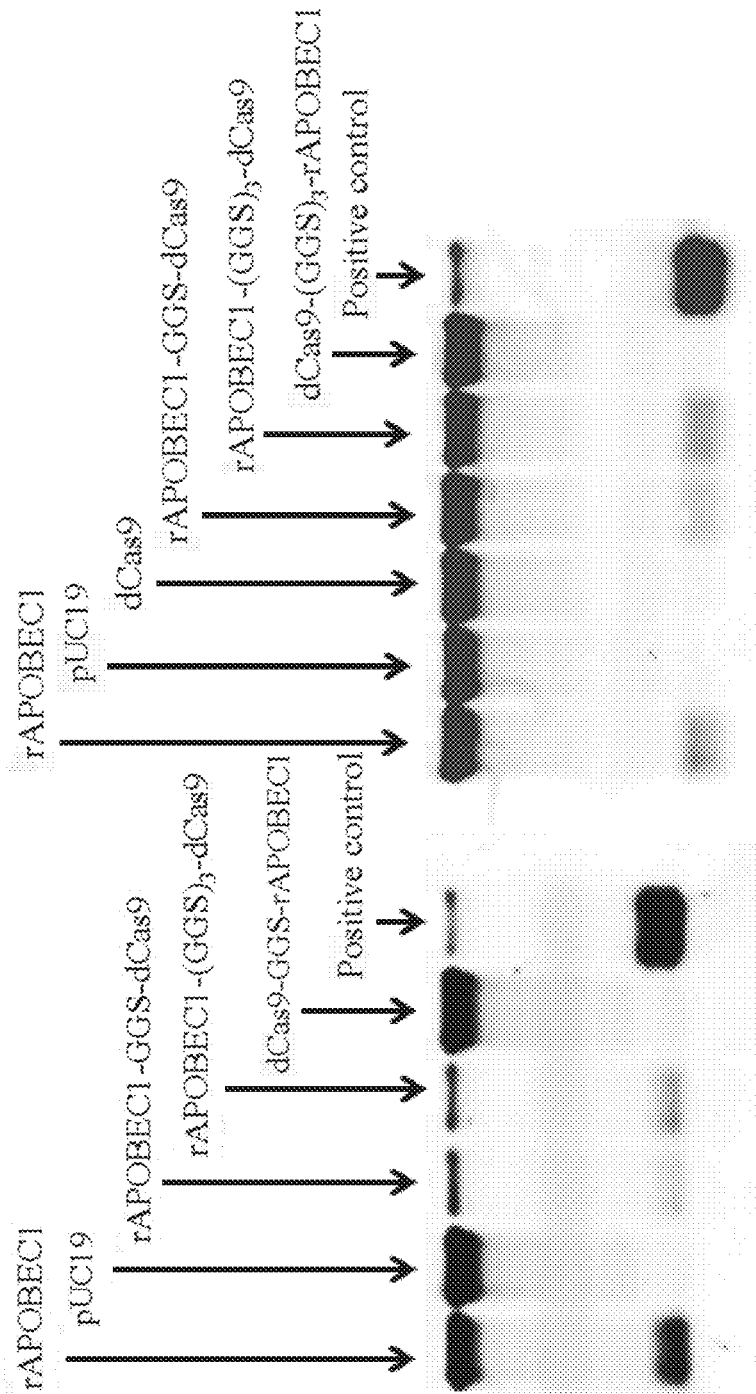
FIG. 2 shows activity of Cas9:deaminase fusion proteins on single stranded DNA substrates.

FIG. 2 shows that the N-terminal deaminase fusions showed significant activity on the single stranded DNA substrates. For this reason, only the N-terminal architecture was chosen for further experiments.

FIG. 3 illustrates double stranded DNA substrate binding by deaminase-dCas9:sgRNA complexes. A number of double stranded deaminase substrate sequences were generated. The sequences are provided below. The structures according to FIG. 3 are identified in these sequences (36 bp: underlined, sgRNA target sequence: bold; PAM: boxed; 21 bp: italicized). All substrates were labeled with a 5'-Cy3 label:

(SEQ ID NO: 616)
2: GTAGGTAGTTAGGATGAATGGAAGGTTGGTATAGTCCCGCGGATTTATTTATTT
AA TGG *ATGACCTCTGGATCCATGGAC*-3'

(SEQ ID NO: 617)
3: GTAGGTAGTTAGGATGAATGGAAGGTTGGTATAGCTTCCGCGGATTTATTTATT
TA TGG *ATGACCTCTGGATCCATGGAC*-3'

-continued (SEQ ID NO: 618)
4: GTAGGTAGTTAGGATGAATGGAAGGTTGGTATAGCC**TTCCGCGGATTTATTTAT
TA**TGGATGACCTCTGGATCCATGGAC-3'

(SEQ ID NO: 619)
5: GTAGGTAGTTAGGATGAATGGAAGGTTGGTATAGCC**ATTCCGCGGATTTATTTA
TT**TGGATGACCTCTGGATCCATGGAC-3'

(SEQ ID NO: 620)
6: GTAGGTAGTTAGGATGAATGGAAGGTTGGTATAGCC**TATTCCGCGGATTTATTT
AT**TGGATGACCTCTGGATCCATGGAC-3'

(SEQ ID NO: 621)
7: GTAGGTAGTTAGGATGAATGGAAGGTTGGTATAGCC**TTATTCCGCGGATTTATT
TA**TGGATGACCTCTGGATCCATGGAC-3'

(SEQ ID NO: 622)
8: GTAGGTAGTTAGGATGAATGGAAGGTTGGTATAGCC**ATTATTCCGCGGATTTAT
TT**TGGATGACCTCTGGATCCATGGAC-3'

(SEQ ID NO: 623)
9: GTAGGTAGTTAGGATGAATGGAAGGTTGGTATAGCC**TATTATTCCGCGGATTTA
TT**TGGATGACCTCTGGATCCATGGAC-3'

(SEQ ID NO: 624)
10: GTAGGTAGTTAGGATGAATGGAAGGTTGGTATAGCC**ATTATATTCCGCGGATTT
AT**TGGATGACCTCTGGATCCATGGAC-3'

(SEQ ID NO: 625)
11: GTAGGTAGTTAGGATGAATGGAAGGTTGGTATAGCC**TATTATATTCCGCGGATT
TA**TGGATGACCTCTGGATCCATGGAC-3'

(SEQ ID NO: 626)
12: GTAGGTAGTTAGGATGAATGGAAGGTTGGTATAGCC**TTATTATATTCCGCGGAT
TT**TGGATGACCTCTGGATCCATGGAC-3'

(SEQ ID NO: 627)
13: GTAGGTAGTTAGGATGAATGGAAGGTTGGTATAGCC**ATTATTATATTCCGCGGA
TT**TGGATGACCTCTGGATCCATGGAC-3'

(SEQ ID NO: 628)
14: GTAGGTAGTTAGGATGAATGGAAGGTTGGTATAGCC**TATTATTATATTCCGCGG
AT**TGGATGACCTCTGGATCCATGGAC-3'

(SEQ ID NO: 629)
15: GTAGGTAGTTAGGATGAATGGAAGGTTGGTATAGCC**ATTATTATTATTACCGCG
GA**TGGATGACCTCTGGATCCATGGAC-3'

(SEQ ID NO: 630)
18: GTAGGTAGTTAGGATGAATGGAAGGTTGGTATAGCC**ATTATTATTATTATTACC
GC**TGGATGACCTCTGGATCCATGGAC-3'

"-":
(SEQ ID NO: 631)
GTAGGTAGTTAGGATGAATGGAAGGTTGGTATAGTAATATTAATTTATTTATTTAA
TGGATGACCTCTGGATCCATGGAC-3'

(SEQ ID NO: 632)
8U: GTAGGTAGTTAGGATGAATGGAAGGTTGGTGTAG**ATTATTATCUGCGGATTTA
T**TGGATGACCTCTGGATCCATGGACAT-3'

*In all substrates except for "8U", the top strand in FIG. 3 is the complement of the sequence specified here. In the case of "8U", there is a "G" opposite the U.

Figure 4:
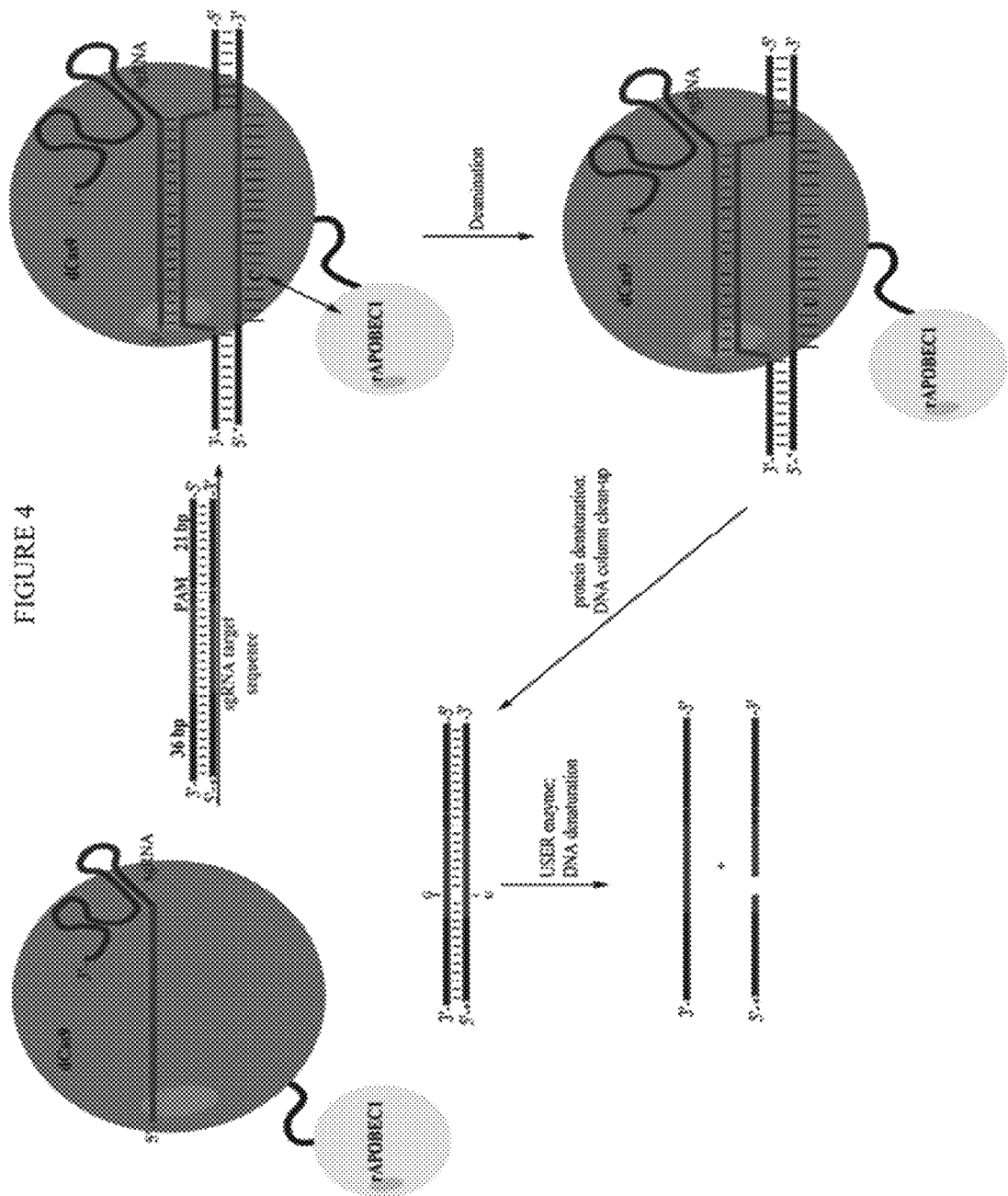
FIG. 4 illustrates a double stranded DNA deamination assay.

FIG. 4 shows the results of a double stranded DNA Deamination Assay. The fusions were expressed and purified with an N-terminal His6 tag via both Ni-NTA and sepharose chromatography. In order to assess deamination on dsDNA substrates, the various dsDNA substrates shown on the previous slide were incubated at a 1:8 dsDNA:fusion protein ratio and incubated at 37° C. for 2 hours. Once the dCas9 portion of the fusion binds to the DNA it blocks access of the USER enzyme to the DNA. Therefore, the fusion proteins were denatured following the incubation and the dsDNA was purified on a spin column, followed by incubation for 45 min with the USER Enzyme and resolution of the resulting DNA substrate and substrate fragments on a 10% TBE-urea gel.

Figure 5:
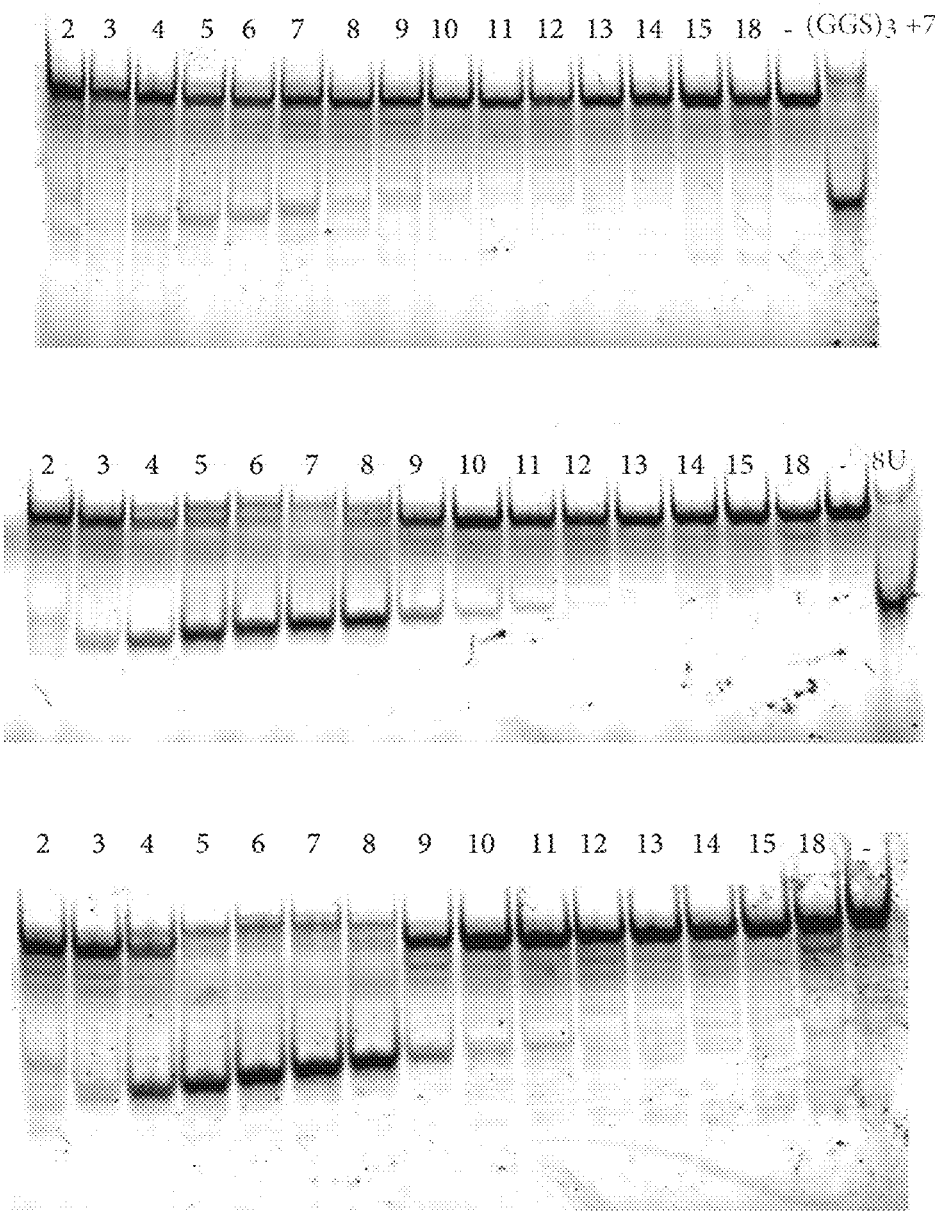
FIG. 5 demonstrates that Cas9 fusions can target positions 3-11 of double-stranded DNA target sequences (numbered according to the schematic in FIG. 5). Upper Gel: 1 µM rAPOBEC1-GGS-dCas9, 125 nM dsDNA, 1 equivalent sgRNA. Mid Gel: 1 µM rAPOBEC1-(GGS)$_3$(SEQ ID NO: 596)-dCas9, 125 nM dsDNA, 1 equivalent sgRNA. Lower Gel: 1.85 µM rAPOBEC1-XTEN-dCas9, 125 nM dsDNA, 1 equivalent sgRNA.

FIG. 5 demonstrates that Cas9 fusions can target positions 3-11 of double-stranded DNA target sequences (numbered according to the schematic in FIG. 3). Upper Gel: 1 µM rAPOBEC1-GGS-dCas9, 125 nM dsDNA, 1 eq sgRNA. Mid Gel: 1 µM rAPOBEC1-(GGS)$_3$-dCas9, 125 nM dsDNA, 1 eq sgRNA. Lower Gel: 1.85 µM rAPOBEC1-XTEN-dCas9, 125 nM dsDNA, 1 eq sgRNA. Based on the data from these gels, positions 3-11 (according to the numbering in FIG. 3) are sufficiently exposed to the activity of the deaminase to be targeted by the fusion proteins tested. Access of the deaminase to other positions is most likely blocked by the dCas9 protein.

The data further indicates that a linker of only 3 amino acids (GGS) is not optimal for allowing the deaminase to access the single stranded portion of the DNA. The 9 amino acid linker [(GGS)$_3$] (SEQ ID NO: 596) and the more structured 16 amino acid linker (XTEN) allow for more efficient deamination.

Figure 6:
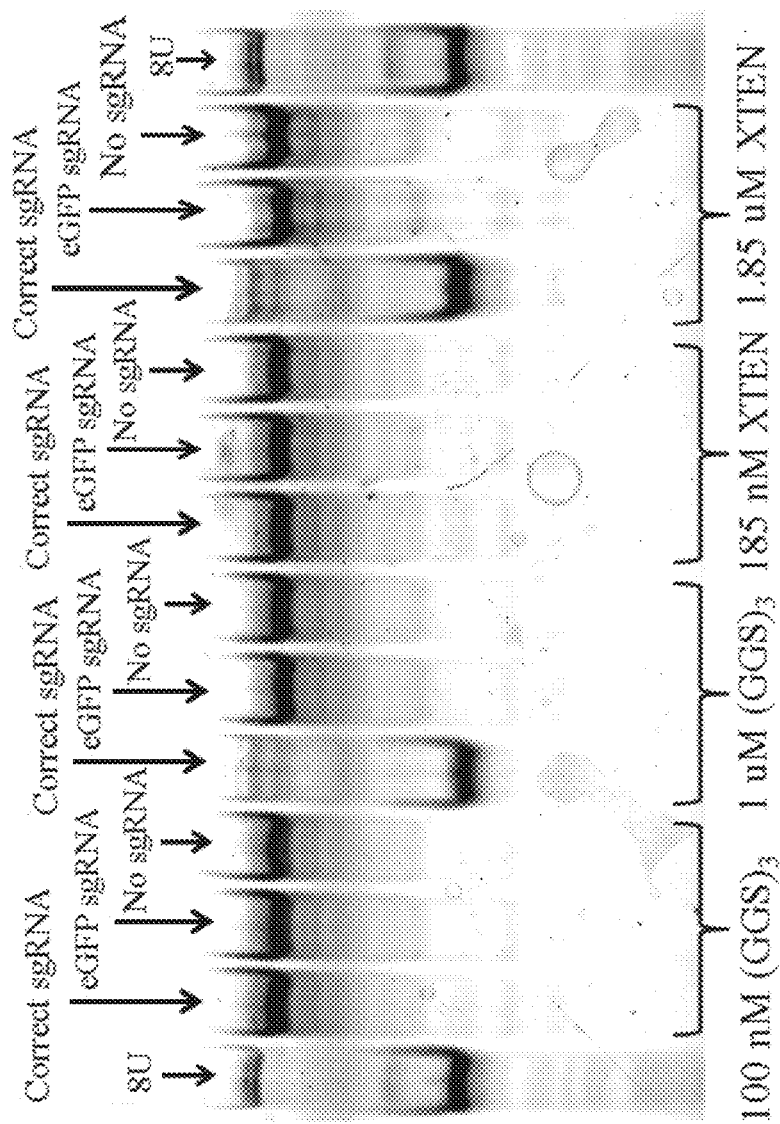
FIG. 6 demonstrates that the correct guide RNA, e.g., the correct sgRNA, is required for deaminase activity.
Figure 7:
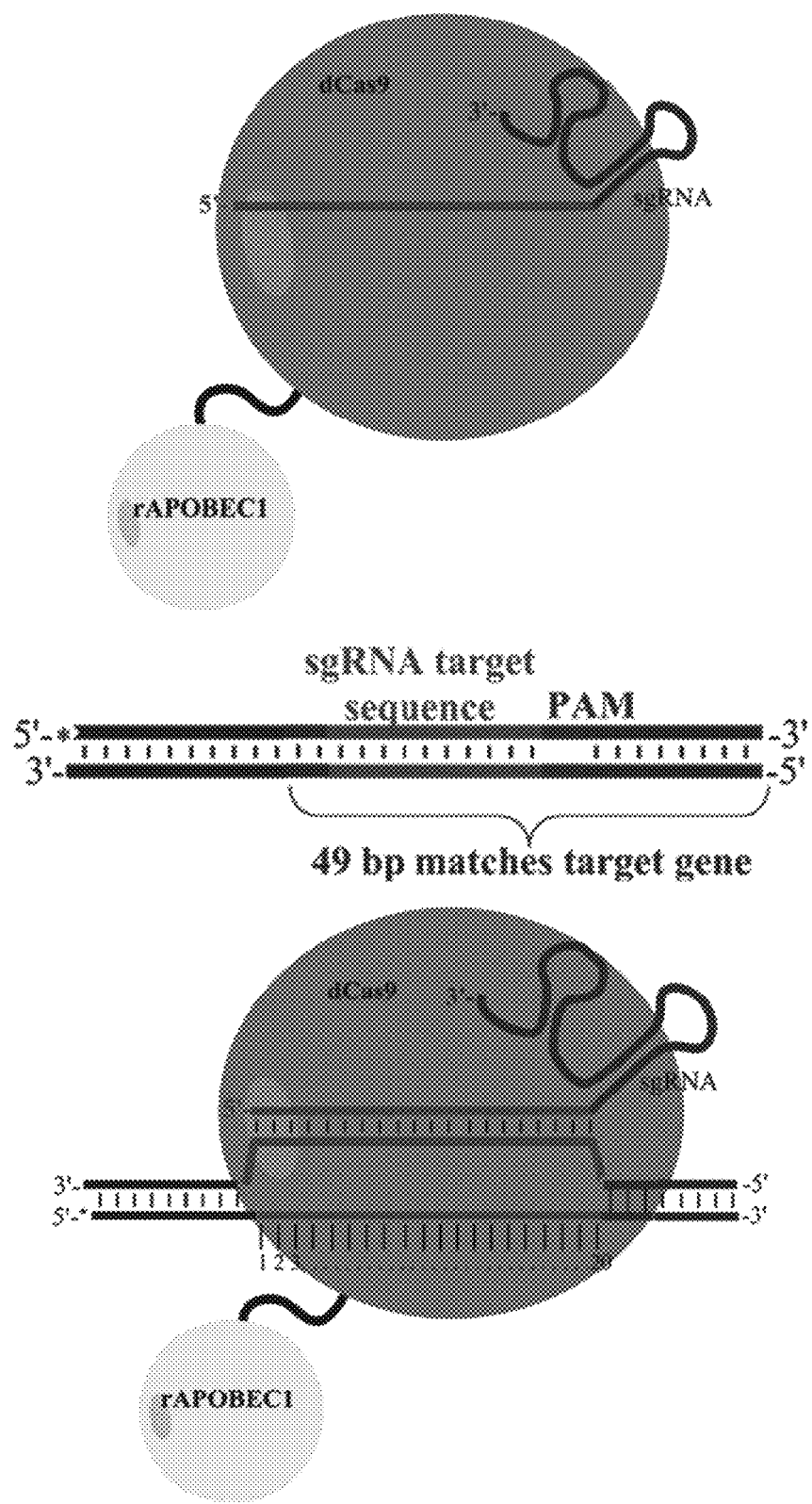
FIG. 7 illustrates the mechanism of target DNA binding of in vivo target sequences by deaminase-dCas9:sgRNA complexes.

FIG. 6 demonstrates that the correct guide RNA, e.g., the correct sgRNA, is required for deaminase activity. The gel shows that fusing the deaminase to dCas9, the deaminase enzyme becomes sequence specific (e.g., using the fusion with an eGFP sgRNA results in no deamination), and also confers the capacity to the deaminase to deaminate dsDNA. The native substrate of the deaminase enzyme is ssDNA, and no deamination occurred when no sgRNA was added. This is consistent with reported knowledge that APOBEC deaminase by itself does not deaminate dsDNA. The data indicates that Cas9 opens the double-stranded DNA helix within a short window, exposing single-stranded DNA that is then accessible to the APOBEC deaminase for cytidine deamination. The sgRNA sequences used are provided below. sequences (36 bp: underlined, sgRNA target sequence: bold; PAM: boxed; 21 bp: italicized) DNA sequence 8:

treatment. APOE4 mutations: mutant codons encoding C11R and C57R mutant APOE4 proteins can be deaminated to revert to the wild-type amino acid with applications in Alzheimer's treatment. eGFP truncations: any of the codons encoding Q158, Q184, Q185 can be deaminated to generate a STOP codon, or the codon encoding M1 can be deaminated to encode I, all of which result in loss of eGFP fluorescence, with applications in reporter systems. eGFP restoration: a mutant codon encoding T65A or Y66C mutant GFP, which does not exhibit substantial fluorescence, can be deaminated to restore the wild-type amino acid and confer fluorescence. PIK3CA mutation: a mutant codon encoding K111E mutant PIK3CA can be deaminated to restore the wild-type amino acid residue with applications in cancer. CTNNB1 mutation: a mutant codon encoding T41A mutant CTNNB1 can be deaminated to restore the wild-type amino acid residue with applications in cancer. HRAS mutation: a mutant codon encoding Q61R mutant HRAS can be deaminated to restore the wild-type amino acid residue with applications in cancer. P53 mutations: any of the mutant codons encoding Y163C, Y236C, or N239D mutant p53 can be deaminated to encode the wild type amino acid sequence with applications in cancer. The feasibility of deaminating these target sequences in double-stranded DNA is demonstrated in FIGS. 7 and 8. FIG. 7 illustrates the mechanism of target DNA binding of in vivo target sequences by deaminase-dCas9:sgRNA complexes.

Figure 8:
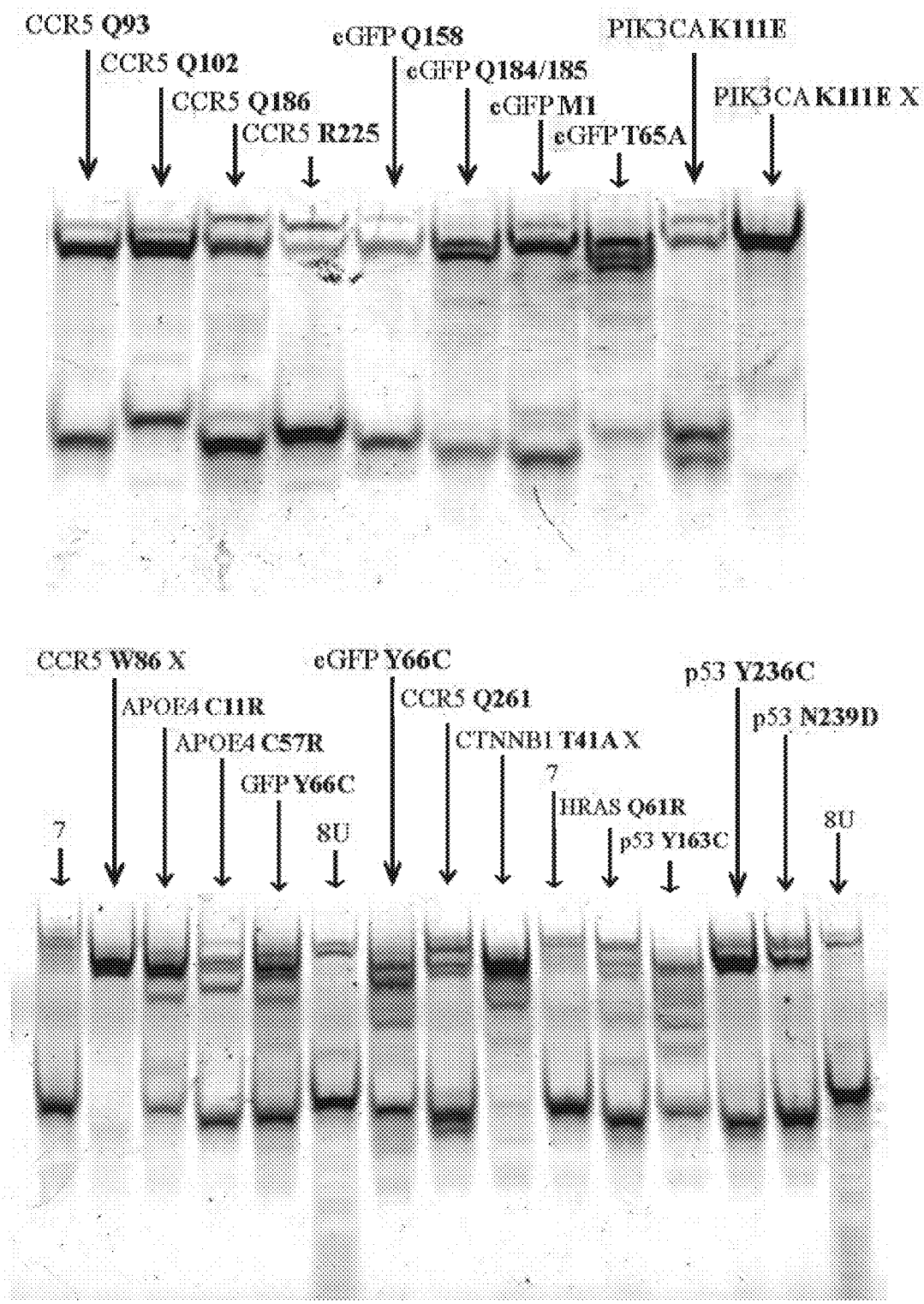
FIG. 8 shows successful deamination of exemplary disease-associated target sequences.

FIG. 8 shows successful deamination of exemplary disease-associated target sequences. Upper Gel: CCR5 Q93: coding strand target in pos. 10 (potential off-targets at positions 2, 5, 6, 8, 9); CCR5 Q102: coding strand target in pos. 9 (potential off-targets at positions 1, 12, 14); CCR5 Q186: coding strand target in pos. 9 (potential off-targets at positions 1, 5, 15); CCR5 R225: coding strand target in pos. 6 (no potential off-targets); eGFP Q158: coding strand target in pos. 5 (potential off-targets at positions 1, 13, 16); eGFP Q184/185: coding strand target in pos. 4 and 7 (potential off-targets at positions 3, 12, 14, 15, 16, 17, 18); eGFP M1: template strand target in pos. 12 (potential off-targets at positions 2, 3, 7, 9, 11) (targets positions 7 and 9 to small degree); eGFP T65A: template strand target in pos. 7 (potential off-targets at positions 1, 8, 17); PIK3CA K111E:

```
                                                             (SEQ ID NO: 633)
5'-Cy3-
GTAGGTAGTTAGGATGAATGGAAGGTTGGTATAGCCATTATTCCGCGGATTTATT
TTGGATGACCTCTGGATCCATGGAC-3'

Correct sgRNA sequence (partial 3' sequence):
                                                             (SEQ ID NO: 634)
5'-AUUAUUCCGCGGAUUUAUUUGUUUUAGAGCUAG...-3' eGFP sgRNA sequence (partial 3'-sequence):
                                                             (SEQ ID NO: 635)
5'-CGUAGGCCAGGGUGGUCACGGUUUUAGAGCUAG...-3'
```

Example 2: Deamination of DNA Target Sequence

Exemplary deamination targets. The dCas9:deaminase fusion proteins described herein can be delivered to a cell in vitro or ex vivo or to a subject in vivo and can be used to effect C to T or G to A transitions when the target nucleotide is in positions 3-11 with respect to a PAM. Exemplary deamination targets include, without limitation, the following: CCR5 truncations: any of the codons encoding Q93, Q102, Q186, R225, W86, or Q261 of CCR5 can be deaminated to generate a STOP codon, which results in a non-functional truncation of CCR5 with applications in HIV template strand target in pos. 2 (potential off-targets at positions 5, 8, 10, 16, 17); PIK3CA K111E: template strand target in pos. 13 (potential off-targets at positions 11, 16, 19) X. Lower Gel: CCR5 W86: template strand target in pos. 2 and 3 (potential off-targets at positions 1, 13) X; APOE4 C11R: coding strand target in pos. 11 (potential off-targets at positions 7, 13, 16, 17); APOE4 C57R: coding strand target in pos. 5) (potential off-targets at positions 7, 8, 12); eGFP Y66C: template strand target in pos. 11 (potential off-targets at positions 1, 4, 6, 8, 9, 16); eGFP Y66C: template strand target in pos. 3 (potential off-targets at positions 1, 8, 17); CCR5 Q261: coding strand target in pos. 10 (potential off-targets at positions 3, 5, 6, 9, 18); CTNNB1 T41A: template strand target in pos. 7 (potential off-targets at positions 1, 13, 15, 16) X; HRAS Q61R: template strand target in pos. 6 (potential off-targets at positions 1, 2, 4, 5, 9, 10, 13); p53 Y163C: template strand target in pos. 6 (potential off-targets at positions 2, 13, 14); p53 Y236C: template strand target in pos. 8 (potential off-targets at positions 2, 4); p53 N239D: template strand target in pos. 4 (potential off-targets at positions 6, 8). Exemplary DNA sequences of disease targets are provided below (PAMs (5'-NGG-3') and target positions are boxed):

```
                                    (SEQ ID NO: 636)
CCR5 Q93: 5'-Cy3-
GTAGGTAGTTAGGATGAATGGAAGGTTGGTAACTATGCTGCCGCC
CAGTGGGACTTTGGAAATACAATGTGTCAACTCTT-3'

(SEQ ID NO: 637)
CCR5 Q102: 5'-Cy3-
GTAGGTAGTTAGGATGAATGGAAGGTTGGTAAAATACAATGTGT
CAACTCTTGACAGGGCTCTATTTTATAGGCTTCTTC-3'

(SEQ ID NO: 638)
CCR5 Q186: 5'-Cy3-
GTAGGTAGTTAGGATGAATGGAAGGTTGGTATTTTCCATACAGT
CAGTATCAATTCTGGAAGAATTTCCAGACATTAAAG-3'

(SEQ ID NO: 639)
CCR5 R225: 5'-Cy3-
GTAGGTAGTTAGGATGAATGGAAGGTTGGTAGCTTCGGTGTCGA
AATGAGAAGAAGAGGCACAGGGCTGTGAGGCTTATC-3'

(SEQ ID NO: 640)
CCR5 W86: 5'-Cy3-
GTAGGTAGTTAGGATGAATGGAAGGTTGGTAGTGAGCCGAGAAGG
GGACAGTAAGAAGGAAAAACAGGTCAGAGATGGCC-3'

(SEQ ID NO: 641)
CCR5 Q261: 5'-Cy3-
GTAGGTAGTTAGGATGAATGGAAGGTTGGTATCCTGAACACCTT
CCAGGAATTCTTTGGCCTGAATAATTGCAGTAGCTC-3'

(SEQ ID NO: 642)
APOE4 C11R: 5'-Cy3-
GTAGGTAGTTAGGATGAATGGAAGGTTGGTAGACATGGAGGAC
GTGCGCGGCCGCCTGGTGCAGTACCGCGGCGAGGTGC-3'

(SEQ ID NO: 643)
APOE4 C57R: 5'-Cy3-
GTAGGTAGTTAGGATGAATGGAAGGTTGGTACTGCAGAAGCGC
CTGGCAGTGTACCAGGCCGGGGCCCGCGAGGGCGCCG-3'

(SEQ ID NO: 644)
eGFP Q158: 5'-Cy3-
GTAGGTAGTTAGGATGAATGGAAGGTTGGTAGCCGACAAGCAGA
AGAACGGCATCAAGGTGAACTTCAAGATCCGCCACA-3'

(SEQ ID NO: 645)
eGFP Q184/185: 5'-Cy3-
GTAGGTAGTTAGGATGAATGGAAGGTTGGTAGACCACTACC
AGCAGAACACCCCCATCGGCGACGGCCCCGTGCTGCTGCC-3'

(SEQ ID NO: 646)
eGFP M1: 5'-Cy3-
GTAGGTAGTTAGGATGAATGGAAGGTTGGTACCTCGCCCTTGCTCA
CCATCTCGAGTCGGCCGCCAGTGTGATGGATATCT-3'

(SEQ ID NO: 647)
eGFP T65A: 5'-Cy3-
GTAGGTAGTTAGGATGAATGGAAGGTTGGTACACGCGTAGGCCA
GGGTGGTCACGAGGGTGGGCCAGGGCACGGGCAGC-3'

(SEQ ID NO: 648)
eGFP Y66C: 5'-Cy3-
GTAGGTAGTTAGGATGAATGGAAGGTTGGTAAAGCACTGCACTC
CGCAGGTCAGGGTGGTCACGAGGGTTGGCCAGGGCA-3'

(SEQ ID NO: 649)
eGFP Y66C: 5'-Cy3-
GTAGGTAGTTAGGATGAATGGAAGGTTGGTACACTCCGCAGGTC
AGGGTGGTCACGAGGGTTGGCCAGGGCACGGGCAGG-3'

(SEQ ID NO: 650)
P1K3CA K111E: 5'-Cy3-
GTAGGTAGTTAGGATGAATGGAAGGTTGGTAGGATCTCTTC
TTCACGGTTGCCTACTGGTTCAATTACTTTTAAAAATGG-3'

(SEQ ID NO: 651)
P1K3CA K111E: 5'-Cy3-
GTAGGTAGTTAGGATGAATGGAAGGTTGGTATTCTCGATTG
AGGATCTCTTCTTCACGGTTGCCTACTGGTTCAATTACT-3'

(SEQ ID NO: 652)
CTNNB1 T41A: 5'-Cy3-
GTAGGTAGTTAGGATGAATGGAAGGTTGGTAAGGAGCTGTGG
CAGTGGCACCAGAATGGATTCCAGAGTCCAGGTAAGAC-3'

(SEQ ID NO: 653)
HRAS Q61R: 5'-Cy3-
GTAGGTAGTTAGGATGAATGGAAGGTTGGTAGTACTCCTCCCGG
CCGGCGGTATCCAGGATGTCCAACAGGCACGTCTCC-3'

(SEQ ID NO: 654)
p53 Y163C: 5'-Cy3-
GTAGGTAGTTAGGATGAATGGAAGGTTGGTATGACTGCTTGCAG
ATGGCCATGGCGCGGACGCGGGTGCCGGGCGGGGT-3'

(SEQ ID NO: 655)
p53 Y236C: 5'-Cy3-
GTAGGTAGTTAGGATGAATGGAAGGTTGGTACTGTTACACATGC
AGTTGTAGTGGATGGTGGTACAGTCAGAGCCAACCT-3'

(SEQ ID NO: 656)
p53 N239D: 5'-Cy3-
GTAGGTAGTTAGGATGAATGGAAGGTTGGTAGGAACTGTCACAC
ATGTAGTTGTAGTGGATGGTGGTACAGTCAGAGCCA-3'
```

Example 3: Uracil Glycosylase Inhibitor Fusion Improves Deamination Efficiency

Direct programmable nucleobase editing efficiencies in mammalian cells by dCas9:deaminase fusion proteins can be improved significantly by fusing a uracil glycosylase inhibitor (UGI) to the dCas9:deaminase fusion protein.

FIG. 9 shows in vitro C→T editing efficiencies in human HEK293 cells using rAPOBEC1-XTEN-dCas9:

rAPOBEC1-XTEN-dCas9-NLS primary sequence (SEQ ID NO: 657)

MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLWV

RLYVLELYCIILGLPPCLNILRRKQPQLTFFTIALQSCHYQRLPPHILWATGLKSGSETP

GTSESATPESDKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFFHRLEESFLV

EEDKKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRED

LLRKQRTFDNGSIPHQIHLGELHAILRRQEDFYPFLKDNREKIEKILTFRIPYYVGPLAR

GNSRFAWMTRKSEETITPWNFEEVVDKGASAQSFIERMTNFDKNLPNEKVLPKHSLL

YEYFTVYNELTKVKYVTEGMRKPAFLSGEQKKAIVDLLFKTNRKVTVKQLKEDYFK

KIECFDSVEISGVEDRFNASLGTYHDLLKIIKDKDFLDNEENEDILEDIVLTLTLFEDRE

MIEERLKTYAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVE

NTQLQNEKLYLYYLQNGRDMYVDQELDINRLSDYDVDAIVPQSFLKDDSIDNKVLT

RSDKNRGKSDNVPSEEVVKKMKNYWRQLLNAKLITQRKFDNLTKAERGGLSELDK

AGFIKRQLVETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRKV

LSMPQVNIVKKTEVQTGGFSKESILPKRNSDKLIARKKDWDPKKYGGFDSPTVAYSV

LVVAKVEKGKSKKLKSVKELLGITIMERSSFEKNPIDFLEAKGYKEVKKDLIIKLPKYS

LFELENGRKRMLASAGELQKGNELALPSKYVNFLYLASHYEKLKGSPEDNEQKQLF

-continued

VEQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD*SGGSPKKKR*

*KV*

EMX1:           5'-GAGTC$_5$C$_6$GAGC$_{10}$AGAAGAAGAAGGG-3'    (SEQ ID NO: 293)

FANCF:          5'-GGAATC$_6$C$_7$C$_8$TTC$_{11}$TGCAGCACCTGG-3'  (SEQ ID NO: 294)

HEK293 site 2:  5'-GAAC$_4$AC$_6$AAAGC$_{11}$ATAGACTGCGGG-3'     (SEQ ID NO: 295)

HEK293 site 3:  5'-GGC$_3$C$_4$C$_5$AGAC$_9$TGAGCACGTGGATGG-3'   (SEQ ID NO: 296)

HEK293 site 4:  5'-GGC$_3$AC$_5$TGC$_8$GGC$_{11}$TGGAGGTGGGGG-3' (SEQ ID NO: 297)

RNF2:           5'-GTC$_3$ATC$_6$TTAGTCATTACCTGAGG-3'           (SEQ ID NO: 298)

*PAMs are boxed, C residues within target window (positions 3-11) are numbered and bolded.

FIG. 10 demonstrates that C→T editing efficiencies on the same protospacer sequences in HEK293T cells are greatly enhanced when a UGI domain is fused to the rAPOBEC1:dCas9 fusion protein.

rAPOBEC1-XTEN-dCas9-UGI-*NLS* primary sequence (SEQ ID NO: 658)

MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLWV

RLYVLELYCIILGLPPCLNILRRKQPQLTFFTIALQSCHYQRLPPHILWATGLKSGSETP

GTSESATPESDKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFFHRLEESFLV

EEDKKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRED

LLRKQRTFDNGSIPHQIHLGELHAILRRQEDFYPFLKDNREKIEKILTFRIPYYVGPLAR

GNSRFAWMTRKSEETITPWNFEEVVDKGASAQSFIERMTNFDKNLPNEKVLPKHSLL

YEYFTVYNELTKVKYVTEGMRKPAFLSGEQKKAIVDLLFKTNRKVTVKQLKEDYFK

KIECFDSVEISGVEDRFNASLGTYHDLLKIIKDKDFLDNEENEDILEDIVLTLTLFEDRE

-continued

```
MIEERLKTYAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVE

NTQLQNEKLYLYYLQNGRDMYVDQELDINRLSDYDVDAIVPQSFLKDDSIDNKVLT

RSDKNRGKSDNVPSEEVVKKMKNYWRQLLNAKLITQRKFDNLTKAERGGLSELDK

AGFIKRQLVETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRKV

LSMPQVNIVKKTEVQTGGFSKESILPKRNSDKLIARKKDWDPKKYGGFDSPTVAYSV

LVVAKVEKGKSKKLKSVKELLGITIMERSSFEKNPIDFLEAKGYKEVKKDLIIKLPKYS

LFELENGRKRMLASAGELQKGNELALPSKYVNFLYLASHYEKLKGSPEDNEQKQLF

VEQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD
```
SGGS**TNLSD
IIEKETGKOLVICIESILMLPEEVEEVIGNKPESDILVHTAYDESTDENVMLLTSDAP
EYKPWALVICIDSNGENKIKML**SGGSPKKKRKV

The percentages in FIGS. 9 and 10 are shown from sequencing both strands of the target sequence. Because only one of the strands is a substrate for deamination, the maximum possible deamination value in this assay is 50%. Accordingly, the deamination efficiency is double the percentages shown in the tables. E.g., a value of 50% relates to deamination of 100% of double-stranded target sequences. When a uracil glycosylase inhibitor (UGI) was fused to the dCas9:deaminase fusion protein (e.g., rAPOBEC1-XTEN-dCas9-[UGI]-NLS), a significant increase in editing efficiency in cells was observed. This result indicates that in mammalian cells, the DNA repair machinery that cuts out the uracil base in a U:G base pair is a rate-limiting process in DNA editing. Tethering UGI to the dVas9:deaminase fusion proteins greatly increases editing yields.

Without UGI, typical editing efficiencies in human cells were in the ~2-14% yield range (FIG. 9 and FIG. 10, "XTEN" entries). With UGI (FIG. 10, "UGI" entries) the editing was observed in the ~6-40% range. Using a UGI fusion is thus more efficient than the current alternative method of correcting point mutations via HDR, which also creates an excess of indels in addition to correcting the point mutation. No indels resulting from treatment with the cas9:deaminase:UGI fusions were observed.

Example 4: Direct, Programmable Conversion of a Target Nucleotide in Genomic DNA without Double-Stranded DNA Cleavage Current genome-editing technologies introduce double-stranded DNA breaks at a target locus of interest as the first step to gene correction.[39,40] Although most genetic diseases arise from mutation of a single nucleobase to a different nucleobase, current approaches to revert such changes are very inefficient and typically induce an abundance of random insertions and deletions (indels) at the target locus as a consequence of the cellular response to double-stranded DNA breaks.[39,40] Reported herein is the development of nucleobase editing, a new strategy for genome editing that enables the direct conversion of one target nucleobase into another in a programmable manner, without requiring double-stranded DNA backbone cleavage. Fusions of CRISPR/Cas9 were engineered and the cytidine deaminase enzyme APOBEC1 that retain the ability to be programmed with a guide RNA, do not induce double-stranded DNA breaks, and mediate the direct conversion of cytidine to uracil, thereby effecting a C→T (or G→A) substitution following DNA replication, DNA repair, or transcription if the template strand is targeted. The resulting "nucleobase editors" convert cytidines within a window of approximately five nucleotides, and can efficiently correct a variety of point mutations relevant to human disease in vitro. In four transformed human and murine cell lines, second- and third-generation nucleobase editors that fuse uracil glycosylase inhibitor (UGI), and that use a Cas9 nickase targeting the non-edited strand, respectively, can overcome the cellular DNA repair response to nucleobase editing, resulting in permanent correction of up to 37% or (~15-75%) of total cellular DNA in human cells with minimal (typically ≤1%) indel formation. In contrast, canonical Cas9-mediated HDR on the same targets yielded an average of 0.7% correction with 4% indel formation. Nucleobase editors were used to revert two oncogenic p53 mutations into wild-type alleles in human breast cancer and lymphoma cells, and to convert an Alzheimer's Disease associated Arg codon in ApoE4 into a non-disease-associated Cys codon in mouse astrocytes. Base editing expands the scope and efficiency of genome editing of point mutations.

The clustered regularly interspaced short palindromic repeat (CRISPR) system is a prokaryotic adaptive immune system that has been adapted to mediate genome engineering in a variety of organisms and cell lines.[41] CRISPR/Cas9 protein-RNA complexes localize to a target DNA sequence through base pairing with a guide RNA, and natively create a DNA double-stranded break (DSB) at the locus specified by the guide RNA. In response to DSBs, endogenous DNA repair processes mostly result in random insertions or deletions (indels) at the site of DNA cleavage through non-homologous end joining (NHEJ). In the presence of a homologous DNA template, the DNA surrounding the cleavage site can be replaced through homology-directed repair (HDR). When simple disruption of a disease-associated gene is sufficient (for example, to treat some gain-of-function diseases), targeted DNA cleavage followed by indel formation can be effective. For most known genetic diseases, however, correction of a point mutation in the target locus, rather than stochastic disruption of the gene, is needed to address or study the underlying cause of the disease.[68]

Motivated by this need, researchers have invested intense effort to increase the efficiency of HDR and suppress NHEJ. For example, a small-molecule inhibitor of ligase IV, an essential enzyme in the NHEJ pathway, has been shown to increase HDR efficiency.[42,43] However, this strategy is challenging in post-mitotic cells, which typically down-regulate HDR, and its therapeutic relevance is limited by the potential risks of inhibiting ligase IV in non-target cells. Enhanced HDR efficiency can also be achieved by the timed delivery of Cas9-guide RNA complexes into chemically synchronized cells, as HDR efficiency is highly cell-cycle dependent.[44] Such an approach, however, is limited to research applications in cell culture since synchronizing cells is highly disruptive. Despite these developments, current strategies to replace point mutations using HDR in most contexts are very inefficient (typically ~0.1 to 5%),[42,43,45,46,75] especially in unmodified, non-dividing cells. In addition, HDR competes with NHEJ during the resolution of double-stranded breaks, and indels are generally more abundant outcomes than gene replacement. These observations highlight the need to develop alternative approaches to install specific modifications in genomic DNA that do not rely on creating double-stranded DNA breaks. A small-molecule inhibitor of ligase IV, an essential enzyme in the NHEJ pathway, has been shown to increase HDR efficiency.[42,43] However, this strategy is challenging in post-mitotic cells, which typically down-regulate HDR, and its therapeutic relevance is limited by the potential risks of inhibiting ligase IV in non-target cells. Enhanced HDR efficiency can also be achieved by the timed delivery of Cas9-guide RNA complexes into chemically synchronized cells, as HDR efficiency is highly cell-cycle dependent.[44] Such an approach, however, is limited to research applications in cell culture since synchronizing cells is highly disruptive. In some cases, it is possible to design HDR templates such that the product of successful HDR contains mutations in the PAM sequence and therefore is no longer a substrate for subsequent Cas9 modification, increasing the overall yield of HDR products,[75] although such an approach imposes constraints on the product sequences. Recently, this strategy has been coupled to the use of ssDNA donors that are complementary to the non-target strand and high-efficiency ribonucleoprotein (RNP) delivery to substantially increase the efficiency of HDR, but even in these cases the ratio of HDR to NHEJ outcomes is relatively low (<2).[83]

Figure 11A:
FIGS. 11A to 11C show NBE1 mediates specific, guide RNA-programmed C to U conversion in vitro.

It was envisioned that direct catalysis of the conversion of one nucleobase to another at a programmable target locus without requiring DNA backbone cleavage could increase the efficiency of gene correction relative to HDR without introducing undesired random indels at the locus of interest. Catalytically dead Cas9 (dCas9), which contains Asp10Ala and His840Ala mutations that inactivate its nuclease activity, retains its ability to bind DNA in a guide RNA-programmed manner but does not cleave the DNA backbone.[16,47] In principle, conjugation of dCas9 with an enzymatic or chemical catalyst that mediates the direct conversion of one nucleobase to another could enable RNA-programmed nucleobase editing. The deamination of cytosine (C) is catalyzed by cytidine deaminases[29] and results in uracil (U), which has the base pairing properties of thymine (T). dCas9 was fused to cytidine deaminase enzymes in order to test their ability to convert C to U at a guide RNA-specified DNA locus. Most known cytidine deaminases operate on RNA, and the few examples that are known to accept DNA require single-stranded DNA.[48] Recent studies on the dCas9-target DNA complex reveal that at least nine nucleotides of the displaced DNA strand are unpaired upon formation of the Cas9:guide RNA:DNA "R-loop" complex.[12] Indeed, in the structure of the Cas9R-loop complex the first 11 nucleotides of the protospacer on the displaced DNA strand are disordered, suggesting that their movement is not highly restricted.[76] It has also been speculated that Cas9 nickase-induced mutations at cytosines in the non-template strand might arise from their accessibility by cellular cytidine deaminase enzymes.[77] Recent studies on the dCas9-target DNA complex have revealed that at least 26 bases on the non-template strand are unpaired when Cas9 binds to its target DNA sequence.[49] It was reasoned that a subset of this stretch of single-stranded DNA in the R-loop might serve as a substrate for a dCas9-tethered cytidine deaminase to effect direct, programmable conversion of C to U in DNA (FIG. 11A).

Figure 11B:
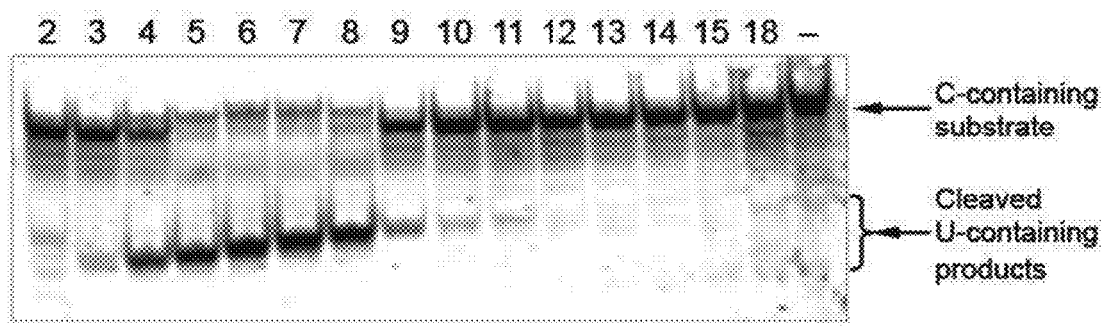
Figure 11C:
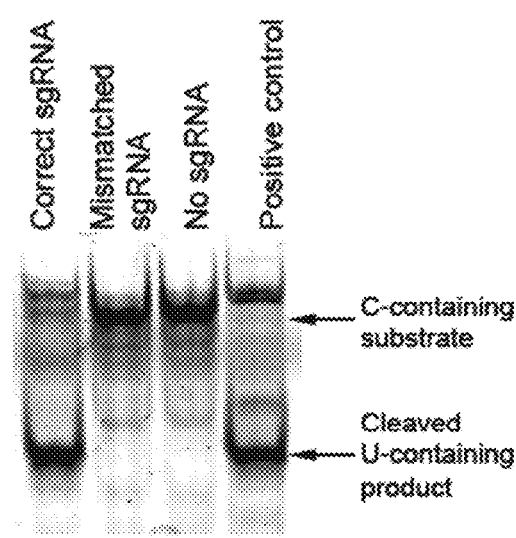
Figure 36A:
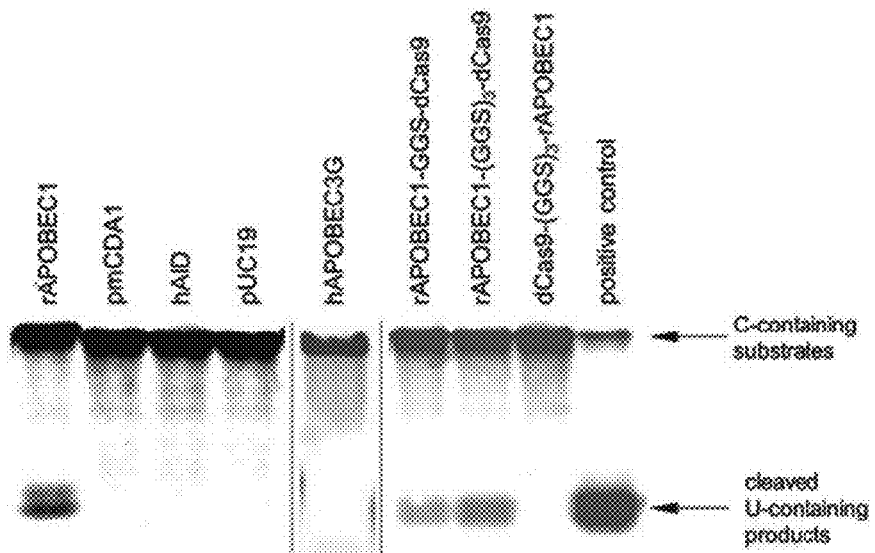
Figure 36B:
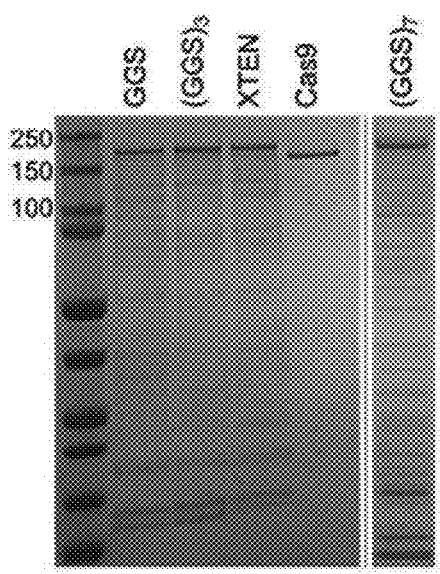
Figure 36C:
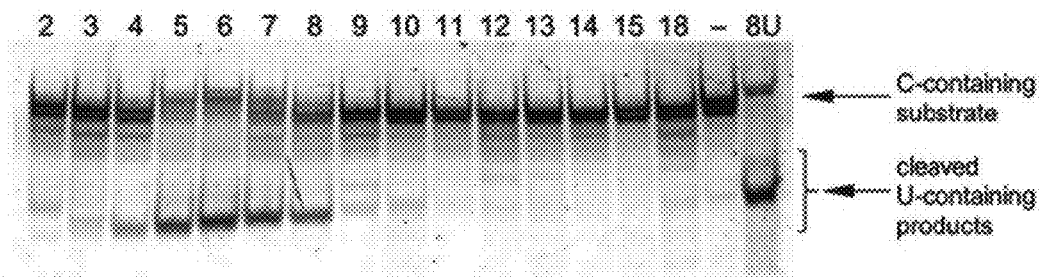

Four different cytidine deaminase enzymes (hAID, hAPOBEC3G, rAPOBEC1, and pmCDA1) were expressed in a mammalian cell lysate-derived in vitro transcription-translation system and evaluated for ssDNA deamination. Of the four enzymes, rAPOBEC1 showed the highest deaminase activity under the tested conditions and was chosen for dCas9 fusion experiments (FIG. 36A). Although appending rAPOBEC1 to the C-terminus of dCas9 abolishes deaminase activity, fusion to the N-terminus of dCas9 preserves deaminase activity on ssDNA at a level comparable to that of the unfused enzyme. Four rAPOBEC1-dCas9 fusions were expressed and purified with linkers of different length and composition (FIG. 36B), and evaluated each fusion for single guide RNA (sgRNA)-programmed dsDNA deamination in vitro (FIGS. 11A to 11C and FIGS. 15A to 15D). Efficient, sequence-specific, sgRNA-dependent C to U conversion was observed in vitro (FIGS. 11A to 11C). Conversion efficiency was greatest using rAPOBEC1-dCas9 linkers over nine amino acids in length. The number of positions susceptible to deamination (the deamination "activity window") increases with linker length was extended from three to 21 amino acids (FIGS. 36C to 36F15A to 15D). The 16-residue XTEN linker[50] was found to offer a promising balance between these two characteristics, with an efficient deamination window of approximately five nucleotides, from positions 4 to 8 within the protospacer, counting the end distal to the protospacer-adjacent motif (PAM) as position 1. The rAPOBEC1-XTEN-dCas9 protein served as the first-generation nucleobase editor (NBE1).

Elected were seven mutations relevant to human disease that in theory could be corrected by C to T nucleobase editing, synthesized double-stranded DNA 80-mers of the corresponding sequences, and assessed the ability of NBE1 to correct these mutations in vitro (FIGS. 16A to 16B). NBE1 yielded products consistent with efficient editing of the target C, or of at least one C within the activity window when multiple Cs were present, in six of these seven targets in vitro, with an average apparent editing efficiency of 44% (FIGS. 16A to 16B). In the three cases in which multiple Cs were present within the deamination window, evidence of deamination of some or all of these cytosines was observed. In only one of the seven cases tested were substantial yields of edited product observed (FIGS. 16A to 16B).

Figures 12B, 13A:
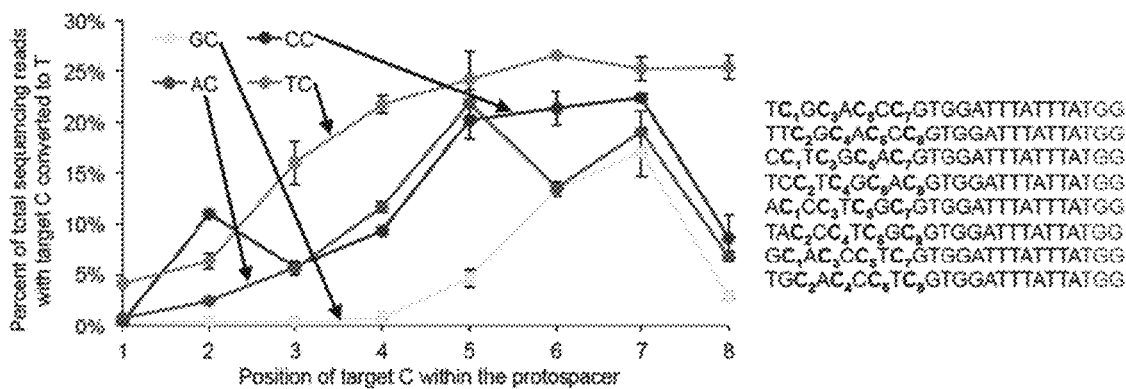

Although the preferred sequence context for APOBEC1 substrates is reported to be CC or TC,[51] it was anticipated that the increased effective molarity of the deaminase and its single-stranded DNA substrate mediated by dCas9 binding to the target locus may relax this restriction. To illuminate the sequence context generality of NBE1, its ability to edit a 60-mer double-stranded DNA oligonucleotide containing a single fixed C at position 7 within the protospacer was assayed, as well as all 36 singly mutated variants in which protospacer bases 1-6 and 8-13 were individually varied to each of the other three bases. Each of these 37 sequences were treated with 1.9 µM NBE1, 1.9 µM of the corresponding sgRNA, and 125 nM DNA for 2 h, similar to standard conditions for in vitro Cas9 assays[52]. High-throughput DNA sequencing (HTS) revealed 50 to 80% C to U conversion of targeted strands (25 to 40% of total sequence reads arising from both DNA strands, one of which is not a substrate for NBE1) (FIG. 12A). The nucleotides surrounding the target C had little effect on editing efficiency was independent of sequence context unless the base immediately 5' of the target C is a G, in which case editing efficiency was substantially lower (FIGS. 12A to 12B). NBE1 activity in vitro was assessed on all four NC motifs at positions 1 through 8 within the protospacer (FIGS. 12A to 12B). In general NBE1 activity on substrates was observed to follow the order TC≥CC≥AC>GC, with maximum editing efficiency achieved when the target C is at or near position 7. In addition, it was observed that the nucleobase editor is highly processive, and will efficiently convert most of all Cs to Us on the same DNA strand within the 5-base activity window (FIG. 17).

Figures 28, 29A:
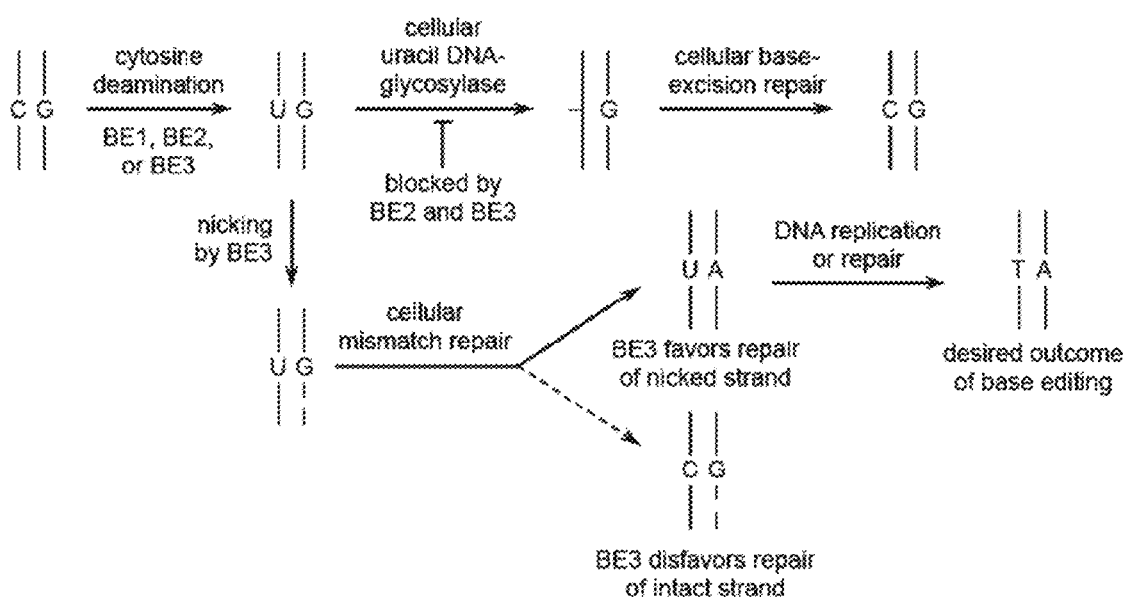
FIG. 28 shows non-target C mutation rates. Shown here are the C to T mutation rates at 2,500 distinct cytosines surrounding the six on-target and 34 off-target loci tested, representing a total of 14,700,000 sequence reads derived from approximately 1.8×106 cells.
FIGS. 29A to 29C show base editing in human cells.

While BE1 efficiently processes substrates in a test tube, in cells a tree of possible DNA repair outcomes determines the fate of the initial U:G product of base editing (FIG. 29A). To test the effectiveness of nucleobase editing in human cells, NBE1 codon usage was optimized for mammalian expression, appended a C-terminal nuclear localization sequence (NLS),[53] and assayed its ability to convert C to T in human cells on 14Cs in six well-studied target sites throughout the human genome (FIG. 37A).[54] The editable Cs were confirmed within each protospacer in vitro by incubating NBE1 with synthetic 80-mers that correspond to the six different genomic sites, followed by HTS (FIGS. 13A to 13C, FIG. 29B and FIG. 25). Next, HEK293T cells were transfected with plasmids encoding NBE1 and one of the six target sgRNAs, allowed three days for nucleobase editing to occur, extracted genomic DNA from the cells, and analyzed the loci by HTS. Although C to T editing in cells at the target locus was observed for all six cases, the efficiency of nucleobase editing was 1.1% to 6.3% or 0.8%-7.7% of total DNA sequences (corresponding to 2.2% to 12.6% of targeted strands), a 6.3-fold to 37-fold or 5-fold to 36-fold decrease in efficiency compared to that of in vitro nucleobase editing (FIGS. 13A to 13C, FIG. 29B and FIG. 25). It was observed that some base editing outside of the typical window of positions 4 to 8 when the substrate C is preceded by a T, which we attribute to the unusually high activity of APOBEC1 for TC substrates.[48]

It was asked whether the cellular DNA repair response to the presence of U:G heteroduplex DNA was responsible for the large decrease in nucleobase editing efficiency in cells (FIG. 29A). Uracil DNA glycosylase (UDG) catalyzes removal of U from DNA in cells and initiates base excision repair (BER), with reversion of the U:G pair to a C:G pair as the most common outcome (FIG. 29A).[55] Uracil DNA glycosylase inhibitor (UGI), an 83-residue protein from *B. subtilis* bacteriophage PBS1, potently blocks human UDG activity ($IC_{50}$=12 µM).[56] UGI was fused to the C-terminus of NBE1 to create the second-generation nucleobase editor NBE2 and repeated editing assays on all six genomic loci. Editing efficiencies in human cells were on average 3-fold higher with NBE2 than with NBE1, resulting in gene conversion efficiencies of up to 22.8% of total DNA sequenced (up to 45.6% of targeted strands) (FIGS. 13A to 13C and FIG. 29B). To test base editing in human cells, BE1 codon usage was optimized for mammalian expression and appended a C-terminal nuclear localization sequence (NLS).[53]

Figure 19:
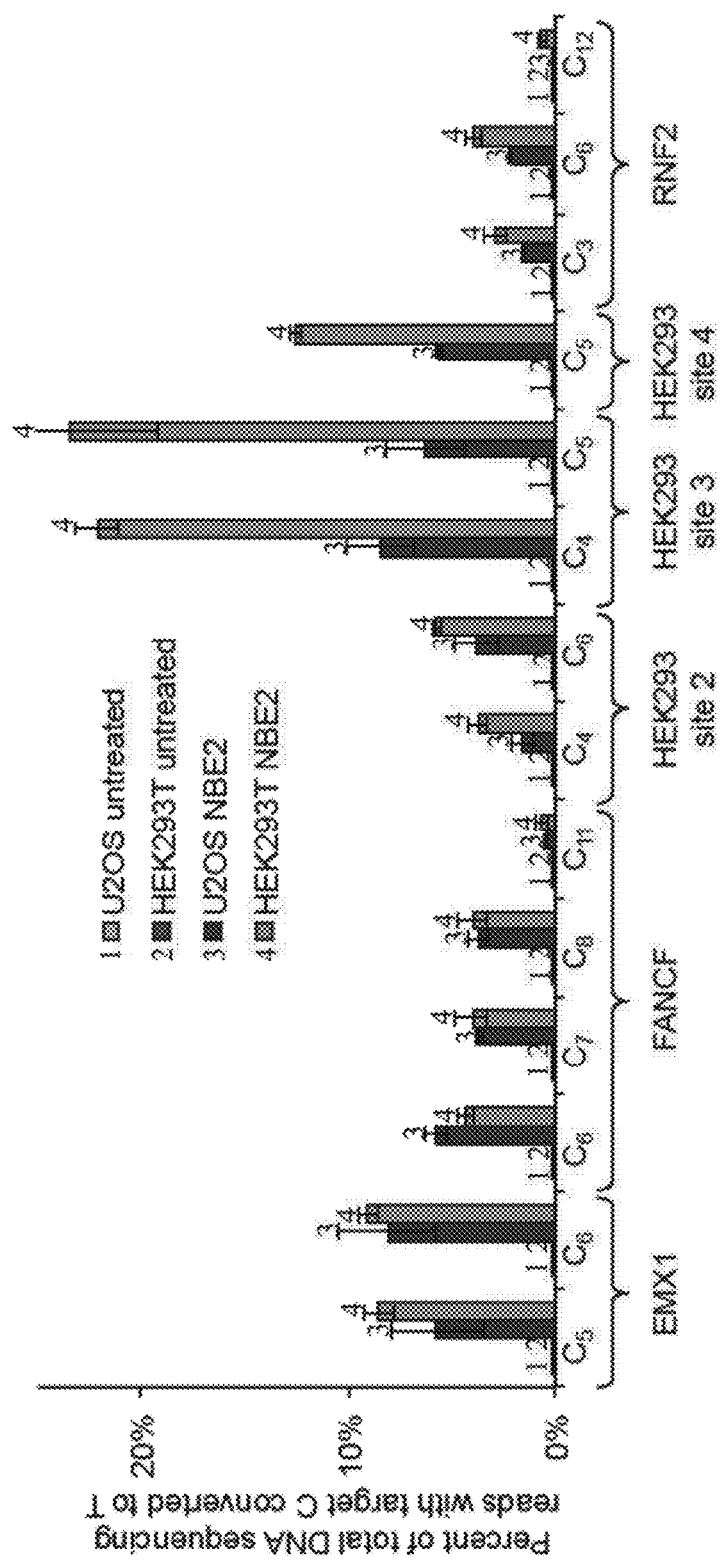
FIG. 19 shows nucleobase editing efficiencies of NBE2 in U2OS and HEK293T cells. Cellular C to T conversion percentages by NBE2 are shown for each of the six targeted genomic loci in HEK293T cells and U2OS cells. HEK293T cells were transfected using lipofectamine 2000, and U2OS cells were nucleofected. U2OS nucleofection efficiency was 74%. Three days after plasmid delivery, genomic DNA was extracted and analyzed for nucleobase editing at the six genomic loci by HTS. Values and error bars reflect the mean and standard deviation of at least two biological experiments done on different days.

Similar editing efficiencies were observed when a separate plasmid overexpressing UGI was co-transfected with NBE1 (FIGS. 18A to 18H). However, while the direct fusion of UGI to NBE1 resulted in no significant increase in C to T mutations at monitored non-targeted genomic locations, overexpression of unfused UGI detectably increased the frequency of C to T mutations elsewhere in the genome (FIGS. 18A to 18H). The generality of NBE2-mediated nucleobase editing was confirmed by assessing editing efficiencies on the same six genomic targets in U2OS cells, and observed similar results with those in HEK293T cells (FIG. 19). Importantly, NBE2 typically did not result in any detectable indels (FIG. 13C and FIG. 29C), consistent with the known mechanistic dependence of NHEJ on double-stranded DNA breaks.[57,78] Together, these results indicate that conjugating UGI to NBE1 can greatly increase the efficiency of nucleobase editing in human cells.

Figure 20:
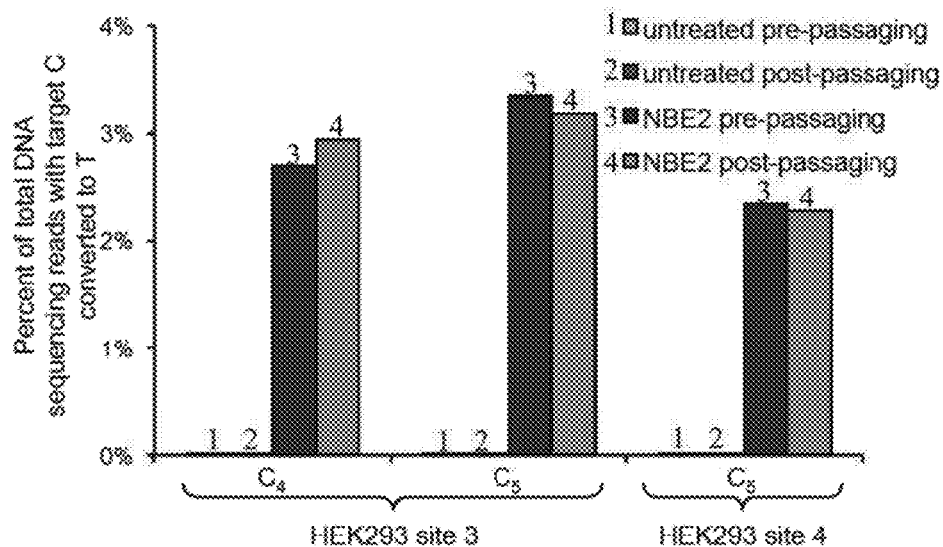
FIG. 20 shows nucleobase editing persists over multiple cell divisions. Cellular C to T conversion percentages by NBE2 are displayed at two genomic loci in HEK293T cells before and after passaging the cells. HEK293T cells were transfected using Lipofectamine 2000. Three days post transfection, the cells were harvested and split in half. One half was subjected to HTS analysis, and the other half was allowed to propagate for approximately five cell divisions, then harvested and subjected to HTS analysis.

The permanence of nucleobase editing in human cells was confirmed by monitoring editing efficiencies over multiple cell divisions in HEK293T cells at two of the tested genomic loci. Genomic DNA was harvested at two time points: three days after transfection with plasmids expressing NBE2 and appropriate sgRNAs, and after passaging the cells and growing them for four additional days (approximately five subsequent cell divisions). No significant change in editing efficiency was observed between the non-passaged cells (editing observed in 4.6% to 6.6% of targeted strands for three different target Cs) and passaged cells (editing observed in 4.6% to 6.4% of targeted strands for the same three target Cs), confirming that the nucleobase edits became permanent following cell division (FIG. 20). Indels will on rare occasion arise from the processing of U:G lesions by cellular repair processes, which involve single-strand break intermediates that are known to lead to indels.[84] Given that several hundred endogenous U:G lesions are generated every day per human cell from spontaneous cytidine deaminase,[85] it was anticipate that the total indel frequency from U:G lesion repair is unlikely to increase from BE1 or BE2 activity at a single target locus.

Figure 13B:
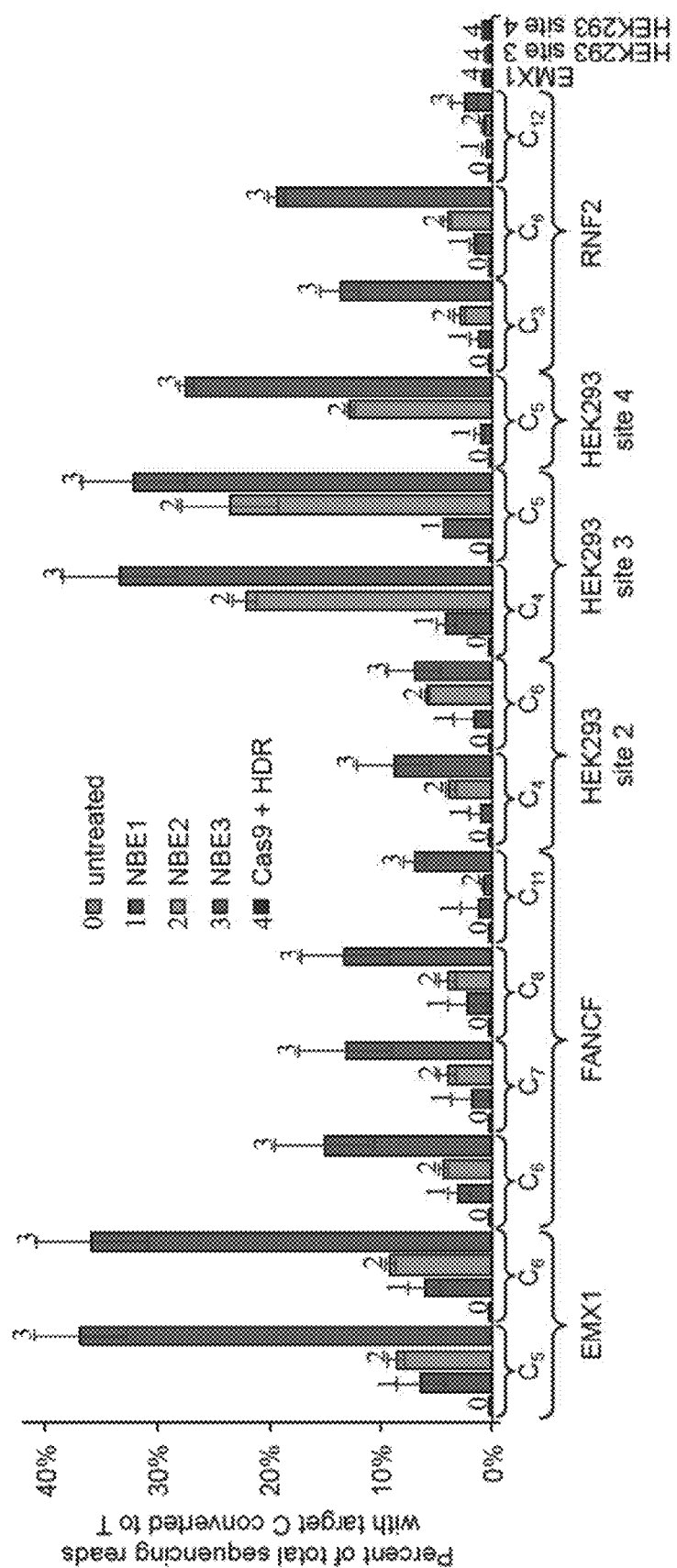
Figure 13C:
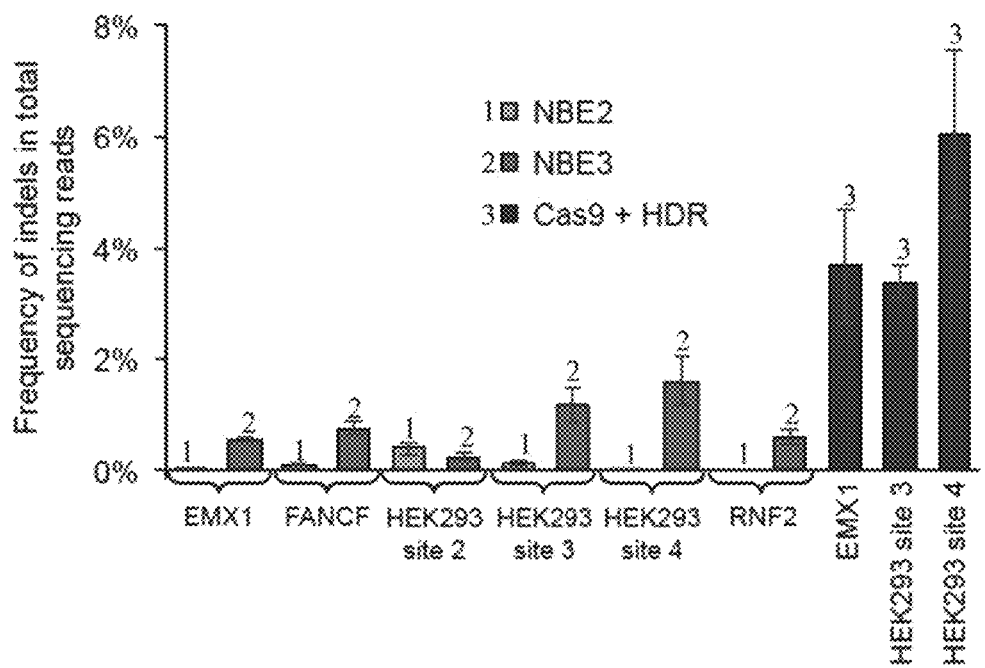
Figure 15A:
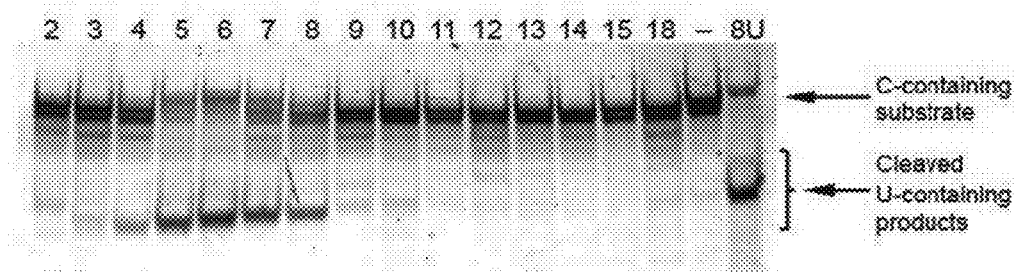
FIGS. 15A to 15D show effects of deaminase-dCas9 linker length and composition on nucleobase editing. Gel-based deaminase assay showing the deamination window of nucleobase editors with deaminase-Cas9 linkers of GGS (FIG. 15A), (GGS)$_3$ (SEQ ID NO: 596) (FIG. 15B), XTEN (FIG. 15C), or (GGS)$_7$ (SEQ ID NO: 597) (FIG. 15D). Following incubation of 1.85 µM editor-sgRNA complexes with 125 nM dsDNA substrates at 37° C. for 2 h, the dye-conjugated DNA was isolated and incubated with USER enzyme (uracil DNA glycosylase and endonuclease VIII) at 37° C. for an additional hour to cleave the DNA backbone at the site of any uracils. The resulting DNA was resolved on a denaturing polyacrylamide gel, and the dye-conjugated strand was imaged. Each lane is numbered according to the position of the target C within the protospacer, or with—if no target C is present. 8U is a positive control sequence with a U synthetically incorporated at position 8.
Figure 15B:
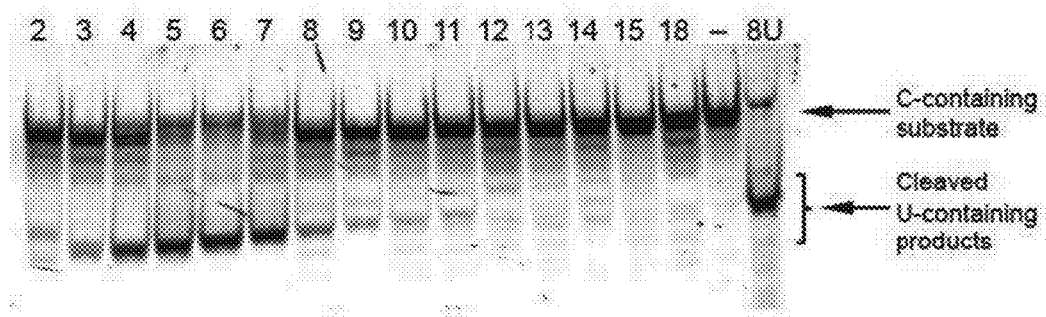
Figure 15C:
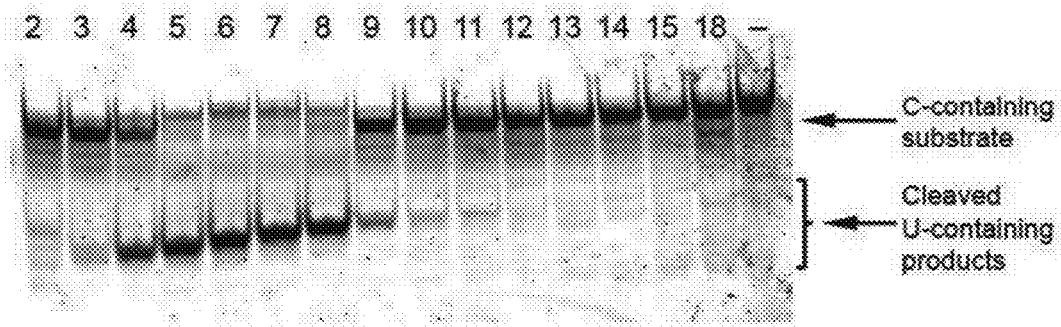
Figure 15D:
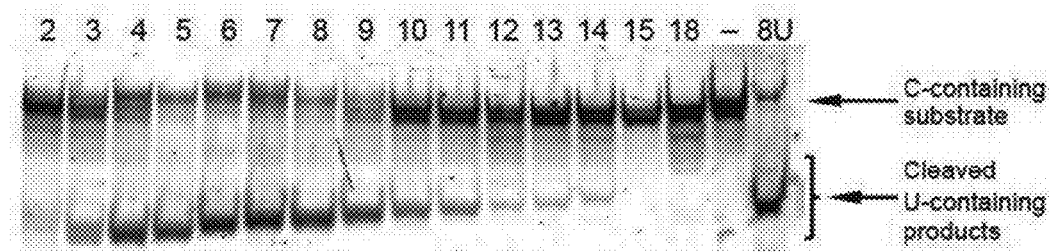
Figure 29B:
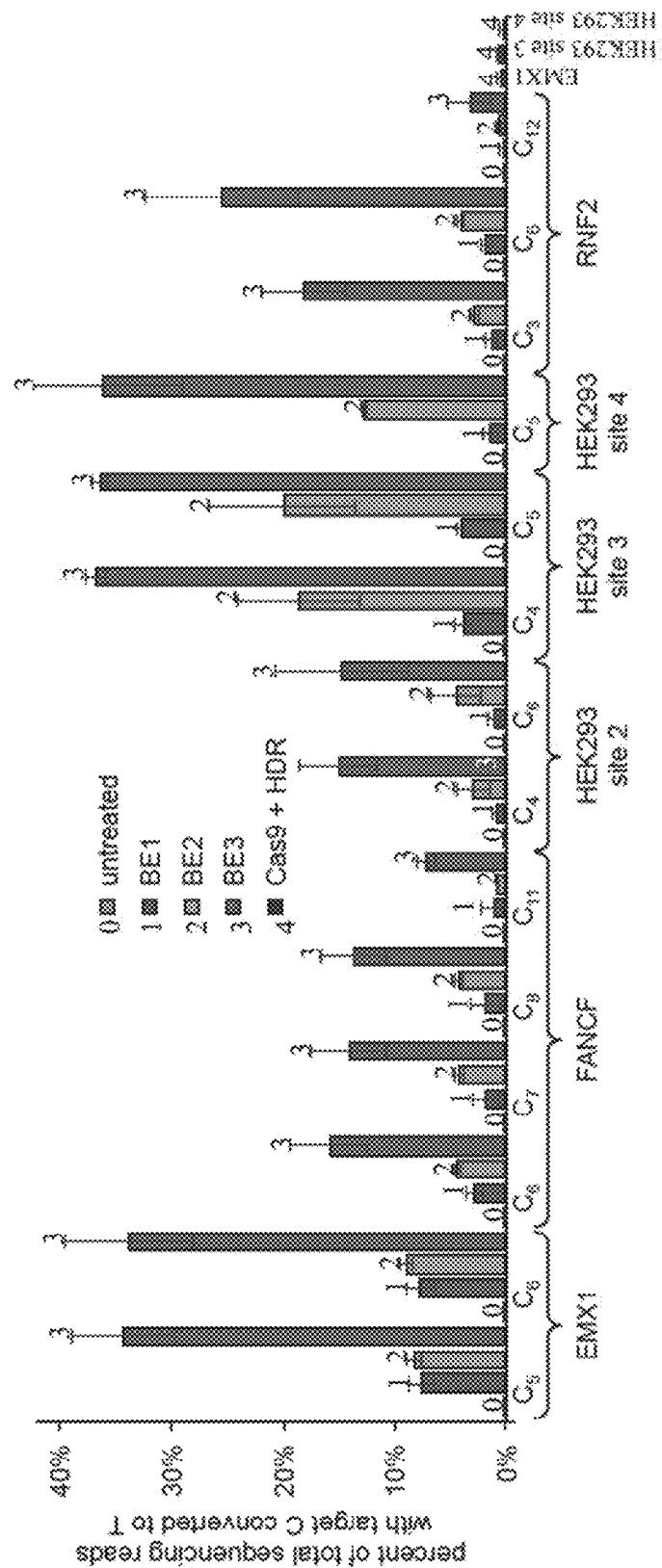
Figure 29C:
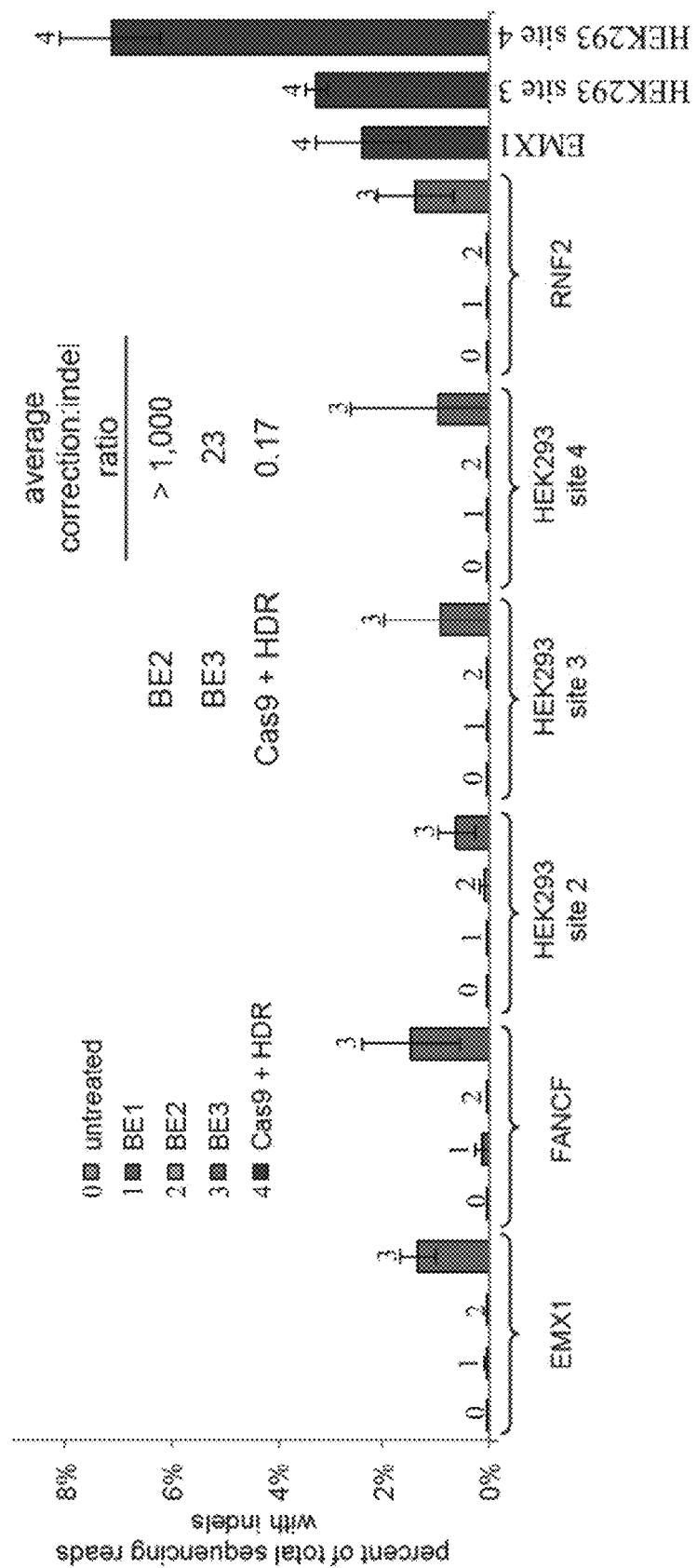
Figure 31:
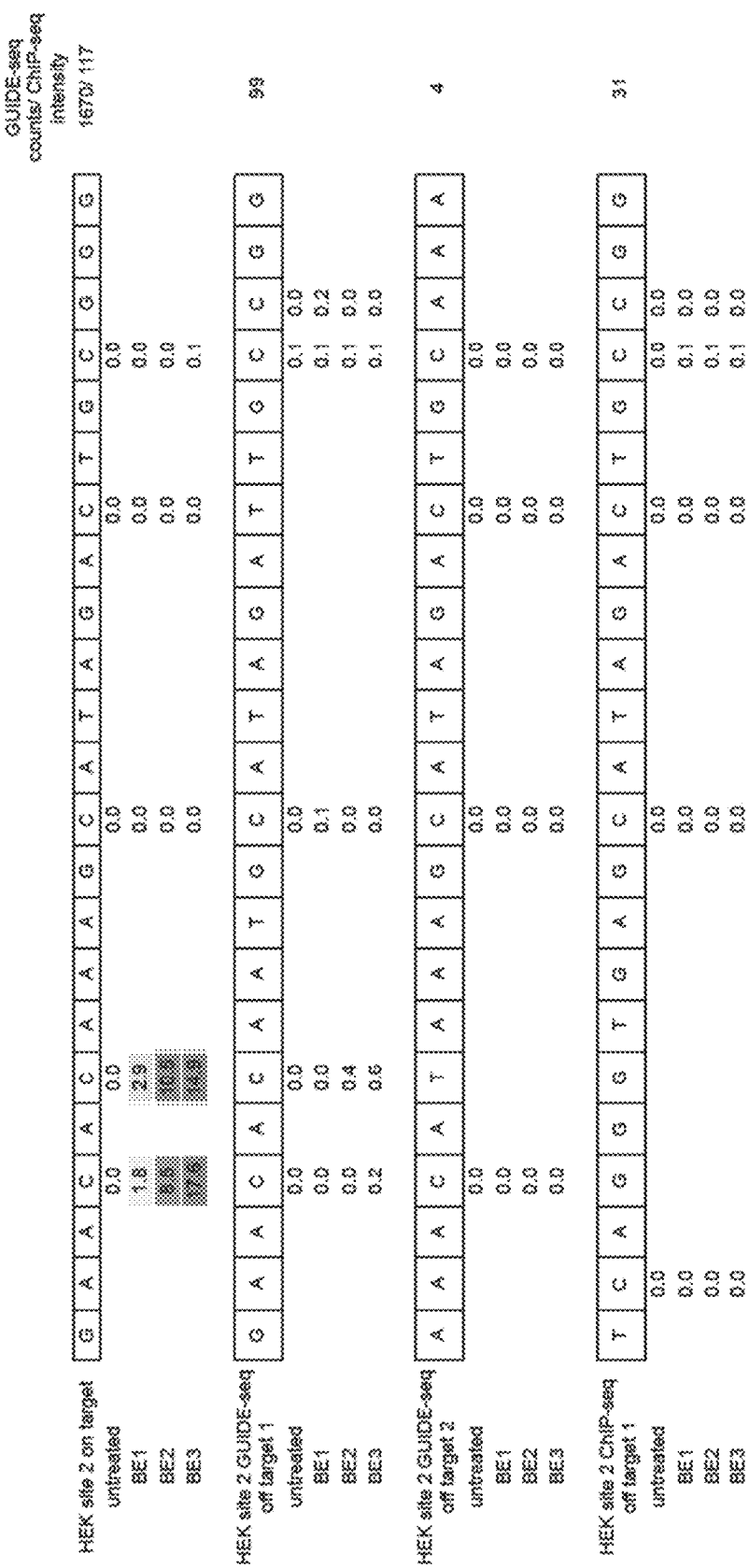
FIG. 31 shows activities of BE1, BE2, and BE3 at HEK293 site 2 off-targets. HEK293T cells were transfected with plasmids expressing BE1, BE2, or BE3 and a sgRNA matching the HEK293 site 2 sequence using Lipofectamine 2000. Three days after transfection, genomic DNA was extracted, amplified by PCR, and analyzed by high-throughput DNA sequencing at the on-target loci, plus all of the known Cas9 and dCas9 off-target loci for the HEK293 site 2 sgRNA, as previously determined by Joung and coworkers using the GUIDE-seq method (63), and Adli and coworkers using chromatin immunoprecipitation high-throughput sequencing (ChIP-seq) experiments (18). Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for BE1, BE2, and BE3. On the far right are displayed the total number of sequencing reads reported, and the ChIP-seq signal intensity reported for each sequence. This figure depicts SEQ ID NOs: 681 to 688 from top to bottom, respectively.
Figure 33:
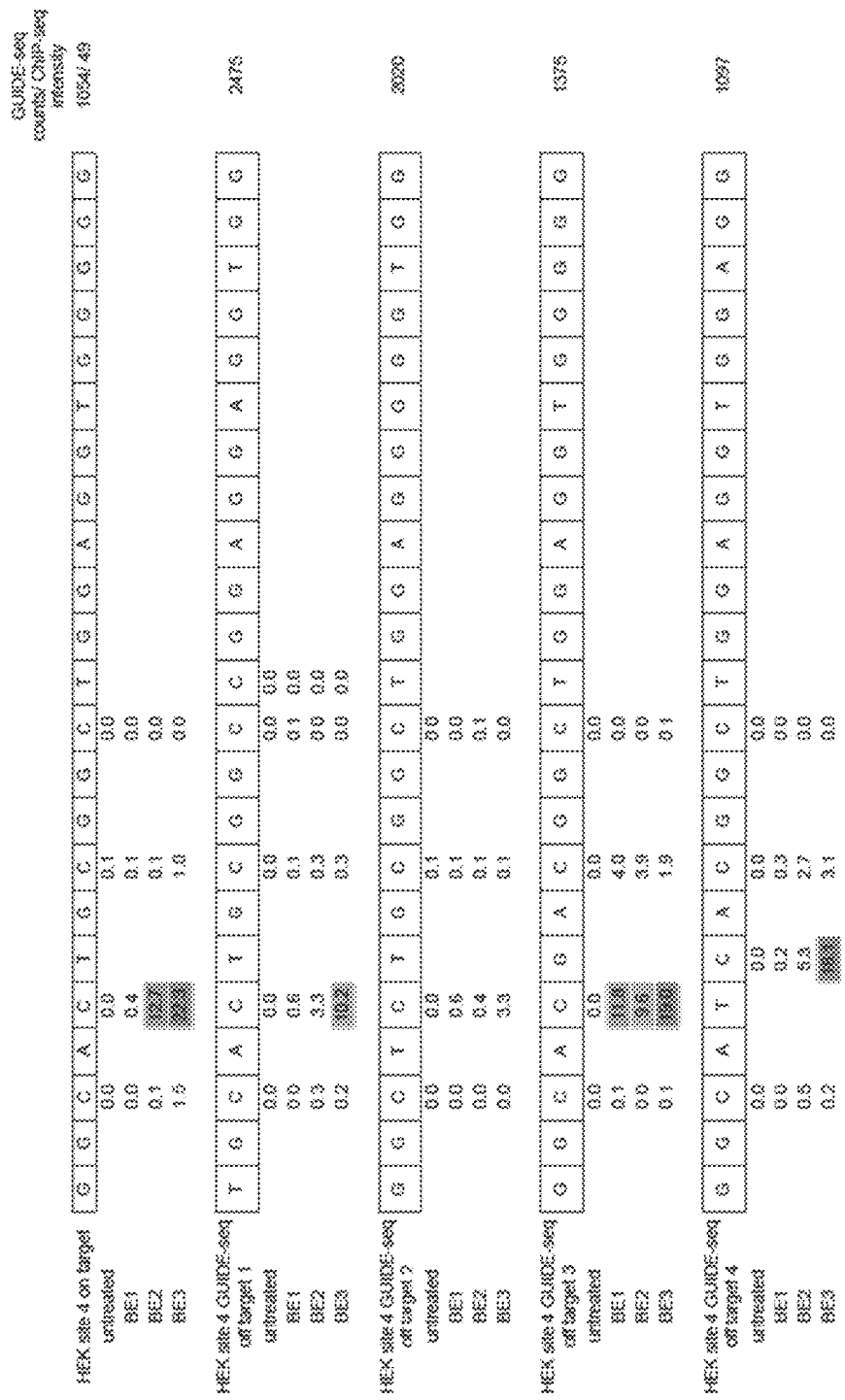
FIG. 33 shows activities of BE1, BE2, and BE3 at HEK293 site 4 off-targets. HEK293T cells were transfected with plasmids expressing BE1, BE2, or BE3 and a sgRNA matching the HEK293 site 4 sequence using Lipofectamine 2000. Three days after transfection, genomic DNA was extracted, amplified by PCR, and analyzed by high-throughput DNA sequencing at the on-target loci, plus the top ten known Cas9 off-target loci and the top five known dCas9 off-target loci for the HEK293 site 4 sgRNA, as previously determined using the GUIDE-seq method[54], and using chromatin immunoprecipitation high-throughput sequencing (ChIP-seq) experiments[61]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for BE1, BE2, and BE3. On the far right are displayed the total number of sequencing reads reported, and the ChIP-seq signal intensity reported for each sequence. This figure depicts SEQ ID NOs: 700 to 712 from top to bottom, respectively.

To further increase the efficiency of nucleobase editing in cells, it was anticipated that nicking the non-edited strand may result in a smaller fraction of edited Us being removed by the cell, since eukaryotic mismatch repair machinery uses strand discontinuity to direct DNA repair to any broken strand of a mismatched duplex (FIG. 29A).[58, 79, 80] The catalytic His residue was restored at position 840 in the Cas9 HNH domain,[47,59] resulting in the third-generation nucleobase editor NBE3 that nicks the non-edited strand containing a G opposite the targeted C, but does not cleave the target strand containing the C. Because NBE3 still contains the Asp10A1a mutation in Cas9, it does not induce double-stranded DNA cleavage. This strategy of nicking the non-edited strand augmented nucleobase editing efficiency in human cells by an additional 1.4- to 4.8-fold relative to NBE2, resulting in up to 36.3% of total DNA sequences containing the targeted C to T conversion on the same six human genomic targets in HEK293T cells (FIGS. 13A to 13C and FIG. 29B). Importantly, only a small frequency of indels, averaging 0.8% (ranging from 0.2% to 1.6% for the six different loci), was observed from NBE3 treatment (FIG. 13C, FIG. 29C, and FIG. 34). In contrast, when cells were treated with wild-type Cas9, sgRNA, and a single-stranded DNA donor template to mediate HDR at three of these loci C to T conversion efficiencies averaging only 0.7% were observed, with much higher relative indel formation averaging 3.9% (FIGS. 13A to 13C and FIG. 29C). The ratio of allele conversion to NHEJ outcomes averaged >1,000 for BE2, 23 for BE3, and 0.17 for wild-type Cas9 (FIG. 3c). We confirmed the permanence of base editing in human cells by monitoring editing efficiencies over multiple cell divisions in HEK293T cells at the HEK293 site 3 and 4 genomic loci (FIG. 38). These results collectively establish that nucleobase editing can effect much more efficient targeted single-base editing in human cells than Cas9-mediated HDR, and with much less (NBE3) or no (NBE2) indel formation.

Next, the off-target activity of NBE1, NBE2, and NBE3 in human cells was evaluated. The off-target activities of Cas9, dCas9, and Cas9 nickase have been extensively studied (FIGS. 23 to 24 and 31 to 33).[54,60-62] Because the sequence preference of rAPOBEC1 has been shown to be independent of DNA bases more than one base from the target C,[63] consistent with the sequence context independence observed in FIGS. 12A to 12B, it was assumed that potential off-target activity of nucleobase editors arises from off-target Cas9 binding. Since only a fraction of Cas9 off-target sites will have a C within the active window for nucleobase editing, off-target nucleobase editing sites should be a subset of the off-target sites of canonical Cas9 variants. For each of the six sites studied, the top ten known Cas9 off-target loci in human cells that were previously determined using the GUIDE-seq method were sequenced (FIGS. 23 to 27 and 31 to 33).[54, 61] Detectable off-target nucleobase editing at only a subset (16/34, 47% for NBE1 and NBE2, and 17/34, 50% for NBE3) of known dCas9 off-target loci was observed. In all cases, the off-target base-editing substrates contained a C within the five-base target window. In general, off-target C to T conversion paralleled off-target Cas9 nuclease-mediated genome modification frequencies (FIGS. 23 to 27). Also monitored were C to T conversions at 2,500 distinct cytosines surrounding the six on-target and 34 off-target loci tested, representing a total of 14,700,000 sequence reads derived from approximately $1.8 \times 10^6$ cells, and observed no detectable increase in C to T conversions at any of these other sites upon NBE1, NBE2, or NBE3 treatment compared to that of untreated cells (FIG. 28). Taken together, these findings suggest that off-target substrates of nucleobase editors include a subset of Cas9 off-target substrates, and that nucleobase editors in human cells do not induce untargeted C to T conversion throughout the genome at levels that can be detected by the methods used here. No substantial change was observed in editing efficiency between non-passaged HEK293T cells (editing observed in 1.8% to 2.6% of sequenced strands for the three target Cs with BE2, and 6.2% to 14.3% with BE3) and cells that had undergone approximately five cell divisions after base editing (editing observed in 1.9% to 2.3% of sequenced strands for the same target Cs with BE2, and 6.4% to 14.5% with BE3), confirming that base edits in these cells are durable (Extended Data FIG. 6).

Finally, the potential of nucleobase editing to correct three disease-relevant mutations in mammalian cells was tested. The apolipoprotein E gene variant APOE4 encodes two Arg residues at amino acid positions 112 and 158, and is the largest and most common genetic risk factor for late-onset Alzheimer's disease.[64] ApoE variants with Cys residues in positions 112 or 158, including APOE2 (Cys112/Cys158), APOE3 (Cys112/Arg158), and APOE3' (Arg112/Cys158) have been shown[65] or are presumed[81] to confer substantially lower Alzheimer's disease risk than APOE4. Encouraged by the ability of NBE1 to convert APOE4 to APOE3' in vitro (FIGS. 16A to 16B), this conversion was attempted in immortalized mouse astrocytes in which the endogenous murine APOE gene has been replaced by human APOE4 (Taconic). DNA encoding NBE3 and an appropriate sgRNA was delivered into these astrocytes by nucleofection (nucleofection efficiency of 25%), extracted genomic DNA from all treated cells two days later, and measured editing efficiency by HTS. Conversion of Arg158 to Cys158 was observed in 58-75% of total DNA sequencing reads (44% of nucleofected astrocytes) (FIGS. 14A to 14C and FIGS. 30A). Also observed was 36-50% editing of total DNA at the third position of codon 158 and 38-55% editing of total DNA at the first position of Leu159, as expected since all three of these Cs are within the active nucleobase editing window. However, neither of the other two C→T conversions results in a change in the amino acid sequence of the ApoE3' protein since both TGC and TGT encode Cys, and both CTG and TTG encode Leu. From >1,500,000 sequencing reads derived from $1 \times 10^6$ cells evidence of 1.7% indels at the targeted locus following NBE3 treatment was observed (FIG. 35). In contrast, identical treatment of astrocytes with wt Cas9 and donor ssDNA resulted in 0.1-0.3% APOE4 correction and 26-40% indels at the targeted locus, efficiencies consistent with previous reports of single-base correction using Cas9 and HDR[45,75] (FIG. 30A and FIG. 40A). Astrocytes treated identically but with an sgRNA targeting the VEGFA locus displayed no evidence of APOE4 base editing (FIG. 34 and FIG. 40A). These results demonstrate how nucleobase editors can effect precise, single-amino acid changes in the coding sequence of a protein as the major product of editing, even when their processivity results in more than one nucleotide change in genomic DNA. The off-target activities of Cas9, dCas9, and Cas9 nickase have been extensively studied.[54, 60-62] In general, off-target C to T conversions by BE1, BE2, and BE3 paralleled off-target Cas9 nuclease-mediated genome modification frequencies.

The dominant-negative p53 mutations Tyr163Cys and Asn239Asp are strongly associated with several types of cancer.[66-67] Both of these mutations can be corrected by a C to T conversion on the template strand (FIGS. 16A to 16B). A human breast cancer cell line homozygous for the p53 Tyr163Cys mutation (HCC1954 cells) was nucleofected with DNA encoding NBE3 and an sgRNA programmed to correct Tyr163Cys. Because the nucleofection efficiency of HCC1954 cells was <10%, a plasmid expressing IRFP was co-nucleofected into these cells to enable isolation of nucleofected cells by fluorescence-activated cell sorting two days after treatment. HTS of genomic DNA revealed correction of the Tyr163Cys mutation in 7.6% of nucleofected HCC1954 cells (FIG. 30B and FIG. 40A to 40B). Also nucleofected was a human lymphoma cell line that is heterozygous for p53 Asn239Asp (ST486 cells) with DNA encoding NBE2 and an sgRNA programmed to correct Asn239Asp with 92% nucleofection efficiency). Correction of the Asn239Asp mutation was observed in 11% of treated ST486 cells (12% of nucleofected ST486 cells). Consistent with the findings in HEK cells, no indels were observed from the treatment of ST486 cells with NBE2, and 0.6% indel formation from the treatment of HCC1954 cells with NBE3. No other DNA changes within at least 50 base pairs of both sides of the protospacer were detected at frequencies above that of untreated controls out of >2,000,000 sequencing reads derived from 2×10$^5$ cells (FIGS. 14A to 14C, FIG. 30B and Table 1). These results collectively represent the conversion of three disease-associated alleles in genomic DNA into their wild-type forms with an efficiency and lack of other genome modification events that is, to our knowledge, not currently achievable using other methods.

Figure 21:
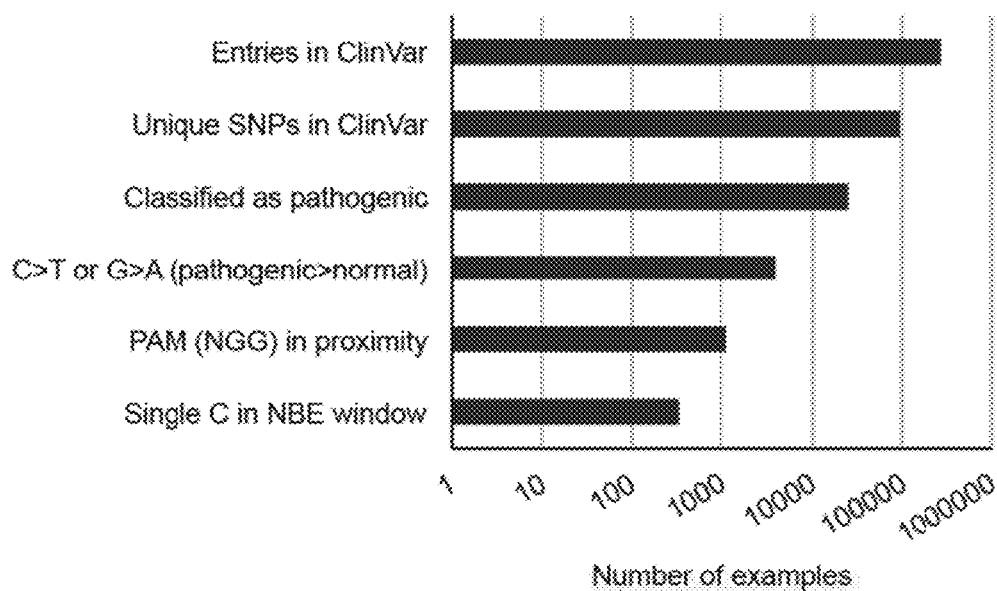
FIG. 21 shows genetic variants from ClinVar that can be corrected in principle by nucleobase editing. The NCBI ClinVar database of human genetic variations and their corresponding phenotypes[68] was searched for genetic diseases that can be corrected by current nucleobase editing technologies. The results were filtered by imposing the successive restrictions listed on the left. The x-axis shows the number of occurrences satisfying that restriction and all above restrictions on a logarithmic scale.
Figure 23:
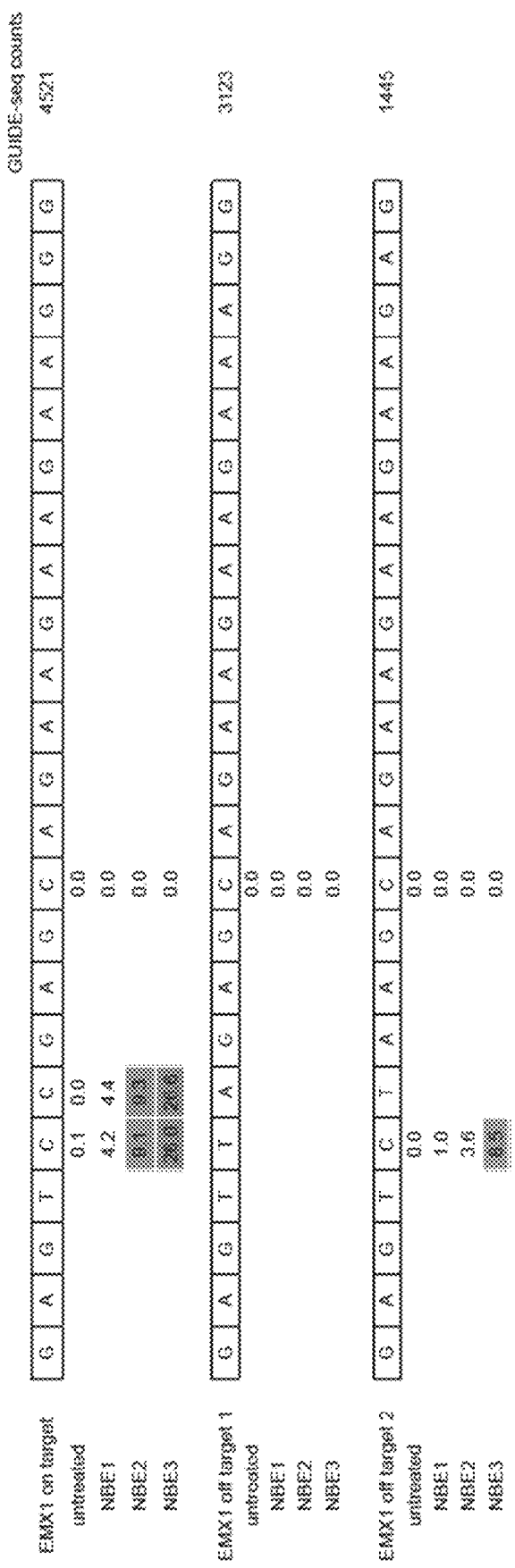
FIG. 23 shows activities of NBE1, NBE2, and NBE3 at EMX1 off-targets. HEK293T cells were transfected with plasmids expressing NBE1, NBE2, or NBE3 and a sgRNA matching the EMX1 sequence using Lipofectamine 2000. Three days after transfection, genomic DNA was extracted, amplified by PCR, and analyzed by high-throughput DNA sequencing at the on-target loci, plus the top ten known Cas9 off-target loci for the EMX1 sgRNA, as previously determined using the GUIDE-seq method[55]. EMX1 off-target 5 locus did not amplify and is not shown. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 293, and 310 through 318 from top to bottom, respectively.
Figure 25:
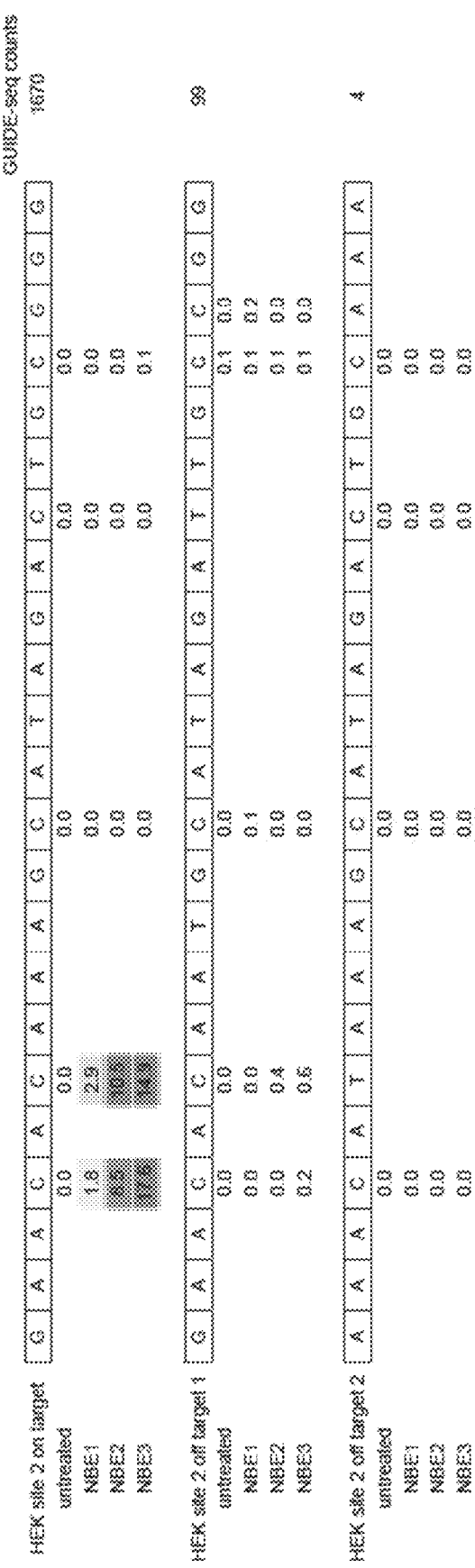
FIG. 25 shows activities of NBE1, NBE2, and NBE3 at HEK293 site 2 off-targets. HEK293T cells were transfected with plasmids expressing NBE1, NBE2, or NBE3 and a sgRNA matching the HEK293 site 2 sequence using Lipofectamine 2000. Three days after transfection, genomic DNA was extracted, amplified by PCR, and analyzed by high-throughput DNA sequencing at the on-target loci, plus all of the known Cas9 off-target loci for the HEK293 site 2 sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 295, 327, and 328 from top to bottom, respectively.

To illuminate the potential relevance of nucleobase editors to address human genetic diseases, the NCBI ClinVar database[68] was searched for known genetic diseases that could in principle be corrected by this approach. ClinVar was filtered by first examining only single nucleotide polymorphisms (SNPs), then removing any nonpathogenic variants. Out of the 24,670 pathogenic SNPs, 3,956 are caused by either a T to C, or an A to G, substitution. This list was further filtered to only include variants with a nearby NGG PAM that would position the SNP within the deamination activity window, resulting in 1,089 clinically relevant pathogenic gene variants that could in principle be corrected by the nucleobase editors described here (FIG. 21 and Table 1). To illuminate the potential relevance of base editors to address human genetic diseases, the NCBI ClinVar database[68] was searched for known genetic diseases that could in principle be corrected by this approach. ClinVar was filtered by first examining only single nucleotide polymorphisms (SNPs), then removing any non-pathogenic variants. Out of the 24,670 pathogenic SNPs, 3,956 are caused by either a T to C, or an A to G, substitution. This list was further filtered to only include variants with a nearby NGG PAM that would position the SNP within the deamination activity window, resulting in 911 clinically relevant pathogenic gene variants that could in principle be corrected by the base editors described here. Of these, 284 contain only one C within the base editing activity window. A detailed list of these pathogenic mutations can be found in Table 1.

TABLE 1

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 755445790 | NM_000391.3(TPP1):c.887-10A>G | TTTYTTTTTTTTTTTTTTGAGG | Ceroid lipofuscinosis, neuronal, 2 |
| 113994167 | NM_000018.3(ACADVL):c.848T>C (p.Val283Ala) | TTTGYGGTGGAGAGGGGCTTCGG, TTGYGGTGGAGAGGGGCTTCGGG | Very long chain acyl-CoA dehydrogenase deficiency |
| 119470018 | NM_024996.5(GFM1):c.521A>G (p.Asn174Ser) | TTGYTAATAAAAGTTAGAAACGG | Combined oxidative phosphorylation deficiency 1 |
| 115650537 | NM_000426.3(LAMA2):c.8282T>C (p.Ile2761Thr) | TTGAYAGGGAGCAAGCAGTTCGG, TGAYAGGGAGCAAGCAGTTCGGG | Merosin deficient congenital muscular dystrophy |
| 587777752 | NM_014946.3(SPAST):c.1688- | TTCYGTAAAACATAAAAGTCAGG | Spastic paraplegia 4, autosomal dominant |
| 794726821 | NM_001165963.1(SCN1A):c.4055T>C (p.Leu1352Pro) | TTCYGGTTTGTCTTATATTCTGG | Severe myoclonic epilepsy in infancy |
| 397514745 | NM_001130089.1(KARS):c.517T>C (p.Tyr173His) | CTTCYATGATCTTCGAGGAGAGG, TTCYATGATCTTCGAGGAGAGG | Deafness, autosomal recessive 89 |
| 376960358 | NM_001202.3(BMP4):c.362A>G (p.His121Arg) | TTCGTGGYGGAAGCTCCTCACGG | Microphthalmia syndromic 6 |
| 606231280 | NM_001287223.1(SCN11A):c.1142T>C (p.Ile381Thr) | CTTCAYTGTGGTCATTTTCCTGG, TTCAYTGTGGTCATTTTCCTGG | Episodic pain syndrome, familial, 3 |
| 387906735 | m.608A>G | TTCAGYGTATTGCTTTGAGGAGG | |
| 199474663 | m.3260A>G | TTAAGTTYTATGCGATTACCGGG | Cardiomyopathy with or without skeletal myopathy |
| 104894962 | NM_003413.3(ZIC3):c.1213A>G (p.Lys405Glu) | TGTGTTYGCGCAGGGAGCTCGGG, ATGTGTTYGCGCAGGGAGCTCG | Heterotaxy, visceral, X-linked |
| 796053181 | NM_021007.2(SCN2A):c.1271T>C (p.Val424Ala) | TGTGGYGGCCATGGCCTATGAGG | not provided |
| 267606788 | NM_000129.3(F13A1):c.728T>C (p.Met243Thr) | TGTGAYGGACAGAGCACAAATGG | Factor xiii, a subunit, deficiency of |

TABLE 1-continued

List of 911 base-editable gene variants associated with human disease with an NGG PAM (SEQ ID NOS: 747 to 1868 appear from top to bottom below, respectively). The "Y" in the protospacer and PAM sequences indicates the base to be edited, e.g., C. (SEQ ID NOS: 747 to 1868 appear from top to bottom below, respectively)

| dbSNP # | Genotype | Protospacer and PAM sequence(s) | Associated genetic disease |
|---|---|---|---|
| 397514503 | NM_003863.3(DPM2):c.68A>G (p.Tyr23Cys) | TGTAGYAGGTGAAGATGATCAGG | Congenital disorder of glycosylation type 1u |
| 104893973 | NM_000416.2(IFNGR1):c.260T>C (p.Ile87Thr) | TGTAATAYTTCTGATCATGTTGG | Disseminated atypical mycobacterial infection, Mycobacterium tuberculosis, susceptibility to |
| 121908466 | NM_005682.6(ADGRG1):c.263A>G (p.Tyr88Cys) | TGGYAGAGGCCCCTGGGGTCAGG | Polymicrogyria, bilateral frontoparietal |
| 147952488 | NM_002437.4(MPV17):c.186+2T>C | TGGYAAGTTCTCCCCTCAACAGG | Navajo neurohepatopathy |
| 21909537 | NM_001145.4(ANG):c.121A>G (p.Lys41Glu) | TGGTTYGGCATCATAGTGCTGGG, GTGGTTYGGCATCATAGTGCTG G | Amyotrophic lateral sclerosis type 9 |
| 121918489 | NM_000141.4(FGFR2):c.1018T>C (p.Tyr340His) | TGGGGAAYATACGTGCTTGGCGG, GGGGAAYATACGTGCTTGGCGG | Crouzon syndrome |
| 121434463 | m.12320A>G | GAGTYGCACCAAAATTTTTGGGG, GGAGTYGCACCAAAATTTTTGG, TGGAGTYGCACCAAAATTTTTG G | Mitochondrial myopathy |
| 121908046 | NM_000403.3(GALE):c.101A>G (p.Asn34Ser) | TGGAAGYTATCGATGACCACAGG | UDPglucose-4-epimerase deficiency |
| 431905512 | NM_003764.3(STX11):c.173T>C (p.Leu58Pro) | TGCYGGTGCCGACGTGAAGCGG | Hemophagocytic lymphohistiocytosis, familial, 4 |
| 121917905 | NM_000124.3(ERCC6):c.2960T>C (p.Leu987Pro) | TGCYAAAAGACCCAAAACAAAGG | Cerebro-oculo-facio-skeletal syndrome |
| 121918500 | NM_000141.4(FGFR2):c.874A>G (p.Lys292Glu) | TGCTYGATCCACTGGATGTGGGG, GTGCTYGATCCACTGGATGTGG, CGTGCTYGATCCACTGGATGTG G | Crouzon syndrome |
| 60431989 | NM_000053.3(ATP7B):c.3443T>C (p.Ile1148Thr) | TGCTGAYTGGAAACCGTGAGTGG | Wilson disease |
| 78950939 | NM_000250.1(MPO):c.518A>G (p.Tyr173Cys) | GTGCGGYATTTGTCCTGCTCCGG, TGCGGYATTTGTCCTGCTCCGG G | Myeloperoxidase deficiency |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 115677373 | NM_201631.3(TGM5):c.763T>C (p.Trp255Arg) | TGCGGAGYGGACGGGCAGCGTGG | Peeling skin syndrome, acral type |
| 5030804 | NM_000551.3(VHL):c.233A>G (p.Asn78Ser) | GCGAYTGCAGAAGATGACCTGGG, TGCGAYTGCAGAAGATGACCTG G | Von Hippel-Lindau syndrome |
| 397508328 | NM_000492.3(CFTR):c.1A>G (p.Met1Val) | GCAYGGTCTCTCGGGCGCTGGGG, TGCAYGGTCTCTCGGGGCGCTGGG, CTGCAYGGTCTCTCGGGCGCTGG | Cystic fibrosis |
| 137853299 | NM_000362.4(TIMP3):c.572A>G (p.Tyr191Cys) | TGCAGYAGCCGCCCTTCTGCCGG | Sorsby fundus dystrophy |
| 121908549 | NM_000334.4(SCN4A):c.3478A>G (p.Ile1160Val) | TGAYGGAGGGATGGCGCCTAGG | |
| 121909337 | NM_001451.2(FOXF1):c.1138T>C (p.Ter380Arg) | TGATGYGAGGCTGCCGCCGCAGG | Alveolar capillary dysplasia with misalignment of pulmonary veins |
| 281875320 | NM_005359.5(SMAD4):c.1500A>G (p.Ile500Met) | TGAGYATGCATAAGCGACGAAGG | Myhre syndrome |
| 730080132 | NM_170707.3(LMNA):c.710T>C (p.Phe237Ser) | TGAGTYTGAGAGCCGGCTGGCGG | Primary dilated cardiomyopathy |
| 281875322 | NM_005359.5(SMAD4):c.1498A>G (p.Ile500Val) | TGAGTAYGCATAAGCGACGAAGG | Hereditary cancer-predisposing syndrome, Myhre syndrome |
| 72556283 | NM_000531.5(OTC):c.527A>G (p.Tyr176Cys) | TGAGGYAATCAGCCAGGATCTGG | not provided |
| 74315311 | NM_020435.3(WC2):c.857T>C (p.Met286Thr) | TGAGAYGGCCCACCTGGGCTTGG, GAGAYGGCCCACCTGGGCTTGGG | Leukodystrophy, hypomyelinating, 2 |
| 121912495 | NM_170707.3(LMNA):c.1139T>C (p.Leu380Ser) | TCTYGGAGGGCGAGGAGGAGAGG | Congenital muscular dystrophy, LMNA-related |
| 128620184 | NM_000061.2(BTK):c.1288A>G (p.Lys430Glu) | TCTYGATGGCCACGTCGTACTGG | X-linked agammaglobulinemia |
| 118192252 | NM_004519.3(KCNQ3):c.1403A>G (p.Asn468Ser) | TCTTTAYTGTTTAAGCCAACAGG | Benign familial neonatal seizures 2, not specified |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 1221909142 | NM_001300.5(KLF6):c.190T>C (p.Trp64Arg) | TCTGYGGACCAAAATCATTCTGG | |
| 104895503 | NM_001127255.1(NLRP7):c.2738A>G (p.Asn913Ser) | TCTGGYTGATACTCAAGTCCAGG | Hydatidiform mole |
| 587783035 | NM_000038.5(APC):c.1744-2A>G | TCCYAGTAAGAACAGATATGG | Familial adenomatous polyposis |
| 72556289 | NM_000531.5(OTC):c.541-2A>G | TCCYAAAAGGCACGGGATGAAGG | not provided |
| 28937313 | NM_005502.3(ABCA1):c.2804A>G (p.Asn935Ser) | TCCAYTGTGGCCCAGGAGGAGG, CGCTCCAYTGTGGCCCAGGAAGG | Tangier disease |
| 143246652 | NM_001003811.1(TEX11):c.511A>G (p.Met171Val) | TCCAYGGTCAAGTCAGCCTCAGG, CCAYGGTCAAGTCAGCCTCAGGG | Spermatogenic failure, X-linked, 2 |
| 587776451 | NM_002049.3(GATA1):c.2T>C (p.Met1Thr) | CTCCAYGGAGTTCCCTGGCCTGG, TCCAYGGAGTTCCCTGGCCTGGG, CCAYGGAGTTCCCTGGCCTGGGG | GATA-1-related thrombocytopenia with dyserythropoiesis |
| 121908403 | NM_021102.3(SPINT2):c.488A>G (p.Tyr163Cys) | TCCAYAGATGAAGTTATTGCAGG | Diarrhea 3, secretory sodium, congenital, syndromic |
| 281874738 | NM_000495.4(COL4A5):c.438+2T>C | CTCCAGYAAGTTATAAAATTTGG, TCCAGYAAGTTATAAAATTTGGG | Alport syndrome, X-linked recessive |
| 730880279 | NM_030653.3(DDX11):c.2271+2T>C | TCCAGGYGCGGGCGTCATGCTGG, CCAGGYGCGGGCGTCATGCTGGG | Warsaw breakage syndrome |
| 28940272 | NM_017890.4(VPS13B):c.8978A>G (p.Asn2993Ser) | TCAYTGATAAGCAGGGCCCAGGG, TTCAYTGATAAGCAGGGCCCAGG | Cohen syndrome, not specified |
| 137852375 | NM_000132.3(F8):c.5372T>C (p.Met1791Thr) | TCAYGGTGAGTTAAGGACAGTGG | Hereditary factor VIII deficiency disease |
| 115677847 | NM_021961.5(TEAD1):c.1261T>C (p.Tyr?His) | TCATATTYACAGGCTTGTAAAGG | not provided |
| 786203989 | NM_016669.9(PAM16):c.226A>G (p.Asn76Asp) | CATAGTYCTGCAGAGGAGGAGGG, TCATAGTYCTGCAGAGGAGGAGG | Chondrodysplasia, megarbane-dagher-melki type |
| 587776437 | NC_012920.1:m.9478T>C | TCAGAAGYTTTTTTCTTCGCAGG | Leigh disease |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121912474 | NM_000424.3(KRT5):c.20T>C (p.Val7Ala) | TCAAGTGYGTCTTCCGAGCGG, CAAGTGYGTCCTTCCGAGCGGG, AAGTGYGTCCTTCCGAGCGGGG, AGTGYGTCCTTCCGAGCGGGGG | Epidermolysis bullosa simplex, Koebner type |
| 104886461 | NM_020533.2(MCOLN1):c.406-2A>G | TACYGTGGGCAGAGAAGGGGAGG, AGGTACYGTGGGCAGAGAGGGG, CAGGTACYGTGGGCAGAGAAGGG | Ganglioside sialidase deficiency |
| 104894275 | NM_000317.2(PTS):c.155A>G (p.Asn52Ser) | TRAAYTGTGCCCATGGCCATTTGG | 6-pyruvoyl-tetrahydropterin synthase deficiency |
| 587777562 | NM_015599.2(PGM3):c.737A>G (p.Asn246Ser) | TAAATGAYTGAGTTTGCCCTTGG | Immunodeficiency 23 |
| 121964906 | NM_000027.3(AGA):c.916T>C (p.Cys306Arg) | GTTATAYGTGCCAATGTGACTGG | Aspartylglycosaminuria |
| 28941769 | NM_000356.3(TCOF1):c.149A>G (p.Tyr50Cys) | GTGTGTAYAGATGTCCAGAAGGG | Treacher collins syndrome 1 |
| 121434464 | m.12297T>C | GTCYTAGGCCCCAAAAATTTTGG | Cardiomyopathy, mitochondrial |
| 121908407 | NM_054027.4(ANKH):c.143T>C (p.Met48Thr) | GTCGAGAYGCTGGCCAGCTACGG, TCGAGAYGCTGGCCAGCTACGGG | Chondrocalcinosis 2 |
| 59151893 | NM_000422.2(KRT17):c.275A>G (p.Asn92Ser) | GTCAYTGAGGTTCTCATGGTGG, GCGGTCAYTGAGGTTCTCATGG | Pachyonychia congenita type 2 |
| 1219909499 | NM_002427.3(MMP13):c.272T>C (p.Met91Thr) | GTCAYGAGAAAAGCCAAGATGCGG, TCAYGAAAAAGCCAAGATGCGG | |
| 61748478 | NM_000552.3(VWF):c.2384A>G (p.Tyr795Cys) | GTCAYAGTTCTGGCACGTTTTGG | von Willebrand disease type 2N |
| 387906889 | NM_006796.2(AFG3L2):c.1847A>G (p.Tyr616Cys) | GTAYAGAGGTATTGTTCTTTTGG | Spastic ataxia 5, autosomal recessive |
| 118203907 | NM_000130.4(F5):c.5189A>G (p.Tyr1730Cys) | GTAGYAGGCCCAAGCCCGACAGG | Factor V deficiency |
| 118203945 | NM_013319.2(UBIAD1):c.305A>G (p.Asn102Ser) | GTAAGTGYTGACCAAATTACCGG | Schnyder crystalline corneal dystrophy |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 267607080 | NM_005633.3(SOS1):c.1294T>C (p.Trp432Arg) | GGTYGGGAGGGAAAAGACATTGG | Noonan syndrome 4, Rasopathy |
| 137852953 | NM_012464.4(TLL1):c.1885A>G (p.Ile629Val) | GGTTAYGGTGCCGTTAAGTTTGG | Atrial septal defect 6 |
| 118203949 | NM_013319.2(UBIAD1):c.695A>G (p.Asn232Ser) | GGTGTTGYTGGAATGGAGAATGG | Schnyder crystalline corneal dystrophy |
| 137852952 | NM_012464.4(TLL1):c.713T>C (p.Val238Ala) | GGGATTGYTGTTCATGAATTGGG | Atrial septal defect 6 |
| 41460449 | m.3394T>C | GGCYATATACAACTACCCAAAGG | Leber optic atrophy |
| 80357281 | NM_007294.3(BRCA1):c.5291T>C (p.Leu1764Pro) | GGCYAGAAATCTGTTGCTATGG, GGCYAGAAATCTGTTGCTATGGG | Familial cancer of breast, Breast-ovarian cancer, familial 1 |
| 5030764 | NM_000174.4(GP9):c.182A>G (p.Asn61Ser) | GGCTGYTGTTGGCCAGCAGAAGG | Bernard-Soulier syndrome type C |
| 72556282 | NM_000531.5(OTC):c.526T>C (p.Tyr176His) | GGCTGATYACCTCACGCTCCAGG, GATYACCTCACGCTCCAGGTTGG | not provided |
| 121913594 | NM_000530.6(MPZ):c.242A>G (p.His81Arg) | GGCATAGYTGGAAGATCTATGAGG | Charcot-Marie-Tooth disease type 1B |
| 587777736 | NM_017617.3(NOTCH1):c.1285T>C (p.Cys429Arg) | GGCAAGYGCATCAACACGCTGGG, GGGCAAGYGCATCAACACGCTGG | Adams-Oliver syndrome 1, Adams-Oliver syndrome 5 |
| 63750912 | NM_016835.4(MAPT):c.1839T>C (p.Asn613=) | GGATAAYATCAAACACGTCCCGG, GATAAYATCAAACACGTCCCGGG | Frontotemporal dementia |
| 121918075 | NM_000371.3(TTR):c.401A>G (p.Tyr134Cys) | GGAGYAGGGGCTCAGCAGGGCGG, ATAGGAGYAGGGGCTCAGCAGGG | Amyloidogenic transthyretin amyloidosis |
| 730882063 | NM_004523.3(KIF11):c.2547+2T>C | GGAGGYAATAACTTTGTAAGTGG | Microcephaly with or without chorioretinopathy, lymphedema, or mental retardation |
| 397516156 | NM_000257.3(MYH7):c.2546T>C (p.Met849Thr) | GGGAGAYGGCCTCCATGAAGGAGG | Primary familial hypertrophic cardiomyopathy, |
| 118204430 | NM_000035.3(ALDOB):c.442T>C (p.Trp148Arg) | GGAAGYGGCGTGCTGTGTGAGG | Hereditary fructosuria |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 200198778 | NM_013332.5(POMT2):c.1997A>G (p.Tyr666Cys) | GGAAGYAGTGGTGGAAGTAGAGG | Congenital muscular dystrophy, Congenital muscular dystrophy-dystroglycanopathy with brain and eye anomalies, type A2, Muscular dystrophy, Congenital muscular dystrophy-dystroglycanopathy with mental retardation, type B2 |
| 754896795 | NM_004006.2(DMD):c.6982A>T (p.Lys2328Ter) | GCTTTTTTTCAAGCTGCCCAAGG | Duchenne muscular dystrophy, Becker muscular dystrophy, Dilated cardiomyopathy 3B |
| 148924904 | NM_000546.5(TP53):c.488A>G (p.Tyr163Cys) | GCTTGYAGATGGCCATGGCGCGG | Hereditary cancer-predisposing syndrome |
| 786204770 | NM_016035.4(COQ4):c.155T>C (p.Leu52Ser) | GCTGTYGGCCGCCGGCTCCGCGG | COENZYME Q10 DEFICIENCY, PRIMARY, 7 |
| 121909520 | NM_001100.3(ACTA1):c.350A>G (p.Asn117Ser) | CGGYTGGCCTTGGGATTGAGGGG, GCGGYTGGCCTTGGGATTGAGGG, CGCGGYTGGCCTTGGGATTGAGG | Nemaline myopathy 3 |
| 587776879 | NM_004656.3(BAP1):c.438-2A>G | GCCYGGGGAAAAACAGAGTCAGG | Tumor predisposition syndrome |
| 727504434 | NM_000501.3(ELN):c.890-2A>G | GCCYGAAAAACAGCCACAGAGG | Supravalvar aortic stenosis |
| 119455953 | NM_000391.3(TPP1):c.1093T>C (p.Cys365Arg) | GCCGGGYGTTGGTCTGTCTCTGG | Ceroid lipofuscinosis, neuronal, 2 |
| 121964983 | NM_000481.3(AMT):c.125A>G (p.His42Arg) | GCCAGGYGGAAGTCATAGAGCGG | Non-ketotichyperglycinemia |
| 121908300 | NM_001005741.2(GBA):c.751T>C (p.Tyr251His) | GCCAGAYACTTTGTGAAGTAAGG, CCAGAYACTTTGTGAAGTAAGG | Gaucher disease, type 1 |
| 786205083 | NM_003494.3(DYSF):c.3443-33A>G | GCCAGAGYGAGTGGCTGGAGTGG | Limb-girdle muscular dystrophy, type 2B |
| 121908133 | NM_175073.2(APTX):c.602A>G (p.His201Arg) | GCCAAYGGTAACGGGCCTTTGGG, AGCCAAYGGTAACGGGCCTTTGG | Adult onset ataxia with oculomotor apraxia |
| 587777195 | NM_005017.3(PCYT1A):c.571T>C (p.Phe191Leu) | GCATGYTTGCTCCAACACAGAGG | Spondylometaphyseal dysplasia with cone-rod dystrophy |
| 431905520 | NM_014714.3(IFT140):c.4078T>C (p.Cys1360Arg) | CAAGCAGYGTGAGCTGCTCCTGG, GCAGYGTGAGCTGCTCCTGGAGG | Renal dysplasia, retinal pigmentary dystrophy, cerebellar ataxia and skeletal dysplasia |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121912889 | NM_001844.4(COL2A1):c.4172A>G (p.Tyr1391Cys) | GCAGTGGYAGGTGATGTTCTGGG | Spondyloperipheral dysplasia, Platyspondylic lethal skeletal dysplasia Torrance type |
| 137854492 | NM_001363.4(DKC1):c.1069A>G (p.Thr357Ala) | GCAGGYAGAGATGACCGCTGTGG | Dyskeratosis congenita X-linked |
| 121434362 | NM_152783.4(D2HGDH):c.1315A>G (p.Asn439Asp) | GCAGGTYACCATCTCCTGGAGGG, TGCAGGTYACCATCTCCTGGAGG | D-2-hydroxyglutaric aciduria 1 |
| 80338732 | NM_002764.3(PRPS1):c.344T>C (p.Met115Thr) | GCAAATAYGCTATCTGTAGCAGG | Charcot-Marie-Tooth disease, X-linked recessive, type 5 |
| 387906675 | NM_000313.3(PROS1):c.701A>G (p.Tyr234Cys) | GATTAYATCTGTAGCCTTCGGGG, AGATTAYATCTGTAGCCTTCGGG, GAGATTAYATCTGTAGCCTTCGG | Thrombophilia due to protein S deficiency, autosomal recessive |
| 28935478 | NM_000061.2(BTK):c.1082A>G (p.Tyr361Cys) | GATGGYAGTTAATGAGCTCAGGG, TGATGGYAGTTAATGAGCTCAGG | |
| 201777056 | NM_005050.3(ABCD4):c.956A>G (p.Tyr319Cys) | GATGAGGYAGATGCACACAAAGG | METHYLMALONIC ACIDURIA AND HOMOCYSTINURIA, cblJ |
| 121918528 | NM_000098.2(CPT2):c.359A>G (p.Tyr120Cys) | GATAGGYACATATCAAACCAGGG, AGATAGGYACATATCAAACCAG G | Carnitine palmitoyltransferase II deficiency, infantile |
| 267607014 | NM_002942.4(ROBO2):c.2834T>C (p.Ile945Thr) | GAGAYTGGAAATTTTGGCCGTGG | Vesicoureteral reflux 2 |
| 281865192 | NM_025114.3(CEP290):c.2991+1655 A>G | GATAYTCACAATTACACACTGGGG, AGATAYTCACAATTACAACTGGG, GAGATAYTCACAATTACAACTG | Leber congenital amaurosis 10 |
| 386833492 | NM_000112.3(SLC26A2):c.-26+2T>C | GAGAGGYAGAGAAGAGGGAAGCGG | Diastrophic dysplasia |
| 587779773 | NM_001101.3(ACTB):c.356T>C (p.Met119Thr) | GAGAAGAYGACCCAGGTGAGTGG | Baraitser-Winter syndrome 1 |
| 121913512 | NM_000222.2(KIT):c.1924A>G (p.Lys642Glu) | GACTTYGAGTTCAGACATGAGGG, GGACTTYGAGTTCAGACATGAGG | |
| 28939072 | NM_006329.3(FBLN5):c.506T>C (p.Ile169Thr) | GACAYTGATGAATGTCGTATGG | Age-related macular degeneration 3 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 104894248 | NM_000525.3(KCNJ11):c.776A>G (p.His259Arg) | GACAYGGTAGATGATCAGCGGGG, TGACAYGGTAGATGATCAGCGGG, ATGACAYGGTAGATGATCAGCGG | Islet cell hyperplasia |
| 387907132 | NM_016464.4(TMEM138):c.287A>G (p.His96Arg) | GACAYGAAGGAGGAGATGCTGAGGG, AGACAYGAAGGAGATGCTGAGG | Joubert syndrome 16 |
| 121918170 | NM_000275.2(OCA2):c.1465A>G (p.Asn489Asp) | GACAYTYCGAGGGTCCCCGATGG | Tyrosinase-positive oculocutaneous albinism |
| 122467173 | NM_014009.3(FOXP3):c.970T>C (p.Phe324Leu) | GACAGAGYTCCTCCACACACATGG | Insulin-dependent diabetes mellitus secretory diarrhea syndrome |
| 137852268 | NM_000133.3(F9):c.1328T>C (p.Ile443Thr) | GAAYATATACCAAGGTATCCCGG | Hereditary factor LX deficiency disease |
| 149054177 | NM_001999.3(FBN2):c.3740T>C (p.Met1247Thr) | GAATGTAYGATAATGAACGGAGG | not specified, Macular degeneration, early-onset |
| 137854488 | NM_212482.1(FN1):c.2918A>G (p.Tyr973Cys) | GAAGTAAYAGGTGACCCCAGGGG | Glomerulopathy with fibronectin deposits 2 |
| 786204027 | NM_005957.4(MTHFR):c.1530+2T>C | GRAAGGYGTGGTAGGGAGGCACGG, AAGGYGTGGTAGGGAGGCACGGG, AGGYGTGGTAGGGAGGCACGGGG | Homocysteinemia due to MTHFR deficiency |
| 104894223 | NM_012193.3(FZD4):c.766A>G (p.Ile256Val) | GAAATAYGATGGGGCGCTCAGGG, AGAAATAYGATGGGGCGCTCAGG | Retinopathy of prematurity |
| 137854474 | NM_000138.4(FBN1):c.3793T>C (p.Cys1265Arg) | CTTGYGTTATGATGGATTCATGG | Marfan syndrome |
| 587784418 | NM_063306.3(SMC1A):c.3254A>G (p.Tyr1085Cys) | CTTAYAGATCTCATCAATGTTGG | Congenital muscular hypertrophy-cerebral syndrome |
| 81002805 | NM_000059.3(BRCA2):c.316+2T>C | CTTAGGYAAGTAATGCAATATGG | Familial cancer of breast, Breast-ovarian cancer, familial 2, Hereditary cancer-predisposing syndrome |
| 121909653 | NM_182925.4(FLT4):c.3104A>G (p.His1035Arg) | CTGYGGATGCACTGGGGTGCGGG, TCTGYGGATGCACTGGGGTGCGG | |
| 786205107 | NM_031226.2(CYP19A1):c.743+2T>C | CTGTGYAAGTAATACAACTTTGG | Aromatase deficiency |
| 587777037 | NM_001283009.1(RTEL1):c.3730T>C (p.Cys1244Arg) | CTGTGTGYGCCAGGGCTGTGGGG | Dyskeratosis congenita, autosomal recessive, 5 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 794728380 | NM_000238.3(KCNH2):c.1945+6T>C | CTGTGAGYGTGCCCAGGGGCGGG, TGAGYGTGCCCAGGGGCGGCGG | Cardiac arrhythmia |
| 267607987 | NM_000251.2(MSH2):c.2005+2T>C | CTGGYAAAAACCTGGTTTTTGG, TGGYAAAAACCTGGTTTTTGGG | Hereditary Nonpolyposis Colorectal Neoplasms |
| 397509397 | NM_006876.2(B4GAT1):c.1168A>G (p.Asn390Asp) | TGATYTTCAGCTCCTTTTGGGG, CTGATYTTCAGCCTCCTTTTGG, GCTGATYTTCAGCCTCCTTTTGG | Congenital muscular dystrophy-dystroglycanopathy with brain and eye anomalies, type A13 |
| 121918381 | NM_000040.1(APOC3):c.280A>G (p.Thr94Ala) | CTGAAGYTGGTCTGACCTCAGGG, GCTGAAGYTGGTCTGACCTCAGG | |
| 104894919 | NM_001015877.1(PHF6):c.769A>G (p.Arg257Gly) | CTCYTGATGTTGTTGTGAGCTGG | Borjeson-Forssman-Lehmann syndrome |
| 267606869 | NM_005144.4(HR):c.-218A>G | CTCYAGGGCCGCAGGTTGGAGGG, GCTCYAGGGCCGCAGGTTGGAGG, GGCGCTCYAGGGCCGCAGGTTGG | Marie Unna hereditary hypotrichosis 1 |
| 139732572 | NM_000146.3(FTL):c.1A>G (p.Met1Val) | CTCAYGGTTGGTTGGCAAGAAGG | L-ferritin deficiency |
| 397515418 | NM_018486.2(HDAC8):c.1001A>G (p.His334Arg) | CTCAYGATCTGGGATCTCAGAGG | Cornelia de Lange syndrome 5 |
| 372395294 | NM_198056.2(SCN5A):c.1247A>G (p.Tyr416Cys) | CTCAYAGGCCATTGCGACCACGG | not provided |
| 104895304 | NM_000431.3(MVK):c.803T>C (p.Ile268Ilr) | CTCAAYAGATGCCATCTCCCTGG | Hyperimmunoglobulin D with periodic fever, Mevalonic aciduria |
| 587777188 | NM_001165899.1(PDE4D):c.1850T>C (p.Ile617Thr) | CTATAYTGTTCATCCCCTCTGGG, ACTATAYTGTTCATCCCCTCTGG | Acrodysostosis 2, with or without hormone resistance |
| 398123026 | NM_003867.3(FGF17):c.560A>G (p.Asn187Ser) | CGTGGYTGGGAGGGCAGCTGG | Hypogonadotropic hypogonadism 20 with or without anosmia |
| 121964924 | NM_001385.2(DPYS):c.1078T>C (p.Trp360Arg) | CGTAATAYGGGAAAAAGGCGTGG, AATAYGGGAAAAAGGCGTGGTGG, ATAYGGGAAAAAGGCGTGGTGGG | Dihydropyrimidinase deficiency |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 587777301 | NM_199189.2(MATR3):c.1864A>G (p.Thr622Ala) | CGGYTGACTCTCAGTCTTCTGG | Myopathy, distal, 2 |
| 200238879 | NM_000527.4(LDLR):c.694+2T>C | ACTGCGYATGGGCGGGGCCAGG, CTGCGYATGGGCGGGGCCAGGG, CGGYATGGGCGGGGCCAGGGTGG | Familial hypercholesterolemia |
| 142951029 | NM_145046.4(CALR3):c.245A>G (p.Lys82Arg) | CGGTYTGAAGCGTGCAGAGATGG | Arrhythmogenic right ventricular cardiomyopathy, Familial hypertrophic cardiomyopathy 19, Hypertrophic cardiomyopathy |
| 786200953 | NM_006785.3(MALT1):c.1019-2A>G | CGCYTTGAAAAAAAAGAAAGGG, TCGCYTTGAAAAAAAAAAGAAAG | Combined immunodeficiency |
| 120074192 | NM_000218.2(KCNQ1):c.418A>G (p.Ser140Gly) | CGCYGAAGATGAGGCAGACCAGG | Atrial fibrillation, familial, 3, Atrial fibrillation |
| 267606887 | NM_005957.4(MTHFR):c.971A>G (p.Asn324Ser) | CGCGGYTGAGGGTGTAGAAGTGG | Homocystinuria due to MTHFR deficiency |
| 118192117 | NM_000540.2(RYR1):c.1205T>C (p.Met402Thr) | CGCAYGATCCACAGCACCAATGG | Congenital myopathy with fiber type disproportion, Central core disease |
| 199473625 | NM_198056.2(SCN5A):c.4978A>G (p.Ile1660Val) | CGAYGTTGAAGAGGGCAGGCAGG, AGCCCGAYGTTGAAGAGGGCAGG | Brugada syndrome |
| 794726865 | NM_000921.4(PDE3A):c.1333A>G (p.Thr445Ala) | CGAGGYGGTGGTGTCCAAGTGG | Brachydactyly with hypertension |
| 606231254 | NM_005740.2(DNAL4):c.153+2T>C | CGAGGYATTGCCAGCAGTGCAGG | Mirror movements 3 |
| 786204826 | NM_004771.3(MMP20):c.611A>G (p.His204Arg) | CGAAAYGTGTATCTCCTCCCAGG | Amelogenesis imperfecta, hypomaturation type, IIA2 |
| 796053139 | NM_021007.2(SCN2A):c.4308+2T>C | CGAAATGYAAGTCTAGTTAGAGG, GAAATGYAAGTCTAGTTAGAGG | not provided |
| 137854494 | NM_005502.3(ABCA1):c.4429T>C (p.Cys1477Arg) | CCTGTGYTCCCCAGGGGCAGG, CTGTGYTCCCCAGGGGCAGGG, TGTGYGTCCCCAGGGGCAGGGG, GTGYGTCCCCAGGGGGCAGGGGG | Tangier disease |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base to be edited,
e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 786205144 | NM_001103.3(ACTN2):c.683T>C (p.Met228Thr) | CCTAAAYGTTGGATGCTGAAGG | Dilated cardiomyopathy IAA |
| 199919568 | NM_007254.3(PNKP):c.1029+2T>C | CCCGGYGAGGCCCTGGGGCGGGG, TCCGGYGAGGCCCTGGGGCGGGG, ATCCGGYGAGGCCCTGGGGCGGG, GATCCGGYGAGGCCCTGGGGCGG | not provided |
| 28939079 | NM_018965.3(TREM2):c.401A>G (p.Asp134Gly) | TGAYCCAGGGGGTCTATGGAGG, CGGTGAYCCAGGGGGTCTATGG, CCGGTGAYCCAGGGGTCTATGG | Polycystic lipomembranous osteodysplasia with sclerosing leukoencephalopathy |
| 193302855 | NM_032520.4(GNPTG):c.610-2A>G | CCCYGAAGGTGGAGGATGCAGGG, GCCCYGAAGGTGGAGGATGCAGG | Mucolipidosis III Gamma |
| 111033708 | NM_000155.3(GALT):c.499T>C (p.Trp167Arg) | CCCTYGGGTGCAGGTTTGTGAGG | Deficiency of UDPglucose-hexose-1-phosphate uridylyltransferase |
| 28933378 | NM_000174.4(GP9):c.70T>C (p.Cys24Arg) | CCAYGGTACCTGCCGCGCCCCTG | Bernard Soulier syndrome, Bernard-Soulier syndrome type C |
| 364897 | NM_000157.3(GBA):c.680A>G (p.Asn227Ser) | CCAYTGGTCTTGAGCCAAGTGGG, TCCAYTGGTCTTGAGCCAAGTGG | Gaucher disease, Subacute neuronopathic Gaucher disease, Gaucher disease, type 1 |
| 796052551 | NM_000833.4(GRIN2A):c.2449A>G (p.Met817Val) | CCAYGTTGTCAATGTCCAGCTGG | not provided |
| 63751006 | NM_002087.3(GRN):c.2T>C (p.Met1Thr) | CCAYGTGACCCTTGGTGAGCTGG | Frontotemporal dementia, ubiquitin-positive |
| 786203997 | NM_001031.4(RPS28):c.1A>G (p.Met1Val) | TGTCCAYGATGGCGGCGCGCGCGG, CCAYGATGGCGGCGCGCGCGGCGG | Diamond-Blackfan anemia with microtia and cleft palate |
| 121908595 | NM_002755.3(MAP2K1):c.389A>G (p.Tyr130Cys) | CCAYAGAAGCCCACGATGTACGG | Cardiofaciocutaneous syndrome 3, Rasopathy |
| 398122910 | NM_000431.3(MVK):c.1039+2T>C | CCAGGYATCCCGGGGTAGGTGG, CAGGYATCCCGGGGTAGGTGGG | Porokeratosis, disseminated superficial actinic 1 |
| 119474039 | NM_020365.4(EIF2B3):c.1037T>C (p.Ile346Thr) | CCAGAYTGTCAGCAAACACCTGG | Leukoencephalopathy with vanishing white matter |
| 587777866 | NM_000076.2(CDKN1C):c.*5+2T>C | CCAAGYGAGTACAGCGCACCTGG, CAAGYGAGTACAGCGCACCTGGG, AAGYGAGTACAGCGCACCTGGGG | Beckwith-Wiedemann syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121918530 | NM_005587.2(MEF2A):c.788A>G (p.Asn263Ser) | AGAYTACCACCACCTGGTGGAGG, CCAAGAYTACCACCACCTGGTGG | |
| 483352818 | NM_000211.4(ITGB2):c.1877+2T>C | CATGYGAGTGCAGGCGGAGCAGG | Leukocyte adhesion deficiency type 1 |
| 460184 | NM_000186.3(CFH):c.3590T>C (p.Val1197Ala) | CAGYTGAATTTGTGTGTAAACGG | Atypical hemolytic-uremic syndrome 1 |
| 1219084 23 | NM_004795.3(KL):c.578A>G (p.His193Arg) | CAGYGGTACAGGGTGACCACGG, CCAGYGGTACAGGGTGACCACGG | |
| 281860300 | NM_005247.2(FGF3):c.146A>G (p.Tyr49Cys) | CAGYAGAGCTTGCGGCGCCGGGG, GCAGYAGAGCTTGCGGCGCCGGG, CGCAGYAGAGCTTGCGGCGCCGG | Deafness with labyrinthine aplasia microtia and microdontia (LAIVIM) |
| 28935488 | NM_000169.2(GLA):c.806T>C (p.Val269Ala) | CAGTTAGYGATTGGCAACTTTGG | Fabry disease |
| 587776514 | NM_173560.3(RFX6):c.380+2T>C | CAGTGGYGAGACTCGCCCGCAGG, AGTGGYGAGACTCGCCCGCAGGG | Mitchell-Riley syndrome |
| 104894117 | NM_178138.4(LHX3):c.332A>G (p.Tyr111Cys) | CAGGTGGYACACGAAGTCCTGGG | Pituitary hormone deficiency, combined 3 |
| 34878913 | NM_000184.2(HBG2):c.125T>C (p.Phe42Ser) | CAGAGGYTCTTTGACAGTTTGG | Cyanosis, transient neonatal |
| 120074124 | NM_000543.4(SMPD1):c.911T>C (p.Leu304Pro) | AGCACYTGTGAGGAAGTTCCTGG, GCACYTGTGAGGAAGTTCCTGGG, CACYTGTGAGGAAGTTCCTGGGG | Sphingomyelin/cholesterol lipidosis,Niemann-Pick disease, type A, Niemann-Pick disease, type B |
| 281860272 | NM_005211.3(CSF1R):c.2320-2A>G | CACYGAGGGAAAGCACTGCAGGG, GCACYGAGGGAAAGCACTGCAGG | Hereditary diffuse leukoencephalopathy with spheroids |
| 128624216 | NM_000033.3(ABCD1):c.443A>G (p.Asn148Ser) | CACTGYTGACGAAGGTAGCAGGG, GCACTGYTGACGAAGGTAGCAGG | Adrenoleukodystrophy |
| 398124257 | NM_012463.3(ATP6V0A2):c.825+2 T>C | CACTGYGAGTAAGCTGGAAGTGG | Cutis laxa with osteodystrophy |
| 267606679 | NM_004183.3(BEST I):c.704T>C (p.Val235Ala) | CACTGGYGTATACACAGGTGAGG | Vitreoretinochoroidopathy dominant |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397514518 | NM_000344.3(SMN1):c.388T>C (p.Tyr130His) | CACTGGAYATGGAAATAGAGAGG | Kugelberg-Welander disease |
| 143946794 | NM_001946.3(DUSP6):c.566A>G (p.Asn189Ser) | CACTAYTGGGGTCTCGTCAAGG | Hypogonadotropic hypogonadism 19 with or without anosmia |
| 397516076 | NM_000256.3(MYBPC3):c.821+2T | GCACGYGAGTGGCCATCCTCAGG, >CCACGYGAGTGGCCATCCTCAGG | Familial hypertrophic cardiomyopathy 4, not specified |
| 149977726 | NM_001257988.1(TYMP):c.665A>G (p.Lys222Arg) | CACGAGTYTCTTACTGAGAATGG, GAGTYTCTTACTGAGAATGGAGG | |
| 121917770 | NM_003361.3(UMOD):c.383A>G (p.Asn128Ser) | CACAYTGACACATGTGGCCAGGG, CCACAYTGACACATGTGGCCAGG | Familial juvenile gout |
| 121909008 | NM_000492.3(CFTR):c.2738A>G (p.Tyr913Cys) | CACATAAVACGAACTGGTGCTGG | Cystic fibrosis |
| 137852819 | NM_003688.3(CASK):c.2740T>C (p.Trp914Arg) | CACAGYGGGTCCCTGTCTCCTGG, ACAGYGGGTCCCTGTCTCCTGGG | FG syndrome 4 |
| 74315320 | NM_024009.2(GM3):c.421A>G (p.Ile141Val) | CAAYGATGAGCTTGAAGATGAGG | Deafness, autosomal recessive |
| 80356747 | NM_001701.3(BAAT):c.967A>G (p.Ile323Val) | CAAYGAAGAGGAATTGCCCCTGG | Atypical hemolytic-uremic syndrome 1 |
| 180177324 | NM_012203.1(GRHPR):c.934A>G (p.Asn312Asp) | CAAGTYGTTAGCTGCCAACAAGG | Primary hyperoxaluria, type II |
| 281860274 | NM_005211.3(CSF1R):c.2381T>C (p.Ile794Thr) | CAAGAYTGGGGACTTCGGGCTGG | Hereditary diffuse leukoencephalopathy with spheroids |
| 398122908 | NM_005334.2(HCFC1):c.-970T>C | CAAGAYGGCGGCTCCCAGGGAGG | Mental retardation 3, X-linked |
| 548076633 | NM_002693.2(POLG):c.3470A>G (p.Asn1157Ser) | CAAGAGGYTGGTGATCTGCAAGG | not provided |
| 120074146 | NM_000019.3(ACAT1):c.935T>C (p.Ile312Thr) | CAAGAAYAGTAGTAAGGCCAGG | Deficiency of acetyl-CoA acetyltransferase |
| 397514489 | NM_005340.6(HINT1):c.250T>C (p.Cys84Arg) | CAAGAAAYGTGCTGCTGATCTGG, AAGAAAYGTGCTGCTGATCTGGG | Gamstorp-Wohlfart syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 587783539 | NM_178151.2(DCX):c.2T>C (p.Met1Thr) | CAAAATAYGGAACTTGATTTTGG | Heterotopia |
| 104894765 | NM_005448.2(BMP15):c.704A>G (p.Tyr235Cys) | ATTGAAAYAGAGTAACAAGAAGG | Ovarian dysgenesis 2 |
| 137852429 | NM_000132.3(F8):c.1892A>G (p.Asn631Ser) | ATGYTGGAGGCTTGGAACTCTGG | Hereditary factor VIII deficiency disease |
| 72558441 | NM_000531.5(OTC):c.779T>C (p.Leu260Ser) | ATGTATYAATTACAGACACTTGG | not provided |
| 398123765 | NM_003494.3(DYSF):c.1284+2T>C | ATGGYAAGGAGCAAGGAGCAGG | Limb-girdle muscular dystrophy, type 2B |
| 387906924 | NM_020191.2(MRPS22):c.644T>C (p.Leu215Pro) | ATCYTAGGGTAAGGTGACTTAGG | Combined oxidative phosphorylation deficiency 5 |
| 397518039 | NM_206933.2(USH2A):c.8559-2A>G | ATCYAAAGCAAAAGACAAGCAGG | Retinitis pigmentosa, Usher syndrome, type 2A |
| 5742905 | NM_000071.2(CBS):c.833T>C (p.Ile278Thr) | ATCATGGGGTGGATCCCGAAGG, TCAYTGGGGTGGATCCCGAAGGG | Homocystinuria due to CBS deficiency, Homocystinuria, pyridoxine-responsive |
| 397507473 | NM_004333.4(BRAF):c.403T>C (p.Phe468Ser) | ATCATYTGGAACAGTCTACAAGG, TCATYTGGAACAGTCTACAAGG | Cardiofaciocutaneous syndrome, Rasopathy |
| 786204056 | NM_000264.3(PTCHH:c.3168+2T>C | ATCATTGYGAGTGTATTATAAGG, TCATTGYGAGTGTATTATAAGGG, CATTGYGAGTGTATTATAAGGG | Gorlin syndrome |
| 72558484 | NM_000531.5(OTC):c.1005+2T>C | ATCATGGYAAGCAAGAAACAAGG | not provided |
| 199473074 | NM_000335.4(SCN5A):c.688A>G (p.Ile230Val) | ATAYAGTTTTCAGGGCCCGGAGG, CTGATAYAGTTTTCAGGGCCCGG | Brugada syndrome |
| 111033273 | NM_206933.2(USH2A):c.1606T>C (p.Cys536Arg) | ATATAGAYGCCCTCTGCTCCCAGG | Usher syndrome, type 2A |
| 72556290 | NM_000531.5(OTC):c.542A>G (p.Glu181Gly) | ATATGTYCCTAAAAGGCACGGG | not provided |
| 121918711 | NM_004612.3(TGFBR1):c.1199A>G (p.Asp400Gly) | ATAGATGYCAGCACGTTTGAAGG | Loeys-Dietz syndrome 1 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 104886288 | NM_000495.4(COL4A5):c.4699T>C (p.Cys1567Arg) | AGTAYGTGAAGCTCCAGCTGTGG | Alport syndrome, X-linked recessive |
| 144637717 | NM_016725.2(FOLRH):c.493+2T>C | CTTCAGGYGAGGGCTGGGGTGGG, AGGYGAGGGCTGGGGTGGCAGG | not provided |
| 72558492 | NM_000531.5(OTC):c.1034A>G (p.Tyr345Cys) | AGGTGAGYAATCTGTCAGCAGGG | not provided |
| 62638745 | NM_000121.3(EPOR):c.1460A>G (p.Asn487Ser) | AGGGYTGGAGTAGGGGCCATCGG | Acute myeloid leukemia, M6 type, Familial erythrocytosis, 1 |
| 387907021 | NM_031427.3(DNAL1):c.449A>G (p.Asn150Ser) | AGGGAYTGCCTACAAACACCAGG | Kartagener syndrome, Ciliary dyskinesia, primary, 16 |
| 397514488 | NM_001161581.1(POC1A):c.398T>C (p.Leu133Pro) | AGCYGTGGGACAAGAGAGCAGCCGG | Short stature, onychodysplasia, facial dysmorphism, and hypotrichosis |
| 154774633 | NM_017882.2(CLN6):c.200T>C (p.Leu67Pro) | AGCYGGTATTCCCTCTCCAGTGG | Adult neuronal ceroid lipofuscinosis |
| 111033700 | NM_000155.3(GALT):c.482T>C (p.Leu161Pro) | AGCYGGGTGCCCAGTACCCTTGG | Deficiency of UDPglucose-hexose-1-phosphate uridylyltransferase |
| 128621198 | NM_000061.2(BTK):c.1223T>C (p.Leu408Pro) | GAGCYGGGACTGGACAATTTGG, AGCYGGGACTGGACAATTTGGG | X-linked agammaglobulinemia |
| 137852611 | NM_000211.4(ITGB2):c.446T>C (p.Leu149Pro) | AGCYAGGTGGCGACCTGCTCCGG | Leukocyte adhesion deficiency |
| 121908838 | NM_003722.4(TP63):c.697A>G (p.Lys233Glu) | AGCTTYTTTGTAGACAGGCATGG | Split-hand/foot malformation 4 |
| 397515869 | NM_000169.2(GLA):c.1153A>G (p.Thr385Ala) | AGCTGTGYGATGAAGCAGGCAGG | not specified |
| 118204064 | NM_000237.2(LPL):c.548A>G (p.Asp183Gly) | GCTGGAYCGAGGCCTTAAAGGG, AGCTGGAYCGAGGCCTTAAAAGG | Hyperlipoproteinemia, type I |
| 128620186 | NM_000061.2(BTK):c.2T>C (p.Met1Thr) | AGCTAYGGCCGCAGTGATTCTGG | X-linked agammaglobulinemia |
| 786204132 | NM_014946.3(SPAST):c.1165A>G (p.Thr389Ala) | ATTGYCTTCCCATTCCCAGGTGG, AGCATTGYCTTCCCATTCCCAGG | Spastic paraplegia 4, autosomal dominant |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 199473661 | NM_000218.2(KCNQ1):c.550T>C (p.Tyr184His) | CAGCAAGBACGTGGGCCTCTGGG, AGCAAGBACGTGGGCCTCTGGGG, GCAAGBACGTGGGCCTCTGGGGG | Congenital long QT syndrome, Cardiac arrhythmia |
| 387907129 | NM_024599.5(RHBDF2):c.557T>C (p.Ile186Thr) | AGAYTGTGGATCCGCTGCCCGG | Howel-Evans syndrome |
| 387906702 | NM_063306.3(SMC1A):c.2351T>C (p.Ile784Thr) | AGAYTGGTGTGCCAACATCCGG | Congenital muscular hypertrophy-cerebral syndrome |
| 193929348 | NM_000525.3(KCNJ11):c.544A>G (p.Ile182Val) | AGAYGAGGGTCTCAGCCCTGCG | Permanent neonatal diabetes mellitus |
| 121908934 | NM_004086.2(COCH):c.1535T>C (p.Met512Thr) | AGATAYGGCTTCTAAACCGAAGG | Deafness, autosomal dominant 9 |
| 397514377 | NM_000060.3(BTD):c.641A>G (p.Asn214Ser) | AGAGGYTGTGTTTACGGTAGCGG | Biotinidase deficiency |
| 72522295 | NM_000531.5(OTC):c.2T>C (p.Met1Thr) | AGAAGAYCTGTTTAATCTGAGG | not provided |
| 201893545 | NM_016247.3(IMPG2):c.370T>C (p.Phe124Leu) | ACTYTTTGGGATCGCACTTCCTGG | Macular dystrophy, vitelliform, 5 |
| 121434469 | m.4290T>C | ACTYTGATAGAGTAAATAATAGG | |
| 121918733 | NM_006920.4(SCN1A):c.269T>C (p.Phe90Ser) | ACTTYTATAGTATTGAATAAAGG, CTTYTATAGTATTGAATAAAGGG | Severe myoclonic epilepsy in infancy |
| 121434471 | m.4291T>C | ACTTYGATAGAGTAAATAATAGG | Hypertension, hypercholesterolemia, and hypomagnesemia, mitochondrial |
| 606231289 | NM_001302946.1(TRNT1):c.497T>C (p.Leu166Ser) | ACTTYATTTGACTACTTTAATGG | Sideroblastic anemia with B-cell immunodeficiency, periodic fevers, and developmental delay |
| 63750067 | NM_000517.4(HBA2):c.*92A>G | CTTYATTCAAAGACCAGGAAGGG, ACTTYATTCAAAGACCAGGAAGG | Hemoglobin H disease, nondeletional |
| 121918734 | NM_006920.4(SCN1A):c.272T>C (p.Ile91Thr) | ACTTTTAYAGTATTGAATAAAGG, CTTTTAYAGTATTGAATAAAGGG | Severe myoclonic epilepsy in infancy |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 137854557 | NM_000267.3(NF1):c.1466A>G (p.Tyr489Cys) | ACTTAYAGCTTCTTGTCTCCAGG | Neurofibromatosis, type 1 |
| 397514626 | NM_018344.5(SLC29A3):c.607T>C (p.Ser203Pro) | ACTGATAYCAGGTGAGAGCCAGG, CTGATAYCAGGTGAGAGCCAGGG | Histiocytosis-lymphadenopathy plus syndrome |
| 118204440 | NM_000512.4(GALNS):c.1460A>G (p.Asn487Ser) | ACCGTYGAGCTGGGGCTGCGCGG, CACGTYGAGCTGGGGCTGCGCGG | Mucopolysaccharidosis, MPS-IV-A |
| 587776843 | NG_012088.1:g.2209A>G | ACCYTATGATCCGCCCGCCTTGG | |
| 137853033 | NM_001080463.1(DYNC2H1):c.4610A>G (p.Gln1537Arg) | ACCYGTGAAGGAACAGAGATGG | Short-rib thoracic dysplasia 3 with or without polydactyly |
| 28933698 | NM_000435.2(NOTCH3):c.1363T>C (p.Cys455Arg) | TTCACCYGTATCTGTATGGCAGG, ACCYGTATCTGTATGGCAGGTGG, ACCYGAGATGCAAAATAGGGAGG, | Cerebral autosomal dominant arteriopathy with subcortical infarcts and leukoencephalopathy |
| 587776766 | NM_000463.2(UGT1A1):c.1085-2A>G | GTGACCYGAGATGCAAAATAGGG, GGTGACCYGAGATGCAAAATAGG | Crigler Najjar syndrome, type 1 |
| 587781628 | NM_001128425.1(MUTYH):c.1187-2A>G | ACCYGAGAGGGGCAGCCAGG | Hereditary cancer-predisposing syndrome, Carcinoma of colon |
| 61755817 | NM_000322.4(PRPH2):c.736T>C (p.Trp246Arg) | ACCTGYGGGTGCGTGGCTGCAGG, CCTGYGGGTGCGTGGCTGCAGGG | Retinitis pigmentosa |
| 121909184 | NM_001089.2(ABCA3):c.1702A>G (p.Asn568Asp) | ACCGTYGTGGCCCAGCAGGACGG | Surfactant metabolism dysfunction, pulmonary, 3 |
| 121434466 | m.4269A>G | ACAYATTCTTAGGTTTGAGGGG, GACAYATTCTTAGGTTTGAGGG, AGACAYATTCTTAGGTTTGAGG | |
| 794726768 | NM_001165963.1(SCN1A):c.1048A>G (p.Met350Val) | ACAYATATCCCCTCTGGACATTGG | Severe myoclonic epilepsy in infancy |
| 28934876 | NM_001382.3(DPAGT1):c.509A>G (p.Tyr170Cys) | ACAYAGTACAGGATTCCTGCGGG, GACAYAGTACAGGATTCCTGCGG | Congenital disorder of glycosylation type 1J |
| 104894749 | NM_000054.4(AVPR2):c.614A>G (p.Tyr205Cys) | ACAYAGGTGCGACGGCCCCAGGG, GACAYAGGTGCGACGGCCCCAGG | Nephrogenic diabetes insipidus, Nephrogenic diabetes insipidus, X-linked |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 128621205 | NM_000061.2(BTK):c.1741T>C (p.Trp581Arg) | ACATTYGGGCTTTTGGTAAGTGG | X-linked agammaglobulinemia |
| 28940892 | NM_000529.2(MC2R):c.761A>G (p.Tyr254Cys) | ACATGYAGCAGGCGCAGTAGGGG, GACATGYAGCAGGCGCAGTAGGG, AGACATGYAGCAGGCGCAGTAGG | ACTH resistance |
| 794726844 | NM_001165963.1(SCN1A):c.1046A>G (p.Tyr349Cys) | ACATAYATCCCCTCTGGACATTGG | Severe myoclonic epilepsy in infancy |
| 587783083 | NM_003159.2(CDKL5):c.449A>G (p.Lys150Arg) | ACAGTYTTAGGACATCATTGTGG | not provided |
| 397514651 | NM_000108.4(DLD):c.140T>C (p.Ile47Thr) | ACAGTTAYAGGTTCTGGTCCTGG, GTTAYAGGTTCTGGTCCTGGAGG | Maple syrup urine disease, type 3 |
| 794727060 | NM_001848.2(COL6A1):c.957+2T>C | ACAAGGYGAGCTGGGCTGCTGG, CAAGGYGAGCGTGGGCTGCTGGG | Ullrich congenital muscular dystrophy, Bethlem myopathy |
| 72554346 | NM_000531.5(OTC):c.284T>C (p.Leu95Ser) | ACAAGATYGTCTACAGAAACAGG | not provided |
| 483353031 | NM_002136.2(HNRNPA1):c.841T>C (p.Phe281Leu) | AATYTTGGAGGCAGAGAAGCTCTGG | Chronic progressive multiple sclerosis |
| 104894271 | NM_000315.2(PTH):c.52T>C (p.Cys18Arg) | AATTYGTTTTCTTACAAAATCGG | Hypoparathyroidism familial isolated |
| 267608260 | NM_015599.2(PGM3):c.248T>C (p.Leu83Ser) | AATGTYGGCACCATCCTCGGGAGG | Immunodeficiency 23 |
| 267606900 | NM_018109.3(MTPAP):c.1432A>G (p.Asn478Asp) | AATGGATYCTGAATGTACAGAGG | Ataxia, spastic, 4, autosomal recessive |
| 796053169 | NM_021007.2(SCN2A):c.387-2A>G | AATAAAGYAGAATATCGTCAAGG | not provided |
| 104894937 | NM_000116.4(TAZ):c.352T>C (p.Cys118Arg) | AAGYGTGTGCCTGTGTGCCGAGG | 3-Methylglutaconic aciduria type 2 |
| 104893911 | NM_001018077.1(NR3C1):c.1712T>C (p.Val571Ala) | AAGYGATTGCAGCAGTGAAATGG | Pseudohermaphroditism, female, with hypokalemia, due to glucocorticoid resistance |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397514472 | NM_004813.2(PEX16):c.992A>G (p.Tyr331Cys) | AAGYAGATTTTCTGCCAGGTGGG, GAAGYAGATTTTCTGCCAGGTGG, GTAGAAGYAGATTTTCTGCCAGG | Peroxisome biogenesis disorder 8B |
| 121918407 | NM_001083112.2(GPD2):c.1904T>C (p.Phe635Ser) | AAGTYTGATGCAGACCAGAAAGG | Diabetes mellitus type 2 |
| 63751110 | NM_000251.2(MSH2):c.595T>C (p.Cys199Arg) | AAGGAAYGTGTTTTACCCGGAGG | Hereditary Nonpolyposis Colorectal Neoplasms |
| 111950945 | NM_000026.2(ADSL):c.674T>C (p.Met225Thr) | AAGAAYGGTGACAGAAAAGGCAGG | Adenylosuccinate lyase deficiency |
| 113993988 | NM_002863.4(PYGL):c.2461T>C (p.Tyr821His) | AAGAAYATGCCCAAAACATCTGG | Glycogen storage disease, type VI |
| 119485091 | NM_022041.3(GAN):c.1268T>C (p.Ile423Thr) | AAGAAAAYCTACGCCATGGGTGG, AAAAYCTACGCCATGGGTGGAGG | Giant axonal neuropathy |
| 137852419 | NM_000132.3(F8):c.1660A>G (p.Ser554Gly) | AACYAGAGTAATAGCGGGTCAGG | Hereditary factor VIII deficiency disease |
| 121964967 | NM_000071.2(CBS):c.1150A>G (p.Lys384Glu) | AACTYGGTCCTGCGGATGGGGG, GGACTYGGTCCTGCGGATGGGG, GGAACTYGGTCCTGCGGATGGG, AGGAACTYGGTCCTGCGGATGG | Homocystinuria,pyridox ne-respons ve |
| 137852376 | NM_000132.3(F8):c.1754T>C (p.Ile585Thr) | AACAGAYAATGTCAGACAAGAGG | Hereditary factor VIII deficiency disease |
| 121917930 | NM_066920.4(SCN1A):c.3577T>C (p.Trp1193Arg) | AACAAYGTGGAACCTGAGAAGG | Generalized epilepsy with febrile seizures plus, type 1, Generalized epilepsy with febrile seizures plus, type 2 |
| 28939717 | NM_003907.2(EIF2B5):c.271A>G (p.Thr91Ala) | AAATGYTTCCTGTACACCTGTG | Leukoencephalopathy with vanishing white matter |
| 80357276 | NM_007294.3(BRCA1):c.122A>G (p.His41Arg) | AAATATGYGGTCACACTTTGTGG | Familial cancer of breast, Breast-ovarian cancer, familial 1 |
| 397515897 | NM_000256.3(MYBPC3):c.1351+2T>C | AAAGGYGGGCCTGGGACCTGAGG | Familial hypertrophic cardiomyopathy 4, Cardiomyopathy |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397514491 | NM_005340.6(HINT I):c.152A>G (p.His51Arg) | AAAAYGTGTTGGTGCTTGAGTGG, GAAAAYGTGTTGGTGCTTGAGGG, AGAAAAYGTGTTGGTGCTTGAGG | Gamstorp-Wohlfart syndrome |
| 387907164 | NM_020894.2(UVSSA):c.94T>C (p.Cys32Arg) | AAAATTYGCAAGTATGTCTTAGG, AAAATTYGCAAGTATGTCTTAGG G | UV-sensitive syndrome 3 |
| 118161496 | NM_025152.2(NUBPL):c.815-277T>C | TGGTTCYAATGGATGTCTGCTGG, GGTTCYAATGGATGTCTGCTGGG | Mitochondrial complex I deficiency |
| 764313717 | NM_005609.2(PYGM):c.425_528del | TGGCTGYCAGGGACCCAGCAAGG, CTGYCAGGGACCCAGCAAGGAGG | |
| 28934568 | NM_003242.5(TGFBR2):c.923T>C (p.Leu308Pro) | AGTTCCYGACGGCTGAGGAGCGG | Loeys-Dietz syndrome 2 |
| 121913461 | NM_007313.2(ABL1):c.814T>C (p.Tyr272His) | CCAGYACGGGGAGGTGTACGAGG, CAGYACGGGGAGGTGTACGAGGG | |
| 377750405 | NM_173551.4(ANKS6):c.1322A>G (p.Gln441Arg) | AGGGCYGTCGGACCTTCGAGTGG, GGGCYGTCGGACCTTCGAGTGGG, GGCYGTCGGACCTTCGAGTGGGG | Nephronophthisis 16 |
| 57639980 | NM_001927.3(DES):c.1034T>C (p.Leu345Pro) | ATTCCCYGATGAGGCAGATGCGG, TTCCCYGATGAGGCAGATGCGGG | Myofibrillar myopathy 1 |
| 147391618 | NM_020320.3(RARS2):c.35A>G (p.Gln12Arg) | ATACCYGGCAAGCAATAGCGCGG | Pontocerebellar hypoplasia type 6 |
| 182650126 | NM_002977.3(SCN9A):c.2215A>G (p.Ile739Val) | GTAAYTGCAAGATCTACAAAAGG | Small fiber neuropathy |
| 80358278 | NM_004700.3(KCNQ4):c.842T>C (p.Leu281Ser) | ACATYGACAACCATCGGCTATGG | DFNA 2 Nonsyndromic Hearing Loss |
| 786204012 | NM_005957.4(MTHFR):c.388T>C (p.Cys130Arg) | GACCYGCTGCCGTCAGCGCCTGG | Homocysteinemia due to MTHFR deficiency |
| 786204037 | NM_005957.4(MTHFR):c.1883T>C (p.Leu628Pro) | TCCCACYGGACAACTGCCTCTGG | Homocysteinemia due to MTHFR deficiency |
| 202147607 | NM_000140.3(FECH):c.1137+3A>G | GTAGAYACCTTAGAGAACAATGG | Erythropoieticprotoporphyria |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 122456136 | NM_005183.3(CACNA1F):c.2267T>C (p.Ile756Thr) | TGCCAYTGCTGTGGACACCTGG | |
| 786204851 | NM_007374.2(SIX6):c.110T>C (p.Leu37Pro) | GTCGCYGCCCGTGGCCCCTGCGG | Cataract, microphthalmia and nystagmus |
| 794728167 | NM_000138.4(FBN1):c.1468+2T>C | ATTGGYACGTGATCCATCCTAGG | Thoracic aortic aneurysms and aortic dissections |
| 121964909 | NM_000027.3(AGA):c.214T>C (p.Ser72Pro) | GACGGYCTGTAGGCTTTGGAGG | Aspartylglycosaminuria |
| 121964978 | NM_000170.2(GLDC):c.2T>C (p.MetIThr) | CGGCCAYGCAGTCCTGTGCCAGG, GGCCAYGCAGTCCTGTGCCAGGG | Non-ketotichyperglycinemia |
| 121965008 | NM_000398.6(CYB5R3):c.446T>C (p.Leu149Pro) | CTGCYGGTCTACCAGGGCAAAGG | METHEMOGLOBINEMIA, TYPE I |
| 121965064 | NM_000128.3(F1 1 ):c.90IT>C (p.Phe301Leu) | TGATYTCTTGGGAGAAGAACTGG | Hereditary factor XI deficiency disease |
| 45517398 | NM_000548.3(TSC2):c.5150T>C (p.Leu1717Pro) | GCCCYGCACGCAAATGTGAGTGG, CCCYGCACGCAAATGTGAGTGGG | Tuberous sclerosis syndrome |
| 786205857 | NM_015662.2(IFT172):c.770T>C (p.Leu257Pro) | TTGTGCYAGGAAGTTATGACAGG | RETINITIS PIGMENTOSA 71 |
| 786205904 | NM_001135669.1(XPR1):c.653T>C (p.Leu218Ser) | GCGTTYACGTGTCCCCCTTTGG, CGTTYACGTGTCCCCCCTTTGGG | BASAL GANGLIA CALCIFICATION, |
| 104893704 | NM_000388.3(CASR):c.2641T>C (p.Phe881Leu) | ACGCYTCAAGGTGGCTGCCCGG, CGCTYTCAAGGTGGCTGCCCGGG | Hypercalciuric hypercalcemia |
| 104893747 | NM_I98159.2(MITF):c.1195T>C (p.Ser399Pro) | ACTTYCCCTTATTCCATCCACGG, CTTYCCCTTATTCCATCCACGGG | Waardenburg syndrome type 2A |
| 104893770 | NM_000539.3(RHO):c.133T>C (p.Phe45Leu) | CATGYTTCTGCTGATCGTGCTGG, ATGYTTCTGCTGATCGTGCTGGG | Retinitis pigmentosa 4 |
| 28937596 | NM_003907.2(EIF2B5):c.1882T>C (p.Trp628Arg) | AGGCCYGGAGCCCTTGTTTTAGG | Leukoencephalopathy with vanishing white matter |
| 104893876 | NM_001151.3(SLC25A4):c.293T>C (p.Leu98Pro) | GCAGCYCTTTCTTAGGGGGTGTGG | Autosomal dominant progressive external ophthalmoplegia with mitochondrial DNA deletions 2 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 104893883 | NM_006005.3(WFS1):c.2486T>C (p.Leu829Pro) | ACCATCCYGGAGGGCCGCCTGGG | WFS1-Related Disorders |
| 104893962 | NM_000165.4(GJA1):c.52T>C (p.Ser18Pro) | CTACYCAACTGTGGAGGGAAGG | Oculodentodigital dysplasia |
| 104893978 | NM_000434.3(NEU1):c.718T>C (p.Trp240Arg) | GCCTCCYGGCGTACGGAAGTGG, CCTCCYGGCGCTACGGAAGTGGG, CTCCYGGCGCTACGGAAGTGGGG | Sialidosis, type II |
| 104894092 | NM_002546.3(TNFRSF11B):c.349T>C (p.Phe117Leu) | TAGAGYTCTGCTTGAAACATAGG | Hyperphosphatasemia with bone disease |
| 104894135 | NM_000102.3(CYP17A1):c.316T>C (p.Ser106Pro) | CATCGCGYCCAACAACCGTAAGG, ATCGCGYCCAACAACCGTAAGGG | Complete combined 17-alpha-hydroxylase/17,20-lyase |
| 104894151 | NM_000102.3(CYP17A1):c.1358T>C (p.Phe453Ser) | AGCTCTYCCTCATCATGGCCTGG | Combined partial 17-alpha-hydroxylase/17,20-lyase deficiency |
| 36015961 | NM_000518.4(HBB):c.344T>C (p.Leu115Pro) | TGTGTGCYGGCCCATCACTTTGG | Beta thalassemia intermedia |
| 104894472 | NM_152443.2(RDH12):c.523T>C (p.Ser175Pro) | TCCYCGGTGGCTCACCACATTGG | Leber congenital amaurosis 13 |
| 104894587 | NM_004870.3(MPDU1):c.356T>C (p.Leu119Pro) | TTCCYGGTCATGCACTACAGAGG | Congenital disorder of glycosylation type 1F |
| 104894588 | NM_004870.3(MPDU1):c.2T>C (p.Met1Thr) | AATAYGGCGGCCAGGCGACGG | Congenital disorder of glycosylation type 1F |
| 104894626 | NM_000304.3(PMP22):c.82T>C (p.Trp28Arg) | TAGCAAYGGATCGTGGGCAATGG | Charcot-Marie-Tooth disease, type IE |
| 104894631 | NM_018129.3(PNPO):c.784T>C (p.Ter262Gln) | ACCTYAACTCTGGGACCTGCTGG | "Pyridoxal 5-phosphate-dependent epilepsy" |
| 104894703 | NM_032551.4(KISS1R):c.305T>C (p.Leu102Pro) | GCCCTGCYGTACCCGCTGCCCGG, TGCYGTACCCGCTGCCCGGCTGG | |
| 104894826 | NM_000166.5(GJB1):c.407T>C (p.Val136Ala) | ATGYCATCAGCGTGGTGTTCCGG | Dejerine-Sottas disease, X-linked hereditary motor and sensory neuropathy |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 104894859 | NM_001122606.1(LAMP2):c.961T>C (p.Trp321Arg) | CAGCTACYGGGATGCCCCCCTGG, AGCTACYGGGATGCCCCCCTGGG | Danon disease |
| 104894931 | NM_006517.4(SLC16A2):c.1313T>C (p.Leu438Pro) | TGAGCYGGTGGGCCCAATGCAGG | Allan-Herndon-Dudley syndrome |
| 104894935 | NM_000330.3(RS1):c.38T>C (p.Leu13Pro) | TTACTTCYCTTTGGCTATGAAGG | Juvenile retinoschisis |
| 104895217 | NM_001065.3(TNFRSF1A):c.175T>C (p.Cys59Arg) | TGCYGTACCAAGTGCCACAAAGG | TNF receptor-associated periodic fever syndrome (TRAPS) |
| 143889283 | NM_003793.3(CTSF):c.692A>G (p.Tyr231Cys) | CTCCAYACTGAGCTGTGCCACGG | Ceroid lipofuscinosis, neuronal, 13 |
| 122459147 | NM_001159702.2(FHL1):c.310T>C (p.Cys104Arg) | GGGGYGCTTCAAGGCCATTGTGG | Myopathy, reducing body, X-linked, childhood-onset |
| 74552543 | NM_020184.3(CNNM4):c.971T>C (p.Leu324Pro) | AAGCTCCYGGACTTTTTCTGGG | Cone-rod dystrophy amelogenesis imperfecta |
| 199476117 | m.10158T>C | AAAYCCACCCCTTACGAGTGCGG | Leigh disease, Leigh syndrome due to mitochondrial complex I deficiency, Mitochondrial complex I deficiency |
| 794727808 | NM_020451.2(SEPN1):c.872+2T>C | TTCCGGYGAGTGGGCCACACTGG | Congenital myopathy with fiber type disproportion, Eichsfeld type congenital muscular dystrophy |
| 140547520 | NM_005022.3(PFN1):c.350A>G (p.Glu117Gly) | CACCTYCTTTGCCCATCAGCAGG | Amyotrophic lateral sclerosis 18 |
| 397514359 | NM_000060.3(BTD):c.445T>C (p.Phe149Leu) | TCACCGCYTCAATGACACAGAGG | Biotinidase deficiency |
| 207460001 | m.15197T>C | CTAYCCCGCCATCCCATACATTGG | Exercise intolerance |
| 397514406 | NM_000060.3(BTD):c.1214T>C (p.Leu405Pro) | TTCACCCYGGTCCCTGTCTGGGG | Biotinidase deficiency |
| 397514516 | NM_061177.3(NRL):c.287T>C (p.Met96Thr) | GAGGCCAYGGAGCTGCTGCAGGG | Retinitis pigmentosa 27 |
| 72554312 | NM_000531.5(OTC):c.134T>C (p.Leu45Pro) | CTCACTCYAAAAACTTTACCGG | Ornithine carbamoyltransferase deficiency |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397514569 | NM_178012.4(TUBB2B):c.350T>C (p.Leu117Pro) | GGTCCYGGATGTGTGGTGAGGAAGG | Polymicrogyria, asymmetric |
| 397514571 | NM_000431.3(MVK):c.122T>C (p.Leu41Pro) | CGGCYTCAACCCCACAGCAATGG, GGCYTCAACCCCACAGCAATGGG | Porokeratosis, disseminated superficial actinic 1 |
| 794728390 | NM_000238.3(KCNH2):c.2396T>C (p.Leu799Pro) | GCCATCCYGGGTATGGGGTGGGG, CCATCCYGGGTATGGGGTGGGGG, CATCCYGGGTATGGGGTGGGGGG | Cardiac arrhythmia |
| 397514713 | NM_001199107.1(TBC1D24):c.686T>C (p.Phe229Ser) | GGTCYTTGACGTCTTCCTGGTGG | Early infantile epileptic encephalopathy 16 |
| 397514719 | NM_080605.3(B3GALT6):c.193A>G (p.Ser65Gly) | CGCYGGGCCACCAGCACTGCCAGG | Spondyloepimetaphyseal dysplasia with joint laxity |
| 730880608 | NM_000256.3(MYBPC3):c.3796T>C (p.Cys1266Arg) | GAGYGCCGCCTGAGGTGCGAGG | Cardiomyopathy |
| 397515329 | NM_001382.3(DPAGT1H:c.503T>C (p.Leu168Pro) | AATCCYGTACTATGTCTACATGG, ATCCYGTACTATGTCTACATGGG, TCCYGTACTATGTCTACATGGGG | Congenital disorder of glycosylation type 1J |
| 397515465 | NM_018127.6(ELAC2):c.460T>C (p.Phe154Leu) | ATAYTTTCTGGTCCATTGAAAGG | Combined oxidative phosphorylation deficiency 17 |
| 397515557 | NM_005211.3(CSF1R):c.2483T>C (p.Phe828Ser) | CATCYTTGACTGTGTCTACACGG | Hereditary diffuse leukoencephalopathy with spheroids |
| 397515599 | NM_194248.2(OTOF):c.3413T>C (p.Leu1138Pro) | AGGTGCYGTTCTGGGGCCTACGG, GGTGCYGTTCTGGGGCCTACGGG | Deafness, autosomal recessive 9 |
| 397515766 | NM_000138.4(FBN1):c.2341T>C (p.Cys781Arg) | GGACAAYGTAGAAATACTCCTGG | Marfan syndrome |
| 565779970 | NM_001429.3(EP300):c.3573T>A (p.Tyr1191Ter) | CTTAYTACAGTTACCAGAACAGG | Rubinstein-Taybi syndrome 2 |
| 786200938 | NM_080605.3(B3GALT6):c.1A>G (p.Met1Val) | AGCTTCAYGGCCCCGCCGCCGGG, TCAYGGCCCCGCCGCCGGGCCGG | Spondyloepimetaphyseal dysplasia with joint laxity |
| 28942087 | NM_000229.1(LCAT):c.698T>C (p.Leu233Pro) | ATCTCYTGGGGCTCCCTGGGG, TCTCYTGGGGCTCCCTGGGGTGG | Norum disease |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 128621203 | NM_000061.2(BTK):c.1625T>C (p.Leu542Pro) | TCGGCCYGTCCAGGTGAGTGTGG | X-linked agammaglobulinemia with growth hormone deficiency |
| 397515412 | NM_006383.3(CIB2):c.368T>C (p.Ile123Thr) | CTTCAYCTGCAAGGAGGACCTGG | Deafness, autosomal recessive 48 |
| 193929364 | NM_000352.4(ABCC8):c.404T>C (p.Leu135Pro) | AAGCYGCTAATTGGTAGTGAGG | Permanent neonatal diabetes mellitus |
| 730880872 | NM_000257.3(MYH7):c.1400T>C (p.Ile467Thr) | TCCAGAYCTTCGATGTGAGTTGG, CGAGAYCTTCGATGTGAGTTGGG | Cardiomyopathy |
| 80356474 | NM_002977.3(SCN9A):c.2543T>C (p.Ile848Thr) | AAGATCAYTGGTAACTCAGTAGG, AGATCAYTGGTAACTCAGTAGGG, GATCAYTGGTAACTCAGTAGGGG | Primary erythromelalgia |
| 80356489 | NM_001164277.1(SLC37A4):c.352T>C (p.Trp118Arg) | GGGCYGGCCCCCATGTGGGAAGG | Glucose-6-phosphate transport defect |
| 80356536 | NM_152296.4(ATP1A3):c.2338T>C (p.Phe780Leu) | GCCCYTCCTGCTGTTCATCATGG | Dystonia 12 |
| 80356596 | NM_194248.2(OTOF):c.3032T>C (p.Leu1011Pro) | GATGCYGGTGTTCGACAACCTGG | Deafness, autosomal recessive 9, Auditory neuropathy, autosomal recessive, 1 |
| 80356689 | NM_000083.2(CLCN1):c.857T>C (p.Val286Ala) | AGGAGYGCTATTTAGCATCGAGG | Myotonia congenita |
| 118203884 | m.4409T>C | AGGYCAGCTAAATAAGCTATCGG | Mitochondrial myopathy |
| 587777625 | NM_173596.2(SLC39A5):c.911T>C (p.Met304Thr) | AGAACAYGCTGGGCTTTTGCGG | Myopia 24, autosomal dominant |
| 587783087 | NM_003159.2(CDKL5):c.602T>C (p.Leu201Pro) | ATTCYTGGGAGCTTAGCGATGG | not provided |
| 118203951 | NM_013319.2(UBIAD1):c.511T>C (p.Ser171Pro) | TCTTGGCYCCTTTCTCTACACAGG, GGCYCCTTTCTCTACACAGGAGG | Schnyder crystalline corneal dystrophy |
| 118204017 | NM_000018.3(ACADVL):c.1372T>C (p.Phe458Leu) | TCGCATCYTCCGGATCTTTGAGG, CGCATCYTCCGGATCTTTGAGGG, GCATCYTCCGGATCTTTGAGGGG | Very long chain acyl-CoA dehydrogenase deficiency |
| 397518466 | NM_000833.4(GRIN2A):c.2T>C (p.Met1Thr) | CTAYGGGCAGAGTGGGCTATTGG | Focal epilepsy with speech disorder with or without mental retardation |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 118204069 | NM_000237.2(LPL):c.337T>C (p.Trp113Arg) | GGACYGGCTGTCACGGGCTCAGG | Hyperlipoproteinemia, type I |
| 118204080 | NM_000237.2(LPL):c.755T>C (p.Ile252Thr) | GTGAYTGCAGAGAGAGGACTTGG | Hyperlipoproteinemia, type I |
| 118204111 | NM_000190.3(HMBS):c.739T>C (p.Cys247Arg) | GCTTCGCYGCATCGCTGAAAGGG | Acute intermittent porphyria |
| 80357438 | NM_007294.3(BRCA1):c.65T>C (p.Leu22Ser) | AAATCTYAGAGTGTCCCATCTGG | Familial cancer of breast, Breast-ovarian cancer, familial 1, Hereditary cancer-predisposing syndrome |
| 139877390 | NM_001040431.2(COA3):c.215A>G (p.Tyr72Cys) | CCAYCTGGGGAGGTAGGTTCAGG | |
| 793888527 | NM_005859.4(PURA):c.563T>C (p.Ile188Th) | GACCAYTGCGCTGCCCGCGCAGG, ACCAYTGCGCTGCCCGCGCAGGG, CCAYTGCGCTGCCCGCGCAGGGG | not provided, Mental retardation, autosomal dominant 31 |
| 561425038 | NM_002878.3(RAD51D):c.1A>G (p.Met1Val) | CGCCCAYGTTCCCGCAGGCCGG | Hereditary cancer-predisposing syndrome |
| 121907934 | NM_024105.3(ALG12):c.473T>C (p.Leu158Pro) | TCCYGCTGGCCCTCGCGGCCTGG | Congenital disorder of glycosylation type 1G |
| 80358207 | NM_153212.2(GM4):c.409T>C (p.Phe137Leu) | CCTCATCYTCAAGGCCGAGGCCGG | Erythrokeratodermia variabilis |
| 80358228 | NM_002353.2(TACSTD2):c.557T>C (p.Leu186Pro) | TCGGCYGCACCCCAAGTTCGTGG | Lattice conical dystrophy Type III |
| 121908076 | NM_138691.2(TMC1):c.1543T>C (p.Cys515Arg) | AGGACCTYGCTGGGAAACAATGG, ACCTYGCTGGGAAACAATGGTGG, CCTYGCTGGGAAACAATGGTGGG | Deafness, autosomal recessive 7 |
| 121908089 | NM_017838.3(NHP2):c.415T>C (p.Tyr139His) | GGAGGCTYACGATGAGTGCCTGG, GGCTYACGATGAGTGCCTGGAGG | Dyskeratosis congenita autosomal recessive 1, Dyskeratosis congenita, autosomal recessive 2 |
| 121908154 | NM_001243133.1(NLRP3):c.926T>C (p.Phe309Ser) | GGTGCCYYTGACGAGCACATAGG | Familial cold urticaria, Chronic infantile neurological, cutaneous and articular syndrome |
| 121908158 | NM_001033855.2(DCLRE1C):c.2T>C (p.Met1Thr) | GGGCTAYGAGTTCTTTCGAGGG, GCGCTAYGAGTTCTTTCGAGGGG | Histiocytic medullary reticulosis |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 796052870 | NM_018129.3(PNP0):c.2T>C (p.Met1Thr) | CCCCAYGACGTGCTGGCTGCGG, CCCAYGACGTGCTGGCTGCGGG, CCCAYGACGTGCTGGCTGCGGGG | not provided |
| 121908318 | NM_020427.2(SLURP1):c.43T>C (p.Trp15Arg) | GCAGCCYGGAGCATGGCTGTGG | Acroerythrokeratoderma |
| 121908352 | NM_022124.5(CDH23):c.5663T>C (p.Phe1888Ser) | CTCACCTYCAACATCACTCGCGG | Deafness, autosomal recessive 12 |
| 121908520 | NM_000030.2(AGXT):c.613T>C (p.Ser205Pro) | CCTGTACYCGGGCTCCCAGAAGG | Primary hyperoxaluria, type I |
| 121908618 | NM_004273.4(CHST3):c.920T>C (p.Leu307Pro) | CGTGCYGGCCTCCGCGCATGGTGG | Spondyloepiphyseal dysplasia with congenital joint dislocations |
| 11694 | NM_006432.3(NPC2):c.199T>C (p.Ser67Pro) | TATTCAGYCTAAAAGCAGCAAGG | Niemann-Pick disease type C2 |
| 121908739 | NM_000022.2(ADA):c.320T>C (p.Leu107Pro) | CCTGCYGGCCAACTCCAAAGTGG | Severe combined immunodeficiency due to ADA deficiency |
| 80359022 | NM_000059.3(BRCA2):c.7958T>C (p.Leu2653Pro) | TGCYTCTTCAACTAAAATACAGG | Familial cancer of breast, Breast-ovarian cancer, familial 2 |
| 121908902 | NM_003880.3(WISP3):c.232T>C (p.Cys78Arg) | AAAATCYGTGCCAAGCAACCAGG, AAATCYGTGCCAAGCAACCAGGG, AATCYGTGCCAAGCAACCAGGGG | Progressive pseudorheumatoid dysplasia |
| 121908947 | NM_006892.3(DNMT3B):c.808T>C (p.Ser270Pro) | CAAGTTCYCCGAGGTGAGTCCGG, AAGTTCYCCGAGGTGAGTCCGGG, AGTTCYCCGAGGTGAGTCCGGGG | Centromeric instability of chromosomes 1, 9 and 16 and immunodeficiency |
| 121909028 | NM_000492.3(CFTR):c.3857T>C (p.Phe1286Ser) | AGCCTYTGGAGTGATACCACAGG | Cystic fibrosis |
| 121909135 | NM_000085.4(CLCNKB):c.1294T>C (p.Tyr432His) | CTTTGTCYATGGTGAGTCTGGGG | Bartter syndrome type 3 |
| 121909143 | NM_001300.5(KLF6):c.506T>C (p.Leu169Pro) | GGAGCYGCCCTCGCCAGGGAAGG | Progressive pseudorheumatoid dysplasia |
| 121909182 | NM_001089.2(ABCA3):c.302T>C (p.Leu101Pro) | GCACYTGTGATCAACATGCGAGG | Surfactant metabolism dysfunction, pulmonary, 3 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121909200 | NM_000503.5(EYA1):c.1459T>C (p.Ser487Pro) | CACTCYCGCTCATTCACTCCGG | Melnick-Fraser syndrome |
| 121909247 | NM_004970.2(IGFALS):c.1618T>C (p.Cys540Arg) | GGACYGTGGCTGCCCTCTCAAGG | Acid-labile subunit deficiency |
| 121909253 | NM_005570.3(LMAN1):c.2T>C (p.Met1Thr) | AGAYGGCGGATCCAGGCAAAGG | Combined deficiency of factor V and factor VIII, 1 |
| 121909385 | NM_000339.2(SLC12A3):c.1868T>C (p.Leu623Pro) | CAACCYGGCCCTCAGCTACTCGG | Familial hypokalemia-hypomagnesemia |
| 121909497 | NM_002427.3(MMP13):c.224T>C (p.Phe75Ser) | TTCTYCGGCTTAGAGGTGACTGG | Spondyloepimetaphyseal dysplasia, Missouri type |
| 121909508 | NM_000751.2(CHRND):c.188T>C (p.Leu63Pro) | AACCYCATCTCCCTGGTGAGAGG | MYASTHENIC SYNDROME, CONGENITAL, 3B, FAST-CHANNEL |
| 121909519 | NM_001100.3(ACTA1):c.287T>C (p.Leu96Pro) | CGAGCYTCGCGTGGCTCCCGAGG | Nemaline myopathy 3 |
| 121909572 | NM_000488.3(SERPINC1):c.667T>C (p.Ser223Pro) | TGGGTGYCCAATAAGACCGAAGG | Antithrombin III deficiency |
| 121909677 | NM_000821.6(GGCX):c.896T>C (p.Phe299Ser) | TATGTYCTCCTACGTCATGCTGG | Pseudoxanthoma elasticum-like disorder with multiple coagulation factor deficiency |
| 121909727 | NM_001018077.1(NR3C1):c.2209T>C (p.Phe737Leu) | CTATTGCYTCCAAACATTTTTGG | Glucocorticoid resistance, generalized |
| 139573311 | NM_000492.3(CFTR):c.1400T>C (p.Leu467Pro) | TTCACYTCTAATGTGATTATGG, TCACYTCTAATGGTGATTATGGG | Cystic fibrosis |
| 121912441 | NM_000454.4(SOD1):c.341T>C (p.Ile114Thr) | CATCAYTGGCCGCACACTGGTGG | Amyotrophic lateral sclerosis type 1 |
| 121912446 | NM_000454.4(SOD1):c.434T>C (p.Leu145Ser) | CGTTYGGCTTGTGGTGTAATTGG, GTTYGGCTTGTGTGGTGTAATTGGG | Amyotrophic lateral sclerosis type 1 |
| 121912463 | NM_000213.3(ITGB4):c.1684T>C (p.Cys562Arg) | GGCCAGYGTGTGTGTGAGCCTGG | Epidermolysis bullosa with pyloric atresia |
| 121912492 | NM_022292.3(LAIVIB2):c.961T>C (p.Cys321Arg) | CCTCAACYGCGAGCAGTGTCAGG | Nephrotic syndrome, type 5, with or without ocular abnormalities |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base to be edited,
e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397516659 | NM_001399.4(EDA):c.2T>C (p.Met1Thr) | GGCCAYGGGCTACCCGGAGGTGG | Hypohidrotic X-linked ectodermal dysplasia |
| 111033589 | NM_021044.2(DHH):c.485T>C (p.Leu162Pro) | GTTGCYGGCGCGCCTCGCAGTGG | 46, XY gonadal dysgenesis, complete, dhh-related |
| 111033622 | NM_000206.2(IL2RG):c.343T>C (p.Cys115Arg) | TGGCYGTCAGTTGCAAAAAAAGG | X-linked severe combined immunodeficiency |
| 1219126613 | NM_001041.3(SI):c.1859T>C (p.Leu620Pro) | ATGCYGGAGTTCAGTTTGTTTGG | Sucrase-isomaltase deficiency |
| 121912619 | NM_016180.4(SLC45A2):c.1082T>C (p.Leu361Pro) | GAGTTYCYCATTTACGAAAGAGG | Oculocutaneous albinism type 4 |
| 61750581 | NM_000552.3(VWF):c.4837T>C (p.Ser1613Pro) | CTGCCYCTGATGAGATCAAGAGG | von Willebrand disease, type 2a |
| 121912653 | NM_000546.5(TP53):c.755T>C (p.Leu252Pro) | CATCCYCACCATCATCACACTGG | Li-Fraumeni syndrome 1 |
| 111033683 | NM_000155.3(GALT):c.386T>C (p.Met129Thr) | AGTCAYGTGCTTCCACCCCTGG | Deficiency of UDPglucose-hexose-1-phosphate uridylyltransferase |
| 111033752 | NM_000155.3(GALT):c.677T>C (p.Leu226Pro) | CAGGAGYACTCAGGAGGTGGG | Deficiency of UDPglucose-hexose-1-phosphate uridylyltransferase |
| 121912729 | NM_000039.1(APOA1):c.593T>C (p.Leu198Ser) | GCGCTYGGCCGCGCGCCTTGAGG | Familial visceral amyloidosis, Ostertag type |
| 769452 | NM_000041.3(APOE):c.137T>C (p.Leu46Pro) | AACYGGGCACTGGGTCGCTTTTGG | |
| 121912762 | NM_016124.4(RHD):c.329T>C (p.Leu110Pro) | ACACYGTTCAGTTATTGGGATGG | |
| 111033824 | NM_000155.3(GALT):c.1138T>C (p.Ter380Arg) | CGCCYGACCACGCCGACCACAGG, GCCYGACCACGCCGACCACAGGG | Deficiency of UDPglucose-hexose-1-phosphate uridylyltransferase |
| 111033832 | NM_000155.3(GALT):c.980T>C (p.Leu327Pro) | TCCYGCGTCTGCCACTGTCCGG | Deficiency of UDPglucose-hexose-1-phosphate uridylyltransferase |
| 730881974 | NM_000455.4(STK11):c.545T>C (p.Leu182Pro) | GGGAACCYGCTGCTCACCACCGG, AACCYGCTGCTCACCACCGGTGG | Hereditary cancer-predisposing syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 1064644 | NM_000157.3(GBA):c.703T>C (p.Ser235Pro) | GGGYCACTCAAGGGACAGCCCGG | Gaucher disease |
| 796052090 | NM_138413.3(HOGA1):c.533T>C (p.Leu178Pro) | GGACCYGCCTGTGGATGCAGTGG | Primary hyperoxaluria, type III |
| 1221913141 | NM_000208.2(INSR):c.779T>C (p.Leu260Pro) | CTACCYGGACGGCAGGTGTGTGG | Leprechaunism syndrome |
| 1221913272 | NM_006218.2(PIK3CA):c.1258T>C (p.Cys420Arg) | GGAACACYGTCCATTGGCATGGG, GAACACYGTCCATTGGCATGGGG | Congenital lipomatous overgrowth, vascular malformations, and epidermal nevi, Neoplasm of ovary, PIK3CA Related Overgrowth Spectrum |
| 61751310 | NM_000552.3(VWF):c.8317T>C (p.Cys2773Arg) | GCTCCYGCTGCTCTCCGACACGG | von Willebrand disease, type 2a |
| 312262799 | NM_024408.3(NOTCH2):c.1438T>C (p.Cys480Arg) | TTCACAYGTCTGTGCATGCCAGG | Alagille syndrome 2 |
| 1221913570 | NM_000426.3(LAIV1A2):c.7691T>C (p.Leu2564Pro) | ATCATTCYTTTGGGAAGTGGAGG, TCATTCYTTTGGGAAGTGGAGGG | Merosin deficient congenital muscular dystrophy |
| 1221913640 | NM_000257.3(MYH7):c.1046T>C (p.Met349Thr) | AACTCCAYGTATAAGCTGACAGG | Familial hypertrophic cardiomyopathy 1, Cardiomyopathy |
| 1221913642 | NM_000257.3(MYH7):c.1594T>C (p.Ser532Pro) | CATCATGYCCATCCTGGAAGAGG | Dilated cardiomyopathy 1S |
| 119463996 | NM_001079802.1(FKTN):c.527T>C (p.Phe176Ser) | GTAGTCYTTCATGAGAGAGTGG | Limb-girdle muscular dystrophy- |
| 587776456 | NM_002049.3(GATA1):c.1240T>C (p.Ter414Arg) | GCTCAYGAGGGCACAGAGCATGG | GATA-1-related thrombocytopenia with dyserythropoiesis |
| 63750654 | NM_000184.2(HBG2):c.-228T>C | ATGCAAAVATCTGTCTGAAACGG | Fetal hemoglobin quantitative trait locus 1 |
| 587776519 | NM_001999.3(FBN2):c.3725-15A>G | AGCAYTGCAACCACATTGTCAGG | Congenital contractural arachnodactyly |
| 78365220 | NM_000402.4(G6PD):c.473T>C (p.Leu158Pro) | TGCCCYCCACCTGGGGTCACAGG | Anemia, nonspherocytic hemolytic, due to G6PD deficiency |
| 63750741 | NM_000179.2(MSH6):c.1346T>C (p.Leu449Pro) | CTGGGGCYGGTATTCATGAAAGG | Hereditary Nonpolyposis Colorectal Neoplasms |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 587776914 | NM_017565.3(FAM20A):c.590-2A>G | GTAATCYGCAAAGGAGGAGAAGG, TAATCYGCAAAGGAGGAGAAGG | Enamel-renal syndrome |
| 5030809 | NM_000551.3(VHL):c.292T>C (p.Tyr98His) | CCCYACCCAACCGCTGCCGCTGG | Von Hippel-Lindau syndrome, Hereditary cancer-predisposing syndrome |
| 199476132 | m.5728T>C | CAATCYACTTCTCCCGCGCCGG, AATCYACTTCTCCCGCCGCCGGG | Cytochrome-c oxidase deficiency, Mitochondrial complex I deficiency |
| 62637012 | NM_014336.4(AIPL1):c.715T>C (p.Cys239Arg) | CTGCCAGYGCCTGCTGAAGAAGG, CCAGYGCCTGCTGAAGAAGGAGG | Leber congenital amaurosis 4 |
| 199476199 | NM_207352.3(CYP4V2):c.1021T>C (p.Ser341Pro) | AAACTGGYCCTTATACCTGTTGG, AACTGGYCCTTATACCTGTTGGG | Bietti crystalline comeoretinal dystrophy |
| 587777183 | NM_006702.4(PNPLA6):c.3053T>C (p.Phe1018Ser) | CCTYTAACCGCAGCATCCATCGG | Boucher Neuhauser syndrome |
| 199476389 | NM_000487.5(ARSA):c.899T>C (p.Leu300Ser) | GGTCTCTYGCGGTGTGAAAGGG | Metachromatic leukodystrophy |
| 199476398 | NM_016599.4(MYOZ2):c.142T>C (p.Ser48Pro) | TTAYCCCATTCAGTAACCGTGG | Familial hypertrophic cardiomyopathy 16 |
| 119456967 | NM_001037633.1(SIL1):c.1370T>C (p.Leu457Pro) | TTGCYGAAGGAGCTGAGATGAGG | Marinesco-Sj\xc3\xb6gren syndrome |
| 730882253 | NM_006888.4(CALM1):c.268T>C (p.Phe90Leu) | GGCAYTCCGAGTCTTTGACAAGG | Long QT syndrome 14 |
| 587777283 | NM_012338.3(TSPAN12):c.413A>G (p.Tyr138Cys) | TAATCCAYAATTTGTCATCCTGG | Exudative vitreoretinopathy 5 |
| 587777306 | NM_015884.3(MBTPS2):c.1391T>C (p.Phe464Ser) | GCTYTGCTTTGGATGGACAATGG | Palmoplantar keratoderma, mutilating, with periorificial keratotic plaques, X-linked |
| 56378716 | NM_000250.1(MPO):c.752T>C (p.Met251Thr) | TCACTCAYGTTCATGCAATGGGG | Myeloperoxidase deficiency |
| 587777390 | NM_005026.3(PIK3CD):c.1246T>C (p.Cys416Arg) | GCAGGACYGCCCCATTGCCTGGG | Activated PI3K-delta syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 587777480 | NM_003108.3(SOX11):c.178T>C (p.Ser60Pro) | TATGGYCCAAGATCGAACGCAGG | Mental retardation, autosomal dominant 27 |
| 587777663 | NM_001288767.1(ARMC5):c.1379T>C (p.Leu460Pro) | GCCCGACYGCGGATGCTGGTGG | Acth-independent macronodular adrenal hyperplasia 2 |
| 61753033 | NM_000350.2(ABCA4):c.5819T>C (p.Leu1940Pro) | AAGGCYACATGACTAACCAAGG | Stargardt disease, Stargardt disease 1, Cone-rod dystrophy 3 |
| 200488568 | NM_002972.3(SBF1):c.4768A>G (p.Thr1590Ala) | CAGGCYCYCCTCTTGCTCAGCCGG | Charcot-Marie-Tooth disease, type 4B3 |
| 132630274 | NM_000377.2(WAS):c.809T>C (p.Leu270Pro) | CGGAGTCYGTTCTCCAGGGCAGG | Severe congenital neutropenia X-linked |
| 132630308 | NM_001399.4(EDA):c.181T>C (p.Tyr61His) | CTGCYACCTAGAGTTGCGCTCGG | Hypohidrotic X-linked ectodermal dysplasia |
| 60934003 | NM_170707.3(LMNA):c.1589T>C (p.Leu530Pro) | ACGGCTCYCATCAACTCCACTGG, CGGCTCYCATCAACTCCACTGGG, GGCTCYCATCAACTCCACTGGGG | Benign scapuloperoneal muscular dystrophy with cardiomyopathy |
| 180177160 | NM_000030.2(AGXT):c.1076T>C (p.Leu359Pro) | GGTGCYGCGGATCGGCCTGCTGG, GTGCYGCGGATCGGCCTGCTGGG | Primary hyperoxaluria, type I |
| 180177222 | NM_000030.2(AGXT):c.449T>C (p.Leu150Pro) | GTGCYGCTGTTCTTAACCACGG, TGCYGCTGTTCTTAACCACGGG | Primary hyperoxaluria, type I |
| 180177254 | NM_000030.2(AGXT):c.661T>C (p.Ser221Pro) | GCTCATCYCCTTCAGTGACAAGG | Primary hyperoxaluria, type I |
| 180177264 | NM_000030.2(AGXT):c.757T>C (p.Cys253Arg) | GGGGCYGTGACGACCAGCCCAGG | Primary hyperoxaluria, type I |
| 180177293 | NM_000030.2(AGXT):c.893T>C (p.Leu298Pro) | GTATCYGCATGGCGGCCTGCAGG | Primary hyperoxaluria, type I |
| 376785840 | NM_001282227.1(CECR1):c.1232A>G (p.Tyr411Cys) | GAAATCAYAGGACAAGCTTTGG | Polyarteritis nodosa |
| 587779393 | NM_000257.3(MYH7):c.4937T>C (p.Leu1646Pro) | GAGCCYCCAGAGCTTGTTGAAGG | Myopathy, distal, 1 |
| 587779410 | NM_012434.4(SLC17A5):c.500T>C (p.Leu167Pro) | ATTGTACYCAGAGCACTAGAAGG | Sialic acid storage disease, severe infantile type |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 587779513 | NM_000090.3(COL3A1):c.2337+2T>C (p.Gly762_Lys779del) | AGGYAACCCTTAATACTACCTGG | Ehlers-Danlos syndrome, type 4 |
| 777539013 | NM_020376.3(PNPLA2):c.757+2T>C | GAACGGYGCGCGACCCCGGCGG, AACGGYGCGCGGACCCCGGCGGG | Neutral lipid storage disease with myopathy |
| 34557412 | NM_012452.2(TNFRSF13B):c.310T>C (p.Cys104Arg) | ACTTCYGTGAGAACAAGCTCAGG | Immunoglobulin A deficiency 2, Common variable |
| 796052970 | NM_001165963.1(SCN1A):c.1094T>C (p.Phe365Ser) | CAAGCTYTGATACCTTCAGTTGG, AAGCTYTGATACCTTCAGTTGGG | not provided |
| 724159989 | NC_012920.1:m.7505T>C | CCTCCAYGACTTTTTCAAAAAGG | Deafness, nonsyndromic sensorineural, mitochondrial |
| 796053222 | NM_014191.3(SCN8A):c.4889T>C (p.Leu1630Pro) | CGTCYGATCAAAGGCGCCAAAGG, GTCYGATCAAAGGCGCCAAAGGG | not provided |
| 118192127 | NM_000540.2(RYR1):c.10817T>C (p.Leu3606Pro) | TACTACCYGGACCAGGTGGGTGG, ACTACCYGGACCAGGTGGGTGGG, CTACCYGGACCAGGTGGGTGGGG | Central core disease |
| 118192170 | NM_000540.2(RYR1):c.14693T>C (p.Ile4898Thr) | AGGCAYTGGGGACGAGATCGAGG | Malignant hyperthermia susceptibility type 1, Central core disease |
| 121917703 | NM_005247.2(FGF3):c.466T>C (p.Ser156Pro) | GTACGTGYCTGTGAACGGCAAGG, TACGTGYCTGTGAACGGCAAGGG | Deafness with labyrinthine aplasia microtia and microdontia (LAIVIM) |
| 690016549 | NM_005211.3(CSF1R):c.2450T>C (p.Leu817Pro) | CCGCCYGCCTGTGAAGTGGATGG | Hereditary diffuse leukoencephalopathy h spheroids |
| 690016552 | NM_005211.3(CSF1R):c.2566T>C (p.Tyr856His) | GAATCCCYACCCTGGCATCCTGG | Hereditary diffuse leukoencephalopathy with spheroids |
| 121917738 | NM_001098668.2(SFTPA2):c.593T>C (p.Phe198Ser) | GGGAGACTYCCGCTACTCAGATGG, GAGACTYCCGCTACTCAGATGGG | Idiopathic fibrosing alveolitis, chronic form |
| 690016559 | NM_005211.3(CSF1R):c.1957T>C (p.Cys653Arg) | AGCCYGTACCCATGGAGGTAAGG, GCCYGTACCCATGGAGGTAAGGG | Hereditary diffuse leukoencephalopathy with spheroids |
| 690016560 | NM_005211.3(CSF1R):c.2717T>C (p.Ile906Thr) | GCAGAYCTGCTCCTTCCTTCAGG | Hereditary diffuse leukoencephalopathy with spheroids |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121917769 | NM_003361.3(UMOD):c.376T>C (p.Cys126Arg) | GGCCACAYGTGTCAATGTGGTGG, GCCACAYGTGTCAATGTGTGGG | Familial juvenile gout |
| 121917773 | NM_003361.3(UMOD):c.943T>C (p.Cys315Arg) | ATGGCACYGCCAGTGCAAACAGG | Glomerulocystic kidney disease with hyperuricemia and isosthenuria |
| 121917818 | NM_007255.2(B4GALT7):c.617T>C (p.Leu206Pro) | TGCYCTCCAAGCAGCACTACCGG | Ehlers-Danlos syndrome progeroid type |
| 121917824 | NM_021615.4(CHST6):c.827T>C (p.Leu276Pro) | GGACCYGGCGCGGGAGCCGCTGG | Macular corneal dystrophy Type I |
| 121917848 | NM_000452.2(SLC10A2):c.728T>C (p.Leu243Pro) | TTTCYTCTGGCTAGAATTGCTGG | Bile acid malabsorption, primary |
| 121918006 | NM_000478.4(ALPL):c.1306T>C (p.Tyr436His) | TGGACAYATGGTGAGACCTCCAGG | Infantile hypophosphatasia |
| 121918010 | NM_000478.4(ALPL):c.979T>C (p.Phe327Leu) | CAAAGGCYTCTCTTGCTGGTGG, GGCYTCTCTTGCTGGTGGAAGG | Infantile hypophosphatasia |
| 121918088 | NM_000371.3(TTR):c.400T>C (p.Tyr134His) | CCCCYACTCCTATTCCACCACGG | |
| 121918110 | NM_001042465.1(PSAP):c.1055T>C (p.Leu352Pro) | GAAGCYGCCGAAGTCCCTGTCGG | Gaucher disease, atypical, due to saposin C deficiency |
| 121918137 | NM_003730.4(RNASET2):c.550T>C (p.Cys184Arg) | CCAGYGCCTTCCACCAAGCCAGG | Leukoencephalopathy, cystic, without megalencephaly |
| 121918191 | NM_001127628.1(FBP1):c.581T>C (p.Phe194Ser) | GGAGTYCATTTTGGTGGACAAGG | Fructose-biphosphatase deficiency |
| 121918306 | NM_006946.2(SPTBN2):c.758T>C (p.Leu253Pro) | ACCAAGCYGTGGATCCCGAAGG, AAGCYGCTGGATCCCGAAGGTGG, AGCYGCTGGATCCCGAAGGTGGG | Spinocerebellar ataxia 5 |
| 121918505 | NM_000141.4(FGFR2):c.799T>C (p.Ser267Pro) | AATGCCYCCACAGTGGTCGGAGG | Pfeiffer syndrome, Neoplasm of stomach |
| 121918643 | NM_003126.2(SPTA1):c.620T>C (p.Leu207Pro) | GTGGAGCYGGTAGCTAAAGAAGG, TGGAGCYGGTAGCTAAAGAAGGG | Hereditary pyropoikilocytosis, Elliptocytosis 2 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121918646 | NM_001024858.2(SPTB):c.604T>C (p.Trp202Arg) | CTCCAGCYGGAAGGATGGCTTGG | Spherocytosis type 2 |
| 121918648 | NM_001024858.2(SPTB):c.6055T>C (p.Ser2019Pro) | ATGCCYCTGTGGCTGAGGCGTGG | |
| 727504166 | NM_000543.4(SMPD1):c.475T>C (p.Cys159Arg) | TGAGGCCYGTGGCCTGCTCCTGG, GAGGCCYGTGGCCTGCTCCTGGG | Niemann-Pick disease, type A, Niemann-Pick disease, type B |
| 193922915 | NM_000434.3(NEU1):c.1088T>C (p.Leu363Pro) | CAGCYATGGCCAGGCCCCAGTGG | Sialidosis, type II |
| 727504419 | NM_000501.3(ELN):c.889+2T>C | CAGGYAACATCTGTCCCAGCAGG, AGGYAACATCTGTCCCAGCAGGG | Supravalvar aortic stenosis |
| 376395543 | NM_000256.3(MYBPC3):c.26-2A>G | GAGACYGAAGGGCCAGGTGGAGG | Primary familial hypertrophic cardiomyopathy, Familial hypertrophic cardiomyopathy 4, Cardiomyopathy |
| 1169305 | NM_000545.6(RNIF1A):c.1720G>A (p.Gly574Ser) | GATGCYGGCAGGGTCCTGGCTGG, ATGCYGGCAGGGTCCTGGCTGGG, TGCYGGCAGGGTCCTGGCTGGGG | Maturity-onset diabetes of the young, type 3 |
| 730880130 | NM_000527.4(LDLR):c.1468T>C (p.Trp490Arg) | CTACYGGACCGACTCTGTCCTGG, TACYGGACCGACTCTGTCCTGGG | Familial hypercholesterolemia |
| 281860286 | NM_018713.2(SLC30A10):c.500T>C (p.Phe167Ser) | GGCGCTTYCGGGGGGCCTCAGGG | Hypermanganesemia with dystonia, polycythemia and cirrhosis |
| 730880306 | NM_145693.2(LPIN1):c.441+2T>C | AAGGYACCGGGGCCTCGCGCGG, AGGYACCGGGGCCTCGCGCGGG | Myoglobinuria, acute recurrent, autosomal recessive |
| 74315452 | NM_000454.4(SOD1):c.338T>C (p.Ile113Thr) | TTGCAYCATTGGCCGCACACTGG | Amyotrophic lateral sclerosis type 1 |
| 730880455 | NM_000169.2(GLA):c.4IT>C (p.Leu14Pro) | CGCGCCYTGCGCTTCGCTTCCTGG | not provided |
| 267606656 | NM_054027.4(ANKH):c.1015T>C (p.Cys339Arg) | AGCTCYGTTTCGTGATGTTTTGG | Craniometaphyseal dysplasia, autosomal dominant |
| 267606687 | NM_033409.3(SLC52A3):c.1238T>C (p.Val413Ala) | AGTTACGYCAAGGTGATGCTGGG | Brown-Vialetto-Van laere syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 267606721 | NM_001928.2(CFD):c.640T>C (p.Cys214Arg) | GGTGYGCGGGGCGTGCTCGAGG, GTGYGCGGGGCCTGCTCGAGG | Complement factor d deficiency |
| 267606747 | NM_001849.3(COL6A2):c.2329T>C (p.Cys777Arg) | CGCCYGCGACAAGCCACAGCAGG | Ullrich congenital muscular dystrophy |
| 431905515 | NM_001044.4(SLC6A3):c.671T>C (p.Leu224Pro) | CTGCACCYYCCACCAGAGCCATGG | Infantile Parkinsonism-dystonia |
| 267606857 | NM_000180.3(GUCY2D):c.2846T>C (p.Ile949Thr) | AGAGAYCGCCAACATGTCACTGG | Cone-rod dystrophy 6 |
| 267606880 | NM_022489.3(INF2):c.125T>C (p.Leu42Pro) | GCTGCYCCAGATGCCCTCTGTGG | Focal segmental glomerulosclerosis 5 |
| 515726191 | NM_015713.4(RRM2B):c.581A>G (p.Glu194Gly) | AACTCCYYCTACAGCAGCAAAGG | RRM2B-related mitochondrial disease |
| 267606917 | NM_004646.3(NPHS1):c.793T>C (p.Cys265Arg) | GCTGCCYGCGYGTGGCCCCGAGGGG, CTGCCGYGCGTGGCCCCGAGGGGG | Finnish congenital nephrotic syndrome |
| 267607104 | NM_001199107.1(TBC1D24):c.751T>C (p.Phe251Leu) | CAAGTTCYTCCACAAGGTGAGGG, TTCYTCCACAAGGTGAGGGCCGG | Myoclonic epilepsy, familial infantile |
| 267607182 | NM_144631.5(ZNF513):c.1015T>C (p.Cys339Arg) | TGGGCGCYGCATGCGAGGAGAGG, CGCYGCATGCGAGGAGAGGCTGG | Retinitis pigmentosa 58 |
| 267607211 | NM_000229.1(LCAT):c.508T>C (p.Trp170Arg) | TATGACYGCGGCTGGAGCCCGG | Norum disease |
| 267607215 | NM_016269.4(LEF1):c.181T>C (p.Ser61Pro) | GAACGAGYCTGAAATCATCCCGG | Sebaceous tumors, somatic |
| 587783580 | NM_178151.2(DCX):c.683T>C (p.Leu228Pro) | AAAAAAYCTACACTCTGGATGG | Heterotopia |
| 587783644 | NM_004004.5(GM2):c.107T>C (p.Leu36Pro) | GATCCYCGTTGTGGCTGCAAAGG | Hearing impairment |
| 587783653 | NM_005682.6(ADGRG1):c.1460T>C (p.Leu487Pro) | CCCTGCYCACCTGCCTTTCCTGG | Polymicrogyria, bilateral frontoparietal |
| 587783863 | NM_000252.2(MTM1):c.958T>C (p.Ser320Pro) | GGAAYCTTTAAAAAAGTGAAGG | Severe X-linked myotubular myopathy |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 267607751 | NM_000249.3(MLH1):c.453+2T>C | ATCACGGYAAGAATGGTACATGG, TCACGGYAAGAATGGTACATGG | Hereditary Nonpolyposis Colorectal Neoplasms |
| 119103227 | NM_000411.6(HLCS):c.710T>C (p.Leu237Pro) | CTATCYTTCTCAGGAGGAGGAAGG | Holocarboxylase synthetase deficiency |
| 119103237 | NM_005787.5(ALG3):c.211T>C (p.Trp71Arg) | GATTGACYGGAAGGCCTACATGG | Congenital disorder of glycosylation type 1D |
| 398122806 | NM_003172.3(SURF1):c.679T>C (p.Trp227Arg) | CCACYGGCATTATCGAGACCTGG | Congenital myasthenic syndrome, acetazolamide-responsive |
| 80338747 | NM_004525.2(LRP2):c.7564T>C (p.Tyr2522His) | GTACCTGYACTGGGCTGACTGGG | Donnai Barrow syndrome |
| 398122838 | NM_001271723.1(FBXO38):c.616T>C (p.Cys206Arg) | TTCCTYGTATCCCAATGCTAAGG | Distal hereditary motor neuronopathy 2D |
| 398122989 | NM_014495.3(ANGPTL3):c.883T>C (p.Phe295Leu) | ACAAAACYTCAATGAAACGTGGG | Hypobetalipoproteinemia, familial, 2 |
| 80338945 | NM_004004.5(GM2):c.269T>C (p.Leu90Pro) | GCTCCYAGTGGGCCATGCACGTGG | Deafness, autosomal recessive 1A, Hearing impairment |
| 80338956 | NM_000334.4(SCN4A):c.2078T>C (p.Ile693Thr) | AAGATCAYTGGCAATTCAGTGGG, AGATCAYTGGCAATTCAGTGGGG, GATCAYTGGCAATTCAGTGGGGG | Hyperkalemic Periodic Paralysis Type 1, Paramyotonia congenita of von Eulenburg |
| 267608131 | NM_000179.2(MSH6):c.4001+2T>C | CGGYAACTAACTAACTATAATGG | Hereditary Nonpolyposis Colorectal Neoplasms |
| 587784573 | NM_004963.3(GUCY2C):c.2782T>C (p.Cys928Arg) | TCCCYGTGCTGCTGGAGTTGTGG, CCCYGTGCTGCTGGAGTTGTGGG | Meconium ileus |
| 267608511 | NM_003159.2(CDKL5):c.659T>C (p.Leu220Pro) | CCAACYTTTTACTATTCAGAAGG | Early infantile epileptic encephalopathy 2 |
| 373842615 | NM_000118.3(ENG):c.1273-2A>G | CCGCCYGCGGGATAAAGCCAGG, CGCCYGCGGGATAAAGCCAGGG | Haemorrhagic telangiectasia 1 |
| 185492581 | NM_000335.4(SCN5A):c.376A>G (p.Lys126Glu) | GAATCTYCACAGCCGCTCTCCGG | Brugada syndrome |
| 200533370 | NM_133499.2(SYN1):c.1699A>G (p.Thr567Ala) | GATGYCTGACGGGTAGCCTGTGG, ATGYCTGACGGGTAGCCTGTGGG | Epilepsy, X-linked, with variable learning disabilities and behavior disorders, not specified |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base to be edited,
e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 118203981 | NM_148960.2(CLDN19):c.269T>C (p.Leu90Pro) | GCTCCYGGGCTTCGTGGCCATGG | Hypomagnesemia 5, renal, with ocular involvement |
| 137853892 | NM_001235.3(SERPINH1):c.233T>C (p.Leu78Pro) | GTCGCYAGGGCTCGTGTCGCTGG, TCGCYAGGGCTCGTGTCGCTGGG | Osteogenesis imperfecta type 10 |
| 118204024 | NM_000263.3(NAGLU):c.142T>C | GGCCGACYTCTCCGTGTCGGTGG | Mucopolysaccharidosis,MPS-III-B |
| 690016563 | NM_005211.3(CSF1R):c.1745T>C (p.Leu582Pro) | CAACCYGCAGTTTGGTGAGATGG | Hereditary diffuse leukoencephalopathy with spheroids |
| 58380626 | NM_000526.4(KRT14):c.1243T>C (p.Tyr415His) | CGCCACCYACCGCCGCCTGCTGG, CACCYACCGCCGCCTGCTGGAGG, ACCYACCGCCGCCTGCTGGAGGG | Epidermolysis bullosa herpetiformis, Dowling- Meara |
| 113994151 | NM_207346.2(TSEN54):c.277T>C (p.Ser93Pro) | TTGAAGYCTCCCGCGGTGAGCGG, AAGYCTCCCGCGGTGAGCGGCGG | Pontocerebellar hypoplasia type 4 |
| 113994206 | NM_004937.2(CTNS):c.473T>C (p.Leu158Pro) | TGGTCYGAGCTTCGACTTCGTGG | Cystinosis |
| 62516109 | NM_000277.1(PAH):c.638T>C (p.Leu213Pro) | CCACTTCYTGAAAAGTACTGTGG | Phenylketonuria |
| 370011798 | NM_001302946.1(TRNT1):c.668T>C (p.Ile223Thr) | GCAAYTGCAGAAAATGCAAAAGG | Sideroblastic anemia with B-cell immunodeficiency, periodic fevers, and developmental delay |
| 62517167 | NM_000277.1(PAH):c.293T>C (p.Leu98Ser) | AAGATCYGAGGCATGACATTGG | Mild non-PKU hyperphenylalanem a |
| 120021720 | NM_001918.3(DBT):c.1150G>A (p.Gly384Ser) | GACYCACAGAGCCCAATTTCTGG | Intermediate maple syrup urine disease type 2 |
| 104886289 | NM_000495.4(COL4A5):c.4756T>C (p.Cys1586Arg) | TCCCCATYGTCCTTCAGGGATGG | Alport syndrome, X-linked recessive |
| 370471013 | NC_012920.1:m.5559A>G | CAACYTACTGAGGCGTTTGAAGG | Leigh disease |
| 121434215 | NM_000487.5(ARSA):c.410T>C (p.Leu137Pro) | GCCTTCCYGCCCCCCCATCAGG | Metachromatic leukodystrophy, adult type |
| 386134128 | NM_000096.3(CP):c.1123T>C (p.Tyr375His) | ACACTACYACATTGCCCGTGAGG | Deficiency of ferroxidase |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121434275 | NM_001127328.2(ACADM):c.1136T>C (p.Ile379Thr) | GTGCAGAYACTTGGAGGCAATGG | Medium-chain acyl-coenzyme A dehydrogenase deficiency |
| 121434276 | NM_001127328.2(ACADM):c.1136T>C (p.Cys248Arg) | CAGCGAYGTTCAGATACTAGAGG | Medium-chain acyl-coenzyme A dehydrogenase deficiency |
| 121434284 | NM_002225.3(IVD):c.134T>C (p.Leu45Pro) | ATGGGCYAAGCGAGGAGCAGAGG | ISOVALERIC ACIDEMIA, TYPE I |
| 121434334 | NM_005908.3(MANBA):c.1513T>C (p.Ser505Pro) | ATTACGYCCAGTCCTACAAATGG, TTACGYCCAGTCCTACAAATGGG, TACGYCCAGTCCTACAAATGGGG | Beta-D-mannosidosis |
| 121434366 | NM_000159.3(GCDH):c.883T>C (p.Tyr295His) | CGCCCGGYACGGCATCGCGTGGG, GCCCGGYACGGCATCGCGTGGGG | Glutaric aciduria, type 1 |
| 60715293 | NM_000424.3(KRT5):c.541T>C (p.Ser181Pro) | GTTTGCCYCCTTCATCGACAAGG | Epidermolysis bullosa herpetiformis, Dowling-Meara |
| 121434409 | NM_001003722.1(GLE1):c.2051T>C (p.Ile684Thr) | AAGGACAYTCCTGTCCCCAAGGG | Lethal arthrogryposis with anterior horn cell disease |
| 121434434 | NM_001287.5(CLCN7):c.2297T>C (p.Leu766Pro) | GGGCCYCGCGCACCTGGTGGTGG | Osteopetrosis autosomal recessive 4 |
| 121434455 | NM_000466.2(PEX1):c.1991T>C (p.Leu664Pro) | GATGACCYTGACCTCATTGCTGG | Zellweger syndrome |
| 199422317 | NM_001099274.1(TINF2):c.862T>C (p.Phe288Leu) | CTGYTTCCCTTTAGGAATCTCGG | Aplastic anemia |
| 104895221 | NM_001065.3(TNFRSF1A):c.349T>C (p.Cys117Arg) | CTCTTCTYGCACAGTGGACCGGG | TNF receptor-associated periodic fever syndrome (TRAPS) |
| 137854459 | NM_000138.4(FBN1):c.4987T>C (p.Cys1663Arg) | GGGACAYGTTACAACACCGTTGG | Marfan syndrome |
| 387907075 | NM_024027.4(COLEC11):c.505T>C (p.Ser169Pro) | CAGCTGYCCTGCCAGGGCCGCGG, AGTGYCCTGCCAGGGCCGCGGG, GCTGYCCTGCCAGGGCCGCGGGG, CTGYCCTGCCAGGGCCGCGGGGG | Carnevale syndrome |
| 1048095 | NM_000352.4(ABCC8):c.674T>C (p.Leu225Pro) | TGCYGTCCAAAGGCACCTACTGG | Permanent neonatal diabetes mellitus |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 796065347 | NM_019074.3(DLL4):c.1168T>C (p.Cys390Arg) | GAAYGTCCCCCAACTTCACCGG | Adams-Oliver syndrome, ADAMS-OLIVER SYNDROME 6 |
| 137852347 | NM_000402.4(G6PD):c.1054T>C (p.Tyr352His) | AGGGYACCTGGACGACCCCACGG | Anemia, nonspherocytic hemolytic, due to G6PD deficiency |
| 74315327 | NM_213653.3(HFE2):c.302T>C (p.Leu101Pro) | GGACCYCGCCTTCCATTCGGCGG | Hemochromatosis type 2A |
| 137852579 | NM_000044.3(AR):c.2033T>C (p.Leu678Pro) | GTCCYGGAAGCCATTGAGCCAGG | |
| 137852636 | NM_001166107.1(IIMGCS2):c.520T>C (p.Phe174Leu) | CCCTCYTCAATGCTGCCAACTGG | mitochondria 3-hydroxy-3-methylglutaryl-CoA synthase deficiency |
| 137852661 | NM_033163.3(FGF8):c.118T>C (p.Phe40Leu) | TTCCCTGYTCCGGGCTGGCCGGG | Kallmann syndrome 6 |
| 121912967 | NM_005215.3(DCC):c.503T>C (p.Met168Thr) | AGCCCAYGCCAACAATCCACTGG | |
| 137852806 | NM_001039523.2(CHRNA1):c.901T>C (p.Phe301Leu) | TGTGYTCCTTCTGGTCATCGTGG | Myasthenic syndrome, congenital, fast-channel |
| 137852850 | NM_182760.3(SUMF1):c.463T>C (p.Ser155Pro) | GGGCACYCCTTTGTCTTTGAAGG | Multiple sulfatase deficiency |
| 137852886 | NM_000158.3(GBE1):c.671T>C (p.Leu224Pro) | AATGTACYACCAAGAATCAAAGG | Glycogen storage disease, type IV, GLYCOGEN STORAGE DISEASE IV, NONPROGRESSIVE HEPATIC |
| 137852911 | NM_000419.3(ITGA2B):c.641T>C (p.Leu214Pro) | CTGGTGCYTGGGGCTCCTGGCG | Glanzmann thrombasthenia |
| 137852948 | NM_138894.3(PKHD1):c.10658T>C (p.Ile3553Thr) | GAGCCCAYTGAAATACGCTCAGG | Polycystic kidney disease, infantile type |
| 137852964 | NM_024960.4(PANK2):c.178T>C (p.Ser60Pro) | ATTGACYCAGTCGATTCAATGG | |
| 137853020 | NM_006899.3(IDH3B):c.395T>C (p.Leu132Pro) | TGCGGCYGAGGTAGGTGGTCTGG, GCGGCYGAGGTAGGTGGTCTGGG | Retinitis pigmentosa 46 |
| 137853249 | NM_033500.2(HK1):c.1550T>C (p.Leu517Ser) | GACTTCYYGGCCCTGGATCTTGG, TTCTYGGCCCTGGATCTTGGAGG | Hemolytic anemia due to hexokinase deficiency |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 137853270 | NM_000444.5(PHEX):c.1664T>C (p.Leu555Pro) | AGCYCCAGAAGCCTTTCTTTTGG | Familial X-linked hypophosphatemic vitamin D refractory rickets |
| 137853325 | NM_003639.4(IKBKG):c.1249T>C (p.Cys417Arg) | TGGAGYGCATTGAGTAGGGCCGG | Hypohidrotic ectodermal dysplasia with immune deficiency, Hyper-IgM immunodeficiency, X-linked, with hypohidrotic ectodermal dysplasia |
| 289332769 | NM_002055.4(GFAP):c.1055T>C (p.Leu352Pro) | GGACCYGCTCAATGTCAAGCTGG | Alexander disease |
| 397507439 | NM_0027694.4(PRSS1):c.116T>C (p.Val39Ala) | TACCAGGYGTCCCTGAATTCTGG | Hereditary pancreatitis |
| 387906446 | NM_000132.3(F8):c.1729T>C (p.Ser577Pro) | AAAGAAYCTGTAGATCAAAGAGG | Hereditary factor VIII deficiency disease |
| 387906482 | NM_000133.3(F9):c.1031T>C (p.Ile344Thr) | ACGAACAYCTTCCTCAAATTGG | Hereditary factor IX deficiency disease |
| 387906508 | NM_000131.4(F7):c.983T>C (p.Phe328Ser) | GACGTYCTCTGAGAGGACGCTGG | Factor VII deficiency |
| 387906532 | NM_001040113.1(MYH11):c.3791T>C (p.Leu1264Pro) | GAAGCYGGAGGCGCCAGGTGCAGG | Aortic aneurysm, familial thoracic 4 |
| 387906658 | NM_002465.3(MYBPC1):c.2566T>C (p.Tyr856His) | CAAACCYATATCCGCAGAGTTGG | Distal arthrogryposis type 1B |
| 387906701 | NM_003491.3(NAA10):c.109T>C | TGGCCTTYCCTGGCCCCAGGTGG, GGCCTTYCCTGGCCCCAGGTGGG GACTTCAYTGAGGACCAGGGTGG, | N-terminal acetyltransferase deficiency |
| 387906717 | NM_000377.2(WAS):c.881T>C (p.Ile294Thr) | ACTTCAYTGAGGACCAGGGTGGG | Severe congenital neutropenia X-linked |
| 387906809 | NM_000287.3(PEX6):c.1601T>C (p.Leu534Pro) | CTTCYGGGCCGGGACCGTGATGG, TTCYGGGCCGGGACCGTGATGGG | Peroxisome biogenesis disorder 4B |
| 387906965 | NM_024513.3(FYCO1):c.4127T>C (p.Leu1376Pro) | CAGCCYGATCCCCATCACTGTGG | Cataract, autosomal recessive congenital 2 |
| 387906967 | NM_006147.3(IRF6):c.65T>C (p.Leu22Pro) | GCCYCTACCCTGGGCTCATCTGG | Van der Woude syndrome, Popliteal pterygium syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 387906982 | NM_025132.3(WDR19):c.20T>C (p.Leu7Pro) | TCTCACYGCTAGAAAAGACTTGG | Asphyxiating thoracic dystrophy 5 |
| 387907072 | NM_032446.2(MEGF10):c.2320T>C (p.Cys774Arg) | GGGCAGYGTACTTGCCGCACTGG | Myopathy, areflexia, respiratory distress, and dysphagia, early-onset, Myopathy, areflexia, respiratory distress, and dysphagia, early-onset, mild variant |
| 137854499 | NM_005502.3(ABCA1):c.6026T>C (p.Phe2009Ser) | GAGTYCTTTGCCCTTTTGAGAGG | Familial hypoalphalipoproteinemia |
| 387907117 | NM_000196.3(HSD11B2):c.1012T>C (p.Tyr338His) | CCGCCGCYATTACCCCGGCCAGG, CGCCGCYATTACCCCGGCCAGGG | Apparent mineralocorticoid excess |
| 387907170 | NM_004453.3(ETFDH):c.1130T>C (p.Leu377Pro) | CCAAAACYCACCTTTCCTGGTGG | |
| 387907205 | NM_033360.3(KRAS):c.211T>C (p.Tyr71His) | GGACCAGYACATGAGGACTGGGG, CCAGYACATGAGGACTGGGGAGG, CAGYACATGAGGACTGGGGAGGG | Cardiofaciocutaneous syndrome 2 |
| 387907240 | NM_024110.4(CARD14):c.467T>C (p.Leu56Pro) | CAGCAGCYGCAGGAGCACCTGGG | Pityriasis rubra pilaris |
| 387907282 | NM_152296.4(ATP1A3):c.2431T>C (p.Ser811Pro) | TGCCATCYCACTGGCGTACGAGG | Alternating hemiplegia of childhood 2 |
| 387907361 | NM_005120.2(MED12):c.3493T>C (p.Ser1165Pro) | AGGACYCTGAGCCAGGGGCCCGG | Ohdo syndrome, X-linked |
| 289933970 | NM_006194.3(PAX9):c.622T>C (p.Leu21Pro) | GGCCGCYGCCCAACGCCATCCGG | Tooth agenesis, selective, 3 |
| 137854472 | NM_000138.4(FBN1):c.3128A>G (p.Lys1043Arg) | TGCACYTGCCGTGGGTGCAGAGG | Cardiomyopathy, not specified |
| 727504261 | NM_000257.3(MYH7):c.2708A>G (p.Glu903Gly) | AGCGCYCCTCAGCATCTGCCAGG | |
| 81002853 | NM_000059.3(BRCA2):c.476-2A>G | ACCACYGGGGGTAAAAAAAGGGG, TACCACYGGGGGTAAAAAAAGGG | Familial cancer of breast, Breast-ovarian cancer, familial 2, Hereditary cancer-predisposing syndrome |
| 119473032 | NM_021020.3(LZTS1):c.355A>G (p.Lys119Glu) | CCCTYCTCGGAGCCCTGTAGAGG | |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 193922801 | NM_000540.2(RYR1):c.7043A>G (p.Glu2348Gly) | TTCYCCTCCACGCTCTCGCCTGG | not provided |
| 36210419 | NM_000218.2(KCNQ1):c.652A>G (p.Lys218Glu) | GCCCCTYGGAGCCCACGCAGAGG | Torsades de pointes, Cardiac arrhythmia |
| 121964989 | NM_000108.4(DLD):c.1483A>G (p.Arg495Gly) | TTCTCYAAAAGTTCTGATAAGG | Maple syrup urine disease, type 3 |
| 28936669 | NM_000095.2(COMP):c.1418A>G (p.Asp473Gly) | ATTGYCGTCGTCGTCGTCGCAGG | not provided |
| 28936696 | NM_018488.2(TBX4):c.1592A>G (p.Gln531Arg) | GTACYGTAAGGAAGATTCTCGGG, GGTACYGTAAGGAAGATTCTCGG | Ischiopatellar dysplasia |
| 121965077 | NM_000137.2(FAH):c.1141A>G (p.Arg381Gly) | TCCYGGGTCTGACCATTCCCAGG | Tyrosinemia type I |
| 794728203 | NM_000138.4(FBN1):c.3344A>G (p.Asp1115Gly) | ACTCAYCAATATCTGCAAAATGG | Thoracic aortic aneurysms and aortic dissections |
| 786205436 | NM_003002.3(SDHD):c.275A>G (p.Asp92Gly) | GAATAGYCCATCGCAGAGCAAGG | Fatal infantile mitochondrial cardiomyopathy |
| 72551317 | NM_000784.3(CYP27A1):c.776A>G (p.Lys259Arg) | AGTCCACYTGGGAGGAGAAGGTGG | Cholestanol storage disease |
| 786205687 | NM_016218.2(POLK):c.1385A>G (p.Asn462Ser) | ATTCACAYTCTTCAACTTAATGG | Malignant tumor of prostate |
| 794728280 | NM_000138.4(FBN1):c.7916A>G (p.Tyr2639Cys) | TGTTCAYACTGGAAGCCCGCGGG, CTGTTCAYACTGGAAGCCGGCGG | Thoracic aortic aneurysms and aortic dissections |
| 28937317 | NM_000335.4(SCN5A):c.3971A>G (p.Asn1324Ser) | GCAYTGACCACCACCTCAAGTGG | Long QT syndrome 3, Congenital long QT syndrome |
| 786205854 | NM_144499.2(GNAT1):c.386A>G (p.Asp129Gly) | CGGAGYCCTTCCACAGCCGCTGG | NIGHT BLINDNESS, CONGENITAL |
| 104893776 | NM_000539.3(RHO):c.533A>G (p.Tyr178Cys) | GGATGYACCTGAGGACAGGCAGG | Retinitis pigmentosa 4 |
| 28937590 | NM_001257342.1(BCS1L):c.232A>G (p.Ser78Gly) | GACACYGAGGTGCTGAGTACGGG, CGACACYGAGGTGCTGAGTACGG | GRACILE syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 104893866 | NM_000320.2(QDPR):c.449A>G (p.Tyr150Cys) | TGCCGYACCGATCATACCTGGG, ATGCCGYACCCGATCATACCTGG | Dihydropteridine reductase deficiency |
| 587776590 | NM_015629.3(PRPF31):c.527+3A>G | GACAYACCCCTGGGTGGTGGAGG, GCGGACAYACCCCTGGGTGGTGG | Retinitis pigmentosa 11 |
| 104894015 | NM_000162.3(GCK):c.641A>G (p.Tyr214Cys) | GTAGYAGCAGGAGATCATCGTGG | Hyperinsulinemic hypoglycemia familial 3 |
| 202247823 | NM_000532.4(PCCB):c.1606A>G (p.Asn536Asp) | ATATYTGCATGTTTTCTCCAAGG | Propionic ac dem a |
| 104894199 | NM_000073.2(CD3G):c.1A>G (p.MetlVal) | CCAYGTCAGTCTCTGTCCTCCGG | Immunodeficiency 17 |
| 104894208 | NM_001814.4(CTSC):c.857A>G (p.Gln286Arg) | CTCCYGAGGGCTTAGGATTGGGG, CCTCCYGAGGGCTTAGGATTGGG, ACCTCCYGAGGGCTTAGGATTGG | Papillon-Lef\xc3\xa8vre syndrome, Haim-Munk syndrome |
| 104894211 | NM_001814.4(CTSC):c.1040A>G (p.Tyr347Cys) | TCCTACAYAGTGTACTCAGAGG | Papillon-Lenxc3\xa8vre syndrome, Periodontitis, |
| 104894290 | NM_000448.2(RAG1):c.2735A>G (p.Tyr912Cys) | CTGYACTGGCAGAGGGATTCTGG | Histiocytic medullary reticulosis |
| 104894354 | NM_000217.2(KCNA1):c.676A>G (p.Tlu.226Ala) | GCGYTTCCACGATGAAGAAGGGG, AGCGYTTCCACGATGAAGAAGGG, CAGCGYTTCCACGATGAAGAAGG | Episodic ataxia type 1 |
| 104894425 | NM_014239.3(EIF2B2):c.638A>G (p.Glu213Gly) | AGTTGTCYCAATACCTGCTTTGG | Leukoencephalopathy with vanishing bite matter, Ovarioleukodystrophy |
| 104894450 | NM_000270.3(PNP):c.383A>G (p.Asp128Gly) | ATAYCTCCAACTTCAAACTTGGG, GATAYCTCCAACTCAAACTTGG | Purine-nucleoside phosphorylase deficiency |
| 147394623 | NM_024887.3(DHDDS):c.124A>G (p.Lys42Glu) | GGACACTYCTTGGCATAGCGACGG | Retinitis pigmentosa 59 |
| 60723330 | NM_005557.3(KRT16):c.374A>G (p.Asn125Ser) | GCGGTCAYTGAGGTTCTGCATGG | Pachyonychia congenita, type 1, Palmoplantar keratoderma, nonepidermolytic, focal |
| 104894634 | NM_030665.3(RAI1):c.4685A>G (p.Gln1562Arg) | CTGCTGCYGTCGTCGTCGCTTGG | Smith-Magenis syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 104894730 | NM_000363.4(TNNI3):c.532A>G (p.Lys178Glu) | CCTYCTTCACCTGCTTGAGGTGG, CCTCCTYCTTCACCTGCTTGAGG | Familial restrictive cardiomyopathy 1 |
| 104894816 | NM_002049.3(GATA1):c.653A>G (p.Asp218Gly) | GTCCTGYCCCTCCGCCACAGTGG | GATA-1-related thrombocytopenia with dyserythropoiesis |
| 794726773 | NM_001165963.1(SCN1A):c.1662+3 A>G | GTGCCAYACCTGTGTGGGAGG | Severe myoclonic epilepsy in infancy |
| 104894861 | NM_000202.6(IDS):c.404A>G (p.Lys135Arg) | AAAGACTYTTCCACCGACATGG | Mucopolysaccharidosis, MPS-II |
| 104894874 | NM_000266.3(NDP):c.125A>G (p.His42Arg) | TGGYGCCTCATGCAGCGTCGAGG | |
| 191205969 | NM_002420.5(TRPM1):c.296T>C (p.Leu99Pro) | AAGCYCTTAATATCTGTGCATGG | Congenital stationary night blindness, type 1C |
| 794727073 | NM_019109.4(ALG1):c.1188-2A>G | TAAACYGCAGAGAACAAGGG, GTAAACYGCAGAGAGAACAAG G | Congenital disorder of glycosylation type 1K |
| 281875236 | NM_001004334.3(GPR179):c.659A>G (p.Tyr220Cys) | CCCACAYATCCATCTGCTCGCGG | Congenital stationary night blindness, type 1E |
| 28939094 | NM_015915.4(ATL1):c.1222A>G (p.Met408Val) | CACCCAYCTTCTTCACCCCTCGG | Spastic paraplegia 3 |
| 281875324 | NM_053359.5(SMAD4):c.989A>G (p.Glu330Gly) | ATCCATTYCAAAGTAAGCAATGG | Juvenile polyposis syndrome, Hereditary cancer-predisposing syndrome |
| 77173848 | NM_000037.3(ANK1):c.-108T>C | GGGCCYGGCCCCGACGTCACAGG | Spherocytosis, type 1, autosomal recessive |
| 150181226 | NM_001159772.1(CANT1):c.671T>C (p.Leu24Pro) | CGTCYGTACGTGGGCGGCCTGGG, GCGTCYGTACGTGGGCGGCCTGG | Desbuquois syndrome |
| 397514253 | NM_000041.3(APOE):c.237-2A>G | CGCCCYGCGGCCGAGAGGGCGGG, GCGCCCYGCGGCCCGAGAGGGCG | Familial type 3 hyperlipoprotenem a |
| 397514348 | NM_000060.3(BTD):c.278A>G (p.Tyr93Cys) | GTTCAYAGATGTCAAGGTTCTGG | Biotinidase deficiency |
| 397514415 | NM_000060.3(BTD):c.1313A>G (p.Tyr438Cys) | GGCAYACAGCTCTTTGGATAAGG | Biotinidase deficiency |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397514501 | NM_007171.3(POMT1):c.430A>G (p.Asn144Asp) | GAGCATYCTCTGTTTCAAAGAGG | Limb-girdle muscular dystrophy- |
| 370382601 | NM_174917.4(ACSF3):c.1A>G (P.MetIVal) | GGCAGCATYGCACTGACAGGCGG | not provided |
| 72554332 | NM_000531.5(OTC):c.238A>G (p.Lys80Glu) | AAGGACTYCCCTTGCAATAAAGG | Ornithine carbamoyltransferase deficiency |
| 397514599 | NM_033109.4(PNPT1):c.1424A>G (p.Glu475Gly) | GACTYCAGATGTAACTCTTATGG | Deafness, autosomal recessive 70 |
| 397514650 | NM_000108.4(DLD):c.1444A>G (p.Arg482Gly) | GACTYCAGCTATATCTTCACAGG | Maple syrup urine disease, type 3 |
| 397514675 | NM_003156.3(STIM1):c.25IA>G (p.Asp84Gly) | TTCCACAYCCACATCACCATTGG | Myopathy with tubular aggregates |
| 794728378 | NM_000238.3(KCNH2):c.1913A>G (p.Lys638Arg) | ATCYTCTCTGAGTTGGTGTTGGG, GATCYTCTCTGAGTTGGTGTTGG | Cardiac arrhythmia |
| 397514711 | NM_002163.2(IRF8):c.238A>G (p.Thr80Ala) | AACCTCGYCTTCCAAGTGGCTGG | Autosomal dominant CD11C+/CD1C+dendritic cell deficiency |
| 397514729 | NM_000388.3(CASR):c.85A>G (p.Lys29Glu) | CCCCCTYCTTTTGGGCTCGCTGG | Hypocalcemia, autosomal dominant 1, with bartter syndrome |
| 397514743 | NM_022114.3(PRDM16):c.2447A>G (p.Asn816Ser) | GCCGCCGYTTTGGCTGGCACGGG | Left ventricular noncompaction 8 |
| 397514757 | NM_005689.2(ABCB6):c.508A>G (p.Ser170Gly) | TGGGCYGTTCCAAGACACCAGGG, GTGGGCYGTTCCAAGACACCAGG | Dyschromatosis universalis hereditaria 3 |
| 28940313 | NM_152443.2(RDH12):c.677A>G (p.Tyr226Cys) | CACTGCGYAGGTGGTGACCCCGG | Leber congenital amaurosis 13 |
| 794728538 | NM_000218.2(KCNQ1):c.1787A>G (p.Glu596Gly) | GTCTYCTACTCGTTCAGGCGGG, TGTCTYCTACTCGTTCAGGCGG | Cardiac arrhythmia |
| 794728569 | NM_000218.2(KCNQ1):c.605A>G (p.Asp202Gly) | AGGYCTGTGGAGTGCAGGAGAGG | Cardiac arrhythmia |
| 794728573 | NM_000218.2(KCNQ1):c.1515-2A>G | GCCYGCAGTGGGAGAGAGAGAGG | Cardiac arrhythmia |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 370874727 | NM_003494.3(DYSF):c.3349-2A>G | CCGCCCYGGAGACACGAAGCTGG | Limb-girdle muscular dystrophy, type 2B |
| 794728859 | NM_198056.2(SCN5A):c.2788-2A>G | ACCYGTCGAGATAATGGGTCAGG | not provided |
| 794728887 | NM_198056.2(SCN5A):c.4462A>G (p.Thr1488Ala) | CCTCTGYCCATGAAGATGTCCTGG | not provided |
| 28940878 | NM_000372.4(TYR):c.125A>G (p.Asp42Gly) | CTCCTGYCCCCGCTCCACGGTGG | Tyrosinase-negative oculocutaneous albinism |
| 397515420 | NM_172107.2(KCNQ2):c.1636A>G (p.Met546Val) | GCAYGACACTGCAGGGGGTGGG, CGCAYGACACTGCAGGGGGTGG, AACCGCAYGACACTGCAGGGGGG | Early infantile epileptic encephalopathy 7 |
| 397515428 | NM_001410.2(MEGF8):c.7099A>G (p.Ser2367Gly) | GACYCCCGTGAAATGATTCCCGG | Carpenter syndrome 2 |
| 143601447 | NM_201631.3(TGM5):c.122T>C (p.Leu41Pro) | TCAACCYCACCCTGTACTTCAGG | Peeling skin syndrome, acral type |
| 397515519 | NM_000207.2(INS):c.*59A>G | GGGCYTTATTCCATCTCTCTCGG | Permanent neonatal diabetes mellitus |
| 397515523 | NM_000370.3(TTPA):c.191A>G (p.Asp64Gly) | CAGGYCCAGATCGAAATCCCGG, CCAGGYCCAGATCGAAATCCCGG | Ataxia with vitamin E deficiency |
| 397515891 | NM_000256.3(MYBPC3):c.1224-2A>G | TACTTGCYGTAGAACAGAAGGGG | Familial hypertrophic cardiomyopathy 4, Cardiomyopathy |
| 397516082 | NM_000256.3(MYBPC3):c.927-2A>G | GTCCCYGTGTCCCGCAGTCTAGG | Familial hypertrophic cardiomyopathy 4, Cardiomyopathy |
| 397516138 | NM_000257.3(MYH7):c.2206A>G (p.Ile736Val) | TATCAAYGAACTGTCCCTCAGGG, CTATCAAYGAACTGTCCCTCAGG | Familial hypertrophic cardiomyopathy 1, Cardiomyopathy, not specified |
| 1154510 | NM_002150.2(HPD):c.97G>A (p.Ala33Thr) | ATGACGYGGCCTGAATCACAGGG, AATGACGYGGCCTGAATCACAGG | 4-Alpha-hydroxyphenylpyruvate hydroxylase deficiency |
| 397516330 | NM_000260.3(MYO7A):c.6439-2A>G | ATATCCYGGGGAGCAGAAAGGG, GATATCCYGGGGAGCAGAAAGG | Usher syndrome, type 1 |
| 72556271 | NM_000531.5(OTC):c.482A>G (p.Asn161Ser) | CAGCCCAYTGATAATTGGGATGG | not provided |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 606231260 | NM_023073.3(C5orf42):c.3290-2A>G | ATCYATCAAATACAAAATTTGG | Orofaciodigital syndrome 6 |
| 587777521 | NM_004817.3(TJP2):c.1992-2A>G | CAGCTCYGAGAAGAAACCACGG, TCAGCTCYGAGAAGAAACCACGG | Progressive familial intrahepatic cholestasis 4 |
| 730080846 | NM_000257.3(MYH7):c.617A>G (p.Lys206Arg) | CTTCYTGCTGCGGTCCCCAATGG | Cardiomyopathy |
| 397517978 | NM_206933.2(USH2A):c.12067-2A>G | TTCCCYGTAAGAAAATTAACAGG | Usher syndrome, type 2A, Retinitis pigmentosa 39 |
| 606231409 | NM_000216.2(ANOS1):c.1A>G (p.Met1Val) | GCACCAYGGCTGCGGGTCGAGGG, GGCACCAYGGCTGCGGGTCGAGG | Kallmann syndrome 1 |
| 80356546 | NM_003334.3(UBA1):c.1639A>G (p.Ser547Gly) | TGGCYTGTCACCCGGATATGTGG | Arthrogryposis multiplex congenita, distal, X-linked |
| 80356584 | NM_194248.2(OTOF):c.766-2A>G | GACCYGCAGGCAGGAGAAGGGGG, TGACCYGCAGGCAGGAGAAGGGG, CTGACCYGCAGGCAGGAGAAGGG, GCTGACCYGCAGGCAGGAGAAGG | Deafness, autosomal recessive 9 |
| 730080930 | NM_000257.3(MYH7):c.1615A>G (p.Met539Val) | GGAACAYGCACTCCTCTTCCAGG | Cardiomyopathy |
| 118203947 | NM_013319.2(UBIAD1):c.355A>G (p.Arg119Gly) | TCCYGTCATCACTCTTTTTGTGG | Schnyder crystalline conical dystrophy |
| 60171927 | NM_000526.4(KRT14):c.368A>G (p.Asn123Ser) | GCCGTCAYTGAGGTTCTGCATGG | Epidermolysis bullosa herpetiformis, Dowling-Meara |
| 199422248 | NM_001363.4(DKC1):c.941A>G (p.Lys314Arg) | AATCYTGGCCCCATAGCAGATGG | Dyskeratosis congenita X-linked |
| 72558467 | NM_000531.5(OTC):c.929A>G (p.Glu310Gly) | TCCACTYCTTCTGGCTTTCTGGG, ATCCACTYCTTCTGGCTTTTCTGG | not provided |
| 72558478 | NM_000531.5(OTC):c.988A>G (p.Arg330Gly) | ACTTTCYGTTTTCTGCCTCTGGG, CACTTTCYGTTTTTCTGCCTCTGG | not provided |
| 118204455 | NM_000505.3(F12):c.158A>G (p.Tyr53Cys) | GGTGGYACTGGAAGGGGAAGTGG | |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base to be edited,
e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 80357477 | NM_007294.3(BRCA1):c (p.Asp1818Gly) | TTGYCCTCTGTCCAGGCATCTGG | Familial cancer of breast, Breast-ovarian cancer, familial 1 |
| 121907908 | NM_024426.4(WT1):c.1021A>G (p.Ser341Gly) | CGCYCTCGTACCCTGTGCTGTGG | Mesothelioma |
| 121907926 | NM_000280.4(PAX6):c.1171A>G (p.Thr391Ala) | GTGGYGCCCGAGTGCCCATTGG | Optic nerve aplasia, bilateral |
| 121908023 | NM_024740.2(ALG9):c.860A>G (p.Tyr287Cys) | TTAYACAAAACAATGTTGAGTGG | Congenital disorder of glycosylation type 1L |
| 121908148 | NM_001243133.1(NLRP3):c.1880A>G (p.Glu627Gly) | ACAATYCCAGCTGGCTGGGCTGG | Familial cold urticaria |
| 121908166 | NM_006492.2(ALX3):c.608A>G (p.Asn203Ser) | CGGYTCTGGAACCAGACCTGGG, GCGGYTCTGGAACCAGACCTGGG, TGCGGYTCTGGAACCAGACCTGG | Frontonasal dysplasia |
| 121908184 | NM_020451.2(SEPN1):c.1A>G (p.Met1Val) | CCCAYGGCTGCGGCTGGCGGCGG, CGGCCCAYGGCTGCGGCTGGCGG | Eichsfeld type congenital muscular dystrophy |
| 121908258 | NM_130468.3(CHST14):c.878A>G (p.Tyr293Cys) | AAGTCAYAGTGCCACGGCACAAGG | Ehlers-Danlos syndrome, musculocontractural type |
| 121908383 | NM_001128425.1(MUTYH):c.1241A>G (p.Gln414Arg) | AAGCYGCTCTGAGGGCTCCCAGG | Neoplasm of stomach |
| 121908580 | NM_004328.4(BCS1L):c.148A>G (p.Thr50Ala) | GTGVGATCATGTAATGCGCCCGG | Mitochondrial complex III deficiency |
| 121908584 | NM_016417.2(GLRX5):c.294A>G (p.Gln98=) | CCTGACCYTGTCGGAGCTCCGGG | Anemia, sideroblastic, pyridoxine-refractory, autosomal recessive |
| 121908635 | NM_022817.2(PER2):c.1984A>G (p.Ser662Gly) | GCCACACYCTCTGCCTTGCCCGG | Advanced sleep phase syndrome, familial |
| 121908655 | NM_003839.3(TNFRSF11A):c.508A>G (p.Arg170Gly) | GGGTCYGCATTTGTCCGTGGAGG | Osteopetrosis autosomal recessive 7 |
| 29001653 | NM_000539.3(RHO):c.886A>G (p.Lys296Glu) | CGCTCTYGGCAAAGAACCTGGG, GCGCTCTYGGCAAAGAACGCTGG | Retinitis pigmentosa 4 |
| 56307355 | NM_006502.2(POLH):c.1603A>G (p.Lys535Glu) | AGACTTTYCTGCTTAAAGAAGGG | Xeroderma pigmentosum, variant type |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121908919 | NM_002977.3(SCN9A):c.1964A>G (p.Lys655Arg) | CCTTTCYTGTGTATTGATTGG | Generalized epilepsy with febrile seizures plus, type 7 not specified |
| 121908939 | NM_006892.3(DNMT3B):c.2450A>G (p.Asp817Gly) | GACACGYCTGTGTAGTGCACAGG | Centromeric instability of chromosomes 1, 9 and 16 and immunodeficiency |
| 121909088 | NM_001005360.2(DNM2):c.1684A>G (p.Lys562Glu) | ACTYCTTCTCTTTTCTCCTGAGGG, TACTYCTTCTCTTTTCTCCTGAGG | Charcot-Marie-Tooth disease, dominant intermediate b, with neutropenia |
| 120074112 | NM_000483.4(APOC2):c.1A>G (p.Met1Val) | GCCCAYAGTGTCCAGAGACCTGG | Apolipoprotein C2 deficiency |
| 121909239 | NM_000314.6(PTEN):c.755A>G (p.Asp252Gly) | ATAYCACCACACACAGGTAACGG | Macrocephaly/autism syndrome |
| 121909251 | NM_198217.2(ING1):c.515A>G (p.Asn172Ser) | TGGYTGCACAGACAGTACGTGGG, CTGGYTGCACAGACAGTACGTGG | Squamous cell carcinoma of the head and neck |
| 121909396 | NM_001174089.1(SLC4A11):c.2518A>G (p.Met840Val) | GATCAYCTTCATGTAGGGCAGGG, AGATCAYCTTCATGTAGGGCAGG | Corneal dystrophy and perceptive deafness |
| 121909533 | NM_000034.3(ALDOA):c.386A>G (p.Asp129Gly) | CCAYCCAACCCTAAGAGAAGAGG | HNSHA due to aldolase A deficiency |
| 128627255 | NM_004006.2(DMD):c.835A>G (p.Thr279Ala) | TGACCGYGATCTGCAGAGAAGGG, CTGACCGYGATCTGCAGAGAAGG | Dilated cardiomyopathy 3B |
| 116929575 | NM_001085.4(SERPINA3):c.1240A>G (p.Met414Val) | GCTCAYGAAGAAGATGTTCTGGG, TGCTCAYGAAGAAGATGTTCTGG | |
| 61748392 | NM_004992.3(MECP2):c.410A>G (p.Glu137Gly) | CAACYCCACTTTAGAGCGAAAGG | Mental retardation, X-linked, syndromic 13 |
| 61748906 | NM_001005741.2(GBA):c.667T>C (p.Trp223Arg) | CCCACTYGGCTCAAGACCAATGG | Gaucher disease, type 1 |
| 199473024 | NM_000238.3(KCNH2):c.3118A>G (p.Ser1040Gly) | CTGCYCTCCACGTCGCCCGGGG, CCTGCYCTCCACGTCGCCCCGGG, GCCTGCYCTCCACGTCGCCCCGG | Sudden infant death syndrome |
| 794728365 | NM_000238.3(KCNH2):c.1129-2A>G | GGACCYGCACCCGGGAAGGCGG | Cardiac arrhythmia |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 72556293 | NM_000531.5(OTC):c.548A>G (p.Tyr183Cys) | AGAGCTAYAGTGTTCCTAAAAGG | not provided |
| 111033244 | NM_000441.1(SLC26A4):c.1151A>G (p.Glu384Gly) | TGAATYCCTAAGGAAGAGACTGG | Pendred syndrome, Enlarged vestibular aqueduct syndrome |
| 111033415 | NM_000260.3(MYO7A):c.1344-2A>G | AGCYGCAGGGCACAGGATGGG, AAGCYGCAGGGGCACAGGGATGG | Usher syndrome, type 1 |
| 121912439 | NM_000454.4(SOD1):c.302A>G (p.Glu101Gly) | AGAATCYYCAATAGACACATCGG | Amyotrophic lateral sclerosis type 1 |
| 121033567 | NM_002769.4(PRSS1):c.68A>G (p.Lys23Arg) | ATCYTGTCATCATCATCAAAGGG, GATCYTGTCATCATCATCAAAGG | Hereditarypancreatitis |
| 121912565 | NM_000901.4(NR3C2):c.2327A>G (p.Gln776Arg) | TCATCYGTTTGCCTGCTAAGCGG | Pseudohypoaldosteronism type 1 autosomal dominant |
| 121912574 | NM_000901.4(NR3C2):c.2915A>G (p.Glu972Gly) | CCGACYCCACCTTGGGCAGCTGG | Pseudohypoaldosteronism type 1 autosomal dominant |
| 121912589 | NM_001173464.1(KIF21A):c.2839A>G (p.Met947Val) | ATTCAYATCTGCCTCCATGTTGG | Fibrosis of extraocular muscles, congenital, 1 |
| 111033661 | NM_000155.3(GALT):c.253-2A>G | ATTCACCYACCGACAAGGATAGG | Deficiency of UDPglucose-hexose-1-phosphate uridylyltransferase |
| 111033669 | NM_000155.3(GALT):c.290A>G (p.Asn97Ser) | GAAGTCGYTGTCAAACAGGAAGG | Deficiency of UDPglucose-hexose-1-phosphate uridylyltransferase |
| 111033682 | NM_000155.3(GALT):c.379A>G (p.Lys127Glu) | TGACCTYACTGGGTGGTGACGGG, ATGACCTYACTGGGTGGTGACGG | Deficiency of UDPglucose-hexose-1-phosphate uridylyltransferase |
| 111033786 | NM_000155.3(GALT):c.950A>G (p.Gln317Arg) | CAGCYGCCAATGGTTCCAGTTGG | Deficiency of UDPglucose-hexose-1-phosphate uridylyltransferase |
| 121912765 | NM_001202.3(BMP4):c.278A>G (p.Glu93Gly) | CCTCCYCCCAGACTGAAGCCGG | Microphthalmia syndromic 6 |
| 121912856 | NM_000094.3(COL7A1):c.425A>G (p.Lys142Arg) | CACCYTGGGACACCAGGTCGGG, TCACCYTGGGGACACCAGGTCGG | Epidermolysis bullosa dystrophica inversa, autosomal recessive |
| 199474715 | NM_152263.3(TPM3):c.505A>G (p.Lys169Glu) | CCAACTYACGAGCCACCTACAGG | Congenital myopathy with fiber type disproportion |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 199474718 | NM_152263.3(TPM3):c.733A>G (p.Arg245Gly) | ATCYCTCAGCAAACTCAGCACGG | Congenital myopathy with fiber type disproportion |
| 121912895 | NM_001844.4(COL2A1):c.2974A>G (p.Arg992Gly) | CCTCYCTCACCACGTTGCCCAGG | Spondyloepimetaphyseal dysplasia Strudwick type |
| 121913074 | NM_000129.3(F13A1):c.851A>G (p.Tyr284Cys) | ATAGGCAYAGATATTGTCCCAGG | Factor xiii, a subunit, deficiency of |
| 121913145 | NM_000208.2(INSR):c.707A>G (p.His236Arg) | GCTGYGGCAACAGAGGCCTTCGG | Leprechaunism syndrome |
| 312262745 | NM_025137.3(SPG11):c.2608A>G (p.Ile870Val) | ACTTAYCCTGGGGAGAAGGATGG | Spastic paraplegia 11, autosomal recessive |
| 121913682 | NM_000222.2(KIT):c.2459A>G (p.Asp820Gly) | AGAAYCATTCTTGATGTCTCTGG | Mast cell disease, systemic |
| 587776757 | NM_000151.3(G6PC):c.230+4A>G | GTTCYTACCACTTAAAGACGAGG | Glycogen storage disease type 1A |
| 61752063 | NM_000330.3(RS1):c.286T>C (p.Trp96Arg) | TTCTTCYGGACTGCAAACAAGG | Juvenile retinoschisis |
| 367543065 | NM_024549.5(TCTN1):c.221-2A>G | AGCAACYGCAGAAAAAAGAGGGG, CAGCAACYGCAGAAAAAGAGAG G | Joubert syndrome 13 |
| 5030773 | NM_000894.2(LHB):c.221A>G (p.Gln74Arg) | CCACCYGAGGCAGGGGCGCAGG | Isolated lutropin deficiency |
| 199476092 | NM_000264.3(PTCH1):c.2479A>G (p.Ser827Gly) | CGTTACYGAAACTCCTGTGTAGG | Gorlin syndrome, Holoprosencephaly 7, not specified |
| 398123158 | NM_000117.2(EMD):c.450-2A>G | CGTTCCCYGAGGCAAAAGAGGGG | not provided |
| 199476103 | RMRP:n.71A>G | ACTTYCCCTAGGCGGAAAGGGG, GACTTYCCCCTAGGCGGAAAGGG, GGACTTYCCCCTAGGCGGAAAGG | Metaphyseal chondrodysplasia, McKusick type, Metaphyseal dysplasia without hypotrichosis |
| 5030856 | NM_000277.1(PAH):c.1169A>G (p.Glu390Gly) | CTCYCTGCCACCTAATACAGGGG, ACTCYCTGCCACGTAATACAGGG, AACTCYCTGCCACGTAATACAGG | Phenylketonuria, Hyperphenylalaninemia, non-Pku |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 5030860 | NM_000277.1(PAH):c.1241A>G (p.Tyr414Cys) | GGGTCGYAGCGAACTGAGAAGGG, TGGGTCGYAGCGAACTGAGAAGG | Phenylketonuria, Hyperphenylalaninem a non-Pku |
| 587777055 | NM_020988.2(GNAO1):c.521A>G (p.Asp174Gly) | GGATGYCCTGCTCGGTGGGCTGG | Early infantile epileptic encephalopathy 17 |
| 587777223 | NM_024301.4(PKRP):c.1A>G (p.MetlVal) | CCGCAYGGGGCCGAAGTCTGGGG, GCCGCAYGGGGCCGAAGTCTGGG, AGCCGCAYGGGGCCGAAGTCTGG | Congenital muscular dystrophy-dystroglycanopathy with brain and eye anomalies type AS |
| 587777479 | NM_003108.3(SOX11):c.347A>G (p.Tyr116Cys) | GTACTTGYAGTCGGGGTAGTCGG | Mental retardation, autosomal dominant 27 |
| 587777496 | NM_020435.3(GJC2):c.-170A>G | TTGYTCCCCCCTCGGCCTCAGGG, ATTGYTCCCCCCCTCGGCCTCAGG | Leukodystrophy, hypomyelinating, 2 |
| 587777507 | NM_022552.4(DNMT3A):c.1943T>C (p.Leu648Pro) | CTCCYGGTGCTGAAGGACTTGGG, GCTCCYGGTGCTGAAGGACTTGG | Tatton-Brown-rahman syndrome |
| 587777557 | NM_018400.3(SCN3B):c.482T>C (p.Met161Thr) | AATCAYGATGTACATCCTTCTGG | Atrial fibrillation, familial, 16 |
| 587777569 | NM_001030001.2(RPS29):c.149T>C (p.Ile50Thr) | GATAYCGTTTCATTAAGGTAGG | Diamond-Blackfan anemia 13 |
| 587777657 | NM_153334.6(SCARF2):c.190T>C (p.Cys64Arg) | CCACGYGCTGCCTGGCTGGAGG | Marden Walker like syndrome |
| 587777689 | NM_005726.5(TSFM):c.57+4A>G | ACTTCYCACCGGGTAGCTCCCGG | Combined oxidative phosphorylation deficiency 3 |
| 796052005 | NM_000255.3(MUT):c.329A>G (p.Tyr110Cys) | GCAYACTGGCGGATGGTCCAGGG, AGCAYACTGGCGGATGGTCCAGG | not provided |
| 587777809 | NM_144596.3(TTC8):c.115-2A>G | GTTCCYGGAAAGCATTAAGAAGG | Retinitis pigmentosa 51 |
| 587777878 | NM_000166.5(GJB1):c.580A>G (p.Met194Val) | TAGCAYGAAGACGGTGAAGACGG | X-linked hereditary motor and sensory neuropathy |
| 74315420 | NM_001029871.3(RSPO4):c.194A>G (p.Gln65Arg) | CGTACYGGCGGATGCCTTCCCGG | Anonychia |
| 180177219 | NM_000030.2(AGXT):c.424-2A>G (p.Gly_142Gln145del) | AGGCCCYGAGGAGAAGCAGGACGG | Primary hyperoxaluria, type I |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 367610201 | NM_002693.2(POLG):c.1808T>C (p.Met603Thr) | CTCAYGGCACTTACCTGGGATGG | not provided |
| 180177319 | NM_012203.1(GRHPR):c.84-2A>G | TCACAGCYGCGGGAAAGGGAGG | Primary hyperoxaluria, type II |
| 796052068 | NM_000030.2(AGXT):c.777-2A>G | GGTACCYGGAAGACACGAGGGGG, TGGTACCYGGAAGACACGAGGGGG | Primary hyperoxaluria, type I |
| 61754010 | NM_000552.3(VWF):c.1583A>G (p.Asn528Ser) | TGCCAYTGTAATTCCCACACAGG | von Willebrand disease, type 2a |
| 587778866 | NM_000321.2(RB1):c.1927A>G (p.Lys643Glu) | ATTYCAATGGCTTCTGGGTCTGG | Retinoblastoma |
| 74435397 | NM_006331.7(EMG1):c.257A>G (p.Asp86Gly) | ATAYCTGGCCGCCGCTTCCCAGG | Bowen-Conradi syndrome |
| 796052527 | NM_000156.5(GAMT):c.1A>G (p.Met1Val) | CGCTCAYGCTGCAGGCTGGACGG | not provided |
| 796052637 | NM_172107.2(KCNQ2):c.848A>G (p.Lys283Arg) | GTACYTGTCCCCGTAGCCAATGG | not provided |
| 724159963 | NM_032228.5(FARH:c.1094A>G (p.Asp365Gly) | GATAYCATACAGGAATGCTGGGG, AGATAYCATACAGGAATGCTGGG, TAGATAYCATACAGGAATGCTGG | Peroxisomal fatty acyl-coa reductase 1 disorder |
| 587779722 | NM_000090.3(COL3A1):c.1762-2A>G (p.Gly588_Gln605del) | CACCCYAAAGAAGAAGAGTGGTCGG | Ehlers-Danlos syndrome, type 4 |
| 118192102 | m.8296A>G | TTTACAGYGGGCTCTAGAGGGGG | Diabetes-deafness syndrome maternally transmitted |
| 727502787 | NM_001077494.3(NEKB2):c.2594A>G (p.Asp865Gly) | CTGYCTTCCTTCACCTCTGCTGG | Common variable immunodeficiency 10 |
| 727503036 | NM_000117.2(EMD):c.266-2A>G | AGCCYTGGGAAGGGGGCAGCGG | Emery-Dreifuss muscular dystrophy 1, X-linked |
| 690016544 | NM_005861.3(STUB1):c.194A>G (p.Asn65Ser) | GGCCCGGYTGGTGTAATACACGG | Spinocerebellar ataxia, autosomal recessive 16 |
| 690016554 | NM_005211.3(CSF1R):c.2655-2A>G | GTATCYGGGAGATAGGACAGAGG | Hereditary diffuse leukoencephalopathy with spheroids |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 118192185 | NM_172107.2(KCNQ2):c.1A>G (p.Met1Val) | GCACCAYGTGCCTGGCGGAGG | Benign familial neonatal seizures 1 |
| 121917869 | NM_012064.3(MIP):c.401A>G (p.Glu134Gly) | AGATCYCCACTGTTGGTTGCCTGG | Cataract 15, multiple types |
| 121918014 | NM_000478.4(ALPL):c.1250A>G (p.Asn417Ser) | AGGCCCAYTGCCATACAGGATGG | Infantile hypophosphatasia |
| 121918036 | NM_000174.4(GP9):c.110A>G (p.Asp37Gly) | GCAGYCCACCCACAGCCCCATGG | Bernard-Soulier syndrome type C |
| 121918089 | NM_000371.3(TTR):c.379A>G (p.Ile127Val) | CGGCAAYGGTGTAGCGCGGGGG, GCGGCAAYGGTGTAGCGCGGGGG | Amyloidogenic transthyretin amyloidosis |
| 121918121 | NM_000823.3(GHRHR):c.985A>G (p.Lys329Glu) | CGACTYGGAGAGACGCCTGCAGG | Isolated growth hormone deficiency type 1B |
| 121918333 | NM_015335.4(MED13L):c.6068A>G (p.Asp2023Gly) | ATATCAYCTAGAGGGAAGGGGGG, CATATCAYCTAGAGGGAAGGGGG | Transposition of great arteries |
| 121918605 | NM_001035.2(RYR2):c.12602A>G (p.Gln4201Arg) | CGGCCAGCYGCATTTCAAAGATGG | Catecholaminergic polymorphic ventricular tachycardia |
| 587781262 | NM_002764.3(PRPS1):c.343A>G (p.Met115Val) | TAGCAYATTTGCAACAGCTTGG | Charcot-Marie-Tooth disease, X-linked recessive, type 5, Deafness, high-frequency sensorineural, X-linked |
| 121918608 | NM_001161766.1(AHCY):c.344A>G (p.Tyr115Cys) | GCGGGYACTTGGTGTGGATGAGG | Hypermethioninemia with s-adenosylhomocysteine hydrolase deficiency |
| 121918613 | NM_000702.3(ATP1A2):c.1033A>G (p.Thr345Ala) | CTGYCAGGGTCAGGCACACCTGG | Familial hemiplegic migraine type 2 |
| 587781339 | NM_000535.5(PMS2):c.904-2A>G | GCAGACCYGCACAAAATACAAGG | Hereditary cancer-predisposing syndrome |
| 121918691 | NM_001128177.1(THRB):c.1324A>G (p.Met442Val) | CTTCAYGTGCAGGAAGCGCTGG | Thyroid hormone resistance, generalized, autosomal dominant |
| 121918692 | NM_001128177.1(THRB):c.1327A>G (p.Lys443Glu) | CCACCTYCATGTGCAGGAAGCGG | Thyroid hormone resistance, generalized, autosomal dominant |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base to be edited,
e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 727504333 | NM_000256.3(MYBPC3):c.2906-2A>G | CCGTTCYGTGGGTATAGAGTGGG, GCCGTTCYGTGGGTATAGAGTGG | Familial hypertrophic cardiomyopathy 4 |
| 730880805 | NM_006204.3(PDE6C):c.1483-2A>G | CTTTCYGTTGAAATAAGGATGGG, TCTTTCYGTTGAAATAAGGATGG | Achromatopsia 5 |
| 281860296 | NM_000551.3(VHL):c.586A>T (p.Lys196Ter) | GGTCTTYCTGCACATTTGGGTGG | Von Hippel-Lindau syndrome |
| 730880444 | NM_000169.2(GLA):c.370-2A>G | GTGAACCYGAAATGAGAGGGGAGG | not provided |
| 756328339 | NM_000256.3(MYBPC3):c.1227-2A>G | GTACCYGGGTGGGGGCCGCAGGG, TGTACCYGGGTGGGGGCCGCAGG | Familial hypertrophic cardiomyopathy 4, Cardiomyopathy |
| 267606643 | NM_013411.4(AK2):c.494A>G (p.Asp165Gly) | TCAYCTTTCATGGGCTCTTTTGG | Reticular dysgenesis |
| 267606705 | NM_005188.3(CBL):c.1144A>G (p.Lys382Glu) | TATTTYACATAGTTGGAATGTGG | Noonan syndrome-like disorder with or without juvenile myelomonocytic leukemia |
| 62642934 | NM_000277.1(PAH):c.916A>G (p.Ile306Val) | GGCCAAYTTCCTGTAATTGGGGG, AGGCCAAYTTCCTGTAATTGGGG | Phenylketonuria, Hyperphenylalaninemia, non-Pku |
| 267606782 | NM_000117.2(EMD):c.1A>G (p.Met1Val) | TCCAYGGCGGGTGCGGGCTCAGG | Emery-Dreifuss muscular dystrophy, X-linked |
| 267606820 | NM_014053.3(FLVCR1):c.361A>G (p.Asn121Asp) | AGGCGGTYGACCAGCGAGTACAGG | Posterior column ataxia with retinitis pigmentosa |

In some embodiments, any of the base editors provided herein may be used to treat a disease or disorder. For example, any base editors provided herein may be used to correct one or more mutations associated with any of the diseases or disorders provided herein. Exemplary diseases or disorders that may be treated include, without limitation, 3-Methylglutaconic aciduria type 2, 46,XY gonadal dysgenesis, 4-Alpha-hydroxyphenylpyruvate hydroxylase deficiency, 6-pyruvoyl-tetrahydropterin synthase deficiency, achromatopsia, Acid-labile subunit deficiency, Acrodysostosis, acroerythrokeratoderma, ACTH resistance, ACTH-independent macronodular adrenal hyperplasia, Activated PI3K-delta syndrome, Acute intermittent porphyria, Acute myeloid leukemia, Adams-Oliver syndrome 1/5/6, Adenylosuccinate lyase deficiency, Adrenoleukodystrophy, Adult neuronal ceroid lipofuscinosis, Adult onset ataxia with oculomotor apraxia, Advanced sleep phase syndrome, Age-related macular degeneration, Alagille syndrome, Alexander disease, Allan-Herndon-Dudley syndrome, Alport syndrome, X-linked recessive, Alternating hemiplegia of childhood, Alveolar capillary dysplasia with misalignment of pulmonary veins, Amelogenesis imperfecta, Amyloidogenic transthyretin amyloidosis, Amyotrophic lateral sclerosis, Anemia (nonspherocytic hemolytic, due to G6PD deficiency), Anemia (sideroblastic, pyridoxine-refractory, autosomal recessive), Anonychia, Antithrombin III deficiency, Aortic aneurysm, Aplastic anemia, Apolipoprotein C2 deficiency, Apparent mineralocorticoid excess, Aromatase deficiency, Arrhythmogenic right ventricular cardiomyopathy, Familial hypertrophic cardiomyopathy, Hypertrophic cardiomyopathy, Arthrogryposis multiplex congenital, Aspartylglycosaminuria, Asphyxiating thoracic dystrophy, Ataxia with vitamin E deficiency, Ataxia (spastic), Atrial fibrillation, Atrial septal defect, atypical hemolytic-uremic syndrome, autosomal dominant CD11C+/CD1C+ dendritic cell deficiency, Autosomal dominant progressive external ophthalmoplegia with mitochondrial DNA deletions, Baraitser-Winter syndrome, Bartter syndrome, Basa ganglia calcification, Beckwith-Wiedemann syndrome, Benign familial neonatal seizures, Benign scapuloperoneal muscular dystrophy, Bernard Soulier syndrome, Beta thalassemia intermedia, Beta-D-mannosidosis, Bietti crystalline corneoretinal dystrophy, Bile acid malabsorption, Biotinidase deficiency, Borjeson-Forssman-Lehmann syndrome, Boucher Neuhauser syndrome, Bowen-Conradi syndrome, Brachydactyly, Brown-Vialetto-Van laere syndrome, Brugada syndrome, Cardiac arrhythmia, Cardiofaciocutaneous syndrome, Cardiomyopathy, Carnevale syndrome, Carnitine palmitoyltransferase II deficiency, Carpenter syndrome, Cataract, Catecholaminergic polymorphic ventricular tachycardia, Central core disease, Centromeric instability of chromosomes 1,9 and 16 and immunodeficiency, Cerebral autosomal dominant arteriopathy, Cerebro-oculo-facio-skeletal syndrome, Ceroid lipofuscinosis, Charcot-Marie-Tooth disease, Cholestanol storage disease, Chondrocalcinosis, Chondrodysplasia, Chronic progressive multiple sclerosis, Coenzyme Q10 deficiency, Cohen syndrome, Combined deficiency of factor V and factor VIII, Combined immunodeficiency, Combined oxidative phosphorylation deficiency, Combined partial 17-alpha-hydroxylase/17,20-lyase deficiency, Complement factor d deficiency, Complete combined 17-alpha-hydroxylase/17,20-lyase deficiency, Cone-rod dystrophy, Congenital contractural arachnodactyly, Congenital disorder of glycosylation, Congenital lipomatous overgrowth, Neoplasm of ovary, PIK3CA Related Overgrowth Spectrum, Congenital long QT syndrome, Congenital muscular dystrophy, Congenital muscular hypertrophy-cerebral syndrome, Congenital myasthenic syndrome, Congenital myopathy with fiber type disproportion, Eichsfeld type congenital muscular dystrophy, Congenital stationary night blindness, Corneal dystrophy, Cornelia de Lange syndrome, Craniometaphyseal dysplasia, Crigler Najjar syndrome, Crouzon syndrome, Cutis laxa with osteodystrophy, Cyanosis, Cystic fibrosis, Cystinosis, Cytochrome-c oxidase deficiency, Mitochondrial complex I deficiency, D-2-hydroxyglutaric aciduria, Danon disease, Deafness with labyrinthine aplasia microtia and microdontia (LAMM), Deafness, Deficiency of acetyl-CoA acetyltransferase, Deficiency of ferroxidase, Deficiency of UDPglucose-hexose-1-phosphate uridylyltransferase, Dejerine-Sottas disease, Desbuquois syndrome, DFNA, Diabetes mellitus type 2, Diabetes-deafness syndrome, Diamond-Blackfan anemia, Diastrophic dysplasia, Dihydropteridine reductase deficiency, Dihydropyrimidinase deficiency, Dilated cardiomyopathy, Disseminated atypical mycobacterial infection, Distal arthrogryposis, Distal hereditary motor neuronopathy, Donnai Barrow syndrome, Duchenne muscular dystrophy, Becker muscular dystrophy, Dyschromatosis universalis hereditaria, Dyskeratosis congenital, Dystonia, Early infantile epileptic encephalopathy, Ehlers-Danlos syndrome, Eichsfeld type congenital muscular dystrophy, Emery-Dreifuss muscular dystrophy, Enamel-renal syndrome, Epidermolysis bullosa dystrophica inversa, Epidermolysis bullosa herpetiformis, Epilepsy, Episodic ataxia, Erythrokeratodermia variabilis, Erythropoietic protoporphyria, Exercise intolerance, Exudative vitreoretinopathy, Fabry disease, Factor V deficiency, Factor VII deficiency, Factor xiii deficiency, Familial adenomatous polyposis, breast cancer, ovarian cancer, cold urticarial, chronic infantile neurological, cutaneous and articular syndrome, hemiplegic migraine, hypercholesterolemia, hypertrophic cardiomyopathy, hypoalphalipoproteinemia, hypokalemia-hypomagnesemia, juvenile gout, hyperlipoproteinemia, visceral amyloidosis, hypophosphatemic vitamin D refractory rickets, FG syndrome, Fibrosis of extraocular muscles, Finnish congenital nephrotic syndrome, focal epilepsy, Focal segmental glomerulosclerosis, Frontonasal dysplasia, Frontotemporal dementia, Fructose-biphosphatase deficiency, Gamstorp-Wohlfart syndrome, Ganglioside sialidase deficiency, GATA-1-related thrombocytopenia, Gaucher disease, Giant axonal neuropathy, Glanzmann thrombasthenia, Glomerulocystic kidney disease, Glomerulopathy, Glucocorticoid resistance, Glucose-6-phosphate transport defect, Glutaric aciduria, Glycogen storage disease, Gorlin syndrome, Holoprosencephaly, GRACILE syndrome, Haemorrhagic telangiectasia, Hemochromatosis, Hemoglobin H disease, Hemolytic anemia, Hemophagocytic lymphohistiocytosis, Carcinoma of colon, Myhre syndrome, leukoencephalopathy, Hereditary factor IX deficiency disease, Hereditary factor VIII deficiency disease, Hereditary factor XI deficiency disease, Hereditary fructosuria, Hereditary Nonpolyposis Colorectal Neoplasm, Hereditary pancreatitis, Hereditary pyropoikilocytosis, Elliptocytosis, Heterotaxy, Heterotopia, Histiocytic medullary reticulosis, Histiocytosis-lymphadenopathy plus syndrome, HNSHA due to aldolase A deficiency, Holocarboxylase synthetase deficiency, Homocysteinemia, Howel-Evans syndrome, Hydatidiform mole, Hypercalciuric hypercalcemia, Hyperimmunoglobulin D, Mevalonic aciduria, Hyperinsulinemic hypoglycemia, Hyperkalemic Periodic Paralysis, Paramyotonia congenita of von Eulenburg, Hyperlipoproteinemia, Hypermanganesemia, Hypermethioninemia, Hyperphosphatasemia, Hypertension, hypomagnesemia, Hypobetalipoproteinemia, Hypocalcemia, Hypogonadotropic hypogonadism, Hypogonadotropic hypogonadism, Hypohidrotic ectodermal dysplasia, Hyper-IgM immunodeficiency, Hypohidrotic X-linked ectodermal dysplasia, Hypomagnesemia, Hypoparathyroidism, Idiopathic fibrosing alveolitis, Immunodeficiency, Immunoglobulin A deficiency, Infantile hypophosphatasia, Infantile Parkinsonism-dystonia, Insulin-dependent diabetes mellitus, Intermediate maple syrup urine disease, Ischiopatellar dysplasia, Islet cell hyperplasia, Isolated growth hormone deficiency, Isolated lutropin deficiency, Isovaleric acidemia, Joubert syndrome, Juvenile polyposis syndrome, Juvenile retinoschisis, Kallmann syndrome, Kartagener syndrome, Kugelberg-Welander disease, Lattice corneal dystrophy, Leber congenital amaurosis, Leber optic atrophy, Left ventricular noncompaction, Leigh disease, Mitochondrial complex I deficiency, Leprechaunism syndrome, Arthrogryposis, Anterior horn cell disease, Leukocyte adhesion deficiency, Leukodystrophy, Leukoencephalopathy, Ovarioleukodystrophy, L-ferritin deficiency, Li-Fraumeni syndrome, Limb-girdle muscular dystrophy-dystroglycanopathy, Loeys-Dietz syndrome, Long QT syndrome, Macrocephaly/autism syndrome, Macular corneal dystrophy, Macular dystrophy, Malignant hyperthermia susceptibility, Malignant tumor of prostate, Maple syrup urine disease, Marden Walker like syndrome, Marfan syndrome, Marie Unna hereditary hypotrichosis, Mast cell disease, Meconium ileus, Medium-chain acyl-coenzyme A dehydrogenase deficiency, Melnick-Fraser syndrome, Mental retardation, Merosin deficient congenital muscular dystrophy, Mesothelioma, Metachromatic leukodystrophy, Metaphyseal chondrodysplasia, Methemoglobinemia, methylmalonic aciduria, homocystinuria, Microcephaly, chorioretinopathy, lymphedema, Microphthalmia, Mild non-PKU hyperphenylalanemia, Mitchell-Riley syndrome, mitochondrial 3-hydroxy-3-methylglutaryl-CoA synthase deficiency, Mitochondrial complex I deficiency, Mitochondrial complex III deficiency, Mitochondrial myopathy, Mucolipidosis III, Mucopolysaccharidosis, Multiple sulfatase deficiency, Myasthenic syndrome, *Mycobacterium tuberculosis*, Myeloperoxidase deficiency, Myhre syndrome, Myoclonic epilepsy, Myofibrillar myopathy, Myoglobinuria, Myopathy, Myopia, Myotonia congenital, Navajo neurohepatopathy, Nemaline myopathy, Neoplasm of stomach, Nephrogenic diabetes insipidus, Nephronophthisis, Nephrotic syndrome, Neurofibromatosis, Neutral lipid storage disease, Niemann-Pick disease, Non-ketotic hyperglycinemia, Noonan syndrome, Noonan syndrome-like disorder, Norum disease, Macular degeneration, N-terminal acetyltransferase deficiency, Oculocutaneous albinism, Oculodentodigital dysplasia, Ohdo syndrome, Optic nerve aplasia, Ornithine carbamoyltransferase deficiency, Orofaciodigital syndrome, Osteogenesis imperfecta, Osteopetrosis, Ovarian dysgenesis, Pachyonychia, Palmoplantar keratoderma, nonepidermolytic, Papillon-Lefxc3xa8vre syndrome, Haim-Munk syndrome, Periodontitis, Peeling skin syndrome, Pendred syndrome, Peroxisomal fatty acyl-coa reductase 1 disorder, Peroxisome biogenesis disorder, Pfeiffer syndrome, Phenylketonuria, Phenylketonuria, Hyperphenylaninemia, non-PKU, Pituitary hormone deficiency, *Pityriasis rubra* pilaris, Polyarteritis nodosa, Polycystic kidney disease, Polycystic lipomembranous osteodysplasia, Polymicrogyria, Pontocerebellar hypoplasia, Porokeratosis, Posterior column ataxia, Primary erythromelalgia, hyperoxaluria, Progressive familial intrahepatic cholestasis, Progressive pseudorheumatoid dysplasia, Propionic acidemia, Pseudohermaphroditism, Pseudohypoaldosteronism, Pseudoxanthoma elasticum-like disorder, Purine-nucleoside phosphorylase deficiency, Pyridoxal 5-phosphate-dependent epilepsy, Renal dysplasia, retinal pigmentary dystrophy, cerebellar ataxia, skeletal dysplasia, Reticular dysgenesis, Retinitis pigmentosa, Usher syndrome, Retinoblastoma, Retinopathy, RRM2B-related mitochondrial disease, Rubinstein-Taybi syndrome, Schnyder crystalline corneal dystrophy, Sebaceous tumor, Severe congenital neutropenia, Severe myoclonic epilepsy in infancy, Severe X-linked myotubular myopathy, onychodysplasia, facial dysmorphism, hypotrichosis, Short-rib thoracic dysplasia, Sialic acid storage disease, Sialidosis, Sideroblastic anemia, Small fiber neuropathy, Smith-Magenis syndrome, Sorsby fundus dystrophy, Spastic ataxia, Spastic paraplegia, Spermatogenic failure, Spherocytosis, Sphingomyelin/cholesterol lipidosis, Spinocerebellar ataxia, Split-hand/foot malformation, Spondyloepimetaphyseal dysplasia, Platyspondylic lethal skeletal dysplasia, Squamous cell carcinoma of the head and neck, Stargardt disease, Sucrase-isomaltase deficiency, Sudden infant death syndrome, Supravalvar aortic stenosis, Surfactant metabolism dysfunction, Tangier disease, Tatton-Brown-rahman syndrome, Thoracic aortic aneurysms and aortic dissections, Thrombophilia, Thyroid hormone resistance, TNF receptor-associated periodic fever syndrome (TRAPS), Tooth agenesis, Torsades de pointes, Transposition of great arteries, Treacher Collins syndrome, Tuberous sclerosis syndrome, Tyrosinase-negative oculocutaneous albinism, Tyrosinase-positive oculocutaneous albinism, Tyrosinemia, UDPglucose-4-epimerase deficiency, Ullrich congenital muscular dystrophy, Bethlem myopathy Usher syndrome, UV-sensitive syndrome, Van der Woude syndrome, popliteal pterygium syndrome, Very long chain acyl-CoA dehydrogenase deficiency, Vesicoureteral reflux, Vitreoretinochoroidopathy, Von Hippel-Lindau syndrome, von Willebrand disease, Waardenburg syndrome, Warsaw breakage syndrome, WFS1-Related Disorders, Wilson disease, Xeroderma pigmentosum, X-linked agammaglobulinemia, X-linked hereditary motor and sensory neuropathy, X-linked severe combined immunodeficiency, and Zellweger syndrome.

The development of nucleobase editing advances both the scope and effectiveness of genome editing. The nucleobase editors described here offer researchers a choice of editing with virtually no indel formation (NBE2), or more efficient editing with a low frequency (here, typically ≥1%) of indel formation (NBE3). That the product of base editing is, by definition, no longer a substrate likely contributes to editing efficiency by preventing subsequent product transformation, which can hamper traditional Cas9 applications. By removing the reliance on double-stranded DNA cleavage and stochastic DNA repair processes that vary greatly by cell state and cell type, nucleobase editing has the potential to expand the type of genome modifications that can be cleanly installed, the efficiency of these modifications, and the type of cells that are amenable to editing. It is likely that recent engineered Cas9 variants[69, 70, 82] or delivery methods[71] with improved DNA specificity, as well as Cas9 variants with altered PAM specificities,[72] can be integrated into this strategy to provide additional nucleobase editors with improved DNA specificity or that can target an even wider range of disease-associated mutations. These findings also suggest that engineering additional fusions of dCas9 with enzymes that catalyze additional nucleobase transformations will increase the fraction of the possible DNA base changes that can be made through nucleobase editing. These results also suggest architectures for the fusion of other DNA-modifying enzymes, including methylases and demathylases, that mau enable additional types of programmable genome and epigenome base editing.

Materials and Methods

Cloning. DNA sequences of all constructs and primers used in this paper are listed in the Supplementary Sequences. Plasmids containing genes encoding NBE1, NBE2, and NBE3 will be available from Addgene. PCR was performed using VeraSeq ULtra DNA polymerase (Enzymatics), or Q5 Hot Start High-Fidelity DNA Polymerase (New England Biolabs). NBE plasmids were constructed using USER cloning (New England Biolabs). Deaminase genes were synthesized as gBlocks Gene Fragments (Integrated DNA Technologies), and Cas9 genes were obtained from previously reported plasmids.[18] Deaminase and fusion genes were cloned into pCMV (mammalian codon-optimized) or pET28b (*E. coli* codon-optimized) backbones. sgRNA expression plasmids were constructed using site-directed mutagenesis. Briefly, the primers listed in the Supplementary Sequences were 5' phosphorylated using T4 Polynucleotide Kinase (New England Biolabs) according to the manufacturer's instructions. Next, PCR was performed using Q5 Hot Start High-Fidelity Polymerase (New England Biolabs) with the phosphorylated primers and the plasmid pFYF1320 (EGFP sgRNA expression plasmid) as a template according to the manufacturer's instructions. PCR products were incubated with DpnI (20 U, New England Biolabs) at 37° C. for 1 h, purified on a QIAprep spin column (Qiagen), and ligated using QuickLigase (New England Biolabs) according to the manufacturer's instructions. DNA vector amplification was carried out using Mach1 competent cells (ThermoFisher Scientific).

In vitro deaminase assay on ssDNA. Sequences of all ssDNA substrates are listed in the Supplementary Sequences. All Cy3-labelled substrates were obtained from Integrated DNA Technologies (IDT). Deaminases were expressed in vitro using the TNT T7 Quick Coupled Transcription/Translation Kit (Promega) according to the manufacturer's instructions using 1 μg of plasmid. Following protein expression, 5 μL of lysate was combined with 35 μL of ssDNA (1.8 μM) and USER enzyme (1 unit) in CutSmart buffer (New England Biolabs) (50 mM potassium acetate, 29 mM Trisacetate, 10 mM magnesium acetate, 100 ug/mL BSA, pH 7.9) and incubated at 37° C. for 2 h. Cleaved U-containing substrates were resolved from full-length unmodified substrates on a 10% TBE-urea gel (Bio-Rad).

Expression and purification of His6-rAPOBEC1-linker-dCas9 fusions. *E. Coli* BL21 STAR (DE3)-competent cells (ThermoFisher Scientific) were transformed with plasmids encoding pET28b-His$_6$-rAPOBEC-linker-dCas9 with GGS, (GGS)$_3$, (SEQ ID NO: 596) XTEN, or (GGS)$_7$ (SEQ ID NO: 597) linkers. The resulting expression strains were grown overnight in Luria-Bertani (LB) broth containing 100 μg/mL of kanamycin at 37° C. The cells were diluted 1:100 into the same growth medium and grown at 37° C. to $OD_{600}$=~0.6. The culture was cooled to 4° C. over a period of 2 h, and isopropyl-β-D-1-thiogalactopyranoside (IPTG) was added at 0.5 mM to induce protein expression. After ~16 h, the cells were collected by centrifugation at 4,000 g and resuspended in lysis buffer (50 mM tris(hydroxymethyl)-aminomethane (Tris)-HCl, pH 7.0, 1 M NaCl, 20% glycerol, 10 mM tris(2-carboxyethyl)phosphine (TCEP, Soltec Ventures)). The cells were lysed by sonication (20 s pulse-on, 20 s pulse-off for 8 min total at 6 W output) and the lysate supernatant was isolated following centrifugation at 25,000 g for 15 min. The lysate was incubated with His-Pur nickel-nitriloacetic acid (nickel-NTA) resin (ThermoFisher Scientific) at 4° C. for 1 h to capture the His-tagged fusion protein. The resin was transferred to a column and washed with 40 mL of lysis buffer. The His-tagged fusion protein was eluted in lysis buffer supplemented with 285 mM imidazole, and concentrated by ultrafiltration (Amicon-Millipore, 100-kDa molecular weight cut-off) to 1 mL total volume. The protein was diluted to 20 mL in low-salt purification buffer containing 50 mM tris(hydroxymethyl)-aminomethane (Tris)-HCl, pH 7.0, 0.1 M NaCl, 20% glycerol, 10 mM TCEP and loaded onto SP Sepharose Fast Flow resin (GE Life Sciences). The resin was washed with 40 mL of this low-salt buffer, and the protein eluted with 5 mL of activity buffer containing 50 mM tris(hydroxymethyl)-aminomethane (Tris)-HCl, pH 7.0, 0.5 M NaCl, 20% glycerol, 10 mM TCEP. The eluted proteins were quantified on a SDSPAGE gel.

In vitro transcription of sgRNAs. Linear DNA fragments containing the T7 promoter followed by the 20-bp sgRNA target sequence were transcribed in vitro using the primers listed in the Supplementary Sequences with the TranscriptAid T7 High Yield Transcription Kit (ThermoFisher Scientific) according to the manufacturer's instructions. sgRNA products were purified using the MEGAclear Kit (ThermoFisher Scientific) according to the manufacturer's instructions and quantified by UV absorbance.

Preparation of Cy3-conjugated dsDNA substrates. Sequences of 80-nucleotide unlabeled strands are listed in the Supplementary Sequences and were ordered as PAGE-purified oligonucleotides from IDT. The 25-nt Cy3-labeled primer listed in the Supplementary Sequences is complementary to the 3' end of each 80-nt substrate. This primer was ordered as an HPLC-purified oligonucleotide from IDT. To generate the Cy3-labeled dsDNA substrates, the 80-nt strands (5 μL of a 100 μM solution) were combined with the Cy3-labeled primer (5 μL of a 100 μM solution) in NEBuffer 2 (38.25 μL of a 50 mM NaCl, 10 mMTris-HCl, 10 mM $MgCl_2$, 1 mM DTT, pH 7.9 solution, New England Biolabs) with dNTPs (0.75 μL of a 100 mM solution) and heated to 95° C. for 5 min, followed by a gradual cooling to 45° C. at a rate of 0.1° C./s. After this annealing period, Klenow exo⁻ (5 U, New England Biolabs) was added and the reaction was incubated at 37° C. for 1 h. The solution was diluted with Buffer PB (250 μL, Qiagen) and isopropanol (50 μL) and purified on a QIAprep spin column (Qiagen), eluting with 50 μL of Tris buffer.

Deaminase assay on dsDNA. The purified fusion protein (20 μL of 1.9 μM in activity buffer) was combined with 1 equivalent of appropriate sgRNA and incubated at ambient temperature for 5 min. The Cy3-labeled dsDNA substrate was added to final concentration of 125 nM and the resulting solution was incubated at 37° C. for 2 h. The dsDNA was separated from the fusion by the addition of Buffer PB (100 μL, Qiagen) and isopropanol (25 μL) and purified on a EconoSpin micro spin column (Epoch Life Science), eluting with 20 μL of CutSmart buffer (New England Biolabs). USER enzyme (1 U, New England Biolabs) was added to the purified, edited dsDNA and incubated at 37° C. for 1 h. The Cy3-labeled strand was fully denatured from its complement by combining 5 μL of the reaction solution with 15 μL of a DMSO-based loading buffer (5 mM Tris, 0.5 mM EDTA, 12.5% glycerol, 0.02% bromophenol blue, 0.02% xylene cyan, 80% DMSO). The full-length C-containing substrate was separated from any cleaved, U-containing edited substrates on a 10% TBE-urea gel (Bio-Rad) and imaged on a GE Amersham Typhoon imager.

Preparation of in vitro-edited dsDNA for high-throughput sequencing (HTS). The oligonucleotides listed in the Supplementary Sequences were obtained from IDT. Complementary sequences were combined (5 μL of a 100

μM solution) in Tris buffer and annealed by heating to 95° C. for 5 min, followed by a gradual cooling to 45° C. at a rate of 0.1° C./s to generate 60-bp dsDNA substrates. Purified fusion protein (20 μL of 1.9 μM in activity buffer) was combined with 1 equivalent of appropriate sgRNA and incubated at ambient temperature for 5 min. The 60-mer dsDNA substrate was added to final concentration of 125 nM and the resulting solution was incubated at 37° C. for 2 h. The dsDNA was separated from the fusion by the addition of Buffer PB (100 μL, Qiagen) and isopropanol (25 μL) and purified on a EconoSpin micro spin column (Epoch Life Science), eluting with 20 μL of Tris buffer. The resulting edited DNA (1 μL was used as a template) was amplified by PCR using the HTS primer pairs specified in the Supplementary Sequences and VeraSeq Ultra (Enzymatics) according to the manufacturer's instructions with 13 cycles of amplification. PCR reaction products were purified using RapidTips (Diffinity Genomics), and the purified DNA was amplified by PCR with primers containing sequencing adapters, purified, and sequenced on a MiSeq high-throughput DNA sequencer (Illumina) as previously described.[73]

Cell culture. HEK293T (ATCC CRL-3216), U2OS (ATCC-HTB-96) and ST486 cells (ATCC) were maintained in Dulbecco's Modified Eagle's Medium plus GlutaMax (ThermoFisher) supplemented with 10% (v/v) fetal bovine serum (FBS) and penicillin/streptomycin (1×, Amresco), at 37° C. with 5% $CO_2$. HCC1954 cells (ATCC CRL-2338) were maintained in RPMI-1640 medium (ThermoFisher Scientific) supplemented as described above. Immortalized rat astrocytes containing the ApoE4 isoform of the APOE gene (Taconic Biosciences) were cultured in Dulbecco's Modified Eagle's Medium plus GlutaMax (ThermoFisher Scientific) supplemented with 10% (v/v) fetal bovine serum (FBS) and 200 μg/mL Geneticin (ThermoFisher Scientific).

Transfections. HEK293T cells were seeded on 48-well collagen-coated BioCoat plates (Corning) and transfected at approximately 85% confluency. Briefly, 750 ng of NBE and 250 ng of sgRNA expression plasmids were transfected using 1.5 μl of Lipofectamine 2000 (ThermoFisher Scientific) per well according to the manufacturer's protocol. Astrocytes, U2OS, HCC1954, HEK293T and ST486 cells were transfected using appropriate AMAXA NUCLEOFECTOR™ II programs according to manufacturer's instructions. 40 ng of infrared RFP (Addgene plasmid 45457)[74] was added to the nucleofection solution to assess nucleofection efficiencies in these cell lines. For astrocytes, U2OS, and ST486 cells, nucleofection efficiencies were 25%, 74%, and 92%, respectively. For HCC1954 cells, nucleofection efficiency was <10%. Therefore, following trypsinization, the HCC1954 cells were filtered through a 40 micron strainer (Fisher Scientific), and the nucleofected HCC1954 cells were collected on a Beckman Coulter MoFlo XDP Cell Sorter using the iRFP signal (abs 643 nm, em 670 nm). The other cells were used without enrichment of nucleofected cells.

High-throughput DNA sequencing of genomic DNA samples. Transfected cells were harvested after 3 d and the genomic DNA was isolated using the Agencourt DNAdvance Genomic DNA Isolation Kit (Beckman Coulter) according to the manufacturer's instructions. On-target and off-target genomic regions of interest were amplified by PCR with flanking HTS primer pairs listed in the Supplementary Sequences. PCR amplification was carried out with Phusion high-fidelity DNA polymerase (ThermoFisher) according to the manufacturer's instructions using 5 ng of genomic DNA as a template. Cycle numbers were determined separately for each primer pair as to ensure the reaction was stopped in the linear range of amplification (30, 28, 28, 28, 32, and 32 cycles for EMX1, FANCF, HEK293 site 2, HEK293 site 3, HEK293 site 4, and RNF2 primers, respectively). PCR products were purified using RapidTips (Diffinity Genomics). Purified DNA was amplified by PCR with primers containing sequencing adaptors. The products were gel-purified and quantified using the QUANT-IT™ PicoGreen dsDNA Assay Kit (ThermoFisher) and KAPA Library Quantification Kit-Illumina (KAPA Biosystems). Samples were sequenced on an Illumina MiSeq as previously described.[73]

Data analysis. Sequencing reads were automatically demultiplexed using MiSeq Reporter (Illumina), and individual FASTQ files were analyzed with a custom Matlab script provided in the Supplementary Notes. Each read was pairwise aligned to the appropriate reference sequence using the Smith-Waterman algorithm. Base calls with a Q-score below 31 were replaced with N's and were thus excluded in calculating nucleotide frequencies. This treatment yields an expected MiSeq base-calling error rate of approximately 1 in 1,000. Aligned sequences in which the read and reference sequence contained no gaps were stored in an alignment table from which base frequencies could be tabulated for each locus.

Indel frequencies were quantified with a custom Matlab script shown in the Supplementary Notes using previously described criteria[71]. Sequencing reads were scanned for exact matches to two 10-bp sequences that flank both sides of a window in which indels might occur. If no exact matches were located, the read was excluded from analysis. If the length of this indel window exactly matched the reference sequence the read was classified as not containing an indel. If the indel window was two or more bases longer or shorter than the reference sequence, then the sequencing read was classified as an insertion or deletion, respectively.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

Supplementary Sequences

Primers used for generating sgRNA transfection plasmids. rev_sgRNA_plasmid was used in all cases. The pFYF1320 plasmid was used as template as noted in Materials and Methods section. SEQ ID NOs: 329-338 appear from top to bottom below, respectively.

```
rev_sgRNA_plasmid    GGTGTTTCGTCCTTTCCACAAG fwd_p53_Y163C        GCTTGCAGATGGCCATGGCGGTTTTAGAGCTAGAAATAGCAAGTTAAAATAAGGC fwd_p53_N239D        TGTCACACATGTAGTTGTAGGTTTTAGAGCTAGAAATAGCAAGTTAAAATAAGGC
```

```
fwd_APOE4_C158R    GAAGCGCCTGGCAGTGTACCGTTTTAGAGCTAGAAATAGCAAGTTAAAATAAGGC fwd_EMX1           GAGTCCGAGCAGAAGAAGAAGTTTTAGAGCTAGAAATAGCAAGTTAAAATAAGGC fwd_FANCF          GGAATCCCTTCTGCAGCACCGTTTTAGAGCTAGAAATAGCAAGTTAAAATAAGGC fwd_HEK293_2       GAACACAAAGCATAGACTGCGTTTTAGAGCTAGAAATAGCAAGTTAAAATAAGGC fwd_HEK293_3       GGCCCAGACTGAGCACGTGAGTTTTAGAGCTAGAAATAGCAAGTTAAAATAAGGC fwd_HEK293_4       GGCACTGCGGCTGGAGGTGGGTTTTAGAGCTAGAAATAGCAAGTTAAAATAAGGC fwd_RNF2           GTCATCTTAGTCATTACCTGGTTTTAGAGCTAGAAATAGCAAGTTAAAATAAGGC
```

Sequences of all ssDNA substrates used in in vitro deaminase assays. SEQ ID NOs: 339-341 appear from top to bottom below, respectively.

```
rAPOBEC1 substrate      Cy3-ATTATTATTATTCCGCGGATTTATTTATTTATTTATTTATTT hAID/pmCDA1 substrate   Cy3-ATTATTATTATTAGCTATTTATTTATTTATTTATTTATTT hAPOBEC3G substrate     Cy3-ATTATTATTATTCCCGGATTTATTTATTTATTTATTTATTT
```

Primers used for generating PCR products to serve as substrates for T7 transcription of sgRNAs for gel-based deaminase assay. rev_gRNA_T7 was used in all cases. The pFYF1320 plasmid was used as template as noted in Materials and Methods section. SEQ ID NOs: 342-365 appear from top to bottom below, respectively.

```
rev_sgRNA_T7                    AAAAAAAGCACCGACTCGGTG fwd_sgRNA_T7_dsDNA_2            TAATACGACTCACTATAGGCCGCGGATTTATTTATTTAAGTTTTAGAGCTAGAAATAGCA fwd_sgRNA_T7_dsDNA_3            TAATACGACTCACTATAGGTCCGCGGATTTATTTATTTAGTTTTAGAGCTAGAAATAGCA fwd_sgRNA_T7_dsDNA_4            TAATACGACTCACTATAGGTTCCGCGGATTTATTTATTAGTTTTAGAGCTAGAAATAGCA fwd_sgRNA_T7_dsDNA_5            TAATACGACTCACTATAGGATTCCGCGGATTTATTTATTGTTTTAGAGCTAGAAATAGCA fwd_sgRNA_T7_dsDNA_6            TAATACGACTCACTATAGGTATTCCGCGGATTTATTTATGTTTTAGAGCTAGAAATAGCA fwd_sgRNA_T7_dsDNA_7            TAATACGACTCACTATAGGTTATTCCGCGGATTTATTTAGTTTTAGAGCTAGAAATAGCA fwd_sgRNA_T7_dsDNA_S            TAATACGACTCACTATAGGATTATTCCGCGGATTTATTTGTTTTAGAGCTAGAAATAGCA fwd_sgRNA_T7_dsDNA_9            TAATACGACTCACTATAGGTATTATTCCGCGGATTTATTGTTTTAGAGCTAGAAATAGCA fwd_sgRNA_T7_dsDNA_10           TAATACGACTCACTATAGGATTATTATCCGGGGATTTATGTTTTAGAGCTAGAAATAGCA fwd_sgRNA_T7_dsDNA_11           TAATACGACTCACTATAGGTATTATATTCCGCGGATTTAGTTTTAGAGCTAGAAATAGCA fwd_sgRNA_T7_dsDNA_12           TAATACGACTCACTATAGGTTATTATATTCCGCGGATTTGTTTTAGAGCTAGAAATAGCA fwd_sgRNA_T7_dsDNA_13           TAATACGACTCACTATAGGATTATTATATTCCGCGGATTGTTTTAGAGCTAGAAATAGCA fwd_sgRNA_T7_dsDNA_14           TAATACGACTCACTATAGGTATTATTATATTCCGCGGATGTTTTAGAGCTAGAAATAGCA fwd_sgRNA_T7_dsDNA_15           TAATACGACTCACTATAGGATTATTATTATTACCGCGGAGTTTTAGAGCTAGAAATAGCA fwd_sgRNA_T7_dsDNA_18           TAATACGACTCACTATAGGATTATTATTATTATTACCGCGTTTTAGAGCTAGAAATAGCA fwd_sgRNA_T7_dsDNA_noC          TAATACGACTCACTATAGGATATTAATTTATTTATTTAAGTTTTAGAGCTAGAAATAGCA fwd_sgRNA_T7_dsDNA_             TAATACGACTCACTATAGGGGAGGACGTGCGCGGCCGCCGTTTTAGAGCTAGAAATAGCA
APOE4_C112R fwd_sgRNA_T7_dsDNA              TAATACGACTCACTATAGGGAAGCGCCTGGCAGTGTACCGTTTTAGAGCTAGAAATAGCA
APOE4_C158R fwd_sgRNA_T7_dsDNA              TAATACGACTCACTATAGGCTGTGGCAGTGGCACCAGAAGTTTTAGAGCTAGAAATAGCA
CTNNB1_T41A fwd_sgRNA_T7_dsDNA              TAATACGACTCACTATAGGCCTCCCGGCCGGCGGTATCCGTTTTAGAGCTAGAAATAGCA
HRAS_081R fwd_sgRNA_T7_dsDNA              TAATACGACTCACTATAGGGCTTGCAGATGGCCATGGCGGTTTTAGAGCTAGAAATAGCA
53_Y163C
```

-continued

```
fwd_sgRNA_T7_dsDNA      TAATACGACTCACTATAGGACACATGCAGTTGTAGTGGAGTTTTAGAGCTAGAAATAGCA
53_Y236C fwd_sgRNA_T7_dsDNA      TAATACGACTCACTATAGGTGTCACACATGTAGTTGTAGGTTTTAGAGCTAGAAATAGCA
53_N23SD
```

Sequences of 80-nucleotide unlabeled strands and Cy3-labeled universal primer used in gel-based dsDNA deaminase assays. SEQ ID NOs: 366-390 appear from top to bottom below, respectively.

```
Cy3-primer         Cy3-GTAGGTAGTTAGGATGAATGGAAGGTTGGTA dsDNA_2            GTCCATGGATCCAGAGGTCATCCATTAAATAAATAAATCCGCGGGGCTATACCAACCTTCCATTCATCCTAACTACCTAC dsDNA_3            GTCCATGGATCCAGAGGTCATCCATAAATAAATAAATCCGCGGAAGCTATACCAACCTTCCATTCATCCTAACTACCTAC dsDNA_4            GTCCATGGATCCAGAGGTCATCCATAATAAATAAATCCGCGGAAGGCTATACCAACCTTCCATTCATCCTAACTACCTAC dsSNA_5            GTCCATGGATCCAGAGGTCATCCAAATAAATAAATCGGCGGAATGGCTATACCAACCTTCCATTCATCCTAACTACCTAC dsDNA_5            GTCCATGGATCCAGAGGTCATCCAATAAATAAATCCGCGGAATAGGCTATACCAACCTTCCATTCATCCTAACTACCTAG dsDNA_7            GTCCATGGATCCAGAGGTCATCCATAAATAAATCCGCGGAATAAGGCTATACCAACCTTCCATTCATCCTAACTACCTAC dsDNA_8            GTCCATGGATCCAGAGGTCATCCAAAATAAATCCGCGGAATAATGGCTATACCAACCTTCCATTCATCCTAACTACCTAC dsDMA_3            GTCCATGGATCCAGAGGTCATCCAAATAAATCCGCGGAATAATAGGCTATACCAACCTTCCATTCATCCTAACTACCTAC dsDMA_10           GTCCATGGATCCAGAGGTCATCCAATAAATCCGCGGATAATAATGGCTATACCAACCTTCCATTCATCCTAACTACCTAC dsDNA_11           GTCCATGGATCCAGAGGTCATCCATAAATCCGCGGAATATAATAGGCTATACCAACCTTCCATTCATCCTAACTACCTAC dsDNA_12           GTCCATGGATCCAGAGGTCATCCAAAATCCGCGGAATATAATAAGGCTATACCAACCTTCCATTCATCCTAACTACCTAC dsDNA_13           GTCCATGGATCCAGAGGTCATCCAAATCCGCGGAATATAATAATGGCTATACCAACCTTCCATTCATCCTAACTACCTAC dsDNA_14           GTCCATGGATCCAGAGGTCATCCAATCCGCGGAATATAATAATAGGCTATACCAACCTTCCATTCATCCTAACTACGTAC dsDNA_15           GTCCATGGATCCAGAGGTCATCCAATCCGCGGTAATAATAATAAGGCTATACCAACCTTCCATTCATCCTAACTACGTAC dsDNA_18           GTCCATGGATGCAGAGGTCATCCAGCGGTAATAATAATAATAATGGCTATACCAACCTTCCATTCATCCTAACTACCTAC dsDNA_noC          GTCCATGGATCCAGAGGTCATCCATTAAATAAATAAATTAATATTACTATACCAACCTTCCATTCATCCTAACTACCTAC dsDNA_8U           5Cy3-GTAGGTGTTAGGATGAATGGAAGGTTGGTAGATATTATCUGCGGATTTATTGGATGAGACCTCTGGATCCATGGACAT dsDNA_APOE_        GCACCTCGCCGCGGTACTGCACCAGGCGGCCGCGCACGTCCTCCATGTCTACCAACCTTCCATTCATCCTAACTACCTAC
C112R d5DNA_APOE_        CGGCGCCCTCGCGGGCCCCGGCCTGGTACACTGCCAGGCGCTTCTGCAGTAOCAACCTTCCATTCATCCTAACTACCTAC
C158R dsDNA_CTNN5        GTCTTACCTGGACTCTGGAATCCATTCTGGTGCCACTGCCACAGCTCCTTACCAACCTTCCATTCATCCTAACTACCTAC
T41A dsDNA_HRAS_        GGAGACGTGCCTGTTGGACATCCTGGATAOCGCCGGaCGGGAGGAGTACTACCAACCTTCCATTCATCCTAACTACCTAC
Q61R dsDNA_p53          ACCCCCGCCCGGCACCCGCGTCCGCGCCATGGCCATCTGCAAGCAGTCATACCAACCTTCCATTCATCCTAACTACCTAC
Y163C dsDNA_p53_         AGGTTGGCTCTGACTGTACCACCATCCACTACAACTGCATGTGTAACAGTACCAACCTTCCATTCATCCTAACTACCTAC
Y236C dsDNA_p53_         TGGCTCTGACTGTACCACCATCCACTACAACTACATGTGTGACAGTTCCTACCAACCTTCCATTCATCCTAACTACCTAC
N239D
```

Primers used for generating PCR products to serve as substrates for T7 transcription of sgRNAs for high-throughput sequencing. rev_gRNA_T7 (above) was used in all cases. The pFYF1320 plasmid was used as template as noted in Materials and Methods section. SEQ ID NOs: 391-442 appear from top to bottom below, respectively.

| | |
|---|---|
| fwd_sgRNA_T7_HTS_base | TAATACGACTCACTATAGGTTATTTCGTGGATTTATTTAGTTTTAGAGCTAGAAATAGCA |
| fwd_sgRNA_T7_HTS_1A | TAATACGACTCACTATAGGATATTTCGTGGATTTATTTA3TTTTAGAGCTAGAAATAGCA |
| fwd_sgRNA_T7_HTS_1C | TAATACGACTCACTATAGGCTATTTCGTGGATTTATTTAGTTTTAGAGCTAGAAATAGCA |
| fwd_sgRNA_T7_HTS_1G | TAATACGACTCACTATAGGGTATTTCGTGSATTTATTTAGTTTTAGAGCTAGAAATAGCA |
| fwd_sgRNA_T7_HTS_2A | TAATACGACTCACTATAGGTAATTTCGTGGATTTATTTAGTTTTAGAGCTAGAAATAGCA |
| fwd_sgRNA_T7_HTS_2C | TAATACGACTCACTATAGGTCATTTCGTGGATTTATTTAGTTTTAGAGCTAGAAATAGCA |
| fwd_sgRNA_T7_HTS_2G | TAATACGACTCACTATAGGTGATTTCGTGGATTTATTTAGTTTTAGAGCTAGAAATAGCA |
| fwd_sgRNA_T7_HTS_3T | TAATACGACTCACTATAGGTTTTTTCGTGGATTTATTTAGTTTTAGAGCTAGAAATAGCA |
| fwd_sgRNA_T7_HTS_3C | TAATACGACTCACTATAGGTTCTTTCGTGGATTTATTTAGTTTTAGAGCTAGAAATAGCA |
| fwd_sgRNA_T7_HTS_3G | TAATACGACTCACTATAGGTTGTTTCGTGGATTTATTTAGTTTTAGAGCTAGAAATAGCA |
| fwd_sgRNA_T7_HTS_4A | TAATACGACTCACTATAGGTTAATTCGTGGATTTATTTAGTTTTAGAGCTAGAAATAGCA |
| fwd_sgRNA_T7_HTS_4C | TAATACGACTCACTATAGGTTACTTCGTGGATTTATTTAGTTTTAGAGCTAGAAATAGCA |
| fwd_sgRNA_T7_HTS_4G | TAATACGACTCACTATAGGTTAGTTCGTGGATTTATTTAGTTTTAGAGCTAGAAATAGCA |
| fwd_sgRNA_T7_HTS_5A | TAATACGACTCACTATAGGTTATATCGTGGATTTATTTAGTTTTAGAGCTAGAAATAGCA |
| fwd_sgRNA_T7_HTS_5C | TAATACGACTCACTATAGGTTATCTCGTGGATTTATTTAGTTTTAGAGCTAGAAATAGCA |
| fwd_sgRNA_T7_HTS_5G | TAATACGACTCACTATAGGTTATGTCGTGGATTTATTTAGTTTTAGAGCTAGAAATAGCA |
| fwd_sgRNA_T7_HTS_6A | TAATACGACTCACTATAGGTTATTACGTGGATTTATTTAGTTTTAGAGCTAGAAATAGCA |
| fwd_sgRNA_T7_HTS_5C | TAATACGACTCACTATAGGTTATTCCGTGGATTTATTTAGTTTTAGAGCTAGAAATAGCA |
| fwd_sgRNA_T7_HTS_6G | TAATACGACTCACTATAGGTTATTGCGTGGATTTATTTAGTTTTAGAGCTAGAAATAGCA |
| fwd_sgRNA_T7_HTS_8A | TAATACGACTCACTATAGGTTATTTCATGGATTTATTTAGTTTTAGAGCTAGAAATAGCA |
| fwd_sgRNA_T7_HTS_8T | TAATACGACTCACTATAGGTTATTTCTTGGATTTATTTAGTTTTAGAGCTAGAAATAGCA |
| fwd_sgRNA_T7_HTS_8C | TAATACGACTCACTATAGGTTATTTCCTGGATTTATTTAGTTTTAGAGCTAGAAATAGCA |
| fwd_sgRNA_T7_HTS_9A | TAATACGACTCACTATAGGTTATTTCGAGGATTTATTTAGTTTTAGAGCTAGAAATAGCA |
| fwd_sgRNA_T7_HTS_9C | TAATACGACTCACTATAGGTTATTTCGCGGATTTATTTAGTTTTAGAGCTAGAAATAGCA |
| fwd_sgRNA_T7_HTS_9G | TAATACGACTCACTATAGGTTATTTCGGGGATTTATTTAGTTTTAGAGCTAGAAATAGCA |
| fwd_sgRNA_T7_HTS_10A | TAATACGACTCACTATAGGTTATTTCGTAGATTTATTTAGTTTTAGAGCTAGAAATAGCA |
| fwd_sgRNA_T7_HTS_10T | TAATACGACTCACTATAGGTTATTTCGTIGATTTATTTAGTTTTAGAGCTAGAAATAGCA |
| fwd_sgRNA_T7_HTS_10C | TAATACGACTCACTATAGGTTATTTCGTCGATTTATTTAGTTTTAGAGCTAGAAATAGCA |
| fwd_sgRNA_T7_HTS_11A | TAATACGACTCACTATAGGTTATTTCGTGAATTTATTTAGTTTTAGAGCTAGAAATAGCA |
| fwd_sgRNA_T7_HTS_11T | TAATACGACTCACTATAGGTTATTTCGTGTATTTATTTAGTTTTAGAGCTAGAAATAGCA |
| fwd_sgRNA_T7_HTS_11C | TAATACGACTCACTATAGGTTATTTCGTGCATTTATTTAGTTTTAGAGCTAGAAATAGCA |
| fwd_sgRNA_T7_HTS_12T | TAATACGACTCACTATAGGTTATTTCGTGGTTTATTTAGTTTTAGAGCTAGAAATAGCA |
| fwd_sgRNA_T7_HTS_12C | TAATACGACTCACTATAGGTTATTTCGTGGCTTTATTTAGTTTTAGAGCTAGAAATAGCA |
| fwd_sgRNA_T7_HTS_12G | TAATACGACTCACTATAGGTTATTTCGTGGGTTTATTTAGTTTTAGAGCTAGAAATAGCA |
| fwd_sgRNA_T7_HTS_13A | TAATACGACTCACTATAGGTTATTTCGTGGAATTATTTAGTTTTAGAGCTAGAAATAGCA |
| fwd_sgRNA_T7_HTS_13C | TAATACGACTCACTATAGGTTATTTCGTGGACTTATTTAGTTTTAGAGCTAGAAATAGCA |
| fwd_sgRNA_T7_HTS_13G | TAATACGACTCACTATAGGTTATTTCGTGGAGTTATTTAGTTTTAGAGCTAGAAATAGCA |
| fwd_sgRNA_77_HTS_multiC | TAATACGACTCACTATAGGTTCCCCCCCGATTTATTTAGTTTTAGAGCTAGAAATAGCA |
| fwd_sgRNA_77_HTS_TCGCACCC_odd | TAATACGACTCACTATAGGCGCACCCGTGGATTTATTTAGTTTTAGAGCTAGAAATAGCA |
| fwd_sgRNA_77_HTS_CCTCGCAC_odd | TAATACGACTCACTATAGGCTCGCACGTGGATTTATTTAGTTTTAGAGCTAGAAATAGCA |
| fwd_sgRNA_77_HTS_ACCCTCGC_odd | TAATACGACTCACTATAGGCCCTCGCGTGGATTTATTTAGTTTTAGAGCTAGAAATAGCA |

```
fwd_sgRNA_77_HTS_GCACCCTC_even    TAATACGACTCACTATAGGCACCCTCGTGGATTTATTTAGTTTTAGAGCTAGAAATAGCA
fwd_sgRNA_T7_HTS_TCGCACCC_even    TAATACGACTCACTATAGGTCGCACCCGTG3ATTTATTAGTTTTAGAGCTAGAAATAGCA
fwd_sgRNA_T7_HTS_CCTCGCAC_even    TAATACGACTCACTATAGGCCTCGCACGTGGATTTATTAGTTTTAGAGCTAGAAATAGCA
fwd_sgRNA_T7_HTS_ACCCTCGC_even    TAATACGACTCACTATAGGACCCTCGCGTG3ATTTATTAGTTTTAGAGCTAGAAATAGCA
fwd_sgRNA_T7_HTS_GCACCCTC_even    TAATACGACTCACTATAGGGCACCCTCGTGGATTTATTAGTTTTAGAGCTAGAAATAGCA
fwd_sgRNA_T7_HTS_EMX1             TAATACGACTCACTATAGGGAGTCCGAGCAGAAGAAGAAGTTTTAGAGCTAGAAATAGCA
fwd_sgRNA_T7_HTS_FANCF            TAATACGACTCACTATAGGGGAATCCCTTCTGCAGCACCGTTTTAGAGCTAGAAATAGCA
fwd_sgRNA_T7_HTS_HEK293_site2     TAATACGACTCACTATAGGGAACACAAAGCATAGACTGCGTTTTAGAGCTAGAAATAGCA
fwd_sgRNA_T7_HTS_HEK293_site3     TAATACGACTCACTATAGGGGCCCAGACTGAGCACGTGAGTTTTAGAGCTAGAAATAGCA
fwd_sgRNA_T7_HTS_HEK293_siie4     TAATACGACTCACTATAGGGGCACTGCGGCTGGAGGTGGGTTTTAGAGCTAGAAATAGCA
fwd_sgRNA_T7_HTS_RNF2             TAATACGACTCACTATAGGGTCATCTTAGTCATTACCTGGTTTTAGAGCTAGAAATAGCA
```

Sequences of in vitro-edited dsDNA for high-throughput sequencing (HTS). Shown are the sequences of edited strands. Reverse complements of all sequences shown were also obtained. dsDNA substrates were obtained by annealing complementary strands as described in Materials and Methods. Oligonucleotides representing the EMX1, FANCF, HEK293 site 2, HEK293 site 3, HEK293 site 4, and RNF2 loci were originally designed for use in the gel-based deaminase assay and therefore have the same 25-nt sequence on their 5'-ends (matching that of the Cy3-primer). SEQ ID NOs: 443-494 appear from top to bottom below, respectively.

```
Base sequence    ACGTAAACGGCCACAAGTTCTTATTTCGTGGATTTATTTATGGCATCTTCTTCAAGGACG
1A               ACGTAAACGGCCACAAGTTCATATTTCGTGGATTTATTTATGGCATCTTCTTCAAGGACG
1C               ACGTAAACGGCCACAAGTTCCTATTTCGTGGATTTATTTATGGCATCTTCTTCAAGGACG
1G               ACGTAAACGGCCACAAGTTCGTATTTCGTGGATTTATTTATGGCATCTTCTTCAAGGACG
2A               ACGTAAACGGCCACAAGTTCTAATTTCGTGGATTTATTTATGGCATCTTCTTCAAGGACG
2C               ACGTAAACGGCCACAAGTTCTCATTTCGTGGATTTATTTATGGCATCTTCTTCAAGGACG
2G               ACGTAAACGGCCACAAGTTCTGATTTCGTGGATTTATTTATGGCATCTTCTTCAAGGACG
3T               ACGTAAACGGCCACAAGTTCTTTTTTCGTGGATTTATTTATGGCATCTTCTTCAAGGACG
3C               ACGTAAACGGCCACAAGTTCTTCTTTCGTGGATTTATTTATGGCATCTTCTTCAAGGACG
3G               ACGTAAACGGCCACAAGTTCTTGTTTCGTGGATTTATTTATGGCATCTTCTTCAAGGACG
4A               ACGTAAACGGCCACAAGTTCTTAATTCGTGGATTTATTTATGGCATCTTCTTCAAGGACG
4C               ACGTAAACGGCCACAAGTTCTTACTTCGTGGATTTATTTATGGCATCTTCTTCAAGGACG
4G               ACGTAAACGGCCACAAGTTCTTAGTTCGTGGATTTATTTATGGCATCTTCTTCAAGGACG
5A               ACGTAAACGGCCACAAGTTCTTATATCGTGGATTTATTTATGGCATCTTCTTCAAGGACG
5C               ACGTAAACGGCCACAAGTTCTTATCTCGTGGATTTATTTATGGCATCTTCTTCAAGGACG
5G               ACGTAAACGGCCACAAGTTCTTATGTCGTGGATTTATTTATGGCATCTTCTTCAAGGACG
5A               ACGTAAACGGCCACAAGTTCTTATTACGTGGATTTATTTATGGCATCTTCTTCAAGGACG
6C               ACGTAAACGGCCACAAGTTCTTATTCCGTGGATTTATTTATGGCATCTTCTTCAAGGACG
5G               ACGTAAACGGCCACAAGTTCTTATTGCGTGGATTTATTTATGGCATCTTCTTCAAGGACG
8A               ACGTAAACGGCCACAAGTTCTTATTTCATGGATTTATTTATGGCATCTTCTTCAAGGACG
8T               ACGTAAACGGCCACAAGTTCTTATTTCTTGGATTTATTTATGGCATCTTCTTCAAGGACG
8C               ACGTAAACGGCCACAAGTTCTTATTTCCTGGATTTATTTATGGCATCTTCTTCAAGGACG
9A               ACGTAAACGGCCACAAGTTCTTATTTCGAGGATTTATTTATGGCATCTTCTTCAAGGACG
9C               ACGTAAACGGCCACAAGTTCTTATTTCGCGGATTTATTTATGGCATCTTCTTCAAGGACG
```

-continued

```
9G                  ACGTAAACGGCCACAAGTTCTTATTTCGGGGATTTATTTATGGCATCTTCTTCAAGGACG

10A                 ACGTAAACGGCCACAAGTTCTTATTTCGTAGATTTATTTATGGCATCTTCTTCAAGGACG

10T                 ACGTAAACGGCCACAAGTTCTTATTTCGTTGATTTATTTATGGCATCTTCTTCAAGGACG

10C                 ACGTAAACGGCCACAAGTTCTTATTTCGTCGATTTATTTATGGCATCTTCTTCAAGGACG

11A                 ACGTAAACGGCCACAAGTTCTTATTTCGTGAATTTATTTATGGCATCTTCTTCAAGGACG

11T                 ACGTAAACGGCCACAAGTTCTTATTTCGTGTATTTATTTATGGCATCTTCTTCAAGGACG

11C                 ACGTAAACGGCCACAAGTTCTTATTTCGTGCATTTATTTATGGCATCTTCTTCAAGGACG

12T                 ACGTAAACGGCCACAAGTTCTTATTTCGTGGTTTATTTATGGCATCTTCTTCAAGGACG

12C                 ACGTAAACGGCCACAAGTTCTTATTTCGTGGCTTTATTTATGGCATCTTCTTCAAGGACG

12G                 ACGTAAACGGCCACAAGTTCTTATTTCGTGGGTTTATTTATGGCATCTTCTTCAAGGACG

13A                 ACGTAAACGGCCACAAGTTCTTATTTCGTGGAATTATTTATGGCATCTTCTTCAAGGACG

13C                 ACGTAAACGGCCACAAGTTCTTATTTCGTGGACTTATTTATGGCATCTTCTTCAAGGACG

13G                 ACGTAAACGGCCACAAGTTCTTATTTCGTGGAGTTATTTATGGCATCTTCTTCAAGGACG multiC              ACGTAAACGGCCACAAGTTCTTCCCCCCCGATTTATTTATGGCATCTTCTTCAAGGACG TCGCACCC_odd        ACGTAAACGGCCACAAGTTTCGCACCCGTGGATTTATTTATGGCATCTTCTTCAAGGACG CCTCGCAC_odd        ACGTAAACGGCCACAAGTTCCTCGCACGTGGATTTATTTATGGCATCTTCTTCAAGGACG ACCCTCGC_odd        ACGTAAACGGCCACAAGTTACCCTCGCGTGGATTTATTTATGGCATCTTCTTCAAGGACG GCACCCTC_odd        ACGTAAACGGCCACAAGTTGCACCCTCGTGGATTTATTTATGGCATCTTCTTCAAGGACG TCGCACCC_even       ACGTAAACGGCCACAAGTATTCGCACCCGTGGATTTATTTATGGCATCTTCTTCAAGGACG CCTCGCAC_even       ACGTAAACGGCCACAAGTATCCTCGCACGTGGATTTATTTATGGCATCTTCTTCAAGGACG ACCCTCGC_even       ACGTAAACGGCCACAAGTATACCCTCGCGTGGATTTATTTATGGCATCTTCTTCAAGGACG GCACCCTC_even       ACGTAAACGGCCACAAGTATGCACCCTCGTGGATTTATTTATGGCATCTTCTTCAAGGACG EMX1_invitro        GTAGGTAGTTAGGATGAATGGAAGGTTGGTAGGCCTGAGTCCGAGCAGAAGAAGAAGGGCTCCCATCACATCAACCGGTG FANCF_invitro       GTAGGTAGTTAGGATGAATGGAAGGTTGGTACTCATGGAATCCCTTCTGCAGCACCTGGATCGCTTTTCCGAGCTTCTGG HEK293_site2_       GTAGGTAGTTAGGATGAATGGAAGGTTGGTAAACTGGAACACAAAGCATAGACTGCGGGCGGGCCAGCCTGAATAGCTG
invitro HEK293_site3_       GTAGGTAGTTAGGATGAATGGAAGGTTGGTACTTGGGGCCCAGACTGAGCACGTGATGGCAGAGGAAAGGAAGCCCTGCT
invitro HEK293_site4_       GTAGGTAGTTAGGATGAATGGAAGGTTGGTACCGGTGGCACTGCGGCTGGAGGTGGGGGTTAAAGCGGAGACTCTGGTGC
invitro RNF2_invitro        GTAGGTAGTTAGGATGAATGGAAGGTTGGTATGGCAGTCATCTTAGTCATTACCTGAGGTCGTTGTAACTCATATAA
```

Primers for HTS of in vitro edited dsDNA. SEQ ID NOs: 495-503 appear from top to bottom below, respectively.

```
fwd_invitro_HTS           ACACTCTTTCCCTACACGAGCTCTTCCGATCTNNNNACGTAAACGGCCACAA rev_invitro_HTS           TGGAGTTCAGACGTGTGCTCTTCCGATCTCGTCCTTGAAGAAGATGC fwd_invitro_HEK_targets   ACACTCTTTCCCTACACGACGCTCTTCCGATCTNNNNGTAGGTAGTTAGGATAATGGAA rev_EMX1_invitro          TGGAGTTCAGACGTGTGCTCTTCCGATCTCACCGGTTGATGTGATGG rev_FANCF_invitro         TGGAGTTCAGACGTGTGCTCTTCCGATCTCCAGAAGCTCGGAAAAGC rev_HEK293_site2_invitro  TGGAGTTCAGACGTGTGCTCTTCCGATCTCAGCTATTCAGGCTGGC rev_HEK293_site3_invitro  TGGAGTTCAGACGTGTGCTCTTCCGATCTAGCAGGGCTTCCTTTC
```

-continued

```
rev_HEK293_site4_invitro   TGGAGTTCAGACGTGTGCTCTTCCGATCTGCACCAGAGTCTCCG rev_RNF2_invitro           TGGAGTTCAGACGTGTGCTCTTCCGATCTTTATATGAGTTACAACGAACACC
```

Primers for HTS of on-target and off-target sites from all mammalian cell culture experiments. SEQ ID NOs: 504-579 and 1869-1900 appear from top to bottom below, respectively.

```
fwd_EMX1_HTS          ACACTCTTTCCCTACACGACGCTCTTCCGATCTNNNNCAGCTCAGCCTGACTGTTGA
rev_EMX1_HTS          TGGAGTTCAGACGTGTGCTCTTCCGATCTCTCGTGGGTTTGTGGTTGC
fwd_FANCF_HTS         ACACTCTTTCCCTACACGACGCTCTTCCGATCTNNNNCATTGCAGAGAGGCGTATCA
rev_FANCF_HTS         TGGAGTTCAGACGTGTGCTCTTCCGATCTGGGGTCCCAGGTGCTGAC
fwd_HEK293_site2_HTS  ACACTCTTTCCCTACACGACGCTCTTCCGATCTNNNNCCAGCCCCATCTGTCAAACT
rev_HEK293_site2_HTS  TGGAGTTCAGACGTGTGCTCTTCCGATCTTGAATGGATTCCTTGGAAACAATGA
fwd_HEK293_Site3_HTS  ACACTCTTTCCCTACACGACGCTCTTCCGATCTNNNNATGTGGGCTGCCTAGAAAGG
rev_HEK293_sit93_HTS  TGGAGTTCAGACGTGTGCTCTTCCGATCTCCCAGCCAAACTTGTCAACC
fwd_HEK293_site4_HTS  ACACTCTTTCCCTACACGACGCTCTTCCGATCTNNNNGAACCCAGGTAGCCAGAGAC
rev_HEK293_site4_HTS  TGGAGTTCAGACGTGTGCTCTTCCGATCTTCCTTTCAACCCGAACGGAG
fwd_RNF2_HTS          ACACTCTTTCCCTACACGACGCTCTTCCGATCTNNNNCTCTTCTTTATTTCCAGCAATGT
rev_RNF2_HTS          TGGAGTTCAGACGTGTGCTCTTCCGATCTGTTTTCATGTTCTAAAAATGTATCCCA
fwd_p53_Y163C_HTS     ACACTCTTTCCCTACACGACGCTCTTCCGATCTNNNNTACAGTACTCCCCTGCCCTC
rev_p53_Y163C_HTS     TGGAGTTCAGACGTGTGCTCTTCCGATCTGCTGCTCACCATCGCTATCT
fwd_p53_N239D_HTS     ACACTCTTTCCCTACACGACGCTCTTCCGATCTNNNNCCTCATCTTGGGCCTGTGTT
rev_p53_N239D_HTS     TGGAGTTCAGACGTGTGCTCTTCCGATCTAAATCGGTAAGAGGTGGGCC
fwd_APOE4_C158R_HTS   ACACTCTTTCCCTACACGACGCTCTTCCGATCTNNNNGCGGACATGGAGGACGTG
rev_APOE4_C158R_HTS   TGGAGTTCAGACGTGTGCTCTTCCGATCTCTGTTCCACCAGGGGCCC
fwd_EMX1_off1_HTS     ACACTCTTTCCCTACACGACGCTCTTCCGATCTNNNNTGCCCAATCATTGATGCTTTT
rev_EMX1_off1_HTS     TGGAGTTCAGACGTGTGCTCTTCCGATCTAGAAACATTTACCATAGACTATCACCT
fwd_EMX1_off2_HTS     ACACTCTTTCCCTACACGACGCTCTTCCGATCTNNNNAGTAGCCTCTTTCTCAATGTGC
rev_EWX1_off2_HTS     TGGAGTTCAGACGTGTGCTCTTCCGATCTGCTTTCACAAGGATGCAGTCT
fwd_EMX1_off3_HTS     ACACTCTTTCCCTACACGACGCTCTTCCGATCTNNNNGAGCTAGACTCCGAGGGGA
rev_EMX1_off3_HTS     TGGAGTTCAGACGTGTGCTCTTCCGATCTTCCTCGTCCTGCTCTCACTT
fwd_EMX1_off4_HTS     ACACTCTTTCCCTACACGACGCTCTTCC3ATCTNNNNAGAGGCTGAAGAGGAAGACCA
rev_EMX1_off4_HTS     TGGAGTTCAGACGTGTGCTCTTCCGATCTGGCCCAGCTGTGCATTCTAT
fwd_EMX1_off6_HTS     ACACTCTTTCCCTACACGACGCTCTTCCGATCTNNNNCCAAGAGGGCCAAGTCCTG
rev_EMX1_off6_HTS     TGGAGTTCAGACGTGTGCTCTTCCGATCTCAGCGAGGAGTGACAGCC
fwd_EMX1_off7_HTS     ACACTCTTTCCCTACACGACGCTCTTCCGATCTNNNNCACTCCACCTGATCTCGGGG
rev_EMX1_off7_HTS     TGGAGTTCAGACGTGTGCTCTTCCGATCTCGAGGAGGGAGGGAGCAG
fwd_EMX1_off8_HTS     ACACTCTTTCCCTACACGACGCTCTTCCGATCTNNNNACCACAAATGCCCAAGAGAC
rev_EMX1_off8_HTS     TGGAGTTCAGACGTGTGCTCTTCCGATCTGACACAGTCAAGGGCCGG
fwd_EMX1_off9_HTS     ACACTCTTTCCCTACACGACGCTCTTCCGATCTNNNNCCCACCTTTGAGGAGGCAAA
rev_EMX1_off9_HTS     TGGAGTTCAGACGTGTGCTCTTCCGATCTTTCCATCTGAGAAGAGAGTGGT
```

-continued

| | |
|---|---|
| fwd_EMX1_off10_HTS | ACACTCTTTCCCTACACGACGCTCTTCCGATCTNNNNGTCATACCTTGGCCCTTCCT |
| rev_EMX1_off10_HTS | TGGAGTTCAGACGTGTGCTCTTCCGATCTTCCCTAGGCCCACACCAG |
| fwd_FANCF_off1_HTS | ACACTCTTTCCCTACACGACGCTCTTCCGATCTNNNNAACCCACTGAAGAAGCAGGG |
| rev_FANCF_off1_HTS | TGGAGTTCAGACGTGTGCTCTTCCGATCTGGTGCTTAATCCGGCTCCAT |
| fwd_FANCF_off2_HTS | ACACTCTTTCCCTACACGACGCTCTTCCGATCTNNNNTCCAGTGTTTCCATCCCGAA |
| rev_FANCF_off2_HTS | TGGAGTTCAGACGTGTGCTCTTCCGATCTCCTCTGACCTCCACAACTCT |
| fwd_FANCF_off3_HTS | ACACTCTTTCCCTACACGACGCTCTTCCGATCTNNNNCTGGGTACAGTTCTGCGTGT |
| rev_FANCF_off3_HTS | TGGAGTTCAGACGTGTGCTCTTCCGATCTTCACTCTGAGCATCGCCAAG |
| fwd_FANCF_off4_HTS | ACACTCTTTCCCTACACGACGCTCTTCCGATCTNNNNGGTTTAGAGCCAGTGAACTAGAG |
| rev_FANCF_off4_HTS | TGGAGTTCAGACGTGTGCTCTTCCGATCTGCAAGACAAAATCCTCTTTATACTTTG |
| fwd_FANCF_off5_HTS | ACACTCTTTCCCTACACGACGCTCTTCCGATCTNNNNGGGAGGGGACGGCCTTAC |
| rev_FANCF_off5_HTS | TGGAGTTCAGACGTGTGCTCTTCCGATCTGCCTCTGGCGAACATGGC |
| fwd_FANCF_off6_HTS | ACACTCTTTCCCTACACGACGCTCTTCCGATCTNNNNTCCTGGTTAAGAGCATGGGC |
| rev_FANCF_off6_HTS | TGGAGTTCAGACGTGTGCTCTTCCGATCTGATTGAGTCCCCACAGCACA |
| fwd_FANCF_off7_HTS | ACACTCTTTCCCTACACGACGCTCTTCCGATCTNNNNCCAGTGTTTCCCATCCCCAA |
| rev_FANCF_off7_HTS | TGGAGTTCAGACGTGTGCTCTTCCGATCTTGACCTCCACAACTGGAAAAT |
| fwd_FANCF_off8_HTS | ACACTCTTTCCCTACACGACGCTCTTCCGATCTNNNNGCTTCCAGACCCACCTGAAG |
| rev_FANCF_off8_HTS | TGGAGTTCAGACGTGTGCTCTTCCGATCTACCGAGGAAAATTGCTTGTCG |
| fwd_HEK293_site2_off1_HTS | ACACTCTTTCCCTACACGACGCTCTTCCGATCTNNNNGTGTGGAGAGTGAGTAAGCCA |
| rev_HEK293_site2_off1_HTS | TGGAGTTCAGACGTGTGCTCTTCCGATCTACGGTAGGATGATTTCAGGCA |
| fwd_HEK293_site2_off2_HTS | ACACTCTTTCCCTACACGACGCTCTTCCGATCTNNNNCACAAAGCAGTGTAGCTCAGG |
| rev_HEK293_site2_off2_HTS | TGGAGTTCAGACGTGTGCTCTTCCGATCTTTTTTGGTACTCGAGTGTTATTCAG |
| fwd_HEK293_site3_off1_HTS | ACACTCTTTCCCTACACGACGCTCTTCCGATCTNNNNTCCCCTGTTGACCTGGAGAA |
| rev_HEK293_site3_off1_HTS | TGGAGTTCAGACGTGTGCTCTTCCGATCTCACTGTACTTGCCCTGACCA |
| fwd_HEK293_site3_off2_HTS | ACACTCTTTCCCTACACGACGCTCTTCCGATCTNNNNTTGGTGTTGACAGGGAGCAA |
| rev_HEK293_site3_off2_HTS | TGGAGTTCAGACGTGTGCTCTTCCGATCTCTGAGATGTGGGCAGAAGGG |
| fwd_HEK293_site3_off3_HTS | ACACTCTTTCCCTACACGACGCTCTTCCGATCTNNNNTGAGAGGGAACAGAAGGGCT |
| rev_HEK293_site3_off3_HTS | TGGAGTTCAGACGTGTGCTCTTCCGATCTGTCCAAAGGCCCAAGAACCT |
| fwd_HEK2S3_site3_off4_HTS | ACACTCTTTCCCTACACGACGCTCTTCCGATCTNNNNTCCTAGCACTTTGGAAGGTCG |
| rev_HEK293_site3_off4_HTS | TGGAGTTCAGACGTGTGCTCTTCCGATCTGCTCATCTTAATCTGCTCAGCC |
| fwd_HEK293_site3_off5_HTS | ACACTCTTTCCCTACACGACGCTCTTCCGATCTNNNNAAAGGAGCAGCTCTTCCTGG |
| rev_HEK293_site3_off5_HTS | TGGAGTTCAGACGTGTGCTCTTCCGATCTGTCTGCACCATCTCCCACAA |
| fwd_HEK293_site4_off1_HTS | ACACTCTTTCCCTACACGACGCTCTTCCGATCTNNNNGGCATGGCTTCTGAGACTCA |
| rev_HEK293_site4_off1_HTS | TGGAGTTCAGACGTGTGCTCTTCCGATCTGTCTCCCTTGCACTCCCTGTCTTT |
| fwd_HEK293_site4_off2_HTS | ACACTCTTTCCCTACACGACGCTCTTCCGATCTNNNNTTTGGCAATGGAGGCATTGG |
| rev_HEK293_site4_off2_HTS | TGGAGTTCAGACGTGTGCTCTTCCGATCTGAAGAGGCTGCCCATGAGAG |
| fwd_HEK293_site4_off3_HTS | ACACTCTTTCCCTACACGACGCTCTTCCGATCTNNNNGGTCTGAGGCTCGAATCCTG |
| rev_HEK293_site4_off3_HTS | TGGAGTTCAGACGTGTGCTCTTCCGATCTCTGTGGCCTCCATATCCCTG |
| fwd_HEK293_site4_off4_HTS | ACACTCTTTCCCTACACGACGCTCTTCCGATCTNNNNTTCCACCAGAACTCAGCCC |
| rev_HEK293_site4_off4_HTS | TGGAGTTCAGACGTGTGCTCTTCCGATCTCCTCGGTTCCTCCACAACAC |
| fwd_HEK293_site4_off5_HTS | ACACTCTTTCCCTACACGACGCTCTTCCGATCTNNNNCACGGGAAGGACAGGAGAAC |

| | |
|---|---|
| rev_HEK293_site4_off5_HTS | TGGAGTTCAGACGTGTGCTCTTCCGATCTGCAGGGGAGGGATAAAGCAG |
| fwd_HEK293_site4_off6_HTS | ACACTCTTTCCCTACACGACGCTCTTCCGATCTNNNNCCACGGGAGATGGCTTATGT |
| rev_HEK293_site4_off6_HTS | TGGAGTTCAGACGTGTGCTCTTCCGATCTCACATCCTCACTGTGCCACT |
| fwd_HEK293_site4_off7_HTS | ACACTCTTTCCCTACACGACGCTCTTCCGATCTNNNNGTCAGTCTCGGCCCCTCA |
| rev_HEK293_site4_off7_HTS | TGGAGTTCAGACGTGTGCTCTTCCGATCTGCCACTGTAAAGCTCTTGGG |
| fwd_HEK293_site4_off8_HTS | AGACTCTTTCCCTACAC3ACGCTCTTCCGATCTNNNNAGGGTAGAGGGACAGAGCTG |
| rev_HEX293_site4_off8_HTS | TGGAGTTCAGACGTGTGCTCTTCCGATCTGGACCCCACATAGTCAGTGC |
| fwd_HEK293_site4_off9_HTS | ACACTCTTTCCCTACACGACGCTCTTCCGATCTNNNNGCTGTCAGCCCTATCTCCATC |
| rev_HEK293_site4_off9_HTS | TGGAGTTCAGACGTGTGCTCTTCCGATCTTGGGCAATTAGGACAGGGAC |
| fwd_HEK293_site4_off10_HTS | ACACTCTTTCCCTACACGACGCTCTTCCGATCTNNNNGCAGCGGAGGAGGTAGATTG |
| rev_HEK293_site4_off10_HTS | TGGAGTTCAGACGTGTGCTCTTCCGATCTCTCAGTACCTGGAGTCCCGA |
| fwd_HEK2_ChIP_off1_HTS | ACACTCTTTCCCTACACGACGCTCTTCCGATCTNNNNGACAGGCTCAGGAAAGCTGT |
| rev_HEK2_ChIP_off1_HTS | TGGAGTTCAGACGTGTGCTCTTCCGATCTACACAAGCCTTTCTCCAGGG |
| fwd_HEK2_ChIP_off2_HTS | ACACTCTTTCCCTACACGACGCTCTTCCGATCTNNNNAATAGGGGGTGAGACTGGGG |
| rev_HEK2_ChIP_off2_HTS | TGGAGTTCAGACGTGTGCTCTTCCGATCTGCCTCAGACGAGACTTGAGG |
| fwd_HEK2_ChIP_off3_HTS | ACACTCTTTCCCTACACGACGCTCTTCCGATCTNNNNGGCCAGCAGGAAAGGAATCT |
| rev_HEK2_ChIp_off3_HTS | TGGAGTTCAGACGTGTGCTCTTCCGATCTTGACTGCACCTGTAGCCATG |
| fwd_HEK2_ChIP_off4_HTS | ACACTCTTTCCCTACACGACGCTCTTCCGATCTNNNNTCAAGGAAATCACCCTGCCC |
| rev_HEK2_ChIP_off4_HTS | TGGAGTTCAGACGTGTGCTCTTCCGATCTAACTTCCTTGGTGTGCAGCT |
| fwd_HEK2_ChIP_off5_HTS | ACACTCTTTCCCTACACGACGCTCTTCCGATCTNNNNATOGGCTCAGCTACGTCATG |
| rev_HEK2_ChIP_off5_HTS | TGGAGTTCAGACGTGTGCTCTTCCGATCTAATAGCAGTGTGGT6GGCAA |
| fwd_HEK3_ChIP_off1_HTS | ACACTCTTTCCCTACACGACGCTCTTCCGATCTNNNNCGCACATCCCTTGTCTCTCT |
| rev_HEK3_ChIP_off1_HTS | TGGAGTTCAGACGTGTGCTCTTCCGATCTCTACTGGAGCACACCCCAAG |
| fwd_HEK3_ChIP_off2_HTS | ACACTCTTTCCCTACACGACGCTCTTCCGATCTNNNNTGGGTCACGTAGCTTTGGTC |
| rev_HEK3_ChIP_off2_HTS | TGGAGTTCAGACGTGTGCTCTTCCGATCTTGGTGGCCATGTGCAACTAA |
| fwd_HEK3_ChIP_off3_HTS | ACACTCTTTCCCTACACGACGCTCTTCCGATCTNNNNCTACTACGTGCCAGCTCAGG |
| rev_HEK3_ChIP_off3_HTS | TGGAGTTCAGACGTGTGCTCTTCCGATCTACCTCCCCTCCTCACTAACC |
| fwd_HEK3_ChIP_off4_HTS | ACACTCTTTCCCTACACGACGCTCTTCCGATCTNNNNGCCTCAGCTCCATTTCCTGT |
| rev_HEK3_ChIP_off4_HTS | TGGAGTTCAGACGTGTGCTCTTCCGATCTAACCTTTATGGCACCAGGGG |
| fwd_HEK3_ChIP_off5_HTS | ACACTCTTTCCCTACACGACGCTCTTCCGATCTNNNNGAGCTCAGCATTAGCAGGCT |
| rev_HEK3_ChIP_off5_HTS | TGGAGTTCAGACGTGTGCTCTTCCGATCTTTCCTGGCTTTCCGATTCCC |
| fwd_HEK4_ChIp_off1_HTS | ACACTCTTTCCCTACACGACGCTCTTCCGATCTNNNNGTGCAATTGGAGGAGGAGCT |
| rev_HEK4_ChIp_off1_HTS | TGGAGTTCAGACGTGTGCTCTTCCGATCTCACCAGCTACAGGCAGAACA |
| fwd_HEK4_ChIP_off3_HTS | ACACTCTTTCCCTACACGACGCTCTTCCGATCTNNNNCCTACCCCCAACACAGATGG |
| rev_HEK4_ChIP_off3_HTS | TGGAGTTCAGACGTGTGCTCTTCCGATCTCCACACAACTCAGGTCCTCC |

Sequences of single-stranded oligonucleotide donor templates (ssODNs) used in HDR studies.

EMX1 sense
(SEQ ID NO: 580)
TCATCTGTGCCCCTCCCTCCCTGGCCCAGGTGAAGGTGTGGTTCCAGAAC

CGGAGGACAAAGTACAAACGGCAGAAGCTGGAGGAGGAAGGGCCTGAGTT

TGAGCAGAAGGAAGGGCTCCCCATCACATCAACCGCGGTGGCGCATTGCCA

CGAAGCAGGCCAATGGGGAGGACATCGATGTCACCTCCAATGACTAGGGT

EMX1 antisense
(SEQ ID NO: 581)
ACCCTAGTCATTGGAGGTGACATCGATGTCCTCCCCATTGGCCTGCTTCG

TGGCAATGCGCCACCGGTTGATGTGATGGGAGCCCTTCTTCTTCTGCTCA

AACTCAGGCCCTTCCTCCTCCAGCTTCTGCCGTTTGTACTTTGTCCTCCG

GTTCTGGAACCACACCTTCACCTGGGCCAGGGAGGGAGGGGCACAGATGA

HEK293 site 3 sense
(SEQ ID NO: 582)
CATGCAATTAGTCTATTTCTGCTGCAAGTAAGGATGCATTTGTAGGCTTG

ATGCTTTTTTTCTGCTTCTCCAGCCCTGGCCTGGGTCAATCCTTGGGGCT

TAGACTGAGCACGTGATGGCAGAGGAAAGGAAGCCCTGCTTCCTCCAGAG

GGCGTCGCAGGACAGCTTTTCCTAGACAGGGGCTAGTATGTGCAGCTCCT

HEK293 site 3 antisense
(SEQ ID NO: 583)
AGGAGCTGCACATACTAGCCCCTGTCTAGGAAAAGCTGTCCTGCGACGCC

CTCTGGAGGAAGCAGGGCTTCCTTTCCTCTGCCATCACGTGCTCAGTCTA

AGCCCCAAGGATTGACCCAGGCCAGGGCTGGAGAAGCAGATAAAAAGCAT

CAAGCCTACAAATGCATGCTTACTTGCAGCAGAAATAGACTAATTGCATG

HEK site 4 sense
(SEQ ID NO: 584)
GGCTGACAAAGGCCGGGCTGGGTGGAAGGAAGGGAGGAAGGGCGAGGCAG

AGGGTCCAAAGCAGGATGACAGGCAGGGGCACCGCGGCGCCCCGGTGGCA

TTGCGGCTGGAGGTGGGGGTTAAAGCGGAGACTCTGGTGCTGTGTGACTA

CAGTGGGGGCCGTGCCCTCTCTGAGCCCCCGCCTCCAGGCCTGTGTGTGT

HEK site 4 antisense
(SEQ ID NO: 585)
ACACACACAGGCCTGGAGGCGGGGGCTCAGAGAGGGCAGGGCCOCCACTG

TAGTCACACAGCACCAGAGTCTCCGCTTTAACCCCCACCTCCAGCCGCAA

TGCCACCGGGGCGCCGCGGTGCCCCTGCCTGTCATCCTGCTTTGGACCCT

CTGCCTCGCCCTTCCTCCCTTCCTTCCACCCAGCCCGGCCTTTGTCAGCC

APOE4 sense
(SEQ ID NO: 743)
AGCACCGAGGAGCTGCGGGTGCGCCTCGCCTCCCACCTGCGCAAGCTGCG

TAAGCGGCTCCTCCGCGATGCCGATGACCTGCAGAAGTGCCTGGCAGTGT

ACCAGGCCGGGGCCCGCGAGGGCGCCGAGCGCGGCCTCAGCGCCATCCGC

GAGCGCCTGGGGCCCCTGGTGGAACAGGGCCGCGTGCGGGCCGCCACTGT

APOE4 antisense
(SEQ ID NO: 744)
ACAGTGGCGGCCCGCACGCGGCCCTGTTCCACCAGGGGCCCCAGGCGCTC

GCGGATGGCGCTGAGGCCGCGCTCGGCGCCCTCGCGGGCCCCGGCCTGGT

ACACTGCCAGGCACTTCTGCAGGTCATCGGCATCGCGGAGGAGCCGCTTA

CGCAGCTTGCGCAGGTGGGAGGCGAGGCGCACCCGCAGCTCCTCGGTGCT p53 Y163C sense
(SEQ ID NO: 745)
ACTCCCCTGCCCTCAACAAGATGTTTTGCCAACTGGCCAAGACCTGCCCT

GTGCAGCTGTGGGTTGATTCCACACCCCCGCCCGGCACCCGCGTCCGCGC

CATGGCCATCTACAAGCAGTCACAGCACATGACGGAGGTTGTGAGGCGCT

GCCCCCACCATGAGCGCTGCTCAGATAGCGATGGTGAGCAGCTGGGGCTG p53 Y163C antisense
(SEQ ID NO: 746)
CAGCCCCAGCTGCTCACCATCGCTATCTGAGCAGCGCTCATGGTGGGGGC

AGCGCCTCACAACCTCCGTCATGTGCTGTGACTGCTTGTAGATGGCCATG

GCGCGGACGCGGGTGCCGGGCGGGGTGTGGAATCAACCCACAGCTGCAC

AGGGCAGGTCTTGGCCAGTTGGCAAAACATCTTGTTGAGGGCAGGGGAGT

Deaminase Gene gBlocks Gene Fragments hAID
(SEQ ID NO: 586)
CATCCTTGGTACCGAGCTCGGATCCAGCCACCATGGATAGCCTCTTGATG

AATAGACGCAAGTTCCTGTATCAGTTTAAAAACGTGAGATGGGCAAAAGG

CCGACGAGAGACATATCTGTGCTATGTCGTTAAGCGCAGAGATTCAGCCA

CCAGTTTCTCTCTCGACTTCGGCTACCTGGGAACAAGAATGGTTGCCAT

GTTGAGCTCCTGTTCCTGAGGTATATCAGCGACTGGGATTTGGACCCAGG

GCGGTGCTATAGGGTGACATGGTTTACCTCCTGGTCACCTTGTTATGACT

GCGCGCGGCATGTTGCCGATTTTCTGAGAGGGAACCCTAACCTGTCTCTG

AGGATCTTCACCGCGCGACTGTACTTCTGTGAGGACCGGAAAGCCGAACC

CGAGGGACTGAGACGCCTCCACAGAGCGGGTGTGCAGATTGCCATAATGA

CCTTTAAGGACTACTTCTACTGCTGGAACACCTTCGTCGAAAATCACGAG

CGGACTTTCAAGGCTTGGGAAGGATTGCATGAAAACAGCGTCAGGCTTTC

CAGGCAGCTTCGCCGCATTCTTCTCCCGTTGTACGAGGTTGATGACCTCA

GAGATGCCTTTAGAACACTGGGACTGTAGGCGGCCGCTCGATTGGTTTGG

TGTGGCTCTAA rAPOBEC1 (mammalian)
(SEQ ID NO: 587)
CATCCTTGGTACCGAGCTCGGATCCAGCCACCATGAGCTCAGAGACTGGC

CCAGTGGCTGTGGACCCCACATTGAGACGGCGGATCGAGCCCCATGAGTT

TGAGGTATTCTTCGATCCGAGAGAGCTCCGCAAGGAGACCTGCCTGCTTT

ACGAAATTAATTGGGGGGCCGGCACTCCATTTGGCGACATACATCACAG

AACACTAACAAGCACGTCGAAGTCAACTTCATCGAGAAGTTCACGACAGA

AAGATATTTCTGTCCGAACACAAGGTGCAGCATTACCTGGTTTCTCAGCT

GGAGCCCATGCGGCGAATGTAGTAGGGCCATCACTGAATTCCTGTCAAGG

TATCCCCACGTCACTCTGTTTATTTACATCGCAAGGCTGTACCACCACGC

TGACCCCGCAATCGACAAGGCCTGCGGGATTTGATCTCTTCAGGTGTGA

CTATCCAAATTATGACTGAGCAGGAGTCAGGATACTGCTGGAGAAACTTT

```
GTGAATTATAGCCCGAGTAATGAAGCCCACTGGCCTAGGTATCCCCATCT
GTGGGTACGACTGTACGTTCTTGAACTGTACTGCATCATACTGGGCCTGC
CTCCTTGTCTCAACATTCTGAGAAGGAAGCAGCCACAGCTGACATTCTTT
ACCATCGCTCTTCAGTCTTGTCATTACCAGCGACTGCCCCCACACATTCT
CTGGGCCACCGGGTTGAAATGAGCGGCCGCTCGATTGGTTTGGTGTGGCT
CTAA
``` pmCDA1
(SEQ ID NO: 588)
```
CATCCTTGGTACCGAGCTCGGATCCAGCCACCATGACAGACGCTGAATAT
GTTAGGATCCATGAAAAACTGGATATCTATACATTTAAGAAGCAGTTCTT
CAATAACAAAAAGTCAGTATCTCACAGATGCTATGTCCTGTTCGAACTCA
AGAGAAGAGGAGAAAGGCGGGCCTGTTTCTGGGGGTACGCGGTTAATAAA
CCCCAGTCCGGGACCGAGAGGGGGATTCACGCCGAGATCTTTTCAATTAG
GAAGGTTGAAGAGTATCTTCGCGACAATCCCGGTCAGTTCACAATTAACT
GGTACAGCTCCTGGAGCCCTTGCGCTGATTGCGCCGAGAAAATACTCGAA
TGGTACAACCAGGAGTTGAGAGGCAATGGCCACACTCTCAAGATTTGGGC
TTGCAAGCTTTACTACGAGAAGAACGCGAGAAATCAGATTGGCTTGTGGA
ACCTCAGGGACAACGGGGTCGGGTTGAATGTTATGGTGTCCGAACATTAC
CAGTGCTGTAGAAAGATCTTCATTCAGTCCAGTCACAATCAGCTGAACGA
GAACAGATGGCTGGAGAAAACACTGAAACGGGCAGAGAAAAGGCGCTCAG
AGCTGAGTATCATGATCCAGGTCAAAATCTCTGCATACAACCAAAAGCCC
GGCTGTATAAGCGGCCGCTCGATTGGTTTGGTGTGGCTCTAA
``` haPOBEC3G
(SEQ ID NO: 589)
```
CATCCTTGGTACCGAGCTCGGATCCAGCCACCATGGAGCTGAAGTATCAC
CCTGAGATGCGGTTTTTCCACTGGTTTAGTAAGTGGCGCAAACTTCATCG
GGATCAGGAGTATGAAGTGACCTGGTATATCTCTTGGTCTCCCTGCACAA
AATGTACACGCGACATGGCCACATTTCTGGCCGAGGATCCAAAGGTGACG
CTCACAATCTTTGTGGCCCGCCTGTATTATTTCTGGGACCCGGATTATCA
GGAGGCACTTAGGTCATTGTGCCAAAAGCGCGACGGACCACGGGCGACTA
TGAAAATCATGAATTATGACGAATTCCAGCATTGCTGGAGTAAGTTTGTG
TACAGCCAGCGGGAGCTGTTCGAGCCCTGGAACAATCTTCCCAAGTACTA
```

```
CATACTGCTTCACATTATGTTGGGGGAGATCCTTCGGCACTCTATGGATC
CTCCTACCTTTACGTTTAACTTTAATAATGAGCCTTGGGTTCGCGGGCGC
CATGAAACCTATTTGTGCTACGAGGTCGAGCGGATGCATAATGATACGTG
GGTCCTGCTGAATCAGAGGAGGGGGTTTCTGTGTAACCAGGCTCCACATA
AACATGGATTTCTCGAGGGGCGGCACGCCGAACTGTGTTTCCTTGATGTG
ATACCTTTCTGGAAGCTCGACCTTGATCAAGATTACAGGGTGACGTGTTT
CACCTCCTGGTCACCCTGCTTCAGTTGCGCCCAAGAGATGGCTAATTTAT
CAGTAAGAACAAGCATGTGTCCCTCTGTATTTTTACAGCCAGAATTTATG
ATGACCAGGGCCGGTGCCAGGAGGGGCTGCGGACACTCGCTGAGGCGGGC
GCGAAGATCAGCATAATGACATACTCCGAATTCAAACACTGTTGGGACAC
TTTTGTGGACCACCAGGGCTGCCCATTTCAGCCGTGGGATGGGCTCGACG
AACATAGTCAGGATCTCTCAGGCCGGCTGCGAGCCATATTGCAGAACCAG
GAGAATTAGGCGGCCGCTCGATTGGTTTGGTGTGGCTCTAA
``` rAPOBEC1 (E. Coli)
(SEQ ID NO: 590)
```
GGCCGGGGATTCTAGAAATAATTTTGTTTAACTTTAAGAAGGAGATATAC
CATGGATGTCTTCTGAAACCGGTCCGGTTGCGGTTGACCCGACCCTGCGT
CGTCGTATCGAACCGCACGAATTCGAAGTTTTCTTCGACCCGCGTGAACT
GCGTAAAGAAACCTGCCTGCTGTACGAAATCAACTGGGGTGGTCGTCACT
CTATCTGGCGTCACACCTCTCAGAACACCAACAAACACGTTGAAGTTAAC
TTCATCGAAAAATTCACCACCGAACGTTACTTCTGCCCGAACACCCGTTG
CTCTATCACCTGGTTCCTGTCTTGGTCTCCGTGCGGTGAATGCTCTCGTG
CGATCACCGAATTCCTGTCTCGTTACCCGCACGTTACCCTGTTCATCTAC
ATCGCGCGTCTGTACCACCACGCGGACCCGCGTAACCGTCAGGGTCTGCG
TGACCTGATCTCTTCTGGTGTTACCATCCAGATCATGACCGAACAGGAAT
CTGGTTACTGCTGGCGTAACTTCGTTAACTACTCTCCGTCTAACGAAGCT
GCACTGGCCGCGTTACTCCGCACCTGTGGGTTCGTCTGTACGTTCTGGAA
CTGTACTGCATCATCCTGGGTCTGCCGCCGTGCCTGAACATCCTGCGTCG
TAAACAGCCGCAGCTGACCTTCTTCACCATCGCGCTGCAGTCTTGCCACT
ACCAGCGTCTGCCGCCGCACATCCTGTGGGCGACCGGTCTGAAAGGTGGT
AGTGGAGGGAGCGGCGGTTCAATGGATAAGAAATAC
```

Amino Acid Sequences of NBE1, NBE2, and NBE3.

NBE1 for E. Coli expression (His$_6$-rAPOBEC1-XTEN-dCas9)
(SEQ ID NO: 591)
```
MGSSHHHHHHMSSETGPVAVDPTLRRRIEPHEFEVFFDPRELRKETCLLYEINWGGRHSIWRHTSQNTN
KHVEVNFIEKFTTERYFCPNTRCSITWFLSWSPCGECSRAITEFLSRYPHVTLFIYIARLYHHADPRNRQGL
RDLISSGVTIQIMTEQESGYCWRNFVNYSPSNEAHWPRYPHLWVRLYVLELYCIILGLPPCLNILRRKQPQ
LTFFTIALQSCHYQRLPPHILWATGLKSGSETPGTSESATPESDKKYSIGLAIGTNSVGWAVITDEYKVPSK
KFKVLGNTDRHSIKKNLIGALLFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFGNLIALSL
GLTPNFKSNFDLAEDAKLQLSKDTYDDDLDNLLAQIGDQYADLFLAAKNLSDAILLSDILRVNTEITKAPLSA
```

-continued

SMIKRYDEHHQDLTLLKALVRQQLPEKYKEIFFDQSKNGYAGYIDGGASQEEFYKFIKPILEKMDGTEELL
VKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTE
GMRKPAFLSGEQKKAIVDLLFKTNRKVTVKQLKEDYFKKIECFDSVEISGVEDRFNASLGTYHDLLKIIKDK
DFLDNEENEDILEDIVLTLTLFEDREMEERLKTYAHLFDDKVMKQLKRRRYTGWGRLSRKLINGIRDKQS
GKTILDFLKSDGFANRNFMQLIHDDSLTFKEDIQKAQVSGQGDSLHEHIANLAGSPAIKKGILQTVKVVDEL
VKVMGRHKPENIVIEMARENQTTQKGQKNSRERMKRIEEGIKELGSQILKEHPVENTQLQNEKLYLYYLQ
NGRDMYVDQELDINRLSDYDVDAIVPQSFLKDDSIDNKVLTRSDKNRGKSDNVPSEEVVKKMKNYWRQL
LNAKLITQRKFDNLTKAERGGLSELDKAGFIKRQLVETRQITKHVAQILDSRMNTKYDENDKLIREVKVITLK
SKLVSDFRKDFQFYKVREINNYHHAHDAYLNAVVGTALIKKYPKLESEFVYGDYKVYDVRKMIAKSEQEIG
KATAKYFFYSNIMNFFKTEITLANGEIRKRPLIETNGETGEIVWDKGRDFATVRKVLSMPQVNIVKKTEVQT
GGFSKESILPKRNSDKLIARKKDWDPKKYGGFDSPTVAYSVLVVAKVEKGKSKKLKSVKELLGITIMERSS
FEKNPIDFLEAKGYKEVKKDLIIKLPKYSLFELENGRKRMLASAGELQKGNELALPSKYVNFLYLASHYEKL
KGSPEDNEQKQLFVEQHKHYLDEIIEQISEFSKRVILADANLDKVLSAYNKHRDKPIREQAENIIHLFTLTINL
GAPAAFKYFDTTIDRKRYTSTKEVLDATLIHQSITGLYETRIDLSQLGGDSGGSPKKKRKV

NBE1 for Mammalian expression (rAPOBEC1-XTEN-dCas9-NLS)
(SEQ ID NO: 592)
MSSETGPVAVDPTLRRRIEPHEFEVFFDPRELRKETCLLYEINWGGRHSIWRHTSQNTNKHVEVNFIEKF
TTERYFCPNTRCSITWFLSWSPCGECSRAITEFLSRYPHVTLFIYIARLYHHADPRNRQGLRDLISSGVTIQ
IMTEQESGYCWRNFVNYSPSNEAHWPRYPHLWVRLYVLELYCIILGLPPCLNILRRKQPQLTFFTIALQSC
HYQRLPPHILWATGLKSGSETPGTSESATPESDKKYSIGLAIGTNSVGWAVITDEYKVPSKKFKVLGNTDR
HSIKKNLIGALLFDSGETAEATRLKRTARRRYTRRKNRICYLQEIFSNEMAKVDDSFFHRLEESFLVEEDKK
HERHPIFGNIVDEVAYHEKYPTIYHLRKKLVDSTDKADLRLIYLALAHMIKFRGHFLIEGDLNPDNSDVDKLF
IQLVQTYNQLFEENPINASGVDAKAISARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQ
DLTLLKALVRQQLPEKYKEIFFDQSKNGYAGYIDGGASQEEFYKFIKPILEKMDGTEELLVKLNREDLLRKQ
RTFDNGSIPHQIHLGELHAILRRQEDFYPFLKDNREKIEKILTFRIPYYVGPLARGNSRFAWMTRKSEETITP
WNFEEVVDKGASAQSFIERMTNFDKNLPNEKVLPKHSLLYEYFTVYNNELTKVKYVTEGMRKPAFLSGEQ
KKAIVDLLFKTNRKVTVKQLKEDYFKKIECFDSVEISGVEDRFNASLGTYHDLLKHKDKDFLDNEENEDILE
DIVLTLTLFEDREMIEERLKTYAHLFDDKVMKQLKRRRYTGWGRLSRKLINGIRDKQSGKTILDFLKSDGFA
NRNFIAGLIHDDSLTFKEDIQKAQVSGQGDSLHEHIANLAGSPAKKGILQPVKVVDELVKVMGRHKPENIVI
EMARENQTTQKGQKNSRERMKRIEEGIKELGSQILKEHPVENTQLQNEKLYLYYLQNGRDMYVDQELDI
NRLSDYDVDAIVPQSFLKDDSIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLIREVKVITLKSKLVSDFRKDFQF
YKVREINNYHHAHDAYLNAVVGTALIKKYPKLESEFVYGDYKVYDVRMIAKSEQEIGKATAKYFFYSNIM
NFFKTEITLANGEIRKRPLIETNGETGEIVWDKGRDFATVRKVLSMPQNIVKKTEVQTGGFSKESILPKRN
SDKLIARKKDWDPKKYGGFDSPTVAYSVLVVAKVEKGKSKKLKSVKELLGITIMERSSFEKNPIDFLEAKG
YKEVKKDLIIKLPKYSLFELENGRKRMLASAGELQKGNELALPSKYVNFLYLASHYEKLKGSPEDNEQKQL
FVEQHKHYLDEIIEQISEFSKRVILADANLDKVLSAYNKHRDKPIREQAENIIHLFTLTNLGAPAAFKYFDTTI
DRKRYTSTKEVLDATLIHQSITGLYETRIDLSQLGGDSGGSPKKKRKV Alternative NBE1 for Mammalian expression with human APOBEC1 (hAPOBEC1-XTEN-dCas9-NLS)

(SEQ ID NO: 5737)

MTSEKGPSTGDPTLRRRIEPWEFDVFYDPRELRKEACLLYEIKWGMSRKIWRSSGKNTTN

HVEVNFIKKFTSERDFHPSMSCSITWFLSWSPCWECSQAIREFLSRHPGVTLVIYVARLFW

HMDQQNRQGLRDLVNSGVTIQIMRASEYYHCWRNFVNYPPGDEAHWPQYPPLWMMLY

ALELHCIILSLPPCLKISRRWQNHLTFFRLHLQNCHYQTIPPHILLATGLIHPSVAWRGSETP

GTSESATPESDKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEGD

LNPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQIH

LGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMR

KPAFLSGEQKKAIVDLLFKTNRKVTVKQLKEDYFKKIECFDSVETSGVEDRFNASLGTYH

DLLKIIKDKDFLDNEENEDILEDIVLTLTLFEDREMIEERLKTYAHLFDDKVMKQLKRRRY

TGWGRLSRKLINGIRDKQSGKTILDFLKSDGFANRNFMQLIHDDSLTFKEDIQKAQVSGQ

GDSLHEHIANLAGSPAIKKGILQTVKVVDELVKVMGRHKPENIVIEMARENQTTQKGQK

NSRERMKRIEEGIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYWRQLLNAKLITQ

RKFDNLTKAERGGLSELDKAGFIKRQLVETRQITKHVAQILDSRMNTKYDENDKLIREVK

VITLKSKLVSDFRKDFQFYKVREINNYHHAHDAYLNAVVGTALIKKYPKLESEFVYGDY

KVYDVRKMIAKSEQEIGKATAKYFFYSNIMNFFKTEITLANGEIRKRPLIETNGETGEIVW

DKGRDFATVRKVLSMPQVNIVKKTEVQTGGFSKESILPKRNSDKLIARKKDWDPKKYGG

FDSPTVAYSVLVVAKVEKGKSKKLKSVKELLGITIMERSSFEKNPIDFLEAKGYKEVKKD

LIIKLPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHLFTL

TNLGAPAAFKYFDTTIDRKRYTSTKEVLDATLIHQSITGLYETRIDLSQLGGDSGGSPKKK

RKV

NBE2 (rAPOBEC1-XTEN-dCas9-UGI-NLS)

(SEQ ID NO: 593)

MSSETGPVAVDPTLRRRIEPHEFEVFFDFRELRKETCLLYEINWGGRHSIWRHTSQNTNKHVEVNFIEKF

TTERYFCPNTRCSITWFLSWSPCGECSRAITEFLSRYPHVTLFIYIARLYHHADPRNRQGLRDLISSGVTIQ

IMTEQESGYCWRNFVNYSPSNEAHWPRYPHLWVRLYVLELYCIILGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETITP

-continued

WNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLRRRYTGWGRLSRKLINGIRDKQSGKTILDFLKSDGFA

NRNFMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDAIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSFEKNPIDFLEAKG

YKEVKKDLIIKLPKYSLFELENGRKRMLASAGELQKGNELALPSKYVNFLYLASHYEKLKGSPEDNEQKQL

FVEQHKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDSGGSTNLSDIIEKETGKQLVIQESILMLPEEVEEVIG

NKPESDILVHTAYDESTDENVMLLTSDAPEYKPWALVIQDSNGENKIKMLSGGSPKKKRKV

NBE3 (rAPOBEC1-XTEN-Cas9n-UGI-NLS)

(SEQ ID NO: 594)

MSSETGPVAVDPTLRRRIEPHEFEVFFDPRELRKETCLLYEINWGGRHSIWRHTSQNTNKHVEVNFIEKF

TTERYFCPNTRCSITWFLSWSPCGECSRAITEFLSRYPHVTLFIYIARLYHHADPRNRQGLRDLISSGVTIQ

IMTEQESGYCWRNFVNYSPSNEAHWPRYPHLWVRLYVLELYCIILGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLRRRYTGWGRLSRKLINGIRDKQSGKTILDFLKSDGFA

NRNFMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDHIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSFEKNPIDFLEAKG

YKEVKKDLIIKLPKYSLFELENGRKRMLASAGELQKGNELALPSKYVNFLYLASHYEKLKGSPEDNEQKQL

FVEQHKHYLDENIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDSGGSTNLSDIIEKETGKQLVIQESILMLPEEVEEVIG

NKPESDILVHTAYDESTDENVMLLTSDAPEYKPWALVQDSNGENKIKMLSGGSPKKKRKV

-continued pmCDA1-XTEN-dCas9-UGI (bacteria)
(SEQ ID NO: 5742)
MTDAEYVRIHEKLDIYTFKKQFFNNKKSVSHRCYVLFELKRRGERRACFWGYAVNKPQS
GTERGIHAEIFSIRKVEEYLRDNPGQFTINWYSSWSPCADCAEKILEWYNQELRGNGHTL
KIWACKLYYEKNARNQIGLWNLRDNGVGLNVMVSEHYQCCRKIFIQSSHNQLNENRWL
EKTLKRAEKRRSELSIMIQVKILHTTKSPAVSGSETPGTSESATPESDKKYSIGLAIGTNSV
GWAVITDEYKVPSKKFKVLGNTDRHSIKKNLIGALLFDSGETAEATRLKRTARRRYTRRK
NRICYLQEIFSNEMAKVDDSFFHRLEESFLVEEDKKHERHPIFGNIVDEVAYHEKYPTIYH
LRKKLVDSTDKADLRLIYLALAHMIKFRGHFLIEGDLNPDNSDVDKLFIQLVQTYNQLFE
ENPINASGVDAKAILSARLSKSRRLENLIAQLPGEKKNGLFGNLIALSLGLTPNFKSNFDLA
EDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYPFLKDNREKIEK
ILTFRIPYYVGPLARGNSRFAWMTRKSEETITPWNFEEVVDKGASAQSFIERMTNFDKNLP
NEKVLPKHSLLYEYFTVYNELTKVKYVTEGMRKPAFLSGEQKKAIVDLLFKTNRKVTVK
QLKEDYFKKIECFDSVETSGVEDRFNASLGTYHDLLKIIKDKDFLDNEENEDILEDIVLTLT
LFEDREMIEERLKTYAHLFDDKVMKQLKRRRYTGWGRLSRKLINGIRDKQSGKTILDFLK
SDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENT
QLQNEKLYLYYLQNGRDMYVDQELDINRLSDYDVDAIVPQSFLKDDSIDNKVLTRSDKN
RGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNY
HHAHDAYLNAVVGTALIKKYPKLESEFVYGDYKVYDVRKMIAKSEQEIGKATAKYFFYS
NIMNFFKTEITLANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEKGKSKKLKSV
KELLGITIMERSSFEKNPIDFLEAKGYKEVKKDLIIKLPKYSLFELENGRKRMLASAGELQ
KGNELALPSKYVNFLYLASHYEKLKGSPEDNEQKQLFVEQHKHYLDEIIEQISEFSKRVIL
ADANLDKVLSAYNKHRDKPIREQAENIIHLFTLTNLGAPAAFKYFDTTIDRKRYTSTKEV
LDATLIHQSITGLYETRIDLSQLGGDSGGSMTNLSDIIEKETGKQLVIQESILMLPEEVEEVI
GNKPESDILVHTAYDESTDENVMLLTSDAPEYKPWALVIQDSNGENKIKML pmCDA1-XTEN-nCas9-UGI-NLS (mammalian construct)
(SEQ ID NO: 5743)
MTDAEYVRIHEKLDIYTFKKQFFNNKKSVSHRCYVLFELKRRGERRACFWGYAVNKPQS
GTERGIHAEIFSIRKVEEYLRDNPGQFTINWYSSWSPCADCAEKILEWYNQELRGNGHTL
KIWACKLYYEKNARNQIGLWNLRDNGVGLNVMVSEHYQCCRKIFIQSSHNQLNENRWL
EKTLKRAEKRRSELSIMIQVKILHTTKSPAVSGSETPGTSESATPESDKKYSIGLAIGTNSV
GWAVITDEYKVPSKKFKVLGNTDRHSIKKNLIGALLFDSGETAEATRLKRTARRRYTRRK
NRICYLQEIFSNEMAKVDDSFFHRLEESFLVEEDKKHERHPIFGNIVDEVAYHEKYPTIYH
LRKKLVDSTDKADLRLIYLALAHMIKFRGHFLIEGDLNPDNSDVDKLFIQLVQTYNQLFE
ENPINASGVDAKAILSARLSKSRRLENLIAQLPGEKKNGLFGNLIALSLGLTPNFKSNFDLA
EDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILE -continued

KMDGTEELLVKLNREDLLRKQRTFDNGSIPHQIHLGELHAILRRQEDFYPFLKDNREKIEK

ILTFRIPYYVGPLARGNSRFAWMTRKSEETITPWNFEEVVDKGASAQSFIERMTNFDKNLP

NEKVLPKHSLLYEYFTVYNELTKVKYVTEGMRKPAFLSGEQKKAIVDLLFKTNRKVTVK

QLKEDYFKKIECFDSVETSGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENT

QLQNEKLYLYYLQNGRDMYVDQELDINRLSDYDVDHIVPQSFLKDDSIDNKVLTRSDKN

RGKSDNVPSEEVVKKMKNYWRQLLNAKLITQRKFDNLTKAERGGLSELDKAGFIKRQL

VETRQITKHVAQILDSRMNTKYDENDKLIREVKVITLKSKLVSDFRKDFQFYKVREINNY

HHAHDAYLNAVVGTALIKKYPKLESEFVYGDYKVYDVRKMIAKSEQEIGKATAKYFFYS

NIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSV

KELLGITIMERS SFEKNPIDFLEAKGYKEVKKDLIIKLPKYSLFELENGRKRMLASAGELQ

KGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEV

LDATLIHQSITGLYETRIDLSQLGGDSGGSTNLSDIIEKETGKQLVIQESILMLPEEVEEVIG

NKPESDILVHTAYDESTDENVMLLTSDAPEYKPWALVIQDSNGENKIKMLSGGSPKKKR

KV huAPOBEC3G-XTEN-dCas9-UGI (bacteria)
(SEQ ID NO: 5744)

MDPPTFTFNFNNEPWVRGRHETYLCYEVERMHNDTWVLLNQRRGFLCNQAPHKHGFLE

GRHAELCFLDVIPFWKLDLDDYRVTCFTSWSPCFSCAQEMAKFISKNKHVSLCIFTARIY

DDQGRCQEGLRTLAEAGAKISIMTYSEFKHCWDTFVDHQGCPFQPWDGLDEHSQDLSGR

LRAILQSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLAQIG

DQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMT

RKSEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVETSGVEDR

FNASLGTYHDLLKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLIHDDSLTFKED

IQKAQVSGQGDSLHEHIANLAGSPAIKKGILQTVKVVDELVKVMGRHKPENIVIEMAREN

QTTQKGQKNSRERMKRIEEGIKELGSQILKEHPVENTQLQNEKLYLYYLQNGRDMYVDQ

ELDINRLSDYDVDAIVPQSFLKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKLE

SEFVYGDYKVYDVRKMIAKSEQEIGKATAKYFFYSNIMNFFKTEITLANGEIRKRPLIETN

```
GETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAK

GYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLYETRIDLSQLGGD

SGGSMTNLSDIIEKETGKQLVIQESILMLPEEVEEVIGNKPESDILVHTAYDESTDENVMLL

TSDAPEYKPWALVIQDSNGENKIKML
``` huAPOBEC3G-XTEN-nCas9-UGI-NLS (mammalian construct)
(SEQ ID NO: 5745)

```
MDPPTFTFNFNNEPWVRGRHETYLCYEVERMHNDTWVLLNQRRGFLCNQAPHKHGFLE

GRHAELCFLDVIPFWKLDLDQDYRVTCFTSWSPCFSCAQEMAKFISKNKHVSLCIFTARIY

DDQGRCQEGLRTLAEAGAKISIMTYSEFKHCWDTFVDHQGCPFQPWDGLDEHSQDLSGR

LRAILQSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLAQIG

DQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMT

RKSEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVETSGVEDR

FNASLGTYHDLLKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLIHDDSLTFKED

IQKAQVSGQGDSLHEHIANLAGSPAIKKGILQTVKVVDELVKVMGRHKPENIVIEMAREN

QTTQKGQKNSRERMKRIEEGIKELGSQILKEHPVENTQLQNEKLYLYYLQNGRDMYVDQ

ELDINRLSDYDVDHIVPQSFLKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKLE

SEFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

WDPKKYGGFDSPTVAYS VLVVAKVEKGKSKKLKSVKELLGITIMERSSFEKNPIDFLEAK

GYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLYETRIDLSQLGGD

SGGSTNLSDIIEKETGKQLVIQESILMLPEEVEEVIGNKPESDILVHTAYDESTDENVMLLT

SDAPEYKPWALVIQDSNGENKIKMLSGGSPKKKRKV
``` huAPOBEC3G (D316R_D317R)-XTEN-nCas9-UGI-NLS (mammalian construct)
(SEQ ID NO: 5746)

```
MDPPTFTFNFNNEPWVRGRHETYLCYEVERMHNDTWVLLNQRRGFLCNQAPHKHGFLE

GRHAELCFLDVIPFWKLDLDQDYRVTCFTSWSPCFSCAQEMAKFISKNKHVSLCIFTARIY

RRQGRCQEGLRTLAEAGAKISIMTYSEFKHCWDTFVDHQGCPFQPWDGLDEHSQDLSGR
```

-continued

LRAILQSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLAQIG

DQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMT

RKSEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVETSGVEDR

FNASLGTYHDLLKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLIHDDSLTFKED

IQKAQVSGQGDSLHEHIANLAGSPAIKKGILQTVKVVDELVKVMGRHKPENIVIEMAREN

QTTQKGQKNSRERMKRIEEGIKELGSQILKEHPVENTQLQNEKLYLYYLQNGRDMYVDQ

ELDINRLSDYDVDHIVPQSFLKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKLE

SEFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAK

GYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLYETRIDLSQLGGD

SGGSTNLSDIIEKETGKQLVIQESILMLPEEVEEVIGNKPESDILVHTAYDESTDENVMLLT

SDAPEYKPWALVIQDSNGENKIKMLSGGSPKKKRKV

Base Calling Matlab Script (SEQ ID NO: 595)
WTnuc = 'GCGGACATGGAGGACGTGCGCGGCCGCCTGGTGCAGTACCGC

GGCGAGGTGCAGGCCATGCTCGGCCAGA

GCACCGAGGAGCTGCGGGTGCGCCTCGCCTCCCACCTGCGCAAGCTGCGT

AAGCGGCTCCTCCGCGATGCCGATGAC

CTGCAGAAGCGCCTGGCAGTGTACCAGGCCGGGGCCCGCGAGGGCGCCGA

GCGCGGCCTCAGCGCCATCCGCGAGCG CCTGGGGCCCCTGGTGGAACA

G';

```
%cycle through fastq files for different samples files=dir('*.fastq');
for d=1:20
filename=files(d).name;
%read fastq file
[header,seqs,qscore]=fastqread(filename);
seqsLength=length(seqs);                              % number of sequences seqsFile=
strrep(filename,'.fastq','');                          % trims off .fastq
%create a directory with the same name as fastq file ifexist(seqsFile,'dir');
   error('Directory already exists. Please rename or move it before moving on.');
end
mkdir(seqsFile);                                       % make directory
wtLength=length(WTnuc);                                % length of wildtype sequence
%% aligning back to the wildtype nucleotide sequence
%
% MN is a matrix of the nucleotide alignment window=1:wtLength;
```

```
sBLength=length(seqs);
% counts number of skips nSkips = 0;
ALN=repmat('',[sBLengthwtLength]);
% iterate through each sequencing read for i = 1:sBLength
%If you only have forward read fastq files leave as is
%If you have R1 foward and R2 is reverse fastq files uncomment the
%next four lines of code and the subsequent end statement
%
%
%
swalign(reverse,WTnuc,'Alphabet','NT');
%
[score,alignment,start]=swalign(seqs{i},WTnuc,'Alphabet','NT');
%
% length of the sequencing read len=
length(alignment(3,:));
% if there is a gap in the alignment, skip = 1 and we will
    % throw away the entire read skip = 0;
    for j = 1:len
if (alignment(3,j) == '-' || alignment(1,j) == '-') skip = 1;
        break;
    end
    %in addition if the qscore for any given base in the read is
        %below 31 the nucleotide is turned into an N (fastq qscores that are not letters)
    ifisletter(qscore{i}(start(1)+j-1)) else
    alignment(1,j) = 'N';
        end
    end
    if skip == 0 && len>10
    ALN(i, start(2):(start(2)+length(alignment)-1))=alignment(1,:);
        end
    end
% with the alignment matrices we can simply tally up the occurrences of
% each nucleotide at each column in the alignment these
% tallies ignore bases annotated as N
% due to low qscores
TallyNTD=zeros(5,wtLength); for i=1:wtLength
TallyNTD(:,i)=[sum(ALN(:,i)=='A'),sum(ALN(:,i)=='C'),sum(ALN(:,i)=='G'),
sum(ALN(:,i)=='T'),sum(ALN(:,i)=='N')];
end
% we then save these tally matrices in the respective folder for
% further processing
save(strcat(seqsFile,'/TallyNTD'),'TallyNTD'); dlmwrite(strcat(seqsFile,'/TallyNTD.txt'),TallyNTD,'precision',
'%.3f','newline','pc'); end % number of sequences ifmod(d,2)==0;
    reverse=seqrcomplement(seqs{i});
    [score,alignment,start]= else end
```

INDEL Detection Matlab Script

```
                                                                (SEQ ID NO: 595)
WTnuc = 'GCGGACATGGAGGACGTGCGCGGCCGCCTGGTGCAGTACCG

CGGCGAGGTGCAGGCCATGCTCGGCCAGA

GCACCGAGGAGCTGCGGGTGCGCCTCGCCTCCCACCTGCGCAAGCTGCGT

AAGCGGCTCCTCCGCGATGCCGATGAC

CTGCAGAAGCGCCTGGCAGTGTACCAGGCCGGGGCCCGCGAGGGCGCCGA

GCGCGGCCTCAGCGCCATCCGCGAGCG  CCTGGGGCCCCTGGTGGAACA

G';
```

```
%cycle through fastq files for different samples files=dir('*.fastq');
%specify start and width of indel window as well as length of each flank indelstart=154;
width=30; flank=10;
for d=1:3
filename=files(d).name;
%read fastq file
[header,seqs,qscore]=fastqread(filename);
seqsLength=length(seqs);                          % number of sequences seqsFile
=strcat(strrep(filename,'.fastq',''),'_INDELS');
%create a directory with the same name as fastq file+_INDELS ifexist(seqsFile,'dir');
        error('Directory already exists. Please rename or move it before moving on.');
end
mkdir(seqsFile);                                  % make directory
wtLength=length(WTnuc);                           % length of wildtype sequence sBLength =
length(seqs);                                     % number of sequences
% initialize counters and cell arrays
nSkips = 0; notINDEL=0;
ins={ };
```

```
dels={ }; NumIns=0;
NumDels=0;
% iterate through each sequencing read for i = 1:sBLength
    %search for 10BP sequences that should flank both sides of the "INDEL WINDOW"
    windowstart=strfind(seqs{i},WTnuc(indelstart-flank:indelstart));
        windowend=strfind(seqs{i},WTnuc(indelstart+width:indelstart+width+flank
));
%if the flanks are found proceed
iflength(windowstart)==1&&length(windowend)==1
%if the sequence length matches the INDEL window length save as
    %not INDEL
if windowend-windowstart==width+flank notINDEL=notINDEL+1;
    %if the sequence is two or more bases longer than the INDEL
    %window length save as an Insertion
elseif windowend-windowstart>=width+flank+2 NumIns=NumIns+1;
    ins{NumDels}=seqs{i};
    %if the sequence is two or more bases shorter than the INDEL
    %window length save as a Deletion
elseif windowend-windowstart<=width+flank-2 NumDels=NumDels+1;
    dels{NumDels}=seqs{i};
    %keep track of skipped sequences that are either one base
    %shorter or longer than the INDEL window width else
    nSkips=nSkips+1;
    end
    %keep track of skipped sequences that do not possess matching flank
    %sequences else
    nSkips=nSkips+1;
       end
    end
    fid=fopen(strcat(seqsFile,'/summary.txt'),'wt');
    fprintf(fid, 'Skipped reads %i\n not INDEL %i\n Insertions %i\n Deletions
%i\n', [nSkips, notINDEL, NumIns, NumDels]); fclose(fid);
    save(strcat(seqsFile,'/nSkips'),'nSkips'); save(strcat(seqsFile,'/notINDEL'),'notINDEL');
    save(strcat(seqsFile,'/NumIns'),'NumIns'); save(strcat(seqsFile,'/NumDels'),'NumDels');
    save(strcat(seqsFile,'/dels'),'dels');
    C = dels;
    fid=fopen(strcat(seqsFile,'/dels.txt'),'wt'); fprintf(fid,'"%s"\n',C{:});
    fclose(fid);
    save(strcat(seqsFile,'/ins'),'ins'); C = ins;
    fid=fopen(strcat(seqsFile,'/ins.txt'), 'wt'); fprintf(fid,'"%s"\n',C{:});
    fclose(fid);
    end
```

Example 5: Cas9 Variant Sequences

The disclosure provides Cas9 variants, for example Cas9 proteins from one or more organisms, which may comprise one or more mutations (e.g., to generate dCas9 or Cas9 nickase). In some embodiments, one or more of the amino acid residues, identified below by an asterek, of a Cas9 protein may be mutated. In some embodiments, the D10 and/or H840 residues of the amino acid sequence provided in SEQ ID NO: 10, or a corresponding mutation in any of the amino acid sequences provided in SEQ ID NOs: 11-260, are mutated. In some embodiments, the D10 residue of the amino acid sequence provided in SEQ ID NO: 10, or a corresponding mutation in any of the amino acid sequences provided in SEQ ID NOs: 11-260, is mutated to any amino acid residue, except for D. In some embodiments, the D10 residue of the amino acid sequence provided in SEQ ID NO: 10, or a corresponding mutation in any of the amino acid sequences provided in SEQ ID NOs: 11-260, is mutated to an A. In some embodiments, the H840 residue of the amino acid sequence provided in SEQ ID NO: 10, or a corresponding residue in any of the amino acid sequences provided in SEQ ID NOs: 11-260, is an H. In some embodiments, the H840 residue of the amino acid sequence provided in SEQ ID NO: 10, or a corresponding mutation in any of the amino acid sequences provided in SEQ ID NOs: 11-260, is mutated to any amino acid residue, except for H. In some embodiments, the H840 residue of the amino acid sequence provided in SEQ ID NO: 10, or a corresponding mutation in any of the amino acid sequences provided in SEQ ID NOs: 11-260, is mutated to an A. In some embodiments, the D10 residue of the amino acid sequence provided in SEQ ID NO: 10, or a corresponding residue in any of the amino acid sequences provided in SEQ ID NOs: 11-260, is a D.

A number of Cas9 sequences from various species were aligned to determine whether corresponding homologous amino acid residues of D10 and H840 of SEQ ID NO: 10 or SEQ ID NO: 11 can be identified in other Cas9 proteins, allowing the generation of Cas9 variants with corresponding mutations of the homologous amino acid residues. The alignment was carried out using the NCBI Constraint-based Multiple Alignment Tool (COBALT(accessible at st-va.ncbi.nlm.nih.gov/tools/cobalt), with the following parameters. Alignment parameters: Gap penalties-11, -1; End-Gap penalties-5, -1. CDD Parameters: Use RPS BLAST on; Blast E-value 0.003; Find Conserved columns and Recompute on. Query Clustering Parameters: Use query clusters on; Word Size 4; Max cluster distance 0.8; Alphabet Regular.

An exemplary alignment of four Cas9 sequences is provided below. The Cas9 sequences in the alignment are: Sequence 1 (S1): SEQ ID NO: 11|WP_010922251| gi 499224711|type II CRISPR RNA-guided endonuclease Cas9 [*Streptococcus pyogenes*]; Sequence 2 (S2): SEQ ID NO: 12|WP_039695303|gi 746743737|type II CRISPR RNA-guided endonuclease Cas9 [*Streptococcus gallolyticus*]; Sequence 3 (S3): SEQ ID NO: 13|WP_045635197|gi 782887988|type II CRISPR RNA-guided endonuclease Cas9 [*Streptococcus mitis*]; Sequence 4 (S4): SEQ ID NO: 14|5AXW_A|gi 924443546|*Staphylococcus aureus* Cas9. The HNH domain (bold and underlined) and the RuvC domain (boxed) are identified for each of the four sequences. Amino acid residues 10 and 840 in S1 and the homologous amino acids in the aligned sequences are identified with an asterisk following the resective amino acid residue.

```
S1     1 --MDKK-YSIGLD*IGTNSVGWAVITDEYKVPSKKFKVLGNTDRHSIKKNLI--GALLEDSG--ETAEATRLKRTARRRYT       73
S2     1 --MTKKNYSIGLD*IGTNSVGWAVITDDYKVPAKKMKVLGNTDKKYIKKNLL--GALLFDSG--ETAEATRLKRTARRRYT       74
S3     1 --M-KKGYSIGLD*IGTNSVGFAVITDDYKVPSKKMKVLGNTDKRFIKKNLI--GALLFDEG--TTAEARRLKRTARRRYT       73
S4     1 GSHMKRNYILGLD*IGITSVGYGII--DYET----------------RDVIDAGVRLFKEANVENNEGRRSKRGARRLKR       61

S1    74 RRKNRICYLQEIFSNEMAKVDDSFEHRLEESELVEEDKKHERHPIFGNIVDEVAYHEKYPTIYHLRKKLVDSTDKADLRL      153
S2    75 RRKNRLRYLQEIFANETAKVDESFFQRLDESFLTDDDKTEDSHPIFGNKAEEDAYHQKFPTIYHLRKHLADSSEKADLRL      154
S3    74 RRKNRLRYLQEIFSEEMSKVDSSFEHRLDDSFLIPEDKRESKYPIFATLTEEKEYHKQFPTIYHLRKQLADSKEKTDLRL      153
S4    62 RRRHRIQRVKKLL--------------FDYNLLTD--------------------HSELSGINPYEARVKGLSQKLSEEE      107

S1   154 IYLALAHNIKERGHFLIEGDLNPDNSDVDKLFIQLVQTYNQLFEENPINASGVDAKAILSARLSKSRRLENLIAQLPGEK      233
S2   155 VYLALAHNIKERGHFLIEGELNAENTDVQKIFADFVGVYNRTFDDSHLSEITVDVASILTEKISKSRRLENLIKYYPTEK      234
S3   154 TYLALAHNIKYRGHFLYEEAFDIKNNDIQKIFNEFISIYDNTFEGSSLSGQNAQVEAIFTDKISKSAKRERVLKLEPDEK      233
S4   108 FSAALLHLAKRRG---------------------VHNVNEVEEDT-----------------------------------      131

S1   234 KNGLFGNLIALSLGLTPNEKSNFDLAEDAKLQLSKDTYDDDLDNLLAQIGDQYADLFLAAKNLSDAILLSDILRVNTEIT      313
S2   235 KNTLFGNLIALALGLQPNEKTNFKLSEDAKLQFSKDTYEEDLEELLGKIGDDYADLFTSAKNLYDAILLSGILTVDDNST      314
S3   234 STGLFSEFLKLIVGNQADFKKHFDLEDKAPLQFSKDTYDEDLENLLGQIGDDFTDLFVSAKKLYDAILLSGILTVTDPST      313
S4   132 -----GNELS------------------TKEQISRN--------------------------------------------      144

S1   314 KAPLSASMIKRYDEHHQDLTLLKALVRQQLPEKYKEIFFDQSKNGYAGYIDGGASQEEFYKFIKPILEKM--DGTEELLV      391
S2   315 KAPLSASMIKRYVEHHEDLEKLKEFIKANKSELYHDIFKDKNKNGYAGYIENGVKQDEFYKYLKNILSKIKIDGSDYFLD      394
S3   314 KAPLSASMIERYENHQNDLAALKQFIKNNLPEKYDEVFSDQSKDGYAGYIDGKTTQETFYKYIKNLLSKF--EGTDYFLD      391
S4   145 ----SKALEEKYVAELQ------------------------------------------------LERLKKDG------      165

S1   392 KLNREDLLRKQRTFDNGSIPHQIHLGELHAILRRQEDFYPFLKDNREKIEKILTFRIPYYVGPLARGNSRFAWMTRKSEE      471
S2   395 KIEREDFLRKQRTFDNGSIPHQIHLQEMHAILRRQGDYYPFLKEKQDRIEKILTFRIPYYVGPLVRKDSRFAWAEYRSDE      474
S3   392 KIEREDFLRKQRTFDNGSIPHQIHLQEMNAILRRQGEYYPFLKDNKEKIEKILTFRIPYYVGPLARGNRDFAWLTRNSDE      471
S4   166 --EVRGSINRFKTSD--------YVKEAKQLLKVQKAYHQLDQSFIDTYIDLLETRRTYYEGP--GEGSPFGW------K      227

S1   472 TITPWNFEEVVDKGASAQSFIERMTNFDKNLPNEKVLPKHSLLYEYFTVYNELTKVKYVTEGMRKPAFLSGEQKKAIVDL      551
S2   475 KITPWNFDKVIDKEKSAEKFITRMTLNDLYLPEEKVLPKHSHVYETYAVYNELTKIKYVNEQGKE-SFFDSNMKQEIFDH      553
S3   472 AIRPWNFEEIVDKASSAEDFINKMTNYDLYLPEEKVLPKHSLLYETFAVYNELTKVKFIAEGLRDYQFLDSGQKKQIVNQ      551
S4   228 DIKEW---------------YEMLMGHCTYFPEELRSVKYAYNADLYNALNDLNNLVITRDENEK---LEYYEKFQIIEN      289

S1   552 LEKTNRKVTVKQLKEDYFKKIECFDSVEISGVEDR---FNASLGTYHDLLKIIKDKDFLDNEENEDILEDIVLTLTLFED      628
S2   554 VFKENRKVTKEKLLNYLNKEFFEYRIKDLIGLDKENKSFNASLGTYHDLKKIL-DKAFLDDKVNEEVIEDIIKTLTLFED      632
S3   552 LEKENRKVTEKDIIHYLHN-VDGYDGIELKGIEKQ---FNASLSTYHDLLKIIKDKEENDDAKNEAILENIVHTLTIFED      627
S4   290 VFKQKKKPTLKQIAKEILVNEEDIKGYRVTSTGKPEF---TNLKVYHDIKDITARKEII---ENAELLDQIAKILTIYQS      363

S1   629 REMIEERLKTYAHLFDDKVMKQLKR-RRYTGWGRLSRKLINGIRDKQSGKTILDFLKSDGFANRNFMQLIHDDSLTFKED      707
S2   633 KDMIHERLQKYSDIFTANQLKKLER-RHYTGWGRLSYKLINGIRNKENNKTILDYLIDDGSANRNFMQLINDDTLPFKQI      711
S3   628 REMIKQRLAQYDSLFDEKVIKALTR-RHYTGWGKLSAKLINGICDKQTGNTILDYLIDDGKINRNFMQLINDDGLSFKEI      706
S4   364 SEDIQEELTNLNSELTQEEIEQISNLKGYTGTHNLSLKAINLILDE------LWHTNDNQIAIFNRLKLVP---------      428

S1   708 IQKAQVSGQG DSLHEHIANLAGSPAIKKGILQTVKVVDELVKVMGRHKPENIVIEMA RENQTT------QKGQKNSRERM      781
```

```
S2   712  IQKSQVVGDV DDIEAVVHDLPGSPAIKKGILQSVKIVDELVKVMG-GNPDNIVIEMA RENQTT------NRGRSQSQQRL   784

S3   707  IQKAQVIGKT DDVKQVVQELSGSPAIKKGILQSIKIVDELVKVMG-HAPESIVIEMA RENQTT------ARGKKNSQQRY   779

S4   429  -KKVDLSQQK EIPTTLVDDFILSPVVKRSFIQSIKVINAIIKKYG--LPNDIIIELA REKNSKDAQKMINEMQKRNRQTN   505

S1   782  KRIEEGIKELGSQIL-------KEHPVENTQLQNEKLYLYYLQNGRDMYVDQELDINRLSD----YDVDH*IVPQSFLKDD   850

S2   785  KKLQNSLKELGSNILNEEKPSYIEDKVENSHLQNDQLFLYYIQNGKDMYTGDELDIDHLSD----YDIDH*IIPQAFIKDD   860

S3   780  KRIEDSLKILASGL---DSNILKENPTDNNQLQNDRLFLYYLQNGKDMYTGEALDINQLSS----YDIDH*IIPQAFIKDD   852

S4   506  ERIEEIIRTTGK---------------ENAKYLIEKIKLHDMQEGKCLYSLEAIPLEDLLNNPFNYEVDH*IIPRSVSFDN   570

S1   851  SIDNKVLTRSDKNRGKSDNVPSEEVVKKMKNYWRQLLNAKLITQRKFDN-LTKAERGGL-SELD------KAGFIKRQLV   922

S2   861  SIDNRVLTSSAKNRGKSDDVPSLDIVRARKAEWVRLYKSGLISKRKFDN-LTKAERGGL-TEAD------KAGFIKRQLV   932

S3   853  SLDNRVLTSSKDNRGKSDNVPSIEVVQKRKAFWQQLLDSKLISERKFNN-LTKAERGGL-DERD------KAGFIKRQLV   924

S4   571  SFNNKVLVKQEEASKKGNRTPFQYLSSSDSKISYETFKKHILNLAKGKGRISKTKKEYLLEERDINRFSVQKDFINRNLV   650

S1   923  ETRQITKHVAQILDSRMNTKYDENDKLIREVKVITLKSKLVSDFRKDFQFYKVREINNYHHAHDAYLNAVVGTALIKKYP  1002

S2   933  ETRQITKHVAQILDARFNTEHDENDKVIRDVKVITLKSNLVSQFRKDFEFYKVREINDYHHAHDAYLNAVVGTALLKKYP  1012

S3   925  ETRQITKHVAQILDARYNTEVNEKDKKNRTVKIITLKSNLVSNFRKEFRLYKVREINDYHHAHDAYLNAVVAKAILKKYP  1004

S4   651  DTRYATRGLMNLLRSYFRVN-------NLDVKVKSINGGFTSFLRRKWKFKKERNKGYKHHAEDALIIA-----------   712

S1  1003  KLESEFVYGDYKVYDVRKMIAKSEQ--EIGKATAYFFYSNIMNFFKTEITLANGEIRKRPLIETNGETGEIVWDKG---  1077

S2  1013  KLASEFVYGEYKKYDIRKFITNSSD-----KATAKYFFYSNLMNFFKTKVKYADGTVFERPIIETNAD-GEIAWNKQ---  1083

S3  1005  KLEPEFVYGEYQKYDLKRYISRSKDPKEVEKATEKYFFYSNLLNFFKEEVHYADGTIVKRENIEYSKDTGEIAWNKE---  1081

S4   713  --NADFIFKEWKKLDKAKKVMENQM------------------------FEEKQAESMPEIETEQEYKEIFITPHQIK   764

S1  1078  -----RDFATVRKVLSMPQVNIVKKTEVQTGGFSKESILPKRNSDKLIARKKD---WDPKKYGGFDSPTVAYSVLVVAKV  1149

S2  1084  -----IDFEKVRKVLSYPQVNIVKKTEVQTGGFSKESILPKGDSDKLIPRKTKKVYWDTKKYGGFDSPTVAYSVFVVADV  1158

S3  1082  -----KDFAIIKKVLSLPQVNIVKKTEVQTGGFSKESILPKGNSDKLIPRKTKDILLDTTKYGGFDSPVIAYSILLIADI  1156

S4   765  HIKDFKDYKYSHRVDKKPNRELINDTLYSTRKDDKGNTLIVNNLNGLYDKDNDKL----KKLIN-KSP----EKLLMYEH   835

S1  1150  EKGKSKKLKSVKELLGITIMERSSFEKNPI-DFLEAKG-----YKEVKKDLIIKLPKYSLFELENGRKRMLASAGELQKG  1223

S2  1159  EKGKAKKLKTVKELVGISIMERSFFEENPV-EFLENKG-----YHNIREDKLIKLPKYSLFEFEGGRRRLLASASELQKG  1232

S3  1157  EKGKAKKLKTVKTLVGITIMEKAAFEENPI-TFLENKG-----YHNVRKENILCLPKYSLFELENGRRRLLASAKELQKG  1230

S4   836  DPQTYQKLK--------LIMEQYGDEKNPLYKYYEETGNYLTKYSKKDNGPVIKKIKYYGNKLNAHLDITDDYPNSRNKV   907

S1  1224  NELALPSKYVNFLYLASHYEKLKGSPEDNEQKQLFVEQHKHYLDEITEQISEFSKRVILADANLDKVLSAYNKH------  1297

S2  1233  NEMVLPGYLVELLYHAHRADNF-----NSTEYLNYVSEHKKEFEKVLSCVEDFANLYVDVEKNLSKIRAVADSM------  1301

S3  1231  NEIVLPVYLTTLLYHSKNVHKL-----DEPGHLEYIQKHRNEFKDLLNLVSEFSQKYVLADANLEKIKSLYADN------  1299

S4   908  VKLSLKPYRFD-VYLDNGVYKFV-----TVKNLDVIK--KENYYEVNSKAYEEAKKLKKISNQAEFIASFYNNDLIKING   979

S1  1298  RDKPIREQAENITHLFTLTNLGAPAAFKYFDTTIDRKRYTSTKEVLDATLIHQSIT--------GLYETRI----DLSQL  1365

S2  1302  DNFSIEEISNSFINLLTLTALGAPADFNFLGEKIPRKRYTSTKECLNATLIHQSIT--------GLYETRI----DLSKL  1369
```

```
S3    1300  EQADIEILANSFINLLTFTALGAPAAFKFFGKDIDRKRYTTVSEILNATLIHQSIT--------GLYETWI----DLSKL    1367

S4     980  ELYRVIGVNNDLLNRIEVNMIDITYR-EYLENMNDKRPPRIIKTIASKT---QSIKKYSTDILGNLYEVKSKKHPQIIKK    1055

S1    1366  GGD                                                                               1368

S2    1370  GEE                                                                               1372

S3    1368  GED                                                                               1370

S4    1056  G--                                                                               1056
```

The alignment demonstrates that amino acid sequences and amino acid residues that are homologous to a reference Cas9 amino acid sequence or amino acid residue can be identified across Cas9 sequence variants, including, but not limited to Cas9 sequences from different species, by identifying the amino acid sequence or residue that aligns with the reference sequence or the reference residue using alignment programs and algorithms known in the art. This disclosure provides Cas9 variants in which one or more of the amino acid residues identified by an asterisk in SEQ ID NOs: 11-14 (e.g., S1, S2, S3, and S4, respectively) are mutated as described herein. The residues D10 and H840 in Cas9 of SEQ ID NO: 10 that correspond to the residues identified in SEQ ID NOs: 11-14 by an asterisk are referred to herein as "homologous" or "corresponding" residues. Such homologous residues can be identified by sequence alignment, e.g., as described above, and by identifying the sequence or residue that aligns with the reference sequence or residue. Similarly, mutations in Cas9 sequences that correspond to mutations identified in SEQ ID NO: 10 herein, e.g., mutations of residues 10, and 840 in SEQ ID NO: 10, are referred to herein as "homologous" or "corresponding" mutations. For example, the mutations corresponding to the D10A mutation in SEQ ID NO: 10 or S1 (SEQ ID NO: 11) for the four aligned sequences above are D11A for S2, D10A for S3, and D13A for S4; the corresponding mutations for H840A in SEQ ID NO: 10 or S1 (SEQ ID NO: 11) are H850A for S2, H842A for S3, and H560A for S4.

A total of 250 Cas9 sequences (SEQ ID NOs: 11-260) from different species were aligned using the same algorithm and alignment parameters outlined above. Amino acid residues homologous to residues 10, and 840 of SEQ ID NO: 10 were identified in the same manner as outlined above. The alignments are provided below. The HNH domain (bold and underlined) and the RuvC domain (boxed) are identified for each of the four sequences. Single residues corresponding to amino acid residues 10, and 840 in SEQ ID NO: 10 are boxed in SEQ ID NO: 11 in the alignments, allowing for the identification of the corresponding amino acid residues in the aligned sequences.

| Accession | Description | SEQ ID NO |
|---|---|---|
| WP_010922251.1 | type II CRISPR RNA-guided endonuclease Cas9 [Streptococcus pyogenes] | SEQ ID NO: 11 |
| WP_039695303.1 | type II CRISPR RNA-guided endonuclease Cas9 [Streptococcus gallolyticus] | SEQ ID NO: 12 |
| WP_045635197.1 | type II CRISPR RNA-guided endonuclease Cas9 [Streptococcus mitis] | SEQ ID NO: 13 |
| 5AXW_A | Cas9, Chain A, Crystal Structure [Staphylococcus Aureus] | SEQ ID NO: 14 |
| WP_009880683.1 | type II CRISPR RNA-guided endonuclease Cas9 [Streptococcus pyogenes] | SEQ ID NO: 15 |
| WP_010922251.1 | type II CRISPR RNA-guided endonuclease Cas9 [Streptococcus pyogenes] | SEQ ID NO: 16 |
| WP_011054416.1 | type II CRISPR RNA-guided endonuclease Cas9 [Streptococcus pyogenes] | SEQ ID NO: 17 |
| WP_011284745.1 | type II CRISPR RNA-guided endonuclease Cas9 [Streptococcus pyogenes] | SEQ ID NO: 18 |
| WP_011285506.1 | type II CRISPR RNA-guided endonuclease Cas9 [Streptococcus pyogenes] | SEQ ID NO: 19 |
| WP_011527619.1 | type II CRISPR RNA-guided endonuclease Cas9 [Streptococcus pyogenes] | SEQ ID NO: 20 |
| WP_012560673.1 | type II CRISPR RNA-guided endonuclease Cas9 [Streptococcus pyogenes] | SEQ ID NO: 21 |
| WP_014407541.1 | type II CRISPR RNA-guided endonuclease Cas9 [Streptococcus pyogenes] | SEQ ID NO: 22 |
| WP_020905136.1 | type II CRISPR RNA-guided endonuclease Cas9 [Streptococcus pyogenes] | SEQ ID NO: 23 |
| WP_023080005.1 | type II CRISPR RNA-guided endonuclease Cas9 [Streptococcus pyogenes] | SEQ ID NO: 24 |
| WP_023610282.1 | type II CRISPR RNA-guided endonuclease Cas9 [Streptococcus pyogenes] | SEQ ID NO: 25 |
| WP_030125963.1 | type II CRISPR RNA-guided endonuclease Cas9 [Streptococcus pyogenes] | SEQ ID NO: 26 |
| WP_030126706.1 | type II CRISPR RNA-guided endonuclease Cas9 [Streptococcus pyogenes] | SEQ ID NO: 27 |
| WP_031488318.1 | type II CRISPR RNA-guided endonuclease Cas9 [Streptococcus pyogenes] | SEQ ID NO: 28 |
| WP_032460140.1 | type II CRISPR RNA-guided endonuclease Cas9 [Streptococcus pyogenes] | SEQ ID NO: 29 |
| WP_032461047.1 | type II CRISPR RNA-guided endonuclease Cas9 [Streptococcus pyogenes] | SEQ ID NO: 30 |
| WP_032462016.1 | type II CRISPR RNA-guided endonuclease Cas9 [Streptococcus pyogenes] | SEQ ID NO: 31 |
| WP_032462936.1 | type II CRISPR RNA-guided endonuclease Cas9 [Streptococcus pyogenes] | SEQ ID NO: 32 |
| WP_032464890.1 | type II CRISPR RNA-guided endonuclease Cas9 [Streptococcus pyogenes] | SEQ ID NO: 33 |
| WP_033888930.1 | type II CRISPR RNA-guided endonuclease Cas9 [Streptococcus pyogenes] | SEQ ID NO: 34 |
| WP_038431314.1 | type II CRISPR RNA-guided endonuclease Cas9 [Streptococcus pyogenes] | SEQ ID NO: 35 |
| WP_038432938.1 | type II CRISPR RNA-guided endonuclease Cas9 [Streptococcus pyogenes] | SEQ ID NO: 36 |
| WP_038434062.1 | type II CRISPR RNA-guided endonuclease Cas9 [Streptococcus pyogenes] | SEQ ID NO: 37 |
| BAQ51233.1 | CRISPR-associated protein, Csn1 family [Streptococcus pyogenes] | SEQ ID NO: 38 |
| KGE60162.1 | hypothetical protein MGAS2111_0903 [Streptococcus pyogenes MGAS2111] | SEQ ID NO: 39 |
| KGE60856.1 | CRISPR-associated endonuclease protein [Streptococcus pyogenes SS1447] | SEQ ID NO: 40 |
| WP_002989955.1 | MULTISPECIES: type II CRISPR RNA-guided endonuclease Cas9 [Streptococcus] | SEQ ID NO: 41 |
| WP_003030001.1 | MULTISPECIES: type II CRISPR RNA-guided endonuclease Cas9 [Streptococcus] | SEQ ID NO: 42 |
| WP_003065552.1 | MULTISPECIES: type II CRISPR RNA-guided endonuclease Cas9 [Streptococcus] | SEQ ID NO: 43 |
| WP_001040076.1 | type II CRISPR RNA-guided endonuclease Cas9 [Streptococcus agalactiae] | SEQ ID NO: 44 |
| WP_001040078.1 | type II CRISPR RNA-guided endonuclease Cas9 [Streptococcus agalactiae] | SEQ ID NO: 45 |
| WP_001040080.1 | type II CRISPR RNA-guided endonuclease Cas9 [Streptococcus agalactiae] | SEQ ID NO: 46 |
| WP_001040081.1 | type II CRISPR RNA-guided endonuclease Cas9 [Streptococcus agalactiae] | SEQ ID NO: 47 |
| WP_001040083.1 | type II CRISPR RNA-guided endonuclease Cas9 [Streptococcus agalactiae] | SEQ ID NO: 48 |
| WP_001040085.1 | type II CRISPR RNA-guided endonuclease Cas9 [Streptococcus agalactiae] | SEQ ID NO: 49 |
| WP_001040087.1 | type II CRISPR RNA-guided endonuclease Cas9 [Streptococcus agalactiae] | SEQ ID NO: 50 |
| WP_001040088.1 | type II CRISPR RNA-guided endonuclease Cas9 [Streptococcus agalactiae] | SEQ ID NO: 51 |
| WP_001040089.1 | type II CRISPR RNA-guided endonuclease Cas9 [Streptococcus agalactiae] | SEQ ID NO: 52 |
| WP_001040090.1 | type II CRISPR RNA-guided endonuclease Cas9 [Streptococcus agalactiae] | SEQ ID NO: 53 |
| WP_001040091.1 | type II CRISPR RNA-guided endonuclease Cas9 [Streptococcus agalactiae] | SEQ ID NO: 54 |
| WP_001040092.1 | type II CRISPR RNA-guided endonuclease Cas9 [Streptococcus agalactiae] | SEQ ID NO: 55 |
| WP_001040094.1 | type II CRISPR RNA-guided endonuclease Cas9 [Streptococcus agalactiae] | SEQ ID NO: 56 |
| WP_001040095.1 | type II CRISPR RNA-guided endonuclease Cas9 [Streptococcus agalactiae] | SEQ ID NO: 57 |
| WP_001040096.1 | type II CRISPR RNA-guided endonuclease Cas9 [Streptococcus agalactiae] | SEQ ID NO: 58 |
| WP_001040097.1 | type II CRISPR RNA-guided endonuclease Cas9 [Streptococcus agalactiae] | SEQ ID NO: 59 |
| WP_001040098.1 | type II CRISPR RNA-guided endonuclease Cas9 [Streptococcus agalactiae] | SEQ ID NO: 60 |
| WP_001040099.1 | type II CRISPR RNA-guided endonuclease Cas9 [Streptococcus agalactiae] | SEQ ID NO: 61 |
| WP_001040100.1 | type II CRISPR RNA-guided endonuclease Cas9 [Streptococcus agalactiae] | SEQ ID NO: 62 |

-continued

| Accession | Description | SEQ ID NO |
|---|---|---|
| WP_001040104.1 | type II CRISPR RNA-guided endonuclease Cas9 [Streptococcus agalactiae] | SEQ ID NO: 63 |
| WP_001040105.1 | type II CRISPR RNA-guided endonuclease Cas9 [Streptococcus agalactiae] | SEQ ID NO: 64 |
| WP_001040106.1 | type II CRISPR RNA-guided endonuclease Cas9 [Streptococcus agalactiae] | SEQ ID NO: 65 |
| WP_001040107.1 | type II CRISPR RNA-guided endonuclease Cas9 [Streptococcus agalactiae] | SEQ ID NO: 66 |
| WP_001040108.1 | type II CRISPR RNA-guided endonuclease Cas9 [Streptococcus agalactiae] | SEQ ID NO: 67 |
| WP_001040109.1 | type II CRISPR RNA-guided endonuclease Cas9 [Streptococcus agalactiae] | SEQ ID NO: 68 |
| WP_001040110.1 | type II CRISPR RNA-guided endonuclease Cas9 [Streptococcus agalactiae] | SEQ ID NO: 69 |
| WP_015058523.1 | type II CRISPR RNA-guided endonuclease Cas9 [Streptococcus agalactiae] | SEQ ID NO: 70 |
| WP_017643650.1 | type II CRISPR RNA-guided endonuclease Cas9 [Streptococcus agalactiae] | SEQ ID NO: 71 |
| WP_017647151.1 | type II CRISPR RNA-guided endonuclease Cas9 [Streptococcus agalactiae] | SEQ ID NO: 72 |
| WP_017648376.1 | type II CRISPR RNA-guided endonuclease Cas9 [Streptococcus agalactiae] | SEQ ID NO: 73 |
| WP_017649527.1 | type II CRISPR RNA-guided endonuclease Cas9 [Streptococcus agalactiae] | SEQ ID NO: 74 |
| WP_017771611.1 | type II CRISPR RNA-guided endonuclease Cas9 [Streptococcus agalactiae] | SEQ ID NO: 75 |
| WP_017771984.1 | type II CRISPR RNA-guided endonuclease Cas9 [Streptococcus agalactiae] | SEQ ID NO: 76 |
| CFQ25032.1 | CRISPR-associated protein [Streptococcus agalactiae] | SEQ ID NO: 77 |
| CFV16040.1 | CRISPR-associated protein [Streptococcus agalactiae] | SEQ ID NO: 78 |
| KLJ37842.1 | CRISPR-associated protein Csn1 [Streptococcus agalactiae] | SEQ ID NO: 79 |
| KLJ72361.1 | CRISPR-associated protein Csn1 [Streptococcus agalactiae] | SEQ ID NO: 80 |
| KLL20707.1 | CRISPR-associated protein Csn1 [Streptococcus agalactiae] | SEQ ID NO: 81 |
| KLL42645.1 | CRISPR-associated protein Csn1 [Streptococcus agalactiae] | SEQ ID NO: 82 |
| WP_047207273.1 | type II CRISPR RNA-guided endonuclease Cas9 [Streptococcus agalactiae] | SEQ ID NO: 83 |
| WP_047209694.1 | type II CRISPR RNA-guided endonuclease Cas9 [Streptococcus agalactiae] | SEQ ID NO: 84 |
| WP_050198062.1 | type II CRISPR RNA-guided endonuclease Cas9 [Streptococcus agalactiae] | SEQ ID NO: 85 |
| WP_050201642.1 | type II CRISPR RNA-guided endonuclease Cas9 [Streptococcus agalactiae] | SEQ ID NO: 86 |
| WP_050204027.1 | type II CRISPR RNA-guided endonuclease Cas9 [Streptococcus agalactiae] | SEQ ID NO: 87 |
| WP_050881965.1 | type II CRISPR RNA-guided endonuclease Cas9 [Streptococcus agalactiae] | SEQ ID NO: 88 |
| WP_050886065.1 | type II CRISPR RNA-guided endonuclease Cas9 [Streptococcus agalactiae] | SEQ ID NO: 89 |
| AHN30376.1 | CRISPR-associated protein Csn1 [Streptococcus agalactiae 138P] | SEQ ID NO: 90 |
| EAO78426.1 | reticulocyte binding protein [Streptococcus agalactiae H36B] | SEQ ID NO: 91 |
| CCW42055.1 | CRISPR-associated protein, SAG0894 family [Streptococcus agalactiae ILRI112] | SEQ ID NO: 92 |
| WP_003041502.1 | type II CRISPR RNA-guided endonuclease Cas9 [Streptococcus anginosus] | SEQ ID NO: 93 |
| WP_037593752.1 | type II CRISPR RNA-guided endonuclease Cas9 [Streptococcus anginosus] | SEQ ID NO: 94 |
| WP_049516684.1 | CRISPR-associated protein Csn1 [Streptococcus anginosus] | SEQ ID NO: 95 |
| GAD46167.1 | hypothetical protein ANG6_0662 [Streptococcus anginosus T5] | SEQ ID NO: 96 |
| WP_018363470.1 | type II CRISPR RNA-guided endonuclease Cas9 [Streptococcus caballi] | SEQ ID NO: 97 |
| WP_003043819.1 | type II CRISPR RNA-guided endonuclease Cas9 [Streptococcus canis] | SEQ ID NO: 98 |
| WP_006269658.1 | type II CRISPR RNA-guided endonuclease Cas9 [Streptococcus constellatus] | SEQ ID NO: 99 |
| WP_048800889.1 | type II CRISPR RNA-guided endonuclease Cas9 [Streptococcus constellatus] | SEQ ID NO: 100 |
| WP_012767106.1 | type II CRISPR RNA-guided endonuclease Cas9 [Streptococcus dysgalactiae] | SEQ ID NO: 101 |
| WP_014612333.1 | type II CRISPR RNA-guided endonuclease Cas9 [Streptococcus dysgalactiae] | SEQ ID NO: 102 |
| WP_015017095.1 | type II CRISPR RNA-guided endonuclease Cas9 [Streptococcus dysgalactiae] | SEQ ID NO: 103 |
| WP_015057649.1 | type II CRISPR RNA-guided endonuclease Cas9 [Streptococcus dysgalactiae] | SEQ ID NO: 104 |
| WP_048327215.1 | type II CRISPR RNA-guided endonuclease Cas9 [Streptococcus dysgalactiae] | SEQ ID NO: 105 |
| WP_049519324.1 | CRISPR-associated protein Csn1 [Streptococcus dysgalactiae] | SEQ ID NO: 106 |
| WP_012515931.1 | type II CRISPR RNA-guided endonuclease Cas9 [Streptococcus equi] | SEQ ID NO: 107 |
| WP_021320964.1 | type II CRISPR RNA-guided endonuclease Cas9 [Streptococcus equi] | SEQ ID NO: 108 |
| WP_037581760.1 | type II CRISPR RNA-guided endonuclease Cas9 [Streptococcus equi] | SEQ ID NO: 109 |
| WP_044232481.1 | type II CRISPR RNA-guided endonuclease Cas9 [Streptococcus equinus] | SEQ ID NO: 110 |
| WP_009854540.1 | type II CRISPR RNA-guided endonuclease Cas9 [Streptococcus gallolyticus] | SEQ ID NO: 111 |
| WP_012962174.1 | type II CRISPR RNA-guided endonuclease Cas9 [Streptococcus gallolyticus] | SEQ ID NO: 112 |
| WP_039695303.1 | type II CRISPR RNA-guided endonuclease Cas9 [Streptococcus gallolyticus] | SEQ ID NO: 113 |
| WP_014334983.1 | type II CRISPR RNA-guided endonuclease Cas9 [Streptococcus infantarius] | SEQ ID NO: 114 |
| WP_003099269.1 | type II CRISPR RNA-guided endonuclease Cas9 [Streptococcus iniae] | SEQ ID NO: 115 |

| Accession | Description | SEQ ID NO |
|---|---|---|
| AHY15608.1 | CRISPR-associated protein Csn1 [Streptococcus iniae] | SEQ ID NO: 116 |
| AHY17476.1 | CRISPR-associated protein Csn1 [Streptococcus iniae] | SEQ ID NO: 117 |
| ESR09100.1 | hypothetical protein IUSA1_08595 [Streptococcus iniae IUSA1] | SEQ ID NO: 118 |
| AGM98575.1 | CRISPR-associated protein Cas9/Csn1, subtype II/NMEMI [Streptococcus iniae SF1] | SEQ ID NO: 119 |
| ALF27331.1 | CRISPR-associated protein Csn1 [Streptococcus intermedius] | SEQ ID NO: 120 |
| WP_018372492.1 | type II CRISPR RNA-guided endonuclease Cas9 [Streptococcus massiliensis] | SEQ ID NO: 121 |
| WP_045618028.1 | type II CRISPR RNA-guided endonuclease Cas9 [Streptococcus mitis] | SEQ ID NO: 122 |
| WP_045635197.1 | type II CRISPR RNA-guided endonuclease Cas9 [Streptococcus mitis] | SEQ ID NO: 123 |
| WP_002263549.1 | type II CRISPR RNA-guided endonuclease Cas9 [Streptococcus mutans] | SEQ ID NO: 124 |
| WP_002263887.1 | type II CRISPR RNA-guided endonuclease Cas9 [Streptococcus mutans] | SEQ ID NO: 125 |
| WP_002264920.1 | type II CRISPR RNA-guided endonuclease Cas9 [Streptococcus mutans] | SEQ ID NO: 126 |
| WP_002269043.1 | type II CRISPR RNA-guided endonuclease Cas9 [Streptococcus mutans] | SEQ ID NO: 127 |
| WP_002269448.1 | type II CRISPR RNA-guided endonuclease Cas9 [Streptococcus mutans] | SEQ ID NO: 128 |
| WP_002271977.1 | type II CRISPR RNA-guided endonuclease Cas9 [Streptococcus mutans] | SEQ ID NO: 129 |
| WP_002272766.1 | type II CRISPR RNA-guided endonuclease Cas9 [Streptococcus mutans] | SEQ ID NO: 130 |
| WP_002273241.1 | type II CRISPR RNA-guided endonuclease Cas9 [Streptococcus mutans] | SEQ ID NO: 131 |
| WP_002275430.1 | type II CRISPR RNA-guided endonuclease Cas9 [Streptococcus mutans] | SEQ ID NO: 132 |
| WP_002276448.1 | type II CRISPR RNA-guided endonuclease Cas9 [Streptococcus mutans] | SEQ ID NO: 133 |
| WP_002277050.1 | type II CRISPR RNA-guided endonuclease Cas9 [Streptococcus mutans] | SEQ ID NO: 134 |
| WP_002277364.1 | type II CRISPR RNA-guided endonuclease Cas9 [Streptococcus mutans] | SEQ ID NO: 135 |
| WP_002279025.1 | type II CRISPR RNA-guided endonuclease Cas9 [Streptococcus mutans] | SEQ ID NO: 136 |
| WP_002279859.1 | type II CRISPR RNA-guided endonuclease Cas9 [Streptococcus mutans] | SEQ ID NO: 137 |
| WP_002280230.1 | type II CRISPR RNA-guided endonuclease Cas9 [Streptococcus mutans] | SEQ ID NO: 138 |
| WP_002281696.1 | type II CRISPR RNA-guided endonuclease Cas9 [Streptococcus mutans] | SEQ ID NO: 139 |
| WP_002282247.1 | type II CRISPR RNA-guided endonuclease Cas9 [Streptococcus mutans] | SEQ ID NO: 140 |
| WP_002282906.1 | type II CRISPR RNA-guided endonuclease Cas9 [Streptococcus mutans] | SEQ ID NO: 141 |
| WP_002283846.1 | type II CRISPR RNA-guided endonuclease Cas9 [Streptococcus mutans] | SEQ ID NO: 142 |
| WP_002872255.1 | type II CRISPR RNA-guided endonuclease Cas9 [Streptococcus mutans] | SEQ ID NO: 143 |
| WP_002288990.1 | type II CRISPR RNA-guided endonuclease Cas9 [Streptococcus mutans] | SEQ ID NO: 144 |
| WP_002289641.1 | type II CRISPR RNA-guided endonuclease Cas9 [Streptococcus mutans] | SEQ ID NO: 145 |
| WP_002290427.1 | type II CRISPR RNA-guided endonuclease Cas9 [Streptococcus mutans] | SEQ ID NO: 146 |
| WP_002295753.1 | type II CRISPR RNA-guided endonuclease Cas9 [Streptococcus mutans] | SEQ ID NO: 147 |
| WP_002296423.1 | type II CRISPR RNA-guided endonuclease Cas9 [Streptococcus mutans] | SEQ ID NO: 148 |
| WP_002304487.1 | type II CRISPR RNA-guided endonuclease Cas9 [Streptococcus mutans] | SEQ ID NO: 149 |
| WP_003305844.1 | type II CRISPR RNA-guided endonuclease Cas9 [Streptococcus mutans] | SEQ ID NO: 150 |
| WP_003307203.1 | type II CRISPR RNA-guided endonuclease Cas9 [Streptococcus mutans] | SEQ ID NO: 151 |
| WP_002310390.1 | type II CRISPR RNA-guided endonuclease Cas9 [Streptococcus mutans] | SEQ ID NO: 152 |
| WP_002352408.1 | type II CRISPR RNA-guided endonuclease Cas9 [Streptococcus mutans] | SEQ ID NO: 153 |
| WP_012997688.1 | type II CRISPR RNA-guided endonuclease Cas9 [Streptococcus mutans] | SEQ ID NO: 154 |
| WP_014677909.1 | type II CRISPR RNA-guided endonuclease Cas9 [Streptococcus mutans] | SEQ ID NO: 155 |
| WP_019312892.1 | type II CRISPR RNA-guided endonuclease Cas9 [Streptococcus mutans] | SEQ ID NO: 156 |
| WP_019313659.1 | type II CRISPR RNA-guided endonuclease Cas9 [Streptococcus mutans] | SEQ ID NO: 157 |
| WP_019314093.1 | type II CRISPR RNA-guided endonuclease Cas9 [Streptococcus mutans] | SEQ ID NO: 158 |
| WP_019315370.1 | type II CRISPR RNA-guided endonuclease Cas9 [Streptococcus mutans] | SEQ ID NO: 159 |
| WP_019803776.1 | type II CRISPR RNA-guided endonuclease Cas9 [Streptococcus mutans] | SEQ ID NO: 160 |
| WP_019805234.1 | type II CRISPR RNA-guided endonuclease Cas9 [Streptococcus mutans] | SEQ ID NO: 161 |
| WP_024783594.1 | type II CRISPR RNA-guided endonuclease Cas9 [Streptococcus mutans] | SEQ ID NO: 162 |
| WP_024784288.1 | type II CRISPR RNA-guided endonuclease Cas9 [Streptococcus mutans] | SEQ ID NO: 163 |
| WP_024784666.1 | type II CRISPR RNA-guided endonuclease Cas9 [Streptococcus mutans] | SEQ ID NO: 164 |
| WP_024784894.1 | type II CRISPR RNA-guided endonuclease Cas9 [Streptococcus mutans] | SEQ ID NO: 165 |
| WP_024786433.1 | type II CRISPR RNA-guided endonuclease Cas9 [Streptococcus mutans] | SEQ ID NO: 166 |
| WP_049473442.1 | CRISPR-associated protein Csn1 [Streptococcus mutans] | SEQ ID NO: 167 |
| WP_049473547.1 | CRISPR-associated protein Csn1 [Streptococcus mutans] | SEQ ID NO: 168 |

| Accession | Description | SEQ ID NO |
|---|---|---|
| EMC03581.1 | hypothetical protein SMU69_09359 [Streptococcus mutans NLML4] | SEQ ID NO: 169 |
| WP_000428612.1 | type II CRISPR RNA-guided endonuclease Cas9 [Streptococcus oralis] | SEQ ID NO: 170 |
| WP_000428613.1 | type II CRISPR RNA-guided endonuclease Cas9 [Streptococcus oralis] | SEQ ID NO: 171 |
| WP_049523028.1 | CRISPR-associated protein Csn1 [Streptococcus parasanguinis] | SEQ ID NO: 172 |
| WP_003107102.1 | type II CRISPR RNA-guided endonuclease Cas9 [Streptococcus parauberis] | SEQ ID NO: 173 |
| WP_054279288.1 | type II CRISPR RNA-guided endonuclease Cas9 [Streptococcus phocae] | SEQ ID NO: 174 |
| WP_049531101.1 | CRISPR-associated protein Csn1 [Streptococcus pseudopneumoniae] | SEQ ID NO: 175 |
| WP_049538452.1 | CRISPR-associated protein Csn1 [Streptococcus pseudopneumoniae] | SEQ ID NO: 176 |
| WP_049549711.1 | CRISPR-associated protein Csn1 [Streptococcus pseudopneumoniae] | SEQ ID NO: 177 |
| WP_007896501.1 | type II CRISPR RNA-guided endonuclease Cas9 [Streptococcus pseudoporcinus] | SEQ ID NO: 178 |
| EFR44625.1 | CRISPR-associated protein, Csn1 family [Streptococcus pseudoporcinus SPIN 20026] | SEQ ID NO: 179 |
| WP_002897477.1 | type II CRISPR RNA-guided endonuclease Cas9 [Streptococcus sanguinis] | SEQ ID NO: 180 |
| WP_002906454.1 | type II CRISPR RNA-guided endonuclease Cas9 [Streptococcus sanguinis] | SEQ ID NO: 181 |
| WP_009729476.1 | type II CRISPR RNA-guided endonuclease Cas9 [Streptococcus sp. F0441] | SEQ ID NO: 182 |
| CQR24647.1 | CRISPR-associated protein [Streptococcus sp. FF10] | SEQ ID NO: 183 |
| WP_000066813.1 | type II CRISPR RNA-guided endonuclease Cas9 [Streptococcus sp. M334] | SEQ ID NO: 184 |
| WP_009754323.1 | type II CRISPR RNA-guided endonuclease Cas9 [Streptococcus sp. taxon 056] | SEQ ID NO: 185 |
| WP_044674937.1 | type II CRISPR RNA-guided endonuclease Cas9 [Streptococcus suis] | SEQ ID NO: 186 |
| WP_044676715.1 | type II CRISPR RNA-guided endonuclease Cas9 [Streptococcus suis] | SEQ ID NO: 187 |
| WP_044680361.1 | type II CRISPR RNA-guided endonuclease Cas9 [Streptococcus suis] | SEQ ID NO: 188 |
| WP_044681799.1 | type II CRISPR RNA-guided endonuclease Cas9 [Streptococcus suis] | SEQ ID NO: 189 |
| WP_049533112.1 | CRISPR-associated protein Csn1 [Streptococcus suis] | SEQ ID NO: 190 |
| WP_029090905.1 | type II CRISPR RNA-guided endonuclease Cas9 [Brochothrix thermosphacta] | SEQ ID NO: 191 |
| WP_065069696.1 | type II CRISPR RNA-guided endonuclease Cas9 [Catenibacterium mitsuokai] | SEQ ID NO: 192 |
| AIT42264.1 | Cas9hc:NLS:HA [Cloning vector pYB196] | SEQ ID NO: 193 |
| WP_034440723.1 | type II CRISPR endonuclease Cas9 [Clostridiales bacterium S5-A11] | SEQ ID NO: 194 |
| AKQ21048.1 | Cas9 [CRISPR-mediated gene targeting vector p(bh5p68-Cas9)] | SEQ ID NO: 195 |
| WP_002636532.1 | type II CRISPR RNA-guided endonuclease Cas9 [Dolosigranulum pigrum] | SEQ ID NO: 196 |
| WP_002364836.1 | MULTISPECIES: type II CRISPR RNA-guided endonuclease Cas9 [Enterococcus] | SEQ ID NO: 197 |
| WP_016631044.1 | MULTISPECIES: type II CRISPR RNA-guided endonuclease Cas9 [Enterococcus] | SEQ ID NO: 198 |
| EMS75795.1 | hypothetical protein H318_06676 [Enterococcus durans IPLA 655] | SEQ ID NO: 199 |
| WP_002373311.1 | type II CRISPR RNA-guided endonuclease Cas9 [Enterococcus faecalis] | SEQ ID NO: 200 |
| WP_002378009.1 | type II CRISPR RNA-guided endonuclease Cas9 [Enterococcus faecalis] | SEQ ID NO: 201 |
| WP_002407324.1 | type II CRISPR RNA-guided endonuclease Cas9 [Enterococcus faecalis] | SEQ ID NO: 202 |
| WP_002413717.1 | type II CRISPR RNA-guided endonuclease Cas9 [Enterococcus faecalis] | SEQ ID NO: 203 |
| WP_010775580.1 | type II CRISPR RNA-guided endonuclease Cas9 [Enterococcus faecalis] | SEQ ID NO: 204 |
| WP_010818269.1 | type II CRISPR RNA-guided endonuclease Cas9 [Enterococcus faecalis] | SEQ ID NO: 205 |
| WP_010824395.1 | type II CRISPR RNA-guided endonuclease Cas9 [Enterococcus faecalis] | SEQ ID NO: 206 |
| WP_016622645.1 | type II CRISPR RNA-guided endonuclease Cas9 [Enterococcus faecalis] | SEQ ID NO: 207 |
| WP_033624816.1 | type II CRISPR RNA-guided endonuclease Cas9 [Enterococcus faecalis] | SEQ ID NO: 208 |
| WP_033625576.1 | type II CRISPR RNA-guided endonuclease Cas9 [Enterococcus faecalis] | SEQ ID NO: 209 |
| WP_033789179.1 | type II CRISPR RNA-guided endonuclease Cas9 [Enterococcus faecalis] | SEQ ID NO: 210 |
| WP_002310644.1 | type II CRISPR RNA-guided endonuclease Cas9 [Enterococcus faecium] | SEQ ID NO: 211 |
| WP_002312694.1 | type II CRISPR RNA-guided endonuclease Cas9 [Enterococcus faecium] | SEQ ID NO: 212 |
| WP_002314015.1 | type II CRISPR RNA-guided endonuclease Cas9 [Enterococcus faecium] | SEQ ID NO: 213 |
| WP_002320716.1 | type II CRISPR RNA-guided endonuclease Cas9 [Enterococcus faecium] | SEQ ID NO: 214 |
| WP_002330729.1 | type II CRISPR RNA-guided endonuclease Cas9 [Enterococcus faecium] | SEQ ID NO: 215 |
| WP_002335161.1 | type II CRISPR RNA-guided endonuclease Cas9 [Enterococcus faecium] | SEQ ID NO: 216 |
| WP_002345439.1 | type II CRISPR RNA-guided endonuclease Cas9 [Enterococcus faecium] | SEQ ID NO: 217 |
| WP_034867970.1 | type II CRISPR RNA-guided endonuclease Cas9 [Enterococcus faecium] | SEQ ID NO: 218 |
| WP_047937432.1 | type II CRISPR RNA-guided endonuclease Cas9 [Enterococcus faecium] | SEQ ID NO: 219 |
| WP_010720994.1 | type II CRISPR RNA-guided endonuclease Cas9 [Enterococcus hirae] | SEQ ID NO: 220 |
| WP_010737004.1 | type II CRISPR RNA-guided endonuclease Cas9 [Enterococcus hirae] | SEQ ID NO: 221 |

| Accession | | Description | SEQ ID NO |
|---|---|---|---|
| WP_034700478.1 | | type II CRISPR RNA-guided endonuclease Cas9 [Enterococcus hirae] | SEQ ID NO: 222 |
| WP_007209003.1 | | type II CRISPR RNA-guided endonuclease Cas9 [Enterococcus italicus] | SEQ ID NO: 223 |
| WP_023519017.1 | | type II CRISPR RNA-guided endonuclease Cas9 [Enterococcus mundtii] | SEQ ID NO: 224 |
| WP_010770040.1 | | type II CRISPR RNA-guided endonuclease Cas9 [Enterococcus phoeniculicola] | SEQ ID NO: 225 |
| WP_048604708.1 | | type II CRISPR RNA-guided endonuclease Cas9 [Enterococcus sp. AM1] | SEQ ID NO: 226 |
| WP_010750235.1 | | type II CRISPR RNA-guided endonuclease Cas9 [Enterococcus villorum] | SEQ ID NO: 227 |
| AII16583.1 | | Cas9 endonuclease [Expression vector pCas9] | SEQ ID NO: 228 |
| WP_029073316.1 | | type II CRISPR RNA-guided endonuclease Cas9 [Kandleria vitulina] | SEQ ID NO: 229 |
| WP_031589969.1 | | type II CRISPR RNA-guided endonuclease Cas9 [Kandleria vitulina] | SEQ ID NO: 230 |
| KDA45870.1 | | CRISPR-associated protein Cas9/Csn1, subtype II/NMEMI [Lactobacillus animalis] | SEQ ID NO: 231 |
| WP_039099354.1 | | type II CRISPR RNA-guided endonuclease Cas9 [Lactobacillus curvatus] | SEQ ID NO: 232 |
| AKP02966.1 | | hypothetical protein ABB45_04605 [Lactobacillus farciminis] | SEQ ID NO: 233 |
| WP_010991369.1 | | type II CRISPR RNA-guided endonuclease Cas9 [Listeria innocua] | SEQ ID NO: 234 |
| WP_033838504.1 | | type II CRISPR RNA-guided endonuclease Cas9 [Listeria innocua] | SEQ ID NO: 235 |
| EHN60060.1 | | CRISPR-associated protein, Csn1 family [Listeria innocua ATCC 33091] | SEQ ID NO: 236 |
| EFR89594.1 | | crispr-associated protein, Csn1 family [Listeria innocua FSL S4-378] | SEQ ID NO: 237 |
| WP_038409211.1 | | type II CRISPR RNA-guided endonuclease Cas9 [Listeria ivanovii] | SEQ ID NO: 238 |
| EFR95520.1 | | crispr-associated protein Csn1 [Listeria ivanovii FSL F6-596] | SEQ ID NO: 239 |
| WP_003723650.1 | | type II CRISPR RNA-guided endonuclease Cas9 [Listeria monocytogenes] | SEQ ID NO: 240 |
| WP_003727705.1 | | type II CRISPR RNA-guided endonuclease Cas9 [Listeria monocytogenes] | SEQ ID NO: 241 |
| WP_003730785.1 | | type II CRISPR RNA-guided endonuclease Cas9 [Listeria monocytogenes] | SEQ ID NO: 242 |
| WP_003733029.1 | | type II CRISPR RNA-guided endonuclease Cas9 [Listeria monocytogenes] | SEQ ID NO: 243 |
| WP_003739838.1 | | type II CRISPR RNA-guided endonuclease Cas9 [Listeria monocytogenes] | SEQ ID NO: 244 |
| WP_014601172.1 | | type II CRISPR RNA-guided endonuclease Cas9 [Listeria monocytogenes] | SEQ ID NO: 245 |
| WP_023548323.1 | | type II CRISPR RNA-guided endonuclease Cas9 [Listeria monocytogenes] | SEQ ID NO: 246 |
| WP_031665337.1 | | type II CRISPR RNA-guided endonuclease Cas9 [Listeria monocytogenes] | SEQ ID NO: 247 |
| WP_031669209.1 | | type II CRISPR RNA-guided endonuclease Cas9 [Listeria monocytogenes] | SEQ ID NO: 248 |
| WP_033920898.1 | | type II CRISPR RNA-guided endonuclease Cas9 [Listeria monocytogenes] | SEQ ID NO: 249 |
| AKI42028.1 | | CRISPR-associated protein [Listeria monocytogenes] | SEQ ID NO: 250 |
| AKI50529.1 | | CRISPR-associated protein [Listeria monocytogenes] | SEQ ID NO: 251 |
| EFR83390.1 | | crispr-associated protein Csn1 [Listeria monocytogenes FSL F2-208] | SEQ ID NO: 252 |
| WP_046323366.1 | | type II CRISPR RNA-guided endonuclease Cas9 [Listeria seeligeri] | SEQ ID NO: 253 |
| AKE81011.1 | | Cas9 [Plant multiplex genome editing vector pYLCRISPR/Cas9Pubi-H] | SEQ ID NO: 254 |
| CU082355.1 | | Uncharacterized protein conserved in bacteria [Roseburia hominis] | SEQ ID NO: 255 |
| WP_033162887.1 | | type II CRISPR RNA-guided endonuclease Cas9 [Sharpea azabuensis] | SEQ ID NO: 256 |
| AGZ01981.1 | | Cas9 endonuclease [synthetic construct] | SEQ ID NO: 257 |
| AKA60242.1 | | nuclease deficient Cas9 [synthetic construct] | SEQ ID NO: 258 |
| AKS40380.1 | | Cas9 [Synthetic plasmid pFC330] | SEQ ID NO: 259 |
| 4UN5_B | | Cas9, Chain B, Crystal Structure | SEQ ID NO: 260 |

| Accession | | Sequence | SEQ ID |
|---|---|---|---|
| WP_010922251 | 1 | MDKK-YSIGLDIGTNSVGWAVITDEYKVPSKKFKVLGNTDRHSIKKNLIGALLFDSGETA-EATRLKRTARRRYT | 73 |
| WP_039695303 | 1 | MTKKnYSIGLDIGTNSVGWAVITDDYKVPAKKMKVLGNTDKKYIKKNLLGALLFDSGETA-EATRLKRTARRRYT | 74 |
| WP_045635197 | 1 | K-KG-YSIGLDIGTNSVGFAVITDDYKVPSKKMKVLGNTDKRFIKKNLIGALLFDEGTTA-EARRLKRTARRRYT | 73 |
| 5AXW_A | 1 | MKRN-YILGLDIGITSVGYGII--DYET--------RDVIDA--GVRLFKEANVEmnEGRRSKRGARRLKR | 61 |
| WP_009880683 | | | |
| WP_010922251 | 1 | MDKK--YSIGLDIGTNSVGWAVITDEYKVPSKKFKVLGNTDRHSIKKNLIGALLFDSGETA-EATRLKRTARRRYT | 73 |
| WP_011054416 | 1 | MDKK--YSIGLDIGTNSVGWAVITDDYKVPSKKLKGLGNTDRHGIKKNLIGALLFDSGETA-EATRLKRTARRRYT | 73 |
| WP_011284745 | 1 | MDKK--YSIGLDIGTNSVGWAVITDDYKVPSKKFKVLGNTDRHSIKKNLIGALLFDSGETA-EATRLKRTARRRYT | 73 |
| WP_011285506 | 1 | MDKK--YSIGLDIGTNSVGWAVITDDYKVPSKKFKVLGNTDRHSIKKNLIGALLFDSGETA-EATRLKRTARRRYT | 73 |
| WP_011527619 | 1 | MDKK--YSIGLDIGTNSVGWAVITDDYKVPSKKFKVLGNTDRHSIKKNLIGALLFDSGEIA-EATRLKRTARRRYT | 73 |
| WP_012560673 | 1 | MDKK--YSIGLDIGTNSVGWAVITDDYKVPSKKFKVLGNTDRHSIKKNLIGALLFGSGETA-EATRLKRTARRRYT | 73 |
| WP_014407541 | 1 | MDKK--YSIGLDIGTNSVGWAVITDDYKVPSKKFKVLGNTDRHSIKKNLIGALLFDSGETA-EATRLKRTARRRYT | 73 |
| WP_020905136 | 1 | MDKK--YSIGLDIGTNSVGWAVITDDYKVPSKKFKVLGNTDRHSIKKNLIGALLFDSGETA-EATRLKRTARRRYT | 73 |

-continued

| ID | Start | Sequence | End |
|---|---|---|---|
| WP_023080005 | 1 | MDKK-YSIGLDIGTNSVGWAVITDDYKVPSKKLKVLGNTDRHGIKKNLIGALLFDSGETA--EATRLKRTARRRYT | 73 |
| WP_023610282 | 1 | MDKK-YSIGLDIGTNSVGWAVITDDYKVPSKKLKVLGNTDRHGIKKNLIGALLFDSGETA--EATRLKRTARRRYT | 73 |
| WP_030125963 | 1 | MDKK-YSIGLDIGTNSVGWAVITDDYKVPSKKFKVLGNTDRHSIKKNLIGALLFDSGETA--EATRLKRTARRRYT | 73 |
| WP_030126706 | 1 | MDKK-YSIGLDIGTNSVGWAVITDDYKVPSKKFKVLGNTDRHGIKKNLIGALLFDSGETA--EATRLKRTARRRYT | 73 |
| WP_031488318 | 1 | MDKK-YSIGLDIGTNSVGWAVITDDYKVPSKKFKVLGNTDRHSIKKNLIGALLFDSGETA--EATRLKRTARRRYT | 73 |
| WP_032460140 | 1 | MDKK-YSIGLDIGTNSVGWAVITDDYKVPSKKFKVLGNTDRHSIKKNLIGALLFDSGETA--EATRLKRTARRRYT | 73 |
| WP_032461047 | 1 | MDKK-YSIGLDIGTNSVGWAVITDDYKVPSKKFKVLGNTERHSIKKNLIGALLFDSGETA--EATRLKRTARRRYT | 73 |
| WP_032462016 | 1 | MDKK-YSIGLDIGTNSVGWAVITDDYKVPSKKFKVLGNTERHSIKKNLIGALLFDSGETA--EATRLKRTARRRYT | 73 |
| WP_032462936 | 1 | MDKK-YSIGLDIGTNSVGWAVITDDYKVPSKKFKVLGNTERHSIKKNLIGALLFDSGEIA--EATRLKRTARRRYT | 73 |
| WP_032464890 | 1 | MDKK-YSIGLDIGTNSVGWAVITDDYKVPSKKFKVLGNTERHSIKKNLIGALLFDSGETA--EATRLKRTARRRYT | 73 |
| WP_033888930 | | ---------------------------------------------------------------------- | |
| WP_038431314 | 1 | MDKK-YSIGLDIGTNSVGWAVITDDYKVPSKKFKVLGNTDRHSIKKNLIGALLFDSGEIA--EATRLKRTARRRYT | 73 |
| WP_038432938 | 1 | MDKK-YSIGLDIGTNSVGWAVITDDYKVPSKKFKVLGNTDRHSIKKNLIGALLFDSGETA--EATRLKRTARRRYT | 73 |
| WP_038434062 | 1 | MDKK-YSIGLDIGTNSVGWAVITDDYKVPSKKFKVLGNTDRHSIKKNLIGALLFDSGETA--EATRLKRTARRRYT | 73 |
| BAQ51233 | | ---------------------------------------------------------------------- | |
| KGE60162 | | ---------------------------------------------------------------------- | |
| KGE60856 | | ---------------------------------------------------------------------- | |
| WP_002989955 | 1 | MDKK-YSIGLDIGTNSVGWAVITDDYKVPSKKFKVLGNTDRHSIKKNLIGALLFDSGEIA--EATRLKRTARRRYT | 73 |
| WP_003030002 | 1 | MDQK-YSIGLDIGTNSVGWAVVTDDYKVPAKKMKVLGNTDKQSIKKNLIGALLFDSGETA--EATRLKRTARRRYT | 73 |
| WP_003065552 | 1 | MTKKnYSIGLDIGTNSVGWSIITDDYKVPAKKMKVLGNTDKKYIKKNLLGALLFDSGETA--EATRLKRTARRRYT | 74 |
| WP_001040076 | 1 | MNKP-YSIGLDIGTNSVGWSIITDDYKVPAKKIRVLGNTDKEYIKKNLIGALLFDSGETA--ADRRLKRTARRRYT | 73 |
| WP_001040078 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040080 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040081 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040083 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040085 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040087 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040088 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040089 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040090 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040091 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040092 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040094 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040095 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040096 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040097 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040098 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040099 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040100 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040104 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040105 | 1 | MNKP-YSIGLDIGTNSVGWSIITDDYKVPAKKMRVLGNTDKEYIKKNLIGALLFDGGNTA--ADRRLKRTSRRRYT | 73 |
| WP_001040106 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040107 | 1 | MNKP-YSIGLDIGTNSVGWSIITDDYKVPAKKMRVLGNTDKEYIKKNLIGALLFDGGNTA--SDRRLKRTARRRYT | 73 |
| WP_001040108 | 1 | MNKP-YSIGLDIGTNSVGWSIITDDYKVPAKKMRVLGNTDKEYIKKNLIGALLFDGGNTA--SDRRLKRTARRRYT | 73 |
| WP_001040109 | 1 | MNKP-YSIGLDIGTNSVGWSIITDDYKVPAKKMRVLGNTDKEYIKKNLIGALLFDGGNTA--SDRRLKRTARRRYT | 73 |
| WP_001040110 | 1 | MNKP-YSIGLDIGTNSVGWSIITDDYKVPAKKMRVLGNTDKEYIKKNLIGALLFDGGNTA--ADRRLKRTARRRYT | 73 |
| WP_015058523 | 1 | MNKP-YSIGLDIGTNSVGWSIITDDYKVPAKKMRVLGNTDKEYIKKNLIGALLFDGGNTA--ADRRLKRTARRRYT | 73 |
| WP_017643650 | 1 | MNKP-YSIGLDIGTNSVGWSIITDDYKVPAKKMRVLGNTDKEYIKKNLIGALLFDGGNTA--SDRRLKRTARRRYT | 73 |
| WP_017647151 | 1 | MNKP-YSIGLDIGTNSVGYSVVTDDYKVPAKKMRVLGNTDKEYIKKNLIGALLFDGGNTA--ADRRLKRTARRRYT | 73 |
| WP_017649527 | 1 | MNKP-YSIGLDIGTNSVGYSVVTDDYKVPAKKMRVLGNTDKEYIKKNLIGALLFDGGNTA--ADRRLKRTSRRRYT | 73 |
| WP_017771611 | 1 | MNKP-YSIGLDIGTNSVGYSVVTDDYKVPAKKMRVLGNTDKEYIKKNLIGALLFDGGNTA--ADRRLKRTARRRYT | 73 |
| WP_017771984 | 1 | MNKP-YSIGLDIGTNSVGWSIITDDYKVPAKKMRVLGNTDKEYIKKNLIGALLFDGGNTA--ADRRLKRTARRRYT | 73 |

-continued

```
CFQ25032          1 MNKP-YSIGLDIGTNSVGWSIITDDYKVPAKKMRVLGNTDKEYIKKNLIGALLFDGGNTA--ADRRLKRTARRRYT 73
CFV16040          1 MNKP-YSIGLDIGTNSVGWSIITDDYKVPAKKMRVLGNTDKEYIKKNLIGALLFDGGNTA--ADRRLKRTARRRYT 73
KLJ37842          1 MNKP-YSIGLDIGTNSVGWSIITDDYKVPAKKMRVLGNTDKEYIKKNLIGALLFDGGNTA--ADRRLKRTARRRYT 73
KLJ72361          1 MNKP-YSIGLDIGTNSVGWSIITDDYKVPAKKMRVLGNTDKEYIKKNLIGALLFDGGNTA--ADRRLKRTARRRYT 73
KLL20707          1 MNKP-YSIGLDIGTNSVGWSIITDDYKVPAKKMRVLGNTDKEYIKKNLIGALLFDGGNTA--ADRRLKRTARRRYT 73
KLL42645          1 MNKP-YSIGLDIGTNSVGYSVVTDDYKVPAKKMRVLGNTDKEYIKKNLIGALLFDGGNTA--SDRRLKRTARRRYT 73
WP_047207273      1 MNKP-YSIGLDIGTNSVGWSIITDDYKVPAKKMRVLGNTDKEYIKKNLIGALLFDGRNTA--ADRRLKRTARRRYT 73
WP_047209694      1 MNKP-YSIGLDIGTNSVGWSIITDDYKVPAKKMRVLGNTDKEYIKKNLIGALLFDGGNTA--ADRRLKRTARRRYT 73
WP_050198062      1 MNKP-YSIGLDIGTNSVGWSIITDDYKVPAKKMRVLGNTDKEYIKKNLIGALLFDGGNTA--ADRRLKRTARRRYT 73
WP_050201642      1 MNKP-YSIGLDIGTNSVGWSIITDDYKVPAKKMRVLGNTDKEYIKKNLIGALLFDGGNTA--ADRRLKRTARRRYT 73
WP_050204027      1 MNKP-YSIGLDIGTNSVGWSIITDDYKVPAKKMRVLGNTDKEYIKKNLIGALLFDGGNTA--SDRRLKRTARRRYT 73
WP_050881965      1 MNKP-YSIGLDIGTNSVGWSIVVTDDYKVPAKKMRVLGNTDKEYIKKNLIGALLFDGGNTA--ADRRLKRTARRRYT 73
WP_050886065      1 MNKP-YSIGLDIGTNSVGWSIITDDYKVPAKKMRVLGNTDKEYIKKNLIGALLFDGGNTA--ADRRLKRTARRRYT 73
AHN30376          1 MNKP-YSIGLDIGTNSVGWSIITDDYKVPAKKMRVLGNTDKEYIKKNLIGALLFDGGNTA--ADRRLKRTARRRYT 73
EAO78426          1 MNKP-YSIGXDIGTNSVGWSIITDDYKVPAKKMRVLGNTDKEYIKKNLIGALLFDGGNTA--ADRRLKRIARRRYT 73
CCW42055          1 MNKP-YSIGLDIGTNSVGWSIITDDYKVPAKKMRVLGNTDKQSIKKNLIGALLFDSGNTA--EATRLKRTARRRYT 73
WP_003041502      1 MNQK-YSIGLDIGTNSVGWAVITDDYKVPAKKMKVLGNTDKQSIKKNLIGALLFDSGETA--EATRLKRTARRRYT 73
WP_037593752      1 MKKE-YSIGLDIGTNSVGWAVITDDYKVPAKKMKVLGNTDKQSIKKNLIGALLFDSGNTA--EATRLKRTARRRYT 74
WP_049516684      1 MKKE-YSIGLDIGTNSVGWAVITDDYKVPAKKMKVLGNTDKQSIKKNLIGALLFDSGETA--EATRLKRTARRRYT 74
GAD46167          1 MKKE-YSIGLDIGTNSVGWAVITDDYKVPAKKMKVLGNTDKQSIKKNLIGALLFDSGETA--EATRLKRTARRRYT 74
WP_018363470      1 MTKKnYSIGLDIGTNSVGWAVITDDYKVPSKKFKVLGNTNRKSIKKNLMGALLFDSGETA--EATRLKRTARRRYT 74
WP_003043819      1 MEKK-YSIGLDIGTNSVGWAVITDDYKVPSKKFKVLGNTDRHSIKKNLIGALLFDSGETA--EATRLKRTARRRYT 73
WP_062695658      1 MGKP-YSIGLDIGTNSVGWAVITDDYKVPSKKFKVLGNTDRHSIKKNLIGALLFDSGETA--EATRLKRTARRRYT 73
WP_048800089      1 MTQK-YSIGLDIGTNSVGWAVITDDYKVPAKKMKILGNTNKQYIKKNLIGALLFDSGETA--KATRLKRTARRRYT 73
WP_012767106      1 MDKK-YSIGLDIGTNSVGWAVITDDYKVPSKKFKVLGNTDRHSIKKNLIGALLFDSGETA--EATRLKRTARRRYT 73
WP_014612333      1 MDKK-YSIGLDIGTNSVGWAVITDDYKVPSKKFKVLGNTDRHSIKKNLIGALLFDSGETA--EATRLKRTARRRYT 73
WP_015017095      1 MDKK-YSIGLDIGTNSVGWAVITDDYKVPSKKFKVLGNTDRHSIKKNLIGALLFDSGETA--EATRLKRTARRRYT 73
WP_015057649      1 MDKK-YSIGLDIGTNSVGWAVITDDYKVPSKKFKVLGNTDRHSIKKNLIGALLFDSGETA--EATRLKRTARRRYT 73
WP_048327215      1 MDKK-YSIGLDIGTNSVGWAVITDDYKVPSKKFKVLGNTDRHSIKKNLIGALLFDSGETA--EVTRLKRTARRRYT 73
WP_049519324      1 MDKK-YSIGLDIGTNSVGWAVITDDYKVPSKKFKVLGNTDRHSIKKNLIGALLFDNGETA--EATRLKRTARRRYT 73
WP_012515931      1 MKKP-YTIALDIGTNSVGWVVVTDDYKVPVPTKKMVLGNTERKTIKKNLIGALLFDSGETA--EGTRLKRTARRRYT 73
WP_021320964      1 MKKP-YTIALDIGTNSVGWVVVTDDYRVPTKKMKVLGNTERKTIKKNLIGALLFDSGETA--EGTRLKRTARPRYT 73
WP_037581760      1 M-EKtYSIGLDIGTNSVGWVVVTDDYKVPAKKMKVLGNTDKKYIKKNLIGALLFDSGETA--EATRLKRAARRRYT 73
WP_004232481      1 MTKKnYSIGLDIGTNSVGWAVITDDYKVPAKKMKVLGNTDKKYIKKNLIGALLFDSGETA--EATRLKRTARRRYT 74
WP_009854540      1 MTEKnYSIGLDIGTNSVGWAVITDDYKVPAKKMKVLGNTDKKYIKKNLIGALLFDNGETA--EATRLKRTARRRYT 74
WP_012962174      1 MTKKnYSIGLDIGTNSVGWAVITDDYKVPAKKMKVLGNTDKKYIKKNLIGALLFDSGETA--EATRLKRTARRRYT 74
WP_039695303      1 M-EKsYSIGLDIGTNSVGFAVITDDYKVPAKKMKVLGNTDRFIKKNLIGALLFDEGTTA--EARRLKRTARRRYT 73
WP_014334983      1 MRKP-YSIGLDIGTNSVGWAVITDDYKVPSKKMVRIQGTTDRTSIKKNLIGALLFDNGETA--EATRLKRTTRRRYT 73
WP_030992269      1 MRKP-YSIGLDIGTNSVGWAVITDDYKVPSKKMVRIQGTTDRTSIKKNLIGALLFDNGETA--EATRLKRTTRRRYT 73
AHY15608          1 MRKP-YSIGLDIGTNSVGWAVITDDYKVPSKKMVRIQGTTDRTSIKKNLIGALLFDNGETA--EATRLKRTTRRRYT 73
AHY17476          1 ---------------------------------------------------------------------------
ESR09100          1 MRKP-YSIGLDIGTNSVGWAVITDDYKVPSKKMVLGNTDKSHIKKNLIGALLFDSGNTA--EATRLKRTTRRRYT 73
AGM98575          1 MKKP-YSIGLDIGTNSVGWAVITDDYKVPAKKMKVLGNTDKSHIKKNLIGALLFDSGNTA--EATRLKRTARRRYT 73
ALF27331          1 MKKP-YSIGLDIGTNSVGWAVMEDYKVPSKKMVLGNTDKSHIKKNLIGALLFDSGETAv--ERRLNRTTSRRYD 74
WP_018372492      1 MKKP-YSIGLDIGTNSVGWAVMEDYKVPSKKMVLGNTDKSHIKKNLIGALLFDSGETAv--ERRLNRTTSRRYD 74
WP_045618028      1 NNKP-YSIGLDIGTNSVGWAVITDDYKVPAKKMVLGNTDKKHFIKKNLIGALLFDSGETTA--EATRLKRTARRRYT 74
WP_045635197      1 K-KG-YSIGLDIGTNSVGFAVITDDYKVPSKKMVLGNTDKRFIKKNLIGALLFDEGTTA--EARRLKRTARRRYT 73
WP_002263549      1 MKKP-YSIGLDIGTNSVGWAVITDDYKVPSKKMVLGNTDKSHIEKNLIGALLFDSGNTA--EDRRLKRTARRRYT 73
WP_002263887      1 MKKP-YSIGLDIGTNSVGWAVITDDYKVPSKKMVLGNTDKSHIKKNLIGALLFDSGNTA--EDRRLKRTARRRYT 73
WP_002264920      1 MKKP-YSIGLDIGTNSVGWAVITDDYKVPAKKMVLGNTDKSHIKKNLIGALLFDNGNTA--EDRRLKRTARRRYT 73
WP_002269043      1 MKKP-YSIGLDIGTNSVGWAVITDDYKVPAKKMVLGNTDKSHIKKNLIGALLFDSGNTA--EDRRLKRTARRRYT 73
WP_002269448      1 MKKP-YSIGLDIGTNSVGWAVITDDYKVPAKKMVLGNTDKSHIKKNLIGALLFDSGNTA--EDRRLKRTARRRYT 73
WP_002271977      1 MKKP-YSIGLDIGTNSVGWAVITDDYKVPAKKMVLGNTDKSHIKKNLIGALLFDSGNTA--EDRRLKRTARRRYT 73
```

| | | |
|---|---|---|
| WP_002272766 | 1 MKKP-YSIGLDIGTNSVGWAVVTDDYKVPAKKMKVLGNTDKSHIKKNLLGALLFDSGNTA-EDRRLKRTARRRYT | 73 |
| WP_002273241 | 1 MKKP-YSIGLDIGTNSVGWAVVTDDYKVPAKKMKVLGNTDKSHIKKNLLGALLFDSGNTA-EDRRLKRTARRRYT | 73 |
| WP_002275430 | 1 MKKP-YSIGLDIGTNSVGWAVVTDDYKVPAKKMKVLGNTDKSHIKKNLLGALLFDSGNTA-ADRRLKRTARRRYT | 73 |
| WP_002276448 | 1 MKKP-YSIGLDIGTNSVGWAVVTDDYKVPAKKMKVLGNTDKSHIKKNLLGALLFDSGNTA-EDRRLKRTARRRYT | 73 |
| WP_002277050 | 1 MKKS-YSIGLDIGTNSVGWAVVTDDYKVPAKKMKVLGNTDKSHIKKNLLGALLFDSGNTA-EDRRLKRTARRRYT | 73 |
| WP_002773364 | 1 MKKP-YSIGLDIGTNSVGWAVVTDDYKVPAKKMKVLGNTDKSHIKKNLLGALLFDSGNTA-EDRRLKRTARRRYT | 73 |
| WP_002279025 | 1 MKKP-YSIGLDIGTNSVGWAVVTDDYKVPAKKMKVLGNTDKSHIKKNLLGALLFDSGNTA-ADRRLKRTARRRYT | 73 |
| WP_002279859 | 1 MKKP-YSIGLDIGTNSVGWAVVTDDYKVPAKKMKVLGNTDKSHIKKNLLGALLFDSGNTA-EDRRLKRTARRRYT | 73 |
| WP_002280230 | 1 MKKP-YSIGLDIGTNSVGWAVVTDDYKVPAKKMKVLGNTDKSHIKKNLLGALLFDSGNTA-ADRRLKRTARRRYT | 73 |
| WP_002281696 | 1 MKKP-YSIGLDIGTNSVGWAVVTDDYKVPAKKMKVLGNTDKSHIKKNLLGALLFDSGNTA-EDRRLKRTARRRYT | 73 |
| WP_002282247 | 1 MKKP-YSIGLDIGTNSVGWAVVTDDYKVPAKKMKVLGNTDKSHIEKNLLGALLFDSGNTA-EDRRLKRTARRRYT | 73 |
| WP_002282906 | 1 MKKP-YSIGLDIGTNSVGWSVVTDDYKVPAKKMKVLGNTDKSHIKKNLLGALLFDSGNTA-EDRRLKRTARRRYT | 73 |
| WP_002283846 | 1 MKKP-YSIGLDIGTNSVGWAVVTDDYKVPAKKMKVLGNTDKSHIKKNLLGALLFDSGNTA-EDRRLKRTARRRYT | 73 |
| WP_002287255 | 1 MKKP-YSIGLDIGTNSVGWAVVTDDYKVSAKKMKVLGNTDKSHIKKNLLGALLFDSGNTA-EDRRLKRTARRRYT | 73 |
| WP_002288990 | 1 MKKP-YSIGLDIGTNSVGWAVVTDDYKVPAKKMKVLGNTDKSHIKKNLLGALLFDSGNTA-EDRRLKRTARRRYT | 73 |
| WP_002289641 | 1 MKKP-YSIGLDIGTNSVGWAVVTDDYKVPAKKMKVLGNTDKSHIKKNLLGALLFDSGNTA-EDRRLKRTTRRRYT | 73 |
| WP_002290427 | 1 MKKP-YSIGLDIGTNSVGWAVVTDDYKVPDKKMKVLGNTDKSHIKKNLLGALLFDSGNTA-EDRRLKRTARRRYT | 73 |
| WP_002295753 | 1 MKKP-YSIGLDIGTNSVGWAVVTDDYKVPAKKMKVLGNTDKSHIKKNLLGALLFDSGNTA-EDRRLKRTARRRYT | 73 |
| WP_002296423 | 1 MKKP-YSIGLDIGTNSVGWAVVTDDYKVPAKKMKVLGNTDKSHIKKNLLGALLFDSGNTA-EDRRLKRTARRRYT | 73 |
| WP_002304487 | 1 MKKP-YSIGLDIGTNSVGWAVVTDDYKVPAKKMKVLGNTDKSHIKKNLLGALLFDSGNTA-EDRRLKRTARRRYT | 73 |
| WP_002305844 | 1 MKKP-YSIGLDIGTNSVGWAVVTDDYKVPAKKMKVLGNTDKSHIKKNLLGALLFDSGNTA-EDRRLKRTARRRYT | 73 |
| WP_002307203 | 1 MKKP-YSIGLDIGTNSVGWAVVTDDYKVPAKKMKVLGNTDKSHIKKNLLGALLFDSGNTA-EDRRLKRTARRRYT | 73 |
| WP_002310390 | 1 MKKP-YSIGLDIGTNSVGWAVVTDDYKVPAKKMKVLGNTDKSHIKKNLLGALLFDSGNTA-EDRRLKRTARRRYT | 73 |
| WP_002352408 | 1 MKKP-YSIGLDIGTNSVGWAVVTDDYKVPAKKMKVLGNTDKSHIKKNLLGALLFDSGNTA-ADRRLKRTARRRYT | 73 |
| WP_012997688 | 1 MKKP-YSIGLDIGTNSVGWAVVTDDYKVPAKKMKVLGNTDKSHIKKNLLGALLFDSGNTA-EDRRLKRTARRRYT | 73 |
| WP_014677909 | 1 MKKP-YSIGLDIGTNSVGWAVVTDDYKVPAKKMKVLGNTDKSHIKKNLLGALLFDSGNTA-EDRRLKRTARRRYT | 73 |
| WP_019312892 | 1 MKKP-YSIGLDIGTNSVGWAVVTDDYKVPAKKMKVLGNTDKSHIKKNLLGALLFDSGNTA-EDRRLKRTARRRYT | 73 |
| WP_019313659 | 1 MKKP-YSIGLDIGTNSVGWAVVTDDYKVPAKKMKVLGNTDKSHIKKNLLGALLFDSGNTA-EDRRLKRTARRRYT | 73 |
| WP_019314093 | 1 MKKP-YSIGLDIGTNSVGWAVVTDDYKVPAKKMKVLGNTDKSHIKKNLLGALLFDSGNTA-ADRRLKRTARRRYT | 73 |
| WP_019315370 | 1 MKKP-YSIGLDIGTNSVGWAVVTDDYKVPAKKMKVLGNTDKSHIKKNLLGALLFDSGNTA-EDRRLKRTTRRRYT | 73 |
| WP_019803776 | 1 MKKP-YSIGLDIGTNSVGWAVVTDDYKVPAKKMKVLGNTDKSHIKKNLLGALLFDSGNTA-EDRRLKRTARRRYT | 73 |
| WP_019805234 | 1 MKKP-YSIGLDIGTNSVGWAVVTDDYKVPAKKMKVLGNTDKSHIKKNLLGALLFDSGNTA-EDRRLKRTARRRYT | 73 |
| WP_024783594 | 1 MKKP-YSIGLDIGTNSVGWAVVTDDYKVPAKKMKVLGNTDKSHIEKNLLGALLFDSGNTA-EDRRLKRTARRRYT | 73 |
| WP_024784288 | 1 MKKP-YSIGLDIGTNSVGWAVVTDDYKVPAKKMKVLGNTDKSHIKKNLLGALLFDSGNTA-ADRRLKRTARRRYT | 73 |
| WP_024784666 | 1 MKKP-YSIGLDIGTNSVGWAVVTDDYKVPAKKMKVLGNTDKSHIKKNLLGALLFDSGNTA-EDRRLKRTARRRYT | 73 |
| WP_024784894 | 1 MKKP-YSIGLDIGTNSVGWAVVTDDYKVPAKKMKVLGNTDKSHIKKNLLGALLFDSGNTA-EDRRLKRTTRRRYT | 73 |
| WP_024786433 | 1 MKKP-YSIGLDIGTNSVGWAVVTDDYKVPAKKMKVLGNTDKSHIKKNLLGALLFDSGNTA-EDRRLKRTARRRYT | 73 |
| WP_049473442 | 1 MKKP-YSIGLDIGTNSVGWAVVTDDYKVPAKKMKVLGNTDKSHIKKNLLGALLFDSGNTA-ADRRLKRTARRRYT | 73 |
| WP_049474547 | 1 MKKP-YSIGLDIGTNSVGWAVVTDDYKVPAKKMKVLGNTDKSHIKKNLLGALLFDSGNTA-EDRRLKRTTRRRYT | 73 |
| EMC03581 | 1 MDL------IGTNSVGWAVVTDDYKVPAKKMKVLGNTDKSHIKKNLLGALLFDSGNTA-EDRRLKRTARRRYT | 66 |
| WP_000428612 | 1 ENKN-YSIGLDIGTNSVGWAVITDDYKVPAKKMKVLGNTDKRPIKKNLIGALLFDEGTTA-EARRLKRTARRRYT | 74 |
| WP_000428613 | 1 ENKN-YSIGLDIGTNSVGWAVITDDYKVPAKKMKVLGNTDKRFIKKNLIGALLFDAGNTA-ADRRLKRTARRRYT | 74 |
| WP_049523028 | 1 K-KP-YSIGLDIGTNSVGWAVITDDYKVPAKKMKVLGNTNKESIKKNLIGTLLFDSGETA-EARRLKRTARRRYT | 73 |
| WP_003107102 | 1 ------MKVLGNTDRQTVKKNMIGTLLFDSGETA-EARRLKRTTRRRYT | 42 |
| WP_054279288 | 1 -KKS-YSIGLDIGTNSVGWAVITDDYKVPAKKMKVLGNTSRQSIKQNMIGALLFDEGPA-ASTVKRTTRRRYT | 75 |
| WP_049531101 | 1 SNKP-YSIGLDIGTNSVGWVITDDYKVPSKKMKVLGNTDKHFIKKNLHGALLFDEGTTA-EDRRLKRTARRRYT | 74 |
| WP_049538452 | 1 SNKP-YSIGLDIGTNSVGWAVITDDYKVPSKKMKVLGNTDKHFIKKNLIGALLFDEGTTA-EDRRLKRTARRRYT | 74 |
| WP_049549711 | 1 ---YS-YSIGLDIGTNSVGWAVINEDYKVPAKKMTVLGNTDRKTIKKNLLGTVLFDSGETA-QARRLKRTNRRRYT | 75 |
| WP_007896501 | 1 --YS-YSIGLDIGTNSVGWAVINEDYKVPAKKMTVFGNTDRKTIKKNLLGTVLFDSGETA-QARRLKRTNRRRYT | 75 |
| EFR44625 | 1 -------MLGTVLFDSGETA-ESRRLKRTNRRRYT | 27 |
| WP_002897477 | 1 K-KP-YSIGLDIGTNSVGWAVITDDYKVPAKKMKVLGNTDKHFIKKNLIGALLFDSGETA-EDRRLKRTSRRRYT | 73 |
| WP_002906454 | 1 K-KP-YSIGLDIGTNSVGWAVITDDYKVPAKKMKVLGNTDKHFIKKNLIGALLFDSGETA-EDRRLKRTARRRYT | 73 |
| WP_009729476 | 1 ENKN-YSIGLDIGTNSVGWSVITDDYKVPSKKMKVLGNTDKHFIKKNLIGALLFDEGTTA-EARRLKRTARRRYT | 74 |

-continued

```
CQR24647            1 MKKP-YSIGLDIGTNSVGWAVTDDYKVPAKKMKVLGNTDKEYIKKNLIGALLFDSGETA--EATRMKRTARRRYT  73
WP_000066813        1 SNKS-YSIGLDIGTNSVGWAVITDDYKVPSKKMKVLGNTDKHFIKKNLIGALLFDEGTTA--EDRRLKRTARRRYT  74
WP_009754323        1 NNNN-YSIGLDIGTNSVGWAVITDDYKVPSKKMRVLGNTDKRPIKKNLIGALLFDEGTTA--EDRRLKRTARRRYT  74
WP_044674937        1 MKKK-YAIGIDIGTNSVGWAVITDDYKVPSKKMKVFGNTEKRYIKKNLLGTLLFDEGNTA--ENRRLKRTARRRYT  73
WP_044676715        1 MKKK-YAIGIDIGTNSVGWSVVTDDYKVPSKKMKVFGNTEKRYIKKNLLGTLLFDEGNTA--ENRRLKRTARRRYT  73
WP_044680361        1 MKKK-YAIGIDIGTNSVGWSVVTDDYKVPSKKMKVFGNTEKRYIKKNLLGTLLFDEGNTA--ENRRLKRTARRRYT  73
WP_044681799        1 MKKK-YAIGLDIGTNSVGWSVVTDDYKVPSKKMKVFGNTEKRYIKKNLLGTLLFDEGNTA--ENRRLKRTARRRYT  73
WP_049533112        1 MDQK-YSIGLDIGTNSVGWAVVTDDYKVPAKKMKVLGNTDKQSIKKNLLGALLFDSGETA--EATRLKRTARRRYT  73
WP_029090905        1 ------------------------------------MWGVSLFEAGKTA--AERRGYRSTRRRLN           27
WP_065066696        1 I-VD-YCIGLDLGTGSVGWAVVDMNHRLMKRN--------GKHLWGSRLFSNAFTA--ANRRASRSIRRRYN      60
AIT42264            1 MDKK-YSIGLDIGTNSVGWAVITDEYKVPSKKPKVLGNTDRHSIKKNLIGALLFDSGETA--EATRLKRTARRRYT  73
WP_034440723        1 -MKN-YTIGLDIGTNSVGWAVIKDDLTLVRKKIKISGNTDKKEVKKNLWGSFLFEQGGTA--QDTRVKRIARRYE   72
AKQ21048            1 MDKK-YSIGLDIGTNSVGWAVITDEYKVPSKKFKVLGNTDRHSIKKNLIGALLFDEGGTA--EATRLKRTARRRYT  73
WP_004636532        1 MQKN-YTIGLDIGTNSVGWAVMKDDYTLLRKRMKVLGNTDIKKIKKNFWGVRLFDEGHTA--KETRLKRGTRRRYQ  73
WP_002364836        1 MKKD-YVIGLDIGTNSVGWAVMTEDYQLVKKMPIYGNTEKKKIKKNFWGVRLFEEGHTA--EDRRLKRTARRRIS   73
WP_016631044        1 ---------------------------------MRLFEEGHTA--EDRRLKRTARRRIS                  24
EMS75795            1 ---------------------------------------------------------                     
WP_002373311        1 MKKD-YVIGLDIGTNSVGWAVMTEDYQLVKKMPIYGNTEKKKIKKNFWGVRLFEEGHTA--EDRRLKRTARRRIS   73
WP_002378009        1 MKKD-YVIGLDIGTNSVGWAVMTEDYQLVKKMPIYGNTEKKKIKKNFWGVRLFEEGHTA--EDRRLKRTARRRIS   73
WP_002407324        1 MKKD-YVIGLDIGTNSVGWAVMTEDYQLVKKMPIYGNTEKKKIKKNFWGVRLFEEGHTA--EDRRLKRTARRRIS   73
WP_002413717        1 MKKD-YVIGLDIGTNSVGWAVMTEDYQLVKKMPIYGNTEKKKIKKNFWGVRLFEEGHTA--EDRRLKRTARRRIS   73
WP_010775580        1 MKKD-YVIGLDIGTNSVGWAVMTEDYQLVKKMPIYGNTEKKKIKKNFWGVRLFEEGHTA--EDRRLKRTARRRIS   73
WP_010818269        1 MKKD-YVIGLDIGTNSVGWAVMTEDYQLVKKMPIYGNTEKKKIKKNFWGVRLFEEGHTA--EDRRLKRTARRRIS   73
WP_010824395        1 MKKD-YVIGLDIGSNSVGWAVMTEDYQLVKKMPIYGNTEKKKIKKNFWGVRLFEEGHTA--EDRRLKRTARRRIS   73
WP_016622645        1 MKKD-YVIGLDIGTNSVGWAVMTEDYQLVKKMPIYGNTEKKKIKKNFWGVRLFEEGHTA--EDRRLKRTARRRIS   73
WP_033624816        1 MKKD-YVIGLDIGTNSVGWAVMTEDYQLVKKMPIYGNTEKKKIKKNFWGVRLFEEGHTA--EDRRLKRTARRRIS   73
WP_002625576        1 MKKD-YVIGLDIGTNSVGWAVMTEDYQLVKKMPIYGNTEKKKIKKNFWGVRLFEEGHTA--EDRRLKRTARRRIS   73
WP_033789179        1 MKKD-YVIGLDIGTNSVGWAVMTEDYQLVKKMPIYGNTEKKKIKKNFWGVRLFEEGHTA--EDRRLKRTARRRIS   73
WP_002310644        1 MKKE-YTIGLDIGTNSVGWSVLTDDYRLVSKKMKVAGNTEKSSTKKNFWGVRLFDEGQTA--EARRSKRTARRRLA  73
WP_002312694        1 MKKE-YTIGLDIGTNSVGWSVLTDDYRLVSKKMKVAGNTEKSSTKKNFWGVRLFDEGQTA--EARRSKRTARRRLA  73
WP_002314015        1 MKKE-YTIGLDIGTNSVGWSVLTDDYRLVSKKMKVAGNTEKSSTKKNFWGVRLFDEGQTA--EARRSKRTARRRLA  73
WP_002320716        1 MKKE-YTIGLDIGTNSVGWSVLTDDYRLVSKKMKVAGNTEKSSTKKNFWGVRLFDEGQTA--EARRSKRTARRRLA  73
WP_002330729        1 MKKE-YTIGLDIGTNSVGWSVLTDDYRLVSKKMKVAGNTEKSSTKKNFWGVRLFDEGQTA--EARRSKRTARRRLA  73
WP_002335161        1 MKKE-YTIGLDIGTNSVGWSVLTDDYRLVSKKMKVAGNTEKSSTKKNFWGVRLFDEGQTA--EARRSKRTARRRLA  73
WP_002345439        1 MTKD-YTIGLDIGTNSVGWSVLTDDYRLVSKKMKVAGNTEKSSTKKNFWGVRLFDEGQTA--EARRSKRTARRRLA  73
WP_034867970        1 MTKD-YTIGLDIGTNSVGWAVLTDDYQLMKRRMSVHGNTEKKKIKKNFWGVRLFDEGQTA--EFRRTKRTNRRRLA  73
WP_047937432        1 MKKE-YTIGLDIGTNSVGWAVLTDDYRLVSKKMKVAGNTEKSSTKKNFWGVRLFDEGQTA--EARRSKRTARRRLA  73
WP_010720994        1 MTKD-YTIGLDIGTNSVGWAVLTDDYQLMKRMSVHGNTEKKKIKKNFWGVRLFDEGQTA--EFRRTKRTNRRRLA   73
WP_010737004        1 MTKD-YTIGLDIGTNSVGWAVLTDDYQLMKERMSVHGNTEKKKIKKNFWGVRLFDEGQTA--EFRRTKRTNRRRLA  73
WP_034700478        1 MTKD-YTIGLDIGTNSVGWAVLTDDYQLMKRMSVHGNTEKKKIKKNFWGARLFDEGQTA--EFRRTKRTNRRRLA   73
WP_072209003        1 MKND-YTIGLDIGTNSVGYSVVTDDYKVISKKNNVFGNTEKKKSIKKNFWGARLFDEGQTA--QEARMKRTSRRRIA 73
WP_023519017        1 MEKE-YTIGLDIGTNSVGWAVLTENYDLVARKMSIQGDSNRKKIKKNFWGVTETRYLKKNLWGVRLFDEGETA--QFRRIKRTNRRRIA 73
WP_010770040        1 MGKE-YTIGLDIGTNSVGWAVLTDDYRLVSKKMKVYGNTETKYLKKNLWGVRLFDEGETA--ADRRLKRTTRRRYS  73
WP_048640708        1 MNCA-YTIGLDIGTNSVGWAVLTDDYRLMAKMPVHSKMEKKKIKKNFWGARLFDEGQTA--ERRRNKRATRRRLR   73
WP_010750235        1 MSRP-YNIGLDIGTSIGWSVVDDQSKLVSVR--------------GKYGYGVRLYDEGQTA--AERRSFRTTRRRLK 61
AII16583            1 ADKK-YSIGLDIGTNSVGWAVLTDDYKVPSKKFKVLGNTDRHSIKKNLIGALLFDSGETA--EATRLKRTARRRIE 112
WP_029073316        1 NNKI-YNIGLDIGDASVGWAVVDEHYNLLKRH--------GKHMWGSRLFTQANTA--VERSSSRSTRRRYN      65
WP_031589969        1 NNNI-YNIGLDIGDASVGWAVVDEHYNLLKRH--------GKHMWGSRLFTQANTA--VERRSSRSTRRRYN      65
KDA45870            1 LKKD-YSIGLDIGTNSVGHAVVTDDYKVPTKMKVFGDTSKKTIKKNMLGVLLFNEGQTA--ADTRLKRGARRRYT   74
WP_039099354        1 MSRP-YNIGLDIGTSSIGWSVVDDQSKLVSVR----------KKNLWGVRLFEGAQTA--KETRLNRSTRRRYR    61
AKP02966            1 KEQP-YNIGLDIGTGSVGWAVLTDQYDIVKRKMKIAGDSEKKQIKKNFWGVRLFDEGQTA--ADRRMARTARRRLA  64
WP_010991369        1 MKKP-YTIGLDIGTNSVGWAVLTDQYDLVKRKMKIAGDSEKKQIKKNFWGVRLFDEGQTA--ADRRMARTARRRIE  73
WP_033838504        1 MKKP-YTIGLDIGTNSVGWAVLTDQYDLVKRKMKIAGDSEKKQIKKNFWGVRLFDEGQTA--ADRRMARTARRRIE  73
```

```
                                -continued

EHN60060           1 MKKP-YTIGLDIGTNSVGWAVLTDQYDLVKRKMKIAGDSEKKQIKKQNFWGVRLFDEQTA--ADRRMARTARRRIE                     76
EFR89594           1                                                                                              
WP_038409211       1 MRKP-YTIGLDIGTNSVGWAVLTDQYNLVKRKMKVAGSAEKKQIKKQNFWGVRLFDEGEVA--AGRRMNRTTRRRIE                     73
EFR_95520                                                                                                         
WP_003723650       1 MKNP-YTIGLDIGTNSVGWAVLTDQYNLVKRKMKVAGNSDKKQIKKQNFWGVRLFDDGQTA--VDRRMNRTARRRIE                     73
WP_003727705       1 MKNP-YTIGLDIGTNSVGWAVLTDQYDLVKRKMKVAGNSDKKQIKKQNFWGVRLFDDGQTA--VDRRMNRTARRRIE                     73
WP_003730785       1 MKNP-YTIGLDIGTNSVGWAVLTDQYDLVKRKMKVAGNSDKKQIKKQNFWGVRLFDDGQTA--VDRRMNRTARRRIE                     73
WP_003733029       1 MKKP-YTIGLDIGTNSVGWAVLTDQYDLVKRKMKVAGNSDKKQIKKQNFWGVRLFEKGETA--AKRRMSRTARRRIE                     73
WP_003739838       1 MKNP-YTIGLDIGTNSVGWAVLTDQYDLVKRKMKISGDSEKKQIKKQNFWGVRLFDEGETA--ADRRMNRTARRRIE                     73
WP_014601172       1 MKNP-YTIGLDIGTNSVGWAVLTDQYDLVKRKMKVAGNSDKKQIKKQNFWGVRLFDDGQTA--VDRRMNRTARRRIE                     73
WP_023548323       1 MKNP-YTIGLDIGTNSVGWAVLTDQYNLVKRKMKVAGNSDKKQIKKQNFWGVRLFDDGQTA--VDRRMNRTARRRIE                     73
WP_031665337       1 MKNP-YTIGLDIGTNSVGWAVLTDQYDLVKRKMKVAGNSDKKQIKKQNFWGVRLFDDGQTA--VDRRMNRTARRRIE                     73
WP_031669209       1 MKKP-YTIGLDIGTNSVGWAVLTDQYDLVKRKMKISGDSEKKQIKKQNFWGVRLFEKGETA--AKRRMSRTARRRIE                     73
WP_033920898       1 MKNP-YTIGLDIGTNSVGWAVLTDQYDLVKRKMKVAGNSDKKQIKKQNFWGVRLFDDGQTA--VDRRMNRTARRRIE                     73
AKI42028           1 MKNP-YTIGLDIGTNSVGWAVLTNQYDLVKRKMKVAGNSDKKQIKKQNFWGVRLFDDGQTA--VDRRMNRTARRRIE                     76
AKI50529           1 MKNP-YTIGLDIGTNSVGWAVLTNQYDLVKRKMKVAGNSDKKQIKKQNFWGVRLFDDGQTA--VDRRMNRTARRRIE                     76
EFR83390                                                                                                          
WP_046323366       1 MKKP-YTIGLDIGTNSVGWAALTDQYDLVKRKMKVAGNSEKKQIKKQNLWGVRLIVDEGKTA--AHRRVNRTTRRRIE                    73
AKE81011           1 ADKK-YSIGLDIGTNSVGWAVITDEYKVPSKKFPKVLGNTDRHSIKKNLIGALLFDSGETA--EATRLKRTARRRYT                     89
CUO82355           1 I-VD-YCIGLDLGTGSVGWAVVDMNHRLMKRN----------GKHLWGSRLFSNAETA--ATRRSSRSIRRRYN                        64
WP_033162887       1 KDIR-YSIGLDIGTNSVGWAVMDEHYELLKKG---------NHHMWGSRLFDAAEPA--ATRRASRSIRRRYN                         65
ADKK-YSIGLDIGTNSVGWAVITDEYKVPSKKFPKVLGNTDRHSIKKNLIGALLFDSGETA--EATRLKRTARRRYT                      106
AGZO1981           1 ADKK-YSIGLDIGTNSVGWAVITDEYKVPSKKFPKVLGNTDRHSIKKNLIGALLFDSGETA--EATRLKRTARRRYT                     73
AKA60242           1 MDKK-YSIGLDIGTNSVGWAVITDEYKVPSKKFPKVLGNTDRHSIKKNLIGALLFDSGETA--EATRLKRTARRRYT                     73
AKS40380           1 MDKK-YSIGLDIGTNSVGWAVITDEYKVPSKKFPKVLGNTDRHSIKKNLIGALLFDSGETA--EATRLKRTARRRYT                     77
4UN5_B             1         YSIGLAIGTNSVGWAVITDEYKVPSKKFPKVLGNTDRHSIKKNLIGALLFDSGETA--EATRLKRTARRRYT                 77
WP_010922251      74 RRKQNRICYLQEIFSNEMAKVDDSFFHRLEE-SFLV--EEDKK---H ERHPIFGNIV-DEVAYHEKYPTIY[I]LRKKLV               143
WP_039695303      75 RRKQNRLRLYLQEIFANEIAKVDESFFQRLDE-SFLT--DDDKT---F DSHPIFGNKA-EEDAYHQKFPTIYHLRKKHLA              144
WP_045635197      74 RRKQNRLRLYLQEIFSEEMSKVDSSFFHRLDD-SFLI--PEDKR---E SKYPIFATLT-EEKEYHKQPPTIYHLRKQLA              143
5AXW_A            62 RRRHRIQRVKKLFD----------YNLLTDhSFLS---------G --NPYEARVK------GLSQKLS                           104
WP_009880683                                                                                                      
WP_010922251      74 RRKQNRICYLQEIFSNEMAKVDDSFFHRLEE-SFLV--EEDKK---H ERHPIFGNIV-DEVAYHEKYPTIYHLRKKLV                 143
WP_011054416      74 RRKQNRICYLQEIFSNEMAKVDDSFFHRLEE-SFLV--EEDKK---H ERHPIFGNIV-DEVAYHEKYPTIYHLRKKLA                 143
WP_011284745      74 RRKQNRICYLQEIFSNEMAKVDDSFFHRLEE-SFLV--EEDKK---H ERHPIFGNIV-DEVAYHEKYPTIYHLRKKLV                 143
WP_011285506      74 RRKQNRICYLQEIFSNEMAKVDDSFFHRLEE-SFLV--EEDKK---H ERHPIFGNIV-DEVAYHEKYPTIYHLRKKLV                 143
WP_011527619      74 RRKQNRICYLQEIFSNEMAKVDDSFFHRLEE-SFLV--EEDKK---H ERHPIFGNIV-DEVAYHEKYPTIYHLRKKLV                 143
WP_012560673      74 RRKQNRICYLQEIFSNEIAKVDDSFFHRLEE-SFLV--EEDKK---H ERHPIFGNIV-DEVAYHEKYPTIYHLRKKLA                 143
WP_014407541      74 RRKQNRICYLQEIFSNEIAKVDDSFFHRLEE-SFLV--EEDKK---H ERHPIFGNIV-DEVAYHEKYPTIYHLRKKLA                 143
WP_020905136      74 RRKQNRICYLQEIFSNEMAKVDDSFFHRLEE-SFLV--EEDKK---H ERHPIFGNIV-DEVAYHEKYPTIYHLRKKLV                 143
WP_023080005      74 RRKQNRICYLQEIFSNEMAKVDDSFFHRLEE-SFLV--EEDKK---H ERHPIFGNIV-DEVAYHEKYPTIYHLRKKLA                 143
WP_023610282      74 RRKQNRICYLQEIFSNEMAKVDDSFFHRLEE-SFLV--EEDKK---H ERHPIFGNIV-DEVAYHEKYPTIYHLRKKLA                 143
WP_030125963      74 RRKQNRICYLQEIFSNEMAKVDDSFFHRLEE-SFLV--EEDKK---H ERHPIFGNIV-DEVAYHEKYPTIYHLRKKLV                 143
WP_030126706      74 RRKQNRICYLQEIFSNEMAKVDDSFFHRLEE-SFLV--EEDKK---H ERHPIFGNIV-DEVAYHEKYPTIYHLRKKLA                 143
WP_031488318      74 RRKQNRICYLQEIFSNEMAKVDDSFFHRLEE-SFLV--EEDKK---H ERHPIFGNIV-DEVAYHEKYPTIYHLRKKLA                 143
WP_032460140      74 RRKQNRICYLQEIFSNEIAKVDDSFFHRLEE-SFLV--EEDKK---H ERHPIFGNIV-DEVAYHEKYPTIYHLRKKLA                 143
WP_032461047      74 RRKQNRICYLQEIFSNEIAKVDDSFFHRLEE-SFLV--EEDKK---H ERHPIFGNIV-DEVAYHEKYPTIYHLRKKLA                 143
WP_032462016      74 RRKQNRICYLQEIFSNEMAKVDDSFFHRLEE-SFLV--EEDKK---H ERHPIFGNIV-DEVAYHEKYPTIYHLRKKLA                 143
WP_032462936      74 RRKQNRICYLQEIFSNEMAKVDDSFFHRLEE-SFLV--EEDKK---H ERHPIFGNIV-DEVAYHEKYPTIYHLRKKLA                 143
WP_032464890      74 RRKQNRICYLQEIFSNEMAKVDDSFFHRLEE-SFLV--EEDKK---H ERHPIFGNIV-DEVAYHEKYPTIYHLRKKLA                 143
WP_033888930                                                                                                      
WP_038431314      74 RRKQNRICYLQEIFSNEMAKVDDSFFHRLEE-SFLV--EEDKK---H ERHPIFGNIV-DEVAYHEKYPTIYHLRKKLA                 143
WP_038432938      74 RRKQNRICYLQEIFSNEMAKVDDSFFHRLEE-SFLV--EEDKK---H ERHPIFGNIV-DEVAYHEKYPTIYHLRKKLA                 143
WP_038434062      74 RRKQNRICYLQEIFSNEMAKVDDSFFHRLEE-SFLV--EEDKK---H ERHPIFGNIV-DEVAYHEKYPTIYHLRKKLV                 143
BAQ51233           1 -----------MAKVDDSFFHRLEE-SFLV--EEDKK---H ERHPIFGNIV-DEVAYHEKYPTIYHLRKKLA                         54
```

-continued

| | | | | |
|---|---|---|---|---|
| KGE60162 | | | | |
| KGE60856 | | | | |
| WP_002989955 | RRNRICYLQEIFSNEMAKVDDSFFHRLEE-SFLV--EEDKK---H | ERHPIFGNIV-DEVAYHEKPTIYHLRKKLV | 143 |
| WP_003030002 | RRRNRLRYLQEIFAEEMNKVDENFFQRLDD-SFLV--DEDKR---G | ERHPIFGNIA-AEVKYHDDFPTIYHLRKHLA | 143 |
| WP_003065552 | RRKNRLRYLQEIFAEEMTKVDDESFFQRLDE-SFLRwGDDNKK---L | GRYPIFGNKA-DVVKYHQEFPTIYHLRKHLA | 146 |
| WP_001040076 | RRRNRILYLQEIFAEEMSKVDDSFFHRLED-SFLV--EEDKR---G | SKYPIFATLQ-EEKYHEKFPTIYHLRKELA | 143 |
| WP_001040078 | RRRNRILYLQEIFAEEMSKVDDSFFHRLED-SFLV--EEDKR---G | SKYPIFATLQ-EEKDYHEKFPTIYHLRKELA | 143 |
| WP_001040080 | RRRNRILYLQEIFAEEMSKVDDSFFHRLED-SFLV--EEDKR---G | SKYPIFATLQ-EEKDYHEKFSTIYHLRKELA | 143 |
| WP_001040081 | RRRNRILYLQEIFAEEMSKVDDSFFHRLED-SFLV--EEDKR---G | SKYPIFATLQ-EEKDYHEKFSTIYHLRKELA | 143 |
| WP_001040083 | RRRNRILYLQEIFAEEMSKVDDSFFHRLED-SFLV--EEDKR---G | SKYPIFATLQ-EEKDYHEKFSTIYHLRKELA | 143 |
| WP_001040085 | RRRNRILYLQEIFAEEMSKVDDSFFHRLED-SFLV--EEDKR---G | SKYPIFATLQ-EEKDYHEKFSTIYHLRKELA | 143 |
| WP_001040087 | RRRNRILYLQEIFAEEMSKVDDSFFHRLED-SFLV--EEDKR---G | SKYPIFATLQ-EEKDYHEKFSTIYHLRKELA | 143 |
| WP_001040088 | RRRNRILYLQEIFAEEMSKVDDSFFHRLED-SFLV--EEDKR---G | SKYPIFATLQ-EEKDYHEKFSTIYHLRKELA | 143 |
| WP_001040089 | RRRNRILYLQEIFAEEMSKVDDSFFHRLED-SFLV--EEDKR---G | SKYPIFATLQ-EEKDYHEKFSTIYHLRKELA | 143 |
| WP_001040090 | RRRNRILYLQEIFAEEMSKVDDSFFHRLED-SFLV--EEDKR---G | SKYPIFATMQ-EEKYHEKFPTIYHLRKELA | 143 |
| WP_001040091 | RRRNRILYLQEIFAEEMSKVDDSFFHRLED-SFLV--EEDKR---G | SKYPIFATMQ-EEKYHEKFPTIYHLRKELA | 143 |
| WP_001040092 | RRRNRILYLQEIFAEEMSKVDDSFFHRLED-SFLV--EEDKR---G | SKYPIFATLQ-EEKDYHEKFSTIYHLRKELA | 143 |
| WP_001040094 | RRRNRILYLQEIFAEEMSKVDDSFFHRLED-SFLV--EEDKR---G | SKYPIFATMQ-EEKYHEKFPTIYHLRKELA | 143 |
| WP_001040095 | RRRNRILYLQEIFAEEMSKVDDSFFHRLED-SFLV--EEDKR---G | SKYPIFATMQ-EEKYHEKFPTIYHLRKELA | 143 |
| WP_001040096 | RRRNRILYLQEIFAEEMSKVDDSFFHRLED-SFLV--EEDKR---G | SKYPIFATMQ-EEKYHEKFPTIYHLRKELA | 143 |
| WP_001040097 | RRRNRILYLQEIFAEEMSKVDDSFFHRLED-SFLV--EEDKR---G | SKYPIFATLQ-EEKYHEKFPTIYHLRKELA | 143 |
| WP_001040098 | RRRNRILYLQEIFAEEMSKVDDSFFHRLED-SFLV--EEDKR---G | SKYPIFATMQ-EEKYHEKFPTIYHLRKELA | 143 |
| WP_001040099 | RRRNRILYLQEIFAEEMSKVDDSFFHRLED-SFLV--EEDKR---G | SKYPIFATMQ-EEKYHEKFPTIYHLRKELA | 143 |
| WP_001040100 | RRRNRILYLQEIFAEEMSKVDDSFFHRLED-SFLV--EEDKR---G | SKYPIFATMQ-EEKYHEKFPTIYHLRKELA | 143 |
| WP_001040104 | RRRNRILYLQEIFAEEMSKVDDSFFHRLED-SFLV--EEDKR---G | SKYXIFATLQ-EEKYHEKFPTIYHLRKELA | 143 |
| WP_001040105 | RRRNRILYLQEIFAEEMSKVDDSFFHRLED-SFLV--EEDKR---G | SKYPIFATMQ-EEKYHEKFPTIYHLRKELA | 143 |
| WP_001040106 | CRRNRILYLQEIFAEEMSKVDDSFFHRLED-SFLV--EEDKR---G | SKYPIFATMQ-EEKYHEKFPTIYHLRKELA | 143 |
| WP_001040107 | RRRNRILYLQEIFAEEMSKVDDSFFHRLED-SFLV--EDDKR---G | SKYPIFATLQ-EEKDYHEKFSTIYHLRKELA | 143 |
| WP_001040108 | RRRNRILYLQEIFAEEMSKVDDSFFHRLED-SFLV--EDDKR---G | SKYPIFATLQ-EEKDYHEKFPTIYHLRKELA | 143 |
| WP_001040109 | RRRNRILYLQEIFAEEMSKVDDSFFHRLED-SFLV--EEDKR---G | SKYPIFATLQ-EEKDYHEKFPTIYHLRKELA | 143 |
| WP_001040110 | RRRNRILYLQEIFAEEMSKVDDSFFHRLED-SFLV--EDDKR---G | SKYPIFATLQ-EEKDYHEKFPTIYHLRKELA | 143 |
| WP_015058523 | RRRNRILYLQEIFAEEMSKVDDSFFHRLED-SFLV--EEDKR---G | SKYPIFATMQ-EEKYHEKFPTIYHLRKELA | 143 |
| WP_017643650 | RRRNRILYLQEIFAEEMSKVDDSFFHRLED-SFLV--EEDKR---G | SKYPIFATMQ-EEKYHEKFPTIYHLRKELA | 143 |
| WP_017647151 | RRRNRILYLQEIFAEEMSKVDDSFFHRLED-SFLV--EEDKR---G | SKYPIFATMQ-EEKYHEKFPTIYHLRKELA | 143 |
| WP_017648376 | RRRNRILYLQEIFAEEMSKVDDSFFHRLED-SFLV--EEDKR---G | SKYPIFATLQ-EEKYHEKFPTIYHLRKELA | 143 |
| WP_017649527 | RRRNRILYLQEIFAEEMSKVDDSFFHRLED-SFLV--EEDKR---G | SKYPIFATLQ-EEKDYHEKFPTIYHLRKELA | 143 |
| WP_017771611 | RRRNRILYLQEIFAEEMSKVDDSFFHRLED-SFLV--EEDKR---G | SKYPIFATMQ-EEKYHEKFPTIYHLRKELA | 143 |
| WP_017771984 | RRRNRILYLQEIFAEEMSKVDDSFFHRLED-SFLV--EEDKR---G | SKYPIFATMQ-EEKYHEKFPTIYHLRKELA | 143 |
| CFQ25032 | RRRNRILYLQEIFAEEMSKVDDSFFHRLED-SFLV--EEDKR---G | SKYPIFATLQ-EEKDYHEKFPTIYHLRKELA | 143 |
| CFV16040 | RRRNRILYLQEIFAEEMSKVDDSFFHRLED-SFLV--EEDKR---G | SKYPIFATLQ-EEKDYHEKFPTIYHLRKELA | 143 |
| KLJ37842 | RRRNRILYLQEIFAEEMSKVDDSFFHRLED-SFLV--EEDKR---G | SKYPIFATLQ-EEKDYHEKFPTIYHLRKELA | 143 |
| KLJ72361 | RRRNRILYLQEIFAEEMSKVDDSFFHRLED-SFLV--EEDKR---G | SKYPIFATLQ-EEKDYHEKFPTIYHLRKELA | 143 |
| KLL20707 | RRRNRILYLQEIFAEEMSKVDDSFFHRLED-SFLV--EEDKR---G | SKYPIFATLQ-EEKDYHEKFPTIYHLRKELA | 143 |
| KLL42645 | RRRNRILYLQEIFAEEMSKVDDSFFHRLED-SFLV--EEDKR---G | SKYPIFATLQ-EEKDYHEKFPTIYHLRKELA | 143 |
| WP_047207273 | RRRNRILYLQEIFAEEMSKVDDSFFHRLED-SFLV--EEDKR---G | SKYPIFATLQ-EEKDYHEKFPTIYHLRKELA | 143 |
| WP_047209694 | RRRNRILYLQEIFAEEMSKVDDSFFHRLED-SFLV--EEDKR---G | SKYPIFATLQ-EEKDYHEKFPTIYHLRKELA | 143 |
| WP_050198062 | RRRNRILYLQEIFAEEMSKVDDSFFHRLED-SFLV--EEDKR---G | SKYPIFATLQ-EEKDYHEKFPTIYHLRKELA | 143 |
| WP_050201642 | RRRNRILYLQEIFAEEMSKVDDSFFHRLED-SFLV--EEDKR---G | SKYPIFATLQ-EEKDYHEKFPTIYHLRKELA | 143 |
| WP_050204027 | RRRNRILYLQEIFAEEMSKVDDSFFHRLED-SFLV--EEDKR---G | SKYPIFATLQ-EEKDYHEKFPTIYHLRKELA | 143 |
| WP_050881965 | RRRNRILYLQEIFAEEMSKVDDSFFHRLED-SFLV--EEDKR---G | SKYPIFATLQ-EEKDYHEKFPTIYHLRKELA | 143 |
| WP_050886065 | RRRNRILYLQEIFAEEMSKVDDSFFHRLED-SFLV--EEDKR---G | SKYPIFATMQ-EEKDYHEKFPTIYHLRKELA | 143 |
| AHN30376 | RRRNRILYLQEIFAEEMSKVDDSFFHRLED-SFLV--EEDKR---G | SKYPIFATLQ-EEKDYHEKFPTIYHLRKELA | 143 |
| EAO78426 | RRRNRILYLQEIFAEEMSKVDDSFFHRLED-SFLV--EEDKR---G | SKYPIFATLQ-EEKDYHEKFPTIYHLRKELA | 143 |

| | | | | |
|---|---|---|---|---|
| CCW42055 | 74 | RRRNRIRLRYLIQEIFAEEMMSKVDDSFFHRLED-SFLV-EEDKR---G | SKYPIFATLQ-EEKDYHEKPTIYHLRKELA | 143 |
| WP_003041502 | 74 | RRRNRLRYLIQEIFAEEMMQVDESFFQRLDD-SFLV-DEDKR---G | ERHPIFGNIA-AEVKYHDEFPTIYHLRKHLA | 143 |
| WP_037593752 | 75 | RRRNRLRYLIQEIFTEEMNKVDENFFQRLDD-SFLV-EEDKQ---G | EEKEYHKKKTIYHLREELA | 144 |
| WP_049516684 | 74 | RRRNRLRYLIQEIFAEEMMQVDESFFQRLDD-SFLV-EEDKQ---G | SRYPIFGTLK-AEVKYHDDFPTIYHLREELA | 143 |
| GAD46167 | 75 | RRRNRLRYLIQEIFTEEMNKVDENFFQRLDE-SFLT-DNDKN---F | SKYPIFGTLK-EEKEYHKKKTIYHLREELA | 144 |
| WP_018363470 | 74 | RRRNRLRYLQDIFTEEMKVDENFFQRLDE-SFLT-DNDKN---F | DSHPIFGNKA-EEDAYHQKPTIYHLRKHLA | 143 |
| WP_003043819 | 74 | RRKNRLRYLIQEIFANEMAKLDDSFFQRLEE-SFLV-EEDKK---N | ERHPIFGNLA-DEVAYHRNYPTIYHLRKKLA | 143 |
| WP_006269658 | 74 | RRRNRLRYLIQEIFTGEMNKVDENFFQRLDD-SFLV-DEDKR---G | ERHPIFGNIA-AEVKYHDDFPTIYHLRKKLA | 143 |
| WP_048800889 | 74 | RRRNRLRYLIQEIFIEEMNKVDENFFQRLDD-SFLV-TEDKR---G | SKYPIFGTLK-EEKEYYKEFETIYHLRKRLA | 143 |
| WP_012767106 | 74 | RRRNRIRYLQEIFSSEMSKVDDSFFHRLEE-SFLV-EEDKK---H | ERHPIFGNIV-DEVAYHEKYPTIYHLRKKLA | 143 |
| WP_014612333 | 74 | RRRNRLRYLIQEIFSSEMSKVDDSFFHRLEE-SFLV-EEDKK---H | ERHPIFGNIV-DEVAYHEKYPTIYHLRKKLA | 143 |
| WP_015017095 | 74 | RRRNRLRYLIQEIFSSEMSKVDDSFFHRLEE-SFLV-EEDKK---H | ERHPIFGNIV-DEVAYHEKYPTIYHLRKKLA | 143 |
| WP_015057649 | 74 | RRRNRLRYLIQEIFSSEMSKVDDSFFHRLEE-SFLV-EEDKK---H | ERHPIFGNIV-DEVAYHKKYPTIYHLRKKLA | 143 |
| WP_048272215 | 74 | RRRNRLRYLIQEIFSSEMSKVDDSFFHRLEE-SFLV-EEDKK---H | ERHPIFGNIV-DEVAYHKKYPTIYHLRKKLA | 143 |
| WP_049519324 | 74 | RRRNRLRYLIQEIFSSEMSKVDDSFFQRLEE-SFLT-LEDKE---G | NKHPIFANLA-DEVAYHKKYPTIYHLRKELV | 143 |
| WP_012515931 | 74 | RRRNRLRYLIKEIFTEEMAKVDDGFFQRLED-SFYV-LEDKE---G | NKHPIFANLA-DEVAYHKKYPTIYHLRKELV | 143 |
| WP_021320964 | 74 | RRRNRLRYLIKEIFTEEMAKVDDGFFQRLED-SFLT-LEDKE---G | NKHPIFANLA-DEVAYHKKYPTIYHLRKELV | 143 |
| WP_037581760 | 74 | RRRNRLRPLKEIFTEEMAKVDDGFFQRLED-SFLT-DDDKT---F | DSHPIFGNKA-EEDTYHQEPPTIYHLRNYLA | 143 |
| WP_044232481 | 74 | RRRNRLRYLIQEIFAEEMAKVDESFFYRLDE-SFLT-TDEKD---F | ERHPIFGNKA-EEDAYHQKPTIYHLRNYLA | 143 |
| WP_009854540 | 74 | RRRNRLRYLIQEIFAEEMAKVDESFFQRLEE-SFLT-TDDKD---F | ERHPIFGNKA-DEIKYHQEFPTIYHLRKHLA | 144 |
| WP_012962174 | 75 | RRRNRLRYLIQEIFAKEMAKVDESFFQRLEE-SFLT-TDDKD---F | DSHPIFGNKA-EEDAYHQKPTIYHLRKYLA | 144 |
| WP_039695303 | 74 | RRRNRLRYLIQEIFANEIAKVDESFFQRLEE-SFLT-DDDKT---F | DSHPIFGNKA-EEDAYHQKPTIYHLRKYLA | 144 |
| WP_014334983 | 74 | RRKYRIKELQKIFSSEMNELDIAFFPRLSE-SFIV-SDDKE---F | ERHPIFGNLK-DEITYHNDYPTIYHLRQTLA | 143 |
| WP_003099269 | 74 | RRKYRIKELQKIFSSEMNELDIAFFPRLSE-SFLV-SDDKE---F | ERHPIFGNLK-DEITYHNDYPTIYHLRQTLA | 143 |
| AHY15608 | 74 | RRKYRIKELQKIFSSEMNELDIAFFPRLSE-SFLV-SDDKE---F | ERHPIFGNLK-DEITYHNDYPTIYHLRQTLA | 143 |
| AHY17476 | | | | |
| ESR09100 | 74 | RRKYRIKELQKIFSSEMNELDIAFFPRLSE-SFLV-SDDKE---F | ENHPIFGNLK-DEITYHNDYPTIYHLRQTLA | 143 |
| AGM98575 | 74 | RRRNRIILYLQKIFSEEMGKVDDSFFHRLED-SFLV-TEDKR---G | ERHPIFGNLE-EEVKYHENFPTIYHLRQYLA | 143 |
| ALF27331 | 74 | RRRNRIRYLQHIFAEEMNRADENFFHRLKE-SFFV-EEDKT---Y | SKYPIFGTLE-EEKNYHKNYPTIYHLRKTLA | 143 |
| WP_018372492 | 75 | RRRNRLRYLIQEIFSEEMGKVDDISFFHRLDD-SFLI-PEDKR---E | SKYPIFATLE-EEKEYHKQPPTIYHLRKHLA | 144 |
| WP_045635197 | 74 | RRKNRLRYLIQEIFSEEMGKVDDSFFHRLED-SFLI-TEDKR---E | SKYPIFATLT-EEKEYHKQNPTIYHLRKQLA | 143 |
| WP_022263887 | 74 | RRRNRIILYLQEIFSEEMGKVDDSFFHRLED-SFLT-DDDKN---F | DSYPIFGNKA-EEDAYHQKPTIYHLRKHLA | 143 |
| WP_022264920 | 74 | RRRNRIILYLQEIFSEEMGKVDDSFFHRLED-SFLV-TEDKR---G | ERHPIFGNLE-EEVKYHENFPTIYHLRKHLA | 143 |
| WP_022269043 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022269448 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022271977 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022272766 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022273241 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022275430 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022276448 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022277050 | 74 | RRRNRIILYLQEIFSEEMGKVDDSFFHRLED-SFLV-DDDKN---F | DSHPIFGNKA-EEDAYHQKPTIYHLRKHLA | 143 |
| WP_022277364 | 74 | RRRNRIILYLQEIFAEEMSKVDDSFFHRLED-SFLV-TEDKR---G | ERHPIFGNLE-EEVKYHENFPTIYHLRQYLA | 143 |
| WP_022279025 | 74 | RRRNRIILYLQEIFSEEMGKVDDSFFHRLED-FFLV-DDDKN---F | DSHPIFGNKA-EEDAYHQKPTIYHLRQYLA | 143 |
| WP_022279859 | 74 | RRRNRIILYLQEIFSEEMGKVDDSFFHRLDE-SFLT-DDDKN---F | DSHPIFGNKA-EEDAYHQKPTIYHLRQYLA | 143 |
| WP_022280230 | 74 | RRRNRIILYLQEIFAEEMSKVDDSFFHRLED-SFLV-TEDKR---G | ERHPIFGNLE-EEVKYHENFPTIYHLRQYLA | 143 |
| WP_022281696 | 74 | RRRNRIILYLQEIFAEEMSKVDDSFFHRLED-SFLV-TEDKR---G | ERHPIFGNLE-EEVKYHENFPTIYHLRKHLA | 143 |
| WP_022282247 | 74 | RRRNRIILYLQEIFAEEMSKVDDSFFHRLED-SFLT-DDDKN---F | DSHPIFGNKA-EEDAYHQKPTIYHLRKHLA | 143 |
| WP_022282906 | 74 | RRRNRIILYLQEIFAEEMSKVDDSFFHRLED-SFLV-TEDKR---G | ERHPIFGNLE-EEVKYHENFPTIYHLRQYLA | 143 |
| WP_022283846 | 74 | RRRNRIILYLQEIFSEEMGKVDDSFFHRLED-SFLV-TEDKR---G | ERHPIFGNLE-EEVKYHENFPTIYHLRQYLA | 143 |
| WP_022287255 | 74 | RRRNRIILYLQEIFAEEMSKVDDSFFHRLED-SFLV-TEDKR---G | ERHPIFGNLE-EEVKYHENFPTIYHLRQYLA | 143 |
| WP_022288990 | 74 | RRRNRIILYLQEIFSEEMGKVDDSFFHRLED-SFLV-TEDKR---G | ERHPIFGNLE-EEVKYHENFPTIYHLRQYLA | 143 |

| | | | |
|---|---|---|---|
| WP_002289641 | 74 | RRRNRILYLQEIFSEEMGKVDDSFFHRLED-SFLV--TEDKR----G ERHPIFGNLE--EEVKYHENFPTIYHLRQYLA | 143 |
| WP_002290427 | 74 | RRRNRILYLQEIFSEEMGKVDDSFFHRLED-SFLV--TEDKR----G ERHPIFGNLE--EEVKYHENFPTIYHLRQYLA | 143 |
| WP_002295753 | 74 | RRRNRILYLQEIFSEEMGKVNDSFFHRLED-SFLV--TEDKR----G ERHPIFGNLE--EEVKYHENFPTIYHLRQYLA | 143 |
| WP_002296423 | 74 | RRRNRILYLQEIFSEEMGKVDDSFFHRLED-SFLV--TEDKR----G ERHPIFGNLE--EEVKYHENFPTIYHLRQYLA | 143 |
| WP_002304487 | 74 | RRRNRILYLQEIFAEEMQDSFFHRLDD-SFLV--EEDKR----G SRYPIFGTLK--EEKKYHKEFKTIYHLREKLA | 143 |
| WP_002305844 | 74 | RRRNRILYLQEIFSEEMDKVDDSFFHRLED-SFLV--TEDKR----G ERHPIFGNLE--EEVKYHENFPTIYHLRQYLA | 143 |
| WP_002307203 | 74 | RRRNRILYLQEIFSEEMGKVDDSFFHRLED-SFLV--TEDKR----G ERHPIFGNLE--EEVKYHENFPTIYHLRQYLA | 143 |
| WP_002310390 | 74 | RRRNRILYLQEIFSEEMGKVDDSFFHRLED-SFLV--TEDKR----G ERHPIFGNLE--EEVKYHENFPTIYHLRQYLA | 143 |
| WP_002352408 | 74 | RRRNRILYLQEIFAEEMSKVDDSFFHRLED-SFLV--TEDKR----G ERHPIFGNLE--EEVKYHENFPTIYHLRQYLA | 143 |
| WP_012997688 | 74 | RRRNRILYLQEIFSEEMGKVDDSFFHRLED-SFLV--TEDKR----G ERHPIFGNLE--EEVKYHENFPTIYHLRQYLA | 143 |
| WP_014677909 | 74 | RRRNRILYLQEIFAEEMSKVDDSFFHRLED-SFLV--TEDKR----G ERHPIFGNLE--EEVKYHENFPTIYHLRQYLA | 143 |
| WP_019312892 | 74 | RRRNRILYLQEIFAEEMSKVDDSFFHRLED-SFLV--TEDKR----G ERHPIFGNLE--EEVKYHENFPTIYHLRQYLA | 143 |
| WP_019313659 | 74 | RRRNRILYLQEIFSEEMGKVDDSFFHRLED-SFLV--TEDKR----G ERHPIFGNLE--EEVKYHENFPTIYHLRQYLA | 143 |
| WP_019314093 | 74 | RRRNRILYLQEIFSEEMGKVDDSFFHRLED-SFLV--TEDKR----G ECHPIFGNLE--EEVKYHENFPTIYHLRQYLA | 143 |
| WP_019315370 | 74 | RRRNRILYLQEIFSEEMGKVDDSFFHRLED-SFLV--TEDKR----G ERHPIFGNLE--EEVKYHENFPTIYHLRQYLA | 143 |
| WP_019803776 | 74 | RRRNRILYLQEIFSEEMGKVDDSFFHRLED-SFLV--TEDKR----G ERHPIFGNLE--EEVKYHENFPTIYHLRQYLA | 143 |
| WP_019805234 | 74 | RRRNRILYLQEIFSEEMGKVDDSFFHRLED-SFLV--TEDKR----G ERHPIFGNLE--EEVKYHENFPTIYHLRQYLA | 143 |
| WP_024783594 | 74 | RRRNRILYLQEIFAEEMSKVDDSFFHRLED-SFLT--DDDKN----F DSHPIFGNKA--EEDAYHQKFPTIYHRKHLA | 143 |
| WP_024784288 | 74 | RRRNRILYLQEIFAEEMSKVDDSFFHRLED-SFLV--TEDKR----G ERHPIFGNLE--EEVKYHENFPTIYHLRQYLA | 143 |
| WP_024784666 | 74 | RRRNRILYLQEIFAEEMSKVDDSFFHRLED-SFLV--TEDKR----G ERHPIFGNLE--EEVKYHENFPTIYHLRQYLA | 143 |
| WP_024784894 | 74 | RRRNRILYLQEIFSEEMGKVDDSFFHRLED-SFLT--DDDKN----F DSHPIFGNKA--EEDAYHQKFPTIYHRKHLA | 143 |
| WP_024786433 | 74 | RRRNRILYLQEIFAEEMNKVDDSFFHRLDE-SFLT--DDDKN----F ERHPIFGNLE--EEVKYENPPTIYYLRKILA | 143 |
| WP_049473442 | 74 | RRRNRILYLQEIFSEEMGKVDDSFFHRLED-SFLV--TEDKR----G ERHPIFGTLE--EEKEYHKQPPTIYYLRKILA | 143 |
| WP_049474547 | 74 | RRRNRILYLQEIFAEEMSKVDDSFFHRLED-SFLV--TEDKR----G ERHPIFGNIK--DEVDYHKNYPTIYHLRKKLA | 143 |
| EMC03581 | 67 | RRKNRILYLQEIFAEEMSKVDDSFFHRLED-SFLI--PEDKR----G SKYPIFATLI--EEKEYHKQPPTIYHLRKQLA | 136 |
| WP_000428612 | 75 | RRKNRLRYLQEIFAEEMNKVDDSFFHRLDD-SFLI--PEDKR----G SKYPIFATLQ--EEKEYHKQPPTIYHLRKQLA | 144 |
| WP_000428613 | 75 | RRKNRLRYLQEIFAAEMNKVDDSFFHRLED-SFLV--PEDKR----G SKYPIFGTLE--EEKEYHKQPPTIYLRKILA | 144 |
| WP_049523028 | 74 | RRKNRLRYLQEIFSEEISKLDSSFFHRLDS-SFLI--PEDKR----G SKYPIFATLE--EEKEYHKKFPTIYHLRKHLA | 143 |
| WP_003107102 | 43 | RRINRKYLQSIFDDEMSKIDSAFFQRIKD-SFLV--PDDKN----D DRHPIFGHKNYPDEEKAYHDNYPTIYHLRKKALA | 112 |
| WP_054279288 | 76 | RRKRCYLRDIFESEMHTIDKHFFLRLED-SFLH--KSDKR----Y EAHPIFGTLQ--EEKAYHDNYPTIYHLRKALA | 145 |
| WP_049531101 | 75 | RRKNRLRYLQEIFSEEISKVDNSFFHRLDD-SFLV--PEDKR----G SKYPIFATLT--EEKEYYKQPPTIYHLRKQLA | 144 |
| WP_049538452 | 75 | RRKNRLRYLQEIFAEEMNKVDDSFFHRLDD-SFLV--PEDKR----G SKYPIFATLA--EEKEYHKQPPTIYHLRKQLA | 144 |
| WP_049549711 | 75 | RRKNRLRYLQEIFSGEMSKVDSSFFHRLDD-SFLV--PEDKR----G SKYPIFATLV--EEKEYHKQFPTIYHLRKQLA | 144 |
| WP_007896501 | 76 | RRRYRLCQLQNIFATEMKVDDTFFQRLSE-SFFY--YQDKA----F DKHPIFGNSK--EERAYHKTYPTIYHLRKDLA | 145 |
| EFR44625 | 28 | RRRYRLCQLQNIFTESMMEIDESFFHRLDD-SFLV--PEDKR----G SKYPIFATLQ--EEKEYHKKFPTIYHLRKQLA | 97 |
| WP_002897477 | 74 | RRRNRILYLQEIFSEEISKLDSSFFHRLDD-SFLV--PEDKR----G SKYPIFATLE--EEKEYHKKFPTIYHLRKHLA | 143 |
| WP_002906454 | 74 | RRKNRLRYLQEIFAEEMSKVDDSFFHRLDD-SFLV--PEDKR----H ERHPIFGNIV--DEVAYHEKYPTIYHLRKHLA | 143 |
| WP_009729476 | 74 | RRKNRLRYLQEIFSEEIGKVDDSFFHRLDD-SFLI--PEDKR----G SKYPIFATLE--EEKEYHKKFPTIYHLRKHLA | 144 |
| CQR24647 | 74 | RRRNRILYLQDIFSPELNQVDESFFHRLED-SFLVa--EDKR----G ERHVIPFGNIA--DEVKYHKEFPTIYHLRKHLA | 143 |
| WP_000066813 | 75 | RRRNRILYLQEIFSQEISKVDDSFFHRLDD-SFLV--PEDKR----G SKYPIFATLV--EEKEYHKKFPTIYHLRKHLA | 144 |
| WP_009754323 | 75 | RRRNRILYLQEIFAEEMSKVDDSFFHRLDD-SFLV--PEDKS----G SKYPIFATLA--EEKEYHKKFPTIYHLRKHLA | 144 |
| WP_044674937 | 74 | RRRNRILYLQEIFAEEINKIDDSFFHRLDD-SFLV--EDKQ----G SKHPIFGTLQ--EEKKYHKQFPTIYHLRKQLA | 143 |
| WP_044676715 | 74 | RRRNRILYLQEIFAEEINKIDDSFFHRLDD-SFLV--EDKQ----G SKHPIFGTLQ--EEKKYHKQPPTIYHLRKHLA | 143 |
| WP_044680361 | 74 | RRRNRILYLQEIFAEEINKIDDSFFQRLDD-SFLIV--EDKQ----G SKHPIFGTLQ--EEKKYHKQPPTIYHLRKHLA | 143 |
| WP_044681799 | 74 | RRRNRILYLQEIFAEEINKIDSFFQRLDD-SFLIV--EDKQ----G SKHPIFGTLQ--EEKKYHKQFPTIYHLRKQLA | 143 |
| WP_049533112 | 28 | HRKFRLRLLEDMFEKEILSKDPSFFIRLKE-AFLSpkDEQKQ----G ERHPIFGNIA--AEVVKYHDDFPTIYHLRKHLA | 97 |
| WP_029090905 | 61 | KRRERILLRAILQDMVLEKDPTFFIRLEHtSFLD--EEDKAkyLG----LFNDKDyTDADYYEQYKTIYHLRYDLI | 100 |
| WP_065506696 | 74 | RRKNRICYLQEIFSNEMAKVDDSFFHRLEE-SFLDKK----H DNYNLFIDEDFNDYTYYYHKYPTIYHLRKALC | 139 |
| AIT42264 | 74 | ERHPIFGNIV--DEVAYHEKYPTIYHLRKKLV | 143 |
| WP_034440723 | 73 | RRKNRICYLQEIFSNEMAKVDDSFFHRLDE-SFLV--EEDKE----Y SKYPIFSNEK--EDKNYDKYPTIYHLRKDLA | 142 |
| AKQ21048 | 74 | RRRNRLRYLQDIFQQPMLAIDENFFHRLDD-SFLV--EEDKL----H ERHPIFGNIV--DEVAYHEKYPTIYHLRKKLV | 143 |
| WP_004636532 | 74 | RRRNRLRYLQAFPEEAMIDLDENFFARLQE-SFLV--PDDKS----Y DRHPIFGSLE--EEVAYHNTYPTIYHLRKKLA | 143 |
| WP_002364836 | 74 | RRRNRLRYLQAFPEEAMTDLDENFFARLQE-SFLV--PEDKK----W HRHPIFAKLE--DEVAYHETYPTIYHLRKKLA | 143 |

-continued

```
WP_016631044    25   RRRNRLRYLQAFFEEAMTDLDENFFARLQE-SFLV--PEDKK---W HRHPIFAKLE-DEVAYHETYPTIYHLRKKLA        94
EMS755795
WP_002373311    74   RRRNRLRYLQAFFEEAMTDLDENFFARLQE-SFLV--PEDKK---W HRHPIFAKLE-DEVAYHETYPTIYHLRKKLA       143
WP_002378009    74   RRRNRLRYLQAFFEEAMTALDENFFARLQE-SFLV--PEDKK---W HRHPIFAKLE-DEVAYHETYPTIYHLRKKLA       143
WP_002407324    74   RRRNRLRYLQAFFEEAMTALDENFFARLQE-SFLV--PEDKK---W HRHPIFAKLE-DEVAYHETYPTIYHLRKKLA       143
WP_002413717    74   RRRNRLRYLQAFFEEAMTDLDENFFARLQE-SFLV--PEDKK---W HRHPIFAKLE-DEVAYHETYPTIYHLRKKLA       143
WP_010775580    74   RRRNRLRYLQAFFEEAMTDLDENFFARLQE-SFLV--PEDKK---W HRHPIFAKLE-DEVAYHETYPTIYHLRKKLA       143
WP_010818269    74   RRRNRLRYLQAFFEEAMTDLDENFFARLQE-SFLV--PEDKK---W HRHPIFAKLE-DEVAYHETYPTIYHLRKKLA       143
WP_010824395    74   RRRNRLRYLQAFFEEAMTALDENFFARLQE-SFLV--PEDKK---W HRHPIFAKLE-DEVAYHETYPTIYHLRKKLA       143
WP_016622645    74   RRRNRLRYLQAFFEEAMTALDENFFARLQE-SFLV--PEDKK---W HRHPIFAKLE-DEVAYHETYPTIYHLRKKLA       143
WP_033624816    74   RRRNRLRYLQAFFEEAMTALDENFFARLQE-SFLV--PEDKK---W HRHPIFAKLE-DEVAYHETYPTIYHLRKKLA       143
WP_033625576    74   RRRNRLRYLQAFFEEAMTALDENFFARLQE-SFLV--PEDKK---W HRHPIFAKLE-DEVAYHETYPTIYHLRKKLA       143
WP_033789179    74   RRRNRLRYLQAFFEEAMTALDENFFARLQE-SFLV--PEDKK---W HRHPIFAKLE-DEVAYHETYPTIYHLRKKLA       143
WP_002310644    74   RRRQRILELQKIFAPEILKIDEHFFARLNE-SFLV--LDEKK---Q SRHPVFATIK-QEKSYHQTYPTIYHLRQALA       143
WP_002312694    74   RRRQRILELQKIFAPEILKIDEHFFARLNE-SFLV--PDEKK---Q SRHPVFATIK-QEKSYHQTYPTIYHLRQALA       143
WP_002314015    74   RRRQRILELQKIFAPEILKIDEHFFARLNE-SFLV--LDEKK---Q SRHPVFATIK-QEKSYHQTYPTIYHLRQALA       143
WP_002320716    74   RRRQRILELQKIFAPEILKIDEHFFARLNE-SFLV--LDEKK---Q SRHPVFATIK-QEKSYHQTYPTIYHLRQALA       143
WP_002330729    74   RRRQRILELQKIFAPEILKIDEHFFARLNE-SFLV--LDEKK---Q SRHPVFATIK-QEKSYHQTYPTIYHLRQALA       143
WP_002335161    74   RRRQRILELQKIFAPEILKIDEHFFARLNE-SFLV--LDEKK---Q SRHPVFATIK-QEKSYHQTYPTIYHLRQALA       143
WP_002345439    74   RRRQRILELQKIFAPEILKIDEHFFARLNE-SFLV--LDEKK---Q SRHPVFATIK-QEKSYHQTYPTIYHLRQALA       143
WP_034867970    74   RRKYRLSKIQDLFAEELCKQDDCFFVRLEE-SFLV--PEEKQ---Y KPASIFPTLE-EEKEYYQKYPTIYHLRQKLV       143
WP_047937432    74   RRRQRILELQKIFAPEILKIDEHFFARLNE-SFLV--LDEKK---Q SRHPVFATIK-QEKSYHQTYPTIYHLRQALA       143
WP_010720994    74   RRKYRLSKIQDLFAEELCKQDDCFFVRLEE-SFLV--PEEKQ---Y KPASIFPTLE-EEKEYYQKYPTIYHLRQKLV       143
WP_010737004    74   RRKYRLSKIQDLFAEELCKQDDCFFVRLEE-SFLV--PEEKQ---Y KPASIFPTLE-EEKEYYQKYPTIYHLRQKLV       143
WP_034700478    74   RRKYRLSKIQDLFAEELCKQDDCFFVRLEE-SFLV--PEEKQ---Y KPASIFPTLE-EEKEYYQKYPTIYHLRQKLV       143
WP_007209003    74   RRRNRICYLQEIFQPEMNHLDNNFFYRLNE-SFLVa-DDAK---Y DKHPIFGTLD-EEIHFHEQPPTIYHLRKYLA         143
WP_023519017    74   RRRQRVLAIQDIFAEEIHKKDPNFFARLEE-GDRV--EADKR---F AKPPVFATLS-EEKNYHRQYPTIYHLRHDLA        143
WP_010770040    74   RRRNRLRCYLQDLFTEEMNQVDANFHRLQE-SFLV--PDEKE---F ERHAIFGKME-EEVSYYREPPTIYHLRKHLA        143
WP_048604708    74   RRRQRISYLQTFPQEEMNRIDPNFFNRLDE-SFLI--BEDKL---S ERHPIFGTIE-EEKAYHKNYATIYHLRQKLA        143
WP_010750235    74   RRKYRILELQKIFSEELLKKDSHFFARLDE-SFLV--PEDKQ---Y ARFPIFPTLL-EEKAYYQNYPTIYHLRKKLV        143
AII16583       113   RRKYRILELQKIFSNENAKVDDSFFHRLEE-SFLV--QEDKKH--H ERHPIFGNIV-DEVAYHDKYPTIYHLRKKLV        182
WP_029073316    66   KRRERIRLLREIMEDMVLDVDPTFFIRLANvSFLD--QEDKKGy1K SNYNLFIDKdFNDKTYDKYPTIYHLRKHLC        144
WP_031589969    66   KRRERIRLLREIMEDMVLDVDPTFFIRLANvSFLD--QEDKKGy1K SNYNLFIDKdENDKTYDKYPTIYHLRKHLC        144
KDA45870        75   RRRERIRLLREIFAPALAKVDPNFFYRLEE-SSLVa-EDKK---Y DVYPIFGKRE-EELLYHDTHKTIYHLRSELA        144
WP_039099354    62   RRKfMRLGLLREIFEPYITPVDDTFFLRKKQ-SNLS--PKDQR---K -QTSLFNDRT--DRAFYDDYPTIYHLRYKLM       132
AKP02966        65   RRKNRINWLNEIFSEELANTDPSFLIRLQN-SWVSkKDPDRK---R DKYNLFIDNPyTDKEYYREPPTIFHLRKELI      137
WP_010991369    74   RRRNRISYLQGIFAEEMSKTDANFFCRLSD-SFYV--DNEKR---N SRHPFFATIE-EEVAYHKNYPTIYHLREELV       143
WP_033838504    74   RRRNRISYLQGIFAEEMSKTDANFFCRLSD-SFYV--DNEKR---N SRHPFFATIE-EEVAYHKNYPTIYHLREELV       143
EHN60060        77   RRRNRISYLQGIFAEEMSKTDANFFCRLSD-SFYV--DNEKR---N SRHPFFATIE-EEVAYHKNYPTIYHLREELV       146
EFR89594
WP_038409211    74   RRRNRIAYLQEIFAAEMAEVDANFFYRLED-SFYI--ESEKR---H SRHPFFATIE-EEVAYHEEYKTIYHLREKLV       143
EFR95520
WP_003723650    74   RRRNRISYLQEIFAVEMANIDANFFCRLND-SFYV--DSEKR---N SRHPFFATIE-EEVAYHDNYRTIYHLREKLV       143
WP_003727705    74   RRRNRISYLQEIFAVEMANIDANFFCRLND-SFYV--DSEKR---N SRHPFFATIE-EEVAYHKNYRTIYHLREELV       143
WP_003730785    74   RRRNRISYLQEIFAVEMANIDANFFCRLND-SFYV--DSEKR---N SRHPFFATIE-EEVAYHKNYRTIYHLREELV       143
WP_003733029    74   RRRNRISYLQEIFAIQMNEVDDNFFNRLKE-SFYA--ESDKK---Y NRHPFFGTVE-EEVAYKDPPTIYHLREELV        143
WP_003739838    74   RRRNRISYLQEIFALEMANIDANFFCRLND-SFYA--DSEKR---N SRHPFFATIE-EEVAYHKNYRTIYHLREELV       143
WP_014601172    74   RRRNRISYLQEIFAVEMANIDANFFCRLND-SFYV--DSEKR---N SRHPFFATIE-EEVAYHKNYRTIYHLREELV       143
WP_023548323    74   RRRNRISYLQEIFAVEMANIDANFFCRLND-SFYV--DSEKR---N SRHPFFATIE-EEVAYHKNYRTIYHLREELV       143
WP_031665337    74   RRRNRISYLQEIFAIQMNEVDDNFFNRLKE-SFYA--ESDKK---Y NRHPFFGTVE-EEVAYYKDPPTIYHLREKLI       143
WP_031669209    74   RRRNRISYLQEIFAVEMANIDANFFCRLND-SFYV--DSEKR---N SRHPFFATIE-EEVAYHKNYRTIYHLREKLI       143
WP_033920898    74   RRRNRISYLQEIFAVEMANIDANFFCRLND-SFYV--DSEKR---N SRHPFFATIE-EEVAYHKNYRTIYHLREELV       143
AKI42028        77   RRRNRISYLQEIFAVEMANIDANFFCRLND-SFYV--DSEKR---N SRHPFFATIE-EEVAYHKNYRTIYHLREELV       146
```

```
AKI50529            77  RRRNRISYLQEIFAVEMANIDANFFCRLND-SFYV--DSEKR---N SRHPFFATIE-EEVAYHKNYRTIYHLREELV                                    146
EFR83390                                                                                                                       
WP_046323366        74  RRRNRISYLQEIFTAEMPEVDANFFYRLED-SFYI--ESEKR---Q SRHPFFATIE-EEVAYHENYRTIYHLREKLV                                    143
AKE81011            90  RRKNRICYIQEIFSNEMAKVDDSFFHRLEE-SFIV--EEDKK---H ERHPIFGNIV-DEVAYHEKYPTIYHLRKKLV                                    159
CU082355            65  KRRERIRLLRALLQDMVLEKDPTFFIRLEHtSFLD--EEDKAkylG DNYNLFIDEDfNDYTYYHKPTIYHLRKALC                                    143
WP_033162887        66  KRRERIRLLRDLLGDMVMEVDPTFFIRLLNvSFLD--EEDKQkm1G DNYNLFIEKDfNDKTYYDKPTIYHLRKELC                                    144
AGZ01981           107  RRKNRICYLQEIFSNEMAKVDDSFFHRLEE-SFLV--EEDKK---H ERHPIFGNIV-DEVAYHEKYPTIYHLRKKLV                                    176
AKA60242            74  RRKNRICYLQEIFSNEMAKVDDSFFHRLEE-SFIV--EEDKK---H ERHPIFGNIV-DEVAYHEKYPTIYHLRKKLV                                    143
AKS40380            74  RRKNRICYLQEIFSNEMAKVDDSFFHRLEE-SFLV--EEDKK---H ERHPIFGNIV-DEVAYHEKYPTIYHLRKKLV                                    143
4UN5_B              78  RRKNRICYLQEIFSNEMAKVDDSFFHRLEE-SFLV--EEDKK---H ERHPIFGNIV-DEVAYHEKYPTIYHLRKKLV                                    147
WP_010922251       144  DSTDKADLRLIYLALAHMIKFRGHFLIEGD-LNPDNSDVDkL- FIQLVQTYNQL--FEEN- INASGVDAK----AI                                    211
WP_039695303       145  DSSEKADLRLVYLALAHMIKFRGHFLIEGE-LNAENTDVQKI- FADFVGVVNRT--FDDS-H LSEITVDVA----SI                                   212
WP_045635197       144  DSKEKTDLRLIYLALAHMIKYRGHFLYEEA-FDIKNNDIQKI- FNEFSISIYDNT--FEGS-S LSGQNAQVE----AI                                  211
5AXW_A             105  EEEFSA-----ALLHLAKRRG---VHNV------NEVE-----         -EDT---    -GN---                                             134
WP_099880683                                                                                                                   
WP_010922251       144  DSTDKADLRLIYLALAHMIKFRGHFLIEGD-LNPDNSDVDKL- FIQLVQTYNQL--FEEN- INASGVDAK----AI                                    211
WP_011054416       144  DSTDKVDLRLIYLALAHMIKFRGHFLIEGD-LNPDNSDVDKL- FIQLVQTYNQL--FEEN- INASGVDAK----AI                                    211
WP_011284745       144  DSTDKADLRLIYLALAHMIKFRGHFLIEGD-LNPDNSDVDKL- FIQLVQTYNQL--FEEN- INASGVDAK----AI                                    211
WP_011285506       144  DSTDKADLRLIYLALAHMIKFRGHFLIEGD-LNPDNSDVDKL- FIQLVQTYNQL--FEEN- INASGVDAK----AI                                    211
WP_011527619       144  DSTDKADLRLIYLALAHMIKFRGHFLIEGD-LNPDNSDVDKL- FIQLVQTYNQL--FEEN- INASGVDAK----AI                                    211
WP_012560673       144  DSTDKADLRLIYLALAHMIKFRGHFLIEGD-LNPDNSDVDKL- FIQLVQTYNQL--FEEN- INASGVDAK----AI                                    211
WP_014407541       144  DSTDKADLRLIYLALAHMIKFRGHFLIEGD-LNPDNSDVDKL- FIQLVQIYNQL--FEEN- INASRVDAK----AI                                    211
WP_020905136       144  DSTDKADLRLIYLALAHMIKFRGHFLIEGD-LNPDNSDVDKL- FIQLVQTYNQL--FEEN- INASRVDAK----AI                                    211
WP_023080005       144  DSTDKVDLRLIYLALAHMIKFRGHFLIEGD-LNPDNSDVDKL- FIQLVQTYNQL--FEEN- INASRVDAK----AI                                    211
WP_023610282       144  DSTDKVDLRLIYLALAHMIKFRGHFLIEGD-LNPDNSDVDKL- FIQLVQTYNQL--FEEN- INASRVDAK----AI                                    211
WP_030125963       144  DSTDKADLRLIYLALAHMIKFRGHFLIEGD-LNPDNSDVDKL- FIQLVQTYNQL--FEEN- INASRVDAK----AI                                    211
WP_030126706       144  DSTDKVDLRLIYLALAHMIKFRGHFLIEGD-LNPDNSDVDKL- FIQLVQTYNQL--FEEN- INASRVDAK----AI                                    211
WP_031488318       144  DSTDKVDLRLIYLALAHMIKFRGHFLIEGD-LNPDNSDVDKL- FIQLVQTYNQL--FEEN- INASRVDAK----AI                                    211
WP_032460140       144  DSTDKADLRLIYLALAHMIKFRGHFLIEGD-LNPDNSDVDKL- FIQLVQTYNQL--FEEN- INASRVDAK----AI                                    211
WP_032461047       144  DSTDKADLRLIYLALAHMIKFRGHFLIEGD-LNPDNSDVDKL- FIQLVQTYNQL--FEEN- INANGVDAK----AI                                    211
WP_032462016       144  DSTDKADLRLIYLALAHMIKFRGHFLIEGD-LNPDNSDVDKL- FIQLVQTYNQL--FEEN- INASRVDAK----AI                                    211
WP_032462936       144  DSTDKADLRLIYLALAHMIKFRGHFLIEGD-LNPDNSDVDKL- FIQLVQTYNQL--FEEN- INASRVDAK----AI                                    211
WP_032464890       144  DSTDKADLRLIYLALAHMIKFRGHFLIEGD-LNPDNSDVDKL- FIQLVQTYNQL--FEEN- INASRVDAK----AI                                    211
WP_033888930         1  ----------------------------PDNSDVDKL- FIQLVQTYNQL--FEEN- INASGVDAK----AI                                         36
WP_038431314       144  DSTDKADLRLIYLALAHMIKFRGHFLIEGD-LNPDNSDVDKL- FIQLVQTYNQL--FEEN- INASRVDAK----AI                                    211
WP_038432938       144  DSTDKVDLRLIYLALAHMIKFRGHFLIEGD-LNPDNSDVDKL- FIQLVQTYNQL--FEEN- INASRVDAK----AI                                    211
WP_038434062       144  DSTDKADLRLIYLALAHMIKFRGHFLIEGG-LNPDNSDVDKL- FIQLVQTYNQL--FEEN- INASRVDAK----AI                                    211
BAQ51233            55  DSTDKADLRLIYLALAHMIKFRGHFLIEGD-LNPDNSDVDKL- FIQLVQTYNQL--FEEN- INASGVDAK----AI                                    122
KGE60856                                                                                                                       
KGE60162                                                                                                                       
WP_002989955       144  DSTDKADLRLIYLALAHMIKFRGHFLIEGD-LNPDNSDVDKL- FIQLVQTYNQL--FEEN-D LLSQNVDVE----AI                                   211
WP_003030002       144  DISQKADLRLVYLALAHMIKFRGHFLIEGQ-LKAENTNVQAL- FKDFVEVYDKT--VEES-H LSEMTVDAL----SI                                   211
WP_003065552       147  DSSEKADLRLVYLALAHMIKFRGHFLIEGE-LNAENTVDQKI- FADFVGVVDRT--FDDS-H LSEITVDAA----SI                                   214
WP_001040076       144  DKQEKADLRLVYLALAHIIKFRGHFLIEDDrFDVRNTDIQKQ- YQAPLEIFDTT--FENN-H LLSQNVDVE----AI                                   211
WP_001040078       144  DKKEKADLRLVYLALAHIIKFRGHFLIEDDsFDVRNTDISKQ- YQDFLEIFNIT--FENN-D LLSQNVDVE----AI                                   212
WP_001040080       144  DKKEKADLRLVYLALAHIIKFRGHFLIEDDsFDVRNTDISKQ- YQDFLEIFNIT--FENN-D LLSQNVDVE----AI                                   212
WP_001040081       144  DKKEKADLRLIYLALAHIIKFRGHFLIEDDsFDVRNTDISKQ- YQDFLEIFNTT--FENN-D LLSQNVDVE----AI                                   212
WP_001040083       144  DKKEKADLRLIYIALAHIIKFRGHFLIEDDsFDVRNTDISKQ- YQDFLEIFNTT--FENN-D LLSQNVDVE----AI                                   212
WP_001040085       144  DKKEKADLRLIYIALAHIIKFRGHFLIEDDsFDVRNTDISKQ- YQDFLEIFNTT--FENN-D LLSQNVDVE----AI                                   212
WP_001040087       144  DKKEKADLRLIYIALAHIIKFRGHFLIEDDsFDVRNTDISKQ- YQDFLEIFNTT--FENN-D LLSQNVDVE----AI                                   212
WP_001040088       144  DKKEKADLRLIYIALAHIIKFRGHFLIEDDsFDVRNTDISKQ- YQDFLEIFNTT--FENN-D LLSQNVDVE----AI                                   212
WP_001040089       144  DKKEKADLRLIYIALAHIIKFRGHFLIEDDsFDVRNTDISKQ- YQDFLEIFNTT--FENN-D LLSQNVDVE----AI                                   212
WP_001040090       144  DKKEKADLRLIYIALAHIIKFRGHFLIEDDsFDVRNTDISKQ- YQDFLEIFNTT--FENN-D LLSQNVDVE----AI                                   212
```

```
WP_001040091      144 DKKEKADLRLIYLALAHIIKFRGHFLIEDDsFDVRNTDIQKQ--YQDFLEIFDTT--FENN-D LLSQNVDVE----AI 212
WP_001040092      144 DKKEKADLRLIYLALAHIIKFRGHFLIEDDrFDVRNTDIQKQ--YQAFLEIFDTS--FENN-H LLSQNVDVE----AI 212
WP_001040094      144 DKKEKADLRLIYLALAHIIKFRGHFLIEDDrFDVRNTDIQKQ--YQAFLEIFDTT--FENN-D LLSQNVDVE----AI 212
WP_001040095      144 DKKEKADLRLIYLALAHIIKFRGHFLIEDDrFDVRNTDIQKQ--YQAFLEIFDTT--FENN-H LLSQNVDVE----AI 212
WP_001040096      144 DKKEKADLRLIYLALAHIIKFRGHFLIEDDrFDVRNTDIQKQ--YQAFLEIFDTT--FENN-D LLSQNVDVE----AI 212
WP_001040097      144 DKKEKADLRLIYLALAHIIKFRGHFLIEDDrFDVRNTDIQKQ--YQAFLEIFDTT--FENN-D LLSQNVDVE----AI 212
WP_001040098      144 DKKEKADLRLIYLALAHIIKFRGHFLIEDDrFDVRNTDIQKQ--YQAFLEIFDTT--FENN-D LLSQNVDVE----AI 212
WP_001040099      144 DKKEKADLRLIYLALAHIIKFRGHFLIEDDrFDVRNTDIQKQ--YQAFLEIFDTT--FENN-D LLSQNVDVE----AI 212
WP_001040100      144 DKKEKADLRLIYLALAHIIKFRGHFLIEDDsFDVRNTDIQKQ--YQDFLEIFDTT--FENN-D LLSQNVDVE----AI 212
WP_001040104      144 DKKEKADLRLIYLALAHIIKFRGHFLIEDDsFDVRNTDISKQ--YQDFLEIFDTT--FENN-H LLSQNVDVE----AI 212
WP_001040105      144 DKKEKADLRLIYLALAHIIKFRGHFLIEDDrFDVRNTDIQKQ--YQAFLEIFDTT--FENN-D LLSQNVDVE----AI 212
WP_001040106      144 DKKEKADLRLIYLALAHIIKFRGHFLIEDDsFDVRNTDISKQ--YQAFLEIFNTT--FENN-D LLSQNVDVE----GI 212
WP_001040107      144 DKKEKANLRLVYLALAHIIKFRGHFLIEDDsFDVRNTDIQKQ--YQAFLEIFDTT--FENN-D LLSQNIDVE----GI 212
WP_001040108      144 DKKEKADLRLVYLALAHIIKFRGHFLIEDDsFDVRNTDIQRQ--YQAFLEIFDTT--FENN-D LLSQNIDVE----GI 212
WP_001040109      144 DKKEKANLRLVYLALAHIIKFRGHFLIEDDsFDVRNTDIQRQ--YQAFLEIFDTT--FENN-D LLSQNIDVE----GI 212
WP_001040110      144 DKKEKADLRLIYLALAHIIKFRGHFLIEDDsFDVRNTDIQRQ--YQAFLEIFDTT--FENN-D LLSQNIDVE----GI 212
WP_015058523      144 DKKEKADLRLIYLALAHIIKFRGHFLIEDDsFDVRNTDIQRQ--YQAFLEIFDTS--FENN-H LLSQNIDVE----GI 212
WP_017643650      144 DKKEKADLRFYLALAHIIKFRGHFLIEDDsFDVRNTDIQRQ--YQAFLEIFDTT--FENN-D LLSQNIDIE----GI 212
WP_017647151      144 DKKEKADLRLVYLALAHIIKFRGHFLIEDDsFDVRNTDIQRQ--YQAFLEIFNTT--FENN-D LLSQNVDVE----AI 212
WP_017648376      144 DKKEKADLRLIYLALAHIIKFRGHFLIEDDsFDVRNTDISKQ--YQDFLEIFNTT--FENN-H LLSQNVDVE----GI 212
WP_017649527      144 DKKEKADLRLIYLALAHIIKFRGHFLIEDDsFDVRNTDIQRQ--YQDFLEIFDTT--FENN-D LLSQNIDVE----AI 212
WP_017771611      144 DKKEKADLRLVYLALAHIIKFRGHFLIEDDsFDVRNTDIQKQ--YQAFLEIFDTT--FENN-H LLSQNIDVE----AI 212
WP_017771984      144 DKKEKADLRLVYLALAHIIKFRGHFLIEDDsFDVRNTDISKQ--YQDFLEIENTT--FENN-D LLSQNVDVE----AI 212
CFQ25032          144 DKKEKADLRLVYLALAHIIKFRGHFLIEDDsFDVRNTDIQKQ--YQDFLEIENTT--FENN-D LLSQNVDVE----AI 212
CFV16040          144 DKKEKADLRLIYLALAHIIKERGHFLIEDDsFDVRNTDIQRQ--YQAFLEIFDTT--FENN-D LLSQNIDVE----GI 212
KLJ37842          144 DKKEKADLRLVYLALAHMIKERGHFLIEDDsFDVRNTDIQKQ--YQDFLEIENTT--FENN-H LLSQNVDVE----AI 212
KLJ72361          144 DKKEKADLRLIYLALAHMIKERGHFLIEDDsFDVRNTDISKQ--YQDFLEIENTT--FENN-H LLSQNVDVE----AI 212
KLL20707          144 DKKEKANLRLVYLALAHIIKERGHFLIEDDsFDVRNTDIQKQ--YQDFLEIENTT--FENN-D LLSQNVDVE----AI 212
KLL42645          144 DKKEKADLRLIYLALAHIIKERGHFLIEDDsFDVRNTDIQRQ--YQAFLEIFDTT--FENN-D LLSQNVDVE----GI 212
WP_047207273      144 DKKEKADLRLIYLALAHIIKERGHFLIEDDsFDVRNTDISKQ--YQDFLEIENTT--FENN-D LLSQNVDVE----AI 212
WP_047209694      144 DKKEKADLRLIYLALAHIIKERGHFLIEDDsFDVRNTDIQKQ--YQAFLEIFDTT--FENN-H LLSQNVDVE----AI 212
WP_050198062      144 DKKEKANLRLVYLALAHIIKERGHFLIEDDsFDVRNTDIQKQ--YQDFLEIENTT--FENN-D LLSQNVDVE----AI 212
WP_050201642      144 DKKEKADLRLIYLALAHIIKERGHFLIEDDsFDVRNTDIQRQ--YQAFLEIFDTT--FENN-D LLSQNVDVE----GI 212
WP_050204027      144 DKKEKADLRLIYLALAHIIKERGHFLIEDDsFDVRNTDIQRQ--YQAFLEIENTT--FENN-D LLSQNVDVE----AI 212
WP_050881965      144 DKKEKADLRLIYLALAHIIKERGHFLIEDDsEDVRNTDISKQ--YQDFLEIENTT--FENN-D LLSQNVDVE----AI 212
WP_050886065      144 DKKEKADLRLIYLALAHIIKERGHFLIEDDsEDVRNTDISKQ--YQAFLEIFDTS--FENN-D LLSQNVDVE----AI 212
AHN30376          144 DKKEKADLRLVYLALAHIIKERGHFLIEDDsEDVRNTDIQKQ--YQAFLEIFNTT--FENN-D LLSQNVDVE----AI 212
EA078426          144 DKKEKADLRLVYLALAHIIKERGHFLIEDDsEDVRNTDIQKQ--YQDFLEIFDTT--FENN-D LLSQNVDVE----AI 212
CCW42055          144 DISQKADLRLIYLALAHIIKERGHFLIEGQ--LKAENTNVQAL--FKDEVEVYDKT--VEES-H LSEITVDAL----SI 211
WP_003041502      144 DISQKADLRLIYLALAHIIKERGHFLIEGQ--LKAENTNVQAL--FKDEVEVYDKT--IEES-H LSEITVDAL----SI 212
WP_037593752      145 NSKEKADLRLIYLALAHIIKERGHFLYEGD--LKAENTDVQAL--FKDEVEEYDKT--IEES-H LSEITVDAL----SI 212
WP_049516684      144 DISQKADLRLIYLALAHMIKERGHFLIEGG--LKAENTNVQAL--FKDEVEVYDKT--VEES-H LSEMTVDAL----SI 212
GAD46167          145 NSKEKADLRLIYLALAHIIKERGHFLIEGE--LKAENTDVQAL--FKDEVEEYDKT--IEES-H LSEITVDAA----SI 212
WP_018363470      144 DSTEKADLRLIYLALAHIIKERGHFLIEGE--LNAENTDVQKL--FTDEVGVDRT--FDDS-H LSEITVDAA----SI 212
WP_003043819      144 DSPEKADLRLIYLALAHIIKERGHFLIEGK--LNAENSDVAKL--FYQLIQTYNQL--FEES-- LDEIEVDAK----GI 211
WP_006299658      144 DTSKKADLRLIYLALAHIIKERGHFLIEGD--LKAENTDVQAL--FYQLIQTYNQL--FEES-- LSEITVDAL----SI 211
WP_048800889      144 DSTGKVDLRLIYLALAHMIKERGHFLIEGQ--LKAENTDVQTL--ENDEVEVYDKT--IEES-H LAEITVDAL----GI 211
WP_012767106      144 DSTDKADLRLIYLALAHMIKERGHFLIEGD--LNPDNSDMDKL--FIQLVQTYNQL--FEEN-- INASRVDAK----AI 211
WP_014612333      144 DSTDKADLRLIYLALAHMIKERGHFLIEGD--LNPDNSDMDKL--FIQLVQTYNQL--FEEK-- INASGVDAK----GI 211
WP_015017095      144 DSTDKADLRLIYLALAHMIKERGHFLIEGD--LNPDNSDVDKL--FIQLVQTYNQL--FEEN-- INASRVDAK----AI 211
WP_015057649      144 DSTDKADLRLIYLALAHMIKERGHFLIEGD--LNPDNSDMDKL--FIQLVQTYNQL--FEEN-- INASRVDAK----AI 211
WP_048272215      144 DSTDKADLRLIYLALAHMIKERGHFLIEGD--LNPDNSDMDKL--FIQLVQTYNQL--FEEN-- INASRVDAK----AI 211
WP_049519324      144 DSTDKADLRLIYLALAHMIKERGHFLIEGD--LNPDNSDVDKL--FIQLVQTYNQL--FEEN-- INASRVDAK----AI 211
```

-continued

```
WP_012515931   144 DNPQKADLRLIYLAVAHIIKERGHFLIEGT-LSSKNNNLQKS--FDHLVDTYNLL--FEEQ--LLTEGINAK----EL 211
WP_021320964   144 DNPQKADLRLIYLAVAHIIKERGHFLIEGT-LSSKNNNLQKS--FDHLVDTYNLL--FEEQ--LLTEGINAK----EL 211
WP_037581760   144 DNPQKADLRLIYLAVAHIIKERGHFLIEGT-LSSKNNNLQKS--FDHLVDTYNLL--FEEQ--LLTEGINAK----EL 211
WP_004232481   144 DSPEKVDLRLIVYLALAHMIKERGHFLIEGQ-LNAENTDVQKI--FADEVGVYDRT--FDDS-H LSEITVDAA---SI 211
WP_009854540   144 DSSEKADLRLIVYLALAHMIKYRGHFLIEGK-LNAENTDVQKL--FTDEVGVYDRT--FDDS-H LSEITVDVA---ST 212
WP_012962174   145 DSHEKADLRLIYLALAHMIKERGHFLIEGE-LNAENTDVQKI--FEAFVEVYDRT--FDDS-N LSEITVDAS---SI 212
WP_039695303   145 DSSEKADLRLIVYLALAHMIKFRGHFLIEGE-LNAENTDVQKL--FADFVGVNRT--FDDS-H LSEITVDVA---SI 212
WP_014334983   144 DSQBKADLRLIVYLALAHMIKYRGHFLIEGE-LNAENTDVQKL--FNVFVETYDKI--VDES-H LSEIEVDAS---SI 211
WP_003099269   144 DSDQKADLRLIYLALAHIIKFRGHFLIEGN-LDSENTDVHVL--FLNLVNIYNNL--FEED--VETASIDAE---KI 211
AHY15608       144 DSDQKADLRLIYLALAHIIKFRGHFLIEGN-LDSENTDVHVL--FLNLVNIYNNL--FEED--VETASIDAE---KI 211
AHY17476       144 DSDQKADLRLIYLALAHIIKFRGHFLIEGN-LDSENTDVHVL--FLNLVNIYNNL--FEED--VETASIDAE---KI 211
ESR09100           ---------------------------------------------------------------------------- 
AGM98575       144 DSDQKADLRLIYLALAHIIKFRGHFLIEGN-LDSENTDVHVL--FLNLVNIYNNL--FEED--VETASIDAE---KI 211
ALF27331       144 DNPEKTDLRLVYLALAHIIKFRGHFLIEGK-FDTRNNDVQRL--FQEFLAVYDNT--FENS-S LQEQNVQVE---KI 211
WP_018372492   144 DTPDKMDIRLIYLALAHIIKYRGHFLIEGD-LDIENIGIQDS--FKSFIEEYNTQ--FGTK--LDSTTKVE----AI 209
WP_045618028   145 DSKEKADFRLISIYLALAHIIKYRGHFLYES-EDIKNNDIQKI--FNEFISIYDNT--FEGS-S LNGQNAQVE---AI 212
WP_045635197   144 DSKEKTDLRLIIYLALAHIIKYRGHFLIEGK-FDIKNNDIQKI--FNEFISIYDNT--FEGS-S LSGQNAQVE---AI 211
WP_002263549   144 DNPEKVDLRLIVYLALAHIIKFRGHFLIEGK-FDTRNNDVQRL--FQEFLAVYDNT--FENS-S LQEQNVQVE---EI 211
WP_002263887   144 DNPEKVDLRLIVYLALAHIIKFRGHFLIEGK-FDTRNNDVQRL--FQEFLAVYDNT--FENS-S LQEQNVQVE---EI 211
WP_002264920   144 DSTEKADLRLIVYLALAHIIKFRGHFLIEGE-LNAENTDVQKI--FADFVGVYDRT--FDDS-H LSEITVDAS---SI 212
WP_002269043   144 DNPEKVDLRLIVYLALAHIIKFRGHFLIEGK-FDTRNNDVQRL--FQEFLAVYDNT--FENS-S LQEQNVQVE---EI 211
WP_002269448   144 DNPEKVDLRLIVYLALAHIIKFRGHFLIEGK-FDTRNNDVQRL--FQEFLAVYDNT--FENS-S LQEQNVQVE---EI 211
WP_002271977   144 DNPEKVDLRLIVYLALAHIIKFRGHFLIEGK-FDTRNNDVQRL--FQEFLAVYDNT--FENS-S LQEQNVQVE---EI 211
WP_002272766   144 DNPEKVDLRLIVYLALAHIIKFRGHFLIEGK-FDTRNNDVQRL--FQEFLAVYDNT--FENS-S LQEQNVQVE---EI 211
WP_002273241   144 DNPEKVDLRLIVYLALAHIIKFRGHFLIEGK-FDTRNNDVQRL--FQEFLAVYDNT--FENS-S LQEQNVQVE---EI 211
WP_002275430   144 DNPEKVDLRLIVYLALAHIIKFRGHFLIEGK-FDTRNNDVQRL--FQEFLAVYDNT--FENS-S LQEQNVQVE---EI 211
WP_002276448   144 DNPEKVDLRLIVYLALAHIIKFRGHFLIEGK-FDTRNNDVQRL--FQEFLAVYDNT--FENS-S LQEQNVQVE---EI 211
WP_002277050   144 DSTEKADLRLIVYLALAHIIKFRGHFLIEGE-LNAENTDVQKL--FADFVGVYDRT--FDDS-H LSEITVDAS---SI 211
WP_002277364   144 DNPEKVDLRLIVYLALAHIIKFRGHFLIEGK-FDTRNNDVQRL--FQEFLAVYDNT--FENS-S LQEQNVQVE---EI 211
WP_002279025   144 DNPEKVDLRLIVYLALAHIIKFRGHFLIEGK-FDTRNNDVQRL--FQEFLAVYDNT--FENS-S LQEQNVQVE---EI 211
WP_002279859   144 DSTEKADLRLIVYLALAHIIKFRGHFLIEGE-LNAENTDVQKL--FADFVGVYDRT--FDDS-H LSEITVDAS---SI 211
WP_002280230   144 DNPEKVDLRLIVYLALAHIIKFRGHFLIEGK-FDTRNNDVQRL--FQEFLAVYDNT--FENS-S LQEQNVQVE---EI 211
WP_002281696   144 DSTEKADLRLIVYLALAHIIKFRGHFLIEGE-LNAENTDVQKL--FADFVGVYDRT--FDDS-H LSEITVDAS---SI 211
WP_002282247   144 DNPEKVDLRLIVYLALAHIIKFRGHFLIEGK-FDTRNNDVQRL--FQEFLAVYDNT--FENS-S LQEQNVQVE---EI 211
WP_002282906   144 DNPEKVDLRLIVYLALAHIIKFRGHFLIEGK-FDTRNNDVQRL--FQEFLAVYDNT--FENS-S LQEQNVQVE---EI 211
WP_002283846   144 DNPEKVDLRLIVYLALAHIIKFRGHFLIEGK-FDTRNNDVQRL--FQEFLAVYDNT--FENS-S LQEQNVQVE---EI 211
WP_002287255   144 DNPEKVDLRLIVYLALAHIIKFRGHFLIEGK-FDTRNNDVQRL--FQEFLAVYDNT--FENS-S LQEQNVQVE---EI 211
WP_002288990   144 DNPEKVDLRLIVYLALAHIIKFRGHFLIEGK-FDTRNNDVQRL--FQEFLAVYDNT--FENS-S LQEQNVQVE---EI 211
WP_002289641   144 DNPEKVDLRLIVYLALAHIIKFRGHFLIEGK-FDTRNNDVQRL--FQEFLAVYDNT--FENS-S LQEQNVQVE---EI 211
WP_002290427   144 DNPEKVDLRLIVYLALAHIIKFRGHFLIEGK-FDTRNNDVQRL--FQEFLAVYDNT--FENS-S LQEQNVQVE---EI 211
WP_002295753   144 DNPEKVDLRLIVYLALAHIIKFRGHFLIEGK-FDTRNNDVQRL--FQEFLAVYDNT--FENS-S LQEQNVQVE---EI 211
WP_002296423   144 NSTEKADLRLVYLSLAHMIKFRGHFLIEGQ-LKAENTNVQAL--FKDFVEVYDKT--VEES-H LSEMTVDAL---SI 211
WP_002304487   144 DNPEKVDLRLIVYLALAHIIKFRGHFLIEGK-FDTRNNDVQKL--FQEFLAVYDNT--FENS-S LQEQNVQVE---EI 211
WP_002305844   144 DNPEKVDLRLIVYLALAHIIKFRGHFLIEGK-FDTRNNDVQKL--FQEFLAVYDNT--FENS-S LQEQNVQVE---EI 211
WP_002307203   144 DNPEKVDLRLIVYLALAHIIKFRGHFLIEGK-FDTRNNDVQKL--FQEFLAVYDNT--FENS-S LQEQNVQVE---EI 211
WP_002310390   144 DNPEKVDLRLIVYLALAHIIKFGGHFLIEGK-FDTRNNDVQKL--FQEFLAVYDNT--FENS-S LQEQNVQVE---EI 211
WP_002352408   144 DNPEKVDLRLIVYLALAHIIKFRGHFLIEGK-FDTRNNDVQKL--FQEFLAVYDNT--FENS-S LQEQNVQVE---EI 211
WP_012997688   144 DNPEKTDLRLIVYLALAHIIKFRGHFLIEGK-FDTRNNDVQKL--FQEFLAVYDNT--FENS-S LQEQNVQVE---EI 211
WP_014677909   144 DNPEKTDLRLIVYLALAHIIKFRGHFLIEGK-FDTRNNDVQKL--FQEFLAVYDNT--FENS-S LQEQNVQVE---EI 211
WP_019312892   144 DNPEKTDLRLIVYLALAHIIKFRGHFLIEGK-FDTRNNDVQKL--FQEFLAVYDNT--FENS-S LQEQNVQVE---EI 211
WP_019313659   144 DNPEKTDLRLIVYLALAHIIKFRGHFLIEGK-FDTRNNDVQKL--FQEFLAVYDNT--FENS-S LQEQNVQVE---EI 211
WP_019314093   144 DNPEKTDLRLIVYLALAHIIKFRGHFLIEGK-FDTRNNDVQKL--FQEFLAVYDNT--FENS-S LQEQNVQVE---EI 211
WP_019315370   144 DNPEKTDLRLIVYLALAHIIKFRGHFLIEGK-FDTRNNDVQKL--FQEFLAVYDNT--FENS-S LQEQNVQVE---EI 211
```

```
                                                   -continued

WP_019803776   144  DNPEKVDLRLIVYLALAHIIKFRGHFLIEGK-FDTRNNDVQRL--FQEFLAVDNT-FENS-S  LQEQNVQVE---EI   211
WP_019805234   144  DNPEKTDLRLIVYLALAHIIKFRGHFLIEGK-FDTRNNDVQRL--FQEFLAVDNT-FENS-S  LQEQNVQVE---EI   211
WP_024783594   144  DNPEKVDLRLIVYLALAHIIKFRGHFLIEGK-FDTRNNDVQRL--FQEFLAVDNT-FENS-S  LQEQNVQVE---EI   211
WP_024784288   144  DSTEKADLRIVYLALAHIIKFRGHFLIEGE-LNAENTDVQKL--FADFVGVDRT-FDDS-H  LSEITVDAS---SI   211
WP_024784666   144  DNPEKVDLRLVYLALAHIIKFRGHFLIEGK-FDTRNNDVQRL--FQEFLAVDNT-FENS-S  LQEQNVQVE---EI   211
WP_024784894   144  DNPEKTDLRLVYLALAHMIKFRGHFLIEGK-FDTRNNDVQRL--FQEFLAVDNT-FENS-S  LQEQNVQVE---EI   211
WP_024786433   144  DSTEKADLRLVYLALAHMIKFRGHFLIEGE-LNAENTDVQKL--FADFVGVDRN-FDDS-H  LSEITVDAS---SI   211
WP_049473442   144  DNPEKVDLRLVYLALAHMIKFRGHFLIEGK-FDTRNNDVQRL--FQEFLAVDNT-FENS-S  LQEQNVQVE---EI   211
WP_049474547   144  DNPEKTDLRLIVYLALAHIIKFRGHFLIEGK-FDTRNNDVQRL--FQEFLAVDNT-FENS-S  LQEQNVQVE---EI   211
EMC03581       137  DNPEKTDLRLIVYLALAHMIKFRGHFLIEGK-FDTRNNDVQRL--FQEFLAVDNT-FENS-S  LQEQNVQVE---EI   204
WP_000428612   145  DSKEKTDLRLIYLALAHMIKYRGHFLYEDT-FDIKNNDIQKI--FNEFISIYNNT-FEGN-S  LSGQNVQVE---AI   212
WP_000428613   144  DSKEKVDLRLIIYLALAHIIKYRGHFLYEDT-FDIKNNDIQKI--FSEFISIYDNT-FEGS-S  LSKGNAQVE---AI   212
WP_049523028   144  DSKEKVDLRLIIYLALAHIIKYRGHFLYEDS-FDIKNNDIQKI--FNEFTILYDNT-FEES-S  LSKGNAQVE---EI   211
WP_003107102   113  DSDEKADLRLIYLALAHIIKFRGHFLIEGD-LDSQNTDVNAL--FLKLVDTYNLM-FEDD--  IDTQTIDAT---VI   180
WP_054279288   146  DNTEKADLRLIYLTLAHMIKYRGHFLIEGA-LSANNTDVQQL--VHALVDAYNIM-FEED--  LDIEAIDVK---AI   213
WP_049531101   145  DSKEKADLRLIYLALAHMIKYRGHFLYEES-FDIKNNDIQKI--FNEFISIYDNT-FEGS-S  LSGQNAQVE---AI   212
WP_049538452   145  DSKEKADLRLIIYLALAHMIKYRGHFLYEEA-FDIKNNDIQKI--FNEFINIYDNT-FEGS-S  LSGQNEQVE---TI   212
WP_049549711   145  DSKEKADLRLIYLALAHMIKYRGHFLYEEA-FDIKNNDIQKI--FNEFISIYDNT-FEGS-S  LSGQNAQVE---AI   212
WP_007896501   146  DRDQKADLRLIYLALSHIIKFRGHFLIEGK-LNSENTDVQKL--FIALVTVYNLL-FEEE--  IAGETCDAK---AL   213
EFR44625        98  DSKEKSDVRLIYLALAHIIKFRGHFLYEET-FDIKNNDIQKI--FIALVTVYNLL-FEEE--  IAGTCDAK---AL    165
WP_002897477   144  DSKEKTDLRLIYLALAHMIKYRGHFLYEES-FDIKNNDIQKI--FNEFINIYDNT-FEGS-S  LSGQNAQVE---AI   211
WP_002906454   144  DSKEKTDLRLIYLALAHMIKYRGHFLYEES-FDIKNNDIQKI--FNEFISIYDNT-FEGS-S  LSGQNAQVE---AI   211
WP_009729476   145  DSKEKTDLRLIYLALAHMIKYRGHFLYEEA-FDIKNNDIQKI--FNEFISIYNNT-FEGN-S  LSGQNVQVE---AI   212
CQR24647       144  DSSEKTDLRLIYLALAHMIKYRGHFLIDEP-IDIRNMNSQNL--FKEFLLAPDGI-QVDC-Y  LASKHTDIS---GI   211
WP_000666813   145  DSKEKTDLRLIYLALAHMIKYRGHFLYEES-FDIKNNDIQKI--FSEFISIYDNT-FEGK-S  LSGQNAQVE---AI   212
WP_009754323   145  DSKEKADLRLIIYLALAHIIKYRGHFLYEES-FDIKNNDIQKI--FNEFINIYDNT-FEGS-S  LSGQNAQVE---AI   212
WP_044674937   144  DSSQKADIRLIYLALAHMIKYRGHELFEGD-LKSENKDVQHL--FNDEVEMFDKT-VEGS-Y  LSENLPNVA---DV   211
WP_044676715   144  DSSQKADIRLIYLALAHMIKYRGHELFEGD-LKSENKDVQHL--FNDEVEMFDKT-VEGS-Y  LSENLPNVA---DV   211
WP_044680361   144  DSSQKADIRLIYLALAHMIKYRGHELFEGD-LKSENKDVQHL--FNDEVEMFDKT-VEGS-Y  LSENLPNVA---DV   211
WP_044681799   144  DSSQKADIRLIYLALAHMIKYRGHELFEGD-LKAENTNVQAL--FKDEVEVYDKT-VEES-H  LSEMTVDAL---SI   211
WP_049533112   101  DISQKADIRLVYLAIHHLIKYRGHFIYEDQtFTTDGNQLQHH--IKAIITMINST1---NR--  IIPETIDINvfeKI  171
WP_029090905   140  SQHRQFDIREVYLAIHHLIKYRGHFLYEGQkFNMDASNIEDK--LSDIFTQFTSFmnIPYEdD  --KKNLEII---EI   210
ESTEKADPLRLIYLALHHIVKYRGHFLYEGN-FNMDASNIEDK--FIQLVQTNQL-FEEN--  INASGVDAK---AI      211
AIT42264       210  ESTEKADPLRLIYLALHHIVKYRGHFLYEGN-FNMDASNIEDK--FIQLVQTNQL-FEEN--  INASGVDAK---AI    217
AKQ21048       143  DSTDKADLRLIYLALAHMIKERGHFLIEGD-LNPDNSDVDKL--FQEFIDSYNEVcaLEDE-N  NDELLTQIE---NI  211
WP_004636532   144  DSTDKADLRLIYLALAHMIKERGHFLIEGD-LKMDGISISES--FQEFIDSYNEVcaLEDE-N  NDELLTQIE---NI  217
WP_002364836   144  DNPEKADLRLIYLALAHIVKYRGHFLIEGE-LNTENTISET--FEOQFLDTYSDI-FKEQ--  LVGDISKVE---EI   210
WP_016631044    95  DSSEQADLRLIIYLALAHLIKYRGHFLIEGK-LSTENISVKEQ--FQQFMIIYNQT-FVNGES  PLPESVLIE---EE   168
EMS75795       ---  -------DSSEQADLRLIYLALAHLIKYRGHFLIEGK-LSTENTSVKEQ--FQQFMIIYNQT-FVNGES  PLPESVLIE---EE  ---
WP_002373311   144  DSSEQADLRLIYLALAHLIKYRGHFLIEGK-LSTENTSVKEQ--FQQFMIIYNQT-FVNGes  PLPESVLIE---EE   217
WP_002378009   144  DSSEQADLRLIIYLALAHLIKYRGHFLIEGK-LSTENISVKEQ--FQQFMIIYNQT-FVNGes  PLPESVLIE---EE  217
WP_002407324   144  DSSEQADLRLIYLALAHLIKYRGHFLIEGK-LSTENISVKEQ--FQQFMIIYNQT-FVNGes  PLPESVLIE---EE   217
WP_002413717   144  DSSEQADLRLIIYLALAHLIKYRGHFLIEGK-LSTENTSVKEQ--FQQFMIIYNQT-FVNGes  PLPESVLIE---EE  217
WP_010775580   144  DSSEQADLRLIIYLALAHLIKYRGHFLIEGK-LSTENTSVKEK--FQQFMIIYNQT-FVNGes  PLPESVLIE---EE  217
WP_010818269   144  DNPEKADLRLIIYTLALAHLVKYRGHFLIEGE-LNTENTISET--FEQFLDTYSDI-FKEO--  LVGDISKVE---EI    210
WP_010824395   144  DSSEQADLRLIIYLALAHLIKYRGHFLIEGK-LSTENISVKEQ--FQQFMIIYNQT-FVNGes  PLPESVLIE---EE  217
WP_016622645   144  DSSEQADLRLIIYLALAHLIKYRGHFLIEGK-LSTENTSVKDQ--FQQFMIIYNQT-FVNGes  PLPESVLIE---EE  217
WP_033624816   144  DSSEQADLRLIYLALAHLIKYRGHFLIEGK-LSTENISVKDQ--FQQFMIIYNQT-FVNGes  PLPESVLIE---EE   217
WP_033625576   144  DSSEQADLRLIIYLALAHLIKYRGHFLIEGK-LSTENISVKEQ--FQQFMVIYNQT-FVNGes  PLPESVLIE---EE  217
WP_033789179   144  DSSEKADIRLVYLAMAHLLKYRGHFLIEGE-LNTENSSVTET--FROFLSTYNQQ-FSEA-D  KLDEAVDCS---FV   216
WP_002310644   144  DSSEKADIRLVYLAMAHLLKYRGHFLIEGE-LNTENSSVTET--FRQFLSTYNQQ-FSEA-G  KLDEAVDCS---FV   216
WP_002312694   144  DSSEKADIRLVYLAMAHLLKYRGHFLIEGE-LNTENSSVTET--FRQFLSTYNQQ-FSEA-G  KLDEAVDCS---FV   216
```

-continued

```
WP_002314015    144 DSSEKADIRLVYLAMAHLLKYRGHFLIEGE-LNTENSSVTET--FRQFLSTNQQ--FSEA-D KLDEAVDCS----FV     216
WP_002320716    144 DSSEKADIRLVYLAMAHLLKYRGHFLIEGE-LNTENSSVTET--FRQFLSTNQQ--FSEA-D KLDEAVDCS----FV     216
WP_002330729    144 DSSEKADIRLVYLAMAHLLKYRGHFLIEGE-LNTENSSVTET--FRQFLSTNQQ--FSEA-D KLDEAVDCS----FV     216
WP_002335161    144 DSSEKADIRLVYLAMAHLLKYRGHFLIEGE-LNTENSSVTET--FRQFLSTNQQ--FSEA-D KLDEAVDCS----FV     216
WP_002345439    144 DSSEKADIRLVYLAMAHLLKYRGHFLIEGE-LNTENSSVTET--FRQFLSTNQQ--FSEA-D KLDEAVDCS----FV     216
WP_034867970    144 DSSTEKEDLRLVYLALAHLLKYRGHFLFEGD-LDTENTSIEES--FRVFLEQYSKQ--SDQP- -LIVHQPVL---TI     209
WP_047937432    144 DSSEKADLRLVYLALAHLLKYRGHFLIEGE-LNTENSSVTET--FRQFLSTNQQ--FSEA-D KLDEAVDCS----FV     216
WP_010720994    144 DSTEKGDLRLVYLALAHLLKYRGHFLFEGD-LDTENTSIEES--FRVFLEQYGKQ--SDQP- -LIVHQPVL---TI     209
WP_010737004    144 DSTEKEDLRLVYLALAHLLKYRGHFLFEGD-LDTENTSIEES--FRVFLEQYGKQ--SDQP- -LIVHQPVL---TI     209
WP_047700478    144 DSTEKEDLRLVYLALAHLLKYRGHFLFEGD-LDTENTSIEES--FRVFLEQYGKQ--SDQP- -LIVHQPVL---TI     209
WP_007209003    144 DGDEKADLRLVYLALAHIIKFRGNFLIEGE-LNTENNSVIELs--KVFVQLNQT1-SELE- FIDESIDFS----EV     214
WP_023519017    144 NSKEQADIRLVYLAIACHLKYRGHFLFEGE-LDTENTSVTEN--YQQFLQAYQQF--FPEP- -IGDLDDAV---PI     209
WP_010770040    144 DTSEQADLRLVYLALAHLLKYRGHFLIEGE-LNTENSSVSET--FRTFIQVNQI--FRENe PLAVPDNIE---EL     212
WP_048604708    144 DAEEKADLRLVYLALAHLLKYRGHFLIEGR-LSTENTSTEET--FKITFLQKYNQT--FN---  PVDETISIG----SI     208
WP_010750235    144 DSTEKADLRLVYLALAHMIKYRGHFLFEGE-LDTENTSVEET--FKEFIDIYNEQ--FEEG- -IIFYKDIP---LI     209
AII16583        183 DSTDKADLRLIYLALAHMIKYRGHFLIEGD-LNPDNSDVDKL--FIQLVQTYNQL--FEEN- INASGVDAK---AI     250
WP_029073316    145 ESKEKEDPRLIIYLALHHIVKYRGNFLYEGQkFSMDVSNIEDK--MIDVLRQFNEIn1FEYVeD --KKIDEVL---NV     215
WP_031589969    145 ESKEKEDPRLIIYLALHHIVKYRGNFLYEGQkFSMDVSNIEDK--MIDVLRQFNEIn1FEYVeD --KKIDEVL---NV     215
KDA45870        145 NNDRPADLRIVYLALAHI IKYRGNELLEGE-IDLRTTDINKV--FAEFSETLNEN--SDENIG --KLDVA----DI     209
WP_039099354    133 TEKRQFDIREIYLAMHHIVKYRGHFLNEAPVSSEKSSEINLVahFDRLNTIFADL-FSESGf -TDKLAEVK---AL     206
AKP02966        138 INKNKADIRLVYLALHHIVKYRGNFTYEHQkFNISTLNSNLS--KELIELNQQLikYDIS- -FPDNCDWNhisDI     208
WP_010991369    144 NSSEKADLRLVYLALAHI IKYRGHFLIEGA-LDTQNTSVDGI--YKQFIQTYNQV--FASGiE KLEDNKDVA----KI     217
WP_033838504    144 NSSEKADLRLVYLALAHI IKYRGHFLIEGA-LDTQNTSVDGI--YKQFIQTYNQV--FASGiE KLEDNKDVA----KI     217
EHN60060        147 NSSEKADLRLVYLALAHI IKYRGHFLIEGA-LDTQNTSVDGI--YKQFIQTYNQV--FASGiE KLEDNKDVA----KI     220
EFR89594            --------------------------------------KELIELNQQLikYDIS- -FPDNCDWNhisDI     208
WP_038409211    144 NSSDKADLRLVYLALAHI IKYRGHFLIEGM-LDTKNTSVDEV--FKQFIQTYNQI--FASDiE RLEENKEVA----EI     217
EFR95520        ----------------------------------------------------------------------
WP_046323366    144 NSSEKADLRLVYLALAHI IKYRGHFLIEGA-LDTKNTSVDEV--YKQFIETYNQV--FMSNiE KVEENIEVA----NI     217
WP_003723650    144 NSSEKADLRLVYLALAHI IKYRGHFLIEGA-LDTKNTSVDEV--YKQFIQTYNQV--FMSNiE KVEENTEVA----SI     217
WP_003727705    144 NSSEKADLRLVYLALAHI IKYRGHFLIEGA-LDTKNTSVDEV--YKQFIQTYNQV--FMSNiE KVEENTEVA----SI     217
WP_003730785    144 NSSEKADLRLVYLALAHI IKYRGHFLIEGA-LDTKNTSIDEV--YKQFIQTYNQV--FMSNiE KVEENTEVA----SI     217
WP_003733029    144 DSQKKADLRLVYLALAHI IKYRGHFLIEGA-LDTKNTSIDEN--FKQFLQIYNQV--FANDiE KTEKNQEVA----QI     217
WP_003739838    144 NSSEKADLRLVYLALAHI IKYRGHFLIEGA-LDTKNTSVDGV--YKQFIQTYNQV--FISNiE KMEENTTVA----DI     217
WP_014601172    144 NSSEKADLRLVYLALAHI IKYRGHFLIEGA-LDTKNTSVDGV--YEQFIQTYNQV--FMSNiE KVEENIEVA----NI     217
WP_023548323    144 NSSEKADLRLVYLALAHI IKYRGHFLIEGA-LDTKNTSVDGV--YEQFILTYNQV--FMSNiE KVEENIEVA----NI     217
WP_031666537    144 NSSEKADLRLVYLALAHI IKYRGHFLIEGA-LDTKNTSVDGV--YEQFLQIYNQV--FANDiE KTEKNQEVA----QI     217
WP_031669209    144 DSQKKADLRLVYLALAHI IKYRGHFLIEGA-LDTKNTSIDEM--FKQFLQIYNQV--FANDiE KTEKNQEVA----QI     217
WP_033920898    144 NSSEKADLRLVYLALAHI IKYRGHFLIEGA-LDTKNTSVDGV--YEQFIQTYNQV--FMSNiE KVEENIEVA----NI     217
AKI42028        147 NSSEKADLRLVYLALAHI IKYRGHFLIEGA-LDTKNTSVDGV--YEQFIQTYNQV--FMSNiE KVEENIEVA----NI     220
AKI50529        147 NSSEKADLRLVYLALAHI IKYRGHFLIEGA-LDTKNTSVDGV--YEQFIQTYNQV--FMSNiE KVEENIEVA----NI     220
EFR83390        -------------------------------------------------------------------------
WP_046323366    144 NSSDKADLRLVYLALAHI IKYRGHFLIIGK-LDTKNTSVDEV--FKQFIKTYNQV--FASDiE RIEENNEVA----KI     217
AKE81011        160 DSTDKADLRLIYLALAHMIKYRGHFLIEGD-LNPDNSDVDKL--FIQLVQTYNQL--FEEN- INASGVDAK---AI     227
CUO82355        144 ESTEKADPRLIIYLALAHMIKYRGHFLYEGQ-LNKNTLFGNLIALGLQPNFKTNF--KLSED-A-- -KKNLEIL---EI     214
WP_033162887    145 ENKEKADPRLIIYLALAHMIKYRGNFLYEGQsFTMDNSDIEER--LSDVFTQFADFmnIPYEdD -SDINSMI---AV     215
AGZ01981        177 DSTDKADLRLIYLALAHMIKYRGHFLIEGD-LNPDNSDVDKL--FIQLVQTYNQL--FEEN- INASGVDAK---AI     244
AKA60242        144 DSTDKADLRLIYLALAHMIKYRGHFLIEGD-LNPDNSDVDKL--FIQLVQTYNQL--FEEN- INASGVDAK---AI     211
AKS40380        144 DSTDKADLRLIYLALAHMIKYRGHFLIEGD-LNPDNSDVDKL--FIQLVQTYNQL--FEEN- INASGVDAK---AI     211
4UN5_B          148 DSTDKADLRLIYLALAHMIKYRGHFLIEGD-LNPDNSDVDKL--FIQLVQTYNQL--FEEN- INASGVDAK---AI     215
WP_010922251    212 LSAR-LSKSRRLENLIAQ-L-PG EKKNGLFGNLIALSLGLTPNFKSNF--DLAED-A--- -KLQ-LSKDTYDDDLDN 277
WP_039695303    213 LTEK-ISKSRRLENLIKY-Y-PT EKKNTLFGNLIALALGLQPNFKTNF--KLSED-A--- -KLQ-FSKDTYEEDLEE 278
WP_045635197    212 FTDK-ISKSAKRERVLKL-F-PD EKSTGLFSEFLKLIVGNQADFKKHF--DLEDK-A--- -PLQ-FSKDTYDEDLEN 277
5AXW_A          135 LSTK--------EQISRN-S--K --------LEEKyVa-ELQ--- 157
WP_009880683        ---------------------------------------------------------
```

| | | | | |
|---|---|---|---|---|
| WP_010922251 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011054416 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011284745 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011285506 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011527619 | 212 | LSAR-LSKSRRLENLIAQ-L-PG | EKKNGLFGNLIALSLGLTPNFKSNF--DLAED-A---KLQ-LSKDTYDDDLDN | 277 |
| WP_012560673 | 212 | LSAR-LSKSRRLENLIAQ-L-PG | EKKNGLFGNLIALSLGLTPNFKSNF--DLAED-A---KLQ-LSKDTYDDDLDN | 277 |
| WP_014407541 | 212 | LSAR-LSKSRRLENLIAQ-L-PG | EKRNGLFGNLIALSLGLTPNFKSNF--DLAED-A---KLQ-LSKDTYDDDLDN | 277 |
| WP_020905136 | 212 | LSAR-LSKSRRLENLIAQ-L-PG | EKRNGLFGNLIALSLGLTPNFKSNF--DLAED-A---KLQ-LSKDTYDDDLDN | 277 |
| WP_023080005 | 212 | LSAR-LSKSRRLENLIAQ-L-PG | EKKNGLFGNLIALSLGLTPNFKSNF--DLAED-A---KLQ-LSKDTYDDDLDN | 277 |
| WP_023610282 | 212 | LSAR-LSKSRRLENLIAQ-L-PG | EKKNGLFGNLIALSLGLTPNFKSNF--DLAED-A---KLQ-LSKDTYDDDLDN | 277 |
| WP_030125963 | 212 | LSAR-LSKSRRLENLIAQ-L-PG | EKKNGLFGNLIALSLGLTPNFKSNF--DLAED-A---KLQ-LSKDTYDDDLDN | 277 |
| WP_030126706 | 212 | LSAR-LSKSRRLENLIAQ-L-PG | EKKNGLFGNLIALSLGLTPNFKSNF--DLAED-A---KLQ-LSKDTYDDDLDN | 277 |
| WP_031488318 | 212 | LSAR-LSKSRRLENLIAQ-L-PG | EKRNGLFGNLIALSLGLTPNFKSNF--DLAED-A---KLQ-LSKDTYDDDLDN | 277 |
| WP_032460140 | 212 | LSAR-LSKSRRLENLIAQ-L-PG | EKKNGLFGNLIALSLGLTPNFKSNF--DLAED-A---KLQ-LSKDTYDDDLDN | 277 |
| WP_032461047 | 212 | LSAR-LSKSRRLENLIAQ-L-PG | EKRNGLFGNLIALSLGLTPNFKSNF--DLAED-A---KLQ-LSKDTYDDDLDN | 277 |
| WP_032462016 | 212 | LSAR-LSKSRRLENLIAQ-L-PG | EKRNGLFGNLIALSLGLTPNFKSNF--DLAED-A---KLQ-LSKDTYDDDLDN | 277 |
| WP_032462936 | 212 | LSAR-LSKSRRLENLIAQ-L-PG | EKKNGLFGNLIALSLGLTPNFKSNF--DLAED-A---KLQ-LSKDTYDDDLDN | 277 |
| WP_032464890 | 212 | LSAR-LSKSRRLENLIAQ-L-PG | EKKNGLFGNLIALLLGLTPNFKSNF--DLAED-A---KLQ-LSKDTYDDDLDN | 277 |
| WP_033888930 | 37 | LSAR-LSKSRRLENLIAQ-L-PG | EKKNGLFGNLIALSLGLTPNFKSNF--DLAED-A---KLQ-LSKDTYDDDLDN | 102 |
| WP_038431314 | 212 | LSAR-LSKSRRLENLIAQ-L-PG | EKKNGLFGNLIALSLGLTPNFKSNF--DLAED-A---KLQ-LSKDTYDDDLDN | 277 |
| WP_038432938 | 212 | LSAR-LSKSRRLENLIAQ-L-PG | EKRNGLFGNLIALSLGLTPNFKSNF--DLAED-T---KLQ-LSKDTYDDDLDN | 277 |
| WP_038434062 | 123 | LSAR-LSKSRRLENLIAQ-L-PG | EKKNGLFGNLIALSLGLTPNFKSNF--DLAED-A---KLQ-LSKDTYDDDLDN | 188 |
| BAQ51233 | | | | |
| KGE60162 | | | | |
| KGE60856 | | | | |
| WP_002989955 | 212 | LSAR-LSKSRRLENLIAQ-L-PG | EKKNGLFGNLIALSLGLTPNFKSNF--DLAED-A---KLQ-LSKDTYDDDLDN | 277 |
| WP_003030002 | 212 | LTEK-VSKSRRLENLIAH-Y-PA | EKKNTLFGNLIALSLGLQPNFKTNF--QLSED-A---KLQ-FSKDTYEEDLEG | 277 |
| WP_003065552 | 215 | LTEK-ISKSRRLENLIKY-Y-PT | EKKNTLFGNLIALGLQPNFKMNF--KLSED-A---KLQ-SYEEDLGE | 280 |
| WP_001040076 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040078 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040080 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040081 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040083 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040085 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040087 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040088 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040089 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040090 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040091 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040092 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040094 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040095 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040096 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040097 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040098 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040099 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040100 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040104 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040105 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040106 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040107 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040108 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040109 | 213 | LTDK-ISKSAKKDRILAR-Y-PN | QKSTGIFAEFLKLIVGNQADFKKHF--NLEDK-T---PLQ-FAKDSYDEDLEN | 278 |

-continued

```
WP_001040110    213 LTDK-ISKSAKKDRILAQ-Y-PN QKSTGIFAEFLKLIVGNQADFKKHF--NLEDK-T---PLQ-FAKDSYDEDLEN 278
WP_015058523    213 LTDK-ISKSAKKDRILAQ-Y-PN QKSTGIFAEFLKLIVGNQADFKKHF--NLEDK-T---PLQ-FAKDSYDEDLEN 278
WP_017643650    213 LTDK-ISKSAKKDRILAR-Y-PN QKSTGIFAEFLKLIVGNQADFKKHF--NLEDK-T---PLQ-FAKDSYDEDLEN 278
WP_017647151    213 LTDK-ISKSAKKDRILAQ-Y-PN QKSTGIFAEFLKLIVGNQADFKKHF--NLEDK-T---PLQ-FAKDSYDEDLEN 278
WP_017648376    213 LTDK-ISKSAKKDRILAQ-Y-PN QKSTGIFAEFLKLIVGNQADFKKHF--NLEDK-T---PLQ-FAKDSYDEDLEN 278
WP_017649527    213 LTDK-ISKSAKKDRILAQ-Y-PN QKSTGIFAEFLKLIVGNQADFKKHF--NLEDK-T---PLQ-FAKDSYDEDLEN 278
WP_017771611    213 LTDK-ISKSAKKDRILAQ-Y-PN QKSTGIFAEFLKLIVGNQADFKKHF--NLEDK-T---PLQ-FAKDSYDEDLEN 278
WP_017771984    213 LTDK-ISKSAKKDRILAQ-Y-PN QKSTGIFAEFLKLIVGNQADFKKYF--NLEDK-T---PLQ-FAKDSYDEDLEN 278
CFQ25032        213 LTDK-ISKSAKKDRILAQ-Y-PN QKSTGIFAEFLKLIVGNQADFKKHF--NLEDK-T---PLQ-FAKDSYDEDLEN 278
CFV16040        213 LTDK-ISKSAKKDRILAQ-Y-PN QKSTGIFAEFLKLIVGNQADFKKYF--NLEDK-T---PLQ-FAKDSYDEDLEN 278
KLJ37842        213 LTDK-ISKSAKKDRILAR-Y-PN QKSTGIFAEFLKLIVGNQADFKKHF--NLEDK-T---PLQ-FAKDSYDEDLEN 278
KLJ72361        213 LTDK-ISKSAKKDRILAQ-Y-PN QKSTGIFAEFLKLIVGNQADFKKYF--NLEDK-T---PLQ-FAKDSYDEDLEN 278
KLL20707        213 LTDK-ISKSAKKDRILAQ-Y-PN QKSTGIFAEFLKLIVGNQADFKKHF--NLEDK-T---PLQ-FAKDSYDEDLEN 278
KLL42645        213 LTDK-ISKSAKKDRILAQ-Y-PN QKSTGIFAEFLKLIVGNQADFKKHF--NLEDK-T---PLQ-FAKDSYDEDLEN 278
WP_047207273    213 LTDK-ISKSAKKDRILAQ-Y-PN QKSTGIFAEFLKLIVGNQADFKKHF--NLEDK-T---PLQ-FAKDSYDEDLEN 278
WP_047209694    213 LTDK-ISKSAKKDRILAR-Y-PN QKSTGIFAEFLKLIVGNQADFKKHF--NLEDK-T---PLQ-FAKDSYDEDLEN 278
WP_050198062    213 LTDK-ISKSAKKDRILAQ-Y-PN QKSTGIFAEFLKLIVGNQADFKKYF--NLEDK-T---PLQ-FAKDSYDEDLEN 278
WP_050201642    213 LTDK-ISKSAKKDRILAQ-Y-PN QKSTGIFAEFLKLIVGNQADFKKHF--NLEDK-T---PLQ-FAKDSYDEDLEN 278
WP_050204027    213 LTDK-ISKSAKKDRILAQ-Y-PN QKSTGIFAEFLKLIVGNQADFKKHF--NLEDK-T---PLQ-FAKDSYDEDLEN 278
WP_050881965    213 LTDK-ISKSAKKDRILAQ-Y-PN QKSTGIFAEFLKLIVGNQADFKKYF--NLEDK-T---PLQ-FAKDSYDEDLEN 278
WP_050886065    213 LTDK-ISKSAKKDRILAQ-Y-PN QKSTGIFAEFLKLIVGNQADFKKYF--NLEDK-T---PLQ-FAKDSYDEDLEN 278
AHN30376        213 LTDK-ISKSAKKDRILAQ-Y-PN QKSTGIFAEFLKLIVGNQADFKKHF--NLEDK-T---PLQ-FAKDSYDEDLEN 278
EA078426        213 LTDK-ISKSAKKDRILAQ-Y-PD QKSTGIFAEFLKLIVGNQADFKKHF--NLEDK-T---PLQ-FAKDSYDEDLEN 278
CCW42055        213 LTEK-VSKSRRLENLIAH-Y-PA EKKNTLFGNLIALFLGLQPNFKTNF--QLSED-A---KLQ-FSKDTYEDDLEG 278
WP_003041502    212 LTEK-VSKSRRLENLIAH-Y-PT EKKNTLFGNLIALSLGLQPNFKTNF--QLSED-A---KLQ-FSKDTYEEDLEE 277
WP_037593752    213 LTEK-VSKSRRLENLVEC-Y-PT EKKNTLFGNLIALSLGLQPNFKTNF--QLSED-A---KLQ-FSKDTYEEDLEG 278
WP_049516684    212 LTEK-VSKSRRLENLIAH-Y-PT EKKNTLFGNLIALSLGLQPNFKTNF--QLSED-A---KLQ-FSKDTYEEDLEE 277
GAD46167        213 LTEK-ISKSRRLENLINN-Y-PK EKKNGLFGNIIALALGLTPNFKSNF--KLSED-A---KLQ-LSKDTYDDDLDE 278
WP_018363470    212 LSAR-LSKSKRLEKLIAV-F-PN EKKNGLFGNIIALALGLSLDLHPNFKTNF--DLTED-A---KLQ-LSKDTYDDDLDE 277
WP_003043819    212 LTEK-VSKSSRLENLIAH-Y-PT EKKNGLFGNIIALALGLSLDLHPNFKTNF--QLSED-A---KLQ-FSKDTYEEDLEG 277
WP_062269658    212 LTEK-VSKSRRLENLVKC-Y-PT EKKNTLFGNLIALSLGLQPNFKTNF--QLSED-A---KLQ-FSKDTYEEDLEE 277
WP_048800889    212 LSAR-LSKSRRLENLIAL-L-PG EKKNGLFGNLIALSLGLTPNFKSNF--DLAED-A---KLQ-LSKDTYDDDLDN 277
WP_042767106    212 LSAR-LSKSRRLENLIAQ-L-PG EKKNGLFGNLIALSLGLTPNFKSNF--DLAED-A---KLQ-LSKDTYDDDLDN 277
WP_014612333    212 LSAR-LSKSRRLENLIAQ-L-PG EKKNGLFGNLIALSLGLTPNFKSNF--DLAED-A---KLQ-LSKDTYDDDLDN 277
WP_015017095    212 LSAR-LSKSRRLENLIAQ-L-PG EKKNGLFGNLIALSLGLQPNFKTNF--DLAED-A---KLQ-LSKDTYDDDLDN 277
WP_015057649    212 LSAR-LSKSRRLENLIAQ-Y-PT EKRNGLFGNLIALSLGLTPNFKSNF--DLAED-A---KLQ-LSKDTYDDDLDN 277
WP_048327215    212 LSAR-LSKSRRLENLIAQ-L-PG EKRNGLFGNLIALSLGLTPNFKSNF--DLAED-A---KLQ-LSKDTYDDDLDN 277
WP_049519324    212 LSAR-LSKSRRLENLIAQ-L-PG EKRNGLFGNLIALSLGLTPNFKSNF--DLAED-A---KLQ-LSKDTYDDDLDN 277
WP_012515931    212 LSAA-LSKSKRLENLISL-I-PG QKKTGIFGNIIALSLGLTPNFKANF--GLSKD-V---KLQ-LAKDTYADDLDS 277
WP_012120964    212 LSAA-LSKSKRLENLISL-I-PG QKKTGIFGNIIALSLGLTPNFKANF--GLSKD-V---KLQ-LAKDTYADDLDS 277
WP_037581760    212 LSAA-LSKSKRLENLISI-I-PG QKKTGIFGNIIALSLGLTPNFKANF--GLSKD-V---KLQ-LAKDTYADDLDS 277
WP_004232481    212 LTEK-ISKSRRLENLIKQ-Y-PT EKKNGLFGNIVALVALGLQPNFKTNF--KLSED-A---KLQ-FSKDTYEDDLEE 278
WP_009854540    213 LTEK-FSKSRRLENLIKH-Y-PT EKKNTLFGNLIALGLQPNFKMNF--KLSED-A---KLQ-FSKDTYEEDLEE 278
WP_012962174    213 LTEK-LSKSRRLENLIKH-Y-PT EKKNTLFGNLIALALGLQPNFKTSF--KLSED-A---KLQ-FSKDTYEEDLEE 278
WP_039695303    213 LTEK-LSKSRRLENLIKY-Y-PT EKKNTLFGNLIALALGLQPNFKTNF--KLSED-A---KLQ-FSKDTYEEDLEE 278
WP_014334983    213 LTEK-LSKSRRLENLIKQ-Y-PT EKKNTLFGNLIALALGLQPNFKTNF--KLSED-A---KLQ-FSKDTYEEDLEE 278
WP_003099269    212 LTSK-TSKSRRLENLIAE-I-PN QKRNMLFGNLVSLALGLTPNFKTNF--ELLED-A---KLQ-ISKDSYEEDLDN 277
AHY15608        -     -                                                                         -
AHY17476        -     -                                                                         -
ESR09100        -     -                                                                         -
AGM98575        212 LTSK-TSKSRRLENLIAE-I-PN QKRNMLFGNLVSLALGLTPNFKTNF--ELLED-A---KLQ-ISKDSYEEDLDN 277
ALF27331        210 LTSK-ISKSAKKDRVLKL-F-PN EKSNGRFAEFLKLIVGNQADFKKHF--ELEEK-A---PLQ-FSKDSYEELEV 277
WP_018372492    210 FTEN-SSKAKRVETILGL-F-PD ETAAGNLDKFLKLMLGNQADFKKVF--DLEEK----iTLQ-FSKDSYEEDLEL 275
```

| ID | Start | Sequence | End |
|---|---|---|---|
| WP_045618028 | 213 | FTDK-ISKSAKRERVLKL-F-PD EKSTGLFSEFLKLIVGNQADFKKHF--DLEEK-A---PLQ-FSKDTYDEDLEN | 278 |
| WP_045635197 | 212 | FTDK-ISKSAKRERVLKL-F-PD EKSTGLFSEFLKLIVGNQADFKKHF--DLEDK-A---PLQ-FSKDTYDEDLEN | 277 |
| WP_002263549 | 212 | LTDK-ISKSAKKDRVLKL-F-PN EKSNGRFAEFLKLIVGNQADFKKHP--ELEEK-A---PLQ-FSKDTYEEELEV | 277 |
| WP_002263887 | 212 | LTEK-ISKSRRLEKLINN-Y-PK EKKNTLFRNLVALSLGLQPNFKTNF--KLSED-A---KLQ-FSKDTYEEDLEE | 277 |
| WP_002264920 | 212 | LTDK-ISKSAKKDRVLKL-F-PN EKSNGRFAEFLKLIVGNQADFKKHF--ELEEK-A---PLQ-FSKDIYEEELEV | 277 |
| WP_002269043 | 212 | LTDK-ISKSAKKDRVLKL-F-PN EKSNGRFAEFLKLIVGNQADFKKHF--ELEEK-A---PLQ-FSKDTYEEELEV | 277 |
| WP_002269448 | 212 | LTDK-ISKSAKKDRVLKL-F-PN EKSNGRFAEFLKLIVGNQADFKKHF--ELEEK-A---PLQ-FSKDTYEEELEV | 277 |
| WP_002271977 | 212 | LTDK-ISKSAKKDRVLKL-F-PN EKSNGRFAEFLKLIVGNQADFKKHF--ELEEK-A---PLQ-FSKDTYEEDLEV | 277 |
| WP_002272766 | 212 | LTDK-ISKSAKKDRVLKL-F-PN EKSNGRFAEFLKLIVGNQADFKKHF--ELEEK-A---PLQ-FSKDTYEEELEE | 277 |
| WP_002273241 | 212 | LTDK-ISKSAKKDRVLKL-F-PN EKSNGRFAEFLKLIVGNQADFKKHF--ELEEK-A---PLQ-FSKDTYEEELEV | 277 |
| WP_002275430 | 212 | LTDK-ISKSAKKDRVLKL-F-PN EKSNGRFAEFLKLIVGNQADFKKHP--ELEEK-A---PLQ-FSKDTYEEELEV | 277 |
| WP_002276448 | 212 | LTDK-ISKSAKKDRVLKL-F-PN EKSNGRFAEFLKLIVGNQADFKKHP--ELEEK-A---PLQ-FSKDTYEEELEV | 277 |
| WP_002277050 | 212 | LTEK-ISKSRRLEKLINN-Y-PK EKKNTLFGNLIALSLGLQPNFKTNF--KLSED-A---KLQ-FSKDTYEEDLEE | 277 |
| WP_002277364 | 212 | LTDK-ISKSAKKDRVLKL-F-PN EKSNGRFAEFLKLIVGNQADFKKHP--ELEEK-A---PLQ-FSKDTYEEELEV | 277 |
| WP_002279025 | 212 | LTDK-ISKSAKKDRVLKL-F-PN EKSNGRFAEFLKLIVGNQADFKKHP--ELEEK-A---PLQ-FSKDTYEEELEV | 277 |
| WP_002279859 | 212 | LTEK-ISKSRRLEKLINN-Y-PK EKKNTLFGNLIALSLGLQPNFKTNF--KLSED-A---KLQ-FSKDTYEEDLEE | 277 |
| WP_002280230 | 212 | LTDK-ISKSAKKDRVLKL-F-PN EKSNGRFAEFLKLIVGNQADFKKHP--ELEEK-A---PLQ-FSKDTYEEELEV | 277 |
| WP_002281696 | 212 | LTDK-ISKSAKKDRVLKL-F-PN EKSNGRFAEFLKLIVGNQADFKKHP--ELEEK-A---PLQ-FSKDTYEEELEV | 277 |
| WP_002282247 | 212 | LTEK-ISKSRRLEKLINN-Y-PK EKKNTLFGNLISLGLQPNFKTNF--KLSED-A---KLQ-FSKDTYEEDLEE | 277 |
| WP_002282906 | 212 | LTDK-ISKSAKKDRVLKL-F-PN EKSNGRFAEFLKLIVGNQADFKKHF--ELEEK-A---PLQ-FSKDTYEEELEV | 277 |
| WP_002283846 | 212 | LTDK-ISKSAKKDRVLKL-F-PN EKSNGRFAEFLKLIVGNQADFKKHP--ELEEK-A---PLQ-FSKDTYEEELEV | 277 |
| WP_002287255 | 212 | LTDK-ISKSAKKDRVLKL-F-PN EKSNGRFAEFLKLIVGNQADFKKHP--ELEEK-A---PLQ-FSKDTYEEELEV | 277 |
| WP_002288990 | 212 | LTDK-ISKSAKKDRVLKL-F-PN EKSNGCFAEFLKLIVGNQADFKKHP--ELEEK-A---PLQ-FSKDTYEEELEV | 277 |
| WP_002289641 | 212 | LTDK-ISKSAKKDRVLKL-F-PN EKSNGRFAEFLKLIVGNQADFKKHP--ELEEK-A---PLQ-FSKDTYEEELEV | 277 |
| WP_002290427 | 212 | LTDK-ISKSAKKDRVLKL-F-PN EKSNGRFAEFLKLIVGNQADFKKHP--ELEEK-A---PLQ-FSKDTYEEELEV | 277 |
| WP_002295753 | 212 | LTDK-ISKSAKKDRVLKL-F-PN EKSNGRFAEFLKLIVGNQADFKKHP--ELEEK-A---PLQ-LSKDTYEEELEV | 277 |
| WP_002296423 | 212 | LTDK-ISKSAKKDRVLKL-F-PN EKSNGRFAEFLKLIVGNQADFKKHP--ELEEK-A---PLQ-FSKDIYEEELEV | 277 |
| WP_002304487 | 212 | LTEK-VSKSRRLENLVEC-Y-PT EKKNTLFGNLIALSLGLQPNFKTNF--QLSED-A---KLQ-FSKDTYEEDLEG | 277 |
| WP_002305844 | 212 | LTDK-ISKSAKKDRVLKL-F-PN EKSNGRFAEFLKLIVGNQADFKKHP--ELEEK-A---PLQ-FSKDTYEEELEV | 277 |
| WP_002307203 | 212 | LTDK-ISKSAKKDRVLKL-F-PN EKSNGRFAEFLKLIVGNQADFKKHP--ELEEK-A---PLQ-LSKDTYEEELEV | 277 |
| WP_002310390 | 212 | LTEK-ISKSRRLEKLINN-Y-PK EKKNTLFGNLIALSLGLQPNFKTNF--KLSED-A---KLQ-FSKDTYEEDLEE | 277 |
| WP_002352408 | 212 | LTDK-ISKSAKKDRVLKL-F-PN EKSNGRFAEFLKLIVGNQADFKKHF--ELEEK-A---PLQ-FSKDTYEEELEV | 277 |
| WP_012997688 | 212 | LTDK-ISKSAKKDRVLKL-F-PN EKSNGRFAEFLKLIVGNQADFKKHF--ELEEK-A---PLQ-FSKDTYEEELEV | 277 |
| WP_014677909 | 212 | LTDK-ISKSAKKDRVLKL-F-PN EKSNGRFAEFLKLIVGNQADFKKHF--ELEEK-A---PLQ-FSKDTYEEELEV | 277 |
| WP_019312892 | 212 | LTDK-ISKSAKKDRVLKL-F-PN EKSNGRFAEFLKLIVGNQADFKKHF--ELEEK-A---PLQ-FSKDIYEEELEV | 277 |
| WP_019313659 | 212 | LTDK-ISKSAKKDRVLKL-F-PN EKSNGRFAEFLKLIIGNQADFKKHF--ELEEK-A---PLQ-FSKDTYEEELEV | 277 |
| WP_019314093 | 212 | LTEK-ISKSRRLEKLINN-Y-PK EKKNTLFGNLIALSLGLQPNFKTNF--KLSED-A---KLQ-LSKDTYEEDLEV | 277 |
| WP_019315370 | 212 | LTDK-ISKSAKKDRVLKL-F-PN EKSNGRFAEFLKLIVGNQADFKKHP--ELEEK-A---PLQ-FSKDTYEEELEV | 277 |
| WP_019803776 | 212 | LTDK-ISKSAKKDRVLKL-F-PN EKSNGRFAEFLKLIVGNQADFKKHP--ELEEK-V---PLQ-FSKDIYEEELEV | 277 |
| WP_019805234 | 212 | LTDK-ISKSAKKDRVLKL-F-PN EKSNGRFAEFLKLIVGNQADFKKHF--ELEEK-A---PLQ-FSKDTYEEELEV | 277 |
| WP_024783594 | 212 | LTDK-ISKSAKKDRVLKL-F-PN EKSNGRFAEFLKLIVGNQADFKKHP--ELEEK-A---PLQ-FSKDTYEEELEV | 277 |
| WP_024784288 | 212 | LTEK-ISKSRRLEKLINN-Y-PK EKKNTLFGNLIALSLGLQPNFKTNF--KLSED-A---KLQ-FSKDTYEEDLEE | 277 |
| WP_024784666 | 212 | LTDK-ISKSAKKDRVLKL-F-PN EKSNGRFAEFLKLIVGNQADFKKHF--ELEEK-A---PLQ-FSKDTYEEELEV | 277 |
| WP_024784894 | 212 | LTDK-ISKSAKKDRVLKL-F-PN EKSNGRFAEFLKLIVGNQADFKKHF--ELEEK-A---PLQ-FSKDTYEEELEV | 277 |
| WP_024786433 | 212 | LTEK-ISKSRRLEKLINN-Y-PK EKKNTLFGNLIALSLGLQPNFKTNF--KLSED-A---KLQ-FSKDTYEEDLEE | 277 |
| WP_049467010 | 212 | LTDK-ISKSAKKDRVLKL-F-PN EKSNGRFAEFLKLIVGNQADFKKHF--ELEEK-A---PLQ-FSKDTYEEELEV | 277 |
| WP_049473442 | 212 | LTDK-ISKSAKKDRVLKL-F-PN EKSNGRFAEFLKLIVGNQADFKKHF--ELEEK-A---PLQ-FSKDTYEEELEV | 277 |
| WP_049474547 | 212 | LTDK-ISKSAKKDRVLKL-F-PN EKSNGRFAEFLKLIVGNQADFKKHF--ELEEK-A---PLQ-FSKDTYEEELEV | 277 |
| EMC03581 | 205 | FTDK-ISKSAKRERVLKL-F-PD EKSTGLFSEFLKLIVGNQADFKKHF--ELEEK-A---PLQ-FSRDTYDEDLEN | 270 |
| WP_000428612 | 213 | FTDK-ISKSAKRERVLKL-F-PD EKSTGLFSEFLKLIVGNQADFKKHF--DLEEK-A---PLQ-FSKDTYDEDLEN | 278 |
| WP_000428613 | 213 | FTDK-ISKSAKRERVLKL-F-PD EKSTGLFSEFLKLIVGNQADFKKHF--DLGEK-A---PLQ-FSKDTYDEDLEN | 278 |
| WP_049523028 | 212 | FTDK-ISKSAKRDRVLKL-F-PD EKSTGLFSEFLKLIVGNQADFKKHF--DLEEK-A---PLQ-FSKDTYEEDLES | 277 |
| WP_003107102 | 181 | LTEK-MSKSRRLENLIAK-I-PN QKKNTLFGNLISLSLGLTPNFKANF--ELSED-A---KLQ-ISKESFEEDLDN | 246 |
| WP_054279288 | 214 | LTEK-ISKTRRLENLISN-I-PG QKKNGLFGNLIALSLGLTPNFKSHF--NLPED-A---KLQ-LAKDTYDEELNN | 279 |

```
WP_049531101   213 FTDK-ISKSTKRERVLKL-F-PD QKSTGLFSEFLKLIVGNQADFKKHF--DLEEK-A---PLQ--FSKDTYDEDLEN 278
WP_049538452   213 FSDK-ISKSAKRERVLKL-F-PD EKSTGLFSEFLKLIVGNQADFKKHF--DLEEK-A---PLQ--FSKDTYDEDLEN 278
WP_049549711   213 FTDK-ISKSAKRERVLKL-F-PD EKSTGLFSEFLKLIVGNQADFKKHF--DLGEK-A---PLQ--FSKDTYDEDLEN 278
WP_007896501   214 LTAK-TSKSKRLESLISE-F-PG QKKNGLFGNLLALALGLRPNFKSNF--GLSED-A---KLQ--ITKDTYEEELDN 279
EFR44625       166 LTAK-TSKSKRLESLISE-F-PG QKKNGLFGNLLALALGLRPNFKSNF--GLSED-A---KLQ--ITKDTYEEELDN 231
WP_002897477   212 FTDK-ISKSAKRERVLKL-F-PD EKSTGLFSEFLKLIVGNQADFKKHF--DLEEK-A---PLQ--FSKDTYDEELEN 277
WP_002906454   213 FTDK-ISKSTKRERVLKL-F-SD EKSTGLFSEFLKLIVGNQADFKKHF--DLEEK-A---PLQ--FSKDTYDEELEN 278
WP_009729476   213 FTDK-ISKSAKRERVLKL-F-PD EKSTGLFSEFLKLIVGNQADFKKHF--DLEEK-A---PLQ--FSRDTYDEDLEN 278
CQR24647       212 ITAK-ISKSRKVEAVLEQ-F-PD QKKNSFFGNMVSLVFGLMPNEKSNF--ELDED-A---KLQ--FSRDSYDEDLEN 277
WP_000066813   213 FTDK-ISKSTKRERVLKL-F-PD EKSTGLFSEFLKLIVGNQADFKKHF--DLEEK-A---PLQ--FSKDTYDEDLEN 278
WP_009754323   213 FTGK-ISKSVKREHVLKL-F-PD EKSTGLFSEFLKLIVGNQADFKKHF--DLGEK-A---SLQ--FSKDTYDEDLEN 278
WP_044674937   212 LVEK-VSKSRRLENILHY-F-PN EKKNGLFGNLLALALGLQPNEKTNF--ELAED-A---KIQ--FSKETYEEDLEE 277
WP_044676715   212 LVEK-VSKSRRLENILHY-F-PN EKKNGLFGNFLTLALGLQPNEKTNF--ELAED-A---KIQ--FSKETYEEDLEE 277
WP_044680361   212 LVEK-VSKSRRLENILHY-F-PN EKKNGLFGNFLALALGLQPNEKTNF--ELAED-A---KIQ--FSKETYEEDLEE 277
WP_044681799   212 LVEK-VSKSRRLENILHY-F-PN EKKNGLFGNFLALALGLQPNEKTNF--ELAED-A---KIQ--FSKETYEEDLEE 277
WP_049533112   212 LTEK-VSKSRRLENLIAH-Y-PA EKKNTLFGNLIALSLGLQPNEKTNF--QLSED-A---KLQ--FSKDTYEEDLEG 277
WP_029090905   172 LLDRmMNRSSKVKFLIEL--TG KQDKPLLKELFNLIVGLKAKPASIFe---QENIATiveTM-nMSTEQVQLDLLT 243
WP_006506696   211 LKKP-LSKKAKVDEVMTL-IaPE KDYKSAFKELVTGIAGNKMNVTKMI1cEPIKQ-Gds-EIK1kFSDSNYDDQFSE 283
AIT42264       212 LSAR-LSKSRRLENLIAQ-L-PG EKKNGLFGNLIALSLGLIPNEKSNF--DLAED-A---KLQ--LSKDTYDDDLDN 277
WP_034440723   218 FKQD-ISRSKKLDQAIAL-F-QG -KRQSLFGIFLTLIVGNKANFQKIF--NLEDD----iKLD--lKEEDYDENLEE 283
AKQ21048       212 LSAR-LSKSRRLENLIAQ-L-PG EKKNGLFGNLIALSLGLIPNEKSNF--DLAED-A---KLQ--LSKDTYDDDLDN 277
WP_004636532   211 LSSK-QSRSRKHEQIMAL-F-PN ENKLGNFGRFMLIVGNTSNFKPVF--DLDDE-Y---KLK--LSDETYEEDLDT 276
WP_002378009   218 LTEK-ASRTKKSSEKVLQQ-F-PQ EKANGLFGQFKLMVGNKADFKKVF--GLEEE-A---KI---tYASESYEEDLEG 283
WP_002407324   218 LTEK-ASRTKKSSEKVLQQ-F-PQ EKANGLFGQFKLMVGNKADFKKVF--GLEEE-A---KI---tYASESYEEDLEG 283
WP_002413717   169 LTEK-ASRTKKSSEKVLQQ-F-PQ EKANGLFGQFKLMVGNKADFKKVF--GLEEE-A---KI---tYASESYEEDLEG 234
EM575795         1 ---------------------- -------------------------  MDEE-A---KI---LSKESYEEELES  20
WP_002373311   218 LTEK-ASRTKKSSEKVLQQ-F-PQ EKANGLFGQFKLMVGNKADFKKVF--GLEEE-A---KI---tYASESYEEDLEG 283
WP_010775580   218 LTEK-ASRTKKSSEKVLQQ-F-PQ EKANGLFGQFKLMVGNKADFKKVF--GLEEE-A---KIKitYASESYEEDLEG 285
WP_010818269   218 LTEK-ASRTKKSSEKVLQQ-F-PQ EKANGLFGQFKLMVGNKADFKKVF--GLEEE-A---KI---tYASESYEEDLEG 283
WP_010824395   218 LTEK-ASRTKKSSEKVLQQ-F-PQ EKANGLFGQFKLMVGNKADFKKVF--GLEEE-A---KI---tYASESYEEDLEG 283
WP_016622645   218 LTEK-ASRTKKSSEKVLQQ-F-PQ EKANGLFGQFKLMVGNKADFKKVF--GLEEE-A---KI---tYASESYEEDLEG 283
WP_033624816   218 LTEK-ASRTKKSSEKVLQQ-F-PQ EKANGLFGQFKLMVGNKADFKKVF--GLEEE-A---KI---tYASESYEEDLEG 283
WP_033625576   218 LTEK-ASRTKKSSEKVLQQ-F-PQ EKANGLFGQFKLMVGNKADFKKVF--GLEEE-A---KI---tYASESYEEDLEG 283
WP_033789179   218 LTEK-ASRTKKSSEKVLQQ-F-PQ EKANGLFGQFKLMVGNKADFKKVF--GLEEE-A---KI---tYASESYEEDLEG 283
WP_002310644   217 FTEK-MSKTKKAETLLKY-F-PH EKSNGYLSQFIKLMVGNQGNFKNVF--GL-EE-A---KLQ--FSKETYEEDLEE 281
WP_002312694   217 FTEK-MSKTKKAETLLKY-F-PH EKSNGYLSQFIKLMVGNQGNFKNVF--GL-EEeA---KLQ--FSKETYEEDLEE 282
WP_002314015   217 FTEK-MSKTKKAETLLKY-F-PH EKSNGYLSQFIKLMVGNQGNFKNVF--GL-EEeA---KLQ--FSKETYEEDLEE 282
WP_002320716   217 FTEK-MSKTKKAETLLKY-F-PH EKSNGYLSQFIKLMVGNQGNFKNVF--GL-EE-A---KLQ--FSKETYEEDLEE 281
WP_002330729   217 FTEK-MSKTKKAETLLKY-F-PH EKSNGYLSQFIKLMVGNQGNFKNVF--GL-EEeA---KLQ--FSKETYEEDLEE 282
WP_002335161   217 FTEK-MSKTKKAETLLKY-F-PH EKSNGYLSQFIKLMVGNQGNFKNVF--GL-EEeA---KLQ--FSKETYEEDLEE 282
WP_002345439   217 FTEK-MSKTKKAETLLKY-F-PH EKSNGYLSQFIKLMVGNQANFKRIF--DL-EAE-V---KLQ--FSKETYEEDLES 282
WP_034867970   210 LTDK-LSKTKKVBEILKY-Y-PT EKINSFFAQCLKLIVGNQANFKRIF--DL-EAE-V---KLQ--FSKETYEEDLES 275
WP_047937432   217 FTEK-MSKTKKAETLLKY-F-PH EKSNGYLSQFIKLMVGNQGNFKNVF--GL-EEeA---KLQ--FSKETYEEDLEE 282
WP_010720994   210 LTDK-LSKTKKVBEILKY-Y-PT EKINSFFAQCLKLIVGNQANFKRIF--DL-EAE-V---KLQ--FSKETYEEDLES 275
WP_010737004   210 LTDK-LSKTKKVEEILKY-Y-PT EKINSFFAQCLKLIVGNQANFKRIF--DL-EAE-V---KLQ--FSKETYEEDLES 275
WP_034700478   210 LTDK-LSKTKKVEEILKY-Y-PT EKINSFFAQCLKLIVGNQANFKRIF--DL-EAE-V---KLQ--FSKETYEEDLES 275
WP_037009003   215 LTQQ-LSKSERADNVLKL-Y-PD EKGTGIFAQFIKLIVGNQGNFKNVF--QL-EED----qKLQ--LSTDDYEENIEN 280
WP_023519017   210 LTER-LSKAKRVEKVLAY-Y-PS EKSTGNFAQFLKLMVGNQANFKKTF--DL-EEE-M---KLN--FTRDCYEBDLNE 275
WP_010770040   213 FSEK-VSRARKVEAILSV-Y-SE EKRNGTFDQFLKMIVGNQRFKKTF--DL-EEED-G---IIQ--IPKEEYEEELET 278
WP_048604708   209 FADK-VSRAKKAEGVLAL-F-PD EKTTGCLAQFLKLIVGNQAF--HLDEE-V---KLQ--FSKEEYDESLEA 274
WP_010750235   210 LTDK-LSKSKKVEKILQY-Y-PK EKTTGCLAQFLKLIVGNQNFKQAF--HLDEE-V---KLQ--lSKETYEEDLEK 275
```

-continued

```
AII16583           251 LSAR-LSKSRRLENLIAQ-L-PG EKKNGLFGNLIALSLGLTPNEKSNF--DLAED-A---KLQ-LSKDTYDDDLDN 316
WP_029073316       216 LKEP-LSKKHKADKAFAL-FdTT KDNKAAYKELCAALAGNKFNVTKMLkeAELHD-EdekDISfkFSDATFDDAFVE 289
WP_031589969       216 LKEP-LSKKHKAEKAFAL-FdTT KDNKAAYKELCAALAGNKFNVTKMLkeAELHD-EdekDISfkFSDATFDDAFVE 289
KDA45870           210 FKDNtFSKTKKSEELLKL---SG -KKNQLAHQLFKMVGNMGSFKKVL--GTDEE---hKLiS--FGKDTYEDDLND 275
WP_039099354       207 LLDNhQSASNRQRQALLLiYtPS KQNKAIATELLKAILGLKAKFNVLT-GlEAEGVktwTLT-FNAENFDEEMVK 285
AKP02966           209 LIGR-GNATQKSSNILNN-F--T KETKKLLKEVINLILGNVAHLNTIFKtSLTKDeE--KLiS-FSGKDIESKLDD 278
WP_010991369       218 LVEK-VTRKEKLERILKL-Y-PG EKSAGMFAQFISLIVGSKGNFQKPF--DLIEK-S---DIE-CAKDSYEEDLES 283
WP_033838504       218 LVEK-VTRKEKLERILKL-Y-PG EKSAGMFAQFISLIVGSKGNFQKPF--DLIEK-S---DIE-CAKDSYEEDLES 283
EHN60060           221 LVEK-VTRKEKLERILKL-Y-PG EKSAGMFAQFISLIVGSKGNFQKPF--DLIEK-S---DIE-CAKDSYEEDLES 286
EFR89594             1 --------------------- ------------LKL-Y-PG EKSTGMFAQFISLIVGSKGNFQKVF--DLIEK-S---EIE-CAKDTYEEDLES 52
WP_038409211       218 LSEK-LTRREKLDKILKL-Y-TG EKSTGMFARFINLIGSKGDFKKVF--DLDEK-A---EIE-CAKDTYEEDLEA 283
EFR95520             1 ------------------------ ------------LKL-Y-PG EKSTGMFAQFISLIVGSKGNFQKVF--DLIEK-T---DIE-CAKDSYEEDLET 
WP_003723650       218 LAGK-FTRREKFERILQL-Y-PG EKSTGMFAQFISLIVGSKGNFQKVF--DLIEK-T---DIE-CAKDSYEEDLET 283
WP_003727705       218 LAGK-FTRREKFERILRL-Y-PG EKSTGMFAQFISLIVGNKGNFQKVF--NLVEK-T---DIN-CAEDSYEEDLEA 283
WP_003730785       218 LAGK-FTRREKFERILRL-Y-PG EKSTGMFAQFISLIVGNKGNFQKVF--NLVEK-T---DIN-CAEDTYDTDLES 283
WP_003733029       218 LAEK-FTRKDKLDKILSL-Y-PG EKTTGVFAQFVNIIVGSTGKEKKHF--NLHEK-K---DIN-CAEDTYDTDLES 283
WP_003739838       218 LAGK-FTRREKFERILQL-Y-PG EKSTGMFAQFISLIVGSKGNFQKVF--DLIVEK-T---DIE-CAKDSYEEDLEA 283
WP_014601172       218 LAGK-FTRREKFERILQL-Y-PG EKSTGMFAQFISLIVGSKGNFQKVF--DLIEK-T---DIE-CAKDSYEEDLEA 283
WP_023548323       218 LAGK-FTRREKFERILQL-Y-PG EKSTGMFAQFISLIVGSKGNFQKVF--DLIEK-T---DIE-CAKDSYEEDLEA 283
WP_031665337       218 LAGK-FTRREKFERILQL-Y-PG EKSTGMFAQFISLIVGSKGNFQKVF--DLIEK-T---DIE-CAKDSYEEDLET 283
WP_031669209       218 LAEK-FTRKDKLDKILSL-Y-PG EKTTGVFAQFVNIIVGSTGKEKKHF--NLHEK-K---DIN-CAEDTYDTDLES 283
WP_033920898       218 LARK-FTRREKFERILQL-Y-PG EKSTGMFAQFISLIVGSKGNFQKVF--DLIEK-T---DIE-CAKDSYEEDLES 283
AKI42028           221 LARK-FTRREKFERILQL-Y-PG EKSTGMFAQFISLIVGSKGNFQKVF--DLIEK-T---DIE-CAKDSYEEDLEA 286
AKI50529           221 LARK-FTRREKFERILQL-Y-PG EKSTGMFAQFISLIVGSKGNFQKVF--DLIEK-T---DIE-CAKDSYEEDLET 286
EFR83390             1 --------------------- --------------------- ------------------------ 
WP_046323366       218 FSEK-LTKREKLDKILNL-Y-PN EKSTDLFAQFISLIIGSKGNEKKPF--NLTEK-T---DIE-CAKDSYEEDLEV 283
AKE81011           228 LSAR-LSKSRRLENLIAQ-L-PG EKKNGLEGNLIALSLGLTPNEKSNF--DLAED-A---KLQ-LSKDTYDDDLDN 293
CU082355           215 LKKP-LSKKAKVDEVMAL-ISPE KEFKSAYKELVTGIAGNKMNVTKMIlcESIKQ-Gds-EIKlkFSDSNYDDQFSE 287
WP_033162887       216 LSKI-YQRSKKADDLLKI-MnPT KEEBKAAYKEFTKALVGLKFNISKMIlaQEVKK-Gdt-DIVleFSNANYDSTIDE 288
AGZ01981           245 LSAR-LSKSRRLENLIAQ-L-PG EKKNGLEGNLIALSLGLTPNEKSNF--DLAED-A---KLQ-LSKDTYDDDLDN 310
AKA60242           212 LSAR-LSKSRRLENLIAQ-L-PG EKKNGLEGNLIALSLGLTPNEKSNF--DLAED-A---KLQ-LSKDTYDDDLDN 277
AKS40380           216 LSAR-LSKSRRLENLIAQ-L-PG EKKNGLEGNLIALSLGLTPNEKSNF--DLAED-A---KLQ-LSKDTYDDDLDN 281
4UN5_B             278 LLAQIGDQYADLFLAAKNLSDAILLSDILRVNTEITKAPLSASMIKRYDEHHQDLTLLKALVRQQ-LPEKYKEIFFDQSK 356
WP_010922251       279 LLGKIGDDYADLFTSAKNLYDAILLSGILTVDDNSTKAPLSASMIKRYVEHHEDLEKLKEFIKAN-KSELYHDIFKDKNK 357
WP_039695303       278 LLGQIGDDFTDLFVSAKKLYDAILLYDAILLSGILTVTDPSTKAPLSASMIKRYENHQNDLAAIKQFIKNN-LPEKYDEVFSDQSK 356
WP_045635197       158 --------------------- --------------------- -------LERLKKDG---- ----LPEKYKEIFFDQSK 168
5AXW_A               1 --------------------- --------------------- LSASMIKRYDEHHQDLTLLKALVRQQ-LPEKYKEIFFDQSK 40
WP_009880683       278 LLAQIGDQYADLFLAAKNLSDAILLSDILRVNTEITKAPLSASMIKRYDEHHQDLTLLKALVRQQ-LPEKYKEIFFDQSK 356
WP_010922251       278 LLAQIGDQYADLFLAAKNLSDAILLSDILRVNTEITKAPLSASMIKRYDEHHQDLTLLKALVRQQ-LPEKYKEIFFDQSK 356
WP_011054416       278 LLAQIGDQYADLFLAAKNLSDATLLSDILRVNSEITKAPLSASMIKRYDEHHQDLTLLKALVRQQ-LPEKYKEIFFDQSK 356
WP_011284745       278 LLAQIGDQYADLFLAAKNLSDAILLSDILRVNSEITKAPLSASMIKRYDEHHQDLTLLKALVRQQ-LPEKYKEIFFDQSK 356
WP_011285506       278 LLAQIGDQYADLFLAAKNLSDAILLSDILRLNSEITKAPLSASMIKRYDEHHQDLTLLKALVRQQ-LPEKYKEIFFDQSK 356
WP_011527619       278 LLAQIGDQYADLFLAAKNLSDAILLSDILRVNSEITKAPLSASMIKRYDEHHQDLTLLKALVRQQ-LPEKYKEIFFDQSK 356
WP_012560673       278 LLAQIGDQYADLFLAAKNLSDAILLSDILRVNSEITKAPLSASMIKRYDEHHQDLTLLKALVRQQ-LPEKYKEIFFDQSK 356
WP_014407541       278 LLAQIGDQYADLFLAAKNLSDAILLSDILRLNSEITKAPLSASMIKRYDEHHQDLTLLKALVRQQ-LPEKYKEIFFDQSK 356
WP_023080005       278 LLAQIGDQYADLFLAAKNLSDAILLSDILRVNSEITKAPLSASMIKRYDEHHQDLTLLKALVRQQ-LPEKYKEIFFDQSK 356
WP_023610282       278 LLAQIGDQYADLFLAAKNLSDAILLSDILRVNSEITKAPLSASMIKRYDEHHQDLTLLKALVRQQ-LPEKYKEIFFDQSK 356
WP_030126706       278 LLAQIGDQYADLFLAAKNLSDAILLSDILRVNSEITKASLSASMIKRYDEHHQDLTLLKALVRQQ-LPEKYKEIFFDQSK 356
WP_031488318       278 LLAQIGDQYADLFLAAKNLSDATLLSDILRVNSEITKAPLSASMIKRYDEHHQDLTLLKALVRQQ-LPEKYKEIFFDQSK 356
WP_032460140       278 LLAQIGDQYADLFLAAKNLSDAILLSDILRVNSEITKAPLSASMIKRYDEHHQDLTLLKALVRQQ-LPEKYKEIFFDQSK 356
WP_032461047       278 LLAQIGDQYADLFLAAKNLSDAILLSDILRVNSEITKAPLSASMIKRYDEHHQDLTLLKALVRQQ-LPEKYKEIFFDQSK 356
```

-continued

```
WP_032462016    278  LLAQIGDQYADLFLAAKNLSDAILLSDILRVNTEITKAPLSASMIKRYDEHHQDLTLLKALVRQQ-LPEKYKEIFFDQSK  356
WP_032462936    278  LLAQIGDQYADLFLAAKNLSDAILLSDILRVNSEITKAPLSASMIKRYDEHHQDLTLLKALVRQQ-LPEKYKEIFFDQSK  356
WP_032464890    278  LLAQIGDQYADLFLAAKNLSDAILLSDILRLNSEITKAPLSASMIKRYDEHHQDLTLLKALVRQQ-LPEKYKEIFFDQSK  356
WP_033888930    103  LLAQIGDQYADLFLAAKNLSDAILLSDILRVNTEITKAPLSASMIKRYDEHHQDLTLLKALVRQQ-LPEKYKEIFFDQSK  181
WP_038431314    278  LLAQIGDQYADLFLAAKNLSDATLLSDILRVNSEITKAPLSASMIKRYDEHHQDLTLLKALVRQQ-LPEKYKEIFFDQSK  356
WP_038432938    278  LLAQIGDQYADLFLAAKNLSDAILLSDILRVNSEITKAPLSASMIKRYDEHHQDLTLLKALVRQQ-LPEKYKEIFFDQSK  356
WP_038434062    278  LLAQIGDQYADLFLAAKNLSDAILLSDILRVNSEITKAPLSASMIKRYDEHHQDLTLLKALVRQQ-LPEKYKEIFFDQSK  356
BAQ51233        189  LLAQIGDQYADLFLAAKNLSDAILLSDILRVNTEITKAPLSASMIKRYDEHHQDLTLLKALVRQQ-LPEKYKEIFFDQSK  267
KGE60162             --------------------------------------------------------------------------------
KGE60856             --------------------------------------------------------------------------------
WP_002989955    278  LLAQIGDQYADLFLAAKNLSDAILLSDILRLNSEITKAPLSASMIKRYDEHHQDLTLLKALVRQQ-LPEKYKEIFFDQSK  356
WP_003030002    278  LLGEIGDEYADLFSAAKNLYDAILLSGILLTVDDNSTKAPLSASMVKRYEEHQKDLKKLKDFIKVN-APDQYNAIFKDKNK  356
WP_003065552    281  LLGKIGDDYADLFTSAKNLYDAILLSGILIVDDNSTKAPLSASMIKRYVEHQEDLEKLKEFIKAN-KSELYHDIFKDKNK  359
WP_001040076    279  LLGQIGDEFADLFSAAKKLYDSVLLSGILTVIDLSTKAPLSTKAPLSASMIQRYDEHREDLKQLKQFVKAS-LPEKYQEIFADSSK  357
WP_001040078    279  LLGQIGDEFADLFSAAKKLYDSVLLSGILTVIDLSTKAPLSASMIQRYDEHREDLKQLKQFVKAS-LPEKYQEIFADSSK  357
WP_001040080    279  LLGQIGDEFADLFSAAKKLYDSVLLSGILTVIDLSTKAPLSASMIQRYDEHREDLKQLKQFVKAS-LPEKYQEIFADSSK  357
WP_001040081    279  LLGQIGDEFADLFSAAKKLYDSVLLSGILTVIDLSTKAPLSASMIQRYDEHREDLKQLKQFVKAS-LPEKYQEIFADSSK  357
WP_001040083    279  LLGQIGDEFADLFSAAKKLYDSVLLSGILTVIDLSTKAPLSASMIQRYDEHREDLKQLKQFVKAS-LPEKYQEIFADSSK  357
WP_001040085    279  LLGQIGDEFADLFSAAKKLYDSVLLSGILTVIDLSTKAPLSASMIQRYDEHREDLKQLKQFVKAS-LPEKYQEIFADSSK  357
WP_001040087    279  LLGQIGDEFADLFSAAKKLYDSVLLSGILTVIDLSTKAPLSASMIQRYDEHREDLKQLKQFVKAS-LPEKYQEIFADSSK  357
WP_001040088    279  LLGQIGDEFADLFSAAKKLYDSVLLSGILTVIDLSTKAPLSASMIQRYDEHREDLKQLKQFVKAS-LPEKYQEIFADSSK  357
WP_001040089    279  LLGQIGDEFADLFSAAKKLYDSVLLSGILTVIDLSTKAPLSASMIQRYDEHREDLKQLKQFVKAS-LPEKYQEIFADSSK  357
WP_001040090    279  LLGQIGDEFADLFSAAKKLYDSVLLSGILTVIDLSTKAPLSASMIQRYDEHREDLKQLKQFVKAS-LPEKYQEIFADSSK  357
WP_001040091    279  LLRQIGDEFADLFSAAKKLYDSVLLSGILTVIDLSTKAPLSASMIQRYDEHREDLKQLKQFVKAS-LPEKYQEIFADSSK  357
WP_001040092    279  LLGQIGDEFADLFSAAKKLYDSVLLSGILTVIDLSTKAPLSASMIQRYDEHREDLKQLKQFVKAS-LPEKYQEIFADSSK  357
WP_001040094    279  LLGQIGDEFADLFSAAKKLYDSVLLSGILTVIDLSTKAPLSAVMIQRYDEHREDLKQLKQFVKAS-LPEKYQEIFADSSK  357
WP_001040095    279  LLGQIGDEFADLFSAAKKLYDSVLLSGILTVIDLSTKAPLSASMIQHYDEHREDLKQLKQFVKAS-LPEKYQEIFADSSK  357
WP_001040096    279  LLGQIGDEFADLFSAAKKLYDSVLLSGILTVIDLSTKAPLSASMIQRYDEHREDLKQLKQFVKAS-LPEKYQEIFADSSK  357
WP_001040097    279  LLGQIGDEFADLFSAAKKLYDSVLLSGILTVIDLSTKAPLSASMIQRYDEHREDLKQLKQFVKAS-LPEKYQEIFADSSK  357
WP_001040098    279  LLGQIGDEFADLFSAAKKLYDSVLLSGILTVIDLSTKAPLSASMIQRYDEHREDLKQLKQFVKAS-LPEKYQEIFADSSK  357
WP_001040099    279  LLGQIGDEFADLFSAAKKLYDSVLLSGILTVIDLSTKAPLSASMIQRYDEHREDLKQLKQFVKAS-LPEKYQEIFADSSK  357
WP_001040100    279  LLGQIGDEFADLFSAAKKLYDSVLLSGILTVIDLSTKAPLSASMIQRYDEHREDLKQLKQFVKAS-LPEKYQEIFADSSK  357
WP_001040104    279  LLGQIGDEFADLFSAAKKLYDSVLLSGILTVIDLSTKAPLSASMIQRYDEHREDLKQLKQFVKAS-LPEKYQEIFADSSK  357
WP_001040105    279  LLGQIGDEFADLFSAAKKLYDSVLLSGILTVIDLSTKAPLSASMIQRYDEHREDLKQLKQFVKAS-LPEKYQEIFADSSK  357
WP_001040106    279  LLGQIGDEFADLFSVAKKLYDSVLLSGILTVIDLSTKAPLSASMIQRYDEHREDLKQLKQFVKAS-LPEKYQEIFADSSK  357
WP_001040107    279  LLGQIGDEFADLFSVAKKLYDSVLLSGILTVIDLSTKAPLSASMIQRYDEHREDLKQLKQFVKAS-LPEKYQEIFTDSSK  357
WP_001040108    279  LLGQIGDEFADLFSVAKKLYDSVLLSGILTVIDLSTKAPLSASMIQRYDEHREDLKQLKQFVKAS-LPEKYQEIFTDSSK  357
WP_001040109    279  LLGQIGDEFADLFSVAKKLYDSVLLSGILTVIDLSTKAPLSASMIQRYDEHREDLKQLKQFVKAS-LPEKYQEIFTDSSK  357
WP_001040110    279  LLGQIGDEFADLFSVAKKLYDSVLLSGILTVIDLSTKAPLSASMIQRYDEHREDLKQLKQFVKAS-LPEKYQEIFADSSK  357
WP_015058523    279  LLGQIGDEFADLFSAAKKLYDSVLLSGILTVIDLSTKAPLSASMIQRYDEHREDLKQLKQFVKAS-LPEKYQEIFADSSK  357
WP_017643650    279  LLGQIGDEFADLFSVAKKLYDSVLLSGILTVIDLSTKAPLSASMIQRYDEHREDLKQLKQFVKAS-LPEKYQEIFADSSK  357
WP_017647151    279  LLGQIGDEFADLFSVAKKLYDSVLLSGILTVIDLSTKAPLSASMIQRYDEHREDLKQLKQFVKAS-LPEKYQEIFADSSK  357
WP_017648376    279  LLGQIGDEFADLFSVAKKLYDSVLLSGILTVIDLSTKAPLSASMIQRYDEHREDLKQLKQFVKAS-LPEKYQEIFTDSSK  357
WP_017649527    279  LLGQIGDEFADLFSVAKKLYDSVLLSGILTVIDLSTKAPLSASMIQRYDEHREDLKQLKQFVKAS-LPEKYQEIFTDSSK  357
WP_017771611    279  LLGQIGDEFADLFSAAKKLYDSVLLSGILTVTALSTKAPLSASMIQRYDEHREDLKQLKQFVKAS-LPEKYQEIFTDSSK  357
WP_017771984    279  LLGQIGDEFADLFSAAKKLYDSVLLSGILTVIDLSTKAPLSASMIQRYDEHREDLKQLKQFVKAS-LPEKYQEIFTDSSK  357
CFQ25032        279  LLGQIGDEFADLFSAAKKLYDSVLLSGILTVIDLSTKAPLSASMIQRYDEHREDLKQLKQFVKAS-LPEKYQEIFADSSK  357
CFV16040        279  LLGQIGDEFADLFSAAKKLYDSVLLSGILTVIDLSTKASLSDSMIQRYDEHREDLKQLKQFVKAS-LPEKYQEIFADSSK  357
KLJ37842        279  LLGQIGDEFADLFSAAKKLYDSVLLSGILTVIDLSTKAPLSASMIQRYDEHREDLKQLKQFVKAS-LPEKYQEIFADSSK  357
KLJ72361        279  LLGQIGDEFADLFSAAKKLYDSVLLSGILTVIDLSTKAPLSASMIQRYDEHREDLKQLKQFVKAS-LPEKYQEIFADSSK  357
KLL20707        279  LLGQIGDEFADLFSAAKKLYDSVLLSGILTVIDLSTKAPLSASMIQRYDEHREDLKQLKQFVKAS-LPEKYQEIFTDSSK  357
KLL42645        279  LLGQIGDEFADLFSVAKKLYDSVLLSGILTVIDLSTKAPLSASMIQRYDEHREDLKQLKQFVKAS-LPEKYQEIFADSSK  357
WP_047207273    279  LLGQIGDEFADLFSAAKKLYDSVLLSGILTVIDLSTKAPLSASMIQRYDEHREDLKQLKQFVKAS-LPEKYQEIFADSSK  357
```

-continued

```
WP_47209694     279 LLGQIGDEFADLFSAAKKLYDSVLLSGILTVIDLSTKAPLSASMIQRYDEHREDLKQLKQFVKAS-LPEKYQEIFADSSK 357
WP_050198062    279 LLGQIGDEFADLFSAAKKLYDSVLLSGILTVIDLSTKAPLSASMIQRYDEHREDLKQLKQFVKAS-LPEKYQEIFADSSK 357
WP_050201642    279 LLGQIGDEFADLFSAAKKLYDSVLLSGILTVIDLSTKAPLSASMIQRYDEHREDLKQLKQFVKAS-LPEKYQEIFADSSK 357
WP_050204027    279 LLGQIGDEFADLFSVAKKLYDSVLLSGILTVIDLSTKAPLSASMIQRYDEHREDLKQLKQFVKAS-LPEKYQEIFTDSSK 357
WP_050881965    279 LLGQIGDEFADLFSAAKKLYDSVLLSGILTVIDLSTKAPLSASMIQRYDEHREDLKQLKQFVKAS-LPEKYQEIFADSSK 357
WP_050886065    279 LLGQIGDEFADLFSAAKKLYDSVLLSGILTVIDLSTKAPLSASMIQRYDEHREDLKQLKQFVKAS-LPEKYQEIFADSSK 357
AHN30376        279 LLGQIGDEFADLFSAAKKLYDSVLLSGILTVIDLSTKAPLSASMIQRYDEHREDLKQLKQFVKAS-LPEKYQEIFADSSK 357
EA078426        279 LLGQIGDEFADLFSAAKKLYDSVLLSGILTVIDLSTKAPLSASMIQRYDEHREDLKQLKQFVKAS-LPEKYQEIFADSSK 357
CCW42055        279 LLGQIGDEFADLFSAAKNLYDAILLSGILTVIDLSTKAPLSASMVKRYEEHQKDLKKKPEDFIKVN-ALDQYNAIFKDKNK 356
WP_003041502    278 LLGEVGDEYADLFASAKNLYDAILLSGILAVDDNTTKAPLSASMVKRYEEHQKDLKKLKDFIKVN-APDQYNAIFKDKNK 357
WP_037593752    279 LLGEIGDEFADLFASAKNLYDAILLSGILAVDDNTTKAPLSASMVKRYEEHQKDLKKLKDFIKVN-APDQYNAIFKDKNK 357
WP_049516684    279 LLGEIGDEYADLFASAKNLYDAILLSGILAVDDNTTKAPLSASMVKRYEEHQKDLKKLKDFIKVN-APAQYDDIFKDETK 357
GAD46167        279 LLGEIGDEYADLFASAKNLYDAILLSGILAVDDNTTKAPLSASMVKRYEEHQKDLKKLKDFIKVN-APDQYNAIFKDKNK 357
WP_018363470    279 LLGKIGDDYADLFTSSKNLYDAILLSGILTVDDNSTKAPLSASMIKRYVEHHEDLEKLKEFIKAN-KSELYHDIFKDKTQ 357
WP_003043819    278 LLGQIGDQYADLFSAAKNLSDAILLSDILRSNSEVTKAPLSASMVKRYDEHHQDLALLIKTLVRQQ-FPEKYAEIFKDDTK 356
WP_006269658    278 FLGEVGDEYADLFASAKNLYDAILLSGILTVDDNSTKAPLSASMVKRYEEHQKDLKKLKDFIKVN-APDQYNAIFKDKNK 356
WP_048800889    278 LLGKIGDDYADLFTSAKNLYDTILLSGILTVDDNSTKAPLSASMIKRYEEHQKDLKKLKDFIKVN-APAQYDDIFKDETK 356
WP_012677106    278 LLAQIGDQYADLFLAAKNLSDAILLSDILRVNSEITKAPLSASMIKRYDEHHQDLTLLKALVRQQ-LPEKYKEIFFDQSK 356
WP_014612333    278 LLAQIGNQYADLFLAAKNLSDAILLSDILRVNSEITKAPLSASMIKRYDEHHQDLTLLKALVRQQ-LPEKYKEIFFDQSK 356
WP_015017095    278 LLAQIGDQYADLFLAAKNLSDAILLSDILRVNSEITKAPLSASMIKRYDEHHQDLTLLKALVRQQ-LPEKYKEIFFDQSK 356
WP_015057649    278 LLAQIGDQYADLFLAAKNLSDAILLSDILRVNSEITKAPLSASMIKRYDEHHQDLTLLKALVRQQ-LPEKYKEIFFDQSK 356
WP_048327215    278 LLAQIGDQYADLFLAAKNLSDAILLSDILRVNSEITKAPLSASMIKRYDEHHQDLTLLKALVRQQ-LPEKYKEIFFDQSK 356
WP_049519324    278 LLAQIGDQYADLFLAAKNLSDAILLSDILTESDEITKAPLSASMVKRYREHHKDLVTLKTLIKDQ-LPEKYQEIFLDKTK 356
WP_012515931    278 LLAQIGDQYADLFLAAKNLSDAILLSDILTESDEITKAPLSASMVKRYREHHKDLVTLKTLIKDQ-LPEKYQEIFLDKTK 356
WP_021320964    278 LLAQIGDQYADLFLAAKNLSDAILLSDILTESDEITRAPLSASMVKRYREHHKDLVTLKTLIKDQ-LPEKYQEIFLDKTK 356
WP_037581760    278 LLAQIGDQYADLFLAAKNLSDAILLSDILTESDEITKAPLSASMVKRYREHHKDLVTLKTLIKDQ-LPEKYQEIFLDKTK 356
WP_044232481    279 LLAQIGDQYADLFTAAKNLSDAILLSGILTVDDNSTKAPLSASMIKRYEEHHEDLEKLKTFIKVN-NFDKYHEIFDKSK 357
WP_009854540    279 LLAQIGDEYADLFTSAKNLYDAILLSGILTVDDNSTKAPLSASMIKRYVEHHEDLEKLKEFIKAN-KSELYHDIFKDKNK 357
WP_012962174    279 LIGKIGDEYADLFTSAKNLYDAILLSGILTVADNTTKAPLSASMIKRYNEHQVDLKKLKEFIKNN-ASDKYDEIFNDKDK 357
WP_039695303    279 LLGKIGDQYADLFSAKNLYDAILLSDILTVKGASTKAPLSASMVQRYEEHQQDLALLIKNLVLKKQ-KLKLYHDIFKDKTK 357
WP_014333493    278 LLAAKLGDDYADLFSAKKLSDAILLSDITTVKGASTKAPLSASMVQRYEEHQQDLALLIKNLVKKQ-IPEKYKEIFDNKEK 356
WP_003099269    278 LLAQIGDQYADLFLAAKKLSDAILLSDITTVKGASTKAPLSASMVQRYEEHQQDLALLIKNLVKKQ-IPEKYKEIFDNKEK 356
AHY15608        278 LLAQIGDQYADLFIAAKKLSDAILLSDITTVKGASTKAPLSASMVQRYEEHQQDLALLKNLVKKQ-IPEKYKEIFDNKEK 356
AHY17476        278 LLAQIGDQYADLFIAAKKLSDAILLSDITTVKGASTKAPLSASMVQRYEEHQQDLALLKNLVKKQ-IPEKYKEIFDNKEK 356
ESR09100            ---------------------------------------------------------------------------------
AGM98575        278 LLAQIGDQYADLFIAAKKLSDAILLSDITTVKGASTKAPLSASMVQRYEEHQQDLALLKNLVKKQ-IPEKYKEIFDNKEK 356
ALF27331        278 LLAQIEDNYAELFLSAKKLYDSILLSGILTVTDVSTKAPLSASMIKRYEEHQMDLAQLKQFIRQK-LSDKYNEVFSDVSK 356
WP_018372492    276 LLSKIDEEYAALFDLAKKVYDAVLLSNILTVKEKNTKAPLSASMIKRYEEHKDDLKAPKRFPRER-LPEKYETMFKDLTK 354
WP_018728028    279 LIVQIGDDFADLFLVAKKLYDAILLSGILTVTDPSTKAPLSASMIDRYENHQKDLAALKQFIKTN-LPEKYDEVFSDQSK 357
WP_045618029    278 LLAQIGDDFTDLFVSAKKLYDAILLSGILTVDGTKAPLSASMIERYENHQNDLAALKQFIKQN-LPEKYDEVFSDQSK 356
WP_045635197    278 LLAQIGDNYAELFLSAKKLYDSILLSGILTVTDVGTKAPLSASMIQRYNEHQMDLAQLKQFIRQK-LSDKYNEVFSDVSK 356
WP_002263549    278 LLAQIGDNYAELFLSAKKLYDSILLSGILTVTDVGTKAPLSASMIQRYNEHQMDLAQLKQFIRQK-LSDKYNEVFSDVSK 356
WP_002263887    278 LLGKIGDDYADLFTLAKNLYDAILLSGILTADDSSTKAPLSASMIKRYAEHHEDLEKLKEFIKAN-KPELYHDIFKDETK 356
WP_002264920    278 LLAQIGDNYAELFLSAKKLYDSILLSGILTVTDVSTKAPLSASMIQRYNEHQMDLAQLKQFIRQK-LSDKYNEVFSDVSK 356
WP_002269043    278 LLAQIGDNYAELFLSAKKLYDSILLSGILTVTDVSTKAPLSASMIQRYNEHQMDLAQLKQFIRQK-LSDKYNEVFSDVSK 356
WP_002269448    278 LLAQIGDNYAELFLSAKKLYDSILLSGILTVTDVSTKAPLSASMIQRYNEHQMDLAQLKQFIRQK-LSDKYNEVFSDVSK 356
WP_002271977    278 LLGKIGDDYADLFTLAKNLYDAILLSGILTADDSSTKAPLSASMIQRYNEHQMDLAQLKQFIRQK-LSDKYNEVFSDVSK 356
WP_002272766    278 LLAQIGDNYAELFLSAKKLYDSILLSGILTVTDVSTKAPLSASMIQRYNEHQMDLAQLKQFIRQK-LSDKYNEVFSDVSK 356
WP_002273241    278 LLAQIGDNYAELFLSAKKLYDSILLSGILTVTDVSTKAPLSASMIQRYNEHQMDLAQLKQFIRQK-LSDKYNEVFSDVSK 356
WP_002275430    278 LLTQIGDNYAELFLSAKKLYDSILLSGILTVTDVSTKAPLSASMIQRYNEHQMDLAQLKQFIRQK-LSDKYNEVFSDVSK 356
WP_002276448    278 LLAQIGDNYAELFLSAKKLYDSILLSGILTVTDVSTKAPLSASMIQRYNEHQMDLAQLKQFIRQK-LSDKYNEVFSDVSK 356
WP_002277050    278 LLGKIGDDYADLFTLAKNLYDAILLSGILTADDSSTKAPLSASMIKRYAEHHEDLEKLKEFIKAN-KPELYHDIFKDETK 356
WP_002273364    278 LLAQIGDNYAELFLSAKKLYDSILLSGILTVTDVSTKAPLSASMIQRYNEHQMDLAQLKQFIRQK-LSDKYNEVFSDVSK 356
WP_002279025    278 LLAQIGDNYAELFLSAKKLYDSILLSGILTADDSSTKAPLSASMIQRYNEHQMDLAQLKQFIRQK-LSDKYNEVFSDVSK 356
```

-continued

| | | | |
|---|---|---|---|
| WP_002279859 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002280230 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002281696 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002282247 | 278 | LLGKIGDDYADLFTLAKNLYDAILLSGIILTVTDVSTKAPLSASMIKRYAEHHEDLEKLKEF IKAN-KPELYHDIFKDETK | 356 |
| WP_002283906 | 278 | LLAQIGDNYAELFLSAKKLYDSILLSGILTVDGTKAPLSASMIQRYNEHQMDLAQLKQFIRQK-LSDKYNEVFSDVSK | 356 |
| WP_002283846 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002287255 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002288990 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002289641 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_002290427 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002295753 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002296423 | 278 | LLAQIGDNYAELFLSAKKLYDSILLSGILTVTDVSTKAPLSASMVKRYKEHKEELAAFKRFIKEK-LPKKYEEIFKDDTK | 356 |
| WP_002304487 | 278 | LLGEIGDEYADLFASAKNLYDAILLSGILAVDDNTTKAPLSASMIQRYNEHQMDLAQLKQFIRQK-LSDKYNEVFSDVSK | 356 |
| WP_002305844 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002307203 | 278 | LLAQIGDNYAELFLSAKKLYDSILLSGILTVTDVGTKAPLSASMIQRYNEHQMDLAQLKQFIRQK-LSDKYNEVFSDVSK | 356 |
| WP_002310390 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002352408 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_012997688 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_014677909 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_019312892 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_019313659 | 278 | LLAQIGDNYAELFLSAKKLYDSILLSGILTVTDVGTQAPLSASMIQRYNEHQMDLAQLKQFIRQK-LSDKYNEVFSDVSK | 356 |
| WP_019314093 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_019315370 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_019803776 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_019805234 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_024783594 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_024784288 | 278 | LLGKIGDDYADLFTLAKNLYDAILLSGILTADDSSTKAPLSASMIKRYAEHHEDLEKLKEF IKRYAEHHEDLEKLKEF IKAN-KPELYHDIFKDETK | 356 |
| WP_024784666 | 278 | LLAQIGDNYAELFLSAKKLYDSILLSGILTVTDVSTKAPLSASMIQRYNEHQMDLVQLKQFIRQK-LSDKYNEVFSDVSK | 356 |
| WP_024784894 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_024786433 | 278 | LLGKIGDDYADLFTLAKNLYDAILLSGILTADDSSTKAPLSASMIKRYAEHHEDLEKLKEF IKAN-KPELYHDIFKDETK | 356 |
| WP_049473442 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_049474547 | 271 | LLAQIGDNYAELFLSAKKLYDSILLSGILTVTDVSTKAPLSASMIQRYNEHQMDLAQLKQFIRQK-LSDKYNEVFSDVSK | 349 |
| EMC03581 | 279 | LLGQIGDDFADLFVAAKKLYDSILLSGILTVTDPSTKAPLSASMIERYENHQKDLATLKQFIKTN-LPEKYDEVFSDQSK | 357 |
| WP_000428612 | 279 | LLGQIGDDFADLFVAAKKLYDSILLSGILTVTDPSTKAPLSASMIERYENHQKDLAVLKQFIKNN-LPEKYDEVFSDQSK | 357 |
| WP_000428613 | 278 | LLGQIGDGFADLFVAKKLYDAILLAGILSVKDPGTKAPLSASMIERYDNHQNDLSALKQFVRRN-LPEKYAEVFSDDSK | 356 |
| WP_049523028 | 278 | LLAQIGDVYADLFVVAKKLYDAILLAGILSVKDPGTKAPLSASMIERYENHQKDLAALKQFIKNN-LSEKYAEVFSDQSK | 356 |
| WP_003107102 | 247 | LLAQIGDGYADLFVAAKNLSDAILLSDILTVKGVNTKAPLSASMVQRFNEHQDDLKLLKKLVKVQ-LPEKYKEIFDIKDK | 325 |
| WP_054279288 | 280 | LLTQIGDEYADLFVAKNLSDAILLSDILTVNGDGTQAPLSASLIKRYEEHRQDLALLLKQMFKEQ-LPDLYRDVFTDENK | 358 |
| WP_049531101 | 279 | LLGQIGDDFADLFVAKKLYDAILLSGILTVTDPSTKAPLSASMIERYENHQKDLAALKQFIKNN-LPEKYDEVFSDQSK | 357 |
| WP_049538452 | 279 | LLGQIGDGFADLFVAKKLYDAILLSGILTVTDPSTKAPLSASMIERYQNHQNDLASLKQFIKNN-LPEKYDEVFSDQSK | 357 |
| WP_049549711 | 279 | LLGQIGDDFADLFVAKKLYDAILLSGILTVTDPSTKAPLSASMIERYENHQKDLTTLKQFIKNN-LPEKYDEVFSDQSK | 357 |
| WP_007896501 | 280 | LLAEIGDHYADLFLAAKNLSDAILLSGILTLSDENTRAPLSDENTRAPLSASMIKRYEEHQEDLALLLKKLVKEQ-MPEKYWEIFSNAKK | 358 |
| EFR44625 | 232 | LLAEIGDHYADLFLAAKNLSDAILLSGILTLSDENTRAPLSDENTRAPLSASMIKRYENHQEDLALLLKKLVKEQ-MPEKYWEIFSNAKK | 310 |
| WP_002897477 | 278 | LLGQIGDFADLFLIAKKLYDAILLSGILTVTDPSTKAPLSASMIERYENHQKDLAALKQFIKNN-LPEKYVEVFSDQSK | 356 |
| WP_002906454 | 278 | LLGQIGDGFADLFVAKKLYDAILLSGILTVTDPSTKAPLSASMIERYENHQKDLAALKQFIKNN-LSEKYAEVFSDQSK | 356 |
| WP_009729476 | 279 | LLGQIGDDFADLFVAKKLYDAILLSGILTVTNPSTKAPLSASMIERYENHQKDLASLKQFIKNN-LPEKYDEVFSDQSE | 357 |
| CQR24647 | 278 | LLGIIGDEYADVFVAAKVYDSILLSGILTTNNHSTKAPLSASMIDRYDEHNSDKKLLRDFIRTNiGKEVFKEVFYDTSK | 357 |
| WP_000066813 | 279 | LLGQIGDDFADLFVAKKLYDAILLSGILTVKDLSTKAPLSASMIERYENHQKDLAALKQFIKNN-LQEKYDEVFSDQSK | 357 |
| WP_009754323 | 279 | LLGQIGDDFADLFVAKKLYDAILLSGILTVTDSTTKAPLSASMIERYENHQKDLAALKQFIKNN-LPEKYDEVFSDQSK | 357 |
| WP_044674937 | 278 | LLGKIGDDYADLFIATKSLYDGILLAGILSTTDSTTKAPLSSSMVNRYEEHKKDLALLKNFIHQN-LSDSYKEVENDKLK | 356 |
| WP_044676715 | 278 | LLGKIGDDYADLFIATKSLYDGILLAGILSTTDSTTKAPLSSSMVNRYEEHKKDLALLKNFIHQN-LSDSYKEVENDKLK | 356 |
| WP_044680361 | 278 | LLGKIGDDYADLFIATKSLYDGILLAGILSTTDSTTKAPLSSSMVNRYEEHKQDLALLKNFIHQN-LSDSYKEVENDKLK | 356 |
| WP_044681799 | 278 | LLGKIGDDYADLFIATKSLYDGILLAGILSTTDSTTKAPLSSSMVNRYEEHKKDLALLKNFIHQN-LSDSYKEVENDKLK | 356 |

```
WP_049533112  278 LLGEIGDEYADLFASAKNLYDAILLSGILTVDDNSTKAPLSASMVKRYEEHQKDLKKLKDFIKVN-APDQYNAIFKDKNK                 356
WP_029090905  244 LADVLADEYDLLLTAQKIYSAIILDESMDGYEYFA-----EAKKESYRKHQBELVLVKKMLKSNaITNDERAKF---EY                 315
WP_006506696  284 VEKDLGE-YVEFVDALHNVYSWVELQTIMGATHTD-NASISEAMVSRYNKHHDDLKLLKLLKDCIKNN-VPNKYFDMFRNDSE             360
AIT42264      278 LLAQIGDQYADLFLAAKNLSDAILLSDILRVNTEITKAPLSASMIKRYDEHHQDLTLLKALVRQQ-LPEKYKEIFFDQSK                356
WP_034440723  284 LLSNIDEGYRDVFLQAKNVYNAIELSKILKTDGKETKAPLSAQMVELYNQHREDLKKYKYDYIKAY-LPEKYGETFKDATK               362
AKQ21048      278 LLAQIGDQYADLFLAAKNLSDAILLSDILRVNTEITKAPLSASMIKRYDEHHQDLTLLKALVRQQ-LPEKYKEIFFDQSK                356
WP_004636532  277 LLGMTDDVFLDVFMAAKNVYDAVEMSAIISTDTGNSKAVLSNQMINFYDEHKVDLAQLKQFKTH-LPDKYYECFSDPSK                 355
WP_002364836  284 LLGEIGDEYSDVFLAAKNVYDAVELSTILADSDKKSHAKLSSSMIVRPTEHQEDLKKFKPKRF IREN-CPDEYDNLFKNEQK             362
WP_016631044  235 ILAKVGDEYSDVFLAAKNVYDAVELSTILADSDKKSHAKLSSSMIVRPTEHQEDLKKFKPKRF IREN-CPDEYDNLFKNEQK             313
EMS75795       21 LLEKSGEEFRDVFLQAKKVYDAILLSTILKQNSKAKLSLGMIERYDSHKKDLEELKQFVKAN-LPEKTAIFFKNEQK                   99
WP_002373311  284 ILAKVGDEYSDVFLAAKNVYDAVELSTILADSDKKSHAKLSSSMIVRPTEHQEDLKKFKPKRF IREN-CPDEYDNLFKNEQK             362
WP_002378009  284 ILAKVGDEYSDVFLAAKNVYDAVELSTILADSDKKSHAKLSSSMIVRPTEHQEDLKNFKPKRF IREN-CPDEYDNLFKNEQK             362
WP_002407324  284 ILAKVGDEYSDVFLAAKNVYDAVELSTILADSDKKSHAKLSSSMIVRPTEHQEDLKNFKRF IREN-CPDEYDNLFKNEQK               362
WP_002413717  286 ILAKVGDEYSDVFLAAKNVYDAVELSTILADSDKKSHAKLSSSMIVRPTEHQEDLKKFKRF IREN-CPDEYDNLFKNEQK               364
WP_010775580  284 ILAKVGDEYSDVFLAAKNVYDAVELSTILADSDKKSHAKLSSSMIVRPTEHQEDLKKFKRF IREN-CPDEYDNLFKNEQK               362
WP_010818269  284 ILAKVGDEYSDVFLAAKNVYDAVELSTILADSDKKSHAKLSSSMIVRPTEHQEDLKKFKRF IREN-CPDEYDNLFKNEQK               362
WP_010824395  284 ILAKVGDEYSDVFLAAKNVYDAVELSTILADSDKKSYAKLSSHAKLSSSMIVRPTEHQEDLKKFKRF IREN-CPDEYDNLFKNEQK         362
WP_016622645  284 ILAKVGDEYSDVFLAAKNVYDAVELSTILADSDKKSHAKLSSSMIVRPTEHQEDLKKFKRF IREN-CPDEYDNLFKNEQK               362
WP_033624816  284 ILAKVGDEYSDVFLAAKNVYDAVELSTILADSDKKSHAKLSSSMIVRPTEHQEDLKKFKRF IREN-CPDEYDNLFKNEQK               362
WP_033625576  284 ILAKVGDEYSDVFLAAKNVYDAVELSTILADSDKKSHAKLSSSMIVRPTEHQEDLKKFKRF IREN-CPDEYDNLFKNEQK               362
WP_033789179  284 ILAKVGDEYSDVFLAAKNVYDAVELSTILADSDKKSHAKLSSSMIVRPTEHQEDLKNFKRF IREN-CPDEYDNLFKNEQK               362
WP_002310644  282 LLEKIGDDYIDLFVQAKNVYDAVLLSEILSDSTKNTRAKLSAGMIRRYDAHKEDLVLLKRFVKEN-LPKKYRAFFGDNSV                360
WP_002312694  283 LLEKIGDDYIDLFVQAKNVYDAVLLSEILSDSTKNTRAKLSAGMIRRYDAHKEDLVLLKRFVKEN-LPKKYRAFFGDNSV                361
WP_002314015  283 LLEKIGDDYIDLFVQAKNVYDAVLLSEILSDSTKNTRAKLSAGMIRRYDAHKEDLVLLKRFVKEN-LPKKYRAFFGDNSV                361
WP_002320716  282 LLEKIGDDYIDLFVQAKNVYDAVLLSEILSDSTKNTRAKLSAGMIRRYDAHKEDLVLLKRFVKEN-LPKKYRAFFGDNSV                360
WP_002330729  283 LLEKIGDDYIDLFVQAKNVYDAVLLSEILSDSTKNTRAKLSAGMIRRYDAHKEDLVLLKRFVKEN-LPKKYRAFFGDNSV                361
WP_002335161  283 LLEKIGDDYIDLFVQAKNVYDAVLLSEILSDSTKNTRAKLSAGMIRRYDAHKEDLVLLKRFVKEN-LPKKYRAFFGDNSV                361
WP_002345439  283 LLEKIGDDYIDLFVQAKNVYDAVLLSEILSDSTKNTRAKLSAGMIRRYDAHKEDLVLLKRFVKEN-LPKKYRAFFGDNSV                361
WP_034867970  276 LLEKIGDEYLDIFIQAKKVHDAILLSEIISSTVKHTRAKLSSGMVERYERHKADLAKFKQFVKEN-VPQKATVFFKDTTK                354
WP_047937432  283 LLEKIGDDYIDLFVQAKNVYDAVLLSEILSDSTKNTRAKLSAGMIRRYDAHKEDLVLLKRFVKEN-LPKKYRAFFGDNSV                361
WP_010720994  276 LLEKIGDEYLDIFIQAKKVHDAILLSEIISSTVKHTQAKLSSGMVERYERHKADLAKFKQFVKEN-VPQKATVFFKDTTK                354
WP_010737004  276 LLEKIGDEYLDIFIQAKKVHDAILLSEIISSTVKHTQAKLSSGMVERYERHKADLAKFKQFVKEN-VPQKATVFFKDTTK                354
WP_034700478  276 LLEKIGDEYLDIFIQAKKVHDAILLSEIISSTVKHTQKLSSGMVERYERHKADLAKFKQFVKEN-VPQKATVFFKDTTK                 354
WP_007209003  281 LLAIIGDEYGDIFVAAQNLYQAILLAGILTSTEK-TRAKLSASMIQRYEEHAKDLKLLKRFVKEH-IPDKYAEIFNDATK                358
WP_023519017  276 LLEKTSDDYAELFLKAKGVYDAILLSGILSKSDDETRAKLSANMKLRFEEHQRDLKQLKELVRRD-LPKKYDFFKNRSK                 354
WP_010770040  279 LLAIIGDEYAELFVAAKNAYSATKSVYDAVALSGILSVTDGDTRAKLSASMVERYEAHQDKLVQFKQFIRKE-LPEMYAPIFRDNSV         357
WP_048604708  275 LLGEIGDEYADLFVEAAKNVYAELSGILTVTDNSTRAKLSASMIKRYEDHKTDLKLFKEFIRKN-LPKEYHEIFNDKNT                 353
WP_010750235  276 LLRKSNEEMIDVFLQVKKVYDAILLSDILSTKMKDTKAKLSAGMIERYQNHKKDLEELKQFVRAH-LHEKVTVFFKDSSK                354
AII16583      317 LLAQIGDQYADLFLAAKNLSDAILLSDILRVNTEITKAPLSASMIKRYDEHHQDLTLLKALVRQQ-LPEKYKEIFFDQSK                395
WP_029073316  290 KQPLLGD-CVEFIDLLHDIYSWVELQNILGSAHTS-EPSISAAMIQRYEDHKNDLKLLKDVIRKY-LPKKYFEVFRDEKS                366
WP_031589969  290 KQPLLGD-CVEFIDLLHDIYSWVELQNILGSAHTS-EPSISAAMIQRYEDHKNDLKLLKDVIRKY-LPKKYFEVFRDEKS                366
KDA45870      276 LLAEAGDQYLDIFVAAKKVYDAAILASILDVKDTQTKTVFSQAMIERYEEHQKDLIELKRVFKKY-LPEKCHDFFSE-PK                353
WP_039099354  286 LESSLDDNAHQIIESLQELYSGVLLAGIVPEMQSLS----QAMITKYDDHQKHLKMLKAVREAL-APEDRQRLKQAYDQ                 359
AKP02966      279 LDSILDDDQFTVLDTANRIYSTITLNEIL----NGESYFSMAKVNQYENHAIDLCKLRDMWHTT---KNEKAV-GLSR                  348
WP_010991369  284 LLALIGDEYAELFVAAKNAYSAVVLSSIITVAETETNAKLSASMIERPDTHEEDLGELKAFIKLH-LPKHYEIFSNTEK                 362
WP_033838504  284 LLALIGDEYAELFVAAKNAYSAVVLSSIITVAETETNAKLSASMIERPDTHEEDLGELKAFIKLH-LPKHYEIFSNTEK                 362
EHN60060      287 LLALIGDEYAELFVAAKNAYSAVVLSSIITVAETETNAKLSASMIERPDTHEEDLGELKAFIKLH-LPKHYEIFSNTEK                 365
AII16583       53 LLAKIGDEYAELFVAAKSTYNAVLSNIITVDTETKAKLSASMIERPDKHAKDLKRLKAFFKMQ-LPEKFNEVFNDIEK                  131
WP_038409211  284 LLAKIGDEYAEIFVAAKSTYNAVLSSIITVTATETNAKLSASMIERPDAHEKELGELKAFIKLH-LPKQYQEIFNNAEI                 362
EFR95520          -----                                                                                        
WP_003723650  284 LLAIIGDEYAELFVAAKNTYNAVVLSSIITVAVLSSIITVTATETNAKLSASMIERPDAHEKELGELKAFIKLH-LPKQYQEIFNNAEI      362
WP_003727705  284 LLAIIGDEYAELFVAAKNTYNAVVLSSIITVATETNAKLSASMIERPDAHEKELGELKAFIKLH-LPKQYQEIFNNAEI                362
WP_003730785  284 LLAIIGDEYAELFVAAKNTYNAVVLSSIITVATETNAKLSASMIERPDAHEKELGELKAFIKLH-LPKQYQEIFNNAEI                362
```

| | | | |
|---|---|---|---|
| WP_003733029 | 284 | LLAIIGDEFAEVFVAAKNAYNAVVLSNIIITVDSTTRAKLSASLIERPENHKEDLKKMKRFVRTY-LPEKYDEIFDDTEK | 362 |
| WP_003739838 | 284 | LLAIIGDEYAELFVAAKNTYNAVVLSSIITVTDTETNAKLSASMIERPDAHEKDLSELKAFIKLH-LPKQYEIFSNVAI | 362 |
| WP_014601172 | 284 | LLAIIGDEYAELFVAAKNTYNAVVLSSIITVTATETNAKLSASMIERPDAHEKDLGELKAFIKLH-LPKQYQEIFNNAAI | 362 |
| WP_023548323 | 284 | LLAIIGDEYAELFVAAKNTYNAVVLSSIITVTDTETNAKLSASMIERPDAHEKDLVELKAFIKLN-LPKQYQEIFNNAAI | 362 |
| WP_031665337 | 284 | LLAIIGDEYAELFVAAKNTYNAVVLSSIITVNDTETNAKLSASMIERPDAHEKDLVELKAFIKLN-LPKQYKEIFSNAAI | 362 |
| WP_031669209 | 284 | LLAIIGDEFAEVFVAAKNAYNAVVLSNIIITVDSTTRAKLSASLIERPENHKEDLKKMKRFVRTY-LPEKYDEIFDDTEK | 362 |
| WP_033920898 | 284 | LLAIIGDEYAELFVAAKNTYNAVVLSSIITVTDTETNAKLSASMIERPDAHEKDLVELKAFIKLN-LPKQYKEIFSNAAI | 362 |
| AKI42028 | 287 | LLAIIGDEYAELFVAAKNTYNAVVLSSIITVTATETNAKLSASMIERPDAHEKDLGELKAFIKLH-LPKQYQEIFNNAAI | 365 |
| AKI50529 | 287 | LLAIIGDEYAELFVAAKNTYNAVVLSSIITVTDTETNAKLSASMIERPDAHEKDLVELKAFIKLN-LPKQYKEIFSNAAI | 365 |
| EFR83390 | | | |
| WP_046323366 | 284 | LLARVGDEYAEIFVAAKNAYNAVVLSSIITVSNTETKAKLSASMIERPDKHDKDLKRMKAFFKVR-LPENFNEVFRNDVEK | 362 |
| AKE81011 | 294 | LLAQIGDQYADLFLAAKNLSDAILLSDILRVNTEITKAPLSASMIKRYDEHHQDLTLLKALVRQQ-LPEKYKEIFFDQSK | 372 |
| CUO82355 | 288 | VENDLGE-YVEFIDSLHNIYSWVELQTIMGATHTD-NASISEAMVSRYNKHHEDLQLLKKCIKDN-VPKKYFDMFRNDSE | 364 |
| WP_033162887 | 289 | LQSELGE-YIEFIEMLHNIYSWELQAILGATHTD-NPSISAMVERYEEHKKDLRVLKKVIREE-LPDKYNEVFRKDNR | 365 |
| AGZ01981 | 311 | LLAQIGDQYADLFLAAKNLSDAILLSDILRVNTEITKAPLSASMIKRYDEHHQDLTLLKALVRQQ-LPEKYKEIFFDQSK | 389 |
| AKA60242 | 278 | LLAQIGDQYADLFLAAKNLSDAILLSDILRVNTEITKAPLSASMIKRYDEHHQDLTLLKALVRQQ-LPEKYKEIFFDQSK | 356 |
| AKS40380 | 278 | LLAQIGDQYADLFLAAKNLSDAILLSDILRVNTEITKAPLSASMIKRYDEHHQDLTLLKALVRQQ-LPEKYKEIFFDQSK | 356 |
| 4UN5_B | 282 | LLAQIGDQYADLFLAAKNLSDAILLSDILRVNTEITKAPLSASMIKRYDEHHQDLTLLKALVRQQ-LPEKYKEIFFDQSK | 360 |
| WP_010922251 | 357 | -NGYAG YIDG G ASQEEFYKFIKPILEK-M--DGTEELLv--KLNREDLLRKQRTFDNGSIPHQIHLGEL | 419 |
| WP_039695303 | 358 | -NGYAG YIEN G VKQDEFYKYLKNILSK-IkiDGSDYFL-DKIEREDFLRKQRTFDNGSIPHQIHLQEM | 422 |
| WP_045635197 | 357 | -DGYAG YIDG K TTQEFFYKYIKNLLSK-F--EGTDYFL-DKIEREDFLRKQRTFDNGSIPHQIHLGEM | 419 |
| 5AXW_A | 169 | ----G SINR - ----------------K---TSDYVk-----------------------EA | 183 |
| WP_009880683 | 41 | -NGYAG YIDG G ASQEEFYKFIKPILEK-M--DGTEELLa--KLNREDLLRKQRTFDNGSIPHQIHLGEL | 103 |
| WP_010922251 | 357 | -NGYAG YIDG G ASQEEFYKFIKPILEK-M--DGTEELLv--KLNREDLLRKQRTFDNGSIPYQIHLGEL | 419 |
| WP_011054416 | 357 | -NGYAG YIDG G ASQEEFYKFIKPILEK-M--DGTEELLa--KLNREDLLRKQRTFDNGSIPYQIHLGEL | 419 |
| WP_011284745 | 357 | -NGYAG YIDG G ASQEEFYKFIKPILEK-M--DGTEELLa--KLNREDLLRKQRTFDNGSIPHQIHLGEL | 419 |
| WP_011285506 | 357 | -NGYAG YIDG G ASQEEFYKFIKPILEK-M--DGTEELLv--KLNREDLLRKQRTFDNGSIPHQIHLGEL | 419 |
| WP_011527619 | 357 | -NGYAG YIDG G ASQEEFYKFIKPILEK-M--DGTEELLa--KLNREDLLRKQRTFDNGSIPHQIHLGEL | 419 |
| WP_012560673 | 357 | -NGYAG YIDG G ASQEEFYKFIKPILEK-M--DGTEELLa--KLNREDLLRKQRTFDNGSIPHQIHLGEL | 419 |
| WP_014407541 | 357 | -NGYAG YIDG G ASQEEFYKFIKPILEK-M--DGTEELLv--KLNREDLLRKQRTFDNGSIPHQIHLGEL | 419 |
| WP_020905136 | 357 | -NGYAG YIDG G ASQEEFYKFIKPILEK-M--DGTEELLa--KLNREDLLRKQRTFDNGSIPHQIHLGEL | 419 |
| WP_023080005 | 357 | -NGYAG YIDG G ASQEEFYKFIKPILEK-M--DGTEELLa--KLNREDLLRKQRTFDNGSIPYQIHLGEL | 419 |
| WP_023610282 | 357 | -NGYAG YIDG G ASQEEFYKFIKPILEK-M--DGTEELLa--KLNREDLLRKQRTFDNGSIPYQIHLGEL | 419 |
| WP_030125963 | 357 | -NGYAG YIDG G ASQEEFYKFIKPILEK-M--DGTEELLa--KLNREDLLRKQRTFDNGSIPHQIHLGEL | 419 |
| WP_030126706 | 357 | -NGYAG YIDG G ASQEEFYKFIKPILEK-M--DGTEELLa--KLNREDLLRKQRTFDNGSIPYQIHLGEL | 419 |
| WP_031488318 | 357 | -NGYAG YIDG G ASQEEFYKFIKPILEK-M--DGTEELLa--KLNREDLLRKQRTFDNGSIPHQIHLGEL | 419 |
| WP_032460140 | 357 | -NGYAG YIDG G ASQEEFYKFIKPILEK-M--DGTEELLa--KLNREDLLRKQRTFDNGSIPHQIHLGEL | 419 |
| WP_032461047 | 357 | -NGYAG YIDG G ASQEEFYKFIKPILEK-M--DGTEELLa--KLNREDLLRKQRTFDNGSIPHQIHLGEL | 419 |
| WP_032462016 | 357 | -NGYAG YIDG G ASQEEFYKFIKPILEK-M--DGTEELLv--KLNREDLLRKQRTFDNGSIPHQIHLGEL | 419 |
| WP_032462936 | 357 | -NGYAG YIDG G ASQEEFYKFIKPILEK-M--DGTEELLa--KLNREDLLRKQRTFDNGSIPYQIHLGEL | 419 |
| WP_032464890 | 357 | -NGYAG YIDG G ASQEEFYKFIKPILEK-M--DGTEELLa--KLNRKDLLRKQRTFDNGSIPHQIHLGEL | 419 |
| WP_033888930 | 182 | -NGYAG YIDG G ASQEEFYKFIKPILEK-M--DGTEELLa--KLNREDLLRKQRTFDNGSIPHQIHLGEL | 244 |
| WP_038431314 | 357 | -NGYAG YIDG G ASQEEFYKFIKPILEK-M--DGTEELLv--KLNREDLLRKQRTFDNGSIPHQIHLGEL | 419 |
| WP_038432938 | 357 | -NGYAG YIDG G ASQEEFYKFIKPILEK-M--DGTEELLa--KLNREDLLRKQRTFDNGSIPYQIHLGEL | 419 |
| WP_038434062 | 268 | -NGYAG YIDG G ASQEEFYKFIKPILEK-M--DGTEELLa--KLNREDLLRKQRTFDNGSIPHQIHLGEL | 330 |
| BAQ51233 | | | |
| KGE60162 | | | |
| KGE60856 | | | |
| WP_002989955 | 357 | -NGYAG YIDG G ASQEEFYKFIKPILEK-M--DGTEELLa--KLNREDLLRKQRTFDNGSIPHQIHLGEL | 419 |
| WP_003030002 | 357 | -KGYAG YIEN G VKQDEFYKYLKGILLQ-I--NGSGDFL-DKIDREDFLRKQRTFDNGSIPHQIHLQEM | 419 |
| WP_003065552 | 360 | -NGYAG YIEN G VKQDEFYKYLKNTLSK-Ia--GSDYFL--DKIEREDFLRKQRTFDNGSIPHQIHLQEM | 422 |
| WP_001040076 | 358 | -DGYAG YIEG K TNQEAFYKYLSKLLTK-Q--EGSEYFL--EKIKNEDFLRKQRTFDNGSIPHQVHLTEL | 420 |
| WP_001040078 | 358 | -DGYAG YIEG K TNQEAFYKYLSKLLTK-Q--EDSENFL--EKIKNEDFLRKQRTFDNGSIPHQVHLTEL | 420 |

| | | | | | |
|---|---|---|---|---|---|
| WP_001040080 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040081 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040083 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040085 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040087 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040088 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040089 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040090 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040091 | 358 | -DGYAG YIEG K | TNQEAFYKYLSKLLTK-Q- | -EDSENFL- | -EKIKNEDFLRKQRTFDNGSIPHQVHLTEL | 420 |
| WP_001040092 | 358 | -DGYAG YIEG K | TNQEAFYKYLSKLLTK-Q- | -EDSEYLL- | -EKIKNEDFLRKQRTFDNGSIPHQVHLTEL | 420 |
| WP_001040094 | 358 | -DGYAG YIEG K | TNQEAFYKYLSKLLTK-Q- | -EDSEYLL- | -EKIKNEDFLRKQRTFDNGSIPHQVHLTEL | 420 |
| WP_001040095 | 358 | -DGYAG YIEG K | TNQEAFYKYLSKLLTK-Q- | -EGSEYLL- | -EKIKNEDFLRKQRTFDNGSIPHQVHLTEL | 420 |
| WP_001040096 | 358 | -DGYAG YIEG K | TNQEAFYKYLSKLLTK-Q- | -EGSEYLL- | -EKIKNEDFLRKQRTFDNGSIPHQVHLTEL | 420 |
| WP_001040097 | 358 | -DGYAG YIEG K | TNQEAFYKYLSKLLTK-Q- | -EGSEYLL- | -EKIKNEDFLRKQRTFDNGSIPHQVHLTEL | 420 |
| WP_001040098 | 358 | -DGYAG YIEG K | TNQEAFYKYLSKLLTK-Q- | -EGSEYLL- | -EKIKNEDFLRKQRTFDNGSIPHQVHLTEL | 420 |
| WP_001040099 | 358 | -DGYAG YIEG K | TNQEAFYKYLSKLLTK-Q- | -EGSEYLL- | -EKIKNEDFLRKQRTFDNGSIPHQVHLTEL | 420 |
| WP_001040100 | 358 | -DGYAG YIEG K | TNQEAFYKYLSKLLTK-Q- | -EGSEYLL- | -EKIKNEDFLRKQRTFDNGSIPHQVHLTEL | 420 |
| WP_001040104 | 358 | -DGYAG YIEG K | TNQGAFYKYLSKLLTK-Q- | -EDSENFL- | -EKIKNEDFLRKQRTFDNGSIPHQVHLTEL | 420 |
| WP_001040105 | 358 | -DGYAG YIEG K | TNQGAFYKYLSKLLTK-Q- | -EGSEYFL- | -EKIKNEDFLRKQRTFDNGSIPHQVHLTEL | 420 |
| WP_001040106 | 358 | -DGYAG YIEG K | TNQGAFYKYLSKLLTK-Q- | -EGSEYFL- | -EKIKNEDFLRKQRTFDNGSIPHQVHLTEL | 420 |
| WP_001040107 | 358 | -DGYAG YIEG K | TNQGAFYKYLSKLLTK-Q- | -EGSEYFL- | -EKIKNEDFLRKQRTFDNGSIPHQVHLTEL | 420 |
| WP_001040108 | 358 | -DGYAG YIEG K | TNQGAFYKYLSKLLTK-Q- | -EGSEYFL- | -EKIKNEDFLRKQRTFDNGSIPHQVHLTEL | 420 |
| WP_001040109 | 358 | -DGYAG YIEG K | TNQGAFYKYLSKLLTK-Q- | -EDSEYFL- | -EKIKNEDFLRKQRTFDNGSIPHQVHLTEL | 420 |
| WP_001040110 | 358 | -DGYAG YIEG K | TNQGAFYKYLSKLLTK-Q- | -EDSEYFL- | -EKIKNEDFLRKQRTFDNGSIPHQVHLTEL | 420 |
| WP_015058523 | 358 | -DGYAG YIEG K | TNQEAFYKYLSKLLTK-Q- | -EDSEYFL- | -EKIKNEDFLRKQRTFDNGSIPHQVHLTEL | 420 |
| WP_017643650 | 358 | -DGYAG YIEG K | TNQEAFYKYLSKLLTK-Q- | -EDSENFL- | -EKIKNEDFLRKQRTFDNGSIPHQVHLTEL | 420 |
| WP_017647151 | 358 | -DGYAG YIEG K | TNQEAFYKYLSKLLTK-Q- | -EDSENFL- | -EKIKNEDFLRKQRTFDNGSIPHQVHLTEL | 420 |
| WP_017648376 | 358 | -DGYAG YIEG K | TNQEAFYKYLSKLLTK-Q- | -EDSENFL- | -EKIKNEDFLRKQRTFDNGSIPHQVHLTEL | 420 |
| WP_017649527 | 358 | -DGYAG YIEG K | TNQEAFYKYLSKLLTK-Q- | -EDSENFL- | -EKIKNEDFLRKQRTFDNGSIPHQVHLTEL | 420 |
| WP_017771611 | 358 | -DGYAG YIEG K | TNQEAFYKYLSKLLTK-Q- | -EDSENFL- | -EKIKNEDFLRKQRTFDNGSIPHQVHLTEL | 420 |
| WP_017771984 | 358 | -DGYAG YIEG K | TNQEAFYKYLSKLLTK-Q- | -EDSENFL- | -EKIKNEDFLRKQRTFDNGSIPHQVHLTEL | 420 |
| CFQ25032 | 358 | -DGYAG YIEG K | TNQEAFYKYLSKLLTK-Q- | -EDSENFL- | -EKIKNEDFLRKQRTFDNGSIPHQVHLTEL | 420 |
| CFV16040 | 358 | -DGYAG YIEG K | TNQEAFYKYLSELLTK-Q- | -EDSENFL- | -EKIKNEDFLREQRTEDNGSIPHQVHLTEL | 420 |
| KLJ37842 | 358 | -DGYAG YIEG K | TNQEAFYKYLSELLTK-Q- | -EDSENFL- | -EKIKNEDFLREQRTEDNGSIPHQVHLTEL | 420 |
| KLJ72361 | 357 | -KGYAG YIES G | VKQDEFYKYLEGILLQ-I- | -NGSGDFL- | -DKIDREDFLREQRTEDNGSIPHIHLQEM | 419 |
| ELL20707 | 358 | -KGYAG YIES G | VKQDEFYKYLEGILLK-I- | -NGSGDFL- | -DKIDCEDFLREQRTEDNGSIPHIHLQEM | 420 |
| KLL42645 | 358 | -NGYAG YIEN G | VKQDEFYKYLENTLSK-I- | -DGSDYFL- | -DKIDREDFLREQRTEDNGSIPHIHLQEM | 420 |
| WP_047207273 | 358 | -KGYAG YIES G | VEQDEFYKYLEGILLK-I- | -NGSGDFL- | -DKIDCEDFLREQRTEDNGSIPHIHLQEM | 420 |
| WP_047209694 | 358 | -KGYAG YIES G | VKQDEFYKYLEGILLK-I- | -NGSGDFL- | -DKIDCEDFLREQRTEDNGSIPHIHLQEM | 420 |
| WP_050198062 | 358 | -DGYAG YIEG K | TNQEAFYKYLSKLLTK-Q- | -EDSENFL- | -EKIKNEDFLREQRTEDNGSIPHQVHLTEL | 420 |
| WP_050201642 | 358 | -DGYAG YIEG K | TNQEAFYKYLSKLLTK-Q- | -EDSENFL- | -EKIKNEDFLREQRTEDNGSIPHQVHLTEL | 420 |
| WP_050204027 | 358 | -DGYAG YIES K | TNQEAFYKYLSELLTK-Q- | -EGSEYLL- | -EKIKNEDFLREQRTEDNGSIPHQVHLTEL | 420 |
| WP_050881965 | 358 | -DGYAG YIEG K | TNQEAFYKYLSELLTK-Q- | -EDSENFL- | -EKIKNEDFLREQRTEDNGSIPHQVHLTEL | 420 |
| WP_050886065 | 358 | -DGYAG YIEG K | TNQEAFYKYLSELLTK-Q- | -EDSENFL- | -EKIKNEDFLREQRTEDNGSIPHQVHLTEL | 420 |
| AHN30376 | 358 | -DGYAG YIEG K | TNQEAFYKYLSELLTK-Q- | -EDSENFL- | -EKIKNEDFLREQRTEDNGSIPHQVHLTEL | 420 |
| EA078426 | 358 | -DGYAG YIEG K | TNQEAFYKYLSELLTK-Q- | -EGSEYLL- | -EKIKNEDFLREQRTEDNGSIPHQVHLTEL | 420 |
| CCW42055 | 357 | -KGYAG YIES G | VKQDEFYKYLEGILLQ-I- | -NGSGDFL- | -DKIDREDFLREQRTEDNGSIPHIHLQEM | 419 |
| WP_003041502 | 358 | -KGYAG YIES G | VKQDEFYKYLEGILLK-I- | -NGSGDFL- | -DKIDCEDFLREQRTEDNGSIPHIHLQEM | 420 |
| WP_037593752 | 358 | -NGYAG YIEN G | VKQDEFYKYLENTLSK-I- | -DGSDYFL- | -DKIDREDFLREQRTEDNGSIPHIHLQEM | 420 |
| WP_049516684 | 358 | -NGYAG YIEN G | VKQDEFYKYLENTLSK-I- | -DGSDYFL- | -DKIDREDFLREQRTEDNGSIPHIHLQEM | 420 |
| GAD46167 | 357 | -KGYAG YIES G | VKQDEFYKYLEGILLK-I- | -NGSGDFL- | -DKIEREDFLREQRTEDNGSIPHIHLQEM | 419 |
| WP_018363470 | 358 | -NGYAG YIEN G | VKQDEFYKYLEGIILTK-I- | -NGSDYFL- | -DKIEREDFLREQRTEDNGSIPHIHLQEM | 420 |
| WP_003043819 | 357 | -NGYAG YVGI G | ATQEEFYKFIKPILEK-M- | -DGAEELLa- | -KLNRDDLLREQRTEDNGSIPHQIHLKEL | 429 |

-continued

```
WP_006269658    357 -KGYAS YIES G VKQDEFYKYLEGILLK-I--NGSGDFL---DKIDREDFLREQRTEDNGSIPHQIHLQEM  419
WP_048800889    357 -NGYAG YIEN G VKQDEFYKYLENTLSK-I--DGSGYFL---DKIDREDFLREQRTEDNGSIPHQIHLGEL  419
WP_012767106    357 -NGYAG YIDG G ASQEEFYKFIKPILEK-M--DGTEELLa--KLNREDLLREQRTEDNGSIPHQIHLGEL  419
WP_014612333    357 -NGYAG YIDG G ASQEEFYKFIKPILEK-M--DGTEELLa--KLNREDLLREQRTEDNGSIPHQIHLGEL  419
WP_015017095    357 -NGYAG YIDG G ASQEEFYKFIKPILEK-M--DGTEELLa--KLNREDLLREQRTEDNGSIPHQIHLGEL  419
WP_015057649    357 -NGYAG YIDG G ASQEEFYKFIKPILEK-M--DGTEELLa--KLNREDLLREQRTEDNGSIPHQIHLGEL  419
WP_048327215    357 -NGYAG YIDG G ASQEEFYKFIKPILEK-M--DGTEELLa--KLNREDLLREQRTEDNGSIPHQIHLGEL  419
WP_049519324    357 -NGYAG YIEG Q VSQEEFYKYLKPILAR-L--DGSEPLLl--KIDREDFLREQRTEDNGSIPHQIHLEEL  419
WP_012515931    357 -NGYAG YIEG Q VSQEEFYKYLKPILAR-L--DGSEPLLl--KIDREDFLREQRTEDNGSIPHQIHLEEL  419
WP_021320964    357 -NGYAG YIEG Q VSQEEFYKYLKPILAR-L--DGSEPLLl--KIDREDFLREQRTEDNGSIPHQIHLEEL  419
WP_037581760    357 -NGYAG YIEG Q VSQEEFYKYLKPILAR-L--DGSEPLLl--KIDREDFLREQRTEDNGSIPHQIHLEEL  419
WP_004232481    357 -NGYAG YIEN G VKQDIFYCHLKSIISE-K--NGGQYFL---DKIREDFLREQRTEDNGSIPYQIHLQEM  419
WP_009854540    358 -NGYAG YIEN G VKQDEFYKYLENTLSK-I--DGSDYFL---DKIREDFLRKQRTFDNGSIPHQIHLQEM  420
WP_012962174    358 -NGYAG YIEN G VKQDEFYKYLETTLSK-I--DGSDYFL---DKIEREDFLRKQRTFDNGSIPHQIHLQEM  420
WP_039695303    358 -NGYAG YIEN G VKQDEFYKYLKNILSK-IkiDGSDYFL---DKIDRDDFLRKQRTFDNGSIPHQIHLQEM  422
WP_014334983    357 -NGYAG YIDN G VKQDEFYKYLKTILTK---DDSDYFL---DKIEREDFLRKQRTFDNGSIPHQIHLQEM  419
WP_003099269    357 -NGYAG YIDG K TSQEEFYKYIKPILLK-L--DGTEKLIs--KLEREDFLRKQRTFDNGSIPHQIHLNEL  419
AHY15608        357 -NGYAG YIDG K TSQEEFYKYIKPILLK-L--DGTEKLIs--KLEREDFLRKQRTFDNGSIPHQIHLNEL  419
AHY17476        357 -NGYAG YIDG K TSQEEFYKYIKPILLK-L--DGTEKLIs--KLEREDFLRKQRTFDNGSIPHQIHLNEL  419
ESR09100        --- ----- ---- - --------------- -- -------- ------------------- ---
AGM98575        357 -NGYAG YIDG K TSQEEFYKYIKPILLK-L--DGTEKLIs--KLEREDFLRKQRTFDNGSIPHQIHLNEL  419
ALF27331        357 -DGYAG YIDG K TNQEAFYKYLKGLLNK-I--ESSGYFL---DKIEREDFLRKQRTFDNGSIPHQIHLQEM  419
WP_018372492    355 -PSYAA YVSG A VTEDDFYKFSKGLLID-V--EGAEYFL---EKIEREDFLRKQRTFDNGAIPNQVHVKEL  432
WP_045618028    358 -DGYAG YIDG K TTQEEFYKYIKNLLSK-I--EGADYFL---DKIEREDFLRKQRTFDNGSIPHQIHLQEM  420
WP_045635197    357 -DGYAG YIDG K TTQETFYKYIKNLLSK-F--EGTDYFL---DKIEREDFLRKQRTFDNGSIPHQIHLQEM  419
WP_002263549    357 -DGYAG YIDG K TNQEAFYKYLKGLLNK-I--EGSGYFL---DKIEREDFLRKQRTFDNGSIPHQIHLQEM  419
WP_002263887    357 -NGYAG YIEN G VKQDEFYKYLKNTLSK-I--AGSDYFL---DKIEREDFLRKQRTFDNGSIPHQIHLQEM  419
WP_002264920    357 -DGYAG YIDG K TNQEAFYKYLKGLLNK-I--AGSDYFL---DKIEREDFLRKQRTFDNGSIPHQIHLQEM  419
WP_002269043    357 -DGYAG YIEN G TNQEAFYKYLKGLLNK-I--EGSGYFL---DKIEREDFLRKQRTFDNGSIPHQIHLQEM  419
WP_002269448    357 -DGYAG YIDG K TNQEAFYKYLKGLLNK-I--EGSGYFL---DKIEREDFLRKQRTFDNGSIPHQIHLQEM  419
WP_002271977    357 -DGYAG YIDG K TNQEAFYKYLKGLLNK-I--EGSGYFL---DKIEREDFLRKQRTFDNGSIPHQIHLQEM  419
WP_002272766    357 -DGYAG YIDG K TNQEAFYKYLKGLLNK-I--EGSGYFL---DKIEREDFLRKQRTFDNGSIPHQIHLQEM  419
WP_002273241    357 -DGYAG YIDG K TNQEAFYKYLKGLLNK-I--EGSGYFL---DKIEREDFLRKQRTFDNGSIPHQIHLQEM  419
WP_002275430    357 -DGYAG YIDG K TNQEAFYKYLKGLLNK-I--EGSGYFL---DKIEREDFLRKQRTFDNGSIPHQIHLQEM  419
WP_002276448    357 -DGYAG YIDG K TNQEAFYKYLKGLLNK-I--EGSGYFL---DKIEREDFLRKQRTFDNGSIPHQIHLQEM  419
WP_002277050    357 -NGYAG YIEN G VKQDEFYKYLKNTLSK-I--AGSDYFL---DKIEREDFLRKQRTFDNGSIPHQIHLQEM  419
WP_002277364    357 -DGYAG YIDG K TNQEAFYKYLKGLLNK-I--EGSGYFL---DKIEREDFLRKQRTFDNGSIPHQIHLQEM  419
WP_002279025    357 -DGYAG YIDG K TNQEAFYKYLKGLLNK-I--EGSGYFL---DKIEREDFLRKQRTFDNGSIPHQIHLQEM  419
WP_002279859    357 -DGYAG YIDG K TNQEAFYKYLKGLLNK-I--EGSGYFL---DKIEREDFLRKQRTFDNGSIPHQIHLQEM  419
WP_002280230    357 -DGYAG YIDG K TNQEAFYKYLKGLLNK-I--EGSGYFL---DKIEREDFLRKQRTFDNGSIPHQIHLQEM  419
WP_002281696    357 -DGYAG YIDG K TNQEAFYKYLKGLLNK-I--TGSDYFL---DQIEREDFLRKQRTFDNGSIPHQIHLQEM  419
WP_002282247    357 -NGYAG YIEN G VKQDEFYKYLKNTLSK-I--TGSDYFL---DKIEREDFLRKQRTFDNGSIPHQIHLQEM  419
WP_002282906    357 -DGYAG YIDG K TNQEAFYKYLKGLLNK-I--EGSGYFL---DKIEREDFLRKQRTFDNGSIPHQIHLQEM  419
WP_002283846    357 -DGYAG YIDG K TNQEAFYKYLKGLLNK-I--EGSGYFL---DKIEREDFLRKQRTFDNGSIPHQIHLQEM  419
WP_002287255    357 -DGYAG YIDG K TNQEAFYKYLKGLLNK-I--EGSGYFL---DKIEREDFLRKQRTFDNGSIPHQIHLQEM  419
WP_002288990    357 -DGYAG YIDG K TNQEAFYKYLKGLLNK-I--EGSGYFL---DKIEREDFLRKQRTFDNGSIPHQIHLQEM  419
WP_002289641    357 -DGYAG YIDG K TNQEAFYKYLKGLLNK-I--EGSGYFL---DKIEREDFLRKQRTFDNGSIPHQIHLQEM  419
WP_002290427    357 -DGYAG YIDG K TNQEAFYKYLKGLLNK-I--EGSGYFL---DKIEREDFLRKQRTFDNGSIPHQIHLQEM  419
WP_002295753    357 -DGYAG YIDG K TNQEAFYKYLKGLLNK-I--EGSGYFL---DKIEREDFLRKQRTFDNGSIPHQIHLQEM  419
WP_002296423    357 -NGYAG YIDG K TNQEAFYKYVKGILNK-V--EGADVWL---DKIDREDFLRKQRTFDNGSIPHQIHLQEM  429
WP_002304487    357 -DGYAG YVGA D ATEEEFYKYVKGILNK-V--EGADVWL---DKIDREDFLRKQRTFDNGSIPHQIHLQEM  429
WP_002305844    357 -NGYAG YIDG K TNQEAFYKYLKGLLNK-I--EGSGYFL---DKIEREDFLRKQRTFDNGSIPHQIHLQEM  419
WP_002307203    357 -DGYAG YIDG K TNQEAFYKYLKGLLNK-I--EGSGYFL---DKIEREDFLRKQRTFDNGSIPHQIHLQEM  419
```

-continued

```
WP_002310390    357 --DGYAG YIDG K TNQEAFYKYLKGLLNK I--EGSGYFL--DKIEREDFLRKQRTFDNGSIPHQIHLQEM    419
WP_002352408    357 --DGYAG YIDG K TNQEAFYKYLKGLLNK I--EGSGYFL--DKIEREDFLRKQRTFDNGSIPHQIHLQEM    419
WP_012997688    357 --DGYAG YIDG K TNQEAFYKYLKGLLNK I--EGSGYFL--DKIEREDFLRKQRTFDNGSIPHQIHLQEM    419
WP_014677909    357 --DGYAG YIDG K TNQEAFYKYLKGLLNK I--EGSGYFL--DKIEREDFLRKQRTFDNGSIPHQIHLQEM    419
WP_019312892    357 --DGYAG YIDG K TNQEAFYKYLKGLLNK I--EGSGYFL--DKIEREDFLRKQRTFDNGSIPHQIHLQEM    419
WP_019313659    357 --DGYAG YIDG K TNQEAFYKYLKGLLNK I--EGSGYFL--DKIEREDFLRKQRTFDNGSIPHQIHLQEM    419
WP_019314093    357 --DGYAG YIDG K TNQEAFYKYLKGLLNK I--EGSGYFL--DKIEREDFLRKQRTFDNGSIPHQIHLQEM    419
WP_019315370    357 --DGYAG YIDG K TNQEAFYKYLKGLLNK I--EGNGYFL--DKIEREDFLRKQRTFDNGSIPHQIHLQEM    419
WP_019803776    357 --DGYAG YIDG K TNQEAFYKYLKGLLNK I--EGSGYFL--DKIEREDFLRKQRTFDNGSIPHQIHLQEM    419
WP_019805234    357 --DGYAG YIDG K TNQEAFYKYLKGLLNK I--EGSGYFL--DKIEREDFLRKQRTFDNGSIPHQIHLQEM    419
WP_024783594    357 --DGYAG YIDG K TNQEAFYKYLKGLLNK I--EGSGYFL--DKIEREDFLRKQRTFDNGSIPHQIHLQEM    419
WP_024784288    357 --NGYAG YIEN G VKQDEFYKYLKNTLSK --TGSDYFL--DQIEREDFLRKQRTFDNGSIPHQIHLQEM    419
WP_024784666    357 --DGYAG YIDG K TNQEAFYKYLKGLLNK I--EGSGYFL--DKIEREDFLRKQRTFDNGSIPHQIHLQEM    419
WP_024784894    357 --DGYAG YIDG K TNQEAFYKYLKGLLNK I--AGSDYFL--DKIEREDFLRKQRTFDNGSIPHQIHLQEM    419
WP_024786433    357 --NGYAG YIEN G VKQDEFYKYLKNTLSK I--EGSGYFL--DKIEREDFLRKQRTFDNGSIPHQIHLQEM    419
WP_049473442    357 --DGYAG YIDG K TNQEAFYKYLKGLLNK I--EGSGYFL--DKIEREDFLRKQRTFDNGSIPHQIHLQEM    419
WP_049474547    357 --DGYAG YIDG K TNQEAFYKYLKGLLNK I--EGNGYFL--DKIEREDFLRKQRTFDNGSIPHQIHLQEM    419
EMC03581        350 --DGYAG YIDG K TNQEAFYKYLKGLLNK I--EGSGYFL--DKIEREDFLRKQRTFDNGSIPHQIHLQEM    412
WP_000428612    358 --DGYAG YIDG K TTQESFYKYIKNLLSK F--EGADYFL--EKIEREDFLRKQRTFDNGSIPHQIHLQEM    420
WP_000428613    358 --DGYAG YIDG K TTQEAFYKYIKNLLSK F--EGTDYFL--EKIEREDFLRKQRTFDNGSIPHQIHLQEM    420
WP_049523028    357 --DGYAG YIDG K TNQEAFYKYIKNLISK I--EGAEYFL--EKIEREDFLRKQRTFDNGSIPHQIHLQEM    419
WP_003107102    326 --NGYAG YING K TSQEDFYKYIKPILSK L--KGAESLis--KLEREDFLRKQRTFDNGSIPHQIHLNEL    388
WP_054279288    359 --DGYAG YISG K TSQEAFYKYIKPILET L--DGAEDFLt--KINREDFLRKQRTFDNGSIPHQIHLGEL    421
WP_049531101    358 --EGYAG YIDS K TTQEAFYKYIKNLLSK F--DGADYFL--DKIEREDFLKKQRTFDNGSIPHQIHLQEM    420
WP_049538452    358 --DGYAG YVDG K TTQEAFYKYIKNLLSK F--EGADYFL--EKIEREDFLRKQRTFDNGSIPHQIHLQEM    420
WP_049549711    358 --DGYAG YIDG K TTQEAFYKYIKNLLSK F--EGTDYFL--EKIEREDFLRKQRTFDNGSIPHQIHLQEM    420
WP_007896501    359 --NGYAG YIEG K VSQDDFYRYIKPILSR L--KGGDEFLa--KIDRDDFLRKQRTFDNGSIPHQIHLKEL    421
EFR44625        311 --NGYAG YIEG K VSQDEFYRYIKPILSR L--KGGDEFLa--KIDRDDFLRKQRTFDNGSIPHQIHLKEL    373
WP_002897477    357 --DGYAG YIEG K TTQEAFYKYIKNLLSK F--EGADYFL--DKIEREDFLRKQRTFDNGSIPHQIHLQEM    419
WP_002906454    357 --DGYAG FIDG K TTQEAFYKYIKNLLSK L--EGADYFL--NKIEREDFLRKQRTFDNGSIPHQIHLQEM    419
WP_009729476    358 --DGYAG YIDG K TTQETFYKYIKNLLSK F--EGADYFL--DKIEREDFLRKQRTFDNGSIPHQVHLDEM    420
CQR24647        358 --NGYAG YIDG K TNQEDFYKYIKNLLQK V--DGGDYFI--EKIEREDFLRKQRTFDNGSIPHQVHLDEM    420
WP_000066813    358 --DGYAG YIDG K TTQEAFYKYIKNLLSK F--EGADYFL--DKIEREDFLKKQRTFDNGSIPHQIHLQEM    420
WP_009754323    358 --DGYAG YIEG K TTQENFYRFIKKAIEK I--EGSNYFI--DKIDREDFLRKQRTFDNGSIPHQIHLQEM    420
WP_044674937    357 --DGYAG YIEG K TTQENFYRFIKKAIEK I--EGNYFI--DKIDREVFLRKQRSFYNSVIPHQIHLQEM    419
WP_044676715    357 --DGYAG YIEG K TTQENFYRFIKKAIEK I--EGSNYFI--DKIDREVFLRKQRSFYNSVIPHQIHLQEM    419
WP_044680361    357 --DGYAG YIEG K TTQENFYRFIKKAIEK I--EGNYFI--DKIDREDFLRKQRTFDNGSIPHQIHLQEM    419
WP_044681799    357 --DGYAG YIEG K TTQENFYRFIKKAIEK I--EGSDYFI--NGSGDFL--DKIDREDFLRKQRTFDNGSIPHQIHLQEM    419
WP_049533112    357 --KGYAG YIEN G VKQDEFYKYLKGILLQ I--NGSGDFL--DKIDREDFLRKQRTFDNGSIPHQIHLQEM    419
WP_029090905    316 fyTDYIG YEES K SKEERLFKHIELLLAKeNv1TTVEHAL1eKNITFASLLPLQRSSRNAVIPYQVHEKEL    403
WP_006506696    361 ksKGYYN YINR K APYDEFYKYVKKCIEK --VdtPEAKQIln--DIELENFLLKQNSRTNGSVPYQMQLDEM    429
AIT42264        357 --NGYAG YIDG G ASQEEFYKFIKPILEK M--DGTEELLv--KLNREDLLRKQRSFYNGVIPYQIHLGEL    419
WP_034440723    363 --NGYAG YIDG K TSQEDFYKFVKAQLKG --eENGEYFL--EAIENENFLRKQRSFYNGVIPYQIHLGEL    425
AKQ21048        357 --NGYAG YIDG G ASQEEFYKFIKPILEK M--DGTEELLv--KLNREDLLRKQRSFYNGVIPYQIHLGEL    419
WP_002436532    356 --NGYAG YIDG K TSQEDFYKYIEKVMKT --IksDKKDYFL--DKIDREVFLRKQRSFYNSVIPHQIHLGEL    420
WP_002364836    363 --DGYAG YIAH A VSQLKFYQVVKKIIQD I--AGAEYFL--EKIAQENFLRKQRTFDNGVIPHQIHLAEL    427
WP_016631044    314 --DGYAG YIAH A VSQLKFYQVVKKIIQD I--AGAEYFL--EKIAQENFLRKQRTFDNGVIPHQIHLAEL    378
EMS75795        100 --NGYAG YIDG K TTQEDFYKFLKKELNG I--AGSERFM--EKVDQENFLLKQRTTANGVIPHQVHLTEL    162
WP_002373311    363 --DGYAG YIAH A VSQLKFYQYVKKIIQD I--AGAEYFL--EKIAQENFLRKQRTFDNGVIPHQIHLAEL    427
WP_002378009    363 --DGYAG YITH A VSQLKFYQYVKKIIQD I--AGAEYFL--EKIAQENFLRKQRTFDNGVIPHQIHLAEL    427
WP_002407324    363 --DGYAG YITH A VSQLKFYQYVKKIIQD I--AGAEYFL--EKIAQENFLRKQRTFDNGVIPHQIHLAEL    427
WP_002413717    363 --DGYAG YIAH A VSQLKFYQYVKKIIQD I--AGAEYFL--EKIAQENFLRKQRTFDNGVIPHQIHLAEL    427
WP_010775580    365 --DGYAG YIAH A VSQLKFYQYVKKIIQD I--AGAEYFL--EKIAQENFLRKQRTFDNGVIPHQIHLAEL    429
```

-continued

```
WP_010818269    363 --DGYAG YIAH A VSQLKFYQYVKKIIQD-I--AGAEYFL---EKIAQENFLRKQRTFDNGVIPHQIHLAEL    427
WP_010824395    363 --DGYAG YITH A VSQLKFYQYVKKIIQD-I--AGAEYFL---EKIAQENFLRKQRTFDNGVIPHQIHLAEL    427
WP_016622645    363 --DGYAG YIAH A VSQLKFYQYVKKIIQD-I--AGAEYFL---EKIAQENFLRKQRTFDNGVIPHQIHLAEL    427
WP_033625576    363 --DGYAG YIAH A VSQLKFYQYVKKIIQD-I--AGAEYFL---EKIAQENFLRKQRTFDNGVIPHQIHLAEL    427
WP_033789179    363 --DGYAG YIAH A VSQLKFYQYVKKIIQD-I--AGAEYFL---EKIAQENFLRKQRTFDNGVIPHQIHLAEL    427
WP_002310644    361 --NGYAG YIEG H ATQEDFYKFVKKELTG-I--RGSEVFL---TKIEQENFLRKQRTFDNGVIPHQIHLTEL    423
WP_002312694    362 --NGYAG YIEG H ATQEAFYKFVKKELTG-I--RGSEVFL---TKIEQENFLRKQRTFDNGVIPHQIHLTEL    424
WP_002314015    362 --NGYAG YIEG H ATQEDFYKFVKKELTG-I--RGSEVFL---TKIEQENFLRKQRTFDNGVIPHQIHLTEL    424
WP_002320716    362 --NGYAG YIEG H ATQEDFYKFVKKELTG-I--RGSEVFL---TKIEQENFLRKQRTFDNGVIPHQIHLTEL    424
WP_002330729    361 --NGYAG YIEG H ATQEDFYKFVKKELTG-I--AGAEYFL---EKIAQENFLRKQRTFDNGVIPHQIHLTEL    423
WP_002335161    362 --NGYAG YIEG H ATQEDFYKFVKKELTG-I--RGSEVFL---TKIEQENFLRKQRTFDNGVIPHQIHLTEL    424
WP_002345439    362 --NGYAG YIEG H ATQEDFYKFVKKELTG-I--RGSEVFL---TKIEQENFLRKQRTFDNGVIPHQIHLTEL    424
WP_034867970    355 --NGYAG YIKG K TTQEEFYKFVKKELSG-V--VGSEPFL---EKIDQETFLLKQRTYTNGVIPHQVHLIEL    417
WP_047937432    362 --NGYAG YIKG K TTQEEFYKFVKKELTG-I--RGSEVFL---TKIEQENFLRKQRTYTNGVIPHQVHLIEL    424
WP_002310994    355 --NGYAG YIKG K TTQEEFYKFVKKELSG-V--VGSEPFL---EKIDQETFLLKQRTYTNGVIPHQVHLIEL    417
WP_010737004    355 --NGYAG YIKG K TTQEEFYKFVKKELSG-V--VGSEPFL---EKIDQETFLLKQRIYDNGVIPHQVHAEEL    417
WP_034700478    355 --NGYAG YIKG K TTQEEFYKFVKKELSG-V--VGSEPFL---EKIDQETFLLKQRTYTNGVIPHQVHLIEL    417
WP_007209003    359 --NGYAG YIDG K TKEEEFYKYLKTTLVQ---ksGYQYFI---EKIEQENFLRKQRIYDNGVIPHQVHAEEL    421
WP_023519017    355 --NGYAG YVKG K ATQEEFYKFLRTELAG-L--EESQsIM---EKIDLEIYLLKQRTFANGVIPHQIHLVEM    417
WP_010770040    358 --SGYAG YVEN S VTQAEFYKYIKKAIEK-V--PGAEYFL---EKIEQETFLDKQRTFNNGVIPHQIHLEEL    422
WP_048604708    354 --DGYAG YIDN S TSQEKFYKYITNLIEK-I--DGAEYFI---KKIENEDFLRKQRTFDNGIIPHQIHLEEL    418
WP_010750235    355 --DGYAG YIDG K TKQADFYKFLKKELTG-V--PGSEPML---AKIDQENFILKQRTPTNGVIPHQVHLTEF    417
AII16583        396 --NGYAG YIDG G ASQEEFYKFIKPILEK-M--DGTEELLv--KLNREDLLRKQRTEDNGSIPHQIHLGEL    458
WP_029073316    367 kkNNYCN YINH K TPVDEFYKYIKKLIEK-IddPDVKTILn--KIELESFMLKQNSRTNGAVPYQMQLDEL    435
WP_031589969    367 kkNNYCN YINH K TPVDEFYKYIKKLIEK-IddPDVKTILn--KIELESFMLKQNSRTNGAVPYQMQLDEL    435
KDA45870        354 -iSGYAG YIDG K VSEEDFYKYTKKTLKG-I--PETEEILq--KIDANNYLRKQRTFDNGAIPHQVHLKEL    417
WP_039099354    360 ------- YVDG K -SKEDFYGDITKALKNnPdhPIVSEIKk--LIELDQFMPKQRTKDNGAIPHQLHQQEL    425
AKP02966        349 --QAYDD YINK K --KELYTSLKKFKLKVaLp-TNLAKEAe--EKISKGTYLVKPRNSENGVVPYQLNKIEM    415
WP_010991369    363 --HGYAG YIDG - TKQADFYKYMKMTLEN-I--EGADYFI---AKIEKENFLRKQRTFDNGAIPHQLHLEEL    425
WP_033838504    363 --HGYAG YIDG - TKQADFYKYMKMTLEN-V--EGADYFI---TKIEEENFLRKQRTFDNGVIPHQLHLEEL    425
EHN60060        366 --HGYAG YIDG - TKQADFYKYMKMTLEN-V--EGADYFI---AKIEKENFLRKQRTFDNGAIPHQLHLEEL    428
EFR89594        132 ------- YIDG - TKQADFYKYMKMTLEN-I--EGADYFI---AKIEKENFLRKQRTFDNGAIPHQLHLEEL    194
WP_038409211    363 --DGYAG YIDG - TTQEKFYKYMKKMLAN-I--DGADYFI---DQIEEENFLRKQRTFDNGTIPHQLHLEEL    425
EFR95520          1 ------- ---- - --MKKMLAN-I--DGADYFI---AKIEEENFLRKQRTFDNGAIPHQLHLEEL     44
WP_003723650    363 --DGYAG YIEG - TKQVDFYKYLKTILEN-I--EGSDYFI---AKIEEENFLRKQRTFDNGAIPHQLHLEEL    425
WP_003727705    363 --DGYAG YIDG - TKQVDFYKYLKTTLEN-V--EGADYFI---TKIEEENFLRKQRTFDNGVIPHQLHLEEL    425
WP_003730785    363 --DGYAG YIDG - TKQVDFYKYLKTTLEN-V--EGADYFI---AKIEEENFLRKQRTFDNGAIPHQLHLEEL    425
WP_003733029    363 --HGYAG YISG - TKQVDFYKYMKATLEK-I--EGADYFI---AKIEEENFLRKQRTFDNGAIPHQLHLEEL    425
WP_003739838    363 --DGYAG YIDG - TKQVDFYKYLKTILEN-I--EGADYFI---AKIEEENFLRKQRTFDNGAIPHQLHLEEL    425
WP_014601172    363 --DGYAG YIDG - TKQVDFYKYLKTILEN-I--EGADYFI---AKIEEENFLRKQRTFDNGAIPHQLHLEEL    425
WP_023548323    363 --DGYAG YIDG - TKQVDFYKYLKTILEN-V--EGSDYFI---TKIEEENFLRKQRTFDNGAIPHQLHLEEL    425
WP_031665337    363 --DGYAG YISG - TKQVDFYKYMKATLEK-I--EGADYFI---AKIEEENFLRKQRTFDNGVIPHQLHLEEL    425
WP_031669209    363 --HGYAG YIDG - TKQVDFYKYMKATLEK-V--EGADYFI---AKIEEENFLRKQRTFDNGAIPHQLHLEEL    425
WP_033920898    363 --DGYAG YIDG - TKQVDFYKYLKTILEN-I--EGADYFI---AKIEEENFLRKQRTFDNGAIPHQLHLEEL    425
AKI42028        366 --DGYAG YIDG - TKQVDFYKYLKTILEN-I--EGADYFI---AKIEEENFLRKQRTFDNGAIPHQLHLEEL    428
AKI50529        366 --DGYAG YIDG - TKQVDFYKYLKTILEN-I--EGADYFI---AKIEEENFLRKQRTFDNGAIPHQLHLEEL    428
EFR83390        363 --DGYAG YIEG - TKQEAFYKYMKMLEH-V---EGADYFI---NQIEEENFLRKQRTFDNGAIPHQLHLEEL    425
WP_046323366    373 --NGYAG YIDG G ASQEEFYKFIKPILEK-M--DGTEELLv--KLNREDLLRKQRTFDNGSIPHQIHLGEL    435
AKE81011        365 kvkGYYN YINR K APVDEFYKFVKKCIEK-VdtPEAKQILh--DIELENFLLKQNSRTNGSVPYQMQLDEM    433
CUO82355        366 kLHNYLG YIKY D TPVEEFYKYIKGLLAK-VdtDEAREILe--RIDLEKFMLKQNSRTNGSIPYQMQKDEM    434
WP_033162887    365 kLHNYLG YIKY D TPVEEFYKYIKGLLAK-VdtDEAREILe--RIDLEKFMLKQNSRTNGSIPYQMQKDEM    434
AG201981        390 --NGYAG YIDG G ASQEEFYKFIKPILEK-M--DGTEELLv--KLNREDLLRKQRTFDNGSIPHQIHLGEL    452
```

```
AKA60242        357 --NGYAG YIDG G ASQEEFYKFYKIPKPILEK-M--DGTEELLV--KLNREDLLRKQRTFDNGSIPHQIHLGEL  419
AKS40380        357 --NGYAG YIDG G ASQEEFYKFYKIPKPILEK-M--DGTEELLV--KLNREDLLRKQRTFDNGSIPHQIHLGEL  419
4UN5_B          361 --NGYAG YIDG G ASQEEFYKFYKIPKPILEK-M--DGTEELLV--KLNREDLLRKQRTFDNGSIPHQIHLGEL  423
WP_010922251    420 HAILRRQEDFYPFLKD--NRE KIEKILTFRIPYYVGPL ARG-n--SRFAWMTR---KSEETITPWNFE[E]VDKGA  486
WP_039695303    423 HAILRRQGDYYPFLKE--KQD RIEKILTFRIPYYVGPL VRKD--SRFAWAEY---RSDEKITPWNFDKVIDKEK  489
WP_045635197    420 NAILRRQGEYYPFLKE--NKE KIEKILTFRIPYYVGPL ARGN--RDFAWLTR---NSDEAIRPWNFEEIVDKAS  486
5AXW_A          184 KQLLKVQKAYHQLDQSfi--D TYIDLLETRRTYEGPG ---Eg-SPFGWKDI-----------------------  229
WP_009980683    104 HAILRRQEDFYPFLKD--NRE KIEKILTFRIPYYVGPL ARG-n--SRFAWMTR---KSEETITPWNFEEVVDKGA  170
WP_010922251    420 HAILRRQEDFYPFLKD--NRE KIEKILTFRIPYYVGPL ARG-n--SRFAWMTR---KSEETITPWNFEEVVDKGA  486
WP_011054416    420 HAILRRQEDFYPFLKD--NRE KIEKILTFRIPYYVGPL ARG-n--SRFAWMTR---KSEETITPWNFEEVVDKGA  486
WP_011284745    420 HAILRRQEDFYPFLKD--NRE KIEKILTFRIPYYVGPL ARG-n--SRFAWMTR---KSEETITPWNFEEVVDKGA  486
WP_011285506    420 HAILRRQEDFYPFLKD--NRE KIEKILTFRIPYYVGPL ARG-n--SRFAWMTR---KSEETITPWNFEEVVDKGA  486
WP_011527619    420 HAILRRQEDFYPFLKD--NRE KIEKILTFRIPYYVGPL ARG-n--SRFAWMTR---KSEETITPWNFEEVVDKGA  486
WP_012560673    420 HAILRRQEDFYPFLKD--NRE KIEKILTFRIPYYVGPL ARG-n--SRFAWMTR---KSEETITPWNFEEVVDKGA  486
WP_014407541    420 HAILRRQEDFYPFLKD--NRE KIEKILTFRIPYYVGPL ARG-n--SRFAWMTR---KSEETITPWNFEEVVDKGA  486
WP_020905136    420 HAILRRQEDFYPFLKD--NRE KIEKILTFRIPYYVGPL ARG-n--SRFAWMTR---KSEETITPWNFEEVVDKGA  486
WP_023080005    420 HAILRRQEDFYPFLKD--NRE KIEKILTFRIPYYVGPL ARG-n--SRFAWMTR---KSEETITPWNFEEVVDKGA  486
WP_023610282    420 HAILRRQEDFYPFLKD--NRE KIEKILTFRIPYYVGPL ARG-n--SRFAWMTR---KSEETITPWNFEEVVDKGA  486
WP_030125963    420 HAILRRQEDFYPFLKD--NRE KIEKILTFRIPYYVGPL ARG-n--SRFAWMTR---KSEETITPWNFEEVVDKGA  486
WP_030126706    420 HAILRRQEDFYPFLKD--NRE KIEKILTFRIPYYVGPL ARG-n--SRFAWMTR---KSEETITPWNFEEVVDKGA  486
WP_031488318    420 HAILRRQEDFYPFLKD--NRE KIEKILTFRIPYYVGPL ARG-n--SRFAWMTR---KSEETITPWNFEEVVDKGA  486
WP_032460140    420 HAILRRQEDFYPFLKD--NRE KIEKILTFRIPYYVGPL ARG-n--SRFAWMTR---KSEETITPWNFEEVVDKGA  486
WP_032461047    420 HAILRRQEDFYPFLKD--NRE KIEKILTFRIPYYVGPL ARG-n--SRFAWMTR---KSEETITPWNFEEVVDKGA  486
WP_032462016    420 HAILRRQEDFYPFLKD--NRE KIEKILTFRIPYYVGPL ARG-n--SRFAWMTR---KSEETITPWNFEEVVDKGA  486
WP_032462936    420 HAILRRQEDFYPFLKD--NRE KIEKILTFRIPYYVGPL ARG-n--SRFAWMTR---KSEETITPWNFEEVVDKGA  486
WP_032464890    420 HAILRRQEDFYPFLKD--NRE KIEKILTFRIPYYVGPL ARG-n--SRFAWMTR---KSEETITPWNFEEVVDKGA  486
WP_033888930    245 HAILRRQEDFYPFLKD--NRE KIEKILTFRIPYYVGPL ARG-n--SRFAWMTR---KSEETITPWNFEEVVDKGA  311
WP_038431314    420 HAILRRQEDFYPFLKD--NRE KIEKILTFRIPYYVGPL ARG-n--SRFAWMTR---KSEETITPWNFEEVVDKGA  486
WP_038432938    420 HAILRRQEDFYPFLKD--NRE KIEKILTFRIPYYVGPL ARG-n--SRFAWMTR---KSEETITPWNFEEVVDKGA  486
WP_038434062    331 HAILRRQEDFYPFLKD--NRE KIEKILTFRIPYYVGPL ARG-n--SRFAWMTR---KSEETITPWNFEEVVDKGA  397
BAQ51233        ---  ------------------------------------------------------------------------
KGE60162        ---  ------------------------------------------------------------------------
KGE60856        420 HAILRRQEDFYPFLKD--NRE KIEKILTFRIPYYVGPL ARG-n--SRFAWMTR---KSEETITPWNFEEVVDKGA  486
WP_002989955    420 HAILRRQEEHYPFLKE--NQD RIEKILTFRIPYYVGPL ARKG--SRFAWAEY---KADEKITPWNFDDILDKEK  486
WP_003030002    420 HAILRRQGDYYPFLKE--NQD RIEKILTFRIPYYVGPL ARKD--SRFSWABY---HSDEKITPWNFDKVIDKEK  486
WP_003065552    423 HAILRRQEDYYPFLKE--NQD RIEKILTFRIPYYVGPL AREK--SDFAWMTR---KTDDSIRPWNFEDLVDKEK  489
WP_001040076    421 RAIIRRQSEYYPFLKE--NQD RIEKILTFRIPYIGPL AREK--SDFAWMTR---KTDDSIRPWNFEDLVDKEK   487
WP_001040078    421 KAIIRRQSEYYPFLKE--NQD RIEKILTFRIPYIGPL AREK--SDFAWMTR---KTDDSIRPWNFEDLVDKEK   487
WP_001040080    421 KAIIRRQSEYYPFLKE--NQD RIEKILTFRIPYIGPL AREK--SDFAWMTR---KTDDSIRPWNFEDLVDKEK   487
WP_001040081    421 KAIIRRQSEYYPFLKE--NQD RIEKILTFRIPYIGPL AREK--SDFAWMTR---KTDDSIRPWNFEDLVDKEK   487
WP_001040083    421 KAIIRRQSEYYPFLKE--NQD RIEKILTFRIPYIGPL AREK--SDFAWMTR---KTDDSIRPWNFEDLVDKEK   487
WP_001040085    421 KAIIRRQSEYYPFLKE--NQD RIEKILTFRIPYIGPL AREK--SDFAWMTR---KTDDSIRPWNFEDLVDKEK   487
WP_001040087    421 KAIIRRQSEYYPFLKE--NQD RIEKILTFRIPYIGPL AREK--SDFAWMTR---KTDDSIRPWNFEDLVDKEK   487
WP_001040088    421 KAIIRRQSEYYPFLKE--NQD RIEKILTFRIPYIGPL AREK--SDFAWMTR---KTDDSIRPWNFEDLVDKEK   487
WP_001040089    421 KAIIRRQSEYYPFLKE--NQD RIEKILTFRIPYIGPL AREK--SDFAWMTR---KTDDSIRPWNFEDLVDKEK   487
WP_001040090    421 KAIIRRQSEYYPFLKE--NQD RIEKILTFRIPYIGPL AREK--SDFAWMTR---KTDDSIRPWNFEDLVDKEK   487
WP_001040091    421 KAIIRRQSEYYPFLKE--NQD RIEKILTFRIPYIGPL AREK--SDFAWMTR---KTDDSIRPWNFEDLVDKEK   487
WP_001040092    421 KAIIRRQSEYYPFLKE--NQN RIEKILTFRIPYIGPL ARGN--SDFAWMTR---KTDDSIRPWNFEDLVDKEK   487
WP_001040094    421 RAIIRRQSEYYPFLKE--NLD RIEKILTFRIPYYVGPL AREK--SDFAWMTR---KTDDSIRPWNFEDLVDKEK   487
WP_001040095    421 RAIIRRQSEYYPFLKE--NLD RIEKILTFRIPYYVGPL AREK--SDFAWMTR---KTDDSIRPWNFEDLVDKEK   487
WP_001040096    421 RAIIRRQSEYYPFLKE--NLD RIEKILTFRIPYYVGPL AREK--SDFAWMTR---KTDDSIRPWNFEDLVDKEK   487
WP_001040097    421 RAIIRRQSEYYPFLKE--NLD RIEKILTFRIPYYVGPL AREK--SDFAWMTR---KTDDSIRPWNFEDLVDKEK   487
WP_001040098    421 RAIIRRQSEYYPFLKE--NLD RIEKILTFRIPYYVGPL AREK--SDFAWMTR---KTDDSIRPWNFEDLVDKEK   487
```

```
-continued

WP_001040099   421 RAIIRRQSEYYPPLKE--NLD RIEKILTFRIPYYVGPL AREK--SDFAWMTR---KTDDSIRPWNFEDLVDKEK 487
WP_001040100   421 RAIIRRQSEYYPPLKE--NLD RIEKILTFRIPYYIGPL AREK--SDFAWMTR---KTDDSIRPWNFEDLVDKEK 487
WP_001040104   421 RAIIRRQSEYYPPLKE--NQD RIEKILTFRIPYYIGPL AREK--SDFAWMTR---KTDDSIRPWNFEDLVDKEK 487
WP_001040105   421 KAIIRRQSEYYPFLKE--NLD RIEKILTFRIPYYIGPL AREK--SDFAWMTR---KTDDSIRPWNFEELVDKEA 487
WP_001040106   421 KAIIRRQSEYYPFLKE--NLD RIEKILTFRIPYYVGPL AREK--SDFAWMTR---KTDDSIRPWNFEELVDKEA 487
WP_001040107   421 KAIIRRQSEYYPFLKE--NLD RIEKILTFRIPYYVGPL AREK--SDFAWMTR---KTDDSIRPWNFEELVDKEA 487
WP_001040108   421 KAIIRRQSEYYPFLKE--NLD RIEKILTFRIPYYVGPL AREK--SDFAWMTR---KTDDSIRPWNFEELVDKEA 487
WP_001040109   421 KAIIRRQSEYYPFLKE--NLD RIEKILTFRIPYYIGPL AREK--SDFAWMTR---KTDDSIRPWNFEELVDKEA 487
WP_001040110   421 KAIIRRQSEYYPFLKE--NLD RIEKILTFRIPYYIGPL AREK--SDFAWMTR---KTDDSIRPWNFEELVDKEA 487
WP_015058523   421 KAIIRRQSEYYPPLKE--NQD RIEKILTFRIPYYIGPL ARGN--SDFAWMTR---KTDDSIRPWNFEDLVDKEK 487
WP_017643650   421 RAIIRRQSEYYPPLKE--NLD RIEKILTFRIPYYIGPL AREK--SDFAWMTR---KTDDSIRPWNFEDLVDKEK 487
WP_017647151   421 KAIIRRQSEYYPFLKE--NLD RIEKILTFRIPYYVGPL AREK--SDFAWMTR---KTDDSIRPWNFEELVDKEA 487
WP_017648376   421 KAIIRRQSEYYPFLKE--NLD RIEKILTFRIPYYVGPL AREK--SDFAWMTR---KTDDSIRPWNFEELVDKEA 487
WP_017649527   421 KAIIRRQSEYYPFLKE--NQD RIEKILTFRIPYYVGPL AREK--SDFAWMTR---KTDDSIRPWNFEELVDKEA 487
WP_017771611   421 KAIIRRQSEYYPFLKE--NLD RIEKILTFRIPYYIGPL AREK--SDFAWMTR---KTDDSIRPWNFEELVDKEA 487
WP_017771984   421 KAIIRRQSEYYPFLKE--NQD RIEKILTFRIPYYIGPL AREK--SDFAWMTR---KTDDSIRPWNFEELVDKEA 487
CFQ25032       421 KAIIRRQSEYYPFLKE--NQD RIEKILTFRIPYYIGPL AREK--SDFAWMTR---KTDDSIRPWNFEDLVDKEK 487
CFV16040       421 KAIIRRQSEYYPFLKE--NLD RIEKILTFRIPYYIGPL AREK--SDFAWMTR---KTDDSIRPWNFEDLVDKEK 487
KLJ37842       421 KAIIRRQSEYYPFLKE--NQD RIEKILTFRIPYYVGPL AREK--SDFAWMTR---KTDDSIRPWNFEDLVDKEK 487
KLJ72361       421 KAIIRRQSEYYPPLKE--NQD RIEKILTFRIPYYIGPL AREK--SDFAWMTR---KTDDSIRPWNFEDLVDKEK 487
KLL20707       421 KAIIRRQSEYYPFLKE--NQD RIEKILTFRIPYYIGPL AREK--SDFAWMTR---KTDDSIRPWNFEDLVDKEK 487
KLL42645       421 KAIIRRQSEYYPFLKE--NLD RIEKILTFRIPYYIGPL AREK--SDFAWMTR---KTDDSIRPWNFEDLVDKEK 487
WP_047207273   421 RAIIRRQSEYYPFLKE--NQD RIEKILTFRIPYYVGPL AREK--SDFAWMTR---KTDDSIRPWNFEDLVDKEK 487
WP_047209694   421 RAIIRRQSEYYPFLKE--NLD RIEKILTFRIPYYVGPL AREK--SDFAWMTR---KTDDSIRPWNFEDLVDKEK 487
WP_050198062   421 KAIIRRQSEYYPFLKE--NQD RIEKILTFRIPYYIGPL AREK--SDFAWMTR---KTDDSIRPWNFEDLVDKEK 487
WP_050201642   421 KAIIRRQSEYYPFLKE--NQD RIEKILTFRIPYYIGPL AREK--SDFAWMTR---KTDDSIRPWNFEDLVDKEK 487
WP_050204027   421 KAIIRRQSEYYPFLKE--NLD RIEKILTFRIPYYIGPL AREK--SDFAWMTR---KTDDSIRPWNFEDLVDKEK 487
WP_050881965   421 KAIIRRQSEYYPFLKE--NQD RIEKILTFRIPYYIGPL AREK--SDFAWMTR---KTDDSIRPWNFEDLVDKEK 487
WP_050886065   421 KDIIRRQSEYYPFLKE--NQD KIEKILTFRIPYYIGPL AREK--SDFAWMTR---KTDDSIRPWNFEDLVDKEK 487
AHN30376       421 KAIIRRQSEYYPFLKE--NQD RIEKILTFRIPYYIGPL ARGN--SDFAWMTR---KTDDSIRPWNFEELVDKEA 487
EA078426       421 RAIIRRQSEYYPFLKE--NLD RIEKILTFRIPYYIGPL AREK--SDFAWMTR---KTDDSIRPWNFEELVDKEA 487
CCW42055       421 KAIIRRQSEYYPFLKE--NQD RIEKILTFRIPYYVGPL AREK--SDFAWAEY---KADEKITPWNFDDILDKEK 486
WP_003041502   420 HAILRRQGEHYPFLKE--NQD KIEKILTFRIPYYVGPL AREK--SRFAWAEY---KADEKITPWNFDDILDKEK 487
WP_037593752   421 HAILRRQGEHYPFLKE--NRE KIEKILTFRIPYYVGPL ARKG--SRFAWAEY---KADEKITPWNFDDILDKEK 487
WP_049516684   420 HAILRRQGEHYPFLKE--NRE KIEKILTFRIPYYVGPL ARKG--SRFAWAEY---KADEKITPWNFDDILDKEK 486
GAD46167       420 HAILRRQGEHYPFLKE--NQD KIEKILTFRIPYYVGPL ARKG--SRFAWAEY---KADEKITPWNFDDILDKEK 486
WP_018363470   430 HAILRRQEFFYPFLKE--NQE EIEKILTFRIPYYVGPL ARKD--SRFAWAEY---RSDEKITPWNFDKVIDKEK 496
WP_003043819   420 HAILRRQGEHYPFLKE--NQD KIEKILTFRIPYYVGPL ARG-n-SRFAWLTR---KSEEAITPWNFEEVVDKGA 486
WP_006269658   420 HAILRRQGEHYPFLKE--NQD KIEKILTFRIPYYVGPL ARKG--SRFAWAEY---KADEKITPWNFDDILDKEK 486
WP_048800889   420 HAILRRQGEHYPFLKE--NQD KIEKILTFRIPYYVGPL VRKG--SRFAWAEY---KSEETITPWNFEEVVDKGA 486
WP_012767106   420 HAILRRQGEDFYPFLKD--NRE KIESLLTFRIPYYVGPL ARG-n-SRFAWMTR---KSEETITPWNFEEVVDKGA 486
WP_014612333   420 HAILRRQGEDFYPFLKD--NRE KIESLLTFRIPYYVGPL ARG-n-SRFAWMTR---KSEETITPWNFEEVVDKGA 486
WP_015017095   420 HAILRRQGEDFYPFLKD--NRE KIESLLTFRIPYYVGPL ARG-n-SRFAWMTR---KADEKITPWNFEEVVDKGA 486
WP_015057649   420 HAILRRQGEHYPFLKE--NRK KIESLLTFRIPYYVGPL ARG-h-SRFAWVKR---KPDGAIRPWNFEEIVDEEA 486
WP_048327215   420 HAILRRQEVEYPFLKE--NRK KIEKILTFRIPYYVGPL ARG-h-SRFAWVKR---KPDGAIRPWNFEEIVDEEA 486
WP_049519324   420 HAILRRQEVEYPFLKD--NRK KIEKILTFRIPYYVGPL ARG-n-SRFAWAKY---KPDGAIRPWNFEEIVDEEA 486
WP_012515931   420 HAILRRQEVEYPFLKE--NQE KIEKILTFRIPYYVGPL ARG-n-SRFAWVKR---KPDGAIRPWNFEEIVDEEA 486
WP_021320964   421 HAILRRQGEHYPFLKE--NRK KIESLLTFRIPYYVGPL ARG-n-SRFAWAKY---KPDGAIRPWNFEEIVDEEA 487
WP_037581760   421 RTILRRQGEHYPFLKE--NQA KIEKILTFRIPYYVGPL ARKN--SRFAWAKY---HSDEPITPWNDEVVDKEK 487
WP_004232481   421 HAILRRQGDYYPFLKE--KQD RIEKILTFRIPYYVGPL VRKD--SRFAWAEY---RSDEKITPWNFDKVIDKEK 487
WP_009854540   421 HAILRRQGEHYAFLKE--NQA KIEKILTFRIPYYVGPL ARKN--SRFAWAEY---HSDEKITPWNFDEIIDKEK 487
WP_012962174   423 HAILRRQGDYYPFLKE--KQD RIEKILTFRIPYYVGPL VRKD--SRFAWAEY---RSDEKITPWNFDKVIDKEK 489
WP_039695303
```

```
WP_014334983    420  HSILRRQGDYYPPLKE--NQA KIEKILTFRIPYYVGPL ARKD--SRFAWANY---HSDEPITPWNFDEVVDKEK  486
WP_003092269    420  KAIIRRQEKFYPFLKE--NQK KIEKLFTFKIPYYIGPL ANG-q-SSFAWLKR---QSNESITPWNFEEVVDQEA  486
AHY15608        420  KAIIRRQEKFYPFLKE--NQK KIEKLFTFKIPYYVGPL ANG-q-SSFAWLKR---QSNESITPWNFEEVVDQEA  486
AHY17476        420  KAIIRRQEKFYPFLKE--NQK KIEKLFTFKIPYYVGPL ANG-q-SSFAWLKR---QSNESITPWNFEEVVDQEA  486
ESR09100        ---  --------------------- ----------------- ----------------------------------  ---
AGM98575        420  RAIIRRQEKFYPFLKE--NQK KIEKLTFKIPYYVGPL ANG-q-SSFAWLKR---QSNESITPWNFEEVVDQEA  486
ALF27331        420  RAIIRRQAEFYPPLAD--NQD RIEKILTFRIPYYIGPL ARGK--SDFSWLSR---KSADKITPWNFDEIVDKES  486
WP_018372492    433  QAIILNQSKYYPFLAE--NKE KIEKILTFRIPYYVGPL ARGN--SSFAWLQR---KSDEAIRPWNFEQVDMET  499
WP_045618028    421  NAIIRRQGEHYPFLQE--NKE KIEKILTFRIPYYVGPL ARGN--RDFAWLTR---NSDQAIRPWNFEEIVDKAS  487
WP_045635197    420  RAIIRRQGEYYPFLKD--NKE KIEKILTFRIPYYVGPL ARGN--RDFAWLTR---NSDEAIRPWNFEEIVDKAS  486
WP_002263549    420  RAIIRRQAEFYPPLAD--NQD RIEKILTFRIPYYVGPL ARGK--SDFAWLSR---KSADKITPWNFDEIVDKES  486
WP_002263887    420  RAIIRRQAEFYPPLAD--NQD RIEKILTFRIPYYVGPL ARGK--SDFAWLSR---KSADKITPWNFDEIVDKES  486
WP_002264920    420  HAILRRQGDYYPPLKE--NQD RIEKILTFRIPYYVGPL ARGK--SDFAWLSR---KSADKITPWNFDEIVDKES  486
WP_002269043    420  RAIIRRQAEFYPPLAD--NQD RIEKILTFRIPYYVGPL ARGK--SDFAWLSR---KSADKITPWNFDEIVDKES  486
WP_002269448    420  RAIIRRQAEFYPPLAD--NQD RIEKILTFRIPYYVGPL ARGK--SDFAWLSR---KSADKITPWNFDEIVDKES  486
WP_002271977    420  RAIIRRQAEFYPPLAD--NQD RIEKILTFRIPYYVGPL ARGK--SDFAWLSR---KSADKITPWNFDEIVDKES  486
WP_002272766    420  RAIIRRQAEFYPPLAD--NQD RIEKILTFRIPYYVGPL ARGK--SDFAWLSR---KSADKITPWNFDEIVDKES  486
WP_002273241    420  RAIIRRQAEFYPPLKE--NQD RIEKILTFRIPYYVGPL ARKN--SRFAWAEY---HSDEAVMPWNFDQVIDKES  486
WP_002275430    420  RAIIRRQAEFYPPLAD--NQD RIEKILTFRIPYYVGPL ARGK--SDFAWLSR---KSADKITPWNFDEIVDKES  486
WP_002276448    420  RAIIRRQSEFYPPLAD--NQD RIEKILTFRIPYYVGPL ARGK--SDFAWLSR---KSADKITPWNFDEIVDKES  486
WP_002277050    420  HAILRRQGDYYPPLKE--NQD RIEKILTFRIPYYVGPL ARKN--SRFAWAEY---HSDEAVMPWNFDQVIDKES  486
WP_002277364    420  RAIIRRQAEFYPPLAD--NQD RIEKILTFRIPYYVGPL ARGK--SDFAWLSR---KSADKITPWNFDEIVDKES  486
WP_002279025    420  RAIIRRQAEFYPPLAD--NQD RIEKILTFRIPYYVGPL ARGK--SDFAWLSR---KSADKITPWNFDEIVDKES  486
WP_002279859    420  RAIIRRQAEFYPPLAD--NQD RIEKILTFRIPYYVGPL ARGK--SDFAWLSR---KSADKITPWNFDEIVDKES  486
WP_002280230    420  RAIIRRQAEFYPPLAD--NQD RIEKILTFRIPYYVGPL ARGK--SDFAWLSR---KSADKITPWNFDEIVDKES  486
WP_002281696    420  RAIIRRQAEFYPPLAD--NQD RIEKILTFRIPYYVGPL ARGK--SDFAWLSR---KSADKITPWNFDEIVDKES  486
WP_002282247    420  HAILRRQGDYYPPLKE--NQD RIEKILTFRIPYYVGPL ARKN--SRFAWAEY---HSDEAVTPWNFDQVIDKES  486
WP_002282906    420  RAIIRRQAEFYPPLAD--NQD RIEKLLTFRIPYYVGPL ARGK--SDFAWLSR---KSADKITPWNFDEIVDKES  486
WP_002283846    420  RAIIRRQAEFYPPLAD--NQD RIEKILTFRIPYYVGPL ARGK--SDFAWLSR---KSADKITPWNFDEIVDKES  486
WP_002287255    420  RAIIRRQAEFYPPLAD--NQD RIEKILTFRIPYYVGPL ARGK--SDFAWLSR---KSADKITPWNFDEIVDKES  486
WP_002288990    420  RAIIRRQAEFYPPLAD--NQD RIEKILTFRIPYYVGPL ASGK--SDFAWLSR---KSADKITPWNFDEIVDKES  486
WP_002289641    420  RAIIRRQAEFYPPLAD--NQD RIEKILTFRIPYYVGPL ARGK--SDFAWLSR---KSADKITPWNFDEIVDKES  486
WP_002290427    420  RAIIRRQAEFYPPLAD--NQD RIEKILTFRIPYYVGPL ARGK--SDFAWLSR---KSADKITPWNFDEIVDKES  486
WP_002295753    420  RAIIRRQAEFYPPLAD--NQD RIEKILTFRIPYYVGPL ARGK--SDFAWLSR---KSADKITPWNFDEIVDKES  486
WP_002296423    420  RAIIRRQAEFYPPLAD--NQD RIEKILTFRIPYYVGPL ARGK--SDFAWLSR---KSADKITPWNFDDILDKEK  486
WP_002304487    430  HAIIRRQGEHYPFLKE--NQD RIEKILTFRIPYYVGPL VRKG--SRFAWAEY---KADEKITPWNFDDILDKEK  496
WP_002305844    420  RAIIRRQAEFYPPLKE--NQD RIEKILTFRIPYYVGPL ARGK--SDFAWLSR---KSADKITPWNFDEIVDKES  486
WP_002307203    420  RAIIRRQAEFYPPLAD--NQD RIEKILTFRIPYYVGPL ARGK--SDFAWLSR---KSADKITPWNFDEIVDKES  486
WP_002310390    420  RAIIRRQAEFYPPLAD--NQD RIEKILTFRIPYYVGPL ARGK--SDFAWLSR---KSADKITPWNFDEIVDKES  486
WP_002352408    420  RAIIRRQAEFYPPLAD--NQD RIEKILTFRIPYYVGPL ARGK--SDFAWLSR---KSADKITPWNFDEIVDKES  486
WP_012997688    420  RAIIRRQAEFYPPLAD--NQD RIEKILTFRIPYYVGPL ARGK--SDFAWLSR---KSADKITPWNFDEIVDKES  486
WP_014677909    420  RAIIRRQAEFYPPLAD--NQD RIEKILTFRIPYYVGPL ARGK--SDFAWLSR---KSADKITPWNFDEIVDKES  486
WP_019312892    420  RAIIRRQAEFYPPLKE--NQD RIEKILTFRIPYYVGPL ARGK--SDFAWLSR---KSADKITPWNFDEIVDKES  486
WP_019313659    420  RAIIRRQAEFYPPLAD--NQD RIEKILTFRIPYYVGPL ARGK--SDFAWLSR---KSADKITPWNFDEIVDKES  486
WP_019314093    420  RAIIRRQAEFYPPLAD--NQD RIEKILTFRIPYYVGPL ARGK--SDFAWLSR---KSADKITPWNFDEIVDKES  486
WP_019315370    420  RAIIRRQAEFYPPLAD--NQD RIEKILTFRIPYYVGPL ARGK--SDFAWLSR---KSADKITPWNFDEIVDKES  486
WP_019803776    420  HAILRRQGDYYPPLKE--NQD RIEKILTFRIPYYVGPL ARGK--SDFAWLSR---HSDEAVTPWNFDQVIDKES  486
WP_019805234    420  RAIIRRQAEFYPPLAD--NQD RIEKILTFRIPYYVGPL ARGK--SDFAWLSR---KSADKITPWNFDEIVDKES  486
WP_024783594    420  RAIIRRQAEFYPPLAD--NQD RIEKILTFRIPYYVGPL ARGK--SDFAWLSR---KSADKITPWNFDEIVDKES  486
WP_024784288    420  HAILRRQGDYYPPLKE--NQD RIEKILTFRIPYYVGPL ARKN--SRFAWAEY---HSDEAVTPWNFDQVIDKES  486
WP_024784666    420  RAIIRRQAEFYPPLAD--NQD RIEKILTFRIPYYVGPL ARGK--SDFAWLSR---KSADKITPWNFDEIVDKES  486
WP_024784894    420  RAIIRRQAEFYPPLAD--NQD RIEKILTFRIPYYVGPL ASGK--SDFAWLSR---KSADKITPWNFDEIVDKES  486
WP_024786433    420  HAILRRQGDYYPPLKE--NQD RIEKILTFRIPYYVGPL ARKN--SRFAWAEY---HSDEAVTPWNFDQVIDKES  486
```

```
-continued

WP_049473442  420  RAIIRRQAEFYPPLAD--NQD  RIEKILTFRIPYYVGPL  ARGK-SDFAWLSR---KSADKITPWNFDEIVDKES  486
WP_049474547  420  RAIIRRQAEFYPPLAD--NQD  RIEKILTFRIPYYVGPL  ASGK-SDFAWLSR---KSADKITPWNFDEIVDKES  486
EMC03581      413  RAIIRRQAEFYPPLAD--NQD  RIEKILTFRIPYYVGPL  ARGK-SDFAWLSR---KSADKITPWNFDEIVDKES  479
WP_000428612  421  NAILRRQGEHYPFLKE--NKE  KIEKILTFRIPYYVGPL  ARGN-RDFAWLTR---NSDQAIRPWNFEEIVDKAS  487
WP_000428613  421  NAILRRQGEHYPFLKD--NKE  KIEKILTFRIPYYVGPL  ARGN-RDFAWLTR---NSDEAIRPWNFEEIVDKAS  487
WP_049523028  420  NAILRHQGEYYPFLKE--NKD  KIEQILTFRIPYYVGPL  ARGN-SDFAWLSR---NSDEAIRPWNFEEMVDKSS  486
WP_003107102  389  KSIIRRQEKYPFLKD--KQV  RIEKIFTFRIPYYVGPL  ANG-n-SSFAWVKR---RSNESITPWNFEEVVEQEA  455
WP_054279288  422  QAILERQQAYYPFIKD--NQE  KIEKILTFRIPYFVGPL  ARG-n-SRFAWLTR---TSDQKITPWNFDEMVDQEA  488
WP_049531101  421  NAILRRQGEHYPFLKE--NRE  KIEKILTFRIPYYVGPL  ARGN-RDFAWLTR---NSDQAIRPWNFEEIVDKAS  487
WP_049538452  421  NAILRRQGEHYPFLKE--NKE  KIEKILTFRIPYYVGPL  ARGN-RDFAWLTR---NSDQAIRPWNFEEIVDKAS  487
WP_049549711  421  NAILRRQGEHYPFLKE--NQD  KIEKILTFRIPYYVGPL  ARGN-RDFAWLTR---NSDQAIRPWNFEEIVDKAS  487
WP_007896501  422  HAILRRQEKYPFLAE--QKE  KIEQLLCFRIPYYVGPL  AKGGn-SSFAWLKR---RSDEPITPWNFKDVVDEEA  489
EFR44625      374  HAILRRQEKYPFLAE--QKE  KIEQLLCFRIPYYVGPL  AKGGn-SSFAWLKR---RSDEPITPWNFKDVVDEEA  441
WP_002897477  420  NAILRRQGEHYPFLKE--NRE  KIEKILTFRIPYYVGPL  ARDN-RDFSWLTR---NSDEPIRPWNFEEVVDKAR  486
WP_002906454  420  NAILRRQGEHYLFLKE--NKE  KIEKILAFRIPYYVGPL  ARGN-RDFAWLTR---NSDQAIRPWNFEEIVDKAS  486
WP_009729476  421  NAILRRQGEHYPFLKE--NKE  KIEKILTFRIPYYVGPL  ARGN-RDFAWLTR---NSDQAIRPWNFEEIVDKAS  487
CQR24647      421  KAILRRQGEFYPFLKE--NAE  KIQQILTFKIPYYVGPL  ARGN-SRFAWASY---NSNEKMTPWNFDNVIDKTS  487
WP_000066813  421  NAILRRQGEHYPPLQE--NKE  KIEKILTFRIPYYVGPL  ARGN-GDFAWLTR---NSDQAIRPWNFEEIVDQAS  487
WP_009754323  421  NAILRRQGEHYPLLKE--NKE  KIEKILTFRIPYYVGPL  ARGN-RDFAWLTR---NSDQAIRPWNFEEIVDKAS  487
WP_044674937  420  HAILRRQEHYPFLVE--NQD  KIEKILTFRIPYYVGPL  ARGK-SEFAWLNR---KSDEKIRPWNFDEMVDKET  486
WP_044767715  420  NAILRRQAEFYPFLVE--NQD  KIEKILTFRIPYYVGPL  ARGK-SEFAWLNR---KSDEKIRPWNFDEMVDKET  486
WP_044680361  420  NAILRRQAEFYPFLVE--NQD  KIEKILTFRIPYYVGPL  ARGK-SEFAWLNR---KSDEKIRPWNFDEMVDKET  486
WP_044681799  420  HAILRRQEHYPFLKE--NQD  KIEKILTFRIPYYVGPL  ARKG-SRFAWAEY---KADEKITPWNFDDILDKEK  486
WP_049533112  420  HAILRRQEHYPFLKE--NQD  KIEKILTFRIPYYVGPL  ARKG-SRFAWAEY---KADEKITPWNFDDILDKEK  486
WP_029090905  404  VAILENQATYYPELLE--QKD  NIHKLLTFRIPYYVGPL  ADQKd-SEFAWMVR---KQAGKITPFNFEEMVDIDA  471
WP_006506696  430  IKIIDNQAEYYPILKE--KRE  QLLSLLTFRIPYYFGPL  ETSEh---AWIKRlegKENQRILPWNYQDIVDVDA  498
AIT42264      420  TAVLDQQREKHYSPLKE--NRD  KIISLLTFRIPYYVGPL  ARGE-SRFAWMTR---sNSEEKIKPWNEDKIVDIDK  486
WP_034440723  426  TAVLDQQREKHYSPLKE--NRD  KIISLLTFRIPYYVGPL  ARG-n-SRFAWMTR---KSEETITPWNFEEVVDKGA  493
AKQ21048      420  HAILRRQEDFYPFIKD--NRE  KIEKILTFRIPYYVGPL  ARG-n-SRFAWMTR---KSEETITPWNFEEVVDKGA  486
WP_004636532  421  QAILDRQSQYYPFLAE--NRD  KIESLVTFRIPYYVGPL  TVSDq-SEFAWMER---QSDEPIRPWNFDEIVNKER  488
WP_002378009  428  QAIHRQAYYPFLKE--NQE  KIEQLVTFRIPYYVGPL  SKGDA-STFAWLKR---QSEEPIRPWNLQETVDLDQ  495
WP_002407324  428  QAIHRQAYYPFLKE--NQE  KIEQLVTFRIPYYVGPL  SKGDA-NTFAWLKR---QSEEPIRPWNLQETVDLDQ  495
WP_002413717  428  QAIHRQAYYPFLKE--NQE  KIEQLVTFRIPYYVGPL  SKGDA-STFAWLKR---QSEEPIRPWNLQETVDLDQ  495
WP_016631044  379  QAIHRQAYYPFLKE--NQE  KIEQLVTFRIPYYVGPL  SKGDA-STFAWLKR---QSEEPIRPWNLQETVDLDQ  446
EMS75795      163  KAIIERQKPYYPSLEE--ARD  KMIRLLTFRIPYYVGPL  AQGEt-SSFAWLER---KTPEKVTPWNATEVIDYSA  231
WP_002373311  428  QAIHRQAYYPFLKE--NQE  KIEQLVTFRIPYYVGPL  SKGDA-STFAWLKR---QSEEPIRPWNLQETVDLDQ  495
WP_010775580  430  QAIHRQAYYPFLKE--NQE  KIEQLVTFRIPYYVGPL  SKGDA-STFAWLKR---QSEEPIRPWNLQETVDLDQ  497
WP_010818269  428  QAIHRQAYYPFLKE--NQE  KIEQLVTFRIPYYVGPL  SKGDA-STFAWLKR---QSEEPIRPWNLQETVDLDQ  495
WP_010824395  428  QAIHRQAYYPFLKE--NQE  KIEQLVTFRIPYYVGPL  SKGDA-STFAWLKR---QSEEPIRPWNLQETVDLDQ  495
WP_016622645  428  QAIHRQAYYPFLKE--NQE  KIEQLVTFRIPYYVGPL  SKGDA-STFAWLKR---QSEEPIRPWNLQETVDLDQ  495
WP_033624816  428  QAIHRQAYYPFLKE--NQK  KIEQLVTFRIPYYVGPL  SKGDA-STFAWLKR---QSEEPIRPWNLQETVDLDQ  495
WP_033625576  428  QAIHRQAYYPFLKE--NQE  KIEQLVTFRIPYYVGPL  SKGDA-STFAWLKR---QNEKPIRPWNLQETVDLDQ  495
WP_033789179  428  QAIHRQAYYPFLKE--NQE  KIEQLVTFRIPYYVGPL  SKGDA-STFAWLKR---QSEEPIRPWNLQETVDLDQ  495
WP_002310644  424  RAIANQKKHYPFLKE--EQE  KLESLLTFKIPYYVGPL  AKKQenSPFAWLIR---KSEEKIKPWNLPEIVDMEG  492
WP_002312694  425  RAIANQKKHYPFLKE--EQE  KLESLLTFKIPYYVGPL  AKKQenSPFAWLIR---KSEEKIKPWNLPEIVDMEG  493
WP_002314015  425  RAIANQKKHYPFLKE--EQE  KLESLLTFKIPYYVGPL  AKKQenSPFAWLIR---KSEEKIKPWNLPEIVDMEG  493
WP_002320716  425  RAIANQKKHYPFLKE--EQE  KLESLLTFKIPYYVGPL  AKKQenSPFAWLIR---KSEEKIKPWNLPEIVDMEG  493
WP_002330729  424  RAIANQKKHYPFLKE--EQE  KLESLLTFKIPYYVGPL  AKKQenSPFAWLIR---KSEEKIKPWNLPEIVDMEG  492
WP_002335161  425  RAIANQKKHYPFLKE--EQE  KLESLLTFKIPYYVGPL  AKKQenSPFAWLIR---KSEEKIKPWNLPEIVDMEG  493
WP_002345439  425  RAIANQKKHYPFLKE--EQE  KLESLLTFKIPYYVGPL  AKKQeaSSFAWLIR---KTAEKINPWNFSEVVDIEK  493
WP_034867970  418  KAIIDQQKQHYPFLEE--AGP  KIIALPKFRIPYYVGPL  AKKQenSPFAWLIR---KTAEKINPWNFSEVVDIEK  486
WP_047937432  425  RAIANQKKHYPFLKE--EQE  KLESLLTFKIPYYVGPL  AKKQenSPFAWLIR---KSEEKIKPWNLPEIVDMEG  493
```

-continued

| | | | | | | |
|---|---|---|---|---|---|---|
| WP_010720994 | 418 | KAIIDQQKQHYPPFLEE--AGP | KIIALFKFRIPYYVGPL | AKEQeaSSFAWIER--- | KTAEKINPWNFSEVDIEK | 486 |
| WP_010737004 | 418 | KAIIDQQKQHYPPFLEE--AGP | KIIALFKFRIPYYVGPL | AKEQeaSSFAWIER--- | KTAEKINPWNFSEVDIEK | 486 |
| WP_034700478 | 418 | KAIIDQQKQHYPPFLEE--AGP | KIIALFKFRIPYYVGPL | AKEQeaSSFAWIER--- | KTAEKINPWNFSEVDIEK | 486 |
| WP_007209003 | 422 | RAILRKQEKYYSFIKE--NHE | KIEQIFKVRIPYYVGPL | AKHNeqSRFAWNIR--- | KSDEPIRPWNMNDVVDENA | 490 |
| WP_023519017 | 418 | REIMDRQKRFYPPLKG--AQG | KIEKLLTFRIPYYVGPL | AQEGq--SPFAWIKR--- | KSPSQITPWNFAEVVDKEN | 485 |
| WP_010770040 | 423 | EAIIQKQATYYPPFLAD--NKE | EMKQLVTFRIPYYVGPL | ADGN----SPFAWLER--- | ISSEPIRPGNLAEVVDIKK | 489 |
| WP_048604708 | 419 | KAILHHQAMYYPPFLQE--KFS | NFVDLLTFRIPYYVGPL | ANGN---SRFSWLSR--- | KSDEPIRPWNLAEVVDLSK | 485 |
| WP_010750235 | 418 | KAIIDQQKQYYPPFIEK--SKE | KMIQLLTFRIPYYVGPL | AQDKetSSFAWLER--- | KTTEKIKPWNAKDVIDYGA | 486 |
| AII16583 | 459 | HAILRRQEDFYPPLKD--NRE | KIEKILTFRIPYYVGPL | ARG-n-SRFAWMTR--- | KSEETITPWNFEEVVDKGA | 525 |
| WP_029073316 | 436 | NKILENQSVYYSDLKD--NED | KIRSILTFRIPYYFGPL | ITKDr-QFDWIIKkegKENERILPWNANEIVDVDK | | 506 |
| WP_031589969 | 436 | NKILENQSVYYSDLKD--NED | KIRSILTFRIPYYFGPL | ITKDr-QFDWIIKkegKENERILPWNANEIVDVDK | | 506 |
| KDA45870 | 418 | VAIVENQGKYYPPFLNE--NKD | KFEKILNFRIPYYVGPL | ARGN--SKFAWLTR--- | a-GEGKITPYNFDEMIDKET | 484 |
| WP_039099354 | 1NPN | DRIIENQQQYYPWLAE--1NPN | KLDELVAFRVPYYVGPL | QQQSsdAKFAWMIR--- | KAEBGQITPWNFDDKVDRQA | 509 |
| AKP02966 | 416 | EKIIDNQSQYYPPFLKE--NKE | KLLSIlsFRIPYYVGPL | -QSSekNPFAWMER--- | KSNGHARPWNFDEIVDREK | 483 |
| WP_010991369 | 426 | EAILHQQAKYYPPFLKE--NYD | KIKSLVTFRIPYFVGPL | ANGQ--SEFAWLTR--- | KADGEIRPWNIEEKVDFGK | 492 |
| WP_033838504 | 426 | EAILHQQAKYYPPFLKE--NYD | KIKSLVTFRIPYFVGPL | ANGQ--SEFAWLTR--- | KADGEIRPWNIEEKVDFGK | 492 |
| EHN60060 | 429 | EAILHQQAKYYPPFLKE--NYD | KIKSLVTFRIPYFVGPL | ANGQ--SEFAWLTR--- | KADGEIRPWNIEEKVDFGK | 495 |
| EFR89594 | 195 | EAILHQQAKYYPPFLKE--NYD | KIKSLVTFRIPYFVGPL | ANGQ--SDFAWLTR--- | KADGEIRPWNIEEKVDFGK | 261 |
| WP_038409211 | 426 | EAILHQQAKYYPPFLRK--DYE | KIRSLVTFRIPYFIGPL | ANGQ--SDFAWLTR--- | KADGEIRPWNIEEKVDFGK | 492 |
| EFR95520 | 45 | EAILHQQAKYYPPFLRK--DYE | KIRSLVTFRIPYFIGPL | ANGQ--SDFAWLTR--- | KADGEIRPWNIEEKVDFGK | 111 |
| WP_003723650 | 426 | EAILHQQAKYYPPFLKE--DYD | KIKSLVTFRIPYFVGPL | ANGQ--SEFAWLTR--- | KADGEIRPWNIEEKVDFGK | 492 |
| WP_003727705 | 426 | EAILHQQAKYYPPFLRE--GYD | KIKSLVTFRIPYFVGPL | ANGQ--SEFAWLTR--- | KDDGEIRPWNIEEKVDFGK | 492 |
| WP_003730785 | 426 | EAILHQQAKYYPPFLRE--GYD | KIKSLVTFRIPYFVGPL | ANGQ--SEFAWLTR--- | KDDGEIRPWNIEEKVDFGK | 492 |
| WP_003733029 | 426 | EAILHQQAKYYPPFLRE--DYE | KIKSLVTFRIPYFVGPL | AKGQ--SDFAWLTR--- | KADGEIRPWNIEEKVDFGK | 492 |
| WP_003739838 | 426 | EAILHQQAKYYPPFLKE--AYD | KIKSLVTFRIPYFVGPL | ANGQ--SDFAWLTR--- | KADGEIRPWNIEEKVDFGK | 492 |
| WP_014601172 | 426 | EAILHQQAKYYPPFLRE--DYE | KIKSLVTFRIPYFVGPL | AKGQ--SEFAWLTR--- | KADGEIRPWNIEEKVDFGK | 492 |
| WP_023548323 | 426 | EAILHQQAKYYTFLKE--DYD | KIKSLVTFRIPYFVGPL | ANGQ--SEFAWLTR--- | KADGEIRPWNIEEKVDFGK | 492 |
| WP_031665337 | 426 | EAILHQQAKYYPPFLRE--DYE | KIKSLVTFRIPYFVGPL | ANGQ--SEFAWLTR--- | KADGEIRPWNIEEKVDFGK | 492 |
| WP_031669209 | 426 | EAILHQQAKYYPPFLRE--DYE | KIKSLVTFRIPYFVGPL | AKGQ--SEFAWLTR--- | KADGEIRPWNIEEKVDFGK | 492 |
| WP_033920898 | 426 | EAILHQQAKYYPPFLRE--DYE | KIKSLVTFRIPYFVGPL | AKGQ--SEFAWLTR--- | KADGEIRPWNIEEKVDFGK | 492 |
| AKI42028 | 429 | EAILHQQAKYYPPFLRE--DYE | KIKSLVTFRIPYFVGPL | AKGQ--SEFAWLTR--- | KADGEIRPWNIEEKVDFGK | 495 |
| AKI50529 | 429 | EAILHQQAKYYPPFLRE--DYE | KIKSLVTFRIPYFVGPL | AKGQ--SEFAWLTR--- | KADGEIRPWNIEEKVDFGK | 495 |
| EFR83390 | | ---------------- | ---------------- | --------------- | ------------------ | |
| WP_046323366 | 426 | EAILHQQAKYYPPFLKV--DYE | KIKSLVTFRIPYFVGPL | ANGQ--SEFSWLTR--- | KADGEIRPWNIEEKVDFGK | 492 |
| AKE81011 | 436 | HAILRRQEDFYPPLKD--NRE | KIEKILTFRIPYYVGPL | ARG-n-SRFAWMTR--- | KSEETITPWNFEEVVDKGA | 502 |
| CUO82355 | 434 | IKIIDNQAKYYPVLKE--KRE | QLLSILTFRIPYYFGPL | ETSEh----AWIKRlegKENQRILPWNYQDTVDVDA | | 502 |
| WP_033162887 | 435 | IQIIDNQSVYYPQLKE--NRD | KLISILEFRIPYFVGPL | AHSE----FAWIKKfedKQKERILPWNIEEQIVDIDA | | 503 |
| AGZ01981 | 453 | HAILRRQEDFYPPLKD--NRE | KIEKILTFRIPYYVGPL | ARG-n-SRFAWMTR--- | KSEETITPWNFEEVVDKGA | 519 |
| AKA60242 | 420 | HAILRRQEDFYPPLKD--NRE | KIEKILTFRIPYYVGPL | ARG-n-SRFAWMTR--- | KSEETITPWNFEEVVDKGA | 486 |
| AKS40380 | 420 | HAILRRQEDFYPPLKD--NRE | KIEKILTFRIPYYVGPL | ARG-n-SRFAWMTR--- | KSEETITPWNFEEVVDKGA | 486 |
| 4UN5_B | 424 | HAILRRQEDFYPPLKD--NRE | KIEKILTFRIPYYVGPL | ARG-n-SRFAWMTR--- | KSEETITPWNFEEVVDKGA | 490 |
| WP_010922251 | 487 | SAQSFIERMTNFDKNLPNEKVLPKHSLLYEYFTVYNELTKVKYT- | EGMRKPaFLSGEQKAIVDLLFK--TNR-KVTV | | | 561 |
| WP_039695303 | 490 | SABKFITRMTLNDLYLPEEKVLPKHSHVYETVAVYNELTKIKYVN- | EQGKES-FFDSNMKQEIFDHVFK--ENR-KVTK | | | 563 |
| WP_045635197 | 487 | SAEDFINRMTNYDLYLPEEKVLPKHSLLYETFAVYNELTKVKFIA- | EGLRDYqFLDSGQKKQIVNQLFK--ENR-KVTE | | | 561 |
| 5AXW_A | 230 | --KEWYEMLMGHCTYFFEELRSVKYAYNADLYNALNDLNNLVITR- | DENEKLeYYE--KPQIIENVFK--QKK-KPTL | | | 299 |
| WP_009880683 | 171 | SAQSFIERMTNFDKNLPNEKVLPKHSLLYEYFTVYNELTKVKYVT- | EGMRKPaFLSGEQKAIVDLLFK--TNR-KVTV | | | 245 |
| WP_010922251 | 487 | SAQSFIERMTNFDKNLPNEKVLPKHSLLYEYFTVYNELTKVKYVT- | EGMRKPaFLSGEQKAIVDLLFK--TNR-KVTV | | | 561 |
| WP_011054416 | 487 | SAQSFIERMTNFDKNLPNEKVLPKHSLLYEYFTVYNELTKVKYVT- | EGMRKPaFLSGEQKAIVDLLFK--TNR-KVTV | | | 561 |
| WP_011284745 | 487 | SAQSFIERMTNFDKNLPNEKVLPKHSLLYEYFTVYNELTKVKYVT- | EGMRKPaFLSGEQKAIVDLLFK--TNR-KVTV | | | 561 |
| WP_011285506 | 487 | SAQSFIERMTNFDKNLPNEKVLPKHSLLYEYFTVYNELTKVKYVT- | EGMRKPaFLSGEQKAIVDLLFK--TNR-KVTV | | | 561 |
| WP_011527619 | 487 | SAQSFIERMTNFDKNLPNEKVLPKHSLLYEYFTVYNELTKVKYVT- | EGMRKPaFLSGEQKAIVDLLFK--TNR-KVTV | | | 561 |
| WP_012560673 | 487 | SAQSFIERMTNFDKNLPNEKVLPKHSLLYEYFTVYNELTKVKYVT- | EGMRKPaFLSGEQKAIVDLLFK--TNR-KVTV | | | 561 |
| WP_014407541 | 487 | SAQSFIERMTNFDKNLPNEKVLPKHSLLYEYFTVYNELTKVKYVT- | EGMRKPaFLSGEQKAIVDLLFK--TNR-KVTV | | | 561 |

-continued

```
WP_020905136      487 SAQSFIERMTNFDKNLPNEKVLPKHSLLYEYFTVYNELTKVKYVT--EGMRKPaFLSGEQKKAIVDLLFK--TNR-KVTV 561
WP_023080005      487 SAQSFIERMTNFDKNLPNEKVLPKHSLLYEYFTVYNELTKVKYVT--EGMRKPaFLSGEQKKAIVDLLFK--TNR-KVTV 561
WP_023610282      487 SAQSFIERMTNFDKNLPNEKVLPKHSLLYEYFTVYNELTKVKYVT--EGMRKPaFLSGEQKKAIVDLLFK--TNR-KVTV 561
WP_030125963      487 SAQSFIERMTNFDKNLPNEKVLPKHSLLYEYFTVYNELTKVKYVT--EGMRKPaFLSGEQKKAIVDLLFK--TNR-KVTV 561
WP_030126706      487 SAQSFIERMTNFDKNLPNEKVLPKHSLLYEYFTVYNELTKVKYVT--EGMRKPaFLSGEQKKAIVDLLFK--TNR-KVTV 561
WP_031488318      487 SAQSFIERMTNFDKNLPNEKVLPKHSLLYEYFTVYNELTKVKYVT--EGMRKPeFLSGEQKKAIVDLLFK--TNR-KVTV 561
WP_032460140      487 SAQSFIERMTNFDKNLPNEKVLPKHSLLYEYFTVYNELTKVKYVT--EGMRKPaFLSGEQKKAIVDLLFK--TNR-KVTV 561
WP_032461047      487 SAQSFIERMTNFDKNLPNEKVLPKHSLLYEYFTVYNELTKVKYVT--EGMRKPaFLSGEQKKAIVDLLFK--TNR-KVTV 561
WP_032462016      487 SAQSFIERMTNFDKNLPNEKVLPKHSLLYEYFTVYNELTKVKYVT--EGMRKPaFLSGEQKKAIVDLLFK--TNR-KVTV 561
WP_032462936      487 SAQSFIERMTNFDKNLPNEKVLPKHSLLYEYFTVYNELTKVKYVT--EGMRKPaFLSGEQKKAIVDLLFK--TNR-KVTV 561
WP_032464890      487 SAQSFIERMTNFDKNLPNEKVLPKHSLLYEYFTVYNELTKVKYVT--EGMRKPaFLSGEQKKAIVDLLFK--TNR-KVTV 561
WP_033888930      312 SAQSFIERMTNFDKNLPNEKVLPKHSLLYEYFTVYNELTKVKYVT--EGMRKPaFLSGEQKKAIVDLLFK--TNR-KVTV 386
WP_038431314      487 SAQSFIERMTNFDKNLPNEKVLPKHSLLYEYFTVYNELTKVKYVT--EGMRKPaFLSGEQKKAIVDLLFK--TNR-KVTV 561
WP_038432938      487 SAQSFIERMTNFDKNLPNEKVLPKHSLLYEYFTVYNELTKVKYVT--EGMRKPaFLSGEQKKAIVDLLFK--TNR-KVTV 561
WP_038434062      487 SAQSFIERMTNFDKNLPNEKVLPKHSLLYEYFTVYNELTKVKYVT--EGMRKPaFLSGEQKKAIVDLLFK--TNR-KVTV 561
BAQ51233          398 SAQSFIERMTNFDKNLPNEKVLPKHSLLYEYFTVYNELTKVKYVT--EGMRKPaFLSGEQKKAIVDLLFK--TNR-KVTV 472
KGE60162              ---------------------------------------------------------------------------
KGE60856              ---------------------------------------------------------------------------
WP_002989955      487 SAQSFIERMTNFDKNLPNEKVLPKHSLLYEYFTVYNELTKVKYVT--EGMRKPaFLSGEQKKAIVDLLFK--TNR-KVTV 561
WP_003030002      487 SAEKFITRMTLNDLYLPEEKVLPKHSLLYETFVYNELTKVKYVN--EQGEAK-FFDANMKQEIFDHVFK--ENR-KVTK 560
WP_003065552      490 SAEKFITRMTLNDLYLPEEKVLPKHSHVYETYAVYNELTKIKVN---EQGKDS-FFDSNMKQEIFNSLFK--ENR-KVTK 563
WP_001040076      488 SAEAFIHRMTNNDLYLPEEKVLPKHSLLYEKFTVYNELTKVRFLA--EGFKDFqFLNRKQKETIENSLEK--EKR-KVTE 562
WP_001040078      488 SAEAFIHRMTNNDFYLPEEKVLPKHSLLYEKFTVYNELTKVRYKN--EQGETY-FFDSNIKQEIFDGVFK--EHR-KVSK 561
WP_001040080      488 SAEAFIHRMTNNDFYLPEEKVLPKHSLLYEKFTVYNELTKVRYKN--EQGETY-FFDSNIKQEIFDGVFK--EHR-KVSK 561
WP_001040081      488 SAEAFIHRMTNNDFYLPEEKVLPKHSLLYEKFTVYNELTKVRYKN--EQGETY-FFDSNIKQEIFDGVFK--EHR-KVSK 561
WP_001040083      488 SAEAFIHRMTNNDFYLPEEKVLPKHSLLYEKFTVYNELTKVRYKN--EQGETY-FFDSNIKQEIFDGVFK--EHR-KVSK 561
WP_001040085      488 SAEAFIHRMTNNDFYLPEEKVLPKHSLLYEKFTVYNELTKVRYKN--EQGETY-FFDSNIKQEIFDGVFK--EHR-KVSK 561
WP_001040087      488 SAEAFIHRMTNNDFYLPEEKVLPKHSLLYEKFTVYNELTKVRYKN--EQGETY-FFDSNIKQEIFDGVFK--EHR-KVSK 561
WP_001040088      488 SAEAFIHRMTNNDFYLPEEKVLPKHSLLYEKFTVYNELTKVRYKN--EQGETY-FFDSNIKQEIFDGVFK--EHR-KVSK 561
WP_001040089      488 SAEAFIHRMTNNDFYLPEEKVLPKHSLLYEKFTVYNELTKVRYKN--EQGETY-FFDSNIKQEIFDGVFK--EHR-KVSK 561
WP_001040090      488 SAEAFIHRMTNNDFYLPEEKVLPKHSLLYEKFTVYNELTKVRYKN--EQGETY-FFDSNIKQEIFDGVFK--EHR-KVSK 561
WP_001040091      488 SAEAFIHRMTNNDFYLPEEKVLPKHSLLYEKFTVYNELTKVRYKN--EQGETY-FFDSNIKQEIFDGVFK--EHR-KVSK 561
WP_001040092      488 SAEAFIHRMTNNDFYLPEEKVLPKHSLLYEKFTVYNELTKVRFLA--EGFKDFqFLNRKQKETIENSLEK--EKR-KVTE 562
WP_001040094      488 SAEAFIHRMTNNDFYLPEEKVLPKHSLLYEKFTVYNELTKVRFLA--EGFKDFqFLNRKQKETIENSLEK--EKR-KVTE 562
WP_001040095      488 SAEAFIHRMTNNDFYLPEEKVLPKHSLLYEKFTVYNELTKVRFLA--EGFKDFqFLNRKQKETIENSLEK--EKR-KVTE 562
WP_001040096      488 SAEAFIHRMTNNDFYLPEEKVLPKHSLLYEKFTVYNELTKVRFLA--EGFKDFqFLNRKQKETIENSLEK--EKR-KVTE 562
WP_001040097      488 SAEAFIHRMTNNDFYLPEEKVLPKHSLLYEKFTVYNELTKVRYKN--EQGETY-FFDSNIKQEIFDGVFK--EHR-KVSK 561
WP_001040098      488 SAEAFIHRMTNNDFYLPEEKVLPKHSLLYEKFTVYNELTKVRFLA--EGFKDFqFLNRKQKETIENSLEK--EKR-KVTE 562
WP_001040099      488 SAEAFIHRMTNNDFYLPEEKVLPKHSLLYEKFTVYNELTKVRYKN--EQGETY-FFDSNIKQEIFDGVFK--EHR-KVSK 561
WP_001040100      488 SAEAFIHRMTNNDFYLPEEKVLPKHSLLYEKFTVYNELTKVRYKN--EQGETY-FFDSNIKQEIFDGVFK--EHR-KVSK 561
WP_001040104      488 SAEAFIHRMTNNDFYLPEEKVLPKHSLLYEKFTVYNELTKVRYKN--EQGETY-FFDSNIKQEIFDGVFK--EHR-KVSK 561
WP_001040105      488 SAEAFIHRMTNNDFYLPEEKVLPKHSLLYEKFTVYNELTKVRFLA--EGFKDFqFLNRKQKETIENSLEK--EKR-KVTE 562
WP_001040106      488 SAEAFIHRMTNNDFYLPEEKVLPKHSLLYEKFTVYNELTKVRYKN--EQGETY-FFDSNIKQEIFDGVFK--EHR-KVSK 561
WP_001040107      488 SAEAFIHRMTNNDFYLPEEKVLPKHSLLYEKFTVYNELTKVRYKN--EQGETY-FFDSNIKQEIFDGVFK--EHR-KVSK 561
WP_001040108      488 SAEAFIHRMTNNDFYLPEEKVLPKHSLLYEKFTVYNELTKVRYKN--EQGETY-FFDSNIKQEIFDGVFK--EHR-KVSK 561
WP_001040109      488 SAEAFIHRMTNNDFYLPEEKVLPKHSLLYEKFTVYNELTKVRYKN--EQGETY-FFDSNIKQEIFDGVFK--EHR-KVSK 561
WP_001040110      488 SAEAFIHRMTNNDFYLPEEKVLPKHSLLYEKFTVYNELTKVRYKN--EQGETY-FFDSNIKQEIFDGVFK--EHR-KVSK 561
WP_015058523      488 SAEAFIHRMTNNDFYLPEEKVLPKHSLLYEKFTVYNELTKVRYKN--EQGETY-FFDSNVKQEIFDGVFK--EHR-KVSK 561
WP_017643650      488 SAEAFIHRMTNNDFYLPEEKVLPKHSLLYEKFTVYNELTKVRFLA--EGFKDFqFLNRKQKETIENSLEK--EKR-KVTE 562
WP_017647151      488 SAEAFIHRMTNNDFYLPEEKVLPKHSLLYEKFTVYNELTKVRYKN--EQGETY-FFDSNIKQEIFDGVFK--EHR-KVSK 561
WP_017648376      488 SAEAFIHRMTNNDFYLPEEKVLPKHSLLYEKFTVYNELTKVRYKN--EQGETY-FFDSNIKQEIFDGVFK--EHR-KVSK 561
WP_017649527      488 SAEAFIHRMTNNDFYLPEEKVLPKHSLLYEKFTVYNELTKVRYKN--EQGETY-FFDSNIKQEIFDGVFK--EHR-KVSK 561
WP_017771611      488 SAEAFIHRMTNNDFYLPEEKVLPKHSLLYEKFTVYNELTKVRYKN--EQGETY-FFDSNIKQEIFDGVFK--EHR-KVSK 561
```

-continued

```
WP_017771984    488  SAEAFIHRMTNNDFYLPEEKVLPKHSLIYEKFTVYNELTKVRYKN-EQGETY-FFDSNIKQEIFDGVFK--EHR-KVSK  561
CFQ25032        488  SAEAFIHRMTNNDFYLPEEKVLPKHSLIYEKFTVYNELTKVRYKN-EQGETY-FFDSNIKQEIFDGVFK--EHR-KVSK  561
CFV16040        488  SAEAFIHRMTNNDFYLPEEKVLPKHSLIYEKFTVYNELTKVRYKN-EQGETY-FFDSNIKQEIFDGVFK--EHR-KVSK  561
KLJ37842        488  SAEAFIHRMTNNDFYLPEEKVLPKHSLIYEKFTVYNELTKVRYKN-EQGETY-FFDSNIKQEIEDGVEK--EHR-KVSK  561
KLJ72361        488  SAEAFIHRMTNNDFYLPEEKVLPKHSLIYEKFTVYNELTKVRYKN-EQGETY-FFDSNIKQEIEDGVEK--EHR-KVSK  561
KLL20707        488  SAEAFIHRMTNNDLYLPEEKVLPKHSLIYEKFTVYNELTKVRYKN-EQGETY-FFDSNIKQEIEDGVEK--EHR-KVSK  561
KLL42645        488  SAEAFIHRMTNNDLYLPEEKVLPKHSLIYEKFTVYNELTKVRYKN-EQGETY-FFDSNIKQEIEDGVEK--EHR-KVSK  561
WP_047207273    488  SAEAFIHRMTNNDLYLPEEKVLPKHSLIYEKFTVYNELTKVRYKN-EQGETY-FFDSNIKQEIEDGVEK--EHR-KVSK  561
WP_047209694    488  SAEAFIHRMTNNDLYLPEEKVLPKHSLIYEKFTVYNELTKVRFLA-EGFKDFqFLNRKQKETIFNLFK--EKR-KVTE  562
WP_050198062    488  SAEAFIHRMTNNDFYLPEEKVLPKHSLIYEKFTVYNELTKVRYKN-EQGETY-FFDSNIKQEIEDGVEK--EHR-KVSK  561
WP_050201642    488  SAEAFIHRMTNNDFYLPEEKVLPKHSLIYEKFTVYNELTKVRYKN-EQGETY-FFDSNIKQEIEDGVEK--EHR-KVSK  561
WP_050204027    488  SAEAFIHRMTNNDFYLPEEKVLPKHSLIYEKFTVYNELTKVRYKN-EQGETY-FFDSNIKQEIEDGVEK--EHR-KVSK  561
WP_050881965    488  SAEAFIHRMTNNDFYLPEEKVLPKHSLIYEKFTVYNELTKVRYKN-EQGETY-FFDSNIKQEIEDGVEK--EHR-KVSK  561
WP_050886065    488  SAEAFIHRMTNNDFYLPEEKVLPKHSLIYEKFTVYNELTKVRYKN-EQGETY-FFDENVKQEIEDGVEK--EHR-KVSK  561
AHN30376        488  SAEAFIHRMTNNDLYLPEEKVLPKHSLIYEKFTVYNELTKVRYKN-EQGETY-FFDSNIKQEIEDGVEK--EHR-KVSK  561
EA078426        488  SAEAFIHRMTNNDLYLPEEKVLPKHSLIYEKFTVYNELTKVRYKN-EQGETY-FFDSNIKQEIEDGVEK--EHR-KVSK  561
CCW42055        488  SAEAFIHCMTNNDLYLPEEKVLPKHSLIYEKFTVYNELTKVKVKN-EQGETY-FFDSNIKQEIEDGVEK--EYR-KVSK  561
WP_003041502    488  SAEKFITRMTLNDLYLPEEKVLPKHELLYETFTVYNELTKVKVVN-EQGEAK-FFDANMKQEIFDHVFK--ENR-KVTK  560
WP_037593752    488  SAEKFITRMTLNDLYLPEEKVLPKHSPLYETFTVYNELTKVKVVN-EQGEAK-FFDTNMKQEIFDHVFK--ENR-KVTK  561
WP_049516684    488  SAEKFITRMTLNDLYLPEEKVLPKHSPLYETFTVYNELTKVKVVN-EQGEAK-FFDTNMKQEIFDHVFK--ENR-KVTK  561
GAD46167        487  SAEKFITRMTLNDLYLPEEKVLPKHSPLYEIFTVYNELTKVKVVN-EQGEAK-FFDTNMKQEIFDHVEK--ENR-KVTK  560
WP_018363470    488  SAEKFITRMTLNDLYLPEEKVLPKHSHVYETFAVYNELTKVKVVN-EQGKDS-FFDSNMKQEIFDHVFK--ENR-KVTK  561
WP_003043819    497  SAQSFIERMTNEDEQLPNKKVLPKHELLYEYFTVYNELTKVKVVT-ERMRKPeFLSGEQKKAIVDLLFK--TNR-KVTV  571
WP_006269658    487  SAQSFIERMTNEDKNLPNEKVLPKHELLYEYFTVYNELTKVKVVT-EGMRKPeFLEGKQKEAIVDLLFK--TNR-KVTV  560
WP_048800889    487  SAQSFIERMTNEDKNLPNEKVLPKHELLYEYFTVYNELTKVKVVT-EGMRKPeFLEGKQKEAIVDLLFK--TNR-KVTV  560
WP_012767106    487  SAQSFIERMTNEDKNLPNEKVLPKHELLYEIFTVYNELTKVKVVT-EGMRKPeFLEGKQKEAIVDLLFK--TNR-KVTV  560
WP_014612333    488  SAQSFIERMTNEDKNLPNEKVLPKHELLYEYFTVYNELTKVKVVT-EGMRKPeFLEGKQKEAIVDLLFK--TNR-KVTV  561
WP_015017095    487  SAQSFIERMTNEDKNLPNEKVLPKHELLYEYFTVYNELTKVKVVT-EGMRKPeFLEGKQKEAIVDLLFK--TNR-KVTV  560
WP_015057649    487  SAQSFIERMTNEDKNLPNEKVLPKHELLYEYFTVYNELTKVKVVT-EGMRKPeFLEGKQKEAIVDLLFK--TNR-KVTV  560
WP_048327215    487  SAQSFIERMTNEDKNLPNEKVLPKHELLYEYFTVYNELTKVKVVT-EGMRKPaELSGEQKKAIVDLLFK--TNR-KVTV  561
WP_049519324    487  SAQSFIERMTNKDDLPNEKVLPKHELLYETFTVYNELTKVKVVT-EGMTRPqFLEADQKQAIVDLLFK--TNR-KVTV  561
WP_012515931    487  SAQIFIEKMTKDDLYLPEEKVLPKHELLYEYFAVYNELTKIKVVN-EGMTRPqFLEADQKQAIVDLLFK--TNR-KVTV  561
WP_021320964    487  SAQIFIEKMTNDDLYLPEEKVLPKHELLYEYFAVYNELTKIKIKVN-EGMTRPqFLEADQKQAIVDLLFK--TNR-KVTV  561
WP_037581760    487  SAQIFIEKMTNDDLYLPEEKVLPKHELLYEYFAVYNELTKIKIKVN-EGMTRPqFLEADQKQAIVDLLFK--TNR-KVTV  561
WP_004232481    487  SAEKFITRMTLNDLYLPEEKVLPKHELLYEYFAVYNELTKIKIKVN-EQGKSP-FFDSNMKQEIFDHVFK--ENR-KVTK  560
WP_009854540    488  SAEKFITRMTLNDLYLPEEKVLPKHELLYEYFAVYNELTKIKIKVN-EQGKEN-FFDANMKQEIFDHVFK--ENR-KVTK  561
WP_012962174    488  SAEKFITRMTLNDLYLPEEKVLPKHELVYETFTVYNELTKVKVVN-EQGKEN-FFDANMKQEIFEHVFK--ENR-KVTK  561
WP_039695303    490  SAEKFITRMTLNDLYLPEEKVLPKHSHVYETFAVYNELTKVKVVN-EQGKES-FFDSNMKQEIFDHVFK--ENR-KVTK  563
WP_014334983    487  SAEKFITRMTLNDLYLPEEKVLPKHSPLYEMFMVYNELTKVKVQT-EQGESP-FFDANMKQEIFDGVFK--ENR-KVTK  560
WP_030099269    487  SAEBFIERMTNFDTYLPEEKVLPKHSPLYEMFMVYNELTKVKVQT-EGMKRPvFLSSEDKEEIVNLLFK--KER-KVTV  560
AHY15608        487  SAEAFIERMTNFDTYLPEEKVLPKHSPLYEMFMVYNELTKVKVQT-EGMKRPvFLSSEDKEEIVNLLFK--KER-KVTV  561
AHY17476        487  SARAFIERMTNFDTYLPEEKVLPKHSPLYEMFMVYNELTKVKVQT-EGMKRPvFLSSEDKEEIVNLLFK--KER-KVTV  561
ESR09100             ------------------------------------------------EGMKRPvFLSSEDKEEIVNLLFK--KER-KVTK  561
AGM98575        487  SAEAFINRMTNVDLYLPNQKVLPKHSLIYEKFTVFNELTKVKYKT-EQGKTA-FFDANMKQEIFDGVFK--VYR-KVTK  560
ALF27331        500  SASRFIEMTLHDLYLPEEKVLPKHSLIYEKFTVFNELTKVKVRFTP-EGGKEV-YFSKTDKENIFDSLFK--RYR-KVTK  573
WP_018372492    488  SAEDFINKMTNVDLYLPEEKVLPKHELLYEKFTVFNELTKVKVFIA-EGLRDYqFLDSGQKQIVTQLFK--EKR-KVTE  562
WP_045618028    488  SAEDFINKMTNVDLYLPEEKVLPKHELLYEKFTVFNELTKVKVFIA-EGLRDYqFLDSGQKQIVNQLFK--ENR-KVTK  561
WP_045635197    487  SAEAFINRMTNVDLYLPNQKVLPKHSLIYEKFTVFNELTKVKVKT-EQGKTA-FFDANMKQEIFDGVFK--VYR-KVTK  560
WP_002263549    487  SAEAFINRMTNVDLYLPNQKVLPKHSLIYEKFTVFNELIKVKYKT-EQGKTA-FFDANMKQEIFDGVFK--VYR-KVTK  560
WP_002263887    487  SVEAFIRNMTNVDLYLPNQKVLPKHSLIYEKFTVFNELTKVKYKT-EQGKTA-FFDANMKQEIFDGVFK--VYR-KVTK  560
WP_002264920    487  SAEAFINRMTNVDLYLPNQKVLPKHSLIYEKFTVFNELTKVKYKT-EQGKTA-FFDANMKQEIFDGVFK--VYR-KVTK  560
WP_002269043    487  SAEAFINRMTNVDLYLPNQKVLPKHSLIYEKFTVFNELTKVKYKT-EQGKTA-FFDANMKQEIFDGVFK--VYR-KVTK  560
WP_002269448    487  SAEAFINRMTNVDLYLPNQKVLPKHSLIYEKFTVFNELTKVKYKT-EQGKTA-FFDANMKQEIFDGVFK--VYR-KVTK  560
```

```
WP_002271977  487  SAEAFIINRMTNYDLYLPNQKVLPKHSLLYEKFTVYNELTKVKYKT-EQGKTA-FFDANMKQEIFDGVFK--VYR-KVTK  560
WP_002272766  487  SAEAFIINRMTNYDLYLPNQKVLPKHSLLYEKFTVYNELTKVKYKT-EQGKTA-FFDANMKQEIFDGVFK--VYR-KVTK  560
WP_002273241  487  SAEAFIINRMTNYDLYLPNQKVLPKHSLLYEKFTVYNELTKVKYKT-EQGKTA-FFDANMKQEIFDGVFK--VYR-KVTK  560
WP_002275430  487  SAEAFIINRMTNYDLYLPNQKVLPKHSPLYEKFTVYNELTKVKYKT-EQGKTA-FFDANMKQEIFDGVFK--VYR-KVTK  560
WP_002276448  487  SAEAFIINRMTNYDLYLPNEKVLPKHSLLYEKFTVYNELTKIKYKT-EIGEAK-FFDANLKQEIFDGLFK--HER-KVTK  560
WP_002277050  487  SAQAFIEHMTNRMTNYDLYLPNQKVLPKHSLLYEKFTVYNELTKVKYVT-EQGKTA-FFDANLKQEIFDGVFK--HER-KVTK  560
WP_002277364  487  SAEAFIINRMTNYDLYLPNQKVLPKHSLLYEKFTVYNELTKVKYKT-EQGKTA-FFDANMKQEIFDGVFK--HER-KVTK  560
WP_002279025  487  SAEAFIINRMTNYDLYLPNQKVLPKHSLLYEKFTVYNELTKVKYKT-EQGETA-FFDANMKQEIFDGVFK--VYR-KVTK  560
WP_002279859  487  SVEAFIINRMTNYDLYLPNQKVLPKHSLLYEKFTVYNELTKVKYKT-EQGKTA-FFDANMKQEIFDGVFK--VYR-KVTK  560
WP_002280230  487  SAEAFIINRMTNYDLYLPNQKVLPKHSLLYEKFTVYNELTKVKYKT-EQGKTA-FFDANMKQEIFDGVFK--VYR-KVTK  560
WP_002281696  487  SAEAFIINRMTNYDLYLPNQKVLPKHSLLYEKFTVYNELTKVKYKT-EQGKTA-FFDANMKQEIFDGLFK--HER-KVTK  560
WP_002282247  487  SAQAFIEHMTNRMTNNDLYLPNEKVLPKHSPLYEKYTVYNELTKIKYVT-EIGEAK-FFDANLKQEIFDGLFK--HER-KVTK  560
WP_002282906  487  SAEAFIINRMTNYDLYLPNQKVLPKHSLLYEKFTVYNELTKVKYKT-EQGKTA-FFDANMKQEIFDGVFK--VYR-KVTK  560
WP_002283846  487  SVEAFIINRMTNYDLYLPNQKVLPKHSLLYEKFTVYNELTKVKYKT-EQGKTA-FFDANMKQEIFDGVFK--VYR-KVTK  560
WP_002287255  487  SVEAFIINRMTNYDLYLPNQKVLPKHSLLYEKFTVYNELTKVKYKT-EQGKTA-FFDANMKQEIFDGVFK--VYR-KVTK  560
WP_002288990  487  SVEAFIINRMTNYDLYLPNQKVLPKHSLLYEKFTVYNELTKVKYKT-EQGKTA-FFDANMKQEIFDGVFK--VYR-KVTK  560
WP_002289641  487  SAEAFIINRMTNYDLYLPNQKVLPKHSLLYEKFTVYNELTKVKYKT-EQGKTA-FFDANMKQEIFDGVFK--VYR-KVTK  560
WP_002290427  487  SAEAFIINRMTNYDLYLPNQKVLPKHSLLYEKFTVYNELTKVKYKT-EQGKTA-FFDANMKQEIFDGVFK--VYR-KVTK  560
WP_002295753  487  SAEAFIINRMTNYDLYLPNQKVLPKHSLLYEKFTVYNELTKVKYKT-EQGKTA-FFDANMKQEIFDGVFK--VYR-KVTK  560
WP_002296423  487  SVEAFIINRMTNYDLYLPNQKVLPKHSLLYEKFTVYNELTKVKYKT-EQGKTA-FFDANMKQEIFDGVFK--VYR-KVTK  560
WP_002304487  497  SAEKFITRMTLNDLYLPEEKVLPKHSLLYETFTVYNELTKVKVVN-EQGEAK-FFDANMKQEIFDHVFK--ENR-KVTK  570
WP_002305844  487  SAEAFIINRMTNYDLYLPNQKVLPKHSLLYEKFTVYNELTKVKYKT-EQGKTA-FFDANMKQEIFDGVFK--VYR-KVTK  560
WP_002307203  487  SVEAFIINRMTNYDLYLPNQKVLPKHSLLYEKFTVYNELTKVKYKT-EQGKTA-FFDANMKQEIFDGVFK--VYR-KVTK  560
WP_002310390  487  SAEAFIINRMTNYDLYLPNQKVLPKHSLLYEKFTVYNELTKVKYKT-EQGKTA-FFDANMKQEIFDGVFK--VYR-KVTK  560
WP_002352408  487  SAEAFIINRMTNYDLYLPNQKVLPKHSLLYEKFTVYNELTKVKYKT-EQGKTA-FFDANMKQEIFDGVFK--VYR-KVTK  560
WP_012997688  487  SAEAFIINRMTNYDLYLPNQKVLPKHSLLYEKFTVYNELTKVKYKT-EQGKTA-FFDANMKQEIFDGVFK--VYR-KVTK  560
WP_014677909  487  SAEAFIINRMTNYDLYLPNQKVLPKHSLLYEKFTVYNELTKVKYKT-EQGKTA-FFDANMKQEIFDGVFK--VYR-KVTK  560
WP_019312892  487  SAEAFIINRMTNYDLYLPNQKVLPKHSLLYEKFTVYNELTKVKYKT-EQGKTA-FFDANMKQEIFDGVFK--VYR-KVTK  560
WP_019313659  487  SAEAFIINRMTNYDLYLPNQKVLPKHSLLYEKFTVYNELTKVKYKT-EIGEAK-FFDANLKQEIFDGLFK--HER-KVTK  560
WP_019314093  487  SVEAFIINRMTNYDLYLPNQKVLPKHSLLYEKFTVYNELTKVKYKT-EQGKTA-FFDANMKQEIFDGVFK--VYR-KVTK  560
WP_019315370  487  SAEAFIINRMTNYDLYLPNQKVLPKHSLLYEKFTVYNELTKVKYKT-EQGKTA-FFDANMKQEIFDGVFK--VYR-KVTK  560
WP_019803776  487  SAEAFIINRMTNYDLYLPNQKVLPKHSLLYEKFTVYNELTKVKYKT-EQGKTA-FFDANMKQEIFDGVFK--VYR-KVTK  560
WP_019805234  487  SAEAFIINRMTNYDLYLPNQKVLPKHSLLYEKFTVYNELTKVKYKT-EQGKTA-FFDANMKQEIFDGVFK--VYR-KVTK  560
WP_024783594  487  SAEAFIINRMTNYDLYLPNQKVLPKHSLLYEKFTVYNELTKVKIKVT-EIGEAK-FFDANLKQEIFDGLFK--HER-KVTK  560
WP_024784288  488  SAQAFIEHMTNRMTNYDLYLPEEKVLPKHSLLYEKFTVYNELTKVKYKT-EQGKTA-FFDANMKQEIFDGVFK--VYR-KVTK  560
WP_024784666  488  SAEDFIINKMTNYDLYLPEEKVLPKHSLLYEKFTVYNELTKVKIKVT-EIGEAK-FFDANLKQEIFDGLFK--HER-KVTK  560
WP_024784894  487  SADRFIHRMTNYDLYLPNQKVLPKHSLLYEKFTAVYNELTKVKFIA-EGLRDYqFLDSGQKKQIVNQLFK--EKR-KVTE  560
WP_024786433  487  SAKVFIERMTNFPDTYLPEEKVLPKHSLLYETFTVYNELTKVKYKT-EQGKTA-FFDANMKQEIFDGVFK--VYR-KVTK  560
WP_049473442  456  SAQAFIERMTNKMTNFDEYLPQEKVLPKHSLLYETFAVYNELTKVKFIA-EGMRKPeFLSSEEKIRIVSNLFK--TER-KVTV  530
WP_049531101  489  SAEAFIINKMTNRDLYLPEEKVLPKHSLLYEKFTAVYNELTKVKFIA-EGMTKPeFLSAGQKEQIVELLFK--KYR-KVTV  563
WP_049538452  488  SADDFIINKMTNYDLYLPEEKVLPKHSLLYEKFTAVYNELTKVKFIA-EGLRDYqFLDSGQKKKIINQLFK--EKR-KVTE  562
WP_049549711  488  SADDFIINKMTNYDLYLPEEKVLPKHSLLYEKFTAVYNELTKVKFIA-EGLRDYqFLDSGQKQIVNQLFK--EKR-KVTE  562
WP_007896501  490  SADDFIINKMTNYDLYLPEEKVLPKHSLLYEKFTAVYNELTKVKFIA-EGLRDYqFLDSGQKQIVNQLFK--EKR-KVTE  564
EFR44625      442  SAQAFIEGMTNRMTNDTYLPEEKVLPKHSLLYEMFTVYNELTKVKYIA-ENMTKPlYLSAEQKEATIDHLFK--QTR-KVTV  516
WP_002897477  487  SAQAFIEGMTNYDLYLPEEKVLPKHSLLYEMFTVYNELTKVKYIA-ENMTKPlYLSAEQKEATIDHLFK--QTR-KVTV  561
WP_002906454  487  SAEDFIINKMTNYDLYLPEEKVLPKHSLLYEKFTAVYNELTKVKFIA-EGLRDYqFLDSGQKKQIVNQLFK--DKR-KVTE  561
```

-continued

```
WP_009729476  488  SAEDFINKMTNDLYLPEEKVLPKHSLLYETFAVYNELTKVKFIA-EGLRDYqFLDSGQKKQIVTQLFK--EKR-KVTE  562
CQR24647      488  SAQAFIERMTNNDLYLPDQKVLPKHSLLYQKFAVYNELTKIKYVT-ETGEAR-LEDVFLKKEIFDGLEK--KER-KVTE  561
WP_000066813  488  SAEDFINKMTNTNDLYLPEEKVLPKHSLLYETFAVYNELTKVKFIA-EGLTRYqFLDKKQKKDIFDTFFKaeNKR-KVTE  564
WP_009754323  488  SAESFINKMTNDLYLPEEKVLPKHSLLYETFAVYNELTKVKFIA-EGLRDYqFFDSGQKKQIVNQLFK--EKR-KVTE  562
WP_044674937  487  SAENFITRMTNVDQYLPDQKVLPKHSLLYEKFAVYNELTKVRYVT-EGMRDYqFLDSGQKKDIVKTLFK--TKR-KVTA  561
WP_044676715  487  SAENFITRMTNVDQYLPDQKVLPKHSLLYEKFAVYNELTKVRYVT-EQGKSF-FFDANMKQEIFDGVEK--VYR-KVTK  560
WP_044680361  487  SAENFITRMTNVDQYLPDQKVLPKHSLLYEKFAVYNELTKVRYVT-EQGKSF-FFDANMKQEIFDGVEK--VYR-KVTK  560
WP_044681799  487  SAENFITRMTNVDQYLPDQKVLPKHSLLYEKFAVYNELTKVKFIA-EGMRDYqFLDSGQKKDIVKTLFK--TKR-KVTA  561
WP_049533112  487  SAEKFITRMTLNDLYLPEEKVLPKHSLLYETFTVYNELTKVKYVN-EQGEAK-FFDANMKQEIFDHVEK--ENR-KVTK  560
WP_029090905  472  SAEKFITRMTNKCTYLIHEDVIPKHSFSYAKFEVLNELANKIRLDG------KP--IDIPLKKRIFEGLFL--EKtKVTQ  540
WP_006506696  499  TAEGFIKRMRSYCTYFPDEEVLPKNSLLVSKYEVNELNKIRVDD------kLLEVDVKNDIYNELFM-KNK-TVTE  567
AIT42264      487  SAQSFIERMTNEDKNLPNEKVLPKHSLLYQKFTIFNELTKVKVT--EGMRKPaELSGEQKAIVDLLFK--TNR-KVTK  561
WP_034440723  494  SAELFIENLTSRDTYLPDEPVLPKHSLLYQKFTIFNELTKISYID-NFSSREKIAIENDLFK---NKsKVTK  567
AKQ21048      487  SAQSFIERMTNEDKNLPNEKVLPKHSLLYEYFTVFNELTKVKVT--EGMRKPaELSGEQKAIVETLFK-qKNR--VRE  561
WP_004636532  489  SAEKFIERMTNMDTYLLEEKVLPKRSLLYQTFEVYNELTKVRYTN-EQGKTE-KLNRQQKAEIIETLFK--TNR-KVTV  562
WP_002364836  496  SATAFIERMTNEDTYLPEKVLPKHSLLYEKFMVFNELTKTKISTD-DRGIKA-NFSGKEKEKIFDYLFK--TRR-KVKK  569
WP_016631044  447  SATAFIERMTNEDTYLPEKVLPKHSLLYEKMVFNELTKISYTD-DRGIKA-NFSGKEKEKIFDYLFK--TRR-KVKK  520
EMS75795      232  SAMKFIQRMINYDTYLPTEKVLPKHSLLYQKYTIFNELTKVAYKD-ERGIKH-QESSKEKREIFKELFQ--KQR-KVTV  305
WP_002373311  496  SATAFIERMTNEDTYLPSEKVLPKHSLLYEKFMVFNELTKISYTD-DRGIKA-NFSGKEKEKIFDYLFK--TRR-KVKK  569
WP_002378009  496  SATAFIERMTNEDTYLPSEKVLPKHSLLYEKFMVFNELTKISYTD-DRGIKA-NFSGKEKEKIFDYLFK--TRR-KVKK  569
WP_002407324  496  SATAFIERMTNEDTYLPSEKVLPKHSLLYEKFMVFNELTKISYTD-DRGIKA-NFSGKEKEKIFDYLFK--TRR-KVKK  569
WP_002413717  498  SATAFIERMTNEDTYLPSEKVLPKHSLLYEKFMVFNELTKISYTD-DRGIKA-NFSGKEKEKIFDYLFK--TRR-KVKK  571
WP_010775580  496  SATAFIERMTNEDTYLPSEKVLPKHSLLYEKFMVFNELTKISYTD-DRGIKA-NFSGKEKEKIFDYLFK--TRR-KVKK  569
WP_010818269  496  SATAFIERMTNEDTYLPSEKVLPKHSLLYEKFMVFNELTKISYTD-DRGIKA-NFSGKEKEKIFDYLFK--TRR-KVKK  569
WP_010824395  496  SATAFIERMTNEDTYLPSEKVLPKHSLLYEKFMVFNELTKISYTD-DRGIKA-NFSGKEKEKIFDYLFK--TRR-KVKK  569
WP_016622645  496  SATAFIERMTNEDTYLPSEKVLPKHSLLYEKFMVFNELTKISYTD-DRGIKA-NFSGKEKEKIFDYLFK--TRR-KVKK  569
WP_033624816  496  SATAFIERMTNEDTYLPSEKVLPKHSLLYEKFMVFNELTKISYTD-DRGIKA-NFSGKEKEKIFDYLFK--TRR-KVKK  569
WP_033625576  496  SATAFIERMTNEDTYLPSEKVLPKHSLLYEKFMVFNELTKISYTD-DRGIKA-NFSGKEKEKIFDYLFK--TRR-KVKK  569
WP_033789179  496  SATAFIERMTNEDTYLPSEKVLPKHSLLYEKFMVFNELTKISYTD-DRGIKA-NFSGKEKEKIFDYLFK--TRR-KVKK  569
WP_002310644  493  SAVRFIERMINTDMYMPHNKVLPKNSLLYQKFSIYNELTKVRYQD-ERGQMN-YFSSIEKKEIFHELFE--KNR-KVTK  566
WP_002312694  494  SAVRFIERMINTDMYMPHNKVLPKNSLLYQKFSIYNELTKVRYQD-ERGQMN-YFSSIEKKEIFHELFE--KNR-KVTK  567
WP_002314015  494  SAVRFIERMNNTDMYIPHNKVLPKNSLLYQKFSIYNELTKVRYQD-ERGQMN-YFSSIEKKEIFHELFE--KNR-KVTK  567
WP_002320716  494  SAVRFIERMINTDMYIPHNKVLPKNSLLYQKFSIYNELTKVRYQD-ERGQMN-YFSSIEKKEIFHELFE--KNR-KVTK  567
WP_002330729  493  SAVRFIERMINTDMYMPHNKVLPKNSLLYQKFSIYNELTKVRYQD-ERGQMN-YESSIEKKEIFHELFE--KNR-KVTK  566
WP_002335161  494  SAVRFIERMINTDMYMPHNKVLPKNSLLYQKFSIYNELTKVRYQD-ERGQMN-YESSIEKKEIFHELFE--KNR-KVTK  567
WP_002345439  494  SAVRFIERMINTDMYMPHNKVLPKNSLLYQKFSIYNELTKVRYQD-ERGQMN-YESSIEKKEIFHELFE--KNR-KVTK  567
WP_034867970  487  SAMRFIQRMFIQDTYLPTEKVLPKNSLLYQKMIFNELTKVKD-ERGVKQ-YFSGDEKQQIFKQLFQ--KERgKITV  561
WP_047937432  494  SAVRFIERMINTDMYMPHNKVLPKNSLLYQKFSIYNELTKVRYQD-ERGQMN-YESSIEKKEIFHELFE--KNR-KVTK  567
WP_010720994  487  SAMRFIQRMTKQDTYLPTEKVLPKNSLLFYQKMIFNELTKVSYKD-ERGVKQ-YFSGDEKQQIFKQLFQ--KERgKITV  561
WP_010737004  487  SAMRFIQRMTKQDTYLPTEKVLPKNSLLYQKMIFNELTKVSYKD-ERGVKQ-YFSGDEKQQIFKQLFQ--KERgKITV  561
WP_034700478  487  SAMRFIQRMTKQDTYLPTEKVLPKNSLLYQKMIFNELTKVSYKD-ERGVKQ-YFSGDEKQQIFKQLFQ--KERgKITV  561
WP_007209003  491  SAVAFIERMTIKDIYL-NENVLPRHSLLYQKQSLLYQRFMIFNELTKVLAD-DRGVFQ-RFSAEEKEDIFEKLFK--SER-KVTK  563
WP_023519017  486  SAIEFIERMTNQDTYLPKEKVLPKHSLLYQRFMIFNELTKVSYTD-ERGKSH-YFSSEQRKIFNELFK--QHP-RVTE  559
WP_010770040  490  SATKFIERMTNEDTYLPKEKVLPKHSMIYEKYMVYNELTKVSVD-ERGMNQ-RFSGEEKKQIVEELFK--QSR-KVTK  563
WP_048604708  486  SAELFIERMTNFDLYLPSEKVLPKNSLLYEKTVYNELTKVSYKD-EQGKVQ-NFSSEEKERIFIDLFK--QHR-KVTK  559
WP_010750235  487  SATKFIQRMINYDTYLPTEKVLPKYSMLYQKYTIFNELTKVAYKD-DRGIKH-QFSSEEKLRIFQELFK--KQR-RVTK  560
AII16583      526  SAQSFIERMTNFDKNLPNEKVLPKHSLLYEYFTVYNELTKVKFVT-EGMRKPaFLSGEQKAIVDLLFK--TNR-KVTV  600
WP_029073316  507  TADEFIKRMRNFCTYFPDEPVMAKNSLTVSKYEVLNEINKLRIND------hLIKRDIKDKMLHTLFM-DHK-SISA  575
WP_031589969  507  TADEFIKRMRNFCTYFPDEPVMAKNSLTVSKYEVLNEINKLRIND------hLIKRDMKDKMLHTLFM-DHK-SISA  575
KDA45870      485  SAEDFIKRMTINDLYLPTEPVLPKHSLLYERYTIFNELAGVRVT-ENGEAK-YEDAQTKRSIFE-LFK1--DR-KVSE  557
WP_039099354  510  SANEFIKRMTTTDTYLLAEDVLPKQSLLYQRFEVLNELNGLKIDD------QPITTE----LKQAIFTDLFM--QKtSVTV  578
AKP02966      484  SSNKFIRRMTVTDSYLVGEPVLPKNSLLYQRYEVLNELANNIRITEniKTNPTGsRLTVETKQHIYNELFK--NYK-KITV  560
WP_010991369  493  SAVDFIEKMTNKDTYLPKENVLPKHSLCYQKYLVYNELTKVRYIN-DQGKTS-YFSSQEKEQIENDLFK--QKR-KVKK  566
```

| | | | | |
|---|---|---|---|---|
| WP_033838504 | 493 | SAVDFIEKMTNKDTYLPKENVLPKHSLCYQKLVYNELTKVRYIN--DQGKTS-YFSGQEKEQIENDLFK--QKR-KVKK | 566 |
| EHN60060 | 496 | SAVDFIEKMTNKDTYLPKENVLPKHSLCYQKLVYNELTKVRYIN--DQGKTS-YFSGQEKEQIENDLFK--QKR-KVKK | 569 |
| EFR89594 | 262 | SAVDFIEKMTNKDTYLPKENVLPKHSLCYQKLVYNELTKVRYIN--DQGKTS-YFSGQEKEQIENDLFK--QKR-KVKK | 335 |
| WP_038409211 | 493 | SAIDFIEKMTNKDTYLPKENVLPKHSLCYQKLVYNELTKVRYIN--DQGKTH-HFSGQEKEQIENDLFK--QQR-KVKK | 566 |
| EFR95520 | 112 | SAIDFIEKMTNKDTYLPKENVLPKHSLCYQKMVYNELTKIRYID--DQGKTH-HFSGQEKQQIFNGLFK--QQR-KVKK | 185 |
| WP_003723650 | 493 | SAVDFIEKMTNKDTYLPKENVLPKHSLCYQKMVYNELTKIRYID--DQGKTN-YFSGQEKQQIFNDLFK--QKR-KVKK | 566 |
| WP_003727705 | 493 | SAVDFIEKMTNKDTYLPKENVLPKHSLCYQKMVYNELTKIRYID--DQGKTN-YFSGREKQQIENDLFK--QKR-KVKK | 566 |
| WP_003730785 | 493 | SAVDFIEKMTNKDTYLPKENVLPKHSLCYQKMVYNELTKIRYID--DQGKTN-YFSGREKQQIENDLFK--QKR-KVKK | 566 |
| WP_003733029 | 493 | SAVDFIEKMTNKDTYLPKENVLPKHSLCYQKMVYNELTKIRYID--DQGKTN-YFSGQEKQQIENDLFK--QKR-KVKK | 566 |
| WP_003739838 | 493 | SAVDFIEKMTNKDTYLPKENVLPKHSLCYQKMVYNELTKIRYID--DQGKTN-YFSGQEKQQIENDYFK--QKR-KVSK | 566 |
| WP_014601172 | 493 | SAVDFIEKMTNKDTYLPKENVLPKHSLCYQKMVYNELTKIRYID--DQGKTN-YFSGQEKQQIENDLFK--QKR-KVKK | 566 |
| WP_023548323 | 493 | SAVDFIEKMTNKDTYLPKENVLPKHSLCYQKMVYNELTKIRYID--DQGKTN-YFSGQEKQQIENDLFK--QKR-KVKK | 566 |
| WP_031665337 | 493 | SAVDFIEKMTNKDTYLPKENVLPKHSLCYQKMVYNELTKIRYID--DQGKTN-YFSGQEKQQIENDLFK--QKR-KVKK | 566 |
| WP_031669209 | 493 | SAVDFIEKMTNKDTYLPKENVLPKHSLCYQKMVYNELTKIRYID--DQGKTN-YESGQEKQQIENDLEK--QKR-KVKK | 566 |
| WP_033920898 | 493 | SAVDFIEKMTNKDTYLPKENVLPKHSLCYQKMVYNELTKIRYID--DQGKTN-YESGQEKQQIENDLEK--QKR-KVKK | 566 |
| AKI42028 | 496 | SAVDFIEKMTNKDTYLPKENVLPKHSLCYQKMVYNELTKIRYID--DQGKTN-YESGQEKQQIENDLEK--QKR-KVKK | 569 |
| AKI50529 | 496 | SAVDFIEKMTNKDTYLPKENVLPKHSLCYQKMVYNELTKIRYID--DQGKTN-YESGQEKQQIENDLEK--QKR-KVKK | 569 |
| EFR83390 | 1 | ------------------------------------------------------IFNDLEK--QKR-KVKK | 14 |
| WP_046323366 | 493 | SAIDFIEKMTNKDTYLPKENVLPKHSLPKHSMCYQKMVYNELTKIRYTD--DQGKTH-YESGQEKQQIENDLEK--QKR-KVKK | 566 |
| AKE81011 | 503 | SAQSFIERMTNEDKNLPNEKVLPKHSLLYEFTVYNELTKVKYIL-DK AFLDDKVNEEVIEDIIKTLTLFEDKDMH | 577 |
| CUO82355 | 503 | TAEGFIKRMRSYCTYFPDEEVLPKNSLIVSKYEVYNELNKIRVDD-------kLLEVDKNDIYNELFM--KNK-TVTE | 571 |
| WP_033162887 | 504 | TAEGFIERMKNTGTYFPDEPVMAKNSLTVSKFEVLNELNKIRING-------kLIAVETKKELLSDLFM--KNK-TITD | 572 |
| AGZ01981 | 520 | SAQSFIERMTNEDKNLPNEKVLPKHSLLYEFTVYNELTKVKYVT--EGMRKPaELSGEQKKAIVDLLFK--TNR-KVTV | 594 |
| AKA60242 | 487 | SAQSFIERMTNEDKNLPNEKVLPKHSLLYEFTVYNELTKVKYVT--EGMRKPaELSGEQKKAIVDLLFK--TNR-KVTV | 561 |
| AKS40380 | 487 | SAQSFIERMTNEDKNLPNEKVLPKHSLLYEFTVYNELTKVKYVT--EGMRKPaELSGEQKKAIVDLLFK--TNR-KVTV | 561 |
| 4UN5_B | 491 | SAQSFIERMTNEDKNLPNEKVLPKHSLLYEFTVYNELTKVKYVT--EGMRKPaELSGEQKKAIVDLLFK--TNR-KVTV | 565 |
| WP_010922251 | 562 | KQLKEDYFKK--IECFDSVEISGVEDR---FNASLGTYHDLLKIIKDK DFLDNEENEDILEDIVLTLFEDREMIE | 633 |
| WP_011527619 | 564 | EKLLNYLNKE--FPEYRIKDLIGLDKEnkSFNASLGTYHDLKKIL-DK AFLDDKVNEEVIEDIIKTLTLFEDKDMIH | 637 |
| WP_012560673 | 562 | KDIIHYLHN---VDGYDGIELKGIEKQ--FNASLSTYHDLLKIYKDK EFMDDAKNEAILENIVHTLTIFEDREMIK | 632 |
| WP_045635197 | 300 | KQIAKEIVNe--EDIKGYRVTSTGKPe--FTNLKVYHDIKDITARK ------ENAELLDQIAKILTIYQSSEDIQ | 368 |
| 5AXW_A | 246 | KQLKEDYFKK--IECFDSVEISGVEDR---FNASLGTYHDLLKIIKDK DFLDNEENEDILEDIVLTLFEDREMIE | 317 |
| WP_099880683 | 562 | KQLKEDYFKK--IECFDSVEISGVEDR---FNASLGTYHDLLKIIKDK DFLDNEENEDILEDIVLTLFEDREMIE | 633 |
| WP_010922251 | 562 | KQLKEDYFKK--IECFDSVEISGVEDR---FNASLGTYHDLLKIIKDK DFLDNEENEDILEDIVLTLFEDREMIE | 633 |
| WP_011054416 | 562 | KQLKEDYFKK--IECFDSVEISGVEDR---FNASLGTYHDLLKIIKDK DFLDNEENEDILEDIVLTLFEDREMIE | 633 |
| WP_011284745 | 562 | KQLKEDYFKK--IECFDSVEISGVEDR---FNASLGTYHDLLKIIKDK DFLDNEENEDILEDIVLTLFEDREMIE | 633 |
| WP_011285506 | 562 | KQLKEDYFKK--IECFDSVEISGVEDR---FNASLGTYHDLLKIIKDK DFLDNEENEDILEDIVLTLFEDREMIE | 633 |
| WP_011527619 | 562 | KQLKEDYFKK--IECFDSVEISGVEDR---FNASLGTYHDLLKIIKDK DFLDNEENEDILEDIVLTLFEDREMIE | 633 |
| WP_012560673 | 562 | KQLKEDYFKK--IECFDSVEISGVEDR---FNASLGTYHDLLKIIKDK DFLDNEENEDILEDIVLTLFEDREMIE | 633 |
| WP_014407541 | 562 | KQLKEDYFKK--IECFDSVEISGVEDR---FNASLGAYHDLLKIIKDK DFLDNEENEDILEDIVLTLFEDRGMIE | 633 |
| WP_020905136 | 562 | KQLKEDYFKK--IECFDSVEISGVEDR---FNASLGTYHDLLKIIKDK DFLDNEENEDILEDIVLTLFEDKEMIE | 633 |
| WP_023080005 | 562 | KQLKEDYFKK--IECFDSVEISGVEDR---FNASLGTYHDLLKIIKDK DFLDNEENEDILEDIVLTLFEDKEMIE | 633 |
| WP_023610282 | 562 | KQLKEDYFKK--IECFDSVEISGVEDR---FNTSLGTYHDLLKIIKDK DFLDNEENEDILEDIVLTLFEDKEMIE | 633 |
| WP_030125963 | 562 | KQLKEDYFKK--IECFDSVEISGVEDR---FNASLGTYHDLLKIIKDK DFLDNEENEDILEDIVLTLFEDREMIE | 633 |
| WP_030126706 | 562 | KQLKEDYFKK--IECFDSVEISGVEDR---FNASLGTYHDLLKIIKDK DFLDNEENEDILEDIVLTLFEDREMIE | 633 |
| WP_031488318 | 562 | KQLKEDYFKK--IECFDSVEISGVEDR---FNASLGTYHDLLKIIKDK DFLDNEENEDILEDIVLTLFEDREMIE | 633 |
| WP_032460140 | 562 | KQLKEDYFKK--IECFDSVEISGVEDR---FNASLGTYHDLLKIIKDK DFLDNEENEDILEDIVLTLFEDREMIE | 633 |
| WP_032461047 | 562 | KQLKEDYFKK--IECFDSVEISGVEDR---FNASLGTYHDLLKIIKDK DFLDNEENEDILEDIVLTLFEDREMIE | 633 |
| WP_032462016 | 562 | KQLKEDYFKK--IECFDSVEISGVEDR---FNASLGTYHDLLKIIKDK DFLDNEENEDILEDIVLTLFEDREMIE | 633 |
| WP_032462936 | 562 | KQLKEDYFKK--IECFDSVEISGVEDR---FNASLGTYHDLLKIIKDK DFLDNEENEDILEDIVLTLFEDREMIE | 633 |
| WP_032464890 | 562 | KQLKEDYFKK--IECFDSVEISGVEDR---FNASLGTYHDLLKIIKDK DFLDNEENEDILEDIVLTLFEDREMIE | 633 |
| WP_033888930 | 387 | KQLKEDYFKK--IECFDSVEISGVEDR---FNASLGTYHDLLKIIKDK DFLDNEENEDILEDIVLTLFEDREMIE | 458 |
| WP_038431314 | 562 | KQLKEDYFKK--IECFDSVEISGVEDR---FNASLGTYHDLLKIIKDK DFLDNEENEDILEDIVLTLFEDREMIE | 633 |
| WP_038432938 | 562 | KQLKEDYFKK--IECFDSVEISGVEDR---FNTSLGTYHDLLKIIKDK DFLDNEENEDILEDIVLTLFEDREMIE | 633 |
| WP_038434062 | 562 | KQLKEDYFKK--IECFDSVEISGVEDR---FNASLGTYHDLLKIIKDK DFLDNEENEDILEDIVLTLFEDREMIE | 633 |

| | | | | |
|---|---|---|---|---|
| BAQ51233 | 473 | KQLKEDYFKK--IECFDSVEISGVEDR---FNASLGTYHDLLKIIKDK | DFLDNEENEDILEDIVLTLFEDREMIE | 544 |
| KGE60162 | | | | |
| KGE60856 | | | | |
| WP_002989955 | 562 | KQLKEDYFKK--IECFDSVEISGVEDR---FNASLGTYHDLLKIIKDK | DFLDNEENEDILEDIVLTLFEDREMIE | 633 |
| WP_003030002 | 561 | DKLLNYLNKE-FEEFRIVNLTGLDKEnkAFNSSLGTYHDLRKIL-DK | SFLDDKANEKTIEDIIQTLTLFEDREMIR | 634 |
| WP_003065552 | 564 | EKLLNYLNKE-FPEYRIKDLIGLDKErkAFNASLGTYHDLRKIL-DK | AFLDDKVNEEVIEDIIKTLTLFEDKDMIH | 637 |
| WP_001040076 | 563 | KDIISFLNK---VDGYEGIAIKGIEKQ---FNASLSTYHDLKKIL-GK | DFLDNTDNELILEDIVQTLTLFEDREMIK | 632 |
| WP_001040078 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040080 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040081 | 562 | KKLLDFLAKE--YEEFRIVDVIGLDKEhkAFNASLGTYHDLEKIL-DK | DFLDNPDNESILEDIIQTLTLFEDREMIK | 635 |
| WP_001040083 | 562 | KKLLDFLAKE--YEEFRIVDVIGLDKEhkAFNASLGTYHDLEKIL-DK | DFLDNPDNESILEDIIQTLTLFEDREMIK | 635 |
| WP_001040085 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040087 | 562 | KKLLDFLAKE--YEEFRIVDVIGLDKEhkAFNASLGTYHDLEKIL-DK | DFLDNPDNESILEDIVQTLTLFEDREMIR | 635 |
| WP_001040088 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040089 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040090 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040091 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040092 | 562 | KQLLDFLAKE--FEEFRIVDVIGLDKEhkAFNASLGTYHDLEKIL-DK | DFLDNPDNESILEDIVQTLTLFEDREMIR | 635 |
| WP_001040094 | 562 | KDIISFLNK---VDGYEGIAIKGIEKQ---FNASLSTYHDLKKIL-GK | DFLDNTDNELILEDIVQTLTLFEDREMIK | 632 |
| WP_001040095 | 563 | KDIISFLNK---VDGYEGIAIKGIEKQ---FNASLSTYHDLKKIL-GK | DFLDNTDNELILEDIVQTLTLFEDREMIR | 632 |
| WP_001040096 | 563 | KDIISFLNK---VDGYEGIAIKGIEKQ---FNASLSTYHDLKKIL-GK | DFLDNTDNELILEDIVQTLTLFEDREMIR | 632 |
| WP_001040097 | 563 | KDIISFLNK---VDGYEGIAIKGIEKQ---FNASLSTYHDLKKIL-GK | DFLDNTDNELILEDIVQTLTLFEDREMIR | 632 |
| WP_001040098 | 563 | KDIISFLNK---VDGYEGIAIKGIEKQ---FNASLSTYHDLKKIL-GK | DFLDNTDNELILEDIVQTLTLFEDREMIR | 632 |
| WP_001040099 | 563 | KDIISFLNK---VDGYEGIAIKGIEKQ---FNASLSTYHDLKKIL-GK | DFLDNTDNELILEDIVQTLTLFEDREMIR | 632 |
| WP_001040100 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040104 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040105 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040106 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040107 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040108 | 562 | KKLLDFLAKE--YEEFRIVDVIGLDKEhkAFNASLGTYHDLEKIL-DK | DFLDNPDNESILEDIVQTLTLFEDREMIK | 635 |
| WP_001040109 | 562 | KKLLDFLAKE--YEEFRIVDVIGLDKEhkAFNASLGTYHDLEKIL-DK | DFLDNPDNESILEDIVQTITLFEDREMIK | 635 |
| WP_001040110 | 562 | KQLLDFLAKE--FEEFRIVDVIGLDKEhkAFNASLGTYHDLKKIL-DK | DFLDNPDNESILEDIVQTLTLFEDREMIK | 635 |
| WP_015058523 | 563 | KDIISFLNK---VDGYEGIAIKGIEKQ---FNASLSTYHDLKKIL-GK | DFLDNTDNELILEDIVQTLTLFEDREMIK | 632 |
| WP_017643650 | 562 | KKLLDFLAKE--YEEFRIVDVIGLDKEhkAFNASLGTYHDLKKIL-DK | DFLDNPDNESILEDIVQTLTLFEDREMIK | 635 |
| WP_017647151 | 562 | KKLLDFLAKE--YEEFRIVDVIGLDKEhkAFNASLGTYHDLEKIL-DK | DFLDNPDNESILEDIVQTLTLFEDREMIK | 635 |
| WP_017648376 | 562 | KKLLDFLAKE--YEEFRIVDVIGLDKEhkAFNASLGTYHDLEKIL-DK | DFLDNPDNESILEDIVQTLTLFEDREMIK | 635 |
| WP_017649527 | 562 | KKLLDFLAKE--YEEFRIVDVIGLDKEhkAFNASLGTYHDLEKIL-DK | DFLDNPDNESILEDIVQTLTLFEDREMIK | 635 |
| WP_017771611 | 562 | KKLLDFLAKE--YEEFRIVDVIGLDKEhkAFNASLGTYHDLEKIL-DK | DFLDNPDNESILEDIVQTLTLFEDREMIK | 635 |
| WP_017771984 | 562 | KKLLDFLAKE--YEEFRIVDVIGLDKEhkAFNASLGTYHDLEKIL-DK | DFLDNPDNESILEDIVQTLTLFEDREMIK | 635 |
| CFQ25032 | 562 | KKLLDFLAKE--YEEFRIVDVIGLDKEhkAFNASLGTYHDLEKIL-DK | DFLDNPDNESILEDIVQTLTLFEDREMIK | 635 |
| CFV16040 | 562 | KKLLDFLAKE--YEEFRIVDVIGLDKEhkAFNASLGTYHDLEKIL-DK | DFLDNPDNESILEDIVQTLTLFEDREMIK | 635 |
| KLJ37842 | 562 | KKLLDFLAKE--YEEFRIVDVIGLDKEhkAFNASLGTYHDLEKIL-DK | DFLDNPDNESILEDIVQTLTLFEDREMIK | 635 |
| KLJ72361 | 562 | KKLLDFLAKE--YEEFRIVDVIGLDKEhkAFNASLGTYHDLEKIL-DK | DFLDNPDNESILEDIVQTLTLFEDREMIK | 635 |
| KLL20707 | 562 | KKLLDFLAKE--YEEFRIVDVIGLDKEhkAFNASLGTYHDLEKIL-DK | DFLDNPDNESILEDIVQTLTLFEDREMIK | 635 |
| KLL42645 | 562 | KKLLDFLAKE--YEEFRIVDVIGLDKEhkAFNASLGTYHDLEKIL-DK | DFLDNPDNESILEDIVQTLTLFEDREMIK | 635 |
| WP_047207273 | 562 | KKLLDFLAKE--YEEFRIVDVIGLDKEhkAFNASLGTYHDLEKIL-DK | DFLDNPDNESILEDIVQTLTLFEDREMIK | 635 |
| WP_047209694 | 563 | KDIISELNK---VDGYEGIAIKGIEKQ---FNASLSTYHDLKKIL-GK | DFLDNTDNELILEDIVQTLTLFEDREMIR | 632 |
| WP_050198062 | 562 | KKLLDFLAKE--YEEFRIVDVIGLDKEhkAFNASLGTYHDLEKIL-DK | DFLDNPDNESILEDIVQTLTLFEDREMIK | 635 |
| WP_050201642 | 562 | KKLLDFLAKE--YEEFRIVDVIGLDKEhkAFNASLGTYHDLEKIL-DK | DFLDNPDNESILEDIVQTLTLFEDREMIK | 635 |
| WP_050204027 | 562 | KKLLDFLAKE--YEEFRIVDVIGLDKEhkAFNASLGTYHDLEKIL-DK | DFLDNPDNESILEDIVQTLTLFEDREMIK | 635 |
| WP_050881965 | 562 | KKLLDFLAKE--YEEFRIVDVIGLDKEhkAFNASLGTYHDLEKIL-DK | DFLDNPDNESILEDIVQTLTLFEDREMIK | 635 |
| WP_050886065 | 562 | KKLLDFLAKE--YEEFRIVDVIGLDKEhkAFNASLGTYHDLEKIL-DK | DFLDNPDNESILEDIVQTLTLFEDREMIK | 635 |
| AHN30376 | 562 | KQLLDFLAKE--FEEFRIVDVTGLDKEhkAFNASLGTYHDLKKIL-DK | DFLDNPDNESILEDIVQTITLFEDREMIK | 635 |

-continued

```
EA078426         562 KKLLDFLAKE--YEEEFRIVDVIGLDKEmkAFNASLGTYHDLEKIL-DK DFLDNPDNESILEDIVQTLTLFEDREMIK 635
CCW42055         562 KQLLDFLAKE--FEEEFRIVDVTGLDKEmkAFNASLGTYHDLEKIL-GK DFLDNPDNESILEDIVQTLTLFEDREMIK 635
WP_003041502     561 DKLLNYLNKE--FEEEFRIVNLTGLDKEmkVENSSLGTYHDLRKIL-NK SFLDNKENAQIIEDIIQTLTLFEDREMIR 634
WP_037593752     562 DKLLNYLNKE--FEEEFRIVNLTGLDKEmkAENSSLGTYHDLRKIL-DK SFLDDKANEKTIEDIIQTLTLFEDREMIR 635
WP_049516684     562 DKLLNYLNKE--FEEEFRIVNLTGLDKEmkAFNASLGTYHDLRKIL-DK SFLDDKVNEKIIEDIIQTLTLFEDREMIR 635
GAD46167         561 DKLLNYLNKE--FEEEFRIVNLTGLDKEmkAENSSLGTYHDLKKIL-DK SFLDDKANEKTIEDIIKTLTLFEDREMIR 634
WP_018363470     562 EKLLNYLDKE--FPEYRIQDLVGLDKEmkSFNASLGTYHDLKKIL-DK SFLDDKVNEEVIEDIIKTLTLFEDREMIQ 635
WP_003043819     572 KQLKEDYFKK--IECEDSVEIIGVEDR----FNASLGTYHDLLKIIKDK DFLDNEENEDILEDIVLTLTLFEDREMIE 643
WP_006269658     561 DKLLNYLNKE--FEEEFRIVNLTGLDKEmkAENSSLGTYHDLRKIL-DK SFLDDKANEKTIEDIIQTLTLFEDREMIR 634
WP_048800889     561 DKLLNYLDKE--FDEEFRIVDLTGLDKEmkAFNASLGTYHDLRKIL-DK SFLDDKANEKTIEDIIQTLTLFEDREMIR 634
WP_012767106     562 KQLKEDYFKK--IECEDSVEISGVEDR----FNASLGTYHDLLKIIKDK DFLDNEENEDILEDIVLTLTLFEDKEMIE 633
WP_014612333     562 KQLKEDYFKK--IECEDSVEISGVEDR----FNASLGTYHDLLKIIKDK DFLDNEENEDILEDIVLTLTLFEDKEMIE 633
WP_015017095     562 KQLKEDYFKK--IECEDSVEISGVEDR----FNASLGTYHDLLKIIKDK DFLDNEENEDILEDIVLTLTLFEDKEMIE 633
WP_015057649     562 KQLKEDYFKK--IECEDSVEISGVEDR----FNASLGTYHDLLKIIKDK DFLDNEENEDILEDIVLTLTLFEDKEMIE 633
WP_048327215     562 KQLKEDYFKK--IECEDSVEISGVEDR----FNASLGTYHDLLKIIKDK DFLDNEENEDILEDIVLTLTLFEDKEMIE 633
WP_049519324     562 KQLKEDYFKK--IECEDSVEISGVEDR----FNASLGTYHDLLKIIKDK DFLDNEENEDILEDIVLTLTLFEDKEMIE 633
WP_012515931     562 KQLKENYFKK--IECEDSVEITGVEDS----FNASLGTYHDLLKIIQDK DFLDNPDNQKIIEDIILTLTLFEDKKMIS 633
WP_021320964     562 KQLKENYFKK--IECWDSVEITGVEDS----FNASLGTYHDLLKIIQDK DFLDNPDNQKIIEDIILTLTLFEDKKMIS 633
WP_037581760     562 KQLKENYFKK--IECWDSVEITGVEDS----FNASLGTYHDLLKIIQDK DFLDNPDNQKIIEDIILTLTLFEDKKMIS 633
WP_004232481     561 AKLLSYLNNE--FEEEFRINDLIGLDKDskSFNASLGTYHDLKKIL-DK SFLDDKTNEQIIEDIVLTLTLFEDRDMIH 634
WP_009854540     562 EKLLNYLNKE--FPEYRIKDLIGLDKEmkSFNASLGTYHDLKKIL-DK AFLDDKVNEEVIEDIIKTLTLFEDKDMIR 635
WP_012962174     562 DKPLNYLNKE--FPEYRIQDLIGLDKEmkSFNASLGTYHDLKKIL-DK SFLDDKTNETIIEDIIQTLTLFEDRDMIR 635
WP_039695303     564 EKLLNYLNKE--FEEEFRINDLLIGLDKDskSFNASLGTYHDLKKIL-DK AFLDDKVNEEVIEDIIKTLTLFEDKDMIH 637
WP_014334983     561 AKLLSYLNNE--FEEEFRINDLLIGLDKDskSFNASLGTYHDLKKIL-DK AFLDDKTNGQIIEDIVLTLTLFEDKDMIH 634
WP_003099269     562 KQLKEEYESK--MKCFHTVTILGVEDR----FNASLGTYHDLLKIFKDK AFLDDEANQDILEBIVWTLTLFEDQAMIE 633
AHY15608         562 KQLKEEYESK--MKCFHTVTILGVEDR----FNASLGTYHDLLKIFKDK AFLDDEANQDILEBIVWTLTLFEDQAMIE 633
AHY17476         562 KQLKEEYESK--MKCFHTVTILGVEDR----FNASLGTYHDLLKIFKDK AFLDDEANQDILEBIVWTLTLFEDQAMIE 633
ESR09100             ----------------------------------------------- ----------------------------
AGM98575         562 KQLKEEYESK--KQLKEEYESK----------FNASLGTYHDLLKIFKDK AFLDDEANQDILEBIVWTLTLFEDQAMIE 633
ALF27331         561 DKLMDFLEKE--FDEEFRIVDLTGLDKEmkAFNASYGTYHDLRKIL-DK DFLDNSKNEKILEDIVLTLTLFEDREMIR 634
WP_018372492     574 RKLKDFIEKEIgYGYIDIDNIKGVEEQ---FNASYTTYQDLLKIGDK EFLDEENKDLLEBIIYILTVFEDRKMIE 647
WP_045618028     563 KDIIQYLHN---VDSYDGIELKGIEKQ---FNASLSTYHDLLKIIKDK EFMDDSKNEAILENIVHTLTIFEDREMIK 633
WP_045635197     562 KDIIHYLHN---VDSYDGIELKGIEKQ---FNASLSTYHDLLKIIKDK EFMDDAKNEAILENIVHTLTIFEDREMIK 632
WP_002263549     561 DKLMDFLEKE--FDEEFRIVDLTGLDKEmkVFNASYGTYHDLCKIL-DK DFLDNSKNEKILEDIVLTLTLFEDREMIR 634
WP_002263887     561 DKLMDFLEKE--FDEEFRIVDLTGLDKEmkVFNASYGTYHDLCKIL-DK DFLDNSKNEKILEDIVLTLTLFEDREMIR 634
WP_002264920     561 DKLMDFLEKE--FDEEFRIVDLTGLDKEmkVFNASYGTYHDLCKIL-DK DFLDNSKNEKILEDIVLTLTLFEDREMIR 634
WP_002269043     561 DKLMDFLEKE--FDEEFRIVDLTGLDKEmkAFNASYGTYHDLRKIL-DK DFLDNSKNEKILEDIVLTLTLFEDREMIR 634
WP_002269448     561 DKLMDFLEKE--FDEEFRIVDLTGLDKEmkAFNASYGTYHDLCKIL-DK DFLDNSKNEKILEDIVLTLTLFEDREMIR 634
WP_002271977     561 DKLMDFLEKE--FDEEFRIVDLTGLDKEmkVFNASYGTYHDLCKIL-DK DFLDNSKNEKILEDIVLTLTLFEDREMIR 634
WP_002272766     561 DKLMDFLEKE--FDEEFRIVDLTGLDKEmkVFNASYGTYHDLCKIL-DK DFLDNSKNEKILEDIVLTLTLFEDREMIR 634
WP_002273241     561 DKLMDFLEKE--FDEEFRIVDLTGLDKEmkVFNASYGTYHDLCKIL-DK DFLDNSKNEKILEDIVLTLTLFEDREMIR 634
WP_002275430     561 DKLMDFLEKE--FDEEFRIVDLTGLDKEmkAFNASYGTYHDLRKIL-DK DFLDNSKNEKILEDIVLLTVFEDRKMIE 634
WP_002276448     561 DKLMDFLEKE--FDEEFRIVDLTGLDKEmkAFNASYGTYHDLCKIL-DK DFLDNSKNEKILENIVHTLTIFEDREMIK 634
WP_002277050     561 DKLMDFLEKE--FDEEFRIVDLTGLDKEmkAFNASYGTYHDLCKIL-DK DFLDNSKNEKILENIVHTLTIFEDREMIK 634
WP_002773364     561 KKLRTFLDKN--FDEEFRIVDIQGLDKEteTENASYATYQDLLKVIKDK VFMDNPENAEILENIVLTLTLFEDREMIR 635
WP_002779025     561 DKLMDFLEKE--FDEEFRIVDLTGLDKEmkAFNASYGTYHDLCKIL-DK DFLDNSKNEKILEDIVLTLTLFEDREMIR 634
WP_002279959     561 DKLMDFLEKE--FDEEFRIVDLTGLDKEmkAFNASYGTYHDLCKIL-DK DFLDNSKNEKILEDIVLTLTLFEDREMIR 634
WP_002280230     561 DKLMDFLEKE--FDEEFRIVDLTGLDKEmkAFNASYGTYHDLCKIL-DK DFLDNSKNEKILEDIVLTLTLFEDREMIR 634
WP_002281696     561 DKLMDFLEKE--FDEEFRIVDLTGLDKEmkAFNASYGTYHDLRKIL-DK DFLDNSKNEKILEDIVLTLTLFEDREMIR 634
WP_002282247     561 KKLRTFLDKN--FDEEFRIVDIQGLDKEteTENASYATYQDLLKVIKDK VFMDNPENAEILENIVLTLTLFEDREMIR 635
WP_002282906     561 DKLMDFLEKE--FDEEFRIVDLTGLDKEmkAFNASYGTYHDLCKIL-DK DFLDNSKNEKILEDIVLTLTLFEDREMIR 634
WP_002283846     561 DKLMDFLEKE--FDEEFRIVDLTGLDKEmkAFNASYGTYHDLRKIL-DK DFLDNSKNEKILEDIVLTLTLFEDREMIR 634
WP_002287255     561 DKLMDFLEKE--FDEEFRIVDLTGLDKEmkAFNASYGTYHDLRKIL-DK DFLDNSKNEKILEDIVLTLTLFEDREMIR 634
```

```
WP_002288990  561  DKLMDFLEKE--FDEFRIVDLTGLDKEhkAFNASYGTYHDLCKIL-DK  DFLDNSKNEKILEDIVLTLFEDREMIR  634
WP_002289641  561  DKLMDFLEKE--FDEFRIVDLTGLDKEhkAFNASYGTYHDLCKIL-DK  DFLDNSKNEKILEDIVLTLFEDREMIR  634
WP_002290427  561  DKLMDFLEKE--FDEFRIVDLTGLDKEhkAFNASYGTYHDLRKIL-DK  DFLDNSKNEKILEDIVLTLFEDREMIR  634
WP_002295753  561  DKLMDFLEKE--FDEFRIVDLTGLDKEmkAFNASYGTYHDLRKIL-DK  DFLDNSKNEKILEDIVLTLFEDREMIR  634
WP_002296423  561  DKLMDFLEKE--FEEFRIVNLTGLDKEhkVENSSLGTYHDLCKIL-NK  SFLDNKENEQIIEDIQTLFEDREMIR  634
WP_002304487  571  DKLINYLNKE--FEEFRIVDLTGLDKEhkVFNASYGTYHDLCKIL-DK  DFLDNSKNEKILEDIVLTLFEDREMIR  644
WP_002305844  561  DKLMDFLEKE--FDEFRIVDLTGLDKEhkVFNASYGTYHDLCKIL-DK  DFLDNSKNEKILEDIVLTLFEDREMIR  634
WP_002307203  561  DKLMDFLEKE--FDEFRIVDLTGLDKEhkAFNASYGTYHDLRKIL-DK  DFLDNSKNEKILEDIVLTLFEDREMIR  634
WP_002310390  561  DKLMDFLEKE--FDEFRIVDLTGLDKEhkAFNASYGTYHDLRKIL-DK  DFLDNSKNEKILEDIVLTLFEDREMIR  634
WP_002352408  561  DKLMDFLEKE--FDEFRIVDLTGLDKEhkAFNASYGTYHDLRKIL-DK  DFLDNSKNEKILEDIVLTLFEDREMIR  634
WP_012997688  561  DKLMDFLEKE--FDEFRIVDLTGLDKEhkAFNASYGTYHDLRKIL-DK  DFLDNSKNEKILEDIVLTLFEDREMIR  634
WP_014677909  561  DKLMDFLEKE--FDEFRIVDLTGLDKEhkAFNASYGTYHDLRKIL-DK  DFLDNSKNEKILEDIVLTLFEDREMIR  634
WP_019312892  561  DKLMDFLEKE--FDEFRIVDLTGLDKEhkAFNASYGTYHDLCKIL-DK  DFLDNSKNEKILEDIVLTLFEDREMIR  634
WP_019313659  561  DKLMDFLEKE--FDEFRIVDLTGLDKEhkVFNASYGTYHDLCKIL-DK  DFLDNSKNEKILEDIVLTLFEDREMIR  634
WP_019314093  561  DKLMDFLEKE--FDEFRIVDLTGLDKEhkAFNASYGTYHDLCKIL-DK  DFLDNSKNEKILEDIVLTLFEDREMIR  634
WP_019315370  561  DKLMDFLEKE--FDEFRIVDLTGLDKEhkVFNASYGTYHDLCKIL-DK  DFLDNSKNEKILEDIVLTLFEDREMIR  634
WP_019803776  561  DKLMDFLEKE--FDEFRIVDLTGLDKEhkAFNASYGTYHDLRKIL-DK  DFLDNSKNEKILEDIVLTLFEDREMIR  634
WP_019805234  561  DKLMDFLEKE--FDEFRIVDLTGLDKEhkVFNASYGTYHDLCKIL-DK  DFLDNSKNEKILEDIVLTLFEDREMIR  634
WP_024783594  561  DKLMDFLEKE--FDEFRIVDIQGLDKEteTFNASYATYQDLLKVIKDK  VFMDNPENAEILENIVLTLFEDREMIK  634
WP_024784288  561  KKLRTFLDKN--FDEFRIVDIQGLDKEteTFNASYATYQDLLKVIKDK  VFMDNPENAEILENIVLTLFEDREMIK  635
WP_024784666  561  DKLMDFLEKE--FDEFRIVDLTGLDKEhkAFNASYGTYHDLRKIL-DK  DFLDNSKNEKILEDIVLTLFEDREMIK  634
WP_024784894  561  KKLRTFLDKN--FDEFRIVDLTGLDKEteTFNASYATYQDLLKVIKDK  VFMDNPENAEILENIVLTLFEDREMIK  635
WP_024786433  561  DKLMDFLEKE--FDEFRIVDLTGLDKEhkVFNASYGTYHDLCKIL-DK  DFLDNSKNEKILEDIVLTLFEDREMIR  634
WP_049473442  561  DKLMDFLEKE--FDEFRIVDLTGLDKEhkVFNASYGTYHDLCKIL-DK  DFLDNSKNEKILEDIVLTLFEDREMIR  634
WP_049474547  554  DKLMDFLEKE--FDEFRIVDLTGLDKEhkAFNASYGTYHDLLKII-DK  DFLDNSKNEKILEDIVLTLFEDREMIR  627
EMC03581      565  KDIIQYLHT---VDGYDGIELKGIEKQ---FNASLSTYHDLLKIIKDK  EFMDDPNNEEILENIVHTLTIFEDREMIK 635
WP_000428612  563  KDIIQFLHN---VDGYDGIELKGIEKQ---FNASLSTYHDLLKIIKDK  EFMDDSKNEEILENIVHTLTIFEDREMIK 633
WP_000428613  562  KDIIHYLHN---VDGYDGIELKGIEKQ---FNSSLSTYHDLLKIIKDK  EFMDDPKNEIFENIVHTLTIFEDRVMIK  632
WP_049523028  531  KQLKENYFNK--IRCLDSITISGVEDK---FNASLGTYHDLLNIIKNQ  KILLDDEQNQDSLEDIVLTLFEDREKMIA 602
WP_003107102  564  KQLKEDFFSK--IECFDTVDISGVEDK---FNASLGTYHDLLKIIKDK  AFLDNSENENIIEDIILTLVHTLFEDREKMIA 635
WP_542792288  563  KDLIHYLHN---VDGYDGIELKGIEKQ---FNASLSTYHDLLKIIKDK  RFMDEPKNQEILENIVHTLTIFEDREMIK 633
WP_049531101  563  KDIIQYLHN---VDGYDGIELKGIEKQ---FNASLSTYHDLLKIIKDK  EFMDDSKNEEILENIVHTLTIFEDREMIK 633
WP_049538452  565  KDIIHYLHT---VDGYDGIELKGIEKQ---FNASLSTYHDLLKIIKDK  EFMDDSKNEAILENIVHTLTIFEDREMIK 636
WP_049549711  517  KDLKEKYFSQ--IEGLENVDVTGVEGA---FNASLGTYNDLLKIIKDK  AFLDDEANAEILEEIVLILTLFQDEKLIE 588
WP_007896501  562  KDLKEKYFSQ--IEGLENVDVTGVEGA---FNANLSTYHDLLKIIKDK  AFLDDEANAEILENIVLILTLFQDEKLIE 632
EFR44625      562  KDIIHYLHN---VDGYDGIELKGIEKQ---FNASLGTYHDLLKIIKDK  EFMDDPKNEILENIVHTLTIFEDREMIK 632
WP_002997477  563  KDIIHYLHN---VDGYDGIELKGIEKQ---FNASLGTYHDLLKIIKDK  EFMDNPKNGEILENIIHTLTIFEDRVMIK 633
WP_002906454  562  KDIIQFLHN---VDGYDGIELKGIEKQ---FNASLGTYHDLLKIIKDK  AFMDDAKNEAILENIVHTLTIFEDREMIK 636
WP_009729476  565  KKIINFLDKN--FDEFRITDIQGLDNEtgNENASYGTYHDLLKIIGDK  EFMDSSDNVDVLEDIVLSLTLFEDREMIK 635
CQR24647      564  KDIIHYLHN---VDGYDGIELKGIEKQ---FNASLSTYHDLLKIIKDK  AFMDDSKNEILENIVHTLTIFEDREMIK 635
WP_000066813  562  KDIIHYLHN---VDGYDGIELKGIEKQ---FNASLSTYHDLLKIIKDK  EFMDNHKNQEILENIVHTLTIFEDREMIK 633
WP_009754323  562  KDIKAYL-EN--SNGYAGVELKGLEEQ---FNASLPTYHDLLKILRDK  AFIDAEENQEILEDIVLTLTLFEDREMIR 632
WP_044674937  541  EKLMDFLGKE--FDEFRIVDLLGLDKDnkSFNASLGTYHDLKKIV-SK  DLLDNPENEDILENVVLTLTLFEDREMIR 634
WP_044676715  562  EKLMDFLGKE--FDEFRIVDLLGLDKDnkSFNASLGTYHDLKKIV-SK  DLLDNPENEDILENVVLTLTLFEDREMIR 634
WP_044680361  561  KDIKAYL-EN--SNGYAGVELKGLEEQ---FNASLPTYHDLLKILRDK  AFIDAEENQEILEDIVLTLTLFEDREMIR 632
WP_044681799  562  DKLLNYLGKE--FDEFRIVDLTGLDKEhkVENSSLGTYHDLRKIL-DK  SFLDNKENEQIIEDIQTLFEDREMIR 634
WP_049533112  541  TSLKKWLAEH--EHMTVSVVQGTQKEt--EFATSLQAEHREVKIF-DR  ETVSNPANEEMFEKIIYwSTVFEDKKIMR 612
WP_029090905  568  KKLKNWLVNNqcCS--KDAEIKGFQKEh-QESTSLTPWIDETNIFGKI  ---DQSNFDLIENIIYDLTVFEDKKIMK  637
AIT42264      ---  ---------- -------------- -- ---------------- -  ---------------------------  ---
WP_034440723  568  KQLKEDYFKK--IECEDSVEISGVEDR---FNSNYSTYIDLSKIPDMK  -LLEKDEDEILEEIIKILTIFEDRKMRK 637
AKQ21048      562  KQLKEDYFKK--IECEDSVEISGVEDR---FNASLGTYHDLLKIIKDK  DFLDNEENEDILENEDIVLTLFEDREMIE 633
WP_004636532  563  KDIANYLEQ---YGYVDGTDIKGVEDK---FNASLSTYNDLAKIDGAK  AYLDDPEYADVWEDIIKILTIFEDKAMRK 633
```

```
WP_002364836   570  KDIIQFYRNE--YN-TEIVTLSGLEED--QFNASFSTYQDLLKCGLTR  AELDHPDNAEKLEDIIKILTIFEDRQRIR  641
WP_016631044   521  KDIIQFYRNE--YN-TEIVTLSGLEED--QFNASFSTYQDLLKCGLTR  AELDHPDNAEKLEDIIKILTIFEDRQRIR  592
EMS75795       306  KKLQQFLSAN--YN-IEDAEILGVDKA--FNSSYATYHDFLDLAKPN   ELLEQPEMNAMFEDIVKILTIFEDREMIR  381
WP_002373311   570  KDIIQFYRNE--YN-TEIVTLSGLEED--QFNASFSTYQDLLKCGLTR  AELDHPDNAEKLEDIIKILTIFEDRQRIR  641
WP_002378009   570  KDIIQFYRNE--YN-TEIVTLSGLEED--QFNASFSTYQDLLKCGLTR  AELDHPDNAEKLEDIIKILTIFEDRQRIR  641
WP_002407324   570  KDIIQFYRNE--YN-TEIVTLSGLEED--QFNASFSTYQDLLKCGLTR  AELDHPDNAEKLEDIIKILTIFEDRQRIR  641
WP_002413717   570  KDIIQFYRNE--YN-TEIVTLSGLEED--QFNASFSTYQDLLKCGLTR  AELDHPDNAEKLEDIIKILTIFEDRQRIR  641
WP_010775580   572  KDIIQFYRNE--YN-TEIVTLSGLEED--QFNASFSTYQDLLKCGLTR  AELDHPDNAEKLEDIIKILTIFEDRQRIR  643
WP_010818269   570  KDIIQFYRNE--YN-TEIVTLSGLEED--QFNASFSTYQDLLKCGLTR  AELDHPDNAEKLEDIIKILTIFEDRQRIR  641
WP_010824395   570  KDIIQFYRNE--YN-TEIVTLSGLEED--QFNASFSTYQDLLKCGLTR  AELDHPDNAEKLEDIIKILTIFEDRQRIR  641
WP_016622645   570  KDIIQFYRNE--YN-TEIVTLSGLEED--QFNASFSTYQDLLKCGLTR  AELDHPDNAEKLEDIIKILTIFEDRQRIR  641
WP_033624816   570  KDIIQFYRNE--YN-TEIVTLSGLEED--QFNASFSTYQDLLKCGLTR  AELDHPDNAEKLEDIIKILTIFEDRQRIR  641
WP_033625576   570  KDIIQFYRNE--YN-TEIVTLSGLEED--QFNASFSTYQDLLKCGLTR  AELDHPDNAEKLEDIIKILTIFEDRQRIR  641
WP_033789179   570  KDIIQFYRNE--YN-TEIVTLSGLEED--QFNASFSTYQDLLKCGLTR  AELDHPDNAEKLEDIIKILTIFEDRQRIR  641
WP_002310644   567  KDLQEFLYLK--YD-IKHAELSGIEKA--FNASYTTYHDFLTMSENK   QWLEDPELASMFEEIIKTLTVFEDREMIK  641
WP_002312694   568  KDLQEFLYLK--YD-IKHAELSGIEKA--FNASYTTYHDFLTMSENK   QWLEDPELASMFEEIIKTLTVFEDREMIK  642
WP_002314015   568  KDLQEFLYLK--YD-IKHAELSGIEKA--FNASYTTYHDFLTMSENK   QWLEDPELASMFEEIIKTLTVFEDREMIK  642
WP_002320716   568  KDLQEFLYLK--YD-IKHAELSGIEKA--FNASYTTYHDFLTMSENK   QWLEDPELASMFEEIIKTLTVFEDREMIK  642
WP_002330729   567  KDLQEFLYLK--YD-IKHAELSGIEKA--FNASYTTYHDFLTMSENK   QWLEDPELASMFEEIIKTLTVFEDREMIK  641
WP_002335161   568  KDLQEFLYLK--YD-IKHAELSGIEKA--FNASYTTYHDFLTMSENK   QWLEDPELASMFEEIIKTLTVFEDREMIK  642
WP_002345439   568  KDLQEFLYLK--YD-IKHAELSGIEKA--FNASYTTYHDFLTMSENK   QWLEDPELASMFEEIIKTLTVFEDREMIK  642
WP_034867970   562  KKLQNFLYTH--YH-IENAQIFGIEKA--FNASYSTYHDFMKLAKTN   EWLEQPEMEPIFEDIVKILTIFEDRQMIK  637
WP_047937432   568  KDLQEFLYLK--YD-IKHAELSGIEKA--FNASYTTYHDFLTMSENK   QWLEDPELASMFEEIIKTLTVFEDREMIK  642
WP_010720994   562  KKLQNFLYTH--YH-IENAQIFGIEKA--FNASYSTYHDFMKLAKTN   EWLEQPEMEPIFEDIVKILTIFEDRQMIK  637
WP_010737004   562  KKLQNFLYTH--YH-IENAQIFGIEKA--FNASYSTYHDFMKLAKTN   EWLEQPEMEPIFEDIVKILTIFEDRQMIK  637
WP_034700478   562  KKLQNFLYTH--YH-IENAQIFGIEKA--FNASYSTYHDFMKLAKTN   EWLEQPEMEPIFEDIVKILTIFEDRQMIK  637
WP_007209003   564  KKLENYLRIE1---SISSPSVKGIEEQ--FNANFGTYLDLKKFDELH   PYLDDEKYQDTLEEVIKVLTVFEDRSMIQ  634
WP_023519017   560  KQLRKFLELN--EQ-IDSTEIKGIETS--FNASYSTYHDLLKLS---   TLLDDPDMTTMFBEIIKILTVFEDREMIR  631
WP_010770040   564  KLLEKFLSNE--FG-LVDVAIKGIE-T--SFNAGYGTYHDFLKIGITR EQLDKEENSETLEEIVKLTVFEDRKMIR   634
WP_048604708   560  KDLSNFLRNE--YN-LDDVIIDGIE-N--KFNASFNTYHDFLKLKIDP KVLDDPANEPMFEEIVKILTIFEDRKMLR  630
WP_010750235   601  KKLQHFLSAN--YN-IECFDSVEISGVEDR--FNSSYATYHDFLELAKPY ELLEQPEMEEMFEDIVLILTLFEDREMVR 636
AII6583        601  KQLKEDYFKK--IECFDSVEISGVEDR--FNSSYATYHDFLELAKPY  DFLDNEENEDILEDIVLITIFEDREMIE    672
WP_029073316   576  NAMKKWLVKNqyFSNTDDIKIEGFQKEn-ACSTSLTPWIDFTKIFGEI ----NNSNVELIEKIIYDVTVFEDKKILR  647
WP_031589969   576  NAMKKWLVKNqyFSNTDDIKIEGFQKEn-ACSTSLTPWIDFTKIFGKI ----NESNYDFIEKIIYDVTVFEDKKILR  647
KDA45870       558  KMVIKHLKVV--MPAIRIQALKGLDNGK-FNASYGTYKDLVDMGVAP  ELlNDEVNSEKWEDIIKILTIFEGRKLIK   630
WP_039099354   579  KNIQDYLVSEk-RYASRPAITGLSDEnk-EFNSTLTTYLDMKKIFGSS --VDDVDKQADLKCIEWSTIFEDGKIYS  650
AKP02966       561  KKLTKWLIAQg---YYKNPILIGLSQKq-EFNSTLTTYLDMKKIFGSS -FMENNKNYNQIELIEWLTIFEDKQILN  632
WP_010991369   567  KDLELFLRNM--SH-VESPTIEGLE-D--SFNSSYSTYHDLLKVGIKQ EILDNPVNTEMLENIVKILTVFEDKRMIK  637
WP_033838504   567  KDLELFLRNM--SH-VESPTIEGLE-D--SFNSSYSTYHDLLKVGIKQ EILDNPVNTEMLENIVKILTVFEDKRMIK  637
EHN60060       570  KDLELFLRNM--SH-VESPTIEGLE-D--SFNSSYSTYHDLLKVGIKQ EILDNPVNTEMLENIVKILTVFEDKRMIK  640
EFR89594       336  KDLELFLRNM--SH-VESPTIEGLE-D--SFNSSYSTYHDLLKVGIKQ EILDNPVNTEMLENIVKILTVFEDKRMIK  406
WP_038409211   567  KDLERFLYTI--NH-IESPTIEGVE-D--AFNSSFATYHDLLQKGGVTQ EILDNPLNADMLEBIVKILTVFEDKRMIK 637
EFR95520       186  KDLERFLYTI--NH-IESPTIEGVE-D--AFNSSFATYHDLQKGGVTQ  EILDNPLNADMLEBIVKILTVFEDKRMIK  256
WP_037723650   567  KDLELFLRNI--NH-IESPTIEGLE-D--SFNASYATYHDLLKVGMKQ EILDNPLNTEILEDIVKILTVFEDKRMIK  637
WP_037727705   567  KDLELFLRNI--NH-IESPTIEGLE-D--SFNASYATYHDLLKVGLKQ EILDNPLNTEILEDIVKILTVFEDKRMIK  637
WP_003730785   567  KDLELFLRNI--NH-IESPTIEGLE-D--SFNASYATYHDLLKVGLKQ EILDNPLNTEILEDIVKILTVFEDKRMIK  637
WP_003733029   567  KDLELFLRNI--NQ-IESPTIEGLE-D--SFNASYATYHDLLKVGMKQ EILDNPVNTEMLENIVKILTVFEDKRMIK  637
WP_003739838   567  KDLEQFLRNM--SH-IESPTIEGLE-D--SFNASYATYHDLLKVGMKQ EVLENPLNTEMLEDIVKILTVFEDKRMIK  637
WP_014601172   567  KDLELFLRNI--NH-IESPTIEGLE-D--SFNASYATYHDLLKVGMKQ EILDNPVNTEMLENIVKILTVFEDKRMIK  637
WP_023548323   567  KDLELFLRNI--NQ-IESPTIEGLE-D--SFNASYATYHDLMKVGIKQ EILDNPLNTEMLEDIVKILTVFEDKRMIK  637
WP_031665337   567  KDLELFLRNI--NH-VESPTIEGLE-D--SFNASYATYHDLMKVGMKQ EILDNPLNTEMLEDIVKILTVFEDKRMIK  637
WP_031669209   567  KDLELFLRNI--NH-VESPTIEGLE-D--SFNASYATYHDLMKVGMKQ EILDNPLNTEMLEDIVKILTVFEDKRMIK  637
WP_033920898   567  KDLELFLRNI--NH-VESPTIEGLE-D--SFNASYATYHDLMKVGIKQ EILDNPLNTEMLEDIVKILTVFEDKRMIK  637
```

```
-continued

AKI42028           570 KDLELFLRNI--NH-IESPTIEGLE-D---SFNASYATYHDLLKVGMKQ EILDNPLNTEMLEDIVKILTVFEDKPMIK                    640
AKI50529           570 KDLELFLRNI--NH-VESPTIEGLE-D---SFNASYATYHDLMKVGIKQ EILDNPLNTEMLEDIVKILTVFEDKRMIK                    640
EFR83390            15 KDLELFLRNI--NQ-IESPTIEGLE-D---SFNASYATYHDLLKVGMKQ EILDNPLNTEMLEDIVKILTVFEDKRMIK                     85
WP_046323366       567 KDLELFLYNM--NH-VESPTVEGVE-D---AFNSSETTYHDLQKVGVPQ EILDDPLNTEMLEEIVKILTLFEDKRMIN                    637
AKE81011           578 KQLKEDYFKK--IECEDSVEISGVEDR----FNASLGTYHDLLKIIKDK DFLDNEENEDILEDIVLTLTLFEDREMIE                    649
CU082355           572 KKLKNWLVNNqCCR--KDAEIKGFQKEn-QESTSLTPWIDETNIFGKI  ----DQSNFDLIEKIIYDLTVFEDKKIMK                    641
WP_033162887       573 KKLKDWLVTHqyYDINEELKIEGYQKD1-QESTSLAPWIDETKIFGEI  ----NASNYQLIEKIIYDISIFEDKKILK                    644
AGZ01981           595 KQLKEDYFKK--IECEDSVEISGVEDR----FNASLGTYHDLLKIIKDK DFLDNEENEDILEDIVLTLTLFEDREMIE                    666
AKA60242           562 KQLKEDYFKK--IECEDSVEISGVEDR----FNASLGTYHDLLKIIKDK DFLDNEENEDILEDIVLTLTLFEDREMIE                    633
AKS40380           562 KQLKEDYFKK--IECEDSVEISGVEDR----FNASLGTYHDLLKIIKDK DFLDNEENEDILEDIVLTLTLFEDREMIE                    633
4UN5_B             566 KQLKEDYFKK--IECEDSVEISGVEDR----FNASLGTYHDLLKIIKDK DFLDNEENEDILEDIVLTLTLFEDREMIE                    637
WP_010922251       634 ERLKTYAHLFDDKVMKQLKR-RRYTGWGRLSRKLINGIRDK QSGKTILDFLK -DGf---ANRNFMQLIHDDSL                       702
WP_039695303       638 ERLQKYSDIFTANQLKKLER-RHYTGWGRLSYKLINGIRNK ENNKTILDYLI DDG---SANRNFMQLINDDTL                       706
WP_045635197       633 QRLAQYDSLFDEKVIKALTR-RHYTGWGKLSAKLINGICDK QTGNTILDYLI DDG---KINRNFMQLINDDGL                       701
5AXW_A             369 EELTNLNSELTQEEIEQISN1KGYTGTHNLSLKAINLILDE ---------LW ----TNDNQIAIFNRLKL                          426
WP_009880683       318 ERLKTYAHLFDDKVMKQLKR-RRYTGWGRLSRKLINGIRDK QSGKTILDFLK -DGf---ANRNFMQLIHDDSL                       386
WP_010922251       634 ERLKTYAHLFDDKVMKQLKR-RRYTGWGRLSRKLINGIRDK QSGKTILDFLK -DGf---ANRNFMQLIHDDSL                       702
WP_011054416       634 ERLKTYANLFDDKVMKQLKR-RRYTGWGRLSRKLINGIRDK QSGKTILDFLK -DGf---ANRNFMQLIHDDSL                       702
WP_011284745       634 ERLKTYAHLFDDKVMKQLKR-RRYTGWGRLSRKLINGIRDK QSGKTILDFLK -DGf---ANRNFMQLIHDDSL                       702
WP_011285506       634 ERLKTYAHLFDDKVMKQLKR-RRYTGWGRLSRKLINGIRDK QSGKTILDFLK -DGf---ANRNFMQLIHDDSL                       702
WP_011527619       634 ERLKTYAHLFDDKVMKQLKR-RRYTVWGRLSRKLINGIRDK QSGKTILDFLK -DGf---ANRNFMQLIHDDSL                       702
WP_012560673       634 ERLKTYAHLFDDKVMKQLKR-RRYTGWGRLSRKLINGIRDK QSGKTILDFLK -DGf---ANRNFMQLIHDDSL                       702
WP_014407541       634 ERLKTYAHLFDDKVMKQLKR-RRYTGWGRLSRKLINGIRDK QSGKTILDFLK -DGf---ANRNFMQLIHDDSL                       702
WP_020905136       634 ERLKTYAHLFDDKVMKQLKR-RRYTGWGRLSRKLINGIRDK QSGKTILDFLK -DGf---ANRNFMQLIHDDSL                       702
WP_023080005       634 ERLKTYAHLFDDKVMKQLKR-RRYTGWGRLSRKLINGIRDK QSGKTILDFLK -DGf---ANRNFMQLIHDDSL                       702
WP_023610282       634 ERLKTYAHLFDDKVMKQLKR-RRYTGWGRLSRKLINGIRDK QSGKTILDFLK -DGf---ANRNFMQLIHDDSL                       702
WP_030125963       634 ERLKTYAHLFDDKVMKQLKR-RRYTGWGRLSRKLINGIRDK QSGKTILDFLK -DGf---ANRNFMQLIHDDSL                       702
WP_030126706       634 ERLKTYAHLFDDKVMKQLKR-RRYTGWGRLSRKLINGIRDK QSGKTILDFLK -DGf---ANRNFMQLIHDDSL                       702
WP_031488318       634 ERLKTYAHLFDDKVMKQLKR-RRYTGWGRLSRKLINGIRDK QSGKTILDFLK -DGf---ANRNFMQLIHDDSL                       702
WP_032460140       634 ERLKTYAHLFDDKVMKQLKR-RRYTGWGRLSRKLINGIRDK QSGKTILDFLK -DGf---ANRNFMQLIHDDSL                       702
WP_032461047       634 ERLKTYAHLFDDKVMKQLKR-RRYTGWGRLSRKLINGIRDK QSGKTILDFLK -DGf---ANRNFMQLIHDDSL                       702
WP_032462016       634 ERLKTYAHLFDDKVMKQLKR-RRYTGWGRLSRKLINGIRDK QSGKTILDFLK -DGf---ANRNFMQLIHDDSL                       702
WP_032462936       634 ERLKKYAHLFDDKVMKQLKR-RRYTGWGRLSRKLINGIRDK QSGKTILDFLK -DGf---ANRNFMQLIHDDSL                       702
WP_032464890       634 ERLKKYANLFDDKVMKQLKR-RRYTGWGRLSRKLINGIRDK QSGKTILDFLK -DGf---ANRNFMQLIHDDSL                       702
WP_033888930       459 ERLKTYAHLFDDKVMKQLKR-RRYTGWGRLSRKLINGIRDK QSGKTILDFLK -DGf---ANRNFMQLIHDDSL                       527
WP_038431314       634 ERLKTYAHLFDDKVMKQLKR-RRYTGWGRLSRKLINGIRDK QSGKTILDFLK -DGf---ANRNFMQLIHDDSL                       702
WP_038432938       634 ERLKTYAHLFDDKVMKQLKR-RRYTGWGRLSRKLINGIRDK QSGKTILDFLK -DGf---ANRNFMQLIHDDSL                       702
WP_038434062       634 ERLKTYAHLFDDKVMKQLKR-RRYTGWGRLSRKLINGIRDK QSGKTILDFLK -DGf---ANRNFMQLIHDDSL                       702
BAQ51233           545 ERLKTYAHLFDDKVMKQLKR-RRYTGWGRLSRKLINGIRDK QSGKTILDFLK -DGf---ANRNFMQLIHDDSL                       613
KGE60162               ------------------------------------------------ ----------- -------------------                       
KGE60856               ------------------------------------------------ ----------- -------------------                       
WP_002989955       634 ERLKTYAHLFDDKVMKQLKR-RRYTGWGRLSRKLINGIRDK QSGKTILDFLK -DGf---ANRNFMQLIHDDSL                       702
WP_003030002       635 QRLQKYSDIFTKAQLKKLER-RHYTGWGRLSYKLINGIRDK ENKKTILDYLI DDG---YANRNFMQLIHDDAL                       703
WP_003065552       638 ERLQKYSDIFTADQLKKLER-RHYTGWGRLSYKLINGIRNK ENQKTILDYLI DDG---SANRNFMQLINDDTL                       706
WP_001040076       633 KRLDIYKDFFTESQLKKLYR-RHYTGWGRLSAKLINGIRNE ENNKTILDYLI DDG---SANRNFMQLINDDGL                       701
WP_001040078       636 KRLENYKDLFTESQLKKLYR-RHYTGWGRLSAKLINGIRNE ENQKTILDYLI DDG---RSNRNFMQLIKDAGL                       704
WP_001040080       636 KRLENYKDLFTESQLKKLYR-RHYTGWGRLSAKLINGIRDK ESQKTILDYLI DDG---RSNRNFMQLINDDGL                       704
WP_001040081       636 KRLENYKDLFTESQLKKLYR-RHYTGWGRLSAKLINGIRDK ESQKTILDYLI DDG---RSNRNFMQLINDDGL                       704
WP_001040083       636 KRLENYKDLFTESQLKKLYR-RHYTGWGRLSAKLINGIRDK ESQKTILDYLI DDG---RSNRNFMQLINDDGL                       704
WP_001040085       636 KRLENYKDLFTESQLKKLYR-RHYTGWGRLSAKLINGIRDK ESQKTILDYLI DDG---RSNRNFMQLINDDGL                       704
WP_001040087       636 KRLENYKDLFTESQLKKLYR-RHYTGWGRLSAKLINGIRDK ESQKTILDYLI DDG---RSNRNFMQLINDDGL                       704
WP_001040088       636 KRLENYKDLFTESQLKKLYR-RHYTGWGRLSAKLINGIRDK ESQKTILDYLI DDG---RSNRNFMQLINDDGL                       704
WP_001040089       636 KRLENYKDLFTESQLKKLYR-RHYTGWGRLSAKLINGIRDK ESQKTILDYLI DDG---RSNRNFMQLINDDGL                       704
```

-continued

| | | | | |
|---|---|---|---|---|
| WP_001040090 | 636 | KRLENYKDLFTESQLKKLYR-RHYTGWGRLSAKLINGIRDK | ESQKTILDYLI | DDG---RSNRNFMQLINDDGL | 704 |
| WP_001040091 | 636 | KRLENYKDLFTESQLKKLYR-RHYTGWGRLSAKLINGIRDK | ESQKTILDYLI | DDG---RSNRNFMQLINDDGL | 704 |
| WP_001040092 | 636 | KRLENYKDLFTESQLKKLYR-RHYTGWGRLSAKLINGIRDR | ESQKTILDYLI | SDG---RANRNFMQLINDDGL | 704 |
| WP_001040094 | 633 | KRLDIYKDFFTESQLKKLYR-RHYTGWGRLSAKLINGIRNK | ENQKTILDYLI | DDG---SANRNFMQLIKDAGL | 701 |
| WP_001040095 | 633 | KRLDIYKDFFTESQLKKLYR-RHYTGWGERLSAKLINGIRNK | ENQKTILDYLI | DDG---SANRNFMQLIKDAGL | 701 |
| WP_001040096 | 633 | KRLDIYKDFFTESQLKKLYR-RHYTGWGRLSAKLINGIRNK | ENQKTILDYLI | DDG---SANRNFMQLIKDAGL | 701 |
| WP_001040097 | 633 | KRLDIYKDFFTESQLKKLYR-RHYTGWGRLSAKLINGIRNK | ENQKTILDYLI | DDG---SANRNFMQLIKDAGL | 701 |
| WP_001040098 | 633 | KRLDIYKDFFTESQLKKLYR-RHYTGWGRLSAKLINGIRNK | ENQKTILDYLI | DDG---SANRNFMQLIKDAGL | 701 |
| WP_001040099 | 633 | KRLDIYKDFFTESQLKKLYR-RHYTGWGRLSAKLINGIRNK | ENQKTILDYLI | DDG---SANRNFMQLIKDAGL | 701 |
| WP_001040100 | 636 | KRLENYKDLFTESQLKKLYR-RHYTGWGRLSAKLINGIRDK | ESQKTILDYLI | DDG---RSNRNFMQLINDDGL | 704 |
| WP_001040104 | 636 | KRLENYKDLFTESQLKKLYR-RHYTGWGRLSAKLINGIRDK | ESQKTILDYLI | DDG---RSNRNFMQLINDDGL | 704 |
| WP_001040105 | 636 | KRLENYKDLFTESQLKKLYR-RHYTGWGRLSAKLINGIRDK | ESQKTILDYLI | DDG---RSNRNFMQLINDDGL | 704 |
| WP_001040106 | 636 | KRLENYKDLFTESQLKKLYR-RHYTGWGRLSAKLINGIRNK | ESQKTILDYLI | SDG---RANRNFMQLIHDDGL | 704 |
| WP_001040107 | 636 | KRLENYKDLFTESQLKKLYR-RHYTGWGRLSAKLINGIRNK | ESQKTILDYLI | SDG---RANRNFMQLIHDDGL | 704 |
| WP_001040108 | 636 | KRLDIYKDFFTESQLKKLYR-RHYTGWGRLSAKLINGIRNK | ENQKTILDYLI | DDG---SANRNFMQLIHDDGL | 704 |
| WP_001040109 | 636 | KRLENYKDLFTESQLKKLYR-RHYTGWGRLSAKLINGIRNK | ESQKTILDYLI | SDG---RANRNFMQLIHDDGL | 704 |
| WP_001040110 | 636 | KRLENYKDLFTESQLKKLYR-RHYTGWGRLSAKLINGIRNK | ESQKTILDYLI | SDG---RANRNFMQLIHDDGL | 704 |
| WP_015058523 | 636 | KRLENYKDLFTESQLKKLYR-RHYTGWGRLSAKLINGIRNK | ESQKTILDYLI | DDG---RANRNFMQLINDDGL | 704 |
| WP_017643650 | 636 | KRLENYKDLFTESQLKKLYR-RHYTGWGRLSAKLINGIRDK | ESQKTILDYLI | DDG---RSNRNFMQLINDDGL | 704 |
| WP_017647151 | 636 | KRLDIYKDFFTESQLKKLYR-RHYTGWGRLSAKLINGIRNK | ENQKTILDYLI | DDG---SANRNFMQLIHDDGL | 701 |
| WP_017648376 | 636 | KRLENYKDLFTESQLKKLYR-RHYTGWGRLSAKLINGIRDR | ESQKTILDYLI | DDG---KSNRNFMQLIHDDGL | 704 |
| WP_017649527 | 636 | KRLENYKDLFTESQLKKLYR-RHYTGWGRLSAKLINGIRDK | ESQKTILDYLI | SDG---RANRNFMQLINDDGL | 704 |
| WP_017771611 | 633 | KRLDIYKDFFTESQLKKLYR-RHYTGWGRLSAKLINGIRNK | ENQKTILDYLI | DDG---SANRNFMQLINDDGL | 701 |
| WP_017771984 | 636 | KRLENYKDLFTESQLKKLYR-RHYTGWGRLSAKLINGIRNK | ESQKTILDYLI | SDG---RANRNFMQLINDDGL | 704 |
| CFQ25032 | 636 | KRLENYKDLFTESQLKKLYR-RHYTGWGRLSAKLINGIRDK | ESQKTILDYLI | DDG---RSNRNFMQLINDDGL | 704 |
| CFV16040 | 636 | KRLENYKDLFTESQLKKLYR-RHYTGWGRLSAKLINGIRDK | ESQKTILDYLI | DDG---RSNRNFMQLINDDGL | 704 |
| KLJ37842 | 636 | KRLENYKDLFTESQLKKLYR-RHYTGWGRLSAKLINGIRDK | ESQKTILDYLI | DDG---RSNRNFMQLINDDGL | 704 |
| KLJ72361 | 636 | KRLENYKDLFTESQLKKLYR-RHYTGWGRLSAKLINGIRDK | ESQKTILDYLI | DDG---RSNRNFMQLINDDGL | 704 |
| KLL20707 | 636 | KRLENYKDLFTESQLKKLYR-RHYTGWGRLSAKLINGIRDK | ESQKTILDYLI | DDG---RSNRNFMQLINDDGL | 704 |
| KLL42645 | 636 | KRLENYKDLFTESQLKKLYR-RHYTGWGRLSAKLINGIRDK | ESQKTILDYLI | DDG---RSNRNFMQLINDDGL | 718 |
| WP_047207273 | 636 | KRLENYKDLFTESQLKKLYR-RHYTGWGRLSAKLINGIRDK | ESQKTILDYLI | SDG---RANRNFMQLINDDGL | 704 |
| WP_047209694 | 633 | KRLDIYKDFFTESQLKKLYR-RHYTGWGRLSAKLINGIRNK | ENQKTILDYLI | DDG---SANRNFMQLINDDGL | 701 |
| WP_050198062 | 636 | KRLENYKDLFTESQLKKLYR-RHYTGWGRLSAKLINGIRDK | ESQKTILDYLI | DDG---RSNRNFMQLINDDGL | 704 |
| WP_050201642 | 636 | KRLENYKDLFTESQLKKLYR-RHYTGWGRLSAKLINGIRDK | ESQKTILDYLI | DDG---RSNRNFMQLINDDGL | 704 |
| WP_050204027 | 636 | KRLENYKDLFTESQLKKLYR-RHYTGWGRLSAKLINGIRDK | ESQKTILDYLI | DDG---RANRNFMQLIHDDGL | 704 |
| WP_050881965 | 636 | KRLENYKDLFTESQLKKLYR-RHYTGWGRLSAKLINGIRNK | ESQKTILDYLI | SDG---RANRNFMQLIHDDGL | 704 |
| WP_050886065 | 636 | KRLENYKDLFTESQLKKLYR-RHYTGWGRLSAKLINGIRDK | ESQKTILDYLI | DDG---RSNRNFMQLINDDGL | 704 |
| AHN30376 | 636 | KRLENYKDLFTESQLKKLYR-RHYTGWGRLSAKLINGIRDK | ESQKTILDYLI | DDG---RANRNFMQLINDDGL | 704 |
| EA078426 | 636 | KRLENYKDLFTESQLKKLYR-RHYTGWGRLSAKLINGIRDK | ESQKTILDYLI | DDG---RSNRNFMQLINDDGL | 704 |
| CCW42055 | 636 | KRLDIYKDFFTESQLKKLYR-RHYTGWGRLSYKLINGIRNK | ENQKTILDYLI | DDG---YANRNFMQLINDDAL | 703 |
| WP_030041502 | 635 | QRLQKYSDIFTKAQLKKLER-RHYTGWGRLSYKLINGIRNK | ENKKTILDYLI | DDG---YANRNFMQLINDDAL | 703 |
| WP_037593752 | 636 | QRLQKYSDIFTTQQLKKLER-RHYTGWGRLSYKLINGIRNK | ENKKTILDYLI | DDG---YANRNFMQLINDDAL | 703 |
| WP_049516684 | 636 | QRLQKYSDIFTKAQLKKLER-RHYTGWGRLSYKLINGIRNK | ENKKTILDYLI | DDG---YANRNFMQLINDDSL | 703 |
| GAD46167 | 635 | QRLQKYSDIFTKAQLKKLER-RHYTGWGRLSYKLINGIRNK | ENNKTILEYLV | DDG---YANRNFMQLINDDTL | 704 |
| WP_018363470 | 636 | KRLENYKDLFTKQQLKKLER-RHYTGWGRLSYKLINGIRNK | ENKKTILDYLI | DDG---SNRNFMQLINDDAL | 712 |
| WP_003043819 | 644 | ERLKTYAHLFDDKVMKQLER-RHYTGWGRLSRKMINGIRDK | QSGKTILDFLK | -DGf---SNRNFMQLIHDDSL | 712 |
| WP_006269658 | 635 | QRLQKYSDIFTKAQLKKLER-RHYTGWGRLSYKLINGIRNK | ENKKTILDYLI | DDG---YANRNFMQLINDDAL | 703 |
| WP_048800889 | 635 | QRLQKYANLFDDKVMKQLKR-RHYTGWGRLSRKLINGIRDK | QSGKTILDFLK | -DGf---ANRNFMQLIHDDSL | 702 |
| WP_012767106 | 634 | ERLKKYANLFDDKVMKQLKR-RHYTGWGRLSRKLINGIRDK | QSGKTILDFLK | -DGf---ANRNFMQLIHDDSL | 702 |
| WP_014612333 | 634 | ERLKKYANLFDDKVMKQLKR-RHYTGWGRLSRKLINGIRDK | QSGKTILDFLK | -DGf---ANRNFIQLIHDDSL | 702 |
| WP_015017095 | 634 | ERLKTYAHLFDDKVMKQLKR-RHYTGWGRLSRKLINGIRDK | QSGKTILDFLK | -DGf---ANRNFIQLIHDDSL | 702 |
| WP_015057649 | 634 | ERLKTYAHLFDDKVMKQLKR-RHYTGWGRLSRKLINGIRDK | QSGKTILDFLK | -DGf---ANRNFMQLIHDDSL | 702 |
| WP_048327215 | 634 | ERLKTYAHLFDDKVMKQLKR-RHYTGWGRLSRKLINGIRDK | QSGKTILDFLK | -DGf---ANRNFIQLIHDDSL | 702 |

-continued

```
WP_049519324  634 ERLKTYAHLFDDKVMKQLKR-RHYTGWGRLSRKLINGIRDK QSGKTILDFLK -DGf---ANRNFIQLIHDDSL 702
WP_012515931  634 KRLDQYAHLFDKVVLNKLER-HHYTGWGRLSGKLINGIRDS QSGKTILDFLK -DGf---ANRNFMQLIHDSEL 702
WP_021320964  634 KRLDQYAHLFDKVVLNKLER-HHYTGWGRLSGKLINGIRDS QSGKTILDFLK -DGf---ANRNFMQLIHDSEL 702
WP_037581760  634 KRLDQYAHLFDKVVLNKLER-HHYTGWGRLSGKLINGIRDS QSGKTILDFLK -DGf---ANRNFMQLIHDSEL 702
WP_004232481  635 ERLQKYSDIFTSQQLKKLER-RHYTGWGRLSYKLINGIRNN ENNKTILDFLI DDG---DANRNFMQLINDDSL 703
WP_009854540  636 ERLQKYSDIFTANQLKKLER-RHYTGWGRLSYKLINGIRNN ENNKTILDYLI DDG---SANRNFMQLINDDTL 704
WP_012962174  636 QRLQKYSDIFTPQQLKKLER-RHYTGWGRLSYKLINGIRNN ENGKSILDYLI DDG---YANRNFMQLISDDTL 704
WP_039695303  638 ERLQKYSDIFTANQLKKLER-RHYTGWGRLSYKLINGIRNN ENNKTILDYLI DDG---SANRNFMQLINDDTL 706
WP_014334983  635 ERLQKYSDFFTSQQLKKLER-RHYTGWGRLSQKLINGIKDS QTGKTILDFLI DDG---HANRNFMQLINDESL 703
WP_030099269  634 RRLVKYADVFEKSVLKKLKR-RHYTGWGRLSQKLINGIKDS QSGKTILGFLK -DGy---ANRNFMQLINDSSL 702
AHY15608      634 RRLVKYADVFEKSVLKKLKK-RHYTGWGRLSQKLINGIKDK QTGKTILGFLK -DGv---ANRNFMQLINDSSL 702
AHY17476      634 RRLVKYADVFEKSVLKKLKK-RHYTGWGRLSQKLINGIKDK QTGKTILGFLK -DGv---ANRNFMQLINDSSL 702
ESR09100          ------------------------------------------- ---------- ------------------- 
AGM98575      634 RRLVKYADVFEKSVLKKLKK-RHYTGWGRLSQKLINGIKDK QTGKTILGFLK -DGy---ANRNFMQLINDSSL 702
ALF27331      635 KRLENYSDLLTKEQVKNLER-RHYTGWGRLSAELIHGIRNN ESRKTILDYLI DDG---NSNRNFMQLINDDAL 703
WP_018372492  648 KRLSELNIPFENKIIKKLAR-KKYTGWGRLSRKLIDGIRNN DDGf---SNRNLMQLINDDGL 716
WP_045618028  634 QRLAHYASIFDEKVIKALTR-RHYTGWGKLSAKLINGIYDK QSKKTILDYLI DDG----EINRNFMQLINDEGL 702
WP_045635197  633 QRLAQYDSLFDERVIKALTR-RHYTGWGKLSAKLINGICDK QTGNTILDYLI DDG---KINRNFMQLINDDGL 701
WP_002263549  635 KRLENYSDLLTKEQVKKLER-RHYTGWGRLSAELIHGIRNN ESRKTILDYLI DDG---NSNRNFMQLINDDAL 703
WP_002263887  635 KRLENYSDLLTKEQLKKLER-RHYTGWGRLSAELIHGIRNN ESRKTILDYLI DDG---NSNRNFMQLINDDAL 703
WP_002264920  635 KRLKNYSDLLTKEQVKKLER-RHYTGWGRLSAELIHGIRNN ESRKTILDYLI DDG---NSNRNFMQLINDDAL 703
WP_002269043  635 KRLENYSDLLTKEQLKKLER-RHYTGWGRLSAELIHGIRNN ESRKTILDYLI DDG---NSNRNFMQLINDDAL 703
WP_002269448  635 KRLENYSDLLTKEQVKKLER-RHYTGWGRLSAELIHGIRNN ESRKTILDYLI DDG---NSNRNFMQLINDDAL 703
WP_002271977  635 KRLENYSDLLTKEQVKKLER-RHYTGWGRLSAELIHGIRNN ESRKTILDYLI DDG---NSNRNFMQLINDDAL 703
WP_002272766  635 KRLENYSDLLTKEQVKKLER-RHYTGWGRLSAELIHGIRNN ESRKTILDYLI DDG---NSNRNFMQLINDDAL 703
WP_002273241  635 KRLENYSDLLTKEQVKKLER-RHYTGWGRLSAELIHGIRNN ESRKTILDYLI DDG---NSNRNFMQLINDDAL 703
WP_002275430  635 KRLENYSDLLTKEQVKKLER-RHYTGWGRLSAELIHGIRNN ESRKTILMDYLI DDG---NSNRNFMQLINDDAL 703
WP_002276448  635 KRLENYSDLLTKEQVKKLER-RHYTGWGRLSAELIHGIRNN ESRKTILDYLI DDG---NSNRNFMQLINDDAL 703
WP_002277050  636 QRLAKYSDLLTKEQVKKVIDQLAR-RHYTGWGRLSAKLLNGIRNN QSCKTMDYLI DDA---QSNRNLMQLITDDNL 704
WP_002277364  635 KRLENYSDLLTKEQVKKLER-RHYTGWGRLSAELIHGIRNN ESRKTILDYLI DDG---NSNRNFMQLINDDAL 703
WP_002279025  635 KRLKNYSDLLTKEQLKKLER-RHYTGWGRLSAELIHGIRNN ESRKTILDYLI DDG---NSNRNFMQLINDDAL 703
WP_002279859  635 KRLENYSDLLTKEQVKKLER-RHYTGWGRLSAELIHGIRNN ESRKTILDYLI DDG---NSNRNFMQLINDDAL 703
WP_002280230  635 KRLENYSDLLTKEQVKKLER-RHYTGWGRLSAELIHGIRNN ESRKTILDYLI DDG---NSNRNFMQLINDDAL 703
WP_002281696  635 KRLENYSDLLTKEQVKKLER-RHYTGWGRLSAELIHGIRNN ESRKTILDYLI DDG---NSNRNFMQLINDDAL 703
WP_002282247  636 QRLAKYADVFDKKVIDQLAR-RHYTGWGRLSAKLLNGIRDG QSCKTILDYLI DDA---QSNRNLMQLITDDNL 704
WP_002282906  635 KRLENYSDLLTKEQVKKLER-RHYTGWGRLSAELIHGIRNN ESRKTILDYLI DDG---NSNRNFMQLINDDAL 703
WP_002283846  635 KRLKNYSDLLTKEQVKKLER-RHYTGWGRLSAELIHGIRNN ESRKTILDYLI DDG---NSNRNFMQLINDDAL 703
WP_002287255  635 KRLENYSDLLTKEQVKKLER-RHYTGWGRLSAELIHGIRNN ESRKTILDYLI DDG---NSNRNFMQLINDDAL 703
WP_002288990  635 KRLENYSDLLTKEQVKKLER-RHYTGWGRLSAELIHGIRNN ESRKTILDYLI DDG---NSNRNFMQLINDDAL 703
WP_002289641  635 KRLENYSDLLTKEQLKKLER-RHYTGWGRLSAELIHGIRNN ESRKTILDYLI DDG---NSNRNFMQLINDDAL 703
WP_002290427  635 KRLENYSDLLTKEQVKKLER-RHYTGWGRLSAELIHGIRNN ESRKTILDYLI DDG---NSNRNFMQLINDDAL 703
WP_002295753  635 KRLENYSDLLTKEQLKKLER-RHYTGWGRLSAELIHGIRNN ESRKTILDYLI DDG---NSNRNFMQLINDDAL 703
WP_002296423  636 QRLQKYSDIFTKAQLKKLER-RHYTGWGRLSYKLINGIRDK QSNKTILGYLI DDG---YSNRNFMQLINDDAL 704
WP_002304487  645 KRLENYSDLLTKEQVKKLER-RHYTGWGRLSAELIHGIRNN ESRKTILDYLI DDG---NSNRNFMQLINDDAL 713
WP_002305844  635 KRLENYSDLLTKEQVKKLER-RHYTGWGRLSAELIHGIRNN ESRKTILDYLI DDG---NSNRNFMQLINDDAL 703
WP_002307203  635 KRLENYSDLLTKEQVKKLER-RHYTGWGRLSAELIHGIRNN ESRKTILDYLI DDG---NSNRNFMQLINDDAL 703
WP_002310390  635 KRLENYSDLLTKEQVKKLER-RHYTGWGRLSAELIHGIRNN ESRKTILDYLI DDG---NSNRNFMQLINDDAL 703
WP_002352408  635 KRLENYSDLLTKEQVKKLER-RHYTGWGRLSAELIHGIRNN ESRKTILDYLI DDG---NSNRNFMQLINDDAL 703
WP_012997688  635 KRLENYSDLLTKEQVKKLER-RHYTGWGRLSAELIHGIRNN ESRKTILDYLI DDG---NSNRNFMQLINDDAL 703
WP_014677909  635 KRLENYSDLLTKEQVKKLER-RHYTGWGRLSAELIHGIRNN ESRKTILDYLI DDG---NSNRNFMQLINDDAL 703
WP_019312892  635 KRLENYSDLLTKEQVKKLER-RHYTGWGRLSAELIHGIRNN ESRKTILDYLI DDG---NSNRNFMQLINDDAL 703
WP_019313659  635 KRLENYSDLLTKEQVKKLER-RHYTGWGRLSAELIHGIRNN ESRKTILDYLI DDG---NSNRNFMQLINDDAL 703
WP_019314093  635 KRLENYSDLLTKEQVKKLER-RHYTGWGRLSAELIHGIRNN ESRKTILDYLI DDG---NSNRNFMQLINDDAL 703
```

```
                    -continued
WP_019315370  635  KRLENYSDLLTKEQVKKLER-RHYTGWGRLSAELIHGIRNK ESRKTLLDYLI DDG---NSNRNFMQLINDDAL  703
WP_019803776  635  KRLENYSDLLTKEQVKKLER-RHYTGWGRLSAELIHGIRNK ESRKTILDYLI DDG---NSNRNFMQLINDDAL  703
WP_019805234  635  KRLKNYSDLLTKEQLKKLER-RHYTGWGRLSAELIHGIRNK ESRKTILDYLI DDG---NSNRNFMQLINDDAL  703
WP_024783594  635  KRLENYSDLLTKEQVKKLER-RHYTGWGRLSAELIHGIRNK ESRKTILDYLI DDG---NSNRNFMQLINDDAL  704
WP_024784288  636  QRLAKYADVFDKKVIDQLAR-RHYTGWGRLSAKLLNGIRDK QSCKTIMDYLI DDA---QSNRNLMQLITDDNL  703
WP_024784666  635  KRLENYSDLLTKEQVKKLER-RHYTGWGRLSAELIHGIRNK ESRKTILDYLI DDG---NSNRNFMQLINDDAL  703
WP_024784894  635  KRLENYSDLLTKEQVKKLER-RHYTGWGRLSAELIHGIRNK ESRKTILDYLI DDG---NSNRNFMQLINDDAL  703
WP_024786433  636  QRLAKYADVFDKKVIDQLAR-RHYTGWGRLSAKLLNGIRDK QSCKTIMDYLI DDA---QSNRNLMQLITDDNL  704
WP_049473442  635  KRLENYSDLLTKEQVKKLER-RHYTGWGRLSAELIHGIRNK ESRKTILDYLI DDG---NSNRNFMQLINDDAL  703
WP_049474547  635  KRLENYSDLLTKEQVKKLER-RHYTGWGRLSAELIHGIRNK ESRKTILDYLI DDG---NSNRNFMQLINDDAL  703
EMC03581      628  KRLENYSDLLTKEQLKKLER-RHYTGWGRLSAELIHGIRNK ESRKTILDYLI DDG---NSNRNFMQLINDDEL  696
WP_000428612  636  QRLAQYDSLFDEKVIKALTR-RHYTGWGKLSSKLINGIRDK QTGNTILDYLM DDG---YNNRNFMQLINDDEL  704
WP_000428613  634  QRLAQYDTLFDEKVIKALTR-RHYTGWGKLSAKLIDGICDK QTGNTILDYLI DDG---KNNRNFMQLINDDGL  702
WP_049523028  633  QRLNQYDSIFDEKVIKALTR-RHYTGWGKLSAKLINGIRDK KTSKTILDYLI DDG---YSNRNFMQLINDDGL  701
WP_003107102  636  KRLSKYESIFDPSILKKLKK-RHYTGWGRLSQKLINGIRDK HTGKTILDFLI -DGq---ANRNFMQLINDDNL  704
WP_054279288  603  NRLAVYEDLFDQNVLKKLQR-RHYTGWGKLSKQLINGMRDK HTGKTILDFLK -DGf---INRNFMQLINDDNL  671
WP_049531101  636  QRLAQYASIFDEKVIKTLTR-RHYTGWGKLSAKLINCIRDR KTGKTILDYLI DDG---YNNRNFMQLINDDGL  704
WP_049538452  634  QRLAQYDSIFDEKVIKALTR-RHYTGWGKLSAKLINGIRDK QTGKTILDYLI DDG---YSNRNFMQLINDDGL  702
WP_049549711  634  QRLAQYDSLFDKKVIKALTR-RHYTGWGKLSAKLINGIRDK QTGNTILDYLI DDG---EINRNFMQLINDDGL  702
WP_078966501  637  KRLAKYANLFEKSVLKKLRK-RHYRGWGRLSRQLIDGMKDK ASGKTILDFLK -DDf---ANRNFIQLINDSSL  705
EFR44625      589  KRLAKYANLFEKSVLKKLRK-RHYRGWGRLSRQLIDGMKDK ASGKTILDFLK -DDf---ANRNFIQLINDSSL  657
WP_002897477  633  QRLAQYDTLFDEKVIKALTR-RHYTGWGKLSAKLINGIRDK QSGKTILDYLI DDD---KINRNFMQLINDDGL  701
WP_002906454  633  QRLAQYDTLFDEKVIKALTR-RHYTGWGKLSAKLINGIRDK QTGKTILEYLI DDG---DCNRNFMQLINDDGL  701
WP_009729476  634  QRLAQYDSLFDEKVIKALTR-RHYTGWGKLSAKLINGISDK QTGKTILDFLK -DGf---ANRNFMQLINDDGL  702
CQR24647      637  QRLLKYEDIFSKKVIANLTR-RHYTGWGRLSAKLINGIRDK HSRKTILDYLI DDG---HSNRNFMQLINDDNL  705
WP_000066813  636  QRLAQYDSLFDEKVIKALTR-RHYTGWGKLSAKLINGIRDK KSGKTILDYLI DDG---EINRNFMQLIHDDGL  704
WP_009754323  634  QRLAQYDSIFDEKVIKALTR-RHYTGWGRLSAKLINGICDK KTGKTILDYLI DDG---YNNRNFMQLINDDGL  702
WP_044674937  633  KRLEKYKDILTEEQRKKLER-RHYTGWGRLSAKLINGILDK VTRKTILDYLI DDG---kHYNRNFMQLINDDTL  701
WP_044676715  635  KRLEKYKDVLTEBQRKKLER-RHYTGWGRLSAKLINGIRDK VTRKTILDYLI DDG---TSNRNFMQLINDDTL  703
WP_044680361  635  KRLEKYKDVLTEBQRKKLER-CHYTGWGRLSYKLINGIRNK ENKKTILDYLI DDG---YANRNFMQLINDDTL  703
WP_044681799  633  QRLQKYSDIFTKAQLKKLER-RFRGWGRLSQRLINRIKTP EDHKLSINEIL --------QTNENFMQIIRNKDY  701
WP_029090905  613  RKLSEYPQLTEQQQVQLAQV-RFRGWGRLSQRLINRIKTP EDHKLSINEIL --------QTNENFMQIIRNKDY  682
WP_006506696  638  RRLKKKYALPDDKVKQILKL-KYKDWSRLSKKLLDGIVAD SV--TVLDVLE ------SRLNLMEIINDKDL  705
AIT42264      634  ERIKTYAHLFDDKVMKQLKR-RRYTGWGLSRKLINGIRDE QSGKTILDFLK -DGf---ANRNFMQLIHDDSL  702
WP_034440723  638  RQLMKFKDKLSEKAINQLSK-RYTGWGQLSERKLINGIRDE DNGcpkNMNRNFMQLINDDTL           710
AKQ21048      634  ERIKTYAHLFDDKVMKQLKR-RRYTGWGLSRKLINGIRDK QSGKTILDFLK -DGf---ANRNFMQLIHDDSL  702
WP_004636532  644  KQLQTYSDTLSPEILKKLER-KHYTGWGRFSKKLINGLRDE GSNKTILDYLK DEGssgPTNRNFMQLIRDNTL  706
WP_002364836  642  TQLSTFKGQFSAEVLKKLER-KHYTGWGRLSKKLINGIYDK ESGKTILGYLI DDGvskHYNRNFMQLINDDSQL 714
WP_016631044  593  TQLSTFKGQFSAEVLKKLER-KHYTGWGRLSKKLINGIYDK ESGKTILDYLV DDGvskHYNRNFMQLINDDSQL 665
EMS75795      382  TQLKYQSVLGDGFEKKLVK-KHYTGWGRLSERLINGIYDK KTNKTILDYLI DDGFpyNRNRNFMQLINDDSL  454
WP_002373311  642  TQLSTFKGQFSAEVLKKLER-KHYTGWGRLSKKLINGIYDK ESGKTILGYLI DDGvskHYNRNFMQLINDDSQL 714
WP_002378009  642  TQLSTFKGQFSAEVLKKLER-KHYTGWGRLSKKLINGIYDK ESGKTILDYLI DDGvskHYNRNFMQLINDDSQL 714
WP_002407324  642  TQLSTFKGQFSAEVLKKLER-KHYTGWGRLSKKLINGIYDK ESGKTILDYLV DDGvskHYNRNFMQLINDDSQL 714
WP_002413717  642  TQLSTFKGQFSAEVLKKLER-KHYTGWGRLSKKLINGIYDK ESGKTILDYLV DDGvskHYNRNFMQLIHDDSL  714
WP_010775580  644  TQLSTFKGQSEEVLKKLER-KHYTGWGRLSKKLINGIYDK ESGKTILDYLI DDGvskHYNRNFMQLINDDSQL 716
WP_010818269  642  TQLSTFKGQFSAEVLKKLER-KHYTGWGRLSKKLINGIYDK ESGKTILGYLI DDGvskHYNRNFMQLINDDSQL 714
WP_010824395  642  TQLSTFKGQFSAEVLKKLER-KHYTGWGRLSKKLINGIYDK ESGKTILDYLI DDGvskHYNRNFMQLINDDSQL 714
WP_016622645  642  TQLSTFKGQFSAEVLKKLER-KHYTGWGRLSKKLINGIYDK ESGKTILDYLV DDGvskHYNRNFMQLINDDSQL 714
WP_033624816  642  TQLSTFKGQFSAEVLKKLER-KHYTGWGRLSKKLINGIYDK ESGKTILDYLI DDGvskHYNRNFMQLINDDSQL 714
WP_033625576  642  TQLSTFKGQFSAEVLKKLER-KHYTGWGRLSKKLINGIYDK ESGKTILDYLI DDGvskHYNRNFMQLINDDSQL 714
WP_033789179  642  TQLSTFKGQSEEVLKKLER-KHYTGWGRLSKELIQGIRDK QSNKTILDYLI DDGvskHYNRNFMQLINDDSQL 714
WP_002310644  642  TRLSHHEATLGKHIIKKLTK-KHYTGWGRLSKELIQGIRDK QSNKTILDYLI DDDfphHRNRNFMQLINDDSL  714
```

-continued

```
WP_002312694  643  TRLSHHEATLGKHIIKKLTK-KHYTGWGRLSKELIQGIRDK QSNKTILDYLI DDDfphHRNRNFMQLINDDSL  715
WP_002314015  643  TRLSHHEATLGKHIIKKLTK-KHYTGWGRLSKELIQGIRDK QSNKTILDYLI DDDfphHRNRNFMQLINDDSL  715
WP_002320716  643  TRLSHHEATLGKHIIKKLTK-KHYTGWGRLSKELIQGIRDK QSNKTILDYLI DDDfphHRNRNFMQLINDDSL  715
WP_002330729  642  TRLSHHEATLGKHIIKKLTK-KHYTGWGRLSKELIQGIRDK QSNKTILDYLI DDDfphHRNRNFMQLINDDSL  714
WP_002335161  643  TRLSHHEATLGKHIIKKLTK-KHYTGWGRLSKELIQGIRDK QSNKTILDYLI DDDfphHRNRNFMQLINDDSL  715
WP_002345439  643  TRLSHHEATLGKHIIKKLTK-KHYTGWGRLSKELIQGIRDK QSNKTILDYLI DDDfphHRNRNFMQLINDDSL  715
WP_034867970  638  HQLSKYQEVFGEKLLKEFAR-KHYTGWGRFSAKLIHGIRDR KTNKTILDYLI DDDvpaNRNRNLMQLINDEHL  710
WP_047937432  643  TRLSHHEATLGKHIIKKLTK-KHYTGWGRLSKELIQGIRDK QSNKTILDYLI DDDfphHRNRNFMQLINDDSL  715
WP_010720994  638  HQLSKYQEVFGEKLLKEFAR-KHYTGWGRFSAKLIHGIRDR KTNKTILDYLI DDDvpaNRNRNLMQLINDEHL  710
WP_010731004  638  HQLSKYQEVFGEKLLKEFAR-KHYTGWGRFSAKLIHGIRDR KTNKTILDYLI DDDvpaNRNRNLMQLINDEHL  710
WP_034700478  638  HQLSKYQEVFGEKLLKEFAR-KHYTGWGRFSAKLIHGIRDR KTNKTILDYLI DDDvpaNRNRNLMQLINDEHL  710
WP_007209003  635  NQLEQLPLNLSTKTIKALSR-RKYTGWGRLSARLIDGIHDK NSGKTILDYLI DESdsyIVNRNRNFMQLINDDHL  707
WP_023519017  632  EQLKPYETVLGLPAIKKLAK-KHYTGWGRLSEKMIQGMREK QSRKTILDYLI DDDfpcNRNRNFMQLINDDHL  704
WP_010770040  635  EQLKKYTYLFDEEVLKKLER-RHYTGWGRLSAKLLNGIKEK RTHKTILDYLI DDGgkqPINRNLMQLINDSDL  707
WP_048604708  631  EQLSKFSDRLSEKTIKDLER-RHYTGWGRLSAKLINGIHDK KTNKTILDYLI DDApkkNINRNRNFMQLINDNRL  703
WP_010750235  637  TQLKKYQRILGEEIFKKLVR-KKYTGWGRLSRKLINGIRDQ KTNKTILDYLI DDDfpyNRNRNLMQLINDDHL  709
AII16583      673  ERLKTYAHLFDDKVMKQLKR-RRYTGWGRLSRKLINGIRDK QSGKTILDFLK -DGf---ANRNFMQLIHDDSL  741
WP_029073316  648  RRLKKEYDLDEEKIKKILKL--KYSGWSRLSKKLLSGIKTK RTPETVLEVME ------TMNNLMQVINDEKL  717
WP_031589969  648  RRLKKEYDLDEEKIKKILKL--KYSGWSRLSKKLLSGIKTK RTPETVLEVME ------TMNNLMQVINDEKL  717
KDA45870      631  RRLENYRDFLGEDILRKLSR-KKYTGWGRLSARLIDGIHDK KTHKTILDCLM EDYs------QNFMQLINDDTY  698
WP_039099354  651  AKLNEIDWLTDQQRVQLAAK--RYRGWGRLSAKLLTQIVN- ANGQRIMDLLW ------TTDNFMRIVHSE-    712
AKP02966      633  EKLHSSNYSYTSDQIKKISN-MRYKGWGRLSKKILTCITTE TNTPKSLQLSN -DLm-wTTNNNFISIISNDKY  706
WP_010991369  638  EQLQQFSDVLDGVVLKKLER-RHYTGWGRLSAKLMGIRDK QSHLTILDYLM DDG----LNRNLMQLINDSNL  706
WP_033838504  638  EQLQQFSDVLDGVVLKKLER-RHYTGWGRLSAKLMGIRDK QSHLTILDYLM DDG----LNRNLMQLINDSNL  706
EHN60060      641  EQLQQFSDVLDGVVLKKLER-RHYTGWGRLSAKLMGIRDK QSHLTILDYLM DDG----LNRNLMQLINDSNL  709
EFR89594      407  EQLQSFSDVLDGSVLDGTIL-RHYTGWGRLSAKLTGIRDK QSHLTILDYLM DDG----LNRNLMQLINDSNL  475
WP_038409211  638  EQLQSFSDVLDGTILKKLER-RHYTGWGRLSAKLTGIRDK HSHLTILDYLM DDG----LNRNLMQLINDSNL  706
EFR95520      257  EQLQSFSDVLDGTILKKLER-RHYTGWGRLSAKLTGIRDK HSHLTILDYLM DDG----LNRNLMQLINDSNL  325
WP_003723650  638  EQLQQFSDVLDGGVVLKKLER-RHYTGWGRLSAKLVGIRDK QSHLTILDYLM DDG----LNRNLMQLINDSNL  706
WP_003727705  638  EQLQQFSDVLDGVVLKKLER-RHYTGWGRLSAKLVGIRDK QSHLTILDYLM DDG----LNRNLMQLINDSNL  706
WP_003730785  638  EQLEQFSDVLDGVVLKKLER-RHYTGWGRLSAKLVGIRDK QSHLTILDYLM DDG----LNRNLMQLINDSNL  706
WP_003733029  638  EQLQQFSDVLDGVVLKKLER-RKYDNWSRLSKKLLDGIVAD SV--TVLDVLE ------SRLNLMEIINDKEL  706
WP_003739838  638  EQLQQFSDVLDGVVLKKLER-RHYTGWGRLSAKLVGIRDK QSHLTILDYLM DDG----LNRNLMQLINDSNL  706
WP_014601172  638  EQLQQFSDVLDGAVLKKLER-RHYTGWGRLSAKLVGIRDK QSHLTILDYLM DDG----LNRNLMQLINDSNL  706
WP_023548323  638  EQLQQFSDVLDGGVLKKLER-RHYTGWGRLSAKLVGIRDK QSHLTILDYLM DDG----LNRNLMQLINDSNL  706
WP_031665337  638  EQLQQFSDVLDGVVLKKLER-RHYTGWGRLSAKLVGIRDK QSHLTILEYLM DDG----LNRNLMQLINDSNL  706
WP_031669209  638  EQLQQFSDVLDGVVLKKLER-RHYTGWGRLSAKLVGIRDK QSHLTILEYLM DDG----LNRNLMQLINDSNL  706
WP_033920898  638  EQLQQFSDVLDGVVLKKLER-RHYTGWGRLSAKLVGIRDK QSHLTILEYLM DDG----LNRNLMQLINDSNL  706
AKI42028      641  EQLQQFSDVLDGVLKKLER-RHYTGWGRLSAKLVGIREK QSHLTILDYLM DDG----LNRNLMQLINDSNL  709
AKI50529      641  EQLQQFSDVLDGVVLKKLER-RHYTGWGRLSAKLVGIREK QSHLTILEYLM DDG----LNRNLMQLINDSNL  709
EFR83390      86   EQLQQFSDVLDGVVLKKLER-RHYTGWGRLSAKLVGIREK QSHLTILEYLM DDG----LNRNLMQLINDSNL  154
WP_046323366  638  ERLQEFSNVLDEAVLKKLER-RHYTGWGRLSAKLLIGIRDK ESHLTILDYLM DDK----HNRNLMQLINDSNL  706
AKE81011      650  ERLKTYAHLFDDKVMKQLKR-RRYTGWGRLSRKLINGIRDK QSGKTILDFLK -DGf---ANRNFMQLIHDDSL  718
CUO82355      642  RRLKKKYALPDDKIKQILKL--KYKDNWSRLSKKLLDGIVAD SV--TVLDVLE ------SRLNLMEIINDKEL  709
WP_033162887  645  RRLKKVYQLDDLLVDKIIKL--NYTGWGRLSKKLLTGMTAD KA--TVLFVLE ------SKNKLMEIINDEKL  712
AGZ01981      667  ERLKTYAHLFDDKVMKQLKR-RRYTGWGRLSRKLINGIRDK QSGKTILDFLK -DGf---ANRNFMQLIHDDSL  735
AKA60242      634  ERLKTYAHLFDDKVMKQLKR-RRYTGWGRLSRKLINGIRDK QSGKTILDFLK -DGf---ANRNFMQLIHDDSL  702
AKS40380      634  ERLKTYAHLFDDKVMKQLKR-RRYTGWGRLSRKLINGIRDK QSGKTILDFLK -DGf---ANRNFMQLIHDDSL  702
4UN5_B        638  ERLKTYAHLFDDKVMKQLKR-RRYTGWGRLSRKLINGIRDK QSGKTILDFLK -DGf---ANRNFMQLIHDDSL  706
WP_010922251  703  TFKEDIQKAQVSG-QGDS-LHEHIANLAGSPAITKKGILQTVKVVDELVKMGrHKPENIVIEMARENQ TTQKGQKNS  777
WP_039695303  707  PFKQIIQKSQVVG-DVDD-IEAVVHDLPGSPAIKKGILQSVKIVDELVKVMG-GNPDNIVIEMARENG TTNRGRSQS  780
WP_045635197  702  SFKEIIQKAQVIG-KTDD-VKQVVQELSGSPAIKKGILQSIKIVDELVKVMG-HAPESIVIEMARENG TTARGKKNS  775
5AXW_A        427  VPKKVDLSQQKEI--PT---TLVDDFILSPVVKRSFIQSIKVINAIIKKYG--LPNDIIIELAREKN  ------S  487
```

-continued

| ID | Start | Sequence | End |
|---|---|---|---|
| WP_009880683 | 387 | TFKEDIQKAQVSG-QGDS-LHEHIANLAGSPAIKKGILQTVKVVDELVKVMGrHKPENIVIEMARENQ TTQKGQKNS | 461 |
| WP_010922251 | 703 | TFKEDIQKAQVSG-QGDS-LHEHIANLAGSPAIKKGILQTVKVVDELVKVMGrHKPENIVIEMARENQ TTQKGQKNS | 777 |
| WP_011054416 | 703 | TFKEDIQKAQVSG-QGDS-LHEHIANLAGSPAIKKGILQTVKVVDELVKVMGrHKPENIVIEMARENQ TTQKGQKNS | 777 |
| WP_011284745 | 703 | TFKEDIQKAQVSG-QGDS-LHEHIANLAGSPAIKKGILQTVKVVDELVKVMGrHKPENIVIEMARENQ TTQKGQKNS | 777 |
| WP_011285506 | 703 | TFKEDIQKAQVSG-QGDS-LHEHIANLAGSPAIKKGILQTVKVVDELVKVMGrHKPENIVIEMARENQ TTQKGQKNS | 777 |
| WP_011527619 | 703 | TFKEDIQKAQVSG-QGDS-LHEHIANLAGSPAIKKGILQTVKVVDELVKVMGrHKPENIVIEMARENQ TTQKGQKNS | 777 |
| WP_012560673 | 703 | TFKEDLQKAQVSG-QGDS-LHEHIANLAGSPAIKKGILQTVKVVDELVKVMGrHKPENIVIEMARENQ TTQKGQKNS | 777 |
| WP_014407541 | 703 | TFKEDIQKAQVSG-QGHS-LHEQIANLAGSPAIKKGILQTVKVVDELVKVMG-HKPENIVIEMARENQ TTQKGQKNS | 776 |
| WP_020905136 | 703 | TFKEAIQKAQVSG-QGDS-LHEQIANLAGSPAIKKGILQTVKVVDELVKVMGrHKPENIVIEMARENQ TTQKGQKNS | 777 |
| WP_023080005 | 703 | TFKEDLQKAQVSG-QGDS-LHEHIANLAGSPAIKKGILQTVKVVDELVKVMG-HKPENIVIEMARENQ TTQKGQKNS | 776 |
| WP_023610282 | 703 | TFKEDIQKAQVSG-QGDS-LHEHIANLAGSPAIKKGILQTVKVVDELVKVMG-HKPENIVIEMARENQ TTQKGQKNS | 776 |
| WP_030125963 | 703 | TFKEDIQKAQVSG-QGDS-LHEHIANLAGSPAIKKGILQTVKVVDELVKVMGrHKPENIVIEMARENQ TTQKGQKNS | 777 |
| WP_030126706 | 703 | TFKEDIQKAQVSG-QGDS-LHEHIANLAGSPAIKKGILQTVKVVDELVKVMGrHKPENIVIEMARENQ TTQKGQKNS | 777 |
| WP_031488318 | 703 | TFKEDIQKAQVSG-QGDS-LHEHIANLAGSPAIKKGILQTVKVVDELVKVMGrHKPENIVIEMARENQ TTQKGQKNS | 777 |
| WP_032460140 | 703 | TFKEDIQKAQVSG-QGDS-LHEHIANLAGSPAIKKGILQTVKVVDELVKVMGrHKPENIVIEMARENQ TTQKGQKNS | 777 |
| WP_032461047 | 703 | TFKEDIQKAQVSG-QGDS-LHEHIANLAGSPAIKKGILQTVKVVDELVKVMGrHKPENIVIEMARENQ TTQKGQKNS | 777 |
| WP_032462016 | 703 | TFKEDIQKAQVSG-QGDS-LHEHIANLAGSPAIKKGILQTVKVVDELVKVMGrHKPENIVIEMARENQ TTQKGQKNS | 777 |
| WP_032462936 | 703 | TFKEDIQKAQVSG-QGDS-LHEHIANLAGSPAIKKGILQTVKVVDELVKVMGrHKPENIVIEMARENQ TTQKGQKNS | 777 |
| WP_032464890 | 703 | TFKEDIQKAQVSG-QGDS-LHEHIANLAGSPAIKKGILQTVKVVDELVKVMGrHKPENIVIEMARENQ TTQKGQKNS | 777 |
| WP_033888930 | 528 | TFKEDIQKAQVSG-QGDS-LHEHIANLAGSPAIKKGILQTVKVVDELVKVMGrHKPENIVIEMARENQ TTQKGQKNS | 602 |
| WP_038431314 | 703 | TFKEDIQKAQVSG-QGDS-LHEHIANLAGSPAIKKGILQTVKIVDELVKVMGrHKPENIVIEMARENQ TTQKGQKNS | 777 |
| WP_038432938 | 703 | TFKEAIQKAQVSG-QGHS-LHEQIANLAGSPAIKKGILQTVKVVDELVKVMG-HKPENIVIEMARENQ TTQKGQKNS | 776 |
| WP_038434062 | 703 | TFKEDIQKAQVSG-QGDS-LHEHIANLAGSPAIKKGILQTVKVVDELVKVMGrHKPENIVIEMARENQ TTQKGQKNS | 777 |
| BAQ51233 | 614 | TFKEDIQKAQVSG-QGDS-LHEHIANLAGSPAIKKGILQTVKVVDELVKVMGrHKPENIVIEMARENQ TTQKGQKNS | 688 |
| KGE60162 | | ---------------------------------------------------------------- ---------- | |
| KGE60856 | 703 | TFKEDIQKAQVSG-QGDS-LHEHIANLAGSPAIKKGILQSVKIVDELVKVMGrHKPENIVIEMARENQ TTQKGQKNS | 777 |
| WP_002989955 | 704 | SFKEEIARAQIIG-DVDD-IANVHDLPGSPAIKKGILQSVKIVDELVKVMG-HNPANIIIEMARENQ MTDKGRRNS | 777 |
| WP_003030002 | 707 | PFKQIIQKSQVVG-DVDD-IEAVVHDLPGSPAIKKGILQSVKIVDELVKVMG-DNPDNIVIEMARENQ TTNRGRSQS | 780 |
| WP_003065552 | 702 | SFKPIIDKARTGS-HSDN-LKEVIGELAGSPAIKKGILQSLKIVDELVKVMG-YEPEQIVVEMARENQ TTAKGLSRS | 775 |
| WP_001040076 | 705 | SFKPIIDKAQAGS-HSDN-LKEVVGELAGSPAIKKGILQSLKIVDELVKVMG-YEPEQIVVEMARENQ TTNQGRRNS | 778 |
| WP_001040078 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040080 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040081 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040083 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040085 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040087 | 705 | SFKSIISKAQSGS-HSDN-LKEVVGELAGSPAIKKGILQSLKIVDELVKVMG-YEPEQIVVEMARENQ TTNQGRRNS | 778 |
| WP_001040088 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040089 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040090 | 702 | SFKPIIDKARTGS-HLDN-LKEVVGELAGSPAIKKGILQSLKIVDELVKVMG-YEPEQIVVEMARENQ TTAKGLSRS | 775 |
| WP_001040091 | 702 | SFKPIIDKARTGS-HLDN-LKEVVGELAGSPAIKKGILQSLKIVDELVKVMG-YEPEQIVVEMARENQ TTAKGLSRS | 775 |
| WP_001040092 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040094 | 702 | SFKPIIDKARTGS-HSDN-LKEVVGELAGSPAIKKGILQSLKIVDELVKVMG-YEPEQIVVEMARENQ TTAKGLSRS | 775 |
| WP_001040095 | 702 | SFKPIIDKARTGS-HLDN-LKEVVGELAGSPAIKKGILQSLKIVDELVKVMG-YEPEQIVVEMARENQ TTAKGLSRS | 775 |
| WP_001040096 | 705 | SFKSIISKAQAGS-HSDN-LKEVVGELAGSPAIKKGILQSLKIVDELVKVMG-YEPEQIVVEMARENQ TTNQGRRNS | 778 |
| WP_001040097 | 702 | SFKPIIDKARTGS-HSDN-LKEVVGELAGSPAIKKGILQSLKIVDELVKVMG-YEPEQIVVEMARENQ TTAKGLSRL | 775 |
| WP_001040098 | 705 | SFKPIIDKAQAGS-HSDN-LKEVVGELAGSPAIKKGILQSLKIVDELVKVMG-YEPEQIVVEMARENQ TTNQGRRNS | 778 |
| WP_001040099 | 702 | SFKPIIDKARTGS-HSDN-LKEVVGELAGSPAIKKGILQSLKIVDELVKVMG-YEPEQIVVEMARENQ TTAKGLSRS | 775 |
| WP_001040100 | 705 | SFKPIIDKAQAGS-HSDN-LKEVVGELAGSPAIKKGILQSLKIVDELVKVMG-YEPEQIVVEMARENQ TTNQGRRNS | 778 |
| WP_001040104 | 702 | SFKPIIDKARTGS-HSDN-LKEVVGELAGSPAIKKGILQSLKIVDELVKVMG-YEPEQIVVEMARENQ TTAKGLSRS | 775 |
| WP_001040105 | 705 | SFKPIIDKAQAGS-HSDN-LKEVVGELAGSPAIKKGILQSLKIVDELVKVMG-YEPEQVVVEMARENQ TTNQGRRNS | 778 |
| WP_001040106 | 705 | SFKPIIDKAQAGS-HSDN-LKEVVGELAGSPAIKKGILQSLKIVDELVKVMG-YEPEQVVVEMARENQ TTNQGRRNT | 778 |
| WP_001040107 | 705 | SFKPIIDKAQAGS-HSDN-LKEVVGELAGSPAIKKGILQSLKIVDELVKVMG-YEPEQVVVEMARENQ TTNQGRRNT | 778 |
| WP_001040108 | 705 | SFKPIIDKAQAGS-HSDN-LKEVVGELAGSPAIKKGILQSLKIVDELVKVMG-YEPEQVVVEMARENQ TTNQGRRNT | 778 |

| | | | |
|---|---|---|---|
| WP_001040109 | 705 | SFKPIIDKAQAGS-HSDN-LKEVVGELAGSPAIKKGILQSLKIVDELVKVMG-YEPEQVVVEMARENQ TTNQGRRNT | 778 |
| WP_001040110 | 705 | SFKPIIDKAQAGS-HSDN-LKEVVGELAGSPAIKKGILQSLKIVDELVKVMG-YEPEQVVVEMARENQ TTNQGRRNT | 778 |
| WP_015058523 | 705 | SFKSIISKAQSGS-HSDN-LKEVVGELAGSPAIKKGILQSLKIVDELVKVMG-YEPEQIVVEMARENQ TTNQGRRNS | 778 |
| WP_017643650 | 702 | SFKPIIDKARTGS-HSDN-LKEVVGELAGSPAIKKGILQSLKIVDELVKVMG-YEPEQIVVEMARENQ TTAKGLSRL | 775 |
| WP_017647151 | 705 | SFKSIISKAQAGS-HSDN-LKEVVGELAGSPAIKKGILQSLKIVDELVKVMG-YEPEQIVVEMARENQ TTNQGRRNS | 778 |
| WP_017648376 | 705 | SFKSIISKAQAGS-HSDN-LKEVVGELAGSPAIKKGILQSLKIVDELVKVMG-YEPEQIVVEMARENQ TTNQGRRNS | 778 |
| WP_017649527 | 705 | SFKSIISKAQAGS-HSDN-LKEVVGELAGSPAIKKGILQSLKIVDELVKVMG-YEPEQIVVEMARENQ TTNQGRRNS | 778 |
| WP_017771611 | 705 | SFKPIIDKAQAGS-HSDN-LKEVVGELAGSPAIKKGILQSLKIVDELVKVMG-YEPEQVVVEMARENQ TTNQGRRNT | 778 |
| WP_017771984 | 705 | SFKSIISKAQAGS-HSDN-LKEVVGELAGSPAIKKGILQSLKIVDELVKVMG-YEPEQIVVEMARENQ TTNQGRRNS | 778 |
| CFQ25032 | 705 | SFKSIISKAQSGS-HSDN-LKEVVGELAGSPAIKKGILQSLKIVDELVKVMG-YEPEQIVVEMARENQ TTNQGRRNS | 778 |
| CFV16040 | 705 | SFKSIISKAQAGS-HSDN-LKEVVGELAGSPAIKKGILQSLKIVDELVKVMG-YEPEQIVVEMARENQ TTNQGRRNS | 778 |
| KLJ37842 | 705 | SFKSIISKAQAGS-HSDN-LKEVVGELAGSPAIKKGILQSLKIVDELVKVMG-YEPEQIVVEMARENQ TTNQGRRNS | 778 |
| KLJ72361 | 719 | SFKSIISKAQAGS-HSDN-LKEVVGELAGSPAIKKGILQSLKIVDELVKVMG-YEPEQIVVEMARENQ TTNKGRRNT | 792 |
| KLL20707 | 705 | SFKSIISKAQAGS-HSDN-LKEVVGELAGSPAIKKGILQSLKIVDELVKVMG-YEPEQIVVEMARENQ TTNQGRRNS | 778 |
| KLL42645 | 702 | SFKPIIDKARTGS-HSDN-LKEVVGELAGSPAIKKGILQSLKIVDELVKVMG-YEPEQIVVEMARENQ TTAKGLSRS | 775 |
| WP_047207273 | 705 | SFKSIISKAQAGS-HSDN-LKEVVGELAGSPAIKKGILQSLKIVDELVKVMG-YEPEQIVVEMARENQ TTNQGRRNS | 778 |
| WP_047209694 | 705 | SFKPIIDKAQAGS-HSDN-LKEVVGELAGSPAIKKGILQSLKIVDELVKVMG-YEPEQVVVEMARENQ TTNQGRRNT | 778 |
| WP_050198062 | 705 | SFKSIISKAQAGS-HSDN-LKEVVGELAGSPAIKKGILQSLKIVDELVKVMG-YEPEQIVVEMARENQ TTNQGRRNS | 778 |
| WP_050201642 | 705 | SFKSIISKAQAGS-HSDN-LKEVVGELAGSPAIKKGILQSLKIVDELVKVMG-YEPEQIVVEMARENQ TTNQGRRNS | 778 |
| WP_050204027 | 705 | SFKSIISKAQAGS-HSDN-LKEVVGELAGSPAIKKGILQSLKIVDELVKVMG-YEPEQIVVEMARENQ TTNQGRRNS | 778 |
| WP_050881965 | 705 | SFKSIISKAQAGS-HSDN-LKEVVGELAGSPAIKKGILQSLKIVDELVKVMG-YEPEQIVVEMARENQ TTNQGRRNS | 778 |
| WP_050886065 | 705 | SFKSIISKAQAGS-HSDN-LKEVVGELAGSPAIKKGILQSLKIVDELVKVMG-YEPEQIVVEMARENQ TTNQGRRNS | 778 |
| AHN30376 | 705 | SFKSIISKAQSGS-HSDN-LKEVVGELAGSPAIKKGILQSLKIVDELVKVMG-YEPEQIVVEMARENQ TTNQGRRNS | 778 |
| EA078426 | 705 | SFKSIISKAQAGS-HSDN-LKEVVGELAGSPAIKKGILQSLKIVDELVKVMG-YEPEQIVVEMARENQ TTNQGRRNS | 778 |
| CCW42055 | 705 | SFKSIISKAQSGS-HSDN-LKEVSELAGSPAIKKGILQSLKIVDELVKVMG-YKPEQIVVEMARENQ TTNQGRRNS | 778 |
| WP_003041502 | 704 | SFKEEIAKAQIIG-DVDD-IANVHDLPGSPAIKKGILQSVKIVDELVKVMG-HNPANIIIEMARENQ TTDRGRRNS | 777 |
| WP_037593752 | 705 | SFKEEIARAQIIG-DVDD-IANVHDLPGSPAIKKGILQSVKIVDELVKVMG-HNPANIIIEMARENQ TTDKGRRNS | 778 |
| WP_049516684 | 705 | SFKEEIARAQIIG-DVDD-IANVHDLPGSPAIKKGILQSVKIVDELVKVMG-HNPANIIIEMARENQ TTDKGRRNS | 778 |
| GAD46167 | 704 | SFKEEIARAQIIG-DVDD-IANVHDLPGSPAIKKGILQSVKIVDELVKVMG-HNPANIIIEMARENQ TTDKGRRNS | 777 |
| WP_018363470 | 705 | SFKQIIQEAQVVG-DVDD-IETVHDLPGSPAIKKGILQSVKIVDELIKVMG-DNPDNIVIEMARENQ TTNRGRSQS | 778 |
| WP_003043819 | 713 | TFKEEIEKAQVSG-QGDS-LHEQIADLAGSPAIKKGILQTVKIVDELVKVMG-HKPENIVIEMARENQ TTTKGLQQS | 786 |
| WP_006269658 | 704 | SFKEEIARAQIID-DVDD-IANVHDLPGSPAIKKGILQSVKIVDELVKVMG-HNPANIIIEMARENQ TTDKGRRNS | 777 |
| WP_048800889 | 704 | PFKQIIKDAQAID-DVDD-IELIVHDLPGSPAIKKGILQSIKIVDELVKVMG-YNPDNIVIEMARENQ TTTKGRRNS | 777 |
| WP_012767106 | 703 | TFKEAIQKAQVSG-QGHS-LHEQIANLAGSPAIKKGILQSVKIVDELVKVMG-HKPENIVIEMARENQ TTQKGQKNS | 776 |
| WP_014612333 | 703 | TFKEAIQKAQVSG-QGHS-LHEQIANLAGSPAIKKGILQSVKIVDELVKVMG-HKPENIVIEMARENQ TTQKGQKNS | 776 |
| WP_015017095 | 703 | TFKEAIQKAQVSG-QGHS-LHEQIANLAGSPAIKKGILQSVKIVDELVKVMG-HKPENIVIEMARENQ TTQKGQKNS | 776 |
| WP_015057649 | 703 | TFKEAIQKAQVSG-QGHS-LHEQIANLAGSPAIKKGILQSVKIVDELVKVMG-HKPENIVIEMARENQ TTQKGQKNS | 776 |
| WP_048327215 | 703 | TFKEAIQKAQVSG-QGHS-LHEQIANLAGSPAIKKGILQSVKIVDELVKVMG-HKPENIVIEMARENQ TTQKGQKNS | 776 |
| WP_049519324 | 703 | TFKEAIQKAQVSG-QGHS-LHEQIANLAGSPAIKKGILQSVKIVDELVKVMG-HKPENIVIEMARENQ TTQKGQKNS | 776 |
| WP_012515931 | 703 | SFIDEIAKAQVIG-KTEY-SKDIVGNLAGSPAIKKGISQTIKIVDELVKIMG-YLPQQIVIEMARENQ TTAQGIKNA | 776 |
| WP_021320964 | 703 | SFIDEIAKAQVIG-KTEY-SKDIVGNLASSPAIKKGISQTIKIVDELVKIMG-YLPQQIVIEMARENQ TTAQGIKNA | 776 |
| WP_037581760 | 703 | SFIDEIAKAQVIG-KTEY-SKDLVGNLAGSPAIKKGISQTIKIVDELVKIMG-YLPQQIVIEMARENQ TTAQGIKNA | 776 |
| WP_004232481 | 704 | SFKTTIQEAQVVG-DVDD-IEAVVHDLPGSPAIKKGILQSVKIVDELVKVMG-HNPQNIVIEMARENQ ITGYGRNRS | 777 |
| WP_009854540 | 703 | PFKQIIQKSQVVG-DVDD-VTSVVRELPGSPAIKKGILQSVKIVDELVKVMG-HNPDNIVIEMARENQ TTNRGRNQS | 778 |
| WP_012962174 | 705 | PFKQIIQKSQVVG-DIDD-VTSVVRELPGSPAIKKGILQSVKIVDELVKVMG-HNPDNIVIEMARENQ TTNRGRNQS | 778 |
| WP_039695303 | 707 | PFKQIIQKSQVVG-DVDD-IEAVVHDLPGSPAIKKGILQSVKIVDELVKVMG-GNPDNIVIEMARENQ TTNRGRRNS | 780 |
| WP_014334983 | 704 | SFKTIIQEAQVVG-DVDD-IEAVVHDLPGSPAIKKGILQSVKIVDELVKVMG-DNPDNIVIEMARENQ TTGYGRNKS | 777 |
| WP_030992269 | 703 | DFAKIIKNEQEKTIKNES-LEETIANLAGSPAIKKGIIQSIKIVDELVKIMG-QNPDNIVIEMARENQ STMQGIKNS | 777 |
| AHY15608 | 703 | DFAKIIKNEQEKTIKNES-LEETIANLAGSPAIKKGIIQSIKIVDELVKIMG-QNPDNIVIEMARENQ STMQGIKNS | 777 |
| AHY17476 | 703 | DFAKIIKNEQEKTIKNES-LEETIANLAGSPAIKKGIIQSIKIVDELVKIMG-QNPDNIVIEMARENQ STMQGIKNS | 777 |
| ESR09100 | | | |
| AGM98575 | 703 | DFAKIIKNEQEKTIKNES-LNQVVSDIAGSPAIKKGIIQSIKIVDELVKIMG-QNPDNIVIEMARENQ STMQGIKNS | 777 |
| ALF27331 | 704 | SFKEEIAKAQVIG-ETDN-LNQVVSDIAGSPAIKKGILQSLKIVDELVKIMG-HQPENIVIEMARENQ FTNQGRRNS | 777 |

| | | | |
|---|---|---|---|
| WP_018372492 | 717 | DFKEIIRKAQTIE-NIDT-NQALVSSLPGSPAIKKGLLQSLNIVDEIIAIMG-YAPTNIVIEMARENQ TTQKGRDNS | 790 |
| WP_045618028 | 703 | SFKEIIQKAQVVG-KTND-VKQVQELPGSPAIKKGILQSIKIVDELVKIMG-HAPESIVIEMARENQ TTARGKKNS | 776 |
| WP_045635197 | 702 | SFKEIIQKAQVIG-KTDD-VKQVQELSGSPAIKKGILQSIKIVDELVKVMG-HAPESIVIEMARENQ TTARGKKNS | 775 |
| WP_002263887 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002264920 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002269043 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002269448 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002271977 | 704 | SFKEEIAKAQVIG-ETDN-LNQVVSDIAGSPAIKKGILQSLKIVDELVKIMG-HQPENIVVEMARENQ FTNQGRQNS | 777 |
| WP_002272766 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002273241 | 704 | SFKEEIAKAQVIG-ETDN-LNQVVSDIAGSPAIKKGILQSLKIVDELVKIMG-HQPENIVVEMARENQ FTKQGRRNS | 777 |
| WP_002275430 | 704 | SFKEEIAKAQVIG-ETDN-LNQVVSDIAGSPAIKKGILQSLKIVDELVKVMG-HQPENIVVEMARENQ FTNQGRRNS | 777 |
| WP_002276448 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002277050 | 705 | TFKDDIVKAQYVD-NSDD-LHQVVQSLAGSPAIKKGILQSLKIVDELVKVMG-KEPEQIVVEMARENQ TTAKGRRNS | 778 |
| WP_002277364 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002279025 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002279859 | 704 | SFKEEIAKAQVIG-ETDN-LNQVVSDIAGSPAIKKGILQSLKIVDELVKIMG-HQPENIVVEMARENQ FTKQGRRNS | 777 |
| WP_002280230 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002281696 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002282247 | 705 | TFKDDIVKAQYVD-NSDD-LHQVVSLAGSPAIKKGILQSLKIVDELVKVMG-KEPEQIVVEMARENQ TTAKGRRNS | 778 |
| WP_002282906 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002283846 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002287255 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002288990 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002289641 | 704 | SFKEEIAKAQVIG-ETDN-LNQVVSDIAGSLAIKKGILQSLKIVDELVKIMG-HQPENIVVEMARENQ FTNQGRRNS | 777 |
| WP_002290427 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002295753 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002296423 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002304487 | 714 | SFKEEIAKAQVIG-EMDG-LNQVVSDIAGSPAIKKGILQSLKIVDELVKVMG-HNPANIVIEMARENQ TTAKGRSS | 787 |
| WP_002305844 | 704 | SFKEEIAKAQVIG-ETDN-LNQVVSDIAGSPAIKKGILQSLKIVDELVKIMG-HQPENIVVEMARENQ FTKQGRRNS | 777 |
| WP_002307203 | 704 | SFKEEIAKAQVIG-ETDN-LNQVVSDIAGSLAIKKGILQSLKIVDELVKIMG-HQPENIVVEMARENQ FTNQGRRNS | 777 |
| WP_002310390 | 704 | SFKEEIAKAQVIG-ETDN-LNQVVSDIAGSPAIKKGILQSLKIVDELVKIMG-HQPENIVVEMARENQ FTNQGRRNS | 777 |
| WP_002352408 | 704 | SFKEEIAKAQVIG-ETDN-LNQVVSDIAGSPAIKKGILQSLKIVDELVKIMG-HQPENIVVEMARENQ FTNQGQRNS | 777 |
| WP_012997688 | 704 | SFKEEIAKAQVIG-ETDN-LNQVVSDIAGSPAIKKGILQSLKIVDELVKIMG-HQPENIVVEMARENQ FTNQGRRNS | 777 |
| WP_014677909 | 705 | TFKDDIVKAQYVD-NSDD-LHQVVQSLAGSPAIKKGILQSLKIVDELVKVMG-KEPEQIVVEMARENQ TTAKGRRNS | 778 |
| WP_019312892 | 704 | SFKEEIAKAQVIG-ETDN-LNQVVSDIAGSPAIKKGILQSLKIVDELVKIMG-HQPENIVVEMARENQ FTNQGRRNS | 777 |
| WP_019313659 | 704 | SFKEEIAKAQVIG-ETDN-LNQVVSDIAGSPAIKKGILQSLKIVDELVKIMG-HQPENIVVEMARENQ FTNQGRRNS | 777 |
| WP_019314093 | 705 | TFKDDIVKAQYVD-NSDD-LHQVVQSLAGSPAIKKGILQSLKIVDELVKIMG-KEPEQIVVEMARENQ FTNQGRRNS | 778 |
| WP_019315370 | 704 | SFKEEIAKAQVIG-ETDN-LNQVVSDIAGSPAIKKGILQSLKIVDELVKIMG-HQPENIVVEMARENQ FTNQGRRNS | 777 |
| WP_019803776 | 704 | SFKEEIAKAQVIG-ETDN-LNQVVSDIAGSPAIKKGILQSLKIVDELVKIMG-HQPENIVVEMARENQ FTNQGRRNS | 777 |
| WP_019805234 | 704 | SFKEEIAKAQVIG-ETDN-LNQVVSDIAGSLAIKKGILQNLKIVDELVKIMG-HQPENIVVEMARENQ FTNQGRRNS | 777 |
| WP_024783594 | 704 | SFKEEIAKAQVIG-ETDN-LNQVVSDIAGSPAIKKGILQSLKIVDELVKIMG-HQPENIVVEMARENQ FTNQGRRNS | 777 |
| WP_024784288 | 705 | TFKDDIVKAQYVD-NSDD-LHQVVQSLAGSPAIKKGILQSLKIVDELVKVMG-KEPEQIVVEMARENQ TTAKGRRNS | 778 |
| WP_024784666 | 704 | SFKEEIAKAQVIG-ETDN-LNQVVSDIAGSPAIKKGILQSLKIVDELVKIMG-HQPENIVVEMARENQ FTNQGRRNS | 777 |
| WP_024784894 | 704 | SFKEEIAKAQVIG-ETDN-LNQVVSDIAGSPAIKKGILQSLKIVDELVKIMG-HQPENIVVEMARENQ FTNQGRRNS | 777 |
| WP_024786433 | 705 | TFKDDIVKAQYVD-NSDD-LHQVVQSLAGSPAIKKGILQSLKIVDELVKVMG-KEPEQIVVEMARENQ TTAKGRRNS | 778 |
| WP_049473442 | 704 | SFKEEIAKAQVIG-ETDN-LNQVVSDIAGSPAIKKGILQSLKIVDELVKIMG-HQPENIVVEMARENQ FTNQGRRNS | 777 |
| WP_049474547 | 704 | SFKEEIAKAQVIG-ETDN-LNQVVSDIAGSPAIKKGILQSLKIVDELVKIMG-HQPENIVVEMARENQ FTNQGRRNS | 777 |
| EMC03581 | 697 | SFKEEIAKAQVIG-ETDN-LNQVVSDIAGSLAIKKGILQSLKIVDELVKIMG-HQPENIVVEMARENQ FTNQGRRNS | 770 |
| WP_000428612 | 705 | SFKEITQKAQVVG-KTDD-VKQVVQELPGSPAIKKGILQSIKIVDELVKVMG-HEPESIVIEMARENQ TTARGKKNS | 778 |
| WP_000428613 | 703 | SFKEIIQKAQVIG-ETND-VKQVQELPGSPAIKKGILQSIKIVDELVKVMG-HTPESIVIEMARENQ TTARGKKNS | 776 |
| WP_049523028 | 702 | SFKEIIQKAQVVG-KTDD-VKQVQELPGSPAIKKGILQSIKIVDEVVKVMG-HAPESVVIEMARENQ TTNKGKSKS | 775 |
| WP_003107102 | 672 | DFASIIKEAQEKTIKSEK-LEEFIANLAGSPAIKKGILQSVKIVDEVVKVMG-YEPSNIVIEMARENQ STQRGINNS | 746 |

-continued

| | | | | |
|---|---|---|---|---|
| WP_054279288 | 705 | SFKEEIKAQEGG-LKDS-INDQIRDLAGSPAIKKGLLQTINIVDEIVKIMG-KAPQHIVVEMARDVQ | KTDIGVKQS | 778 |
| WP_049531101 | 703 | SFKEIIQESQVVG-KPDD-VKQIVQELPGSSAIKKGILQSIKILVDELVKVMG-HDPESIVIEMARENQ | TTARGKKNS | 776 |
| WP_049538452 | 703 | SFKEIIQKAQVFG-KTND-VKQVVQELPGSPAIKKGILQSIKIVEELVKVMG-HEPESIVIEMARENQ | TTTRGKKNS | 776 |
| WP_049549711 | 703 | SFKKIIQKSQVVG-ETDD-VKQVVRELPGSPAIKKGILQSIKIVDELVKVMD-HAPESIVIEMARENQ | TTARGKKNS | 776 |
| WP_007896501 | 706 | DFEKLIDDAQKKAiKRES-LTEAVANLAGSPAIKKGILQSLKVVDEIVKVMG-HNPDNIVIEMSRENQ | TTAQGLKNA | 780 |
| EFR44625 | 658 | DFEKLIDDAQKKAiKRES-LTEAVANLAGSPAIKKGILQSLKVVDEIVKVMG-HNPDNIVIEMSRENQ | TTAQGLKNA | 732 |
| WP_002897477 | 702 | SFKEIIQKAQVVG-KTDD-VKQVVQELPGSPAIKKGILQSIKIVDELVKVMG-YALESIVIEMARENQ | TTARGKKNS | 775 |
| WP_002906454 | 703 | SFKEIIQKAQVVG-KTDD-VKQVVEIPGSPAIKKGILQSIKIVDELVKVMG-HNPESIVIEMARENQ | TTAKGKKNS | 775 |
| WP_009729476 | 706 | SFKEIIQKAQVVG-KTND-VKQVVQELPGSPAIKKGILQSIKIVDELVKVMG-HAPESIVIEMARENQ | TTARGKKNS | 779 |
| CQR24647 | 705 | SFKDEIANSQVIG-DGDD-LHQVVQELAGSPAIKKGILQSIKIVDELVKVMG-YNPEQIVVEMARENQ | TTARGRNNS | 778 |
| WP_000066813 | 703 | SFKEIIQKAQVFG-KTND-VKQVVQELPGSPAIKKGILQSIKIVEELVKVMG-HAPESIVIEMARENQ | TTARGKKNS | 776 |
| WP_009754323 | 702 | SFKEIIQKAQVVG-KTND-LTQVVRELSGSPAIKKGILQSIKIVDELVKIMG-YAPESIVIEMARENQ | TTAKGKKNS | 775 |
| WP_044674937 | 704 | SFVDEIRLAQGSG-EAED-YRAEVQNLAGSPAIKKGILQSLKIVDELIEVMG-YDPBHIVVEMARENQ | FTNQGRRNS | 777 |
| WP_044676715 | 704 | SFVDEIRLAQGSG-EAED-YRAEVQNLAGSPAIKKGILQSLKIVDELIEVMG-YDPEHIVVEMARENQ | FTNQGRRNS | 777 |
| WP_044680361 | 702 | SFVDEIRLAQGSG-EAED-YRAEVQNLAGSPAIKKGILQSLKIVDELIEVMG-YDPEHIVVEMARENQ | FTNQGRRNS | 775 |
| WP_044681799 | 704 | SFVDEIRLAQGSG-EAED-YRAEVQNLAGSPAIKKGILQSLKIVDELVEVMG-YDPEHIVVEMARENQ | FTNQGRRNS | 777 |
| WP_049533112 | 704 | SEKEETAKAQVIG-ETDD-LNQVVSDIAGSPAIKKGILQSLKIVDELVKVMG-YNPANIVIEMARENQ | TTDKGRRNS | 777 |
| WP_029090905 | 683 | LFKKIIEEQFENEtALLN--KQRIDELAASPANKKGIWQATKIVKELEKVLQ-QPAENIFIEFARSDE | ES----KRS | 752 |
| WP_006506696 | 706 | GYAQMIEEATSCPeDGKE-TYEEVERLAGSPALKRGIWQSLQIVEEITKVMK-CRPKYIYIEFERSEE | ----KERT | 776 |
| AIT42264 | 703 | TEKEDIQKAQVSG-QGDS-LHEHIANLAGSPAIKGIIQTVKVVDELVKVMGrHKPENIVIEMARENQ | TTQKGQKNS | 777 |
| WP_034440723 | 711 | SFKEKIRKAQDIN-QVND-IKEIVKDLPGSPAIKKGIYQSIRIVDEIIRKMK-DRPKNIVIEMARENQ | TTQEGKNKS | 784 |
| AKQ21048 | 703 | TEKEDIQKAQVSG-QGDS-LHEHIANLAGSPAIKKGIIQTVKVVDELVKVMGrHKPENIVIEMARESQ | TTKKGKDLS | 777 |
| WP_004636532 | 707 | SFKKKIEDAQTIE-DTTH-IYDTVAELPGSPAIKGIRQALKIVEEIIDIIG-YEPENIVVEMARENQ | TTSTGKRRS | 780 |
| WP_002364836 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_016631044 | 666 | SFKNAIQKAQSSE-HEET-LSETVNELAGSPAIKKGIWQSLKIYQSLKIVDELVAIMG-YAPKRIVVEMARENQ | TTSTGKRRS | 739 |
| EMS75795 | 455 | SFKEELANELALA-GNQS-LLEVVEALLGSPAIKKGIWQTLKIVEELIEIIG-YNPKNIVVEMARENQ | RT----NRS | 524 |
| WP_002373311 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_002378009 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_002407324 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_002413717 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_010777580 | 717 | SFKNAIQKAQSSE-HEET-LSETVNELAGSPAIKKGIWQSLKIYQSLKIVDELVAIMG-YAPKRIVVEMARENQ | TTSTGKRRS | 790 |
| WP_010818269 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_010824395 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_016622645 | 715 | SFKNAIQKAQSSE-HEET-LSETVNELAGSPAIKKGIWQSLKIYQSLKIVDELVAIMG-YAPKRIVVEMARENQ | TTSTGKRRS | 788 |
| WP_033624816 | 715 | SFKKEIKKAQMIT-DTEN-LEEIVKELTGSPAIKKGILQSLKIYQSLKIVDELVAIMG-YEPANIVVEMARENQ | TTGRGLKSS | 788 |
| WP_033625576 | 715 | SFKKEIKKAQMIT-DTEN-LEEIVKELTGSPAIKKGILQSLKIYQSLKIVDELVAIMG-YEPANIVVEMARENQ | TTGRGLKSS | 788 |
| WP_033789179 | 715 | SFKKEIKKAQMIT-DTEN-LEEIVKELTGSPAIKKGILQSLKIYQSLKIVDELVAIMG-YEPANIVVEMARENQ | TTGRGLKSS | 788 |
| WP_002310644 | 715 | SFKKEIKKAQMIT-DTEN-LEEIVKELTGSPAIKKGILQSLKIYQSLKIVDELVGIMG-YEPANIVVEMARENQ | TTGRGLKSS | 788 |
| WP_002322694 | 716 | SFKKEIKKAQMIT-DTEN-LEEIVKELTGSPAIKKGILQSLKIYQSLKIVDEIVGIMG-YEPANIVVEMARENQ | TTGRGLKSS | 789 |
| WP_002314015 | 715 | SFKKEIKKAQMIT-DTEN-LEEIVKELTGSPAIKKGILQSLKIYQSLKIVDEIVGIMG-YEPANIVIEMARENQ | TTGRGLKSS | 788 |
| WP_002320716 | 716 | SFKEEIAKATVFS-KHKS-LVDVIQDLPGSPAIKKGIWQSLKIVEELIAIIG-YKPKNIVIEMARENQ | TTGRGLKSS | 789 |
| WP_002330729 | 716 | SFKEEIAKATVFS-KHKS-LVDVIQDLPGSPAIKKGIWQSLKIVEELIAIIG-YKPKNIVIEMARENQ | TTGRGLKSS | 789 |
| WP_002335161 | 716 | SFKEEIAKATVFS-KHKS-LVDVIQDLPGSPAIKKGIWQSLKIVEELIAIIG-YKPKNIVIEMARENQ | TTGRGLKSS | 789 |
| WP_002345439 | 711 | SFKEEIAKATVFS-KHKS-LVDVIQDLPGSPAIKKGIWQSLKIVEELIAIIG-YKPKNIVIEMARENQ | KT----HRT | 780 |
| WP_034867970 | 711 | SFKEEIAKATVFS-KHKS-LVDVIQDLPGSPAIKKGIWQSLKIVEELIAIIG-YKPKNIVIEMARENQ | KT----HRT | 780 |
| WP_034700478 | 711 | SFKEEIAKATVFS-KHKS-LVDVIQDLPGSPAIKKGIWQSLKIVEELIAIIG-YKPKNIVIEMARENQ | KT----HRT | 780 |
| WP_047937432 | 708 | SFKKIIEDSQPYK-EQQS-AEEIVSELSGSPAIKKGILQSLKIVDELVAIMG-YKPKNIVIEMARENQ | TTGRGKQNS | 781 |
| WP_023519017 | 705 | SPKETIANELIMS-DSNV-LLDQVKAIPGSPAVKKGIWQSIKIVEELIGIIG-KAPKNIVIEMARENQ | RTSR----S | 774 |
| WP_010770040 | 708 | SFKSEIAEAQSDM-NTED-LHEVVQNLAGSPAIKKGIWQSIKIVDELVDIMG-SLPKNIVVEMARENQ | TTSRGRTNS | 781 |
| WP_048604708 | 704 | TFKEEIBEQLKA-NSBEsLIEIVQNLAGSPAIKKGIFQSLKIVDELVEIMG-YAPTNIVEMARENQ | TTANGRRNS | 778 |

-continued

| ID | Seq | End |
|---|---|---|
| WP_010750235 | 710 SFKEEIAKELTLS-DKQS-LLEVVEAIPGSPAIKKGIWQTLKIVEELIAIIG-YKPKNIVIEMARENQ TTTGGKNRS | 783 |
| AII16583 | 742 TFKEDIQKAQVSG-QGDS-LHEHIANLAGSPAIKKGILQTVKVVDELVKVMGrHKPENIVIEMARENQ TTQKGQKNS | 816 |
| WP_029073316 | 718 GFKKTIDDANSTSvSGKF-SYAEVQELAGSPAIKRGIWQALLIVDEIKKIMK-HEPAHVYIEFARNED ----KERK | 788 |
| WP_031589969 | 718 GFKKTIDDANSTSvSGKF-SYAEVQELAGSPAIKRGIWQALLIVDEIKKIMK-HEPAHVYIEFARNED ----KERK | 788 |
| KDA45870 | 699 SFKETIKNAQVIE-KEET-LAKTVQELPGSPAIKKGILQSLEIVDEIIKVMG-YKPKSIVVEMARETQ --THGTRKR | 771 |
| WP_039099354 | 713 DFDKLITEANQMM-LAENdVQDVINDLYTSPQNKKALRQILLVVNDIQKAMKgQAPERILIEFAREDE VNPRLSVQR | 788 |
| AKP02966 | 707 DFKNYIENHNLNKnEDQN-ISNLVNDIHVSPALKRGITQSIKIVQEIVKFMG-HAPKYIFIEVTRETK TTSRGKRIQ | 785 |
| WP_010991369 | 707 SFKSIIEKEQVTT-ADKD-IQSIVADLAGSPAIKKGILQSLKIVDELVSVMG-YPPQTIVVEMARENQ TTGKGKNNS | 780 |
| WP_033838504 | 710 SFKSIIEKEQVTT-ADKD-IQSIVADLAGSPAIKKGILQSLKIVDELVSVMG-YPPQTIVVEMARENQ TTGKGKNNS | 783 |
| EHN60060 | 476 SFKSIIEKEQVTT-ADKD-IQSIVADLAGSPAIKKGILQSLKIVDELVSVMG-YPPQTIVVEMARENQ TTGKGKNNS | 549 |
| EFR89594 | 326 SFKSIIEKEQVST-ADKG-IQSIVAELAGSPAIKKGILQSLKIVDELVGIMG-YPPQTIVVEMARENQ TTGKGKNNS | 399 |
| WP_038409211 | 707 SFKSIIEKEQVST-ADKG-IQSIVAELAGSPAIKKGILQSLKIVDELVGIMG-YPPQTIVVEMARENQ TTGKGKNNS | 780 |
| EFR95520 | 707 SFKSIIEKEQVST-TDKD-LQSIVADLAGSPAIKKGILQSLKIVDELVSIMG-YPPQTIVVEMARENQ TTGKGKNNS | 780 |
| WP_003723650 | 707 SFKSIIEKEQVST-TDKD-LQSIVADLAGSPAIKKGILQSLKIVDELVSIMG-YPPQTIVVEMARENQ TTGKGKNNS | 780 |
| WP_003727705 | 707 SFKSIIEKEQVST-TDKD-LQSIVADLAGSPAIKKGILQSLKIVDELVSIMG-YPPQTIVVEMARENQ TTGKGKNNS | 780 |
| WP_003730785 | 707 SFKSIIEKEQVST-TDKD-LQSIVADLAGSPAIKKGILQSLKIVDELVSIMG-YPPQTIVVEMARENQ TTGKGKNNS | 780 |
| WP_003733029 | 707 SFKSIIEKEQVST-ADKD-IQSIVAELAGSPAIKKGILQSLKIVDELVSIMG-YPPQTIVVEMARENQ TTGKGKNNS | 780 |
| WP_003739838 | 707 SFKSIIEKEQVST-TDKD-LQSIVADLAGSPAIKKGILQSLKIVDELVSIMG-YPPQTIVVEMARENQ TTVKGKNNS | 780 |
| WP_014601172 | 707 SFKSIIEKEQVST-ADKD-LQSIVADLAGSPAIKKGILQSLKIVDELVSIMG-YPPQTIVVEMARENQ TTNKGKNNS | 780 |
| WP_023548323 | 707 SFKSIIEKEQVST-ADKD-LQSIVADLAGSPAIKKVEELVSVMG-YPPQTIVVEMARENQ TTNKGKNNS | 780 |
| WP_031665337 | 707 SFKSIIEKEQVST-TDKD-LQSIVAELAGSPAIKKGILQSLKIVDELVSIMG-YPPQTIVVEMARENQ TTNKGKNNS | 780 |
| WP_031669209 | 707 SFKSIIEKEQVST-ADKD-LQSIVADLAGSPAIKKGILQSLKIVDELVSIMG-YPPQTIVVEEMARENQ TTGKGKNNS | 780 |
| WP_033920898 | 707 SFKSIIEKEQVST-TDKD-LQSIVADLAGSPAIKKGILQSLKIVDELVSIMG-YPPQTIVVEMARENQ TTGKGKNNS | 780 |
| AKI42028 | 710 SFKSIIEKEQVST-ADKD-LQSIVADLAGSPAIKKGILQSLKVVEELVSVMG-YPPQTIVVEMARENQ TTGKGKNNS | 783 |
| AKI50529 | 710 SFKSIIEKEQVST-ADKD-LQSIVADLAGSPAIKKGILQSLKVVEELVSVMG-YPPQTIVVEMARENQ TTGKGKNNS | 783 |
| EFR83390 | 155 SFKSIIEKEQVST-ADKD-IQSIVADLAGSPAIKKGILQSLKIVDELVSIMG-YPPQTIVVEMARENQ TTGKGKNNS | 228 |
| WP_046323366 | 707 SFKSIIEKEQVST-ADKD-LQSIVADLAGSPAIKKGILQSLKIVDELVSIMG-YPPQTIVVEMARENQ TTGKGKNNS | 780 |
| AKE81011 | 719 TFKEDIQKAQVSG-QGDS-LHEHIANLAGSPAIKKGILQTVKVVDELVKVMGrHKPENIVIEMARENQ TTQKGQKNS | 793 |
| CUO82355 | 710 GYAQMIEEASSCPkDGKF-TYEEVAKLAGSPALKRGIWQSLQIVEEITKVMK-CRPKYIYIEPERSEE ----KVRK | 780 |
| WP_033162887 | 713 GYKQIIEESNMQDiEGPF-KYDEVKKLAGSPAIKKGIWQALLVVREITKFMK-HEPSHIYIEFAREEQ ----KERT | 783 |
| AGZ01981 | 736 TFKEDIQKAQVSG-QGDS-LHEHIANLAGSPAIKKGILQTVKVVDELVKVMGrHKPENIVIEMARENQ TTQKGQKNS | 810 |
| AKA60242 | 703 TFKEDIQKAQVSG-QGDS-LHEHIANLAGSPAIKKGILQTVKVVDELVKVMGrHKPENIVIEMARENQ TTQKGQKNS | 777 |
| AKS40380 | 703 TFKEDIQKAQVSG-QGDS-LHEHIANLAGSPAIKKGILQTVKVVDELVKVMGrHKPENIVIEMARENQ TTQKGQKNS | 777 |
| 4UN5_B | 707 TFKEDIQKAQVSG-QGDS-LHEHIANLAGSPAIKKGILQTVKVVDELVKVMGrHKPENIVIEMARENQ TTQKGQKNS | 781 |
| WP_010922251 | 778 RERMKRIEEGIK ELGS QILKEHP--VE---NTQLQNEKLYLYYLQNGRDMYVDQEL--D--INRLSDYDVDEH | 841 |
| WP_039695303 | 781 QQRLKKLQNSLK PSYI E----DK--VE--NSHLQNDQLFLYYIQNGKDMYTGDEL--D--IDHLSDYDIDHI | 851 |
| WP_045635197 | 776 QQRYKRIEDSLK ILAS NILKENP-TD--NNQLQNDRLFLYYLQNGKDMYTGEAL--D--INQLSSYDIDHI | 843 |
| 5AXW_A | 488 KDAQKMINEMQK QTNE EIIRITGk-E---NAKYLIEKIKIHDMQPGKCLYSLEAIpIEdILNNPNYEVDHI | 561 |
| WP_009880683 | 462 RERMKRIEEGIK ELGS DILKEYP--VE----NTQLQNEKLYLYYLQNGRDMYVDQEL--D--INRLSDYDVDHI | 525 |
| WP_010922251 | 778 RERMKRIEEGIK ELGS QILKEYP--VE----NTQLQNEKLYLYYLQNGRDMYVDQEL--D--INRLSDYDVDHI | 841 |
| WP_011054416 | 778 RERMKRIEEGIK ELGS QILKEYP--VE----NTQLQNEKLYLYYLQNGRDMYVDQEL--D--INRLSDYDVDHI | 841 |
| WP_011284745 | 778 RERMKRIEEGIK ELGS QILKEYP--VE----NTQLQNEKLYLYYLQNGRDMYVDQEL--D--INRLSDYDVDHI | 841 |
| WP_011285506 | 778 RERMKRIEEGIK ELGS QILKEYP--VE----NTQLQNEKLYLYYLQNGRDMYVDQEL--D--INRLSDYDVDHI | 841 |
| WP_011527619 | 778 RERMKRIEEGIK ELGS QILKEYP--VE----NTQLQNEKLYLYYLQNGRDMYVDQEL--D--INRLSDYDVDHI | 841 |
| WP_012560673 | 777 RERMKRIEEGIK ELGS QILKEHP--VE----TTQLQNEKLYLYYLQNGRDMYVDQEL--D--INRLSDYDVDHI | 840 |
| WP_014407541 | 777 RERMKRIEEGIK ELGS QILKEHP--VE----NTQLQNEKLYLYYLQNGRDMYVDQEL--D--INRLSDYDVDHI | 840 |
| WP_020905136 | 778 RERMKRIEEGIK ELGS QILKEYP--VE----NTQLQNEKLYLYYLQNGRDMYVDQEL--D--INRLSDYDVDHI | 841 |
| WP_023080005 | 777 RERMKRIEEGIK ELGS DILKEYP--VE----NTQLQNEKLYLYYLQNGRDMYVDQEL--D--INRLSDYDVDHI | 840 |
| WP_023610282 | 778 RERMKRIEEGIK ELGS DILKEYP--VE----NTQLQNEKLYLYYLQNGRDMYVDQEL--D--INRLSDYDVDHI | 841 |
| WP_030125963 | 778 RERMKRIEEGIK ELGS DILKEYP--VE----NTQLQNEKLYLYYLQNGRDMYVDQEL--D--INRLSDYDVDHI | 841 |
| WP_030126706 | 778 RERMKRIEEGIK ELGS DILKEYP--VE----NTQLQNEKLYLYYLQNGRDMYVDQEL--D--INRLSDYDVDHI | 841 |
| WP_031488318 | 778 RERMKRIEEGIK ELGS DILKEYP--VE----NTQLQNEKLYLYYLQNGRDMYVDQEL--D--INRLSDYDVDHI | 841 |
| WP_032460140 | 778 RERMKRIEEGIK ELGS DILKEYP--VE----NTQLQNEKLYLYYLQNGRDMYVDQEL--D--INRLSDYDVDHI | 841 |

```
                                -continued
WP_032461047   778 RERMKRIEEGIK ELGS DILKEYP -VE- -NTQLQNEKLYLYYLQNGRDMVDQEL- -D- -INRLSDYDVDHI 841
WP_032462016   778 RERMKRIEEGIK ELGS QILKEHP -VE- -NTQLQNEKLYLYYLQNGRDMYVDQEL- -D- -INRLSDYDVDHI 841
WP_032462936   778 RERMKRIEEGIK ELGS DILKEHP -VE- -NTQLQNEKLYLYYLQNGRDMYVDQEL- -D- -INRLSDYDVDHI 841
WP_032464890   603 RERMKRIEEGIK ELGS QILKEHP -VE- -NTQLQNEKLYLYYLQNGRDMYVDQEL- -D- -INRLSDYDVDHI 666
WP_033888930   778 RERMKRIEEGIK ELGS QILKEHP -VE- -NTQLQNEKLYLYYLQNGRDMYVDQEL- -D- -INRLSDYDVDHI 841
WP_038431314   777 RERMKRIEEGIK ELGS DILKEYP -VE- -NTQLQNEKLYLYYLQNGRDMVDQEL- -D- -INRLSDYDVDHI 840
WP_038432938   778 RERMKRIEEGIK ELGS QILKEHP -VE- -NTQLQNEKLYLYYLQNGRDMYVDQEL- -D- -INRLSDYDVDHI 841
WP_038434062   689 RERMKRIEEGIK ELGS ------- ---- ------------------------QEL- -D- -INRLSGYDVDHI 752
BAQ51233         1 ------------ ---- ------- ---- ----------------------------- --- --------------- 16
KGE60162
KGE60856
WP_002989955   778 RERMKRIEEGIK ELGS QILKEHP -VE- -NTQLQNEKLYLYYLQNGRDMVDQEL- -D- -INRLSDYDVDHI 841
WP_003030002   778 QQRLKLLQDSLK PVNI K---- -N-- -NQQLQNDRLFLYYIQNGKDMYTGETL- -D- -INNLSDYDIDHI 840
WP_003065552   781 QQRLKKLQNSLK PSYI E---- -DK- -NSHLQNDQLFLYYIQNGKDMYTGDEL- -D- -IDHLSDYDIDHI 851
WP_001040076   776 RQRLTTLRESLA NLKS EKKPKYV -KD- -qveNHHLSDDRLFLYLQNGKDMYTDDEL- -D- -IDNLSQYDIDHI 846
WP_001040078   779 RQRYKLLDDGVK NLKS NILKEYP -TD- -NQALQNERLFLYIQNGKDMYTGEAL- -D- -IDNLSQYDIDHI 846
WP_001040080   779 RQRYKLLDDGVK NLKS NILKEYP -TD- -NQALQNERLFLYIQNGKDMYTGEAL- -D- -IDNLSQYDIDHI 846
WP_001040081   779 RQRYKLLDDGVK NLKS NILKEYP -TD- -NQALQNERLFLYIQNGKDMYTGEAL- -D- -IDNLSQYDIDHI 846
WP_001040083   779 RQRYKLLDDGVK NLKS NILKEYP -TD- -NQALQNERLFLYIQNGKDMYTGEAL- -D- -IDNLSQYDIDHI 846
WP_001040085   779 RQRYKLLDDGVK NLKS NILKEYP -TD- -NQALQNERLFLYIQNGKDMYTGEAL- -D- -IDNLSQYDIDHI 846
WP_001040087   779 RQRYKLLDDGVK NLKS NILKEYP -TD- -NQALQNERLFLYIQNGKDMYTGEAL- -D- -IDNLSQYDIDHI 846
WP_001040088   779 RQRYKLLDDGVK NLKS NILKEYP -TD- -NQALQNERLFLYIQNGKDMYTGEAL- -D- -IDNLSQYDIDHI 846
WP_001040089   779 RQRYKLLDDGVK NLKS NILKEYP -TD- -NQALQNERLFLYIQNGKDMYTGEAL- -D- -IDNLSQYDIDHI 846
WP_001040090   779 RQRYKLLDDGVK NLKS NILKEYP -TD- -NQALQNERLFLYIQNGKDMYTGEAL- -D- -IDNLSQYDIDHI 846
WP_001040091   779 RQRYKLLDDGVK NLKS NILKEYP -TD- -NQALQNERLFLYIQNGKDMYTGEAL- -D- -IDNLSQYDIDHI 846
WP_001040092   779 RQRYKLLEDGVK NLKS DILKEYP -TD- -NQALQNERLFLYIQNGKDMYTGEAL- -D- -IDNLSQYDIDHI 846
WP_001040094   776 RQRLTTLRESLA NLKS EKKPKYV -KD- -qveNHHLSDDRLFLYLQNGKDMYTDDEL- -D- -IDNLSQYDIDHI 846
WP_001040095   776 RQRLTTLRESLA NLKS EKKPKYV -KD- -qveNHHLSDDRLFLYLQNGKDMYTDDEL- -D- -IDNLSQYDIDHI 846
WP_001040096   776 RQRLTTLRESLA NLKS EKKPKYV -KD- -qveNHHLSDDRLFLYLQNGKDMYTDDEL- -D- -IDNLSQYDIDHI 846
WP_001040097   776 RQRLTTLRESLA NLKS EKKPKYV -KD- -qveNHHLSDDRLFLYLQNGKDMYTDDEL- -D- -IDNLSQYDIDHI 846
WP_001040098   779 RQRYKLLDDGVK NLKS NILKEYP -TD- -NQALQNERLFLYIQNGKDMYTGEAL- -D- -IDNLSQYDIDHI 846
WP_001040099   779 RQRYKLLDDGVK NLKS NILKEYP -TD- -NQALQNERLFLYIQNGKDMYTGEAL- -D- -IDNLSQYDIDHI 846
WP_001040100   776 RQRLTTLRESLA NLKS EKKPKYV -KD- -qveNHHLSDDRLFLYLQNGKDMYTDDEL- -D- -IDNLSQYDIDHI 846
WP_001040104   779 RQRYKLLDDGVK NLKS NILKEYP -TD- -NQALQNERLFLYIQNGKDMYTGEAL- -D- -IDNLSQYDIDHI 846
WP_001040105   779 RQRYKLLDDGVK NLKS NILKEYP -TD- -NQALQNERLFLYIQNGKDMYTGEAL- -D- -IDNLSQYDIDHI 846
WP_001040106   779 RQRYKLLEEGVK NLKS NILKEYP -TD- -NQALQNERLFLYIQNGKDMYTGEAL- -D- -IDNLSQYDIDHI 846
WP_001040107   779 RQRYKLLEEGVK NLKS NILKEYP -TD- -NQALQNERLFLYIQNGKDMYTGEAL- -D- -IDNLSQYDIDHI 846
WP_001040108   779 RQRYKLLEEGVK NLKS NILKEYP -TD- -NQALQNERLFLYIQNGKDMYTGEAL- -D- -IDNLSQYDIDHI 846
WP_001040109   779 RQRYKLLEEGVK NLKS NILKEYP -TD- -NQALQNERLFLYIQNGKDMYTGEAL- -D- -IDNLSQYDIDHI 846
WP_001040110   779 RQRYKLLEEGVK NLKS NILKEYP -TD- -NQALQNERLFLYIQNGKDMYTGEAL- -D- -IDNLSQYDIDHI 846
WP_015058523   779 RQRYKLLDDGVK NLKS DILKEYP -TD- -NQALQNERLFLYIQNGKDMYTGEAL- -D- -IDNLSQYDIDHI 846
WP_017643650   776 RQRLTTLRESLA NLKS EKKPKYV -KD- -qveNHHLSDDRLFLYLQNGKDMYTDDEL- -D- -IDNLSQYDIDHI 846
WP_017647151   779 RQRYKLLDDGVK NLKS NILKEYP -TD- -NQALQNERLFLYIQNGKDMYTGEAL- -D- -IDNLSQYDIDHI 846
WP_017648376   779 RQRYKLLDDGVK NLKS NILKEYP -TD- -NQALQNERLFLYIQNGKDMYTGEAL- -D- -IDNLSQYDIDHI 846
WP_017649527   779 RQRYKLLDDGVK NLKS NILKEYP -TD- -NQALQNERLFLYIQNGKDMYTGEAL- -D- -IDNLSQYDIDHI 846
WP_017771611   779 RQRYKLLDDGVK NLKS NILKEYP -TD- -NQALQNERLFLYIQNGKDMYTGEAL- -D- -IDNLSQYDIDHI 846
WP_017771984   779 RQRYKLLDDGVK NLKS NILKEYP -TD- -NQALQNERLFLYIQNGKDMYTGEAL- -D- -IDNLSQYDIDHI 846
CFQ25032       779 RQRYKLLDDGVK NLKS NILKEYP -TD- -NQALQNERLFLYIQNGKDMYTGEAL- -D- -IDNLSQYDIDHI 846
CFV16040       779 RQRYKLLDDGVK NLKS NILKEYP -TD- -NQALQNERLFLYIQNGKDMYTGEAL- -D- -IDNLSQYDIDHI 846
KLJ37842       779 RQRYKLLEEGVK NLKS NILKEYP -TD- -NQALQNERLFLYIQNGKDMYTGEAL- -D- -IDNLSQYDIDHI 846
KLJ72361       793 RQRYKLLEEGVK NLKS NILKEYP -TD- -NQALQNERLFLYIQNGKDMYTGEAL- -D- -IDNLSQYDIDHI 860
KLL20707       779 RQRYKLLDDGVK NLKS NILKEYP -TD- -NQALQNERLFLYIQNGKDMYTGEAL- -D- -IDNLSQYDIDHI 846
KLL42645       779 RQRYKLLEEGVK NLKS NILKEYP -TD- -NQALQNERLFLYIQNGKDMYTGEAL- -D- -IDNLSQYDIDHI 846
```

```
-continued

WP_047202273   779 RQRYKLLDDGVK NLAS NILKEYP-TD---NQALQNERLFLYYLQNGRDMYTGEAL--D---IDNLSQYDIDHI 846
WP_047209694   776 RQRLTTLRESLA NLKS EKKPKYV-KDqveNHHLSDDRLFLYYLQNGKDMYTDDEL--D---IDNLSQYDIDHI 846
WP_050198062   779 RQRYKLLDDGVK NLAS NILKEYP-TD---NQALQNERLFLYYLQNGKDMYTGEAL--D---IDNLSQYDIDHI 846
WP_050201642   779 RQRYKLLDDGVK NLAS NILKEYP-TD---NQALQNERLFLYYLQNGRDMYTGEAL--D---IDNLSQYDIDHI 846
WP_050204027   779 RQRYKLLEEGVK NLAS NILKEYP-TD---NQALQNERLFLYYLQNGRDMYTGEAL--D---IDNLSQYDIDHI 846
WP_050881965   779 RQRYKLLDDGVK NLAS NILKEYP-TD---NQALQNERLFLYYLQNGRDMYTGEAL--D---IDNLSQYDIDHI 846
WP_050886065   779 RQRYKLLDDGVK NLAS NILKEYP-TD---NQALQNERLFLYYLQNGRDMYTGEAL--D---IDNLSQYDIDHI 846
AHN30376       779 RQRYKLLEDGVK NLAS DILKEYP-TD---NQALQNERLFLYYLQNGRDMYTGEAL--D---IDSLSQYDIDHI 846
EA078426       779 RQRYKLLDDGVK NLAS NILKEYP-TD---NQALQNERLFLYYLQNGRDMYTEKAL--D---IDNLSQYDIDHI 846
CCW42055       779 RQRYKLLDDGVR NLAS NILKEYP-TD---NQALQNERLFLYYLQNGRDMYTDDEL--D---IDNLSQYDIDHI 846
WP_003041502   778 QQRLKLLQDSLK PVNI K------N-VE---NQQLQNDRLFLYIQNGRDMYTGETL--D---INNLSQYDIDHI 840
WP_037593752   778 QQRLKLLQDSLK PVNI K------N-VE---NQQLQNDRLFLYIQNGRDMYTGETL--D---INNLSQYDIDHI 841
WP_049516684   779 QQRLKLLQDSLK PVNI K------N-VE---NQQLQNDRLFLYIQNGKDMYTGETL--D---INNLSQYDIDHI 841
GAD46167       778 QQRLKLLQDSLK PSYI E---DK--N-VE---NQQLQNDQLFLYIQNGKDMYTGDEL--D---IDHLSDYDIDHI 840
WP_018363470   787 RERKKRIEGIK ELES QILKENP-VE---NTQLQNEKLYLYYLQNGRDMYTVDQEL--D---INRLSDYDVDHI 849
WP_003043819   778 QQRLKLLQDSLK PVNI K------N-VE---NQQLQNDRLFLYIQNGRDMYTVDQEL--D---INNLSQYDIDHI 850
WP_006269658   778 QQRLKLLQDSLT PVSI K------N-VE---NQQLQNDRLFLYIQNGRDMYTGETL--D---IHHLSDYDIDHI 840
WP_048800889   777 RERMKRIEGIK ELGS QILKEHP-VE---NTQLQNEKLYLYYLQNGRDMYTGEEL--D---INRLSDYDVDHI 840
WP_012767106   777 RERMKRIEGIK ELGS QILKEHP-VE---NTQLQNEKLYLYYLQNGRDMYTVDQEL--D---INRLSDYDVDHI 840
WP_014612333   777 RERMKRIEGIK ELGS QILKEHP-VE---NTQLQNEKLYLYYLQNGRDMYTVDQEL--D---INRLSDYDVDHI 840
WP_015017095   777 RERMKRIEGIK ELGS QILKEHP-VE---NTQLQNDRLYLYYLQNGRDMYTVDQEL--D---INRLSDYDVDHI 840
WP_015057649   777 RERMKRIEGIK ELGS QILKEHP-VE---NTQLQNDRLYLYYLQNGRDMYTVDQEL--D---INRLSDYDVDHI 840
WP_048277215   777 RERMKRIEGIK ELGS QILKEHP-VE---NTQLQNDRLYLYYLQNGRDMYTVDQEL--D---INRLSDYDVDHI 840
WP_049519324   777 RERMKRIEGIK ELGS QILKEHP-VE---NTQLQNDRLYLYYLQNGRDMYTVDQEL--D---IDYLSDYDIDHI 840
WP_012515931   777 RQRMRKLEETAK KLGS NILKEHP-VD---NSQLQNDRLYLYYLQNGRDMYTGDEL--D---IDYLSSYDIDHI 840
WP_021320964   777 RQRMRKLEETAK KLGS NILKEHP-VD---NSQLQNDKRLYLYYLQNGRDMYTGDDL--D---IDYLSSYDIDHI 840
WP_037581760   778 NQRLKRLQDSLK PSYV D---SK--VE---NSHLQNDQLFLYYLQNGRDMYTGDDL--D---IDHLSDYDIDHI 848
WP_009854540   779 QQRLKKLQSSLK PSYI E---GK--VE---NSHLQNDQLFLYYLQNGKDMYTGDEL--D---IDRLSDYDIDHI 849
WP_012962174   779 QQRLKKLQDSLK PSYI E---DK--VE---NSHLQNDQLFLYYLQDGKDMYTGDEL--D---IDRLSDYDIDHI 851
WP_039695303   779 NQRLKRLQDSLK PSYV D---SK--VE---NSHLQNDRLYLYYLQDGKDMYTGEEL--D---IDRLSDYDIDHI 848
WP_014334983   778 RQRLRKLEEVHK NTGS KILKEYN-VS---NTQLQSDRLYLYLLQGKDMYTGKEL--D---YDNLSQYDIDHI 841
WP_003099269   778 RQRLRKLEEVHK NTGS KILKEYN-VS---NTQLQSDRLYLYLLQGKDMYTGKEL--D---YDNLSQYDIDHI 841
AHY15608       ---- ------------- ---- ---------- ---------------------------------------- ---
AHY17476       778 RQRLRKLEEVHK NTGS KILKEYN-VS---NTQLQSDRLYLYLLQGKDMYTGKEL--D---YDNLSQYDIDHI 841
ESR09100       778 RQRLRKGLTDSIK EFGS QILKEHP-VE---NSQLQNDRLFLYYLQNGKDMYTGEEL--D---IDYLSQYDIDHI 841
AGM98575       791 AQRLKKIEDGIK -LGS DLLKQNP-IQd--NKDLQKEKLFLYYMQNGIDLYTGQPLncD--PDSLAFYDVDHI 857
ALF27331       777 QQRYKIRIEDALK NLAH NILKEHP-TD---NIQLQNDRLFLYYMQNGIDLYTGKSL--D---INQLSSCDIDHI 844
WP_018372492   776 QQRYLIKEDSLK ILAS NILKEHP-VE---NNQLQNDRLFLYYLQNGKDMYTGEAL--D---INQLSSYDIDHI 843
WP_045618028   778 QQRLKGLTDSIK EFGS QILKEHP-VE---NSQLQNDRLFLYYLQNGKDMYTGEEL--D---IDYLSQYDIDHI 841
WP_045635197   778 QQRLKGLTDSIK EFGS QILKEHP-VE---NSQLQNDRLFLYYLQNGKDMYTGEEL--D---IDYLSQYDIDHI 841
WP_002263549   778 QQRLKGLTDSIK EFGS QILKEHP-VE---NSQLQNDRLFLYYLQNGKDMYTGEEL--D---IDYLSQYDIDHI 841
WP_002263887   778 QQRLKGLTDSIK EFGS QILKEHP-VE---NSQLQNDRLFLYYLQNGKDMYTGEEL--D---IDYLSQYDIDHI 841
WP_002644920   778 QQRLKGLTDSIK EFGS QILKEHP-VE---NSQLQNDRLFLYYLQNGKDMYTGEEL--D---IDYLSQYDIDHI 841
WP_002269043   778 QQRLKGLTDSIK EFGS QILKEHP-VE---NSQLQNDRLFLYYLQNGKDMYTGEEL--D---IDYLSQYDIDHI 841
WP_002269448   778 QQRLKGLTDSIK EFGS QILKEHP-VE---NSQLQNDRLFLYYLQNGKDMYTGEEL--D---IDYLSQYDIDHI 841
WP_002271977   778 QQRLKGLTDSIK EFGS QILKEHP-VE---NSQLQNDRLFLYYLQNGKDMYTGEEL--D---IDYLSQYDIDHI 841
WP_002272766   778 QQRLKGLTDSIK EFGS QILKEHP-VE---NSQLQNDRLFLYYLQNGKDMYTGEEL--D---IDYLSQYDIDHI 841
WP_002273241   778 QQRLKGLTDSIK EFGS QILKEHP-VE---NSQLQNDRLFLYYLQNGKDMYTGEEL--D---IDYLSQYDIDHI 841
WP_002275430   778 QQRLKGLTDSIK EFGS QILKEHP-VE---NSQLQNDRLFLYYLQNGKDMYTGEEL--D---IDYLSQYDIDHI 841
WP_002276448   779 QQRLKRLKEAIK DLNH KILKEHP-TD---NQALQNNRLFLYYLQNGRDMYTGESL--D---INRLSDYDIDHV 846
WP_002277050   779 QQRLKRLKEAIK DLNH KILKEHP-TD---NQALQNNRLFLYYLQNGRDMYTGESL--D---INRLSDYDIDHV 846
WP_002277364   778 QQRLKGLTDSIK EFGS QILKEHP-VE---HSQLQNDRLFLYYLQNGKDMYTGEEL--D---IDYLSQYDIDHI 841
```

```
-continued

WP_002279025   778 QQRLKGLTDSIK EFGS QILKEHP-VE---NSQLQNDRLFLYYLQNGRDMYTGEEL--D--IDYLSQYDIDHI 841
WP_002279859   778 QQRLKGLTDSIK EFGS QILKEHP-VE---NSQLQNDRLFLYYLQNGRDMYTGEEL--D--IDYLSQYDIDHI 841
WP_002280230   778 QQRLKGLTDSIK EFGS QILKEHP-VE---NSQLQNDRLFLYYLQNGRDMYTGEEL--D--IDYLSQYDIDHI 841
WP_002281696   778 QQRLKGLTDSIK EFGS QILKEHP-VE---NSQLQNDRLFLYYLQNGRDMYTGEEL--D--IDYLSQYDIDHI 841
WP_002282247   779 QQRLKRLKEAIK DLNH KILKEHP-TD---NQALQNDRLFLYYLQNGRDMYTGEEL--D--INRLSDYDIDHV 846
WP_002282906   778 QQRLKGLTDSIK EFGS QILKEHP-VE---NSQLQNDRLFLYYLQNGRDMYTGEEL--D--IDYLSQYDIDHI 841
WP_002283846   778 QQRLKGLTDSIK EFGS QILKEHP-VE---NSQLQNDRLFLYYLQNGRDMYTGEEL--D--IDYLSQYDIDHI 841
WP_002287255   778 QQRLKGLTDSIK EFGS QILKEHP-VE---HSQLQNDRLFLYYLQNGRDMYTGEEL--D--IDYLSQYDIDHI 841
WP_002288990   778 QQRLKGLTDSIK EFGS QILKEHP-VE---NSQLQNDRLFLYYLQNGRDMYTGEEL--D--IDYLSQYDIDHI 841
WP_002289641   778 QQRLKGLTDSIK EFGS QILKEHP-VE---NSQLQNDRLFLYYLQNGRDMYTGEEL--D--IDYLSQYDIDHI 841
WP_002290427   778 QQRLKGLTDSIK EFGS QILKEHP-VE---NSQLQNDRLFLYYLQNGRDMYTGEEL--D--IDYLSQYDIDHI 841
WP_002295753   778 QQRLKGLTDSIK EFGS QILKEHP-VE---NSQLQNDRLFLYYLQNGRDMYTGEEL--D--IDYLSQYDIDHI 841
WP_002296423   788 QKRYKRLEEAIK DLNH KILKEHP-TD---NQALQNDRLFLYYLQNGRDMYTEDPL--D--INRLSDYDIDHI 855
WP_002304487   778 QQRLKGLTDSIK EFGS QILKEHP-VE---NSQLQNDRLFLYYLQNGRDMYTGEEL--D--IDYLSQYDIDHI 841
WP_002305844   778 QQRLKGLTDSIK EFGS QILKEHP-VE---NSQLQNDRLFLYYLQNGRDMYTGEEL--D--IDYLSQYDIDHI 841
WP_002307203   778 QQRLKGLTDSIK EFGS QILKEHP-VE---NSQLQNDRLFLYYLQNGRDMYTGEEL--D--IDYLSQYDIDHI 841
WP_002310390   778 QQRLKGLTDSIK EFGS QILKEHP-VE---NSQLQNDRLFLYYLQNGRDMYTGEEL--D--IDYLSQYDIDHI 841
WP_002352408   778 QQRLKGLTDSIK EFGS QILKEHP-VE---NSQLQNDRLFLYYLQNGRDMYTGEEL--D--IDYLSQYDIDHI 841
WP_012997688   778 QQRLKGLTDSIK EFGS QILKEHP-VK---NSQLQNDRLFLYYLQNGRDMYTGEEL--D--IDYLSQYDIDHI 841
WP_014677909   778 QQRLKGLTDSIK EFGS QILKEHP-VE---NSQLQNDRLFLYYLQNGRDMYTGEEL--D--IDYLSQYDIDHI 841
WP_019312892   778 QQRLKGLTDSIK EFGS QILKEHP-VE---NSQLQNDRLFLYYLQNGRDMYTGEEL--D--IDYLSQYDIDHI 841
WP_019313659   778 QQRLKGLTDSIK EFGS QILKEHP-VE---NSQLQNDRLFLYYLQNGRDMYTGEEL--D--IDYLSQYDIDHI 841
WP_019314093   778 QQRLKGLTDSIK EFGS QILKEHP-VE---NSQLQNDRLFLYYLQNGRDMYTGEEL--D--IDYLSQYDIDHI 841
WP_019315370   778 QQRLKGLTDSIK EFGS QILKEHP-TD---NQLQNDRLFLYYLQNGRDMYTGESL--D--IDYLSDYDIDHV 841
WP_019803776   778 QQRLKGLTDSIK EFGS QILKEHP-VE---NSQLQNDRLFLYYLQNGRDMYTGEEL--D--IDYLSQYDIDHI 841
WP_019805234   778 QQRLKGLTDSIK EFGS QILKEHP-VE---NSQLQNDRLFLYYLQNGRDMYTGEEL--D--IDYLSQYDIDHI 841
WP_024783594   778 QQRLKGLTDSIK EFGS QILKEHP-TD---NQALQNDRLFLYYLQNGRDMYTGEEL--D--INRLSDYDIDHV 846
WP_024784288   779 QQRLKRLKEAIK DLNH KILKEHP-TD---NSQLQNDRLFLYYLQNGRDMYTGESL--D--IDYLSDYDIDHV 846
WP_024784666   778 QQRLKGLTDSIK EFGS QILKEHP-VE---HSQLQNDRLFLYYLQNGRDMYTGEEL--D--IDYLSQYDIDHI 841
WP_024784894   778 QQRLKGLTDSIK EFGS QILKEHP-VE---NSQLQNDRLFLYYLQNGRDMYTGEEL--D--IDYLSQYDIDHI 841
WP_024786433   778 QQRLKGLTDSIK EFGS QILKEHP-TD---NQLQNDRLFLYYLQNGRDMYTGESL--D--INRLSDYDIDHV 841
WP_049473442   779 QQRLKRLKEAIK DLNH KILKEHP-VE---NSQLQNDRLFLYYLQNGRDMYTGEEL--D--IDYLSQYDIDHV 846
WP_049474547   778 QQRLKGLTDSIK EFGS QILKEHP-VE---NSQLQNDRLFLYYLQNGRDMYTGEEL--D--IDYLSQYDIDHI 841
EMC03581       771 RERLRKLEEVHK NIGS KILKEHE-IS---NAQLQSDRVYLYLLQDGKDMYTGKDL--D--ISNLSHYDIDHI 834
WP_000428612   779 QQRYKRIEDSLK ILAS KLLKEHP-TD---NIQLQNDRLYLYLYLQNGKDMYTGEEL--D--INQLSSYDIDHI 846
WP_000428613   777 QQRYKRIEDALK NLAS NILKEHP-TN---NIQLQNDRLFLYYLQNGKDMYTGKPL--D--INQLSSYDIDHI 844
WP_049523028   776 QQRLKTLSDAIS ELG- NILKEHP-TD---NIQLQNDRLFLYYLQNGKDMYTGEAL--D--INQLSNYDIDHI 839
WP_003107102   747 RERLRKLEEVHK NIGS KILKEHE-IS---NAQLQSDRVYLYLLQDGKDMYTGKDL--D--FDRLSQYDIDHI 810
WP_054279288   779 RERMKRVQEVLK KLGS QLLKEHP-VE---NFQLQNERLYLYLYLQNGKDMYTGEEL--S--ISNLSHYDIDHI 842
WP_049531101   777 QQRYKRIEDSLK NILKEHP-TD---NILQNDQLYLYLYLQNGKDMYTGNPL--D--INHLSSYDIDHI 844
WP_049538452   777 QQRYKRIENSLK ILAS NILKEHP-TD---NNQLQNDRLFLYYLQNGKDMYTGEEL--D--INQLSSCDIDHI 844
WP_049549711   777 QQRYKRIEDSLK ILAS NILKEHP-TD---NIQLQNDRLFLYYLQNGKDMYTGEAL--D--INQLSSYDIDHI 844
WP_007896501   781 RQRLKKIKEVHK KTGS RILEDNserIT---NLTLQDNRLYLYLLQDGKDMYTGQDL--D--INNLSQYDIDHI 846
EFR44625       733 RQRLKKIKEVHK KTGS RILEDNserIT---NLTLQDNRLYLYLLQDGKDMYTGQDL--D--INNLSQYDIDHI 798
WP_002974477   776 QQRYKRIEDALK NLAP NILKEHP-TD---NIQLKNDRLFLYYLQNGKDMYTGKPL--D--INQLSSYDIDHI 843
WP_002906454   777 QQRYKRIEDALK NLAP NILKEHP-TD---NIQLQNDRLFLYYLQNGKDMYTGKPL--D--INQLSSYDIDHI 844
WP_009729476   780 QQRYKRIEDSLK ILAS KILKEHP-TD---NIQLQNDRLFLYYLQNGKDMYTGEAL--D--INQLSSCDIDHI 843
CQR24647       779 QQRLGSLITKAIQ DFGS DILKRYP-VE---NNQLQNDQLYLYLYLQNGKDMYTGKPL--E--INHLSNYDIDHI 844
WP_009754323   779 QQRYKRIEDSLK NLAS NILKEHP-TD---NIQLQNDRLFLYYLQNGKDMYTGKPL--E--INHLSNYDIDHI 846
WP_044674937   776 QQRYKKIENAIK NLNS NLKEYP-TN---NQALQNDRLFLYYLQNGKDMYTDEEL--D--IDQLSQYDIDHI 843
WP_044676715   778 QQRYKKIENAIK NLNS KILKEYP-TN---NIQLQNDRLFLYYLQNGKDMYTDEEL--D--IDQLSQYDIDHI 845
WP_044680361   778 QQRYKKIENAIK NLNS KILKEYP-TN---NQALQNDRLFLYYLQNGKDMYTDEEL--D--IDQLSQYDIDHI 845
```

-continued

| | | | | |
|---|---|---|---|---|
| WP_044681799 | 776 QQRYKKIENAIK NLNS KILKEYP-TN---NQALQNDRLFLYYLQNGKDMYTDEEL--D--IDQLSQYDIDHI | | | 843 |
| WP_049533112 | 778 QQRLKLLQDSLK PVNI K-----N--VE--NQQLQNDRLFLYYIQNGKDMYTGETL--D--INNLSQYDIDHI | | | 840 |
| WP_029090905 | 753 TPRDKFIEKAYA ETDT EHLKELK--Qr-SKQLSSQRLFLFIQNGKDMYSGEHL--D--IERLDSYEVDHI | | | 823 |
| WP_006506696 | 777 ESKIKKLENVYK DEQT SVLEELKg-FDn-TKKISSDSLFLYFTQLGKCMYSGKKL--D--IDSLDKYQIDHI | | | 849 |
| AIT42264 | 778 RERMKRIEEGIK ELGS QILKEHP-VE--NTQLQNEKLYLYLQNGRDMYVDQEL--D--INRLSDYDVDHI | | | 841 |
| WP_034440723 | 785 KARLKKQEGLE NLDS HVEKQAL--D--EEMLKSPKYYLYCLQNGKDIYTGKDL--D--IGQLQTYDIDHI | | | 848 |
| AKQ21048 | 778 RERMKRIEEGIK ELGS QILKEHP-VE--NTQLQNEKLYLYLQNGRDMVDQEL--D--INRLSDYDVDHI | | | 841 |
| WP_004636532 | 781 KERLEKLTEAIK EFDG --VKVKD--LK--NENLRNDRLYLYYLQNGRDMYTNEPL--D--INNLSKYDIDHI | | | 845 |
| WP_002364836 | 789 IQRLKIVEKAMA EIGS NLLKEQP-TT--NEQLRDTRLFLYYMQNGKDMYTGDEL--S--LHRLSHYDIDHI | | | 852 |
| WP_016663104 | 740 IQRLKIVEKAMA EIGS NLLKEQP-TT--NEQLRDTRLFLYYMQNGKDMYTGDEL--S--LHRLSHYDIDHI | | | 803 |
| EMS75795 | 525 KPRLKALEEALK SFDS PLLKEQP-VD--NQALQDRLYLYLQNGKDMYTGEAL--D--IDRLSEYDIDHI | | | 588 |
| WP_002373311 | 789 IQRLKIVEKAMA EIGS NLLKEQP-TT--NEQLRDTRLFLYYMQNGKDMYTGDEL--S--LHRLSHYDIDHI | | | 852 |
| WP_033789179 | 789 IQRLKIVEKAMA EIGS NLLKEQP-TT--NEQLRDTRLFLYYMQNGKDMYTGDEL--S--LHRLSHYDIDHI | | | 852 |
| WP_002378009 | 789 IQRLKIVEKAMA EIGS NLLKEQP-TT--NEQLRDTRLFLYYMQNGKDMYTGDEL--S--IHRLSHYDIDHI | | | 852 |
| WP_002407324 | 789 IQRLKIVEKAMA EIGS NLLKEQP-TT--NEQLRDTRLFLYYMQNGKDMYTGDEL--S--LHRLSHYDIDHI | | | 852 |
| WP_002413717 | 789 IQRLKIVEKAMA EIGS NLLKEQP-TT--NEQLRDTRLFLYYMQNGKDMYTGDEL--S--LHRLSHYDIDHI | | | 852 |
| WP_010775580 | 791 IQRLKIVEKAMA EIGS NLLKEQP-TT--NEQLRDTRLFLYYMQNGKDMYTGDEL--S--LHRLSHYDIDHI | | | 854 |
| WP_010818269 | 789 IQRLKIVEKAMA EIGS NLLKEQP-TT--NEQLRDTRLFLYYMQNGKDMYTGDEL--S--LHRLSHYDIDHI | | | 852 |
| WP_010824395 | 789 IQRLKIVEKAMA EIGS NLLKEQP-TT--NEQLRDTRLFLYYMQNGKDMYTGDEL--S--LHRLSHYDIDHI | | | 852 |
| WP_016622645 | 789 IQRLKIVEKAMA EIGS NLLKEQP-TT--NEQLRDTRLFLYYMQNGKDMYTGDEL--S--LHRLSHYDIDHI | | | 852 |
| WP_033624816 | 789 IQRLKIVEKAMA EIGS NLLKEQP-TT--NEQLRDTRLFLYYMQNGKDMYTGDEL--S--LHRLSHYDIDHI | | | 852 |
| WP_033625576 | 789 IQRLKIVEKAMA EIGS NLLKEQP-TT--NEQLRDTRLFLYYMQNGKDMYTGDEL--S--LHRLSHYDIDHI | | | 852 |
| WP_033789179 | 789 IQRLKIVEKAMA EIGS NLLKEQP-TT--NEQLRDTRLFLYYMQNGKDMYTGDEL--S--IHRLSHYDIDHI | | | 852 |
| WP_002310644 | 789 RPRLKALEESLK DFGS QLLKEYP-TD--NSSLQKDRLYLYLYLQNGRDMYTGAPL--D--IHRLSDYDIDHI | | | 852 |
| WP_002312694 | 790 RPRLKALEESLK DFGS QLLKEYP-TD--NSSLQKDRLYLYLYLQNGRDMYTGAPL--D--IHRLSDYDIDHI | | | 853 |
| WP_002314015 | 790 RPRLKALEESLK DFGS QLLKEYP-TD--NSSLQKDRLYLYLYLQNGRDMYTGAPL--D--IHRLSDYDIDHI | | | 853 |
| WP_002320716 | 790 RPRLKALEESLK DFGS QLLKEYP-TD--NSSLQKDRLYLYLYLQNGRDMYTGAPL--D--IHRLSDYDIDHI | | | 853 |
| WP_002330729 | 789 RPRLKALEESLK DFGS QLLKEYP-TD--NSSLQKDRLYLYLYLQNGRDMYTGAPL--D--IHRLSDYDIDHI | | | 852 |
| WP_002335161 | 790 RPRLKALEESLK DFGS QLLKEYP-TD--NSSLQKDRLYLYLYLQNGRDMYTGAPL--D--IHRLSDYDIDHI | | | 853 |
| WP_002345439 | 790 RPRLKALEESLK DFGS QLLKEYP-TD--NSSLQKDRLYLYLYLQNGRDMYTGAPL--D--IHRLSDYDIDHI | | | 853 |
| WP_034867970 | 781 SPRLKALENGLK QIGS TLLKEQP-TD--NKALQKERLYLYLYLQNGRDMYTGEPL--E--IENLHQYEVDHI | | | 844 |
| WP_047937432 | 790 KPRLKALEESLK DFGS QLLKEYP-TD--NSSLQKDRLYLYLYLQNGRDMYTGAPL--D--IHRLSDYDIDHI | | | 853 |
| WP_010720994 | 781 KPRLKALENGLK QIGS TLLKEQP-TD--NKALQKERLYLYLYLQNGRDMYTGEPL--E--IENLHQYEVDHI | | | 844 |
| WP_010737004 | 781 SPRLKALENGLK QIGS TLLKEQP-TD--NKALQKERLYLYLYLQNGRDMYTGEPL--E--IENLHQYEVDHI | | | 844 |
| WP_034700478 | 781 KPRLKALENGLK QIGS TLLKEQP-TD--NKALQKERLYLYLYLQNGRDMYTGEPL--E--IENLHQYEVDHI | | | 844 |
| WP_007209003 | 782 KPRLKGIENGLK EFSD SVLKGSS-ID--NKQLQNDRLYLYLYLQNGKDMYTGHEL--D--IDHLSTYDIDHI | | | 845 |
| WP_023519017 | 775 RPRLKALEEALK NIDS PLLKDYP-TD--NQALQDRLYLFLQNGKSLYSEESL--E--INKLSDYQVDHI | | | 838 |
| WP_010770040 | 782 NPRMKALEEAMR NLRS NLLKEYP-TD--NQALQNDRLYLYLQNGKDMYTGLDL--S--LHNLSSYDIDHI | | | 845 |
| WP_048604708 | 779 RPRLKNLEKAID DLDS QLLKERP-VD--NKALQKDRLYLYLYLQNGKDMYTNEEL--D--IHKLSTYDIDHI | | | 842 |
| WP_010750235 | 784 KPRLKSLEEALK NFDS QLLKEYP-VE--NTQLQNDRLYLYLQNGRDMYTGESL--D--IDRLSEYDIDHI | | | 847 |
| AII16583 | 817 RERMKRIEEGIK ELGS QILKEHP-VE--NTQLQNDRLYLYLQNGRDMVDQEL--D--INRLSDYDVDHI | | | 880 |
| WP_029073316 | 789 DSFVNQMLKLYK DFED EANKHLKg-EDa-KSKIRSERLKLYYTQMGKCMYGKSL--D--IDRLDTYQVDHI | | | 860 |
| WP_031589969 | 789 DSFVNQMLKLYK DFED EANKHLKg-EDa-KSKIRSERLKLYYTQMGKCMYTGKSL--D--IDRLDTYQVDHI | | | 860 |
| KDA45870 | 772 EDRVQQIVKNLK ELPK ------P--S--NAELSDERKYLYCLQNGRDMYTGAPL--D--YDHLQFYDVDHI | | | 833 |
| WP_039099354 | 789 KRQVEQVVQNIS EL-- EIRNELK---D--LSSERIMYFLQNGKSLYSEESL--N--INKLSDYQVDHI | | | 856 |
| AKP02966 | 786 RLQSKLLNKANG -LVP EELKKHKn-D---LSSERIMYFLQNGKSLYSEESL--N--INKLSDYQVDHI | | | 858 |
| WP_010991369 | 781 RPRYKSLEKAIK EFGS QILKEHP-TD--NQELRNNRLYLYLYLQNGKDMYTGQDL--D--IHNLSNYDIDHI | | | 844 |
| WP_033838504 | 781 RPRYKSLEKAIK EFGS QILKEHP-TD--NQELRNNRLYLYLYLQNGKDMYTGQDL--D--IHNLSNYDIDHI | | | 844 |
| EHN60060 | 782 RPRYKSLEKAIK EFGS QILKEHP-TD--NQELRNNRLYLYLYLQNGKDMYTGQDL--D--IHNLSSYDIDHI | | | 847 |
| EFR89594 | 550 RPRYKSLEKAIK EFGS QILKEHP-TD--NQELRNNRLYLYLYLQNGKDMYTGQDL--D--IHNLSNYDIDHI | | | 613 |
| WP_038409211 | 781 KPRFISLEKAIK EFGS QILKEHP-TD--NQCLKNDRLYLYLYLQNGKDMYTGKEL--D--IHNLSNYDIDHI | | | 844 |
| EFR95520 | 400 KPRFISLEKAIK EFGS QILKEHP-TD--NQCLKNDRLYLYLYLQNGKDMYTGKEL--D--IHNLSNYDIDHI | | | 463 |
| WP_003723650 | 781 KPRYKSLEKAIK EFGS QILKEHP-TD--NQELKNNRLYLYLYLQNGKDMYTGQEL--D--IHNLSNYDIDHI | | | 844 |
| WP_003727705 | 781 KPRYKSLEKAIK DFGS QILKEHP-TD--NQELKNNRLYLYLQNGKDIYTGQEL--D--IHNLSNYDIDHI | | | 844 |

-continued

| | | | | |
|---|---|---|---|---|
| WP_003730785 | 781 | KPRYKSLEKAIK DFGS QILKEHP--TD---NQELKNNRLYLYYLQNGKDIYTGQEL---D---IHNLSNYDIDHI | | 844 |
| WP_003733029 | 781 | KPRYKSLEKAIK EFGS QILKEHP--TD---NQELKNNRLYLYYLQNGKDMYTGQEL---D---IHNLSNYDIDHI | | 844 |
| WP_003739838 | 781 | RPRYKSLEKAIK EFGS QILKEHP--TD---NQELRNNRLYLYYLQNGKDMYTGQEL---D---IHNLSNYDIDHI | | 844 |
| WP_014601172 | 781 | KPRYKSLEKAIK EFGS KILKEHP--TD---NQELKNNRLYLYYLQNGKDMYTGQEL---D---IHNLSNYDIDHI | | 844 |
| WP_023548323 | 781 | KPRYKSLEKAIK EFGS QILKEHP--TD---NQELKNNRLYLYYLQNGKDMYTGQEL---D---IHNLSNYDIDHI | | 844 |
| WP_031665337 | 781 | KPRYKSLEKAIK EFGS QILKEHP--TD---NQELKNNRLYLYYLQNGKDMYTGQEL---D---IHNLSNYDIDHI | | 844 |
| WP_031669209 | 781 | KPRYKSLEKAIK EFGS QILKEHP--TD---NQELKNNRLYLYYLQNGKDMYTGQEL---D---IHNLSNYDIDHI | | 844 |
| WP_033920898 | 781 | KPRYKSLEKAIK EFGS QILKEHP--TD---NQELKNNRLYLYYLQNGKDMYTGQEL---D---IHNLSNYDIDHI | | 844 |
| AKI42028 | 784 | KPRYKSLEKAIK EFGS QILKEHP--TD---NQELKNNRLYLYYLQNGKDMYTGQEL---D---IHNLSNYDIDHI | | 847 |
| AKI50529 | 784 | KPRYKSLEKAIK EFGS KILKEHP--TD---NQELKNNRLYLYYLQNGKDMYTGQEL---D---IHNLSNYDIDHI | | 847 |
| EFR83390 | 229 | RPRYKSLEKAIK EFGS QILKEHP--TD---NQELKNNRLYLYYLQNGKDMYTGQEL---D---IHNLSNYDIDHI | | 292 |
| WP_046323366 | 781 | KPRFTSLEKAIK ELGS QILKEHP--TD---NQGLKNDRLYLYYLQNGRDMYTGQEL---D---IHNLSNYDIDHV | | 844 |
| AKE81011 | 794 | RERMKRIEEGIK ELGS QILKEHP--VE---NTQLQNEKLYLYFTQLGKCMYSGKKL---D---IDSLDKYQIDHI | | 857 |
| CUO82355 | 781 | ESKIAKLQKIYE DEQT SVLEELKg-FDn--TKKISSDSLFLYFTQLGKCMYSGKKL---D---IDSLDKYQIDHI | | 853 |
| AKE81011 | 784 | ESKIAKLQKIYE NLQT QVYESLKr-EDa--KKRMETDALYLYYLQMGKSMYSGKPL---D---IDKLSTYQIDHI | | 855 |
| AGZ01981 | 811 | RERMKRIEEGIK ELGS QILKEHP--VE---NTQLQNEKLYLYYLQNGRDMYVDQEL---D---INRLSDYDVDHI | | 874 |
| AKA60242 | 778 | RERMKRIEEGIK ELGS QILKEHP--VE---NTQLQNEKLYLYYLQNGRDMYVDQEL---D---INRLSDYDVDHI | | 841 |
| AKS40380 | 778 | RERMKRIEEGIK ELGS QILKEHP--VE---NTQLQNEKLYLYYLQNGRDMYVDQEL---D---INRLSDYDVDAI | | 841 |
| 4UN5_B | 782 | RERMKRIEEGIK ELGS QILKEHP--VE---NTQLQNEKLYLYYLQNGRDMYVDQEL---D---INRLSDYDVDAI | | 845 |
| WP_010922251 | 842 | VPQSFLKDDSIDNKVLTRSDKNRG-KSDN--VP S---EEVVKKMKN-YWRQLLNAKLITQRKEDNLTKA--ERGGLSE | | 910 |
| WP_039995303 | 852 | IPQAFIKDDSIDNRVLTSSAKNRG-KSDN--VP S---LDIVRARKA-EMVRLYKSGLISKRKFPDNLTKA--ERGGLTE | | 920 |
| WP_045635197 | 844 | IPQAFIKDSLDNRVLTSSKDNRG-KSDN--VP S---IEVVQKRKA-FWQQLLDSKLISERKFPNNLTKA--ERGGLDE | | 912 |
| 5AXW_A | 562 | IPRSVSFPDNSFNNKVLVKQEEASK-KGNR--TP FGy-LSSSDSKI-SYETFKKHILNLAKGKGRISKTk--KEYLLEE | | 632 |
| WP_009880683 | 526 | VPQSFLKDDSIDNKVLTRSDKNRG-KSDN--VP S---EEVVKKMKN-YWKQLLNAKLITQRKFPDNLTKA--ERGGLSE | | 594 |
| WP_010922251 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_011054416 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_011284745 | 842 | VPQSFLKDDSIDNKVLTRSDKNRG-KSNN--VP S---EEVVKKMKN-YWKQLLNAKLITQRKFPDNLTKA--ERGGLSE | | 910 |
| WP_011285506 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_011527619 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_012560673 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_014407541 | 841 | VPQSFIKDDSIDNKVLTRSDKNRG-KSDN--VP S---EEVVKKMKN-YWKQLLNAKLITQRKFPDNLTKA--ERGGLSE | | 909 |
| WP_020905136 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_023080005 | 841 | VPQSFLKDDSIDNKVLTRSDKNRG-KSDN--VP S---EEVVKKMKN-YWKQLLNAKLITQRKFPDNLTKA--ERGGLSE | | 909 |
| WP_023610282 | 841 | VPQSFIKDDSIDNKVLTRSDKNRG-KSDN--VP S---EEVVKKMKN-YWKQLLNAKLITQRKFPDNLTKA--ERGGLSE | | 909 |
| WP_030125963 | 842 | VPQSFIKDDSIDNKVLTRSDKNRG-KSDN--VP S---EEVVKKMKN-YWKQLLNAKLITQRKFPDNLTKA--ERGGLSE | | 910 |
| WP_030126706 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_031488318 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_032460140 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_032461047 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_032462016 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_032462936 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_032464890 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_033888930 | 667 | VPQSFIKDDSIDNKVLTRSDKNRG-KSDN--VP S---EEVVKKMKN-YWKQLLNAKLITQRKFPDNLTKA--ERGGLSE | | 735 |
| WP_038431314 | 842 | VPQSFLKDDSIDNKVLTRSDKNRG-KSDN--VP S---EEVVKKMKN-YWKQLLNAKLITQRKFPDNLTKA--ERGGLSE | | 910 |
| WP_038432938 | 841 | VPQSFLKDDSIDNRVLTSSAKNRG-KSDD--VP S---EEVVKKMKN-YWKQLLNAKLITQRKFPDNLTKA--ERGGLSE | | 909 |
| WP_038434062 | 753 | VPQSFLKDDSIDNKVLTRSDKNRG-KSDN--VP S---EEVVKKMKN-YWKQLLNAKLITQRKFPDNLTKA--ERGGLSE | | 821 |
| BAQ51233 | 17 | ---------------------------------- | | 85 |
| KGE60162 | | | | |
| KGE60856 | | | | |
| WP_002989955 | 842 | VPQSFLKDDSIDNKVLTRSDKNRG-KSDN--VP S---EEVVKKMKN-YWRQLLNAKLITQRKFPDNLTKA--ERGGLSE | | 910 |
| WP_003030002 | 841 | IPQAFIKDNSLDNRVLTRSDKNRG-KSDD--VP S---IEVVHEMKS-FWSKLLSVKLITQRKFPDNLTKA--ERGGLSE | | 909 |
| WP_003065552 | 852 | IPQAFIKDDSIDNRVLTSSAKNRG-KSDD--VP S---LDIVRARKA-EMVRLYKSGLISKRKFPDNLTKA--ERGGLTE | | 920 |
| WP_001040076 | 847 | IPQAFIKDDSIDNRVLVSSAKNRG-KSDD--VP S---LEIVDCKV-FWKKLLDAKLMSQRKYDNLTKA--ERGGLTS | | 915 |

-continued

| | | | | | |
|---|---|---|---|---|---|
| WP_001040078 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040080 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040081 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040083 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040085 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040087 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040088 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040089 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040090 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040091 | 847 | IPQAFIKDDSIDNRVLVSSAKNRG-KSDD--VP | S--LEIVKDCKV-FWKKLLDAKLISQRKYDNLTKA--ERGGLTS | 915 |
| WP_001040092 | 847 | VPQAFIKDDSIDNRVLVSSAKNRG-KSDD--VP | S--LEIVKDCKV-FWKKLLDAKLMSQRKYDNLTKA--ERGGLTS | 915 |
| WP_001040094 | 847 | IPQAFIKDDSIDNRVLVSSAKNRG-KSDD--VP | S--VEIVKDCKV-FWKKLLDAKLMSQRKYDNLTKA--ERGGLTP | 915 |
| WP_001040095 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040096 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040097 | 847 | VPQAFIKDDSIDNRVLVSSAKNRG-KSDD--VP | S--VEIVKDCKV-FWKKLLDAKLMSQRKYDNLTKA--ERGGLTS | 915 |
| WP_001040098 | 847 | VPQAFIKDDSIDNRVLVSSAKNRG-KSDD--VP | S--VEIVKDCKV-FWKKLLDAKLMSQRKYDNLTKA--ERGGLTS | 915 |
| WP_001040099 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040100 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040104 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040105 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040106 | 847 | VPQAFIKDDSIDNRVLVSSAKNRG-KSDD--VP | S--IDIVKARKA-FWKKLLDAKLMSQRKYDNLTKA--ERGGLTS | 915 |
| WP_001040107 | 847 | VPQAFIKDDSIDNRVLVSSAKNRG-KSDD--VP | S--IDIVKARKA-FWKKLLDAKLMSQRKYDNLTKA--ERGGLTS | 915 |
| WP_001040108 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_001040109 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_001040110 | 847 | VPQAFIKDDSIDNRVLVSSAKNRG-KSDN--VP | S--IDIVKARKA-FWKKLLDAKLMSQRKYDNLTKA--ERGGLTP | 915 |
| WP_015058523 | 847 | IPQAFIKDDSIDNRVLVSSAKNRG-KSDD--VP | S--VEIVKDCKV-FWKKLLDAKLISQRKYDNLTKA--ERGGLTS | 915 |
| WP_017643650 | 847 | IPQAFIKDDSIDNRVLVSSAKNRG-KSDN--VP | S--IDIVKARKA-FWKKLLDAKLMSQRKYDNLTKA--ERGGLTS | 915 |
| WP_017647151 | 847 | IPQAFIKDDSIDNRVLVSSAKNRG-KSDN--VP | S--VEIVKDCKV-FWKKLLDAKLMSQRKYDNLTKA--ERGGLTS | 915 |
| WP_017648376 | 847 | IPQAFIKDDSIDNRVLVSSAKNRG-KSDN--VP | S--LEIVKDCKV-FWKKLLDAKLMSQRKYDNLTKA--ERGGLTS | 915 |
| WP_017649527 | 847 | IPQAFIKDDSIDNRVLVSSAKNRG-KSDN--VP | S--IDIVKARKA-FWKKLLDAKLMSQRKYDNLTKA--ERGGLTS | 915 |
| WP_017771611 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_017771984 | 847 | IPQAFIKDDSIDNRVLVSSAKNRG-KSDN--VP | S--LEIVKDCKV-FWKKLLDAKLMSQRKYDNLTKA--ERGGLTS | 915 |
| CFQ25032 | 847 | IPQAFIKDDSIDNRVLVSSAKNRG-KSDD--VP | S--LEIVKDCKV-FWKKLLDAKLMSQRKYDNLTKA--ERGGLTS | 915 |
| CFV16040 | 847 | IPQAFIKDDSIDNRVLVSSAKNRG-KSDD--VP | S--LEIVKDCKV-FWKKLLDAKLMSQRKYDNLTKA--ERGGLTS | 915 |
| KLJ37842 | 847 | IPQAFIKDDSIDNRVLVSSAKNRG-KSDD--VP | S--LEIVKDCKV-FWKKLLDAKLMSQRKYDNLTKA--ERGGLTS | 915 |
| KLJ72361 | 847 | IPQAFIKDDSIDNRVLVSSAKNRG-KSDD--VP | S--LEIVKDCKV-FWKKLLDAKLMSQRKYDNLTKA--ERGGLTS | 915 |
| KLL20707 | 861 | IPQAFIKDDSIDNRVLVSSAKNRG-KSDD--VP | S--LEIVKDCKV-FWKKLLDAKLMSQRKYDNLTKA--ERGGLTS | 929 |
| KLL42645 | 847 | VPQAFIKDDSIDNRVLVSSAKNRG-KSDD--VP | S--IDIVKARKA-FWKKLLDAKLMSQRKYDNLTKA--ERGGLTS | 915 |
| WP_047207273 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_047209694 | 847 | IPQAFIKDDSIDNRVLVSSAKNRG-KSDD--VP | S--VEIVKDCKV-FWKKLLDAKLMSQRKYDNLTKA--ERGGLTS | 915 |
| WP_050198062 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_050201642 | 847 | IPQAFIKDDSIDNRVLVSSENRG-KSDN--VP | S--IDIVKARKA-FWKKLLDAKLMSQRKYDNLTKA--ERGGLTS | 915 |
| WP_050204027 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_050881965 | 847 | IPQAFIKDDSIDNRVLVSSAKNRG-KSDD--VP | S--LEIVKDCKV-FWKKLLDAKLMSQRKYDNLTKA--ERGGLTP | 915 |
| WP_050886065 | 847 | IPQAFIKDDSIDNRVLVSSAKNRG-KSDD--VP | S--LEIVKDCKV-FWKKLLDAKLMSQRKYDNLTKA--ERGGLTS | 915 |
| AHN30376 | 847 | IPQAFIKDDSIDNRVLVSSAKNRG-KSDD--VP | S--LEIVKDCKV-FWKKLLDAKLMSQRKYDNLTKA--ERGGLTS | 915 |
| EA078426 | 847 | IPQAFIKDDSIDNRVLVSSAKNRG-KSDD--VP | S--LEIVCARKA-DWMRLRKAGLISQRKFDNLTKA--ERGGLTS | 915 |
| CCW42055 | 841 | IPQAYIKDDSFDNRVLTSSENRG-KSDN--VP | S--IEVVCARKA-DWMRLRKAGLISQRKFDNLTKA--ERGGLTS | 909 |
| WP_003041502 | 842 | IPQAFIKDNSLDNRVLTRSDKNRG-KSDD--VP | S--IEVVHEMKS-FWSKLLSVKLITQRKFDNLTKA--ERGGLTE | 910 |
| WP_037593752 | 842 | IPQAFIKDNSLDNRVLTRSDKNRG-KSDD--VP | S--IEVVHEMKS-FWSKLLSVKLITQRKFDNLTKA--ERGGLTE | 910 |
| WP_049516684 | 841 | IPQAFIKDNSLDNRVLTRSDKNRG-KSDD--VP | S--IEVVHEMKS-FWSKLLSVKLITQRKFDNLTKA--ERGGLTE | 909 |
| GAD46167 | 850 | IPQAFIKDDSIDNRVLTSSAKNRG-KSDD--VP | S--LGIVRARKA-EWVRLYKSGLISKRKFDNLTKA--ERGGLTE | 918 |
| WP_018363470 | 850 | IPQAFIKDDSIDNRVLTSSAKNRG-KSDD--VP | S--LGIVRARKA-EWVRLYKSGLISKRKFDNLTKA--ERGGLTE | 918 |

-continued

```
WP_003043819    851 VPQSFIKDDSIDNKVLTRSVENRG-KSDN--VP S--EEVVKKMKN-YWRQLLNAKLITQRKFPDNLTKA--ERGGLSE 919
WP_066269658    841 IPQAFIKDDSIDNSLDNRVLTRSDKNRG-KSDD--VP S--IEVVHEMKS-FWSKLLSVKLITQRKFPDNLTKA--ERGGLTE 909
WP_048800089    841 IPQAFIKDDSIDNRVLTSSAKNRG-KSDN--VP N--LEVVCDRKA-DWIRLREAGLISQRKFPDNLTKA--ERGGLTE 909
WP_012767106    841 VPQSFIKDDSIDNKILTRSDKNRG-KSDN--VP S--BEEVVKKMKN-YWRQLLNAKLITQRKFPDNLTKA--ERGGLSE 909
WP_014612333    841 VPQSFIKDDSIDNKVLTRSDKNRG-KSDD--VP S--EEVVKKMKN-YWRQLLNAKLITQRKFPDNLTKA--ERGGLSE 909
WP_015017095    841 VPQSFIKDDSIDNKVLTRSDKNRG-KSDD--VP S--EEVVKKMKN-YWRQLLNAKLITQRKFPDNLTKA--ERGGLSE 909
WP_015057649    841 VPQSFIKDDSIDNKVLTRSDKNRG-KSDD--VP S--EEVVKKMKN-YWRQLLNAKLITQRKFPDNLTKA--ERGGLSE 909
WP_048327215    841 VPQSFIKDDSIDNKVLTRSDKNRG-KSDD--VP S--EEVVKKMKN-YWRQLLNAKLITQRKFPDNLTKA--ERGGLSE 909
WP_049519324    841 VPQSFIKDDSIDNKVLTRSDKNRG-KSDD--VP S--EEVVKKMKN-YWRQLLNAKLITQRKFPDNLTKA--ERGGLSE 909
WP_012515931    841 IPQSFIKNNSIDNKVLTSQGANRG-KLDN--VP S--EAIVRKMKG-YWQSLLRAGAISKQKFPDNLTKA--ERGGLTQ 909
WP_021320964    841 IPQSFIKNNSIDNKVLTSQGANRG-KLDN--VP S--EAIVRKMKG-YWQSLLRAGAISKQKFPDNLTKA--ERGGLTQ 909
WP_037581760    841 IPQSFIKNNSIDNKVLTSSAKNRG-KSDD--VP S--IEIVRNRKS-YWYKLYKSGLISKRKFPDNLTKA--ERGGLTE 909
WP_004232481    849 IPQAFIKDNSIDNRVLTSSAKNRG-KSDD--VP S--IEIVRNRKS-VWYKLYKSGLISKRKFPDNLTKA--ERGGLTE 917
WP_009854540    850 IPQAFIKDDSIDNRVLTSSAKNRG-KSDD--VP S--LDIVRARKA-EWVRLYKSGLISKRKFPDNLTKA--ERGGLTE 918
WP_012962174    850 IPQAFIKDDSIDNRVLTSSAKNRG-KSDD--VP S--LDIVHDRKA-DWIRLYKSGLISKRKFPDNLTKA--ERGGLTE 918
WP_039695303    852 IPQAFIKDDSIDNRVLTSSAKNRG-KSDD--VP S--LDIVRARKA-EWVRLYKSGLISKRKFPDNLTKA--ERGGLTE 920
WP_014334983    849 IPQSFIKDNSIDNTVLTTQASNRG-KSDN--VP S--IEIVRNRRS-YWYKLYKSGLISKRKFPDNLTKA--ERGGLTE 917
WP_003099269    842 IPQSFIKDNSIDNTVLITQASNRG-KSDN--VP N--IETVNKMKS-FWYKQLKSGAISQRKFDHLTKA--ERGALSD 910
AHY15608        842 IPQSFIKDNSIDNTVLTTQASNRG-KSDN--VP N--IETVNKMKS-FWYKQLKSGAISQRKFDHLTKA--ERGALSD 910
AHY17476        842 IPQSFIKDNSIDNTVLITQASNRG-KSDN--VP N--IETVNKMKS-FWYKQLKSGAISQRKFDHLTKA--ERGALSD 910
ESR09100        --- ---------------------------- -- --------------------------------------- ---
AGM98575        842 IPQAFIKDNSIDNTVLTTQASNRG-KSDN--VP N--IETVNKMKS-FWYKQLKSGAISQRKFDHLTKA--ERGALSD 910
ALF27331        858 VPRSYIKNDSFDNKVLTSSKGNRK-KLDD--VP A--KEVVEKMEN-TWRRLHAAGLISDIKLSYLMKGe----LTE 923
WP_018372492    845 IPQAFIKDNSIDNRVLTSSKENRG-KSDN--VP S--KDVVRKMKS-YWSKLLSAKLITQRKFPDNLTKA--ERGGLDE 913
WP_045618028    844 IPQAFIKDNSIDNRVLTSSKDNRG-KSDN--VP S--LEIVQKRKA-FWQQLLDSKLISERKFPNNLTKA--ERGGLDE 912
WP_045635197    842 IPQAFIKDNSIDNRVLTSSKENRG-KSDN--VP S--IEVVQKRKA-FWQQLLDSKLISERKFPNNLTKA--ERGGLTD 910
WP_002263549    842 IPQAFIKDNSIDNRVLTSSKENRG-KSDN--VP S--KDVVRKMKS-YWSKLLSAKLITQRKFPDNLTKA--ERGGLTD 910
WP_002263887    842 IPQAFIKDNSIDNRVLTSSKENRG-KSDN--VP S--KDVVRKMKS-YWSKLLSAKLITQRKFPDNLTKA--ERGGLTD 910
WP_002264920    842 IPQAFIKDNSIDNRVLTSSKENRG-KSDN--VP S--KDVVRKMKS-YWSKLLSAKLITQRKFPDNLTKA--ERGGLTD 910
WP_002269043    842 IPQAFIKDNSIDNRVLTSSKENRG-KSDN--VP S--KDVVRKMKS-YWSKLLSAKLITQRKFPDNLTKA--ERGGLTD 910
WP_002269448    847 IPQAFIKDNSIDNRVLTSSKANRG-KSDD--VP S--BDVVRKMKS-YWSKLLSAKLITQRKFPDNLTKG--ERGGLTD 912
WP_002271977    842 IPQAFIKDNSIDNRVLTSSKENRG-KSDN--VP S--KDVVRKMKS-YWSKLLSAKLITQRKFPDNLTKA--ERGGLTD 910
WP_002272766    842 IPQAFIKDNSIDNRVLTSSKENRG-KSDN--VP S--KDVVRKMKP-YWSKLLSAKLITQRKFPDNLTKA--ERGGLTD 910
WP_002273241    842 IPQAFIKDNSIDNRVLTSSKENRG-KSDN--VP S--KDVVRKMKP-YWSKLLSAKLITQRKFPDNLTKA--ERGGLTD 910
WP_002275430    842 IPQAFIKDNSIDNRVLTSSKENRG-KSDN--VP S--KDVVRKMKP-YWSKLLSAKLITQRKFPDNLTKA--ERGGLTD 910
WP_002276448    842 IPQAFIKDNSIDNRVLTSSKENRG-KSDN--VP S--KDVVRKMKS-YWSKLLSSGLISAKLITQRKFPDNLTKA--ERGGLTD 910
WP_002777050    847 IPQAFIKDNSIDNRVLTSSKANRG-KSDN--VP S--BDVVNRMRP-FWNKLLSSGLISQRKYNNLTKK--E---LTP 912
WP_002777364    842 IPQAFIKDNSIDNRVLTSSKENRG-KSDN--VP S--KNVVRKMKS-YWSKLLSAKLITQRKFPDNLTKA--ERGGLTD 910
WP_002779025    842 IPQAFIKDNSIDNRVLTSSKENRG-KSDN--VP S--KDVVRKMKP-YWSKLLSAKLITQRKFPDNLTKA--ERGGLTD 910
WP_002779859    842 IPQAFIKDNSIDNRVLTSSKENRG-KSDN--VP S--KDVVRKMKP-YWSKLLSAKLITQRKFPDNLTKG--ERGGLTD 910
WP_002780230    842 IPQAFIKDNSIDNRVLTSSKENRG-KSDN--VP S--BDVVRKMKS-YWSKLLSAKLITQRKFPDNLTKA--ERGGLTD 910
WP_002281696    847 IPQAFIKDNSIDNRVLTSSKENRG-KSDN--VP S--KNVVRKMKS-YWSKLLSAKLITQRKFPDNLTKA--ERGGLTD 910
WP_002282247    847 IPQAFIKDNSIDNRVLTSSKENRG-KSDN--VP S--BDVVNRMRP-FWNKLLSISGLISQRKYNNLTKK--E---LTL 912
WP_002282906    842 IPQAFIKDNSIDNRVLTSSKENRG-KSDN--VP S--KDVVRKMKP-YWSKLLSAKLITQRKFPDNLTKA--ERGGLTD 910
WP_002283846    842 IPQAFIKDNSIDNRVLTSSKENRG-KSDN--VP S--KNVVRKMKS-YWSKLLSAKLITQRKFPDNLTKA--ERGGLTD 910
WP_002287255    842 IPQAFIKDNSIDNRVLTSSKENRG-KSDN--VP S--KNVVRKMKS-YWSKLLSAKLITQRKFPDNLTKA--ERGGLTD 910
WP_002288990    842 IPQAFIKDNSIDNRVLTSSKENRG-KSDN--VP S--KDVVRKMKS-YWSKLLSAKLITQRKFPDNLTKA--ERGGLTD 910
WP_002289641    842 IPQAFIKDNSIDNRVLTSSKENRG-KSDN--VP S--KDVVRKMKP-YWSKLLSAKLITQRKFPDNLTKA--ERGGLTD 910
WP_002290427    842 IPQAFIKDNSIDNRVLTSSKENRG-KSDN--VP S--KDVVRKMKP-YWSKLLSAKLITQRKFPDNLTKG--ERGGLTD 910
WP_002295753    842 IPQAFIKDNSIDNRVLTSSKENRG-KSDN--VP S--KDVVRKMKS-YWSKLLSAKLITQRKFPDNLTKA--ERGGLTD 910
WP_002296423    842 IPQAFIKDNSIDNRVLTSSKENRG-KSDN--VP S--KNVVRKMKS-YWSKLLSAKLITQRKFPDNLTKA--ERGGLTD 910
WP_002304487    856 IPQAFIKDNSIDNRVLTRSDKNRG-KSDD--VP S--BEVVHKMKP-FWSKLLSAKLITQRKFPDNLTKA--ERGGLTD 924
WP_002305844    842 IPQAFIKDNSIDNRVLTSSKENRG-KSDD--VP S--KDVVRKMKS-YWSKLLSAKLITQRKFPDNLTKA--ERGGLTD 910
```

-continued

```
WP_002307203   842 IPQAFIKDNSIDNRVLTSSKENRG-KSDD--VP S--KDVVRKMKS-YWSKLLSAKLITQRKFPDNLTKA--ERGGLTD 910
WP_002310390   842 IPQAFIKDNSIDNRVLTSSKENRG-KSDD--VP S--KDVVRKMKS-YWSKLLSAKLITQRKFPDNLTKA--ERGGLTD 910
WP_002352408   842 IPQAFIKDNSIDNRVLTSSKENRG-KSDD--VP S--KDVVRKMKS-YWSKLLSAKLITQRKFPDNLTKA--ERGGLTD 910
WP_012997688   842 IPQAFIKDNSIDNRVLTSSKENRG-KSDD--VP S--KNVVRKMKS-YWSKLLSAKLITQRKFPDNLTKA--ERGGLTD 910
WP_014677909   842 IPQAFIKDNSIDNRVLTSSKENRG-KSDD--VP S--KDVVRKMKS-YWSKLLSAKLITQRKFPDNLTKA--ERGGLTD 910
WP_019312892   842 IPQAFIKDNSIDNRVLTSSKENRG-KSDD--VP S--KNVVRKMKS-YWSKLLSAKLITQRKFPDNLTKA--ERGGLTD 910
WP_019313659   842 IPQAFIKDNSIDNRVLTSSKENRG-KSDD--VP S--KDVVRKMKS-YWSKLLSAKLITQRKFPDNLTKA--ERGGLTD 910
WP_019314093   842 IPQAFIKDNSIDNRVLTSSKENRG-KSDD--VP S--KDVVRKMKP-YWSKLLSAKLITQRKFPDNLTKA--ERGGLTD 910
WP_019315370   842 IPQAFIKDNSIDNRVLTSSKENRG-KSDD--VP S--KDVVRKMKS-YWSKLLSAKLITQRKFPDNLTKA--ERGGLTD 910
WP_019803776   842 IPQAFIKDNSIDNRVLTSSKENRG-KSDD--VP S--KDVVRKMKS-YWSKLLSAKLITQRKFPDNLTKA--ERGGLTD 910
WP_019805234   842 IPQAFIKDNSIDNRVLTSSKENRG-KSDD--VP S--KDVVRKMKS-YWSKLLSAKLITQRKFPDNLTKG--ERGGLTD 910
WP_024783594   842 IPQAFIKDNSIDNRVLTSSKENRG-KSDD--VP S--KDVVRKMKS-YWSKLLSAKLITQRKFPDNLTKA--ERGGLTD 910
WP_024784288   847 IPQAFIKDNSIDNRVLTSSKANRG-KSDD--VP S--EDVVNRMRP-FWNKLLSSGLISQRKYNNLTKK--E---LTL 912
WP_024784666   842 IPQAFIKDNSIDNRVLTSSKENRG-KSDD--VP S--KNVVRKMKS-YWSKLLSAKLITQRKFPDNLTKA--ERGGLTD 910
WP_024784894   842 IPQAFIKDNSIDNRVLTSSKENRG-KSDD--VP S--KDVVRKMKS-YWSKLLSSGLISQRKYNNLTKA--ERGGLTD 910
WP_024786433   847 IPQAFIKDNSIDNRVLTSSKANRG-KSDD--VP S--SDVVNRMRP-FWNKLLSSGLISQRKYNNLTKK--E---LTL 912
WP_049473442   842 IPQAFIKDNSIDNRVLTSSKENRG-KSDD--VP S--KDVVRKMKP-YWSKLLSAKLITQRKFPDNLTKA--ERGGLTD 910
WP_049474547   842 IPQAFIKDNSIDNRVLTSSKENRG-KSDD--VP S--KDVVRKMKS-YWSKLLSAKLITQRKFPDNLTKA--ERGGLTD 910
EMC03581       835 IPQAFIKDNSIDNRVLTSLKDNRG-KSDN--VP S--KNVVRKMKS-YWSKLLSAKLITQRKFPDNLTKA--ERGGLTD 903
WP_000428612   847 VPQAFIKDDSLDNRVLTSLKDNRG-KSDN--VP S--IEVVEKMKT-FWQQLLDSKLISYRKFPNNLTKA--ERGGLDE 915
WP_000428613   845 IPQAFIKDDSLDNRVLTSSKDNRG-KSDN--VP S--LEIVEKMKG-FWQQLLDSKLISERKFPNNLTKA--ERGGLDE 913
WP_049523028   840 IPQAFIKDDSLDNRVLTSSKDNRG-KSDN--VP S--IEVVQKRKA-FWQQLLDSKLISERKFPNNLTKA--KRGGLDE 908
WP_003107102   811 IPQAFIKDDSLDNRVLTSSKDNRG-KSDN--VP Y--IAIVNKMKS-YWQHQLKSGAISQRKEDNLTKA--ERGGLSE 879
WP_054279288   843 IPRSFIKDDSIDNKVLTRSEHNRG-KTDN--VP S--LEVVQKRKA-FWQKLLDTKVISQRKFPDNLTKA--ERGGLQE 911
WP_049531101   845 IPQAFIKDDSLDNRVLTSSKDNRG-KSDN--VP S--LEVVQKRKA-FWQQLLESKLISERKFPNNLTKA--ERGGLNE 913
WP_049538452   845 IPQAFIKDDSLDNRVLTSSKDNRG-KSDN--VP C--LEVVDKMKV-FWQQLLDFKLISYRKFPNNLTKA--ERGGLDE 913
WP_049549711   845 IPQAFIKDDSLDNRVLTSSKDNRG-KSDN--VP S--IEVVRDMKD-VWRRQLANGAISRQKFDHLTKA--ERDGLNE 915
WP_007896501   847 IPQSFIKDNSLDNLVLTTQKANRG-KSDN--VP S--IEVVRDMKDr-VWRRQLANGAISRQKFDHLTKAer-ERDGLNE 916
EFR44625       799 IPQSFIKDNSIDNLVLTTQKANRG-KSDN--VP S--IEVVRDMKDr-VWRRQLANGAISRQKFDHLTKA--ERGGLAD 868
WP_002897477   844 IPQAFIKDDSIDNRVLTSSKDNRG-KSDN--VP S--LEVVQKRKA-FWQQLLDSKLISERKFPNNLTKA--ERGGLDE 912
WP_002906454   844 IPQAFIKDDSLDNRVLTSSKDNRG-KSDN--VP S--IEVVQKRKA-FWQQLLDSKLISERKFPNNLTKA--KRGGLDE 912
WP_009729476   845 IPQAFIKDDSLDNRVLTSAKNRG-KSDN--VP S--LEVVDKMKV-FWQQLLDSKLISYRKFPNNLTKA--ERGGLNE 913
CQR24647       844 IPQSFIKDNSLDNRVLTNSKSNRG-KSDN--VP S--NEVVEKMKA-FWQQLLDSKLISERKFPNNLTKAer-ERGGLNE 912
WP_000066813   847 IPQAFIKDDSLDNRVLTKSAKNRG-KSDN--VP S--LEVVEKMKA-FWKRLRKA-FWQQLLDSKLISERKFPNNLTKA--ERGGLDE 917
WP_009754323   845 IPQAFIKDDSLDNRVLTKSAKNRG-KSDN--VP S--LEIVHKKKN-FWKQLLDSQLISQRKFPNLLTKA--ERGGLDE 913
WP_044674937   844 IPQAFIKDDSLDNKVLTKSAKNRG-KSDN--VP S--LEIVHKKKN-YWRQLLNAKLITQRKFPDNLTKA--ERGGLTN 912
WP_044676715   846 IPQAFIKDDSLDNKVLTKSAKNRG-KSDN--VP S--LEIVHCKKN-FWKQLLDSQLISQRKFPDNLLTKA--ERGGLTN 914
WP_044680361   846 IPQAFIKDDSLDNKVLTKSAKNRG-KSDN--VP S--LEIVHKKKN-FWKQLLDSQLISQRKFPDNLTKA--ERGGLTN 914
WP_044681799   844 IPQAFIKDDSLDNKVLTKSAKNRG-KSDN--VP S--LEIVHKKKN-FWKQLLDSQLISQRKFPDNLTKA--ERGGLTN 912
WP_049533112   841 IPQSFIKDDSFDNLVLVSSKENRL-KMDD--VP D--QKVVIRMRR-YWEKLLRANLISERKFAYLTKLe--LTP 909
WP_029090905   824 LPQSYIKDNSIENLALVKKVENQR-KKDS11LN S--SIINQNYS-RWEQLKNAGLIGEKKFPNLTRTk----ITD 890
WP_006506696   850 VPQSLVKDDSEDNRVLVVPSENQR-KLDD1vVP ---FDIRDKMYR-FWKLLPDHELISPKKFYSLIKTe----YTE 916
AIT42264       842 VPQSFIKDDSIDNKVLTRSDKNRG-KSDN--VP S--EEVVKKMKN-YWRQLLNAKLITQRKFPDNLTKGk----ERGGLSE 910
AKQ34440723    849 IPRSFIKDDSIDNKVLTRSEHNRG-KSDN--VP Sp--DIVRQQKG-FWKQLLRAGLMSQRKFNNLTKA-----LTD 914
AKQ21048       842 VPQSFIKDDSLDNKVLTRSDHNRG-KLDN--VP S--EEVVKKMKN-YWRQLLNAKLITQRKFPDNLTKA--ERGGLSE 910
WP_004636532   846 IPQSFTTDNSIDNKVLVSRTKNQGnKSDD--VP S--INIVHKMKP-FWRQLHKAGLISDRKFKNLLTKA--EHGGLTE 915
WP_002364836   853 IPQSFMKDDSLDNLVLVLGSTENRG-KSDD--VP S--KEVVKDMKA-YWEKLYAAGLISQRKFQRLQTKG--EQGGLTL 921
WP_016631044   804 IPQSFMKDDSLDNLVLVLGSTENRG-KSDD--VP S--KEVVKDMKA-YWEKLYAAGLISQRKFQRLQTKG--EQGGLTL 872
EMS75795       589 IPRSFIVDNSIDNLVLVLSSKENRL-KMDD--VP D--QKVVIRMRR-YWEKLLRANLISERKFAYLTKLe--LTP 654
WP_002373311   853 IPQSFMKDDSLDNLVLVLGSTENRG-KSDD--VP S--KKVVKKMKA-YWEKLYAAGLISQRKFQRLTKG--EQGGLTL 921
WP_002378009   853 IPQSFMKDDSLDNLVLVLGSTENRG-KSDD--VP S--KEVVKDMKA-YWEKLYAAGLISQRKFQRLTKG--EQGGLTL 921
WP_002407324   853 IPQSFMKDDSLDNLVLVLGSTENRG-KSDD--VP S--KEVVKDMKA-YWEKLYAAGLISQRKFQRLTKG--EQGGLTL 921
WP_002413717   853 IPQSFMKDDSLDNLVLVLGSTENRG-KSDD--VP S--KEVVKDMKA-YWEKLYAAGLISQRKFQRLTKG--EQGGLTL 921
```

-continued

```
WP_010775580    855  IPQSFMKDDSLDNLVLVGSTENRG-KSDD--VP   S--KEVVKKMKA-YWEKLYAAGLISQRKFQRLTKG--EQGGLTL  923
WP_010818269    853  IPQSFMKDDSLDNLVLVGSTENRG-KSDD--VP   S--KEVVKDMKA-YWEKLYAAGLISQRKFQRLTKG--EQGGLTL  921
WP_010824395    853  IPQSFMKDDSLDNLVLVGSTENRG-KSDD--VP   S--KEVVKDMKA-YWEKLYAAGLISQRKFQRLTKG--EQGGLTL  921
WP_016622645    853  IPQSFMKDDSLDNLVLVGSTENRG-KSDD--VP   S--KEVVKDMKA-YWEKLYAAGLISQRKFQRLTKG--EQGGLTL  921
WP_033624816    853  IPQSFMKDDSLDNLVLVGSTENRG-KSDD--VP   S--KEVVKDMKA-YWEKLYAAGLISQRKFQRLTKG--EQGGLTL  921
WP_033625576    853  IPQSFMKDDSLDNLVLVGSTENRG-KSDD--VP   S--KEVVKDMKA-YWEKLYAAGLISQRKFQRLTKG--EQGGLTL  921
WP_033789179    853  IPQSFMKDDSLDNLVLVGSTENRG-KSDD--VP   S--KEVVKDMKA-YWEKLYAAGLISQRKFQRLTKG--EQGGLTL  921
WP_002110644    854  IPRSFTTDNSIDNKVLVSSKENRL-KKDD--VP   S--EKVVKKMRS-FWYDLYSSKLISKRKLDNLTKIk----LTE  918
WP_002112694    854  IPRSFTTDNSIDNKVLVSSKENRL-KKDD--VP   S--EKVVKKMRS-FWYDLYSSKLISKRKLDNLTKIk----LTE  919
WP_002314015    854  IPRSFTTDNSIDNKVLVSSKENRL-KKDD--VP   S--EKVVKKMRS-FWYDLYSSKLISKRKLDNLTKIk----LTE  919
WP_002320716    854  IPRSFTTDNSIDNKVLVSSKENRL-KKDD--VP   S--EKVVKKMRS-FWYDLYSSKLISKRKLDNLTKIk----LTE  919
WP_002330729    853  IPRSFTTDNSIDNKVLVSSKENRL-KKDD--VP   S--EKVVKKMRS-FWYDLYSSKLISKRKLDNLTKIk----LTE  918
WP_002335161    854  IPRSFTTDNSIDNKVLVSSKENRL-KKDD--VP   S--EKVVKKMRS-FWYDLYSSKLISKRKLDNLTKIk----LTE  919
WP_002345439    854  IPRSFIVDNSIDDKVLVASKQNQK-KRDD--VP   K--KQIVNEQRI-FWNQLKEAKLISTKKYAYLIKIe----LTP  919
WP_034867970    845  IPRSFIVDNSIDNKVLVASKQNQK-KRDD--VP   K--KQIVNEQRI-FWNQLKEAKLISPKKYAYLIKIe----LTP  910
WP_047937432    854  IPRSFIVDNSIDNKVLVASKQNQK-KRDD--VP   K--KQIVNEQRI-FWDLYSSKLISKRKLDNLTKIe----LTE  919
WP_010720994    845  IPRSFIVDNSIDNKVLVASKQNQK-KRDD--VP   K--KQIVNEQRI-FWNQLKEAKLISPKKYAYLIKIe----LTP  910
WP_010773004    845  IPRSFIVDNSIDNKVLVASKQNQK-KRDD--VP   K--KQIVNEQRI-FWNQLKEAKLISPKKYAYLIKIe----LTP  910
WP_034700478    854  IPRSFIVDNSIDNRVLTSKSNRG-KRDD--VP    N--KQIVNEQRI-FWNQLKEAKLISERKYTNLTKKe----LTE  919
WP_007209003    846  IPQSFLTDNSIDNRVLTSKSNPG-KRDD--VP    S--BERVKTMDR-FWRKLLNAKLISERKYTNLTKKe----LTE  911
WP_023519017    839  IPRSFIVDNSLDNKVLVSSKVNRG-KLDN--AP   D--PLVVKRMRS-HWEKLHQAKLISDKKLANLTKQn----LTE  904
WP_010770040    846  VPQSFTDNSLDNRVLVSSKENRG-KKDD--VP    S--KEVVQKNIT-LWETLKNSNLISQKKYDNLTKG--LRGGLTE  914
WP_048604708    843  IPQSFITDNSIDNKVLTSSKNRG-KLDD--VP    S--KEVVKKMRA-FWESLYRSGLISKKKFPDNLVKA--ESGGLSE  911
WP_010750235    848  IPRSFIVDHSLDNKVLVSSKENRL-KKDD--VP   S--SKVVKRMKA-YWEKLLRANLISERKFSYLTKIe----LTD  913
AII16583        881  VPQSFLKDDSIDNKVLTRSDKNRG-KSDN--VP   S--BEVVKKMKN-YWRQLLNAKLITQRKFDNLTKA--ERGGLSE  949
WP_029073316    861  VPQSLLKDDSIDNKVLVLSSENQR-KLDD1vIP   ---EMIRNKMFG-FWNKLYENKLISPKKFYSLIKSe----YSD  927
WP_031589969    861  VPQSLLKDDSIDNKVLVLSSENQR-KLDD1vIP   ---SSIRNKMYG-FWEKLFNNKLISPKKFYSLIKTe----FNE  927
KDA45870        834  IPQSFLKDDSIENKVLTIKKENVR-KTNG--LP   S--EAVIQKMGS-FWKKLLDAGAMTNKKYDNLRRN1--HGGLNE  902
WP_039099354    857  LPQSFIKDNSLDNRVLVSQRMNRS-KADQ--VP   S--VELGQKMQI-QWEQMLRAGLITKKKYDNLTLNp---------  923
AKP02966        859  LPRTYIPDDSLENKALVLAKENQR-KADD11LN   S--NVIDKNLE-RWTYMLNNNMMGLKKFKNLTRRv----ITD  925
WP_010991369    845  VPQSFITDNSIDNLVLTSSAGNRE-KGDD--VP   P--LEIVRKRKA-FWEKLYQGNLMSKRKFPDYLTKA--ERGGLTE  913
WP_003838504    845  VPQSFITDNSIDNLVLTSSAGNRE-KGDD--VP   P--LEIVRKRKA-FWEKLYQGNLMSKRKFPDYLTKA--ERGGLTE  913
EHN60060        848  VPQSFITDNSIDNLVLTSSAGNRE-KGGD--VP   P--LEIVQKRKI-FWEKLYQGNLMSKRKFPDYLTKA--ERGGLTE  916
EFR89594        614  VPQSFITDNSIDNLVLTSSAGNRE-KGND--VP   P--LEIVQKRKI-FWEKLYQGNLMSKRKFPDYLTKA--ERGGLTE  682
WP_038409211    845  IPQSFITDNSIDNRVLVSSTANRE-KGDN--VP   L--LEIVRKRKA-FWEKLYQAKLMSKRKFPDYLTKA--ERGGLTE  913
EFR95520        464  IPQSFITDNSIDNLVLTSSAGNRE-KGDN--VP   L--LEIVRKRKA-FWEKLYQAKLMSKRKFPDYLTKA--ERGGLTE  532
WP_003723650    845  VPQSFITDNSIDNLVLTSSAGNRE-KGGD--VP   P--LEIVRKRKI-FWEKLYQGNLMSKRKFPDYLTKA--ERGGLTE  913
WP_003727705    845  VPQSFITDNSIDNLVLTSSAGNRE-KGDN--VP   P--LEIVRKRKI-FWEKLYQGNLMSKRKFPDYLTKA--ERGGLTE  913
WP_003730785    845  VPQSFITDNSIDNLVLTSSAGNRE-KGGD--VP   P--LEIVRKRKI-FWEKLYQGNLMSKRKFPDYLTKA--ERGGLTE  913
WP_003733029    845  VPQSFITDNSVDNLVLTSSAGNRE-KGGD--VP   P--LEIVRKRKI-FWEKLYQGNLMSKRKFPDYLTKA--ERGGLTE  913
WP_003739838    845  VPQSFITDNSIDNLVLTSSAGNRE-KGDN--VP   P--LEIVQKRKI-FWEKLFQGNLMSKRKFPDYLTKA--ERGGLTE  913
WP_014601172    845  VPQSFITDNSIDNLVLTSSAGNRE-KGGD--VP   P--LEIVQKRKI-FWEKLYQGNLMSKRKFPDYLTKA--ERGGLTD  913
WP_023548323    845  VPQSFITDNSIDNLVLTSSAGNRE-KGDN--VP   P--LEIVQKRKI-FWEKLYQGNLMSKRKFPDYLTKA--ERGGLTE  913
WP_031665337    848  VPQSFITDNSIDNLVLTSSAGNRE-KGDN--VP   P--LEIVRKRKI-FWEKLYQGNLMSKRKFPDYLTKA--ERGGLTE  916
WP_031669209    845  VPQSFITDNSIDNLVLTSSAGNRE-KGDN--VP   P--LEIVRKRKI-FWEKLYQGNLMSKRKFPDYLTKA--ERGGLTE  913
WP_033920898    845  VPQSFITDNSIDNLVLTSSAGNRE-KGDN--VP   P--LEIVRKRKI-FWEKLYQGNLMSKRKFPDYLTKA--ERGGLTE  913
AKI42028        848  VPQSFITDNSIDNLVLTSSAGNRE-KGGD--VP   P--LEIVQKRKI-FWEKLYQGNLMSKRKFPDYLTKA--ERGGLTD  916
AKI50529        848  VPQSFITDNSIDNLVLTSSAGNRE-KGDN--VP   P--LEIVQKRKI-FWEKLYQGNLMSKRKFPDYLTKA--ERGGLTE  916
EFR83390        293  VPQSFITDNSIDNLVLTSSAANRE-KGDN--VP   S--LEVVRKRKV-YWEKLYQAKLINAKLITQRKFDNLTKA--ERGGLTE  361
WP_046323366    845  VPQSFIVDNSIDNKVLTRSDKNRG-KSDN--VP   S--BEVVKKMKN-YWRQLLNAKLITQRKFDNLTKA--ERGGLTE  913
AKE81011        858  VPQSLVKDDSFDNRVLVLPSENQR-KLDD1vVP   ---FDIRDKMYR-FWKLLFPDHELISPKKFYSLIKTe----YTE  926
CU083235        854  VPQSLVKDDSFDNRVLVLPSENQM-KLDSetVP   ---FEIRNKMIG-FWQMLHENGLMSNKKFFSLIRTd----FSD  920
WP_033162887    856  LPQSLIKDDSFDNRVLVLPEENQM-KLDSetVP   ---FEIRNKMIG-FWQMLHENGLMSNKKFFSLIRTd----FSD  922
```

```
AGZ01981           875 VPQSFLKDDSIDNKVLTRSDKNRG-KSDN--VP S--EEVVKKMKN-YWRQLLNAKLITQRKFPDNLTKA--ERGGLSE 943
AKA60242           842 VPQSFLKDDSIDNKVLTRSDKNRG-KSDN--VP S--EEVVKKMKN-YWRQLLNAKLITQRKFPDNLTKA--ERGGLSE 910
AKS40380           842 VPQSFLKDDSIDNKVLTRSDKNRG-KSDN--VP S--EEVVKKMKN-YWRQLLNAKLITQRKFPDNLTKA--ERGGLSE 910
4UN5_B             846 VPQSFLKDDSIDNKVLTRSDKNRG-KSDN--VP S--EEVVKKMKN-YWRQLLNAKLITQRKFPDNLTKA--ERGGLSE 914
WP_010922251       911 LD KAGFIKRQLVETRQITKHVAQILDSRMNTKYDENDKLIR--EVKVITLKSKLVSDFRKDF QFYKVREINNY 981
WP_039695303       921 AD KVGFIKRQLVETRQITKHVAQILDARFNTEHDENDKVIR--DVKVITLKSNLVSQFRKDF EFYKVREINDY 991
WP_045635197       913 RD KVGFIKRQLVETRQITKHVAQILDARYNTEVNEKDKKNR--TVKIITLKSNLVSNERKEF RLYKVREINDY 983
5AXW_A             633 RD QKDFINRNLVDTRYATRGLMNLLRSYFR------VNn1DVKVKSINGGFTSFLRRKW KFKKERNKGYK 702
WP_009880683       595 LD KAGFIKRQLVETRQITKHVAQILDSRMNTKYDENDKLIR--EVKVITLKSKLVSDERKDF QFYKVREINNY 665
WP_010922251       911 LD KAGFIKRQLVETRQITKHVAQILDSRMNTKYDENDKLIR--EVKVITLKSKLVSDERKDF QFYKVREINNY 981
WP_011054416       911 LD KAGFIKRQLVETRQITKHVAQILDSRMNTKYDENDKLIR--EVKVITLKSKLVSDERKDF QFYKVREINNY 981
WP_011284745       911 LD KAGFIKRQLVETRQITKHVAQILDSRMNTKYDENDKLIR--EVKVITLKSKLVSDERKDF QFYKVREINNY 981
WP_011285506       911 LD KVGFIKRQLVETRQITKHVAQILDSRMNTKYDENDKLIR--EVKVITLKSKLVSDERKDF QFYKVREINNY 981
WP_011527619       911 LD KAGFIKRQLVETRQITKHVAQILDSRMNTKYDENDKLIR--EVKVITLKSKLVSDERKDF QFYKVREINNY 981
WP_012560673       911 LD KAGFIKRQLVETRQITKHVAQILDSRMNTKYDENDKLIR--EVKVITLKSKLVSDERKDF QFYKVREINNY 981
WP_014407541       910 LD KAGFIKRQLVETRQITKHVAQILDSRMNTKYDENDKLIR--EVKVITLKSKLVSDERKDF QFYKVREINNY 980
WP_020905136       911 LD KAGFIKRQLVETRQITKHVAQILDSRMNTKYDENDKLIR--EVKVITLKSKLVSDERKDF QFYKVREINNY 981
WP_023080005       910 LD KAGFIKRQLVETRQITKHVAQILDSRMNTKYDENDKLIR--EVKVITLKSKLVSDERKDF QFYKVREINNY 980
WP_023610282       910 LD KAGFIKRQLVETRQITKHVAQILDSRMNTKYDENDKLIR--EVKVITLKSKLVSDERKDF QFYKVREINNY 980
WP_030125963       911 LD KAGFIKRQLVETRQITKHVAQILDSRMNTKYDENDKLIR--EVKVITLKSKLVSDERKDF QFYKVREINNY 981
WP_030126706       911 LD KAGFIKRQLVETRQITKHVAQILDSRMNTKYDENDKLIR--EVKVITLKSKLVSDERKDF QFYKVREINNY 981
WP_031488318       911 LD KAGFIKRQLVETRQITKHVAQILDSRMNTKYDENDKLIR--EVKVITLKSKLVSDERKDF QFYKVREINNY 981
WP_032460140       911 LD KAGFIKRQLVETRQITKHVAQILDSRMNTKYDENDKLIR--EVKVITLKSKLVSDERKDF QFYKVREINNY 981
WP_032461047       911 LD KAGFIKRQLVETRQITKHVAQILDSRMNTKYDENDKLIR--EVKVITLKSKLVSDERKDF QFYKVREINNY 981
WP_032462016       911 LD KAGFIKRQLVETRQITKHVAQILDSRMNTKYDENDKLIR--EVKVITLKSKLVSDERKDF QFYKVREINNY 981
WP_032462936       911 LD KAGFIKRQLVETRQITKHVAQILDSRMNTKYDENDKLIR--EVKVITLKSKLVSDERKDF QFYKVREINNY 981
WP_032464890       911 LD KAGFIKRQLVETRQITKHVAQILDSRMNTKYDENDKLIR--EVKVITLKSKLVSDERKDF QFYKVREINNY 981
WP_033888930       736 LD KAGFIKRQLVETRQITKHVAQILDSRMNTKYDENDKLIR--EVKVITLKSKLVSDERKDF QFYKVREINNY 806
WP_038431314       911 LD KAGFIKRQLVETRQITKHVAQILDSRMNTKYDENDKLIR--EVKVITLKSKLVSDERKDF QFYKVREINNY 981
WP_038432938       910 LD KAGFIKRQLVETRQITKHVAQILDSRMNTKYDENDKLIR--EVKVITLKSKLVSDERKDF QFYKVREINNY 980
WP_038434062       911 LD KAGFIKRQLVETRQITKHVAQILDSRMNTKYDENDKLIR--EVKVITLKSKLVSDERKDF QFYKVREINNY 981
BAQ51233           822 LD KVGFIKRQLVETRQITKHVAQILDSRMNTKYDENDKLIR--EVKVITLKSKLVSDERKDF QFYKVREINNY 892
KGE60162            86 -- -------------------------------------------------------- ----------- 156
KGE60856           911 -- KAGFIKRQLVETRQITKHVAQILDSRMNTKYDENDKLIR--EVKVITLKSNLVSDERKDF QFYKVREINNY 981
WP_002989955       910 ED KAGFIKRQLVETRQITKHVAQILDERFNTEFDGNKRPIR--NVKIITLKSNLVSNFRKEF ELYKVREINDY 980
WP_003030002       921 AD KAGFIKRQLVETRQITKHVAQILDARFNTESDENDKVIR--DVKVITLKSNLVSQFRKDF EFYKVREINDY 991
WP_003065552       916 DD KARFIQRQLVETRQITKHVARILDERFNNELDSKGRRIR--KVKIVTLKSNLVSNFRKEF VFYKIREVNDY 986
WP_001040076       916 DD KARFIQRQLVETRQITKHVARILDERFNNELDSKGRRIR--KVKIVTLKSNLVSNFRKEF GFYKIREVNDY 986
WP_001040078       916 DD KARFIQRQLVETRQITKHVARILDERFNNELDSKGRRIR--KVKIVTLKSNLVSNFRKEF GFYKIREVNNY 986
WP_001040080       916 DD KARFIQRQLVETRQITKHVARILDERFNNELDSKGRRIR--KVKIVTLKSNLVSNFRKEF GFYKIREVNNY 986
WP_001040081       916 DD KARFIQRQLVETRQITKHVARILDERFNNELDSKGRRIR--KVKIVTLKSNLVSNFRKEF GFYKIREVNNY 986
WP_001040083       916 DD KARFIQRQLVETRQITKHVARILDERFNNELDSKGRRIR--KVKIVTLKSNLVSNFRKEF GFYKIREVNNY 986
WP_001040085       916 DD KARFIQRQLVETRQITKHVARILDERFNNELDSKGRRIR--KVKIVTLKSNLVSNFRKEF GFYKIREVNNY 986
WP_001040087       916 DD KARFIQRQLVETRQITKHVARILDERFNNELDSKGRRIR--KVKIVTLKSNLVSNFRKEF GFYKIREVNNY 986
WP_001040088       916 DD KARFIQRQLVETRQITKHVARILDERFNNELDSKGRRIR--KVKIVTLKSNLVSNFRKEF GFYKIREVNNY 986
WP_001040089       916 DD KARFIQRQLVETRQITKHVARILDERFNNELDSKGRRIR--KVKIVTLKSNLVSNFRKEF GFYKIREVNNY 986
WP_001040090       916 DD KARFIQRQLVETRQITKHVARILDERFNNELDSKGRRIR--KVKIVTLKSNLVSNFRKEF GFYKIREVNNY 986
WP_001040091       916 DD KARFIQRQLVETRQITKHVARILDERFNNELDSKGRRIR--KVKIVTLKSNLVSNFRKEF GFYKIREVNNY 986
WP_001040092       916 DD KARFIQRQLVETRQITKHVARILDERFNNELDSKGRRIR--KVKIVTLKSNLVSNFRKEF GFYKIREVNNY 986
WP_001040094       916 DD KARFIQRQLVETRQITKHVARILDERFNNELDSKGRRIR--KVKIVTLKSNLVSNFRKEF GFYKIREVNNY 986
WP_001040095       916 DD KARFIQRQLVETRQITKHVARILDERFNNELDSKGRRIR--KVKIVTLKSNLVSNFRKEF GFYKIREVNNY 986
WP_001040096       916 DD KARFIQRQLVETRQITKHVARILDERFNNELDSKGRRIR--KVKIVTLKSNLVSNFRKEF GFYKIREVNNY 986
WP_001040097       916 DD KARFIQRQLVETRQITKHVARILDERFNNELDDNNKPIR--KVKIVTLKSNLVSNFRKEF GFYKIREVNNY 986
```

| | | | | |
|---|---|---|---|---|
| WP_001040098 | 916 | DD KARFIQRQLVETRQITKHVARILDERFNNELDSKGRRIR--KVKIVTLKSNLVSNFRKEF GFYKIREVNNY | 986 |
| WP_001040099 | 916 | DD KARFIQRQLVETRQITKHVARILDERFNNELDSKGRRIR--KVKIVTLKSNLVSNFRKEF GFYKIREVNNY | 986 |
| WP_001040100 | 916 | DD KARFIQRQLVETRQITKHVARILDERFNNELDSKGRRIR--KVKIVTLKSNLVSNFRKEF GFYKIREVNNY | 986 |
| WP_001040104 | 916 | DD KARFIQRQLVETRQITKHVARILDERFNNELDSKGRRIR--KVKIVTLKSNLVSNFRKEF GFYKIREVNNY | 986 |
| WP_001040105 | 916 | DD KARFIQRQLVETRQITKHVARILDERFNNELDSKGRRIR--KVKIVTLKSNLVSNFRKEF GFYKIREVNNY | 986 |
| WP_001040106 | 916 | DD KARFIQRQLVETRQITKHVARILDERFNNELDSKGRRIR--KVKIVTLKSNLVSNFRKEF GFYKIREVNDY | 986 |
| WP_001040107 | 916 | DD KARFIQRQLVETRQITKHVARILDERFNNELDSKGRRIR--KVKIVTLKSNLVSNFRKEF GFYKIREVNDY | 986 |
| WP_001040108 | 916 | DD KARFIQRQLVETRQITKHVARILDERFNNELDSKGRRIR--KVKIVTLKSNLVSNFRKEF GFYKIREVNDY | 986 |
| WP_001040109 | 916 | DD KARFIQRQLVETRQITKHVARILDERFNNELDSKGRRIR--KVKIVTLKSNLVSNFRKEF GFYKIREVNDY | 986 |
| WP_001040110 | 916 | DD KAGFIQRQLVETRQITKHVARILDERFNNELDSKGRRIR--KVKIVTLKSNLVSNFRKEF GFYKIREVNDY | 986 |
| WP_015058523 | 916 | DD KARFIQRQLVETRQITKHVARILDERFNNKVDDNNKPIR--KVKIVTLKSNLVSNFRKEF GFYKIREVNNY | 986 |
| WP_017643650 | 916 | DD KARFIQRQLVETRQITKHVARILDERFNNELDSKGRRIR--KVKIVTLKSNLVSNFRKEF GFYKIREVNNY | 986 |
| WP_017647151 | 916 | DD KARFIQRQLVETRQITKHVARILDELFNNELDSKGRRIR--KVKIVTLKSNLVSNFRKEF GFYKIREVNNY | 986 |
| WP_017648376 | 930 | DD KARFIQRQLVETRQITKHVARILDERFNNELDSKGRRIR--KVKIVTLKSNLVSNFRKEF GFYKIREVNNY | 1000 |
| WP_017649527 | 916 | DD KARFIQRQLVETRQITKHVARILDERFNNELDSKGRRIR--KVKIVTLKSNLVSNFRKEF GFYKIREVNDY | 986 |
| WP_017771611 | 916 | DD KARFIQRQLVETRQITKHVARILDERFNNELDSKGRRIR--KVKIVTLKSNLVSNFRKEF GFYKIREVNNY | 986 |
| WP_017771984 | 916 | DD KARFIQRQLVETRQITKHVARILDERFNNELDSKGRRIR--KVKIVTLKSNLVSNFRKEF GFYKIREVNNY | 986 |
| CFQ25032 | 916 | DD KARFIQRQLVEIRQITKHVARILDERFNNELDSKGRRIR--KVKIVTLKSNLVSNFRKEF GFYKIREVNNY | 986 |
| CFV16040 | 916 | DD KARFIQRQLVETRQITKHVARILDERFNNELDSKGRRIR--KVKIVTLKSNLVSNFRKEF GFYKIREVNNY | 986 |
| KLJ37842 | 916 | DD KARFIQRQLVETRQITKHVASILDERFNNELDSKGRRIR--KVKIVTLKSNLVSNFRKEF GFYKIREVNNY | 986 |
| KLJ72361 | 916 | DD KARFIQRQLVETRQITKHVARILDERFNNELDSKGRRIR--KVKIVTVKSNLVSNFRKEF GFYKIREVNNY | 986 |
| KLL20707 | 916 | DD KARFIQRQLVETRQITKHVARILDERFNNELDSKGRRIR--KVKIVTLKSNLVSNFRKEF GFYKIREVNNY | 986 |
| KLL42645 | 916 | DD KARFIQRQLVETRQITKHVARILDERFNNELDSKGRRIR--KVKIVTLKSNLVSNFRKEF GFYKIREVNDY | 986 |
| WP_047207273 | 916 | DD KARFIQRQLVETRQITKHVARILDERFNNELDSKGRRIR--KVKIVTLKSNLVSNFRKEF GFYKIREVNNY | 986 |
| WP_047209694 | 916 | DD KARFIQRQLVETRQITKHVARILDERFNNELDSKGRRIR--KVKIVTLKSNLVSNFRKEF GFYKIREVNNY | 986 |
| WP_050198062 | 916 | DD KARFIQRQLVETRQITKHVARILDERFNNELDSKGRRIR--KVKIVTLKSNLVSNFRKEF GFYKIREVNNY | 986 |
| WP_050201642 | 916 | DD KARFIQRQLVETRQITKHVARILDERFNNELDSKGRRIR--KVKIVTLKSNLVSNFRKEF GFYKIREVNDY | 986 |
| WP_050204027 | 916 | DD KARFIQRQLVETRQITKHVARILDERFNNELDSKGRRIR--KVKIVTLKSNLVSNFRKEF GFYKIREVNNY | 986 |
| WP_050881965 | 916 | DD KARFIQRQLVETRQITKHVARILDERFNNELDSKGRRIR--KVKIVTLKSNLVSNFRKEF GFYKIREVNNY | 986 |
| WP_050886065 | 916 | DD KARFIQRQLVETRQITKHVARILDERFNNKVDDNNKPIR--KVKIVTLKSNLVSNFRKEF GFYKIREVNNY | 986 |
| AHN30376 | 916 | DD KARFIQRQLVETRQITKHVARILDERFNNELDSKGRRIR--KVKIVTLKSNLVSNFRKEF GFYKIREVNNY | 986 |
| EA078426 | 916 | DD KARFIQRQLVETRQITKHVARILDERFNNELDSKGRRIR--KVKIVTLKSNLVSNFRKEF GFYKIREVNNY | 986 |
| CCW42055 | 916 | DD KARFIQRQLVETRQITKHVARILDERFNNELDSKGRRIR--KVKIVTLKSNLVSNFRKEF GFYKIREVNDY | 986 |
| WP_003041502 | 910 | ND KAGFIKRQLVETRQITKHVAQVLDARFNAKHDENKKVIR--DVKIITLKSNLVSNFRKEF KFYKVREINDY | 980 |
| WP_037593752 | 911 | ED KAGFIKRQLVETRQITKHVAQILDERFNTEFDGAQRRIR--NVKIITLKSNLVSNFRKEF ELYKVREINDY | 981 |
| WP_049516684 | 911 | ED KAGFIKRQLVETRQITKHVAQILDERFNTEFDGAQRRIR--NVKIITLKSNLVSNFRKEF ELYKVREINDY | 981 |
| GAD46167 | 910 | ED KAGFIKRQLVETRQITKHVAQILDERFNTERDENDKVIR--DVKVITLKSNLVSDFRKEF ELYKVREINDY | 980 |
| WP_018363470 | 919 | AD KAGFIKRQLVETRQITKHVAQILDARFNTERDENDKVIR--DVKVITLKSNLVSQFRKEF KFYKVREINDY | 989 |
| WP_003043819 | 920 | AD KAGFIKRQLVETRQITKHVARILDSRMNTKRDKNDKPIR--EVKVITLKSKLVSDFRKDF QLYKVRDINNY | 990 |
| WP_066269658 | 910 | ED KAGFIQRQLVETRQITKHVARILDSRMNTKYDENDKLIR--NVKIITLKSNLVSNFRKEF ELYKVREINDY | 980 |
| WP_048800089 | 910 | ND KAGFIHRQLVETRQITKHVAQILDARFNPKRDDNKKVIR--DVKIITLKSKLVSQFPRRDF KLYKVREINDY | 980 |
| WP_012767106 | 910 | LD KAGFIKRQLVETRQITKHVAQILDSRMNTKYDENDKLIR--EVKVITLKSKLVSDFRKDF QFYKVREINDY | 980 |
| WP_014612333 | 910 | LD KAGFIKRQLVETRQITKHVAQILDSRMNTKYDENDKLIR--EVKVITLKSKLVSDFRKDF QFYKVREINDY | 980 |
| WP_015017095 | 910 | LD KAGFIKRQLVETRQITKHVAQILDSRMNTKYDENDKLIR--EVKVITLKSKLVSDFRKDF QFYKVREINDY | 980 |
| WP_015057649 | 910 | LD KAGFIKRQLVETRQITKHVAQILDSRFNTEFDDHNKLIR--KVHIITLKSKLVSDFRKEF GLYKIRDINHY | 980 |
| WP_048327215 | 910 | LD KAGFIKRQLVETRQITKHVAQILDSRFNTEFDDHNKLIR--KVHIITLKSKLVSDFRKEF GLYKIRDINHY | 980 |
| WP_049519324 | 910 | LD KAGFIKRQLVETRQITKHVAQILDSRFNTEFDDHNKLIR--KVHIITLKSKLVSDFRKEF GLYKIRDINHY | 980 |
| WP_012515931 | 910 | VD KAGFIQRQLVETRQITKHVAQILDSRMNTKYDENDKLIR--KVHIITLKSKLVSDFRKEF GLYKIRDINHY | 980 |
| WP_021320964 | 910 | VD KAGFIQRQLVETRQITKHVAQILDSRFNTEFDDHNKRIR--KVHIITLKSKLVSDFRKEF GLYKIRDINHY | 980 |
| WP_037581760 | 910 | VD KAGFIQLQLVETRQITKHVAQILDSRFNTERDENDKVIR--KVHIITLKSKLVSDFRKEF GLYKIRDINHY | 980 |
| WP_004232481 | 918 | TD KAGFIKRQLVETRQITKHVAQILDSRFNTKCCDENDKVIR--DVKVITLKSSLVSQFRKEF KFYKVREINDY | 988 |
| WP_009854540 | 919 | AD KAGFIKRQLVETRQITKHVAQILDARFNTEHDENDKVIR--DVKVITLKSNLVSQFPRKDF EFYKVREINDY | 989 |
| WP_012962174 | 919 | ND KAGFIKRQLVETRQITKHVAQILDSRFNTERDENDKVIR--NVKVITLKSNLVSNFRKEF KFYKVREINDY | 989 |

| | | | | |
|---|---|---|---|---|
| WP_039695303 | 921 | AD KAGFIKRQLVETRQITKHVAQILDARFNTEHDENDKVIR--DVKVITLKSNLVSQFRKDF | EFYKVREINDY | 991 |
| WP_014334983 | 918 | AD KAGFIKRQLVETRQITKHVAQILDARFNTKRDENDKVIR--DVKVITLKSNLVSQFRKEF | KFYKLREINDY | 988 |
| WP_003099269 | 911 | FD KAGFIRRQLVETRQITKHVAQILDSRFNSLTEDSKSNR--NVKIITLKSKMVSDFRKDF | GFYKLREVNDY | 981 |
| AHY15608 | 911 | FD KAGFIKRQLVETRQITKHVAQILDSRFNSLTEDSKSNR--NVKIITLKSKMVSDFRKDF | GFYKLREVNDY | 981 |
| AHY17476 | 911 | FD KAGFIKRQLVETRQITKHVAQILDSRFNSLTEDSKSNR--NVKIITLKSKMVSDFRKEF | GFYKLREVNDY | 981 |
| ESR09100 | | -- -------------------------------------------------------- | ---------- | |
| AGM98575 | 911 | FD KAGFIKRQLVETRQITKHVAQILDSRFNSLTEDSKSNR--NVKIITLKSKMVSDFRKDF | GFYKLREVNDY | 981 |
| ALF27331 | 911 | DD KAGFIKRQLVETRQITKHVARILDERFNTETDENNKKIR--QVKIVTLKSNLVSNFRKEF | ELYKVREINDY | 981 |
| WP_018372492 | 924 | ED KAGFIRRQLVETRQITKHVARLLDEKLNRKKNENGEKLR--TTKIITLKSVFASRFRANF | DLYKLRELNHY | 994 |
| WP_045618028 | 914 | RD KVGFIKRQLVETRQITKHVAQILDARFNTEVTEKDKKDR--SVKIITLKSNLVSNFRKEF | RLYKVREINDY | 984 |
| WP_045635197 | 913 | RD KVGFIKRQLVETRQITKHVAQILDARYNTEVNEKDKKNR--TVKIITLKSNLVSNFRKEF | RLYKVREINDY | 983 |
| WP_002263549 | 911 | DD KAGFIKRQLVETRQITKHVARILDERFNTETDENNKKIR--QVKIVTLKSNLVSNFRKEF | ELYKVREINDY | 981 |
| WP_002263887 | 911 | DD KAGFIKRQLVETRQITKHVARILDERFNTETDENNKKIR--QVKIVTLKSNLVSNFRKEF | ELYKVREINDY | 981 |
| WP_002264920 | 911 | DD KAGFIKRQLVETRQITKHVARILDERFNTETDENNKKIR--QVKIVTLKSNLVSNFRKEF | ELYKVREINDY | 981 |
| WP_002269043 | 911 | DD KAGFIKRQLVETRQITKHVARILDERFNTETDENNKKIR--QVKIVTLKSNLVSNFRKEF | ELYKVREINDY | 981 |
| WP_002269448 | 911 | DD KAGFIKRQLVETRQITKHVARILDERFYTETDENNKKIR--QVKIVTLKSNLVSNFRKEF | ELYKVREINDY | 981 |
| WP_002271977 | 911 | DD KAGFIKRQLVETRQITKHVARILDERFYTETDENNKKIR--QVKIVTLKSNLVSNFRKEF | ELYKVREINDY | 981 |
| WP_002272766 | 911 | DD KAGFIKRQLVETRQITKHVARILDERFNTETDENNKKIR--QVKIVTLKSNLVSNFRKEF | ELYKVREINDY | 981 |
| WP_002273241 | 911 | DD KAGFIKRQLVETRQITKHVARILDERFNTETDENNKKIR--QVKIVTLKSNLVSNFRKEF | ELYKVREINDY | 981 |
| WP_002275430 | 911 | DD KAGFIKRQLVETRQITKHVARILDERFNTETDENNKKIR--QVKIVTLKSNLVSNFRKEF | ELYKVREINDY | 981 |
| WP_002276448 | 911 | DD KAGFIKRQLVETRQITKHVARILDERFNTETDENNKKIR--QVKIVTLKSNLVSNFRKEF | ELYKVREINDY | 981 |
| WP_002277050 | 913 | DD KAGFIKRQLVETRQITKHVARMLDERFNKEFDDNNKKIR--RVKIVTLKSNLVSSFRKEF | ELYKVREINDY | 983 |
| WP_002277364 | 911 | DD KAGFIKRQLVETRQITKHVARILDERFHTETDENNKKIR--QVKIVTLKSNLVSNFRKEF | ELYKVREINDY | 981 |
| WP_002279025 | 911 | DD KAGFIKRQLVETRQITKHVARILDERFNTETDENNKKIR--QVKIVTLKSNLVSNFRKEF | ELYKVREINDY | 981 |
| WP_002279859 | 911 | DD KAGFIKRQLVETRQITKHVARILDERFNTETDENNKKIR--QVKIVTLKSNLVSNFRKEF | ELYKVREINDY | 981 |
| WP_002280230 | 911 | DD KAGFIKRQLVETRQITKHVARILDERFYTETDENNKKIR--QVKIVTLKSNLVSNFRKEF | ELYKVREINDY | 981 |
| WP_002281696 | 911 | DD KAGFIKRQLVETRQITKHVARILDERFHTETDENNKKIR--QVKIVTLKSNLVSNFRKEF | ELYKVREINDY | 981 |
| WP_002282247 | 913 | DD KAGFIKRQLVETRQITKHVARMLDERFNKEFDDNNKKIR--RVKIVTLKSNLVSSFRKEF | ELYKVREINDY | 983 |
| WP_002282906 | 911 | DD KAGFIKRQLVETRQITKHVARILDERFNTETDENNKKIR--QVKIVTLKSNLVSNFRKEF | ELYKVREINDY | 981 |
| WP_002283846 | 911 | DD KAGFIKRQLVETRQITKHVARILDERFNTETDENNKKIR--QVKIVTLKSNLVSNFRKEF | ELYKVREINDY | 981 |
| WP_002287255 | 911 | DD KAGFIKRQLVETRQITKHVARILDERFHTETDENNKKIR--QVKIVTLKSNLVSNFRKEF | ELYKVREINDY | 981 |
| WP_002288990 | 911 | DD KAGFIKRQLVETRQITKHVARILDERFNTETDENNKKIR--QVKIVTLKSNLVSNFRKEF | ELYKVREINDY | 981 |
| WP_002289641 | 925 | DD KAGFIKRQLVETRQITKHVARILDERFHTETDENNKKIR--QVKIVTLKSNLVSNFRKEF | ELYKVREINDY | 995 |
| WP_002290427 | 911 | DD KAGFIKRQLVETRQITKHVARILDERFNTETDENNKKIR--QVKIVTLKSNLVSNFRKEF | ELYKVREINDY | 981 |
| WP_002295753 | 911 | DD KAGFIKHQLVETRQITKHVARILDERFYTETDENNKKIR--QVKIVTLKSNLVSNFRKEF | ELYKVREINDY | 981 |
| WP_002296423 | 911 | DD KAGFIKRQLVETRQITKHVARILDERFNTETDENNKKIR--QVKIVTLKSNLVSNFRKEF | ELYKVREINDY | 981 |
| WP_002304487 | 911 | DD KAGFIKRQLVETRQITKHVARILDERFHTETDENNKKIR--QVKIVTLKSNLVSNFRKEF | ELYKVREINDY | 981 |
| WP_002305844 | 911 | DD KAGFIKRQLVETRQITKHVARILDERFHTETDENNKKIR--QVKIVTLKSNLVSNFRKEF | ELYKVREINDY | 981 |
| WP_002307203 | 911 | DD KAGFIKRQLVETRQITKHVARILDERFHTETDENNKKIR--QVKIVTLKSNLVSNFRKEF | ELYKVREINDY | 981 |
| WP_002310390 | 911 | DD KAGFIKRQLVETRQITKHVARILDERFHTETDENNKKIR--QVKIVTLKSNLVSNFRKEF | ELYKVREINDY | 981 |
| WP_002352408 | 911 | DD KAGFIKRQLVETRQITKHVARILDERFNTETDENNKKIR--QVKIVTLKSNLVSNFRKEF | ELYKVREINDY | 981 |
| WP_012997688 | 911 | DD KAGFIKRQLVETRQITKHVARILDERFHTETDENNKKIR--QVKIVTLKSNLVSNFRKEF | ELYKVREINDY | 981 |
| WP_014677909 | 911 | DD KAGFIKRQLVETRQITKHVARILDERFYTETDENNKKIR--QVKIVTLKSNLVSNFRKEF | ELYKVREINDY | 981 |
| WP_019312892 | 911 | DD KAGFIKRQLVETRQITKHVARILDERFHTETDENNKKIR--QVKIVTLKSNLVSNFRKEF | ELYKVREINDY | 981 |
| WP_019313659 | 911 | DD KAGFIKRQLVETRQITKHVARILDERFHTETDENNKKIR--QVKIVTLKSNLVSNFRKEF | ELYKVREINDY | 981 |
| WP_019314093 | 911 | DD KAGFIKRQLVETRQITKHVARILDERFHTETDENNKKIR--QVKIVTLKSNLVSNFRKEF | ELYKVREINDY | 981 |
| WP_019315370 | 911 | DD KAGFIKRQLVETRQITKHVARILDERFHTETDENNKKIR--QVKIVTLKSNLVSNFRKEF | ELYKVREINDY | 981 |
| WP_019803776 | 911 | DD KAGFIKRQLVETRQITKHVARILDERFHTETDENNKKIR--QVKIVTLKSNLVSNFRKEF | ELYKVREINDY | 981 |
| WP_019805234 | 911 | DD KAGFIKRQLVETRQITKHVARILDERFHTETDENNKKIR--QVKIVTLKSNLVSNFRKEF | ELYKVREINDY | 981 |
| WP_024783594 | 913 | DD KAGFIKRQLVETRQITKHVARMLDERFNTETDENNKKIR--RVKIVTLKSNLVSSFRKEF | ELYKVREINDY | 983 |
| WP_024784288 | 911 | DD KAGFIKRQLVETRQITKHVARILDERFNTETDENNKKIR--QVKIVTLKSNLVSNFRKEF | ELYKVREINDY | 981 |
| WP_024784666 | 911 | DD KAGFIKRQLVETRQITKHVARILDERFNTETDENNKKIR--QVKIVTLKSNLVSNFRKEF | ELYKVREINDY | 981 |
| WP_024784894 | 911 | DD KAGFIKRQLVETRQITKHVARILDERFNTETDENNKKIR--QVKIVTLKSNLVSNFRKEF | ELYKVREINDY | 981 |

-continued

| | | | | |
|---|---|---|---|---|
| WP_024786433 | 913 | DD KAGFIKRQLVETRQITKHVARMLDERFNKEFDDNNKIR--RVKIVTLKSNLVSSFRKEF | ELYKVREINDY | 983 |
| WP_049473442 | 911 | DD KAGFIKRQLVETRQITKHVARILDERFNTETDENNKKIR--QVKIVTLKSNLVSNFRKEF | ELYKVREINDY | 981 |
| WP_049474547 | 911 | DD KAGFIKRQLVETRQITKHVARILDERFNTETDENNKKIR--QVKIVTLKSNLVSNFRKEF | ELYKVREINDY | 981 |
| EMC03581 | 904 | DD KAGFIKRQLVETRQITKHVARILDERFHTETDENNKKIR--QVKIVTLKSNLVSNFRKEF | ELYKVREINDY | 974 |
| WP_000428612 | 916 | RD KVGFIKRQLVETRQITKHVAQILDARYNTEVNEKDKKNR--TVKIITLKSNLVSNFRKEF | RLYKIREINDY | 986 |
| WP_002364836 | 909 | RD KVGFIKRQLVETRQITKHVAQILDDRFNAEVNEKNQKLR--SVKIITLKSNLVSNFRKEF | GLYKVREINDY | 979 |
| WP_003107102 | 880 | YD KAGFIKRQLVETRQITKHVAQILNNRFNNNVDDSSKNKR--PVKIITLKSKMVSDFRKEF | GFYKIREVNDY | 950 |
| WP_054279288 | 912 | SD KANFIQRQLVETRQITKHVAQILDSRFNTERDEKDRPIR--RVKVITLKSKFVSDFRQDF | GFYKLREINDY | 982 |
| WP_049531101 | 914 | RD KVGFIRRQLVETRQITKHVAQILDDRFNTKVNEKNQKIR--TVKIITLKSNLVSNFRKEF | RLYKVREINDY | 984 |
| WP_049538452 | 914 | RD KVGFIRRQLVETRQITKHVAQILDSRFNTEVTEKDKKNR--NVKIITLKSNLVSNFRKEF | RLYKVREINDY | 984 |
| WP_049549711 | 916 | LD KVGFIKRQLVETRQITKHVAQILDARFNKEVTEKDKKNR--NVKIITLKSKIVSDFRKDF | GLYKLREVNNY | 986 |
| WP_007896501 | 917 | SD KARFLRRQLVETRQITKHVAQLLDDSRFNSKSNQNKKLAR--NVKIITLKSKIVSDFRKDF | GLYKLREVNNY | 987 |
| EFR44625 | 869 | SD KARFIRRQLVETOQITKHVAQLLDDRFNSKSNQNKKLAR--NVKIITLKSNLVSNFRKEF | GLYKLREVNNY | 939 |
| WP_002897477 | 913 | RD KVGFIRRQLVETRQITKHVAQLLDTRENTEVKEKNQKIR--TVKIITLKSNLVSNFRKEF | GLYKVREINDY | 983 |
| WP_002906454 | 913 | RD KVGFIRRQLVETRQITKHVAQLLDTRENTNEVNEQKIR--TVKIITLKSNLVSNFRKEF | GLYKVREINDY | 983 |
| WP_009729476 | 914 | LD KVGFIKRQLVETRQITKHVAQILDARFNKEVTEKDKKNR--TVKIITLKSNLVSNFRKEF | ELYKVREINDY | 984 |
| CQR24647 | 913 | ED KAGFIKRQLVETRQITKHVAQILDERFNRDFDKNDKRIR--NVKIITLKSNLVSNFRKEF | GFYKVREINNF | 983 |
| WP_000066813 | 918 | LD KVGFIKRQLVETRQITKHVAQFLDARFNKEVTEKDKKNR--NVKIITLKSNLVSNFRKEF | EFIKNRNVNDY | 988 |
| WP_009754323 | 914 | RD KVGFIKRQLVETRQITKHVARILDARENTVSEKNQKIR--SVKIITLKSNLVSNFRKEF | KLYKVREINDY | 984 |
| WP_044674937 | 913 | ED KARFIQRQLVETRQITKHVAQILDTRENTKLDEAGNRIRdpKVNIITLKSNLVSQFRKDY | QLYKVREINNY | 985 |
| WP_044676715 | 915 | ED KARFIQRQLVETRQITKHVAQILDTRENTKLDEAGNRIRdpKVNIITLKSNLVSQFRKDY | QLYKVREINNY | 987 |
| WP_044680361 | 915 | ED KARFIQRQLVETRQITKHVAQILDTRENTKLDEAGNRIRdpKVNIITLKSNLVSQFRKDY | QLYKVREINNY | 987 |
| WP_044681799 | 913 | ED KARFIQRQLVETRQITKHVAQILDTRENTKLDEAGNRIRdpKVNIITLKSNLVSQFRKDY | QLYKVREINDY | 985 |
| WP_049533112 | 910 | ND KAGFIKRQLVETRQITKHVAQVLDARFANKHDENKKVIR--DVKIITLKSNLVSQFRKDF | KFYKVREINDY | 980 |
| WP_029090905 | 891 | RD KEGFIARQLVETRQITKHVTQLLQQEY--------K-dTTKVFAIKATLVSGLRRKF | EFIKNRNVNDY | 951 |
| WP_006506696 | 917 | ED EERFINRQLVETRQITKHVTQIIEDHYST------TKVAAIRANLSHEFRVKN | HIYKNRDINDY | 976 |
| AIT42264 | 911 | LD KAGFIKRQLVETRQITKHVAQILDSRMNTKYDENDKLIR--EVKVITLKSKLVSDERKDF | DFYKVREINNY | 981 |
| WP_034440723 | 915 | RD RQQFINRQLVETRQITKHVANLLSHHLNEK----KEVG--EINIVLLKSALTSQFRKKE | QFYKVREINNY | 980 |
| AKQ21048 | 911 | LD KAGFIKRQLVETRQITKHVAQILDSRMNTKYDENDKLIR--EVKVITLKSKLVSDERKDF | KLYKVREINDY | 981 |
| WP_004636532 | 916 | AD RAHFLNRQLVETRQITKHVANLLDSQYNTAEEQ----R--INIVLLKSSMTSRFRKEF | KLYKVREINDY | 980 |
| WP_002364836 | 922 | ED KAHFIQRQLVETRQITKHVAQILDDRFNTEVNAKSKE------K--KVQIITLKASLTSQFRSIF | GLYKVREINDY | 987 |
| WP_016631044 | 873 | ED KAHFIQRQLVETRQITKHVAQILDQRYNAKSKE-------K--KVQIITLKASLTSQFRSIF | GLYKVREVNDY | 938 |
| EMS75795 | 655 | ED KAHFIQRQLVETRQITKHVAAILDQYFN-QPEE-SK-NK--GIRIITLKSLVSQFRKTF | GINKVREINNH | 722 |
| WP_002373311 | 922 | ED KAHFIQRQLVETRQITKHVAQILDQRYNAKSKE-------K--KVQIITLKASLTSQFRSIF | GLYKVREVNDY | 987 |
| WP_002378009 | 922 | ED KAHFIQRQLVETRQITKHVAQILDQRYNAKSKE-------K--KVQIITLKASLTSQFRSIF | GLYKVREVNDY | 987 |
| WP_002407324 | 922 | ED KAHFIQRQLVETRQITKHVAQILDQRYNAKSKE-------K--KVQIITLKASLTSQFRSIF | GLYKVREVNDY | 987 |
| WP_002413717 | 922 | ED KAHFIQRQLVETRQITKHVAQILDQRYNANSKE-------K--KVQIITLKASLTSQFRSIF | GLYKVREVNDY | 987 |
| WP_010777580 | 924 | ED KAHFIQRQLVETRQITKHVAQILDQRYNAKSKE-------K--KVQIITLKASLTSQFRSIF | GLYKVREVNDY | 989 |
| WP_010818269 | 922 | ED KAHFIQRQLVETRQITKHVAQILDQRYNAKSKE-------K--KVQIITLKASLTSQFRSIF | GLYKVREVNDY | 987 |
| WP_010824395 | 922 | ED KAHFIQRQLVETRQITKHVAQILDLYNAKSKE-------K--KVQIITLKASLTSQFRSIF | GLYKVREVNDY | 987 |
| WP_016622645 | 922 | ED KAHFIQRQLVETRQITKHVAQILDQRYNAKSKE-------K--KVQIITLKASLTSQFRSIF | GLYKVREVNDY | 987 |
| WP_033624816 | 922 | ED KAHFIQRQLVETRQITKHVAQILDQRYNAKSKE-------K--KVQIITLKASLTSQFRSIF | GLYKVREVNDY | 987 |
| WP_033625576 | 922 | ED KAHFIQRQLVETRQITKHVAQILDQRYNAKSKE-------K--KVQIITLKASLTSQFRSIF | GLYKVREVNDY | 987 |
| WP_337789179 | 922 | ED KAHFIQRQLVETRQITKHVAQILHHREN-KAEDTNEPIR--KVRIITLKSALVSQFRNRF | GLYKVREVNDY | 987 |
| WP_002310644 | 919 | ED KAHFIQRQLVETRQITKHVAGILHHREN-KAEDTNDPIR--KVRIITLKSALVSQFRNRF | GIYKVREINEY | 988 |
| WP_002312694 | 920 | ED KAHFIQRQLVETRQITKHVAGILHHREN-KAEDTNEPIR--KVRIITLKSALVSQFRNRF | GIYKVREVNDY | 989 |
| WP_002314015 | 920 | ED KAHFIQRQLVETRQITKHVAGILHHREN-KAEDTNEPIR--KVRIITLKSALVSQFRNRF | GIYKVREINEY | 989 |
| WP_002320716 | 920 | ED KAHFIQRQLVETRQITKHVAGILHHREN-KAEDTNEPIR--KVRIITLKSALVSQFRNRF | GIYKVREVNDY | 989 |
| WP_002330729 | 919 | ED KAHFIQRQLVETRQITKHVAGILHHREN-KAEDTNEPIR--KVRIITLKSALVSQFRNRF | GIYKVREINEY | 988 |
| WP_002335161 | 920 | ED KAHFIQRQLVETRQITKHVAGILHHREN-KAEDTNEPIR--KVRIITLKSALVSQFRNRF | GIYKVREVNDY | 989 |
| WP_002345439 | 920 | ED KAHFIQRQLVETRQITKHVAGILHHREN-KAEDTNEPIR--KVRIITLKSALVSQFRNRF | GIYKVREINEY | 989 |
| WP_034867970 | 911 | ED KARFIQRQLVETRQITKHVANILHQSFN-QEEEGTD-CD--GVQIITLKATLTSQFRQTF | GLYKVREINPH | 979 |

```
WP_047937432  920 ED KAGFIKRQLVETRQITKHVAGILHHRFN-KAEDTNEPIR--KVRIITLKSALVSQFRNRF GIYKVREINEY  989
WP_010720994  911 ED KARFIQRQLVETRQITKHVANILHQSFN-QEEEGTD-CD--GVQITLKATLTSQFRQTF GLYKVREINPH  979
WP_010737004  911 ED KARFIQRQLVETRQITKHVANILHQSFN-QEEEGTD-CD--GVQITLKATLTSQFRQTF GLYKVREINPH  979
WP_034700478  911 ED KARFIQRQLVETRQITKHVANILHQSFN-QEEEGTD-CD--GVQITLKATLTSQFRQTF GLYKVREINPH  979
WP_007209003  912 SD KAGFLKRQLVETRQITKHVATILDSKFNE--DSNNRDVQ-----IITLKSALVSEFRKTF NLYKVREINDL  977
WP_023515917  905 AD KARFIQRQLVETRQITKHVANLLHQHFN-LPEEVSA-TE--KTSIITLKSTLTSQFRQMF DIYKVREINHH  973
WP_010770040  915 DD RAHFIKRQLVETRQITKHVARILDQRFNSQKDEEGKTIR--AVRVVTLKSSLTSQFRKQF AIHKVREINDY  985
WP_048604708  912 DD KAGFIHRQLVETRQITKNVARILHQRFNSEKDEEGNLIR--KVRIITLKSALTSQFRKNY GIYKVREINDY  982
WP_010750235  914 DD KARFIQRQLVETRQITKHVAAILHQYFN-QTQELEK-EK--DIRIITLKSSLVSQFRQVF GIHKVREINHH  982
AII16583      950 LD KAGFIKRQLVETRQITKHVAQILDSRMNTKYDENDKLIR--EVKVITLKSKLVSDERKDF QFYKVREINNY 1020
WP_029073316  928 KD KERFINRQIVETRQITKHVAQIISNHYET----------TKVVTVRADLSHAFRERY HIYKNRDINDF  987
WP_031589969  928 KD QERFINRQIVETRQITKHVAQIINHYEN----------TKVVTVRADLSHQFRERY HIYQNRDINDF  987
KDA45870      903 KL KERFIERQLVETRQITKYVAQLLDQRLN--YDNGVELD-eKIAIVTLKAQLASQFRSEF KLRKVRALNNL  972
WP_039099354  924 -D MKGFINRQLVETRQVIKLATNLLMEQYGED--------NQGTTCIQ-----ARANLSTAFRKAL ELVKRNINDF  990
AKP02966      926 KD KLGFIHRQLVQTSQMVKGVANILNSMYK---NQGTTCIQ-----QVRIVTLKSALVSQFRKQF QLYKVRDINDF  999
WP_010991369  914 AD KARFIHRQLVETRQITKNVANILHQRFNYEKDDHGNTMK--QVRIVTLKSALVSQFRKQF QLYKVRDVNDY  984
WP_033838504  914 AD KARFIHRQLVETRQITKNVANILHQRFNYEKDDHGNTMK--QVRIVTLKSALVSQFRKQF QLYKVRDVNDY  984
EHN60060      917 AD KARFIHRQLVETRQITKNVANILHQRFNYEKDDHGNTMK--QVRIVTLKSALVSQFRKQF QLYKVRDVNDY  987
EFR89594      683 AD KATFIHRQLVETRQITKNVANILHQRFNYGKDDHGNTMK--QVRIVTLKSALVSQFRKQF QLYKVRGVNDY  753
WP_038409211  914 AD KANFIQRQLVETRQITKNVANILYQRFNCKQDENGNEVE--QVRIVTLKSTLVSQFRKQF QLYKVREVNDY  984
EFR95520      533 AD KANFIQRQLVETRQITKNVANILYQRFNCKQDENGNEVE--QVRIVTLKSTLVSQFRKQF QLYKVREVNDY  603
WP_003723650  914 AD KARFIHRQLVETRQITKNVANILYQRFNKETDNHGNTME--QVRIVTLKSALVSQFRKQF QLYKVREVNGY  984
WP_003727705  914 AD KARFIHRQLVETRQITKNVANILYQRFNKETDNHGNTME--QVRIVTLKSALVSQFRKQF QLYKVREVNDY  984
WP_003730785  914 AD KARFIHRQLVETRQITKNVANILHQRFNKETDNHGNTME--QVRIVTLKSALVSQFRKQF QLYKVREVNDY  984
WP_003733029  914 AD KARFIHRQLVETRQITKNVANILHQRFNKTDGNKDTME--TVRIVTLKSALVSQFRKQF QLYKVREVNDY  984
WP_003739838  914 AD KARFIHRQLVETRQITKNVANILHQRFNNETDNHGNNME--QVRIVMLKSALVSQFRKQF QLYKVREVNDY  984
WP_014601172  914 AD KARFIHRQLVETRQITKNVANILHQRFNNETDNHGNTME--QVRIVTLKSALVSQFRKQF QLYKVREVNDY  984
WP_023548323  914 AD KARFIHRQLVETRQITKNVANILHQRFNNETDDNEDTME--PVRIVTLKSALVSQFRKQF QLYKVREVNDY  984
WP_031665337  914 AD KARFIHRQLVETRQITKNVANILHQRFNKETDNHGNTME--QVRIVTLKSALVSQFRKQF QLYKVREVNDY  984
WP_031669209  914 AD KARFIHRQLVETRQITKNVANILHQRFNNETDGNKDTME--TVRIVTLKSALVSQFRKQF QLYKVREVNDY  984
WP_033920898  914 AD KARFIHRQLVETRQITKNVANILHQRFNNETDDNEDTME--QVRIVTLKSALVSQFRKQF QFYKVREVNDY  984
AKI42028      917 AD KARFIHRQLVETRQITKNVANILHQRFNNETDDNEDTME--PVRIVTLKSALVSQFRKQF QLYKVREVNDY  987
AKI50529      917 AD KARFIHRQLVETRQITKNVANILHQRFNNETDNHGNTME--QVRIVTLKSALVSQFRKQF QLYKVREVNDY  987
EFR83390      362 AD KARFIHRQLVETRQITKNVANILHQRFNCKKDESGNVIE--QVRIVTLKAALVSQFRKQF QLYKVREVNDY  432
WP_046323366  914 LD KARFIKRQLVETRQITKHVANILHQRFNCKKDESGNVIE--QVRIVTLKSKLVSDENDKLIR-EVKVITLKSKLVSDFRKDF QFYKVREINDY  984
AKE81011      927 LD KARFIKRQLVETRQITKHVAQILDSRMNLKYDENDKLIR--EVKVITLKSKLVSDFRKDF QFYKVREINNY  997
CUO82355      921 RD EERFINRQLVETRQITKNVTQIIEDHYST--------TKVAAIRANLSHEFRVKN HIYQNRDINDY  980
WP_033162887  923 KD KERFINRQLVETRQITKNVAVIIKNVAVIINDHYTN----------TNIVTVRAELSHQFRERY KIYKNRDINDF  982
AGZ01981      944 LD KAGFIKRQLVETRQITKHVAQILDSRMNTKYDENDKLIR--EVKVITLKSKLVSDFRKDF QFYKVREINNY 1014
AKA60242      911 LD KAGFIKRQLVETRQITKHVAQILDSRMNTKYDENDKLIR--EVKVITLKSKLVSDFRKDF QFYKVREINNY  981
AKS40380      911 LD KAGFIKRQLVETRQITKHVAQILDSRMNTKYDENDKLIR--EVKVITLKSKLVSDFRKDF QFYKVREINNY  981
4UN5_B        915 LD KAGFIKRQLVETRQITKHVAQILDSRMNTKYDENDKLIR--EVKVITLKSKLVSDFRKDF QFYKVREINNY  985
WP_010922251  982 HHAHDAYLNAVVGTALIKKYPKL-ESEFVYGDYKVYDV S---EQE1--GK ATAKY--F-FYSNIM-NFFKTEIT 1051
WP_039695303  992 HHAHDAYLNAVVGTALLKKYPKL-ASEFVYGEYKKYDI S---SD-----KATAK--YfFYSNLM-NFFKTKVK 1058
WP_045635197  984 HHAHDAYLNAVVAKAILKKYPKL-EPEFVYGEYQKYDL SkdpKEV--EK ATEKY--F-FYSNLL-NFFKEEVH 1055
5AXW_A        703 HHAEDALI---------IaNADPIFKEWNKLDK Nq-mFE----EK ETEQEYkEiFITPHQiKHIKDFKD  771
WP_009880683  666 HHAHDAYLNAVVGTALIKKYPKL-ESEFVYGDYKVYDI S---EQE1--GK ATAKY--F-FYSNIM-NFFKTEIT  735
WP_010922251  982 HHAHDAYLNAVVGTALIKKYPKL-ESEFVYGDYKVYDI S---EQE1--GK ATAKY--F-FYSNIM-NFFKTEIT 1051
WP_010954416  982 HHAHDAYLNAVVGTALIKKYPKL-ESEFVYGDYKVYDI S---EQE1--GK ATAKY--F-FYSNIM-NFFKTEIT 1051
WP_011284745  982 HHAHDAYLNAVVGTALIKKYPKL-ESEFVYGDYKVYDV S---EQE1--GK ATAKY--F-FYSNIM-NFFKTEIT 1051
WP_011285506  982 HHAHDAYLNAVVGTALIKKYPKL-ESEFVYGDYKVYDV S---EQE1--GK ATAKY--F-FYSNIM-NFFKTEIT 1051
WP_011527619  982 HHAHDAYLNAVVGTALIKKYPKL-ESEFVYGDYKVYDI S---EQE1--GK ATAKY--F-FYSNIM-NFFKTEIT 1051
WP_012560673  982 HHAHDAYLNAVVGTALIKKYPKL-ESEFVYGDYKVYDI S---EQE1--GK ATAKY--F-FYSNIM-NFFKTEIT 1051
```

```
-continued

WP_014407541  981  HHAHDAYLNAVVGTALIKKYPKL-ESEFVYGDYKVYDV  S---EQEi--GK  ATAKY--F-FYSNIM-NFFKTEIT  1050
WP_020905136  982  HHAHDAYLNAVVGTALIKKYPKL-ESEFVYGDYKVYDV  S---EQEi--GK  ATAKY--F-FYSNIM-NFFKTEIT  1051
WP_023080005  981  HHAHDAYLNAVVGTALIKKYPKL-ESEFVYGDYKVYDV  S---EQEi--GK  ATAKY--F-FYSNIM-NFFKTEIT  1050
WP_023610282  982  HHAHDAYLNAVVGTALIKKYPKL-ESEFVYGDYKVYDV  S---EQEi--GK  ATAKY--F-FYSNIM-NFFKTEIT  1051
WP_030125963  981  HHAHDAYLNAVVGTALIKKYPKL-ESEFVYGDYKVYDV  S---EQEi--GK  ATAKY--F-FYSNIM-NFFKTEIT  1050
WP_030126706  982  HHAHDAYLNAVVGTALIKKYPKL-ESEFVYGDYKVYDV  S---EQEi--GK  ATAKY--F-FYSNIM-NFFKTEIT  1051
WP_031488318  982  HHAHDAYLNAVVGTALIKKYPKL-ESEFVYGDYKVYDV  S---EQEi--GK  ATAKY--F-FYSNIM-NFFKTEIT  1051
WP_032460140  982  HHAHDAYLNAVVGTALIKKYPKL-ESEFVYGDYKVYDV  S---EQEi--GK  ATAKY--F-FYSNIM-NFFKTEIT  1051
WP_032461047  982  HHAHDAYLNAVVGTALIKKYPKL-ESEFVYGDYKVYDI  S---EQEi--GK  ATAKY--F-FYSNIM-NFFKTEIT  1051
WP_032462016  982  HHAHDAYLNAVVGTALIKKYPKL-ESEFVYGDYKVYDV  S---EQEi--GK  ATAKY--F-FYSNIM-NFFKTEIT  1051
WP_032462936  982  HHAHDAYLNAVVGTALIKKYPKL-ESEFVYGDYKVYDV  S---EQEi--GK  ATAKY--F-FYSNIM-NFFKTEIT  1051
WP_032464890  982  HHAHDAYLNAVVGTALIKKYPKL-ESEFVYGDYKVYDV  S---EQEi--GK  ATAKY--F-FYSNIM-NFFKTEIT  1051
WP_033888930  807  HHAHDAYLNAVVGTALIKKYPKL-ESEFVYGDYKVYDV  S---EQEi--GK  ATAKY--F-FYSNIM-NFFKTEIT  876
WP_038431314  982  HHAHDAYLNAVVGTALIKKYPKL-ESEFVYGDYKVYDV  S---EQEi--GK  ATAKY--F-FYSNIM-NFFKTEIT  1051
WP_038432938  981  HHAHDAYLNAVVGTALIKKYPKL-ESEFVYGDYKVYDV  S---EQEi--GK  ATAKY--F-FYSNIM-NFFKTEIT  1050
WP_038434062  982  HHAHDAYLNAVVGTALIKKYPKL-ESEFVYGDYKVYDV  S---EQEi--GK  ATAKY--F-FYSNIM-NFFKTEIT  1051
BAQ51233      893  HHAHDAYLNAVVGTALIKKYPKL-ESEFVYGDYKVYDV  S---EQEi--GK  ATAKY--F-FYSNIM-NFFKTEIT  962
KGE60162      157  HHAHDAYLNAVVGTALIKKYPKL-ESEFVYGDYKVYDV  S---EQEi--GK  ATAKY--F-FYSNIM-NFFKTEIT  226
KGE60856      ---  --------------------------------------  ------------  ------------------------  ----
WP_002989955  982  HHAHDAYLNAVVGTALIKKYPKL-ESEFVYGDYKVYDV  S---EQEi--GK  ATAKY--F-FYSNIM-NFFKTEIT  1051
WP_003030002  981  HHAHDAYLNAVVGNALLLKKYPKL-EPEFVYGEYPKYN  S---YR----sRK  SATEK-F1FYSNIL-RFFKKE--  1041
WP_003065552  992  HHAHDAYLNAVVGTALLKKYPKI-ASEFVYGEYKKYDI  S---SD------  KATAK-YfFYSNLM-NFFKRVIR  1058
WP_001040076  987  HHAHDAYLNAVVAKAILTKYPQL-EPEFVYGLYRRKK-  L---SKI----VR  ATRKM-F-FYSNLM-NMFKRVVR  1057
WP_001040078  987  HHAHDAYLNAVVAKAILTKYPQL-EPEFVYGDYPKYN  S---YKT---RK  ATEKL-F-FYSNIM-NFFKTKVT  1049
WP_001040080  987  HHAHDAYLNAVVAKAILTKYPQL-EPEFVYGDYPKYN  S---YKT---RK  ATEKL-F-FYSNIM-NFFKTKVT  1049
WP_001040081  987  HHAHDAYLNAVVAKAILTKYPQL-EPEFVYGDYPKYN  S---YKT---RK  ATEKL-F-FYSNIM-NFFKTKVT  1049
WP_001040083  987  HHAHDAYLNAVVAKAILTKYPQL-EPEFVYGDYPKYN  S---YKT---RK  ATEKL-F-FYSNIM-NFFKTKVT  1049
WP_001040085  987  HHAHDAYLNAVVAKAILTKYPQL-EPEFVYGDYPKYN  S---YKT---RK  ATEKL-F-FYSNIM-NFFKTKVT  1049
WP_001040087  987  HHAHDAYLNAVVAKAILTKYPQL-EPEFVYGDYPKYN  S---YKT---RK  ATEKL-F-FYSNIM-NFFKTKVT  1049
WP_001040088  987  HHAHDAYLNAVVAKAILTKYPQL-EPEFVYGDYPKYN  S---YKT---RK  ATEKL-F-FYSNIM-NFFKTKVT  1049
WP_001040089  987  HHAHDAYLNAVVAKAILTKYPQL-EPEFVYGDYPKYN  S---YKT---RK  ATEKL-F-FYSNIM-NFFKTKVT  1049
WP_001040090  987  HHAHDAYLNAVVAKAILTKYPQL-EPEFVYGDYPKYN  S---YKT---RK  ATEKL-F-FYSNIM-NFFKTKVT  1049
WP_001040091  987  HHAHDAYLNAVVAKAILTKYPQL-EPEFVYGDYPKYN  S---YKT---RK  ATEKL-F-FYSNIM-NFFKTKVT  1049
WP_001040092  987  HHAHDAYLNAVVAKAILTKYPQL-EPEFVYGDYPKYN  S---YKT---RK  ATEKL-F-FYSNIM-NFFKTKVT  1049
WP_001040094  987  HHAHDAYLNAVVAKAILTKYPQL-EPEFVYGDYPKYN  S---YKT---RK  ATEKL-F-FYSNIM-NFFKTKVT  1049
WP_001040095  987  HHAHDAYLNAVVAKAILTKYPQL-EPEFVYGDYPKYN  S---YKT---RK  ATEKL-F-FYSNIM-NFFKTKVT  1049
WP_001040096  987  HHAHDAYLNAVVAKAILTKYPQL-EPEFVYGDYPKYN  S---YKT---RK  ATEKL-F-FYSNIM-NFFKTKVT  1049
WP_001040097  987  HHAHDAYLNAVVAKAILTKYPQL-EPEFVYGDYPKYN  S---YKT---RK  ATEKL-F-FYSNIM-NFFKTKVT  1049
WP_001040098  987  HHAHDAYLNAVVAKAILTKYPQL-EPEFVYGDYPKYN  S---YKT---RK  ATEKL-F-FYSNIM-NFFKTKVT  1049
WP_001040099  987  HHAHDAYLNAVVAKAILTKYPQL-EPEFVYGDYPKYN  S---YKT---RK  ATEKL-F-FYSNIM-NFFKTKVT  1049
WP_001040100  987  HHAHDAYLNAVVAKAILTKYPQL-EPEFVYGDYPKYN  S---YKT---RK  ATEKL-F-FYSNIM-NFFKTKVT  1049
WP_001040104  987  HHAHDAYLNAVVAKAILTKYPQL-EPEFVYGDYPKYN  S---YKT---RK  ATEKL-F-FYSNIM-NFFKTKVT  1049
WP_001040105  987  HHAHDAYLNAVVAKAILTKYPQL-EPEFVYGDYPKYN  S---YKT---RK  ATEKL-F-FYSNIM-NFFKTKVT  1049
WP_001040106  987  HHAHDAYLNAVVAKAILTKYPQL-EPEFVYGDYPKYN  S---YKT---RK  ATEKL-F-FYSNIM-NFFKTKVT  1049
WP_001040107  987  HHAHDAYLNAVVAKAILTKYPQL-EPEFVYGDYPKYN  S---YKT---RK  ATEKL-F-FYSNIM-NFFKTKVT  1049
WP_001040108  987  HHAHDAYLNAVVAKAILTKYPQL-EPEFVYGDYPKYN  S---YKT---RK  ATEKL-F-FYSNIM-NFFKTKVT  1049
WP_001040109  987  HHAHDAYLNAVVAKAILTKYPQL-EPEFVYGDYPKYN  S---YKT---RK  ATEKL-F-FYSNIM-NFFKTKVT  1049
WP_001040110  987  HHAHDAYLNAVVAKAILTKYPQL-EPEFVYGDYPKYN  S---YKT---RK  ATEKL-F-FYSNIM-NFFKTKVT  1049
WP_015058523  987  HHAHDAYLNAVVAKAILTKYPQL-EREFVYGDYPKYN  S---YKT---RK  ATEKL-F-FYSNIM-NFFKTKVT  1049
WP_017643650  987  HHAHDAYLNAVVAKAILTKYPQL-EPEFVYGDYPKYN  S---YKT---RK  ATEKL-F-FYSNIM-NFFKTKVT  1049
WP_017647151  987  HHAHDAYLNAVVAKAILTKYPQL-EPEFVYGDYPKYN  S---YKT---RK  ATEKL-F-FYSNIM-NFFKTKVT  1049
WP_017648376  987  HHAHDAYLNAVVAKAILTKYPQL-EPEFVYGDYPKYN  S---YKT---RK  ATEKL-F-FYSNIM-NFFKTKVT  1049
WP_017649527  987  HHAHDAYLNAVVAKAILTKYPQL-EPEFVYGDYPKYN  S---YKT---RK  ATEKL-F-FYSNIM-NFFKTKVT  1049
```

```
WP_017771611   987 HHAHDAYLNAVLNAVVAKAILTKYPQL-EPEFVYGDYPKYN-S---YKT---RK ATEKL-F-FYSNIM-NFFKTKVT 1049
WP_017771984   987 HHAHDAYLNAVLNAVVAKAILTKYPQL-EPEFVYGDYPKYN-S---YKT---RK ATEKL-F-FYSNIM-NFFKTKVT 1049
CFQ25032       987 HHAHDAYLNAVLNAVVAKAILTKYPQL-EPEFVYGDYPKYN-S---YKT---RK ATEKL-F-FYSNIM-NFFKTKVT 1049
CFV16040       987 HHAHDAYLNAVLNAVVAKAILTKYPQL-EPEFVYGDYPKYN-S---YKT---RK ATEKL-F-FYSNIM-NFFKTKVT 1049
KLJ37842       987 HHAHDAYLNAVLNAVVAKAILTKYPQL-EPEFVYGDYPKYN-S---YKT---RK ATEKL-F-FYSNIM-NFFKTKVT 1049
KLJ72361       987 HHAHDAYLNAVLNAVVAKAILTKYPQL-EPEFVYGDYPKYN-S---YKT---RK ATEKL-F-FYSNIM-NFFKTKVT 1049
KLL20707      1001 HHAHDAYLNAVLNAVVAKAILTKYPQL-EPEFVYGDYPKYN-S---YKT---RK ATEKL-F-FYSNIM-NFFKTKVT 1063
KLL42645       987 HHAHDAYLNAVLNAVVAKAILTKYPQL-EPEFVYGDYPKYN-S---YKT---RK ATEKL-F-FYSNIM-NFFKTKVT 1049
WP_047207273   987 HHAHDAYLNAVLNAVVAKAILTKYPQL-EPEFVYGDYPKYN-S---YKT---RK ATEKL-F-FYSNIM-NFFKTKVT 1049
WP_047209694   987 HHAHDAYLNAVLNAVVAKAILTKYPQL-EPEFVYGDYPKYN-S---YKT---RK ATEKL-F-FYSNIM-NFFKTKVT 1049
WP_050198062   987 HHAHDAYLNAVLNAVVAKAILTKYPQL-EPEFVYGDYPKYN-S---YKT---RK ATEKL-F-FYSNIM-NFFKTKVT 1049
WP_050201642   987 HHAHDAYLNAVLNAVVAKAILTKYPQL-EPEFVYGDYPKYN-S---YKT---RK ATEKL-F-FYSNIM-NFFKTKVT 1049
WP_050204027   987 HHAHDAYLNAVLNAVVAKAILTKYPQL-EPEFVYGDYPKYN-S---YKT---RK ATEKL-F-FYSNIM-NFFKTKVT 1049
WP_050881965   987 HHAHDAYLNAVLNAVVAKAILTKYPQL-EPEFVYGDYPKYN-S---YKT---RK ATEKL-F-FYSNIM-NFFKTKVT 1049
WP_050886065   987 HHAHDAYLNAVLNAVVAKAILTKYPQL-EPEFVYGDYPKYN-S---YKT---RK ATEKL-F-FYSNIM-NFFKTKVT 1049
AHN30376       987 HHAHDAYLNAVLNAVVAKAILTKYPQL-EPEFVYGDYPKYN-S---YKT---RK ATEKL-F-FYSNIM-NFFKTKVT 1049
EA078426       987 HHAHDAYLNAVLNAVVAKAILTKYPQL-EPEFVYGDYPKYN-S---YKT---RK ATEKL-F-FYSNIM-NFFKTKVT 1049
CCW42055       987 HHAHDAYLNAVLNAVVAKAILTKYPQL-ASEFVYGEFKKYDV-S---DK---eIG KATAK-YfFYSNIM-NFFKKEVK 1050
WP_003041502   981 HHAHDAYLNAVIGTALLKKYPKL-ASEFVYGEFKKYDV-S---DK---eIG KATAK-YfFYSNIM-NFFKKEVK 1050
WP_037593752   982 HHAHDAYLNAVVGNALLLKYPQL-EPEFVYGDYPKYN-S---YR---sRK SATEK-F1FYSNIL-RFFKKE-- 1042
WP_049516684   981 HHAHDAYLNAVVGNALLLKYPQL-EPEFVYGDYPKYN-S---YR---sRK SATEK-F1FYSNIL-RFFKKE-- 1041
GAD46167       990 HHAHDAYLNAVVGNALLLKYPQL-EPEFVYGDYPKYN-S---YR---sRK SATEK-F1FYSNIL-RFFKKE-- 1062
WP_018363470   991 HHAHDAYLNAVVGTALLKKYPKL-APEFVYGDYKKYDV-S---SDDhseMG KATAK-YfFYSNLM-NFFKRVIR 1060
WP_003043819   981 HHAHDAYLNAVVGTALLKKYPKL-APEFVYGDYKKYDV-S---EQEi-GK ATAKR-F-FYSNIM-NFFKTEVK 1041
WP_006269658   981 HHAHDAYLNAVVGTALLKKYPKL-EPEFVYGEYPKYN-S---YR---sRK SATEK-F1FYSNIL-RFFKKE-- 1051
WP_048800889   981 HHAHDAYLNAVVGTALLKKYPKL-TSEFVYGEYKKYDV-S---DND---eIG KATAK-YfFYSNIM-NFFKTEVK 1050
WP_012767106   981 HHAHDAYLNAVVGTALIKKYYTKL-ESEFVYGDYKKYDI-S---EQEi-GK ATAKR-F-FYSNIM-NFFKTEIT 1050
WP_014612333   981 HHAHDAYLNAVVGTALIKKYPKL-ESEFVYGDYKKYDV-S---EQEi-GK ATAKR-F-FYSNIM-NFFKTEIT 1050
WP_015017095   981 HHAHDAYLNAVVGTALIKKYPKL-ESEFVYGDYKKYDI-S---EQEi-GK ATAKR-F-FYSNIM-NFFKTEIT 1050
WP_015057649   981 HHAHDAYLNAVVGTALIKKYPKL-ESEFVYGDYKKYDV-S---EQEi-GK ATAKR-F-FYSNIM-NFFKTEVK 1050
WP_048327215   981 HHAHDAYLNAVVGTALIKKYPKL-ESEFVYGDYKKYDV-S---EQEi-GK ATAKR-F-FYSNIM-NFFKTEIT 1050
WP_049519324   981 HHAHDAYLNAVVGTALIKKYPKL-ESEFVYGDYKKYDV-S---EQEi-GK ATAKR-F-FYSNIM-NFFKTEIT 1050
WP_012515931   981 HHAHDAYLNAVVAKAILGKYPKL-APEFVYGDYPKYN-S---FKEr--QK ATQKM-L-FYSNIL-KFFKDQES 1043
WP_021320964   981 HHAHDAYLNAVVAKAILGKYPKL-APEFVYGDYPKYN-S---FKEr--QK ATQKT-L-FYSNIL-KFFKDQES 1043
WP_037581760   981 HHAHDAYLNAVVAKAILGKYPKL-APEFVYGDYPKYN-S---FKEi--QK ATQKT-L-FYSNIL-KFFKDQES 1061
WP_004232481   989 HHAHDAYLNAVVGTALLKKYPKL-EPEFVYGEYKKKYD-S---SDNhseLG KATAK-YfFYSNIM-NFFKTEVK 1056
WP_009854540   990 HHAHDAYLNAVVGTALLKKYPKL-APEFVYGEYKKKYD-S---SD----GK KATAK-YfFYSNLL-NFFKKEVH 1056
WP_012962174   990 HHAHDAYLNAVVGTALLKKYPKL-APEFVYGEYKKKYD-S---GD------- KATAK-YfFYSNLM-NFFKRVIR 1058
WP_039695303   992 HHAHDAYLNAVVGTALLKKYPKL-ASEFVYGEYKKKYD-S---SD------- KATAK-YfFYSNLM-NFFKTKVK 1058
WP_014334983   989 HHAHDAYLNAVVGTALLKKYPKL-TPEFVYGDYKHYDL-P---SDDyseMG KATAK-YfFYSNLM-NFFKTEVK 1061
WP_003099269   982 HHAHDAYLNAVVGTALLKKYPKL-EAEFVYGDYKHYDL-P---DSS1-GK ATTRM-F-FYSNLM-NFFKKEIK 1051
AHY15608       982 HHAHDAYLNAVVGTALLKKYPKL-EAEFVYGDYKHYDL-P---DSS1-GK ATTRM-F-FYSNLM-NFFKKEIK 1051
AHY17476       982 HHAHDAYLNAVVGTALLKKYPKL-EAEFVYGDYKHYDL-P---DSS1-GK ATTRM-F-FYSNIM-NFFKKEIK 1051
ESR09100           HHAQDAYLNAVVGTALLKKYPKL-EAEFVYGDYKHYDL-P---DSS1-GK ATTRM-F-FYSNLM-NFFKKEIK 1051
AGM98575       982 HHAQDAYLNAVVGTALLKKYPKL-EAEFVYGDYKHYDL-P---DSS1-GK ATTRM-F-FYSNIM-NFFKKEIK 1051
ALF27331       982 HHAHDAYLNAVIGKALLGVYPQL-ERELVYGSYVKESI-G---HK----ATAKK-F-FYSNIM-NFFKKD-- 1041
WP_018372492   995 HHAHDPYLNAVIGKALLGVYPQL-EPEFVYGQKYDL TkdpKEV---FS---RK ATERM--rMNNIL-KFISKD-- 1055
WP_045618028   985 HHAHDPYLNAVIGKALLKVYPKF-EPEFVYGQKYDL SkdpKEV---EK ATEKY-F-FYSNLL-NFFKKEEVH 1056
WP_045635197   984 HHAHDAYLNAVAKAILGVYPQL-EPEFVYGQKYDL---EK ATEKY-F-FYSNLL-NFFKKEEVH 1055
WP_012962174   990 HHAHDAYLNAVIGKALLGVYPQL-EPEFVYGDYPHFH---G---HK---eNK ATAKK-F-FYSNIM-NFFKKD-- 1041
WP_002263887   982 HHAHDAYLNAVIGKALLGVYPQL-EPEFVYGDYPHFH---G---HK---eNK ATAKK-F-FYSNIM-NFFKKD-- 1041
WP_002264920   982 HHAHDAYLNAVIGKALLGVYPQL-EPEFVYGDYPHFH---G---HK---eNK ATAKK-F-FYSNIM-NFFKKD-- 1041
WP_002269043   982 HHAHDAYLNAVIGKALLGVYPQL-EPEFVYGDYPHFH---G---HK---eNK ATAKK-F-FYSNIM-NFFKKD-- 1041
```

```
WP_002269448   982 HHAHDAYLNAVIGKALLGVYPQL-EPEFVYGDYPHFH G---HK----eNK ATAKK--F-FYSNIM-NFFKKD--  1041
WP_002271977   982 HHAHDAYLNAVIGKALLGVYPQL-EPEFVYGDYPHFH G---HK----eNK ATAKK--F-FYSNIM-NFFKKD--  1041
WP_002272766   982 HHAHDAYLNAVIGKALLGVYPQL-EPEFVYGDYPHFH G---HE----eNK ATAKK--F-FYSNIM-NFFKKD--  1041
WP_002273241   982 HHAHDAYLNAVIGKALLGVYPQL-EPEFVYGDYPHFH G---HK----eNK ATAKK--F-FYSNIM-NFFKKD--  1041
WP_002275430   982 HHAHDAYLNAVIGKALLGVYPQL-EPEFVYGDYPHFH G---HE----eNK ATAKK--F-FYSNIM-NFFKKD--  1041
WP_002276448   982 HHAHDAYLNAVIGKALLGVYPQL-EPEFVYGDYPHFH G---HK----eNK ATAKK--F-FYSNIM-NFFKKD--  1041
WP_002277050   984 HHAHDAYLNAVVVKALLVKYPKL-EPEFVYGEYPKYN S---YR----eRK ATQKM--F-FYSNIM-NMFKSKVK  1046
WP_002277364   982 HHAHDAYLNAVIGKALLGVYPQL-EPEFVYGDYPHFH G---HK----eNK ATAKK--F-FYSNIM-NFFKKD--  1041
WP_002279025   982 HHAHDAYLNAVIGKALLGVYPQL-EPEFVYGDYPHFH G---HE----eNK ATAKK--F-FYSNIM-NFFKKD--  1041
WP_002279859   982 HHAHDAYLNAVIGKALLGVYPQL-EPEFVYGDYPHFH G---HK----eNK ATAKK--F-FYSNIM-NFFKKD--  1041
WP_002280230   982 HHAHDAYLNAVIGKALLGVYPQL-EPEFVYGDYPHFH G---HK----eNK ATAKK--F-FYSNIM-NFFKKD--  1041
WP_002281696   984 HHAHDAYLNAVIGKALLVKYPKL-EPEFVYGEYPKYN S---YR----eRK ATQKM--F-FYSNIM-NMFKSKVK  1046
WP_002282247   982 HHAHDAYLNAVIGKALLGVYPQL-EPEFVYGEYPKYN S---YR----eRK ATQKM--F-FYSNIM-NMFKSKVK  1041
WP_002282906   982 HHAHDAYLNAVIGKALLGVYPQL-EPEFVYGDYPHFH G---HK----eNK ATAKK--F-FYSNIM-NFFKKD--  1041
WP_002283846   982 HHAHDAYLNAVIGKALLGVYPQL-EPEFVYGDYPHFH G---HE----eNK ATAKK--F-FYSNIM-NFFKKD--  1041
WP_002287255   982 HHTHDAYLNAVIGKALLGVYPQL-EPEFVYGDYPHFH G---HK----eNK ATAKK--F-FYSNIM-NFFKKD--  1041
WP_002288990   982 HHAHDAYLNAVIGKALLGVYPQL-EPEFVYGDYPHFH G---HK----eNK ATAKK--F-FYSNIM-NFFKKD--  1041
WP_002289641   982 HHAHDAYLNAVIGKALLGVYPQL-EPEFVYGDYPHFH G---HK----eNK ATAKK--F-FYSNIM-NFFKKD--  1041
WP_002290427   982 HHAHDAYLNAVIGKALLGVYPQL-EPEFVYGDYPHFH G---HE----eNK ATAKK--F-FYSNIM-NFFKKD--  1041
WP_002295753   982 HHAHDAYLNAVIGKALLGVYPQL-EPEFVYGDYPHFH G---HK----eNK ATAKK--F-FYSNIM-NFFKKD--  1041
WP_002296423   982 HHAHDAYLNAVIGKALLGVYPQL-EPEFVYGDYPHFH G---HK----eNK ATAKK--F-FYSNIM-NFFKKD--  1041
WP_002304487   996 HHAHDAYLNAVIGKALLGVYPQL-EPEFVYGDYPHFH G---HK----eNK ATAKK--F-FYSNIM-NFFKKG--  1055
WP_002305844   982 HHAHDAYLNAVIGKALLGVYPQL-EPEFVYGDYPHFH G---HK----eNK ATAKK--F-FYSNIM-NFFKKD--  1041
WP_002307203   982 HHAHDAYLNAVIGKALLGVYPQL-EPEFVYGDYPHFH G---HK----eNK ATAKK--F-FYSNIM-NFFKKD--  1041
WP_002310390   982 HHAHDAYLNAVIGKALLGVYPQL-EPEFVYGDYPHFH G---HK----eNK ATAKK--F-FYSNIM-NFFKKD--  1041
WP_003352408   982 HHAHDAYLNAVIGKALLGVYPQL-EPEFVYGDYPHFH G---HK----eNK ATAKK--F-FYSNIM-NFFKKD--  1041
WP_012997688   982 HHAHDAYLNAVIGKALLGVYPQL-EPEFVYGDYPHFH G---HK----eNK ATAKK--F-FYSNIM-NFFKKD--  1041
WP_014677909   982 HHAHDAYLNAVIGKALLGVYPQL-EPEFVYGDYPHFH G---HK----eNK ATAKK--F-FYSNIM-NFFKKD--  1041
WP_019312892   982 HHAHDAYLNAVIGKALLGVYPQL-EPEFVYGDYPHFH G---HK----eNK ATAKK--F-FYSNIM-NFFKKD--  1041
WP_019313659   982 HHAHDAYLNAVIGKALLGVYPQL-EPEFVYGDYPHFH G---HK----eNK ATAKK--F-FYSNIM-NFFKKD--  1041
WP_019314093   982 HHAHDAYLNAVIGKALLGVYPQL-EPEFVYGDYPHFH G---HE----eNK ATAKK--F-FYSNIM-NFFKKD--  1041
WP_019315370   982 HHAHDAYLNAVIGKALLGVYPQL-EPEFVYGDYPHFH G---HK----eNK ATAKK--F-FYSNIM-NFFKKD--  1041
WP_019803776   982 HHAHDAYLNAVIGKALLGVYPQL-EPEFVYGDYPHFH G---HK----eNK ATAKK--F-FYSNIM-NFFKKD--  1041
WP_019805234   982 HHAHDAYLNAVIGKALLGVYPQL-EPEFVYGDYPHFH G---HK----eNK ATAKK--F-FYSNIM-NFFKKD--  1041
WP_024784288   982 HHAHDAYLNAVIGKALLGVYPQL-EPEFVYGDYPHFH G---HK----eNK ATAKK--F-FYSNIM-NFFKKD--  1041
WP_024784288   984 HHAHDAYLNAVVVKALLVKYPKL-EPEFVYGEYLKYN S---YR----eRK ATQKM--F-FYSNIM-NMFKSKVK  1046
WP_024784666   982 HHAHDAYLNAVIGKALLGVYPQL-EPEFVYGDYPHFH G---HK----eNK ATAKK--F-FYSNIM-NFFKKD--  1041
WP_024784894   982 HHAHDAYLNAVIGKALLGVYPQL-EPEFVYGDYPHFH G---HK----eNK ATAKK--F-FYSNIM-NFFKKD--  1041
WP_024786433   984 HHAHDAYLNAVVVKALLVKYPKL-EPEFVYGEYPKYN S---YR----eRK ATQKM--F-FYSNIM-NMFKSKVK  1046
WP_024973442   982 HHAHDAYLNAVIGKALLGVYPQL-EPEFVYGDYPHFH G---HE----eNK ATAKK--F-FYSNIM-NFFKKD--  1041
WP_024974547   982 HHAHDAYLNAVIGKALLGVYPQL-EPEFVYGDYPHFH G---HK----eNK ATAKK--F-FYSNIM-NFFKKD--  1041
EMC03581       975 HHAHDAYLNAVIGKALLGVYPQL-EPEFVYGDYPHFH G---HK----eNK ATAKK--F-FYSNIM-NFFKKD--  1034
WP_000428612   987 HHAHDAYLNAVAKAILKKYPKL-EPEFVYGDYQKYDL SkdpKEI---EK ATEKY--F-FYSNLL-NFFKEEVH  1058
WP_000428613   985 HHAHDAYLNAVAKAILKKYPKL-EPEFVYGDYQKYDL SmpKEV---EK ATEKY--F-FYSNLL-NFFKEEVH  1056
WP_049523028   980 HHAHDAYLNAVAKAILKKYPKL-EPEFVYGDYQKYDL TkdpKEI---EK ATEKY--F-FYSNLL-NFFKDKVY  1051
WP_003107102   951 HHAHDAYLNAVGTALLKKYPKL-EAEFVYGDYKHYDL S---DTS1--GK ATAKM--F-FYSNIM-NFFKKEVR  1020
WP_054279288   983 HHAHDAYLNAVGTALLKMYPKL-ASEFVYGDYQKYDL S---GKAs--GH ATAKY--F-FYSNLL-NFFKSEVK  1052
WP_049531101   985 HHAHDAYLNAVAKAILKKYPKL-EPEFVYGDYQKYDL SrdpKEI---EK ATEKY--F-FYSNLL-NFFKEEVH  1056
WP_049538452   985 HHAHDAYLNAVAKAILKKYPKL-EPEFVYGDYQKYDL SkdpKDI---EK ATEKY--F-FYSNLL-NFFKEEVH  1056
WP_049549711   987 HHAHDAYLNAVAKAILKKYPKL-EPEFVYGDYQKNDL SkdpKDI---EK ATEKV--F-FYSNLL-NFFKEEVH  1058
WP_007896501   988 HHAHDAYLNAVGTALLKKYPKL-EAEFVYGDYKHFDL S---DPS1--GK ATAKV--F-FYSNIM-NFFKEELS  1057
EFR44625       940 HHAHDAYLNAVGTALLKKYPKL-EAEFVYGDYKHFDL S---DPS1--GK ATAKV--F-FYSNIM-NFFKEELS  1009
WP_002897477   984 HHAHDAYLNAVVAKAILKKYPKL-EPEFVYGDYQKYDL FkpsKEI---EK ATEKY--F-FYSNLL-NFFKEEVL  1055
```

| ID | Seq | N1 | Seq2 | Seq3 | N2 |
|---|---|---|---|---|---|
| WP_002906454 | 984 | HHAAHDAYLNAVVAKAILKKYPKL-EPEFVYGDYQKYDL | SkasNTI---DK | ATEKY--F-FYSNLL-NFFKEKVR | 1055 |
| WP_009729476 | 985 | HHAAHDAYLNAVVAKAILKKYPKL-EPEFVYGDYQKYDL | SkdpKEI---EK | ATEKY--F-FYSNLL-NFFKEEVH | 1056 |
| CQR24647 | 984 | HHAAHDAYLNAVAKALLIRYPKL-EPEFVYGEYPKYN- | S---YRE--RK | ATEKM--F-FYSNIM-NMFKTTIK | 1046 |
| WP_000066813 | 989 | HHAAHDAYLNAVLAKAILKKYPKL-EPEFVYGDYQKYDL | srepKEV---EK | ATQKY--F-FYSNIL-NFFKEEVH | 1060 |
| WP_009754323 | 985 | HHAAHDAYLNAVVAKAILKKYPKL-EPEFVYGDYQKYDL | skdpKEV---EK | ATEKY--F-FYSNIL-NFFKEEVH | 1056 |
| WP_044674937 | 988 | HHAAHDAYLNAVVATALLKKYPQL-APEFVYGDYPKYN- | S---YKS--RK | ATEKV--L-FYSNIM-NFFRRVLV | 1048 |
| WP_044676715 | 988 | HHAAHDAYLNAVVATALLKKYPQL-APEFVYGDYPKYN- | S---YKS--RK | ATEKV--L-FYSNIM-NFFRRVLV | 1050 |
| WP_044680361 | 986 | HHAAHDAYLNAVVATALLKKYPQL-APEFVYGDYPKYN- | S---YKS--RK | ATEKV--L-FYSNIM-NFFRRVLV | 1048 |
| WP_044681799 | 986 | HHAAHDAYLNAVVATALLKKYPQL-APEFVYGDYPKYN- | S---YKS--RK | ATEKY--L-FYSNIM-NFFRRVLV | 1050 |
| WP_049533112 | 981 | HHAAHDAYLNAVIGTALLKKYPKL-ASEFVYGEFKKYDV | S---DK--eIG | KATAK-YfFYSNLM-NFFKKEVK | 1050 |
| WP_029090905 | 977 | HHAAHDAFLVAFLGTNIITSNYPKI-EMEYLFKGYQHYLN | ---Ev--GK | AAKPKftF-IVENLS-------- | 1007 |
| WP_006506696 | 982 | HHAHQDAFIVAFLGTNIITSNYPKI-EMEYLFKGYQHYLN | ---NKNd--QK | ---g---FVINSM-NYPY-EV- | 1038 |
| AIT42264 | 981 | HHAHDAYLNAVVGTALIKKYPKL-ESEFVYGDYKVYDV | S---EQEi--GK | ATAKY--F-FYSNIM-NFFKTEIT | 1051 |
| WP_034440723 | 982 | HHGHDAYLNGVIALKLELYPYM-AKDLIYGKYSYHRK | G------g- | ATQAK--Y-KMSNII-ERFSQDL- | 1041 |
| AKQ21048 | 981 | HHAAHDAYLNAVVATTIMKVYPNL-KPQFVYGQYKKTSM | S---EQEi--GK | ATAKY--F-FYSNIM-KFFKKEKV | 1051 |
| WP_004636532 | 988 | HHAAHDAYLNCVVATTLLKVYPNL-APEFVYGEYPKFQT | ---FKE--EK | ATARK--H-FYSNIT-KFFTEED | 1042 |
| WP_002364836 | 939 | HHGQDAYLNCVVATTLLKVYPNL-APEFVYGEYPKFQT | ---FKE--NK | ATAKA--I-IYTNLL-RFFTED | 1047 |
| WP_016631044 | 723 | HHGQDAYLNCVVATTLLKVYPNL-APEFVYGEYPKFQT | ---FKE--NK | ATAKA--I-IYTNLL-RFFTED | 998 |
| EMS75795 | 988 | HHGQDAYLNCVVATLLKVYPNL-APEFVYGNYTKFNL | ---AT--eNK | ATAKK--E-FYSNIL-RFFBEKE | 782 |
| WP_002373311 | 988 | HHGQDAYLNCVVATTLLKVYPNL-APEFVYGEYPKFQA | ---FKE--NK | ATAKT--I-IYTNLM-RFFTEED | 1047 |
| WP_002378009 | 988 | HHGQDAYLNCVVATTLLKVYPNL-APEFVYGEYPKFQT | ---FKE--NK | ATAKA--I-IYTNLL-RFFTED | 1047 |
| WP_002407324 | 988 | HHGQDAYLNCVVATTLLKVYPNL-APEFVYGEYPKFQT | ---FKE--NK | ATAKA--I-IYTNLL-RFFTED | 1047 |
| WP_002413717 | 990 | HHGQDAYLNCVVATTLLKVYPNL-APEFVYGEYPKFQT | ---FKE--NK | ATAKA--I-IYTNLL-RFFTED | 1049 |
| WP_010775580 | 988 | HHGQDAYLNCVVATTLLKVYPNL-APEFVYGEYPKFQT | ---FKE--NK | ATAKA--I-IYTNLL-RFFTED | 1047 |
| WP_010818269 | 988 | HHGQDAYLNCVVATTLLKVYPNL-APEFVYGEYPKFQT | ---FKE--NK | ATAKA--I-IYTNLL-RFFTED | 1047 |
| WP_010824395 | 988 | HHGQDAYLNCVVATTLLKVYPNL-APEFVYGEYPKFQT | ---FKE--NK | ATAKT--I-IYTNLL-RFFTED | 1047 |
| WP_016622645 | 988 | HHGQDAYLNCVVATTLLKVYPNL-APEFVYGEYPKFQT | ---FKE--NK | ATAKA--I-IYTNLL-RFFTED | 1047 |
| WP_033624816 | 988 | HHGQDAYLNCVVATTLLKVYPNL-APEFVYGEYPKFQA | ---FKE--NK | AMAKA--I-IYTNLL-RFFTED | 1047 |
| WP_033625576 | 988 | HHGQDAYLNCVVATTLLKVYPNL-APEFVYGEYPKFQA | ---FKE--NK | ATAKA--I-IYTNLL-RFFTED | 1047 |
| WP_033789179 | 988 | HHGQDAYLNCVVATTLLKVYPNL-APEFVYGEYPKFQA | ---FKE--NK | ATAKA--I-IYTNLM-RFFTEV- | 1047 |
| WP_002310644 | 989 | HHAAHDAYLNGVVALALLKKYPOL-APEFVYGEYLKFNA | ---HK--aNK | ATVKK--E-FYSNIM-KFFESD- | 1048 |
| WP_002312694 | 990 | HHAAHDAYLNGVVALALLKKYPOL-APEFVYGEYLKFNA | ---HK--aNK | ATVKK--E-FYSNIM-KFFESD- | 1049 |
| WP_002314015 | 990 | HHAAHDAYLNGVVALALLKKYPOL-APEFVYGEYLKFNA | ---HK--aNK | ATVKK--E-FYSNIM-KFFESD- | 1049 |
| WP_002320716 | 990 | HHAAHDAYLNGVVALALLKKYPOL-APEFVYGEYLKFNA | ---HK--aNK | ATVKK--E-FYSNIL-KFFLESD- | 1049 |
| WP_002330729 | 990 | HHAAHDAYLNGVVALALLKKYPOL-APEFVYGEYLKFNA | ---HK--aNK | ATVKK--E-FYSNIM-KFFESD- | 1048 |
| WP_002335161 | 990 | HHAAHDAYLNGVVALALLKKYPOL-APEFVYGEYLKFNA | ---HK--aNK | ATVKK--E-FYSNIM-KFFESD- | 1049 |
| WP_002345439 | 990 | HHAAHDAYLNGVVALALLKKYPOL-APEFVYGEYLKFNA | ---HK--eNK | ATAKK--E-FYSNIM-KFFESD- | 1049 |
| WP_034867970 | 980 | HHAAHDAYLNGFIANVLLKRYPNL-APEFVYGKVKYSL | ---AR--eNK | ATAKK--E-FYSNIL-KFLESD- | 1039 |
| WP_047937432 | 990 | HHAAHDAYLNGVIALALLKRYPNL-APEFVYGEYLKFNA | ---HK--aNK | ATVKK--E-FYSNIM-KFFESD- | 1049 |
| WP_010720994 | 980 | HHAAHDAYLNGFIANVLLKRYPNL-APEFVYGKVKYSL | ---AR--eNK | ATAKK--E-FYSNIL-KFLESD- | 1039 |
| WP_010737004 | 980 | HHAAHDAYLNGFIANVLLKRYPNL-APEFVYGKVKYSL | ---AR--eNK | ATAKK--E-FYSNIL-KFLESD- | 1039 |
| WP_034700478 | 980 | HHAAHDAYLNGFIANVLLKRYPNL-APEFVYGKVKYSL | ---AR--eNK | ATAKK--E-FYSNIL-KFLESD- | 1039 |
| WP_007209003 | 978 | HHAAHDAYLNAVVALSLLRVYPOL-KPEFVYGKNS- | ---IHDq--NK | ATIKK--qFYSNIT-RYFASK- | 1037 |
| WP_023519017 | 974 | HHAAHDAYLNGVVAMTLLGTYIGHRFESL-APEFVYGSYIKGDI | ---NQ---NK | ATAKK--E-FYSNIM-KFFASE- | 1033 |
| WP_010770040 | 986 | HHGHDAYLNGVVANSLLRVYPOL-QPEFVYGDYPKFNA | ---YKA--NK | ATAKK--Q-LYTNIM-KFFAED- | 1045 |
| WP_048604708 | 983 | HHAAHDAYLNGVVATALLKIYPOL-EPEFVYGEFHRFNA | ---FKE--NK | ATAKK--Q-FYSNLM-EFSKSD- | 1042 |
| WP_010750235 | 983 | HHAAHDAYLNAVVALALLKKYPRL-APEFVYGSFAKFHL | ---VK--eNK | ATAKK--F-FYSNIL-KFFFEKE- | 1042 |
| AII16583 | 1021 | HHAAHDAYIATILGTYIGHRFESL-ESEFVYGDYKVYDV | S---EQEi--GK | ATAKY--F-FYSNIT-NFFKTEIT | 1090 |
| WP_029073316 | 988 | HHAAHDAYIATILGTYIGHRFESL-DAKYIYGEYQKIFR | ---NKNk--DK | ---KDg--FILNSM-RNLYADK- | 1052 |
| WP_031589969 | 988 | HHAAHDAYIATILGTYIGHRFESL-DAKYIYGEYKRIFR | ---QKNk--GK | ---NDg--FILNSM-RNIYADK- | 1052 |
| KDA45870 | 973 | HHAAHDAYLNAVVANLIMAKYPEL-EPEFVYGKYRKTK- | ---FKG1--GK | ATAKN--t1YANVL-YFLKENEV | 1034 |
| WP_039099354 | 991 | HHAFDAYLTAFVGLYLLKRYPKL-KPYPVYGEYQKAS- | ---QQ--DK | ---RN--F---NFL-NGLKKD- | 1043 |
| AKP02966 | 1000 | HHAAQDAYLASFLGTYRLRRFPTD-EMLLMNGEYNKFYG | ---KEIysKK | -SRKN-gF-IISPLV------- | 1062 |

-continued

```
WP_010991369   985  HHAHDAYLNGVVANTLLKVYPQL-EPEFVYGDYHQFDW ----NK ATAKK---Q-FYTNIM LFFAQK--  1044
WP_033838504   985  HHAHDAYLNGVVANTLLKVYPQL-EPEFVYGDYHQFDW ----FKA---NK ATAKK---Q-FYTNIM LFFAQK--  1044
EHN60060       988  HHAHDAYLNGVVANTLLKVYPQL-EPEFVYGDYHQFDW ----FKA---NK ATAKK---Q-FYTNIM LFFAQK--  1047
EFR89594       754  HHAHDAYLNGVVANTLLKVYPQL-EPEFVYGDYHQFDW ----FKA---NK ATAKK---Q-FYTNIM LFFAQK--  813
WP_038409211   985  HHAHDAYLNGVVANTLLKVYPQL-EPEFVYGDYHQFDW ----FKA---NK ATAKK---Q-FYTNIM LFFAQK--  1044
EFR95520       604  HHAHDAYLNGVVANTLLKVYPQL-EPEFVYGDYHQFDW ----FKA---NK ATAKK---Q-FYTNIM RFFAKE--  663
WP_003723650   985  HHAHDAYLNGVVANTLLKVYPQL-EPEFVYGDYHQFDW ----FKA---NK ATAKK---Q-FYTNIM LFFAQK--  1044
WP_003727705   985  HHAHDAYLNGVVANTLLKVYPQL-EPEFVYGDYHQFDW ----FKA---NK ATAKK---Q-FYTNIM LFFAQK--  1044
WP_003730785   985  HHAHDAYLNGVVANTLLKVYPQL-EPEFVYGEYHQFDW ----FKA---NK ATAKK---Q-FYTNIM LFFAQK--  1044
WP_003733029   985  HHAHDAYLNGVVANTLLKVYPQL-EPEFVYGEYHQFDW ----FKA---NK ATAKK---Q-FYTNIM LFFAQK--  1044
WP_003739838   985  HHAHDAYLNGVVANTLLKVYPQL-EPEFVYGEYHQFGW ----FKA---NK ATAKK---Q-FYTNIM LFFAQK--  1044
WP_014601172   985  HHAHDAYLNGVVANTLLKVYPQL-EPEFVYGEYHQFDW ----FKA---NK ATAKK---Q-FYTNIM LFFGQK--  1044
WP_023548323   985  HHAHDAYLNGVVANTLLKVYPQL-EPEFVYGEYHQFDW ----FKA---NK ATAKK---Q-FYTNIM LFFAQK--  1044
WP_031665337   985  HHAHDAYLNGVVANTLLKVYPQL-EPEFVYGEYHQFDW ----FKA---NK ATAKK---Q-FYTNIM LFFAQK--  1044
WP_031669209   985  HHAHDAYLNGVVANTLLKVYPQL-EPEFVYGEYHQFDW ----FKA---NK ATAKK---Q-FYTNIM LFFAQK--  1044
WP_003920898   985  HHAHDAYLNGVVANTLLKVYPQL-EPEFVYGEYHQFDW ----FKA---NK ATAKK---Q-FYTNIM LFFAQK--  1044
AKI42028       988  HHAHDAYLNGVVANTLLKVYPQL-EPEFVYGEYHQFDW ----FKA---NK ATAKK---Q-FYTNIM LFFAQK--  1047
AKI50529       988  HHAHDAYLNGVVANTLLKVYPQL-EPEFVYGEYHQFDW ----FKA---NK ATAKK---Q-FYTNIM LFFGQK--  1047
EFR83390       433  HHAHDAYLNGVVANTLLKVYPQL-EPEFVYGEYHQFDW ----FKA---NK ATAKK---Q-FYTNIM LFFAKK--  492
WP_046323366   985  HHAHDAYLNCVVANTLLKVYPQL-ESEFVYGDYKVYDV S---EQEi-GK ATAKY---F-FYSNIM-NFFKTEIT  1044
AKE81011       998  HHAHDAYIVALIGGFMRDRYPNMhDSKAVYSEYMKMFR ----NKNd-QK -----g---FVINSM-NYPY-EV--  1067
CUO82355       981  HHAHDAYIACIVCQFMHQNFEHL-DAKIIYGQYK---- ------KNy---KK ---NYg----FILNSM-NHLQSDI  1042
AGZ01981      1015  HHAHDAYLNAVVGTALIKKYPKL-ESEFVYGDYKVYDV S---EQEi-GK ATAKY---F-FYSNIM-NFFKTEIT  1084
AKA60242       982  HHAHDAYLNAVVGTALIKKYPKL-ESEFVYGDYKVYDV S---EQEi-GK ATAKY---F-FYSNIM-NFFKTEIT  1051
AK540380       982  HHAHDAYLNAVVGTALIKKYPKL-ESEFVYGDYKVYDV S---EQEi-GK ATAKY---F-FYSNIM-NFFKTEIT  1051
4UN5_B         986  HHAHDAYLNAVVGTALIKKYPKL-ESEFVYGDYKVYDV S---EQEi-GK ATAKY---F-FYSNIM-NFFKTEIT  1055
WP_010922251  1052  LAN-GEIRKRPLIE TNGET-GE-IVWDKGRDFATVRKVLS-MPQVNIVKKTEVQT GGFSK ESIL-PKR-  1114
WP_039695303  1059  YAD-GTVFERPLIE T-NAD-GE-IAWNKQIDFEKVRKVLS-YPQVNIVKKVETQT GGFSK ESIL-PKG-  1120
WP_045635197  1056  YAD-GTIVKRENIE Y-SKDLGE-IAWNKEKDFAIIKKVLS-LPQVNIVKKREVQT GGFSK ESIL-PKG-  1118
5AXW_A         772  YKYsHRVDKKPNRE VNNLN-GL---YDKDND--KLKKLINkSPEKLLMYHHDPQT --YQK KLIMeQYGd  852
WP_009880683   736  LAN-GEIRKRPLIE TNGET-GE-IVWDKGRDFATVRKVLS-MPQVNIVKKTEVQT GGFSK ESIL-PKR-  798
WP_010922251  1052  LAN-GEIRKRPLIE TNGET-GE-IVWDKGRDFATVRKVLS-MPQVNIVKKTEVQT GGFSK ESIL-PKR-  1114
WP_011054416  1052  LAN-GEIRKRPLIE TNGET-GE-IVWDKGRDFATVRKVLS-MPQVNIVKKTEVQT GGFSK ESIL-PKR-  1114
WP_011284745  1052  LAN-GEIRKRPLIE TNGET-GE-IVWDKGRDFATVRKVLS-MPQVNIVKKTEVQT GGFSK ESIL-PKR-  1114
WP_011285506  1052  LAN-GEIRKRPLIE TNGET-GE-IVWDKGRDFATVRKVLS-MPQVNIVKKTEVQT GGFSK ESIL-PKR-  1114
WP_011527619  1052  LAN-GEIRKRPLIE TNGET-GE-IVWDKGRDFATVRKVLS-MPQVNIVKKTEVQT GGFSK ESIL-PKR-  1114
WP_012560673  1051  LAN-GEIRKRPLIE TNGET-GE-IVWDKGRDFATVRKVLS-MPQVNIVKKTEVQT GGFSK ESIL-PKR-  1113
WP_014407541  1052  LAN-GEIRKRPLIE TNGET-GE-IVWDKGRDFATVRKVLS-MPQVNIVKKTEVQT GGFSK ESIL-PKR-  1114
WP_020905136  1052  LAN-GEIRKRPLIE TNGET-GE-IVWDKGRDFATVRKVLS-MPQVNIVKKTEVQT GGFSK ESIL-PKR-  1114
WP_023080005  1051  LAN-GEIRKRPLIE TNGET-GE-IVWDKGRDFATVRKVLS-MPQVNIVKKTEVQT GGFSK ESIL-PKR-  1113
WP_023610282  1051  LAN-GEIRKRPLIE TNGET-GE-IVWDKGRDFATVRKVLS-MPQVNIVKKTEVQT GGFSK ESIL-PKR-  1113
WP_030125963  1052  LAN-GEIRKRPLIE TNGET-GE-IVWDKGRDFATVRKVLS-MPQVNIVKKTEVQT GGFSK ESIL-PKR-  1114
WP_030126706  1052  LAN-GEIRKRPLIE TNGET-GE-IVWDKGRDFATVRKVLS-MPQVNIVKKTEVQT GGFSK ESIL-PKR-  1114
WP_031488318  1052  LAN-GEIRKRPLIE TNGET-GE-IVWDKGRDFATVRKVLS-MPQVNIVKKTEVQT GGFSK ESIL-PKR-  1114
WP_032460140  1052  LAN-GEIRKRPLIE TNGET-GE-IVWDKGRDFATVRKVLS-MPQVNIVKKTEVQT GGFSK ESIL-PKR-  1114
WP_032461047  1052  LAN-GEIRKRPLIE TNGET-GE-IVWDKGRDFATVRKVLS-MPQVNIVKKTEVQT GGFSK ESIL-PKR-  1114
WP_032462016  1052  LAN-GEIRKRPLIE TNGET-GE-IVWDKGRDFATVRKVLS-MPQVNIVKKTEVQT GGFSK ESIL-PKR-  1114
WP_032462936  1052  LAN-GEIRKRPLIE TNGET-GE-IVWDKGRDFATVRKVLS-MPQVNIVKKTEVQT GGFSK ESIL-PKR-  1114
WP_032464890  1052  LAN-GEIRKRPLIE TNGET-GE-IVWDKGRDFATVRKVLS-MPQVNIVKKTEVQT GGFSK ESIL-PKR-  1114
WP_033888930   877  LAN-GEIRKRPLIE TNGET-GE-IVWDKGRDFATVRKVLS-MPQVNIVKKTEVQT GGFSK ESIL-PKR-  939
WP_038431314  1052  LAN-GEIRKRPLIE TNGET-GE-IVWDKGRDFATVRKVLS-MPQVNIVKKTEVQT GGFSK ESIL-PKR-  1114
WP_038432938  1051  LAN-GEIRKRPLIE TNGET-GE-IVWDKGRDFATVRKVLS-MPQVNIVKKTEVQT GGFSK ESIL-PKR-  1113
```

-continued

```
WP_038434062    1052 LAN-GEIRKRPLIE TNGET-GE-IVWDKGRDFATVRKVLS-MPQVNIVKKTEVQT GGFSK ESIL-PKR- 1114
BAQ51233         963 LAN-GEIRKRPLIE TNGET-GE-IVWDKGRDFATVRKVLS-MPQVNIVKKTEVQT GGFSK ESIL-PKR- 1025
KGE60162         227 LAN-GEIRKRPLIE TNGET-GE-IVWDKGRDFATVRKVLS-MPQVNIVKKTEVQT GGFSK ESIL-PKR-  289
KGE60856           1 ------------IE ----IE---IVWDKGRDFATVRKVLS-MPQVNIVKKTEVQT GGFSK ESIL-PKR-   52
WP_002989955    1052 LAN-GEIRKRPLIE TNGET-GE-IVWDKGRDFATVRKVLS-MPQVNIVKKTEEQT GGFSK ESIL-PKR- 1114
WP_003030002    1042 ------------DIQ T-NED-GE-IAWNKEKHIKILRKVLS-YPQVNIVKKTEQT GGFSK ESIL-PKG- 1093
WP_003065552    1059 YSN-GKVIVRPVVE Y-SKD-TEdIAWDKKKSNERTICKVLS-YPQVNIVKKVETQT GGFSK ESIL-PKG- 1121
WP_001040076    1058 LAD-GTVVVKDDIE TGRYM-GK-TAWDKKKKHFATVRKVLS-YPQVNIVKKTEIQT GGFSK ESIL-AHG- 1120
WP_001040078    1050 LAD-GSIVVRPVIE TGRYM-GK-TAWDKKKKHFATVRKVLS-YPQVNIVKKTEIQT GGFSK ESIL-AHG- 1112
WP_001040080    1050 LAD-GTVVVKDDIE VNNDT-GE-IVWDKKKKHFATVRKVLS-YPQVNIVKKTEIQT GGFSK ESIL-AHG- 1112
WP_001040081    1050 LAD-GTVVVKDDIE VNNDT-GE-IVWDKKKKHFATVRKVLS-YPQVNIVKKTEIQT GGFSK ESIL-AHG- 1112
WP_001040083    1050 LAD-GTVVVKDDIE VNNDT-GE-IVWDKKKKHFATVRKVLS-YPQNNIVKKTEIQT GGFSK ESIL-AHG- 1112
WP_001040085    1050 LAD-GTVVVKDDIE VNNDT-GE-IVWDKKKKHFATVRKVLS-YPQNNIVKKTEIQT GGFSK ESIL-AHG- 1112
WP_001040087    1050 LAD-GTVVVKDDIE VNNDT-GE-IVWDKKKKHFATVRKVLS-YPQNNIVKKTEIQT GGFSK ESIL-AHG- 1112
WP_001040088    1050 LAD-GTVVVKDDIE VNNDT-GE-IVWDKKKKHFATVRKVLS-YPQNNIVKKTEIQT GGFSK ESIL-AHG- 1112
WP_001040089    1050 LAD-GTVVVKDDIE VNNDT-GE-IVWDKKKKHFATVRKVLS-YPQNNIVKKTEIQT GGFSK ESIL-AHG- 1112
WP_001040090    1050 LAD-GTVVVKDDIE VNNDT-GE-IVWDKKKKHFATVRKVLS-YPQVNIVKKTEIQT GGFSK ESIL-AHG- 1112
WP_001040091    1050 LAD-GTVVVKDDIE VNNDT-GE-IVWDKKKKHFATVRKVLS-YPQVNIVKKTEVQT GGFSK ESIL-AHG- 1112
WP_001040092    1050 LAD-ETVVVKDDIE VNNET-GE-IAWDKKKKHFATVRKVLS-YPQVNIVKKTEIQT GGFSK ESIL-AHS- 1112
WP_001040094    1050 LAD-GTVVVKDDIE VNNDT-GE-IVWDKKKKHFATVRKVLS-YPQVNIVKKTEIQT GGFSK ESIL-AHG- 1112
WP_001040095    1050 LAD-GTVVVKDDIE VNNDT-GE-IVWDKKKKHFATVRKVLS-YPQVNIVKKTEVQT GGFSK ESIL-AHG- 1112
WP_001040096    1050 LAD-GTVVVKDDIE VNNDT-GE-IVWDKKKKHFATVRKVLS-YPQNNIVKKTEIQT GGFSK ESIL-AHG- 1112
WP_001040097    1050 LAD-GTVVVKDDIE VNNDT-GE-IVWDKKKKHFATVRKVLS-YPQNNIVKKTEIQT GGFSK ESIL-AHG- 1112
WP_001040098    1050 LAD-GTVVVKDDIE VNNDT-GE-IVWDKKKKHFATVRKVLS-YPQVNIVKKTEIQT GGFSK ESIL-AHG- 1112
WP_001040099    1050 LAD-GTVVVKDDIE VNNDT-GE-IVWDKKKKHFATVRKVLS-YPQVNIVKKTEIQT GGFSK ESIL-AHG- 1112
WP_001040100    1050 LAD-GTVVVKDDIE VNNDT-GE-IVWDKKKKHFATVRKVLS-YPQVNIVKKTEIQT GGFSK ESIL-AHG- 1112
WP_001040104    1050 LAD-GTVVVKDDIE VNNDT-GE-IVWDKKKKHFATVRKVLS-YPQVNIVKKTEIQT GGFSK ESIL-AHG- 1112
WP_001040105    1050 LAD-GTVVVKDDIE VNNDT-GE-IVWDKKKKHFATVRKVLS-YPQVNIVKKTEIQT GGFSK ESIL-AHG- 1112
WP_001040106    1050 LAD-GTVVVKDDIE VNNDT-GE-IVWDKKKKHFATVRKVLS-YPQVNIVKKTEIQT GGFSK ESIL-AHG- 1112
WP_001040107    1050 LAD-GTVVVKDDIE VNNDT-GE-IVWDKKKKHFATVRKVLS-YPQVNIVKKTEIQT GGFSK ESIL-AHG- 1112
WP_001040108    1050 LAD-GTVVVKDDIE VNNDT-GE-IVWDKKKKHFATVRKVLS-YPQNNIVKKTEIQT GGFSK ESIL-AHG- 1112
WP_001040109    1050 LAD-GTVVVKDDIE VNNDT-GE-IVWDKKKKHFATVRKVLS-YPQNNIVKKTEIQT GGFSK ESIL-AHG- 1112
WP_001040110    1050 LAD-GTVVVKDDIE VNNDT-GE-IVWDKKKKHFATVRKVLS-YPQNNIVKKTEIQT GGFSK ESIL-AHG- 1112
WP_015058523    1050 LAD-GTVVVKDDIE VNNET-GE-IAWDKKKKHFATVRKVLS-YPQNNIVKKTEIQT GGFSK ESIL-AHS- 1112
WP_017643650    1050 LAD-GTVVVKDDIE VNNDT-GE-IVWDKKKKHFATVRKVLS-YPQNNIVKKTEIQT GGFSK ESIL-AHG- 1112
WP_017647151    1050 LAD-GTVVVKDDIE VNNDT-GE-IVWDKKKKHFATVRKVLS-YPQNNIVKKTEIQT GGFSK ESIL-AHG- 1112
WP_017648376    1050 LAD-GTVVIKDDIE VNNDT-GE-IVWDKKKKHFATVRKVLS-YPQNNIVKKTEIQT GGFSK ESIL-AHG- 1112
WP_017649527    1050 LAD-GTVVVKDDIE VNNDT-GE-IVWDKKKKHFATVRKVLS-YPQNNIVKKTEIQT GGFSK ESIL-AHG- 1112
WP_017771611    1050 LAD-GTVVVKDDIE VNNDT-GE-IVWDKKKKHFATVRKVLS-YPQNNIVKKTEIQT GGFSK ESIL-AHG- 1112
WP_017771984    1050 LAD-GTVVVKDDIE VNNDT-GE-IVWDKKKKHFATVRKVLS-YPQNNIVKKTEIQT GGFSK ESIL-AHG- 1112
CFQ25032        1050 LAD-GTVVVKDDIE VNNDT-GE-IVWDKKKKHFATVRKVLS-YPQNNIVKKTEIQT GGFSK ESIL-AHG- 1112
CFV16040        1050 LAD-GTVVVKDDIE VNNDT-GE-IVWDKKKKHFATVRKVLS-YPQNNIVKKTEIQT GGFSK ESIL-AHG- 1112
KLJ37842        1050 LAD-GTVVVKDDIE VNNDT-GE-IVWDKKKKHFATVRKVLS-YPQNNIVKKTEIQT GGFSK ESIL-AHG- 1112
KLJ72361        1064 LAD-GTVVVKDDIE VNNDT-GE-IVWDKKKKHFATVRKVLS-YPQNNIVKKTEIQT GGFSK ESIL-AHG- 1126
KLL20707        1050 LAD-GTVVVKDDIE VNNDT-GE-IVWDKKKKHFATVRKVLS-YPQNNIVKKTEIQT GGFSK ESIL-AHG- 1112
KLL42645        1050 LAD-GTVVVKDDIE VNNDT-GE-IVWDKKKKHFATVRKVLS-YPQNNIVKKTEIQT GGFSK ESIL-AHG- 1112
WP_047207273    1050 LAD-GTVVVKDDIE VNNDT-GE-IVWDKKKKHFATVRKVLS-YPQNNIVKKTEIQT GGFSK ESIL-AHG- 1112
WP_047209694    1050 LAD-GTVVVKDDIE VNNDT-GE-IVWDKKKKHFATVRKVLS-YPQNNIVKKTEIQT GGFSK ESIL-AHG- 1112
WP_050198062    1050 LAD-GTVVVKDDIE VNNDT-GE-IVWDKKKKHFATVRKVLS-YPQNNIVKKTEIQT GGFSK ESIL-AHG- 1112
WP_050201642    1050 LAD-GTVVVKDDIE VNNDT-GE-IVWDKKKKHFATVRKVLS-YPQNNIVKKTEIQT GGFSK ESIL-AHG- 1112
WP_050204027    1050 LAD-GTVVVKDDIE VNNDT-GE-IVWDKKKKHFATVRKVLS-YPQNNIVKKTEIQT GGFSK ESIL-AHG- 1112
WP_050881965    1050 LAD-GTVVVKDDIE VNNDT-GE-IVWDKKKKHFATVRKVLS-YPQNNIVKKTEIQT GGFSK ESIL-AHG- 1112
WP_050886065    1050 LAD-GTVVVKDDIE VNNDT-GE-IVWDKKKKHFATVRKVLS-YPQNNIVKKTEIQT GGFSK ESIL-AHG- 1112
```

```
                                                                                                                       -continued AHN30376        1050 LAD-ETVVVKDDIE VNNET-GE-IAWDKKKHFATVRKVLS-YPQVNIVKKTEVQT GGFSK ESIL-AHS- 1112
EA078426        1050 LAD-GTVVVKDDIE VNNDT-GE-IVWDKKKHFATVRKVLS-YPQVNIVKKTEIQT GGFSK ESIL-AHG- 1112
CCW42055        1050 LAD-GTVVVKDDIE VNNDT-GE-IVWDKKKHFATVRKVLS-YPQNNIVKKTEIQT GGFSK ESIL-AHG- 1112
WP_003041502    1051 FAD-GTVVERPDIE T-SED-GE-IAWNKQTDFKIVRKVLS-YPQNNIVKKTEIQT HGLDR PSPK-PKP- 1122
WP_037593752    1043 ---------DIQ   T-NED-GE-IAWNKEKHIKILRKVLS-YPQVNIVKKEEQT GGFSK ESIL-PKG- 1094
WP_049516684    1042 ---------DIQ   T-NED-GE-IAWNKEKHIKILRKVLS-YPQVNIVKKEEQT GGFSK ESIL-PKG- 1093
GAD46167        1042 ---------DIQ   T-NED-GE-IAWNKEKHIKILRKVLS-YPQVNIVKKEEQT GGFSK ESIL-PKG- 1093
WP_018363470    1063 YSN-GKVIVRPVVE Y-SKDtGE-IAWNKRTDFEKVRKVLA-MPQVNIVKKTEVQT GGFSK ESIL-SKR- 1125
WP_003043819    1061 LAN-GEIRKRPLIE TNGET-GE-VVWNKEKDFATVRKVLS-YPQVNIVKKTEEQT GGFSK ESIL-PKG- 1123
WP_066269658    1042 ---------DIQ   T-NED-GE-IAWNKEKHIKILRKVLS-YPQVNIVKKTEEQT GGFSK ESIL-PKG- 1093
WP_048800889    1052 FAD-GTVVVKDDIE T-SED-GE-IVWDKGTDFKIVRKVLS-YPQNNIVKKTEVQT GRFSK ESIY-ARG- 1113
WP_012767106    1051 LAN-GEIRKRPLIE TNEET-GE-IVWDKGRDFATVRKVLS-MPQVNIVKKTEVQT GALTN ESIY-ARG- 1113
WP_014612333    1051 LAN-GEIRKRPLIE TNEET-GE-IVWDKGRDFATVRKVLS-MPQVNIVKKTEVQT GALTN ESIY-ARG- 1113
WP_015017095    1051 LAN-GEIRKRPLIE TNEET-GE-IVWDKGRDFATVRKVLS-MPQVNIVKKTEVQT GALTN ESIY-ARG- 1113
WP_015057649    1051 LAN-GEIRKRPLIE TNEET-GE-IVWDKGRDFATVRKVLS-MPQVNIVKKTEVQT GALTN ESIY-ARG- 1113
WP_048327215    1051 LAN-GEIRKRPLIE TNEET-GE-IVWDKGRDFATVRKVLS-MPQVNIVKKTEVQT GALTN ESIY-ARG- 1113
WP_049519324    1051 LAN-GEIRKRPLIE TNEET-GE-IVWDKGRDFATVRKVLS-MPQVNIVKKTEVQT GALTN ESIY-ARG- 1113
WP_012515931    1044 L--------H     VNSD--GE-EIWNANKHLPIIKNVLS-IPQVNIVKKTEVQT GGFYK ESIL-SKG- 1094
WP_021320964    1044 L--------H     VNSD--GE-EIWNANKHLPIIKNVLS-IPQVNIVKKTEVQT GGFYK ESIL-SKG- 1094
WP_037581760    1044 L--------H     VNSD--GE-EIWNANKHLPIIKNVLS-IPQVNIVKKTEVQT GGFYK ESIL-SKG- 1094
WP_004324481    1062 YAD-GRVFERPDIE T-NAD-GE-VVWNKQRDFNIVRKVLS-YPQVNIVRKVLS  GGFSK ESIL-PKG- 1123
WP_009854540    1057 YAD-GTVFERPIIE T-NAD-GE-IAWNKQIDFEKVRKVLS-LPQVNIVKKVETQT GGFSK ESIL-PKG- 1118
WP_012962174    1059 YSN-GKVVRPVIE  C-SKDtGE-IAWNKQTDFEKVRKVLS-YPQVNIVKKVETQT GGFSK ESIL-PKG- 1119
WP_039695303    1059 YSN-GKVVVRPVIE C-SKDtGE-IAWNKQTDFEKVRKVLS-YPQVNIVKKVETQT GGFSK ESIL-PKG- 1120
WP_014334983    1062 YAD-GRVFERPDIE T-NAD-GE-VVWNKQKDPDIVRKVMS-YPQVNIVKKVEAQT GGFSK ESIL-SKG- 1123
WP_003099269    1052 LAD-DTIFTRPQIE VNTET-GE-IVWDKVKDMQTIRKVMS-YPQVNIVMKTEVQT GGFSK ESIW-PKG- 1114
AHY17476        1052 LAD-DTIFTRPQIE VNTET-GE-IVWDKVKDMQTIRKVMS-YPQVNIVMKTEVQT GGFSK ESIW-PKG- 1114
ESR09100        1052 LAD-DTIFTRPQIE VNTET-GE-IVWDKVKDMQTIRKVMS-YPQVNIVMKTEVQT GGFSK ESIW-PKG- 1114
AGM98575        1052 LAD-DTIFTRPQIE VNTET-GE-IIWKKDEHISNIKKVLS-YPQVNIVKKVEEQT GGFSK ESIW-PKG- 1114
ALF27331        1056 --K------      -DQEtGE-IVWDKKEIENIVKKVIY-SSPVNIVKKREEQS GALFK QSNM-AVGy 1108
WP_018372492    1056 YAD-GTIVKRENIE Y-SKDtGE-IVWDKKEIENIVKKVIY-SSPVNIVKKREEQS GALFD GGLFD 1124
WP_045618028    1057 YAD-GTIVKRENIE Y-SKDtGE-IAWNKEKDFATIKKVLS-LPQVNIVKKEREVQT GGLFD NNIV-SKKk 1118
WP_045635197    1056 YAD-GTIVKRENIE Y-SKDtGE-IAWNKEKDFAIIKKVLS-LPQVNIVKKREVQT GGFSK ESIL-PKG- 1118
WP_002263549    1042 ---------DVR   T-DKN-GE-IIWKKDEHISNIKKVLS-YPQVNIVKKVEEQT GGFSK ESIL-PKG- 1093
WP_002263887    1042 ---------DVR   T-DKN-GE-IIWKKDEHISNIKKVLS-YPQVNIVKKVEEQT GGFSK ESIL-PKG- 1093
WP_002264920    1042 ---------DVR   T-DKN-GE-IIWKKDEYISNIKKVLS-YPQVNIVKKVEEQT GGFSK ESIL-PKG- 1093
WP_002269043    1042 ---------DVR   T-DKN-GE-IIWKKDEHISNIKKVLS-YPQVNIVKKVEEQT GGFSK ESIL-PKG- 1093
WP_002269448    1042 ---------DVR   T-DRN-GE-IIWKKDEHISNIKKVLS-YPQVNIVKKVEEQT GGFSK ESIL-PKG- 1093
WP_002271977    1042 ---------DVR   T-DKN-GE-IIWKKDEHISNIKKVLS-YPQVNIVKKVEEQT GGFSK ESIL-PKG- 1093
WP_002272766    1042 ---------DVR   T-DKN-GE-IAWDKTKHITTVKKVLS-YPQVNIVKKVEEQT GGLFD ----PKS- 1093
WP_002273241    1042 ---------DVR   T-DKN-GE-IIWKKDEHISNIKKVLS-YPQVNIVKKVEEQT GGFSK ESIL-PKG- 1093
WP_002275430    1042 ---------DVR   T-DKN-GE-IIWKKDEHITTVKKVLS-YPQVNIVKKVEEQT GGFSK ESIL-PKG- 1093
WP_002276448    1042 ---------DVR   T-DKN-GE-IIWKKDEHISNIKKVLS-YPQVNIVKKVEEQT GGFSK ESIL-PKG- 1093
WP_002277050    1047 LAD-DQIVERPMIE VNDET-GE-IAWDKTKHITTVKKVLS-YPQVNIVKKVEEQT GGLFD ----PKS- 1111
WP_002277364    1042 ---------DVR   T-DRN-GE-IIWKKDEHISNIKKVLS-YPQVNIVKKVEEQT GGFSK ESIL-PKG- 1093
WP_002279025    1042 ---------DVR   T-DKN-GE-IIWKKDEHISNIKKVLS-YPQVNIVKKVEEQT GGFSK ESIL-PKG- 1093
WP_002279859    1042 ---------DVR   T-DKN-GE-IIWKKDEHISNIKKVLS-YPQVNIVKKVEEQT GGFSK ESIL-PKG- 1093
WP_002280230    1042 ---------DVR   T-DKN-GE-IIWKKDEHISNIKKVLS-YPQVNIVKKVEEQT GGFSK ESIL-PKG- 1093
WP_002281696    1047 LAD-DQIVERPMIE VNDET-GE-IAWDKTKHITTVKKVLS-YPQVNIVKKVEEQT GGLFD ----PKS- 1111
WP_002282247    1042 ---------DVR   I-DKN-GE-IIWKKDEHISNIKKVLS-YPQVNIVKKVEEQT GGFSK ESIL-PKG- 1093
WP_002282906    1042 ---------DVR   T-DKN-GE-IIWKKDEHISNIKKVLS-YPQVNIVKKVEEQT GGFSK ESIL-PKG- 1093
WP_002283846    1042 ---------DVR   T-DKN-GE-IIWKKDEHISNIKKVLS-YPQVNIVKKVEEQT GGFSK ESIL-PKG- 1093
```

```
-continued

WP_002872255  1042  ------------DVR  T-DKN-GE  IIWKKDEHISNIKKVLS-YPQVNIVKKVEEQT  GGFSK  ESIL-PKG-  1093
WP_002288990  1042  ------------DVR  T-DKN-GE  IIWKKDEHISNIKKVLS-YPQVNIVKKVEEQT  GGFSK  ESIL-PKG-  1093
WP_002289641  1042  ------------DVR  T-DKN-GE  IIWKKDEHISNIKKVLS-YPQVNIVKKVEEQT  GGFSK  ESIL-PKG-  1093
WP_002290427  1042  ------------DVR  T-DKN-GE  IIWKKDEHISNIKKVLS-YPQVNIVKKVEEQT  GGFSK  ESIL-PKG-  1093
WP_002295753  1042  ------------DVR  T-DKN-GE  IIWKKDEHISNIKKVLS-YPQVNIVKKVEEQT  GGFFK  ESIL-PKG-  1093
WP_002296423  1042  ------------DVR  T-DKN-GE  IIWKKDEHISNIKKVLS-YPQVNIVKKVEEQT  GGFSK  ESIL-PKG-  1093
WP_002304487  1056  ------------DVR  T-DKN-GE  IIWKKDEHISNIKKVLS-YPQVNIVKKVEEQT  GGFSK  ESIL-PKG-  1107
WP_002305844  1056  ------------DVR  T-DKN-GE  IIWKKDEHISNIKKVLS-YPQVNIVKKVEEQT  GGFSK  ESIL-PKG-  1107
WP_002307203  1042  ------------DVR  T-DKN-GE  IIWKKDEHISNIKKVLS-YPQVNIVKKVEEQT  GGFSK  ESIL-PKG-  1093
WP_002310390  1042  ------------DVR  T-DKN-GE  IIWKKDEYISNIKKVLS-YPQVNIVKKVEEQT  GGFSK  ESIL-PKG-  1093
WP_002352408  1042  ------------DVR  T-DKN-GE  IIWKKDEYISNIKKVLS-YPQVNIVKKVEEQT  GGFSK  ESIL-PKG-  1093
WP_012997688  1042  ------------DVR  T-DKN-GE  IIWKKDEHISNIKKVLS-YPQVNIVKKVEEQT  GGFSK  ESIL-PKG-  1093
WP_014677909  1042  ------------DVR  T-DKN-GE  IIWKKDEHISNIKKVLS-YPQVNIVKKVEEQT  GGFFK  ESIL-PKG-  1093
WP_019312892  1042  ------------DVR  T-DKN-GE  IIWKKDEYISNIKKVLS-YPQVNIVKKVEEQT  GGFSK  ESIL-PKG-  1093
WP_019313659  1042  ------------DVR  T-DKN-GE  IIWKKDEHISNIKKVLS-YPQVNIVKKVEEQT  GGFSK  ESIL-PKG-  1093
WP_019314093  1042  ------------DVR  T-DKN-GE  IIWKKDEYISNIKKVLS-YPQVNIVKKVEEQT  GGFSK  ESIL-PKG-  1093
WP_019315370  1042  ------------DVR  T-DKN-GE  IIWKKDEHISNIKKVLS-YPQVNIVKKVEEQT  GGFSK  ESIL-PKG-  1093
WP_019803776  1042  ------------DVR  T-DKN-GE  IIWKKDEHISNIKKVLS-YPQVNIVKKVEEQT  GGFSK  ESIL-PKG-  1093
WP_019805234  1042  ------------DVR  T-DKN-GE  IIWKKDEHISNIKKVLS-YPQVNIVKKVEEQT  GGFFK  ESIL-PKG-  1093
WP_024783594  1042  ------------DVR  T-DKN-GE  IIWKKDEHISNIKKVLS-YPQVNIVKKVEEQT  GGFSK  ESIL-PKG-  1093
WP_024784288  1047  LAD-DQIVERPMIE  VNDET-GE  IAWDKTKHITTVKKVLS-YPQVNIVKKVEEQT  GGLFD  ------PKS-  1111
WP_024784666  1042  ------------DVR  T-DKN-GE  IIWKKDEHISNIKKVLS-YPQVNIVKKVEEQT  GGFSK  ESIL-PKG-  1093
WP_024784894  1042  ------------DVR  T-DKN-GE  IIWKKDEHISNIKKVLS-YPQVNIVKKVEEQT  GGFSK  ESIL-PKG-  1093
WP_024786433  1047  LAD-DQIVERPMIE  VNDET-GE  IAWDKTKHITTVKKVLS-YPQVNIVKKVEEQT  GGLFD  ------PKS-  1111
WP_049473442  1042  ------------DVR  T-DKN-GE  IIWKKDKFGTVRKVLS-APQVNIVKKVEEQT  GGFSN  ETIL-SKR-  1093
WP_049474547  1042  ------------DVR  T-DKN-GE  IIWKKDEHISNIKKVLS-YPQVNIVKKVEEQT  GGFSK  ESIL-PKG-  1093
EMC03581      1035  ------------DVR  T-DKN-GE  IIWKKDEHISNIKKILS-LSQVNIVKKTEEQT  GGLFD  NNIV-SKKk  1086
WP_000428612  1059  YAD-GTIVKRENIE  Y-SKDtGE  IAWNKEKDFATIKKVLS-LPQVNIVKKVEEQT  GGLFD  NNIV-SKEk  1121
WP_000428613  1057  YAD-GTIVKRENIE  Y-SKDtGE  IAWNKEKDFATIKKVLS-YPQVNIVKKREVQT  GGFSK  ESIL-PKG-  1119
WP_049523028  1052  YAD-GTIIQRGNVE  Y-SKDtGE  IAWNKKRDFAIVRKVLS-YPQVNIVKKVEEQT  GGFSK  ESIL-PKG-  1114
WP_003107102  1021  LAD-GTVITRPQIE  TNTET-GE  IVWDKVKDIKTIRKVLS-IPQINVVKKTEVQT  GGFSK  ESIL-SKR-  1083
WP_054279288  1053  LAN-GNIIKRSPIE  VNKET-GE  IAWDKTKDFGTVRKVLS-APQVNIVKKTEIQT  GGFSN  ETIL-SKR-  1115
WP_049531101  1057  YAD-GTIVKRENIE  Y-SKDtGE  IAWNKEIDFATIRKILS-LSQVNIVKKTEEQT  GGLFD  NNIV-SKKK  1124
WP_049538452  1057  YAD-GTIVKRENIE  Y-SKDtGE  IAWNKEKDFATIKKILS-LPQVNIVKKTEEQT  GGLFD  NNIV-SKKK  1124
WP_049549711  1059  YAD-GTIKKRENIE  Y-SKDtGE  IAWNKEKDFATIKKVLS-YPQVNIVKKTEEQT  GGLFD  NNIV-SKEK  1126
WP_007896501  1058  LAD-GTLMKRPVIE  TNTET-GE  VVWDKVKDFKTIRKVLS-YPQVNIVKKTEIQS  GAFSK  ESVL-SKG-  1120
EFR44625      1010  LAD-GTLMKRPVIE  TNTET-GE  IVWDKTKHFANVKKVLS-YPQVNIVKKTEIQS  ESVL  ESVL-SKG-  1072
WP_002897477  1056  YAD-GTIRKRENIE  Y-SNDtGE  IAWNKEKDFATIKKVLS-LPQVNIVKKTEEQT  GGLFD  NNIV-SKKK  1118
WP_002906454  1056  YAD-GTIVKRENIE  Y-SKDtGE  IAWNKEKDFVTIKKVLS-YPQVNIVKKREVQT  GGFSK  ESIL-PKG-  1123
WP_009729476  1057  YAD-GTIVKRENIE  Y-SKDtGE  IAWNKEKDFVTIKKVLS-YPQVSIVKKVEEQT  GGFSK  ESIL-PKG-  1119
CQR24647      1047  LAD-GRVVEKPVIE  ANEET-GE  IAWDKTKHFANVKKVLS-YPQVSIVKKVEEQT  GGFSK  ESIL-PKG-  1109
WP_000066813  1061  YAD-GTIVKRENIE  Y-SKDtGE  IAWNKEKDFVTIKKVLS-LPQVNIVKKVEEQT  GGLFD  NNIV-SKKK  1123
WP_009754323  1057  YAD-GTIVKRENIE  Y-SKDtGE  IAWNKEKDFVTIKKVLS-YPQVNIVKKREVQT  GGFSK  ESIL-PKG-  1119
WP_044674937  1049  YSKtGEVRIRPVIE  VNKET-GE  IVWDKKSDFRTVRKVLS-YPQVNVVKKVEMQT  GGFSK  ESIL-QHG-  1112
WP_044676715  1051  YSKtGEVRIRPVIE  VNKET-GE  IVWDKKSDFRTVRKVLS-YPQVNNVKKVEMQT  GGFSK  ESIL-QHG-  1114
WP_044680361  1051  YSKtGEVRIRPVIE  VNKET-GE  IVWDKKSDFRTVRKVLS-YPQVNVVKKVEMQT  GGFSK  ESIL-QHG-  1114
WP_044681799  1049  YSKtGEVRIRPVIE  VNKET-GE  IVWDKKSDFKTVRKVLS-YPQVNVVKKVEMQT  GGFSK  ESIL-QHG-  1112
WP_049533112  1051  YSKtGEVRIRPVIE  VNKET-GE  IVWDKTKHFIVRKIVS-YPQVNIVKKTEVQT  HGLDR  PSPK-PKP-  1122
WP_029090905  1008  FAD-GTVVERPDIE  T-SED-GE  IAWNKQTDFKIVRKVLS-FKQCNIVRKVEEQS  GALFK  ETIY-PVEe  1061
EFR44625      1039  -KQ----------------Q  ------GK  LIWNP-DLINEIKKCFY-YKDCYCTTKLDQKS  GQLFN  -TVL-SNDa  1084
AIT42264      1052  LAN-GEIRKRPLIE  TNGET-GE  IVWDKGRDFATVRKVLS-MPQVNIVKKTEVQT  GGFSK  ESIL-PKR-  1114
WP_034440723  1042  ------------LA  --NPD-GE  IAWEKDKDLNTIRKVLS-SKQINIIKKABEGK  GRLFK  ETIN-SRPs  1092
AKQ21048      1052  LAN-GEIRKRPLIE  TNGET-GE  IVWDKGRDFATVRKVLS-MPQVNIVKKTEVQT  GGFSK  ESIL-PKR-  1114
```

-continued

| | | | | | |
|---|---|---|---|---|---|
| WP_004636532 | 1043 | ------------- | VNEET-GE- ILWDTERHLSTIKRVLS-WKQMNIVKKVEKQK GQLWK ETIY-PKG- | 1092 |
| WP_002364836 | 1048 | --E--------P | RFTKD-GE- ILWSN-SYLKTIKKELN-YHQMNIVKKVEVQK GGFSK ESIK-PKG- | 1098 |
| WP_016631044 | 999 | --E--------P | RFTKD-GE- ILWSN-SYLKTIKKELN-YHQMNIVKKVEVQK GGFSK ESIK-PKG- | 1049 |
| EMS75795 | 783 | --E--------Y | SYDEN-GE- IFWDKARHIPQIKKVIS-SHQVNIVKKVEVQT GGFYK ETVN-PKG- | 834 |
| WP_002373311 | 1048 | --E--------P | RFTKD-SE- ILWSN-SYLKTIKKELN-YHQMNIVKKVEVQK GGFSK ESIK-PKG- | 1098 |
| WP_002378009 | 1048 | --E--------P | RFTKD-GE- ILWSN-SYLKTIKKELN-YHQMNIVKKVEVQK GGFSK ESIK-PKG- | 1098 |
| WP_002407324 | 1048 | --E--------P | RFTKD-GE- ILWSN-SYLKTIKKELN-YHQMNIVKKVEVQK GGFSK ESIK-PKG- | 1098 |
| WP_002413717 | 1048 | --E--------P | RFTKD-GE- ILWSN-SYLKTIKKELN-YHQMNIVKKVEVQK GGFSK ESIK-PKG- | 1098 |
| WP_010775580 | 1050 | --E--------P | RFTKD-GE- ILWSN-SYLKTIKKELN-YHQMNIVKKVEVQK GGFSK ESIK-PKG- | 1100 |
| WP_010818269 | 1048 | --E--------P | RFTKD-GE- ILWSN-SYLKTIKKELN-YHQMNIVKKVEVQK GGFSK ESIK-PKG- | 1098 |
| WP_010824395 | 1048 | --E--------P | RFTKD-GE- ILWSN-SYLKTIKKELN-YHQMNIVKKVEVQK GGFSK ESIK-PKG- | 1098 |
| WP_016622645 | 1048 | --E--------P | RFTKD-GE- ILWSN-SYLKTIKKELN-YHQMNIVKKVEVQK GGFSK ESIK-PKG- | 1098 |
| WP_033624816 | 1048 | --E--------P | RFTKD-GE- ILWSN-SYLKTIKKELN-YHQMNIVKKVEVQK GGFSK ESIK-PKG- | 1098 |
| WP_033625576 | 1048 | --E--------P | RFTKD-GE- ILWSN-SYLKTIKKELN-YHQMNIVKKVEVQK GGFSK ESIK-PKG- | 1098 |
| WP_033789179 | 1048 | --E--------P | RFTKD-GE- ILWSN-SYLKTIKKELN-YHQMNIVKKVEVQK GGFSK ESIK-PKG- | 1098 |
| WP_002310644 | 1049 | --T--------P | VCDEN-GE- IFWDKSKSIAQVKKVIN-HHHMNIVKKTEIQK GGFSE ETVE-PKK- | 1100 |
| WP_002112694 | 1050 | --T--------P | VCDEN-GE- IFWDKSKSIAQVKKVIN-HHHMNIVKKTEIQK GGFSE ETVE-PKK- | 1100 |
| WP_002314015 | 1050 | --T--------P | VCDEN-GE- IFWDKSKSIAQVKKVIN-HHHMNIVKKTEIQK GGFSE ETVE-PKK- | 1101 |
| WP_002320716 | 1050 | --T--------P | VCDEN-GE- IFWDKSKSIAQVKKVIN-HHHMNIVKKTEIQK GGFSE ETVE-PKK- | 1101 |
| WP_002330729 | 1049 | --T--------P | VCDEN-GE- IFWDKSKSIAQVKKVIN-HHHMNIVKKTEIQK GGFSE ETVE-PKK- | 1100 |
| WP_002335161 | 1050 | --T--------P | VCDEN-GE- IFWDKSKSIAQVKKVIN-HHHMNIVKKTEIQK GGFSE ETVE-PKK- | 1101 |
| WP_002345439 | 1050 | --T--------P | VCDEN-GE- IYWEKSHHLPRIKKVLS-SHQVNVKKVEQQK GGFSK ETVE-SKE- | 1101 |
| WP_034879970 | 1040 | --T--------P | FCDEN-GE- IYWEKSHHLPRIKKVLS-SHQVNVKKVEQQK GGFSK ETVE-SKE- | 1091 |
| WP_010720994 | 1040 | --T--------P | FCDEN-GE- IYWEKSHHLPRIKKVLS-SHQVNVKKVEQQK GGFYK ETVN-SKE- | 1091 |
| WP_010737004 | 1040 | --E--------P | FCDEN-GE- IYWEKSHHLPRIKKVLS-SHQVNVKKVEQQK GGFYK ETVN-SKE- | 1091 |
| WP_034700478 | 1040 | --E--------P | FCDEN-GE- IYWEKSHHLPRIKKVLS-SHQVNVKKVEQQK GGFYK ETVN-SKE- | 1091 |
| WP_007209003 | 1038 | --D--------I | INDD-GE- ILNNKQETIAQVIKTLG-MHQVNVKKVEIQK GGFYK ESIQ-PKG- | 1089 |
| WP_023519017 | 1034 | --D--------I | ICDEQ-GE- VIMNKKRDLSTIKKTIG-AHQVNIVKKVEKQK GGFYK ETIN-SKA- | 1085 |
| WP_010770040 | 1046 | --A--------V | IIDEN-GE- ILWDK-KNIATVKKVMS-YPQMNIVKKPEIQT GSFSK ETIK-PKG- | 1096 |
| WP_048604708 | 1043 | --K--------V | IIDEN-GE- ILWNQ-KKIVTVKKVMN-YRQMNIVKKVEIQK GGFSK ESIL-PKG- | 1093 |
| WP_010750235 | 1043 | --E--------Q | FCDEN-GE- IFWDKRKHIQQIKKVIS-SHQVNIVKKVEVQT GGFYK ETVN-TKE- | 1094 |
| AII16583 | 1091 | LAN-GEIRKRPLIE | TNGET-GE- IVWDKGRDFATVRKVLS-MPQVNIVKKTEVQT GSFSK ESIL-PKR- | 1153 |
| WP_029073316 | 1053 | --D--------- | ----T-GE- EWISRIKKCFY-YKDCFVTKKLEENN GSFFN -TVR-PNDe | 1099 |
| WP_031589969 | 1053 | --D--------- | ----T-GE- IVWDP-NYIDRIKKCFY-YKDCFVTKKLEENN GTFFN -TVL-PNDt | 1099 |
| KDA45870 | 1035 | YPF--------- | ----WDKARDLPTIKRYLY-RAQVNKVRKAERQT GGFSD EMLV-PKS- | 1078 |
| WP_039099354 | 1044 | --E--------- | LVDEN-TEaVIWNKESGLAYLNKIYQ-FKKILVTREVHENS GALFN QTLYaAKDd | 1097 |
| AKP02966 | 1063 | --N--------- GTTQ | -DRNtGE- IIWNVG- FRDKILKIFN-YHQCNVTRKTEIKT GQFYD QTIYsPKNp | 1118 |
| WP_010991369 | 1045 | --D--------R | IIDEN-GE- ILWDK-KYLDTVKKVMS-YRQINIVKKTEIQK GEFSN ATIK-PKG- | 1095 |
| WP_033838504 | 1045 | --D--------R | IIDEN-GE- ILWDK-KYLETIKKVLD-YRQMNIVKKTEIQK GEFSN VTPN-PKG- | 1095 |
| EHN60060 | 1048 | --E--------R | IIDEN-GE- ILWDK-KYLDTVKKVMS-YRQMNIVKKTEIQK GEFSN ATIK-PKG- | 1098 |
| EFR89594 | 814 | --D--------R | IIDEN-GE- ILWDK-KYLETIKKVLD-YRQMNIVKKTEIQK GEFSN ATIK-PKG- | 864 |
| WP_038409211 | 1045 | --N--------Q | IIDKN-GE- ILWDN-RYLDTIKKVLS-YRQMNIVKKTEIQK GEFSN ATVN-PKG- | 1095 |
| EFR95520 | 664 | --N--------Q | IIDKN-GE- ILWDN-RYLDTIKKVLS-YRQMNIVKKTEIQK GEFSN ATVN-PKG- | 714 |
| WP_037723650 | 1045 | --E--------R | IIDEN-GE- ILWDK-KYLETIKKVLD-YRQMNIVKKTEIQK GEFSN ATIK-PKG- | 1095 |
| WP_037727705 | 1045 | --E--------R | IIDEN-GE- ILWDK-KYLETIKKVLD-YRQMNIVKKTEIQK GEFSN ATIK-PKG- | 1095 |
| WP_037730785 | 1045 | --E--------R | IIDEN-GE- ILWDK-KYLETIKKVLD-YRQMNIVKKTEIQK GEFSN ATIK-PKG- | 1095 |
| WP_003730785 | 1045 | --E--------R | IIDEN-GE- ILWDK-KYLETIKKVLG-YRQINIVKKTEIQK GEFSK VTPN-PKG- | 1095 |
| WP_003739838 | 1045 | --E--------R | IIDEN-GE- ILWDK-KYLETIKKVLG-YRQMNIVKKTEIQK GEFSK ATIK-PKG- | 1095 |
| WP_014601172 | 1045 | --E--------R | IIDEN-GE- ILWDK-KYLETIKKVLN-YRQMNIVKKTEIQK GEFSN QNPK-PRG- | 1095 |
| WP_023548323 | 1045 | --E--------R | IIDEN-GE- ILWDK-KYLETIKKVLD-YRQMNIVKKTEIQK GEFSK ATIK-PKG- | 1095 |
| WP_031665337 | 1045 | --E--------R | IIDEN-GE- ILWDK-KYLETIKKVLD-YRQMNIVKKTEIQK GEFSN VTPN-PKG- | 1095 |
| WP_031669209 | 1045 | --D--------R | IIDEN-GE- ILWDK-RYLETVKKVLG-YRQMNIVKKTEIQK GEFSN VTPN-PKG- | 1095 |

```
                                                    -continued

WP_033920898  1045  -E----------R  IIDEN-GE-ILWDK-KYLETIKKVLN-YRQMNIVKKTEIQK  GEFSN  QNPK-PRG-                                                            1095
AKI42028      1048  -E----------R  IIDEN-GE-ILWDK-KYLETIKKVLD-YRQMNIVKKTEIQK  GEFSK  ATIK-PKG-                                                            1098
AKI50529      1048  -E----------R  IIDEN-GE-ILWDK-KYLETIKKVLN-YRQMNIVKKTEIQK  GEFSN  QNPK-PRG-                                                            1098
EFR83390       493  -E----------R  IIDEN-GE-ILWDK-KYLETIKKVLN-YRQMNIVKKTEIQK  GEFSK  ATIK-PKG-                                                             543
WP_046323366  1045  -D----------R  IIDEN-GE-ILWDK-KYLDTIKKVLN-YRQMNIVKKTEIQK  GEFSN  ATAN-PKG-                                                            1095
AKE81011      1068  LAN-GEIRKRPLIE  TNGET-GE-IVWDKGRDFATVRKVLS-MPQVNIVKKTEVQT  GGFSK  ESIL-PKR-                                                            1130
CUO82355      1043  -D-----------  ------GK-LIWNP-DLINEIKKCFY-YKDCYCTTKLDQKS  GQMFN  -TVL-PNDa                                                            1088
WP_033162887  1085  -D-----------  ------T-GE-VMWDP-AKIGKIKSCFY-YKDVVTKKLEQNS  GTLFN  -TVL-PNDa                                                            1089
AGZ01981      1052  LAN-GEIRKRPLIE  TNGET-GE-IVWDKGRDFATVRKVLS-MPQVNIVKKTEVQT  GGFSK  ESIL-PKR-                                                            1147
AKA60242      1052  LAN-GEIRKRPLIE  TNGET-GE-IVWDKGRDFATVRKVLS-MPQVNIVKKTEVQT  GGFSK  ESIL-PKR-                                                            1114
AKS40380      1056  LAN-GEIRKRPLIE  TNGET-GE-IVWDKGRDFATVRKVLS-MPQVNIVKKTEVQT  GGFSK  ESIL-PKR-                                                            1118
4UN5_B        1115  -NSD KLIA---    RKKDW-DPKKYGGFDSPTVAYSV-LVVAK--VE--KGKSKKLKSVKELLGITIME  RSSFEK                                                          1176
WP_010922251  1121  -DSD KLIPRTkKV-YW-DTKKYGGFDSPTVAYSV-FVVAD--VE--KGKAKKLKTVKELVGISIME  RSFFEE                                                              1185
WP_039695303  1119  -NSD KLIPRKT-KDILL-DTTKYGGFDSPVIAYSI-LLIAD--IE--KGKAKKLKTVKTLVGITIME  KAAFEE                                                               1183
WP_045635197   853  -EKN -LYKYYReTGNYL---TKYSKKDNGPVIKKI----------------KYYGNKLNAHLDITDDYPNS  -VKLSL                                                              912
5AXW_A         799  -NSD KLIA---    RKKDW-DPKKYGGFDSPTVAYSV-LVVAK--VE--KGKSKKLKSVKELVGITIME  RSSFEK                                                              860
WP_009880683  1115  -NSD KLIA---    RKKDW-DPKKYGGFDSPTVAYSV-LVVAK--VE--KGKSKKLKSVKELVGITIME  RSSFEK                                                            1176
WP_010922251  1115  -NSD KLIA---    RKKDW-DPKKYGGFDSPTVAYSV-LVVAK--VE--KGKSKKLKSVKELLGITIME  RSSFEK                                                            1176
WP_011054416  1115  -NSD KLIA---    RKKDW-DPKKYGGFDSPTVAYSV-LVVAK--VE--KGKSKKLKSVKELLGITIME  RSSFEK                                                            1176
WP_011284745  1115  -NSD KLIA---    RKKDW-DPKKYGGFDSPTVAYSV-LVVAK--VE--KGKSKKLKSVKELLGITIME  RSSFEK                                                            1176
WP_011285506  1115  -NSD KLIA---    RKKDW-DPKKYGGFDSPTVAYSV-LVVAK--VE--KGKSKKLKSVKELLGITIME  RSSFEK                                                            1176
WP_011527619  1115  -NSD KLIA---    RKKDW-DPKKYGGFDSPTVAYSV-LVVAK--VE--KGKSKKLKSVKELLGITIME  RSSFEK                                                            1176
WP_012560673  1115  -NSD KLIA---    RKKDW-DPKKYGGFDSPTVAYSV-LVVAK--VE--KGKSKKLKSVKELLGITIME  RSSFEK                                                            1176
WP_014407541  1114  -NSD KLIA---    RKKDW-DPKKYGGFDSPTVAYSV-LVVAK--VE--KGKSKKLKSVKELLGLTIME  RSSFEK                                                            1175
WP_020905136  1115  -NSD KLIA---    RKKDW-DPKKYGGFDSPTVAYSV-LVVAK--VE--KGKSKKLKSVKELLGITIME  RSSFEK                                                            1176
WP_023080005  1115  -NSD KLIA---    RKKDW-DPKKYGGFDSPTVAYSV-LVVAK--VE--KGKSKKLKSVKELLGITIME  RSSFEK                                                            1175
WP_023610282  1114  -NSD KLIA---    RKKDW-DPKKYGGFDSPTVAYSV-LVVAK--VE--KGKSKKLKSVKELLGITIME  RSSFEK                                                            1175
WP_030125963  1115  -NSD KLIA---    RKKDW-DPKKYGGFDSPTVAYSV-LVVAK--VE--KGKSKKLKSVKELLGITIME  RSSFEK                                                            1176
WP_030126706  1115  -NSD KLIA---    RKKDW-DPKKYGGFDSPTVAYSV-LVVAK--VE--KGKSKKLKSVKELLGITIME  RSSFEK                                                            1176
WP_031488318  1115  -NSD KLIA---    RKKDW-DPKKYGGFDSPTVAYSV-LVVAK--VE--KGKSKKLKSVKELLGITIME  RSSFEK                                                            1176
WP_032460140  1115  -NSD KLIA---    RKKDW-DPKKYGGFDSPTVAYSV-LVVAK--VE--KGKSKKLKSVKELVGITIME  RSSFEK                                                            1176
WP_032461047  1115  -NSD KLIA---    RKKDW-DPKKYGGFDSPTVAYSV-LVVAK--VE--KGKSKKLKSVKELVGITIME  RSSFEK                                                            1176
WP_032462016  1115  -NSD KLIA---    RKKDW-DPKKYGGFDSPTVAYSV-LVVAK--VE--KGKSKKLKSVKELLGITIME  RSSFEK                                                            1176
WP_032462936  1115  -NSD KLIA---    RKKDW-DPKKYGGFDSPTVAYSV-LVVAK--VE--KGKSKKLKSVKELLGITIME  RSSFEK                                                            1176
WP_032464890  1115  -NSD KLIA---    RKKDW-DPKKYGGFDSPTVAYSV-LVVAK--VE--KGKSKKLKSVKELLGITIME  RSSFEK                                                            1176
WP_033888930   940  -NSD KLIA---    RKKDW-DPKKYGGFDSPTVAYSV-LVVAK--VE--KGKSKKLKSVKELLGITIME  RSSFEK                                                            1001
WP_038431314  1115  -NSD KLIA---    RKKDW-DPKKYGGFDSPTVAYSV-LVVAK--VE--KGKSKKLKSVKELLGITIME  RSSFEK                                                            1176
WP_038432938  1114  -NSD KLIA---    RKKDW-DPKKYGGFDSPTVAYSV-LVVAK--VE--KGKSKKLKSVKELLGITIME  RSSFEK                                                            1175
WP_038434062  1026  -NSD KLIA---    RKKDW-DPKKYGGFDSPTVAYSV-LVVAK--VE--KGKSKKLKSVKELLGITIME  RSSFEK                                                            1087
BAQ51233       290  -NSD KLIA---    RKKDW-DPKKYGGFDSPTVAYSV-LVVAK--VE--KGKSKKLKSVKELLGITIME  RSSFEK                                                             351
KGE60162        53  -NSD KLIA---    RKKDW-DPKKYGGFDSPTVAYSV-LVVAK--VE--KGKSKKLKSVKELLGITIME  RSSFEK                                                             114
KGE60856      1115  -NSD KLIPRKT-KNSYW-NPKKYGGFDSPTVAYSV-LVFAD--VE--KGKSKKLKRVQDMVGITIME  KKRFEK                                                            1176
WP_002989955  1094  -ESD KLIPRKT-KA-YW-DTKKYGGFDSPTVAYSV-LVFAD--VE--KGKAKKLKTVKELVGISIME  RSFFEE                                                            1158
WP_003030002  1122  -DSD KLIPRKTkKA-YW-DTKKYGGFDSPVIAYSI-FVVAD--VE--KGKAKKLKTVKELVGISIME  RSFFEE                                                            1186
WP_003065552  1121  -NSD KLIPRKT-KDIYL-DPKKYGGFDSPIVAYSV-LVVAD--IK--KGKAQKLKTVTELLGITIME  RSFFEK                                                            1185
WP_001040076  1113  -NSD KLIPRKT-KDIYL-DPKKYGGFDSPIVAYSV-LVVAD--IK--KGKAQKLKTVTELLGITIME  RSRFEK                                                            1177
WP_001040078  1113  -NSD KLIPRKT-KDIYL-DPKKYGGFDSPIVAYSV-LVVAD--IK--KGKAQKLKTVTELLGITIME  RSKFEK                                                            1177
WP_001040080  1113  -NSD KLIPRKT-KDIYL-DPKKYGGFDSPIVAYSV-LVVAD--IK--KGKAQKLKTVTELLGITIME  RSRFEK                                                            1177
WP_001040081  1113  -NSD KLIPRKT-KDIYL-DPKKYGGFDSPIVAYSV-LVVAD--IK--KGKAQKLKTVTELLGITIME  RSRFEK                                                            1177
WP_001040083  1113  -NSD KLIPRKT-KDIYL-DPKKYGGFDSPIVAYSV-LVVAD--IK--KGKAQKLKTVTELLGITIME  RSRFEK                                                            1177
WP_001040085  1113  -NSD KLIPRKT-KDIYL-DPKKYGGFDSPIVAYSV-LVVAD--IK--KGKAQKLKTVTELLGITIME  RSRFEK                                                            1177
WP_001040087  1113  -NSD KLIPRKT-KDIYL-DPKKYGGFDSPIVAYSV-LVVAD--IK--KGKAQKLKTVTELLGITIME  RSRFEK                                                            1177
WP_001040088  1113  -NSD KLIPRKT-KDIYL-DPKKYGGFDSPIVAYSV-LVVAD--IK--KGKAQKLKTVTELLGITIME  RSRFEK                                                            1177
```

-continued

```
WP_001040089    1113 -NSD KLIPRKT-KDIYL-DPKKYGGFDSPIVAYSV-LVVAD--IK--KGKAQKLKTVTELLGITIME RSRFEK 1177
WP_001040090    1113 -NSD KLIPRKT-KDIYL-DPKKYGGFDSPIVAYSV-LVVAD--IK--KGKAQKLKTVTELLGITIME RSRFEK 1177
WP_001040091    1113 -NSD KLIPRKT-KDIYL-DPKKYGGFDSPIVAYSV-LVVAD--IK--KGKAQKLKTVTELLGITIME RERFEK 1177
WP_001040092    1113 -NSD KLIPRKT-KDIYL-DPKKYGGFDSPIVAYSV-LVLAD--IK--KGKAQKLKTVTELLGITIME RSRFEK 1177
WP_001040094    1113 -NSD KLIPRKT-KDIYL-DPKKYGGFDSPIVAYSV-LVVAD--IK--KGKAQKLKTVTELLGITIME RSRFEK 1177
WP_001040095    1113 -NSD KLIPRKT-KDIYL-DPKKYGGFDSPIVAYSV-LVVAD--IK--KGKAQKLKTVKELLGITIME RSRFEK 1177
WP_001040096    1113 -NSD KLIPRKT-KDIYL-DPKKYGGFDSPIVAYSV-LVVAD--IK--KGKAQKLKTVTELLGITIME RSRFEK 1177
WP_001040097    1113 -NSD KLIPRKT-KDIYL-DPKKYGGFDSPKVAYSV-LVVAD--IK--KGKAQKLKTVTELLGITIME RSRFEK 1177
WP_001040098    1113 -NSD KLIPRKT-KDIYL-DPKKYGGFDSPIVAYSV-LVVAD--IK--KGKAQKLKTVTELLGITIME RSRFEK 1177
WP_001040099    1113 -NSD KLIPRKT-KDIYL-DPKKYGGFDSPIVAYSV-LVVAD--IK--KGKAQKLKTVTELLGITIME RSRFEK 1177
WP_001040100    1113 -NSD KLIPRKT-KDIYL-DPKKYGGFDSPIVAYSV-LVVAD--IK--KGKAQKLKTVTELLGITIME RSRFEK 1177
WP_001040104    1113 -NSD KLIPRKT-KDIYL-DPKKYGGFDSPIVAYSV-LVVAD--IK--KGKAQKLKTVTELLGITIME RSRFEK 1177
WP_001040105    1113 -NSD KLIPRKT-KDIYL-DPKKYGGFDSPIVAYSV-LVVAD--IK--KGKAQKLKTVTELLGITIME RPRFEK 1177
WP_001040106    1113 -NSD KLIPRKT-KDIYL-DPKKYGGFDSPIVAYSV-LVVAD--IK--KGKAQKLKTVTELLGITIME RPRFEK 1177
WP_001040107    1113 -NSD KLIPRKT-KDIYL-DPKKYGGFDSPIVAYSV-LVVAD--IK--KGKAQKLKTVTELLGITIME RPRFEK 1177
WP_001040108    1113 -NSD KLIPRKT-KDIYL-DPKKYGGFDSPIVAYSV-LVVAD--IK--KGKAQKLKTVTELLGITIME RPRFEK 1177
WP_001040109    1113 -NSD KLIPRKT-KDIYL-DPKKYGGFDSPIVAYSV-LVVAD--IK--KGKAQKLKTVTELLGITIME RPRFEK 1177
WP_001040110    1113 -NSD KLIPRKT-KDIYL-DPKKYGGFDSPIVAYSV-LVLAD--IK--KGKAQKLKTVTELLGITIME RPRFEK 1177
WP_015058523    1113 -NSD KLIPRKT-KDIYL-DPKKYGGFDSPIVAYSV-LVVAD--IK--KGKAQKLKTVKELLGITIME RERFEK 1177
WP_017643650    1113 -NSD KLIPRKT-KDIYL-DPKKYGGFDSPIVAYSV-LVVAD--IK--KGKAQKLKTVTELLGITIME RSRFEK 1177
WP_017647151    1113 -NSD KLIPRKT-KDIYL-DPKKYGGFDSPIVAYSV-LVVAD--IK--KGKAQKLKTVTELLGITIME RSRFEK 1177
WP_017648376    1127 -NSD KLIPRKT-KDIYL-DPKKYGGFDSPIVAYSV-LVVAD--IK--KGKAQKLKTVTELLGITIME RSRFEK 1191
WP_017649527    1113 -NSD KLIPRKT-KDIYL-DPKKYGGFDSPIVAYSV-LVVAD--IK--KGKAQKLKTVTELLGITIME RPRFEK 1177
WP_017771611    1113 -NSD KLIPRKT-KDIYL-DPKKYGGFDSPIVAYSV-LVVAD--IK--KGKAQKLKTVTELLGITIME RSRFEK 1177
WP_017771984    1113 -NSD KLIPRKT-KDIYL-DPKKYGGFDSPIVAYSV-LVAAD--IK--KGKAQKLKTVTELLGITIME RSRFEK 1177
CFQ25032        1113 -NSD KLIPRKT-KDIYL-DPKKYGGFDSPIVAYSV-LVVAD--IK--KGKAQKLKTVTELLGITIME RSRFEK 1177
CFV16040        1113 -NSD KLIPRKT-KDIYL-DPKKYGGFDSPIVAYSV-LVLAD--IK--KGKAQKLKTVTELLGITIME RSRFEK 1177
KLJ37842        1113 -NSD KLIPRKT-KDIYL-DPKKYGGFDSPIVAYSV-LVVAD--IK--KGKAQKLKTVTELLGITIME RSRFEK 1177
KLJ72361        1113 -NSD KLIPRKT-KDIYL-DPKKYGGFDSPIVAYSV-LVVAD--IK--KGKAQKLKTVTELLGITIME RSRFEK 1177
KLL20707        1113 -NSD KLIPRKT-KDIYL-DPKKYGGFDSPIVAYSV-LVVAD--IK--KGKAQKLKTVTELLGITIME RSRFEK 1177
KLL42645        1113 -NSD KLIPRKT-KDIYL-DPKKYGGFDSPIVAYSV-LVVAD--IK--KGKAQKLKTVTELLGITIME RPRFEK 1177
WP_047207273    1113 -NSD KLIPRKT-KDIYL-DPKKYGGFDSPIVAYSV-LVVAD--IK--KGKAQKLKTVTELLGITIME RSRFEK 1177
WP_047209694    1113 -NSD KLIPRKT-KDIYL-DPKKYGGFDSPIVAYSV-LVVAD--IK--KGKAQKLKTVTELLGITIME RSRFEK 1177
WP_050198062    1113 -NSD KLIPRKT-KDIYL-DPKKYGGFDSPIVAYSV-LVVAD--IK--KGKAQKLKTVTELLGITIME RSRFEK 1177
WP_050201642    1113 -NSD KLIPRKT-KDIYL-DPKKYGGFDSPIVAYSV-LVVAD--IK--KGKAQKLKTVTELLGITIME RSRFEK 1177
WP_050204027    1113 -NSD KLIPRKT-KDIYL-DPKKYGGFDSPIVAYSV-LVVAD--IK--KGKAQKLKTVTELLGITIME RSRFEK 1177
WP_050881965    1113 -NSD KLIPRKT-KDIYL-DPKKYGGFDSPIVAYSV-LVVAD--IK--KGKAQKLKTVTELLGITIME RSRFEK 1177
WP_050886065    1113 -NSD KLIPRKT-KDIYL-DPKKYGGFDSPIVAYSV-LVLAD--IK--KGKAQKLKTVTELLGITIME RERFEK 1177
AHN30376        1113 -NSD KLIPRKT-KDIYL-DPKKYGGFDSPIVAYSV-LVVAD--IK--KGKAQKLKTVTELLGITIME RSRFEK 1177
EA078426        1113 -NSD KLIPRKT-KDIYL-DPKKYGGFDSPIVAYSV-LVVAD--IK--KGKAQKLKTVTELLGITIME RSRFEK 1177
CCW42055        1123 -DSS ENLVGVK-RNL---DPKKYGYAGISNSYAV-LVKAI--IE--KGVKKETMVLEFQGISILD RITFEK 1185
WP_003041502    1095 -ESD KLIPRKT-KNSYW-NPKKYGGFDSPVVAYSI-LVFAD--VE--KGKSKKLRKVQDMVGITIME KKRFEK 1159
WP_037593752    1095 -ESD KLIPRKT-KNSYW-NPKKYGGFDSPVVAYSI-LVFAD--VE--KGKSKKLRKVQDMVGITIME KKRFEK 1159
WP_049516684    1094 -ESD KLIPRKT-KNSYW-NPKKYGGFDSPVVAYSI-LVFAD--VE--KGKSKKLRKVQDMVGITIME KKRFEK 1158
GAD46167        1094 -ESD KLIPRKT-KNSYW-NPKKYGGFDSPVVAYSI-LVFAD--VE--KGKSKKLRKVQDMVGITIME KKRFEK 1158
WP_018363470    1126 -DSD KLIPRKTkKV-LW-EPKKYGGEDSPTTAYSV-LVVAK--VE--KGKTKKLKTVKELVGISIME RSFFEK 1190
WP_003043819    1124 -ESA KLIP----RKKGW-DTRKYGGFGSPTTAYSI-LVVAK--VE--KGKAKKLSVKVLVGITIME KGSYEK 1185
WP_066269658    1094 -ESD KLIP----RKKGW-KNSYW-DTRKYGGFGSPTTAYSI-LVFAD--VE--KGKSKKLRKVQDMVGITIME KGSYEK 1158
WP_048800889    1114 -DSD KLIARKTkEN-YW-DTRKYGGEDSPTVAYSV-LVFAD--IK--KGKAKKLTVKELVGISIME RPFFEK 1178
WP_012767106    1114 -SFD KLIS----RKHRF-ESSKYGGEGSPTVTYSV-LVVAKsKVQ-DGKVKKIKTGKELIGMTLLD KLVFEK 1177
WP_014612333    1114 -SFD KLIS----RKHRF-ESSKYGGEGSPTVTYSV-LVVAKsKVQ-DGKVKKIKTGKELIGTLLD KLVFEK 1177
WP_015017095    1114 -SFD KLIS----RKHRF-ESSKYGGEGSPTVTYSV-LVVAKsKVQ-DGKVKKIKTGKELIGITLLD KLVFEK 1177
WP_015057649    1114 -SFD KLIS----RKHRF-ESSKYGGEGSPTVTYSV-LVVAKsKVQ-DGKVKKIKTGKELIGITLLD KLVFEK 1177
```

```
-continued

WP_048327215   1114  -SFD KLIS----RKHRF-ESSKYGGEGSPTVTYSV-LVVAKcKVQ--DGKVKKIKTGKELIGITLLD KLVFEK  1177
WP_049519324   1114  -SFD KLIS----RKHRF-ESSKYGGEGSPTVTYSV-LVVAKsKVQ--DGKVKKIKTGKELIGITLLD KLVFEK  1177
WP_012515931   1095  -NSD KLIP----RKNNW-DTRKYGGFDSPTVAYSV-LVIAK--ME--KGKAKVLKPVKEMVGITIME RTAFEE  1156
WP_021320964   1095  -NSD KLIP----RKNNW-DTRKYGGFDSPTVAYSV-LVIAK--ME--KGKAKVLKPVKEMVGITIME RTAFEE  1156
WP_037581760   1124  -DSD KLIP----RKNNW-DTRKYGGFDSPTVAYSV-LVIAK--ME--KGKAKVLKPVKEMVGITIME RIAFEE  1188
WP_044232481   1119  -DSD KLIPRKTKKL-QW-ETQKYGGEDSPTVAYSV-LVVAD--VE--KGKTRKLKTVKELVGISIME RSFFEE  1183
WP_009854540   1120  -DSD KLIPRKTKKV-YW-DTKKYGGEDSPTVAYSV-FVVAD--VE--KGKAKKLKTVKELVGISIME RSFFEE  1184
WP_012962174   1121  -NSD KLIPRKTKKF-RW-DTPKYGGEDSPNIAYSV-FVIAD--VE--KGKAKKLKTVKELVGISIME RSFFEE  1185
WP_039695303   1124  -DSD KLIPRKTKKV-YW-DTKKYGGFDSPTVAYSV-FVVAD--VE--KGKAKKLKTVKELVGISIME RSFFEE  1188
WP_014334983   1115  -DSD KLIA-----RKKSW-NTKKYGGFDSPIIAYSV-LVVAD--IE--KGKAKKLKTVKELVGIKIME QDEFEK  1176
WP_003099269   1115  -DSD KLIA-----RKKSW-DPKKYGGFDSPIIAYSV-LVVAK--IA--KGKTQKLKTIKELVGIKIME QDEFEK  1176
AHY15608       1115  -DSD KLIA-----RKKSW-DPKKYGGFDSPIIAYSV-LVIAD--IA--KGKTQKLKTIKELVGIKIME QDEFEK  1176
AHY17476          1  -----                                                            ME QDEFEK     8
ESR09100       1115  -DSD KLIA-----RKKSW-DPKKYGGFDSPIIAYSV-LVVAK--IA--KGKTQKLKTIKELVGIKIME QDEFEK  1176
AGM98575       1094  -NSD KLIPRKT-KKFYW-DTKKYGGFDSPIVAYSI-LVVAK--IE--KGKSKKLKLVKDLVGITIME RTIFEK  1158
ALF27331       1109  -NN  KLIP----RKKDW-SVDKYGGFIEPAESYSLaIFYTD-IN---GKKPKKKKSTIIAISRME   KKDYEK  1167
WP_018372492   1125  vvDAS KLTPIKS-G---L-SPEKYGGYARPTIAYSV-LVIAD--IE--KGKARKLKRIKEMVGITVQD KKKFEA  1188
WP_045618028   1119  -NSD KLIPRKT-KDILL-DTTKYGGFDSPVIAYSI-LLIAD--IE--KGKARKLKTVKTLVGITIME KAAFEE  1183
WP_045635197   1094  -NSD KLIPRKT-KKFYW-DTKKYGGFDSPIVAYSI-LVIAD--IE--KGKSKKLKTVKALVGVTIME KMTFER  1158
WP_002263549   1094  -DSD KLIPRKT-KKFYW-DTKKYGGFDSPIVAYSI-LVIAD--IE--KGKSKKLKTVKALVGVTIME KMTFER  1158
WP_002263887   1094  -DSD KLIA-----RKKSW-DPKKYGGFDSPIIAYSV-LVVAK--IA--KGKTQKLKTIKELVGIKIME QDEFEK  1158
WP_002264920   1094  -NSD KLIPRKT-KKFYW-DTKKYGGFDSPIVAYSI-LVIAD--IE--KGKSKKLKTVKALVGVTIME KMTFER  1158
WP_002269043   1094  -NSD KLIPRKT-KKFYW-DTKKYGGFDSPIVAYSI-LVIAD--IE--KGKSKKLKLVKDLVGITIME RTIFEK  1158
WP_002269448   1094  -NSD KLIPRKT-KKFYW-DTKKYGGFDSPIVAYSI-LVIAD--IE--KGKSKKLKTVKALVGVTIME KMTFER  1158
WP_002271977   1094  -NSD KLIPRKT-KKFYW-DTKKYGGFDSPIVAYSI-LVIAD--IE--KGKSKKLKTVKALVGVTIME KMTFER  1158
WP_002272766   1094  -NSD KLIPRKT-KKFYW-DTKKYGGFDSPIVAYSI-LVIAD--IE--KGKSKKLKTVKALVGVTIME KMTFER  1158
WP_002273241   1094  -NSD KLIPRKT-KKFYW-DTKKYGGFDSPIVAYSI-LVIAD--IE--KGKSKKLKTVKALVGVTIME KMTFER  1158
WP_002275430   1094  -NSD KLIPRKT-KKFYW-DTKKYGGFDSPIVAYSI-LVIAD--IE--KGKSKKLKTVKALVGVTIME KMTFER  1158
WP_002276448   1094  -NSD KLIPRKT-KKFYW-DTKKYGGFDSPIVAYSI-LVIAD--IE--KGKSKKLKTVKALVGVTIME KMTFER  1158
WP_002277050   1112  -PLE KLVPLKK---AL-NPEKYGGYQKPTTAYPI-LLIVD------TKQLIPISVMD          KKRFEQ  1166
WP_002773364   1094  -NSD KLIPRKT-KKFYW-DTKKYGGFDSPIVAYSI-LVIAD--IE--KGKSKKLKTVKALVGVTIME KMTFER  1158
WP_002279025   1094  -NSD KLIPRKT-KKFYW-DTKKYGGFDSPIVAYSI-LVIAD--IE--KGKSKKLKTVKALVGVTIME KMTFER  1158
WP_002279859   1094  -DSD KLIPRKT-KKFYW-DTKKYGGFDSPIVAYSI-LVIAD--IE--KGKSKKLKTVKALVGVTIME KMTFER  1158
WP_002280230   1094  -NSD KLIPRKT-KKFYW-DTKKYGGFDSPIVAYSI-LVIAD--IE--KGKSKKLKTVKALVGVTIME KMTFER  1158
WP_002281696   1094  -NSD KLIPRKT-KKFYW-DTKKYGGFDSPIVAYSI-LVIAD--IE--KGKSKKLKTVKALVGVTIME KMTFER  1158
WP_002282247   1112  -PLE KLVPLKK---AL-NPEKYGGYQKPTTAYPI-LLIVD------TKQLIPISVMD          KKRFEQ  1166
WP_002282906   1094  -NSD KLIPRKT-KKFYW-DTKKYGGFDSPIVAYSI-LVIAD--IE--KGKSKKLKTVKALVGVTIME KMTFER  1158
WP_002283846   1094  -NSD KLIPRKT-KKFYW-DTKKYGGFDSPIVAYSI-LVIAD--IE--KGKSKKLKTVKALVGVTIME KMTFER  1158
WP_002287255   1108  -NSD KLIPRKT-KKFYW-DTKKYGGFDSPIVAYSI-LVIAD--IE--KGKSKKLKTVKALVGVTIME KMTFER  1172
WP_002288990   1094  -NSY KLIPRKT-KKFYW-DTKKYGGFDSPIVAYSI-LVIAD--IE--KGKSKKLKTVKALVGVTIME KMTFER  1158
WP_002289641   1094  -DSD KLIPRKT-KKFYW-DTKKYGGFDSPIVAYSI-LVIAD--IE--KGKSKKLKTVKALVGVTIME KMTFER  1158
WP_002290427   1094  -NSD KLIPRKT-KKFYW-DTKKYGGFDSPIVAYSI-LVIAD--IE--KGKSKKLKTVKALVGVTIME KMTFER  1158
WP_002295753   1094  -DSD KLIPRKT-KKFYW-DTKKYGGFDSPIVAYSI-LVIAD--IE--KGKSKKLKTVKALVGVTIME KMTFER  1158
WP_002296423   1094  -NSD KLIPRKT-KKFYW-DTKKYGGFDSPIVAYSI-LVIAD--IE--KGKSKKLKTVKALVGVTIME KMTFER  1158
WP_003044487   1094  -NSD KLIPRKT-KKFYW-DTKKYGGFDSPIVAYSI-LVIAD--IE--KGKSKKLKTVKALVGVTIME KMTFER  1158
WP_003055844   1094  -NSD KLIPRKT-KKFYW-DTKKYGGFDSPIVAYSI-LVIAD--IE--KGKSKKLKTVKALVGVTIME KMTFER  1158
WP_003072203   1094  -NSD KLIPRKT-KKFYW-DTKKYGGFDSPIVAYSI-LVIAD--IE--KGKSKKLKTVKALVGVTIME KMTFER  1158
WP_003102390   1094  -DSD KLIPRKT-KKFYW-DTKKYGGFDSPIVAYSI-LVIAD--IE--KGKSKKLKTVKALVGVTIME KMTFER  1158
WP_003252408   1094  -NSD KLIPRKT-KKFYW-DTKKYGGFDSPIVAYSI-LVIAD--IE--KGKSKKLKTVKALVGVTIME KMTFER  1158
WP_012997688   1094  -NSD KLIPRKT-KKFYW-DTKKYGGFDSPIVAYSI-LVIAD--IE--KGKSKKLKTVKALVGVTIME KMTFER  1158
WP_014677909   1094  -NSD KLIPRKT-KKFYW-DTKKYGGFDSPIVAYSI-LVIAD--IE--KGKSKKLKTVKALVGVTIME KMTFER  1158
WP_019312892   1094  -NSD KLIPRKT-KKFYW-DTKKYGGFDSPIVAYSI-LVIAD--IE--KGKSKKLKTVKALVGVTIME KMTFER  1158
WP_019313659   1094  -NSD KLIPRKT-KKFYW-DTKKYGGFDSPIVAYSI-LVIAD--IE--KGKSKKLKTVKALVGVTIME KMTFER  1158
```

```
                                                                                                   -continued WP_019314093     1094  -NSD KLIPRKT-KKFYW-DTKKYGGFDSPIVAYSI-LVIAD--IE--KGKSKKLKTVKALVGVTIME KMTFER  1158
WP_019315370     1094  -NSD KLIPRKT-KKFYW-DTKKYGGFDSPIVAYSI-LVIAD--IE--KGKSKKLKTVKALVGVTIME KMTFER  1158
WP_019803776     1094  -NSD KLIPRKT-KKFYW-DTKKYGGFDSPIVAYSI-LVIAD--IE--KGKSKKLKTVKALVGVTIME KMTFER  1158
WP_019805234     1094  -DSD KLIPRKT-KKFYW-DTKKYGGFDSPIVAYSI-LVIAD--IE--KGKSKKLKTVKALVGVTIME KMTFER  1158
WP_024783594     1094  -NSD KLIPRKT-KKFYW-DTKKYGGFDSPIVAYSI-LVIAD--IE--KSKSKKLKTVKALVGVTIME KMTFER  1158
WP_024784288     1112  -PLE KLVPLKK----AL-NPEKYGGYQKPTTAYPI LLIVD---------TKQLIPISVMD KKRFEQ  1166
WP_024784666     1094  -NSD KLIPRKT-KKFYW-DTKKYGGFDSPIVAYSI-LVIAD--IE--KGKSKKLKTVKALVGVTIME KMTFER  1158
WP_024784894     1094  -NSD KLIPRKT-KKFYW-DTKKYGGFDSPIVAYSI-LVIAD--IE--KGKSKKLKTVKALVGVTIME KMTFER  1158
WP_024786433     1112  -PLE KLVPLKK----AL-NPEKYGGYQKPTTAYPI LLIVD---------TKQLIPISVMD KKRFEQ  1166
WP_049473442     1094  -NSD KLIPRKT-KKFYW-DTKKYGGFDSPIVAYSI-LVIAD--IE--KGKSKKLKTVKALVGVTIME KMTFER  1158
WP_049474547     1094  -NSD KLIPRKT-KKFYW-DTKKYGGFDSPIVAYSI-LVIAD--IE--KGKSKKLKTVKALVGVTIME KMTFER  1158
EMC03581         1087  -NSD KLIPRKT-KKFYW-DTKKYGGFDSPIVAYSI-LVIAD--IE--KGKSKKLKTVKALVGVTIME KMTFER  1151
WP_000428612     1122  -NSD KLIPRKT-KDILW-DTTKYGGFDSPVIAYSI-LLIAD--IE--KGKAKRLKTVKTLVGITIME KATFEK  1186
WP_000428613     1120  -NSD KLIPRKT-KDILW-ETTKYGGFDSPVIAYSI-LLIAD--IE--KGKAKKLKTVKTLVGITIME KAAFEE  1184
WP_049523028     1115  -NSD KLIPRKT-KNVQL-DTTKYGGFDSPIIAYSV-LVVAD--VE--KGKSQKTKSVKELVGITIME KVKFEA  1179
WP_003107102     1084  -DSD KLIP----RKNNW-DTTKYGGFDSPIIAYSV-LVVAK--VT--KGKSQKTKSVKELVGITIME QNEFEK  1145
WP_054279288     1116  -KSS KLIP----RKNKWrDTTKYGGNTPTVAYSV-LVVAK--VE--KGKAKKLKPVKELVGITIME RTKFEA  1178
WP_049531101     1125  vvDAS KLIPIKS-G---L-SPEKYGGYARPTIAYSV-LVIAD--IE--KGKAKKLKRIKEMVGITIQD KKKFEA  1188
WP_049538452     1125  vvDAS KLIPIKS-G---L-SPEKYGGYARPTIAYSV-LVIAD--IE--KGKTKKLKRIKEMIGITVQD KKIFES  1188
WP_049549711     1127  vvDAS KLIPIKS-G---L-SPEKYGGYARPTIAYSV-LVIAD--IE--KGKTKKLKRIKEMVGITIQD KKKFEA  1190
WP_007896501     1121  -NSD KLIE----DPKKYGGFDSPNTAYSI-FVVAK--VA--KRKAQKLKTVKEIVGITIME QAEYEK  1182
EFR44625         1073  -NSD KLIE----RKKGW-DPKKYGGFDSPNTAYSI-FVVAK--VA--KRKAQKLKTVKEIVGITIME QAEYEK  1134
WP_002897477     1119  -NSD KLIE----RKKGW-DTTKYGGFDSPVIAYSI-LVIAD--IE--KGKAKKLKTVKTLVGITIME KAAFEE  1183
WP_002906454     1124  vvDAS KLIPIKS-S---L-SPEKYGGYARPTIAYSV-LVIAD--IE--IEkgKGKAKKLKRIKEIVGITIQD KKKFES  1189
WP_009729476     1120  -NSD KLIP----KDILW-DTTKYGGFDSPVIAYSI-LLIAD--IE--KGKAKKLKTVKTLVGITIME KDAFEH  1184
CQR24647         1110  -GSD KLIARKT-KNNYL-STQKYGGFDSPTVAYSI-MFVAD--IE--KGKSRLKTVKEMIGITIME RSRFES  1174
WP_000066813     1124  -NSD KLIP----KEILW-DTTKYGGFDSPVIAYSI-LLIAD--IE--KGKAKKLKTVKTLVGITIME KATFEK  1188
WP_009754323     1120  -NSD KLIP----KDILW-DTTKYGGFDSPVIAYSI-LLIAD--IE--KGKAKKLKTVKTLVGITIME KAAFEK  1184
WP_044674937     1113  -DSD KLIP----EKFYL-DTKKYGGFDSPTIAYSV-LLIAD--IE--KGKAKKLKRVKELIGITIME RMAFEK  1177
WP_044676715     1115  -DSD KLIP----EKFYL-DTKKYGGFDSPTIAYSV-LLIAD--IE--KGKAKKLKRVKELIGITIME RMAFEK  1179
WP_044680361     1115  -DSD KLIP----EKFYL-DTKKYGGFDSPTIAYSV-LLIAD--IE--KGKAKKLKRVKELIGITIME RMAFEK  1179
WP_044681799     1113  -DSD KLIP----EKFYL-DTKKYGGFDSPTIAYSV-LLIAD--IE--KGKAKKLKRVKELIGITIME RMAFEK  1177
WP_049533112     1123  -DSS ENLVGVK-RNL---DPKKYGGYAGISNSYAV-LVKA1--IE--KGVKKKETMVLEFQGISILD RITFEK  1185
WP_029090905     1062  -SSS KTIP----LKKHL-DTAIYGGYTAVNYASYA---LIQ--FK---KGRKLK--REIIGIPLAV QTRIDN  1117
WP_006506696     1085  haDKG AVVP----vNKNRS-DVHKYGGFPSG--LQYTI---VA--IEggKKKGKKTELVKKISGVPLHL KAASIN  1149
AIT42264         1115  KRIP----IKNNL-DPNIYGGYIEEKMAYYI---AlnyLE-NGKTKK---AIVGISIKD KDFEG  1176
WP_034440723     1093  k-KTE KRIP----IKNNL-DPNIYGGYIEEKMAYYI---AlnyLE-NGKTKK---AIVGISIKD KDFEG  1149
AKQ21048         1115  -NSD KLIA----RKKDW-DPKKYGGFDSPTVAYSV-LVVAK--VE--KGKSKKLKSVKELLGITIME RSSFEK  1176
WP_004636532     1093  -DSS KLIP----VKEGM-DPQKYGGLsQVSEAFAV-VIT----HE--KGKKKQLK--SDLISIPIVD QKAYEQ  1150
WP_002364836     1099  -PSN KLIP----VKNGL-DPQKYGGFDSPIVAYTV-LF----T--HE--KGK-KPL-IKQEILGITIME KTRFEQ  1156
WP_016631044     1050  -PSN KLIP----VKNGL-DPQKYGGFDSPVVAYTV-LF----T--HE--KGK-KPL-IKQEILGITIME KTRFEQ  1107
EMS75795         835   -KPD KLIQ----RKAGW-DVSKYGGFGSPVVAYAV-AFI----YE--KGKAR--KKAKAIEGITIME QSLFEQ  892
WP_002373311     1099  -PSN KLIP----VKNGL-DPQKYGGFDSPVVAYTV-LF----T--HE--KGK-KPL-IKQEILGITIME KTRFEQ  1156
WP_002378009     1099  -PSN KLIP----VKNGL-DPQKYGGFDSPVVAYTV-LF----T--HE--KGK-KPL-IKQEILGITIME KTRFEQ  1156
WP_002407324     1099  -PSN KLIP----VKNGL-DPQKYGGFDSPVVAYTV-LF----T--HE--KGK-KPL-IKQEILGITIME KTRFEQ  1156
WP_002413717     1101  -PSN KLIP----VKNGL-DPQKYGGFDSPVVAYTV-LF----T--HE--KGK-KPL-IKQEILGITIME KTRFEQ  1158
WP_010775580     1099  -PSN KLIP----VKNGL-DPQKYGGFDSPVVAYTV-LF----T--HE--KGK-KPL-IKQEILGITIME KTRFEQ  1156
WP_010818269     1099  -PSN KLIP----VKNGL-DPQKYGGFDSPVVAYTV-LF----T--HE--KGK-KPL-IKQEILGITIME KTRFEQ  1156
WP_010824395     1099  -PSN KLIP----VKNGL-DPQKYGGFDSPVVAYTV-LF----T--HE--KGK-KPL-IKQEILGITIME KTRFEQ  1156
WP_016222645     1099  -PSN KLIP----VKNGL-DPQKYGGFDSPVVAYTV-LF----T--HE--KGK-KPL-IKQEILGITIME KTRFEQ  1156
WP_033624816     1099  -PSN KLIP----VKNGL-DPQKYGGFDSPVVAYTV-LF----T--HE--KGK-KPL-IKQEILGITIME KTKFEQ  1156
WP_033625576     1099  -PSN KLIP----VKNGL-DPQKYGGFDSPVVAYTV-LF----T--HE--KGK-KPL-IKQEILGITIME KTRFEQ  1156
WP_033789179     1099  -PSN KLIP----VKNGL-DPQKYGGFDSPVVAYTV-LF----T--HE--KGK-KPL-IKQEILGITIME KTRFEQ  1156
```

```
WP_002310644   1101  -DSS KLLP-----RKNNW-DPAKYGGLGSPNVAYTV-AFT-----YE--KGKAR--KRTNALEGITIME REAFEQ  1158
WP_002312694   1102  -DSS KLLP-----RKNNW-DPAKYGGLGSPNVAYTV-AFT-----YE--KGKAR--KRTNALEGITIME REAFEQ  1159
WP_002314015   1102  -DSS KLLP-----RKNNW-DPAKYGGLGSPNVAYTV-AFT-----YE--KGKAR--KRTNALEGITIME REAFEQ  1159
WP_002320716   1102  -DSS KLLP-----RKNNW-DPAKYGGLGSPNVAYTV-AFT-----YE--KGKAR--KRTNALEGITIME REAFEQ  1159
WP_002330729   1101  -DSS KLLP-----RKNNW-DPAKYGGLGSPNVAYTV-AFT-----YE--KGKAR--KRTNALEGITIME REAFEQ  1158
WP_002335161   1102  -DSS KLLP-----RKNNW-DPAKYGGLGSPNVAYTV-AFT-----YE--KGKAR--KRTNALEGITIME REAFEQ  1159
WP_002345439   1102  -DSS KLLP-----RKNNW-DPTKYGGLGSPNVAYTV-AFT-----YE--KGKAR--KRTNALEGITIME REAFEQ  1159
WP_034867970   1092  -KPD KLIE-----RKNNW-DVTKYGGFGSPVIAYAI-AFV-----YA--KGKTQ--KKTRALEGITIME QAAFEK  1149
WP_047937432   1102  -DSS KLLP-----RKNNW-DPAKYGGLGSPNVAYTV-AFT-----YE--KGKAR--KRTNALEGITIME REAFEQ  1159
WP_010720994   1092  -KPD KLIE-----RKNNW-DVTKYGGFGSPVIAYAI-AFV-----YA--KGKTQ--KKTKALEGITIME QAAFEK  1149
WP_010737004   1092  -KPD KLIE-----RKNNW-DVTKYGGFGSPVIAYAI-AFV-----YA--KGKTQ--KKTRAIEGITIME QAAFEK  1149
WP_034700478   1092  -KPD KLIE-----RKNNW-DVTKYGGFGSPVIAYAI-AFV-----YA--KGKTQ--KKTRAIEGITIME QAAFEK  1149
WP_007209003   1090  -ESQ KLIR-----RKQQW-NTKKYGGFDSPVVAYAI-----LLS--FD--KGK-RKARSFK-IVGITIQD RESFEG  1147
WP_023351917   1086  -NPE KLIP-----RKASL-DPLKYGGYGSPLVAYTV-IFI-----FE--KGKQK--KVTKGIEGITVME QLRFEQ  1143
WP_010770040   1097  -DSD KLIS-----RKTNW-SPKLYGGFDSPQVAYSV-II--T---YE--KGK-KKVRA-KAIVGITIME QSLFKK  1154
WP_048604708   1094  -DSD KLIS-----RKKEW-DTTKYGGFDSPNMAYSV-II------YE--KGK-TRKLV-KTIVGITIME RAAFEK  1151
WP_010750235   1095  -KPD KLIK-----RKNNW-DVTKYGGFGSPVVAYAV-VFT-----YE--KGKNH--KKAKAIEGITIME QALFEK  1152
AII16583       1154  -NSD KLIA-----RKKDW-DPKKYGGFDSPTVAYSV-LVVAK---VE--KGKSKKLKSVKELLGITIME RSSFEK  1215
WP_029073316   1100  hsBKG AKVP-----vNKLRS-NVHKYGGFEG--LKYSI------VA--IKgkKKKGKKIIDVNKLVGIPLMY KNVDDE  1164
WP_031589969   1100  nsDKD ATVP-----vNKYRS-NVHKYGGFSG--VNSFI------VA--IKgkKKKGKKVIEVNKLTGIPLMY KNADEE  1164
KDA45870       1079  -DSG KLLP-----RKEGL-DPVKYGGYAKAVESYAV-LITAD-eVK--KGKTKKKVKT---LVNIPIID SKKYEA  1138
WP_039099354   1098  k-ASG QLIPAKQdRPTAL----YGGYSGKTVAYMC---IVR--IKnkKGDLYKVCGVETSWLAQLKQ KKAFLK  1170
AKP02966       1119  KLIA-----QKKDM-DPNIYGGFSGDNKSSIT---IVK--ID----NNKIKPVA--IPIRLIN ---DK  1172
WP_010991369   1096  -NSS KLIS-----RKTNW-DPMKYGGLDSPNMAYAV-VI------E--YA--KGK-NKLVFEKKIIRVTIME RKAFEK  1154
WP_033838504   1096  -NSS KLIS-----RKTNW-DPMKYGGLDSPNMAYAV-VI------E--YA--KGK-NKLVFEKKIIRVTIME RKAFEK  1154
EHN60060       1099  -NSS KLIS-----RKTNW-DPMKYGGLDSPNMAYAV-VI------E--YA--KGK-NKLVFEKKIIRVTIME RKAFEK  1157
EFR89594       865   -NSS KLIS-----RKTNW-DPMKYGGLDSPNMAYAV-VI------E--YA--KGK-NKLVFEKKIIRVTIME RKAFEK  923
WP_038409211   1096  -NSS KLIS-----RKADW-DPMKYGGFDSPNMAYAV-VI------E--YE--KRK-KKTVIKKELIQINIME RVAFEK  1154
EFR95520       715   -NSS KLIS-----RKADW-NPIKYGGFDSPNMAYSI-VI------E--YB--KRK-KKTVIKKELIQINIME KNADEE  773
WP_003723650   1096  -NSS KLIP-----RKENW-DPMKYGGLDSPNMAYAV-II------E--HA--KGK-KKIVIEKKLIQINIME RKMFEK  1154
WP_003727705   1096  -NSS KLIP-----RKENW-DPMKYGGLDSPNMAYAV-II------E--HA--KGK-KKIVIEKKLIQINIME RKMFEK  1154
WP_003730785   1096  -NSS KLIP-----RKENW-DPMKYGGLDSPNMAYAI-II------E--YA--KGK-KKIVIEKKLIQINIME RKMFEK  1154
WP_003733029   1096  -KSN KLIP-----RKDW-DPIKYGGFDSPNMAYAV-III-----E--YE--KQK-RKVRIEKKLIQINIME REAFEK  1154
WP_003739838   1099  -NSS KLIP-----RKENW-DPMKYGGLDSPNMAYAV-II------E--HA--KGK-KKVFEKKLIRITIME RKAFEK  1157
WP_014601172   1096  -NSS KLIP-----RKENW-DPMKYGGLDSPNMAYAV-II------E--HE--KGK-KKLIPEKKLIRITIME RKAFEK  1154
WP_023548323   1096  -DSS KLIP-----RKENW-DPMKYGGLDSPNMAYAV-III-----E--HE--KRK-KKVTIEKKLIQINIME RKAFEK  1154
WP_031665337   1096  -NSS KLIP-----RKENW-DPMKYGGLDSPNMAYAV-III-----E--HA--KGK-KRIVIEKKLIQINIME RKMFEK  1154
WP_031669209   1096  -KSN KLIP-----RKKDW-DPIKYGGFDSPNMAYAV-III-----E--YB--KQK-RKVRIEKKLIQINIME REAFEK  1154
WP_033920898   1096  -DSS KLIP-----KKTNL-NPIKYGGFEGSNMAYAI-II------E--HE--KRK-KKVTIEKKLIPEKKIRITIME RKAFEK  1154
AKI42028       1099  -NSS KLIP-----RKENW-DPMKYGGLDSPNMAYAV-II------E--HA--KGK-KKVTIEKKLIQINIME RKMFEK  1157
AKI50529       1099  -DSS KLIP-----KKTNL-NPIKYGGFEGSNMAYAI-II------E--HE--KRK-KKVTIEKKLIQINIME RKAFEK  1157
EFR83390       544   -NSS KLIP-----RKDW-DPIKYGGFDSPNMAYAV-II------E--HA--KGK-KRK-KKIVIEKKLIQINIME RKMFEK  602
WP_046323366   1096  -NSD KLIA-----RKADW-DPIKYGGFDSPNMAYAI-VI------E--HE--KRK-KGKSKKLKSVKELLGITIME RTAFEK  1154
AKE81011       1131  AVIP-----vNKNRK-DVNKYGGFSG--LQYVI-----AA--IEgtKKKGKKKLVKRKLSGIPLYL KQADIK  1192
CUO82355       1089  hsAKG ATVP-----vNKYRA-DVHKYGGFGN---VQSII-----VA--IEgkKKKKGKKLIDVRKLTSIPLHL KNAPVE  1153
WP_033162887   1090  -NSD KLIA-----RKKDW-DPKKYGGFDSPTVAYSV-LVVAK---VE--KGKSKKLKSVKELLGITIME RSSFEK  1154
AGZ01981       1148  -NSD KLIA-----RKKDW-DPKKYGGFDSPTVAYSV-LVVAK---VE--KGKSKKLKSVKELLGITIME RSSFEK  1209
AKA60242       1115  -NSD KLIA-----RKKDW-DPKKYGGFDSPTVAYSV-LVVAK---VE--KGKSKKLKSVKELLGITIME RSSFEK  1176
AKS40380       1115  -NSD KLIA-----RKKDW-DPKKYGGFDSPTVAYSV-LVVAK---VE--KGKSKKLKSVKELLGITIME RSSFEK  1176
4UN5_B         1119  -NSD KLIA-----RKKDW-DPKKYGGFDSPTVAYSV-LVVAK---VE--KGKSKKLKSVKELLGITIME RSSFEK  1180
WP_010922251   1177  NPI---DFLE--AKGYKE--V-KKDLIIK--LPKYSLFE--LENGRKRMLAS -gELQKGNELALPSKYVNFLYLA  1239
WP_039695303   1186  NPV---EFLE--NKGYHN--I-REDKLIK--LPKYSLFE---FEGGRRRLLAS ASELQKGNEMVLPGYLVELLYHA  1248
WP_045635197   1184  NPI---TFLE--NKGYHN--V-RKENILC--LPKYSLFE--LENGRRRLLAS AKELQKGNEIVLPVYLTTLLYHS  1246
```

-continued

```
5AXW_A             913  KPYrfdVYLD---NGVVKFvtV-KNLDVIK----KENYYE---VNSKAYEEAKK-KKISNQAEFIASFYNNDLIKIN      978
WP_009880683       861  DPV----DFLE---AKGYKE--V-RKDLIIK--LPKYSLFE--LENGRKRMLAS-GELQKGNELALPSKYVNFLYLA      923
WP_010922251      1177  NPI----DFLE---AKGYKE--V-RKDLIIK--LPKYSLFE--LENGRKRMLAS-GELQKGNELALPSKYVNFLYLA     1239
WP_011054416      1177  DPI----DFLE---AKGYKE--V-RKDLIVK--LPKYSLFE--LENGRKRMLAS-GELQKGNELALPSKYVNFLYLA     1239
WP_011284745      1177  NPI----DFLE---AKGYKE--V-RKDLIIK--LPKYSLFE--LENGRKRMLAS-GELQKGNELALPSKYVNFLYLA     1239
WP_011285506      1177  NPI----DFLE---AKGYKE--V-KKDLIIK--LPKYSLFE--LENGRKRMLAS-GELQKGNELALPSKYVNFLYLA     1239
WP_011527619      1177  DPV----DFLE---AKGYKE--V-RKDLIIK--LPKYSLFE--LENGRKRMLAS-GELQKGNELALPSKYVNFLYLA     1239
WP_012560673      1177  DPV----DFLE---AKGYKE--V-KKDLIIK--LPKYSLFE--LENGRKRMLAS-GELQKGNELALPSKYVNFLYLA     1239
WP_014407541      1176  NPI----DFLE---AKGYKE--V-KKDLIIK--LPKYSLFE--LENGRKRMLAS-GELQKGNELALPSKYVNFLYLA     1238
WP_020905136      1177  NPI----DFLE---AKGYKE--V-RKDLIIK--LPKYSLFE--LENGRKRMLAS-GELQKGNELALPSKYVNFLYLA     1239
WP_023080005      1176  NPI----DFLE---AKGYKE--V-RKDLIIK--LPKYSLFE--LENGRKRMLAS-GELQKGNELALPSKYVNFLYLA     1238
WP_023610282      1176  NPI----DFLE---AKGYKE--V-RKDLIIK--LPKYSLFE--LENGRKRMLAS-GELQKGNELALPSKYVNFLYLA     1238
WP_030125963      1177  NPI----DFLE---AKGYKE--V-RKDLIIK--LPKYSLFE--LENGRKRMLAS-GELQKGNELALPSKYVNFLYLA     1239
WP_030126706      1177  NPI----DFLE---AKGYKE--V-RKDLIIK--LPKYSLFE--LENGRKRMLAS-GELQKGNELALPSKYVNFLYLA     1239
WP_031488318      1177  NPI----DFLE---AKGYKE--V-RKDLIIK--LPKYSLFE--LENGRKRMLAS-GELQKGNELALPSKYVNFLYLA     1239
WP_032460140      1177  DPV----DFLE---AKGYKE--V-RKDLIIK--LPKYSLFE--LENGRKRMLAS-GELQKGNELALPSKYVNFLYLA     1239
WP_032461047      1177  DPV----DFLE---AKGYKE--V-RKDLIIK--LPKYSLFE--LENGRKRMLAS-GELQKGNELALPSKYVNFLYLA     1239
WP_032462016      1177  NPI----DFLE---AKGYKE--V-KKDLIIK--LPKYSLFE--LENGRKRMLAS-GELQKGNELALPSKYVNFLYLA     1239
WP_032462936      1177  NPI----DFLE---AKGYKE--V-RKDLIIK--LPKYSLFE--LENGRKRMLAS-GELQKGNELALPSKYVNFLYLA     1239
WP_032464890      1177  NPI----DFLE---AKGYKE--V-RKDLIIK--LPKYSLFE--LENGRKRMLAS-GELQKGNELALPSKYVNFLYLA     1239
WP_033888930      1002  NPI----DFLE---AKGYKE--V-KKDLIIK--LPKYSLFE--LENGRKRMLAS-GELQKGNELALPSKYVNFLYLA     1064
WP_038431314      1177  NPI----DFLE---AKGYKE--V-RKDLIIK--LPKYSLFE--LENGRKRMLAS-GELQKGNELALPSKYVNFLYLA     1239
WP_038432938      1176  NPI----DFLE---AKGYKE--V-RKDLIIK--LPKYSLFE--LENGRKRMLAS-GELQKGNELALPSKYVNFLYLA     1238
WP_038434062      1177  NPI----DFLE---AKGYKE--V-RKDLIIK--LPKYSLFE--LENGRKRMLAS-GELQKGNELALPSKYVNFLYLA     1239
BAQ51233          1088  NPI----DFLE---AKGYKE--V-RKDLIIK--LPKYSLFE--LENGRKRMLAS-GELQKGNELALPSKYVNFLYLA     1150
KGE60162           352  DPI----DFLE---AKGYKE--V-RKDLIIK--LPKYSLFE--LENGRKRMLAS-GELQKGNELALPSKYVNFLYLA      414
KGE60856           115  NPI----DFLE---AKGYKE--V-RKDLIIK--LPKYSLFE--LENGRKRMLAS-GELQKGNELALPSKYVNFLYLA      177
WP_002989955      1177  NPI----DFLE---AKGYKE--V-RKDLIIK--LPKYSLFE--LENGRKRMLAS-GELQKGNELALPSKYVNFLYLA     1239
WP_003030002      1159  HPV----DFLE---QRGYRN--V-RLEKIIK--LPKYSLFE--LENKRRLLAS  ARELQKGNELVIPQRFTTLLYHS     1221
WP_003065552      1187  NPV----EFLE---NKGYHN--I-REDKLIK--LPKYSLFE--FEGGKRRLLAS ASELQKGNEMVIPGHLVKLLYHA     1249
WP_001040076      1186  NPS----AFLE---SKGYLN--I-RTDKLII--LPKYSLFE--LENGRRRLLAS AGELQKGNELALPTQFMKFLYLA     1248
WP_001040078      1178  NPS----AFLE---SKGYLN--I-RDDKLMI--LPKYSLFE--LENGRRRLLAS AGELQKGNELALPTQFMKFLYLA     1240
WP_001040080      1178  NPS----AFLE---SKGYLN--I-RADKLII--LPKYSLFE--LENGRRRLLAS AGELQKGNELALPTQFMKFLYLA     1240
WP_001040081      1178  NPS----AFLE---SKGYLN--I-RADKLII--LPKYSLFE--LENGRRRLLAS AGETIDRLQKGNELALPTQFMKFLYLA   1240
WP_001040083      1178  NPS----AFLE---SKGYLN--I-RADKLII--LPKYSLFE--LENGRRRLLAS AGELQKGNELALPTQFMKFLYLA     1240
WP_001040085      1178  NPS----AFLE---SKGYLN--I-RADKLII--LPKYSLFE--LENGRRRLLAS AGELQKGNELALPTQFMKFLYLA     1240
WP_001040087      1178  NPS----AFLE---SKGYLN--I-RADKLII--LPKYSLFE--LENGRRRLLAS AGELQKGNELALPTQFMKFLYLA     1240
WP_001040088      1178  NPS----AFLE---SKGYLN--I-RDDKLMI--LPKYSLFE--LENGRRRLLAS AGELQKGNELALPTQFMKFLYLA     1240
WP_001040089      1178  NPS----AFLE---SKGYLN--I-RDDKLMI--LPKYSLFE--LENGRRRLLAS AGELQKGNELALPTQFMKFLYLA     1240
WP_001040090      1178  NPS----AFLE---SKGYLN--I-RDDKLMI--LPKYSLFE--LENGRRRLLAS AGELQKGNELALPTQFMKFLYLA     1240
WP_001040091      1178  NPS----AFLE---SKGYLN--I-RADKLII--LPKYSLFE--LENGRRRLLAS AGELQKGNELALPTQFMKFLYLA     1240
WP_001040092      1178  NPS----AFLE---SKGYLN--I-RTDKLII--LPKYSLFE--LENGRRRLLAS AGELQKGNELALPTQYMKFLYLA     1240
WP_001040094      1178  NPS----AFLE---SKGYLN--I-RDDKLII--LPKYSLFE--LENGRRRLLAS AGELQKGNELALPTQFMKFLYLA     1240
WP_001040095      1178  NPS----AFLE---SKGYLN--I-RTDKLII--LPKYSLFE--LENGRRRLLAS AGELQKGNELALPTQFMKFLYLA     1240
WP_001040096      1178  NPS----AFLE---SKGYLN--I-RDDKLMI--LPKYSLFE--LENGRRRLLAS AGELQKGNELALPTQFMKFLYLA     1240
WP_001040097      1178  NPS----AFLE---SKGYLN--I-RDDKLMI--LPKYSLFE--LENGRRRLLAS AGELQKGNELALPTQYMKFLYLA     1240
WP_001040098      1178  NPS----AFLE---SKGYLN--I-RDDKLMI--LPKYSLFE--LENGRRRLLAS ADELQKGNELALPTQFMKFLYLA     1240
WP_001040099      1178  NPS----AFLE---SKGYLN--I-RDDKLMI--LPKYSLFE--LENGRRRLLAS AGELQKGNELALPTQFMKFLYLA     1240
WP_001040100      1178  NPS----AFLE---SKGYLD--I-RDDKLMI--LPKYSLFE--LENGRRRLLAS AGELQKGNELALPTQFMKFLYLA     1240
WP_001040104      1178  NPS----AFLE---SKGYLN--I-RDDKLMI--LPKYSLFE--LENGRRRLLAS AGELQKGNELALPTQYMKFLYLA     1240
WP_001040105      1178  NPS----AFLE---SKGYLN--I-RDDKLMI--LPKYSLFE--LENGRRRLLAS AGELQKGNELALPTQFMKFLYLA     1240
WP_001040106      1178  NPS----AFLE---SKGYLN--I-RDDKLMI--LPKYSLFE--LENGRRRLLAS AGELQKGNELALPTQYMKFLYLA     1240
WP_001040107      1178  NPS----AFLE---SKGYLN--I-RDDKLMI--LPKYSLFE--LENGRRRLLAS AGELQKGNELALPTQFMKFLYLA     1240
```

-continued

| | | | | | | |
|---|---|---|---|---|---|---|
| WP_001040108 | 1178 | NPS---AFLE---SKGYLN---I-RDDKLMI--LPKYSLFE---LENGRRRLLAS | AGELQKGNELALPTQYMKFLYLA | 1240 |
| WP_001040109 | 1178 | NPS---AFLE---SKGYLN---I-RDDKLMI--LPKYSLFE---LENGRRRLLAS | AGELQKGNELALPTQYMKFLYLA | 1240 |
| WP_001040110 | 1178 | NPS---AFLE---SKGYLN---I-RDDKLMI--LPKYSLFE---LENGRRRLLAS | AGELQKGNELALPTQYMKFLYLA | 1240 |
| WP_015058523 | 1178 | NPS---AFLE---SKGYLN---I-RTDKLJI--LPKYSLFE---LENGRRRLLAS | ADELQKGNELALPTQYMKFLYLA | 1240 |
| WP_017643650 | 1178 | NPS---AFLE---SKGYLN---I-RDDKLMI--LPKYSLFE---LENGRRRLLAS | AGELQKGNELALPTQFMKFLYLA | 1240 |
| WP_017647151 | 1178 | NPS---AFLE---SKGYLN---I-RDDKLMI--LPKYSLFE---LENGRRRLLAS | AGELQKGNELALPTQFMKFLYLA | 1240 |
| WP_017648376 | 1178 | NPS---AFLE---SKGYLN---I-RDDKLMI--LPKYSLFE---LENGRRRLLAS | AGELQKGNELALPTQFMKFLYLA | 1240 |
| WP_017649527 | 1178 | NPS---AFLE---SKGYLN---I-RADKLJI--LPKYSLFE---LENGRRRLLAS | AGELQKGNELALPTQYMKFLYLA | 1240 |
| WP_017771611 | 1178 | NPS---AFLE---SKGYLN---I-RDDKLMI--LPKYSLFE---LENGRRRLLAS | AGELQKGNELALPTQFMKFLYLA | 1240 |
| WP_017771984 | 1178 | NPS---AFLE---SKGYLN---I-RADKLJI--LPKYSLFE---LENGRRRLLAS | AGELQKGNELALPTQFMKFLYLA | 1240 |
| CFQ25032 | 1178 | NPS---AFLE---SKGYLN---I-RADKLJI--LPKYSLFE---LENGRRRLLAS | AGELQKGNELALPTQFMKFLYLA | 1240 |
| CFV16040 | 1178 | NPS---AFLE---SKGYLN---I-RADKLJI--LPKYSLFE---LENGRRRLLAS | AGELQKGNELALPTQYMKFLYLA | 1240 |
| KLJ37842 | 1178 | NPS---AFLE---SKGYLN---I-RADKLJI--LPKYSLFE---LENGRRRLLAS | AGELQKGNELALPTQFMKFLYLA | 1240 |
| KLJ72361 | 1192 | NPS---AFLE---SKGYLN---I-RADKLJI--LPKYSLFE---LENGRRRLLAS | AGELQKGNELALPTQYMKFLYLA | 1254 |
| KLL20707 | 1178 | NPS---AFLE---SKGYLN---I-RDDKLMI--LPKYSLFE---LENGRRRLLAS | AGELQKGNELALPTQFMKFLYLA | 1240 |
| KLL42645 | 1178 | NPS---AFLE---SKGYLN---I-RADKLJI--LPKYSLFE---LENGRRRLLAS | AGELQKGNELALPTQFMKFLYLA | 1240 |
| WP_047207273 | 1178 | NPS---AFLE---SKGYLN---I-RDDKLMI--LPKYSLFE---LENGRRRLLAS | AGELQKGNELALPTQFMKFLYLA | 1240 |
| WP_047209694 | 1178 | NPS---AFLE---SKGYLN---I-RADKLJI--LPKYSLFE---LENGRRRLLAS | AGELQKGNELALPTQFMKFLYLA | 1240 |
| WP_050198062 | 1178 | NPS---AFLE---SKGYLN---I-RDDKLMI--LPKYSLFE---LENGRRRLLAS | AGELQKGNELALPTQFMKFLYLA | 1240 |
| WP_050201642 | 1178 | NPS---AFLE---SKGYLN---I-RADKLJI--LPKYSLFE---LENGRRRLLAS | AGELQKGNELALPTQFMKFLYLA | 1240 |
| WP_050204027 | 1178 | NPS---AFLE---SKGYLN---I-RDDKLMI--LPKYSLFE---LENGRRRLLAS | AGELQKGNELALPTQYMKFLYLA | 1240 |
| WP_050881965 | 1178 | NLS---AFLE---SKGYLN---I-RADKLJI--LPKYSLFE---LENGRRRLLAS | AGELQKGNELALPTQFMKFLYLA | 1240 |
| WP_050886065 | 1178 | NPS---AFLE---SKGYLN---I-RTDKLJI--LPKYSLFE---LENGRRRLLAS | AGELQKGNELALPTQYMKFLYLA | 1240 |
| AHN30376 | 1178 | NPS---AFLE---SKGYLN---I-RADKLJI--LPKYSLFE---LENGRRRLLAS | AGELQKGNELALPTQFMKFLYLA | 1240 |
| EA078426 | 1178 | NPS---AFLE---SKGYLN---I-RTDKLJI--LPKYSLFE---LENGRRRLLAS | AGELQKGNELALPTQFMKFLYLA | 1240 |
| CCW42055 | 1186 | DKR---AFIL---GKGYKD---I-K--KIIE--LKDGSRRMLAS | RGEIHKGNELFVPQKFTTLLYHS | 1253 |
| WP_003041502 | 1160 | DPLE---QRGYRN---V-RLEKIIK--LPKYSLFE---LENKRRRLLAS | ARELQKGNELVIPQRFTTLLYHS | 1222 |
| WP_037593752 | 1160 | HPV---DFLE---QRGYRN---V-RLEKIIK--LPKYSLFE---LENKRRRLLAS | ARELQKGNELVIPQRFTTLLYHS | 1222 |
| WP_049516684 | 1159 | NPV---DFLE---QRGYRN---V-RLEKIIK--LPKYSLFE---LENKRRRLLAS | ARELQKGNELVIPQRFTTLLYHS | 1221 |
| GAD46167 | 1191 | NPV---EFIK---NKGYQN---V-QEDKLMK--LPKYSLFE---LENKRRRLLAS | ATELQKGNEIMLSAHLVALLYHA | 1253 |
| WP_018363470 | 1186 | DPI---GFLE---AKGYKD---I-KKELFK--LPKYSLFE---LENKRRRLLAS | --ELQKANELVLPQHLVRLLYYT | 1248 |
| WP_003043819 | 1159 | DPV---DFLE---QRGYRN---V-RLEKIIK--LPKYSLFE---LENKRRRLLAS | AKELQKGNELVIPQRFTTLLYHS | 1221 |
| WP_006269658 | 1179 | MFLE---SKGYRN---I-QKDKLIK--LPKYSLFE---LENKRRRLLAS | AVELQKGNEMVLPQYLNNLLYHA | 1241 |
| WP_048800889 | 1178 | NPI---KFIE---DKGYGN---V-QIDKCIK--LPKYSLFE---FENGTRRMLAS | RGDLQKANEMFLPAKLVTLLY-- | 1245 |
| WP_012767106 | 1178 | NPL---KFIE---DKGYGN---V-QIDKCIK--LPKYSLFE---FENGTRRMLAS | RGDLQKANEMFLPAKLVTLLY-- | 1245 |
| WP_014612333 | 1157 | NPV---VFLE---ARGYRE---I-QEHLIIK--LPKYSLFE---LENGRRRLLAS | -SELQKGNELFLPVDYMTFLYLA | 1219 |
| WP_012515931 | 1157 | NPV---VFLE---AKGYRE---I-QEHLIIK--LPKYSLFE---LENGRRRLLAS | -SELQKGNELFLPVDYMTFLYLA | 1219 |
| WP_021320964 | 1184 | NPV---VFLE---AKGYHN---V-QEHLJIK--LPKYSLFE---LENGRRRLLAS | -SELQKGNELFLPVDYMTFLYLA | 1251 |
| WP_037581760 | 1189 | NPV---SFLE---NKGYHN---V-REDKLIK--LPKYSLFE---LENGRRRLLAS | ATELQKGNEVVLPQYMVNLLYHS | 1251 |
| WP_044232481 | 1184 | NPV---EFLE---NKGYHN---V-QEDKLIK--LPKYSLFE---LENGRRRLLAS | ASELQKGNEMVLPGYLVELLYHA | 1246 |
| WP_009854540 | 1185 | NPV---VFLE---VFLE---NKGYHN---V-QEDNLIK--LPKYSLFE---LENGRRRLLAS | ASELQKGNEVVLSRHLVELLYHN | 1247 |
| WP_012962174 | 1186 | NPV---EFLE---NKGYHN---I-REDKLIK--LPKYSLFE---LENGRRRLLAS | ASELQKGNEMVLPGYLVELLYHA | 1248 |
| WP_039695303 | 1189 | NPV---SFLE---NKGYHN---V-QEDKLIK--LPKYSLFE---LENGRRRLLAS | ATELQKGNEVMLPAHLVELLYHA | 1251 |
| WP_014334983 | 1177 | DPI---AFLE---KKGYQD---I-QTSSIIK--LPKYSLFE---LENGRRKLLAS | --ELQKGNELALPNKYVKFLYLA | 1239 |
| WP_003099269 | 1177 | DPI---AFLE---KKGYQD---I-QTSSIIK--LPKYSLFE---LENGRRKLLAS | --ELQKGNELALPNKYVKFLYLA | 1239 |
| AHY15608 | 1177 | DPI---AFLE---KKGYQD---I-QTSSIIK--LPKYSLFE---LENGRRKLLAS | ELQKGNELALPNKYVKFLYLA | 1239 |
| AHY17476 | 9 | DPI---AFLE---KKGYQD---I-QTSSIIK--LPKYSLFE---LENGRRKLLAS | KELQKGNELALPNKYVKFLYLA | 71 |
| ESR09100 | 1177 | DPI---AFLE---KKGYQD---I-QTSSIIK--LPKYSLFE---LENGRKRLLAS | ELQKGNELALPNKYVKFLYLA | 1239 |
| AGM98575 | | | | |

-continued

```
ALF27331        1159 NPV---AFLE---RKGYRN--V-QEENIVK--LPKYSLFE---LENGRRRLLAS ARELQKGNEIVLPNHLGTMLYHA 1221
WP_018372492    1168 EPEr---FLA--QKGFER--V-EKT--IK--LPKYSLFE---MEKGRRRLLAS SGELQKGNQVLLPEHLIRLLSYA 1228
WP_045618028    1189 NPI---AYLE--ECGYKN--I-NPNLIIK--LPKYSLFE---FNNGQRRLLAS SIELQKGNELIVPYHFTALLYHA 1251
WP_045635197    1184 NPI---TFIE--NKGYHN--V-RKENILC--LPKYSLFE---LENGRRRLLAS AKELQKGNEIVLPVYLTTLLYHS 1246
WP_002263549    1159 DPV---AFLE---RKGYRN--V-QEENIIK--LPKYSLFK---LENGRKRLLAS ARELQKGNEIVLPNHLGTLLYHA 1221
WP_002263887    1159 DPV---AFLE---RKGYRN--V-QEENIIK--LPKYSLFK---LENGRKRLLAS ARELQKGNEIVLPNHLGTLLYHA 1221
WP_002264920    1159 DPV---AFLE---RKGYRN--V-QEENIIK--LPKYSLFK---LENGRKRLLAS ARELQKGNEIVLPNHLGTLLYHA 1221
WP_002269043    1159 DPV---AFLE---RKGYRN--V-QEENIIK--LPKYSLFK---LENGRKRLLAS ARELQKGNEIVLPNHLGTLLYHA 1221
WP_002269448    1159 DPV---AFLE---RKGYRN--V-QEENIIK--LPKYSLFK---LENGRKRLLAS ARELQKGNEIVLPNHLGTLLYHA 1221
WP_002271977    1159 DPV---AFLE---RKGYRN--V-QEENIIK--LPKYSLFK---LENGRKRLLAS ARELQKGNEIVLPNHLGTLLYHA 1221
WP_002272766    1159 DPV---AFLE---RKGYRN--V-QEENIIK--LPKYSLFK---LENGRKRLLAS ARELQKGNEIVLPNHLGTLLYHA 1221
WP_002273241    1159 DPV---AFLE---RKGYRN--V-QEENIIK--LPKYSLFK---LENGRKRLLAS ARELQKGNEIVLPNHLGTLLYHA 1221
WP_002275430    1159 DPV---AFLE---RKGYRN--V-QEENIIK--LPKYSLFK---LENGRKRLLAS ARELQKGNEIVLPNHLGTLLYHA 1221
WP_002276448    1159 DPV---AFLE---RKGYRN--V-QEENIIK--LPKYSLFK---LENGRKRLLAS ARELQKGNEIVLPNHLGTLLYHA 1221
WP_002277050    1167 NPV---KFLK--DKGYQQ--I-EKNNFVK--LPKYTLVD---IGNGIKRLWAS SKEVHKGNQLVVSKKSQDLLYHA 1229
WP_002277364    1159 DPV---AFLE---RKGYRN--V-QEENIIK--LPKYSLFK---LENGRKRLLAS ARELQKGNEIVLPNHLGTLLYHA 1221
WP_002279025    1159 DPV---AFLE---RKGYRN--V-QEENIIK--LPKYSLFK---LENGRKRLLAS ARELQKGNEIVLPNHLGTLLYHA 1221
WP_002279859    1159 DPV---AFLE---RKGYRN--V-QEENIIK--LPKYSLFK---LENGRKRLLAS ARELQKGNEIVLPNHLGTLLYHA 1221
WP_002280230    1159 DPI---AFLE---RKGYRN--V-QEENIIK--LPKYSLFK---LENGRKRLLAS ARELQKGNEIVLPNHLGTLLYHA 1221
WP_002281696    1159 DPV---AFLE---RKGYRN--V-QEENIIK--LPKYSLFK---LENGRKRLLAS ARELQKGNEIVLPNHLGTLLYHA 1221
WP_002282247    1167 NPV---KFIK--DKGYQQ--I-EKNNFVK--LPKYTLVD---IGNGIKRLWAS SKEVHKGNQLVVSKKSQDLLYHA 1229
WP_002282906    1159 DPV---AFLE---RKGYRN--V-QEENIIK--LPKYSLFK---LENGRKRLLAS ARELQKGNEIVLPNHLGTLLYHA 1221
WP_002283846    1159 DPV---AFLE---RKGYRN--V-QEENIIK--LPKYSLFK---LENGRKRLLAS ARELQKGNEIVLPNHLGTLLYHA 1221
WP_002287255    1159 DPV---AFLE---RKGYRN--V-QEENIIK--LPKYSLFK---LENGRKRLLAS ARELQKGNEIVLPNHLGTLLYHA 1221
WP_002288990    1159 DPV---AFLE---RKGYRN--V-QEENIIK--LPKYSLFK---LENGRKRLLAS ARELQKGNEIVLPNHLGTLLYHA 1221
WP_002289641    1159 DPV---AFLE---RKGYRN--V-QEENIIK--LPKYSLFK---LENGRKRLLAS ARELQKGNEIVLPNHLGTLLYHA 1221
WP_002290427    1159 DPV---AFLE---RKGYRN--V-QEENIIK--LPKYSLFK---LENGRKRLLAS ARELQKGNEIVLPNHLGTLLYHA 1221
WP_002295753    1159 DPI---AFLE---RKGYRN--V-QEENIIK--LPKYSLFK---LENGRKRLLAS ARELQKGNEIVLPNHLGTLLYHA 1221
WP_002296423    1159 DPV---AFLE---RKGYRN--V-QEENIIK--LPKYSLFK---LENGRKRLLAS ARELQKGNEIVLPNHLGTLLYHA 1221
WP_002304487    1173 DPV---AFLE---RKGYRN--V-QEENIIK--LPKYTLVD---IGNGIKRLWAS ARELQKGNEIVLPNHLETLLYHA 1235
WP_002305844    1159 DPV---AFLE---RKGYRN--V-QEENIIK--LPKYSLFK---LENGRKRLLAS ARELQKGNEIVLPNHLGTLLYHA 1221
WP_002307203    1159 DPI---AFLE---RKGYRN--V-QEENIIK--LPKYSLFK---LENGRKRLLAS ARELQKGNEIVLPNHLGTLLYHA 1221
WP_002310390    1159 DPI---AFLE---RKGYRN--V-QEENIIK--LPKYSLFK---LENGRKRLLAS ARELQKGNEIVLPDHLGTLLYHA 1221
WP_002352408    1159 DPV---AFLE---RKGYRN--V-QEENIIK--LPKYSLFK---LENGRKRLLAS ARELQKGNEIVLPNHLGTLLYHA 1221
WP_012997688    1159 DPV---AFLE---RKGYRN--V-QEENIIK--LPKYSLFK---LENGRKRLLAS ARELQKGNEIVLPNHLGTLLYHA 1221
WP_014677909    1167 NPV---KFLK--DKGYQQ--I-EKNNFVK--LPKYTLVD---IGNGIKRLWAS SKEVHKGNQLVVSKKSQDLLYHA 1229
WP_019312892    1159 DPV---AFLE---RKGYRN--V-QEENIIK--LPKYSLFK---LENGRKRLLAS ARELQKGNEIVLPNHLGTLLYHA 1221
WP_019313659    1159 DPV---AFLE---RKGYRN--V-QEENIIK--LPKYSLFK---LENGRKRLLAS ARELQKGNEIVLPNHLGTLLYHA 1221
WP_019314093    1167 NPI---KFLK--DKGYQQ--I-EKNNFVK--LPKYTLVD---IGNGIKRLWAS SKEVHKGNQLVVSKKSQDLLYHA 1229
WP_019315370    1159 DPV---AFLE---RKGYRN--V-QEENIIK--LPKYSLFK---LENGRKRLLAS ARELQKGNEIVLPNHLGTLLYHA 1221
WP_019803776    1159 DPV---AFLE---RKGYRN--V-QEENIIK--LPKYSLFK---LENGRKRLLAS ARELQKGNEIVLPNHLGTLLYHA 1221
WP_019805234    1159 DPV---AFLE---RKGYRN--V-QEENIIK--LPKYSLFK---LENGRKRLLAS ARELQKGNEIVLPNHLGTLLYHA 1221
WP_024783594    1159 DPV---AFLE---RKGYRN--V-QEENIIK--LPKYSLFK---LENGRKRLLAS ARELQKGNEIVLPNHLGTLLYHA 1221
WP_024784288    1167 NPV---KFLK--DKGYQQ--I-EKNNFVK--LPKYTLVD---IGNGIKRLWAS SKEVHKGNQLVVSKKSQDLLYHA 1229
WP_024784666    1159 DPV---AFLE---RKGYRN--V-QEENIIK--LPKYSLFK---LENGRKRLLAS ARELQKGNEIVLPNHLGTLLYHA 1221
WP_024784894    1159 DPV---AFLE---RKGYRN--V-QEENIIK--LPKYSLFK---LENGRKRLLAS ARELQKGNEIVLPNHLGTLLYHA 1221
WP_024786433    1167 NPV---KFLK--DKGYQQ--I-EKNNFVK--LPKYTLVD---IGNGIKRLWAS SKEVHKGNQLVVSKKSQDLLYHA 1229
WP_049473442    1159 DPV---AFLE---RKGYRN--V-QEENIIK--LPKYSLFK---LENGRKRLLAS ARELQKGNEIVLPNHLGTLLYHA 1221
WP_049474547    1159 DPV---AFLE---RKGYRN--V-QEENIIK--LPKYSLFK---LKNGRRRMLAS AKELQKGNEIVLPVHLTTLLYHA 1221
EMC03581        1152 SPI---AFLE---NKGYHN--V-RKENILC--LPKYSLFE---LKNGRRRMLAS AKELQKGNEIVLPVHLTTLLYHA 1214
WP_000428612    1187 SPI---AFLE---NKGYHN--V-RKENILC--LPKYSLFE---LKNGRRRMLAS AKELQKGNEIVLPVHLTTLLYHS 1249
WP_000428613    1185 NPI---TFIE--NKGYHN--V-RKENILC--LPKYSLFE---LENGRRRLLAS AKELQKGNEIVLPVYLTTLLYHS 1247
WP_049523028    1180 NPV---AFLE---GKGYQN--V-VEENIIR--LPKYSLFE---LENGRRRMLAS AKELQKGNEMVLPSYLIALLYHA 1242
```

-continued

| | | | | |
|---|---|---|---|---|
| WP_003107102 | 1146 | DRI---TFLE---KKGYQD--I-QESLIIK--LPKFSLFE---LENGKRLLAS | -ELQKGNELSLPNKYIQFLYLA | 1208 |
| WP_054272288 | 1179 | NPI---AFLE---SKGYHD--I-QEHLMIT--LPKYSLFE---LENGRRLLAS | -ELQKGNEMVLPQHLVTFLYRV | 1241 |
| WP_049531101 | 1189 | NPT---AYLE---EYGYKN--I-NPNLIIK--LPKYSLFK---FNDGQRLLAS | SIELQKGNELILPYHFTLLYHA | 1251 |
| WP_049538452 | 1191 | NPI---AYLE---ECGYKN--I-NPNLIIK--LPKYSLFE---FNGGQRLLAS | SIELQKGNELILPYHFTALLYHT | 1253 |
| WP_049549711 | 1183 | NPI---AYLE---ECGYKN--I-NPNLIIK--LPKYSLFE---LENGRRLLAS | SIELQKGNELILPYHFTALLYHA | 1245 |
| WP_007896501 | 1135 | DNI---AFLE---KKGYQD--I-QEKLLIK--LPKYSLFE---LENGRRLLAS | -EFQKGNELALSGKYMKFLYLA | 1197 |
| EFR44625 | 1184 | DNI---AFLE---KKGYQD--I-QEKLLIK--LPKYSLFE---LENGRRLLAS | -EFQKGNELALSGKYMKFLYLA | 1246 |
| WP_002897477 | 1190 | NPI---TFLE---NKGYHN--V-RKENILC--LPKYSLFE---LENGRRLLAS | AKELQKGNEIVLPVCLITLLYHS | 1252 |
| WP_002906454 | 1185 | NPV---TYLE---ECGYKN--I-NSNLIIK--LPKYSLFE---FNDGQRLLAS | SIELQKGNELILPYHLTALLYHS | 1247 |
| WP_009729476 | 1175 | NPI---AFLE---NKGYHN--V-CKENILC--LPKYSLFE---LENGRRLLAS | AIELQKCNEIVLPVYLITLLYHS | 1237 |
| CQR24647 | 1189 | NSV---TFLE---EKGYRN--I-RENTLIK--FPKYSLFE---LESGRRMLAS | AKELQKGNEMFLPQQFVNLLYHA | 1251 |
| WP_000066813 | 1185 | NPI---TFLE---NKGYHN--V-RKENILC--LPKYSLFE---LENGRRLLAS | AKELQKGNEIVLPVYLITLLYHS | 1247 |
| WP_009754323 | 1178 | NPI---EFLE---HKGYKN--I-LEKNIIK--LPKYSLFE---LENGRRLLAS | AKELQKGNEMILPPHLVTLLYHS | 1240 |
| WP_044674937 | 1180 | NPI---EFLE---HKGYKN--I-LEKNIIK--LPKYSLFE---LENGRRLLAS | AKELQKGNEMILPPHLVTLLYHS | 1242 |
| WP_044676715 | 1180 | NPI---EFLE---HKGYKN--I-LEKNIIK--LPKYSLFE---LENGRRLLAS | AKELQKGNEMILPPHLVTLLYHS | 1242 |
| WP_044680361 | 1178 | NPI---EFLE---HKGYKN--I-LEKNIIK--LPKYSLFE---LENGRRLLAS | AKELQKGNEMILPPHLVTLLYHS | 1240 |
| WP_044681799 | 1186 | DKR---AFLL---GKGYKD--I-K--KIIE--LPKYSLFE---LKDGSRRMLAS | RGEIHKGNELIVPQKFTTLLYHA | 1253 |
| WP_049533112 | 1118 | SETslqAYIA---EQIKSE--VeILN----grILKYQLIS----NNNGNRLYIAG | -SERHNARQLIVSDEAAKVIWLI | 1181 |
| WP_029090905 | 1150 | EKI---TFLE---eKEGlSD--VrIIK----Dn-IPVNQMIEm----DGGEYLLTS | -EYVNARQLVLNEKQCALIADI | 1211 |
| WP_006506696 | 1177 | NPI---DFLE---AKGYKE--V-KKDLIIK--LPKYSLFE---LENGKRMLAS | -GELQKGNELALPSKYVNFLYLA | 1239 |
| AIT42264 | 1150 | QTT---EYLG---KIGFNK--AsIIN----S-FKNYTLFE---LENGSRRMIVG | KGELQKGNQMVLPQNLLEFVYHL | 1217 |
| WP_034440723 | 1177 | NPI---DFLE---AKGYKE--V-KKDLIIK--LPKYSLFE---LENGKRMLAS | -GELQKGNELALPSKYVNFLYLA | 1239 |
| AKQ21048 | 1151 | HPT---AYLE---EAGYNN--P-TV--LHE--LPKYQLFE---LEDGSRRMIAS | AKEFQKGNQMVLPLELVELLYHA | 1211 |
| WP_004636532 | 1157 | NPI---LFLE---EKGFLR--P-RV--LMK--LPKYTLYE---FPEGRRRLLAS | AKEAQKGNQMVLPEHLLTLLYHA | 1217 |
| WP_002364836 | 1108 | NPI---LFLE---EKGFLR--P-RV--LMK--LPKYTLYE---FPEGRRRLLAS | AKEAQKGNQMVLPEHLLTLLYHA | 1168 |
| WP_016631044 | 893 | DPI---GFLS---NKGYSN--V-TKF--IK--LsKYTLYE---LENGRRRLLAS | -KEAQKANSFILPEKLVTLLYHA | 953 |
| EM575795 | 1157 | NPI---LFLE---EKGFLR--P-RV--LMK--LPKYTLYQ---FPEGRRRLLAS | AKEAQKGNQMVLPEHLLTLLYHA | 1217 |
| WP_002373311 | 1157 | NPI---LFLE---EKGFLR--P-RV--LMK--LPKYTLYE---FPEGRRRLLAS | AKEAQKGNQMVLPEHLLTLLYHA | 1217 |
| WP_002378009 | 1157 | NPI---LFLE---EKGFLR--P-RV--LMK--LPKYTLYE---FPEGRRRLLAS | AKEAQKGNQMVLPEHLLTLLYHA | 1217 |
| WP_002407324 | 1159 | NPI---LFLE---EKGFLR--P-RV--LMK--LPKYTLYE---FPEGRRRLLAS | AKEAQKGNQMVLPERLLTLLYHA | 1219 |
| WP_002413717 | 1157 | NPI---LFLE---EKGFLR--P-RV--LMK--LPKYTLYE---FPEGRRRLLAS | AKEAQKGNQMVLPEHLLTLLYHA | 1217 |
| WP_010775580 | 1159 | NPI---LFLE---EKGFLR--P-RV--LMK--LPKYTLYE---FPEGRRRLLAS | AKEAQKGNQMVLPEHLLTLLYHA | 1219 |
| WP_010818269 | 1157 | NPI---LFLE---EKGFLR--P-RV--LMK--LPKYTLYE---FPEGRRRLLAS | AKEAQKGNQMVLPEHLLTLLYHA | 1217 |
| WP_010824395 | 1157 | NPI---LFLE---EKGFLR--P-RV--LMK--LPKYTLYE---FPEGRRRLLAS | AKEAQKGNQMVLPEHLLTLLYHA | 1217 |
| WP_016622645 | 1159 | SPV---LFLK---NKGYEQ--A-EIE--MK--LPKYALFE---LENGRKRMVAS | -KEAQKANSFLLPEHLVTLLYHA | 1219 |
| WP_023112694 | 1160 | SPV---LFLK---NKGYEQ--A-EIE--MK--LPKYALFE---LENGRKRMVAS | -KEAQKANSFLLPEHLVTLLYHA | 1220 |
| WP_033624816 | 1160 | SPV---LFLK---NKGYEQ--A-EIE--MK--LPKYALFE---LENGRKRMVAS | -KEAQKANSFLLPEHLVTLLYHA | 1220 |
| WP_023114015 | 1160 | SPV---LFLK---NKGYEQ--A-EIE--MK--LPKYALFE---LENGRKRMVAS | -KEAQKANSFLLPEHLVTLLYHA | 1220 |
| WP_033625576 | 1160 | SPV---LFLK---NKGYEQ--A-EIE--MK--LPKYALFE---LENGRKRMVAS | -KEAQKANSFLLPEHLVTLLYHA | 1220 |
| WP_033789179 | 1159 | SPV---LFLK---NKGYEQ--A-EIE--MK--LPKYALFE---LENGRKRMVAS | -KEAQKANSFLLPEHLVTLLYHA | 1219 |
| WP_002310644 | 1160 | SPV---LFLK---NKGYEQ--A-EIE--MK--LPKYALFE---LENGRKRMVAS | -KEAQKANSFLLPEHLVTLLYHA | 1220 |
| WP_002335161 | 1160 | SPV---LFLK---NKGYEQ--A-EIE--MK--LPKYALFE---LENGRKRMVAS | -KEAQKANSFLLPEHLVTLLYHA | 1220 |
| WP_002345439 | 1160 | SPV---LFLK---NKGYEQ--A-EIE--MK--LPKYALFE---LENGRKRMVAS | -KEAQKANSFLLPEHLVTLLYHA | 1220 |
| WP_034867970 | 1150 | DPT---TFLK---NKGFPQ--V-TEF--IK--LPKYTLFE---FDNGRRRFLAS | -KESQKGNPFILSDQLVTLLYHA | 1210 |
| WP_047937432 | 1160 | SPV---LFLK---NKGYEQ--A-EIE--MK--LPKYALFE---LENGRKRMVAS | -KEAQKANSFLLPEHLVTLLYHA | 1220 |
| WP_010720994 | 1150 | DPT---TFLK---DKGFPQ--V-TEF--IK--LPKYTLFE---FDNGRRRFLAS | -KESQKGNPFILSDQLVTLLYHA | 1210 |
| WP_010737004 | 1150 | DPT---TFLK---DKGFPQ--V-TEF--IK--LPKYTLFE---FDNGRRRFLAS | -KESQKGNPFILSDQLVTLLYHA | 1210 |
| WP_034700478 | 1150 | DPT---TFLK---DKGFPH--V-TEF--IK--LPKYTLFE---FDNGRRRFLAS | -KESQKGNPFILSDQLVTLLYHA | 1210 |
| WP_007209003 | 1148 | NPIl---YLS---KKDYHN--pkVEAI----LPKYSLFE---FENGRRRMVAS | -SETQKGNQLIIPGHLMELLYHS | 1208 |
| WP_023519017 | 1144 | DPR---EFLK---TKGYBG--V-KQW--LI--LPKYILFE---AQGGYRRMIAS | -QETQKANSLIILPENLVTLLYHA | 1204 |
| WP_010770040 | 1155 | DPV---SLLE---EKGYAN--P-EV--LIH--LPKYTLYE---LENGRRLLAS | ANEAQKGNQLVLPASLVTLLYHA | 1215 |

-continued

```
WP_048604708   1152 NER----EFLK---NKGYQN--P-QI--CMK-LPKYSLYE---FDDGRRRLlAS AKEAQKGNQMVLPAHLVTFLYHA 1212
WP_010750235   1153 DPI----SFlI---EKGYSN--V-NQF--IK-LPKYTLFE---LANGQRRMLAS -QELQKANSFILPEKLVTLLYHA 1213
AII16583       1216 NPI----DFlE---AKGYKE--V-KKDLIIK-LPKYSLFE---LENGRKRMLAS -GELQKGNELALPSKYVNFLYLA 1278
WP_029073316   1165 TKI----NYIK--eSEGLEE--VkIIK----E--ILKNQlIET---NGGLFYVTS -EIVNARQLILDFNCTRIIDGI 1225
WP_031589969   1165 IKI----NYLK--qAEDLEE--VqIGK----E--ILKNQlIEk----DGGLYYIVA -EIINAKQLIINESQTKLVCEI 1225
KDA45870       1139 DPT----AYlA---SRGYTNvtNsFIL------PKYSLLEd---PEGRRRYlAS -KEFQKANELILPQHLVELLYWv 1199
WP_039099354   1171 QKI-spQPTKv---KKQKGtIV-KVVEDFEv-IAPHILINqrfFDNGQELTLGS ---HNEQELILDKTAVKLLNGA 1241
AKP02966       1173 KTL-qNWlE----ENVKHKks IqlIK---Nn-VPIGQlIY-----SKKVGLlS -REIANRQQLILPPEHSALLRIL 1237
WP_010991369   1155 DEK----AFlE---EQGYRQ--P-KV--LAK-LPKYTLYE---CEEGRRRMLAS ANEAQKGNQQVLPNHLVTLLHHA 1215
WP_033838504   1155 DEK----AFlE---EQGYRQ--P-KV--LAK-LPKYTLYE---CEEGRRRMLAS ANEAQKGNQQVLPNHLVTLLHHv 1215
EHN60060       1158 NPI----DFlE---AKGYKE--V-KKDLIIK-LPKYSLFE---LENGRKRMLAS -GELQKGNELALPSKYVNFLYLA 1218
EFR89594        924 DEK----AFlE---EQGYRQ--P-KV--LAK-LPKYTLYE---CEEGRRRMLAS ANEAQKGNQQVLPNHLVTLLHHv  984
WP_038409211   1155 DQK----AFlE---EKGYYS--P-KV--LTK-IPKYTLYE---CENGRRRMLGS ANEAQKGNQMVLPNHLMTLLYHA 1215
EFR95520        774 DQK----AFlE---EKGYYS--P-KV--LTK-IPKYTLYE---CENGRRRMLGS ANEAQKGNQMVLPNHLMTLLYHA  834
WP_003723650   1155 DEE----AFlE---EKGYRH--P-KV--LTK-LPKYTLYE---CEKGRRRMLSS ANEAQKGNQLVLSNHLVSLLYHA 1215
WP_003727705   1155 DEE----AFlE---EKGYRH--P-KV--LTK-LPKYTLYE---CEKGRRRMLSS ANEAQKGNQLVLSNHLVSLLYHA 1215
WP_003730785   1155 DEE----AFlE---EKGYHQ--P-KV--LTK-LPKYTLYE---CEKGRRRMLAS ANEAQKGNQLVLSNHLVSLLYHA 1215
WP_003733029   1155 DEE----AFlE---EKGYHQ--P-KV--LIK-VPKYTLYE---CKNGRRRMLGS ANEAHKGNQMLLPNHLMALLYHA 1215
WP_003739838   1155 DEK----SFlE---KQGYRQ--P-KV--LTK-LPKYTLYE---CENGRRRMLAS ANEAQKGNQQVLKGQLITLLHHA 1215
WP_014601172   1155 DEE----AFlE---EKGYRH--P-KV--LTK-LPKYTLYE---CEKGRRRMLAS ANEAQKGNQLVLSNHLVSLLYHA 1215
WP_023548323   1155 DEK----VFlE---GKGYHQ--P-KV--LTK-LPKYALYE---CENGRRRMLGS ANEVHKGNQMLLPNHLMTLLYHA 1215
WP_031665337   1155 DEK----AFlE---EKGYRH--P-KV--LTK-LPKYTLYE---CEKGRRRMLGS ANEAQKGNQLVLSNHLVSLLYHA 1215
WP_031669209   1155 DEK----TFlE---GKGYHQ--P-KV--LIK-VPKYTLYE---CENGRRRMLAS ANEAHKGNQMLLPNHLMLLLYHA 1215
WP_033920898   1155 DEK----VFlE---GKGYHQ--P-KV--LTK-LPKYALYE---CENGRRRMLGS ANEVHKGNQMLLPNHLMTLLYHA 1215
AKI42028       1158 DEE----AFlE---EKGYRH--P-KV--LTK-LPKYTLYE---CEKGRRRMLAS ANEAQKGNQLVLSNHLVSLLYHA 1218
AKI50529       1158 DEK----VFlE---GKGYHQ--P-KV--LTK-LPKYALYE---CENGRRRMLGS ANEVHKGNQMLLPNHLMTLLYHA 1218
EFR83390        603 DQK----EFlE---GKGYRH--P-KV--ITK-IPKYTLYE---CENGRRRMLGS ANEAQKGNQMVLPNHLMTLLYHA  663
WP_046323366   1155 NPI----DFlE---AKGYKE--V-KKDLIIK-LPKYSLFE---LENGRKRMLAS -GELQKGNELALPSKYVNFLYLA 1215
AKE81011       1193 HRAD----NFNS-TEYLN--YVSEHKKFEKVLsCVEDFANLYDVE-KNLSKIR-A VAD-SM--DNFSIEE-       1255
CU082355       1154 EQI----EYVE-kEEKLSD--VkIIK---Nn-IPLNQlIEi-------DGRQYLLTS -ECVNAMQLVLNEEQCKLIADI 1215
WP_033162887   1210 EQL----SYIASpeHEDLID--VrIVK----E--ILKNQlIEi-------DGGLYYVTS -EYVTARQLSLNEQSCKLISEI 1217
AGZ01981       1177 NPI----DFlE---AKGYKE--V-KKDLIIK-LPKYSLFE---LENGRKRMLAS -GELQKGNELALPSKYYNFLYLA 1272
AKA60242       1177 NPI----DFlE---AKGYKE--V-KKDLIIK-LPKYSLFE---LENGRKRMLAS -GELQKGNELALPSKYVNFLYLA 1239
AK540380       1181 NPI----DFlE---AKGYKE--V-KKDLIIK-LPKYSLFE---LENGRKRMLAS -GELQKGNELALPSKYVNFLYLA 1239
4UN5_B         1247 KNVH---KLDE-PGHLE--YIQKHRNEFKDLLNLVSEFSQKVLAD--ANLEKIK-S LYA-DN--EQADIEI-       1243
5AXW_A          979 GELYRVIgVNNDILNRIE---VNMIDITYREYLENMDKRPPRIIKTIaSKTQSIK-K LYbvKSk--KHPQIIKg      1056
WP_009880683    924 SHYEKLKgSPEDnEQKQL-FVEQHKHYLDEIIEQISEFSKRVILAD--ANLDKVL-S AYN-KH---RDKPIREq      989
WP_010922251   1240 SHYEKLKgSPEDnEQKQL-FVEQHKHYLDEIIEQISEFSKRVILAD--ANLDKVL-S AYN-KH---RDKPIREq      1305
WP_010922251   1240 SHYEKLKgSPEDnEQKQL-FVEQHKHYLDEIIEQISEFSKRVILAD--ANLDKVL-S AYN-KH---RDKPIREq      1305
WP_039695303   1243 SHYEKLKgSPEDnEQKQL-FVEQHKHYLDEIIEQISEFSKRVILAD--ANLDKVL-S AYN-KH---RDKPIREq      1308
WP_045635197   1241 SHYEKLKgSPEDnEQKQL-FVEQHKHYLDEIIEQISEFSKRVILAD--ANLDKVL-S AYN-KH---RDKPIREq      1306
WP_011054416   1240 SHYEKLKgSPEDnEQKQL-FVEQHKHYLDEIIEQISEFSKRVILAD--ANLDKVL-S AYN-KH---RDKPIREq      1305
WP_011284745   1240 SHYEKLKgSPEDnEQKQL-FVEQHKHYLDEIIEQISEFSKRVILAD--ANLDKVL-S AYN-KH---RDKPIREq      1305
WP_011285506   1240 SHYEKLKgSPEDnEQKQL-FVEQHKHYLDEIIEQISEFSKRVILAD--ANLDKVL-S AYN-KH---RDKPIREq      1305
WP_011527619   1240 SHYEKLKgSPEDnEQKQL-FVEQHKHYLDEIIEQISEFSKRVILAD--ANLDKVL-S AYN-KH---RDKPIREq      1305
WP_012560673   1239 SHYEKLKgSPEDnEQKQL-FVEQHKHYLDEIIEQISEFSKRVILAD--ANLDKVL-S AYN-KH---RDKPIREq      1304
WP_014407541   1240 SHYEKLKgSPEDnEQKQL-FVEQHKHYLDEIIEQISEFSKRVILAD--ANLDKVL-S AYN-KH---RDKPIREq      1305
WP_020905136   1240 SHYEKLKgSPEDnEQKQL-FVEQHKHYLDEIIEQISEFSKRVILAD--ANLDKVL-S AYN-KH---RDKPIREq      1305
WP_023080005   1239 SHYEKLKgSPEDnEQKQL-FVEQHKHYLDEIIEQISEFSKRVILAD--ANLDKVL-S AYN-KH---RDKPIREq      1304
WP_023610282   1239 SHYEKLKgSPEDnEQKQL-FVEQHKHYLDEIIEQISEFSKRVILAD--ANLDKVL-S AYN-KH---RDKPIREq      1304
WP_030125963   1240 SHYEKLKgSPEDnEQKQL-FVEQHKHYLDEIIEQISEFSKRVILAD--ANLDKVL-S AYN-KH---RDKPIREq      1305
WP_030126706   1240 SHYEKLKgSPEDnEQKQL-FVEQHKHYLDEIIEQISEFSKRVILAD--ANLDKVL-S AYN-KH---RDKPIREq      1305
WP_031488318   1240 SHYEKLKgSPEDnEQKQL-FVEQHKHYLDEIIEQISEFSKRVILAD--ANLDKVL-S AYN-KH---RDKPIREq      1305
```

```
WP_032460140  SHYEKLKgSPEDnEQKQL--FVEQHKHYLDEIIEQISEFSKRVILAD--ANLDKVL-S  AYN-KH---RDKPIREq  1305
WP_032461047  SHYEKLKgSPEDnEQKQL--FVEQHKHYLDEIIEQISEFSKRVILAD--ANLDKVL-S  AYN-KH---RDKPIREq  1305
WP_032462016  SHYEKLKgSPEDnEQKQL--FVEQHKHYLDEIIEQISEFSKRVILAD--ANLDKVL-S  AYN-KH---RDKPIREq  1305
WP_032464890  SHYEKLKgSPEDnEQKQL--FVEQHKHYLDEIIEQISEFSKRVILAD--ANLDKVL-S  AYN-KH---RDKPIREq  1305
WP_033888930  SHYEKLKgSPEDnEQKQL--FVEQHKHYLDEIIEQISEFSKRVILAD--ANLDKVL-S  AYN-KH---RDKPIREq  1130
WP_038431314  SHYEKLKgSPEDnEQKQL--FVEQHKHYLDEIIEQISEFSKRVILAD--ANLDKVL-S  AYN-KH---RDKPIREq  1305
WP_038432938  SHYEKLKgSPEDnEQKQL--FVEQHKHYLDEIIEQISEFSKRVILAD--ANLDKVL-S  AYN-KH---RDKPIREq  1304
WP_038434062  SHYEKLKgSPEDnEQKQL--FVEQHKHYLDEIIEQISEFSKRVILAD--ANLDKVL-S  AYN-KH---RDKPIREq  1305
BAQ51233      SHYEKLKgSPEDnEQKQL--FVEQHKHYLDEIIEQISEFSKRVILAD--ANLDKVL-S  AYN-KH---RDKPIREq  1216
KGE60162      SHYEKLKgSPEDnEQKQL--FVEQHKHYLDEIIEQISEFSKRVILAD--ANLDKVL-S  AYN-KH---RDKPIREq  480
KGE60856      SHYEKLKgSPEDnEQKQL--FVEQHKHYLDEIIEQISEFSKRVILAD--ANLDKVL-S  AYN-KH---RDKPIREq  243
WP_002989955  SHYEKLKgSPEDnEQKQL--FVEQHKHYLDEIIEQISEFSKRVILAD--ANLDKVL-S  AYN-KH---RDKPIREq  1305
WP_003030002  YQIE----KNYE-PEHRE--YVEKHKDEFKELLEYISVFSRKVYLAD--NNLTKIE-M  LFS-KN---KDAEVSS-  1281
WP_003065552  QRIN----SENS-TKYLD--YVSAHKKEFEKVLSCVEDFANLYVDVE--KNLSKIR-A  VAD-SM---DNFSIEE-  1309
WP_001040076  SRYNESKgKPEEIEKKQE--FVNQHVSYFDDIPQIINDFSKRVILAD--ANLEKIN-R  LYQ-DNK--ENIPVDE-  1314
WP_001040078  SRYNESKgKPEEIEKKQE--FVNQHVSYFDDILQLINDFSKRVILAD--ANLEKIN-K  LYQ-DNK--ENISVDE-  1306
WP_001040080  SRYNESKgKPEEIEKKQE--FVNQHVSYFDDILQLINDFSKRVILAD--ANLEKIN-K  LYQ-DNK--ENISVDE-  1306
WP_001040081  SRYNESKgKPEEIEKKQE--FVNQHVSYFDDILQLINDFSKRVILAD--ANLEKIN-K  LYQ-DNK--ENISVDE-  1306
WP_001040083  SRYNESKgKPEEIEKKQE--FVNQHVSYFDDILQLINDFSKRVILAD--ANLEKIN-K  LYQ-DNK--ENISVDE-  1306
WP_001040085  SRYNESKgKPEEIEKKQE--FVNQHVSYFDDILQLINDFSKRVILAD--ANLEKIN-K  LYQ-DNK--ENISVDE-  1306
WP_001040087  SRYNESKgKPEEIEKKQE--FVNQHVSYFDDILQLINDFSKRVILAD--ANLEKIN-K  LYQ-DNK--ENIPVDE-  1306
WP_001040088  SRYNESKgKPEEIEKKQE--FVNQHVSYFDDILQLINDFSKRVILAD--ANLEKIN-K  LYQ-DNK--ENIPVDE-  1306
WP_001040089  SRYNESKgKPEEIEKKQE--FVNQHVSYFDDILQLINDFSKRVILAD--ANLEKIN-K  LYQ-DNK--ENIPVDE-  1306
WP_001040090  SRYNESKgKPEEIEKKQE--FVNQHVSYFDDILQLINDFSKRVILAD--ANLEKIN-K  LYQ-DNK--ENIPVDE-  1306
WP_001040091  SRYNESKgKPEEIEKKQE--FVNQHISYFDDILQLINDFSKRVILAD--ANLEKIN-K  LYS-DNK--DNTPVDE-  1306
WP_001040092  SRYNELKgKPEEIEKKQE--FVNQHVSYFDDILQLINDFSNRVILAD--ANLEKIN-K  LYQ-DNK--ENIPVDE-  1306
WP_001040094  SRYNELKgKPEEIEQKQE--FVVQHVSYFDDILQIINDFSNRVILAD--ANLEKIN-K  LYQ-DNK--ENIPVDE-  1306
WP_001040095  SRYNELKgKPEEIEQKQE--FVVQHVSYFDDILQIINDFSNRVILAD--ANLEKIN-K  LYQ-DNK--ENIPVDE-  1306
WP_001040096  SRYNELKgKPEEIEQKQE--FVVQHVSYFDDILQIINDFSNRVILAD--ANLEKIN-K  LYQ-DNK--ENIPVDE-  1306
WP_001040097  SRYNELKgKPEEIEQKQE--FVVQHVSYFDDILQIINDFSNRVILAD--ANLEKIN-K  LYQ-DNK--ENIPVDE-  1306
WP_001040098  SRYNELKgKPEEIEQKQE--FVVQHVSYFDDILQIINDFSNRVILAD--ANLEKIN-K  LYQ-DNK--ENIPVDE-  1306
WP_001040099  SRYNELKgKPEEIEKKQE--FVNQHVSYFDDILQLINDFSKRVILAD--ANLEKIN-K  LYQ-DNK--ENIPVDE-  1306
WP_001040100  SRYNESKgKPEEIEKKQE--FVNQHVSYFDDILQLINDFSKRVILAD--ANLEKIN-K  LYQ-DNK--ENISVDE-  1306
WP_001040104  SRYNELKgKPEEIEKKQE--FVNQHVSYFDDILQLINDFSNRVILAD--ANLEKIN-K  LYQ-DNK--ENIPVDE-  1306
WP_001040105  SRYNELKgKPEEIEKKQE--FVNQHVSYFDDILQLINDFSNRVILAD--ANLEKIN-K  LYQ-DNK--ENIPVDE-  1306
WP_001040106  SRYNELKgKPEEIEKKQE--FVNQHVSYFDDILQLINDFSNRVILAD--ANLEKIN-K  LYQ-DNK--ENIPVDE-  1306
WP_001040107  SRYNELKgKPEEIEKKQE--FVNQHVSYFDDILQLINDFSNRVILAD--ANLEKIN-K  LYQ-DNK--ENIPVDE-  1306
WP_001040108  SRYNELKgKPEEIEKKQE--FVNQHVSYFDDILQLINDFSNRVILAD--ANLEKIN-K  LYQ-DNK--ENIPVDE-  1306
WP_001040109  SRYNELKgKPEEIEKKQE--FVNQHVSYFDDILQLINDFSNRVILAD--ANLEKIN-K  LYQ-DNK--ENIPVDE-  1306
WP_001040110  SRYNESKgKPEEIEKKQE--FVNQHVSYFDDILQLINDFSKRVILAD--ANLEKIN-K  LYS-DNK--DNTPVDE-  1306
WP_015058523  SRYNESKgKPEEIEKKQE--FVNQHVSYFDDILQLINDFSKRVILAD--ANLEKIN-K  LYQ-DNK--ENIPVDE-  1306
WP_017643650  SRYNESKgKPEEIEKKQE--FVNQHVSYFDDILQLINDFSKRVILAD--ANLEKIN-K  LYQ-DNK--ENIPVDE-  1306
WP_017647151  SRYNESKgKPEEIEKKQE--FVNQHVSYFDDILQLINDFSKRVILAD--ANLEKIN-K  LYQ-DNK--ENIPVDE-  1306
WP_017648376  SRYNESKgKPEEIEKKQE--FVNQHVSYFDDILQLINDFSKRVILAD--ANLEKIN-K  LYQ-DNK--ENIPVDE-  1306
WP_017649527  SRYNESKgKPEEIEKKQE--FVNQHVSYFDDILQLINDFSKRVILAD--ANLEKIN-K  LYQ-DNK--ENIPVDE-  1306
WP_017771611  SRYNESKgKPEEIEKKQE--FVNQHVSYFDDILQLINDFSKRVILAD--ANLEKIN-K  LYQ-DNK--ENIPVDE-  1306
WP_017771984  SRYNESKgKPEEIEKKQE--FVNQHVSYFDDILQLINDFSKRVILAD--ANLEKIN-K  LYQ-DNK--ENIPVDE-  1306
CFQ25032      SRYNESKgKPEEIEKKQE--FVNQHVSYFDDILQLINDFSKRVILAD--ANLEKIN-K  LYQ-DNK--ENIPVDE-  1306
CFV16040      SRYNESKgKPEEIEKKQE--FVNQHVSYFDDILQLINDFSKRVILAD--ANLEKIN-K  LYQ-DNK--ENIPVDE-  1306
KLJ37842      SRYNESKgKPEEIEKKQE--FVNQHVSYFDDILQLINDFSKRVILAD--ANLEKIN-K  LYQ-DNK--ENIPVDE-  1306
KLJ72361      SRYNESKgKPEEIEKKQE--FVNQHVSYFDDILQLINDFSKRVILAD--ANLEKIN-K  LYQ-DNK--ENIPVDE-  1306
KLL20707      SRYNESKgKPEEIEKKQE--FVNQHVSYFDDILQLINDFSKRVILAD--ANLEKIN-K  LYQ-DNK--ENIPVDE-  1320
```

```
KLL42645           1241 SRYNELkgKPEEiEQKQE--FVVQHVSYFDDILQIINDFSNRVILAD--ANLEKIN-K LYQ-DNk--ENISVDE- 1306
WP_047207273       1241 SRYNESkgKPEEiEKKQE--FVNQHVSYFDDILQIINDFSKRVILAD--ANLEKIN-K LYQ-DNk--ENISVDE- 1306
WP_047209694       1241 SRYNELkgKPEEiEQKQE--FVVQHVSYFDDILQIINDFSNRVILAD--ANLEKIN-K LYQ-DNk--ENIPVDE- 1306
WP_050198062       1241 SRYNESkgKPEEiEKKQE--FVNQHVSYFDDILQIINDFSKRVILAD--ANLEKIN-K LYQ-DNk--ENISVDE- 1306
WP_050201642       1241 SRYNESkgKPEEiEKKQE--FVVQHVSYFDDILQIINDFSNRVILAD--ANLEKIN-K LYQ-DNk--ENISVDE- 1306
WP_050204027       1241 SRYNELkgKPEEiEQKQE--FVVQHVSYFDDILQIINDFSNRVILAD--ANLEKIN-K LYQ-DNk--ENISVDE- 1306
WP_050881965       1241 SRYNESkgKPEEiEKKQE--FVNQHVSYFDDILQIINDFSKRVILAD--ANLEKIN-K LYQ-DNk--ENISVDE- 1306
WP_050886065       1241 SRYNESkgKPEEiEKKQE--FVNQHVSYFDDILQIINDFSKRVILAD--ANLEKIN-K LYS-DNk--DNTPVDE- 1306
AHN30376           1241 SRYNESkgKPEEiEKKQE--FVNQHVSYFDDILQIINDFSKRVILAD--ANLEKIN-K LYQ-DNk--ENISVDE- 1306
EA078426           1241 SRYNESkgKPEEiEKKQE--FVNQHVSYFDDILQIINDFSNRVILAD--ANLEKIN-K LYQ-DNk--ENISVDE- 1306
CCW42055           1241 SRYNESkgKPEEiEKKQE--FVNQHVSYFDDILQIINDFSNRVILAD--ANLEKIN-E AVA-DF--DSKSNEE- 1306
WP_003041502       1254 KRIN---NPIN-KDHIE--YVKKHRDDFKELLNYVLEFNEKVGAT-KNGRLK-E AVA-DF--DSKSNEE- 1313
WP_037593752       1223 YQIE----KNYE-PEHRE--YVEKHKDEFKELLEYISVFSRKVLAD--NNLTKIE-M LFS-KN--KDAEVSS- 1282
WP_049516684       1223 YRIE----KDYE-PEHRE--YVEKHKDEFKELLEYISVFSRKVVLAD--NNLTKIE-M LFS-KN--KDAEVSS- 1282
GAD46167           1222 YQIE----KNYE-PEHRE--YVEKHKDEFKELLEYISVFSRKVLAD--NNLTKIE-M LFS-KN--KDAEVSS- 1281
WP_018363470       1254 HRIG----NFNS-AEHLK--YVSEHKKEFEEVLSCVENFANVVDVE--KNLsKIR-A AAD-SM--DNFSIEE- 1313
WP_003043819       1249 QNISATTgSNNLg------YIEQHREEFKEIFEKIIDFSEKYILKN--KVNSNLK-S SFD-EQfavSDSIl--1 1310
WP_006269658       1222 YRIE----KDYE-PEHRE--YVEKHKDEFKELLEYISVFSRKVVLAD--NNLTKIE-M LFS-KN--KDAEVSS- 1281
WP_048800889       1242 HRID----NSDN-SEHLK--YITEHKEEFGKLLSYIENFAKSVDVD--KNLEKIQ-L AVE-KI--DSFSVKE- 1301
WP_012767106       1246 -HAHKIEsSKE--LEHEA--YILDHYNDLYQLLSYIERFASLYDVE--KNISKVK-E LFS-NI--ESYSISEi 1308
WP_014612333       1246 -HAHKIEsSKE--LEHEA--YILDHYNDLYQLLSYIERFASLYDVE--KNISKVK-E LFS-NI--ESYSISEi 1308
WP_015017095       1246 -HAHKIEsSKE--LEHEA--YILDHYNDLYQLLSYIERFASLYDVE--KNISKVK-E LFS-NI--ESYSISEi 1308
WP_015057649       1246 -HAHKIEsSKE--LEHEA--YILDHYNDLYQLLSYIERFASLYDVE--KNISKVK-E LFS-NI--ESYSISEi 1308
WP_048277215       1246 -HAHKIEsSKE--LEHEA--YILDHYNDLYQLLSYIERFASLYDVE--KNISKVK-E LFS-NI--ESYSISEi 1308
WP_049519324       1246 -HAHKIEsSKE--LEHEA--YILDHYNDLYQLLSYIERFASLYDVE--KNISKVK-E LFS-NI--ESYSISEi 1308
WP_012515931       1220 AHYHELTgSSEDvLRKKY--FVDRHLHYFDDIIQMINDFAERHILAS--SNLEKIN-H TYH-NN--SDLPINEr 1285
WP_013209064       1220 AHYHELTgSSEDvLRKKY--FVERHLHYFDDIIQMINDFAERHILAS--SNLEKIN-H TYH-NN--SDLPINEr 1285
WP_037581760       1220 AHYHELTgSSEDvLRKKY--FVERHLHYFDDIIQMINDFAERHILAS--SNLEKIN-H TYH-NN--SDLPVNEr 1285
WP_004232481       1252 QHVN----NSHK-PEHLN--YVKQHKDEFKDIPNLIISIARINILKP--KVVDNL-- -IN EF--TEYGQED- 1308
WP_009854540       1247 HRAD----NFNS-TEYLN--YVSEHKKEFEKVLSCVEDFANLYVDVE--KNLSKIR-A VAD-SM--DNFSIEE- 1306
WP_012962174       1248 HRVN----SFNN-SEHLK--YVSEHKKEFGEVLSCVENFAKSVVDVE--KNLGKIR-A VAD-KI--DTFSIED- 1307
WP_039695303       1249 HRAD----NENS-TEYLN--YVSEHKKEFEKVLSCVEDFANLYVDVE--KNLSKIR-A VAD-SM--DNFSIEE- 1308
WP_014334983       1252 HRID----SFNS-TEHLK--YVSEHKKEFEKVLSCVENFSNLYVDVE--KNLSKVR-A AAE-SM--TNFSLEE- 1311
WP_003099269       1240 SHYTKFTgKEEDrEKKRS--YVESHLYYFDEIMQIIVEYSNRYILAD--SNLIKIQ-N LYK-EKq--NFSIEEq 1305
AHYI5608           1240 SHYTKFTgKEEDrEKKRS--YVESHLYYFXEVKSSF----------- ---------- 1273
AHYI7476           1240 SHYTKFTgKEEDrEKKRS--YVESHLYXFX----------------- ---------- 1267
ESR09100           72   SHYTKFTgKEEDrEKKRS--YVESHLYYFDEIMQIIVEYSNRYILAD--SNLIKIQ-N LYK-Ek--DNFSIEEq- 137
AGM98575           1240 SHYTKFTgKEEDrEKKRS--YVESHLYYFDVRLSQVFRVTNVEF--- ---------- 1281
ALF27331           1222 KKVDVLVkSKDD---DYD--LEEHRAEFAELLDCIKKFNDMYILAS--SNLEKIE-E LYA-QN--NNKDITE- 1289
WP_018372492       1229 KVDE-PKHLD--KVDE-PKHLD--YVKKHKDEFKELLDVVSNFSKKNILAE--SNLEKIE-E LYA-QN--DAPIEE- 1289
WP_045618028       1252 QRIN----KISE-PIHKQ--YVETHQSEFKPLLTAIISLSKKYI-QK--PNVESL-- LQQ-AF--DQSDKDIyq 1310
WP_045635197       1247 KNVH----KLDE-PGHLE--YIQKHRNEFKDLLNLVSEFSQKVLAD--ANLEKIK-S LYA-DN--EQADIEI- 1306
WP_002263549       1222 KNIH----KVDE-PKHLD--YVDKHKDEFKELLDVVSNFSKKYTLAE--GNLEKIK-E LYA-QN--NGEDLKE- 1281
WP_002263887       1222 KNIH----KVDE-PKHLD--YVDKHKDEFKELLDVVSNFSKKYTLAE--GNLEKIK-E LYA-QN--NGEDLKE- 1281
WP_002264920       1222 KNIH----KVDE-PKHLD--YVDKHKDEFKELLDVVSNFSKKYTLAE--GNLEKIK-E LYA-QN--NGEDLKE- 1281
WP_002269043       1222 KNIH----KVDE-PKHLD--YVDKHKDEFKELLDVVSNFSKKYTLAE--GNLEKIK-E LYA-QN--NGEDLKE- 1281
WP_002269448       1222 KNIH----KVDE-PKHLD--YVDKHKDEFKELLDVVSNFSKKYTLAE--GNLEKIK-E LYA-QN--NGEDLKE- 1281
WP_002271977       1222 KNIH----KVDE-PKHLD--YVDKHKDEFKELLDVVSNFSKKYTLAE--GNLEKIK-E LYA-QN--NGEDLKE- 1281
WP_002272766       1222 KNIH----KVDE-PKHLD--YVDKHKDEFKELLDVVSNFSKKYTLAE--GNLEKIK-E LYA-QN--NGEDLKE- 1281
WP_002273241       1222 KNIH----KVDE-PKHLD--YVDKHKDEFKELLDVVSNFSKKYTLAE--GNLEKIK-E LYA-QN--NGEDLKE- 1281
WP_002275430       1222 KNIH----KVDE-PKHLD--YVDKHKDEFKELLDVVSNFSKKYTLAE--GNLEKIK-E LYA-QN--NGEDLKE- 1281
WP_002276448       1222 KNIH----KVDE-PKHLD--YVDKHKDEFKELLDVVSNFSKKYTLAE--GNLEKIK-E LYA-QN--NGEDLKE- 1281
WP_002277050       1230 HHL-----DN-DYSNE---YVKNHYQQFPDILFNEITSFSKKCKLGK--EHIQKIE-E AYSkER--DSASIEE- 1287
```

```
                                                                                                                      -continued WP_002273364   KNIH----KVDE-PKHLD-YVDKHKDEFKELLDVVSNFSKKYTLAE--GNLEKIK-E LYA-QN---NGEDLKE--   1281
WP_002279025   KNIH----KVDE-PKHLD-YVDKHKDEFKELLDVVSNFSKKYTLAE--GNLEKIK-E LYA-QN---NGEDLKE--   1281
WP_002279859   KNIH----KVDE-PKHLD-YVDKHKDEFKELLDVVSNFSKKYTLAE--GNLEKIK-E LYA-QN---NGEDLKE--   1281
WP_002280230   KNIH----KVDE-PKHLD-YVDKHKDEFKELLDVVSNFSKKYTLAE--GNLEKIK-E LYA-QN---NGEDLKE--   1281
WP_002281696   KNIH----KVDE-PKHLD-YVDKHKDEFKELLDVVSNFSKKYTLAE--GNLEKIK-E LYA-QN---NGEDLKE--   1281
WP_002282247   HHL-------DN-DYSNE-YVKNHYQQFDILFNEITSFSKKCKLGK--EHIQKIE-E AYSKER---DFASIEE--   1287
WP_002282906   KNIH----KVDE-PKHLD-YVDKHKDEFKELLDVVSNFSKKYTLAE--GNLEKIK-E LYA-QN---NGEDLKE--   1281
WP_002283846   KNIH----KVDE-PKHLD-YVDKHKDEFKELLDVVSNFSKKYTLAE--GNLEKIK-E LYA-QN---NGEDLKE--   1281
WP_002287255   KNIH----KVDE-PKHLD-YVDKHKDEFKELLDVVSNFSKKYTLAE--GNLEKIK-E LYA-QN---NGEDLKE--   1281
WP_002288990   KNIH----KVDE-PKHLD-YVDKHKDEFKELLDVVSNFSKKYTLAE--GNLEKIK-E LYA-QN---NGEDLKE--   1281
WP_002289641   KNIH----KVDE-PKHLD-YVDKHKDEFKELLDVVSNFSKKYTLAE--GNLEKIK-E LYA-QN---NGEDLKE--   1281
WP_002290427   KNIH----KVDE-PKHLD-YVDKHKDEFKELLDVVSNFSKKYTLAE--GNLEKIK-E LYA-QN---NGEDLKE--   1281
WP_002295753   KNIH----KVDE-PKHLD-YVDKHKDEFKELLDVVSNFSKKYTLAE--GNLEKIK-E LYA-QN---NGEDLKE--   1281
WP_002296423   KNIH----KVDE-PKHLD-YVDKHKDEFKELLDVVSNFSKKYTLAE--GNLEKIK-E LYA-QN---NGEDLKE--   1281
WP_002304487   KNIH----KVDE-PKHLD-YVDKHKDEFKELLDVVSNFSKKYTLAE--GNLEKIK-E LYA-QN---NGEDLKE--   1295
WP_002305844   KNIH----KVDE-PKHLD-YVDKHKDEFKELLDVVSNFSKKYTLAE--GNLEKIK-E LYA-QN---NGEDLKE--   1281
WP_002307203   KNIH----KVDE-PKHLD-YVDKHKDEFKELLDVVSNFSKKYTLAE--GNLEKIK-E LYA-QN---NGEDLKE--   1281
WP_002310390   KNIH----KVDE-PKHLD-YVDKHKDEFKELLDVVSNFSKKYTLAE--GNLEKIK-E LYA-QN---NGEDLKE--   1281
WP_002352408   KNIH----KVDE-PKHLD-YVDKHKDEFKELLDVVSNFSKKYTLAE--GNLEKIK-E LYA-QN---NGEDLKE--   1281
WP_012997688   KNIH----KVDE-PKHLD-YVDKHKDEFKELLDVVSNFSKKYTLAE--GNLEKIK-E LYA-QN---NGEDLKE--   1281
WP_014677909   KNIH----KVDE-PKHLD-YVDKHKDEFKELLDVVSNFSKKYTLAE--GNLEKIK-E LYA-QN---NGEDLKE--   1281
WP_019312892   KNIH----KVDE-PKHLD-YVDKHKDEFKELLDVVSNFSKKYTLAE--GNLEKIK-E LYA-QN---NGEDLKE--   1281
WP_019313659   KNIH----KVDE-PKHLD-YVDKHKDEFKELLDVVSNFSKKYTLAE--GNLEKIK-E LYA-QN---NGEDLKE--   1281
WP_019314093   HHL-------DN-DYSNE-YVKNHYQQFDILFNEITSFSKKCKLGK--EHIQKIE-E AYSKER---DFASIEE--   1287
WP_019315370   KNIH----KVDE-PKHLD-YVDKHKDEFKELLDVVSNFSKKYTLAE--GNLEKIK-E LYA-QN---DSASIEE--   1281
WP_019803776   KNIH----KVDE-PKHLD-YVDKHKDEFKELLDVVSNFSKKYTLAE--GNLEKIK-E LYA-QN---NGEDLKE--   1281
WP_019805234   KNIH----KVDE-PKHLD-YVDKHKDEFKELLDVVSNFSKKYTLAE--GNLEKIK-E LYA-QN---NGEDLKE--   1281
WP_024783594   KNIH----KVDE-PKHLD-YVDKHKDEFKELLDVVSNFSKKYTLAE--GNLEKIK-E LYA-QN---NGEDLKE--   1281
WP_024784288   HHL-------DN-DYSNE-YVKNHYQQFDILFNEITSFSKKCKLGK--EHIQKIE-E AYSKER---DFASIEE--   1287
WP_024784666   KNIH----KVDE-PKHLD-YVDKHKDEFKELLDVVSNFSKKYTLAE--GNLEKIK-E LYA-QN---NGEDLKE--   1281
WP_024784894   KNIH----KVDE-PKHLD-YVDKHKDEFKELLDVVSNFSKKYTLAE--GNLEKIK-E LYA-QN---NGEDLKE--   1281
WP_024786433   HHL-------DN-DYSNE-YVKNHYQQFDILFNEITSFSKKCKLGK--EHIQKIE-E AYSKER---DSASIEE--   1287
WP_049473442   KNIH----KVDE-PKHLD-YVDKHKDEFKELLDVVSNFSKKYTLAE--GNLEKIK-E LYA-QN---NGEDLKE--   1281
WP_049474547   KNIH----KVDE-PKHLD-YVDKHKDEFKELLDVVSNFSKKYTLAE--GNLEKIK-E LYA-QN---NGEDLKE--   1281
EMC03581       KNIH----KVDE-PEHLE-YIQKHRNEFKGLLNLVSEFSQKTVLAD--ANLEKIK-N LYA-DN---EQADIEI--   1274
WP_000428612   KNIH----RLDE-PEHLE-YIQKHRNEFKDLLNLVSEFSQKYVLAD--ANLEKIK-N LYA-DN---EQADIEI--   1309
WP_000428613   KNVH----KLDE-PEHLE-YIQKHRNEFKDLLNLVSEFSQKYVLAD--ANLEKIQ-N LYA-DN---EQADIEI--   1307
WP_049523028   KRIQ----KKDE-PEHLE-YIKQHHSEFNDLLNFVSEFSQKYVLAE--SNLEKIK-N LYI-DN---EQTNMEE--   1302
WP_003107102   SRYTSFSGKEED-REKHRH-FVESHLHYFDEIKDIIADFSRRYLAD--ANLEKIL-T LYN-EKn---QFSIEEq-   1274
WP_054279288   SKRDK---gTQSEnME-----YISNHLKKFIEIFPHYIIRYAEKNVIKP--KVIERLN-D TENqKF---NDSDLTE1-   1303
WP_049531101   QRIN----KISE-PIHKQ--YVETHQSEFEELLTTIISLSKKYI--QK-PIVESL-- LQQ-AF---EQADKDIyq   1310
WP_049538452   QRIN----KISE-PIHKQ--YVEAHQNEFKELLTTIIISLSKKYI--QK-PIVESL-- LHQ-AF---EQADNDIyq   1312
WP_049549711   QRIN----KFSE-PIHKQ--YVEAHQNEFKELLTTIIISLSKKYI--QK-PNVESL-- LYK-KK---EAYSINEq-   1311
WP_007896501   SRYDKLsKIEseQQKKL--FVEQHLHYFDEILDIVVKHATCYIKAE--NNLKKII-S LYK-KK---EAYSINEq-   1263
EFR44625       SRYDKLsKIEseQQKKL--FVEQHLHYFDEILDIVVKHATCYIKAE--NNLKKII-S LYK-KK---EAYSINEq-   1263
WP_002897477   KNLH----KLDE-PEHLE-YIQKHRNEFKDLLNLVSEFSQKVLAE--ANLEKIK-D LYA-DN---EQADIEI--   1306
WP_002906454   QRIN----KISE-PIHKQ--YVEAHQNEFKELLTTIIISLSKKYI--QK-PNVELL-- LQQ-AF---DQADKDIyq   1311
WP_009729476   KNVH----KLDE-PGHLE-YIQKHRNEFKDLLNLVSEFSQKVLAD--ANLEKIK-N LYA-DN---EQADIEI--   1307
CQR24647       QHAN----KEDS----VI--YLEKHRHLSELFHHIIGVSEKTILKP--KVEMTLN-N AFE-KHf--EFDEVSE--   1295
WP_000066813   KNVH----KLDE-PEHLE-YIQKHRYEFKDLLNLVSEFSQKVLAD--ANLEKIK-N LYA-DN---EQADIEI--   1311
WP_009754323   KNVH----KLDE-PEHLE-YIQKHRYEFKDLLNLVSEFSQKVLAE--ANLEKIK-S LYV-DN---EQADIEI--   1307
WP_044674937   SNIH----KITE-PIHLN-YVNKNKHEFKELLRHISDFSTRYILAQ--DRLSKIE-E LYD-KN---DGDDISD--   1300
WP_044676715   SNIH----KITE-PIHLN-YVNKNKHEFKELLRHISDFSTRYILAQ--DRLSKIE-E LYD-KN---DGDDISD--   1302
```

```
                              -continued

WP_044680361  1243  SNIH----KITE-PIHLN--YVNKNKHEFKELLRHISDFSTRYILAQ--DRLSKIE-E LYD-KN---DGDDISD--  1302
WP_044681799  1241  SNIH----KITE-PIHLN--YVNKNKHEFKELLRHISDFSTRYILAQ--DRLSKIE-E LYD-KN---DGDDISD--  1300
WP_049533112  1254  KRIN----NPIN-KDHIF--YVKKHRDDFKELLNYVLEFNEKYVGAT--KNGERLK-E AVA-DF---DSKSNEE--  1313
WP_029090905  1182  STKQA------DE-AMFLKyyRLEHLEAVFEEL---IRKQAADYQIFE--KLIKKIEvN FYS-----c----TYNEk  1240
WP_006506696  1212  YNAIYKQ-DYDNlDDIlMi-----------QLYIELTNKMKVLYPAY-rGIAEKFE-S YVV-----i----SKEEk  1268
AIT42264      1240  SHYEKLKgSPEDrEQKQL--FVEQHKHYLDEIIEQISEFSKRVILAD--ANlDKVL-S AYN-KH---RDKPIREq-  1305
WP_034440723  1218  KHYNE-----DE-TSHK--FIVEHKAYFDELLNYIVEFANKYLELE--NSIEKIK-D LYH----gKGPDVEEke  1276
AKQ21048      1240  SHYEKLKgSPEDrEQKQL--FVEQHKHYLDEIIEQISEFSKRVILAD--ANlDKVL-S AYN-KH---RDKPIREq-  1305
WP_004636532  1212  NRYDKVK------FPDSIE-YVHDNLAKFDDLLEYVIDFSNKYINAD--KNVQKIQ-K IYK-EH---GTEDVEL--  1271
WP_002364836  1218  KQCLL-----PNQ-SESLA--YVEQHQPEFQEILERVVDFAEVHTLAK--SKVQQIV-K LFE-AN---QTADVKE--  1277
WP_016631044  1169  KQCLL-----PNQ-SESLA--YVEQHQPEFQEILERVVDFAEVHTLAK--SKVQQIV-K LFE-AN---QTADVKE--  1228
EM575795       954  QHYDEIAhKESF-----D--YVNDHLSFREILDQVIDFSNRYTIAA--KNTEKIA-E LFE-AN---QESTVQS--  1013
WP_002373311  1218  KQCLL-----PNQ-SESLA--YVEQHQPEFQEILERVVDFAEVHTLAK--SKVQQIV-K LFE-AN---QTADVKE--  1277
WP_002378009  1218  KQCLL-----PNQ-SESLA--YVEQHQPEFQEILERVVDFAEVHTLAK--SKVQQIV-K LFE-AN---QTADVKE--  1277
WP_002407324  1218  KQCLL-----PNQ-SESLA--YVEQHQPEFQEILERVVDFAEVHTLAK--SKVQQIV-K LFE-AN---QTADVKE--  1277
WP_002413717  1218  KQCLL-----PNQ-SESLA--YVEQHQPEFQEILERVVDFAEVHTLAK--SKVQQIV-K LFE-AN---QTADVKE--  1277
WP_010775580  1220  KQCLL-----PNQ-SESLA--YVEQHQPEFQEILERVVDFAEVHTLAK--SKVQQIV-K LFE-AN---QTADVKE--  1279
WP_010818269  1218  KQCLL-----PNQ-SESLA--YVEQHQPEFQEILERVVDFAEVHTLAK--SKVQQIV-K LFE-AN---QTADVKE--  1277
WP_010824395  1218  KQCLL-----PNQ-SESLA--YVEQHQPEFQEILERVVDFAEVHTLAK--SKVQQIV-K LFE-AN---QTADVKE--  1277
WP_016222645  1218  KQCLL-----PNQ-SESLA--YVEQHQPEFQEILERVVDFAEVHTLAK--SKVQQIV-K LFE-AN---QTADVKE--  1277
WP_033624816  1218  KQCLL-----PNQ-SESLA--YVEQHQPEFQEILERVVDFAEVHTLAK--SKVQQIV-K LFE-AN---QTADVKE--  1277
WP_033625576  1218  KQCLL-----PNQ-SESLA--YVEQHQPEFQEILERVVDFAEVHTLAK--SKVQQIV-K LFE-TN---QTADVKE--  1277
WP_033789179  1218  KQCLL-----PNQ-SESLA--YVEQHQPEFQEILERVVDFAEVHTLAK--SKVQQIV-K LFE-AN---QTDDLAK--  1277
WP_002310644  1220  KQYDEISHKESF-----D--YVNEHHKEFSEVFARVLEFAGKYTLAE--KNIEKLE-K IYK-EN---QTDDLAK--  1279
WP_002312694  1221  KQYDEISHKESF-----D--YVNEHHKEFSEVFARVLEFAGKYTLAE--KNIEKLE-K IYK-EN---QTDDLAK--  1280
WP_002314015  1221  KQYDEISHKESF-----D--YVNEHHKEFSEVFARVLEFAGKYTLAE--KNIEKLE-K IYK-EN---QTDDLAK--  1280
WP_002320716  1220  KQYDEISHKESF-----D--YVNEHHKEFSEVFARVLEFAGKYTLAE--KNIEKLE-K IYK-EN---QTDDLAK--  1279
WP_002330729  1221  KQYDEISHKESF-----D--YVNEHHKEFSEVFARVLEFAGKYTLAE--KNIEKLE-K IYK-EN---QTDDLAK--  1280
WP_002335161  1221  KQYDEISHKESF-----D--YVNEHHKEFSEVFARVLEFAGKYTLAE--KNIEKLE-K IYK-EN---QTDDLAK--  1280
WP_002345439  1221  KQYDEISHKESF-----D--YVNEHHKEFSEVFARVLEFAGKYTLAE--KNIEKLE-K IYK-EN---QTDDLAK--  1280
WP_034867970  1211  QHYDKITyQESF-----D--YVNTHLSDFSAILTEVLAFAEKYTLAD--KNIERIQ-E LYE-EN---KYGEISM--  1270
WP_034937432  1221  KQYDEISHKESF-----D--YVNTHLSDFSAILTEVLAFAEKYTLAD--KNIERIQ-E IYK-EN---QTDDLAK--  1280
WP_010720994  1211  QHYDKITyQESF-----D--YVNTHLSDFSAILTEVLAFAEKYTLAD--KNIERIQ-E LYE-EN---KYGEISM--  1270
WP_010737004  1211  QHYDKITyQESF-----D--YVNTHLSDFSAILTEVLAFAEKYTLAD--KNIERIQ-E LYE-EN---KYGEISM--  1270
WP_034700478  1209  KKIIN--gKNSD----SVS--YIQNNKEKFREIFEYIVDFSSKYISAD--ANLNKIE-K IFE-NNFh----KASEqe  1269
WP_007209003  1205  RHYDEINhKVSF-----D--YVNAHKEGENDIPDFISDEGVRYIAP--QHLEKIK-V AYE-EN---KEVDLKE--  1264
WP_023519017  1216  KQVDE-----DS-GKSEE--YVREHRAEFAEILNYVQAFSETKILAN--KNLQTIL-K LYE-EN---KEADIKE--  1274
WP_010770040  1213  KHCNE-----KP-D-SLK--YVTEHQSGFSEIMAHVKDFAEKYTLVD--KNLEKIL-S LYA-KN---MDSEVKE--  1270
WP_048604708  1214  NHYDEIAyKDSY-----D--YVNEHFSNFQDIILDKVIIFABKYTSAP--QKLNQII-A TYE-KN---QEADRKI--  1273
WP_010750235  1279  SHYEKLKgSPEDrEQKQL--FVEQHKHYLDEIIEQISEFSKRVILAD--ANlDKVL-S AYN-KH---RDKPIREq-  1344
AII16583      1226  YKAMKYK-NYSElSQEEIm-----------NVVDIFVEKLKLYYPTY-KNIATNFE-N FEN-----i----SDEEK  1282
WP_029073316  1226  YKAMKYK-NYDNIdSEKIi-----------DLYRLLINKMELYYPEYrKQLVKKFE-D LKV-----i----SIEEk  1283
WP_031589969  1200  NAKDG-----EQKLE-----DHKAEFKELPDKIMEFADKYVVAP--KNSEKIR-R LYE-ENq------DATPme  1253
KDA45870      1242  LPLTQ-----SElAEQV-----YDEILDQVMHYFPLYDTNQfrAKLsAGKaA DGN-KMv-----QVGQqv  1306
WP_039099354  1238  QIPDE-----DpDQILAf----YDKNILVEIlQELITKMKKFYPFY--KNEQEFLaS FNQ----------ATTSEk  1296
AKP02966      1216  ANCEV-----SD-GKSLD--YIESNREMFAELLAHVSEFAKRYTLAE--ANLNKIN-Q LFE-QN---KEGDIKA--  1274
WP_010991369  1216  ANCEV-----SD-GKSLD--YIESNREMFAELLAHVSEFAKRYTLAE--ANLNKIN-Q LFE-QN---KEGDIKA--  1274
WP_033838504  1219  ANCEV-----SD-GKSLD--YIESNREMFAELLAHVSEFAKRYTLAE--ANLNKIN-Q LFE-QN---KEGDIKA--  1277
EHN60060       985  ANCEV-----SD-GKSLD--YIESNREMFAELLAHVSEFAKRYTLAE--ANLNKIN-Q LFE-QN---KEGDIKA--  1043
EFR89594      1216  KNCEA-----ND-GESLA--YIEMHREMFAELLAYISEFAKRYTLAN--DRLEKIN-M FFE-QN---KKGDIKV--  1274
WP_038409211   835  KNCEA-----ND-GESLA--YIEMHREMFAELLAYISEFAKRYTLAN--DRLEKIN-M FFE-QN---KKGDIKV--   893
EFR95520      1216  KNCEA-----SD-GKSLK--YIEAHRETFSELLAQVSEFATRYTLAD--ANLSKIN-N LFE-QN---KEGDIKA--  1274
WP_003723650
```

```
-continued

WP_003727705   1216 KNCEA------SD-GKSLK--YIEAHRETFSELLAQVSEFATKYTLAD--ANLSKIN-N LFE-QN---KEGDIKA-- 1274
WP_003730785   1216 KNCEA------SD-GKSLK--YIEAHRETFSELLAQVSEFATKYTLAD--ANLSKIN-N LFE-QN---KEGDIKA-- 1274
WP_003733029   1216 EKYEA------ID-GESLA--YIEVHRALFDELLAYISEFARKYTLSN--DRLDEIN-M LYE-RN---KDGDVKS-- 1274
WP_003739838   1216 KNCEA------SD-GKSLD--YIESNREMFGELLAHVSEFAKRYTLAD--ANLSKIN-M LFE-QN---KDNDIKV-- 1274
WP_014601172   1216 KNCEA------SD-GKSLK--YIEAHRETFSELLAQVSEFATRYTLAD--ANLSKIN-N LFE-RN---KEGDIQA-- 1274
WP_023548323   1216 EKREA------ID-GESLA--YIEAHKAVFGELLAHISEFARKYTLAN--DKLDEIN-M LYE-RN---KDGDVKS-- 1274
WP_031665337   1216 KNCEA------SD-GKSLK--YIEAHRETFSEATRYTLAD--ANLSKIN-N LFE-QN---KEGDIKA-- 1274
WP_031669209   1216 EKYEA------ID-GESLA--YIEVHRALFDELLAYISEFARKYTLSN--DRLDEIN-M LYE-RN---KDGDVKS-- 1274
WP_033920898   1216 EKREA------ID-GESLA--YIEAHKAVFGELLAHISEFARKYTLAN--DKLDEIN-M LYE-RN---KDGDVKS-- 1274
AKI42028       1216 KNCEA------SD-GKSLK--YIEAHRETFSELLAQVSEFATRYTLAD--ANLSKIN-N LFE-QN---KEGDIQA-- 1277
AKI50529       1219 EKREA------ID-GESLA--YIEAHKAVFGELLAHISEFARKYTLAN--DKLDEIN-M LYE-RN---KDGDVKS-- 1277
EFR83390        664 ------------------------------------------------------------------KEGDIKX--  722
WP_046323366   1216 KNCEA------SD-GKSLK--YTEAHRETFSELLAQVSFATRYTLAD--ANLSKIN-T IFE-QN---KSGDVKV-- 1274
AKE81011       1256 SHYEKLkgSPEDnEQKQL-FVEQHKHYLDEIIEQISEFSKKVILAD--ANLDKVL-S AYN-KH---RDKPIREq- 1321
CUO82355       1216 YNAIYKQ-DFDG1DNMLMi---------QLYLQLQKMDTLYPAY-mGIVEKFE-K FVS--i----SKEEk-- 1272
WP_031162887   1218 YAAMLKK-RYEY1DEEEIf---------DLYLQLQKMDTLYPAY-kGIAKRFF-D FKN--i----DVVEk-- 1274
AGZ01981       1273 SHYEKLkgSPEDnEQKQL-FVEQHKHYLDEIIEQISEFSKRVILAD--ANLDKVL-S AYN-KH---RDKPIREq- 1338
AKA60242       1240 SHYEKLkgSPEDnEQKQL-FVEQHKHYLDEIIEQISEFSKRVILAD--ANLDKVL-S AYN-KH---RDKPIREq- 1305
AK540380       1240 SHYEKLkgSPEDnEQKQL-FVEQHKHYLDEIIEQISEFSKRVILAD--ANLDKVL-S AYN-KH---RDKPIREq- 1305
4UN5_B         1244 SHYEKLkgSPEDnEQKQL-FVEQHKHYLDEIIEQISEFSKRVILAD--ANLDKVL-S AYN-KH---RDKPIREq- 1309
WP_010922251   1306 -AE---NII HLFTLTNLGAP-AAFKYFD--TTI--DRK--R-YTSTKEVL DATLIHQSITGLYETRIDLSQl- 1365
WP_039695303   1309 ISN---SFI NLLJTLTALGAP-ADFNFLG--EKI--PRK--R-YTSTKECL NATLIHQSITGLYETRIDLSKl- 1369
WP_045635197   1307 LAN---SFI NLLTFTALGAP-AAFKFFG--KDI--DRK--R-YTTVSEIL NATLIHQSITGLYETWIDLSKl- 1367
5AXW_A                -AE---NII HLFTLTNLGAP-AAFKYFD--TTI--DRK--R-YTSTKEVL DATLIHQSITGLYETRIDLSQl-
WP_009880683    990 -AE---NII HLFTLTNLGAP-AAFKCFD--TTI--GRN--R-YKSIKEVL DATLIHQSITGLYETRIDLSQl- 1049
WP_010922251   1306 -AE---NII HLFTLTNLGAP-AAFKYFD--TTI--DRK--R-YTSTKEVL DATLIHQSITGLYETRIDLSQl- 1365
WP_011054416   1306 -AE---NII HLFTLTNLGAP-AAFKYFD--TTI--DRK--R-YTSTKEVL DATLIHQSITGLYETRIDLSQl- 1365
WP_011284745   1306 -AE---NII HLFTLTNLGAP-AAFKYFD--TTI--DRK--R-YTSTKEVL DATFIHQSITGLYETRIDLSQl- 1365
WP_011285506   1306 -AE---NII HLFTLTNLGAP-AAFKYFD--TTI--DRK--R-YTSTKEVL DATLIHQSITGLYETRIDLSQl- 1365
WP_011527619   1306 -AE---NII HLFTLTNFGAP-AAFIYPD--TTI--DRK--R-YTSTKEVL DATFIHQSITGLYETRIDLSQl- 1365
WP_012560673   1306 -AE---NII HLFTLTNLGAP-AAFKYFD--TTI--GRN--R-YKSIKEVL DATLIHQSITGLYETRIDLSQl- 1365
WP_014407541   1306 -AE---NII HLFTLTNLGAP-AAFKYFD--TTI--DRK--R-YTSTKEVL DATLIHQSITGLYETRIDLSQl- 1364
WP_020905136   1305 -AE---NII HLFTLTNLGAP-AAFKYFD--TTI--DRK--R-YTSTKEVL DATLIHQSITGLYETRIDLSQl- 1364
WP_023080005   1305 -AK---NII HLFTLTNLGAP-AAFKYFD--TTI--ERN--R-YKSIKEVL DATLIHQSITGLYETRIDLSQl- 1364
WP_023610282   1305 -AK---NII HLFTLTNLGAP-AAFKYFD--TTI--ERN--R-YKSIKEVL DATLIHQSITGLYETRIDLSQl- 1364
WP_023612963   1306 -AE---NII HLFTLTNLGAP-AAFKYFD--TTI--DRK--R-YTSTKEVL DATFIHQSITGLYETRIDLSQl- 1365
WP_030125963   1306 -AE---NII HLFTLTNLGAP-AAFKYFD--TTI--DRK--R-YTSTKEVL DATLIHQSITGLYETRIDLSQl- 1365
WP_030126706   1306 -AE---NII HLFTLTNFGAP-AAFIYPD--TTI--DRK--R-YTSTKEVL DATFIHQSITGLYETRIDLSQl- 1365
WP_031488318   1306 -AE---NII HLFTLTNLGAP-AAFKYFD--TTI--GRN--R-YKSIKEVL DATLIHQSITGLYETRIDLSQl- 1365
WP_032460140   1306 -AE---NII HLFTLTNLGAP-TAFKYFD--TTI--DRK--R-YTSTKEVL DATLIHQSITGLYETRIDLSQl- 1365
WP_032461047   1306 -AE---NII HLFTLTNLGAP-AAFKYFD--TTI--DRK--R-YTSTKEVL DATLIHQSITGLYETRIDLSQl- 1365
WP_032462016   1306 -AE---NII HLFTLTNLGAP-AAFKYFD--TTI--DRK--R-YTSTKEVL DATLIHQSITGLYETRIDLSQl- 1365
WP_032462936   1306 -AE---NII HLFTLTNLGAP-AAFKYFD--TTI--DRK--R-YTSTKEVL DATLIHQSITGLYETRIDLSQl- 1365
WP_022464890   1306 -AE---NII HLFTLTNLGAP-AAFKYFD--TTI--DRK--R-YTSTKEVL DATFIHQSITGLYETRIDLSQl- 1365
WP_033888930   1131 -AE---NII HLFTLTNLGAP-TAFKYFD--TTI--GRN--R-YKSIKEVL DATLIHQSITGLYETRIDLSQl- 1190
WP_038431314   1306 -AE---NII HLFTLTNLGAP-AAFKYFD--TTI--DRK--R-YTSTKEVL DATLIHQSITGLYETRIDLSQl- 1365
WP_038432938   1305 -AK---NII HLFTLTNLGAP-AAFKYFD--TTI--ERN--R-YKSIKEVL DATLIHQSITGLYETRIDLSQl- 1364
WP_038434062   1306 -AE---NII HLFTLTNLGAP-AAFKYFD--TTI--GRN--R-YKSIKEVL DATLIHQSITGLYETRIDLSQl- 1365
BAQ51233       1217 -AE---NII HLFTLTNLGAP-AAFKYFD--TTI--DRK--R-YTSTKEVL DATLIHQSITGLYETRIDLSQl- 1276
KGE60162        481 -AE---NII HLFTLTNLGAP-AAFKYFD--TTI--DRK--R-YTSTKEVL DATLIHQSITGLYETRIDLSQl-  540
KGE60856        244 -AE---NII HLFTLTNLGAP-AAFKYFD--TTI--DRK--R-YTSTKEVL DATLIHQSITGLYETRIDLSQl-  303
WP_002989955   1306 -AE---NII HLFTLTNLGAP-TAFKYFD--TTI--DRK--R-YTSTKEVL DATFIHQSITGLYETRIDLSQl- 1365
WP_003030002   1282 LAK---SFI SLLTFTAFGAP-AAFNFFG--ENI--DRK--R-YTSVTECL NATLIHQSITGLYETRIDLSKl- 1342
WP_003065552   1310 ISN---SFI NLLTLTALGAP-ADFNFLG--EKI--PRK--R-YTSTKECL NATLIHQSITGLYETRIDLSKI- 1370
```

-continued

| | | | | | | |
|---|---|---|---|---|---|---|
| WP_001040076 | 1307 | LAN---NII | NLFTFTSLGAP-AAFKFFD--KIV--DRK-R-YTSTKEVL | NSTLIHQSITGLYETRIDLGKL-- | 1367 |
| WP_001040078 | 1315 | LAN---NII | NLFTFTSLGAP-AAFKFFD--KIV--DRK-R-YTSTKEVL | NSTLIHQSITGLYETRIDLSKL-- | 1375 |
| WP_001040080 | 1307 | LAN---NII | NLFTFTSLGAP-AAFKFFD--KIV--DRK-R-YTSTKEVL | NSTLIHQSITGLYETRIDLGKL-- | 1367 |
| WP_001040081 | 1307 | LAN---NII | NLFTFTSLGAP-AAFKFFD--KIV--DRK-R-YTSTKEVL | NSTLIHQSITGLYETRIDLGKL-- | 1367 |
| WP_001040083 | 1307 | LAN---NII | NLFTFTSLGAP-AAFKFFD--KIV--DRK-R-YTSTKEVL | NSTLIHQSITGLYETRIDLGKL-- | 1367 |
| WP_001040085 | 1307 | LAN---NII | NLFTFTSLGAP-AAFKFFD--KIV--DRK-R-YTSTKEVL | NSTLIHQSITGLYETRIDLGKL-- | 1367 |
| WP_001040087 | 1307 | LAN---NII | NLFTFTSLGAP-AAFKFFD--KIV--DRK-R-YTSTKEVL | NSTLIHQSITGLYETRIDLGKL-- | 1367 |
| WP_001040088 | 1307 | LAN---NII | NLFTFTSLGAP-AAFKFFD--KIV--DRK-R-YTSTKEVL | NSTLIHQSITGLYETRIDLGKL-- | 1367 |
| WP_001040089 | 1307 | LAN---NII | NLFTFTSLGAP-AAFKFFD--KIV--DRK-R-YTSTKEVL | NSTLIHQSITGLYETRIDLGKL-- | 1367 |
| WP_001040090 | 1307 | LAN---NII | NLFTFTSLGAP-AAFKFFD--KIV--DRK-R-YTSTKEVL | NSTLIHQSITGLYETRIDLGKL-- | 1367 |
| WP_001040091 | 1307 | LAN---NII | NLFTFTSLGAP-AAFKFFD--KIV--DRK-R-YTSTKEVL | NSTLIHQSITGLYETRIDLGKL-- | 1367 |
| WP_001040092 | 1307 | LAK---NII | NLFTFTSLGAP-AAFKFFD--KSV--DRK-R-YTSTKEVL | DSTLIHQSITGLYETRIDLGKL-- | 1367 |
| WP_001040094 | 1307 | LAN---NII | NLFTFTSLGAP-AAFKFFD--KIV--DRK-R-YTSTKEVL | NSTLIHQSITGLYETRIDLGKL-- | 1367 |
| WP_001040095 | 1307 | LAN---NII | NLFTFTSLGAP-AAFKFFD--KIV--DRK-R-YTSTKEVL | NSTLIHQSITGLYETRIDLGKL-- | 1367 |
| WP_001040096 | 1307 | LAN---NII | NLFTFTSLGAP-AAFKFFD--KIV--DRK-R-YTSTKEVL | NSTLIHQSITGLYETRIDLGKL-- | 1367 |
| WP_001040097 | 1307 | LAN---NII | NLFTFTSLGAP-AAFKFFD--KIV--DRK-R-YTSTKEVL | NSTLIHKSITGLYETRIDLGKL-- | 1367 |
| WP_001040098 | 1307 | LAN---NII | NLFTFTSLGAP-AAFKFFD--KIV--DRK-R-YTSTKEVL | NSTLIHQSITGLYETRIDLGKL-- | 1367 |
| WP_001040099 | 1307 | LAN---NII | NLFTFTSLGAP-AAFKFFD--KIV--DRK-R-YTSTKEVL | NSTLIHQFITGLYETRIDLGKL-- | 1367 |
| WP_001040100 | 1307 | LAN---NII | NLFTFTSLGAP-AAFKFFD--KIV--DRK-R-YTSTKEVL | DSTLIHQSITGLYETRIDLGKL-- | 1367 |
| WP_001040104 | 1307 | LAK---NII | NLFTFTSLGAP-AAFKFFD--KSV--DRK-R-YTSTKEVL | NSTLIHQSITGLYETRIDLGKL-- | 1367 |
| WP_001040105 | 1307 | LAN---NII | NLFTFTSLGAP-AAFKFFD--KIV--DRK-R-YTSTKEVL | NSTLIHQSITGLYETRIDLGKL-- | 1367 |
| WP_001040106 | 1307 | LAN---NII | NLFTFTSLGAP-AAFKFFD--KIV--DRK-R-YTSTKEVL | NSTLIHQSITGLYETRIDLGKL-- | 1367 |
| WP_001040107 | 1307 | LAN---NII | NLFTFTSLGAP-AAFKFFD--KIV--DRK-R-YTSTKEVL | NSTLIHQSITGLYETRIDLGKL-- | 1367 |
| WP_001040108 | 1307 | LAN---NII | NLFTFTSLGAP-AAFKFFD--KIV--DRK-R-YTSTKEVL | NSTLIHQSITGLYETRIDLGKL-- | 1367 |
| WP_001040109 | 1307 | LAN---NII | NLFTFTSLGAP-AAFKFFD--KIV--DRK-R-YTSTKEVL | NSTLIHQSITGLYETRIDLGKL-- | 1367 |
| WP_001040110 | 1307 | LAN---NII | NLFTFTSLGAP-AAFKFFD--KIV--DRK-R-YTSTKEVL | NSTLIHQSITGLYETRIDLGKL-- | 1367 |
| WP_015058523 | 1307 | LAN---NII | NLFTFTSLGAP-AAFKFFD--KIV--DRK-R-YTSTKEVL | NSTLIHQSITGLYETRIDLGKL-- | 1367 |
| WP_017643650 | 1307 | LAN---NII | NLFTFTSLGAP-AAFKFFD--KIV--DRK-R-YTSTKEVL | NSTLIHQSITGLYETRIDLGKL-- | 1367 |
| WP_017647151 | 1307 | LAN---NII | NLFTFTSLGAP-AAFKFFD--KIV--DRK-R-YTSTKEVL | NSTLIHQSITGLYETRIDLGKL-- | 1367 |
| WP_017648376 | 1307 | LAN---NII | NLFTFTSLGAP-AAFKFFD--KIV--DRK-R-YTSTKEVL | NSTLIHQSITGLYETRIDLGKL-- | 1367 |
| WP_017649527 | 1307 | LAN---NII | NLFTFTSLGAP-AAFKFFD--KIV--DRK-R-YTSTKEVL | NSTLIHQSITGLYETRIDLGKL-- | 1367 |
| WP_017771611 | 1307 | LAN---NII | NLFTFTSLGAP-AAFKFFD--KIV--DRK-R-YTSTKEVL | NSTLIHQSITGLYETRIDLGKL-- | 1367 |
| WP_017771984 | 1307 | LAN---NII | NLFTFTSLGAP-AAFKFFD--KIV--DRK-R-YTSTKEVL | NSTLIHQSITGLYETRIDLGKL-- | 1367 |
| CFQ25032 | 1307 | LAN---NII | NLFTFTSLGAP-AAFKFFD--KIV--DRK-R-YTSTKEVL | NSTLIHQSITGLYETRIDLGKL-- | 1367 |
| CFV16040 | 1307 | LAN---NII | NLFTFTSLGAP-AAFKFFD--KIV--DRK-R-YTSTKEVL | NSTLIHQSITGLYETRIDLGKL-- | 1367 |
| KLJ37842 | 1307 | LAN---NII | NLFTFTSLGAP-AAFKFFD--KIV--DRK-R-YTSTKEVL | NSTLIHQSITGLYETRIDLGKL-- | 1367 |
| KLJ72361 | 1307 | LAN---NII | NLFTFTSLGAP-AAFKFFD--KIV--DRK-R-YTSTKEVL | NSTLIHQSITGLYETRIDLGKL-- | 1367 |
| KLL20707 | 1321 | LAN---NII | NLFTFTSLGAP-AAFKFFD--KIV--DRK-R-YTSTKEVL | NSTLIHQSITGLYETRIDLGKL-- | 1381 |
| KLL42645 | 1307 | LAN---NII | NLFTFTSLGAP-AAFKFFD--KIV--DRK-R-YTSTKEVL | NSTLIHQSITGLYETRIDLGKL-- | 1367 |
| WP_047207273 | 1307 | LAN---NII | NLFTFTSLGAP-AAFKFFD--KIV--DRK-R-YTSTKEVL | NSTLIHQSITGLYETRIDLGKL-- | 1367 |
| WP_047209694 | 1307 | LAN---NII | NLFTFTSLGAP-AAFKFFD--KIV--DRK-R-YTSTKEVL | NSTLIHQSITGLYETRIDLGKL-- | 1367 |
| WP_050198062 | 1307 | LAN---NII | NLFTFTSLGAP-AAFKFFD--KIV--DRK-R-YTSTKEVL | NSTLIHQSITGLYETRIDLGKL-- | 1367 |
| WP_050201642 | 1307 | LAN---NII | NLFTFTSLGAP-AAFKFFD--KIV--DRK-R-YTSTKEVL | NSTLIHQSITGLYETRIDLGKL-- | 1367 |
| WP_050204027 | 1307 | LAN---NII | NLFTFTSLGAP-AAFKFFD--KII--DRK-R-YTSTKEVL | NSTLIHQSITGLYETRIDLGKL-- | 1367 |
| WP_050881965 | 1307 | LAN---NII | NLFTFTSLGAP-AAFKFFD--KIV--DRK-R-YTSTKEVL | NSTLIHQSITGLYETRIDLGKL-- | 1367 |
| WP_050886065 | 1307 | LAN---NII | NLFTFTSLGAP-AAFKFFD--KIV--DRK-R-YTSTKEVL | NSTLIHQSITGLYETRIDLGKL-- | 1367 |
| AHN30376 | 1307 | LAK---NII | NLFTFTSLGAP-AAFKFFD--KSV--DRK-R-YTSTKEVL | DSTLIHQSITGLYETRIDLGKL-- | 1367 |
| EA078426 | 1307 | LAN---NII | NLFTFTSLGAP-AAFKFFD--KIV--DRK-R-YTSTKEVL | NSTLIHQSITGLYETRIDLGKL-- | 1367 |
| CCW42055 | 1307 | LAN---NII | NLFTFTSLGAP-AAFKFFD--KIV--DRK-R-YTSTKEVL | NSTLIHQSITGLYETRIDLGKL-- | 1367 |
| WP_003041502 | 1314 | ICT---SFL | GLFELTSLGSA-SDFEFLG--VKI--PRY-RdYTPSSLLK | DSTLIHQSITGLYETRIDLSKL-- | 1383 |
| WP_037593752 | 1283 | LAK---SFI | SLLTFTAFGAP-AAFNFFG--ENI--DRK-R-YTSVTECL | NATLIHQSITGLYETRIDLSKL-- | 1343 |
| WP_049516684 | 1283 | LAK---SFI | SLLTFTAFGAP-AAFNFFG--ENI--DRK-R-YTSVTECL | NATLIHQSITGLYETRIDLSKL-- | 1343 |
| GAD46167 | 1282 | LAK---SFI | SLLTFTAFGAP-AAFNFFG--ENI--DRK-R-YTSVTECL | NATLIHQSITGLYETRIDLSKL-- | 1342 |

```
WP_018363470   1314   ISD---SFI NLLTLTALGAP-ADFNFLG--BKI--PRK--R-YNSTKECL NATLIHQSITGLYETRIDLSKL--   1374
WP_003043819   1311   -SN---SFV SLLKYTSFGAS-GGFTFLD--LDVkqGRLJ-R-YQTVTEVL DATLIYQSITGLYETRTDLSQL--   1372
WP_006269658   1282   LAK---SFI SLLTFTAFGAP-AAFNFFG--ENI--DRK--R-YTSVTECL NATLIHQSITGLYETRIDLSKL--   1342
WP_048800889   1302   ISN---SFI HLLTLTALGAP-ADFNFJG--EKI--PRK--R-YTSTKECL NATLIHQSITGLYETRIDLSKL--   1362
WP_012767106   1309   -CS---SVI NLLTLTASGAP-ADFKFLG--TTI--PRK--R-YGSPQSIL SSTLIHQSITGLYETRIDLSQL--   1368
WP_014613333   1309   -CS---SVI NLLTLTASGAP-ADFKFLG--TTI--PRK--R-YGSPQSIL SSTLIHQSITGLYETRIDLSQL--   1368
WP_015017095   1309   -CS---SVI NLLTLTASGAP-ADFKFLG--TTI--PRK--R-YGSPQSIL SSTLIHQSITGLYETRIDLSQL--   1368
WP_015057649   1309   -CS---SVI NLLTLTASGAP-ADFKFLG--TTI--PRK--R-YGSPQSIL SSTLIHQSITGLYETRIDLSQL--   1368
WP_048272215   1309   -CS---SVI NLLTLTASGAP-ADFKFLG--TTI--PRK--R-YGSPQSIL SSTLIHQSITGLYETRIDLSQL--   1368
WP_049519324   1286   -AE---NII NVFTFVALGAP-AAFKFFD--ATI--DRK--R-YTSTKEVL NATLIHQSVTGLYETRIDLSQL--   1345
WP_012515931   1286   -AE---NII NVFTFVALGAP-AAFKFFD--ATI--DRK--R-YTSTKEVL NATLIHQSVTGLYETRIDLSQL--   1345
WP_021320964   1286   -AE---NII NVFTFVALGAP-AAFKFFD--ATI--DRK--R-YTSTKEVL NATLIHQSVTGLYETRIDLSKL--   1345
WP_037581760   1309   ISSlseSFI NLLKFISPGAP-GAFKFLK--LDV--KQSnlR-YKSTTEAL SATLIHQSVTGLYETRIDLSKL--   1374
WP_004232481   1307   LAS---SFI NLLTLTALGAP-ADFNFLG--EKI--PRK--R-YTSTKECL TATLIHQSITGLYETRIDLSKL--   1367
WP_009854540   1308   ISI---SFV NLLTLTALGAP-ADFKFLG--EKI--PRK--R-YTSTKECL NATLIHQSITGLYETRIDLSKL--   1368
WP_039695303   1308   ISN---SFI NLLTLTALGAP-ADFNFLG--EKI--PRK--R-YTSTKECL NATLIHQSITGLYETRIDLSKL--   1369
WP_014334983   1312   ISA---SFI NLLTLTALGAP-ADFNFLG--EKI--PRK--R-YTSTKECL SATLIHQSVTGLYETRIDLSKL--   1372
WP_030099269   1306   -AI---NML NLFTFTDLGAP-SAFKFFN--GDI--DRK--R-YSSTNEII NSTLIYQSPTGLYETRIDLSKL--   1365
AHY17476        --    --------- ----------- ----- -- --- --- -- ---------- -----------------------    --
AHY17476        138   -AI---NML NLFTFTDLGAP-SAFKFFNg--DI--DRK--R-YSSTNEII NSTLIYQSPTGLYETRIDLSRL--   197
ESR09100        --    --------- ----------- ----- -- --- --- -- ---------- -----------------------    --
AGM98575        --    --------- ----------- ----- -- --- --- -- ---------- -----------------------    --
ALF27331       1282   LAS---SFI NLLTFTAIGAP-AAFKFFD--NNI--DRK--R-YTSTTEIL NATLIHQSITGLYETRIDLSRL--   1342
WP_018372492   1290   -SFV---SFV -LLNFTMMGAA-TDFKFPG--QII--PRK--R-YPSTTECL KSTLIHQSITGLYETRIDLSKL--   1350
WP_045610828   1311   LSE---SFI SLLKLISFGAP-GTFKFLG--VEI--SQSnvR-YQSVSSCF NATLIHQSITGLYETRIDLSKL--   1373
WP_045635197   1307   LAN---SFI NLLTFTAIGAP-AAFKFPG--KDI--DRK--R-YTTVSEIL NATLIHQSITGLYETWIDLSKL--   1367
WP_002263549   1282   LAS---SFI NLLTFTAIGAP-ATFKFFD--KNI--DRK--R-YTSTTEIL NATLIHQSITGLYETRIDLNKL--   1342
WP_002263887   1282   LAS---SFI NLLTFTAIGAP-ATFKFFD--KNI--DRK--R-YTSTTEIL NATLIHQSITGLYETRIDLNKL--   1342
WP_002264920   1282   LAS---SFI NLLTFTAIGAP-ATFKFFD--KNI--DRK--R-YTSTTEIL NATLIHQSITGLYETRIDLNKL--   1342
WP_002269043   1282   LAS---SFI NLLTFTAIGAP-ATFKFFD--KNI--DRK--R-YTSTTEIL NATLIHQSITGLYETRIDLNKL--   1342
WP_002269448   1282   LAS---SFI NLLTFTAIGAP-ATFKFFD--KNI--DRK--R-YTSTTEIL NATLIHQSITGLYETRIDLSKL--   1342
WP_002271977   1282   LAS---SFI NLLTFTAIGAP-ATFKFFD--KNI--DRK--R-YTSTTEIL NATLIHQSITGLYETRIDLSKL--   1342
WP_002272766   1282   LAS---SFI NLLTFTAIGAP-ATFKFFD--KNI--DRK--R-YTSTTEIL NATLIHQSITGLYETRIDLSKL--   1342
WP_002273241   1282   LAS---SFI NLLTFTAIGAP-ATFKFFD--KNI--DRK--R-YTSTTEIL NATLIHQSITGLYETRIDLSKL--   1342
WP_002275430   1282   LAS---SFI NLLTFTAIGAP-AAFKFFD--KNI--DRK--R-YTSTTEIL NATLIHQSITGLYETRIDLSKL--   1342
WP_002276448   1282   LAS---SFI NLLTFTAIGAP-ATFKFFD--KNI--DRK--R-YTSTTEIL NATLIHQSITGLYETRIDLSKL--   1342
WP_002277050   1288   LAD---GFI KLLGFTQLGAT-SPFSFLG--IKL--NQK--Q-YTGKKDYL EATLIHQSITGLYETRIDLNKL--   1352
WP_002277364   1282   LAS---SFI NLLTFTAIGAP-ATFKFFD--KNI--DRK--R-YTSTTEIL NATLIHQSITGLYETRIDLNKL--   1342
WP_002279025   1282   LAS---SFI NLLTFTAIGAP-ATFKFFD--KNI--DRK--R-YTSTTEIL NATLIHQSITGLYETRIDLNKL--   1342
WP_002279859   1282   LAS---SFI NLLTFTAIGAP-ATFKFFD--KNI--DRK--R-YTSTTEIL NATLIHQSITGLYETRIDLSKL--   1342
WP_002280230   1282   LAS---SFI NLLTFTAIGAP-ATFKFFD--KNI--DRK--R-YTSTTEIL NATLIHQSITGLYETRIDLSKL--   1342
WP_002281696   1282   LSS---SFI NLLTFTAIGAP-ATFKFFD--KNI--DRK--R-YTSTTEIL NATLIHQSITGLYETRIDLSKL--   1342
WP_002282247   1288   LAD---GFI KLLGFTQLGAT-SPFSFLG--IKL--NQK--Q-YTGKKDYL EATLIHQSITGLYETRIDLSKL--   1352
WP_002282906   1282   LAS---SFI NLLTFTAIGAP-ATFKFFD--KNI--DRK--R-YTSTTEIL NATLIHQSITGLYETRIDLSKL--   1342
WP_002283846   1282   LAS---SFI NLLTFTAIGAP-ATFKFFD--KNI--DRK--R-YTSTTEIL NATLIHQSITGLYETRIDLSKL--   1342
WP_002287255   1282   LAS---SFI NLLTFTAIGAP-ATFKFFD--KNI--DRK--R-YTSTTEIL NATLIHQSITGLYETRIDLSKL--   1342
WP_002288990   1282   LAS---SFI NLLTFTAIGAP-ATFKFFD--KNI--DRK--R-YTSTTEIL NATLIHQSITGLYETRIDLSKL--   1342
WP_002289641   1282   LAS---SFI NLLTFTAIGAP-ATFKFFD--KNI--DRK--R-YTSTTEIL NATLIHQSITGLYETRIDLSKL--   1342
WP_002290427   1282   LAS---SFI NLLTFTAIGAP-ATFKFFD--KNI--DRK--R-YTSTTEIL NATLIHQSITGLYETRIDLSKL--   1342
WP_002295753   1282   LAS---SFI NLLTFTAIGAP-ATFKFFD--KNI--DRK--R-YTSTTEIL NATLIHQSITGLYETRIDLSKL--   1342
WP_002296423   1282   LAS---SFI NLLTFTAIGAP-ATFKFFD--KNI--DRK--R-YTSTTEIL NATLIHQSITGLYETRIDLSKL--   1342
WP_002304487   1296   LAS---SFI NLLTFTAIGAP-AAFKFFD--KNI--DRK--R-YTSTTEIL NATLIHQSITGLYETRIDLNKL--   1356
```

-continued

| ID | | | | | | | |
|---|---|---|---|---|---|---|---|
| WP_002305844 | 1282 | LAS---SFI | NLLTFTAIGAP-ATFKFFD--KNI--DRK--R-YTSTTEIL | NATLIHQSITGLYETRIDLSKL-- | 1342 |
| WP_002307203 | 1282 | LAS---SFI | NLLTFTAIGAP-ATFKFFD--KNI--DRK--R-YTSTTEIL | NATLIHQSITGLYETRIDLSKL-- | 1342 |
| WP_002310390 | 1282 | LAS---SFI | NLLTFTAIGAP-ATFKFFD--KNI--DRK--R-YTSTTEIL | NATLIHQSITGLYETRIDLSKL-- | 1342 |
| WP_002352408 | 1282 | LAS---SFI | NLLTFTAIGAP-ATFKFFD--KNI--DRK--R-YTSTTEIL | NATLIHQSITGLYETRIDLSKL-- | 1342 |
| WP_012997688 | 1282 | LAS---SFI | NLLTFTAIGAP-ATFKFFD--KNI--DRK--R-YTSTTEIL | NATLIHQSITGLYETRIDLSKL-- | 1342 |
| WP_014677909 | 1282 | LAS---SFI | NLLTFTAIGAP-ATFKFFD--KNI--DRK--R-YTSTTEIL | NATLIHQSITGLYETRIDLSKL-- | 1342 |
| WP_019312892 | 1282 | LAS---SFI | NLLTFTAIGAP-ATFKFFD--KNI--DRK--R-YTSTTEIL | NATLIHQSITGLYETRIDLSKL-- | 1342 |
| WP_019313659 | 1282 | LAS---SFI | NLLTFTAIGAP-ATFKFFD--KNI--DRK--R-YTSTTEIL | NATLIHQSITGLYETRIDLNKL-- | 1342 |
| WP_019314093 | 1282 | LAS---SFI | NLLTFTAIGAP-AAFKFFD--KNI--DRK--R-YTSTTEIL | NATLIHQSITGLYETRIDLSKL-- | 1342 |
| WP_019315370 | 1282 | LSS---SFI | NLLTFTAIGAP-AAFKFFD--KNI--DRK--R-YTSTTEIL | NATLIHQSITGLYETRIDLSKL-- | 1342 |
| WP_019803776 | 1282 | LSE---SFI | NLLTFTAIGAP-ATFKFFD--KNI--DRK--R-YTSTTEIL | NATLIHQSITGLYETRIDLNKL-- | 1342 |
| WP_019805234 | 1282 | LAS---SFI | NLLTFTAIGAP-ATFKFFD--KNI--DRK--R-YTSTTEIL | NATLIHQSITGLYETRIDLSKL-- | 1342 |
| WP_024783594 | 1282 | LAS---SFI | NLLTFTAIGAP-ATFKFFD--KNI--DRK--R-YTSTTEIL | NATLIHQSITGLYETRIDLSKL-- | 1342 |
| WP_024784288 | 1288 | LAD---GFI | KLLGFTQLGAT-SPFSFLG--IKL--NQK--Q-YTGKKDYL | EATLIHQSITGLYETRIDLSKL-- | 1352 |
| WP_024784666 | 1282 | LAS---SFI | NLLTFTAIGAP-ATFKFFD--KNI--DRK--R-YTSTTEIL | NATLIHQSITGLYETRIDLSKL-- | 1342 |
| WP_024784894 | 1282 | LAS---SFI | NLLTFTAIGAP-ATFKFFD--KNI--DRK--R-YTSTTEIL | NATLIHQSITGLYETRIDLSKL-- | 1342 |
| WP_024786433 | 1288 | LAD---GFI | KLLGFTQLGAT-SPFSFLG--IKL--NQK--Q-YTGKKDYL | EATLIHQSITGLYETRIDLSKL-- | 1352 |
| WP_049473442 | 1282 | LAS---SFI | NLLTFTAIGAP-ATFKFFD--KNI--DRK--R-YTSTTEIL | NATLIHQSITGLYETRIDLSKL-- | 1342 |
| WP_049474547 | 1282 | LAS---SFI | NLLTFTAIGAP-ATFKFFD--KNI--DRK--R-YTSTTEIL | KATLIHQSITGLYETRIDLNKL-- | 1342 |
| EMC03581 | 1275 | LAS---SFI | NLLTFTAIGAP-ATFKFFD--KNI--DRK--R-YTSTTEIL | NATLIHQSITGLYETRIDLSKL-- | 1335 |
| WP_000428612 | 1310 | LAN---SFI | NLLTFSLGAP-AAFKFPG--KDV--DRK--R-YTTVSEIL | NATLIHQSITGLYETRIDLSKL-- | 1370 |
| WP_000428613 | 1308 | LSE---SFI | SLLKLTSFGAP-AAFKFLG--VEI--SQSsvR-YKPNSQFL | DTTLIHQSITGLYETRIDLSKL-- | 1368 |
| WP_049523028 | 1303 | IAN---SFI | NLLTFTAPGAP-AVFKFPG--KDI--ERK--R-YSTVTEIL | KATLIHQSITGLYETRIDLSKL-- | 1363 |
| WP_003107102 | 1275 | -AT---NML | NLPFTFTGLGAP-ATLKFFN--VDI--DRK--R-YTSSTEIL | NSTLIRQSITGLYETRIDLSKL-- | 1334 |
| WP_054279288 | 1304 | -SI---SFL | NLPFKFTSFGAP-BKFTFLN--SEIkqDDV--R-YRSTKECL | NSTLIHQSVTGLYETRIDLSQF-- | 1365 |
| WP_049531101 | 1311 | LSE---SFI | SLLKLTSFGAP-GAFRFLG--VEI--SQSnvR-YQSVSSCF | NATLIHQSITGLYETRIDLSKL-- | 1373 |
| WP_049538452 | 1313 | LSE---SFI | SLLKLTSFGAP-GAFKFLG--VBI--SQSsvR-YKPNSQFL | DATLIHQSITGLYETRIDLSKL-- | 1373 |
| WP_049549711 | 1313 | LSE---SFI | SLLKLTSFGAP-GAFKFLG--AEI--SQSsvR-YKPNSQFL | DTTLIHQSITGLYETRIDLSKL-- | 1375 |
| WP_007896501 | 1312 | -AL---NML | NLFIFTSLGAP-STFVFFD--ETI--DRK--R-YTTSDVL | NGILIQQSITGLYETRIDLSRP-- | 1371 |
| EFR44625 | 1264 | -AL---NML | NLFIFTSLGAP-STFVFFD--ETI--DRK--R-YTTSDVL | NGILIQQSITGLYETRIDLSRF-- | 1323 |
| WP_002897477 | 1307 | LAN---SFI | NLLTFTAIGAP-AAFKFPG--KDV--DRK--R-YTTVSEIL | NATLIHQSITGLYETRIDLSKL-- | 1367 |
| WP_002906454 | 1312 | LSE---SFI | SLLKLTSFGAP-GAFKFLG--VEI--SQSsvR-YKPNSQFL | DTTLIHQSITGLYETRIDLSKL-- | 1374 |
| WP_009729476 | 1308 | LAN---SFI | NLLTFTAIGAP-AAFKFPG--KDV--DRK--R-YTTVSEIL | NATLIHQSITGLYETRIDLSKL-- | 1368 |
| CQR24647 | 1296 | LAQ---SFI | SLLKFTAPGAP-GGFKFLD--ADI--KQSnlR-YQTVTEVL | SSTLIHQSVTGLYETRIDLSKL-- | 1358 |
| WP_000066813 | 1312 | LAN---SFI | NLLTFTAIGAP-AAFKFLG--KDV--DRK--R-YTTVSEIL | NATLIHQSITGLYETRIDLSKL-- | 1372 |
| WP_009754323 | 1308 | LAN---SFI | NLLTFTAIGAP-AAFKFPG--KDV--DRK--R-YTTVSEIL | NATLIHQSITGLYETRIDLSKL-- | 1368 |
| WP_044674937 | 1301 | LTS---SFV | NLLTFTAIGAP-AAFKFLG--SVI--DRK--R-YTSIAEIL | EATLIHQSVTGLYETRIDLSKL-- | 1361 |
| WP_044676715 | 1303 | LTS---SFV | NLLTFTAIGAP-AAFKFLG--SVI--DRK--R-YTSIAEIL | EATLIHQSVTGLYETRIDLSKL-- | 1363 |
| WP_044680361 | 1301 | LTS---SFV | NLLTFTAIGAP-AAFKFLG--SVI--DRK--R-YTSIAEIL | EATLIHQSVTGLYETRIDLSKL-- | 1363 |
| WP_044681799 | 1301 | LTS---SFV | NLLTFTAIGAP-AAFKFLG--AEI--DRK--R-YTSIAEIL | EATLIHQSVTGLYETRIDLSKL-- | 1361 |
| WP_049533112 | 1314 | ICT---SFL | GLPELTSLGSA-SDFEFLG--VKI--PRY--RdYTPSSLLK | DSTLIHQSITGLYETRIDLSKL-- | 1383 |
| WP_029090905 | 1241 | -VK---VI | ELLKITQANATnGDLKLLK---M-sNREg-R-LGSVSVAL | DFKIINQSVTGLYQSIEDYNN--- | 1300 |
| WP_006506696 | 1269 | -AN---II | QMLIVMHRGPQnGNIVyDDf--KI-sDRIg-R-LKTKNHNL | NIVFISQSPTGIYTKKYKL---- | 1329 |
| AIT42264 | 1306 | -AE---NII | HLPTLTNLGAP-AAFKYFD--TTI--DRK--R-YTSTKEVL | DATLIHQSITGLYETRIDLSQL-- | 1365 |
| WP_034440723 | 1277 | LVE---SFI | NLLAITTKCGPA-ADITFLG--EKI--SRK--R-YRSTNCLW | GSEVIFQSPTGLYETRLRLE--- | 1335 |
| AKQ21048 | 1306 | -AE---NII | HLPTLTNLGAP-AAFKYFD--TTI--DRK--R-YTSTKEVL | DATLIHQSITGLYETRIDLSQL-- | 1365 |
| WP_004636532 | 1272 | TVE---SFV | NLMTFTAMGAP-ATFKYYG--ESI--TRS--R-YTSITEFR | GSTLIFQSITGLYETRYKL----- | 1329 |
| WP_002364836 | 1278 | IAA---SFI | QLMQFNAMGAP-STFKFFQ--KDI--ERA--R-YTSIKEIF | DATIIYQSPTGLYETRRKV----- | 1335 |
| WP_016631044 | 1229 | IAA---SFI | QLMQFNAMGAP-STFKFFQ--KDI--ERA--R-YTSIKEIF | DATIIYQSPTGLYETRRKV----- | 1286 |
| EM575795 | 1014 | LSQ---SFI | NLMQLNAMGAP-ADFKFFD--VII--PRK--R-YPSLTEIW | ESTITYQSTTGLRETRTRMATLwd | 1076 |
| WP_002373311 | 1278 | IAA---SFI | QLMQFNAMGAP-STFKFFQ--KDI--ERA--R-YTSIKEIF | DATIIYQSTTGLYETRRKV----- | 1335 |
| WP_002378009 | 1278 | IAA---SFI | QLMQFNAMGAP-STFKFFQ--KDI--ERA--R-YTSIKEIF | DATIIYQSTTGLYETRRKV----- | 1335 |
| WP_002407324 | 1278 | IAA---SFI | QLMQFNAMGAP-STFKFFQ--KDI--ERA--R-YTSIKEIF | DATIIYQSTTGLYETRRKV----- | 1335 |

-continued

```
WP_002413717   1278 IAA---SFI QLMQFNAMGAP-STFKFFQ--KDI--ERA-R-YTSIKEIF DATIIYQSTTGLYETRRKV----  1335
WP_010775580   1280 IAA---SFI QLMQFNAMGAP-STFKFFQ--KDI--ERA-R-YTSIKEIF DATIIYQSTTGLYETRRKV----  1337
WP_010818269   1278 IAA---SFI QLMQFNAMGAP-STFKFFQ--KDI--ERA-R-YTSIKEIF DATIIYQSTTGLYETRRKV----  1335
WP_010824395   1278 IAA---SFI QLMQFNAMGAP-STFKFFQ--KDI--ERA-R-YTSIKEIF DATIIYQSTTGLYETRRKV----  1335
WP_016622645   1278 IAA---SFI QLMQFNAMGAP-STFKFFQ--KDI--ERA-R-YTSIKEIF DATIIYQSTTGLYETRRKV----  1335
WP_033625576   1278 IAA---SFI QLMQFNAMGAP-STFKFFQ--KDI--ERA-R-YTSIKEIF DATIIYQSTTGLYETRRKV----  1335
WP_033789179   1278 IAA---SFI QLMQFNAMGAP-STFKFFQ--KDI--ERA-R-YTSIKEIF DATIIYQSTTGLYETRRKV----  1335
WP_002310644   1280 LAS---SFV NLMQFNAMGAP-ADFKFFD--VTI--PRK-R-YTSLTEIW QSTIIHQSITGLYETRIRMGK--  1339
WP_002312694   1281 LAS---SFV NLMQFNAMGAP-ADFKFFD--VTI--PRK-R-YTSLTEIW QSTIIHQSITGLYETRIRMGK--  1340
WP_002314015   1281 LAS---SFV NLMQFNAMGAP-ADFKFFD--VTI--PRK-R-YTSLTEIW QSTIIHQSITGLYETRIRMGK--  1340
WP_002320716   1281 LAS---SFV NLMQFNAMGAP-ADFKFFD--VTI--PRK-R-YTSLTEIW QSTIIHQSITGLYETRIRMGK--  1340
WP_002330729   1280 LAS---SFV NLMQFNAMGAP-ADFKFFD--VTI--PRK-R-YTSLTEIW QSTIIHQSITGLYETRIRMGK--  1339
WP_002335161   1281 LAS---SFV NLMQFNAMGAP-ADFKFFD--VTI--PRK-R-YTSLTEIW QSTIIHQSITGLYETRIRMGK--  1340
WP_002345439   1281 LAS---SFV NLMQFNAMGAP-ADFKFFD--VTI--PRK-R-YTSLTEIW QSTIIHQSITGLYETRIRMGK--  1340
WP_034867970   1281 LAS---SFV NLMQFNAMGAP-ADFKFFD--VTI--PRK-R-YTSLTEIW QSTIIHQSVTGLYETRIRMGDLwa 1340
WP_047937432   1271 IAQ---SFL QLLQFNAIGAP-ADFKFFG--VTI--PRK-R-YTSLTEIW DATIIYQSVTGLYETRIRMGDLwa 1333
WP_010720994   1271 IAQ---SFL QLLQFNAIGAP-ADFKFFG--VTI--PRK-R-YTSLTEIW DATIIYQSVTGLYETRIRMGDLwa 1333
WP_010737004   1271 IAQ---SFL QLLQFNAIGAP-ADFKFFG--ETI--PRS-R-YTSVNELL EATIINQSITGLYETRRKL---- 1332
WP_034700478   1271 IAQ---SFL QLLQFNAIGAP-ADFKFFG--VTI--PRK-R-YTSLTEIW DATIIYQSVTGLYETRIRMGDLwa 1333
WP_007209003   1270 IAK---SFI NLLTFTAMGAP-ADFEFFG--EKI--PRK-R-YVSISEII DAVFIHQSITGLYETRVRLTEV- 1330
WP_023519917   1265 MID---AIL SLLKFTLFGAS-VEFKFFD--IKI--LK-R-YKSLTDIW EATIIYQSVTGLYERRVEVRKLwd 1326
WP_010770040   1275 IAE---SFV NLMKFSAYGAP-MDFKFFG--ETI--PRS-R-YTSVGELL SATINQSITGLYETRRKL----  1332
WP_048604708   1271 IAQ---SFV DLMQLNAFGAP-ADFKFFE--ETI--PRK-R-YTSVNELL EATIINQSITGLYETRRKL----  1328
WP_010750235   1274 MAH---SFV NLMQFNALGAP-ADFKFFD--TTI--TRK-R-YTSLTEIW QSTIIYQSVTGLYETRRRMADLwd 1336
AII16583       1345 -AE---NII HLFTLTNLGAP-AAFKYFD--TTI--DRK-R-YTSTKEVL DATLIHQSITGLYETRIDLSQL- 1404
WP_029073316   1283 -CE---VI  QMLVVMHAGPQnGNITFDDf--KL-sNRIg-R-LNCKTISL TTVFIADSPTGMYSKKYKL---  1343
WP_031589969   1284 -CN---II  QILATLHCNSSiGKIMYSDf--KI-sTTIg-R-LNGRTISL DISFIAESPTGMYSKKYKL---  1344
KDA45870       1254 LGK---NFV ELLRYTADGAA-SDFKFFG--ENI--PRK-R-YNSAGSLL NGTLIYQSKTGLYETRIDLGKL  1314
WP_039099354   1307 ILDr--V  -LIGLHANAAV-SDLGVLKisTPL--GKM--Q--QPSGIS DTQIIYQSPTGLFERRVALRDL  1368
AKP02966       1297 INS1-eELI TLLHANSTSAH-LIFNNIE-kKAP--GRK------THGLT DTDFIYQSVTGLYETRIHIE-  1356
WP_010991369   1275 IAQ---SFV DLMAFNAMGAP-ASFKFFE--BRK--DRK-R-YNNLKELL NSTIIYQSITGLYESRKRL---  1332
WP_033838504   1275 IAQ---SFV DLMAFNAMGAP-ASFKFFE--TTI--BRK-R-YNNLKELL NSTIIYQSITGLYESRKRL---  1332
EHN60060       1278 IAQ---SFV DLMAFNAMGAP-ASFKFFE--ATI--BRK-R-YNNLKELL SATIIYQSITGLYEARKRL---  1335
EFR89594       1044 IAQ---SFV DLMAFNAMGAP-ASFKFFE--TTI--BRK-R-YNNLKELL NSTIIYQSITGLYESRKRL---  1101
WP_038409211   1275 IAK---SFD KLKVFNAFGAP-RDFEFFE--TTI--KRK-R-YYNIKELL NATIIYQSITGLYEARKRL---  1332
EFR95520       894  IAK---SFD KLKVFNAFGAP-KDFNFFG--TTI--KRK-R-YYNIKELL NATIIYQSITGLYEARKRL---  951
WP_003723650   1275 IAQ---SFV DLMAFNAMGAP-ASFKFFE--ATI--DRK-R-YTNLKELL SSTIIYQSITGLYESRKRL---  1332
WP_003727705   1275 IAQ---SFV DLMAFNAMGAP-ASFKFFE--ATI--DRK-R-YTNLKELL SSTIIYQSITGLYESRKRL---  1332
WP_003730785   1275 IAQ---SFV DLMAFNAMGAP-ASFKFFE--ATI--DRK-R-YTNLKELL SSTIIYQSITGLYESRKRL---  1332
WP_003733029   1275 IAE---SFV SLKKFNAFGVH-QDFSFFG--TKI--DRK-R-YTNLKELL NSTIIYQSITGLYESRKRL---  1332
WP_003739838   1275 IAQ---SFV NLMAFNAMGAP-ASFKFFE--ATI--BRK-R-YTNLKELL SATIIYQSITGLYEARKRL---  1332
WP_014601172   1275 IAQ---SFV DLMAFNAMGAP-ASFKFFE--ATI--DRK-R-YTNLKELL SSTIIYQSITGLYESRKRL---  1332
WP_023548323   1275 IAE---SFV SLKKFNAFGVH-KDFNFFG--TTI--KRK-R-YTNLKELL NSTIIYQSITGLYESRKRL---  1332
WP_031665337   1275 IAE---SFV DLMAFNAMGAP-ASFKFFE--ATI--DRK-R-YTNLKELL SSTIIYQSITGLYESRKRL---  1332
WP_031669209   1275 IAE---SFV SLKKFNAFGVH-KDFNFFG--TKI--BRK-R-YTNLKELL NSTIIYQSITGLYESRKRL---  1332
WP_033920898   1278 IAE---SFV SLKKFNAFGVH-QDFSFFG--TKI--DRK-R-YTNLKELL SSTIIYQSITGLYESRKRL---  1335
AKI42028       1275 IAQ---SFV DLMVFNAMGAP-ASFKYFE--TNI--BRK-R-YNNLKELL NATIIYQSITGLYEARKRL---  1332
AKI50529       723  -AE---NII HLFTLTNLGAP-AAFKYFD--TTI--DRK-R-YTSTKEVL DATLIHQSITGLYETRIDLSQL- 780
EFR83390       1275 IAQ---SFV NLLEFNAMGAP-ASFKYFE--TNI--BRK-R-YNNLKELL NATIIYQSITGLYEARKRL---  1332
WP_046323366   1322 -AE---NII HLFTLTNLGAP-AAFKYFD--TTI--DRK-R-YTSTKEVL DATLIHQSITGLYETRIDLSQL- 1381
AKE81011       1273 -AN---VI  QMLIIMHKGPQnGNIIYDDf--NV-gKRIg-R-LNGRFFYL NIEFISQSPTGIYTKKYL---  1333
CUO82355
```

```
                                                       -continued

WP_033162887    1275 -CD----VI QLLIMHAGPMnGNIMYDDf--KF-tNRig-R-FTHKNIDL KTTFISTSVTGLFSKKYKL----- 1335
AGZ01981        1339 -AE----NII HLFTLTNLGAP-AAFKYFD--TTI--DRK--R-YTSTKEVL DATLIHQSITGLYETRIDLSQL-- 1398
AKA60242        1306 -AE----NII HLFTLTNLGAP-AAFKYFD--TTI--DRK--R-YTSTKEVL DATLIHQSITGLYETRIDLSQL-- 1365
AKS40380        1306 -AE----NII HLFTLTNLGAP-AAFKYFD--TTI--DRK--R-YTSTKEVL DATLIHQSITGLYETRIDLSQL-- 1365
4UN5_B          1310 -AE----NII HLFTLTNLGAP-AAFKYFD--TTI--DRK--R-YTSTKEVL DATLIHQSITGLYETRIDLSQL-- 1369

WP_010922251    1366 GGD 1368
WP_010922251    1370 GEE 1372
WP_039695303    1368 GED 1370
WP_045635197    ---  ---
5AXW_A          1050 GGD 1052
WP_009880683    1366 GGD 1368
WP_010922251    1366 GGD 1368
WP_011054416    1366 GGD 1368
WP_011284745    1366 GGD 1368
WP_011285506    1366 GGD 1368
WP_011527619    1366 GGD 1368
WP_012560673    1365 GGD 1367
WP_012560673    1366 GGD 1368
WP_014407541    1365 GGD 1367
WP_020905136    1365 GGD 1367
WP_023080005    1366 GGD 1368
WP_023610282    1366 GGD 1368
WP_030125963    1366 GGD 1368
WP_030126706    1366 GGD 1368
WP_031488318    1366 GGD 1368
WP_032460140    1366 GGD 1368
WP_032461047    1366 GGD 1368
WP_032462016    1366 GGD 1368
WP_032462936    1366 GGD 1368
WP_032464890    1366 GGD 1368
WP_033888930    1191 GGD 1193
WP_038431314    1366 GGD 1368
WP_038432938    1365 GGD 1367
WP_038434062    1366 GGD 1368
BAQ51233        1277 GGD 1279
KGE60162        541  GGD 543
KGE60856        304  GGD 306
WP_002989955    1366 GGD 1368
WP_003030002    1343 GED 1345
WP_003065552    1371 GEE 1373
WP_001040076    1368 GGD 1370
WP_001040078    1376 GED 1378
WP_001040080    1368 GED 1370
WP_001040081    1368 GED 1370
WP_001040083    1368 GED 1370
WP_001040085    1368 GED 1370
WP_001040087    1368 GED 1370
WP_001040088    1368 GGD 1370
WP_001040089    1368 GGD 1370
WP_001040090    1368 GGD 1370
WP_001040091    1368 GGD 1370
WP_001040092    1368 GED 1370
WP_001040094    1368 GED 1370
WP_001040095    1368 GEG 1370
```

-continued

| | | |
|---|---|---|
| WP_001040096 | 1368 GEG | 1370 |
| WP_001040097 | 1368 GED | 1370 |
| WP_001040098 | 1368 GED | 1370 |
| WP_001040099 | 1368 GED | 1370 |
| WP_001040100 | 1368 GED | 1370 |
| WP_001040104 | 1368 GED | 1370 |
| WP_001040105 | 1368 GED | 1370 |
| WP_001040106 | 1368 GED | 1370 |
| WP_001040107 | 1368 GED | 1370 |
| WP_001040108 | 1368 GED | 1370 |
| WP_001040109 | 1368 GED | 1370 |
| WP_001040110 | 1368 GED | 1370 |
| WP_015058523 | 1368 GED | 1370 |
| WP_017643650 | 1368 GED | 1370 |
| WP_017647151 | 1368 GED | 1370 |
| WP_017648376 | 1368 GED | 1370 |
| WP_017649527 | 1368 GED | 1370 |
| WP_017771611 | 1368 GED | 1370 |
| WP_017771984 | 1368 GED | 1370 |
| CFQ25032 | 1368 GED | 1370 |
| CFV16040 | 1368 GED | 1370 |
| KLJ37842 | 1368 GGD | 1370 |
| KLJ72361 | 1382 GED | 1384 |
| KLL20707 | 1368 GED | 1370 |
| KLL42645 | 1368 GED | 1370 |
| WP_047207273 | 1368 GED | 1370 |
| WP_047209694 | 1368 GED | 1370 |
| WP_050198062 | 1368 GED | 1370 |
| WP_050201642 | 1368 GED | 1370 |
| WP_050204027 | 1368 GED | 1370 |
| WP_050881965 | 1368 GED | 1370 |
| WP_050886065 | 1368 GED | 1370 |
| AHN30376 | 1368 GED | 1370 |
| EA078426 | 1368 GED | 1370 |
| CCW42055 | 1384 GED | 1386 |
| WP_003041502 | 1344 GED | 1346 |
| WP_037593752 | 1344 GED | 1346 |
| WP_049516684 | 1343 GED | 1345 |
| GAD46167 | 1375 GEE | 1377 |
| WP_018363470 | 1373 GEE | 1375 |
| WP_003043819 | 1343 GED | 1345 |
| WP_006269658 | 1363 GED | 1365 |
| WP_048800889 | 1369 GGD | 1371 |
| WP_012767106 | 1369 GGD | 1371 |
| WP_014612333 | 1369 GGD | 1371 |
| WP_015017095 | 1369 GGD | 1371 |
| WP_015057649 | 1369 GEN | 1348 |
| WP_048327215 | 1346 GEN | 1348 |
| WP_049519324 | 1346 GEN | 1348 |
| WP_012515931 | 1346 GEN | 1348 |
| WP_021320964 | 1346 GEN | 1348 |
| WP_037581760 | 1346 GEN | 1348 |
| WP_004232481 | 1375 GEE | 1377 |

-continued

| | | |
|---|---|---|
| WP_009854540 | 1368 GEE | 1370 |
| WP_012962174 | 1369 GEE | 1371 |
| WP_039695303 | 1370 GEE | 1372 |
| WP_014334983 | 1373 GEE | 1375 |
| WP_003099269 | 1366 GGK | 1368 |
| AHY15608 | - - | |
| AHY17476 | - - | |
| ESR09100 | 198 GGK | 200 |
| AGM98575 | - - | |
| ALF27331 | 1343 GGD | 1345 |
| WP_018372492 | 1351 GGD | 1353 |
| WP_045618028 | 1374 GEN | 1376 |
| WP_045635197 | 1368 GED | 1370 |
| WP_002263549 | 1343 GGD | 1345 |
| WP_002263887 | 1343 GGD | 1345 |
| WP_002264920 | 1343 GGD | 1345 |
| WP_002269043 | 1343 GGD | 1345 |
| WP_002269448 | 1343 GGD | 1345 |
| WP_002271977 | 1343 GGD | 1345 |
| WP_002272766 | 1343 GGD | 1345 |
| WP_002273241 | 1343 GGD | 1345 |
| WP_002275430 | 1343 GGD | 1345 |
| WP_002276448 | 1343 GGD | 1345 |
| WP_002277050 | 1353 GGD | 1355 |
| WP_002277364 | 1343 GGD | 1345 |
| WP_002279025 | 1343 GGD | 1345 |
| WP_002279859 | 1343 GGD | 1345 |
| WP_002280230 | 1343 GGD | 1345 |
| WP_002281696 | 1343 GGD | 1345 |
| WP_002282247 | 1353 GGD | 1355 |
| WP_002282906 | 1343 GGD | 1345 |
| WP_002283846 | 1343 GGD | 1345 |
| WP_002287255 | 1343 GGD | 1345 |
| WP_002288990 | 1343 GGD | 1345 |
| WP_002289641 | 1343 GGD | 1345 |
| WP_002290427 | 1343 GGD | 1345 |
| WP_002295753 | 1343 GGD | 1345 |
| WP_002296423 | 1343 GGD | 1345 |
| WP_002304487 | 1357 GGD | 1359 |
| WP_002305844 | 1343 GGD | 1345 |
| WP_002307203 | 1343 GGD | 1345 |
| WP_002310390 | 1343 GGD | 1345 |
| WP_002352408 | 1343 GGD | 1345 |
| WP_012997688 | 1343 GGD | 1345 |
| WP_014677909 | 1343 GGD | 1345 |
| WP_019312892 | 1343 GGD | 1345 |
| WP_019313659 | 1343 GGD | 1345 |
| WP_019314093 | 1343 GGD | 1345 |
| WP_019315370 | 1343 GGD | 1345 |
| WP_019803776 | 1343 GGD | 1345 |
| WP_019805234 | 1343 GGD | 1345 |
| WP_024783594 | 1343 GGD | 1345 |
| WP_024784288 | 1353 GGD | 1355 |

-continued

| | | | |
|---|---|---|---|
| WP_024784666 | 1343 | GGD | 1345 |
| WP_024784894 | 1343 | GGD | 1345 |
| WP_024786433 | 1353 | GGD | 1355 |
| WP_049473442 | 1343 | GGD | 1345 |
| WP_049474547 | 1343 | GGD | 1345 |
| EMC03581 | 1336 | GGD | 1338 |
| WP_000428612 | 1371 | GED | 1373 |
| WP_000428613 | 1369 | GED | 1371 |
| WP_049523028 | 1364 | GEE | 1366 |
| WP_003107102 | 1335 | GGD | 1337 |
| WP_054279288 | 1366 | GED | 1368 |
| WP_049531101 | 1374 | GED | 1376 |
| WP_049538452 | 1374 | GED | 1376 |
| WP_049549711 | 1376 | GED | 1378 |
| WP_007896501 | 1372 | GED | 1374 |
| EFR44625 | 1324 | GGD | 1326 |
| WP_002897477 | 1368 | GEE | 1370 |
| WP_002906454 | 1375 | GED | 1377 |
| WP_009729476 | 1369 | GED | 1371 |
| CQR24647 | 1359 | GGE | 1361 |
| WP_000066813 | 1373 | GED | 1375 |
| WP_009754323 | 1369 | GED | 1371 |
| WP_044674937 | 1362 | GGD | 1364 |
| WP_044676715 | 1364 | GGD | 1366 |
| WP_044680361 | 1364 | GGD | 1366 |
| WP_044681799 | 1362 | GGD | 1364 |
| WP_049533112 | 1384 | GED | 1386 |
| WP_029090905 | | - - | |
| WP_006506696 | | - - | |
| A1T42264 | 1366 | GGD | 1389 |
| WP_034440723 | | | |
| AKQ21048 | 1366 | GGD | 1384 |
| WP_004636532 | 1330 | -ED | 1332 |
| WP_002364836 | 1336 | -VD | 1337 |
| WP_016631044 | 1287 | -VD | 1288 |
| EMS75795 | 1077 | GEQ | 1079 |
| WP_002373311 | 1336 | -VD | 1337 |
| WP_002378009 | 1336 | -VD | 1337 |
| WP_002407324 | 1336 | -VD | 1337 |
| WP_002413717 | 1338 | -VD | 1339 |
| WP_010775580 | 1336 | -VD | 1337 |
| WP_010818269 | 1336 | -VD | 1337 |
| WP_010824395 | 1336 | -VD | 1337 |
| WP_016622645 | 1336 | -VD | 1337 |
| WP_033624816 | 1336 | -VD | 1337 |
| WP_033789179 | 1336 | -VD | 1337 |
| WP_002310644 | | - - | |
| WP_002312694 | | - - | |
| WP_002314015 | | - - | |
| WP_002320716 | | - - | |
| WP_002330729 | | - - | |
| WP_002335161 | | - - | |

-continued

| | | |
|---|---|---|
| WP_002345439 | | |
| WP_034867970 | 1334 | --- |
| WP_047937432 | | |
| WP_010720994 | 1334 | GEQ |
| WP_010737004 | 1334 | GEQ |
| WP_034700478 | 1334 | GEQ |
| WP_007209003 | | --- |
| WP_023519017 | 1327 | GER |
| WP_010770040 | 1333 | -VD |
| WP_048604708 | 1329 | -GD |
| WP_010750235 | 1337 | GVQ |
| AII16583 | 1405 | GGD |
| WP_029073316 | | |
| WP_031589969 | | |
| KDA45870 | | |
| WP_039099354 | | |
| AKP02966 | | |
| WP_010991369 | 1333 | -DD |
| WP_033838504 | 1333 | -DD |
| EHN60060 | 1336 | -DD |
| EFR89594 | 1102 | -DD |
| WP_038409211 | 1333 | -ED |
| EFR95520 | 952 | -ED |
| WP_003723650 | 1333 | -DD |
| WP_003727705 | 1333 | -DD |
| WP_003730785 | 1333 | -DD |
| WP_003733029 | 1333 | -DN |
| WP_003739838 | 1333 | -DG |
| WP_014601172 | 1333 | -DD |
| WP_023548323 | 1333 | -DS |
| WP_031665337 | 1333 | -DD |
| WP_031669209 | 1333 | -DN |
| WP_033920898 | 1333 | -DS |
| AKI42028 | 1336 | -DD |
| AKI50529 | 1336 | -DS |
| EFR83390 | 781 | -DD |
| WP_046323366 | 1333 | -DD |
| AKE81011 | 1382 | GGD |
| CUO82355 | | --- |
| WP_033162887 | | |
| AGZ01981 | 1399 | GGD |
| AKA60242 | 1366 | GGD |
| AKS40380 | 1366 | GGD |
| 4UN5_B | 1370 | GGD |

| | |
|---|---|
| | 1336 |
| | 1336 |
| | 1336 |
| | 1336 |
| | 1330 |
| | 1334 |
| | 1330 |
| | 1339 |
| | 1424 |
| | 1334 |
| | 1334 |
| | 1337 |
| | 1103 |
| | 1334 |
| | 953 |
| | 1334 |
| | 1334 |
| | 1334 |
| | 1334 |
| | 1334 |
| | 1334 |
| | 1334 |
| | 1334 |
| | 1334 |
| | 1334 |
| | 1337 |
| | 1337 |
| | 782 |
| | 1334 |
| | 1400 |
| | 1417 |
| | 1368 |
| | 1376 |
| | 1372 |

TABLE 2

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000071.2 (CBS):c.833T>C (p.Ile278Thr) | 875 | CBS | 2540 | ['CTGAAGCCGC GCCCTCTGCAG ATCAYTGGGGT GGATCCCGAA GGGTCCATC'] | 2703-2704 | ['ATCAYTGGGGTG GATCCCGAAGG', 'TCAYTGGGGTGGA TCCCGAAGGG'] | 2907-2908 | ['ATCAYTGGGGTG GATCCCGAAGG', 'TCAYTGGGGTGG ATCCCGAAGGG'] |
| NM_001385.2 (DPYS):c.1078T>C (p.Trp360Arg) | 1807 | DPYS | 2541 | ['TGTTGAAGAT CGGATGTCCGT AATAYGGGAA AAAGGCGTGG TGGGTTTCAC'] | 2705-2707 | ['CGTAATAYGGGA AAAAGGCGTGG', 'AATAYGGGAAAA AGGCGTGGTGG', 'ATAYGGGAAAAA GGCGTGGTGGG'] | 2909-2911 | ['CGTAATAYGGGA AAAAGGCGTGG', 'AATAYGGGAAAA AGGCGTGGTGG', 'ATAYGGGAAAAA GGCGTGGTGGG'] |
| NM_000027.3 (AGA):c.916T>C (p.Cys306Arg) | 175 | AGA | 2542 | ['TCCAGAATTC TTTGGGGCTGT TATAYGTGCCA ATGTGACTGGA AGTTACGG'] | 2708 | ['GTTATAYGTGCC AATGTGACTGG'] | 2912 | ['GTTATAYGTGCC AATGTGACTGG'] |
| NM_000035.3 (ALDOB):c.442T>C (p.Trp148Arg) | 229 | ALDOB | 2543 | ['GAAAGATGGT GTTGACTTTGG GAAGYGGCGT GCTGTGCTGAG GATTGCCGA'] | 2709 | ['GGAAGYGGCGTG CTGTGCTGAGG'] | 2913 | ['GGAAGYGGCGT GCTGTGCTGAGG'] |
| NM_173560.3 (RFX6):c.380+2T>C | 222546 | RFX6 | 2544 | ['GCAGACACAG CTCACGCTGCA GTGGYGAGAC TCGCCCGCAGG GTACACTGA'] | 2710-2711 | ['CAGTGGYGAGAC TCGCCCGCAGG', 'AGTGGYGAGACTC GCCCGCAGGG'] | 2914-2915 | ['CAGTGGYGAGAC TCGCCCGCAGG', 'AGTGGYGAGACT CGCCCGCAGGG'] |
| NM_153704.5 (TMEM67):c.1843T>C (p.Cys615Arg) | 91147 | TMEM67 | 2545 | ['AGAACGTTTT GTCACTTATGT TGGAHGTGCCT TTGCTCTGAAG GTAAGTTT'] | 2712 | ['TGGAHGTGCCTTT GCTCTGAAGG'] | 2916 | ['TGGAHGTGCCTT TGCTCTGAAGG'] |
| NM_000124.3 (ERCC6):c.2960T>C (p.Leu987Pro) | 2074 | ERCC6 | 2546 | ['AAGCAGTTTT TGACAAATAG AGTGCYAAAA GACCCAAAAC AAAGGCGGTTT'] | 2713 | ['TGCYAAAAGACC CAAAACAAAGG'] | 2917 | ['TGCYAAAAGACC CAAAACAAAGG'] |
| NM_020435.3 (GJC2):c.857T>C (p.Met286Thr) | 57165 | GJC2 | 2547 | ['TGCCTGCTGC TCAACCTCTGT GAGAYGGCCC ACCTGGGCTTG GGCAGCGCG'] | 2714 | ['TGAGAYGGCCCA CCTGGGCTTGG'] | 2918-2919 | ['TGAGAYGGCCCA CCTGGGCTTGG', 'GAGAYGGCCCAC CTGGGCTTGGG'] |
| NM_000920.3 (PC):c.434T>C (p.Val145Ala) | 5091 | PC | 2548 | ['CGGTTTATTG GGCCAAGCCC AGAAGBGGTC CGCAAGATGG GAGACAAGGTG'] | 2715 | ['CCAGAAGBGGTC CGCAAGATGGG'] | 2920 | ['CCAGAAGBGGTC CGCAAGATGGG'] |
| NM_000026.2 (ADSL):c.674T>C (p.Met225Thr) | 158 | ADSL | 2549 | ['TCCAAGGTAG AGCAGCTTGAC AAGAYGGTGA CAGAAAAGGC AGGATTTAAG'] | 2716 | ['AAGAYGGTGACA GAAAAGGCAGG'] | 2921 | ['AAGAYGGTGAC AGAAAAGGCAGG'] |
| NM_000391.3 (TPP1):c.1093T>C (p.Cys365Arg) | 1200 | TPP1 | 2550 | ['TCTCTCAGGT GACAGTGGGG CCGGGYGTTG GTCTGTCTCTG GAAGACACCA'] | 2717 | ['GCCGGGYGTTGG TCTGTCTCTGG'] | 2922 | ['GCCGGGYGTTGG TCTGTCTCTGG'] |
| NM_004183.3 (BEST1):c.704T>C (p.Val235Ala) | 7439 | BEST1 | 2551 | ['TACGACTGGA TTAGTATCCCA CTGGYGTATAC ACAGGTGAGG ACTAGGCTG'] | 2718 | ['CACTGGYGTATA CACAGGTGAGG'] | 2923 | ['CACTGGYGTATA CACAGGTGAGG'] |
| NM_000019.3 (ACAT1):c.935T>C (p.Ile312Thr) | 38 | ACAT1 | 2552 | ['CTCAATGTTA CACCACTGGCA AGAAYAGTAG GTAAGGCCAG GCGAGGTGGC'] | 2719 | ['CAAGAAYAGTAG GTAAGGCCAGG'] | 2924 | ['CAAGAAYAGTA GGTAAGGCCAGG'] |

TABLE 2-continued

T to C changes with NGG PAM. Table 2 shows a list of T to C mutations that may
be corrected using any of the base editors provided herein. GRNAs and gRNAall indicate the
protospacer and PAM sequence, where the PAM sequence is the last 3 nucleotides of each of
the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000543.4 (SMPD1):c.911T>C (p.Leu304Pro) | 6609 | SMPD1 | 2553 | ['CGGGCCCTGA CCACCGTCACA GCACYTGTGA GGAAGTTCCTG GGGCCAGTG'] | 2720 | ['CACYTGTGAGGA AGTTCCTGGGG'] | 2925-2927 | ['AGCACYTGTGAG GAAGTTCCTGG', 'GCACYTGTGAGG AAGTTCCTGGG', 'CACYTGTGAGGA AGTTCCTGGGG'] |
| NM_000527.4 (LDLR):c.694+2T>C | 3949 | LDLR | 2554 | ['ACAAATCTGA CGAGGAAAAC TGCGGYATGG GCGGGGCCAG GGTGGGGGCGG'] | 2721 | ['CGGYATGGGCGG GGCCAGGGTGG'] | 2928-2930 | ['ACTGCGGYATGG GCGGGGCCAGG', 'CTGCGGYATGGG CGGGGCCAGGG', 'CGGYATGGGCGG GGCCAGGGTGG'] |
| NM_012464.4 (TLL1):c.713T>C (p.Val238Ala) | 7092 | TLL1 | 2555 | ['AAGAACTGTG ATAAATTTGGG ATTGYTGTTCA TGAATTGGGTC ATGTGATA'] | 2722 | ['GGGATTGYTGTTC ATGAATTGGG'] | 2931 | ['GGGATTGYTGTT CATGAATTGGG'] |
| NM_000112.3 (SLC26A2):c.-26+2T>C | 1836 | SLC26A2 | 2556 | ['CCTGCAGCGG CCCGGACCCG AGAGGYGAGA AGAGGGAAGC GGACCAGGGA A'] | 2723 | ['GAGAGGYGAGAA GAGGGAAGCGG'] | 2932 | ['GAGAGGYGAGA AGAGGGAAGCGG'] |
| NM_001005741.2 (GBA):c.751T>C (p.Tyr251His) | 2629 | GBA | 2557 | ['CATCTACCAC CAGACCTGGG CCAGAYACTTT GTGAAGTAAG GGATCAGCAA'] | 2724 | ['GCCAGAYACTTT GTGAAGTAAGG'] | 2933-2934 | ['GCCAGAYACTTT GTGAAGTAAGG', 'CCAGAYACTTTGT GAAGTAAGGG'] |
| NM_020365.4 (EIF2B3):c.1037T>C (p.Ile346Thr) | 8891 | EIF2B3 | 2558 | ['CCACCAGTCC ATTCGTCAGCC CAGAYTGTCA GCAAACACCT GGTAAGTGCT'] | 2725 | ['CCAGAYTGTCAG CAAACACCTGG'] | 2935 | ['CCAGAYTGTCAG CAAACACCTGG'] |
| NM_022041.3 (GAN):c.1268T>C (p.Ile423Thr) | 8139 | GAN | 2559 | ['TGCTATGCAG CTATGAAAAA GAAAAYCTAC GCCATGGGTG GAGGCTCCTAC'] | 2726 | ['AAGAAAAYCTAC GCCATGGGTGG'] | 2936-2937 | ['AAGAAAAYCTAC GCCATGGGTGG', 'AAAAYCTACGCC ATGGGTGGAGG'] |
| NM_054027.4 (ANKH):c.143T>C (p.Met48Thr) | 56172 | ANKH | 2560 | ['GCTGTCAAGG AGGATGCAGT CGAGAYGCTG GCCAGCTACG GGCTGGCGTAC'] | 2727-2728 | ['GTCGAGAYGCTG GCCAGCTACGG', 'TCGAGAYGCTGGC CAGCTACGGG'] | 2938-2939 | ['GTCGAGAYGCTG GCCAGCTACGG', 'TCGAGAYGCTGG CCAGCTACGGG'] |
| NM_006329.3 (FBLN5):c.506T>C (p.Ile169Thr) | 10516 | FBLN5 | 2561 | ['TTGCTTGCAT TTCTGTTTCCA GACAYTGATG AATGTCGCTAT GGTTACTGC'] | 2729 | ['GACAYTGATGAA TGTCGCTATGG'] | 2940 | ['GACAYTGATGAA TGTCGCTATGG'] |
| NM_004086.2 (COCH):c.1535T>C (p.Met512Thr) | −1 | — | 2562 | ['GCACCTCTGG ATGACCTGAA AGATAYGGCTT CTAAACCGAA GGAGTCTCAT'] | 2730 | ['AGATAYGGCTTC TAAACCGAAGG'] | 2941 | ['AGATAYGGCTTC TAAACCGAAGG'] |
| NM_002942.4 (ROBO2):c.2834T>C (p.Ile945Thr) | 6092 | ROBO2 | 2563 | ['AATAGCAACA GTGGCCCAAAT GAGAYTGGAA ATTTTGGCCGT GGAGGTAAG'] | 2731 | ['GAGAYTGGAAAT TTTGGCCGTGG'] | 2942 | ['GAGAYTGGAAAT TTTGGCCGTGG'] |
| NM_001300.5 (KLF6):c.190T>C (p.Trp64Arg) | 1316 | KLF6 | 2564 | ['CAAATTTGAC AGCCAGGAAG ATCTGYGGACC AAAATCATTCT GGCTCGGGA'] | 2732 | ['TCTGYGGACCAA AATCATTCTGG'] | 2943 | ['TCTGYGGACCAA AATCATTCTGG'] |
| NM_030653.3 (DDX11):c.2271+2T>C | 1663 | DDX11 | 2565 | ['CTGGCATATT CCAGGTGCATC CAGGYGCGGG CGTCATGCTGG GCTTGGGTC'] | 2733 | ['TCCAGGYGCGGG CGTCATGCTGG'] | 2944-2945 | ['TCCAGGYGCGGG CGTCATGCTGG', 'CCAGGYGCGGGC GTCATGCTGGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001451.2 (FOXF1):c.1138T>C (p.Ter380Arg) | 2294 | FOXF1 | 2566 | ['CCAAGACATC AAGCCTTGCGT GATGYGAGGC TGCCGCCGCAG GCCCTCCTG'] | 2734 | ['TGATGYGAGGCT GCCGCCGCAGG'] | 2946 | ['TGATGYGAGGCT GCCGCCGCAGG'] |
| NM_000435.2 (NOTCH3):c.1363T>C (p.Cys455Arg) | 4854 | NOTCH3 | 2567 | ['CCTCGACCGC ATAGGCCAGTT CACCYGTATCT GTATGGCAGGT GGGTGGTG'] | 2735 | ['ACCYGTATCTGTA TGGCAGGTGG'] | 294-72948 | ['TTCACCYGTATC TGTATGGCAGG', 'ACCYGTATCTGTA TGGCAGGTGG'] |
| NM_002427.3 (MMP13):c.272T>C (p.Met91Thr) | 4322 | MMP13 | 2568 | ['CTTGACGATA ACACCTTAGAT GTCAYGAAAAA AGCCAAGATG CGGGGTTCCT'] | 2736-2737 | ['GTCAYGAAAAAG CCAAGATGCGG', 'TCAYGAAAAAGCC AAGATGCGGG'] | 2949-2950 | ['GTCAYGAAAAA GCCAAGATGCGG', 'TCAYGAAAAAGC CAAGATGCGGG'] |
| NM_000211.4 (ITGB2):c.446T>C (p.Leu149Pro) | 3689 | ITGB2 | 2569 | ['GATGACCTCA GGAATGTCAA GAAGCYAGGT GGCGACCTGCT CCGGGCCCTC'] | 2738 | ['AGCYAGGTGGCG ACCTGCTCCGG'] | 2951 | ['AGCYAGGTGGCG ACCTGCTCCGG'] |
| NM_005502.3 (ABCA1):c.4429T>C (p.Cys1477Arg) | 19 | ABCA1 | 2570 | ['CAAAATCAAG AAGATGCTGCC TGTGYGTCCCC CAGGGGCAGG GGGGCTGCC'] | 2739-2740 | ['CCTGTGYGTCCCC CAGGGGCAGG', 'CTGTGYGTCCCCC AGGGGCAGGG'] | 2952-2955 | ['CCTGTGYGTCCCC CAGGGGCAGG', 'CTGTGYGTCCCCC AGGGGCAGGG', 'TGTGYGTCCCCCA GGGGCAGGGG', 'GTGYGTCCCCCA GGGGCAGGGGG'] |
| m.12297T>C | 4568 | MT-TL2 | 2571 | ['AAAGGATAAC AGCTATCCATT GGTCYTAGGCC CCAAAAATTTT GGTGCAAC'] | 2741 | ['GTCYTAGGCCCC AAAAATTTTGG'] | 2956 | ['GTCYTAGGCCCC AAAAATTTTGG'] |
| m.4290T>C | 4565 | MT-TI | 2572 | ['AAATATGTCT GATAAAAGAG TTACTYTGATA GAGTAAATAA TAGGAGCTTA'] | 2742 | ['ACTYTGATAGAG TAAATAATAGG'] | 2957 | ['ACTYTGATAGAG TAAATAATAGG'] |
| m.4291T>C | 4565 | MT-TI | 2573 | ['AATATGTCTG ATAAAAGAGT TACTTYGATAG AGTAAATAAT AGGAGCTTAA'] | 2743 | ['ACTTYGATAGAG TAAATAATAGG'] | 2958 | ['ACTTYGATAGAG TAAATAATAGG'] |
| m.3394T>C | 4535 | MT-ND1 | 2574 | ['GCTTACCGAA CGAAAAATTCT AGGCYATATA CAACTACGCA AAGGCCCCAA'] | 2744 | ['GGCYATATACAA CTACGCAAAGG'] | 2959 | ['GGCYATATACAA CTACGCAAAGG'] |
| NM_002764.3 (PRPS1):c.344T>C (p.Met115Thr) | 5631 | PRPS1 | 2575 | ['ATCTCAGCCA AGCTTGTTGCA AATAYGCTATC TGTAGCAGGTG CAGATCAT'] | 2745 | ['GCAAATAYGCTA TCTGTAGCAGG'] | 2960 | ['GCAAATAYGCTA TCTGTAGCAGG'] |
| NM_000132.3 (F8):c.5372T>C (p.Met1791Thr) | 2157 | F8 | 2576 | ['AGAGCAGAA GTTGAAGATA ATATCAYGGTG AGTTAAGGAC AGTGGAATTAC'] | 2746 | ['TCAYGGTGAGTT AAGGACAGTGG'] | 2961 | ['TCAYGGTGAGTT AAGGACAGTGG'] |
| NM_000132.3 (F8):c.1754T>C (p.Ile585Thr) | 2157 | F8 | 2577 | ['CCTTTCAATA TATGTAATTAA CAGAYAATGT CAGACAAGAG GAATGTCATC'] | 2747 | ['AACAGAYAATGT CAGACAAGAGG'] | 2962 | ['AACAGAYAATGT CAGACAAGAGG'] |
| NM_000133.3 (F9):c.1328T>C (p.Ile443Thr) | 2158 | F9 | 2578 | ['TGTGCAATGA AAGGCAAATA TGGAAYATAT ACCAAGGTATC CCGGTATGTC'] | 2748 | ['GAAYATATACCA AGGTATCCCGG'] | 2963 | ['GAAYATATACCA AGGTATCCCGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000169.2 (GLA):c.806T>C (p.Val269Ala) | −1 | — | 2579 | ['TTATTTCATTC TTTTTCTCAGT TAGYGATTGGC AACTTTGGCCT CAGCTGG'] | 2749 | ['CAGTTAGYGATT GGCAACTTTGG'] | 2964 | ['CAGTTAGYGATT GGCAACTTTGG'] |
| NM_000116.4 (TAZ):c.352T>C (p.Cys118Arg) | 6901 | TAZ | 2580 | ['CTCCCACTTC TTCAGCTTGGG CAAGYGTGTG CCTGTGTGCCG AGGTGAGCT'] | 2750 | ['AAGYGTGTGCCT GTGTGCCGAGG'] | 2965 | ['AAGYGTGTGCCT GTGTGCCGAGG'] |
| NM_000061.2 (BTK):c.2T>C (p.Met1Thr) | 695 | BTK | 2581 | ['GGTGAACTCC AGAAAGAAGA AGCTAYGGCC GCAGTGATTCT GGAGAGCATC'] | 2751 | ['AGCTAYGGCCGC AGTGATTCTGG'] | 2966 | ['AGCTAYGGCCGC AGTGATTCTGG'] |
| NM_000061.2 (BTK):c.1223T>C (p.Leu408Pro) | 695 | BTK | 2582 | ['AAGGACCTGA CCTTCTTGAAG GAGCYGGGGA CTGGACAATTT GGGTAGTG'] | 2752 | ['AGCYGGGGACTG GACAATTTGGG'] | 2967-2968 | ['GAGCYGGGGACT GGACAATTTGG', 'AGCYGGGGACTG GACAATTTGGG'] |
| NM_000061.2 (BTK):c.1741T>C (p.Trp581Arg) | 695 | BTK | 2583 | ['CAAGTTCAGC AGCAAATCTG ACATTYGGGCT TTTGGTAAGTG GATAAGATT'] | 2753 | ['ACATTYGGGCTTT TGGTAAGTGG'] | 2969 | ['ACATTYGGGCTT TTGGTAAGTGG'] |
| NM_014009.3 (FOXP3):c.970T>C (p.Phe324Leu) | 50943 | FOXP3 | 2584 | ['GATTCATCCC CACCCTCTGAC AGAGYTCCTCC ACAACATGGA CTACTTCAA'] | 2754 | ['GACAGAGYTCCT CCACAACATGG'] | 2970 | ['GACAGAGYTCCT CCACAACATGG'] |
| NM_003688.3 (CASK):c.2740T>C (p.Trp914Arg) | 8573 | CASK | 2585 | ['TGAGCTCGTG TGCACAGCCCC ACAGYGGGTC CCTGTCTCCTG GGTCTATTA'] | 2755-2756 | ['CACAGYGGGTCC CTGTCTCCTGG', 'ACAGYGGGTCCCT GTCTCCTGGG'] | 2971-2972 | ['CACAGYGGGTCC CTGTCTCCTGG', 'ACAGYGGGTCCC TGTCTCCTGGG'] |
| NM_004992.3 (MECP2):c.464T>C (p.Phe155Ser) | 4204 | MECP2 | 2586 | ['GACACATCCC TGGACCCTAAT GATTBTGACTT CACGGTAACTG GGAGAGGG'] | 2757 | ['GATTBTGACTTCA CGGTAACTGG'] | 2973-2974 | ['GATTBTGACTTC ACGGTAACTGG', 'ATTBTGACTTCAC GGTAACTGGG'] |
| NM_000431.3 (MVK):c.803T>C (p.Ile268Thr) | 4598 | MVK | 2587 | ['ATCGTGGCCC CCCTCCTGACC TCAAYAGATG CCATCTCCCTG GAGTGTGAG'] | 2758 | ['CTCAAYAGATGC CATCTCCCTGG'] | 2975 | ['CTCAAYAGATGC CATCTCCCTGG'] |
| NM_021961.5 (TEAD1):c.1261T>C (p.Tyr?His) | 7003 | TEAD1 | 2588 | ['TGAACACGGA GCACAACATC ATATTYACAGG CTTGTAAAGGA CTGAACATG'] | 2759 | ['TCATATTYACAG GCTTGTAAAGG'] | 2976 | ['TCATATTYACAG GCTTGTAAAGG'] |
| NM_005633.3 (SOS1):c.1294T>C (p.Trp432Arg) | 6654 | SOS1 | 2589 | ['CGAGATTCAG AAGAATATTG ATGGTYGGGA GGGAAAAGAC ATTGGACAGTG'] | 2760 | ['GGTYGGGAGGGA AAAGACATTGG'] | 2977 | ['GGTYGGGAGGG AAAAGACATTGG'] |
| NM_006920.4 (SCN1A):c.3577T>C (p.Trp1193Arg) | −1 | — | 2590 | ['TGTGGAAGAA GGCAGAGGAA AACAAYGGTG GAACCTGAGA AGGACGTGTTT'] | 2761 | ['AACAAYGGTGGA ACCTGAGAAGG'] | 2978 | ['AACAAYGGTGG AACCTGAGAAGG'] |
| NM_000141.4 (FGFR2):c.1018T>C (p.Tyr340His) | 2263 | FGFR2 | 2591 | ['TGTAACTTTT GAGGACGCTG GGGAAYATAC GTGCTTGGCGG GTAATTCTAT'] | 2762-2763 | ['TGGGGAAYATAC GTGCTTGGCGG', 'GGGGAAYATACGT GCTTGCGGG'] | 2979-2980 | ['TGGGGAAYATAC GTGCTTGGCGG', 'GGGGAAYATACG TGCTTGGCGGG'] |
| NM_000174.4 (GP9):c.70T>C (p.Cys24Arg) | 2815 | GP9 | 2592 | ['GGCCACCAAG GACTGCCCCAG CCCAYGTACCT GCCGCGCCCTG GAAACCAT'] | 2764 | ['CCCAYGTACCTG CCGCGCCCTGG'] | 2981 | ['CCCAYGTACCTG CCGCGCCCTGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000175.3 (GPI):c.1574T>C (p.Ile525Thr) | 2821 | GPI | 2593 | ['CTGGGAAAGC AGCTGGCTAA GAAAABAGAG CCTGAGCTTGA TGGCAGTGCT'] | 2765 | ['AAAABAGAGCCT GAGCTTGATGG'] | 2982 | ['AAAABAGAGCCT GAGCTTGATGG'] |
| NM_000315.2 (PTH):c.52T>C (p.Cys18Arg) | 5741 | PTH | 2594 | ['AGTTATGATT GTCATGTTGGC AATTYGTTTTC TTACAAAATCG GATGGGAA'] | 2766 | ['AATTYGTTTTCTT ACAAAATCGG'] | 2983 | ['AATTYGTTTTCTT ACAAAATCGG'] |
| NM_000222.2 (KIT):c.1676T>C (p.Val559Ala) | 3815 | KIT | 2595 | ['CCCATGTATG AAGTACAGTG GAAGGNTGTT GAGGAGATAA ATGGAAACAAT'] | 2767 | ['AAGGNTGTTGAG GAGATAAATGG'] | 2984 | ['AAGGNTGTTGAG GAGATAAATGG'] |
| NM_016835.4 (MAPT):c.1839T>C (p.Asn613=) | 4137 | MAPT | 2596 | ['AGTCCAAGTG TGGCTCAAAG GATAAYATCA AACACGTCCCG GGAGGCGGCA'] | 2768-2769 | ['GGATAAYATCAA ACACGTCCCGG', 'GATAAYATCAAAC ACGTCCCGGG'] | 2985-2986 | ['GGATAAYATCAA ACACGTCCCGG', 'GATAAYATCAAA CACGTCCCGGG'] |
| NM_170707.3 (LMNA):c.1139T>C (p.Leu380Ser) | 4000 | LMNA | 2597 | ['GAGATCCACG CCTACCGCAAG CTCTYGGAGG GCGAGGAGGA GAGGTGGGCT'] | 2770 | ['TCTYGGAGGGCG AGGAGGAGAGG'] | 2987 | ['TCTYGGAGGGCG AGGAGGAGAGG'] |
| NM_000424.3 (KRT5):c.20T>C (p.Val7Ala) | 3852 | KRT5 | 2598 | ['GCCACCATGT CTCGCCAGTCA AGTGYGTCCTT CCGGAGCGGG GGCAGTCGT'] | 2771-2773 | ['TCAAGTGYGTCCT TCCGGAGCGG', 'CAAGTGYGTCCTT CCGGAGCGGG', 'AAGTGYGTCCTTC CGGAGCGGGG'] | 2988-2991 | ['TCAAGTGYGTCC TTCCGGAGCGG', 'CAAGTGYGTCCTT CCGGAGCGGG', 'AAGTGYGTCCTTC CGGAGCGGGG', 'AGTGYGTCCTTCC GGAGCGGGG'] |
| NM_000184.2 (HBG2):c.125T>C (p.Phe42Ser) | 3048 | HBG2 | 2599 | ['GTTGTCTACC CATGGACCCA GAGGTYCTTTG ACAGCTTTGGC AACCTGTCC'] | 2774 | ['CAGAGGTYCTTT GACAGCTTTGG'] | 2992 | ['CAGAGGTYCTTT GACAGCTTTGG'] |
| NM_000515.4 (GH1):c.291+6T>C | 2688 | GH1 | 2600 | ['AGGAAACAC AACAGAAATC CGTGAGYGGA TGCCTTCTCCC CAGGCGGGGAT'] | 2775 | ['TGAGYGGATGCC TTCTCCCCAGG'] | 2993 | ['TGAGYGGATGCC TTCTCCCCAGG'] |
| NM_002087.3 GRN):c.2T>C (p.Met1Thr) | 2896 | GRN | 2601 | ['TCCTTGGTAC TTTGCAGGCAG ACCAYGTGGA CCCTGGTGAGC TGGGTGGCC'] | 2776 | ['CCAYGTGGACCC TGGTGAGCTGG'] | 2994 | ['CCAYGTGGACCC TGGTGAGCTGG'] |
| NM_001083112.2 (GPD2):c.1904T>C (p.Phe635Ser) | 2820 | GPD2 | 2602 | ['AGGTATAAGA AGAGATTTCAT AAGTYTGATGC AGACCAGAAA GGCTTTATT'] | 2777 | ['AAGTYTGATGCA GACCAGAAAGG'] | 2995 | ['AAGTYTGATGCA GACCAGAAAGG'] |
| NM_00101807 7.1(NR3C1):c.1712T>C (p.Val571Ala) | 2908 | NR3C1 | 2603 | ['CTCAACATGT TAGGAGGGCG GCAAGYGATT GCAGCAGTGA AATGGGCAAAG'] | 2778 | ['AAGYGATTGCAG CAGTGAAATGG'] | 2996 | ['AAGYGATTGCAG CAGTGAAATGG'] |
| NM_006306.3 (SMC1A):c.2351T>C (p.11e784Thr) | 8243 | SMC1A | 2621 | ['GTGTTTGAAG AGTTTTGTCGG GAGAYTGGTG TGCGCAACATC CGGGAGTTT'] | 2798 | ['AGAYTGGTGTGC GCAACATCCGG'] | 3017 | ['AGAYTGGTGTGC GCAACATCCGG'] |
| NM_002242.4 (KCN.113):c.722T>C (p.Leu241Pro) | −1 | — | 2622 | ['TGGTGTAATG GAGTGATAGT ACGTTDGTGGA AAGATGAAGA ATGGACATTC'] | 2799 | ['GTTDGTGGAAAG ATGAAGAATGG'] | 3018 | ['GTTDGTGGAAAG ATGAAGAATGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000199.3 (SGSH):c.892T>C (p.Ser298Pro) | 6448 | SGSH | 2623 | ['CCCCAGCGTT TGGGTGCTCC GGGGRTGACA CCAGTAAGGG TTCAGCAGTG'] | 2800 | ['TCCGGGGRTGAC ACCAGTAAGGG'] | 3019 | ['TCCGGGGRTGAC ACCAGTAAGGG'] |
| NM_020191.2 (MRPS22):c.644T>C (p.Leu215Pro) | 56945 | MRPS22 | 2624 | ['CCAATAATTT TCAAGGAAGA AAATCYTAGG GTAAGGTGACT TAGGTTTTAT'] | 2801 | ['ATCYTAGGGTAA GGTGACTTAGG'] | 3020 | ['ATCYTAGGGTAA GGTGACTTAGG'] |
| NM_017882.2 (CLN6):c.200T>C (p.Leu67Pro) | 54982 | CLN6 | 2625 | ['CCCCATTCTTC CATTTGCTCCG CAGCYGGTATT CCCTCTCGAGT GGTTTCCA'] | 2802 | ['AGCYGGTATTCC CTCTCGAGTGG'] | 3021 | ['AGCYGGTATTCC CTCTCGAGTGG'] |
| NM_014874.3 (MFN2):c.1392+2T>C | 9927 | MFN2 | 2626 | ['GTAGTCCTCA AGGTTTATAAG AATGWGAGTC ATGGAGCAAC AGGTCCTCTT'] | 2803 | ['AATGWGAGTCAT GGAGCAACAGG'] | 3022 | ['AATGWGAGTCA TGGAGCAACAGG'] |
| NM_024599.5 (RHBDF2):c.557T>C (p.Ile186Thr) | 79651 | RHBDF2 | 2627 | ['GCTTACCGCC CCCTCCCTTC CAGAYTGTGG ATCCGCTGGCC CGGGGCCGG'] | 2804 | ['AGAYTGTGGATC CGCTGGCCCGG'] | 3023 | ['AGAYTGTGGATC CGCTGGCCCGG'] |
| NM_020894.2 (UVSSA):c.94T>C (p.Cys32Arg) | 57654 | UVSSA | 2628 | ['GAAAATGAA GGAACTGAAG AAAATTYGCA AGTATGTCTTA GGGTTCAGTAA'] | 2805 | ['AAAATTYGCAAG TATGTCTTAGG'] | 3024-3025 | ['AAAATTYGCAAG TATGTCTTAGG', 'AAAATTYGCAAGT ATGTCTTAGGG'] |
| NM_001161581.1 (POC1A):c.398T>C (p.Leu133Pro) | 25886 | POC1A | 2629 | ['GCCAGTGATG ACAAGACTGTT AAGCYGTGGG ACAAGAGCAG CCGGGAATGT'] | 2806 | ['AGCYGTGGGACA AGAGCAGCCGG'] | 3026 | ['AGCYGTGGGACA AGAGCAGCCGG'] |
| NM_005340.6 (HINT1):c.250T>C (p.Cys84Arg) | 3094 | HINT1 | 2630 | ['ACACTTAATG ATTGTTGGCAA GAAAYGTGCT GCTGATCTGGG CCTGAATAA'] | 2807- 2808 | ['CAAGAAAYGTGC TGCTGATCTGG', 'AAGAAAYGTGCT GCTGATCTGGG'] | 3027-3028 | ['CAAGAAAYGTGC TGCTGATCTGG', 'AAGAAAYGTGCT GCTGATCTGGG'] |
| NM_000495 (COL4A5):c.438+2T>C | 1287 | COL4A5 | 2631 | ['TTTCCTGGTT ACAGGGTCCTC CAGYAAGTTAT AAAATTTGGG ATTATGAT'] | 2809 | ['TCCAGYAAGTTA TAAAATTTGGG'] | 3029-3030 | ['CTCCAGYAAGTT ATAAAATTTGG', 'TCCAGYAAGTTA TAAAATTTGGG'] |
| NM_000344.3 (SMN1):c.388T>C (p.Tyr130His) | 6606 | SMN1 | 2632 | ['AACCTGTGTT GTGGTTTACAC TGGAYATGGA AATAGAGAGG AGCAAAATCT'] | 2810 | ['CACTGGAYATGG AAATAGAGAGG'] | 3031 | ['CACTGGAYATGG AAATAGAGAGG'] |
| NM_005334.2 (HCFC1):c.-970T>C | 3054 | HCFC1 | 2633 | ['TTAGTTGTTA CTTCTTCACAC AAGAYGGCGG CTCCCAGGGA GGAGGCATGA'] | 2811 | ['CAAGAYGGCGGC TCCCAGGGAGG'] | 3032 | ['CAAGAYGGCGG CTCCCAGGGAGG'] |
| NM_000431.3 (MVK):c.1039+2T>C | 4598 | MVK | 2634 | ['GTGGCATCAC ACTCCTCAAGC CAGGYATCCC GGGGTAGGT GGGCCAGGCT'] | 2812 | ['CCAGGYATCCCG GGGTAGGTGG'] | 3033-3034 | ['CCAGGYATCCCG GGGTAGGTGG', 'CAGGYATCCCGG GGGTAGGTGGG'] |
| NM_018344.5 (SLC29A3):c.607T>C (p.Ser203Pro) | 55315 | SLC29A3 | 2635 | ['TATGAGGAAC TCCCAGGCACT GATAYCAGGT GAGAGCCAGG GTCCGGGCAG'] | 2813 | ['ACTGATAYCAGG TGAGAGCCAGG'] | 3035-3036 | ['ACTGATAYCAGG TGAGAGCCAGG', 'CTGATAYCAGGT GAGAGCCAGGG'] |
| NM_000108.4 (DLD):c.140T>C (p.Ile47Thr) | 1738 | DLD | 2636 | ['GTAGTTGATG CTGATGTAACA GTTAYAGGTTC TGGTCCTGGAG GATATGTT'] | 2815 | ['ACAGTTAYAGGT TCTGGTCCTGG', 'GTTAYAGGTTCTG GTCCTGGAGG'] | 3037-3038 | ['ACAGTTAYAGGT TCTGGTCCTGG', 'GTTAYAGGTTCTG GTCCTGGAGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_004333.4 (BRAF):c.1403T>C (p.Phe468Ser) | 673 | BRAF | 2637 | ['GGACAAAGA ATTGGATCTGG ATCATYTGGAA CAGTCTACAAG GGAAAGTGG'] | 2816-2817 | ['ATCATYTGGAAC AGTCTACAAGG', 'TCATYTGGAACAG TCTACAAGGG'] | 3039-3040 | ['ATCATYTGGAAC AGTCTACAAGG', 'TCATYTGGAACA GTCTACAAGGG'] |
| NM_000540.2 (RYR1):c.1205T>C (p.Met402Thr) | 6261 | RYR1 | 2638 | ['CAGGAGGAGT CCCAGGCCGCC CGCAYGATCC ACAGCACCAA TGGCCTATAC'] | 2818 | ['CGCAYGATCCAC AGCACCAATGG'] | 3041 | ['CGCAYGATCCAC AGCACCAATGG'] |
| NM_000256.3 (MYBPC3):c.1351+2T>C | 4607 | MYBPC3 | 2639 | ['GTAGCACGGA GCTCTTTGTGA AAGGYGGGCC TGGGACCTGA GGATGTGGGA'] | 2819 | ['AAAGGYGGGCCT GGGACCTGAGG'] | 3042 | ['AAAGGYGGGCCT GGGACCTGAGG'] |
| NM_000256.3 (MYBPC3):c.821+2T>C | 4607 | MYBPC3 | 2640 | ['CCTCCTATCA GCCTTCCGCCG CACGYGAGTG GCCATCCTCAG GGCCTGGGG'] | 2820 | ['CACGYGAGTGGC CATCCTCAGGG'] | 3043-3044 | CCATCCTCAGG', 'CACGYGAGTGGC CATCCTCAGGG'] |
| NM_000257.3 (MYH7):c.2546T>C (p.Met849Thr) | 4625 | MYH7 | 2641 | ['AAGAGTGCAG AAAGAGAGAA GGAGAYGGCC TCCATGAAGG AGGAGTTCACA'] | 2821 | ['GGAGAYGGCCTC CATGAAGGAGG'] | 3045 | ['GGAGAYGGCCTC CATGAAGGAGG'] |
| NM_206933.2 (USH2A):c.1606T>C (p.Cys536Arg) | 7399 | USH2A | 2642 | ['CGACACAACA AGCCAGCCAT ATAGAYGCCTC TGCTCCCAGGA GAGCTTCAC'] | 2822 | ['ATATAGAYGCCT CTGCTCCCAGG'] | 3046 | ['ATATAGAYGCCT CTGCTCCCAGG'] |
| NM_000059.3 (BRCA2):c.316+2T>C | 675 | BRCA2 | 2643 | ['TAGATAAATT CAAATTAGACT TAGGYAAGTA ATGCAATATGG TAGACTGGG'] | 2823 | ['CTTAGGYAAGTA ATGCAATATGG'] | 3047 | ['CTTAGGYAAGTA ATGCAATATGG'] |
| NM_007294.3 (BRCA1):c.5291T>C (p.Leu1764Pro) | 672 | BRCA1 | 2644 | ['CTCTTCTTCC AGATCTTCAGG GGGCYAGAAA TCTGTTGCTAT GGGCCCTTC'] | 2824 | ['GGCYAGAAATCT GTTGCTATGG'] | 3048-3049 | ['GGGCYAGAAATC TGTTGCTATGG', 'GGCYAGAAATCT GTTGCTATGGG'] |
| NM_001130089.1(KARS):c.517T>C (p.Tyr173His) | 3735 | KARS | 2645 | ['AGCTTCTGGG GGAAAGCTCA TCTTCYATGAT CTTCGAGGAG AGGGGTGAA'] | 2825 | ['TTCYATGATCTTC GAGGAGAGGG'] | 3050-3051 | ['CTTCYATGATCT TCGAGGAGAGG', 'TTCYATGATCTTC GAGGAGAGGG'] |
| NM_001283009.1(RTEL1):c.3730T>C (p.Cys1244Arg) | -1 | — | 2646 | ['CGGGCCCCTC TCAGCAGGCT TGTGYGCCAG GGCTGTGGGG CAGAGGACGT'] | 2826 | ['CTGTGTGYGCCA GGGCTGTGGGG'] | 3052 | ['CTGTGTGYGCCA GGGCTGTGGGG'] |
| NM_005554.3 (KRT6A):c.1406T>C (p.Leu469Pro) | 3853 | KRT6A | 2647 | ['GAGATCGCCA CCTACCGCAAG CTGCBGGAGG GTGAGGAGTG CAGGTGGGTA'] | 2827 | ['TGCBGGAGGGTG AGGAGTGCAGG'] | 3053 | ['TGCBGGAGGGTG AGGAGTGCAGG'] |
| NM_000218.2 (KCNQ1):c.550T>C (p.Tyr184His) | 3784 | KCNQ1 | 2648 | ['CTGGTCCGCC GGCTGCCGCA GCAAGBACGT GGGCCTCTGGG GGCGGCTGCG'] | 2828 | ['AGCAAGBACGTG GGCCTCTGGGG'] | 3054-3056 | ['CAGCAAGBACGT GGGCCTCTGGG', 'AGCAAGBACGTG GGCCTCTGGGG', 'GCAAGBACGTGG GGCCTCTGGGG'] |
| NM_198056.2 (SCN5A):c.5624T>C (p.Met1875Thr) | 6331 | SCN5A | 2649 | ['GAGATGGACG CCCTGAAGATC CAGAHGGAGG AGAAGTTCATG GCAGCCAAC'] | 2829 | ['CCAGAHGGAGGA GAAGTTCATGG'] | 3057 | ['CCAGAHGGAGG AGAAGTTCATGG'] |
| NM_006920.4 (SCN1A):c.269T>C (p.Phe90Ser) | 6323 | SCN1A | 2650 | ['TGTTGTGTTC CTGTCTTACAG ACTTYTATAGT ATTGAATAAA GGGAAGGCC'] | 2830-2831 | ['ACTTYTATAGTAT TGAATAAAGG', 'CTTYTATAGTATT GAATAAAGGG'] | 3058-3059 | ['ACTTYTATAGTA TTGAATAAAGG', 'CTTYTATAGTATT GAATAAAGGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_006920.4 (SCN1A):c.272T>C (p.Ile91Thr) | 6323 | SCN1A | 2651 | ['TGTGTTCCTG TCTTACAGACT TTTAYAGTATT GAATAAAGGG AAGGCCATC'] | 2832-2833 | ['ACTTTTAYAGTAT TGAATAAAGG', 'CTTTTAYAGTATT GAATAAAGGG'] | 3060-3061 | ['ACTTTTAYAGTA TTGAATAAAGG', 'CTTTTAYAGTATT GAATAAAGGG'] |
| NM_006514.3 (SCN10A):c.1661T>C (p.Leu554Pro) | 6336 | SCN10A | 2652 | ['GGAGTCAGGG TTGCTGGGTTG AGGARGAGGG CTTCTAGGGAG GGGGCCTTG'] | 2834-2836 | ['GAGGARGAGGGC TTCTAGGGAGG', 'AGGARGAGGGCTT CTAGGGAGG', 'GGARGAGGGCTTC TAGGGAGGGG'] | 3062-3064 | ['GAGGARGAGGG CTTCTAGGGAGG', 'AGGARGAGGGCT TCTAGGGAGGG', 'GGARGAGGGCTT CTAGGGAGGGG'] |
| NM_000251.2 (MSH2):c.2005+2T>C | 4436 | MSH2 | 2653 | ['AACAGATGTT CCACATCATTA CTGGYAAAAA ACCTGGTTTTT GGGCTTTGT'] | 2837-2838 | ['CTGGYAAAAAAC CTGGTTTTTGG', 'TGGYAAAAAACCT GGTTTTTGGG'] | 3065-3066 | ['CTGGYAAAAAAC CTGGTTTTTGG', 'TGGYAAAAAACC TGGTTTTTGGG'] |
| NM_000251.2 (MSH2):c.595T>C (p.Cys199Arg) | 4436 | MSH2 | 2654 | ['CCTCATCCAG ATTGGACCAA AGGAAYGTGT TTACCCGGAG GAGAGACTGC'] | 2839 | ['AAGGAAYGTGTT TTACCCGGAGG'] | 3067 | ['AAGGAAYGTGTT TTACCCGGAGG'] |
| NM_001005741.2 (GBA):c.667T>C (p.Trp223Arg) | 2629 | GBA | 2655 | ['TTCACCGCTC CATTGGTCTTG AGCCRAGTGG GTGATGTCCAG GGGCTGGCA'] | 2840 | ['GCCRAGTGGGTG ATGTCCAGGGG'] | 3068-3070 | ['GAGCCRAGTGGG TGATGTCCAGG', 'AGCCRAGTGGGT GATGTCCAGGG', 'GCCRAGTGGGTG ATGTCCAGGGG'] |
| NM_003494.3 (DYSF):c.1284+2T>C | 8291 | DYSF | 2656 | ['GAGGTCAGCT TTGCGGGGAA AATGGYAAGG AGCAAGGGAG CAGGAGGGTTC'] | 2841 | ['ATGGYAAGGAGC AAGGGAGCAGG'] | 3071 | ['ATGGYAAGGAG CAAGGGAGCAGG'] |
| NM_012463.3 (ATP6V0A2):c.825+2T>C | 2354 | ATP6V50A2 | 2657 | ['ACCCGCATCC AGGATCTCTAC ACTGYGAGTA AGCTGGAAGT GGATTGCCTC'] | 2842 | ['CACTGYGAGTAA GCTGGAAGTGG'] | 3072 | ['CACTGYGAGTAA GCTGGAAGTGG'] |
| NM_016725.2 (FOLR1):c.493+2T>C | 2348 | FOLR1 | 2658 | ['ACAAGGGCTG GAACTGGACTT CAGGYGAGGG CTGGGGTGGG CAGGAATGGA'] | 2843 | ['AGGYGAGGGCTG GGGTGGGCAGG'] | 3073-3074 | ['CTTCAGGYGAGG GCTGGGGTGGG', 'AGGYGAGGGCTG GGGTGGGCAGG'] |
| NM_003764.3 (STX11):c.173T>C (p.Leu58Pro) | 8676 | STX11 | 2659 | ['GACATTCAGG ATGAAAACCA GCTGCYGGTG GCCGACGTGA AGCGGCTGGGA'] | 2844 | ['TGCYGGTGGCCG ACGTGAAGCGG'] | 3075 | ['TGCYGGTGGCCG ACGTGAAGCGG'] |
| NM_014714.3 (1FT140):c.4078T>C (p.Cys1360Arg) | 9742 | IFT140 | 2660 | ['GGACCCCAAG GAGTCCATCAA GCAGYGTGAG CTGCTCCTGGA GGAACCAGA'] | 2845 | ['GCAGYGTGAGCT GCTCCTGGAGG'] | 3076-3077 | ['CAAGCAGYGTGA GCTGCTCCTGG', 'GCAGYGTGAGCT GCTCCTGGAGG'] |
| NM_000531.5 (OTC):c.1005+2T>C | 5009 | OTC | 2661 | ['GAAAACAGA AAGTGGACAA TCATGGYAAG CAAGAAACAA GGAATGGAGGAT'] | 2846 | ['ATCATGGYAAGC AAGAAACAAGG'] | 3078 | ['ATCATGGYAAGC AAGAAACAAGG'] |
| NM_000531.5 (OTC):c.158T>C (p.Ile53Thr) | 5009 | OTC | 2662 | ['CTAAAAAACT TACCGGAGA AGAAABTAAA TATATGCTATG GCTATCAGCA'] | 2847 | ['AAGAAABTAAAT ATATGCTATGG'] | 3079 | ['AAGAAABTAAAT ATATGCTATGG'] |
| NM_000531.5 (OTC):c.284T>C (p.Leu95Ser) | 5009 | OTC | 2663 | ['GAGAAAAGA AGTACTCGAAC AAGATYGTCTA CAGAAACAGG TAAGTCCACT'] | 2848 | ['ACAAGATYGTCT ACAGAAACAGG'] | 3080 | ['ACAAGATYGTCT ACAGAAACAGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000531.5 (OTC):c.2T>C (p.Met1Thr) | 5009 | OTC | 2664 | ['CGTCCTTTAC ACAATTAAAA GAAGAYGCTG TTTAATCTGAG GATCCTGTTA'] | 2849 | ['AGAAGAYGCTGT TTAATCTGAGG'] | 3081 | ['AGAAGAYGCTGT TTAATCTGAGG'] |
| NM_000531.5 (OTC):c.526T>C (p.Tyr176His) | 5009 | OTC | 2665 | ['CCATCCTATC CAGATCCTGGC TGATYACCTCA CGCTCCAGGTT GGTTTATT'] | 2850 | ['GGCTGATYACCT CACGCTCCAGG'] | 3082-3083 | ['GGCTGATYACCT CACGCTCCAGG', 'GATYACCTCACG CTCCAGGTTGG'] |
| NM_000531.5 (OTC):c.779T>C (p.Leu260Ser) | 5009 | OTC | 2666 | ['GAAGCAGCGC ATGGAGGCAA TGTATYAATTA CAGACACTTGG ATAAGCATG'] | 2851 | ['ATGTATYAATTAC AGACACTTGG'] | 3084 | ['ATGTATYAATTA CAGACACTTGG'] |
| NM_000322.4 (PRPH2):c.736T>C (p.Trp246Arg) | 5961 | PRPH2 | 2667 | ['CCACCAGACG GAGGAGCTCA ACCTGYGGGT GCGTGGCTGCA GGGCTGCCCT'] | 2852-2853 | ['ACCTGYGGGTGC GTGGCTGCAGG', 'CCTGYGGGTGCGT GGCTGCAGGG'] | 3085-3086 | ['ACCTGYGGGTGC GTGGCTGCAGG', 'CCTGYGGGTGCG TGGCTGCAGGG'] |
| NM_000211.4 (ITGB2):c.1877+2T>C | 3689 | ITGB2 | 2668 | ['CCCCTCACCC TGTGGCAAGTA CATGYGAGTG CAGGCGGAGC AGGCAGGGCG'] | 2854 | ['CATGYGAGTGCA GCGGAGCAGG'] | 3087 | ['CATGYGAGTGCA GCGGAGCAGG'] |
| NM_015474.3 (SAMHD1):c.1106T>C (p.Leu369Ser) | 25939 | SAMHD1 | 2669 | ['TTTGTGTTGA TAAGCTCTACG GTGTRAAGAGT TGCGAGTGTGG AACATGTC'] | 2855 | ['GGTGTRAAGAGT TGCGAGTGTGG'] | 3088 | ['GGTGTRAAGAGT TGCGAGTGTGG'] |
| NM_001101.3 (ACTB):c.356T>C (p.Met119Thr) | 60 | ACTB | 2670 | ['AACCCCAAGG CCAACCGCGA GAAGAYGACC CAGGTGAGTG GCCCGCTACCT'] | 2856 | ['GAGAAGAYGACC CAGGTGAGTGG'] | 3089 | ['GAGAAGAYGAC CCAGGTGAGTGG'] |
| NM_015713.4 (RRM2B):c.368T>C (p.Phe123Ser) | 50484 | RRM2B | 2671 | ['CTCGATGAGA ATTTGAAAGCC ATAGRAACAG CGAGCCTCTGG AACCTGCAC'] | 2857 | ['CCATAGRAACAG CGAGCCTCTGG'] | 3090 | ['CCATAGRAACAG CGAGCCTCTGG'] |
| NM_015599.2 (PGM3):c.248T>C (p.Leu83Ser) | 5238 | PGM3 | 2672 | ['TTGGTTGATC CTTTGGGTGAA ATGTYGGCACC ATCCTGGGAG GAACATGCC'] | 2858 | ['AATGTYGGCACC ATCCTGGGAGG'] | 3091 | ['AATGTYGGCACC ATCCTGGGAGG'] |
| NM_002136.2 (HNRNPA1):c.817T>C (p.Phe273Leu) | 3178 | HNRNPA1 | 2673 | ['GAATTACAAC AATCAGTCTTC AAATBTTGGAC CCATGAAGGG AGGAAATTT'] | 2859-2861 | ['TTCAAATBTTGGA CCCATGAAGG', 'TCAAATBTTGGAC CCATGAAGGG', 'AATBTTGGACCCA TGAAGGGAGG'] | 3092-3094 | ['TTCAAATBTTGG ACCCATGAAGG', 'TCAAATBTTGGAC CCATGAAGGG', 'AATBTTGGACCC ATGAAGGGAGG'] |
| NM_002136.2 (HNRNPA1):c.841T>C (p.Phe281Leu) | 3178 | HNRNPA1 | 2674 | ['TTTTGGACCC ATGAAGGGAG GAAATYTTGG AGGCAGAAGC TCTGGCCCCTA'] | 2862 | ['AATYTTGGAGGC AGAAGCTCTGG'] | 3095 | ['AATYTTGGAGGC AGAAGCTCTGG'] |
| NM_022552.4 (DNMT3A):c.2705T>C (p.Phe902Ser) | 1788 | DNMT3A | 2675 | ['CGCAAAATAC TCCTTCAGCGG AGCGRAGAGG TGGCGGATGA CTGGCACGCT'] | 2863 | ['GCGRAGAGGTGG CGGATGACTGG'] | 3096 | ['GCGRAGAGGTGG CGGATGACTGG'] |
| NM_000076.2 (CDKN1C):c.*5+2T>C | 1028 | CDKN1C | 2676 | ['GCGCAAGAG GCTGCGGTGA GCCAAGYGAG TACAGCGCACC TGGGGGGGCGC'] | 2864-2866 | ['CCAAGYGAGTAC AGCGCACCTGG', 'CAAGYGAGTACA GCGCACCTGGG', 'AAGYGAGTACAG CGCACCTGGGG'] | 3097-3099 | ['CCAAGYGAGTAC AGCGCACCTGG', 'CAAGYGAGTACA GCGCACCTGGG', 'AAGYGAGTACAG CGCACCTGGGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NC_012920.1:m.9478T>C | 4514 | MTCO3 | 2677 | ['ATAATCCTAT TTATTACCTCA GAAGYTTTTT CTTCGCAGGAT TTTTCTGA'] | 2867 | ['TCAGAAGYTTTTT TCTTCGCAGG'] | 3100 | ['TCAGAAGYTTTT TTCTTCGCAGG'] |
| NM_002049.3 (GATA1):c.2T>C (p.Met1Thr) | 2623 | GATA1 | 2678 | ['CGCAGGTTAA TCCCCAGAGGC TCCAYGGAGTT CCCTGGCCTGG GGTCCCTG'] | 2868-2869 | ['TCCAYGGAGTTC CCTGGCCTGGG', 'CCAYGGAGTTCC TGGCCTGGGG'] | 3101-3103 | ['CTCCAYGGAGTT CCCTGGCCTGG', 'TCCAYGGAGTTC CCTGGCCTGGG', 'CCAYGGAGTTCC CTGGCCTGGGG'] |
| NM_005740.2 (DNAL4):c.153+2T>C | 10126 | DNAL4 | 2679 | ['GAGAAATTCT CCAACAACAA CGAGGYATTG CCAGCAGTGC AGGCGGCCCCT'] | 2870 | ['CGAGGYATTGCC AGCAGTGCAGG'] | 3104 | ['CGAGGYATTGCC AGCAGTGCAGG'] |
| NM_001287223.1 (SCN11A):c.1142T>C (p.Ile381Thr) | 11280 | SCN11A | 2680 | ['GGGCTCTACT CAGTCTTCTTC TTCAYTGTGGT CATTTTCCTGG GCTCCTTC'] | 2871 | ['TTCAYTGTGGTCA TTTTCCTGGG'] | 3105-3106 | ['CTTCAYTGTGGT CATTTTCCTGG', 'TTCAYTGTGGTCA TTTTCCTGGG'] |
| NM_001302946.1 (TRNT1):c.497T>C (p.Leu166Ser) | 51095 | TRNT1 | 2681 | ['TAATGAATAG GTTTTGATGGC ACTTYATTTGA CTACTTTAATG GTTATGAA'] | 2872 | ['ACTTYATTTGACT ACTTTAATGG'] | 3107 | ['ACTTYATTTGAC TACTTTAATGG'] |
| NM_178151.2 (DCX):c.2T>C (p.Met1Thr) | 1641 | DCX | 2682 | ['AGGTCTCTGA GGTTCCACCAA AATAYGGAAC TTGATTTTGGA CACTTTGAC'] | 2873 | ['CAAAATAYGGAA CTTGATTTTGG'] | 3108 | ['CAAAATAYGGA ACTTGATTTTGG'] |
| NM_000169.2 (GLA):c.758T>C (p.Ile253Thr) | −1 | — | 2683 | ['TGGACATCTT TTAACCAGGA GAGAAYTGTT GATGTTGCTGG ACCAGGGGGT'] | 2874 | ['GAGAGAAYTGTT GATGTTGCTGG'] | 3109 | ['GAGAGAAYTGTT GATGTTGCTGG'] |
| NM_170707.3 (LMNA):c.710T>C (p.Phe237Ser) | 4000 | LMNA | 2684 | ['ATTGACAATG GGAAGCAGCG TGAGTYTGAG AGCCGGCTGG CGGATGCGCTG'] | 2875 | ['TGAGTYTGAGAG CCGGCTGGCGG'] | 3110 | ['TGAGTYTGAGAG CCGGCTGGCGG'] |
| NM_000256.3 (MYBPC3):c.3330+2T>C | 4607 | MYBPC3 | 2685 | ['CAGAAAGCCG ACAAGAAGAC CATGGBGAGC CCAGGGTCTGG GGTCCCCACG'] | 2876-2878 | ['ACCATGGBGAGC CCAGGGTCTGG', 'CCATGGBGAGCCC AGGGTCTGGG', 'CATGGBGAGCCCA GGGTCTGGGG'] | 3111-3113 | ['ACCATGGBGAGC CCAGGGTCTGG', 'CCATGGBGAGCC CAGGGTCTGGG', 'CATGGBGAGCCC AGGGTCTGGGG'] |
| NM_005957.4 (MTHFR):c.1530+2T>C | 4524 | MTHFR | 2686 | ['AGCGGGGGCT ATGTCTTCCAG AAGGYGTGGT AGGGAGGCAC GGGGTGCCCC'] | 2879-2881 | ['GAAGGYGTGGTA GGGAGGCACGG', 'AAGGYGTGGTAG GGAGGCACGGG', 'AGGYGTGGTAGG GAGGCACGGGG'] | 3114-3116 | ['GAAGGYGTGGTA GGGAGGCACGG', 'AAGGYGTGGTAG GGAGGCACGGG', 'AGGYGTGGTAGG GAGGCACGGGG'] |
| NM_000264.3 (PTCH1):c.3168+2T>C | 5727 | PTCH1 | 2687 | ['AACCCCTGGA CGGCCGGGAT CATTGYGAGTG TATTATAAGGG GCTTTGTGG'] | 2882-2884 | ['ATCATTGYGAGT GTATTATAAGG', 'TCATTGYGAGTGT ATTATAAGGG', 'CATTGYGAGTGTA TTATAAGGGG'] | 3117-3119 | ['ATCATTGYGAGT GTATTATAAGG', 'TCATTGYGAGTGT ATTATAAGGG', 'CATTGYGAGTGT ATTATAAGGGG'] |
| NM_000030.2 (AGXT):c.322T>C (p.Trp108Arg) | 189 | AGXT | 2688 | ['CTTCCTGGTT GGGGCCAATG GCATTYGGGG GCAGCGAGCC GTGGACATCGG'] | 2885 | ['CATTYGGGGGCA GCGAGCCGTGG'] | 3120 | ['CATTYGGGGGCA GCGAGCCGTGG'] |
| NM_000023.2 (SGCA):c.371T>C (p.Ile124Thr) | 6442 | SGCA | 2689 | ['ACTCGGCAGA GGCTGGTGCTG GAGAYTGGGG ACCCAGAAGG TACCTCTAGC'] | 2886 | ['CTGGAGAYTGGG GACCCAGAAGG'] | 3121 | ['CTGGAGAYTGGG GACCCAGAAGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001103.3 (ACTN2):c.683T>C (p.Met228Thr) | 88 | ACTN2 | 2690 | ['GAGAAGCACC TGGATATTCCT AAAAYGTTGG ATGCTGAAGGT GAGATGAAA'] | 2887 | ['CCTAAAAYGTTG GATGCTGAAGG'] | 3122 | ['CCTAAAAYGTTG GATGCTGAAGG'] |
| NM_001165963.1 (SCN1A):c.4055T>C (p.Leu1352Pro) | −1 | — | 2691 | ['ATTCCATCCA TCATGAATGTG CTTCYGGTTTG TCTTATATTCT GGCTAATT'] | 2888 | ['TTCYGGTTTGTCT TATATTCTGG'] | 3123 | ['TTCYGGTTTGTC TTATATTCTGG'] |
| NM_001165963.1 (SCN1A):c.1265T>C (p.Val422Ala) | 6323 | SCN1A | 2692 | ['CTAATAAATT TGATCCTGGCT GTGGHGGCCA TGGCCTACGAG GAACAGAAT'] | 2889 | ['TGTGGHGGCCAT GGCCTACGAGG'] | 3124 | ['TGTGGHGGCCAT GGCCTACGAGG'] |
| NM_000426.3 (LAMA2):c.8282T>C (p.Ile2761Thr) | 3908 | LAMA2 | 2693 | ['GCAGAATCAG AACCAGCTCTT TTGAYAGGGA GCAAGCAGTTC GGGCTTTCA'] | 2890-2891 | ['TTGAYAGGGAGC AAGCAGTTCGG', 'TGAYAGGGAGCA AGCAGTTCGGG'] | 3125-3126 | ['TTGAYAGGGAGC AAGCAGTTCGG', 'TGAYAGGGAGCA AGCAGTTCGGG'] |
| NM_000257.3 (MYH7):c.5117T>C (p.Leu1706Pro) | −1 | — | 2694 | ['TCCCGGAAGC TGGCGGAGCA GGAGCYGATT GAGACTAGTG AGCGGGTGCAG'] | 2892 | ['AGCYGATTGAGA CTAGTGAGCGG'] | 3127 | ['AGCYGATTGAGA CTAGTGAGCGG'] |
| NM_001399.4 (EDA):c.396+2T>C | 1896 | EDA | 2695 | ['TCTGACTCCC AGGACGGGCA CCAGGKGAGT CACCTAGTAGG GGCGGCGGCG'] | 2893-2894 | ['ACCAGGKGAGTC ACCTAGTAGGG', 'CCAGGKGAGTCAC CTAGTAGGGG'] | 3128-3130 | ['CACCAGGKGAGT CACCTAGTAGG', 'ACCAGGKGAGTC ACCTAGTAGGG', 'CCAGGKGAGTCA CCTAGTAGGGG'] |
| NM_001848.2 (COL6A1):c.957+2T>C | 1291 | COL6A1 | 2696 | ['TCCAGGGGAC CCAAGGGCTA CAAGGYGAGC GTGGGCTGCTG GGAGGGGGA'] | 2895-2896 | ['ACAAGGYGAGCG TGGGCTGCTGG', 'CAAGGYGAGCGT GGGCTGCTGGG'] | 3131-3132 | ['ACAAGGYGAGC GTGGGCTGCTGG', 'CAAGGYGAGCGT GGGCTGCTGGG'] |
| NM_000238.3 (KCNH2):c.1945+6T>C | 3757 | KCNH2 | 2697 | ['CTGCGTCATG CTCATTGGCTG TGAGYGTGCCC AGGGGCGGGC GGCGGGGAG'] | 2897-2898 | ['CTGTGAGYGTGC CCAGGGGCGGG', 'TGAGYGTGCCCAG GGGCGGGCGG'] | 3133-3134 | ['CTGTGAGYGTGC CCAGGGGCGGG', 'TGAGYGTGCCCA GGGGCGGGCGG'] |
| NM_021007.2 (SCN2A):c.1271T>C (p.Val424Ala) | 6326 | SCN2A | 2698 | ['CTAATAAATT TGATCTTGGCT GTGGYGGCCA TGGCCTATGAG GAACAGAAT'] | 2899 | ['TGTGGYGGCCAT GGCCTATGAGG'] | 3135 | ['TGTGGYGGCCAT GGCCTATGAGG'] |
| NM_021007.2 (SCN2A):c.4308+2T>C | 6326 | SCN2A | 2699 | ['TATGCAGCTG TTGATTCACGA AATGYAAGTCT AGTTAGAGGG AAATTGTTT'] | 2900-2901 | ['CGAAATGYAAGT CTAGTTAGAGG', 'GAAATGYAAGTCT AGTTAGAGGG'] | 3136-3137 | ['CGAAATGYAAGT CTAGTTAGAGG', 'GAAATGYAAGTC TAGTTAGAGGG'] |
| NM_000083.2 (CLCN1):c.1283T>C (p.Phe428Ser) | 1180 | CLCN1 | 2700 | ['CCCCGCGAAG CCATCAGTACT TTGTYTGACAA CAATACATGG GTGAAACAC'] | 2902-2903 | ['CTTTGTYTGACAA CAATACATGG', 'TTTGTYTGACAAC AATACATGGG'] | 3138-3139 | ['CTTTGTYTGACA ACAATACATGG', 'TTTGTYTGACAAC AATACATGGG'] |
| NM_004550.4 (NDUFS2):c.875T>C (p.Met292Thr) | 4720 | NDUFS2 | 2701 | ['CATTATGCTC TCCACAGTGGA GTGAYGCTTCG GGGCTCAGGC ATCCAGTGG'] | 2904 | ['GGAGTGAYGCTT CGGGGCTCAGG'] | 3140 | ['GGAGTGAYGCTT CGGGGCTCAGG'] |
| NM_000546.5 (TP53):c.584T>C (p.Ile195Thr) | 7157 | TP53 | 2702 | ['CACACGCAAA TTTCCTTCCAC TCGGRTAAGAT GCTGAGGAGG GGCCAGACC'] | 2905-2906 | ['CTCGGRTAAGAT GCTGAGGAGGG', 'TCGGRTAAGATGC TGAGGAGGGG'] | 3141-3143 | ['ACTCGGRTAAGA TGCTGAGGAGG', 'CTCGGRTAAGAT GCTGAGGAGGG', 'TCGGRTAAGATG CTGAGGAGGGG'] |

TABLE 3

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_017547.3 (FOXRED1):c.1289A>G (p.Asn430Ser) | 55572 | FOXRED1 | 5084 | ['GTGGGCCCCCACC CGCTAGTTGTCAVC ATGTACTTTGCTACT GGCTTCAGT'] | 5261 | ['CCACCCGCTAGT TGTCAVCATGT'] | 5464-5466 | ['CCCACCCGCTAG TTGTCAVCATG', 'CCACCCGCTAGTT GTCAVCATGT', 'CCCGCTAGTTGTC AVCATGTACT'] |
| NM_000071.2 (CBS):c.1150A>G (p.Lys384Glu) | 875 | CBS | 5085 | ['GGTGACTCCCCCAT CCCGCAGGACCRAG TTCCTGAGCGACAG GTGGATGCT'] | 5262 | ['CCCCATCCCGCA GGACCRAGTTC'] | 5467-5470 | ['CCCCCATCCCGC AGGACCRAGTT', 'CCCCATCCCGCA GGACCRAGTTC', 'CCCATCCCGCAG GACCRAGTTCC', 'CCATCCCGCAGG ACCRAGTTCCT'] |
| NM_000552.3 (VWF):c.2384A>G (p.Tyr795Cys) | 7450 | VWF | 5086 | ['GAGTGTACCAAAA CGTGCCAGAACTRT GACCTGGAGTGCAT GAGCATGGGC'] | 5263 | ['CCAAAACGTGCC AGAACTRTGAC'] | 5471 | ['CCAAAACGTGCC AGAACTRTGAC'] |
| NM_000552.3 (VWF):c.1583A>G (p.Asn528Ser) | 7450 | VWF | 5087 | ['ACCTGCGGCCTGT GTGGGAATTACART GGCAACCAGGGCGA CGACTTCCTT'] | 5264 | ['CCTGTGTGGGAA TTACARTGGCA'] | 5472 | ['CCTGTGTGGGAA TTACARTGGCA'] |
| NM_000308.2 (CTSA):c.1238A>G (p.Tyr413Cys) | 5476 | CTSA | 5088 | ['CTTTAGAAATACC AGATCCTATTATRTA ATGGAGATGTAGAC ATGGCCTGC'] | 5265 | ['CCAGATCCTATT ATRTAATGGAG'] | 5473 | ['CCAGATCCTATT ATRTAATGGAG'] |
| NM_000277.1 (PAH):c.916A>G (p.Ile306Val) | 5053 | PAH | 5089 | ['TTCTATTTTCCCCC AATTACAGGAARTT GGCCTTGCCTCTCTG GGTGCACC'] | 5266 | ['CCCCCAATTACA GGAARTTGGCC'] | 5474-5476 | ['CCCCCAATTACA GGAARTTGGCC', 'CCCCAATTACAG GAARTTGGCCT', 'CCCAATTACAGG AARTTGGCCTT'] |
| NM_000512.4 (GALNS):c.1460A>G (p.Asn487Ser) | 2588 | GALNS | 5090 | ['TTGGTCCCCGCGCA GCCCCAGCTCARCG TGTGCAACTGGGCG GTCATGGTA'] | 5267 | ['CCGCGCAGCCCC AGCTCARCGTG'] | 5477 | ['CCGCGCAGCCCC AGCTCARCGTG'] |
| NM_013319.2 (UBIAD1):c.305A>G (p.Asn102Ser) | 29914 | UBIAD1 | 5091 | ['GTGCACGGGGCCG GTAATTTGGTCARC ACTTACTATGACTTT TCCAAGGGC'] | 5268 | ['CCGGTAATTTGG TCARCACTTAC'] | 5478 | ['CCGGTAATTTGG TCARCACTTAC'] |
| NM_013319.2 (UBIAD1):c.695A>G (p.Asn232Ser) | 29914 | UBIAD1 | 5092 | ['AGCACCGAGGCCA TTCTCCATTCCARCA ACACCAGGGACATG GAGTCCGAC'] | 5269 | ['CCATTCTCCATT CCARCAACACC'] | 5479 | ['CCATTCTCCATT CCARCAACACC'] |
| NM_000275.2 (OCA2):c.1465A>G (p.Asn489Asp) | 4948 | OCA2 | 5093 | ['TGCCACTGCCATCG GGGACCCTCCARAT GTCATTATTGTTTCC AACCAAGA'] | 5270 | ['CCATCGGGGACC CTCCARATGTC'] | 5480 | ['CCATCGGGGACC CTCCARATGTC'] |
| NM_001127255.1 (NLRP7):c.2738A>G (p.Asn913Ser) | −1 | — | 5094 | ['CTCACAAACCTGG ACTTGAGTATCARC CAGATAGCTCGTGG ATTGTGGATT'] | 5271 | ['CCTGGACTTGAG TATCARCCAGA'] | 5481 | ['CCTGGACTTGAG TATCARCCAGA'] |
| NM_152783.4 (D2HGDH):c.1315A>G (p.Asn439Asp) | 728294 | D2HGDH | 5095 | ['TGCCCTTGTCCCTC CAGGAGATGGTRAC CTGCACCTCAATGT GACGGCGGA'] | 5272 | ['CCTCCAGGAGAT GGTRACCTGCA'] | 5482-5483 | ['CCCTCCAGGAGA TGGTRACCTGC', 'CCTCCAGGAGAT GGTRACCTGCA'] |
| NM_022132.4 (MCCC2):c.1309A>G (p.Ile437Val) | 64087 | MCCC2 | 5096 | ['TGTGGCCTGTGCCC AAGTGCCTAAGDTA ACCCTCATCATTGG GGGCTCCTA'] | 5273 | ['CCCAAGTGCCTA AGDTAACCCTC'] | 5484 | ['CCCAAGTGCCTA AGDTAACCCTC'] |
| NM_000022.2 (ADA):c.219-2A>G | 100 | ADA | 5097 | ['TTCCCAACCCCTTT CTTCCCTTCCCRGGG GCTGCCGGGAGGCT ATCAAAAG'] | 5274 | ['CCCCTTTCTTCCC TTCCCRGGGG'] | 5485-5487 | ['CCCCTTTCTTCCC TTCCCRGGGG', 'CCCTTTCTTCCCT TCCCRGGGGC', 'CCTTTCTTCCCTT CCCRGGGGCT'] |
| NM_017780.3 (CHD7):c.3082A>G (p.Ile1028Val) | 55636 | CHD7 | 5098 | ['TTTAGTAATTGCCC CATTGTCCACARTC CCCAACTGGGAAAG GGAATTCCG'] | 5275 | ['CCCCATTGTCCA CARTCCCCAAC'] | 5488 | ['CCCCATTGTCCA CARTCCCCAAC'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000483.4 (APOC2):c.1A>G (p.MetIVal) | −1 | — | 5099 | ['TCAATGTTCCAGGT CTCTGGACACTRTG GGCACACGACTCCT CCCAGCTCT'] | 5276 | ['CCAGGTCTCTGG ACACTRTGGGC'] | 5489 | ['CCAGGTCTCTGG ACACTRTGGGC'] |
| NM_000391.3 (TPP1):c.887-10A>G | 1200 | TPP1 | 5100 | ['TGTCCCTCATGCCG GCCTGGATTTTYTTT TTTTTTTTTTTGAG GGATGGG'] | 5277 | ['CCGGCCTGGATT TTYTTTTTTTT'] | 5490 | ['CCGGCCTGGATT TTYTTTTTTTT'] |
| NM_017890.4 (VPS13B):c.8978A>G (p.Asn2993Ser) | 157680 | VPS13B | 5101 | ['CTTCTGCCCTGGGC CCTGCTTATCARTG AATCCAAATGGGAC CTCTGGCTA'] | 5278 | ['CCTGGGCCCTGC TTATCARTGAA'] | 5491 | ['CCTGGGCCCTGC TTATCARTGAA'] |
| NM_000226.3 (KRT9):c.482A>G (p.Asn161Ser) | 3857 | KRT9 | 5102 | ['GAGAAGAGCACCA TGCAGGAACTCADT TCTCGGCTGGCCTCT TACTTGGAT'] | 5279 | ['CCATGCAGGAAC TCADTTCTCGG'] | 5492 | ['CCATGCAGGAAC TCADTTCTCGG'] |
| NM_000529.2 (MC2R):c.761A>G (p.Tyr254Cys) | 4158 | MC2R | 5103 | ['CCAAGTAACCCT ACTGCGCCTGCTRC ATGTCTCTCTTCCAG GTGAACGGC'] | 5280-5281 | ['CCCCTACTGCGCC TGCTRCATGTC', 'CCTACTGCGCCTG CTRCATGTCT'] | 5493-5495 | ['CCCCTACTGCGC CTGCTRCATGT', 'CCCTACTGCGCCT GCTRCATGTC', 'CCTACTGCGCCTG CTRCATGTCT'] |
| NM_005957.4 (MTHFR):c.971A>G (p.Asn324Ser) | 4524 | MTHFR | 5104 | ['CCAGGCCTCCACTT CTACACCCTCARCC GCGAGATGGCTACC ACAGAGGTG'] | 5282 | ['CCACTTCTACAC CCTCARCCGCG'] | 5496 | ['CCACTTCTACAC CCTCARCCGCG'] |
| NM_000403.3 (GALE):c.101A>G (p.Asn34Ser) | 2582 | GALE | 5105 | ['GGCTACTTGCCTGT GGTCATCGATARCT TCCATAATGCCTTCC GTGGTGAG'] | 5283 | ['CCTGTGGTCATC GATARCTTCCA'] | 5497 | ['CCTGTGGTCATC GATARCTTCCA'] |
| NM_000356.3 (TCOF1):c.149A>G (p.Tyr50Cys) | 6949 | TCOF1 | 5106 | ['CAGCCCGTAACCC TTCTGGACATCTRTA CACACTGGCAACAG TAAGTGGTG'] | 5284-5285 | ['CCCTTCTGGACA TCTRTACACAC', 'CCTTCTGGACATC TRTACACACT'] | 5498-5499 | ['CCCTTCTGGACA TCTRTACACAC', 'CCTTCTGGACATC TRTACACACT'] |
| NM_012464.4 (TLL1):c.1885A>G (p.Ile629Val) | 7092 | TLL1 | 5107 | ['ACTTCTTACCAAAC TTAACGGCACCRTA ACCACCCCTGGCTG GCCCAAGGA'] | 5286 | ['CCAAACTTAACG GCACCRTAACC'] | 5500 | ['CCAAACTTAACG GCACCRTAACC'] |
| NM_000112.3 (SLC26A2):c.1273A>G (p.Asn425Asp) | 1836 | SLC26A2 | 5108 | ['GGAAATGTATGCC ATTGGCTTTTGTRAT ATCATCCCTTCCTTC TTCCACTG'] | 5287 | ['CCATTGGCTTTT GTRATATCATC'] | 5501 | ['CCATTGGCTTTT GTRATATCATC'] |
| NM_000157.3 (GBA):c.680A>G (p.Asn227Ser) | 2629 | GBA | 5109 | ['ACATCACCCACTTG GCTCAAGACCARTG GAGCGGTGAATGGG AAGGGGTCA'] | 5288 | ['CCACTTGGCTCA AGACCARTGGA'] | 5502 | ['CCACTTGGCTCA AGACCARTGGA'] |
| NM_175073.2 (APTX):c.602A>G (p.His201Arg) | 54840 | APTX | 5110 | ['GATAAATACCCAA AGGCCCGTTACCRT TGGCTGGTCTTACC GTGGACCTCC'] | 5289-5290 | ['CCCAAAGGCCCG TTACCRTTGGC', 'CCAAAGGCCCGT TACCRTTGGCT'] | 5503-5504 | ['CCCAAAGGCCCG TTACCRTTGGC', 'CCAAAGGCCCGT TACCRTTGGCT'] |
| NM_020638.2 (FGF23):c.211A>G (p.Ser71Gly) | 8074 | FGF23 | 5111 | ['TGGCGCACCCCAT CAGACCATCTACRG TGAGTAGGGCTTCA GGCTGGGAAG'] | 5291 | ['CCCCATCAGACC ATCTACRGTGA'] | 5505-5507 | ['CCCCATCAGACC ATCTACRGTGA', 'CCCATCAGACCA TCTACRGTGAG', 'CCATCAGACCAT CTACRGTGAGT'] |
| NM_021102.3 (SPINT2):c.488A>G (p.Tyr163Cys) | 10653 | SPINT2 | 5112 | ['AGGAACTCCTGCA ATAACTTCATCTRTG GAGGCTGCCGGGGC AATAAGAAC'] | 5292 | ['CCTGCAATAACT TCATCTRTGGA'] | 5508 | ['CCTGCAATAACT TCATCTRTGGA'] |
| NM_004795.3 (KL):c.578A>G (p.His193Arg) | 9365 | KL | 5113 | ['GTGCAGCCCGTGG TCACCCTGTACCRCT GGGACCTGCCCCAG CGCCTGCAG'] | 5293 | ['CCGTGGTCACCC TGTACCRCTGG'] | 5509 | ['CCGTGGTCACCC TGTACCRCTGG'] |
| NM_012193.3 (FZD4):c.766A>G (p.Ile256Val) | −1 | — | 5114 | ['GTTTTCCTACCCTG AGCGCCCCATCRTA TTTCTCAGTATGTGC TATAATAT'] | 5294-5295 | ['CCCTGAGCGCCC CATCRTATTTC', 'CCTGAGCGCCCC ATCRTATTTCT'] | 5510-5511 | ['CCCTGAGCGCCC CATCRTATTTC', 'CCTGAGCGCCCC ATCRTATTTCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001099274.1 (TINF2):c.838A>G (p.Lys280Glu) | 26277 | TINF2 | 5115 | ['ATGGGCCTCCACT AGGGGAGGCCATDA GGAGCGCCCCACAG TCATGCTGTT'] | 5296 | ['CCACTAGGGGAG GCCATDAGGAG'] | 5512 | ['CCACTAGGGGAG GCCATDAGGAG'] |
| NM_005682.6 (ADGRG1):c.263A>G (p.Tyr88Cys) | 9289 | ADGRG1 | 5116 | ['TCCTTCCCTGACCC CAGGGGCCTCTRCC ACTTCTGCCTCTACT GGAACCGA'] | 5297 | ['CCCCAGGGGCCT CTRCCACTTCT'] | 5513 | ['CCCCAGGGGCCT CTRCCACTTCT'] |
| NM_000369.2 (TSHR):c.1856A>G (p.Asp619Gly) | 7253 | TSHR | 5117 | ['CCGCAGTACAACC CAGGGGACAAAGRT ACCAAAATTGCCAA GAGGATGGCT'] | 5298 | ['CCCCAGGGGACAA AGRTACCAAAA'] | 5514 | ['CCCCAGGGGACAA AGRTACCAAAA'] |
| NM_024009.2 (GJB3):c.497A>G (p.Asn166Ser) | 2707 | GJB3 | 5118 | ['ATGCCGCGCCTGG TGCAGTGTGCCADC GTGGCCCCCTGCCC CAACATCGTG'] | 5299 | ['CCTGGTGCAGTG TGCCADCGTGG'] | 5515 | ['CCTGGTGCAGTG TGCCADCGTGG'] |
| NM_003722.4 (TP63):c.697A>G (p.Lys233Glu) | 8626 | TP63 | 5119 | ['TATCCGCGCCATGC CTGTCTACAAARAA GCTGAGCACGTCAC GGAGGTGGT'] | 5300 | ['CCATGCCTGTCT ACAAARAAGCT'] | 5516 | ['CCATGCCTGTCT ACAAARAAGCT'] |
| NM_003494.3 (DYSF):c.3443-33A>G | 8291 | DYSF | 5120 | ['CAGCTCTTAACCAC TCCAGCCACTCRCT CTGGCACCTCTGTTT TTTCCCTT'] | 5301 | ['CCACTCCAGCCA CTCRCTCTGGC'] | 5517 | ['CCACTCCAGCCA CTCRCTCTGGC'] |
| NM_003494.3 (DYSF):c.1285-2A>G | 8291 | DYSF | 5121 | ['AACTTGTCCCCTCC CTGTGTCTTCTRGCT GTGCAGCAAGATCT TGGAGAAG'] | 5302 | ['CCCCTCCCTGTG TCTTCTRGCTG'] | 5518-5520 | ['CCCCTCCCTGTG TCTTCTRGCTG', 'CCCTCCCTGTGTC TTCTRGCTGT', 'CCTCCCTGTGTCT TCTRGCTGTG'] |
| NM_002408.3 (MGAT2):c.785A>G (p.His262Arg) | 4247 | MGAT2 | 5122 | ['CTTATACTTTTCCT AGAAGAGGATCRCT ACTTAGCCCCAGAC TTTTACCAT'] | 5303 | ['CCTAGAAGAGGA TCRCTACTTAG'] | 5521 | ['CCTAGAAGAGGA TCRCTACTTAG'] |
| NM_000492.3 (CFTR):c.2738A>G (p.Tyr913Cys) | 1080 | CFTR | 5123 | ['GTGATTATCACCA GCACCAGTTCGTRT TATGTGTTTTACATT TACGTGGGA'] | 5304 | ['CCAGCACCAGTT CGTRTTATGTG'] | 5522 | ['CCAGCACCAGTT CGTRTTATGTG'] |
| NM_001814.4 (CTSC):c.857A>G (p.Gln286Arg) | 1075 | CTSC | 5124 | ['TCTCAGACCCCAAT CCTAAGCCCTCRGG AGGTTGTGTCTTGTA GCCAGTAT'] | 5305 | ['CCCCAATCCTAA GCCCTCRGGAG'] | 5523-5525 | ['CCCCAATCCTAA GCCCTCRGGAG', 'CCCAATCCTAAG CCCTCRGGAGG', 'CCAATCCTAAGC CCTCRGGAGGT'] |
| NM_005144.4 (HR):c.-218A>G | 55806 | HR | 5125 | ['TCCGACCCCTCCAA CCTGCGGCCCTRGA GCGCCCCGCCGCC CCGGGGGAA'] | 5306 | ['CCTCCAACCTGC GGCCCTRGAGC'] | 5526-5527 | ['CCTCCAACCTGC GGCCCTRGAGC', 'CCAACCTGCGGC CCTRGAGCGCC'] |
| NM_018488.2 (TBX4):c.1592A>G (p.Gln531Arg) | 9496 | TBX4 | 5126 | ['TCCTTGTCCCGAGA ATCTTCCTTACRGTA CCATTCAGGAATGG GGACTGTG'] | 5307 | ['CCCGAGAATCTT CCTTACRGTAC'] | 5528-5529 | ['CCCGAGAATCTT CCTTACRGTAC', 'CCGAGAATCTTCC TTACRGTACC'] |
| NM_001089.2 (ABCA3):c.1702A>G (p.Asn568Asp) | 21 | ABCA3 | 5127 | ['ACAGATCACCGTC CTGCTGGGCCACRA CGGTGCCGGGAAGA CCACCACCCT'] | 5308 | ['CCGTCCTGCTGG GCCACRACGGT'] | 5530 | ['CCGTCCTGCTGG GCCACRACGGT'] |
| NM_000525.3 (KCNDJ11):c.776A>G (p.His259Arg) | 37671 | KCNJ1 | 5128 | ['CTGGTGGCCCCGCT GATCATCTACCRTG TCATTGATGCCAAC AGCCCACTC'] | 5309-5310 | ['CCCCGCTGATCA TCTACCRTGTC', 'CCCGCTGATCATC TACCRTGTCA'] | 5531-5533 | ['CCCCGCTGATCA TCTACCRTGTC', 'CCCGCTGATCATC TACCRTGTCA', 'CCGCTGATCATCT ACCRTGTCAT'] |
| NM_005587.2 (MEF2A):c.788A>G (p.Asn263Ser) | 4205 | MEF2A | 5129 | ['TCTCCCCCTCCACC AGGTGGTGGTARTC TTGGAATGAACAGT AGGAAACCA'] | 5311 | ['CCACCAGGTGGT GGTARTCTTGG'] | 5534 | ['CCACCAGGTGGT GGTARTCTTGG'] |
| NM_000098.2 (CPT2):c.359A>G (p.Tyr120Cys) | 1376 | CPT2 | 5130 | ['TTTTTAGGACCCTG GTTTGATATGTRCCT ATCTGCTCGAGACT CCGTTGTT'] | 5312 | ['CCTGGTTTGATA TGTRCCTATCT'] | 5535-5536 | ['CCCTGGTTTGAT ATGTRCCTATC', 'CCTGGTTTGATAT GTRCCTATCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_178138.4 (LHX3):c.332A>G (p.Tyr111Cys) | 8022 | LHX3 | 5131 | ['GTGCGCCGCGCCC AGGACTTCGTGTRC CACCTGCACTGCTTT GCCTGCGTC'] | 5313-5314 | ['CCCAGGACTTCG TGTRCCACCTG', 'CCAGGACTTCGT GTRCCACCTGC'] | 5537-5538 | ['CCCAGGACTTCG TGTRCCACCTG', 'CCAGGACTTCGT GTRCCACCTGC'] |
| NM_005502.3 (ABCA1):c.2804A>G (p.Asn935Ser) | 19 | ABCA1 | 5132 | ['CAGATCACCTCCTT CCTGGGCCACARTG GAGCGGGGAAGAC GACCACCATG'] | 5315 | ['CCTCCTTCCTGG GCCACARTGGA'] | 5539-5540 | ['CCTCCTTCCTGG GCCACARTGGA', 'CCTTCCTGGGCCA CARTGGAGCG'] |
| m.3260A>G | 4567 | MT-TL1 | 5133 | ['GATGGCAGAGCCC GGTAATCGCATARA ACTTAAAACTTTAC AGTCAGAGGT'] | 5316-5317 | ['CCCGGTAATCGC ATARAACTTAA', 'CCGGTAATCGCA TARAACTTAAA'] | 5541-5542 | ['CCCGGTAATCGC ATARAACTTAA', 'CCGGTAATCGCA TARAACTTAAA'] |
| m.4269A>G | 4565 | MT-TI | 5134 | ['GCATTCCCCCTCAA ACCTAAGAAATRTG TCTGATAAAAGAGT TACTTTGAT'] | 5318-5319 | ['CCCTCAAACCTA AGAAATRTGTC', 'CCTCAAACCTAA GAAATRTGTCT'] | 5543-5544 | ['CCCTCAAACCTA AGAAATRTGTC', 'CCTCAAACCTAA GAAATRTGTCT'] |
| m.14495A>G | 4541 | MT-ND6 | 5135 | ['TCCAAAGACAACC ATCATTCCCCCTRA ATAAATTAAAAAAA CTATTAAACC'] | 5320 | ['CCATCATTCCCC CTRAATAAATT'] | 5545 | ['CCATCATTCCCC CTRAATAAATT'] |
| NM_002764.3 (PRPS1):c.341A>G (p.Asn114Ser) | 5631 | PRPS1 | 5136 | ['CCAATCTCAGCCA AGCTTGTTGCAART ATGCTATCTGTAGC AGGTGCAGAT'] | 5321 | ['CCAAGCTTGTTG CAARTATGCTA'] | 5546 | ['CCAAGCTTGTTG CAARTATGCTA'] |
| NM_000054.4 (AVPR2):c.614A>G (p.Tyr205Cys) | 554 | AVPR2 | 5137 | ['GCGGAGCCCTGGG GCCGTCGCACCTRT GTCACCTGGATTGC CCTGATGGTG'] | 5322 | ['CCTGGGGCCGTC GCACCTRTGTC'] | 5547 | ['CCTGGGGCCGTC GCACCTRTGTC'] |
| NM_000033.3 (ABCD1):c.443A>G (p.Asn148Ser) | 215 | ABCD1 | 5138 | ['ATCGCCCTCCCTGC TACCTTCGTCARCA GTGCCATCCGTTAC CTGGAGGGC'] | 5323-5324 | ['CCCTGCTACCTT CGTCARCAGTG', 'CCTGCTACCTTCG TCARCAGTGC'] | 5548-5549 | ['CCCTGCTACCTT CGTCARCAGTG', 'CCTGCTACCTTCG TCARCAGTGC'] |
| NM_000061.2 (BTK):c.1082A>G (p.Tyr361Cys) | 695 | BTK | 5139 | ['AGCACCATCCCTG AGCTCATTAACTRC CATCAGCACAACTC TGCAGGTGAG'] | 5325-5326 | ['CCCTGAGCTCAT TAACTRCCATC', 'CCTGAGCTCATTA ACTRCCATCA'] | 5550-5551 | ['CCCTGAGCTCAT TAACTRCCATC', 'CCTGAGCTCATTA ACTRCCATCA'] |
| NM_003413.3 (ZIC3):c.1213A>G (p.Lys405Glu) | 7547 | ZIC3 | 5140 | ['CTACACGCACCCG AGCTCCCTGCGCRA ACACATGAAGGTAA TTACCTCTTT'] | 5327 | ['CCCGAGCTCCCTG CGCRAACACAT'] | 5552-5553 | ['CCCGAGCTCCCT GCGCRAACACA', 'CCGAGCTCCCTGC GCRAACACAT'] |
| NM_005448.2 (BMP15):c.704A>G (p.Tyr235Cys) | 9210 | BMP15 | 5141 | ['TTGGACATTGCCTT CTTGTTACTCTRTTT CAATGATACTCATA AAAGCATT'] | 5328 | ['CCTTCTTGTTACT CTRTTTCAAT'] | 5554 | ['CCTTCTTGTTACT CTRTTTCAAT'] |
| NM_001363.4 (DKC1):c.1069A>G (p.Thr357Ala) | 1736 | DKC1 | 5142 | ['ATTAATGACCACA GCGGTCATCTCTRC CTGCGACCATGGTA TAGTAGCCAA'] | 5329 | ['CCACAGCGGTCA TCTCTRCCTGC'] | 5555 | ['CCACAGCGGTCA TCTCTRCCTGC'] |
| NM_000481.3 (AMT):c.125A>G (p.His42Arg) | 275 | AMT | 5143 | ['CGCAGGACACCGC TCTATGACTTCCRCC TGGCCCACGGCGGG AAAATGGTG'] | 5330 | ['CCGCTCTATGAC TTCCRCCTGGC'] | 5556 | ['CCGCTCTATGAC TTCCRCCTGGC'] |
| NM_003361.3 (UMOD):c.383A>G (p.Asn128Ser) | 7369 | UMOD | 5144 | ['TGCCACGCCCTGG CCACATGTGTCART GTGGTGGGCAGCTA CTTGTGCGTA'] | 5331 | ['CCTGGCCACATG TGTCARTGTGG'] | 5557-5558 | ['CCCTGGCCACAT GTGTCARTGTG', 'CCTGGCCACATGT GTCARTGTGG'] |
| NM_001382.3 (DPAGT1):c.509A>G (p.Tyr170Cys) | 1798 | DPAGT1 | 5145 | ['TCTCTCCCCGCAGG AATCCTGTACTRTGT CTACATGGGGCTGC TGGCAGTG'] | 5332 | ['CCGCAGGAATCC TGTACTRTGTC'] | 5559 | ['CCGCAGGAATCC TGTACTRTGTC'] |
| NM_001128177.1 (THRB):c.1324A>G (p.Met442Val) | 7068 | THRB | 5146 | ['CTGCCATGCCAGC CGCTTCCTGCACRT GAAGGTGGAATGCC CCACAGAACT'] | 5333 | ['CCAGCCGCTTCC TGCACRTGAAG'] | 5560 | ['CCAGCCGCTTCC TGCACRTGAAG'] |
| NM_000141.4 (FGFR2):c.874A>G (p.Lys292Glu) | 2263 | FGFR2 | 5147 | ['TGCCCAGCCCCAC ATCCAGTGGATCRA GCACGTGGAAAAGA ACGGCAGTAA'] | 5334 | ['CCCACATCCAGT GGATCRAGCAC'] | 5561-5563 | ['CCCCACATCCAG TGGATCRAGCA', 'CCCACATCCAGT GGATCRAGCAC', 'CCACATCCAGTG GATCRAGCACG'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: Flanks | Flanks | SEQ ID NO: GRNAs | GRNAs | SEQ ID NO: gRNAall | gRNAall |
|---|---|---|---|---|---|---|---|---|
| NM_000371.3 (TTR):c.401A>G (p.Tyr134Cys) | 7276 | TTR | 5148 | ['ACCATTGCCGCCCT GCTGAGCCCCTRCT CCTATTCCACCACG GCTGTCGTC'] | 5335-5337 | ['CCGCCCTGCTGA GCCCCTRCTCC', 'CCCTGCTGAGCCC CTRCTCCTAT', 'CCTGCTGAGCCCC TRCTCCTATT'] | 5564-5566 | ['CCGCCCTGCTGA GCCCCTRCTCC', 'CCCTGCTGAGCCC CTRCTCCTAT', 'CCTGCTGAGCCCC TRCTCCTATT'] |
| NM_000371.3 (TTR):c.379A>G (p.Ile127Val) | 7276 | TTR | 5149 | ['CGACTCCGGCCCC CGCCGCTACACCRT TGCCGCCCTGCTGA GCCCCTACTC'] | 5338 | ['CCCCCGCCGCTA CACCRTTGCCG'] | 5567-5569 | ['CCCCCGCCGCTA CACCRTTGCCG', 'CCCCGCCGCTAC ACCRTTGCCGC', 'CCCGCCGCTACA CCRTTGCCGCC'] |
| NM_000174.4 (GP9):c.182A>G (p.Asn61Ser) | 2815 | GP9 | 5150 | ['ACCCGCCACCTTCT GCTGGCCAACARCA GCCTTCAGTCCGTG CCCCCGGGA'] | 5339 | ['CCTTCTGCTGGC CAACARCAGCC'] | 5570 | ['CCTTCTGCTGGC CAACARCAGCC'] |
| NM_000222.2 (KIT):c.1924A>G (p.Lys642Glu) | 3815 | KIT | 5151 | ['ACGGGAAGCCCTC ATGTCTGAACTCRA AGTCCTGAGTTACC TTGGTAATCA'] | 5340-5341 | ['CCCTCATGTCTG AACTCRAAGTC', 'CCTCATGTCTGAA CTCRAAGTCC'] | 5571-5572 | ['CCCTCATGTCTG AACTCRAAGTC', 'CCTCATGTCTGAA CTCRAAGTCC'] |
| NM_000530.6 (MPZ):c.242A>G (p.His81Arg) | 4359 | MPZ | 5152 | ['TCCCCTCATTCCTC ATAGATCTTCCRCT ATGCCAAGGGACAA CCCTACATT'] | 5342 | ['CCTCATAGATCT TCCRCTATGCC'] | 5573 | ['CCTCATAGATCT TCCRCTATGCC'] |
| NM_000233.3 (LHCGR):c.1733A>G (p.Asp578Gly) | -1 | — | 5153 | ['AAAATGGCAATCC TCATCTTCACCGRTT TCACCTGCATGGCA CCTATCTCT'] | 5343 | ['CCTCATCTTCAC CGRTTTCACCT'] | 5574 | ['CCTCATCTTCAC CGRTTTCACCT'] |
| NM_000421.3 (KRT10):c.1374-2A>G | -1 | — | 5154 | ['CCGCCGCGTCCGC CGCCTCCGGAACYA AACGGGGTGAGGTC ACATTCGGTT'] | 5344 | ['CCGCCGCCTCCG GAACYAAACGG'] | 5575 | ['CCGCCGCCTCCG GAACYAAACGG'] |
| NM_000422.2 (KRT17):c.274A>G (p.Asn92Asp) | 3872 | KRT17 | 5155 | ['TGAGAAGGCCACC ATGCAGAACCTCVA TGACCGCCTGGCCT CCTACCTGGA'] | 5345 | ['CCACCATGCAGA ACCTCVATGAC'] | 5576-5577 | ['CCACCATGCAGA ACCTCVATGAC', 'CCATGCAGAACC TCVATGACCGC'] |
| NM_000422.2 (KRT17):c.275A>G (p.Asn92Ser) | 3872 | KRT17 | 5156 | ['GAGAAGGCCACCA TGCAGAACCTCART GACCGCCTGGCCTC CTACCTGGAC'] | 5346 | ['CCACCATGCAGA ACCTCARTGAC'] | 5578-5579 | ['CCACCATGCAGA ACCTCARTGAC', 'CCATGCAGAACC TCARTGACCGC'] |
| NM_000823.3 (GHRHR):c.985A>G (p.Lys329Glu) | 2692 | GHRHR | 5157 | ['TTGTCTTTCCTGCA GGCGTCTCTCCRAG TCGACACTTTTCCTG ATCCCACT'] | 5347 | ['CCTGCAGGCGTC TCTCCRAGTCG'] | 5580 | ['CCTGCAGGCGTC TCTCCRAGTCG'] |
| NM_000407.4 (GP1BB):c.338A>G (p.Tyr113Cys) | -1 | — | 5158 | ['GCCGGCCGCCCCG AGCGTGCGCCCTDC CGCGACCTGCGTTG CGTGGCGCCC'] | 5348-5349 | ['CCCCGAGCGTGC GCCCTDCCGCG', 'CCCGAGCGTGCG CCCTDCCGCGA'] | 5581-5583 | ['CCCCGAGCGTGC GCCCTDCCGCG', 'CCCGAGCGTGCG CCCTDCCGCGA', 'CCGAGCGTGCGC CCTDCCGCGAC'] |
| NM_001146040.1 (GLRA1):c.920A>G (p.Tyr307Cys) | 2741 | GLRA1 | 5159 | ['CCTCCACCCCCACT CTAGGTGTCCTVTGT GAAAGCCATTGACA TTTGGATG'] | 5350-5351 | ['CCCCACTCTAGG TGTCCTVTGTG', 'CCCACTCTAGGTG TCCTVTGTGA'] | 5584-5586 | ['CCCCACTCTAGG TGTCCTVTGTG', 'CCCACTCTAGGTG TCCTVTGTGA', 'CCACTCTAGGTGT CCTVTGTGAA'] |
| NM_182925.4 (FLT4):c.3104A>G (p.His1035Arg) | 2324 | FLT4 | 5160 | ['CGCCTCCCCGCACC CCAGTGCATCCRCA GAGACCTGGCTGCT CGGAACATT'] | 5352 | ['CCGCACCCCAGT GCATCCRCAGA'] | 5587 | ['CCGCACCCCAGT GCATCCRCAGA'] |
| NM_212482.1 (FN1):c.2918A>G (p.Tyr973Cys) | 2335 | FN1 | 5161 | ['ACCGGGCTGTCCC CTGGGGTCACCTRT TACTTCAAAGTCTTT GCAGTGAGC'] | 5353-5354 | ['CCCCTGGGGTCA CCTRTTACTTC', 'CCCTGGGGTCAC CTRTTACTTCA'] | 5588-5589 | ['CCCCTGGGGTCA CCTRTTACTTC', 'CCCTGGGGTCAC CTRTTACTTCA'] |
| NM_000121.3 (EPOR):c.1460A>G (p.Asn487Ser) | 2057 | EPOR | 5162 | ['GGCTTATCCGATG GCCCCTACTCCARC CCTTATGAGAACAG CCTTATCCCA'] | 5355 | ['CCGATGGCCCCT ACTCCARCCCT'] | 5590 | ['CCGATGGCCCCT ACTCCARCCCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001735.2 (C5):c.1115A>G (p.Lys372Arg) | 727 | C5 | 5163 | ['CGTCTACCCCCTCA CCCAATCTACCYTG ATGGGATATGGAAT CCCAGGCTT'] | 5356-5357 | ['CCCCTCACCCAA TCTACCYTGAT', 'CCCTCACCCAATC TACCYTGATG'] | 5591-5593 | ['CCCCTCACCCAA TCTACCYTGAT', 'CCCTCACCCAATC TACCYTGATG', 'CCTCACCCAATCT ACCYTGATGG'] |
| NM_001844.4 (COL2A1):c.4172A>G (p.Tyr1391Cys) | 1280 | COL2A1 | 5164 | ['ACGGAAGGCTCCC AGAACATCACCTRC CACTGCAAGAACAG CATTGCCTAT'] | 5358-5359 | ['CCCAGAACATCA CCTRCCACTGC', 'CCAGAACATCAC CTRCCACTGCA'] | 5594-5595 | ['CCCAGAACATCA CCTRCCACTGC', 'CCAGAACATCAC CTRCCACTGCA'] |
| NM_001904.3 (CTNNB1):c.121A>G (p.Thr41Ala) | 1499 | CTNNB1 | 5165 | ['CTCTGGAATCCATT CTGGTGCCACTNCC ACAGCTCCTTCTCTG AGTGGTAA'] | 5360 | ['CCATTCTGGTGC CACTNCCACAG'] | 5596 | ['CCATTCTGGTGC CACTNCCACAG'] |
| NM_000040.1 (APOC3):c.280A>G (p.Thr94Ala) | 345 | APOC3 | 5166 | ['GGATTTGGACCCT GAGGTCAGACCARC TTCAGCCGTGGCTG CCTGAGACCT'] | 5361-5362 | ['CCCTGAGGTCAG ACCARCTTCAG', 'CCTGAGGTCAGA CCARCTTCAGC'] | 5597-5598 | ['CCCTGAGGTCAG ACCARCTTCAG', 'CCTGAGGTCAGA CCARCTTCAGC'] |
| NM_000488.3 (SERPINC1):c.655A>G (p.Asn219Asp) | 462 | SERPINC1 | 5167 | ['TGCAGAGCAATCC AGAGCGGCCATCRA CAAATGGGTGTCCA ATAAGACCGA'] | 5363 | ['CCAGAGCGGCCA TCRACAAATGG'] | 5599 | ['CCAGAGCGGCCA TCRACAAATGG'] |
| NM_001085.4 (SERPINA3):c.1240A>G (p.Met414Val) | 12 | SERPINA3 | 5168 | ['TACAGACACCCAG AACATCTTCTTCRTG AGCAAAGTCACCAA TCCCAAGCA'] | 5364 | ['CCCAGAACATCT TCTTCRTGAGC'] | 5600-5601 | ['CCCAGAACATCT TCTTCRTGAGC', 'CCAGAACATCTTC TTCRTGAGCA'] |
| NM_001145.4 (ANG):c.121A>G (p.Lys41Glu) | −1 | — | 5169 | ['CTTCCTGACCCAGC ACTATGATGCCRAA CCACAGGGCCGGGA TGACAGATA'] | 5365 | ['CCAGCACTATGA TGCCRAACCAC'] | 5602-5603 | ['CCCAGCACTATG ATGCCRAACCA', 'CCAGCACTATGA TGCCRAACCAC'] |
| NM_001100.3 (ACTA1):c.350A>G (p.Asn117Ser) | 58 | ACTA1 | 5170 | ['GAGGCCCCCCTCA ATCCCAAGGCCARC CGCGAGAAGATGAC CCAGATCATG'] | 5366 | ['CCTCAATCCCAA GGCCARCCGCG'] | 5604-5605 | ['CCCTCAATCCCA AGGCCARCCGC', 'CCTCAATCCCAA GGCCARCCGCG'] |
| NM_014053.3 (FLVCR1):c.361A>G (p.Asn121Asp) | 28982 | FLVCR1 | 5171 | ['GATCTTCAGCCTGT ACTCGCTGGTCRAC GCCTTTCAGTGGAT CCAGTACAG'] | 5367 | ['CCTGTACTCGCT GGTCRACGCCT'] | 5606 | ['CCTGTACTCGCT GGTCRACGCCT'] |
| NM_000334.4 (SCN4A):c.4078A>G (p.Met1360Val) | 6329 | SCN4A | 5172 | ['GAAGCAGGCCTTC GACATCACCATCRT GATCCTCATCTGCCT CAACATGGT'] | 5368 | ['CCTTCGACATCA CCATCRTGATC'] | 5607 | ['CCTTCGACATCA CCATCRTGATC'] |
| NM_004519.3 (KCNQ3):c.1403A>G (p.Asn468Ser) | 3786 | KCNQ3 | 5173 | ['GAACCAAAGCCTG TTGGCTTAAACART AAAGAGCGTTTCCG CACGGCCTTC'] | 5369 | ['CCTGTTGGCTTA AACARTAAAGA'] | 5608 | ['CCTGTTGGCTTA AACARTAAAGA'] |
| NM_007375.3 (TARDBP):c.800A>G (p.Asn267Ser) | 23435 | TARDBP | 5174 | ['AATGCCGAACCTA AGCACAATAGCART AGACAGTTAGAAAG AAGTGGAAGA'] | 5370 | ['CCTAAGCACAAT AGCARTAGACA'] | 5609 | ['CCTAAGCACAAT AGCARTAGACA'] |
| NM_032520.4 (GNPTG):c.6102A>G | 84572 | GNPTG | 5175 | ['TGCTGCCCCTGCAT CCTCCACCTTCRGG GCCATGAGAAGTTG CTGAGGACA'] | 5371 | ['CCTGCATCCTCC ACCTTCRGGGC'] | 5610 | ['CCTGCATCCTCC ACCTTCRGGGC'] |
| NM_000495.4 (COL4A5):c.466-2A>G | 1287 | COL4A5 | 5176 | ['AGAACTTCCATTG ATGGCTTCTTTTGG GTGAACCAGGTAGT ATAATTATG'] | 5372 | ['CCATTGATGGCT TCTTTTRGGGT'] | 5611 | ['CCATTGATGGCT TCTTTTRGGGT'] |
| NM_000495.4 (COL4A5):c.1340-2A>G | 12875 | COMA | 5177 | ['TTGCTATCCTTTCT TTATCTTACTCRGGT GATGAGATATGTGA ACCAGGCC'] | 5373 | ['CCTTTCTTTATCT TACTCRGGTG'] | 5612 | ['CCTTTCTTTATCT TACTCRGGTG'] |
| NM_000060.3 (BTD):c.278A>G (p.Tyr93Cys) | 686 | BTD | 5178 | ['CTCATGAACCAGA ACCTTGACATCTRT GAACAGCAAGTGAT GACTGCAGCC'] | 5374 | ['CCAGAACCTTGA CATCTRTGAAC'] | 5613 | ['CCAGAACCTTGA CATCTRTGAAC'] |
| NM_000060.3 (BTD):c.641A>G (p.Asn214Ser) | 686 | BTD | 5179 | ['CTTGTTGACCGCTA CCGTAAACACARCC TCTACTTTGAGGCA GCATTCGAT'] | 5375 | ['CCGCTACCGTAA ACACARCCTCT'] | 5614 | ['CCGCTACCGTAA ACACARCCTCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000094.3 (COL7A1):c.425A>G (p.Lys142Arg) | 1294 | COL7A1 | 5180 | ['CAGCTGGCCCGAC CTGGTGTCCCCARG GTGATCCCTACCCC TACCATGCCT'] | 5376 | ['CCCGACCTGGTG TCCCCARGGTG'] | 5615- 5616 | ['CCCGACCTGGTG TCCCCARGGTG', 'CCGACCTGGTGTC CCCARGGTGA'] |
| NM_005247.2 (FGF3):c.146A>G (p.Tyr49Cys) | 2248 | FGF3 | 5181 | ['GGGGCGCCCCGGC GCCGCAAGCTCTRC TGCGCCACGAAGTA CCACCTCCAG'] | 5377- 5378 | ['CCCGGCGCCGCA AGCTCTRCTGC', 'CCGGCGCCGCAA GCTCTRCTGCG'] | 5617- 5618 | ['CCCGGCGCCGCA AGCTCTRCTGC', 'CCGGCGCCGCAA GCTCTRCTGCG'] |
| NM_000313.3 (PROS1):c.701A>G (p.Tyr234Cys) | 5627 | PROS1 | 5182 | ['TGTGAATGCCCCG AAGGCTACAGATRT AATCTCAAATCAAA GTCTTGTGAA'] | 5379- 5380 | ['CCCGAAGGCTAC AGATRTAATCT', 'CCGAAGGCTACA GATRTAATCTC'] | 5619- 5621 | ['CCCCGAAGGCTA CAGATRTAATCT', 'CCCGAAGGCTAC AGATRTAATCT', 'CCGAAGGCTACA GATRTAATCTC'] |
| NM_004612.3 (TGFBR1):c.134A>G (p.Asn45Ser) | 7046 | TGFBR1 | 5183 | ['TTCTGCCACCTCTG TACAAAAGACARTT TTACTTGTGTGACA GATGGGCTC'] | 5381 | ['CCTCTGTACAAA AGACARTTTTA'] | 5622 | ['CCTCTGTACAAA AGACARTTTTA'] |
| m.608A>G | 4558 | MT-TF | 5184 | ['GTAGCTTACCTCCT CAAAGCAATACRCT GAAAATGTTTAGAC GGGCTCACA'] | 5382 | ['CCTCCTCAAAGC AATACRCTGAA'] | 5623- 5624 | ['CCTCCTCAAAGC AATACRCTGAA', 'CCTCAAAGCAAT ACRCTGAAAAT'] |
| NM_001376.4 (DYNC1H1):c.2909A>G (p.Tyr970Cys) | 1778 | DYNC1H1 | 5185 | ['CTAAGAATAACCA ATCAGGTAATCTRC TTGAATCCACCAAT TGAAGAGTGC'] | 5383 | ['CCAATCAGGTAA TCTRCTTGAAT'] | 5625 | ['CCAATCAGGTAA TCTRCTTGAAT'] |
| NM_000459.4 (TEK):c.2690A>G (p.Tyr897Cys) | 7010 | TEK | 5186 | ['ATGCTCTCTTCCTT CCCTCCAGGCTVCT TGTACCTGGCCATT GAGTACGCG'] | 5384 | ['CCTTCCCTCCAG GCTVCTTGTAC'] | 5626 | ['CCTTCCCTCCAG GCTVCTTGTAC'] |
| NM_014191.3 (SCN8A):c.5302A>G (p.Asn1768Asp) | 6334 | SCN8A | 5187 | ['CATGTACATTGCCA TCATCCTGGAGRAC TTCAGTGTAGCCAC AGAGGAAAG'] | 5385 | ['CCATCATCCTGG AGRACTTCAGT'] | 5627 | ['CCATCATCCTGG AGRACTTCAGT'] |
| NM_002552.4 (ORC4):c.521A>G (p.Tyr174Cys) | 5000 | ORC4 | 5188 | ['CATCATAAAAACC AAACACTTCTCTRT AATCTTTTTGACATT TCTCAGTCT'] | 5386 | ['CCAAACACTTCT CTRTAATCTTT'] | 5628 | ['CCAAACACTTCT CTRTAATCTTT'] |
| NM_004813.2 (PEX16):c.992A>G (p.Tyr331Cys) | 9409 | PEX16 | 5189 | ['TACTTGCCCACCTG GCAGAAAATCTRCT TCTACAGTTGGGC TGACAGACC'] | 5387- 5388 | ['CCACCTGGCAGA AAATCTRCTTC', 'CCTGGCAGAAAA TCTRCTTCTAC'] | 5629- 5630 | ['CCACCTGGCAGA AAATCTRCTTC', 'CCTGGCAGAAAA TCTRCTTCTAC'] |
| NM_016952.4 (CDON):c.2368A>G (p.Thr790Ala) | 50937 | CDON | 5190 | ['GTTTTTGTTTTCCC TCAAAGGTTCARCA TACAAATTTAGGGT CATTGCCAT'] | 5389 | ['CCCTCAAAGGTT CARCATACAAA'] | 5631 | ['CCCTCAAAGGTT CARCATACAAA'] |
| NM_016464.4 (TMEM138):c.287A>G (p.His96Arg) | 51524 | TMEM138 | 5191 | ['TACTTTGCCCTCAG CATCTCCCTTCRTGT CTGGGTCATGGTAA GAGTGGCA'] | 5390- 5391 | ['CCCTCAGCATCT CCCTTCRTGTC', 'CCTCAGCATCTCC CTTCRTGTCT'] | 5632- 5633 | ['CCCTCAGCATCT CCCTTCRTGTC', 'CCTCAGCATCTCC CTTCRTGTCT'] |
| NM_005022.3 (PFN1):c.350A>G (p.Glu117Gly) | 5216 | PFN1 | 5192 | ['GTTGATCAAACCA CCGTGGACACCTYC TTTGCCCATCAGCA GGACTAGCGC'] | 5392 | ['CCACCGTGGACA CCTYCTTTGCC'] | 5634 | ['CCACCGTGGACA CCTYCTTTGCC'] |
| NM_022787.3 (NMNAT1):c.817A>G (p.Asn273Asp) | 64802 | NMNAT1 | 5193 | ['GGTCATCCTGGCCC CTTTGCAGAGARAC ACTGCAGAAGCTAA GACATAGGA'] | 5393 | ['CCCCTTTGCAGA GARACACTGCA'] | 5635 | ['CCCCTTTGCAGA GARACACTGCA'] |
| NM_005340.6 (HINT1):c.152A>G (p.His51Arg) | 3094 | HINT1 | 5194 | ['GACATTTCCCCTCA AGCACCAACACRTT TTCTGGTGATACCC AAGAAACAT'] | 5394- 5396 | ['CCCCTCAAGCAC CAACACRTTTT', 'CCCTCAAGCACC AACACRTTTTC', 'CCTCAAGCACCA ACACRTTTTCT'] | 5636- 5638 | ['CCCCTCAAGCAC CAACACRTTTT', 'CCCTCAAGCACC AACACRTTTTC', 'CCTCAAGCACCA ACACRTTTTCT'] |
| NM_005211.3 (CSF1R):c.2320-2A>G | 1436 | CSF1R | 5195 | ['GACTAACCCTGCA GTGCTTTCCCTCRGT GCATCCACCGGGAC GTGGCAGCG'] | 5397 | ['CCTGCAGTGCTT TCCCTCRGTGC'] | 5639 | ['CCTGCAGTGCTT TCCCTCRGTGC'] |

TABLE 3-continued

A to G with NGG PAM. Table 2 shows a list of A to G mutations that may be
corrected using any of the base editors provided herein. GRNAs and gRNAall indicate the
protospacer and PAM sequence, where the PAM sequence is the last 3 nucleotides of each of
the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001039958.1 (MESP2):c.271A>G (p.Lys91Glu) | 145873 | MESP2 | 5196 | ['GCGGCAGAGCGCC AGCGAGCGGGAGRA ACTGCGCATGCGCA CGCTGGCCCG'] | 5398 | ['CCAGCGAGCGGG AGRAACTGCGC'] | 5640 | ['CCAGCGAGCGGG AGRAACTGCGC'] |
| NM_001099274.1 (TINF2):c.850A>G (p.Thr284Ala) | 26277 | TINF2 | 5197 | ['TAGGGGAGGCCAT AAGGAGCGCCCCRC AGTCATGCTGTTTCC CTTTAGGAA'] | 5399 | ['CCATAAGGAGCG CCCCRCAGTCA'] | 5641 | ['CCATAAGGAGCG CCCCRCAGTCA'] |
| NM_003863.3 (DPM2):c.68A>G (p.Tyr23Cys) | 8818 | DPM2 | 5198 | ['GCCGTTAGCCTGAT CATCTTCACCTRCTA CACCGCCTGGGTGA TTCTCTTG'] | 5400 | ['CCTGATCATCTT CACCTRCTACA'] | 5642 | ['CCTGATCATCTT CACCTRCTACA'] |
| NM_000530.6 (MPZ):c.347A>G (p.Asn116Ser) | 4359 | MPZ | 5199 | ['AAGGATGGCTCCA TTGTCATACACARC CTAGACTACAGTGA CAATGGCACG'] | 5401 | ['CCATTGTCATAC ACARCCTAGAC'] | 5643 | ['CCATTGTCATAC ACARCCTAGAC'] |
| NM_000138.4 (FBN1):c.3058A>G (p.Thr1020Ala) | 2200 | FBN1 | 5200 | ['ACCCGGATTTGCC ACAAAAGAAATTRC AAATGGAAAGCCTT TCTTCAAAGG'] | 5402 | ['CCACAAAAGAA ATTRCAAATGGA'] | 5644 | ['CCACAAAAGAA ATTRCAAATGGA'] |
| NM_000169.2 (GLA):c.1153A>G (p.Thr385Ala) | -1 | — | 5201 | ['GGCCTGTAATCCTG CCTGCTTCATCRCAC AGCTCCTCCCTGTG AAAAGGAA'] | 5403 | ['CCTGCCTGCTTC ATCRCACAGCT'] | 5645 | ['CCTGCCTGCTTC ATCRCACAGCT'] |
| NM_000257.3 (MYH7):c.2206A>G (p.Ile736Val) | 4625 | MYH7 | 5202 | ['AGCGGCCATCCCT GAGGGACAGTTCRT TGATAGCAGGAAGG GGGCAGAGAA'] | 5404 | ['CCCTGAGGGACA GTTCRTTGATA'] | 5646-5647 | ['CCCTGAGGGACA GTTCRTTGATA', 'CCTGAGGGACAG TTCRTTGATAG'] |
| NM_018972.2 (GDAP1):c.368A>G (p.His123Arg) | 54332 | GDAP1 | 5203 | ['AGCATGTATTACCC ACGGGTACAACRTT ACCGAGAGCTGCTT GACTCCTTG'] | 5405 | ['CCCACGGGTACA ACRTTACCGAG'] | 5648 | ['CCCACGGGTACA ACRTTACCGAG'] |
| NM_001946.3 (DUSP6):c.566A>G (p.Asn189Ser) | 1848 | DUSP6 | 5204 | ['ACTACCATCCGAG TCTGTTGCACTAYTG GGGTCTCGGTCAAG GTCAGACTC'] | 5406 | ['CCGAGTCTGTTG CACTAYTGGGG'] | 5649 | ['CCGAGTCTGTTG CACTAYTGGGG'] |
| NM_003867.3 (FGF17):c.560A>G (p.Asn187Ser) | 8822 | FGF17 | 5205 | ['TACCAAGGCCAGC TGCCCTTCCCCARCC ACGCCGAGAAGCAG AAGCAGTTC'] | 5407 | ['CCAGCTGCCCTT CCCCARCCACG'] | 5650 | ['CCAGCTGCCCTT CCCCARCCACG'] |
| NM_015560.2 (OPA1):c.1146A>G (p.Ile382Met) | 4976 | OPA1 | 5206 | ['TTTTTATTTTTCCT GAGTAGACCATRTC CTTAAATGTAAAAG GCCCTGGAC'] | 5408 | ['CCTGAGTAGACC ATRTCCTTAAA'] | 5651 | ['CCTGAGTAGACC ATRTCCTTAAA'] |
| NM_002972.3 (SBF1):c.1249A>G (p.Met417Val) | 6305 | SBF1 | 5207 | ['AAGGCCATGCCCT CCAGCACCTTCAYC AGGAAATCGTCCTC TACCAGCCCA'] | 5409 | ['CCCTCCAGCACC TTCAYCAGGAA'] | 5652-5653 | ['CCCTCCAGCACC TTCAYCAGGAA', 'CCTCCAGCACCTT CAYCAGGAAA'] |
| NM_006876.2 (B4GAT1):c.1168A>G (p.Asn390Asp) | 11041 | B4GAT1 | 5208 | ['GTTCCATCCCCAAA AGGAGGCTGAAAT CAGCACAATAAGAT CCTATATCG'] | 5410 | ['CCAAAAGGAGG CTGAAARATCAGC'] | 5654-5656 | ['CCCCAAAAGGAG GCTGAAARATCA', 'CCCAAAAGGAGG CTGAAARATCAG', 'CCAAAAGGAGGC TGAAARATCAGC'] |
| NM_000218.2 (KCNQ1):c.332A>G (p.Tyr111Cys) | 3784 | KCNQ1 | 5209 | ['CGCACCCACGTCC AGGGCCGCGTCTRC AACTTCCTCGAGCG TCCCACCGGC'] | 5411 | ['CCAGGGCCGCGT CTRCAACTTCC'] | 5657 | ['CCAGGGCCGCGT CTRCAACTTCC'] |
| NM_000492.3 (CFTR):c.1A>G (p.MetIVal) | 1080 | CFTR | 5210 | ['CAGGGACCCCAGC GCCCGAGAGACCRT GCAGAGGTCGCCTC TGGAAAAGGC'] | 5412 | ['CCAGCGCCCGAG AGACCRTGCAG'] | 5658-5659 | ['CCCAGCGCCCGA GAGACCRTGCA', 'CCAGCGCCCGAG AGACCRTGCAG'] |
| NM_007294.3 (BRCA1):c.122A>G (p.His41Arg) | 672 | BRCA1 | 5211 | ['GAACCTGTCTCCAC AAGTGTGACCRCA TATTTTGCAAGTAA GTTTGAATG'] | 5413 | ['CCACAAAGTGTG ACCRCATATTT'] | 5660 | ['CCACAAAGTGTG ACCRCATATTT'] |
| NM_007294.3 (BRCA1):c.44852A>G | 672 | BRCA1 | 5212 | ['GTTTTCTCCTTCCA TTTATCTTTCTRGGT CATCCCCTTCTAAAT GCCCATC'] | 5414 | ['CCTTCCATTTATC TTTCTRGGTC'] | 5661-5662 | ['CCTTCCATTTATC TTTCTRGGTC', 'CCATTTATCTTTC TRGGTCATCC'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_014795.3 (ZEB2):c.3134A>G (p.His1045Arg) | 9839 | ZEB2 | 5213 | ['AAACACAAGCACC ACCTTATCGAGCRC TCAAGGCTTCACTC GGGCGAGAAG'] | 5415 | ['CCACCTTATCGA GCRCTCAAGGC'] | 5663 | ['CCACCTTATCGA GCRCTCAAGGC'] |
| NM_001287.5 (CLCN7):c.296A>G (p.Tyr99Cys) | 1186 | CLCN7 | 5214 | ['TGTCCCGGCCTGCA GAGCTTGGACTRTG ACAACAGTGAGAAC CAGCTGTTC'] | 5416 | ['CCTGCAGAGCTT GGACTRTGACA'] | 5664 | ['CCTGCAGAGCTT GGACTRTGACA'] |
| NM_080605.3 (B3GALT6):c.1A>G (p.MetlVal) | 126792 | B3GALT6 | 5215 | ['CGCCACGCCCGCC GCAGCAGCTTCAYG GCGCCCGCGCCGGG CCGGCGGCCC'] | 5417 | ['CCCGCCGCAGCA GCTTCAYGGCG'] | 5665-5667 | ['CCCGCCGCAGCA GCTTCAYGGCG', 'CCGCCGCAGCAG CTTCAYGGCGC', 'CCGCAGCAGCTT CAYGGCGCCCG'] |
| NM_000207.2 (1NS):c.*59A>G | −1 | — | 5216 | ['TCCTGCACCGAGA GAGATGGAATAARG CCCTTGAACCAGCC CTGCTGTGCC'] | 5418 | ['CCGAGAGAGATG GAATAARGCCC'] | 5668 | ['CCGAGAGAGATG GAATAARGCCC'] |
| NM_000784.3 (CYP27A1):c.1061A>G (p.Asp354Gly) | 1593 | CYP27A1 | 5217 | ['TGGGCCCTGTACC ACCTCTCAAAGGRC CCTGAGATCCAGGA GGCCTTGCAC'] | 5419 | ['CCACCTCTCAAA GGRCCCTGAGA'] | 5669 | ['CCACCTCTCAAA GGRCCCTGAGA'] |
| NM_000540.2 (RYRO:c.14572A>G (p.Asn4858Asp) | 6261 | RYR1 | 5218 | ['CTACCTGTACACCG TGGTGGCCTTCRAC TTCTTCCGCAAGTTC TACAACAA'] | 5420 | ['CCGTGGTGGCCT TCRACTTCTTC'] | 5670 | ['CCGTGGTGGCCT TCRACTTCTTC'] |
| NM_000238.3 (KCNH2):c.1478A>G (p.Tyr493Cys) | 3757 | KCNH2 | 5219 | ['CACCCCGGCCGCA TCGCCGTCCACTNC TTCAAGGGCTGGTT CCTCATCGAC'] | 5421 | ['CCGCATCGCCGT CCACTNCTTCA'] | 5671 | ['CCGCATCGCCGT CCACTNCTTCA'] |
| NM_000335.4 (SCN5A):c.688A>G (p.Ile230Val) | 6331 | SCN5A | 5220 | ['CCGAGTCCTCCGG GCCCTGAAAACTRT ATCAGTCATTTCAG GTGAAAATCA'] | 5422 | ['CCGGGCCCTGAA AACTRTATCAG'] | 5672 | ['CCGGGCCCTGAA AACTRTATCAG'] |
| NM_000169.2 (GLA):c.548-2A>G | −1 | — | 5221 | ['TATTTTACCCATTG TTTTCTCATACRGGT TATAAGCACATGTC CTTGGCCC'] | 5423 | ['CCCATTGTTTTCT CATACRGGTT'] | 5673-5674 | ['CCCATTGTTTTCT CATACRGGTT', 'CCATTGTTTTCTC ATACRGGTTA'] |
| NM_000146.3 (FTL):c.1A>G (p.MetlVal) | 2512 | FTL | 5222 | ['GTTAGCTCCTTCTT GCCAACCAACCRTG AGCTCCCAGATTCG TCAGAATTA'] | 5424 | ['CCTTCTTGCCAA CCAACCRTGAG'] | 5675 | ['CCTTCTTGCCAA CCAACCRTGAG'] |
| NM_000531.5 (OTC):c.1034A>G (p.Tyr345Cys) | 5009 | OTC | 5223 | ['GTCATGGTGTCCCT GCTGACAGATTRCT CACCTCAGCTCCAG AAGCCTAAA'] | 5425-5426 | ['CCCTGCTGACAG ATTRCTCACCT', 'CCTGCTGACAGA TTRCTCACCTC'] | 5676-5677 | ['CCCTGCTGACAG ATTRCTCACCT', 'CCTGCTGACAGA TTRCTCACCTC'] |
| NM_000531.5 (OTC):c.350A>G (p.His117Arg) | 5009 | OTC | 5224 | ['TGTTTTCTTACCAC ACAAGATATTCDTT TGGGTGTGAATGAA AGTCTCACG'] | 5427 | ['CCACACAAGATA TTCDTTTGGGT'] | 5678 | ['CCACACAAGATA TTCDTTTGGGT'] |
| NM_000531.5 (OTC):c.524A>G (p.Asp175Gly) | 5009 | OTC | 5225 | ['TACCATCCTATCCA GATCCTGGCTGDTT ACCTCACGCTCCAG GTTGGTTTA'] | 5428 | ['CCAGATCCTGGC TGDTTACCTCA'] | 5679 | ['CCAGATCCTGGC TGDTTACCTCA'] |
| NM_000531.5 (OTC):c.527A>G (p.Tyr176Cys) | 5009 | OTC | 5226 | ['CATCCTATCCAGAT CCTGGCTGATTRCCT CACGCTCCAGGTTG GTTTATTT'] | 5429 | ['CCAGATCCTGGC TGATTRCCTCA'] | 5680 | ['CCAGATCCTGGC TGATTRCCTCA'] |
| NM_000531.5 (OTC):c.542A>G (p.Glu181Gly) | 5009 | OTC | 5227 | ['TCTCCTTCATCCCG TGCCTTTAGGRAC ACTATAGCTCTCTG AAAGGTCTT'] | 5430 | ['CCGTGCCTTTTA GGRACACTATA'] | 5681-5682 | ['CCGTGCCTTTT AGGRACACTAT', 'CCGTGCCTTTTAG GRACACTATA'] |
| NM_024301.4 (FKRP):c.1A>G (p.MetlVal) | 79147 | FKRP | 5228 | ['CCAGCTAGCCCCA GACTTCGGCCCCRT GCGGCTCACCCGCT GCCAGGCTGC'] | 5431 | ['CCCCAGACTTCG GCCCCRTGCGG'] | 5683-5685 | ['CCCCAGACTTCG GCCCCRTGCGG', 'CCCAGACTTCGG CCCCRTGCGGC', 'CCAGACTTCGGC CCCRTGCGGCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000321.2 (RBO:c.1927A>G (p.Lys643Glu) | 5925 | RB1 | 5229 | ['AGCCTTCCAGACC CAGAAGCCATTGRA ATCTACCTCTCTTTC ACTGTTTTA'] | 5432 | ['CCCAGAAGCCAT TGRAATCTACC'] | 5686 | ['CCCAGAAGCCAT TGRAATCTACC'] |
| NM_015713.4 (RRM2B):c.581A>G (p.Glu194Gly) | 50484 | RRM2B | 5230 | ['AAAAGATCCTGAG AAGAAAACTCCTYC TACAGCAGCAAAGG CCACCACTCT'] | 5433 | ['CCTGAGAAGAAA ACTCCTYCTAC'] | 5687 | ['CCTGAGAAGAAA ACTCCTYCTAC'] |
| NM_000219.5 (KCNE1):c.242A>G (p.Tyr81Cys) | 3753 | KCNE1 | 5231 | ['CACTCGAACGACC CATTCAACGTCTDC ATCGAGTCCGATGC CTGGCAAGAG'] | 5434 | ['CCCATTCAACGT CTDCATCGAGT'] | 5688 | ['CCCATTCAACGT CTDCATCGAGT'] |
| NM_003108.3 (SOX11):c.347A>G (p.Tyr116Cys) | 6664 | SOX11 | 5232 | ['AAGCACATGGCCG ACTACCCCGACTRC AAGTACCGGCCCCG GAAAAAGCCC'] | 5435 | ['CCGACTACCCCG ACTRCAAGTAC'] | 5689 | ['CCGACTACCCCG ACTRCAAGTAC'] |
| NM_002764.3 (PRPSO:c.343A>G (p.Met115Val) | 5631 | PRPS1 | 5233 | ['AATCTCAGCCAAG CTTGTTGCAAATRTG CTATCTGTAGCAGG TGCAGATCA'] | 5436 | ['CCAAGCTTGTTG CAAATRTGCTA'] | 5690 | ['CCAAGCTTGTTG CAAATRTGCTA'] |
| NM_000546.5 (TP53):c.1101-2A>G | 7157 | TP53 | 5234 | ['TCTCCTCCCTGCTT CTGTCCTACRGCC ACCTGAAGTCCAAA AAGGGTCA'] | 5437 | ['CCTGCTTCTGTCT CCTACRGCCA'] | 5691 | ['CCTGCTTCTGTCT CCTACRGCCA'] |
| NM_000166.5 (GJB1):c.580A>G (p.Met194Val) | 2705 | GJB1 | 5235 | ['CGAGAAAACCGTC TTCACCGTCTTCRTG CTAGCTGCCTCTGG CATCTGCAT'] | 5438 | ['CCGTCTTCACCG TCTTCRTGCTA'] | 5692 | ['CCGTCTTCACCG TCTTCRTGCTA'] |
| NM_003159.2 (CDKL5):c.449A>G (p.Lys150Arg) | 6792 | CDKL5 | 5236 | ['TTAATCAGCCACA ATGATGTCCTAARA CTGTGTGACTTTGGT AAGTTAAAA'] | 5439 | ['CCACAATGATGT CCTAARACTGT'] | 5693 | ['CCACAATGATGT CCTAARACTGT'] |
| NM_000053.3 (ATP7B):c.122A>G (p.Asn41Ser) | 540 | ATP7B | 5237 | ['ATCCAGACCACCTT CATAGCCAACAYTG TCAAAAGCAAAACT CTTCTTCAT'] | 5440 | ['CCACCTTCATAG CCAACAYTGTC'] | 5694-5695 | ['CCACCTTCATAG CCAACAYTGTC', 'CCTTCATAGCCAA CAYTGTCAAA'] |
| NM_006306.3 (SMC1A):c.3254A>G (p.Tyr1085Cys) | 8243 | SMC1A | 5238 | ['GTGGCTACCAACA TTGATGAGATCTRT AAGGCCCTGTCCCG CAATAGCAGT'] | 5441 | ['CCAACATTGATG AGATCTRTAAG'] | 5696 | ['CCAACATTGATG AGATCTRTAAG'] |
| NM_005154.4 (USP8):c.2150A>G (p.Tyr717Cys) | 9101 | USP8 | 5239 | ['GAACCTTCCAAAC TGAAGCGCTCCTDC TCCTCCCAGATAT AACCCAGGCT'] | 5442 | ['CCAAACTGAAGC GCTCCTDCTCC'] | 5697 | ['CCAAACTGAAGC GCTCCTDCTCC'] |
| NM_000117.2 (EMD):c.266-2A>G | 2010 | EMD | 5240 | ['TCTGCTACCGCTGC CCCCCTTCCCARGG CTACAATGACGACT ACTATGAAG'] | 5443 | ['CCGCTGCCCCCC TTCCCARGGCT'] | 5698 | ['CCGCTGCCCCCC TTCCCARGGCT'] |
| NM_207352.3 (CYP4V2):c.1393A>G (p.Arg465Gly) | 285440 | CYP4V2 | 5241 | ['CTACGTGCCCTTCT CTGCTGGCCCCRGG AACTGTATAGGTTT GTATCCATC'] | 5444 | ['CCCTTCTCTGCT GGCCCCRGGAA'] | 5699-5700 | ['CCCTTCTCTGCT GGCCCCRGGAA', 'CCTTCTCTGCTGG CCCCRGGAAC'] |
| NM_000546.5 (TP53):c.709A>G (p.Met237Val) | 7157 | TP53 | 5242 | ['CTGTACCACCATCC ACTACAACTACRTG TGTAACAGTTCCTG CATGGGCGG'] | 5445 | ['CCATCCACTACA ACTACRTGTGT'] | 5701 | ['CCATCCACTACA ACTACRTGTGT'] |
| NM_016069.9 (PAM16):c.226A>G (p.Asn76Asp) | −1 | — | 5243 | ['CTCACCCGTCCCCT CTCCTCTGCAGRAC TATGAACACTTATTT AAGGTGAA'] | 5446 | ['CCTCTCCTCTGC AGRACTATGAA'] | 5702-5704 | ['CCCCTCTCCTCT GCAGRACTATG', 'CCCTCTCCTCTGC AGRACTATGA', 'CCTCTCCTCTGCA GRACTATGAA'] |
| NM_006785.3 (MALT1):c.1019-2A>G | 10892 | MALT1 | 5244 | ['AACACCCCCTTTCT TTTTTTTCAARGCG AAGGACAAGGTTGC CCTTTTGA'] | 5447 | ['CCTTTCTTTTTTT TTCAARGCGA'] | 5705 | ['CCTTTCTTTTTTT TTCAARGCGA'] |
| NM_004771.3 (MMP20):c.611A>G (p.His204Arg) | 9313 | MMP20 | 5245 | ['GGAGAAGGCCTGG GAGGAGATACACRT TTCGACAATGCTGA GAAGTGGACT'] | 5448 | ['CCTGGGAGGAGA TACACRTTTCG'] | 5706 | ['CCTGGGAGGAGA TACACRTTTCG'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_003159.2 (CDKL5):c.458A>G (p.Asp153Gly) | 6792 | CDKL5 | 5246 | ['CACAATGATGTCCT AAAACTGTGTGRCT TTGGTAAGTTAAAA AGAAATTAA'] | 5449 | ['CCTAAAACTGTG TGRCTTTGGTA'] | 5707 | ['CCTAAAACTGTG TGRCTTTGGTA'] |
| NM_001204830.1 (LIPT1):c.535A>G (p.Thr179Ala) | −1 | — | 5247 | ['CCGGACTACTGCCT ATCACCATTGCRCTT TATTATGTAGTACTG ATGGGAC'] | 5450 | ['CCTATCACCATT GCRCTTTATTA'] | 5708 | ['CCTATCACCATT GCRCTTTATTA'] |
| NM_000921.4 (PDE3A):c.1333A>G (p.Thr445Ala) | 5139 | PDE3A | 5248 | ['AGTTTCTTCCACTT GGACCACCACCRCC TCGGCCACAGGTCT ACCCACCTT'] | 5451 | ['CCACTTGGACCA CCACCRCCTCG'] | 5709 | ['CCACTTGGACCA CCACCRCCTCG'] |
| NM_000182.4 (HADHA):c.9192A>G | 3030 | HADHA | 5249 | ['TTGCTCAATTCCAG TCTTTACCACCYAA AAAACATATAAAGC ACTTGCTCA'] | 5452 | ['CCAGTCTTTACC ACCYAAAAAAC'] | 5710 | ['CCAGTCTTTACC ACCYAAAAAAC'] |
| NM_000169.2 (GLA):c.620A>G (p.Tyr207Cys) | −1 | — | 5250 | ['GTGTACTCCTGTGA GTGGCCTCTTTRTAT GTGGCCCTTTCAAA AGGTGAGA'] | 5453 | ['CCTGTGAGTGGC CTCTTTRTATG'] | 5711 | ['CCTGTGAGTGGC CTCTTTRTATG'] |
| NM_000238.3 (KCNH2):c.2582A>G (p.Asn861Ser) | 3757 | KCNH2 | 5251 | ['TGGTCCAGCCTGG AGATCACCTTCANC CTGCGAGATGTGAG TTGGCTGCCC'] | 5454 | ['CCTGGAGATCAC CTTCANCCTGC'] | 5712 | ['CCTGGAGATCAC CTTCANCCTGC'] |
| NM_000218.2 (KCNQ1):c.605A>G (p.Asp202Gly) | 3784 | KCNQ1 | 5252 | ['GCTCCCCCTCTCCT GCACTCCACAGRCC TCATCGTGGTCGTG GCCTCCATG'] | 5455 | ['CCTGCACTCCAC AGRCCTCATCG'] | 5713 | ['CCTGCACTCCAC AGRCCTCATCG'] |
| NM_012203.1 (GRHPR):c.934A>G (p.Asn312Asp) | 9380 | GRHPR | 5253 | ['CACCATGTCCTTGT TGGCAGCTAACRAC TTGCTGGCTGGCCT GAGAGGGGA'] | 5456 | ['CCTTGTTGGCAG CTAACRACTTG'] | 5714 | ['CCTTGTTGGCAG CTAACRACTTG'] |
| NM_021007.2 (SCN2A):c.3872A>G | 6326 | SCN2A | 5254 | ['ACTTTGTCTTCCTT GACGATATTCTRCTT TATTCAATATGCTCA TTATGTG'] | 5457 | ['CCTTGACGATAT TCTRCTTTATT'] | 5715 | ['CCTTGACGATAT TCTRCTTTATT'] |
| NM_002693.2 (POLG):c.2840A>G (p.Lys947Arg) | 8542 | POLG | 5255 | ['GTGGGCATCAGCC GTGAGCATGCCARA ATCTTCAACTACGG CCGCATCTAT'] | 5458 | ['CCGTGAGCATGC CARAATCTTCA'] | 5716 | ['CCGTGAGCATGC CARAATCTTCA'] |
| NM_020533.2 (MCOLN1):c.1406A>G (p.Asn469Ser) | 57192 | MCOLN1 | 5256 | ['TCTGAGTGCCTGTT CTCGCTCATCARTG GGGACGACATGTTT GTGACGTTC'] | 5459 | ['CCTGTTCTCGCT CATCARTGGGG'] | 5717 | ['CCTGTTCTCGCT CATCARTGGGG'] |
| NM_000069.2 (CACNA1S):c.3526-2A>G | 779 | CACNA1S | 5257 | ['TCGCTTTCCCATCC TTTTCCTTCCCRGGG'] | 5460 | ['CCCATCCTTTTCC TTCCCRGGGC'] CTACTTTGGAGACC CCTGGAAT'] | 5718-5719 | ['CCCATCCTTTTCC TTCCCRGGGC', 'CCATCCTTTTCCT TCCCRGGGCT'] |
| NM_017662.4 (TRPM6):c.3173A>G (p.Tyr1058Cys) | 140803 | TRPM6 | 5258 | ['CAAGCTGTCTACCT CTTCGTGCAATRTAT CATCATGGTGAACC TGTTGATT'] | 5461 | ['CCTCTTCGTGCA ATRTATCATCA'] | 5720 | ['CCTCTTCGTGCA ATRTATCATCA'] |
| NM_006642.3 (SDCCAG8):c.2212A>G | 10806 | SDCCAG8 | 5259 | ['AATAAACCCTCTG CTTTTGCTCTATRGT TAATCAGCTCAAAG ATTTGTTGC'] | 5462 | ['CCTCTGCTTTTGC TCTATRGTTA'] | 5721 | ['CCTCTGCTTTTGC TCTATRGTTA'] |
| NM_003560.2 (PLA2G6):c.1349-2A>G | 8398 | PLA2G6 | 5260 | ['CAGCATGCCCTGCT CTGTGCCTCACRGA ACTACAGGATCTCA TGCACATCT'] | 5463 | ['CCCTGCTCTGTG CCTCACRGAAC'] | 5722-5723 | ['CCCTGCTCTGTG CCTCACRGAAC', 'CCTGCTCTGTGCC TCACRGAACT'] |

Example 6: Next Generation C to T Editors

Other families of cytidine deaminases as alternatives to base editor 3 (BE3) constructs were examined. The different C to T editors were developed to have a narrow or different editing window, alternate sequence specificity to expand targetable substrates, and to have higher activity.

Using the methods described in Example 4, the pmCDA1 (cytidine deaminase 1 from *Petromyzon marinus*) activity at the HeK-3 site is evaluated (FIG. 42). The pmCDA1-nCas9-UGI-NLS (nCas9 indicates the Cas9 nickase described herein) construct is active on some sites (e.g., the C bases on the complementary strand at position 9, 5, 4, and 3) that are not accessible with rAPOBEC1 (BE3).

The pmCDA1 activity at the HeK-2 site is given in FIG. 43. The pmCDA1-XTEN-nCas9-UGI-NLS construct is active on sites adjacent to "G," while rAPOBEC1 analog (BE3 construct) has low activity on "C"s that are adjacent to "G"s, e.g., the C base at position 11 on the complementary strand.

The percent of total sequencing reads with target C converted to T (FIG. 44), C converted to A (FIG. 45), and C converted to G (FIG. 46) are shown for CDA and APOBEC1 (the BE3 construct).

The huAPOBEC3G activity at the HeK-2 site is shown in FIG. 47. Two constructs were used: huAPOBEC3G-XTEN-nCas9-UGI-NLS and huAPOBEC3G*(D316R_D317R)-XTEN-nCas9-UGI-NLS. The huAPOBEC3G-XTEN-nCas9-UGI-NLS construct has different sequence specificity than rAPOBEC1 (BE3), as shown in FIG. 47, the editing window appears narrow, as indicated by APOBEC3G's decreased activity at position 4 compared to APOBEC1. Mutations made in huAPOBEC3G (D316R and D317R) increased ssDNA binding and resulted in an observable effect on expanding the sites which were edited (compare APOBEC3G with APOBEC3G_RR in FIG. 47). Mutations were chosen based on APOBEC3G crystal structure, see: Holden et al., Crystal structure of the anti-viral APOBEC3G catalytic domain and functional implication. *Nature.* (2008); 121-4, the entire contents of which are incorporated herein by reference.

Example 7: pmCDA1/huAPOBEC3G/rAPOBEC1 Work in *E. coli*

LacZ selection optimization for the A to I conversion was performed using a bacterial strain with lacZ encoded on the F plasmid. A critical glutamic acid residue was mutated (e.g., GAG to GGG, Glu to Gly mutation) so that G to A by a cytidine deaminase would restore lacZ activity (FIG. 48). Strain CC102 was selected for the selection assay. APOBEC1 and CDA constructs were used in a selection assay to optimize G to A conversion.

To evaluate the the effect of copy number of the plasmids encoding the deaminase constructs on lacZ reversion frequency, the CDA and APOBEC1 deaminases were cloned into 4 plasmids with different replication origins (hence different copy numbers), SC101, CloDF3, RSF1030, and PUC (copy number: PUC>RSF1030>CloDF3>SC101) and placed under an inducible promoter. The plasmids were individually transformed into *E. coli* cells harboring F plasmid containing the mutated LacZ gene. The expression of the deaminases were induced and LacZ activity was detected for each construct (FIG. 49). As shown in FIG. 49, CDA exhibited significantly higher activity than APOBEC1 in all instances, regardless of the plasmid copy number the deaminases were cloned in. Further, In terms of the copy number, the deaminase activity was positively correlated with the copy number of the plasmid they are cloned in, i.e., PUC>CloDF3>SC101.

LacZ reversions were confirmed by sequencing of the genomic DNA at the lacZ locus. To obtain the genomic DNA containing the corrected LacZ gene, cells were grown media containing X-gal, where cells having LacZ activity form blue colonies. Blue colonies were selected and grown in minimal media containing lactose. The cells were spun down, washed, and re-plated on minimal media plates (lactose). The blue colony at the highest dilution was then selected, and its genomic DNA was sequenced at the lacZ locus (FIG. 50).

A chloramphenicol reversion assay was designed to test the activity of different cytidine deaminases (e.g., CDA, and APOBEC1). A plasmid harboring a mutant CAT1 gene which confers chloramphenicol resistance to bacteria is constructed with RSF1030 as the replication origin. The mutant CAT1 gene encodings a CAT1 protein that has a H195R (CAC to CGC) mutation, rendering the protein inactive (FIG. 51). Deamination of the C base-paired to the G base in the CGC codon would convert the codon back to a CAC codon, restoring the activity of the protein. As shown in FIG. 52, CDA outperforms rAPOBEC in *E. coli* in restoring the activity of the chloramphenicol resistance gene. The minimum inhibitory concentration (MIC) of chlor in S1030 with the selection plasmid (pNMG_ch_5) was approximately 1 µg/mL. Both rAPOBEC-XTEN-dCas9-UGI and CDA-XTEN-dCas9-UGI induced DNA correction on the selection plasmid (FIG. 53).

Next, the huAPOBEC3G-XTEN-dCas9-UGI protein was tested in the same assay. Interestingly, huAPOBEC3G-XTEN-dCas9-UGI exhibited different sequence specificity than the rAPOBEC1-XTEN-dCas9-UGI fusion protein. Only position 8 was edited with APOBEC3G-XTEN-dCas9-UGI fusion, as compared to the rAPOBEC11-XTEN-dCas9-UGIfusion (in which positions 3, 6, and 8 were edited) (FIG. 54).

Example 8: C to T Base Editors with Less Off Target Editing

Current base editing technologies allow for the sequence-specific conversion of a C:G base pair into a T:A base pair in genomic DNA. This is done via the direct catalytic conversion of cytosine to uracil by a cytidine deaminase enzyme and thus, unlike traditional genome editing technologies, does not introduce double-stranded DNA breaks (DSBs) into the DNA as a first step. See, Komor, A. C., Kim, Y. B., Packer, M. S., Zuris, J. A., and Liu, D. R. (2016), "Programmable editing of a target base in genomic DNA without double-stranded DNA cleavage." Nature 533, 420-424; the entire contents of which are incorporated by reference herein. Instead, catalytically dead SpCas9 (dCas9) or a SpCas9 nickase (dCas9(A840H)) is tethered to a cytidine deaminase enzyme such as rAPOBEC1, pmCDA1, or hAPOBEC3G. The genomic locus of interest is encoded by an sgRNA, and DNA binding and local denaturation is facilitated by the dCas9 portion of the fusion. However, just as wt dCas9 and wt Cas9 exhibit off-target DNA binding and cleavage, current base editors also exhibit C to T editing at Cas9 off-target loci, which limits their therapeutic usefulness.

It has been reported that the introduction of just three to four mutations into SpCas9 that neutralize nonspecific electrostatic interactions between the protein and the sugar-phosphate backbone of its target DNA, increases the DNA binding specificity of SpCas9. See, Kleinstiver, B. P., Pattanayak, V., Prew, M. S., Tsai, S. Q., Nguyen, N. T., Zheng, Z., and Joung, J. K. (2016) "High-fidelity CRISPR-Cas9 nucleases with no detectable genome-wide off-target effects." Nature 529, 490-495; and Slaymaker, I. M., Gao, L., Zetsche, B., Scott, D. A., Yan, W. X., and Zhang, F. (2015) "Rationally engineered Cas9 nucleases with improved specificity. Science 351, 84-88; the entire contents of each are hereby incorporated by reference herein. Four reported neutralizing mutations were therefore incorporated into the initially reported base editor BE3 (SEQ ID NO:

285), and found that off-target C to T editing of this enzyme is also drastically reduced (FIG. 55), with no decrease in on-target editing (FIG. 56).

As shown in FIG. 55, HEK293T cells were transfected with plasmids expressing BE3 or HF-BE3 and a sgRNA matching the EMX1 sequence using Lipofectamine 2000. Three days after transfection, genomic DNA was extracted, amplified by PCR, and analyzed by high-throughput DNA sequencing at the on-target locus, plus the top ten known Cas9 off-target loci for the EMX1 sgRNA, as previously determined by Joung and coworkers using the GUIDE-seq method. See Tsai, S. Q., Zheng, Z., Nguyen, N. T., Liebers, M., Topkar, V. V., Thapar, V., Wyvekens, N., Khayter, C., Iafrate, A. J., Le, L. P., et al. (2015) "GUIDE-seq enables genome-wide profiling of off-target cleavage by CRISPR-Cas nucleases." Nat Biotech 33, 187-197; the entire contents of which are incorporated by reference herein. EMX1 off-target 5 locus did not amplify and is not shown. Sequences of the on-target and off-target protospacers and protospacer adjacent motifs (PAMs) are displayed (FIG. 55). Cellular C to T conversion percentages, defined as the percentage of total DNA sequencing reads with T at each position of an original C within the protospacer, are shown for BE3 and HF-BE3.

In FIG. 56, HEK293T cells were transfected with plasmids expressing BE3 or HF-BE3 and sgRNAs matching the genomic loci indicated using Lipofectamine 2000. Three days after transfection, genomic DNA was extracted, amplified by PCR, and analyzed by high-throughput DNA sequencing at the on-target loci. The percentage of total DNA sequencing reads with all four bases at the target Cs within each protospacer are shown for treatment with BE3 or HF-BE3 (FIG. 56). Frequencies of indel formation are shown as well.

```
Primary Protein Sequence
of HF-BE3 (SEQ ID NO: 285):
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKSGSETPGTSESATPESDKKYS

IGLAIGTNSVGWAVITDEYKVPSKKFKVLGNTDRHSIKKNLIGALLFDSG

ETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYL

ALAHMIKFRGHFLIEGDLNPDNSDVDKLFIQLVQTYNQLFEENPINASGV

DAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSK

NGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLA

RGNSRFAWMTRKSEETITPWNFEEVVDKGASAQSFIERMTAFDKNLPNEK

VLPKHSLLYEYFTVYNELTKVKYVTEGMRKPAFLSGEQKKAIVDLLFKTN

RKVTVKQLKEDYFKKIECFDSVEISGVEDRFNASLGTYHDLLKIIKDKDF

LDNEENEDILEDIVLTLTLFEDREMIEERLKTYAHLFDDKVMKQLKRRRY

TGWGALSRKLINGIRDKQSGKTILDFLKSDGFANRNFMALIHDDSLTFKE

DIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKV

LTRSDKNRGKSDNVPSEEVVKKMKNYWRQLLNAKLITQRKFDNLTKAERG

GLSELDKAGFIKRQLVETRAITKHVAQILDSRMNTKYDENDKLIREVKVI

TLKSKLVSDFRKDFQFYKVREINNYHHAHDAYLNAVVGTALIKKYPKLES

EFVYGDYKVYDVRKMIAKSEQEIGKATAKYFFYSNIMNFFKTEITLANGE

IRKRPLIETNGETGEIVWDKGRDFATVRKVLSMPQVNIVKKTEVQTGGFS

KESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFEL

ENGRKRMLASAGELQKGNELALPSKYVNFLYLASHYEKLKGSPEDNEQKQ

LFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLY

ETRIDLSQLGGDSGGSTNLSDIIEKETGKQLVIQESILMLPEEVEEVIGN

KPESDILVHTAYDESTDENVMLLTSDAPEYKPWALVIQDSNGENKIKMLS

GGSPKKKRKV
```

Example 9: Development of Base Editors that Use Cas9 Variants and Modulation of the Base Editor Processivity to Increase the Target Range and Precision of the Base Editing Technology Unlike traditional genome editing platforms, base editing technology allows precise single nucleotide changes in the DNA without inducing double-stranded breaks (DSBs). See, Komor, A. C. et al. *Nature* 533, 420-424 (2016). The current generation of base editor uses the NGG PAM exclusively. This limits its ability to edit desired bases within the genome, as the base editor needs to be placed at a precise location where the target base is placed within a 4-base region (the 'deamination window'), approximately 15 bases upstream of the PAM. See, Komor, A. C. et al. *Nature* 533, 420-424 (2016). Moreover, due to the high processivity of cytidine deaminase, the base editor may convert all cytidines within its deamination window into thymidines, which could induce amino acid changes other than the one desired by the researcher. See, Komor, A. C. et al. *Nature* 533, 420-424 (2016).

Expanding the Scope of Base Editing Through the Development of Base Editors with Cas9 Variants Cas9 homologs and other RNA-guided DNA binders that have different PAM specificities were incorporated into the base editor architecture. See, Kleinstiver, B. P. et al. *Nature* 523, 481-485 (2015); Kleinstiver, B. P. et al. Nature Biotechnology 33, 1293-1298 (2015); and Zetsche, B. et al. *Cell* 163, 759-771 (2015); the entire contents of each are incorporated by reference herein. Furthermore, innovations that have broadened the PAM specificities of various Cas9 proteins were also incorporated to expand the target reach of the base editor even more. See, Kleinstiver, B. P. et al. *Nature* 523, 481-485 (2015); and Kleinstiver, B. P. et al. *Nature Biotechnology* 33, 1293-1298 (2015). The current palette of base editors is summarized in Table 4.

TABLE 4

New base editors made from Cas9 Variants

| Species | PAM | Base Editor Name | Reference for Cas9 variant |
|---|---|---|---|
| S. pyogenes | ...NGG | BE3 | Wild-type |
|  | ...NGA | VQR BE3 or EQR BE3 | Kleinstiver, B. P. et al. |
|  | ...NGCG | VRER BE3 | Kleinstiver, B. P. et al. |
| S. aureus | ...NNGRRT | SaBE3 | Wild-type |
|  | ...NNNRRT | SaKKH BE3 | Kleinstiver, B. P. et al. |
| L. bacterium | TTTN... | dCpf1 BE2 | Zetsche, B. et al. |

Modulating Base Editor's Processivity Through Site-Directed Mutagenesis of rAPOBEC1

It was reasoned that the processivity of the base editor could be modulated by making point mutations in the deaminase enzyme. The incorporation of mutations that slightly reduce the catalytic activity of deaminase in which the base editor could still catalyze on average one round of cytidine deamination but was unlikely to access and catalyze another deamination within the relevant timescale were pursued. In effect, the resulting base editor would have a narrower deamination window.

rAPOBEC1 mutations probed in this work are listed in Table 5. Some of the mutations resulted in slight apparent impairment of rAPOBEC1 catalysis, which manifested as preferential editing of one cytidine over another when multiple cytidines are found within the deamination window. Combining some of these mutations had an additive effect, allowing the base editor to discriminate substrate cytidines with higher stringency. Some of the double mutants and the triple mutant allowed selective editing of one cytidine among multiple cytidines that are right next to one another (FIG. 57).

TABLE 5 rAPOBEC1 Point Mutations Investigated

| rAPOBEC1 mutation studied in this work | Corresponding mutation in APOBEC3G | Reference |
|---|---|---|
| H121R/H122R | D315R/D316R | Holden, L. G. et al. |
| R126A | R320A | Chen, K-M. et al. |
| R126E | R320E | Chen, K-M. et al. |
| R118A | R313A | Chen, K-M. et al. |
| W90A | W285A | Chen, K-M. et al. |
| W90Y | W285Y |  |
| R312E | R326E |  |

Base Editor PAM Expansion and Processivity Modulation

The next generation of base editors were designed to expand editable cytidines in the genome by using other RNA-guided DNA binders (FIG. 58). Using a NGG PAM only allows for a single target within the "window" whereas the use of multiple different PAMs allows for Cas9 to be positioned anywhere to effect selective deamination. A variety of new base editors have been created from Cas9 variants (FIG. 59 and Table 4). Different PAM sites (NGA, FIG. 60; NGCG, FIG. 61; NNGRRT, FIG. 62; and NNHRRT, FIG. 63) were explored. Selective deamination was successfully achieved through kinetic modulation of cytidine deaminase point mutagenesis (FIG. 65 and Table 5).

The effect of various mutations on the deamination window was then investigated in cell culture using spacers with multiple cytidines (FIGS. 66 and 67).

Further, the effect of various mutations on different genomic sites with limited numbers of cytidines was examined (FIGS. 68 to 71). It was found that approximately one cytidine will be edited within the deamination window in the spacer, while the rest of the cytidines will be left intact. Overall, the preference for editing is as follows: $C_6 > C_5 \gg C_7 \approx C_4$.

Base Editing Using Cpf1

Cpf1, a Cas9 homolog, can be obtained as AsCpf1, LbCpf1, or from any other species. Schematics of fusion constructs, including BE2 and BE3 equivalents, are shown in FIG. 73. The BE2 equivalent uses catalytically inactive Cpf2 enzyme (dCpf1) instead of Cas9, while the BE3 equivalent includes the Cpf1 mutant, which nicks the target strand. The bottom schematic depicts different fusion architectures to combine the two innovations illustrated above it (FIG. 73). The base editing results of HEK293T cell TTTN PAM sites using Cpf1 BE2 were examined with different spacers (FIGS. 64A to 64C). In some embodiments, Cpf1 may be used in place of a Cas9 domain in any of the base editors provided herein. In some embodiments, the Cpf1 is a protein that is at lesst 50%, 55%, 60%, 65%, 70%, 75%, 80%, 85%, 90%, 95%, 98%, 99%, or 99.5% identical to SEQ ID NO 313.

```
Full Protein Sequence of Cpf1 (SEQ ID NO: 313):
MSIYQEFVNKYSLSKTLRFELIPQGKTLENIKARGLILDDEKRAKDYKKA

KQIIDKYHQFFIEEILSSVCISEDLLQNYSDVYFKLKKSDDDNLQKDFKS

AKDTIKKQISEYIKDSEKFKNLFNQNLIDAKKGQESDLILWLKQSKDNGI

ELFKANSDITDIDEALEIIKSFKGWTTYFKGFHENRKNVYSSNDIPTSII

YRIVDDNLPKFLENKAKYESLKDKAPEAINYEQIKKDLAEELTFDIDYKT

SEVNQRVFSLDEVFEIANFNNYLNQSGITKFNTIIGGKFVNGENTKRKGI

NEYINLYSQQINDKTLKKYKMSVLFKQILSDTESKSFVIDKLEDDSDVVT

TMQSFYEQIAAFKTVEEKSIKETLSLLFDDLKAQKLDLSKIYFKNDKSLT

DLSQQVFDDYSVIGTAVLEYITQQIAPKNLDNPSKKEQELIAKKTEKAKY

LSLETIKLALEEFNKHRDIDKQCRFEEILANFAAIPMIFDEIAQNKDNLA

QISIKYQNQGKKDLLQASAEDDVKAIKDLLDQTNNLLHKLKIFHISQSED

KANILDKDEHFYLVFEECYFELANIVPLYNKIRNYITQKPYSDEKFKLNF

ENSTLANGWDKNKEPDNTAILFIKDDKYYLGVMNKKNNKIFDDKAIKENK

GEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSI

DEFYREVENQGYKLTFENISESYIDSVVNQGKLYLFQIYNKDFSAYSKGR

PNLHTLYWKALFDERNLQDVVYKLNGEAELFYRKQSIPKKITHPAKEAIA

NKNKDNPKKESVFEYDLIKDKRFTEDKFFFHCPITINFKSSGANKFNDEI

NLLLKEKANDVHILSIDRGERHLAYYTLVDGKGNIIKQDTFNIIGNDRMK

TNYHDKLAAIEKDRDSARKDWKKINNIKEMKEGYLSQVVHEIAKLVIEYN

AIVVFEDLNFGFKRGRFKVEKQVYQKLEKMLIEKLNYLVFKDNEFDKTGG

VLRAYQLTAPFETFKKMGKQTGIIYYVPAGFTSKICPVTGFVNQLYPKYE

SVSKSQEFFSKFDKICYNLDKGYFEFSFDYKNFGDKAAKGKWTIASFGSR

LINFRNSDKNHNWDTREVYPTKELEKLLKDYSIEYGHGECIKAAICGESD
```

-continued

KKFFAKLTSVLNTILQMRNSKTGTELDYLISPVADVNGNFFDSRQAPKNM

PQDADANGAYHIGLKGLMLLGRIKNNQEGKKLNLVIKNEEYFEFVQNRNN

Example 10: Increased Fidelity of Base Editing

Examining the difference between plasmid delivery of BE3 and HF-BE3, it was found that the two edit on-target loci with comparable efficiency (FIGS. 74 and 75). However, HF-BE3 edited off-target loci much less than BE3, meaning that HF-BE3 has a much higher DNA specificity than BE3 (FIG. 76). Deaminase protein lipofection to HEK cells demonstrated that protein delivery of BE3 results in comparable on-target activity, but much better specificity, than plasmid DNA delivery of BE3. Using improved transfection procedures and better plasmids (n=2), the experiment used the following conditions: protein delivery was 125 nM Cas9:sgRNA complex, plasmid delivery was 750ng BE3/HF-BE3 plasmid+250ng sgRNA plasmid, and lipofection was with 1.5 µL of Lipofectamine 2000 per well. EMX-1 off target site 2 and FANCF off-target site 1 showed the most off-target editing with BE3, compared to all of the off-targets assayed (FIGS. 77 and 78), while HEK-3 showed no significant editing at off-targets for any of the delivery methods (FIG. 79). HEK-4 shows some C-to-G editing on at the on-target site, while its off-target sites 1, 3, and 4 showed the most off-target editing of all the assayed sites (FIG. 80). Delivery of BE3 Protein Via Micro-Injection to Zebrafish TYR guide RNAs were tested in an in vitro assay for sgRNA activity (FIGS. 81 and 82). The % HTS reads shows how many C residues were converted to T residues during a 2h incubation with purified BE3 protein and PCR of the resulting product. Experiments used an 80-mer synthetic DNA substrate with the target deamination site in 60 bp of its genomic context. This is not the same as % edited DNA strands because only one strand was nicked, so the product is not amplified by PCR. The proportion of HTS reads edited is equal to x/(2−x), where x is the actual proportion of THS reads edited. For 60% editing, the actual proportion of bases edited is 75%. "Off target" is represents BE3 incubated with the same DNA substrate, while bound to an off-target sgRNA. It was found sgRNAs sgRH_13, sgHR_17, and possibly sgHR_16 appeared to be promising targets for in vivo injection experiments.

The delivery of BE3 protein in was tested in vivo in zebrafish. Zebrafish embryos (n=16-24) were injected with either scrambled sgRNA, sgHR_13, sgHR_16, or sgHR_17 and purified BE3. Three embryos from each condition were analyzed independently (single embryo) and for each condition, all of the injected embryos were pooled and sequenced as a pool. The results are shown in FIGS. 83 to 85.

Example 11: Uses of Base Editors to Treat Disease

Base editors or complexes provided herein (e.g., BE3) may be used to modify nucleic acids. For example, base editors may be used to change a cytosine to a thymine in a nucleic acid (e.g., DNA). Such changes may be made to, inter alia, alter the amino acid sequence of a protein, to destroy or create a start codon, to create a stop codon, to disrupt splicing donors, to disrupt splicing acceptors or edit regulatory sequences. Examples of possible nucleotide changes are shown in FIG. 86.

Base editors or complexes provided herein (e.g., BE3) may be used to edit an isoform of Apolipoprotein E in a subject. For example, an Apolipoprotein E isoform may be edited to yield an isoform associated with a lower risk of developing Alzheimer's disease. Apolipoprotein E has four isoforms that differ at amino acids 112 and 158. APOE4 is the largest and most common genetic risk factor for late-onset Alzheimer's disease. Arginine residue 158 of APOE4, encoded by the nucleic acid sequence CGC, may be changed to a cysteine by using a base editor (e.g., BE3) to change the CGC nucleic acid sequence to TGC, which encodes cysteine at residue 158. This change yields an APOE3r isoform, which is associated with lower Alzheimer's disease risk. See FIG. 87.

It was tested whether base editor BE3 could be used to edit APOE4 to APOE3r in mouse astrocytes (FIG. 88). APOE 4 mouse astrocytes were nucleofected with Cas9+ template or BE3, targeting the nucleic acid encoding Arginine 158 of APOE4. The Cas9+ template yielded only 0.3% editing with 26% indels, while BE3 yielded 75% editing with 5% indels. Two additional base-edited cytosines are silent and do not yield changes to the amino acid sequence (FIG. 88).

Base editors or complexes provided herein may be used to treat prion protein diseases such as Creutzfeldt-Jakob disease and fatal familial insomnia, for example, by introducing mutations into a PRNP gene. Reverting PRNP mutations may not yield therapeutic results, and intels in PRNP may be pathogenic. Accordingly, it was tested whether PRNP could be mutated using base editors (e.g., BE3) to introduce a premature stop codon in the PRNP gene. BE3, associated with its guide RNA, was introduced into HEK cells or glioblastoma cells and was capable of editing the PRNP gene to change the encoded arginine at residue 37 to a stop codon. BE3 yielded 41% editing (FIG. 89).

Additional genes that may be edited include the following: APOE editing of Arg 112 and Arg 158 to treat increased Alzheimer's risk; APP editing of Ala 673 to decrease Alzheimer's risk; PRNP editing of Arg 37 to treat fatal familial insomnia and other prion protein diseases; DMD editing of the exons 23 and 51 splice sites to treat Duchenne muscular dystrophy; FTO editing of intron 1 to treat obesity risk; PDS editing of exon 8 to treat Pendred syndrome (genetic deafness); TMC1 editing of exon 8 to treat congenital hearing loss; CYBB editing of various patient-relevant mutations to treat chronic granulomatous disease. Additional diseases that may be treated using the base editors provided herein are shown in Table 6, below.

UGI also plays a key role. Knocking out UDG (which UGI inhibits) was shown to dramatically improve the cleanliness and efficiency of C to T base editing (FIG. 90). Furthermore, base editors with nickase and without UGI were shown to produce a mixture of outcomes, with very high indel rates (FIG. 91).

Example 12: Expanding the Targeting Scope of Base Editing

Base editing is a new approach to genome editing that uses a fusion protein containing a catalytically defective *Streptococcus pyogenes* Cas9, a cytidine deaminase, and an inhibitor of base excision repair to induce programmable, single-nucleotide C→T (or G→A) changes in DNA without generating double-strand DNA breaks, without requiring a donor DNA template, and without inducing an excess of stochastic insertions and deletions. The development of five new C→T (or G→A) base editors that use natural and engineered Cas9 variants with different protospacer-adjacent motif (PAM) specificities to expand the number of sites that can be targeted by base editing by 2.5-fold are described herein. Additionally, new base editors containing mutated cytidine deaminase domains that narrow the width of the apparent editing window from approximately 5 nucleotides to 1 or 2 nucleotides were engineered, enabling the discrimination of neighboring C nucleotides that would previously be edited with comparable efficiency. Together, these developments substantially increase the targeting scope of base editing.

CRISPR-Cas9 nucleases have been widely used to mediate targeted genome editing[2]. In most genome editing applications, Cas9 forms a complex with a single guide RNA (sgRNA) and induces a double-stranded DNA break (DSB) at the target site specified by the sgRNA sequence. Cells primarily respond to this DSB through the non-homologous end-joining (NHEJ) repair pathway, which results in stochastic insertions or deletions (indels) that can cause frameshift mutations that disrupt the gene. In the presence of a donor DNA template with a high degree of homology to the sequences flanking the DSB, gene correction can be achieved through an alternative pathway known as homology directed repair (HDR).[34] Unfortunately, under most non-perturbative conditions HDR is inefficient, dependent on cell state and cell type, and dominated by a larger frequency of indels.[3,4] As most of the known genetic variations associated with human disease are point mutations[5], methods that can more efficiently and cleanly make precise point mutations are needed.

Base editing, which enables targeted replacement of a C:G base pair with a T:A base pair in a programmable manner without inducing DSBs[1], has been recently described. Base editing uses a fusion protein between a catalytically inactivated (dCas9) or nickase form of *Streptococcus pyogenes* Cas9 (SpCas9), a cytidine deaminase such as APOBEC1, and an inhibitor of base excision repair such as uracil glycosylase inhibitor (UGI) to convert cytidines into uridines within a five-nucleotide window specified by the sgRNA.[1] The third-generation base editor, BE3, converts C:G base pairs to T:A base pairs, including disease-relevant point mutations, in a variety of cell lines with higher efficiency and lower indel frequency than what can be achieved using other genome editing methods[1]. Subsequent studies have validated the deaminase-dCas9 fusion approach in a variety of settings[6,7].

Efficient editing by BE3 requires the presence of an NGG PAM that places the target C within a five-nucleotide window near the PAM-distal end of the protospacer (positions 4-8, counting the PAM as positions 21-23)[1]. This PAM requirement substantially limits the number of sites in the human genome that can be efficiently targeted by BE3, as many sites of interest lack an NGG 13- to 17-nucleotides downstream of the target C. Moreover, the high activity and processivity of BE3 results in conversion of all Cs within the editing window to Ts, which can potentially introduce undesired changes to the target locus. Herein, new C:G to T:A base editors that address both of these limitations are described.

It was thought that any Cas9 homolog that binds DNA and forms an "R-loop" complex[8] containing a single-stranded DNA bubble could in principle be converted into a base editor. These new base editors would expand the number of targetable loci by allowing non-NGG PAM sites to be edited. The Cas9 homolog from *Staphylococcus aureus* (SaCas9) is considerably smaller than SpCas9 (1053 vs. 1368 residues), can mediate efficient genome editing in mammalian cells, and requires an NNGRRT PAM[9]. SpCas9 was replaced with SaCas9 in BE3 to generate SaBE3 and transfected HEK293T cells with plasmids encoding SaBE3 and sgRNAs targeting six human genomic loci (FIGS. 92A and 92B). After 3 d, the genomic loci were subjected to high-throughput DNA sequencing (HTS) to quantify base editing efficiency. SaBE3 enabled C to T base editing of target Cs at a variety of genomic sites in human cells, with very high conversion efficiencies (approximately 50-75% of total DNA sequences converted from C to T, without enrichment for transfected cells) arising from targeting Cs at positions 6-11. The efficiency of SaBE3 on NNGRRT-containing target sites in general exceeded that of BE3 on NGG-containing target sites[1]. Perhaps due to its higher average efficiency, SaBE3 can also result in detectable base editing at target Cs at positions outside of the canonical BE3 activity window (FIG. 92C). In comparison, BE3 showed significantly reduced editing under the same conditions (0-11%), in accordance with the known SpCas9 PAM preference (FIG. 106A)[10]. These data show that SaBE3 can facilitate very efficient base editing at sites not accessible to BE3.

The targeting range of base editors was further expanded by applying recently engineered Cas9 variants that expand or alter PAM specificities. Joung and coworkers recently reported three SpCas9 mutants that accept NGA (VQR-Cas9), NGAG (EQR-Cas9), or NGCG(VRER-Cas9) PAM sequences[11]. In addition, Joung and coworkers engineered a SaCas9 variant containing three mutations (SaKKH-Cas9) that relax its PAM requirement to NNNRRT[12]. The SpCas9 portion of BE3 was replaced with these four Cas9 variants to produce VQR-BE3, EQR-BE3, VRER-BE3, and SaKKH-BE3, which target NNNRRT, NGA, NGAG, and NGCG PAMs respectively. HEK293T cells were transfected with plasmids encoding these constructs and sgRNAs targeting six genomic loci for each new base editor, and measured C to T base conversions using HTS.

SaKKH-BE3 edited sites with NNNRRT PAMs with efficiencies up to 62% of treated, non-enriched cells (FIG. 92D). As expected, SaBE3 was unable to efficiently edit targets containing PAMs that were NNNHRRT (where H=A, C, or T) (FIG. 92D). VQR-BE3, EQR-BE3, and VRER-BE3 exhibited more modest, but still substantial base editing efficiencies of up to 50% of treated, non-enriched cells at genomic loci with the expected PAM requirements with an editing window similar to that of BE3 (FIGS. 92E and 92F). Base editing efficiencies of VQR-BE3, EQR-BE3, and VRER-BE3 in general closely paralleled the reported PAM requirements of the corresponding Cas9 nucleases; for example, EQR-BE3 was unable to efficiently edit targets containing NGAH PAM sequences (FIG. 92F). In contrast, BE3 was unable to edit sites with NGA or NGCG PAMs efficiently (0-3%), likely due to its PAM restrictions (FIG. 106B).

Collectively, the properties of SaBE3, SaKKH-BE3, VQR-BE3, EQR-BE3, and VRER-BE3 establish that base editors exhibit a modularity that facilitates their ability to exploit Cas9 homologs and engineered variants.

Next, base editors with altered activity window widths were developed. All Cs within the activity window of BE3 can be efficiently converted to Ts[1]. The ability to modulate the width of this window would be useful in cases in which it is important to edit only a subset of Cs present in the BE3 activity window.

The length of the linker between APOBEC1 and dCas9 was previously observed to modulate the number of bases that are accessible by APOBEC1 in vitro[1]. In HEK293T cells, however, varying the linker length did not significantly modulate the width of the editing window, suggesting that in the complex cellular milieu, the relative orientation and flexibility of dCas9 and the cytidine deaminase are not strongly determined by linker length (FIG. 96). Next, it was thought that truncating the 5' end of the sgRNA might narrow the base editing window by reducing the length of single-stranded DNA accessible to the deaminase upon formation of the RNA-DNA heteroduplex. HEK293T cells were co-transfected with plasmids encoding BE3 and sgRNAs of different spacer lengths targeting a locus with multiple Cs in the editing window. No consistent changes in the width of base editing when using truncated sgRNAs with 17- to 19-base spacers were observed (FIGS. 95A to 95B). Truncating the sgRNA spacer to fewer than 17 bases resulted in large losses in activity (FIG. 95A).

As an alternative approach, it was thought that mutations to the deaminase domain might narrow the width of the editing window through multiple possible mechanisms. First, some mutations may alter substrate binding, the conformation of bound DNA, or substrate accessibility to the active site in ways that reduce tolerance for non-optimal presentation of a C to the deaminase active site. Second, because the high activity of APOBEC1 likely contributes to the deamination of multiple Cs per DNA binding event,[1, 13, 14] mutations that reduce the catalytic efficiency of the deaminase domain of a base editor might prevent it from catalyzing successive rounds of deamination before dissociating from the DNA. Once any C:G to T:A editing event has taken place, the sgRNA no longer perfectly matches the target DNA sequence and re-binding of the base editor to the target locus should be less favorable. Both strategies were tested in an effort to discover new base editors that distinguish among multiple cytidines within the original editing window.

Given the absence of an available APOBEC1 structure, several mutations previously reported to modulate the catalytic activity of APOBEC3G, a cytidine deaminase from the same family that shares 42% sequence similarity of its active site-containing domain to that of APOBEC1, were identified[15]. Corresponding APOBEC1 mutations were incorporated into BE3 and evaluated their effect on base editing efficiency and editing window width in HEK293T cells at two C-rich genomic sites containing Cs at positions 3, 4, 5, 6, 8, 9, 10, 12, 13, and 14 (site A); or containing Cs at positions 5, 6, 7, 8, 9, 10, 11, and 13 (site B).

The APOBEC1 mutations R118A and W90A each led to dramatic loss of base editing efficiency (FIG. 97C). R132E led to a general decrease in editing efficiency but did not change the substantially narrow the shape of the editing window (FIG. 97C). In contrast, several mutations that narrowed the width of the editing window while maintaining substantial editing efficiency were found (FIGS. 93A and 97C). The "editing window width" was defined to represent the artificially calculated window width within which editing efficiency exceeds the half-maximal value for that target. The editing window width of BE3 for the two C-rich genomic sites tested was 5.0 (site A) and 6.1 (site B) nucleotides.

R126 in APOBEC1 is predicted to interact with the phosphate backbone of ssDNA[13]. Previous studies have shown that introducing the corresponding mutation into APOBEC3G decreased catalysis by at least 5-fold[14]. Interestingly, when introduced into APOBEC1 in BE3, R126A and R126E increased or maintained activity relative to BE3 at the most strongly edited positions (C5, C6, and C7), while decreasing editing activity at other positions (FIGS. 93A and 97C). Each of these two mutations therefore narrowed the width of the editing window at site A and site B to 4.4 and 3.4 nucleotides (R126A), or to 4.2 and 3.1 nucleotides (R126E), respectively (FIGS. 93A and 97C).

W90 in APOBEC1 (corresponding to W285 in APOBEC3G) is predicted to form a hydrophobic pocket in the APOBEC3G active site and assist in substrate binding[13]. Mutating this residue to Ala abrogated APOBEC3G's catalytic activity[13]. In BE3, W90A almost completely abrogated base editing efficiency (FIG. 97C). In contrast, it was found that W90Y only modestly decreased base editing activity while narrowing the editing window width at site A and site B to 3.8 and 4.9 nucleotides, respectively (FIG. 93A). These results demonstrate that mutations to the cytidine deaminase domain can narrow the activity window width of the corresponding base editors.

W90Y, R126E, and R132E, the three mutations that narrowed the editing window without drastically reducing base editing activity, were combined into doubly and triply mutated base editors. The double mutant W90Y+R126E resulted in a base editor (YE1-BE3) with BE3-like maximal editing efficiencies, but substantially narrowed editing window width (width at site A and site B=2.9 and 3.0 nucleotides, respectively (FIG. 93A). The W90Y+R132E base editor (YE2-BE3) exhibited modestly lower editing efficiencies (averaging 1.4-fold lower maximal editing yields across the five sites tested compared with BE3), and also substantially narrowed editing window width (width at site A and site B=2.7 and 2.8 nucleotides, respectively) (FIG. 97C). The R126E+R132E double mutant (EE-BE3) showed similar maximal editing efficiencies and editing window width as YE2-BE3 (FIG. 97C). The triple mutant W90Y+R126E+R132E (YEE-BE3) exhibited 2.0-fold lower average maximal editing yields but very little editing beyond the C6 position and an editing window width of 2.1 and 1.4 nucleotides for site A and site B, respectively (FIG. 97C). These data taken together indicate that mutations in the cytidine deaminase domain can strongly affect editing window widths, in some cases with minimal or only modest effects on editing efficiency.

The base editing outcomes of BE3, YE1-BE3, YE2-BE3, EE-BE3, and YEE-BE3 were further compared in HEK293T cells targeting four well-studied human genomic sites that contain multiple Cs within the BE3 activity window[1]. These target loci contained target Cs at positions 4 and 5 (HEK site 3), positions 4 and 6 (HEK site 2), positions 5 and 6 (EMX1), or positions 6, 7, 8, and 11 (FANCF). BE3 exhibited little (<1.2-fold) preference for editing any Cs within the position 4-8 activity window. In contrast, YE1-BE3, exhibited a 1.3-fold preference for editing C5 over C4 (HEK site 3), 2.6-fold preference for C6 over C4 (HEK site 2), 2.0-fold preference for C5 over C6 (EMX1), and 1.5-fold preference for C6 over C7 (FANCF) (FIG. 93B). YE2-BE3 and EE-BE3 exhibited somewhat greater positional specificity (narrower activity window) than YE1-BE3, averaging 2.4-fold preference for editing C5 over C4 (HEK site 3), 9.5-fold preference for C6 over C4 (HEK site 2), 2.9-fold preference for C5 over C6 (EMX1), and 2.6-fold preference for C7 over C6 (FANCF) (FIG. 93B). YEE-BE3 showed the greatest positional selectivity, with a 2.9-fold preference for editing C5 over C4 (HEK site 3), 29.7-fold preference for C6 over C4 (HEK site 2), 7.9-fold preference for C5 over C6 (EMX1), and 7.9-fold preference for C7 over C6 (FANCF) (FIG. 93B). The findings establish that mutant base editors can discriminate between adjacent Cs, even when both nucleotides are within the BE3 editing window.

The product distributions of these four mutants and BE3 were further analyzed by HTS to evaluate their apparent processivity. BE3 generated predominantly T4-T5 (HEK site 3), T4-T6 (HEK site 2), and T5-T6 (EMX1) products in treated HEK293T cells, resulting in, on average, 7.4-fold more products containing two Ts, than products containing a single T. In contrast, YE1-BE3, YE2-BE3, EE-BE3, and YEE-BE3 showed substantially higher preferences for singly edited C4-T5, C4-T6, and T5-C6 products (FIG. 93C). YE1-BE3 yielded products with an average single-T to double-T product ratio of 1.4. YE2-BE3 and EE-BE3 yielded products with an average single-T to double-T product ratio of 4.3 and 5.1, respectively (FIG. 93C). Consistent with the above results, the YEE-BE3 triple mutant favored single-T products by an average of 14.3-fold across the three genomic loci. (FIG. 93C). For the target site in which only one C is within the target window (HEK site 4, at position C5), all four mutants exhibited comparable editing efficiencies as BE3 (FIG. 98). These findings indicate that these BE3 mutants have decreased apparent processivity and can favor the conversion of only a single C at target sites containing multiple Cs within the BE3 editing window. These data also suggest a positional preference of C5>C6>C7≈C4 for these mutant base editors, although this preference could differ depending on the target sequence.

The window-modulating mutations in APOBEC1 were applied to VQR-BE3, allowing selective base editing of substrates at sites targeted by NGA PAM (FIG. 107A). However, when these mutations were applied to SaKKH-BE3, a linear decrease in base editing efficiency was observed without the improvement in substrate selectivity, suggesting a different kinetic equilibrium and substrate accessibility of this base editor than those of BE3 and its variants (FIG. 107B).

The five base editors with altered PAM specificities described in this study together increase the number of disease-associated mutations in the ClinVar database that can in principle be corrected by base editing by 2.5-fold (FIGS. 94A and 94B). Similarly, the development of base editors with narrowed editing windows approximately doubles the fraction of ClinVar entries with a properly positioned NGG PAM that can be corrected by base editing without comparable modification of a non-target C (from 31% for BE3 to 59% for YEE-BE3) (FIGS. 94A and 94B).

In summary, the targeting scope of base editing was substantially expanded by developing base editors that use Cas9 variants with different PAM specificities, and by developing a collection of deaminase mutants with varying editing window widths. In theory, base editing should be possible using other programmable DNA-binding proteins (such as Cpf1[16]) that create a bubble of single-stranded DNA that can serve as a substrate for a single-strand-specific nucleotide deaminase enzyme.

Materials and Methods

Cloning. PCR was performed using Q5 Hot Start High-Fidelity DNA Polymerase (New England Biolabs). Plasmids for BE and sgRNA were constructed using USER cloning (New England Biolabs), obtained from previously reported plasmids[1]. DNA vector amplification was carried out using NEB 10 beta competent cells (New England Biolabs).

Cell culture. HEK293T (ATCC CRL-3216) were cultured in Dulbecco's Modified Eagle's Medium plus GlutaMax (ThermoFisher) supplemented with 10% (v/v) fetal bovine serum (FBS), at 37° C. with 5% $CO_2$. Immortalized rat astrocytes containing the ApoE4 isoform of the APOE gene (Taconic Biosciences) were maintained in Dulbecco's Modified Eagle's Medium plus GlutaMax (ThermoFisher Scientific) supplemented with 10% (v/v) fetal bovine serum (FBS) and 200 µg/mL Geneticin (ThermoFisher Scientific).

Transfections. HEK293T cells were seeded on 48-well collagen-coated BioCoat plates (Corning) and transfected at approximately 85% confluency. 750 ng of BE and 250 ng of sgRNA expression plasmids were transfected using 1.5 µl of Lipofectamine 2000 (ThermoFisher Scientific) per well according to the manufacturer's protocol.

High-throughput DNA sequencing of genomic DNA samples. Transfected cells were harvested after 3 d and the genomic DNA was isolated using the Agencourt DNAdvance Genomic DNA Isolation Kit (Beckman Coulter) according to the manufacturer's instructions. Genomic regions of interest were amplified by PCR with flanking HTS primer pairs listed in the Supplementary Sequences. PCR amplification was carried out with Phusion hot-start II DNA polymerase (ThermoFisher) according to the manufacturer's instructions. PCR products were purified using RapidTips (Diffinity Genomics). Secondary PCR was performed to attach sequencing adaptors. The products were gel-purified and quantified using the KAPA Library Quantification Kit-Illumina (KAPA Biosystems). Samples were sequenced on an Illumina MiSeq as previously described[1].

Data analysis. Nucleotide frequencies were assessed using a previously described MATLAB script[1]. Briefly, the reads were aligned to the reference sequence via the Smith-Waterman algorithm. Base calls with Q-scores below 30 were replaced with a placeholder nucleotide (N). This quality threshold results in nucleotide frequencies with an expected theoretical error rate of 1 in 1000.

Analyses of base editing processivity were performed using a custom python script. This program trims sequencing reads to the 20 nucleotide protospacer sequence as determined by a perfect match for the 7 nucleotide sequences that should flank the target site. These targets were then consolidated and sorted by abundance to assess the frequency of base editing products.

Bioinformatic analysis of the ClinVar database of human disease-associated mutations was performed in a manner similar to that previously described but with small adjustments[1]. These adjustments enable the identification of targets with PAMs of customizable length and sequence. In addition, this improved script includes a priority ranking of target C positions (C5>C6>C7>C8≈C4), thus enabling the identification of target sites in which the on-target C is either the only cytosine within the window or is placed at a position with higher predicted editing efficiency than any off-target C within the editing window.

REFERENCES FOR EXAMPLE 12

1 Komor, A. C. et al. Programmable editing of a target base in genomic DNA without double-stranded DNA cleavage. *Nature* 533, 420-424 (2016).
2 Sander, J. D. & Joung, J. K. CRISPR-Cas systems for editing, regulating and targeting genomes. *Nature biotechnology* 32, 347-355 (2014).
3 Cong, L. et al. Multiplex genome engineering using CRISPR/Cas systems. *Science* 339, 819-823 (2013).
4 Ran, F. A. et al. Genome engineering using the CRISPR-Cas9 system. *Nat. Protocols* 8, 2281-2308 (2013).
5 Landrum, M. J. et al. ClinVar: public archive of interpretations of clinically relevant variants. *Nucleic Acids Res.* 44, D862-D868 (2015).
6 Nishida, K. et al. Targeted nucleotide editing using hybrid prokaryotic and vertebrate adaptive immune systems. *Science* 353, aaf8729-1-8 (2016).

7 Ma, Y. et al. Targeted AID-mediated mutagenesis (TAM) enables efficient genomic diversification in mammalian cells. *Nat. Methods* doi:10.1038/nmeth.4027 (2016).
8 Jiang, F. et al. Structures of a CRISPR-Cas9 R-loop complex primed for DNA cleavage. *Science* 351, 867-71 (2016).
9 Ran, F. A. et al. In vivo genome editing using *Staphylococcus aureus* Cas9. *Nature* 520, 186-191 (2015).
10 Zhang, Y. et al. Comparison of non-canonical PAMs for CRISPR/Cas9-mediated DNA cleavage in human cells. *Sci. Rep.* 4, (2014).
11 Kleinstiver, B. P. et. al. Engineered CRISPR-Cas9 nucleases with altered PAM specificities. *Nature* 523, 481-485 (2015).
12 Kleinstiver, B. P. et. al. Broadening the targeting range of *Staphylococcus aureus* CRISPR-Cas9 by modifying PAM recognition. *Nat. Biotechnol.* 33, 1293-1298 (2015).
13 Holden, L. G. et al. Crystal structure of the anti-viral APOBEC3G catalytic domain and functional implications. *Nature* 452, 121-124 (2008).
14 Chen, K.-M. et al. Structure of the DNA deaminase domain of the HIV-1 restriction factor APOBEC3G. *Nature* 452, 116-119 (2008).
15 Harris, R. S., Petersen-Mahrt, S. K. & Neuberger, M. S. RNA Editing Enzyme APOBEC1 and Some of Its Homologs Can Act as DNA Mutators. *Molecular Cell* 10, 1247-1253 (2002).
16 Zetsche, B. et al. Cpf1 Is a Single RNA-Guided Endonuclease of a Class 2 CRISPR-Cas System. *Cell* 163, 759-771 (2015).

Example 13

Using improved transfection procedures and better plasmids, biological replicates (n=3) were used to install the four HF mutations into the Cas9 portion of BE3. The mutations do not significantly effect on-targeting editing with plasmid delivery (FIG. 99). At the tested concentration, BE3 protein delivery works; however, the on-target editing is lower than for plasmid delivery (FIG. 100). Protein delivery of BE3 with the HF mutations installed reduces on-targeting editing efficiency but still yields some edited cells (FIG. 101).

Both lipofection and installing HF mutations were shown to decrease off-target deamination events. For the four sites shown in FIG. 102, the off-target sitest (OT) with the highest GUIDE-Seq reads and deamination events were assayed (Komor et al., *Nature*, 2016). The specificity ratio was calculated by dividing the off-target editing by the on-target editing at the closest corresponding C. In cases where off-target editing was not detectable, the ratio was set to 100. Thus, a higher specificity ratio indicates a more specific construct. BE3 plasmid delivery showed much higher off-target/on-target editing than protein delivery of BE3, plasmid delivery of HF-BE3, or protein delivery of HF-BE3 (FIGS. 102 and 105).

Purified proteins HF-BE3 and BE3 were analyzed in vitro for their capabilities to convert C to T residues at different positions in the spacer with the most permissive motif. Both BE3 and HF-BE3 proteins were found to have the same "window" for base editing (FIGS. 103 and 104).

A list of the disease targets is given in Table 9. The base to be edited in Table 9 is indicated in bold and underlined.

TABLE 9

Base Editor Disease Targets

| GENE | DISEASE | SPACER | PAM | EDITOR | DEFECT | CELL |
|---|---|---|---|---|---|---|
| RB1 | RETINOBLASTOMA | AATCTAGTAAA TAAATTGATGT | AAAAGT | SAKKH-BE3 | SPLICING IMPAIRMENT | J82 |
| PTEN | CANCER | GACCAACGGCT AAGTGAAGA | TGA | VQR-BE3 | W111R | MC116 |
| PIK3CA | CANCER | TCCTTTCTTCA CGGTTGCCT | ACTGGT | SAKKH-BE3 | K111R | CRL-5853 |
| PIK3CA | CANCER | CTCCTGCTCAG TGATTTCAG | AGA | VQR-BE3 | Q546R | CRL-2505 |
| TP53 | CANCER | TGTCACACATG TAGTTGTAG | TGG | YEE-BE3 | N239D | SNU475 |
| HRAS | CANCER | CCTCCCGGCCG GCGGTATCC | AGG | YEE-BE3 | Q61R | MC/CAR |

TABLE 6

Exemplary diseases that may be treated using base editors.

| Disease target | gene symbol | Base changed | sgRNA (PAM) | Base editor |
|---|---|---|---|---|
| Prion disease | PRNP | R37* | GGCAGCCGATACCCGGGGCA (GGG) GGGCAGCCGATACCCGGGGC (AGG) | BE3 |
| Pendred syndrome | Slc26a4 | c.919-2A>G | TTATTGTCCGAAATAAAGA (AGA) ATTGTCCGAAATAAAGAAG (AGG) TTGTCCGAAATAAAGAAGA (GGA) GTCCGAAATAAAGAAGAGGAAAA (AAT) GTCCGAAATAAAGAAGAGGAAAAA (ATT) | BE3 (VQR SaCas9) |

TABLE 6-continued

Exemplary diseases that may be treated using base editors.

| Disease target | gene symbol | Base changed | sgRNA (PAM) | Base editor |
|---|---|---|---|---|
| Congenital deafness | Tmc1 | c.545A>G | CAGGAAGCACGAGGCCACTG (AGG)<br>AACAGGAAGCACGAGGCCAC (TGA)<br>AGGAAGCACGAGGCCACTGA (GGA) | BE3<br>YE-BE3<br>YEE-BE3 |
| Acquired deafness | SNHL | S33F | TTGGATTCTGGAATCCATTC (TGG) | BE3 |
| Alzheimer's Disease | APP | A673T | TCTGCATCCATCTTCACTTC (AGA) | BE3 VQR |
| Niemann-Pick Disease Type C | NPC1 | I1061T | CTTACAGCCAGTAATGTCAC (CGA) | BE3 VQR |

The protospacer and PAM sequences are shown in the sgRNA (PAM) column.
The PAM sequence is shown in parentheses and with the base to be edited indicated by underlining.

Additional exemplary genes in the human genome that may be targeted by the base editors or complexes of this disclosure are provided herein in Tables 7 and 8. Table 7 includes gene mutations that may be corrected by changing a cytosine (C) to a thymine (T), for example, using a BE3 nucleobase editor. Table 8 includes gene mutations that may be corrected by changing a guanine (G) to an adenine (A), for example, using a BE3 nucelobase editor.

Lengthy table referenced here

US12344869-20250701-T00001

Please refer to the end of the specification for access instructions.

Lengthy table referenced here

US12344869-20250701-T00002

Please refer to the end of the specification for access instructions.

REFERENCES

1. Humbert O, Davis L, Maizels N. Targeted gene therapies: tools, applications, optimization. *Crit Rev Biochem Mol.* 2012; 47(3):264-81. PMID: 22530743.
2. Perez-Pinera P, Ousterout D G, Gersbach C A. Advances in targeted genome editing. *Curr Opin Chem Biol.* 2012; 16(3-4):268-77. PMID: 22819644.
3. Urnov F D, Rebar E J, Holmes M C, Zhang H S, Gregory P D. Genome editing with engineered zinc finger nucleases. *Nat Rev Genet.* 2010; 11(9):636-46. PMID: 20717154.
4. Joung J K, Sander J D. TALENs: a widely applicable technology for targeted genome editing. *Nat Rev Mol Cell Biol.* 2013; 14(1):49-55. PMID: 23169466.
5. Charpentier E, Doudna J A. Biotechnology: Rewriting a genome. *Nature.* 2013; 495, (7439):50-1. PMID: 23467164.
6. Pan Y, Xia L, Li A S, Zhang X, Sirois P, Zhang J, Li K. Biological and biomedical applications of engineered nucleases. *Mol Biotechnol.* 2013; 55(1):54-62. PMID: 23089945.
7. De Souza, N. Primer: genome editing with engineered nucleases. *Nat Methods.* 2012; 9(1):27. PMID: 22312638.
8. Santiago Y, Chan E, Liu P Q, Orlando S, Zhang L, Urnov F D, Holmes M C, Guschin D, Waite A, Miller J C, Rebar E J, Gregory P D, Klug A, Collingwood T N. Targeted gene knockout in mammalian cells by using engineered zinc-finger nucleases. *Proc Natl Acad Sci USA.* 2008; 105(15):5809-14. PMID: 18359850.
9. Cargill M, Altshuler D, Ireland J, Sklar P, Ardlie K, Patil N, Lane C R, Lim E P, Kalyanaraman N, Nemesh J, Ziaugra L, Friedland L, Rolfe A, Warrington J, Lipshutz R, Daley G Q, Lander E S. Characterization of single-nucleotide polymorphisms in coding regions of human genes. *Nat Genet.* 1999; 22(3):231-8. PMID: 10391209.
10. Jansen R, van Embden J D, Gaastra W, Schouls L M. Identification of genes that are associated with DNA repeats in prokaryotes. *Mol Microbiol.* 2002; 43(6):1565-75. PMID: 11952905.
11. Mali P, Esvelt K M, Church G M. Cas9 as a versatile tool for engineering biology. *Nat Methods.* 2013; 10(10):957-63. PMID: 24076990.
12. Jore M M, Lundgren M, van Duijin E, Bultema J B, Westra E R, Waghmare S P, Wiedenheft B, Pul U, Wurm R, Wagner R, Beijer M R, Barendregt A, Shou K, Snijders A P, Dickman M J, Doudna J A, Boekema E J, Heck A J, van der Oost J, Brouns S J. Structural basis for CRISPR RNA-guided DNA recognition by Cascade. *Nat Struct Mol Biol.* 2011; 18(5):529-36. PMID: 21460843.
13. Horvath P, Barrangou R. CRISPR/Cas, the immune system of bacteria and archaea. *Science.* 2010; 327(5962): 167-70. PMID: 20056882.
14. Wiedenheft B, Sternberg S H, Doudna J A. RNA-guided genetic silencing systems in bacteria and archaea. *Nature.* 2012; 482(7385):331-8. PMID: 22337052.
15. Gasiunas G, Siksnys V. RNA-dependent DNA endonuclease Cas9 of the CRISPR system: Holy Grail of genome editing? *Trends Microbiol.* 2013; 21(11):562-7. PMID: 24095303.
16. Qi L S, Larson M H, Gilbert L A, Doudna J A, Weissman J S, Arkin A P, Lim W A. Repurposing CRISPR as an RNA-guided platform for sequence-specific control of gene expression. *Cell.* 2013; 152(5):1173-83. PMID: 23452860.
17. Perez-Pinera P, Kocak D D, Vockley C M, Adler A F, Kabadi A M, Polstein L R, Thakore P I, Glass K A, Ousterout D G, Leong K W, Guilak F, Crawford G E, Reddy T E, Gersbach C A. RNA-guided gene activation by CRISPR-Cas9-based transcription factors. *Nat Methods.* 2013; 10(10):973-6. PMID: 23892895.

18. Mali P, Aach J, Stranges P B, Esvelt K M, Moosburner M, Kosuri S, Yang L, Church G M. CAS9 transcriptional activators for target specificity screening and paired nickases for cooperative genome engineering. *Nat Biotechnol.* 2013; 31(9):833-8. PMID: 23907171.

19. Gilbert L A, Larson M H, Morsut L, Liu Z, Brar G A, Torres S E, Stern-Ginossar N, Brandman O, Whitehead E H, Doudna J A, Lim W A, Weissman J S, Qi L S. CRISPR-mediated modular RNA-guided regulation of transcription in eukaryotes. *Cell.* 2013; 154(2):442-51. PMID: 23849981.

20. Larson M H, Gilbert L A, Wang X, Lim W A, Weissman J S, Qi L S. CRISPR interference (CRISPRi) for sequence-specific control of gene expression. *Nat Protoc.* 2013; 8(11):2180-96. PMID: 24136345.

21. Mali P, Yang L, Esvelt K M, Aach J, Guell M, DiCarlo J E, Norville J E, Church G M. RNA-guided human genome engineering via Cas9. *Science.* 2013; 339(6121): 823-6. PMID: 23287722.

22. Cole-Strauss A, Yoon K, Xiang Y, Byrne B C, Rice M C, Gryn J, Holloman W K, Kmiec E B. Correction of the mutation responsible for sickle cell anemia by an RNA-DNA oligonucleotide. *Science.* 1996; 273(5280):1386-9. PMID: 8703073.

23. Tagalakis A D, Owen J S, Simons J P. Lack of RNA-DNA oligonucleotide (chimeraplast) mutagenic activity in mouse embryos. *Mol Reprod Dev.* 2005; 71(2):140-4. PMID: 15791601.

24. Ray A, Langer M. Homologous recombination: ends as the means. *Trends Plant Sci.* 2002; 7(10):435-40. PMID 12399177.

25. Britt A B, May G D. Re-engineering plant gene targeting. *Trends Plant Sci.* 2003; 8(2):90-5. PMID: 12597876.

26. Vagner V, Ehrlich S D. Efficiency of homologous DNA recombination varies along the *Bacillus subtilis* chromosome. *J Bacteriol.* 1988; 170(9):3978-82. PMID: 3137211.

27. Saleh-Gohari N, Helleday T. Conservative homologous recombination preferentially repairs DNA double-strand breaks in the S phase of the cell cycle in human cells. *Nucleic Acids Res.* 2004; 32(12):3683-8. PMID: 15252152.

28. Lombardo A, Genovese P, Beausejour C M, Colleoni S, Lee Y L, Kim K A, Ando D, Urnov F D, Galli C, Gregory P D, Holmes M C, Naldini L. Gene editing in human stem cells using zinc finger nucleases and integrase-defective lentiviral vector delivery. *Nat Biotechnol.* 2007; 25(11): 1298-306. PMID: 17965707.

29. Conticello S G. The AID/APOBEC family of nucleic acid mutators. *Genome Biol.* 2008; 9(6):229. PMID: 18598372.

30. Reynaud C A, Aoufouchi S, Faili A, Weill J C. What role for AID: mutator, or assembler of the immunoglobulin mutasome?*Nat Immunol.* 2003; 4(7):631-8.

31. Bhagwat A S. DNA-cytosine deaminases: from antibody maturation to antiviral defense. *DNA Repair (Amst).* 2004; 3(1):85-9. PMID: 14697763.

32. Navaratnam N, Sarwar R. An overview of cytidine deaminases. *Int J Hematol.* 2006; 83(3):195-200. PMID: 16720547.

33. Holden L G, Prochnow C, Chang Y P, Bransteitter R, Chelico L, Sen U, Stevens R C, Goodman M F, Chen X S. Crystal structure of the anti-viral APOBEC3G catalytic domain and functional implications. *Nature.* 2008; 456 (7218):121-4. PMID: 18849968.

34. Chelico L, Pham P, Petruska J, Goodman M F. Biochemical basis of immunological and retroviral responses to DNA-targeted cytosine deamination by activation-induced cytidine deaminase and APOBEC3G. *J Biol Chem.* 2009; 284(41). 27761-5. PMID: 19684020.

35. Pham P, Bransteitter R, Goodman M F. Reward versus risk: DNA cytidine deaminases triggering immunity and disease. *Biochemistry.* 2005; 44(8):2703-15. PMID 15723516.

36. Chen X, Zaro J L, Shen W C. Fusion protein linkers: property, design and functionality. *Adv Drug Deliv Rev.* 2013; 65(10):1357-69. PMID: 23026637.

37. Lee J W, Soung Y H, Kim S Y, Lee H W, Park W S, Nam S W, Kim S H, Lee J Y, Yoo N J, Lee S H. PIK3C A gene is frequently mutated in breast carcinomas and hepatocellular carcinomas. *Oncogene.* 2005; 24(8):1477-80. PMID: 15608678.

38. Ikediobi O N, Davies H, Bignell G, Edkins S, Stevens C, O'Meara S, Santarius T, Avis T, Barthorpe S, Brackenbury L, Buck G, Butler A, Clements J, Cole J, Dicks E, Forbes S, Gray K, Halliday K, Harrison R, Hills K, Hinton J, Hunter C, Jenkinson A, Jones D, Kosmidou V, Lugg R, Menzies A, Mironenko T, Parker A, Perry J, Raine K, Richardson D, Shepherd R, Small A, Smith R, Solomon H, Stephens P, Teague J, Tofts C, Varian J, Webb T, West S, Widaa S, Yates A, Reinhold W, Weinstein J N, Stratton M R, Futreal P A, Wooster R. Mutation analysis of 24 known cancer genes in the NCI-60 cell line set. *Mol Cancer Ther.* 2006; 5(11):2606-12. PMID: 17088437.

39. Cox, D. B., Platt, R. J. & Zhang, F. Therapeutic genome editing: prospects and challenges. *Nature medicine* 21, 121-131, doi:10.1038/nm.3793 (2015).

40. Hilton, I. B. & Gersbach, C. A. Enabling functional genomics with genome engineering. *Genome research* 25, 1442-1455, doi:10.1101/gr.190124.115 (2015).

41. Sander, J. D. & Joung, J. K. CRISPR-Cas systems for editing, regulating and targeting genomes. *Nature biotechnology* 32, 347-355, doi: 10.1038/nbt.2842 (2014).

42. Maruyama, T. et al. Increasing the efficiency of precise genome editing with CRISPR-Cas9 by inhibition of non-homologous end joining. *Nature biotechnology* 33, 538-542, doi:10.1038/nbt.3190 (2015).

43. Chu, V. T. et al. Increasing the efficiency of homology-directed repair for CRISPR-Cas9-induced precise gene editing in mammalian cells. *Nature biotechnology* 33, 543-548, doi:10.1038/nbt.3198 (2015).

44. Lin, S., Staahl, B. T., Alla, R. K. & Doudna, J. A. Enhanced homology-directed human genome engineering by controlled timing of CRISPR/Cas9 delivery. *eLife* 3, e04766, doi:10.7554/eLife.04766 (2014).

45. Cong, L. et al. Multiplex genome engineering using CRISPR/Cas systems. *Science* 339,819-823, doi:10.1126/science.1231143 (2013).

46. Rong, Z., Zhu, S., Xu, Y. & Fu, X. Homologous recombination in human embryonic stem cells using CRISPR/Cas9 nickase and a long DNA donor template. *Protein & cell* 5, 258-260, doi:10.1007/s13238-014-0032-5 (2014).

47. Jinek, M. et al. A Programmable Dual-RNA-Guided DNA Endonuclease in Adaptive Bacterial Immunity. *Science* 337, 816-821, doi:10.1126/science.1225829 (2012).

48. Harris, R. S., Petersen-Mahrt, S. K. & Neuberger, M. S. RNA Editing Enzyme APOBEC1 and Some of Its Homologs Can Act as DNA Mutators. *Molecular Cell* 10, 1247-1253 (2002).

49. Jinek, M. et al. Structures of Cas9 endonucleases reveal RNA-mediated conformational activation. *Science* 343, 1247997, doi:10.1126/science.1247997 (2014).
50. Schellenberger, V. et al. A recombinant polypeptide extends the in vivo half-life of peptides and proteins in a tunable manner. *Nature biotechnology* 27, 1186-1190, doi: 10.1038/nbt.1588 (2009).
51. Saraconi, G., Severi, F., Sala, C., Mattiuz, G. & Conticello, S. G. The RNA editing enzyme APOBEC1 induces somatic mutations and a compatible mutational signature is present in esophageal adenocarcinomas. *Genome biology* 15,417-(2014).
52. Anders, C., Niewoehner, O., Duerst, A. & Jinek, M. Structural basis of PAM-dependent target DNA recognition by the Cas9 endonuclease. *Nature* 513, 569-573, doi:10.1038/nature13579 (2014).
53. Cong, L. et al. Multiplex genome engineering using CRISPR/Cas systems. *Science* 339, 819-823 (2013).
54. Tsai, S. Q. et al. GUIDE-seq enables genome-wide profiling of off-target cleavage by CRISPR-Cas nucleases. *Nature biotechnology* 33, 187-197, doi:10.1038/nbt.3117 (2015).
55. Kunz, C., Saito, Y. & Schar, P. DNA Repair in mammalian cells: Mismatched repair: variations on a theme. *Cellular and molecular life sciences*: CMLS 66, 1021-1038, doi:10.1007/s00018-009-8739-9(2009).
56. D., M. C. et al. Crystal structure of human uracil-DNA glycosylase in complex with a protein inhibitor: protein mimicry of DNA. *Cell* 82, 701-708 (1995).
57. Caldecott, K. W. Single-strand break repair and genetic disease. *Nature reviews. Genetics* 9, 619-631, doi:10.1038/nrg2380 (2008).
58. Fukui, K. DNA mismatch repair in eukaryotes and bacteria. *Journal of nucleic acids* 2010, doi:10.4061/2010/260512 (2010).
59. Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences* 109, E2579-E2586, doi: 10.1073/pnas.1208507109 (2012).
60. Ran, F. A. et al. In vivo genome editing using *Staphylococcus aureus* Cas9. *Nature* 520, 186-191, doi:10.1038/nature14299 (2015).
61. Kuscu, C., Arslan, S., Singh, R., Thorpe, J. & Adli, M. Genome-wide analysis reveals characteristics of off-target sites bound by the Cas9 endonuclease. *Nature biotechnology* 32, 677-683, doi:10.1038/nbt.2916(2014).
62. Wu, X. et al. Genome-wide binding of the CRISPR endonuclease Cas9 in mammalian cells. *Nature biotechnology* 32, 670-676, doi:10.1038/nbt.2889 (2014).
63. Beale, R. C. L. et al. Comparison of the Differential Context-dependence of DNA Deamination by APOBEC Enzymes: Correlation with Mutation Spectra in Vivo. *Journal of Molecular Biology* 337, 585-596, doi:10.1016/j.jmb.2004.01.046 (2004).
64. Kim, J., Basak, J. M. & Holtzman, D. M. The role of apolipoprotein E in Alzheimer's disease. *Neuron* 63,287-303, doi: 10.1016/j.neuron.2009.06.026 (2009).
65. Liu, C. C., Kanekiyo, T., Xu, H. & Bu, G. Apolipoprotein E and Alzheimer disease: risk, mechanisms and therapy. *Nature reviews. Neurology* 9, 106-118, doi:10.1038/nrneurol.2012.263 (2013).
66. Sjöblom, T. et al. The Consensus Coding Sequences of Human Breast and Colorectal Cancers. *Science* 314, 268-274, doi:10.1126/science.1133427 (2006).
67. Stephens, P. J. et al. The landscape of cancer genes and mutational processes in breast cancer. *Nature* 486, 400-404, doi:10.1038/nature11017 (2012).
68. Landrum, M. J. et al. ClinVar: public archive of interpretations of clinically relevant variants. *Nucleic Acids Research*, doi:10.1093/nar/gkv1222 (2015).
69. Slaymaker, I. M. et al. Rationally engineered Cas9 nucleases with improved specificity. *Science*, doi: 10.1126/science.aad5227 (2015).
70. Davis, K. M., Pattanayak, V., Thompson, D. B., Zuris, J. A. & Liu, D. R. Small molecule-triggered Cas9 protein with improved genome-editing specificity. *Nature chemical biology* 11, 316-318, doi:10.1038/nchembio.1793 (2015).
71. Zuris, J. A. et al. Cationic lipid-mediated delivery of proteins enables efficient protein-based genome editing in vitro and in vivo. *Nature biotechnology* 33, 73-80, doi: 10.1038/nbt.3081 (2015).
72. Kleinstiver, B. P. et al. Engineered CRISPR-Cas9 nucleases with altered PAM specificities. *Nature* 523,481-485, doi: 10.1038/nature14592 (2015).
73. Pattanayak, V. et al. High-throughput profiling of off-target DNA cleavage reveals RNA-programmed Cas9 nuclease specificity. *Nature Biotechnology* 31, 839-843, doi:10.1038/nbt.2673 (2013).
74. Shcherbakova, D. M. & Verkhusha, V. V. Near-infrared fluorescent proteins for multicolor in vivo imaging. *Nature Methods* 10, 751-754, doi:10.1038/nmeth.2521 (2013).
75. Ran, F. A. et al. Genome engineering using the CRISPR-Cas9 system. *Nat. Protocols* 8, 2281-2308, doi:10.1038/nprot.2013.143 (2013).
76. Jiang, F. et al. Structures of a CRISPR-Cas9 R-loop complex primed for DNA cleavage. *Science*, doi:10.1126/science.aad8282 (2016).
77. Tsai, S. Q. et al. Dimeric CRISPR RNA-guided FokI nucleases for highly specific genome editing. *Nat Biotech* 32, 569-576, doi:10.1038/nbt.2908 (2014).
78. Lieber, M. R., Ma, Y., Pannicke, U. & Schwarz, K. Mechanism and regulation of human non-homologous DNA end-joining. *Nat Rev Mol Cell Biol* 4, 712-720 (2003).
79. Heller, R. C. & Marians, K. J. Replisome assembly and the direct restart of stalled replication forks. *Nat Rev Mol Cell Biol* 7, 932-943 (2006).
80. Pluciennik, A. et al. PCNA function in the activation and strand direction of MutLα endonuclease in mismatch repair. *Proceedings of the National Academy of Sciences of the United States of America* 107, 16066-16071, doi: 10.1073/pnas.1010662107 (2010).
81. Seripa, D. et al. The missing ApoE allele. *Annals of human genetics* 71, 496-500, doi:10.1111/j.1469-1809.2006.00344.x (2007).
82. Kleinstiver, B. P. et al. High-fidelity CRISPR-Cas9 nucleases with no detectable genome-wide off-target effects. *Nature* 529, 490-495, doi:10.1038/nature16526 (2016).
83. Richardson, C. D., Ray, G. J., DeWitt, M. A., Curie, G. L. & Corn, J. E. Enhancing homology-directed genome editing by catalytically active and inactive CRISPR-Cas9 using asymmetric donor DNA. *Nat Biotech* 34, 339-344, doi:10.1038/nbt.3481 (2016).
84. Simonelli, V., Narciso, L., Dogliotti, E. & Fortini, P. Base excision repair intermediates are mutagenic in mammalian cells. *Nucleic acids research* 33, 4404-4411, doi: 10.1093/nar/gki749 (2005).

85. Barnes, D. E. & Lindahl, T. Repair and Genetic Consequences of Endogenous DNA Base Damage in Mammalian Cells. *Annual Review of Genetics* 38, 445-476, doi: doi:10.1146/annurev.genet.38.072902.092448 (2004).

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

LENGTHY TABLES

The patent contains a lengthy table section. A copy of the table is available in electronic form from the USPTO web site (https://seqdata.uspto.gov/?pageRequest=docDetail&DocID=US12344869B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US12344869B2). An electronic copy of the sequence listing will also be available from the USPTO upon request and payment of the fee set forth in 37 CFR 1.19(b)(3).

What is claimed is:
1. A complex comprising:
   (i) a Cas9 protein;
   (ii) a cytidine deaminase;
   (iii) a uracil glycosylase inhibitor (UGI) protein; and
   (iv) a guide RNA (gRNA);
   wherein the complex deaminates a cytidine in a target nucleic acid sequence.
2. The complex of claim 1, wherein the Cas9 protein is a Cas9 nickase (nCas9).
3. The complex of claim 2, wherein the nCas9 comprises an amino acid sequence having at least 85% sequence identity to the amino acid sequence provided in SEQ ID NO: 10, and wherein the amino acid sequence provided in SEQ ID NO: 10 further comprises a D10A mutation, or a corresponding mutation in any of the amino acid sequences provided in SEQ ID NOs: 11-260, and 4273-4276.
4. The complex of claim 2, wherein the nCas9 comprises one or more of N497A, R661A, Q695A, or Q926A mutations in the amino acid sequence provided in SEQ ID NO: 10, or one or more corresponding mutations in any of the amino acid sequences provided in SEQ ID NOs: 11-260, and 4273-4276.
5. The complex of claim 1, wherein the Cas9 protein is a nuclease-inactive Cas9 (dCas9).
6. The complex of claim 5, wherein the dCas9 comprises an amino acid sequence having at least 85% sequence identity to the amino acid sequence provided in SEQ ID NO: 10, and wherein the amino acid sequence provided in SEQ ID NO: 10 further comprises a D10A mutation, or a corresponding mutation in any of the amino acid sequences provided in SEQ ID NOs: 11-26, and 4273-4276.
7. The complex of claim 6, wherein the dCas9 comprises an H840A mutation in the amino acid sequence provided in SEQ ID NO: 10, or a corresponding mutation in any of the amino acid sequences provided in SEQ ID NOs: 11-260, and 4273-4276.
8. The complex of claim 5, wherein the dCas9 comprises one or more of N497A, R661A, Q695A, or Q926A mutations in the amino acid sequence provided in SEQ ID NO: 10, or one or more corresponding mutations in any of the amino acid sequences provided in SEQ ID NOs: 11-260, and 4273-4276.
9. The complex of claim 1, wherein the Cas9 protein is selected from the group consisting of a *Staphylococcus aureus* Cas9 protein (SaCas9), a nuclease inactive SaCas9 (dSaCas9), a SaCas9 nickase (nSaCas9), a *Streptococcus pyogenes* Cas9 protein (SpCas9), a nuclease inactive SpCas9 (dSpCas9), and a SpCas9 nickase (nSpCas9).
10. The complex of claim 9, wherein the SaCas9 comprises the amino acid sequence provided in SEQ ID NO: 4273 or 4274.
11. The complex of claim 10, wherein the SaCas9 comprises one or more of E781K, N967K, or R1014H mutations in the amino acid sequence provided in SEQ ID NO: 4273, or one or more corresponding mutations in any of the amino acid sequences provided in SEQ ID NOs: 10-260 and 4274-4276.
12. The complex of claim 9, wherein the SpCas9 comprises the amino acid sequence provided in SEQ ID NO: 4276.
13. The complex of claim 9, wherein the SpCas9 comprises a D9A mutation in the amino acid sequence provided in SEQ ID NO: 4276, or a corresponding mutation in any of the amino acid sequences provided in SEQ ID NOs: 10-260, and 4273-4276.

14. The complex of claim 1, wherein the Cas9 protein is derived from *Corynebacterium ulcerous, Corynebacterium diphtheria, Spiroplasma syrphidicola, Prevotella intermedia, Spiroplasma taiwanense, Streptococcus iniae, Belliella baltica, Psychroflexus torquisI, Streptococcus thermophilus, Listeria innocua, Campylobacter jejuni*, or *Neisseria meningitidis*.
15. The complex of claim 14, wherein the Cas9 protein is derived from *Neisseria meningitidis*.
16. The complex of claim 1, wherein the cytidine deaminase:
   (i) is an apolipoprotein B mRNA-editing complex (APOBEC) family deaminase;
   (ii) comprises an amino acid sequence that is at least 85% identical to any of the amino acid sequences of SEQ ID NO: 266-284, 607-610, 5724-5736, and 5738-5741;
   (iii) comprises any of the amino acid sequences of SEQ ID NO: 266-284, 607-610, 5724-5736, and 5738-5741;
   (iv) is a rat APOBEC1 (rAPOBEC1) deaminase comprising one or more mutations selected from the group consisting of W90Y, R126E, and R132E of SEQ ID NO: 284, or one or more corresponding mutations in another APOBEC deaminase;
   (v) is a human APOBEC1 (hAPOBEC1) deaminase comprising one or more mutations selected from the group consisting of W90Y, Q126E, and R132E of SEQ ID NO: 5724, or one or more corresponding mutations in another APOBEC deaminase;
   (vi) is a human APOBEC3G (hAPOBEC3G) deaminase comprising one or more mutations selected from the group consisting of W285Y, R320E, and R326E of SEQ ID NO: 275, or one or more corresponding mutations in another APOBEC deaminase;
   (vii) is an activation-induced deaminase (AID); or
   (viii) is a cytidine deaminase 1 from *Petromyzon marinus* (pmCDA1).
17. The complex of claim 1, wherein the cytidine deaminase is a cytidine deaminase from a human or a rat.
18. The complex of claim 16, wherein the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase.
19. The complex of claim 16, wherein the APOBEC family deaminase is an APOBEC3G deaminase.
20. The complex of claim 1, wherein the UGI protein comprises an amino acid sequence that is at least 85% identical to any one of SEQ ID NOs: 322-324 and 600.
21. The complex of claim 1, wherein the UGI protein comprises an amino acid sequence set forth in any one of SEQ ID NOs: 322-324 and 600.
22. The complex of claim 1, wherein the gRNA comprises a nucleotide sequence of at least 10 contiguous nucleotides that is complementary to the target nucleic acid sequence.
23. The complex of claim 1, wherein the gRNA is from 15-100 nucleotides long.
24. The complex of claim 1, wherein the target nucleic acid sequence is a DNA sequence.
25. The complex of claim 1, wherein the target sequence is in the genome of a eukaryote.
26. The complex of claim 25, wherein the eukaryote is a mammal.
27. The complex of claim 26, wherein the mammal is human.
28. The complex of claim 1, wherein the target nucleic acid sequence comprises a sequence associated with a disease or disorder, and wherein the deamination of the cytidine results in a sequence that is not associated with the disease or disorder.

29. A method of nucleic acid editing, the method comprising contacting a target nucleic acid molecule with the complex of claim 1, wherein the method results in deamination of a cytidine in the target nucleic acid molecule.

30. The method of claim 29, wherein the gRNA comprises a nucleotide sequence of at least 10 contiguous nucleotides that is complementary to the target nucleic acid molecule.

31. The method of claim 29, wherein the target nucleic acid molecule comprises a sequence associated with a disease or disorder, and wherein the deamination of the cytidine results in a sequence that is not associated with the disease or disorder.

32. The method of claim 29, wherein the target nucleic acid molecule comprises a point mutation associated with a disease or disorder, and wherein the deamination corrects the point mutation.

33. The method of claim 32, wherein the target nucleic acid molecule comprises a T to C point mutation, and wherein the deamination of the mutant C base results in a nucleic acid sequence that is not associated with the disease or disorder.

34. The method of claim 31, wherein the target nucleic acid sequence associated with the disease or disorder encodes a protein and wherein the deamination introduces a stop codon into the sequence associated with the disease or disorder, resulting in a truncation of the encoded protein.

* * * * *

UNITED STATES PATENT AND TRADEMARK OFFICE
CERTIFICATE OF CORRECTION

| | | |
|---|---|---|
| PATENT NO. | : 12,344,869 B2 | Page 1 of 1 |
| APPLICATION NO. | : 17/527011 | |
| DATED | : July 1, 2025 | |
| INVENTOR(S) | : David R. Liu et al. | |

It is certified that error appears in the above-identified patent and that said Letters Patent is hereby corrected as shown below:

In the Specification

At Column 1, Lines 35-38, please change the paragraph:
"This invention was made with Government support under grant number EB022376 (formerly GM065400) awarded by the National Institutes of Health. The Government has certain rights in the invention."

To:
-- This invention was made with government support under EB022376 awarded by the National Institutes of Health. The government has certain rights in the invention. --

Signed and Sealed this
Fifth Day of August, 2025

Coke Morgan Stewart
*Acting Director of the United States Patent and Trademark Office*